US012503439B2

(12) United States Patent
Miller et al.

(10) Patent No.: US 12,503,439 B2
(45) Date of Patent: Dec. 23, 2025

(54) HETEROARYL COMPOUNDS FOR THE TREATMENT OF PAIN

(71) Applicant: VERTEX PHARMACEUTICALS INCORPORATED, Boston, MA (US)

(72) Inventors: Mark Thomas Miller, Rancho Santa Fe, CA (US); Dennis James Hurley, San Marcos, CA (US); Timothy Donald Neubert, San Diego, CA (US); Vijayalaksmi Arumugam, San Marcos, CA (US); Sara Sabina Hadida Ruah, La Jolla, CA (US); Jason McCartney, Cardiff by the Sea, CA (US); Jinglan Zhou, San Diego, CA (US); Jaclyn Chau, San Diego, CA (US); Robert Martin Demoret, San Diego, CA (US); Senait G. Ghirmai, San Diego, CA (US); Roman Askatovich Valiulin, San Diego, CA (US); Alexander Fredrick Kintzer, Carlsbad, CA (US); David Robert Slochower, San Diego, CA (US); Kathleen Aertgeerts, San Diego, CA (US); Elizabeth Mary Beck, Abingdon (GB); James Jun Bon Mui, Watford (GB); Miranda Adele Wright, Oxford (GB); Ronald Marcellus Alphonsus Knegtel, Abingdon (GB); Ewa Iwona Chudyk, Wantage (GB); Joanne Louise Pinder, Didcot (GB); James Dodd, Wallingford (GB); Iain Simpson, Oxford (GB)

(73) Assignee: VERTEX PHARMACEUTICALS INCORPORATED, Boston, MA (US)

( * ) Notice: Subject to any disclaimer, the term of this patent is extended or adjusted under 35 U.S.C. 154(b) by 39 days.

(21) Appl. No.: 18/137,939

(22) Filed: Apr. 21, 2023

(65) Prior Publication Data

US 2023/0373925 A1 Nov. 23, 2023

Related U.S. Application Data

(60) Provisional application No. 63/333,875, filed on Apr. 22, 2022.

(51) Int. Cl.

| | |
|---|---|
| ***C07D 215/233*** | (2006.01) |
| ***C07D 239/91*** | (2006.01) |
| ***C07D 401/04*** | (2006.01) |
| ***C07D 401/14*** | (2006.01) |
| ***C07D 471/04*** | (2006.01) |
| ***C07D 519/00*** | (2006.01) |

(52) U.S. Cl.

CPC ....... *C07D 215/233* (2013.01); *C07D 239/91* (2013.01); *C07D 401/04* (2013.01); *C07D 401/14* (2013.01); *C07D 471/04* (2013.01); *C07D 519/00* (2013.01); *C07B 2200/05* (2013.01)

(58) Field of Classification Search

CPC .. A61P 25/02; A61P 29/00; A61P 9/06; C07B 2200/05; C07D 215/233; C07D 239/91; C07D 401/04; C07D 401/14; C07D 405/14; C07D 471/04; C07D 519/00

See application file for complete search history.

(56) References Cited

U.S. PATENT DOCUMENTS

| | | | |
|---|---|---|---|
| 4,923,874 | A | 5/1990 | McMahon et al. |
| 5,294,612 | A | 3/1994 | Bacon et al. |
| 5,304,121 | A | 4/1994 | Sahatjian |
| 5,403,842 | A | 4/1995 | Leonardi et al. |
| 5,817,674 | A | 10/1998 | Clemence et al. |
| 5,886,026 | A | 3/1999 | Hunter et al. |
| 6,060,477 | A | 5/2000 | Piazza et al. |
| 6,099,562 | A | 8/2000 | Ding et al. |
| 6,200,980 | B1 | 3/2001 | Piazza et al. |
| 8,389,734 | B2 | 3/2013 | Chen |
| 8,466,188 | B2 | 6/2013 | Chafeev et al. |
| 8,519,137 | B2 | 8/2013 | Joshi |
| 8,779,197 | B2 | 7/2014 | Chen |
| 8,841,483 | B2 | 9/2014 | Joshi |
| 8,865,771 | B2 | 10/2014 | Chen |
| 8,883,840 | B2 | 11/2014 | Chafeev et al. |

(Continued)

FOREIGN PATENT DOCUMENTS

| | | |
|---|---|---|
| CA | 2112425 | 12/1993 |
| CA | 2228535 | 2/1998 |

(Continued)

OTHER PUBLICATIONS

Amine, M.S., "Synthesis, behavior and biological activities of 1,3-benzoxazin-4-ones with a bulky substituent in the 2-position," Egyptian Journal of Chemistry (1997), 40(3), pp. 231-238.

Kassab, E.A., et al., "Synthesis and Behavior of a Static Benzoxazinone Derivative towards Nitrogen and Sulphur Nucleophiles,"Egyptian Journal of Chemistry (2001), 44(1-3), pp. 169-179.

Abdullaha, Mohd et al., "Discovery of Quinazolin-4(3H)-ones as NLRP3 Inflammasome Inhibitors: Computational Design, Metal-Free Synthesis, and in Vitro Biological Evaluation," Journal of Organic Chemistry (2019), 84(9), pp. 5129-5140.

Akopian, A.N., L. Sivilotti, and J.N. Wood, A tetrodotoxin-resistant voltage-gated sodium channel expressed by sensory neurons. Nature, 1996. 379(6562): p. 257-62).

Alam, Md Toufique; Maiti, Saikat; Mal, Prasenjit, "The mechanochemical synthesis of quinazolin-4(3h)-ones by controlling the reactivity of IBX," Beilstein Journal of Organic Chemistry (2018), 14, pp. 2396-2403.

(Continued)

*Primary Examiner* — Jeffrey H Murray
*Assistant Examiner* — Daniel John Burkett
(74) *Attorney, Agent, or Firm* — Barnes & Thornburg, LLP; Steve M. Sturlis; Joshua E. Ney

(57) ABSTRACT

Compounds, and pharmaceutically acceptable salts thereof, useful as inhibitors of sodium channels are provided. Also provided are pharmaceutical compositions comprising the compounds or pharmaceutically acceptable salts and methods of using the compounds, pharmaceutically acceptable salts, and pharmaceutical compositions in the treatment of various disorders, including pain.

35 Claims, No Drawings

(56) References Cited

U.S. PATENT DOCUMENTS

| | | | |
|---|---|---|---|
| 9,051,270 | B2 | 6/2015 | Hadida-Ruah |
| 9,108,903 | B2 | 8/2015 | Hadida-Ruah |
| 9,139,529 | B2 | 9/2015 | Hadida-Ruah |
| 9,163,042 | B2 | 10/2015 | Anderson |
| 9,393,235 | B2 | 7/2016 | Hadida-Ruah |
| 9,421,196 | B2 | 8/2016 | Hadida-Ruah |
| 9,464,102 | B2 | 10/2016 | Anderson |
| 9,758,483 | B2 | 9/2017 | Hadida-Ruah |
| 9,783,501 | B2 | 10/2017 | Hadida-Ruah |
| 9,828,397 | B2 | 11/2017 | Anderson |
| 10,087,143 | B2 | 10/2018 | Hadida Ruah |
| 10,253,054 | B2 | 4/2019 | Anderson |
| 10,647,661 | B2 | 5/2020 | Ahmad |
| 10,738,009 | B2 | 8/2020 | Hadida Ruah |
| 10,787,472 | B2 | 9/2020 | Anderson |
| 11,203,571 | B2 | 12/2021 | Hadida-Ruah et al. |
| 11,358,977 | B2 | 6/2022 | Jiang et al. |
| 11,529,337 | B2 | 12/2022 | Agarwal et al. |
| 11,603,351 | B2 | 3/2023 | Ahmad et al. |
| 11,673,864 | B2 | 6/2023 | Hadida Ruah et al. |
| 11,773,119 | B2 | 10/2023 | Anderson et al. |
| 11,827,627 | B2 | 11/2023 | Beck et al. |
| 11,834,441 | B2 | 12/2023 | Durrant et al. |
| 11,919,887 | B2 | 3/2024 | Durrant et al. |
| 12,247,021 | B2 | 3/2025 | Durrant et al. |
| 2004/0229909 | A1 | 11/2004 | Kiyama et al. |
| 2005/0020592 | A1 | 1/2005 | Dominguez et al. |
| 2005/0142383 | A1 | 6/2005 | Igarashi et al. |
| 2006/0142248 | A1 | 6/2006 | Bricker et al. |
| 2007/0203236 | A1 | 8/2007 | Smith et al. |
| 2007/0238733 | A1 | 10/2007 | Joshi et al. |
| 2008/0176225 | A1 | 7/2008 | Roffler et al. |
| 2008/0188467 | A1 | 8/2008 | Wong et al. |
| 2008/0234332 | A1 | 9/2008 | Cai et al. |
| 2008/0312235 | A1 | 12/2008 | Lane et al. |
| 2009/0048306 | A1 | 2/2009 | Bagal et al. |
| 2009/0099233 | A1 | 4/2009 | Joshi et al. |
| 2009/0118333 | A1 | 5/2009 | Chen et al. |
| 2009/0118338 | A1 | 5/2009 | Chen et al. |
| 2009/0326020 | A1 | 12/2009 | Miller et al. |
| 2010/0129367 | A1 | 5/2010 | Roffler et al. |
| 2011/0257196 | A1 | 10/2011 | Lu et al. |
| 2011/0306607 | A1 | 12/2011 | Hadida-Ruah et al. |
| 2011/0312905 | A1 | 12/2011 | Cohen et al. |
| 2012/0015908 | A1 | 1/2012 | Kuo et al. |
| 2012/0071524 | A1 | 3/2012 | Lu et al. |
| 2012/0196869 | A1 | 8/2012 | Hadida Ruah et al. |
| 2012/0220605 | A1 | 8/2012 | Pajouhesh et al. |
| 2012/0245136 | A1 | 9/2012 | Hadida-Ruah et al. |
| 2012/0264749 | A1 | 10/2012 | Hadida-Ruah et al. |
| 2013/0158031 | A1 | 6/2013 | Cai et al. |
| 2013/0231370 | A1 | 9/2013 | Chen et al. |
| 2013/0274243 | A1 | 10/2013 | Bagal et al. |
| 2013/0281397 | A1 | 10/2013 | McLure et al. |
| 2013/0303535 | A1 | 11/2013 | Tsuboi et al. |
| 2014/0005181 | A1 | 1/2014 | Smith et al. |
| 2014/0187533 | A1 | 7/2014 | Pajouhesh et al. |
| 2014/0213616 | A1 | 7/2014 | Hadida-Ruah et al. |
| 2014/0221435 | A1 | 8/2014 | Hadida-Ruah et al. |
| 2014/0228371 | A1 | 8/2014 | Hadida-Ruah et al. |
| 2014/0296313 | A1 | 10/2014 | Bagal et al. |
| 2014/0323477 | A1 | 10/2014 | Crawford et al. |
| 2015/0005304 | A1 | 1/2015 | Hadida-Ruah et al. |
| 2015/0166589 | A1 | 6/2015 | Anderson et al. |
| 2015/0246028 | A1 | 9/2015 | Hadida-Ruah et al. |
| 2015/0328196 | A1 | 11/2015 | Hadida-Ruah et al. |
| 2015/0336945 | A1 | 11/2015 | Hadida-Ruah et al. |
| 2016/0009743 | A1 | 1/2016 | Anderson et al. |
| 2016/0043331 | A1 | 2/2016 | Li et al. |
| 2016/0152561 | A1 | 6/2016 | Hadida-Ruah et al. |
| 2016/0376295 | A1 | 12/2016 | Anderson et al. |
| 2017/0037009 | A1 | 2/2017 | Hadida-Ruah et al. |
| 2018/0016235 | A1 | 1/2018 | Hadida-Ruah et al. |
| 2018/0044361 | A1 | 2/2018 | Anderson et al. |
| 2019/0016671 | A1 | 1/2019 | Ahmad et al. |
| 2019/0106398 | A1 | 4/2019 | Cohen et al. |
| 2019/0248745 | A1 | 8/2019 | Hadida Ruah et al. |
| 2019/0276483 | A1 | 9/2019 | Anderson et al. |
| 2019/0343817 | A1 | 11/2019 | Agarwal et al. |
| 2019/0375753 | A1 | 12/2019 | Bui et al. |
| 2020/0377535 | A1 | 12/2020 | Anderson et al. |
| 2021/0047271 | A1 | 2/2021 | Hadida Ruah et al. |
| 2021/0052610 | A1 | 2/2021 | Agarwal et al. |
| 2021/0094906 | A1 | 4/2021 | Ahmad et al. |
| 2021/0155643 | A1 | 5/2021 | Jiang et al. |
| 2021/0198241 | A1 | 7/2021 | Durrant |
| 2022/0110923 | A1 | 4/2022 | Thomson |
| 2023/0009251 | A1 | 1/2023 | Beck |
| 2023/0062053 | A1 | 3/2023 | Thomson |
| 2023/0286907 | A1 | 9/2023 | Ahmad et al. |
| 2023/0286961 | A1 | 9/2023 | Durrant et al. |
| 2023/0373925 | A1 | 11/2023 | Miller et al. |
| 2023/0382910 | A1* | 11/2023 | Miller .................. C07D 215/48 |
| 2024/0182455 | A1 | 6/2024 | Beck et al. |
| 2024/0285596 | A1 | 8/2024 | Karkare et al. |
| 2024/0294512 | A1 | 9/2024 | Beck et al. |
| 2024/0368135 | A1 | 11/2024 | Beck et al. |
| 2024/0391907 | A1 | 11/2024 | Durrant et al. |
| 2024/0400544 | A1 | 12/2024 | Beck et al. |

FOREIGN PATENT DOCUMENTS

| | | | | |
|---|---|---|---|---|
| CA | 2354175 | | 7/2001 | |
| CA | 2359383 | | 10/2001 | |
| CN | 104761524 | | 7/2015 | |
| CN | 105936635 | | 9/2016 | |
| CN | 106946775 | | 7/2017 | |
| CN | 106977486 | | 7/2017 | |
| CN | 107365326 | | 11/2017 | |
| CN | 107661333 | | 2/2018 | |
| CN | 107773562 | | 3/2018 | |
| CN | 108329366 | | 7/2018 | |
| CN | 108623562 | | 10/2018 | |
| CN | 108623587 | | 10/2018 | |
| CN | 108623588 | | 10/2018 | |
| CN | 110498784 | | 11/2019 | |
| CN | 111153899 | | 5/2020 | |
| CN | 111217776 | | 6/2020 | |
| CN | 111808019 | | 10/2020 | |
| CN | 111848731 | | 10/2020 | |
| CN | 112047880 | | 12/2020 | |
| CN | 112225695 | | 1/2021 | |
| CN | 112300051 | | 2/2021 | |
| CN | 112300069 | | 2/2021 | |
| CN | 112390745 | | 2/2021 | |
| CN | 112409331 | | 2/2021 | |
| CN | 112441969 | | 3/2021 | |
| CN | 112457294 | | 3/2021 | |
| CN | 112479996 | | 3/2021 | |
| CN | 112778288 | | 5/2021 | |
| CN | 112812014 | | 5/2021 | |
| CN | 113200926 | | 8/2021 | |
| CN | 113754594 | | 12/2021 | |
| CN | 114591293 | | 6/2022 | |
| CN | 112390745 | B * | 10/2022 | .............. A61P 13/00 |
| DE | 2162096 | | 7/1972 | |
| DE | 102015121035 | A1 | 6/2017 | |
| EP | 0304001 | | 2/1989 | |
| EP | 0304155 | | 2/1989 | |
| EP | 0347146 | | 12/1989 | |
| EP | 0351058 | | 1/1990 | |
| EP | 0352960 | | 1/1990 | |
| EP | 0498723 | | 8/1992 | |
| EP | 0531901 | | 3/1993 | |
| EP | 0558245 | | 9/1993 | |
| EP | 0591785 | | 4/1994 | |
| EP | 0811613 | | 12/1997 | |
| EP | 0856310 | | 8/1998 | |
| EP | 1321811 | | 6/2003 | |
| EP | 1321812 | | 6/2003 | |
| EP | 2524918 | | 11/2012 | |
| EP | 3309154 | | 4/2018 | |
| JP | H04164070 | A | 6/1992 | |
| JP | 2001081451 | | 3/2001 | |

(56) References Cited

FOREIGN PATENT DOCUMENTS

| | | |
|---|---|---|
| JP | 2002189128 | 7/2002 |
| JP | 2005008789 | 1/2005 |
| JP | 2007230145 | 9/2007 |
| JP | 2009203350 | 9/2009 |
| JP | 2016079098 | 5/2016 |
| JP | 2017218449 | 12/2017 |
| WO | WO 1988/006588 | 9/1988 |
| WO | WO 1993/004077 | 3/1993 |
| WO | WO 1993/017007 | 9/1993 |
| WO | WO 1995/015758 | 6/1995 |
| WO | WO 1996/028448 | 9/1996 |
| WO | WO 1996/030540 | 10/1996 |
| WO | WO 1997/014419 | 4/1997 |
| WO | WO 1998/004257 | 2/1998 |
| WO | WO 1998/018466 | 5/1998 |
| WO | WO 1998/027080 | 6/1998 |
| WO | WO 1998/039332 | 9/1998 |
| WO | WO 1999/054333 | 10/1999 |
| WO | WO 1999/062518 | 12/1999 |
| WO | WO 2000/024745 | 5/2000 |
| WO | WO 2000/031063 | 6/2000 |
| WO | WO 2001/027112 | 4/2001 |
| WO | WO 2001/027113 | 4/2001 |
| WO | WO 2001/049685 | 7/2001 |
| WO | WO 2001/081340 | 11/2001 |
| WO | WO 2002/003995 | 1/2002 |
| WO | WO 2002/008748 | 1/2002 |
| WO | WO 2002/026713 | 4/2002 |
| WO | WO 2002/055012 | 7/2002 |
| WO | WO 2002/070515 | 9/2002 |
| WO | WO 2002/074774 | 9/2002 |
| WO | WO 2003/037871 | 5/2003 |
| WO | WO 2004/003103 | 1/2004 |
| WO | WO 2004/016607 | 2/2004 |
| WO | WO 2004/058787 | 7/2004 |
| WO | WO 2005/000309 | 1/2005 |
| WO | WO 2005/043630 | 5/2005 |
| WO | WO 2005/047279 | 5/2005 |
| WO | WO 2005/071096 | 8/2005 |
| WO | WO 2005/100345 | 10/2005 |
| WO | WO 2005/100353 | 10/2005 |
| WO | WO 2005/103052 | 11/2005 |
| WO | WO 2006/011050 | 2/2006 |
| WO | WO 2006/030807 | 3/2006 |
| WO | WO 2006/037958 | 4/2006 |
| WO | WO 2006/038041 | 4/2006 |
| WO | WO 2006/072000 | 7/2006 |
| WO | WO 2006/094604 | 9/2006 |
| WO | WO 2006/100119 | 9/2006 |
| WO | WO 2006/120251 | 11/2006 |
| WO | WO 2006/138418 | 12/2006 |
| WO | WO 2007/002701 | 1/2007 |
| WO | WO 2007/057782 | 5/2007 |
| WO | WO 2007/071632 | 6/2007 |
| WO | WO 2007/079180 | 7/2007 |
| WO | WO 2007/095187 | 8/2007 |
| WO | WO 2007/097940 | 8/2007 |
| WO | WO 2007/126765 | 11/2007 |
| WO | WO 2007/128460 | 11/2007 |
| WO | WO 2008/024139 | 2/2008 |
| WO | WO 2008/030120 | 3/2008 |
| WO | WO 2008/033743 | 3/2008 |
| WO | WO 2008/033744 | 3/2008 |
| WO | WO 2008/033745 | 3/2008 |
| WO | WO 2008/033746 | 3/2008 |
| WO | WO 2008/033749 | 3/2008 |
| WO | WO 2008/037607 | 4/2008 |
| WO | WO 2008/067389 | 6/2008 |
| WO | WO 2008/068470 | 6/2008 |
| WO | WO 2008/074474 | 6/2008 |
| WO | WO 2008/081455 | 7/2008 |
| WO | WO 2008/094507 | 8/2008 |
| WO | WO 2008/115262 | 9/2008 |
| WO | WO 2008/135826 | 11/2008 |
| WO | WO 2008/142384 | 11/2008 |
| WO | WO 2009/036012 | 3/2009 |
| WO | WO 2009/036016 | 3/2009 |
| WO | WO 2009/036055 | 3/2009 |
| WO | WO 2009/036066 | 3/2009 |
| WO | WO 2009/086012 | 7/2009 |
| WO | WO 2009/102498 | 8/2009 |
| WO | WO 2009/114470 | 9/2009 |
| WO | WO 2009/129372 | 10/2009 |
| WO | WO 2009/147431 | 12/2009 |
| WO | WO 2010/025906 | 3/2010 |
| WO | WO 2010/037127 | 4/2010 |
| WO | WO 2010/037129 | 4/2010 |
| WO | WO 2010/038081 | 4/2010 |
| WO | WO 2010/048149 | 4/2010 |
| WO | WO 2010/070523 | 6/2010 |
| WO | WO 2010/080996 | 7/2010 |
| WO | WO 2010/129864 | 11/2010 |
| WO | WO 2010/139483 | 12/2010 |
| WO | WO 2010/142216 | 12/2010 |
| WO | WO 2011/026240 | 3/2011 |
| WO | WO 2011/037731 | 3/2011 |
| WO | WO 2011/047320 | 4/2011 |
| WO | WO 2011/109059 | 9/2011 |
| WO | WO 2011/130628 | 10/2011 |
| WO | WO 2011/140425 | 11/2011 |
| WO | WO 2011/160024 | 12/2011 |
| WO | WO 2012/009519 | 1/2012 |
| WO | WO 2012/015914 | 2/2012 |
| WO | WO 2012/016133 | 2/2012 |
| WO | WO 2012/049460 | 4/2012 |
| WO | WO 2012/069856 | 5/2012 |
| WO | WO 2012/073138 | 6/2012 |
| WO | WO 2012/080729 | 6/2012 |
| WO | WO 2012/094328 | 7/2012 |
| WO | WO 2012/106499 | 8/2012 |
| WO | WO 2012/106534 | 8/2012 |
| WO | WO 2012/112743 | 8/2012 |
| WO | WO 2012/116440 | 9/2012 |
| WO | WO 2012/125613 | 9/2012 |
| WO | WO 2012/125973 | 9/2012 |
| WO | WO 2012/148808 | 11/2012 |
| WO | WO 2012/149157 | 11/2012 |
| WO | WO 2012/151512 | 11/2012 |
| WO | WO 2012/170371 | 12/2012 |
| WO | WO 2013/014170 | 1/2013 |
| WO | WO 2013/022740 | 2/2013 |
| WO | WO 2013/045854 | 4/2013 |
| WO | WO 2013/049559 | 4/2013 |
| WO | WO 2013/061205 | 5/2013 |
| WO | WO 2013/086229 | 6/2013 |
| WO | WO 2013/093484 | 6/2013 |
| WO | WO 2013/109521 | 7/2013 |
| WO | WO 2013/114250 | 8/2013 |
| WO | WO 2013/131018 | 9/2013 |
| WO | WO 2013/134518 | 9/2013 |
| WO | WO 2014/000713 | 1/2014 |
| WO | WO 2014/018741 | 1/2014 |
| WO | WO 2014/020285 | 2/2014 |
| WO | WO 2014/029684 | 2/2014 |
| WO | WO 2014/033448 | 3/2014 |
| WO | WO 2014/066795 | 5/2014 |
| WO | WO 2014/070978 | 5/2014 |
| WO | WO 2014/078479 | 5/2014 |
| WO | WO 2014/082379 | 6/2014 |
| WO | WO 2014/082380 | 6/2014 |
| WO | WO 2014/108407 | 7/2014 |
| WO | WO 2014/120808 | 8/2014 |
| WO | WO 2014/120815 | 8/2014 |
| WO | WO 2014/120820 | 8/2014 |
| WO | WO 2014/128188 | 8/2014 |
| WO | WO 2014/139326 | 9/2014 |
| WO | WO 2014/179496 | 11/2014 |
| WO | WO 2014/201173 | 12/2014 |
| WO | WO 2014/201206 | 12/2014 |
| WO | WO 2015/010065 | 1/2015 |
| WO | WO 2015/015318 | 2/2015 |
| WO | WO 2015/025228 | 2/2015 |
| WO | WO 2015/035051 | 3/2015 |
| WO | WO 2015/035062 | 3/2015 |

(56) References Cited

FOREIGN PATENT DOCUMENTS

| | | | |
|---|---|---|---|
| WO | WO 2015/085238 | | 6/2015 |
| WO | WO 2015/089361 | | 6/2015 |
| WO | WO 2015/120777 | | 8/2015 |
| WO | WO 2015/135094 | | 9/2015 |
| WO | WO 2015/157559 | | 10/2015 |
| WO | WO 2015/197981 | | 12/2015 |
| WO | WO 2016/141035 | | 9/2016 |
| WO | WO 2016/141855 | | 9/2016 |
| WO | WO 2016/174072 | | 11/2016 |
| WO | WO 2016/174075 | | 11/2016 |
| WO | WO 2017/017631 | | 2/2017 |
| WO | WO 2017/059385 | | 4/2017 |
| WO | WO 2017/103615 | | 6/2017 |
| WO | WO 2016/093285 | | 9/2017 |
| WO | WO 2017/156194 | | 9/2017 |
| WO | WO 2017/220205 | | 12/2017 |
| WO | WO 2018/020242 | | 2/2018 |
| WO | WO 2018/033742 | | 2/2018 |
| WO | WO 2018/071283 | | 4/2018 |
| WO | WO 2018/114933 | | 6/2018 |
| WO | WO 2018/130152 | | 7/2018 |
| WO | WO 2018/161033 | | 9/2018 |
| WO | WO 2018/183781 | | 10/2018 |
| WO | WO 2018/183782 | | 10/2018 |
| WO | WO 2018/186365 | | 10/2018 |
| WO | WO 2018/204765 | | 11/2018 |
| WO | WO 2018/213426 | | 11/2018 |
| WO | WO 2018/226976 | | 12/2018 |
| WO | WO 2019/014352 | | 1/2019 |
| WO | WO 2019/018119 | | 1/2019 |
| WO | WO 2019/028456 | | 2/2019 |
| WO | WO 2019/121392 | | 6/2019 |
| WO | WO 2019/137201 | | 7/2019 |
| WO | WO 2019/213006 | | 11/2019 |
| WO | WO 2019/222238 | | 11/2019 |
| WO | WO 2019/238057 | | 12/2019 |
| WO | WO 2019/246343 | | 12/2019 |
| WO | WO 2020/003219 | | 1/2020 |
| WO | WO 2020/014243 | | 1/2020 |
| WO | WO 2020/014246 | | 1/2020 |
| WO | WO 2020/113759 | | 1/2020 |
| WO | WO 2020/042618 | | 3/2020 |
| WO | WO 2020/051207 | | 3/2020 |
| WO | WO 2020/072835 | | 4/2020 |
| WO | WO 2020/087170 | | 5/2020 |
| WO | WO 2020/092187 | | 5/2020 |
| WO | WO 2020/092667 | | 5/2020 |
| WO | WO 2020/094156 | | 5/2020 |
| WO | WO 2020/113373 | | 6/2020 |
| WO | WO 2020/117626 | | 6/2020 |
| WO | WO 2020/118036 | | 6/2020 |
| WO | WO 2020/140959 | | 7/2020 |
| WO | WO 2020/144375 | | 7/2020 |
| WO | WO 2020/146612 | | 7/2020 |
| WO | WO 2020/146682 | | 7/2020 |
| WO | WO 2020/151728 | | 7/2020 |
| WO | WO 2020/154492 | | 7/2020 |
| WO | WO 2020/261114 | A1 | 12/2020 |
| WO | WO 2021/011727 | | 1/2021 |
| WO | WO 2021/032074 | | 2/2021 |
| WO | WO 2021/047622 | | 3/2021 |
| WO | WO 2021/105512 | | 6/2021 |
| WO | WO 2021/126995 | | 6/2021 |
| WO | WO 2021/133917 | | 7/2021 |
| WO | WO 2021/155253 | | 8/2021 |
| WO | WO 2021/252818 | | 12/2021 |
| WO | WO 2021/252820 | | 12/2021 |
| WO | WO 2021/252822 | | 12/2021 |
| WO | WO 2021/257418 | | 12/2021 |
| WO | WO 2021/257420 | | 12/2021 |
| WO | WO 2021/257490 | | 12/2021 |
| WO | WO 2022/036297 | | 2/2022 |
| WO | WO 2022/235558 | | 11/2022 |
| WO | WO 2022/235859 | | 11/2022 |
| WO | WO 2022/263498 | | 12/2022 |

OTHER PUBLICATIONS

Antunes, Joao E., et al., "In silico prediction of novel phosphodiesterase type-5 inhibitors derived from Sildenafil, Vardenafil and Tadalafil," BioOrganic & Medicinal Chemistry (2008), 16(16), pp. 7599-7606.
Anzola, Marcello and Winssinger, Nicolas, "Turn On of a Ruthenium (II) Photocatalyst by DNA-Templated Ligation," Chemistry—A European Journal (2019), 25(1), pp. 334-342.
Banerji, Biswadip et aL., "Regioselective Synthesis of Quinazolinone-/Phenanthridine-Fused Heteropolycycles by Pd-Catalyzed Direct Intramolecular Aerobic Oxidative C—H Amination from Aromatic Strained Amides,"Chemistry—A European Journal (2016), 22(10), pp. 3506-3512.
Berge, S. M., et al. describe pharmaceutically acceptable salts in detail in J. Pharmaceutical Sciences. Jan. 1977. 66. p. 1-19.
Berggren, Kiera N., et al., "An improved formulation of SYPRO Ruby protein gel stain: Comparison with the original formulation and with a ruthenium II tris (bathophenanthroline disulfonate) formulation," Proteomics (2002), 2(5), pp. 486-498.
Black, J.A., et al., Multiple sodium channel isoforms and mitogen-activated protein kinases are present in painful human neuromas. Ann. Neurol., 2008. 64(6): p. 644-53.
Blair, N.T. and B.P. Bean, Roles of tetrodotoxin (TTX)-sensitive Na+ current, TTX-resistant Na+ current, and Ca2+ current in the action potentials of nociceptive sensory neurons. J. Neurosci., 2002. 22(23): p. 10277-90).
Broughton, B.J., et al., "Antiallergic activity of 2-phenyl-8-azapurin-6-ones," Journal of Medicinal Chemistry (1975), 18(11), pp. 1117-1122.
Bunnage, Mark E., et al., "Highly potent and selective chiral inhibitors of PDE5: An illustration of Pfeiffer's Rule," BioOrganic & Medicinal Chemistry Letters (2008), 18(23), pp. 6033-6036.
Catterall, W. A., Goldin, A. L., and Waxman, S. G., International Union of Pharmacology. XLVII. Nomenclature and structure-function relationships of voltage-gated sodium channels. Pharmacol. Rev. 57 (4), p. 397 (2005)).
Chahine, M, Chatelier, A., Babich, O., and Krupp, J. J., Voltage-gated sodium channels in neurological disorders. CNS Neurol. Disord. Drug Targets 7 (2), p. 144-58 (2008).
Chavan, Subhash P. and Rasapalli, Sivappa, "A short and efficient general synthesis of luotonin A, B and E," Tetrahedron (2004), 60(44), pp. 9931-9935.
Chen, H.F. et al., Virtual Screening and Rational Drug Design Method Using Structure Generation System Based on 3D-QSAR and Docking. SAR and QSAR in Environmental Research, 2003, 14(4), pp. 251-264.
Choi, J.S. and S.G. Waxman, Physiological interactions between NaV1.7 and NaV1.8 sodium channels: a computer simulation study. J. Neurophysiol. (2011) 106(6): p. 3173-84;
Choi, Jin Ho et al., "Ru(II)-Catalyzed C—H addition and oxidative cyclization of 2-aryl quinazolinones with activated aldehydes," Organic & Biomolecular Chemistry (2020), 18(47), pp. 9611-9622.
Coward, K., et al., Immunolocalization of SNS/PN3 and NaN/SNS2 sodium channels in human pain states. Pain, 2000. 85(1-2): p. 41-50.
Credille, Cy V. et al., SAR Exploration of Tight-Binding Inhibitors of Influenza Virus PA Endonuclease. Journal of Medicinal Chemistry, 2019. 62(21): pp. 9438-9449.
Dalai, Suryakanta et al., "Cyclopropyl Building Blocks in organic synthesis. 124. Access to variously substituted 5, 6, 7, 8—tetrahydro-3H-quinazolin-4-ones via Diels-Alder adducts of phenyl vinyl sulfone to cyclobutene-annelated pyrimidinones," European Journal of Organic Chemistry (2006), 12, pp. 2753-2765.
Dalai, Suryakanta, "New Applications of Methyl 2-chloro-2-cyclopropylideneacetate Towards the Synthesis of Biologically Important Heterocycles," Georg-August Univ. of Goettingen (2005).
Da Silva, Gustavo et al, "Lewis Acid Catalyzed Diels-Alder Reactions of (E)—1-Methyl-2-styrylquinolin-4(1H)-ones with ortho-Benzoquinodimethane: Synthesis of New 2-(3-Arylnaphthalen-2-yl)-1-methquuinolin-4(1H)-ones," Synthesis (2016), 48(24), pp. A-F.
Devkota, Shreedhar et al., "Direct Construction of Diverse Polyheterocycles Bearing Pyrrolidinediones via Rh(III)-Catzlyzed

(56) References Cited

OTHER PUBLICATIONS

Cascade C—H Activation/Spirocyclization," Advanced Synthesis & Catalysis (2019), 361(24), pp. 5587-5595.
Dieleman, J.P., et al., Incidence rates and treatment of neuropathic pain conditions in the general population. *Pain*, 2008. 137(3): p. 681-8.
Diwu, Zhenjun et al., "Fluorescent molecular probes I. The synthesis and biological properties of an ELF β-glucuronidase substrate that yields fluorescent precipitates at the enzymic activity sites," Tetrahedron (1997) vol. 53, Issue 21, pp. 7159-7164.
Dong, X.W., et al., Small interfering RNA-mediated selective knockdown of NaV1.8 tetrodotoxin-resistant sodium channel reverses mechanical allodynia in neuropathic rats. Neuroscience, 2007. 146(2): p. 812-21.
England, S., Voltage-gated sodium channels: the search for subtype-selective analgesics. Expert Opin. Investig. Drugs 17 (12), p. 1849-64 (2008).
Feng, Yadong et al. "Palladium-catzlyzed oxidative homocoupling of 2-arylquinazolinones," Chinese Chemical Letters (2020), 31(12), pp. 3263-3266.
Fornwald J. A., et al., Gene Expression in Mammalian Cells Using BacMam, a Modified Baculovirus System, 1350 Methods in Molecular Biology 95-116 (2016).
Gaddamidi, Venkat et al., "Metabolism of [14C] Chlorantraniliprole in the Lactating Goat," Journal of Agricultural and Food Chemistry (2011), 59(4), pp. 1316-1323.
Gonzalez, J.E. and Tsien, R.Y., "Improved indicators of cell membrane potential that use fluorescence resonance energy transfer," (1997) Chem. Biol. 4, 269-277.
Gonzalez, J.E. and Tsien, R.Y., "Voltage Sensing by Fluorescence Resonance Energy Transfer in Single Cells," (1995) Biophys. J. 69, 1272-1280.
Harbeson, S.L. and R. D. Tung, Deuterium In Drug Discovery and Development, Ann. Rep. Med. Chem. 2011, 46, 403-417.
Huang, C. J., et al. Characterization of voltage-gated sodium channel blockers by electrical stimulation and fluorescence detection of membrane potential, 24 Nature Biotech. 439-46 (2006).
Huang, H.L., et al., Proteomic profiling of neuromas reveals alterations in protein composition and local protein synthesis in hyper-excitable nerves. Mol. Pain, 2008. 4: p. 33.
Huang, Tianle et al., "One-Pot Construction of Diverse Products using Versatile Cyclopropenones," Advanced Synthesis & Catalysis (2021), 363 (21), pp. 4899-4904.
Huang, Zhentao et al., "Redox supramolecular self-assemblies nonlinearly enhance fluorescence to identify cancer cells," Chemical Communications (2018), 54(42), pp. 5385-5388.
Huang, Zhentao et al., "Supramolecular assemblies mimicking neutrophil extracellular traps for MRSE infection control," Biomaterials (2020), 253, pp. 120124.
Ibric, Amra et al., "A facile oxidative opening of the C-ring in luotonin A and derivatives," Molecules (2017), 22(9), pp. 1540/1-1540/12.
International Search Report and Written Opinion for PCT/U82023/019469, Jul. 7, 2023, 9 pgs.
Jarvis, M.F., et al., A-803467, a potent and selective NaV1.8 sodium channel blocker, attenuates neuropathic and inflammatory pain in the rat. Proc. Natl. Acad. Sci. U S A, 2007. 104(20): p. 8520-5.
Joshi, S.K., et al., Involvement of the TTX-resistant sodium channel NaV1.8 in inflammatory and neuropathic, but not post-operative, pain states. Pain, 2006. 123(1-2): pp. 75-82.
Krafte, D. S. and Bannon, A. W., "Sodium channels and nociception: recent concepts and therapeutic opportunities", Current Opinion in Pharmacology, 8(1), 2008, pp. 50-56, (XP002540499).
Lai, J., et al., Inhibition of neuropathic pain by decreased expression of the tetrodotoxin-resistant sodium channel, NaV1.8. Pain, 2002. 95(1-2): p. 143-52.
Li, Ke et al., "In Situ Imaging of Furin Activity with a Highly Stable Probe by Releasing of Precipitating Fluorochrome," Analytical Chemistry (2018), 90(19), pp. 1-10.
List of Registry Compounds from CAS STN® Registry Database, with dates of entry in database.
Liu, Xuexin et al., "Three-Component Couplings among Heteroarenes, Difluorocyclopropenes, and Water via C—H Activation," Organic Letters (2021), 23(17), pp. 6831-6835.
Mohammed, Shabber, et al., "Iodine Catalyzed Oxidative Synthesis of Quinazolin-4(3H)-ones and Pyrazolo [4,3-d] pyrimidin-7 (6H)-ones via Amination of sp3 C—H Bond," Journal of Organic Chemistry (2015), 80(13), pp. 6915-6921.
Naleway, John J. et al., "Synthesis and Use of New Fluorogenic Precipitating Substrates," Tetrahedron Letters, (1994), 35(46), pp. 8569-8572.
Ou-Yang, Juan et al., "Detecting and imaging of γ-Glutamytranspeptidase activity in serum, live cells, and pathological tissues with a high signal-stability probe by releasing a precipitating fluorochrome," ACS Sensors (2018), 3(7), pp. 1354-1361.
Plaskon, Andrey S., et al., "A Synthesis of 5-hetaryl-3-(2-hydroxybenzoyl) pyrroles," Tetrahedron (2008), 64(25), pp. 5933-5943.
Prost, Maxime et al., "Tagging Live Cells that Express Specific Peptidase Activity with Solid-State Fluorescence," ChemBioChem (2014), 15(10), pp. 1413-1417.
Qiu, F., et al., Increased expression of tetrodotoxin-resistant sodium channels NaV1.8 and NaV1.9 within dorsal root ganglia in a rat model of bone cancer pain. Neurosci. Lett., 512(2): p. 61-6).
Rawson, David J. et al., "The Discovery of UK-369003, a novel PDE5 inhibitor with the potential for oral bioavailability and dose-proportional pharmacokinetics," BioOrganic & Medicinal Chemistry (2012), 20(1), pp. 498-509.
Renganathan, M., T.R. Cummins, and S.G. Waxman, Contribution of Na(V)1.8 sodium channels to action potential electrogenesis in DRG neurons. J. Neurophysiol., 2001. 86(2): p. 629-40.
Roza, C., et al., The tetrodotoxin-resistant Na+ channel NaV1.8 is essential for the expression of spontaneous activity in damaged sensory axons of mice. J. Phvsiol., 2003. 550(Pt 3): p. 921-6).
Ruangsri, S., et al., Relationship of axonal voltage-gated sodium channel 1.8 (NaV1.8) mRNA accumulation to sciatic nerve injury-induced painful neuropathy in rats. J. Biol. Chem. 286(46): p. 39836-47).
Rukavishnikov, Aleksey et al., "Fluorogenic cephalosporin Substrates for β-lactamase TEM-1," Analytical Biochemistry (2011), 419(1), pp. 9-16.
Rush, A.M., et al., A single sodium channel mutation produces hyper- or hypoexcitability in different types of neurons. Proc. Natl. Acad. Sci. USA, 2006. 103(21): p. 8245-50).
Rush, A.M. and T.R. Cummins, "Painful Research: Identification of a Small-Molecule Inhibitorthat Selectively Targets NaV1.8 Sodium Channels", Mol. Interv., 2007. 7(4): p. 192-5.
Sacramento, Manoela et al., "Selective Synthesis of 2-(1,2,3-Triazolyl) Quinazolinones through Copper-Catalyzed Multicomponent Reaction," Catalysts (2021), 11(10), pp. 1170.
Salazar, Chase A. et al., "Tailored quinones support high-turnover Pd catlysts for oxidative C—H arylation with o2," Science (2020), 370(6523), pp. 1454-1460.
Schuerer, Stephen C. et al., "Prospective Exploration of Synthetically Feasible, Medicinally Relevant Chemical Space," Journal of Chemical Information and Modeling (2005), 45(2), pp. 239-248.
Shi, Yuesen et al., "Divergent Construction of Diverse Scaffolds through Catalyst-Controlled C—H Activation Cascades of Quinazolinones and Cyclopropenones," Chemistry A European Journal, Vol. 27, Iss. 53, Sep. 20, 2021, p. 13346-13351.
Soderpalm, B., Anticonvulsants: aspects of their mechanisms of action. Eur. J. Pain 6 Suggl. A, p. 3-9 (2002).
Strickland, I.T., et al., Changes in the expression of NaV1.7, NaV1.8 and NaV1.9 in a distinct population of dorsal root ganglia innervating the rat knee joint in a model of chronic inflammatory joint pain. Eur. J. Pain, 2008. 12(5): p. 564-72.
Sun, W., et al., Reduced conduction failure of the main axon of polymodal nociceptive C-fibers contributes to painful diabetic neuropathy in rats. Brain, 135(Pt 2): p. 359-75.
Terrett, Nicholas K. et al., "Sildenafil (Viagra™), a potent and selective inhibitor of type cGMP phosphodiesterase with utility for

(56) References Cited

OTHER PUBLICATIONS the treatment of male erectile dysfunction," Bioorganic & Medicinal Chemistry Letters (1996), 6(15), pp. 1819-1824.
Thorn-Seshold, et al., "A robust, high-sensitivity stealth probe for peptidases," Chemical Communications (2012), 48(50), pp. 6253-6255.
Voitenko, Z.V. et al., "Esters of o-(4-oxo-3,4-dihydro-2-quinazolinyl) benzoic acid and 5, 11-dihydroisoindolo [2, 1-a] quinazolinone-5 derivatives as β-cyclodextrin modifiers," Dopovidi Natsional'noi Akademii Nauk Ukraini (2005), (8), pp.132-138.
Wang, G. K., Mitchell, J., and Wang, S. Y., Block of persistent late Na+ currents by antidepressant sertraline and paroxetine. J. Membr. Biol. 222 (2), p. 79-90 (2008).
Wang, Xingwei et al., "A novel fluorescent probe based on ESIPT and AIE processes for the detection of hydrogen peroxide and glucose and its application in nasopharyngeal carcinoma imaging," Analytical Methods (2017), 9(12), pp. 1872-1875.
Wei, Lin-Su et al, "Gold (III)-Catalyzed Selective Cyclization of Alkynyl Quinazolinone-Tethered Pyrroles: Synthesis of Fused Quinazolinone Scaffolds." Journal of Organic Chemistry (2018). 83(12). pp. 6719-6727.
Xiang, Haoyue et al., "Pot, atom and step economic synthesis: a diversity-oriented approach to construct 2-substituted pyrrolo [2,1-f] [1, 2, 4] triazin-4(3H)-ones," RSC Advances (2013), 3(17), pp. 5807-5810.
Yang, Wenge et al., "Hydroxyphenquuinazolinone-based turn-on fluorescent probe for β-galactosidase activity detection and application in livinq cells." Dyes and Piqments (2018). 156. pp. 100-107.
Yang, Ning-Hong et al., "A facile approach to synthesize NH-3-aryloxindoles at room temperature by Rh(III)-catalized C—H activation," Catalysis Communications (2020), 136, p. 105904.
Yiangou, Y., et al., SNS/PN3 and SNSZ/NaN sodium channel-like immunoreactivity in human adult and neonate injured sensory nerves. FEBS Lett., 2000. 467(2-3): p. 249-52.
Zhang, Yuanguang et al., "Rhodium (III)-catalyzed C—H amination of 2-arquuinazolin-4(3H)-one with N-alkyl-o-benzoyl-hydroxylamines," Tetrahedron (2018), 74(19), pp. 2330-2337.
Zhao, Zhou et al., "A novel HPQ-based turn-on fluorescent probe for detection of fluoride ions in living cells," Tetrahedron Letters (2017), 58(43), pp. 4129-4132.
Zhou, Mingjie, et al., "A fluorogenic substrate for β-glucuronidase: applications in fluorometric, polyacrylamide gel and histochemical assays," Journal of Biochemical and Biophysical Methods (1996), 33(3), pp. 197-205.
Zhou, Liyi et al., "Localizable and Photoactivatable Fluorophore for Spatiotemporal Two-Photon Bioimaging," Analytical Chemistry (2015), 87(11), pp. 5626-5631.
Zhou, Xi-Rui et al., "Gag Protein Oriented Supramolecular Nets as Potential HIV Traps," Bioconjugate Chemistry (2021), 32(1), pp. 106-110.

* cited by examiner

HETEROARYL COMPOUNDS FOR THE TREATMENT OF PAIN

CROSS-REFERENCE TO RELATED APPLICATIONS

This application claims the benefit of U.S. Provisional Application No. 63/333,875, filed Apr. 22, 2022, which is incorporated by reference in its entirety.

BACKGROUND

Pain is a protective mechanism that allows healthy animals to avoid tissue damage and to prevent further damage to injured tissue. Nonetheless there are many conditions where pain persists beyond its usefulness, or where patients would benefit from inhibition of pain. Neuropathic pain is a form of chronic pain caused by an injury to the sensory nerves (Dieleman, J. P., et al., Incidence rates and treatment of neuropathic pain conditions in the general population. *Pain,* 2008. 137(3): p. 681-8). Neuropathic pain can be divided into two categories, pain caused by generalized metabolic damage to the nerve and pain caused by a discrete nerve injury. The metabolic neuropathies include post-herpetic neuropathy, diabetic neuropathy, and drug-induced neuropathy. Discrete nerve injury indications include post-amputation pain, post-surgical nerve injury pain, and nerve entrapment injuries like neuropathic back pain.

Voltage-gated sodium channels ($Na_V$s) are involved in pain signaling. $Na_V$s are biological mediators of electrical signaling as they mediate the rapid upstroke of the action potential of many excitable cell types (e.g. neurons, skeletal myocytes, cardiac myocytes). The evidence for the role of these channels in normal physiology, the pathological states arising from mutations in sodium channel genes, preclinical work in animal models, and the clinical pharmacology of known sodium channel modulating agents all point to the central role of $Na_V$s in pain sensation (Rush, A. M. and T. R. Cummins, *Painful Research: Identification of a Small-Molecule Inhibitor that Selectively Targets $Na_V$1.8 Sodium Channels. Mol. Interv.,* 2007. 7(4): p. 192-5); England, S., Voltage-gated sodium channels: the search for subtype-selective analgesics. *Expert Opin. Investig. Drugs* 17 (12), p. 1849-64 (2008); Krafte, D. S. and Bannon, A. W., Sodium channels and nociception: recent concepts and therapeutic opportunities. *Curr. Opin. Pharmacol.* 8 (1), p. 50-56 (2008)). $Na_V$s mediate the rapid upstroke of the action potential of many excitable cell types (e.g. neurons, skeletal myocytes, cardiac myocytes), and thus are involved in the initiation of signaling in those cells (Hille, Bertil, *Ion Channels of Excitable Membranes*, Third ed. (Sinauer Associates, Inc., Sunderland, M A, 2001)). Because of the role $Na_V$s play in the initiation and propagation of neuronal signals, antagonists that reduce $Na_V$ currents can prevent or reduce neural signaling and $Na_V$ channels have been considered likely targets to reduce pain in conditions where hyper-excitability is observed (Chahine, M., Chatelier, A., Babich, O., and Krupp, J. J., Voltage-gated sodium channels in neurological disorders. *CNS Neurol. Disord. Drug Targets* 7 (2), p. 144-58 (2008)). Several clinically useful analgesics have been identified as inhibitors of $Na_V$ channels. The local anesthetic drugs such as lidocaine block pain by inhibiting $Na_V$ channels, and other compounds, such as carbamazepine, lamotrigine, and tricyclic antidepressants that have proven effective at reducing pain have also been suggested to act by sodium channel inhibition (Soderpalm, B., Anticonvulsants: aspects of their mechanisms of action. *Eur. J. Pain* 6 Suppl. A, p. 3-9 (2002); Wang, G. K., Mitchell, J., and Wang, S. Y., Block of persistent late $Na^+$ currents by antidepressant sertraline and paroxetine. *J. Membr. Biol.* 222 (2), p. 79-90 (2008)).

The $Na_V$s form a subfamily of the voltage-gated ion channel super-family and comprises 9 isoforms, designated $Na_V$1.1-$Na_V$1.9. The tissue localizations of the nine isoforms vary. $Na_V$1.4 is the primary sodium channel of skeletal muscle, and $Na_V$1.5 is primary sodium channel of cardiac myocytes. $Na_V$s 1.7, 1.8 and 1.9 are primarily localized to the peripheral nervous system, while $Na_V$s 1.1, 1.2, 1.3, and 1.6 are neuronal channels found in both the central and peripheral nervous systems. The functional behaviors of the nine isoforms are similar but distinct in the specifics of their voltage-dependent and kinetic behavior (Catterall, W. A., Goldin, A. L., and Waxman, S. G., International Union of Pharmacology. XLVII. Nomenclature and structure-function relationships of voltage-gated sodium channels. *Pharmacol. Rev.* 57 (4), p. 397 (2005)).

Upon their discovery, $Na_V$1.8 channels were identified as likely targets for analgesia (Akopian, A. N., L. Sivilotti, and J. N. Wood, A tetrodotoxin-resistant voltage-gated sodium channel expressed by sensory neurons. *Nature,* 1996. 379 (6562): p. 257-62). Since then, $Na_V$1.8 has been shown to be a carrier of the sodium current that maintains action potential firing in small dorsal root ganglia (DRG) neurons (Blair, N. T. and B. P. Bean, Roles of tetrodotoxin (TTX)-sensitive $Na^+$ current, TTX-resistant $Na^+$ current, and $Ca^{2+}$ current in the action potentials of nociceptive sensory neurons. *J. Neurosci.,* 2002. 22(23): p. 10277-90). $Na_V$1.8 is involved in spontaneous firing in damaged neurons, like those that drive neuropathic pain (Roza, C., et al., The tetrodotoxin-resistant $Na^+$ channel $Na_V$1.8 is essential for the expression of spontaneous activity in damaged sensory axons of mice. *J. Physiol.,* 2003. 550(Pt 3): p. 921-6; Jarvis, M. F., et al., A-803467, a potent and selective $Na_V$1.8 sodium channel blocker, attenuates neuropathic and inflammatory pain in the rat. *Proc. Natl. Acad. Sci. USA,* 2007. 104(20): p. 8520-5; Joshi, S. K., et al., Involvement of the TTX-resistant sodium channel $Na_V$1.8 in inflammatory and neuropathic, but not post-operative, pain states. *Pain,* 2006. 123 (1-2): pp. 75-82; Lai, J., et al., Inhibition of neuropathic pain by decreased expression of the tetrodotoxin-resistant sodium channel, $Na_V$1.8. *Pain,* 2002. 95(1-2): p. 143-52; Dong, X. W., et al., *Small interfering RNA-mediated selective knockdown of Nav* 1.8 tetrodotoxin-resistant sodium channel reverses mechanical allodynia in neuropathic rats. *Neuroscience,* 2007. 146 (2): p. 812-21; Huang, H. L., et al., Proteomic profiling of neuromas reveals alterations in protein composition and local protein synthesis in hyper-excitable nerves. *Mol. Pain,* 2008. 4: p. 33; Black, J. A., et al., Multiple sodium channel isoforms and mitogen-activated protein kinases are present in painful human neuromas. *Ann. Neurol.,* 2008. 64(6): p. 644-53; Coward, K., et al., Immunolocalization of SNS/PN3 and NaN/SNS2 sodium channels in human pain states. *Pain,* 2000. 85 (1-2): p. 41-50; Yiangou, Y., et al., SNS/PN3 and SNS2/NaN sodium channel-like immunoreactivity in human adult and neonate injured sensory nerves. *FEBS Lett.,* 2000. 467 (2-3): p. 249-52; Ruangsri, S., et al., Relationship of axonal voltage-gated sodium channel 1.8 ($Na_V$1.8) mRNA accumulation to sciatic nerve injury-induced painful neuropathy in rats. *J. Biol. Chem.* 286 (46): p. 39836-47). The small DRG neurons where $Na_V$1.8 is expressed include the nociceptors involved in pain signaling. $Na_V$1.8 mediates large amplitude action potentials in small neurons of the dorsal root ganglia (Blair, N. T. and B. P. Bean, Roles of tetrodotoxin (TTX)-sensitive $Na^+$ current, TTX-resistant $Na^+$ current, and $Ca^{2+}$ current in the action potentials of nociceptive sensory neurons. *J. Neurosci.,* 2002. 22 (23): p. 10277-90). $Na_V1.8$ is necessary for rapid repetitive action potentials in nociceptors, and for spontaneous activity of damaged neurons. (Choi, J. S. and S. G. Waxman, Physiological interactions between $Na_V1.7$ and $Na_V1.8$ sodium channels: a computer simulation study. *J. Neurophysiol.* 106 (6): p. 3173-84; Renganathan, M., T. R. Cummins, and S. G. Waxman, Contribution of $Na(_V)1.8$ sodium channels to action potential electrogenesis in DRG neurons. *J. Neurophysiol.,* 2001. 86(2): p. 629-40; Roza, C., et al., The tetrodotoxin-resistant $Na^+$ channel $Na_V1.8$ is essential for the expression of spontaneous activity in damaged sensory axons of mice. *J. Physiol.,* 2003. 550(Pt 3): p. 921-6). In depolarized or damaged DRG neurons, $Na_V1.8$ appears to be a driver of hyper excitability (Rush, A. M., et al., A single sodium channel mutation produces hyper- or hypoexcitability in different types of neurons. *Proc. Natl. Acad. Sci. USA,* 2006. 103(21): p. 8245-50). In some animal pain models, $Na_V1.8$ mRNA expression levels have been shown to increase in the DRG (Sun, W., et al., Reduced conduction failure of the main axon of polymodal nociceptive C-fibers contributes to painful diabetic neuropathy in rats. *Brain,* 135(Pt 2): p. 359-75; Strickland, I. T., et al., Changes in the expression of $Na_V1.7$, $Na_V1.8$ and $Na_V1.9$ in a distinct population of dorsal root ganglia innervating the rat knee joint in a model of chronic inflammatory joint pain. *Eur. J. Pain,* 2008. 12(5): p. 564-72; Qiu, F., et al., Increased expression of tetrodotoxin-resistant sodium channels $Na_V1.8$ and $Na_V1.9$ within dorsal root ganglia in a rat model of bone cancer pain. *Neurosci. Lett.,* 512(2): p. 61-6).

The inventors have discovered that some voltage-gated sodium channel inhibitors have limitations as therapeutic agents due to, for example, a poor therapeutic window (e.g., due to a lack of $Na_V$ isoform selectivity, low potency, and/or other reasons). Accordingly, there remains a need to develop selective voltage-gated sodium channel inhibitors, such as selective $Na_V1.8$ inhibitors.

SUMMARY

In one aspect, the invention relates to a compound described herein, or a pharmaceutically acceptable salt thereof.

In another aspect, the invention relates to a pharmaceutical composition comprising the compound, or a pharmaceutically acceptable salt thereof, and one or more pharmaceutically acceptable carriers or vehicles.

In still another aspect, the invention relates to a method of inhibiting a voltage gated sodium channel in a subject by administering the compound, pharmaceutically acceptable salt, or pharmaceutical composition to the subject.

In yet another aspect, the invention relates to a method of treating or lessening the severity in a subject of a variety of diseases, disorders, or conditions, including, but not limited to, chronic pain, gut pain, neuropathic pain, musculoskeletal pain, acute pain, inflammatory pain, cancer pain, idiopathic pain, postsurgical pain (e.g., bunionectomy pain, herniorrhaphy pain or abdominoplasty pain), visceral pain, multiple sclerosis, Charcot-Marie-Tooth syndrome, incontinence, pathological cough, and cardiac arrhythmia, by administering the compound, pharmaceutically acceptable salt, or pharmaceutical composition to the subject.

DETAILED DESCRIPTION

In one aspect, the invention relates to a compound of formula (I)

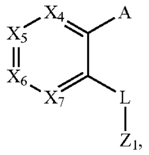

I or a pharmaceutically acceptable salt thereof, wherein:

A is

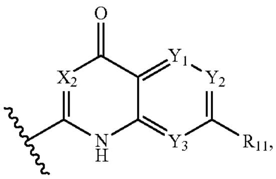

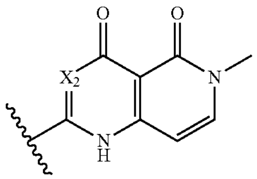

,

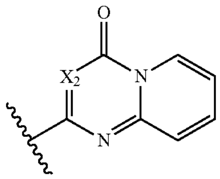

, or

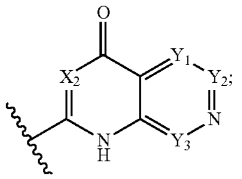

L is —O—, a single bond, —O—$C(R)_2$—, —$C(R)_2$—, —$C(R)_2$—O—, or —N(R)—;

each R is independently H, halo, or $C_1$-$C_6$ alkyl;

$X_2$ is N or $CR_2$;

$X_4$ is N or $CR_4$;

$X_5$ is N or $CR_5$;

$X_6$ is N or $CR_6$;

$X_7$ is N or $CR_7$;

$Y_1$ is N or $CR_{1a}$;

$Y_2$ is N, N—O—, or $CR_{2a}$;

$Y_3$ is N or $CR_{3a}$;

$R_2$ is H, halo, $C_1$-$C_6$ alkyl, ($C_1$-$C_6$ alkylene)-$NR_8R_9$, $C_2$-$C_6$ alkenyl, $C_1$-$C_6$ alkoxy, ($C_1$-$C_6$ alkylene)-OH, $C(O)OR_8$, or $CH(OH)(CH_2)_m(CHOH)_n(CH_2)_pH$;

$R_4$, $R_5$, $R_6$, and $R_7$ are defined as follows:

(i) $R_4$, $R_5$, $R_6$, and $R_7$ are each independently H, halo, $C_1$-$C_6$ alkyl, $C_1$-$C_6$ haloalkyl, or $C_3$-$C_6$ cycloalkyl optionally substituted with one or more alkyl, halo, or OH;

(ii) $R_4$ and $R_7$ are each independently is H, halo, $C_1$-$C_6$ alkyl, $C_1$-$C_6$ haloalkyl, or $C_3$-$C_6$ cycloalkyl optionally substituted with one or more halo; and $R_5$ and $R_6$, together with the carbon atoms to which they are attached, form a ring of formula:

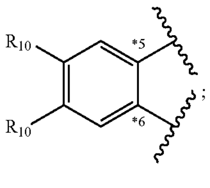

(iii) $R_4$ and $R_7$ are each independently is H, halo, $C_1$-$C_6$ alkyl, $C_1$-$C_6$ haloalkyl, $C_3$-$C_6$ cycloalkyl, or $C_3$-$C_6$ cycloalkyl substituted with one or more halo; and $R_5$ and $R_6$, together with the carbon atoms to which they are attached, form a ring of formula:

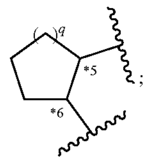

$R_8$ and $R_9$ are each independently H or $C_1$-$C_6$ alkyl;

each $R_{10}$ is independently H or halo;

$R_{1a}$ is H, halo, CN, $C_1$-$C_6$ alkyl, OH, $C(O)NR_{12}R_{13}$, $C_1$-$C_6$ alkoxy, $NR_{12}R_{13}$, $NR_8C(O)NR_8R_9$, ($C_1$-$C_6$ alkylene)-$C(O)NR_8R_9$, ($C_1$-$C_6$ alkylene)-OH, C(O)$OR_{12}$, $OR_{12}$, $CH(OH)(CH_2)_m(CHOH)_n(CH_2)_pH$, N═S(═O)$(CH_3)_2$, N═S(═O)R'R", 5-10 membered heteroaryl, or 4-10 membered heterocyclyl, wherein the heterocyclyl or heteroaryl in said 5-10 membered heteroaryl or 4-10 membered heterocyclyl is optionally substituted with 1-4 substituents selected from OH, halo, oxo, $C(O)NR_8R_9$, $NR_8R_9$, $C_1$-$C_6$ alkyl, $C_1$-$C_6$ alkoxy, ($C_1$-$C_6$ alkylene)-OH, ($C_1$-$C_6$ alkylene)-O—($C_1C_6$ alkyl), and ($C_1$-$C_6$ alkylene)-$NR_8R_9$;

R' and R", together with the S atom to which they are attached, form a 4-7 membered heterocyclyl;

$R_{11}$, $R_{2a}$, and $R_{3a}$ are each independently H, halo, CN, $C_1$-$C_6$ alkyl, $C(O)NR_8R_9$, or $C_1$-$C_6$ alkoxy;

$R_{12}$ and $R_{13}$ are each independently H, C(O)($C_1$-$C_6$ alkyl), ($C_1$-$C_6$ alkylene)-$NR_8R_9$, $CH_2CH(OH)(CH_2)_m(CHOH)_n(CH_2)_pH$, $C_1$-$C_6$ alkyl optionally substituted with one or more OH, indanyl, ($C_1$-$C_6$ alkylene)-($C_3$-$C_6$ cycloalkyl), ($C_1$-$C_6$ alkylene)-phenyl, ($C_1$-$C_6$ alkylene)-(5 membered heterocyclyl), $C_4$-$C_7$ cycloalkyl, $C_6$-$C_{10}$ aryl, 5-6 membered heteroaryl, or 4-7 membered heterocyclyl, wherein the indanyl, ($C_1$-$C_6$ alkylene)-($C_3$-$C_6$ cycloalkyl), ($C_1$-$C_6$ alkylene)-phenyl, ($C_1$-$C_6$ alkylene)-(5 membered heterocyclyl), $C_4$-$C_7$ cycloalkyl, $C_6$-$C_{10}$ aryl, 5-6 membered heteroaryl, or 4-7 membered heterocyclyl is optionally substituted with 1-4 substituents selected from OH, oxo, $C_1$-$C_6$ alkyl, ($C_1$-$C_6$ alkylene)-OH, and $C_1$-$C_6$ alkoxy;

$Z_1$ is 3-10 membered cycloalkyl, 3-10 membered cycloalkenyl, phenyl, 4-10 membered heterocyclyl, or 5-6 membered heteroaryl, wherein said 3-10 membered cycloalkyl, 3-10 membered cycloalkenyl, phenyl, 4-10 membered heterocyclyl, or 5-6 membered heteroaryl may be unsubstituted or may be substituted with 1-4 substituents selected from halo, OH, $CD_3$, $C_1$-$C_6$ alkyl, $C_1$-$C_6$ alkoxy, $C_1$-$C_6$ haloalkyl, $CH_2OH$, C(O)H, and $C_1$-$C_6$ haloalkoxy;

m, n, and p are each independently 0 or 1; and q is 1, 2, or 3, wherein when $X_2$ is N, then:

L is O, and $Z_1$ is phenyl, wherein said phenyl is substituted with 2-4 substituents selected from halo, OH, $C_1$-$C_6$ alkyl, $C_1$-$C_6$ alkoxy, $C_1$-$C_6$ haloalkyl, and $C_1$-$C_6$ haloalkoxy; or L is a single bond, and $Z_1$ is 4-10 membered heterocyclyl, wherein said 4-10 membered heterocyclyl is substituted with 2-4 substituents selected from halo, OH, $C_1$-$C_6$ alkyl, $C_1$-$C_6$ alkoxy, $C_1$-$C_6$ haloalkyl, and $C_1$-$C_6$ haloalkoxy; and wherein when $X_2$, $X_4$, $X_5$, $X_6$ and $X_7$ are each CH, L is a single bond, and $Z_1$ is phenyl, then said phenyl is substituted with 1-4 substituents selected from halo, OH, $C_1$-$C_6$ alkyl, $C_1$-$C_6$ alkoxy, $C_1$-$C_6$ haloalkyl, and $C_1$-$C_6$ haloalkoxy.

For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry," Thomas Sorrell, University Science Books, Sausalito: 1999, and "March's Advanced Organic Chemistry," 5$^{th}$ Ed., Ed.: Smith, M. B. and March, J., John Wiley & Sons, New York: 2001, the entire contents of which are hereby incorporated by reference.

As used herein, the term "compounds of the invention" refers to the compounds of formulas (I), (II), and (III), and all of the embodiments thereof (e.g., formulas (I-A-1), etc.), as described herein, and to the compounds identified in Table A and Table B.

As described herein, the compounds of the invention comprise multiple variable groups (e.g., $R_1$, $X_1$, $R_{1a}$, etc.). As one of ordinary skill in the art will recognize, combinations of groups envisioned by this invention are those combinations that result in the formation of stable or chemically feasible compounds. The term "stable," in this context, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The chemical structures depicted herein are intended to be understood as they would be understood by one of ordinary skill in the art. For example, with respect to formulas (I), (I-A-1), (I-A-2), (I-B-1), (I-C-1), and (I-C-2), $X_4$ and $X_5$ are connected by a single bond, $X_5$ and $X_6$ are connected by a double bond, and $X_6$ and $X_7$ are connected by a single bond, even though the bonds between these groups may be obscured by the atom labels in the chemical structures. Using a different ChemDraw style, formula (I) could be drawn as follows to show the bonds in question:

I

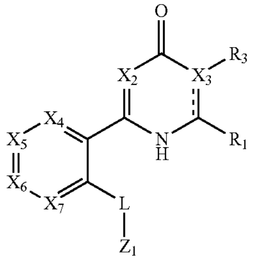

Moreover, a substituent depicted as "$CF_3$" or "$F_3C$" in a chemical structure refers to a trifluoromethyl substituent, regardless of which depiction appears in the chemical structure.

As used herein, the term "halo" means F, Cl, Br or I.

As used herein, the term "alkyl" refers to a straight or branched hydrocarbon chain radical group consisting solely of carbon and hydrogen atoms, containing no unsaturation, and having the specified number of carbon atoms, which is attached to the rest of the molecule by a single bond. For example, a "$C_1$-$C_6$ alkyl" group is an alkyl group having between one and six carbon atoms.

As used herein, the term "alkenyl" refers to a straight or branched hydrocarbon chain radical group consisting solely of carbon and hydrogen atoms, containing one or more carbon-carbon double bonds, and having the specified number of carbon atoms, which is attached to the rest of the molecule by a single bond. For example, a "$C_2$-$C_6$ alkenyl" group is an alkenyl group having between two and six carbon atoms.

As used herein, the term "cycloalkyl" refers to a stable, non-aromatic, mono- or bicyclic (fused, bridged, or spiro) saturated hydrocarbon radical consisting solely of carbon and hydrogen atoms, having the specified number of carbon ring atoms, and which is attached to the rest of the molecule by a single bond. For example, a "$C_3$-$C_8$ cycloalkyl" group is a cycloalkyl group having between three and eight carbon atoms.

As used herein, the term "haloalkyl" refers to an alkyl group having the specified number of carbon atoms, wherein one or more of the hydrogen atoms of the alkyl group are replaced by halo groups. For example, a "$C_1$-$C_6$ haloalkyl" group is an alkyl group having between one and six carbon atoms, wherein one or more of the hydrogen atoms of the alkyl group are replaced by halo groups.

As used herein, the term "alkoxy" refers to a radical of the formula —$OR_a$ where $R_a$ is an alkyl group having the specified number of carbon atoms. For example, a "$C_1$-$C_6$ alkoxy" group is a radical of the formula —$OR_a$ where $R_a$ is an alkyl group having the between one and six carbon atoms.

As used herein, the term "haloalkoxy" refers to an alkoxy group having the specified number of carbon atoms, wherein one or more of the hydrogen atoms of the of the alkyl group are replaced by halo groups.

As used herein, the term "alkylene" refers to a divalent, straight or branched hydrocarbon chain radical group consisting solely of carbon and hydrogen atoms, containing no unsaturation, and having the specified number of carbon atoms, which is attached to the rest of the molecule by two single bonds. For example, a "$C_1$-$C_6$ alkylene" group is an alkylene group having between one and six carbon atoms.

As used herein, the term "cycloalkenyl" refers to a stable, non-aromatic, mono- or bicyclic (fused, bridged, or spiro) hydrocarbon radical consisting solely of carbon and hydrogen atoms, containing one or more carbon-carbon double bonds, and having the specified number of carbon ring atoms, which is attached to the rest of the molecule by a single bond. For example, a "$C_3$-$C_8$ cycloalkenyl" group is a cycloalkenyl group having between three and eight carbon atoms.

As used herein, the term "heterocyclyl" refers to a stable, non-aromatic, mono-, bi-, or tricyclic (fused, bridged, or spiro) radical in which one or more ring atoms is a heteroatom (e.g., a heteroatom independently selected from N, O, P, and S), which has the specified number of ring atoms, which is attached to the rest of the molecule by a single bond. Heterocyclic rings can be saturated or can contain one or more double or triple bonds. In some embodiments, the "heterocyclyl" group has the indicated number of ring members, in which one or more ring members is a heteroatom independently selected from oxygen, sulfur, nitrogen, and phosphorus, and each ring in the ring system contains 3 to 7 ring members. For example, a 6-membered heterocyclyl includes a total of 6 ring members, at least one of which is a heteroatom (e.g., a heteroatom independently selected from N, O, P, and S).

As used herein, the term "heteroaryl" refers to a stable mono-, bi-, or tricyclic radical having the specified number of ring atoms, wherein at least one ring in the system is aromatic, at least one aromatic ring in the system contains one or more heteroatoms (e.g., one or more heteroatoms independently selected from N, O, P, and S). In some embodiments, each ring in the system contains 3 to 7 ring members. For example, a 6-membered heteroaryl includes a total of 6 ring members, at least one of which is a heteroatom selected from N, S, O, and P. The term "heteroaryl" may be used interchangeably with the term "heteroaryl ring" or the term "heteroaromatic".

As used herein, the term "optionally substituted" refers to a group that is either unsubstituted or substituted with the subsequently identified substituents. For example, a group that is "optionally substituted with 1-2 halo" is either unsubstituted, substituted with 1 halo group, or substituted with 2 halo groups.

As used herein, labels such as "*5" and "*6", such as those shown in the following structure, designate the atoms to which the corresponding R groups (in this case, the $R_5$ and $R_6$ groups, respectively) are attached.

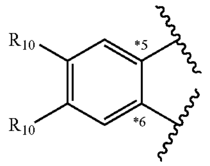

Similarly, the labels "*8" and "*9" in the following structure designate the atoms to which the $R_{8a}$ and $R_{9a}$ groups, respectively, are attached.

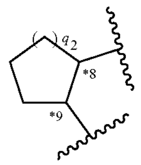

Unless otherwise specified, the compounds of the invention, whether identified by chemical name or chemical structure, include all stereoisomers (e.g., enantiomers and diastereomers), double bond isomers (e.g., (Z) and (E)), conformational isomers, and tautomers of the compounds identified by the chemical names and chemical structures provided herein. In addition, single stereoisomers, double bond isomers, conformational isomers, and tautomers as well as mixtures of stereoisomers, double bond isomers, conformational isomers, and tautomers are within the scope of the invention.

As used herein, in any chemical structure or formula, a non-bold, straight bond attached to a stereocenter of a compound, such as in

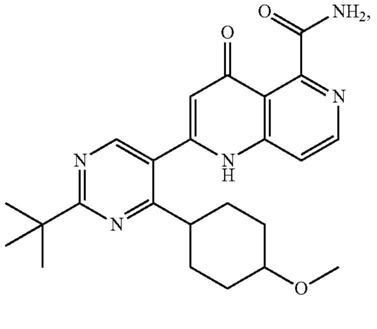 [SMILES: COC1CCC(c2nc(C(C)(C)C)ncc2-c2cc(=O)c3c(C(N)=O)nccc3[nH]2)CC1]

denotes that the configuration of the stereocenter is unspecified. The compound may have any configuration, or a mixture of configurations, at the stereocenter.

As used herein, in any chemical structure or formula, a bold or hashed straight bond attached to a stereocenter of a compound, such as in

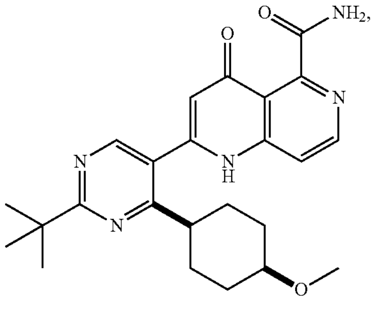

denotes the relative stereochemistry of the stereocenter, relative to other stereocenter(s) to which bold or hashed straight bonds are attached.

As used herein, in any chemical structure or formula, a bold or hashed wedge bond attached to a stereocenter of a compound, such as in

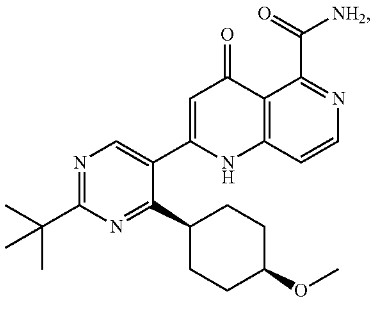 [SMILES: CO[C@H]1CC[C@@H](c2nc(C(C)(C)C)ncc2-c2cc(=O)c3c(C(N)=O)nccc3[nH]2)CC1]

denotes the absolute stereochemistry of the stereocenter, as well as the relative stereochemistry of the stereocenter, relative to other stereocenter(s) to which bold or hashed wedge bonds are attached.

As used herein, the prefix "rac-," when used in connection with a chiral compound, refers to a racemic mixture of the compound. In a compound bearing the "rac-" prefix, the (R)- and (S)-designators in the chemical name reflect the relative stereochemistry of the compound.

As used herein, the prefix "rel-," when used in connection with a chiral compound, refers to a single enantiomer of unknown absolute configuration. In a compound bearing the "rel-" prefix, the (R)- and (S)-designators in the chemical name reflect the relative stereochemistry of the compound, but do not necessarily reflect the absolute stereochemistry of the compound. Where the relative stereochemistry of a given stereocenter is unknown, no stereochemical designator is provided. In some instances, the absolute configuration of some stereocenters is known, while only the relative configuration of the other stereocenters is known. In these instances, the stereochemical designators associated with the stereocenters of known absolute configuration are marked with an asterisk (*), e.g., (R*)- and (S*)-, while the stereochemical designators associated with stereocenters of unknown absolute configuration are not so marked. The unmarked stereochemical designators associated with the stereocenters of unknown absolute configuration reflect the relative stereochemistry of those stereocenters with respect to other stereocenters of unknown absolute configuration, but do not necessarily reflect the relative stereochemistry with respect to the stereocenters of known absolute configuration.

As used herein, the term "compound," when referring to the compounds of the invention, refers to a collection of molecules having identical chemical structures, except that there may be isotopic variation among the constituent atoms of the molecules. The term "compound" includes such a collection of molecules without regard to the purity of a given sample containing the collection of molecules. Thus, the term "compound" includes such a collection of molecules in pure form, in a mixture (e.g., solution, suspension, colloid, or pharmaceutical composition, or dosage form) with one or more other substances, or in the form of a hydrate, solvate, or co-crystal.

In the specification and claims, unless otherwise specified, any atom not specifically designated as a particular isotope in any compound of the invention is meant to represent any stable isotope of the specified element. In the Examples, where an atom is not specifically designated as a particular isotope in any compound of the invention, no effort was made to enrich that atom in a particular isotope, and therefore a person of ordinary skill in the art would understand that such atom likely was present at approximately the natural abundance isotopic composition of the specified element.

As used herein, the term "stable," when referring to an isotope, means that the isotope is not known to undergo spontaneous radioactive decay. Stable isotopes include, but are not limited to, the isotopes for which no decay mode is identified in V. S. Shirley & C. M. Lederer, Isotopes Project, Nuclear Science Division, Lawrence Berkeley Laboratory, Table of Nuclides (January 1980).

As used herein in the specification and claims, "H" refers to hydrogen and includes any stable isotope of hydrogen, namely $^1H$ and D. In the Examples, where an atom is designated as "H," no effort was made to enrich that atom in a particular isotope of hydrogen, and therefore a person of ordinary skill in the art would understand that such hydrogen atom likely was present at approximately the natural abundance isotopic composition of hydrogen.

As used herein, "$^1H$" refers to protium. Where an atom in a compound of the invention, or a pharmaceutically acceptable salt thereof, is designated as protium, protium is present at the specified position at at least the natural abundance concentration of protium.

As used herein, "D," "d," and "$^2$H" refer to deuterium.

In some embodiments, the compounds of the invention, and pharmaceutically acceptable salts thereof, include each constituent atom at approximately the natural abundance isotopic composition of the specified element.

In some embodiments, the compounds of the invention, and pharmaceutically acceptable salts thereof, include one or more atoms having an atomic mass or mass number which differs from the atomic mass or mass number of the most abundant isotope of the specified element ("isotope-labeled" compounds and salts). Examples of stable isotopes which are commercially available and suitable for the invention include without limitation isotopes of hydrogen, carbon, nitrogen, oxygen, and phosphorus, for example $^2$H, $^{13}$C, $^{15}$N, $^{18}$O, $^{17}$O, and $^{31}$P, respectively.

The isotope-labeled compounds and salts can be used in a number of beneficial ways, including as medicaments. In some embodiments, the isotope-labeled compounds and salts are deuterium ($^2$H)-labeled. Deuterium ($^2$H)-labeled compounds and salts are therapeutically useful with potential therapeutic advantages over the non-$^2$H-labeled compounds. In general, deuterium ($^2$H)-labeled compounds and salts can have higher metabolic stability as compared to those that are not isotope-labeled owing to the kinetic isotope effect described below. Higher metabolic stability translates directly into an increased in vivo half-life or lower dosages, which under most circumstances would represent a preferred embodiment of the present invention. The isotope-labeled compounds and salts can usually be prepared by carrying out the procedures disclosed in the synthesis schemes, the examples and the related description, replacing a non-isotope-labeled reactant by a readily available isotope-labeled reactant.

The deuterium ($^2$H)-labeled compounds and salts can manipulate the rate of oxidative metabolism of the compound by way of the primary kinetic isotope effect. The primary kinetic isotope effect is a change of the rate for a chemical reaction that results from exchange of isotopic nuclei, which in turn is caused by the change in ground state energies of the covalent bonds involved in the reaction. Exchange of a heavier isotope usually results in a lowering of the ground state energy for a chemical bond and thus causes a reduction in the rate-limiting bond breakage. If the bond breakage occurs in or in the vicinity of a saddle-point region along the coordinate of a multi-product reaction, the product distribution ratios can be altered substantially. For example, if deuterium is bonded to a carbon atom at a non-exchangeable position, rate differences of $k_H/k_D$=2-7 are typical. For a further discussion, see S. L. Harbeson and R. D. Tung, *Deuterium In Drug Discovery and Development*, Ann. Rep. Med. Chem. 2011, 46, 403-417, incorporated in its entirety herein by reference.

The concentration of an isotope (e.g., deuterium) incorporated at a given position of an isotope-labeled compound of the invention, or a pharmaceutically acceptable salt thereof, may be defined by the isotopic enrichment factor. The term "isotopic enrichment factor," as used herein, means the ratio between the abundance of an isotope at a given position in an isotope-labeled compound (or salt) and the natural abundance of the isotope.

Where an atom in a compound of the invention, or a pharmaceutically acceptable salt thereof, is designated as deuterium, such compound (or salt) has an isotopic enrichment factor for such atom of at least 3000 (~45% deuterium incorporation). In some embodiments, the isotopic enrichment factor is at least 3500 (~52.5% deuterium incorporation), at least 4000 (~60% deuterium incorporation), at least 4500 (~67.5% deuterium incorporation), at least 5000 (~75% deuterium incorporation), at least 5500 (~82.5% deuterium incorporation), at least 6000 (~90% deuterium incorporation), at least 6333.3 (~95% deuterium incorporation), at least 6466.7 (~97% deuterium incorporation), at least 6600 (~99% deuterium incorporation), or at least 6633.3 (~99.5% deuterium incorporation).

In some embodiments, the invention relates to a compound of formula (I), or a pharmaceutically acceptable salt thereof, wherein:

A is

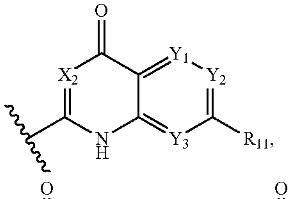

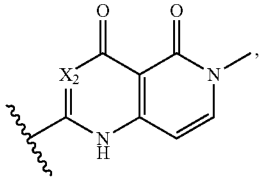

or

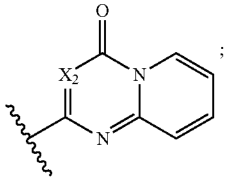

;

$R_{1a}$ is H, halo, CN, $C_1$-$C_6$ alkyl, OH, C(O)$NR_{12}R_{13}$, $C_1$-$C_6$ alkoxy, $NR_{12}R_{13}$, ($C_1$-$C_6$ alkylene)-C(O)$NR_8R_9$, ($C_1$-$C_6$ alkylene)-OH, C(O)$OR_{12}$, CH(OH)$(CH_2)_m$$(CHOH)_n$$(CH_2)_p$H, or N═S(═O)$(CH_3)_2$; and $R_{12}$ and $R_{13}$ are each independently H, C(O)($C_1$-$C_6$ alkyl), ($C_1$-$C_6$ alkylene)-$NR_8R_9$, $CH_2CH(OH)(CH_2)_m$$(CHOH)_n$$(CH_2)_p$H, $C_1$-$C_6$ alkyl optionally substituted with one or more OH.

In some embodiments, the invention relates to a compound of formula (I), or a pharmaceutically acceptable salt thereof, wherein A is

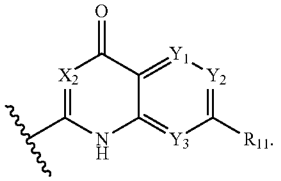

In some embodiments, the invention relates to a compound of formula (I), or a pharmaceutically acceptable salt thereof, wherein:

L is a single bond or —C(R)$_2$—;

$X_2$ is $CR_2$;

$Z_1$ is 4-10 membered cycloalkyl, 3-10 membered cycloalkenyl, phenyl, or 5-6 membered heteroaryl, wherein said 4-10 membered cycloalkyl, 3-10 membered cycloalkenyl, phenyl, or 5-6 membered heteroaryl may be unsubstituted or may be substituted with 1-4 substituents selected from halo, OH, $C_1$-$C_6$ alkyl, $C_1$-$C_6$ alkoxy, $C_1$-$C_6$ haloalkyl, and $C_1$-$C_6$ haloalkoxy.

In some embodiments, the invention relates to a compound of formula (I), or a pharmaceutically acceptable salt thereof, wherein R is H or $C_1$-$C_6$ alkyl.

In some embodiments, the invention relates to a compound of formula (I-A-1)

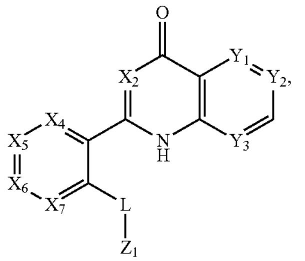

I-A-1 or a pharmaceutically acceptable salt thereof, wherein L, $X_2$, $X_4$, $X_5$, $X_6$, $X_7$, $Y_1$, $Y_2$, $Y_3$, and $Z_1$ are defined as set forth above in connection with formula (I), or any embodiment thereof.

In some embodiments, the invention relates to a compound of formula (I-A-2)

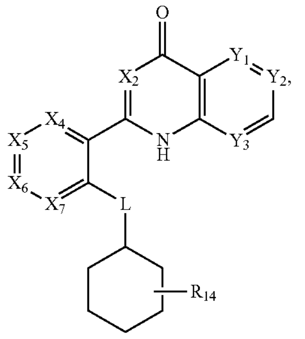

I-A-2 or a pharmaceutically acceptable salt thereof, wherein L, $X_2$, $X_4$, $X_5$, $X_6$, $X_7$, $Y_1$, $Y_2$, and $Y_3$ are defined as set forth above in connection with formula (I), or any embodiment thereof. Each $R_{14}$ is selected from halo, OH, $C_1$-$C_6$ alkyl, $C_1$-$C_6$ alkoxy, $C_1$-$C_6$ haloalkyl, and $C_1$-$C_6$ haloalkoxy.

In some embodiments, the invention relates to a compound of formula (I), or a pharmaceutically acceptable salt thereof, wherein:

L is a single bond;

$X_2$ is $CR_2$;

$R_{1a}$ is H, halo, CN, OH, $C(O)NR_{12}R_{13}$, $C_1$-$C_6$ alkoxy, —$NR_{12}R_{13}$, ($C_1$-$C_6$ alkylene)-$C(O)NR_8R_9$, ($C_1$-$C_6$ alkylene)-OH, $C(O)OR_{12}$, $CH(OH)(CH_2)_m(CHOH)_n(CH_2)_pH$, or $N{=}S({=}O)(CH_3)_2$;

$Z_1$ is 4-10 membered heterocyclyl, wherein said 4-10 membered heterocyclyl may be unsubstituted or may be substituted with 1-4 substituents selected from halo, OH, $C_1$-$C_6$ alkyl, $C_1$-$C_6$ alkoxy, $C_1$-$C_6$ haloalkyl, and $C_1$-$C_6$ haloalkoxy.

In some embodiments, the invention relates to a compound of formula (I), or a pharmaceutically acceptable salt thereof, wherein:

L is a single bond;

$X_2$ is $CR_2$;

$R_{1a}$ is H, halo, CN, OH, $C(O)NR_{12}R_{13}$, $C_1$-$C_6$ alkoxy, —$NR_{12}R_{13}$, ($C_1$-$C_6$ alkylene)-$C(O)NR_8R_9$, ($C_1$-$C_6$ alkylene)-OH, $C(O)OR_{12}$, $CH(OH)(CH_2)_m(CHOH)_n(CH_2)_pH$, or $N{=}S({=}O)(CH_3)_2$;

$Z_1$ is 5-10 membered heterocyclyl, wherein said 5-10 membered heterocyclyl may be unsubstituted or may be substituted with 1-4 substituents selected from halo, OH, $C_1$-$C_6$ alkyl, $C_1$-$C_6$ alkoxy, $C_1$-$C_6$ haloalkyl, and $C_1$-$C_6$ haloalkoxy.

In some embodiments, the invention relates to a compound of formula (I-A-1) or (I-A-2), or a pharmaceutically acceptable salt thereof, wherein R is H or $C_1$-$C_6$ alkyl.

In some embodiments, the invention relates to a compound of formula (I-B-1)

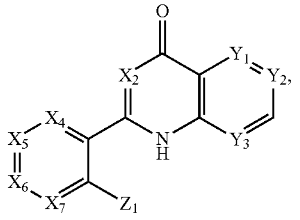

I-B-1 or a pharmaceutically acceptable salt thereof, wherein $X_2$, $X_4$, $X_5$, $X_6$, $X_7$, $Y_1$, $Y_2$, $Y_3$, and $Z_1$ are defined as set forth above in connection with formula (I), or any embodiment thereof.

In some embodiments, the invention relates to a compound of formula (I-B-2)

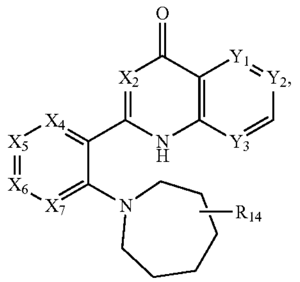

I-B-2 or a pharmaceutically acceptable salt thereof, wherein $X_2$, $X_4$, $X_5$, $X_6$, $X_7$, $Y_1$, $Y_2$, $Y_3$, and $Z_1$ are defined as set forth above in connection with formula (I), including any embodiment thereof. Each $R_{14}$ is selected from halo, OH, $C_1$-$C_6$ alkyl, $C_1$-$C_6$ alkoxy, $C_1$-$C_6$ haloalkyl, and $C_1$-$C_6$ haloalkoxy.

In some embodiments, the invention relates to a compound of formula (I), or a pharmaceutically acceptable salt thereof, wherein:

L is O, —O—$C(R)_2$—, or —$C(R)_2$—O—;

$Z_1$ is phenyl, 4-10 membered heterocyclyl, or 5-6 membered heteroaryl, wherein said phenyl, 4-10 membered heterocyclyl, or 5-6 membered heteroaryl may be unsubstituted or may be substituted with 1-4 substituents selected from halo, OH, $C_1$-$C_6$ alkyl, $C_1$-$C_6$ alkoxy, $C_1$-$C_6$ haloalkyl, $CH_2OH$, C(O)H, and $C_1$-$C_6$ haloalkoxy.

In some embodiments, the invention relates to a compound of formula (I), or a pharmaceutically acceptable salt thereof, wherein:

L is O, —O—$C(R)_2$—, or —$C(R)_2$—O—;

$Z_1$ is phenyl, 5-10 membered heterocyclyl, or 5-6 membered heteroaryl, wherein said phenyl, 5-10 membered heterocyclyl, or 5-6 membered heteroaryl may be unsubstituted or may be substituted with 1-4 substituents selected from halo, OH, $C_1$-$C_6$ alkyl, $C_1$-$C_6$ alkoxy, $C_1$-$C_6$ haloalkyl, $CH_2OH$, C(O)H, and $C_1$-$C_6$ haloalkoxy.

In some embodiments, the invention relates to a compound of formula (I-C-1)

I-C-1

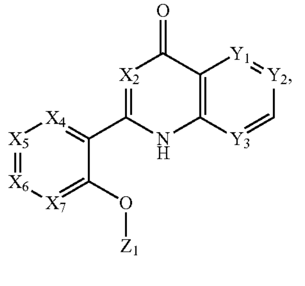

or a pharmaceutically acceptable salt thereof, wherein $X_2$, $X_4$, $X_5$, $X_6$, $X_7$, $Y_1$, $Y_2$, $Y_3$, and $Z_1$ are defined as set forth above in connection with formula (I), or any embodiment thereof.

In some embodiments, the invention relates to a compound of formula (I-C-2)

I-C-2

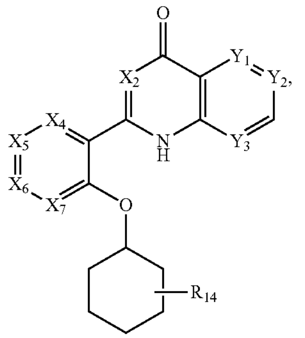

or a pharmaceutically acceptable salt thereof, wherein $X_2$, $X_4$, $X_5$, $X_6$, $X_7$, $Y_1$, $Y_2$, and $Y_3$ are defined as set forth above in connection with formula (I), or any embodiment thereof. Each $R_{14}$ is selected from halo, OH, $C_1$-$C_6$ alkyl, $C_1$-$C_6$ alkoxy, $C_1$-$C_6$ haloalkyl, and $C_1$-$C_6$ haloalkoxy.

In some embodiments, the invention relates to a compound of formula (I), or a pharmaceutically acceptable salt thereof, wherein:

L is —O— or a single bond;

$X_4$ is $CR_4$;

$X_6$ is $CR_6$;

$R_4$, $R_5$, $R_6$, and $R_7$ are each independently H, halo, $C_1$-$C_6$ alkyl, $C_1$-$C_6$ haloalkyl, or $C_3$-$C_6$ cycloalkyl optionally substituted with one or more halo;

$Z_1$ is 3-10 membered cycloalkyl or phenyl wherein said 3-10 membered cycloalkyl or phenyl may be unsubstituted or may be substituted with 1-4 substituents selected from halo, $C_1$-$C_6$ alkyl, $C_1$-$C_6$ alkoxy, and $C_1$-$C_6$ haloalkyl.

In some embodiments, the invention relates to a compound of formula (I), or a pharmaceutically acceptable salt thereof, wherein:

A is

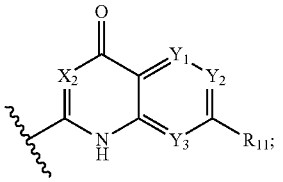

$X_2$ is $CR_2$;

$Y_1$ is $CR_{1a}$;

$Y_2$ is N or $CR_{2a}$;

$Y_3$ is $CR_{3a}$;

$R_{11}$, $R_{2a}$, and $R_{3a}$ are each H;

$R_{1a}$ is $C(O)NR_{12}R_{13}$, $NR_{12}R_{13}$, $NR_8C(O)NR_8R_9$, $OR_{12}$, N═S(═O)R'R", 5-10 membered heteroaryl, or 4-10 membered heterocyclyl, wherein the heterocyclyl or heteroaryl in said 5-10 membered heteroaryl or 4-10 membered heterocyclyl is optionally substituted with 1-4 substituents selected from OH, halo, oxo, $C(O)NR_8R_9$, $NR_8R_9$, $C_1$-$C_6$ alkyl, $C_1$-$C_6$ alkoxy, ($C_1$-$C_6$ alkylene)-OH, ($C_1$-$C_6$ alkylene)-O—($C_1C_6$ alkyl), and ($C_1$-$C_6$ alkylene)-$NR_8R_9$;

R' and R", together with the S atom to which they are attached, form a 4-7 membered heterocyclyl; and $R_{12}$ and $R_{13}$ are each independently H, C(O)($C_1$-$C_6$ alkyl), ($C_1$-$C_6$ alkylene)-$NR_8R_9$, $CH_2CH(OH)(CH_2)_m(CHOH)_n(CH_2)_pH$, $C_1$-$C_6$ alkyl optionally substituted with one or more OH, indanyl, ($C_1$-$C_6$ alkylene)-($C_3$-$C_6$ cycloalkyl), ($C_1$-$C_6$ alkylene)-phenyl, ($C_1$-$C_6$ alkylene)-(5 membered heterocyclyl), $C_4$-$C_7$ cycloalkyl, $C_6$-$C_{10}$ aryl, 5-6 membered heteroaryl, or 4-7 membered heterocyclyl, wherein the indanyl, ($C_1$-$C_6$ alkylene)-($C_3$-$C_6$ cycloalkyl), ($C_1$-$C_6$ alkylene)-phenyl, ($C_1$-$C_6$ alkylene)-(5 membered heterocyclyl), $C_4$-$C_7$ cycloalkyl, $C_6$-$C_{10}$ aryl, 5-6 membered heteroaryl, or 4-7 membered heterocyclyl is optionally substituted with 1-4 substituents selected from OH, oxo, $C_1$-$C_6$ alkyl, ($C_1$-$C_6$ alkylene)-OH, and $C_1$-$C_6$ alkoxy.

In some embodiments, the invention relates to a compound of formula (I), or a pharmaceutically acceptable salt thereof, wherein:

L is —O—;

A is

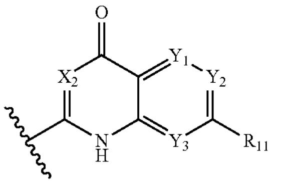

or

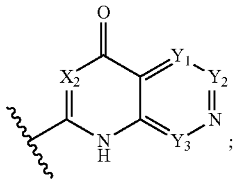

;

$X_2$ is $CR_2$;

$X_4$ is $CR_4$;

$X_5$ is $CR_5$;

$X_6$ is $CR_6$;

$Y_1$ is $CR_{1a}$;

$Y_3$ is $CR_{3a}$;

$R_2$ is H;

$R_4$, $R_5$, $R_6$, and $R_7$ are each independently H, halo, $C_1$-$C_6$ alkyl, or $C_1$-$C_6$ haloalkyl;

$R_8$ and $R_9$ are each independently H or $C_1$-$C_6$ alkyl;

$R_{1a}$ is $C(O)NR_{12}R_{13}$ or $NR_8C(O)NR_8R_9$;

$R_{12}$ and $R_{13}$ are each H; and $Z_1$ is phenyl wherein said phenyl may be unsubstituted or may be substituted with 1-4 substituents selected from halo or $C_1$-$C_6$ alkyl. In some embodiments, the invention relates to a compound of any one of formulas (I), (I-A-1), (I-A-2), (I-B-1), (I-B-2), (I-C-1), and (I-C-2), or a pharmaceutically acceptable salt thereof, wherein $Y_2$ is N. In other embodiments, $Y_2$ is $^+NO^-$. In some embodiments, $Y_2$ is $CR_{2a}$; and $R_{2a}$ is H, halo, CN, $C_1$-$C_6$ alkyl, $C(O)NR_8R_9$, or $C_1$-$C_6$ alkoxy. In some embodiments, $R_{2a}$ is H. In some embodiments, $R_{2a}$ is halo. In some embodiments, $R_{2a}$ is CN. In some embodiments, $R_{2a}$ is $C_1$-$C_6$ alkyl. In some embodiments, $R_{2a}$ is $C(O)NR_8R_9$. In some embodiments, $R_{2a}$ is $C_1$-$C_6$ alkoxy.

In some embodiments, the invention relates to a compound of any one of formulas (I), (I-A-1), (I-A-2), (I-B-1), (I-B-2), (I-C-1), and (I-C-2), or a pharmaceutically acceptable salt thereof, wherein $X_4$ is $CR_4$; $X_5$ is N; $X_6$ is $CR_6$; $X_7$ is $CR_7$. In some embodiments, $X_4$ is $CR_4$; $X_5$ is N; $X_6$ is $CR_6$; $X_7$ is N. In some embodiments, $X_4$ is $CR_4$; $X_5$ is $CR_5$; $X_6$ is N; $X_7$ is $CR_7$. In some embodiments, $X_4$ is $CR_4$; $X_5$ is $CR_5$; $X_6$ is $CR_6$; $X_7$ is N.

In some embodiments, the invention relates to a compound of any one of formulas (I), (I-A-1), (I-A-2), (I-B-1), (I-B-2), (I-C-1), and (I-C-2), or a pharmaceutically acceptable salt thereof, wherein $R_4$, $R_5$, $R_6$, and $R_7$ are each independently H, halo, $C_1$-$C_6$ alkyl, $C_1$-$C_6$ haloalkyl, or $C_3$-$C_6$ cycloalkyl optionally substituted with one or more alkyl, halo, or OH. In some embodiments, $R_4$, $R_5$, $R_6$, and $R_7$ are each independently H, halo, $C_1$-$C_6$ alkyl, $C_1$-$C_6$ haloalkyl, or $C_3$-$C_6$ cycloalkyl substituted with one or more halo. In some embodiments, $R_4$, $R_5$, $R_6$, and $R_7$ are each independently H, halo, $C_1$-$C_6$ alkyl, $C_1$-$C_6$ haloalkyl, or $C_3$-$C_6$ cycloalkyl substituted with one, two, or three halo. In some embodiments, $R_4$ is H, halo, or $C_1$-$C_6$ alkyl. In some embodiments, $R_5$ is H, halo, or $C_1$-$C_6$ haloalkyl. In some embodiments, $R_5$ is H or $C_1$-$C_6$ haloalkyl. In some embodiments, $R_5$ is F. In some embodiments, $R_5$ is $—CF_3$. In some embodiments, $R_6$ is H, $C_1$-$C_6$ alkyl, $C_1$-$C_6$ haloalkyl, or $C_3$-$C_6$ cycloalkyl substituted with two halo. In some embodiments, $R_6$ is H. In some embodiments, $R_6$ is $—CF_3$. In some embodiments, $R_6$ is $C_4$ cycloalkyl substituted with two F. In some embodiments, $R_7$ is H.

In some embodiments, the invention relates to a compound of any one of formulas (I), (I-A-1), (I-A-2), (I-B-1), (I-B-2), (I-C-1), and (I-C-2), or a pharmaceutically acceptable salt thereof, wherein $Y_1$ is $CR_{1a}$. In some embodiments, $R_{1a}$ is $C(O)NR_{12}R_{13}$. In some embodiments, $R_{1a}$ is H. In some embodiments, $R_{1a}$ is halo. In some embodiments, $R_{1a}$ is CN. In some embodiments, $R_{1a}$ is $C_1$-$C_6$ alkyl. In some embodiments, $R_{1a}$ is OH. In some embodiments, $R_{1a}$ is $C_1$-$C_6$ alkoxy. In some embodiments, $R_{1a}$ is $NR_{12}R_{13}$. In some embodiments, $R_{1a}$ is ($C_1$-$C_6$ alkylene)-$C(O)NR_8R_9$. In some embodiments, $R_{1a}$ is ($C_1$-$C_6$ alkylene)-OH. In some embodiments, $R_{1a}$ is $C(O)OR_{12}$. In some embodiments, $R_{1a}$ is $OR_{12}$. In some embodiments, $R_{1a}$ is $NR_8C(O)NR_8R_9$. In some embodiments, $R_{1a}$ is N═S(═O)R'R" wherein R' and R", together with the S atom to which they are attached, form a 4-7 membered heterocyclyl. In some embodiments, $R_{1a}$ is a 5-10 membered heteroaryl wherein the 5-10 membered heteroaryl is optionally substituted with 1-4 substituents selected from OH, halo, oxo, $C(O)NR_8R_9$, $NR_8R_9$, $C_1$-$C_6$ alkyl, $C_1$-$C_6$ alkoxy, ($C_1$-$C_6$ alkylene)-OH, ($C_1$-$C_6$ alkylene)-O—($C_1C_6$ alkyl), and ($C_1$-$C_6$ alkylene)-$NR_8R_9$. In some embodiments, $R_{1a}$ is a 4-10 membered heterocyclyl, wherein the 4-10 membered heterocyclyl is optionally substituted with 1-4 substituents selected from OH, halo, oxo, $C(O)NR_8R_9$, $NR_8R_9$, $C_1$-$C_6$ alkyl, $C_1$-$C_6$ alkoxy, ($C_1$-$C_6$ alkylene)-OH, ($C_1$-$C_6$ alkylene)-O—($C_1C_6$ alkyl), and ($C_1$-$C_6$ alkylene)-$NR_8R_9$.

In some embodiments, the invention relates to a compound of any one of formulas (I), (I-A-1), (I-A-2), (I-B-1), (I-B-2), (I-C-1), and (I-C-2), or a pharmaceutically acceptable salt thereof, wherein $X_2$ is $CR_2$. In some embodiments, $R_2$ is H. In some embodiments, $R_2$ is halo. In some embodiments, $R_2$ is $C_1$-$C_6$ alkyl. In some embodiments, $R_2$ is ($C_1$-$C_6$ alkylene)-$NR_8R_9$. In some embodiments, $R_2$ is $C_2$-$C_6$ alkenyl. In some embodiments, $R_2$ is $C_1$-$C_6$ alkoxy. In some embodiments, $R_2$ is ($C_1$-$C_6$ alkylene)-OH. In some embodiments, $R_2$ is $C(O)OR_8$. In some embodiments, $R_2$ is $CH(OH)(CH_2)_m(CHOH)_n(CH_2)_pH$.

In some embodiments, the invention relates to a compound of formula (I), or a pharmaceutically acceptable salt thereof, wherein L is O, a single bond, O—$C(R)_2$, $C(R)_2$, $C(R)_2$—O, or N(R). In some embodiments, L is O. In some embodiments, L is a single bond. In some embodiments, L is O—$C(R)_2$. In some embodiments, L is $C(R)_2$. In some embodiments, L is $C(R)_2$—O. In some embodiments, L is N(R).

In some embodiments, the invention relates to a compound of formula (I), or a pharmaceutically acceptable salt thereof, wherein L is O, a single bond, O—$C(R)_2$, $C(R)_2$, $C(R)_2$—O, or N(R), and R is H or $C_1$-$C_6$ alkyl. In some embodiments, L is O. In some embodiments, L is a single bond. In some embodiments, L is O—$C(R)_2$, and R is H or $C_1$-$C_6$ alkyl. In some embodiments, L is $C(R)_2$, and R is H or $C_1$-$C_6$ alkyl. In some embodiments, L is $C(R)_2$—O, and R is H or $C_1$-$C_6$ alkyl. In some embodiments, L is N(R), and R is H or $C_1$-$C_6$ alkyl.

In some embodiments, the invention relates to a compound of any one of formulas (I), (I-A-1), (I-A-2), (I-B-1), (I-B-2), (I-C-1), and (I-C-2), or a pharmaceutically acceptable salt thereof, wherein $R_{12}$ and $R_{13}$ are each H. In some embodiments, $R_{12}$ and $R_{13}$ are each independently H or $C_1$-$C_6$ alkyl. In some embodiments, $R_{12}$ and $R_{13}$ are each independently H or $C_1$-$C_6$ alkyl optionally substituted with one or more OH.

In some embodiments, the invention relates to a compound of any one of formulas (I), (I-A-1), (I-A-2), (I-B-1), (I-B-2), (I-C-1), and (I-C-2), or a pharmaceutically acceptable salt thereof, wherein $R_{12}$ is $C(O)(C_1$-$C_6$ alkyl). In some embodiments, $R_{12}$ is ($C_1$-$C_6$ alkylene)-$NR_8R_9$. In some embodiments, $R_{12}$ is $CH_2CH(OH)(CH_2)_m(CHOH)_n(CH_2)_pH$. In some embodiments, $R_{12}$ is indanyl wherein the indanyl is optionally substituted with 1-4 substituents selected from OH, oxo, $C_1$-$C_6$ alkyl, ($C_1$-$C_6$ alkylene)-OH, and $C_1$-$C_6$ alkoxy. In some embodiments, $R_{12}$ is ($C_1$-$C_6$ alkylene)-($C_3$-$C_6$ cycloalkyl) wherein the ($C_1$-$C_6$ alkylene)-($C_3$-$C_6$ cycloalkyl) is optionally substituted with 1-4 substituents selected from OH, oxo, $C_1$-$C_6$ alkyl, ($C_1$-$C_6$ alkylene)-OH, and $C_1$-$C_6$ alkoxy. In some embodiments, $R_{12}$ is ($C_1$-$C_6$ alkylene)-phenyl wherein the ($C_1$-$C_6$ alkylene)-phenyl is optionally substituted with 1-4 substituents selected from OH, oxo, $C_1$-$C_6$ alkyl, ($C_1$-$C_6$ alkylene)-OH, and $C_1$-$C_6$ alkoxy. In some embodiments, $R_{12}$ is ($C_1$-$C_6$ alkylene)-(5 membered heterocyclyl) wherein the ($C_1$-$C_6$ alkylene)-(5 membered heterocyclyl) is optionally substituted with 1-4 substituents selected from OH, oxo, $C_1$-$C_6$ alkyl, ($C_1$-$C_6$ alkylene)-OH, and $C_1$-$C_6$ alkoxy. In some embodiments, $R_{12}$ is $C_4$-$C_7$ cycloalkyl wherein the $C_4$-$C_7$ cycloalkyl is optionally substituted with 1-4 substituents selected from OH, oxo, $C_1$-$C_6$ alkyl, ($C_1$-$C_6$ alkylene)-OH, and $C_1$-$C_6$ alkoxy. In some embodiments, $R_{12}$ is $C_6$-$C_{10}$ aryl wherein the $C_6$-$C_{10}$ aryl is optionally substituted with 1-4 substituents selected from OH, oxo, $C_1$-$C_6$ alkyl, ($C_1$-$C_6$ alkylene)-OH, and $C_1$-$C_6$ alkoxy. In some embodiments, $R_{12}$ is 5-6 membered heteroaryl wherein the 5-6 membered heteroaryl is optionally substituted with 1-4 substituents selected from OH, oxo, $C_1$-$C_6$ alkyl, ($C_1$-$C_6$ alkylene)-OH, and $C_1$-$C_6$ alkoxy. In some embodiments, $R_{12}$ is 4-7 membered heterocyclyl wherein the 4-7 membered heterocyclyl is optionally substituted with 1-4 substituents selected from OH, oxo, $C_1$-$C_6$ alkyl, ($C_1$-$C_6$ alkylene)-OH, and $C_1$-$C_6$ alkoxy. In some embodiments, $R_{12}$ is $C_3$-$C_6$ cycloalkyl or 5-6 membered heterocyclyl wherein the $C_3$-$C_6$ cycloalkyl or 5-6 membered heterocyclyl is optionally substituted with 1-4 substituents of $C_1$-$C_6$ alkoxy.

In some embodiments, the invention relates to a compound of any one of formulas (I-A-2), (I-B-2), and (I-C-2), or a pharmaceutically acceptable salt thereof, wherein $R_{14}$ is halo, OH, $C_1$-$C_6$ alkyl, $C_1$-$C_6$ alkoxy, $C_1$-$C_6$ haloalkyl, or $C_1$-$C_6$ haloalkoxy. In some embodiments, $R_{14}$ is halo. In some embodiments, $R_{14}$ is $C_1$-$C_6$ alkyl. In some embodiments, $R_{14}$ is $C_1$-$C_6$ haloalkyl. In some embodiments, $R_{14}$ is $C_1$-$C_6$ haloalkoxy. In some embodiments, $R_{14}$ is OH. In some embodiments, $R_{14}$ is $C_1$-$C_6$ alkoxy.

In some embodiments, the invention relates to a compound of any one of formulas (I), (I-A-1), (I-B-1), and (I-C-1), or a pharmaceutically acceptable salt thereof, wherein $Z_1$ is 3-10 membered cycloalkyl, 3-10 membered cycloalkenyl, phenyl, 5-10 membered heterocyclyl, or 5-6 membered heteroaryl, wherein said 3-10 membered cycloalkyl, 3-10 membered cycloalkenyl, phenyl, 5-10 membered heterocyclyl, or 5-6 membered heteroaryl may be unsubstituted or may be substituted with 1-4 substituents selected from halo, OH, $C_1$-$C_6$ alkyl, $C_1$-$C_6$ alkoxy, $C_1$-$C_6$ haloalkyl, $CH_2OH$, C(O)H, and $C_1$-$C_6$ haloalkoxy. In some embodiments, said 3-10 membered cycloalkyl, 3-10 membered cycloalkenyl, phenyl, 5-10 membered heterocyclyl, or 5-6 membered heteroaryl is substituted with D, $OCD_3$, or $CD_3$.

In some embodiments, the invention relates to a compound of any one of formulas (I), (I-A-1), (I-B-1), and (I-C-1), or a pharmaceutically acceptable salt thereof, wherein $Z_1$ is 4-10 membered cycloalkyl, 3-10 membered cycloalkenyl, phenyl, or 5-6 membered heteroaryl. In some embodiments, $Z_1$ is 4-10 membered cycloalkyl. In some embodiments, $Z_1$ is 4-7 membered cycloalkyl. In some embodiments, $Z_1$ is 5-6 membered cycloalkyl. In some embodiments, $Z_1$ is cyclohexane. In some embodiments, $Z_1$ is phenyl. In some embodiments, $Z_1$ is 5-6 membered heteroaryl. In some embodiments, the 4-10 membered cycloalkyl, 4-7 membered cycloalkyl, 5-6 membered cycloalkyl, or cyclohexane is substituted with 1, 2, 3, or 4 substituents selected from halo and $C_1$-$C_6$ haloalkyl. In some embodiments, the 4-10 membered cycloalkyl, 4-7 membered cycloalkyl, 5-6 membered cycloalkyl, or cyclohexane is substituted with 1, 2, 3, or 4 halo. In some embodiments, the 4-10 membered cycloalkyl, 4-7 membered cycloalkyl, 5-6 membered cycloalkyl, or cyclohexane is substituted with 1, 2, 3, or 4 $C_1$-$C_6$ haloalkyl.

In some embodiments, the invention relates to a compound of any one of formulas (I), (I-A-1), (I-B-1), and (I-C-1), or a pharmaceutically acceptable salt thereof, wherein $Z_1$ is 4-10 membered heterocyclyl. In some embodiments, $Z_1$ is 5-10 membered heterocyclyl. In some embodiments, $Z_1$ is 5-9 membered heterocyclyl. In some embodiments, $Z_1$ is 6-9 membered heterocyclyl. In some embodiments, $Z_1$ is 6-8 membered heterocyclyl. In some embodiments, $Z_1$ is 6-7 membered heterocyclyl. In some embodiments, $Z_1$ is 7-8 membered heterocyclyl. In some embodiments, $Z_1$ is 7 membered heterocyclyl.

In some embodiments, the invention relates to a compound of any one of formulas (I), (I-A-1), (I-B-1), and (I-C-1), or a pharmaceutically acceptable salt thereof, wherein $Z_1$ is phenyl or 4-10 membered heterocyclyl. In some embodiments, $Z_1$ is phenyl or 5-10 membered heterocyclyl. In some embodiments, $Z_1$ is phenyl. In some embodiments, $Z_1$ is 4-10 membered heterocyclyl. In some embodiments, $Z_1$ is 5-10 membered heterocyclyl. In some embodiments, the phenyl is substituted with 1, 2, 3, or 4 substituents selected from halo, OH, $C_1$-$C_6$ alkyl, $C_1$-$C_6$ alkoxy, $C_1$-$C_6$ haloalkyl, $CH_2OH$, C(O)H, and $C_1$-$C_6$ haloalkoxy. In some embodiments, the phenyl is substituted with 1, 2, 3, or 4 substituents selected from halo, $C_1$-$C_6$ alkyl, $C_1$-$C_6$ alkoxy, $CH_2OH$, C(O)H, and $C_1$-$C_6$ haloalkyl. In some embodiments, the phenyl is substituted with 2 substituents selected from halo, $C_1$-$C_6$ alkyl, $C_1$-$C_6$ alkoxy, $CH_2OH$, C(O)H, and $C_1$-$C_6$ haloalkyl.

In some embodiments, the invention relates to a compound of any one of formulas (I), (I-A-1), (I-A-2), (I-B-1), (I-B-2), (I-C-1), and (I-C-2), or any embodiment thereof, i.e., the compound in non-salt form.

In some embodiments, the invention relates to a compound of formula (II) or (III)

II

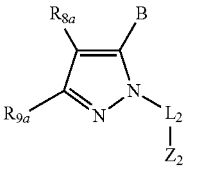

or

III

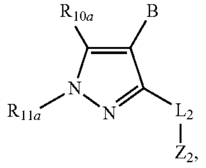

or a pharmaceutically acceptable salt thereof, wherein:

B is

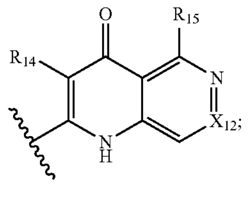

$L_2$ is a single bond or —$CH_2$—;

$X_{12}$ is CH or N;

$R_{14}$ is H, halo, or $C_1$-$C_6$ alkoxy;

$R_{8a}$ and $R_{9a}$ are defined as follows:

(i) $R_{8a}$ and $R_{9a}$ are each independently H, halo, $C_1$-$C_6$ alkyl, $C_1$-$C_6$ haloalkyl, or $C_3$-$C_6$ cycloalkyl optionally substituted with 1-4 substituents selected from $C_1$-$C_6$ alkyl, halo, and $C_1$-$C_6$ haloalkyl;

(ii) $R_{8a}$ and $R_{9a}$, together with the carbon atoms to which they are attached, form a ring of formula:

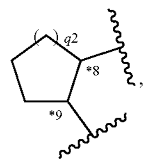

wherein said ring is optionally substituted with 1-4 $C_1$-$C_6$ alkyl;

$R_{10a}$ is H, halo, $C_1$-$C_6$ alkyl, $C_1$-$C_6$ haloalkyl, or $C_3$-$C_6$ cycloalkyl optionally substituted with 1-4 substituents selected from $C_1$-$C_6$ alkyl, halo, and $C_1$-$C_6$ haloalkyl;

$R_{11a}$ is H or $C_1$-$C_6$ alkyl;

$R_{15}$ is $C(O)NR_{16}R_{17}$ or 5 membered heteroaryl wherein the 5 membered heteroaryl is optionally substituted with 1-4 $C_1$-$C_6$ alkyl;

$R_{16}$ and $R_{17}$ are each independently H or $C_1$-$C_6$ alkyl;

$Z_2$ is $C_4$-$C_6$ cycloalkyl or phenyl, wherein said $C_4$-$C_6$ cycloalkyl or phenyl is optionally substituted with 1-4 substituents selected from halo and $C_1$-$C_6$ alkyl; and $q_2$ is 1, 2, or 3.

In some embodiments, the invention relates to a compound of formula (II)

II

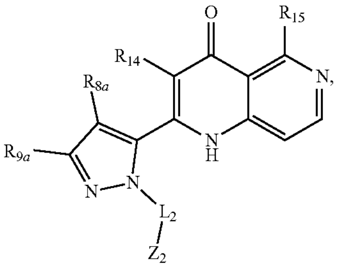

or a pharmaceutically acceptable salt thereof, wherein $R_{14}$, $R_{15}$, $R_{8a}$, $R_{9a}$, $L_2$, and $Z_2$ are defined as set forth above in connection with formula (II), or any embodiment thereof.

In some embodiments, the invention relates to a compound of formula (III)

III

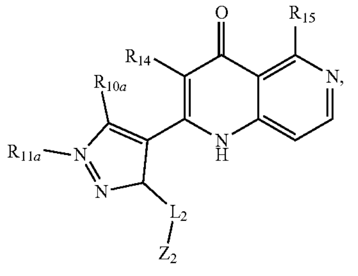

or a pharmaceutically acceptable salt thereof, wherein $R_{14}$, $R_{15}$, $R_{10a}$, $R_{11a}$, $L_2$, and $Z_2$ are defined as set forth above in connection with formula (III), or any embodiment thereof.

In some embodiments, the invention relates to a compound of any one of formulas (II) and (III), or a pharmaceutically acceptable salt thereof, wherein $L_2$ is a single bond. In some embodiments, $L_2$ is $—CH_2—$.

In some embodiments, the invention relates to a compound of any one of formulas (II) and (III), or a pharmaceutically acceptable salt thereof, wherein $R_{14}$ is H, halo or $C_1$-$C_6$ alkyloxy. In some embodiments, $R_{14}$ is H. In some embodiments, $R_{14}$ is halo. In some embodiments, $R_{14}$ is Br. In some embodiments, $R_{14}$ is $C_1$-$C_6$ alkoxy. In some embodiments, $R_{14}$ is methoxy.

In some embodiments, the invention relates to a compound of any one of formulas (II) and (III), or a pharmaceutically acceptable salt thereof, wherein $R_{15}$ is $C(O)NR_{16}R_{17}$ or a 5 membered heteroaryl wherein the 5 membered heteroaryl is optionally substituted with 1-4 $C_1$-$C_6$ alkyl. In some embodiments, $R_{15}$ is $C(O)NR_{16}R_{17}$. In some embodiments, $R_{15}$ is a 5 membered heteroaryl wherein the 5 membered heteroaryl is optionally substituted with 1-4 $C_1$-$C_6$ alkyl. In some embodiments, $R_{15}$ is a 5 membered heteroaryl wherein the 5 membered heteroaryl is optionally substituted with 1-2 methyl.

In some embodiments, the invention relates to a compound of any one of formulas (II) and (III), or a pharmaceutically acceptable salt thereof, wherein wherein $R_{16}$ and $R_{17}$ are each independently H or $C_1$-$C_6$ alkyl. In some embodiments, $R_{16}$ and $R_{17}$ are each independently H. In some embodiments, $R_{16}$ and $R_{17}$ are each independently $C_1$-$C_6$ alkyl.

In some embodiments, the invention relates to a compound of any one of formulas (II) and (III), or a pharmaceutically acceptable salt thereof, wherein $R_{8a}$ is H, halo, $C_1$-$C_6$ alkyl, $C_1$-$C_6$ haloalkyl, or $C_3$-$C_6$ cycloalkyl optionally substituted with 1-4 substituents selected from $C_1$-$C_6$ alkyl, halo, and $C_1$-$C_6$ haloalkyl. In some embodiments, $R_{8a}$ is H. In some embodiments, $R_{8a}$ is halo. In some embodiments, $R_{8a}$ is $C_1$-$C_6$ alkyl. In some embodiments, $R_{8a}$ is $C_1$-$C_6$ haloalkyl. In some embodiments, $R_{8a}$ is $C_3$-$C_6$ cycloalkyl optionally substituted with 1-4 substituents selected from $C_1$-$C_6$ alkyl, halo, and $C_1$-$C_6$ haloalkyl. In some embodiments, $R_{8a}$ is H. In some embodiments, $R_{8a}$ is Br. In some embodiments, $R_{8a}$ is Cl.

In some embodiments, the invention relates to a compound of any one of formulas (II) and (III), or a pharmaceutically acceptable salt thereof, wherein $R_{9a}$ is H, halo, $C_1$-$C_6$ alkyl, $C_1$-$C_6$ haloalkyl, or $C_3$-$C_6$ cycloalkyl optionally substituted with 1-4 substituents selected from $C_1$-$C_6$ alkyl, halo, and $C_1$-$C_6$ haloalkyl. In some embodiments, $R_{9a}$ is $C_1$-$C_6$ alkyl. In some embodiments, $R_{9a}$ is $C_1$-$C_6$ haloalkyl. In some embodiments, $R_{9a}$ is $C_3$-$C_6$ cycloalkyl optionally substituted with 1-4 substituents selected from $C_1$-$C_6$ alkyl, halo, and $C_1$-$C_6$ haloalkyl. In some embodiments, $R_{9a}$ is tert-butyl. In some embodiments, $R_{9a}$ is $—CH_2CF_3$. In some embodiments, $R_{9a}$ is $C_3$ cycloalkyl optionally substituted with 1-4 substituents selected from $C_1$-$C_6$ alkyl, halo, and $C_1$-$C_6$ haloalkyl. In some embodiments, $R_{9a}$ is $C_3$ cycloalkyl optionally substituted with one $—CF_3$. In some embodiments, $R_{9a}$ is $C_4$ cycloalkyl optionally substituted with 1-4 substituents selected from $C_1$-$C_6$ alkyl, halo, and $C_1$-$C_6$ haloalkyl. In some embodiments, $R_{9a}$ is $C_4$ cycloalkyl optionally substituted with one substituent $—CF_3$. In some embodiments, $R_{9a}$ is $C_4$ cycloalkyl optionally substituted with 1-2 substituents of F. In some embodiments, $R_{9a}$ is $C_4$ cycloalkyl optionally substituted with 1-2 substituents of $C_1$-$C_6$ alkyl. In some embodiments, $R_{9a}$ is $C_4$ cycloalkyl optionally substituted with 1-2 substituents of methyl. In some embodiments, $R_{9a}$ is $C_4$ cycloalkyl optionally substituted with 1-2 substituents selected from halo and $C_1$-$C_6$ alkyl. In some embodiments, $R_{9a}$ is $C_4$ cycloalkyl optionally substituted with 1-2 substituents selected from F and methyl. In some embodiments, $R_{9a}$ is $C_5$ cycloalkyl optionally substituted with 1-4 substituents selected from $C_1$-$C_6$ alkyl, halo, and $C_1$-$C_6$ haloalkyl. In some embodiments, $R_{9a}$ is $C_5$ cycloalkyl optionally substituted with one substituent —$CF_3$.

In some embodiments, the invention relates to a compound of any one of formulas (II) and (III), or a pharmaceutically acceptable salt thereof, wherein $R_{10a}$ is H, halo, $C_1$-$C_6$ alkyl, $C_1$-$C_6$ haloalkyl, or $C_3$-$C_6$ cycloalkyl optionally substituted with 1-4 substituents selected from $C_1$-$C_6$ alkyl, halo, and $C_1$-$C_6$ haloalkyl. In some embodiments, $R_{10a}$ is H. In some embodiments, $R_{10a}$ is $C_1$-$C_6$ alkyl.

In some embodiments, the invention relates to a compound of any one of formulas (II) and (III), or a pharmaceutically acceptable salt thereof, wherein $R_{11a}$ is H, halo or $C_1$-$C_6$ alkyl. In some embodiments, $R_{11a}$ is H. In some embodiments, $R_{11a}$ is $C_1$-$C_6$ alkyl. In some embodiments, the invention relates to a compound of any one of formulas (II) and (III), or a pharmaceutically acceptable salt thereof, wherein $Z_1$ is 4-10 membered cycloalkyl, 3-10 membered cycloalkenyl, phenyl, or 5-6 membered heteroaryl. In some embodiments, $Z_1$ is 4-10 membered cycloalkyl.

In some embodiments, the invention relates to a compound of any one of formulas (II) and (III), or a pharmaceutically acceptable salt thereof, wherein $Z_2$ is $C_1$-$C_6$ cycloalkyl or phenyl wherein the $C_1$-$C_6$ cycloalkyl or phenyl are optionally substituted with 1-4 substituents selected from halo and $C_1$-$C_6$ alkyl. In some embodiments, $Z_2$ is $C_4$ cycloalkyl wherein the $C_4$ cycloalkyl is optionally substituted with 1-4 substituents selected from halo and $C_1$-$C_6$ alkyl. In some embodiments, $Z_2$ is $C_4$ cycloalkyl wherein the $C_4$ cycloalkyl is optionally substituted with 1-4 substituents of F. In some embodiments, $Z_2$ is cyclohexane wherein the cyclohexane is optionally substituted with 1-4 substituents selected from F and $CF_3$. In some embodiments, $Z_2$ is phenyl, wherein the phenyl is optionally substituted with 1-4 substituents selected from F and methyl.

In some embodiments, the invention relates to a compound of any one of formulas (II) and (1111), or any embodiment thereof, i.e., the compound in non-salt form.

In some embodiments, the invention relates to a compound selected from Table A, or a pharmaceutically acceptable salt thereof. In other embodiments, the invention relates to a compound selected from Table A, i.e., the compound in non-salt form.

TABLE A

| Compound Structures and Names. |
| --- |
| 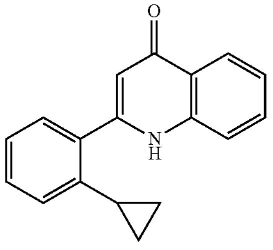 [SMILES: O=c1cc(-c2ccccc2C2CC2)[nH]c2ccccc12] |
| 2-(2-cyclopropylphenyl)-1H-quinolin-4-one |

TABLE A-continued

| Compound Structures and Names. |
| --- |
| 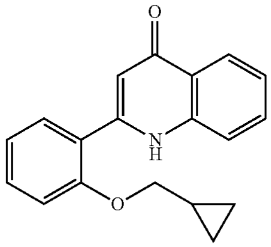 [SMILES: O=c1cc(-c2ccccc2OCC2CC2)[nH]c2ccccc12] |
| 2-[2-(cyclopropylmethoxy)phenyl]-1H-quinolin-4-one |
| 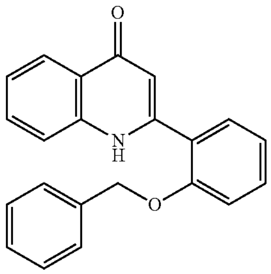 [SMILES: O=c1cc(-c2ccccc2OCc2ccccc2)[nH]c2ccccc12] |
| 2-(2-benzyloxyphenyl)-1H-quinolin-4-one |
| 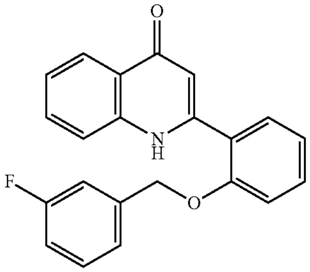 [SMILES: O=c1cc(-c2ccccc2OCc2cccc(F)c2)[nH]c2ccccc12] |
| 2-[2-[(3-fluorophenyl)methoxy]phenyl]-1H-quinolin-4-one |
| 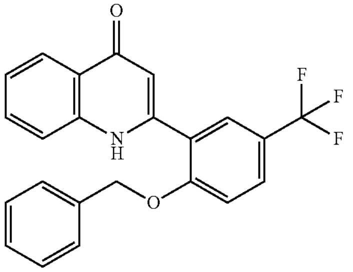 [SMILES: O=c1cc(-c2cc(C(F)(F)F)ccc2OCc2ccccc2)[nH]c2ccccc12] |
| 2-[2-benzyloxy-5-(trifluoromethyl)phenyl]-1H-quinolin-4-one |

TABLE A-continued

| Compound Structures and Names. |
|---|
| 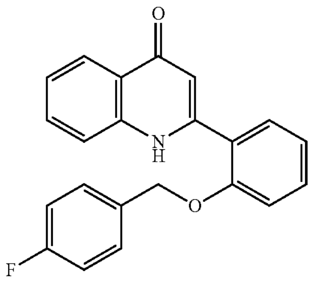 [SMILES: O=c1cc(-c2ccccc2OCc2ccc(F)cc2)[nH]c2ccccc12] |
| 2-[2-[(4-fluorophenyl)methoxy]phenyl]-1H-quinolin-4-one |
| 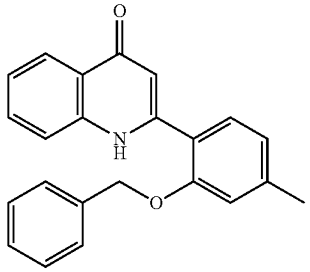 [SMILES: Cc1ccc(-c2cc(=O)c3ccccc3[nH]2)c(OCc2ccccc2)c1] |
| 2-(2-benzyloxy-4-methyl-phenyl)-1H-quinolin-4-one |
| 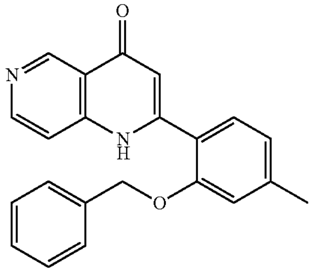 [SMILES: Cc1ccc(-c2cc(=O)c3cnccc3[nH]2)c(OCc2ccccc2)c1] |
| 2-(2-benzyloxy-4-methyl-phenyl)-1H-1,6-naphthyridin-4-one |
| 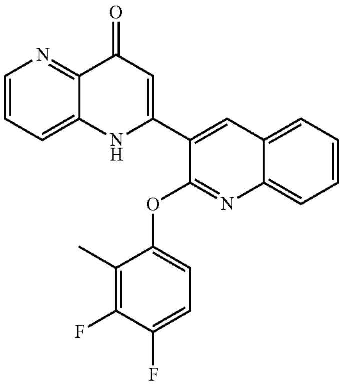 [SMILES: Cc1c(Oc2nc3ccccc3cc2-c2cc(=O)c3ncccc3[nH]2)ccc(F)c1F] |
| 2-[2-(3,4-difluoro-2-methyl-phenoxy)-3-quinolyl]-1H-1,5-naphthyridin-4-one |

TABLE A-continued

| Compound Structures and Names. |
|---|
| 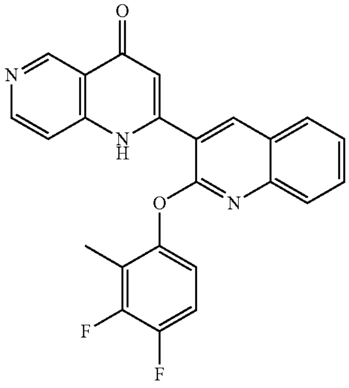 [SMILES: Cc1c(Oc2nc3ccccc3cc2-c2cc(=O)c3cnccc3[nH]2)ccc(F)c1F] |
| 2-[2-(3,4-difluoro-2-methyl-phenoxy)-3-quinolyl]-1H-1,6-naphthyridin-4-one |
| 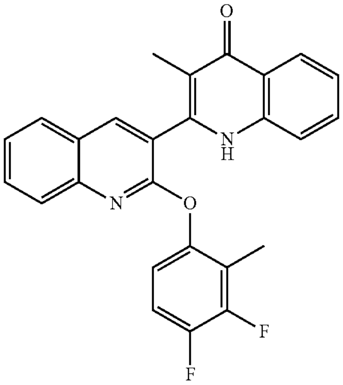 [SMILES: Cc1c(Oc2nc3ccccc3cc2-c2[nH]c3ccccc3c(=O)c2C)ccc(F)c1F] |
| 2-[2-(3,4-difluoro-2-methyl-phenoxy)-3-quinolyl]-3-methyl-1H-quinolin-4-one |
| 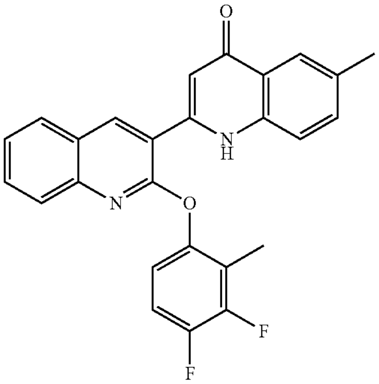 [SMILES: Cc1ccc2[nH]c(-c3cc4ccccc4nc3Oc3ccc(F)c(F)c3C)cc(=O)c2c1] |
| 2-[2-(3,4-difluoro-2-methyl-phenoxy)-3-quinolyl]-6-methyl-1H-quinolin-4-one |

TABLE A-continued

| Compound Structures and Names. |
|---|
| 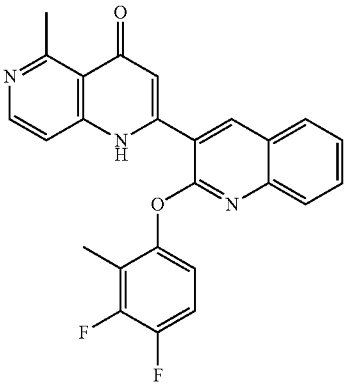 [SMILES: Cc1c(Oc2nc3ccccc3cc2-c2cc(=O)c3c(C)nccc3[nH]2)ccc(F)c1F] |
| 2-[2-(3,4-difluoro-2-methyl-phenoxy)-3-quinolyl]-5-methyl-1H-1,6-naphthyridin-4-one |
| 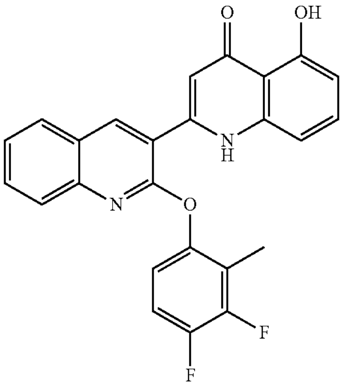 [SMILES: Cc1c(Oc2nc3ccccc3cc2-c2cc(=O)c3c(O)cccc3[nH]2)ccc(F)c1F] |
| 2-[2-(3,4-difluoro-2-methyl-phenoxy)-3-quinolyl]-5-hydroxy-1H-quinolin-4-one |
| 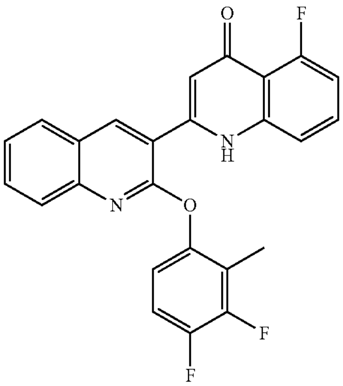 [SMILES: Cc1c(Oc2nc3ccccc3cc2-c2cc(=O)c3c(F)cccc3[nH]2)ccc(F)c1F] |
| 2-[2-(3,4-difluoro-2-methyl-phenoxy)-3-quinolyl]-5-fluoro-1H-quinolin-4-one |

TABLE A-continued

| Compound Structures and Names. |
|---|
| 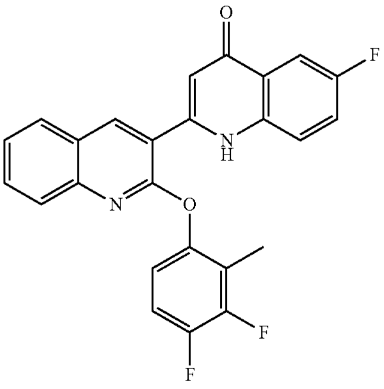 [SMILES: Cc1c(Oc2nc3ccccc3cc2-c2cc(=O)c3cc(F)ccc3[nH]2)ccc(F)c1F] |
| 2-[2-(3,4-difluoro-2-methyl-phenoxy)-3-quinolyl]-6-fluoro-1H-quinolin-4-one |
| 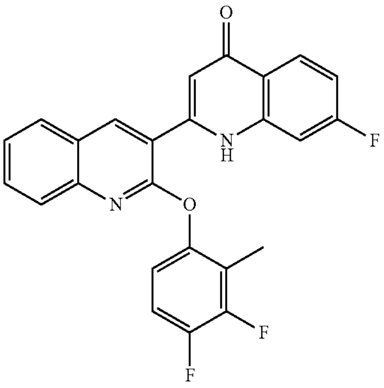 [SMILES: Cc1c(Oc2nc3ccccc3cc2-c2cc(=O)c3ccc(F)cc3[nH]2)ccc(F)c1F] |
| 2-[2-(3,4-difluoro-2-methyl-phenoxy)-3-quinolyl]-7-fluoro-1H-quinolin-4-one |
| 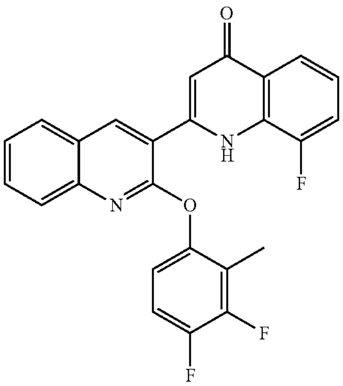 [SMILES: Cc1c(Oc2nc3ccccc3cc2-c2cc(=O)c3cccc(F)c3[nH]2)ccc(F)c1F] |
| 2-[2-(3,4-difluoro-2-methyl-phenoxy)-3-quinolyl]-8-fluoro-1H-quinolin-4-one |

TABLE A-continued

Compound Structures and Names.

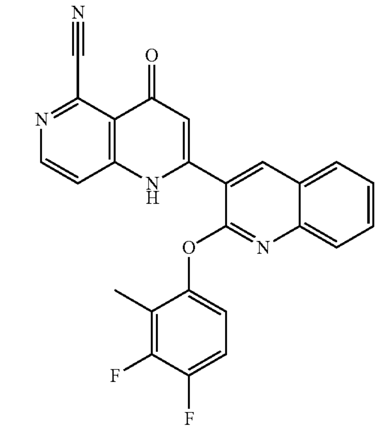 [SMILES: Cc1c(Oc2nc3ccccc3cc2-c2cc(=O)c3c(C#N)nccc3[nH]2)ccc(F)c1F]

2-[2-(3,4-difluoro-2-methyl-pheoxy)-3-quinolyl]-4-oxo-1H-1,6-naphthyridine-5-carbonitrile

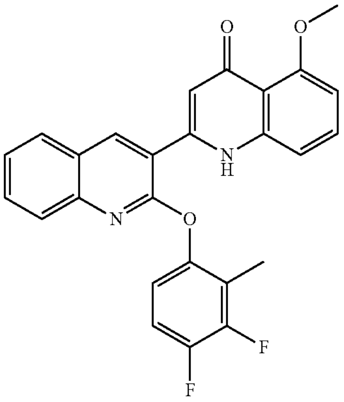 [SMILES: COc1cccc2[nH]c(-c3cc4ccccc4nc3Oc3ccc(F)c(F)c3C)cc(=O)c12]

2-[2-(3,4-difluoro-2-methyl-phenoxy)-3-quinolyl]-5-methoxy-1H-quinolin-4-one

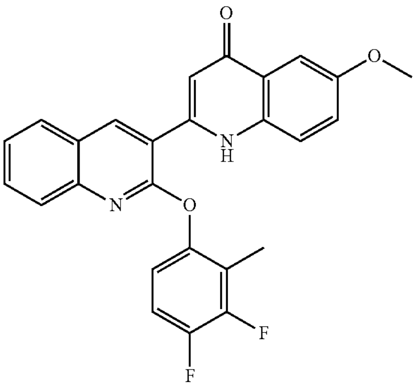 [SMILES: COc1ccc2[nH]c(-c3cc4ccccc4nc3Oc3ccc(F)c(F)c3C)cc(=O)c2c1]

2-[2-(3,4-difluoro-2-methyl-phenoxy)-3-quinolyl]-6-methoxy-1H-quinolin-4-one

TABLE A-continued

Compound Structures and Names.

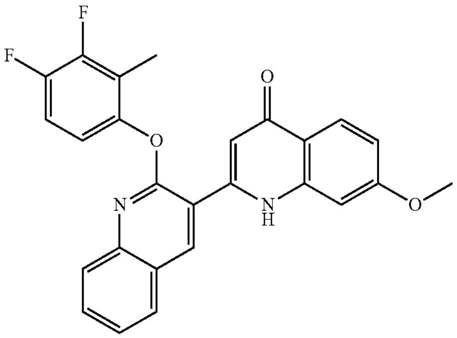 [SMILES: COc1ccc2c(=O)cc(-c3cc4ccccc4nc3Oc3ccc(F)c(F)c3C)[nH]c2c1]

2-[2-(3,4-difluoro-2-methyl-phenoxy)-3-quinolyl]-7-methoxy-1H-quinolin-4-one

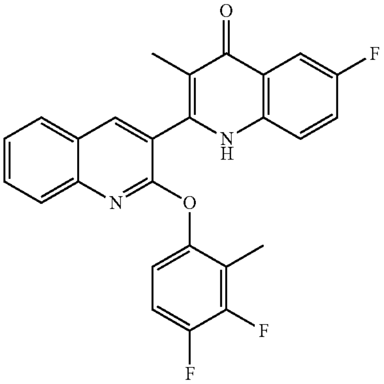 [SMILES: Cc1c(Oc2nc3ccccc3cc2-c2[nH]c3ccc(F)cc3c(=O)c2C)ccc(F)c1F]

2-[2-(3,4-difluoro-2-methyl-phenoxy)-3-quinolyl]-6-fluoro-3-methyl-1H-quinolin-4-one

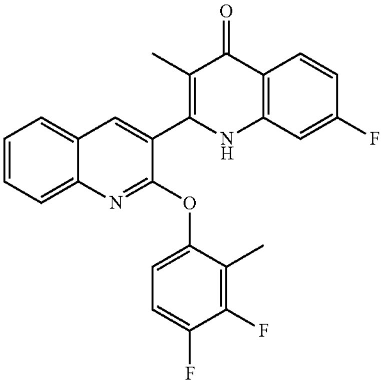 [SMILES: Cc1c(Oc2nc3ccccc3cc2-c2[nH]c3cc(F)ccc3c(=O)c2C)ccc(F)c1F]

2-[2-(3,4-difluoro-2-methyl-phenoxy)-3-quinolyl]-7-fluoro-3-methyl-1H-quinolin-4-one TABLE A-continued

| Compound Structures and Names. |
|---|
| 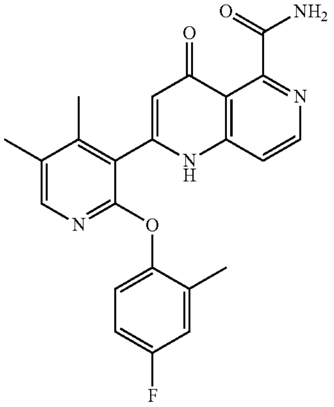 [SMILES: Cc1cc(F)ccc1Oc1ncc(C)c(C)c1-c1cc(=O)c2c(C(N)=O)nccc2[nH]1] 2-[2-(4-fluoro-2-methyl-phenoxy)-4,5-dimethyl-3-pyridyl]-4-oxo-1H-1,6-naphthyridine-5-carboxamide |
| 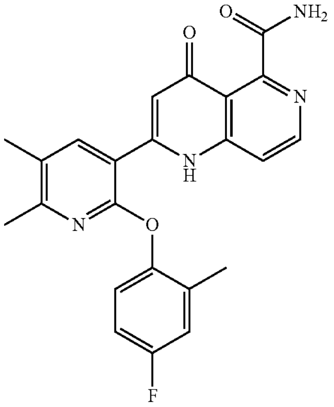 [SMILES: Cc1cc(F)ccc1Oc1nc(C)c(C)cc1-c1cc(=O)c2c(C(N)=O)nccc2[nH]1] 2-[2-(4-fluoro-2-methyl-phenoxy)-5,6-dimethyl-3-pyridyl]-4-oxo-1H-1,6-naphthyridine-5-carboxamide |
| 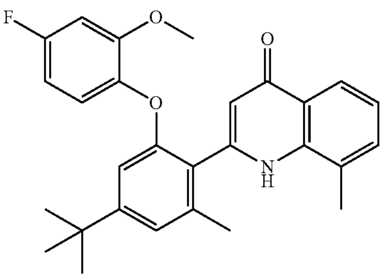 [SMILES: COc1cc(F)ccc1Oc1cc(C(C)(C)C)cc(C)c1-c1cc(=O)c2cccc(C)c2[nH]1] 2-[4-tert-butyl-2-(4-fluoro-2-methoxy-phenoxy)-6-methyl-phenyl]-8-methyl-1H-quinolin-4-one |

TABLE A-continued

| Compound Structures and Names. |
|---|
| 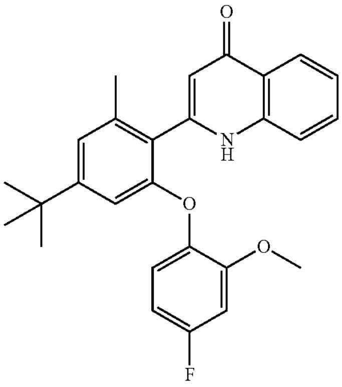 [SMILES: COc1cc(F)ccc1Oc1cc(C(C)(C)C)cc(C)c1-c1cc(=O)c2ccccc2[nH]1] 2-[4-tert-butyl-2-(4-fluoro-2-methoxy-phenoxy)-6-methyl-phenyl]-1H-quinolin-4-one |
| 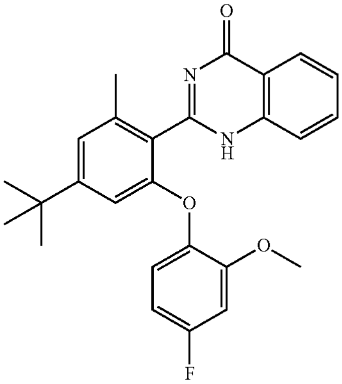 [SMILES: COc1cc(F)ccc1Oc1cc(C(C)(C)C)cc(C)c1-c1nc(=O)c2ccccc2[nH]1] 2-[4-tert-butyl-2-(4-fluoro-2-methoxy-phenoxy)-6-methyl-phenyl]-1H-quinolin-4-one |
| 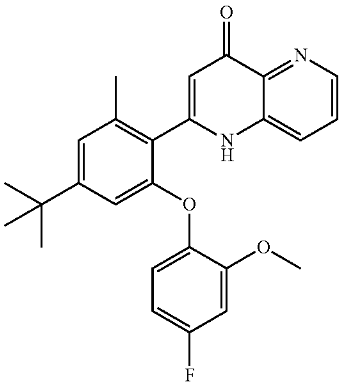 [SMILES: COc1cc(F)ccc1Oc1cc(C(C)(C)C)cc(C)c1-c1cc(=O)c2ncccc2[nH]1] 2-[4-tert-butyl-2-(4-fluoro-2-methoxy-phenoxy)-6-methyl-phenyl]-1H-1,5-naphthyridin-4-one |

TABLE A-continued

| Compound Structures and Names. |
| --- |
| 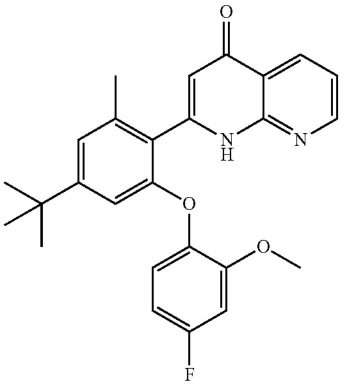 [SMILES: COc1cc(F)ccc1Oc1cc(C(C)(C)C)cc(C)c1-c1cc(=O)c2cccnc2[nH]1] |
| 2-[4-tert-butyl-2-(4-fluoro-2-methoxy-phenoxy)-6-methyl-phenyl]-1H-1,8-naphthyridin-4-one |
| 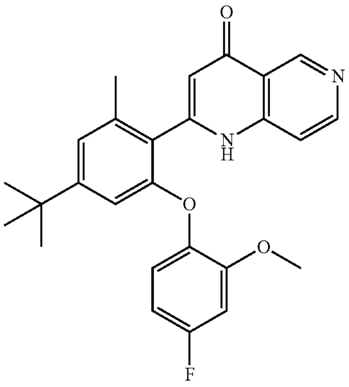 [SMILES: COc1cc(F)ccc1Oc1cc(C(C)(C)C)cc(C)c1-c1cc(=O)c2cnccc2[nH]1] |
| 2-[4-tert-butyl-2-(4-fluoro-2-methoxy-phenoxy)-6-methyl-phenyl]-1H-1,6-naphthyridin-4-one |
| 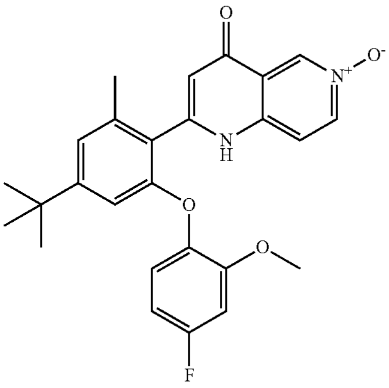 [SMILES: COc1cc(F)ccc1Oc1cc(C(C)(C)C)cc(C)c1-c1cc(=O)c2c[n+]([O-])ccc2[nH]1] |
| 2-[4-tert-butyl-2-(4-fluoro-2-methoxy-phenoxy)-6-methyl-phenyl]-6-oxido-1H-1,6-naphthyridin-6-ium-4-one |

TABLE A-continued

| Compound Structures and Names. |
| --- |
| 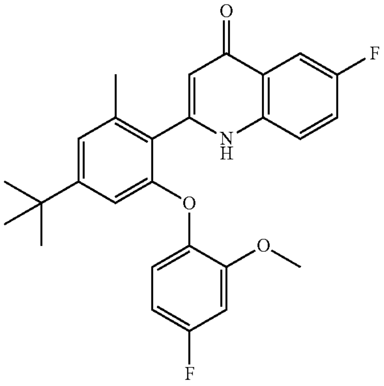 [SMILES: COc1cc(F)ccc1Oc1cc(C(C)(C)C)cc(C)c1-c1cc(=O)c2cc(F)ccc2[nH]1] |
| 2-[4-tert-butyl-2-(4-fluoro-2-methoxy-phenoxy)-6-methyl-phenyl]-6-fluoro-1H-quinolin-4-one |
| 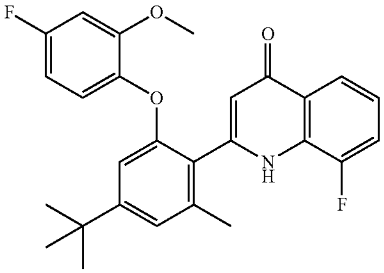 |
| 2-[4-tert-butyl-2-(4-fluoro-2-methoxy-phenoxy)-6-methyl-phenyl]-8-fluoro-1H-quinolin-4-one |
| 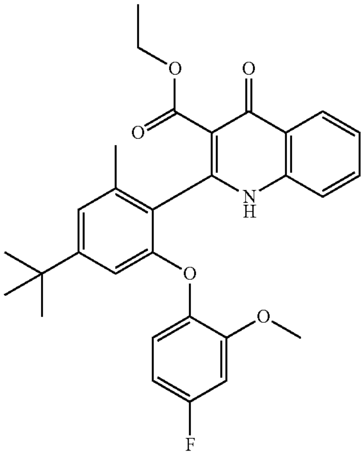 [SMILES: CCOC(=O)c1c(-c2c(C)cc(C(C)(C)C)cc2Oc2ccc(F)cc2OC)[nH]c2ccccc2c1=O] |
| ethyl 2-[4-tert-butyl-2-(4-fluoro-2-methoxy-phenoxy)-6-methyl-phenyl]-4-oxo-1H-quinoline-3-carboxylate |

TABLE A-continued

| Compound Structures and Names. |
|---|
| 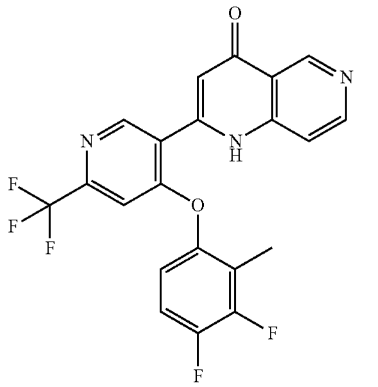 [SMILES: Cc1c(Oc2cc(C(F)(F)F)ncc2-c2cc(=O)c3cnccc3[nH]2)ccc(F)c1F] |
| 2-[4-(3,4-difluoro-2-methyl-phenoxy)-6-(trifluoromethyl)-3-pyridyl]-1H-1,6-naphthyridin-4-one |
| 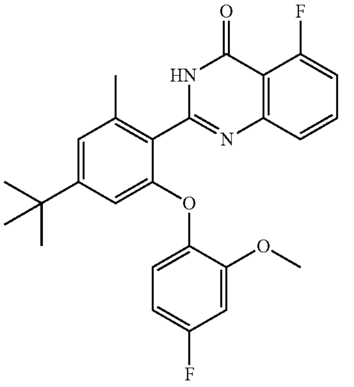 [SMILES: COc1cc(F)ccc1Oc1cc(C(C)(C)C)cc(C)c1-c1nc2cccc(F)c2c(=O)[nH]1] |
| 2-[4-tert-butyl-2-(4-fluoro-2-methoxy-phenoxy)-6-methyl-phenyl]-5-fluoro-3H-quinazolin-4-one |
| 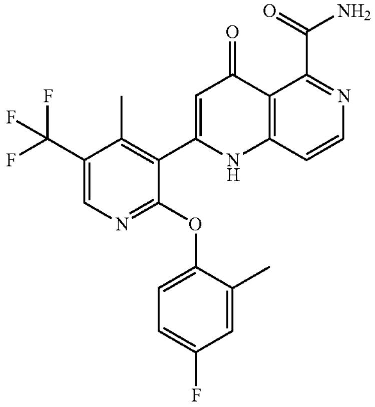 [SMILES: Cc1cc(F)ccc1Oc1ncc(C(F)(F)F)c(C)c1-c1cc(=O)c2c(C(N)=O)nccc2[nH]1] |
| 2-[2-(4-fluoro-2-methyl-phenoxy)-4-methyl-5-(trifluoromethyl)-3-pyridyl]-4-oxo-1H-1,6-naphthyridine-5-carboxamide |

TABLE A-continued

| Compound Structures and Names. |
|---|
| 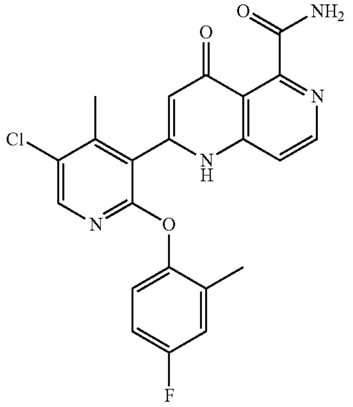 [SMILES: Cc1cc(F)ccc1Oc1ncc(Cl)c(C)c1-c1cc(=O)c2c(C(N)=O)nccc2[nH]1] |
| 2-[5-chloro-2-(4-fluoro-2-methyl-phenoxy)-4-methyl-3-pyridyl]-4-oxo-1H-1,6-naphthyridine-5-carboxamide |
| 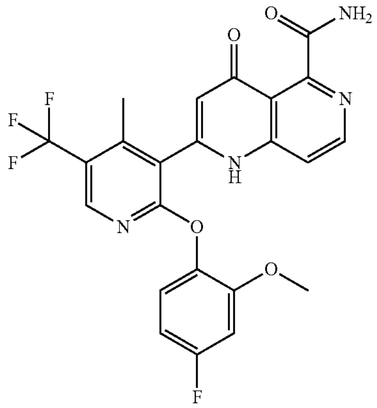 [SMILES: COc1cc(F)ccc1Oc1ncc(C(F)(F)F)c(C)c1-c1cc(=O)c2c(C(N)=O)nccc2[nH]1] |
| 2-[2-(4-fluoro-2-methoxy-phenoxy)-4-methyl-5-(trifluoromethyl)-3-pyridyl]-4-oxo-1H-1,6-naphthyridine-5-carboxamide |
| 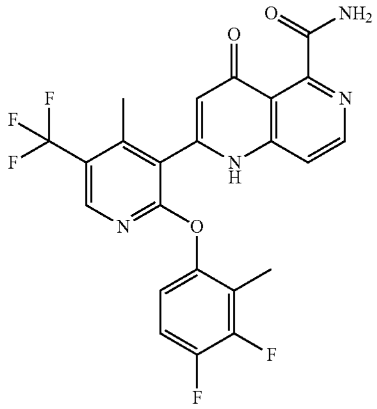 [SMILES: Cc1c(Oc2ncc(C(F)(F)F)c(C)c2-c2cc(=O)c3c(C(N)=O)nccc3[nH]2)ccc(F)c1F] |
| 2-[2-(3,4-difluoro-2-methyl-phenoxy)-4-methyl-5-(trifluoromethyl)-3-pyridyl]-4-oxo-1H-1,6-naphthyridine-5-carboxamide |

TABLE A-continued

Compound Structures and Names.

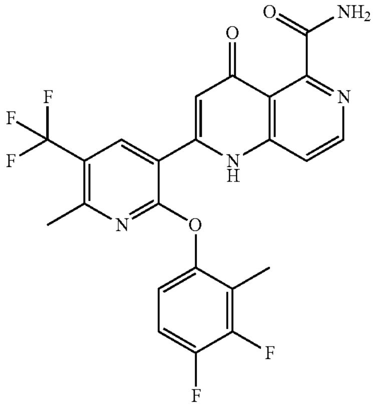 [SMILES: Cc1nc(Oc2ccc(F)c(F)c2C)c(-c2cc(=O)c3c(C(N)=O)nccc3[nH]2)cc1C(F)(F)F]

2-[2-(3,4-difluoro-2-methyl-phenoxy)-6-methyl-5-(trifluoromethyl)-3-pyridyl]-4-oxo-1H-1,6-naphthyridine-5-carboxamide

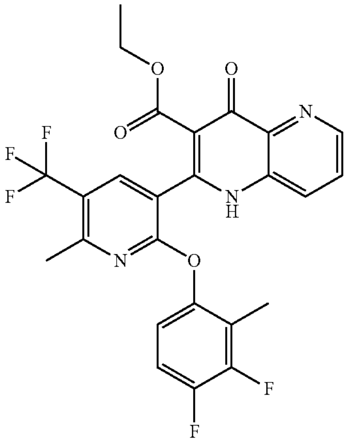 [SMILES: CCOC(=O)c1c(-c2cc(C(F)(F)F)c(C)nc2Oc2ccc(F)c(F)c2C)[nH]c2cccnc2c1=O]

ethyl 2-[2-(3,4-difluoro-2-methyl-phenoxy)-6-methyl-5-(trifluoromethyl)-3-pyridyl]-4-oxo-1H-1,5-naphthyridine-3-carboxylate

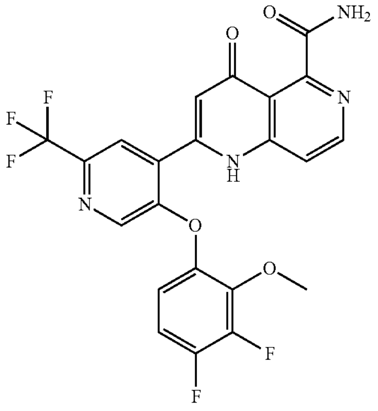 [SMILES: COc1c(Oc2cnc(C(F)(F)F)cc2-c2cc(=O)c3c(C(N)=O)nccc3[nH]2)ccc(F)c1F]

2-[5-(3,4-difluoro-2-methoxy-phenoxy)-2-(trifluoromethyl)-4-pyridyl]-4-oxo-1H-1,6-naphthyridine-5-carboxamide TABLE A-continued Compound Structures and Names.

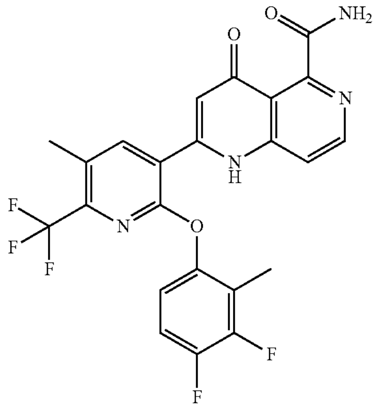 [SMILES: Cc1cc(-c2cc(=O)c3c(C(N)=O)nccc3[nH]2)c(Oc2ccc(F)c(F)c2C)nc1C(F)(F)F]

2-[2-(3,4-difluoro-2-methyl-phenoxy)-5-methyl-6-(trifluoromethyl)-3-pyridyl]-4-oxo-1H-1,6-naphthyridine-5-carboxamide

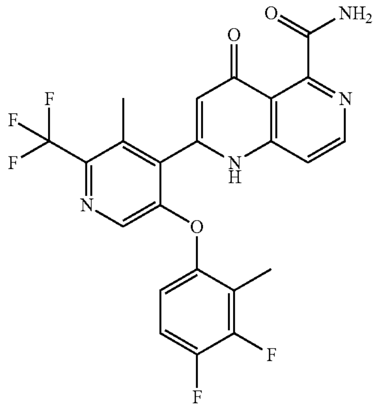 [SMILES: Cc1c(Oc2cnc(C(F)(F)F)c(C)c2-c2cc(=O)c3c(C(N)=O)nccc3[nH]2)ccc(F)c1F]

2-[5-(3,4-difluoro-2-methyl-phenoxy)-3-methyl-2-(trifluoromethyl)-4-pyridyl]-4-oxo-1H-1,6-naphthyridine-5-carboxamide

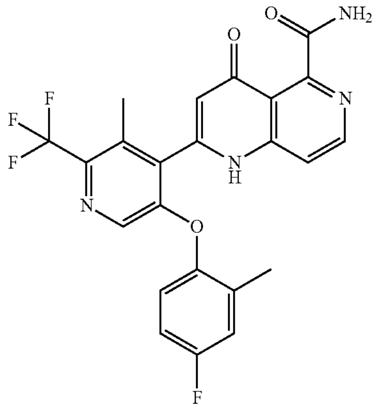 [SMILES: Cc1cc(F)ccc1Oc1cnc(C(F)(F)F)c(C)c1-c1cc(=O)c2c(C(N)=O)nccc2[nH]1]

2-[5-(4-fluoro-2-methyl-phenoxy)-3-methyl-2-(trifluoromethyl)-4-pyridyl]-4-oxo-1H-1,6-naphthyridine-5-carboxamide TABLE A-continued

| Compound Structures and Names. |
| --- |
| 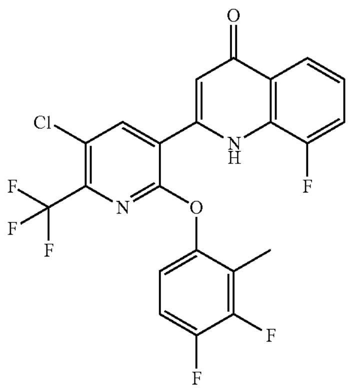 [SMILES: Cc1c(Oc2nc(C(F)(F)F)c(Cl)cc2-c2cc(=O)c3cccc(F)c3[nH]2)ccc(F)c1F] |
| 2-[5-chloro-2-(3,4-difluoro-2-methyl-phenoxy)-6-(trifluoromethyl)-3-pyridyl]-8-fluoro-1H-quinolin-4-one |
| 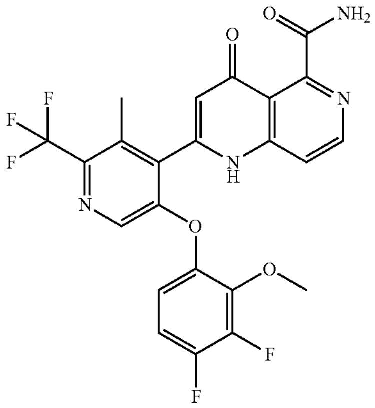 [SMILES: COc1c(Oc2cnc(C(F)(F)F)c(C)c2-c2cc(=O)c3c(C(N)=O)nccc3[nH]2)ccc(F)c1F] |
| 2-[5-(3,4-difluoro-2-methoxy-phenoxy)-3-methyl-2-(trifluoromethyl)-4-pyridyl]-4-oxo-1H-1,6-naphthyridine-5-carboxamide |
| 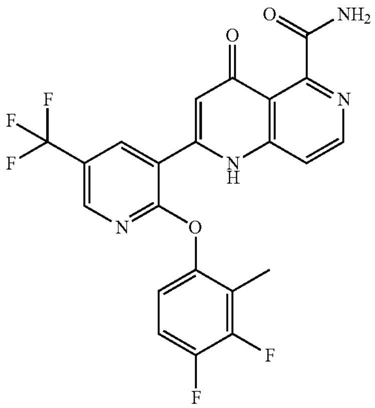 [SMILES: Cc1c(Oc2ncc(C(F)(F)F)cc2-c2cc(=O)c3c(C(N)=O)nccc3[nH]2)ccc(F)c1F] |
| 2-[2-(3,4-difluoro-2-methyl-phenoxy)-5-(trifluoromethyl)-3-pyridyl]-4-oxo-1H-1,6-naphthyridine-5-carboxamide |

TABLE A-continued

| Compound Structures and Names. |
| --- |
| 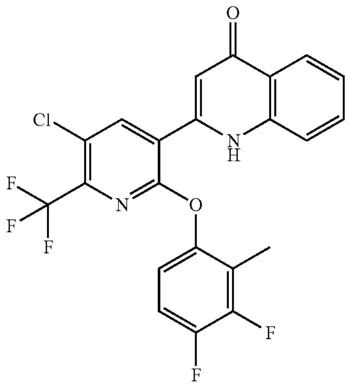 [SMILES: Cc1c(Oc2nc(C(F)(F)F)c(Cl)cc2-c2cc(=O)c3ccccc3[nH]2)ccc(F)c1F] |
| 2-[5-chloro-2-(3,4-difluoro-2-methyl-phenoxy)-6-(trifluoromethyl)-3-pyridyl]-1H-quinolin-4-one |
| 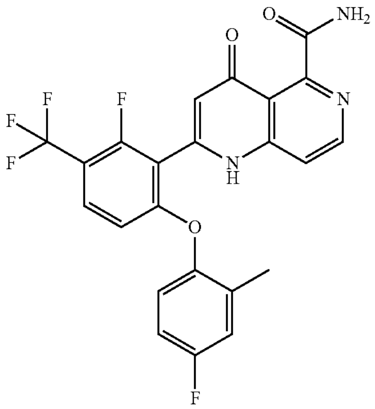 [SMILES: Cc1cc(F)ccc1Oc1ccc(C(F)(F)F)c(F)c1-c1cc(=O)c2c(C(N)=O)nccc2[nH]1] |
| 2-[2-fluoro-6-(4-fluoro-2-methyl-phenoxy)-3-(trifluoromethyl)phenyl]-4-oxo-1H-1,6-naphthyridine-5-carboxamide |
| 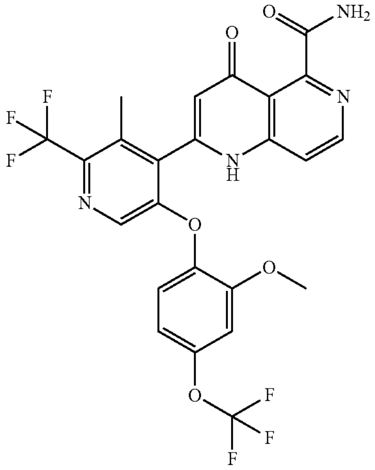 [SMILES: COc1cc(OC(F)(F)F)ccc1Oc1cnc(C(F)(F)F)c(C)c1-c1cc(=O)c2c(C(N)=O)nccc2[nH]1] |
| 2-[5-[2-methoxy-4-(trifluoromethoxy)phenoxy]-3-methyl-2-(trifluoromethyl)-4-pyridyl]-4-oxo-1H-1,6-naphthyridine-5-carboxamide |

TABLE A-continued

| Compound Structures and Names. |
|---|
| 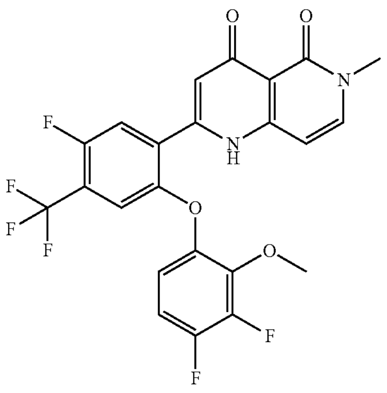 [SMILES: COc1c(Oc2cc(C(F)(F)F)c(F)cc2-c2cc(=O)c3c(=O)n(C)ccc3[nH]2)ccc(F)c1F] |
| 2-[2-(3,4-difluoro-2-methoxy-phenoxy)-5-fluoro-4-(trifluoromethyl)phenyl]-6-methyl-1H-1,6-naphthyridine-4,5-dione |
| 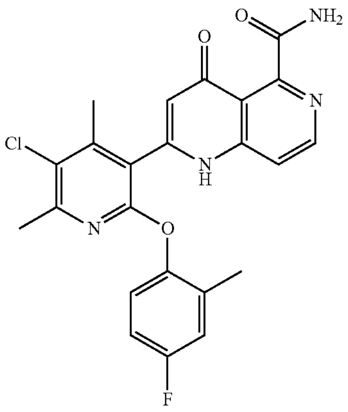 [SMILES: Cc1cc(F)ccc1Oc1nc(C)c(Cl)c(C)c1-c1cc(=O)c2c(C(N)=O)nccc2[nH]1] |
| 2-[5-chloro-2-(4-fluoro-2-methyl-phenxoy)-4,6-dimethyl-3-pyridyl]-4-oxo-1H-1,6-naphthyridine-5-carboxamide |
| 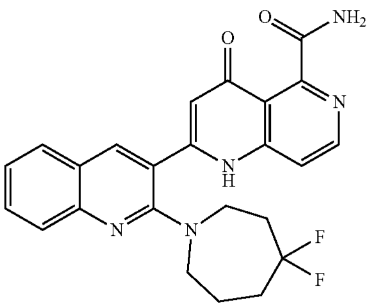 [SMILES: NC(=O)c1nccc2[nH]c(-c3cc4ccccc4nc3N3CCCC(F)(F)CC3)cc(=O)c12] |
| 2-[2-(4,4-difluoroazepan-1-yl)-3-quinolyl]-4-oxo-1H-1,6-naphthyridine-5-carboxamide |

TABLE A-continued

| Compound Structures and Names. |
|---|
| 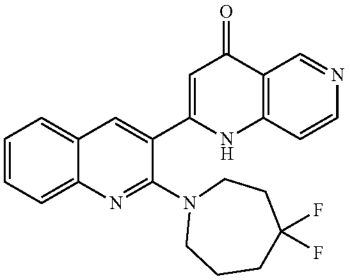 [SMILES: O=c1cc(-c2cc3ccccc3nc2N2CCCC(F)(F)CC2)[nH]c2ccncc12] |
| 2-[2-(4,4-difluoroazepan-1-yl)-3-quinolyl]-1H-1,6-naphthyridin-4-one |
| 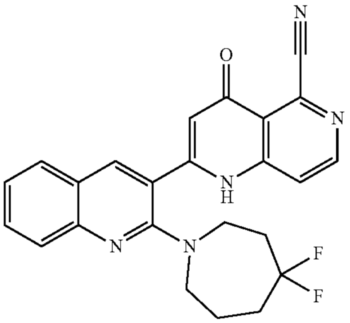 [SMILES: N#Cc1nccc2[nH]c(-c3cc4ccccc4nc3N3CCCC(F)(F)CC3)cc(=O)c12] |
| 2-[2-(4,4-difluoroazepan-1-yl)-3-quinolyl]-4-oxo-1H-1,6-naphthyridine-5-carbonitrile |
| 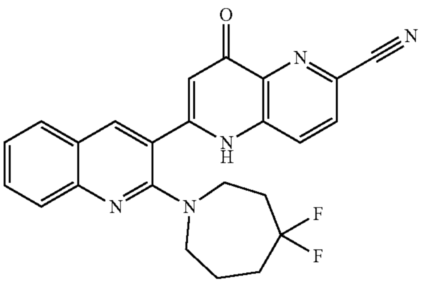 [SMILES: N#Cc1ccc2[nH]c(-c3cc4ccccc4nc3N3CCCC(F)(F)CC3)cc(=O)c2n1] |
| 6-[2-(4,4-difluoroazepan-1-yl)-3-quinolyl]-8-oxo-5H-1,5-naphthyridine-2-carbontrile |
| 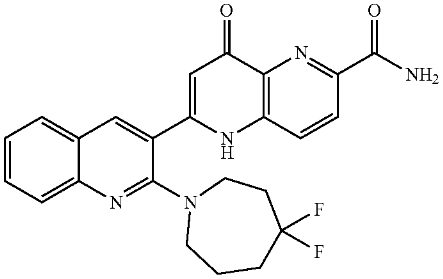 [SMILES: NC(=O)c1ccc2[nH]c(-c3cc4ccccc4nc3N3CCCC(F)(F)CC3)cc(=O)c2n1] |
| 6-[2-(4,4-difluoroazepan-1-yl)-3-quinolyl]-8-oxo-5H-1,5-naphthyridine-2-carboxamide |

TABLE A-continued

| Compound Structures and Names. |
| --- |
| 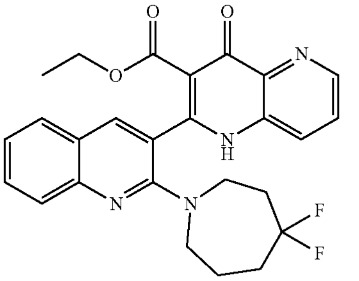 [SMILES: CCOC(=O)c1c(-c2cc3ccccc3nc2N2CCCC(F)(F)CC2)[nH]c2cccnc2c1=O] ethyl 2-[2-(4,4-difluoroazepan-1-yl)-3-quinolyl]-4-oxo-1H-1,5-naphthyridine-3-carboxylate |
| 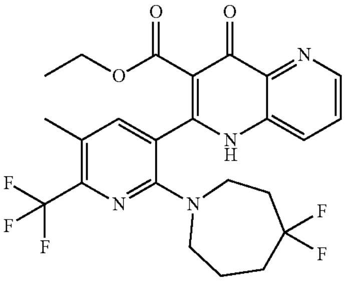 [SMILES: CCOC(=O)c1c(-c2cc(C)c(C(F)(F)F)nc2N2CCCC(F)(F)CC2)[nH]c2cccnc2c1=O] ethyl 2-[2-(4,4-difluoroazepan-1-yl)-5-methyl-6-(trifluoromethyl)-3-pyridyl]-4-oxo-1H-1,5-naphthyridine-3-carboxylate |
| 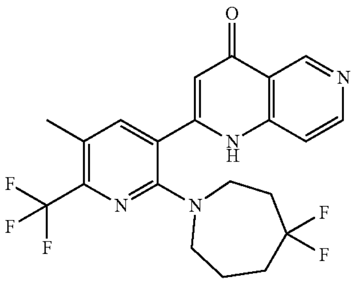 [SMILES: Cc1cc(-c2cc(=O)c3cnccc3[nH]2)c(N2CCCC(F)(F)CC2)nc1C(F)(F)F] 2-[2-(4,4-difluoroazepan-1-yl)-5-methyl-6-(trifluoromethyl)-3-pyridyl]-1H-1,6-naphthyridine-4-one |
| 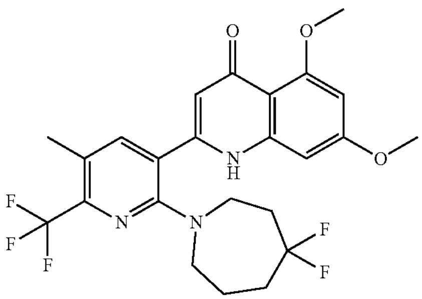 [SMILES: COc1cc(OC)c2c(=O)cc(-c3cc(C)c(C(F)(F)F)nc3N3CCCC(F)(F)CC3)[nH]c2c1] 2-[2-(4,4-difluoroazepan-1-yl)-5-methyl-6-(trifluoromethyl)-3-pyridyl]-5,7-dimethoxy-1H-quinolin-4-one |

TABLE A-continued

| Compound Structures and Names. |
| --- |
| 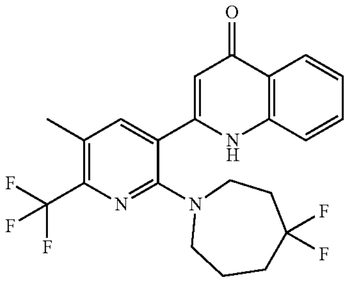 [SMILES: Cc1cc(-c2cc(=O)c3ccccc3[nH]2)c(N2CCCC(F)(F)CC2)nc1C(F)(F)F] 2-[2-(4,4-difluoroazepan-1-yl)-5-methyl-6-(trifluoromethyl)-3-pyridyl]-1H-quinolin-4-one |
| 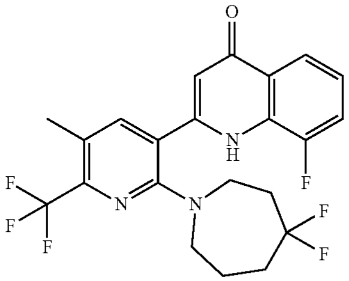 [SMILES: Cc1cc(-c2cc(=O)c3cccc(F)c3[nH]2)c(N2CCCC(F)(F)CC2)nc1C(F)(F)F] 2-[2-(4,4-difluoroazepan-1-yl)-5-methyl-6-(trifluoromethyl)-3-pyridyl]-8-fluoro-1H-quinolin-4-one |
| 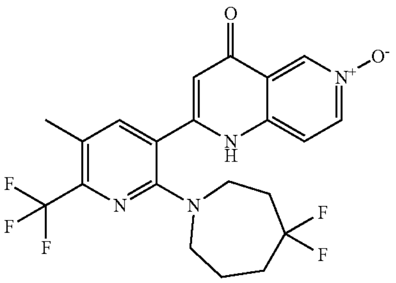 [SMILES: Cc1cc(-c2cc(=O)c3c[n+]([O-])ccc3[nH]2)c(N2CCCC(F)(F)CC2)nc1C(F)(F)F] 2-[2-(4,4-difluroazepan-1-yl)-5-methyl-6-(trifluoromethyl)-3-pyridyl]-6-oxide-1H-1,6-naphthyridin-6-ium-4-one |
| 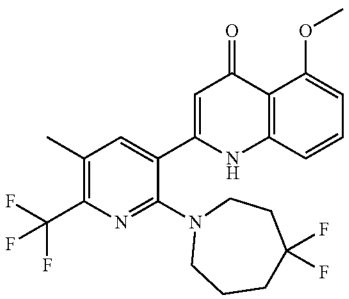 [SMILES: COc1cccc2[nH]c(-c3cc(C)c(C(F)(F)F)nc3N3CCCC(F)(F)CC3)cc(=O)c12] 2-[2-(4,4-difluoroazepan-1-yl)-5-methyl-6-(trifluoromethyl)-3-pyridyl]-5-methoxy-1H-quinolin-4-one |

TABLE A-continued

| Compound Structures and Names. |
| --- |
| 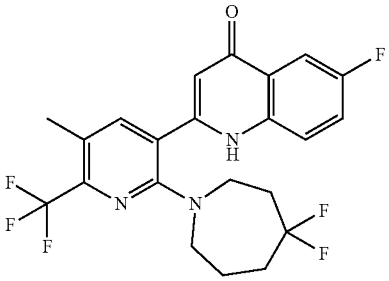 [SMILES: Cc1cc(-c2cc(=O)c3cc(F)ccc3[nH]2)c(N2CCCC(F)(F)CC2)nc1C(F)(F)F] |
| 2-[2-(4,4-difluoroazepan-1-yl)-5-methyl-6-(trifluoromethyl)-3-pyridyl]-6-fluoro-1H-quinolin-4-one |
| 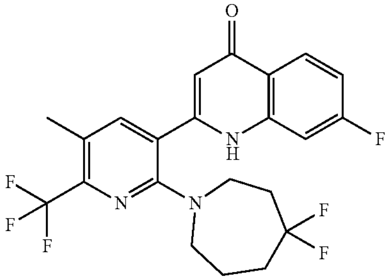 [SMILES: Cc1cc(-c2cc(=O)c3ccc(F)cc3[nH]2)c(N2CCCC(F)(F)CC2)nc1C(F)(F)F] |
| 2-[2-(4,4-difluoroazepan-1-yl)-5-methyl-6-(trifluoromethyl)-3-pyridyl]-7-fluoro-1H-quinolin-4-one |
| 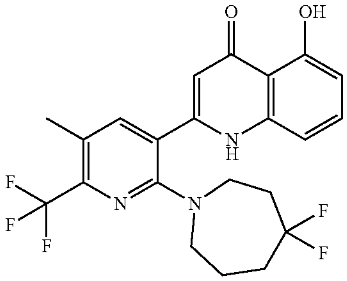 [SMILES: Cc1cc(-c2cc(=O)c3c(O)cccc3[nH]2)c(N2CCCC(F)(F)CC2)nc1C(F)(F)F] |
| 2-[2-(4,4-difluoroazepan-1-yl)-5-methyl-6-(trifluoromethyl)-3-pyridyl]-5-hydroxy-1H-quinolin-4-one |
| 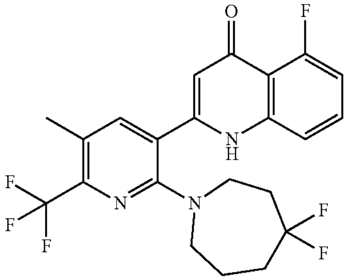 [SMILES: Cc1cc(-c2cc(=O)c3c(F)cccc3[nH]2)c(N2CCCC(F)(F)CC2)nc1C(F)(F)F] |
| 2-[2-(4,4-difluoroazepan-1-yl)-5-methyl-6-(trifluoromethyl)-3-pyridyl]-5-fluoro-1H-quinolin-4-one |

TABLE A-continued

| Compound Structures and Names. |
| --- |
| 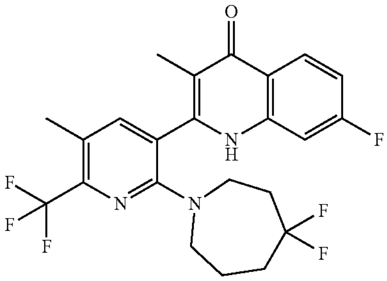 [SMILES: Cc1cc(-c2[nH]c3cc(F)ccc3c(=O)c2C)c(N2CCCC(F)(F)CC2)nc1C(F)(F)F] |
| 2-[2-(4,4-difluoroazepan-1-yl)-5-methyl-6-(trifluoromethyl)-3-pyridyl]-7-fluoro-3-methyl-1H-quinolin-4-one |
| 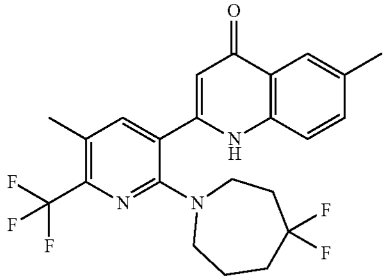 [SMILES: Cc1ccc2[nH]c(-c3cc(C)c(C(F)(F)F)nc3N3CCCC(F)(F)CC3)cc(=O)c2c1] |
| 2-[2-(4,4-difluoroazepan-1-yl)-5-methyl-6-(trifluoromethyl)-3-pyridyl]-6-methyl-1H-quinolin-4-one |
| 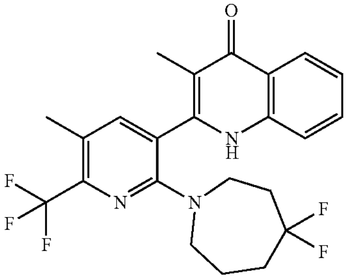 [SMILES: Cc1cc(-c2[nH]c3ccccc3c(=O)c2C)c(N2CCCC(F)(F)CC2)nc1C(F)(F)F] |
| 2-[2-(4,4-difluoroazepan-1-yl)-5-methyl-6-(trifluoromethyl)-3-pyridyl]-3-methyl-1H-quinolin-4-one |
| 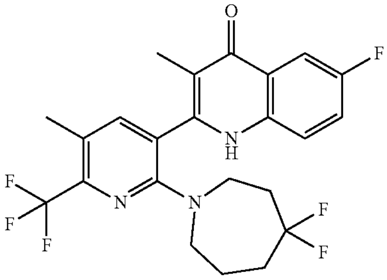 [SMILES: Cc1cc(-c2[nH]c3ccc(F)cc3c(=O)c2C)c(N2CCCC(F)(F)CC2)nc1C(F)(F)F] |
| 2-[2-(4,4-difluoroazepan-1-yl)-5-methyl-6-(trifluoromethyl)-3-pyridyl]-6-fluoro-3-methyl-1H-quinolin-4-one |

TABLE A-continued

| Compound Structures and Names. |
|---|
| 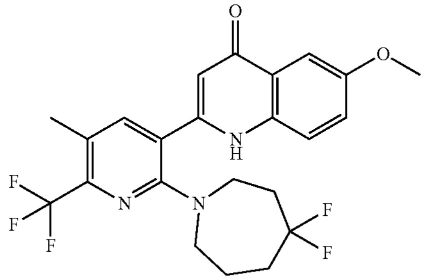 [SMILES: COc1ccc2[nH]c(-c3cc(C)c(C(F)(F)F)nc3N3CCCC(F)(F)CC3)cc(=O)c2c1] |
| 2-[2-(4,4-difluoroazepan-1-yl)-5-methyl-6-(trifluoromethyl)-3-pyridyl]-6-methoxy-1H-quinolin-4-one |
| 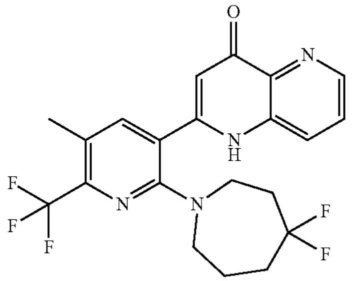 [SMILES: Cc1cc(-c2cc(=O)c3ncccc3[nH]2)c(N2CCCC(F)(F)CC2)nc1C(F)(F)F] |
| 2-[2-(4,4-difluoroazepan-1-yl)-5-methyl-6-(trifluoromethyl)-3-pyridyl]-1H-1,5-naphthyridin-4-one |
| 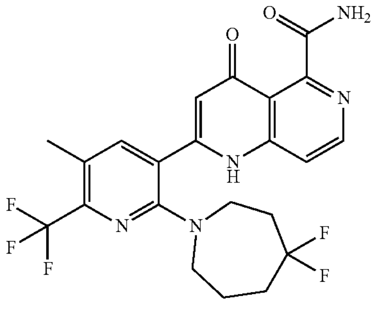 [SMILES: Cc1cc(-c2cc(=O)c3c(C(N)=O)nccc3[nH]2)c(N2CCCC(F)(F)CC2)nc1C(F)(F)F] |
| 2-[2-(4,4-difluoroazepan-1-yl)-5-methyl-6-(trifluoromethyl)-3-pyridyl]-4-oxo-1H-1,6-naphthyridine-5-carboxamide |
| 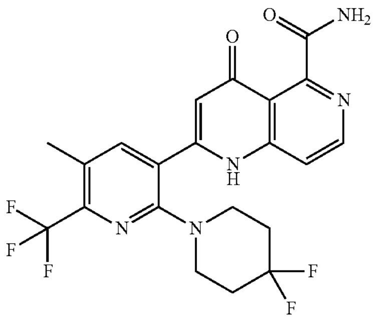 [SMILES: Cc1cc(-c2cc(=O)c3c(C(N)=O)nccc3[nH]2)c(N2CCC(F)(F)CC2)nc1C(F)(F)F] |
| 2-[2-(4,4-difluoro-1-piperidyl)-5-methyl-6-(trifluoromethyl)-3-pyridyl]-4-oxo-1H-1,6-naphthyridine-5-carboxamide |

TABLE A-continued

| Compound Structures and Names. |
|---|
| 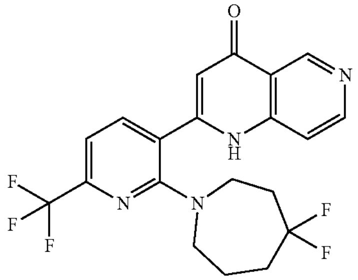 [SMILES: O=c1cc(-c2ccc(C(F)(F)F)nc2N2CCCC(F)(F)CC2)[nH]c2ccncc12] |
| 2-[2-(4,4-difluoroazepan-1-yl)-6-(trifluoromethyl)-3-pyridyl]-1H-1,6-naphthyridin-4-one |
| 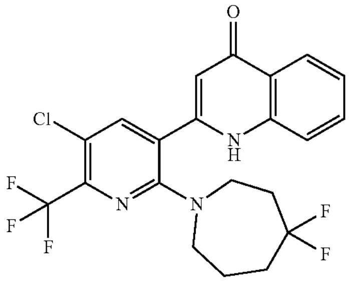 |
| 2-[5-chloro-2-(4,4-difluoroazepan-1-yl)-6-(trifluoromethyl)-3-pyridyl]-1H-quinolin-4-one |
| 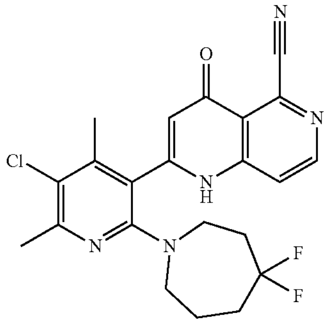 [SMILES: Cc1nc(N2CCCC(F)(F)CC2)c(-c2cc(=O)c3c(C#N)nccc3[nH]2)c(C)c1Cl] |
| 2-[5-chloro-2-(4,4-difluoroazepan-1-yl)-4,6-dimethyl-3-pyridyl]-4-oxo-1H-1,6-naphthyridine-5-carbonitrile |
| 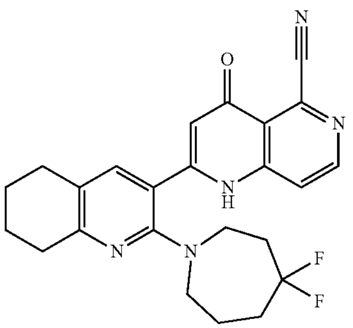 [SMILES: N#Cc1nccc2[nH]c(-c3cc4c(nc3N3CCCC(F)(F)CC3)CCCC4)cc(=O)c12] |
| 2-[2-(4,4-difluoroazepan-1-yl)-5,6,7,8-tetrahydroquinolin-3-yl]-4-oxo-1H-1,6-naphthyridine-5-carbonitrile |

TABLE A-continued

| Compound Structures and Names. |
|---|
| 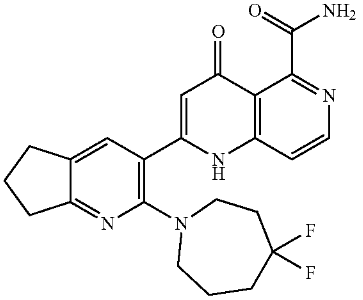 [SMILES: NC(=O)c1nccc2[nH]c(-c3cc4c(nc3N3CCCC(F)(F)CC3)CCC4)cc(=O)c12] 2-[2-(4,4-difluoroazepan-1-yl)-6,7-dihydro-5H-cyclopenta[b]pyridin-3-yl]-4-oxo-1H-1,6-naphthyridine-5-carboxamide |
| 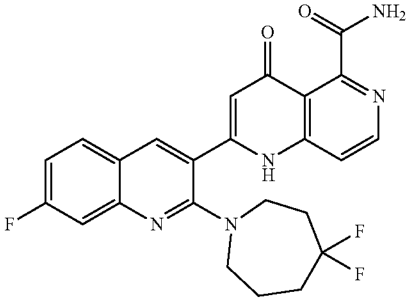 [SMILES: NC(=O)c1nccc2[nH]c(-c3cc4ccc(F)cc4nc3N3CCCC(F)(F)CC3)cc(=O)c12] 2-[2-(4,4-difluoroazepan-1-yl)-7-fluoro-3-quinolyl]-4-oxo-1H-1,6-naphthyridine-5-carboxamide |
| 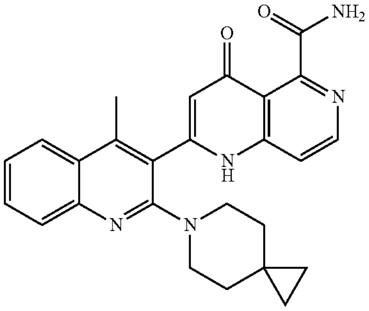 [SMILES: Cc1c(-c2cc(=O)c3c(C(N)=O)nccc3[nH]2)c(N2CCC3(CC2)CC3)nc2ccccc12] 2-[2-(6-azaspiro[2.5]octan-6-yl)-4-methyl-3-quinolyl]-4-oxo-1H-1,6-naphthyridine-5-carboxamide |
| 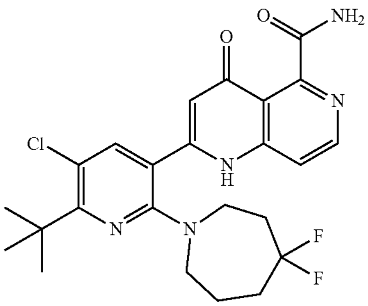 [SMILES: CC(C)(C)c1nc(N2CCCC(F)(F)CC2)c(-c2cc(=O)c3c(C(N)=O)nccc3[nH]2)cc1Cl] 2-[6-tert-butyl-5-chloro-2-(4,4-difluoroazepan-1-yl)-3-pyridyl]-4-oxo-1H-1,6-naphthyridine-5-carboxamide |

TABLE A-continued

| Compound Structures and Names. |
|---|
| 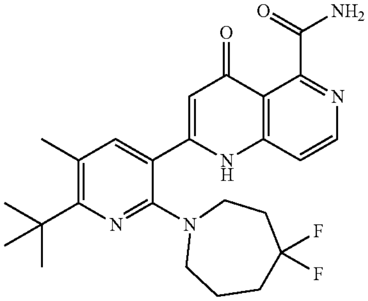 [SMILES: Cc1cc(-c2cc(=O)c3c(C(N)=O)nccc3[nH]2)c(N2CCCC(F)(F)CC2)nc1C(C)(C)C] 2-[6-tert-butyl-2-(4,4-difluoroazepan-1-yl)-5-methyl-3-pyridyl]-4-oxo-1H-1,6-naphthyridine-5-carboxamide |
| 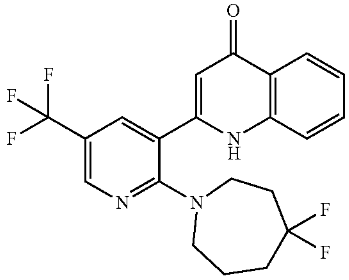 [SMILES: O=c1cc(-c2cc(C(F)(F)F)cnc2N2CCCC(F)(F)CC2)[nH]c2ccccc12] 2-[2-(4,4-difluoroazepan-1-yl)-5-(trifluoromethyl)-3-pyridyl]-1H-quinolin-4-one |
| 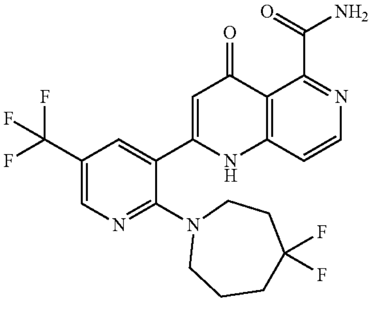 [SMILES: NC(=O)c1nccc2[nH]c(-c3cc(C(F)(F)F)cnc3N3CCCC(F)(F)CC3)cc(=O)c12] 2-[2-(4,4-difluoroazepan-1-yl)-5-(trifluoromethyl)-3-pyridyl]-4-oxo-1H-1,6-naphthyridine-5-carboxamide |
| 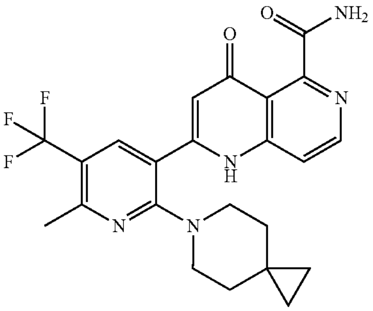 [SMILES: Cc1nc(N2CCC3(CC2)CC3)c(-c2cc(=O)c3c(C(N)=O)nccc3[nH]2)cc1C(F)(F)F] 2-[2-(6-azaspiro[2.5]octan-6-yl)-6-methyl-5-(trifluoromethyl)-3-pyridyl]-4-oxo-1H-1,6-naphthyridine-5-carboxamide |

TABLE A-continued

Compound Structures and Names.

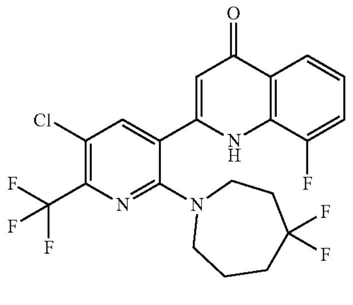 [SMILES: O=c1cc(-c2cc(Cl)c(C(F)(F)F)nc2N2CCCC(F)(F)CC2)[nH]c2c(F)cccc12]

2-[5-chloro-2-(4,4-difluoroazepan-1-yl)-6-(trifluoromethyl)-3-pyridyl]-8-fluoro-1H-quinolin-4-one

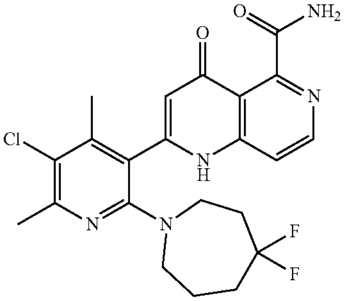 [SMILES: Cc1nc(N2CCCC(F)(F)CC2)c(-c2cc(=O)c3c(C(N)=O)nccc3[nH]2)c(C)c1Cl]

2-[5-chloro-2-(4,4-difluoroazepan-1-yl)-4,6-dimethyl-3-pyridyl]-4-oxo-1H-1,6-naphthyridine-5-carboxamide

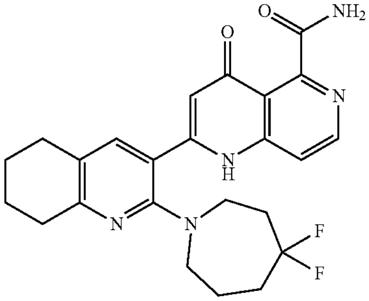 [SMILES: NC(=O)c1nccc2[nH]c(-c3cc4c(nc3N3CCCC(F)(F)CC3)CCCC4)cc(=O)c12]

2-[2-(4,4-difluoroazepan-1-yl)-5,6,7,8-tetrahydroquinolin-3-yl]-4-oxo-1H-1,6-naphthyridine-5-carboxamide

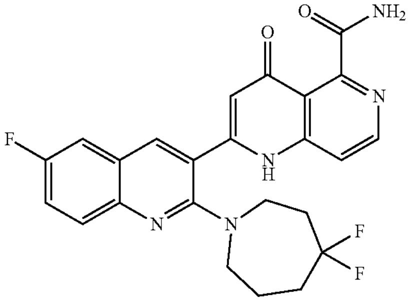 [SMILES: NC(=O)c1nccc2[nH]c(-c3cc4cc(F)ccc4nc3N3CCCC(F)(F)CC3)cc(=O)c12]

2-[2-(4,4-difluoroazepan-1-yl)-6-fluoro-3-quinolyl]-4-oxo-1H-1,6-naphthyridine-5-carboxamide TABLE A-continued Compound Structures and Names.

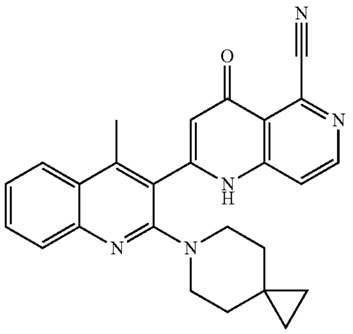 [SMILES: Cc1c(-c2cc(=O)c3c(C#N)nccc3[nH]2)c(N2CCC3(CC2)CC3)nc2ccccc12]

2-[2-(6-azaspiro[2.5]octan-6-yl)-4-methyl-3-quinolyl]-4-oxo-1H-1,6-naphthyridine-5-carbonitrile

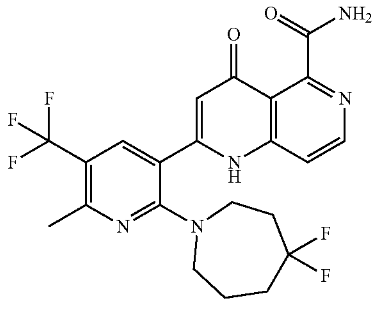 [SMILES: Cc1nc(N2CCCC(F)(F)CC2)c(-c2cc(=O)c3c(C(N)=O)nccc3[nH]2)cc1C(F)(F)F]

2-[2-(4,4-difluoroazepan-1-yl)-6-methyl-5-(trifluoromethyl)-3-pyridyl]-4-oxo-1H-1,6-naphthyridine-5-carboxamide

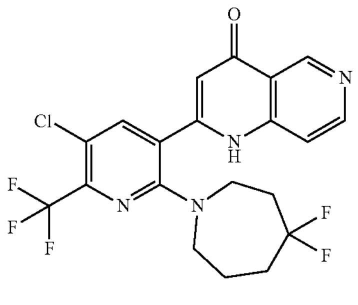 [SMILES: O=c1cc(-c2cc(Cl)c(C(F)(F)F)nc2N2CCCC(F)(F)CC2)[nH]c2ccncc12]

2-[5-chloro-2-(4,4-difluoroazepan-1-yl)-6-(trifluoromethyl)-3-pyridyl]-1H-1,6-naphthyridin-4-one

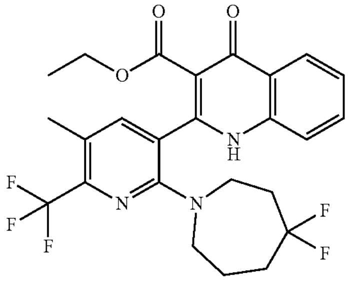 [SMILES: CCOC(=O)c1c(-c2cc(C)c(C(F)(F)F)nc2N2CCCC(F)(F)CC2)[nH]c2ccccc2c1=O]

ethyl 2-[2-(4,4-difluoroazepan-1-yl)-5-methyl-6-(trifluoromethyl)-3-pyridyl]-4-oxo-1H-quinoline-3-carboxylate TABLE A-continued

| Compound Structures and Names. |
|---|
| 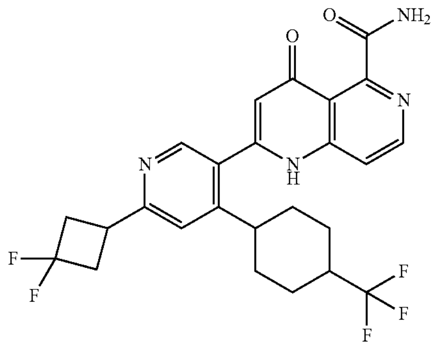 [SMILES: NC(=O)c1nccc2[nH]c(-c3cnc(C4CC(F)(F)C4)cc3C3CCC(C(F)(F)F)CC3)cc(=O)c12] |
| 2-[6-(3,3-difluorocyclobutyl)-4-[4-(trifluoromethyl)cyclohexyl]-3-pyridyl]-4-oxo-1H-1,6-naphthyridine-5-carboxamide |
| 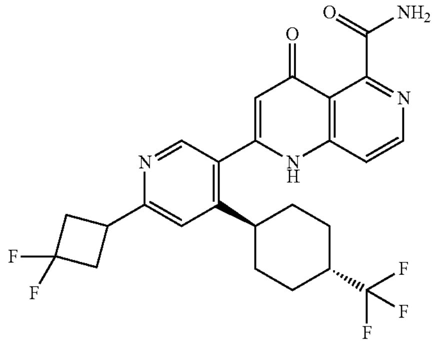 [SMILES: NC(=O)c1nccc2[nH]c(-c3cnc(C4CC(F)(F)C4)cc3[C@H]3CC[C@H](C(F)(F)F)CC3)cc(=O)c12] |
| 2-[6-(3,3-difluorocyclobutyl)-4-((1r,4r)-4-(trifluoromethyl)cyclohexyl)-3-pyridyl]-4-oxo-1H-1,6-naphthyridine-5-carboxamide |
| 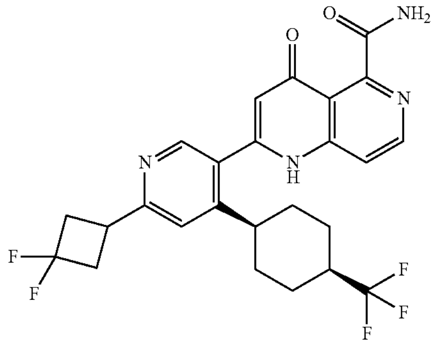 [SMILES: NC(=O)c1nccc2[nH]c(-c3cnc(C4CC(F)(F)C4)cc3[C@H]3CC[C@@H](C(F)(F)F)CC3)cc(=O)c12] |
| 2-[6-(3,3-difluorocyclobutyl)-4-((1s,4s)-4-(trifluoromethyl)cyclohexyl]-3-pyridyl]-4-oxo-1H-1,6-naphthyridine-5-carboxamide (cis isomer) |

TABLE A-continued

| Compound Structures and Names. |
|---|
| 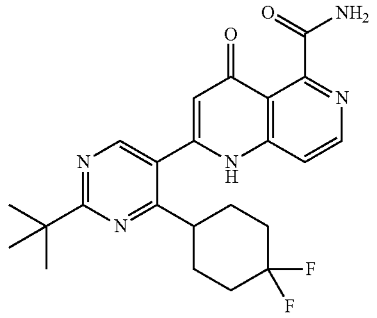 [SMILES: CC(C)(C)c1ncc(-c2cc(=O)c3c(C(N)=O)nccc3[nH]2)c(C2CCC(F)(F)CC2)n1] |
| 2-[2-tert-butyl-4-(4,4-difluorocyclohexyl)pyrimidin-5-yl]-4-oxo-1H-1,6-naphthyridine-5-carboxmaide |
| 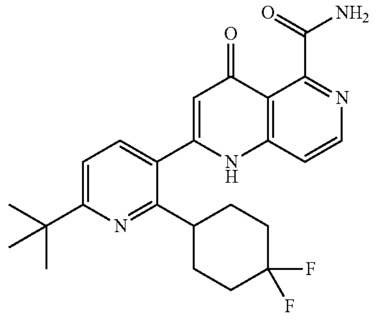 [SMILES: CC(C)(C)c1ccc(-c2cc(=O)c3c(C(N)=O)nccc3[nH]2)c(C2CCC(F)(F)CC2)n1] |
| 2-[6-tert-butyl-2-(4,4-difluorocyclohexyl)-3-pyridyl]-4-oxo-1H-1,6-naphthyridine-5-carboxamide |
| 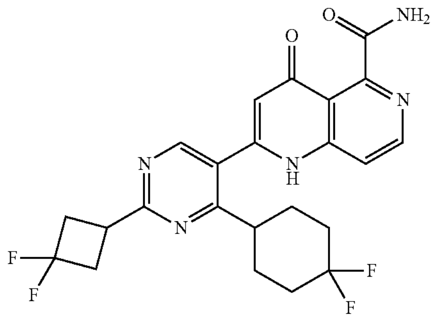 [SMILES: NC(=O)c1nccc2[nH]c(-c3cnc(C4CC(F)(F)C4)nc3C3CCC(F)(F)CC3)cc(=O)c12] |
| 2-[2-(3,3-difluorocyclobutyl)-4-(4,4-difluorocyclohexyl)pyrimidin-5-yl]-4-oxo-1H-1,6-naphthyridine-5-carboxamide |
| 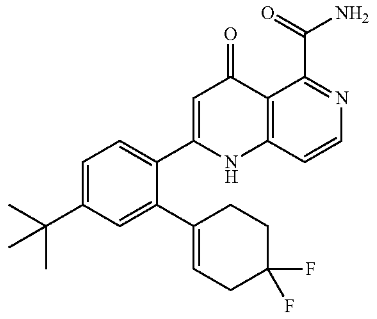 [SMILES: CC(C)(C)c1ccc(-c2cc(=O)c3c(C(N)=O)nccc3[nH]2)c(C2=CCC(F)(F)CC2)c1] |
| 2-[4-tert-butyl-2-(4,4-difluorocyclohexen-1-yl)phenyl]-4-oxo-1H-1,6-naphthyridine-5-carboxamide |

TABLE A-continued

| Compound Structures and Names. |
| --- |
| 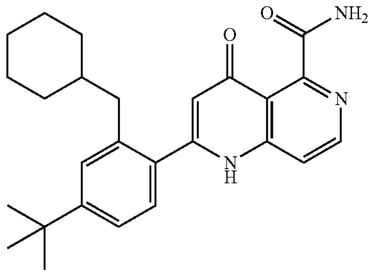 [SMILES: CC(C)(C)c1ccc(-c2cc(=O)c3c(C(N)=O)nccc3[nH]2)c(CC2CCCCC2)c1] 2-[4-tert-butyl-2-(cyclohexylmethyl)phenyl]-4-oxo-1H-1,6-naphthyridine-5-carboxamide |
| 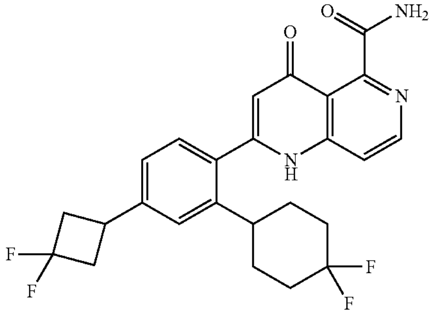 [SMILES: NC(=O)c1nccc2[nH]c(-c3ccc(C4CC(F)(F)C4)cc3C3CCC(F)(F)CC3)cc(=O)c12] 2-[4-(3,3-difluorocyclobutyl)-2-(4,4-difluorocyclohexyl)phenyl]-4-oxo-1H-1,6-naphthyridine-5-carboxamide |
| 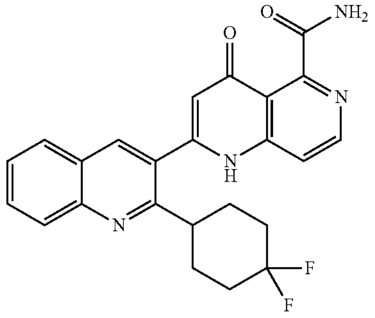 [SMILES: NC(=O)c1nccc2[nH]c(-c3cc4ccccc4nc3C3CCC(F)(F)CC3)cc(=O)c12] 2-[2-(4,4-difluorocyclohexyl)-3-quinolyl]-4-oxo-1H-1,6-naphthyridine-5-carboxamide |
| 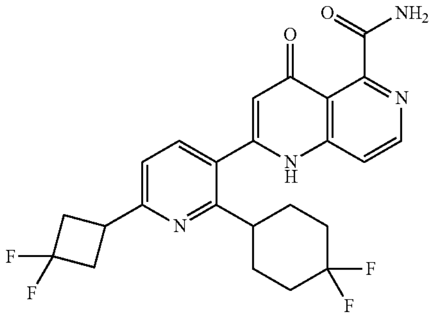 [SMILES: NC(=O)c1nccc2[nH]c(-c3ccc(C4CC(F)(F)C4)nc3C3CCC(F)(F)CC3)cc(=O)c12] 2-[6-(3,3-difluorocyclobutyl)-2-(4,4-difluorocyclohexyl)-3-pyridyl]-4-oxo-1H-1,6-naphthyridine-5-carboxamide |

TABLE A-continued

| Compound Structures and Names. |
| --- |
| 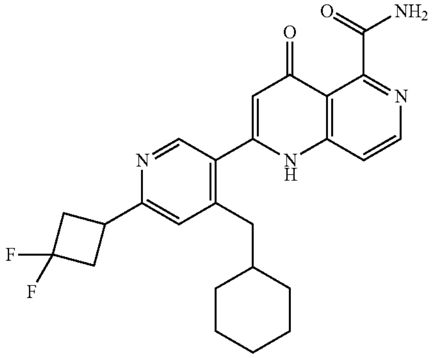 [SMILES: NC(=O)c1nccc2[nH]c(-c3cnc(C4CC(F)(F)C4)cc3CC3CCCCC3)cc(=O)c12] 2-[4-(cyclohexylmethyl)-6-(3,3-difluorocyclobutyl)-3-pyridyl]-4-oxo-1H-1,6-naphthyridine-5-carboxamide |
| 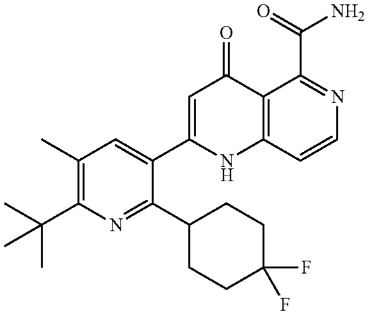 [SMILES: Cc1cc(-c2cc(=O)c3c(C(N)=O)nccc3[nH]2)c(C2CCC(F)(F)CC2)nc1C(C)(C)C] 2-[6-tert-butyl-2-(4,4-difluorocyclohexyl)-5-methyl-3-pyridyl]-4-oxo-1H-1,6-naphthyridine-5-carboxamide |
| 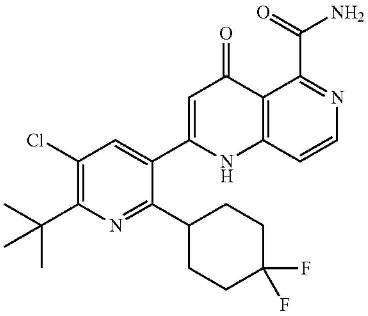 [SMILES: CC(C)(C)c1nc(C2CCC(F)(F)CC2)c(-c2cc(=O)c3c(C(N)=O)nccc3[nH]2)cc1Cl] 2-[6-tert-butyl-5-chloro-2-(4,4-difluorocyclohexyl)-3-pyridyl]-4-oxo-1H-1,6-naphthyridine-5-carboxamide |

TABLE A-continued

| Compound Structures and Names. |
|---|
| 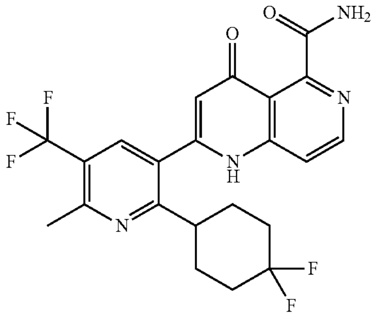 [SMILES: Cc1nc(C2CCC(F)(F)CC2)c(-c2cc(=O)c3c(C(N)=O)nccc3[nH]2)cc1C(F)(F)F] |
| 2-[2-(4,4-difluorocyclohexyl)-6-methyl-5-(trifluoromethyl)-3-pyridyl]-4-oxo-1H-1,6-naphthyridine-5-carboxamide |
| 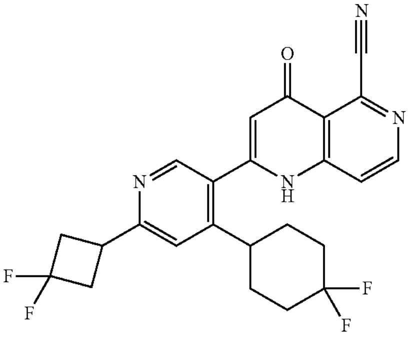 [SMILES: N#Cc1nccc2[nH]c(-c3cnc(C4CC(F)(F)C4)cc3C3CCC(F)(F)CC3)cc(=O)c12] |
| 2-[6-(3,3-difluorocyclobutyl)-4-(4,4-difluorocyclohexyl)-3-pyridyl]-4-oxo-1H-1,6-naphthyridine-5-carbonitrile |
| 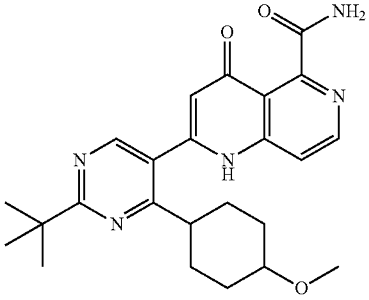 [SMILES: COC1CCC(c2nc(C(C)(C)C)ncc2-c2cc(=O)c3c(C(N)=O)nccc3[nH]2)CC1] |
| 2-[2-tert-butyl-4-(4-methoxycyclohexyl)pyrimidin-5-yl]-4-oxo-1H-1,6-naphthyridine-5-carboxamide |
| 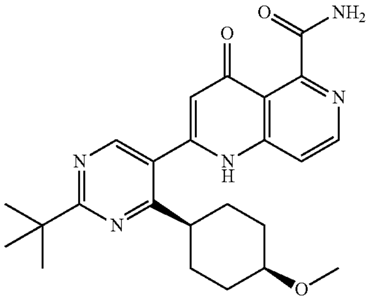 [SMILES: CO[C@H]1CC[C@@H](c2nc(C(C)(C)C)ncc2-c2cc(=O)c3c(C(N)=O)nccc3[nH]2)CC1] |
| 2-[2-tert-butyl-4-((1s,4s)-4-methoxycyclohexyl)pyrimidin-5-yl]-4-oxo-1H-1,6-naphthyridine-5-carboxamide |

TABLE A-continued

| Compound Structures and Names. |
|---|
| 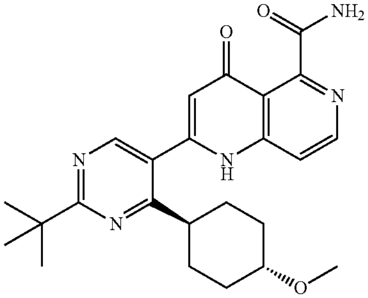 [SMILES: CO[C@H]1CC[C@H](c2nc(C(C)(C)C)ncc2-c2cc(=O)c3c(C(N)=O)nccc3[nH]2)CC1] |
| 2-[2-tert-butyl-4-((1r,4r)-4-methoxycyclohexyl)pyrimidin-5-yl]-4-oxo-1H-1,6-naphthyridine-5-carboxamide |
| 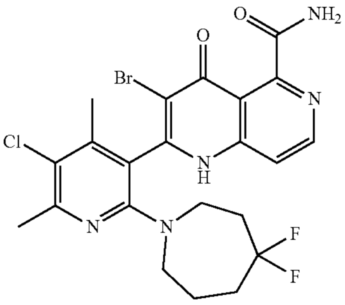 [SMILES: Cc1nc(N2CCCC(F)(F)CC2)c(-c2[nH]c3ccnc(C(N)=O)c3c(=O)c2Br)c(C)c1Cl] |
| 3-bromo-2-[5-chloro-2-(4,4-difluoroazepan-1-yl)-4,6-dimethyl-3-pyridyl]-4-oxo-1H-1,6-naphthyridine-5-carboxamide |
| 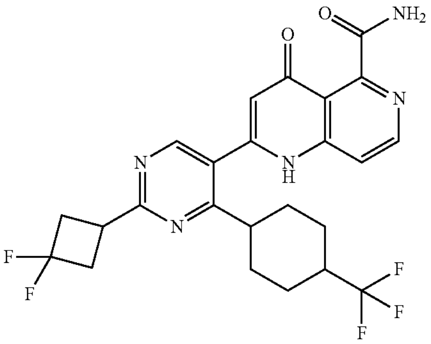 [SMILES: NC(=O)c1nccc2[nH]c(-c3cnc(C4CC(F)(F)C4)nc3C3CCC(C(F)(F)F)CC3)cc(=O)c12] |
| 2-[2-(3,3-difluorocyclobutyl)-4-[4-(trifluoromethyl)cyclohexyl]pyrimidin-5-yl]-4-oxo-1H-1,6-naphthyridine-5-carboxamide |

TABLE A-continued

| Compound Structures and Names. |
|---|
| 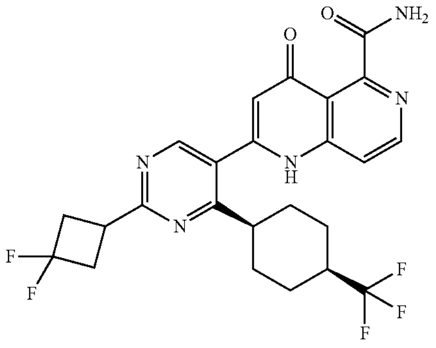 [SMILES: NC(=O)c1nccc2[nH]c(-c3cnc(C4CC(F)(F)C4)nc3[C@H]3CC[C@@H](C(F)(F)F)CC3)cc(=O)c12] |
| 2-[2-(3,3-difluorocyclobutyl)-4-((1s,4s)-4-(trifluoromethyl)cyclohexyl]pyrimidin-5-yl]-4-oxo-1H-1,6-naphthyridine-5-carboxamide |
| 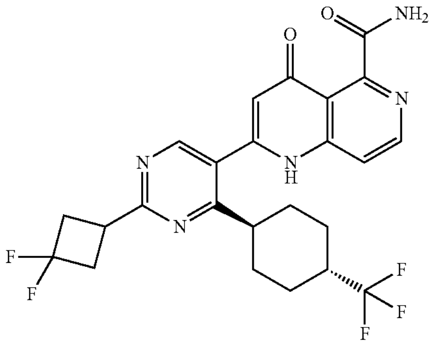 [SMILES: NC(=O)c1nccc2[nH]c(-c3cnc(C4CC(F)(F)C4)nc3[C@H]3CC[C@H](C(F)(F)F)CC3)cc(=O)c12] |
| 2-[2-(3,3-difluorocyclobutyl)-4-((1r,4r)-4-(trifluoromethyl)cyclohexyl]pyrimidin-5-yl]-4-oxo-1H-1,6-naphthyridine-5-carboxamide |
| 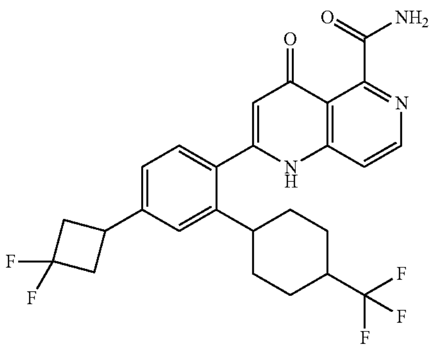 [SMILES: NC(=O)c1nccc2[nH]c(-c3ccc(C4CC(F)(F)C4)cc3C3CCC(C(F)(F)F)CC3)cc(=O)c12] |
| 2-[4-(3,3-difluorocyclobutyl)-2-[4-(trifluoromethyl)cyclohexyl]phenyl]-4-oxo-1H-1,6-naphthyridine-5-carboxamide |

TABLE A-continued

| Compound Structures and Names. |
|---|
| 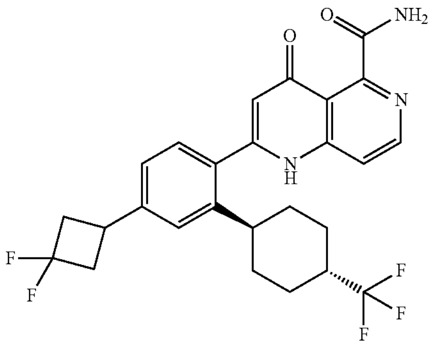 [SMILES: NC(=O)c1nccc2[nH]c(-c3ccc(C4CC(F)(F)C4)cc3[C@H]3CC[C@H](C(F)(F)F)CC3)cc(=O)c12] |
| 2-[4-(3,3-difluorocyclobutyl)-2-((1r,4r)-4-(trifluoromethyl)cyclohexyl)phenyl]-4-oxo-1H-1,6-naphthyridine-5-carboxamide |
| 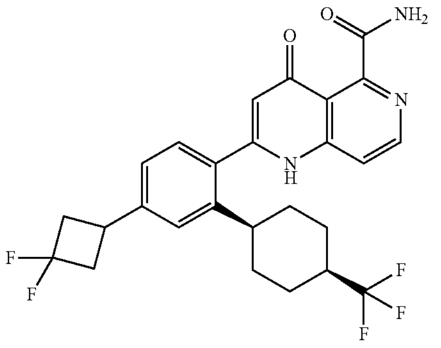 [SMILES: NC(=O)c1nccc2[nH]c(-c3ccc(C4CC(F)(F)C4)cc3[C@H]3CC[C@@H](C(F)(F)F)CC3)cc(=O)c12] |
| 2-[4-(3,3-difluorocyclobutyl)-2-((1s4s)-4-(trifluoromethyl)cyclohexyl)phenyl]-4-oxo-1H-1,6-naphthyridine-5-carboxamide |
| 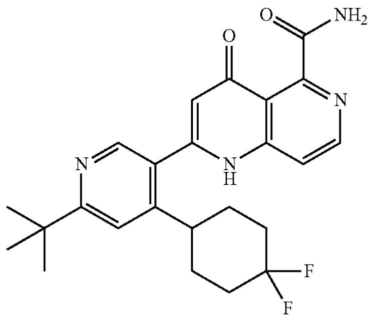 [SMILES: CC(C)(C)c1cc(C2CCC(F)(F)CC2)c(-c2cc(=O)c3c(C(N)=O)nccc3[nH]2)cn1] |
| 2-[6-tert-butyl-4-(4,4-difluorocyclohexyl)-3-pyridyl]-4-oxo-1H-1,6-naphthyridine-5-carboxamide |

TABLE A-continued

Compound Structures and Names.

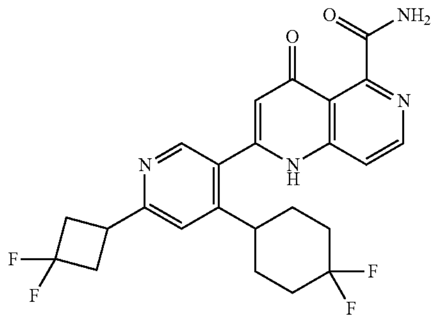 [SMILES: NC(=O)c1nccc2[nH]c(-c3cnc(C4CC(F)(F)C4)cc3C3CCC(F)(F)CC3)cc(=O)c12]

2-[6-(3,3-difluorocyclobutyl)-4-(4,4-difluorocyclohexyl)-3-pyridyl]-4-oxo-1H-1,6-naphthyridine-5-carboxamide

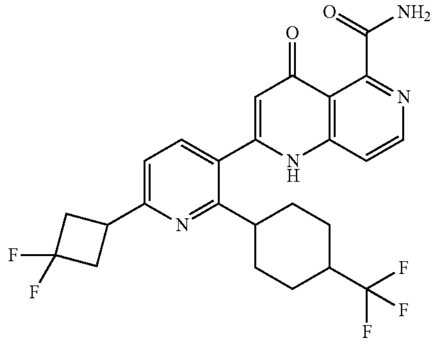 [SMILES: NC(=O)c1nccc2[nH]c(-c3ccc(C4CC(F)(F)C4)nc3C3CCC(C(F)(F)F)CC3)cc(=O)c12]

2-[6-(3,3-difluorocyclobutyl)-2-[4-(trifluoromethyl)cyclohexyl]-3-pyridyl]-4-oxo-1H-1,6-naphthyridine-5-carboxamide

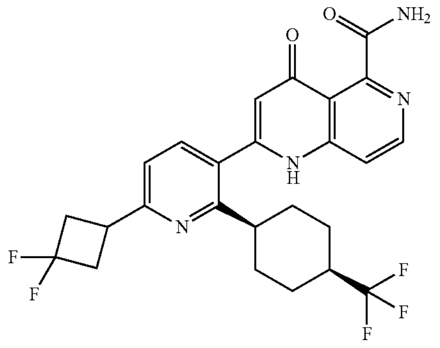 [SMILES: NC(=O)c1nccc2[nH]c(-c3ccc(C4CC(F)(F)C4)nc3[C@H]3CC[C@@H](C(F)(F)F)CC3)cc(=O)c12]

2-[6-(3,3-difluorocyclobutyl)-2-((1s,4s)-4-(trifluoromethyl)cyclohexyl)-3-pyridyl]-4-oxo-1H-1,6-naphthyridine-5-carboxamide TABLE A-continued Compound Structures and Names.

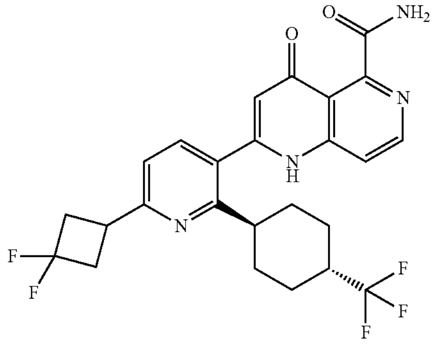

2-[6-(3,3-difluorocyclobutyl)-2-((1r,4r)-4-(trifluoromethyl)cyclohexyl)-3-pyridyl]-4-oxo-1H-1,6-naphthyridine-5-carboxamide

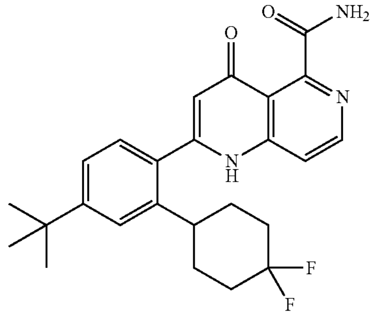 [SMILES: CC(C)(C)c1ccc(-c2cc(=O)c3c(C(N)=O)nccc3[nH]2)c(C2CCC(F)(F)CC2)c1]

2-[4-tert-butyl-2-(4,4-difluorocyclohexyl)phenyl]-4-oxo-1H-1,6-naphthyridine-5-carboxamide

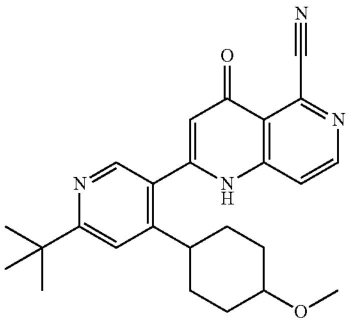 [SMILES: COC1CCC(c2cc(C(C)(C)C)ncc2-c2cc(=O)c3c(C#N)nccc3[nH]2)CC1]

2-[6-tert-butyl-4-(4-methoxycyclohexyl)-3-pyridyl]-4-oxo-1H-1,6-naphthyridine-5-carbonitrile

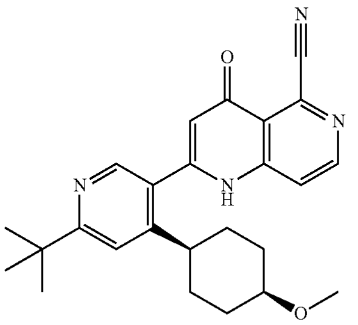 [SMILES: CO[C@H]1CC[C@@H](c2cc(C(C)(C)C)ncc2-c2cc(=O)c3c(C#N)nccc3[nH]2)CC1]

2-[6-tert-butyl-4-((1s,4s)-4-methoxycyclohexyl)-3-pyridyl]-4-oxo-1H-1,6-naphthyridine-5-carbonitrile TABLE A-continued Compound Structures and Names.

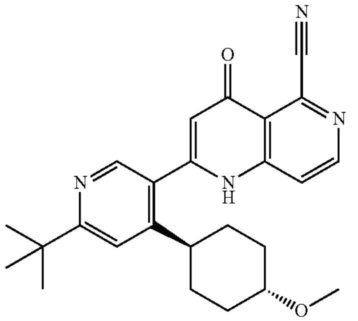 [SMILES: CO[C@H]1CC[C@H](c2cc(C(C)(C)C)ncc2-c2cc(=O)c3c(C#N)nccc3[nH]2)CC1]

2-[6-tert-butyl-4-((1r,4r)-4-methoxycyclohexyl)-3-pyridyl]-4-oxo-1H-1,6-naphthyridine-5-carbonitrile

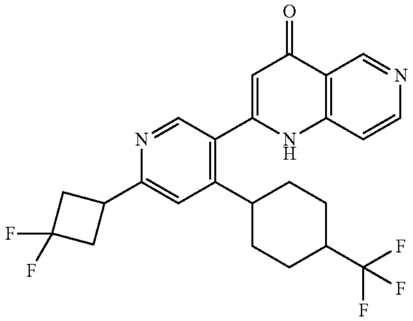 [SMILES: O=c1cc(-c2cnc(C3CC(F)(F)C3)cc2C2CCC(C(F)(F)F)CC2)[nH]c2ccncc12]

2-[6-(3,3-difluorocyclobutyl)-4-[4-(trifluoromethyl)cyclohexyl]-3-pyridyl]-1H-1,6-naphthyridin-4-one

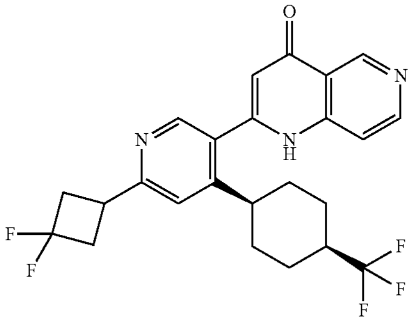 [SMILES: O=c1cc(-c2cnc(C3CC(F)(F)C3)cc2[C@H]2CC[C@@H](C(F)(F)F)CC2)[nH]c2ccncc12]

2-[6-(3,3-difluorocyclobutyl)-4-((1s,4s)-4-(trifluoromethyl)cyclohexyl)-3-pyridyl]-1H-1,6-naphthyridin-4-one TABLE A-continued Compound Structures and Names.

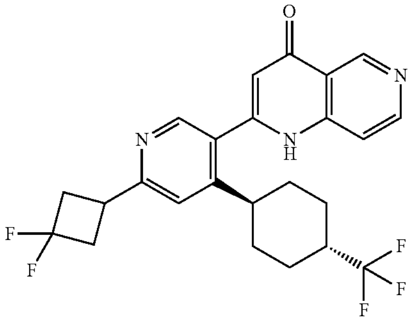 [SMILES: O=c1cc(-c2cnc(C3CC(F)(F)C3)cc2[C@H]2CC[C@H](C(F)(F)F)CC2)[nH]c2ccncc12]

2-[6-(3,3-difluorocyclobutyl)-4-((1r,4r)-4-(trifluoromethyl)cyclohexyl)-3-pyridyl]-1H-1,6-naphthyridin-4-one

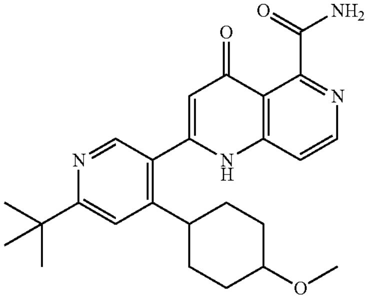 [SMILES: COC1CCC(c2cc(C(C)(C)C)ncc2-c2cc(=O)c3c(C(N)=O)nccc3[nH]2)CC1]

2-[6-tert-butyl-4-(4-methoxycyclohexyl)-3-pyridyl]-4-oxo-1H-1,6-naphthyridine-5-carboxamide

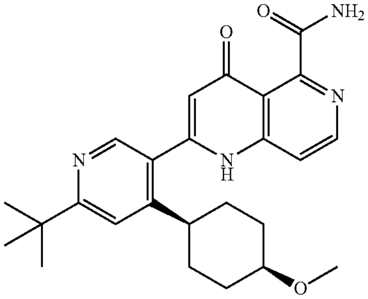 [SMILES: CO[C@H]1CC[C@@H](c2cc(C(C)(C)C)ncc2-c2cc(=O)c3c(C(N)=O)nccc3[nH]2)CC1]

2-[6-tert-butyl-4-((1r,4s)-4-methoxycyclohexyl)-3-pyridyl]-4-oxo-1H-1,6-naphthyridine-5-carboxamide

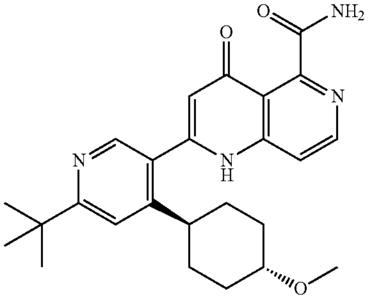 [SMILES: CO[C@H]1CC[C@H](c2cc(C(C)(C)C)ncc2-c2cc(=O)c3c(C(N)=O)nccc3[nH]2)CC1]

2-[6-tert-butyl-4-((1r,4r)-4-methoxycyclohexyl)-3-pyridyl]-4-oxo-1H-1,6-naphthyridine-5-carboxamide TABLE A-continued

| Compound Structures and Names. |
| --- |
| 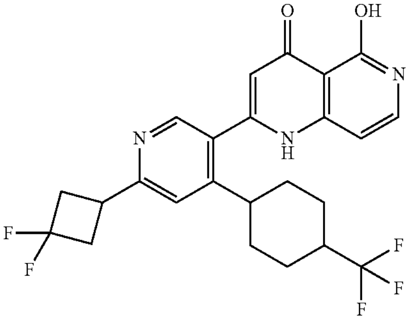 [SMILES: O=c1cc(-c2cnc(C3CC(F)(F)C3)cc2C2CCC(C(F)(F)F)CC2)[nH]c2ccnc(O)c12] |
| 2-[6-(3,3-difluorocyclobutyl)-4-[4-(trifluoromethyl)cyclohexyl]-3-pyridyl]-5-hydroxy-1H-1,6-naphthyridin-4-one |
| 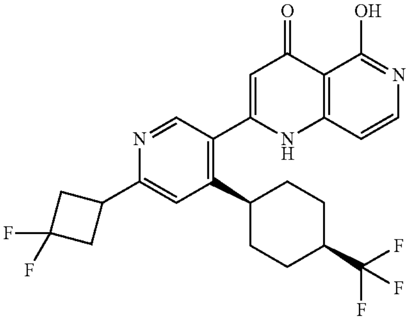 [SMILES: O=c1cc(-c2cnc(C3CC(F)(F)C3)cc2[C@H]2CC[C@@H](C(F)(F)F)CC2)[nH]c2ccnc(O)c12] |
| 2-[6-(3,3-difluorocyclobutyl)-4-((1s,4s)-4-(trifluoromethyl)cyclohexyl)-3-pyridyl]-5-hydroxy-1H-1,6-naphthyridin-4-one |
| 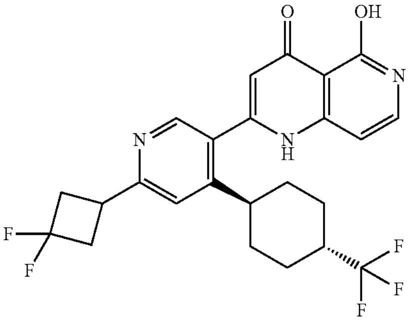 [SMILES: O=c1cc(-c2cnc(C3CC(F)(F)C3)cc2[C@H]2CC[C@H](C(F)(F)F)CC2)[nH]c2ccnc(O)c12] |
| 2-[6-(3,3-difluorocyclobutyl)-4-((1r,4r)-4-(trifluoromethyl)cyclohexyl)-3-pyridyl]-5-hydroxy-1H-1,6-naphthyridin-4-one |

TABLE A-continued

| Compound Structures and Names. |
| --- |
| 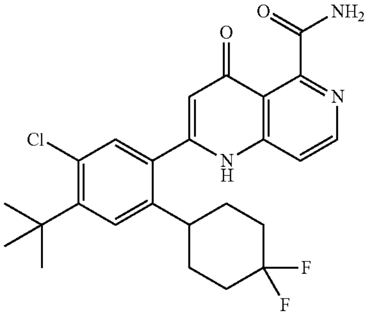 |
| 2-[4-tert-butyl-5-chloro-2-(4,4-difluorocyclohexyl)phenyl]-4-oxo-1H-1,6-naphthyridine-5-carboxamide |
| 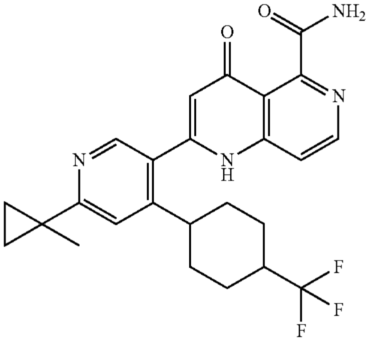 [SMILES: CC1(c2cc(C3CCC(C(F)(F)F)CC3)c(-c3cc(=O)c4c(C(N)=O)nccc4[nH]3)cn2)CC1] |
| 2-[6-(1-methylcyclopropyl)-4-[4-(trifluoromethyl)cyclohexyl]-3-pyridyl]-4-oxo-1H-1,6-naphthyridine-5-carboxamide |
| 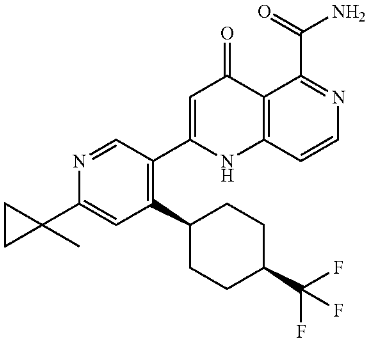 [SMILES: CC1(c2cc([C@H]3CC[C@@H](C(F)(F)F)CC3)c(-c3cc(=O)c4c(C(N)=O)nccc4[nH]3)cn2)CC1] |
| 2-[6-(1-methylcyclopropyl)-4-((1s,4s)-4-(trifluoromethyl)cyclohexyl)-3-pyridyl]-4-oxo-1H-1,6-naphthyridine-5-carboxamide |

Compound Structures and Names.

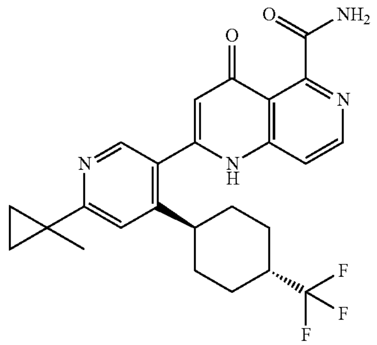 [SMILES: CC1(c2cc([C@H]3CC[C@H](C(F)(F)F)CC3)c(-c3cc(=O)c4c(C(N)=O)nccc4[nH]3)cn2)CC1]

2-[6-(1-methylcyclopropyl)-4-((1r,4r)-4-(trifluoromethyl)cyclohexyl)-3-pyridyl]-4-oxo-1H-1,6-naphthyridine-5-carboxamide

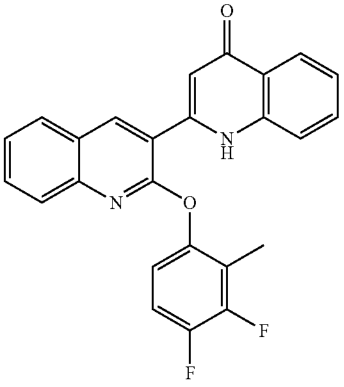 [SMILES: Cc1c(Oc2nc3ccccc3cc2-c2cc(=O)c3ccccc3[nH]2)ccc(F)c1F]

2-[2-(3,4-difluoro-2-methyl-phenoxy)-3-quinolyl]-1H-quinolin-4-one

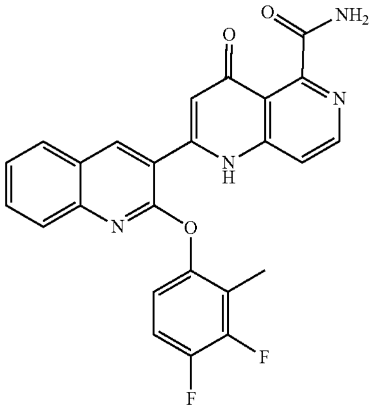 [SMILES: Cc1c(Oc2nc3ccccc3cc2-c2cc(=O)c3c(C(N)=O)nccc3[nH]2)ccc(F)c1F]

2-[2-(3,4-difluoro-2-methyl-phenoxy)-3-quinolyl]-4-oxo-1H-1,6-naphthyridine-5-carboxamide Compound Structures and Names.

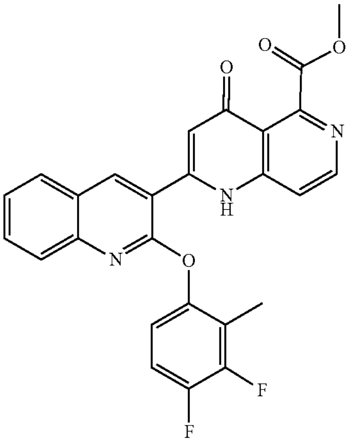 [SMILES: COC(=O)c1nccc2[nH]c(-c3cc4ccccc4nc3Oc3ccc(F)c(F)c3C)cc(=O)c12]

methyl 2-[2-(3,4-difluoro-2-methyl-phenoxy)-3-quinolyl]-4-oxo-1H-1,6-naphthyridine-5-carboxylate

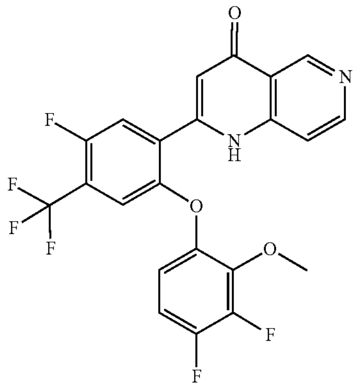 [SMILES: COc1c(Oc2cc(C(F)(F)F)c(F)cc2-c2cc(=O)c3cnccc3[nH]2)ccc(F)c1F]

2-[2-(3,4-difluoro-2-methoxy-phenoxy)-5-fluoro-4-(trifluoromethyl)phenyl]-1H-1,6-naphthyridin-4-one

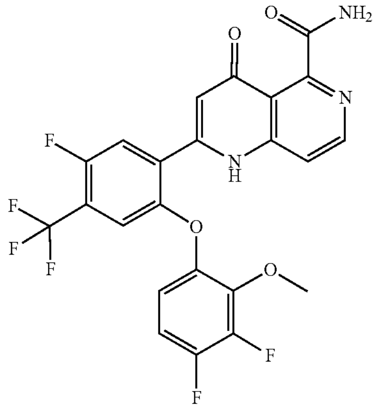 [SMILES: COc1c(Oc2cc(C(F)(F)F)c(F)cc2-c2cc(=O)c3c(C(N)=O)nccc3[nH]2)ccc(F)c1F]

2-[2-(3,4-difluoro-2-methoxy-phenoxy)-5-fluoro-4-(trifluoromethyl)phenyl]-4-oxo-1H-1,6-naphthyridine-5-carboxamide TABLE A-continued

| Compound Structures and Names. |
| --- |
| 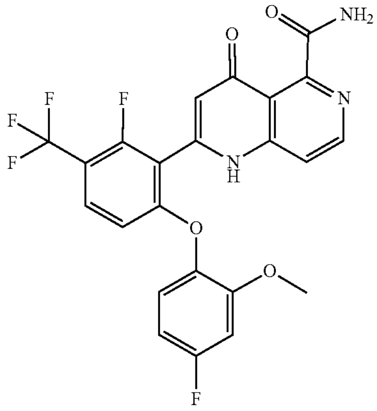 [SMILES: COc1cc(F)ccc1Oc1ccc(C(F)(F)F)c(F)c1-c1cc(=O)c2c(C(N)=O)nccc2[nH]1] |
| 2-[2-fluoro-6-(4-fluoro-2-methoxy-phenoxy)-3-(trifluoromethyl)phenyl]-4-oxo-1H-1,6-naphthyridine-5-carboxamide |
| 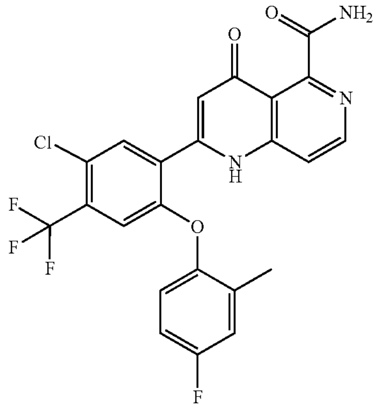 [SMILES: Cc1cc(F)ccc1Oc1cc(C(F)(F)F)c(Cl)cc1-c1cc(=O)c2c(C(N)=O)nccc2[nH]1] |
| 2-[5-chloro-2-(4-fluoro-2-methyl-phenoxy)-4-(trifluoromethyl)phenyl]-4-oxo-1H-1,6-naphthyridine-5-carboxamide |
| 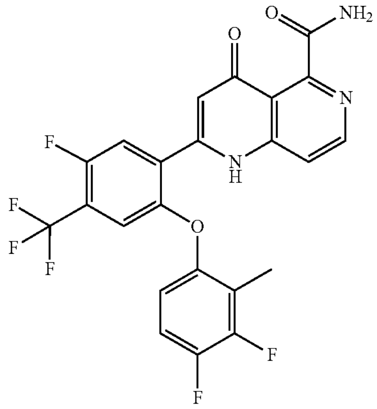 [SMILES: Cc1c(Oc2cc(C(F)(F)F)c(F)cc2-c2cc(=O)c3c(C(N)=O)nccc3[nH]2)ccc(F)c1F] |
| 2-[2-(3,4-difluoro-2-methyl-phenoxy)-5-fluoro-4-(trifluoromethyl)phenyl]-4-oxo-1H-1,6-naphthyridine-5-carboxamide |

TABLE A-continued

| Compound Structures and Names. |
| --- |
| 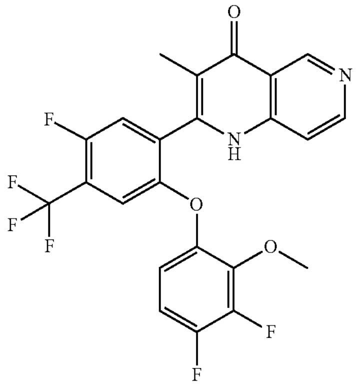 [SMILES: COc1c(Oc2cc(C(F)(F)F)c(F)cc2-c2[nH]c3ccncc3c(=O)c2C)ccc(F)c1F] |
| 2-[2-(3,4-difluoro-2-methoxy-phenoxy)-5-fluoro-4-(trifluoromethyl)phenyl]-3-methyl-1H-1,6-naphthyridine-4-one |
| 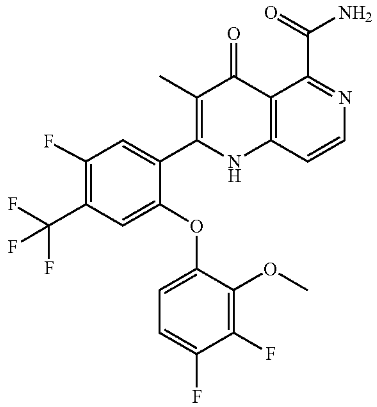 [SMILES: COc1c(Oc2cc(C(F)(F)F)c(F)cc2-c2[nH]c3ccnc(C(N)=O)c3c(=O)c2C)ccc(F)c1F] |
| 2-[2-(3,4-difluoro-2-methoxy-phenoxy)-5-fluoro-4-(trifluoromethyl)phenyl]-3-methyl-4-oxo-1H-1,6-naphthyridine-5-carboxamide |
| 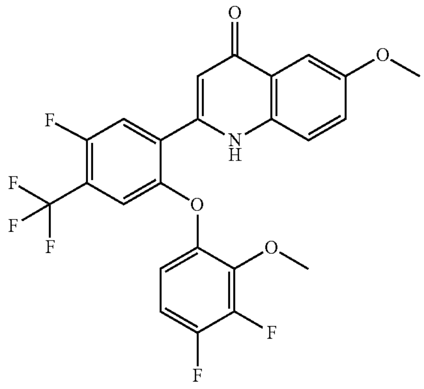 [SMILES: COc1ccc2[nH]c(-c3cc(F)c(C(F)(F)F)cc3Oc3ccc(F)c(F)c3OC)cc(=O)c2c1] |
| 2-[2-(3,4-difluoro-2-methoxy-phenoxy)-5-fluoro-4-(trifluoromethyl)phenyl]-6-methoxy-1H-quinolin-4-one |

TABLE A-continued

| Compound Structures and Names. |
| --- |
| 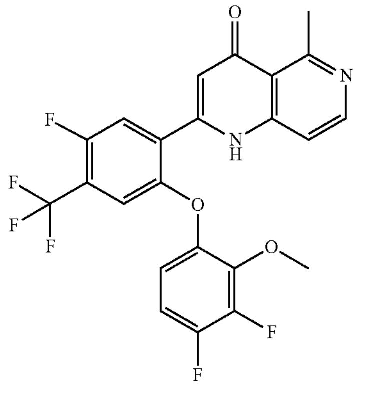 [SMILES: COc1c(Oc2cc(C(F)(F)F)c(F)cc2-c2cc(=O)c3c(C)nccc3[nH]2)ccc(F)c1F] |
| 2-[2-(3,4-difluoro-2-methoxy-phenoxy)-5-fluoro-4-(trifluoromethyl)phenyl]-5-methyl-1H-1,6-naphthyridin-4-one |
| 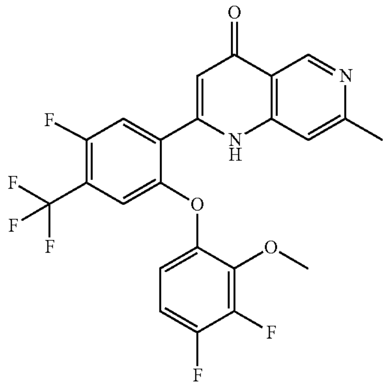 [SMILES: COc1c(Oc2cc(C(F)(F)F)c(F)cc2-c2cc(=O)c3cnc(C)cc3[nH]2)ccc(F)c1F] |
| 2-[2-(3,4-difluoro-2-methoxy-phenoxy)-5-fluoro-4-(trifluoromethyl)phenyl]-7-methyl-1H-1,6-naphthyridin-4-one |
| 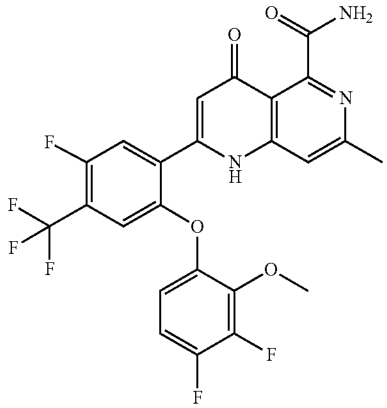 [SMILES: COc1c(Oc2cc(C(F)(F)F)c(F)cc2-c2cc(=O)c3c(C(N)=O)nc(C)cc3[nH]2)ccc(F)c1F] |
| 2-[2-(3,4-difluoro-2-methoxy-phenoxy)-5-fluoro-4-(trifluoromethyl)phenyl]-7-methyl-4-oxo-1H-1,6-naphthyridine-5-carboxamide |

TABLE A-continued

| Compound Structures and Names. |
| --- |
| 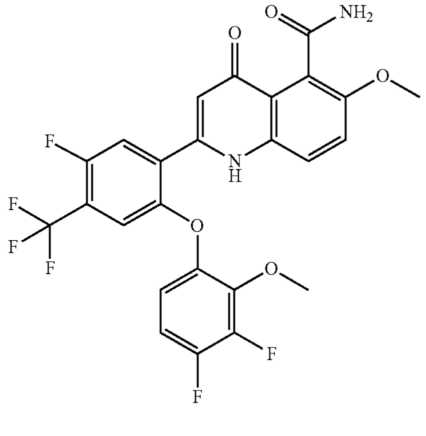 [SMILES: COc1ccc2[nH]c(-c3cc(F)c(C(F)(F)F)cc3Oc3ccc(F)c(F)c3OC)cc(=O)c2c1C(N)=O] |
| 2-[2-(3,4-difluoro-2-methoxy-phenoxy)-5-fluoro-4-(trifluoromethyl)phenyl]-6-methoxy-4-oxo-1H-quinoline-5-carboxamide |
| 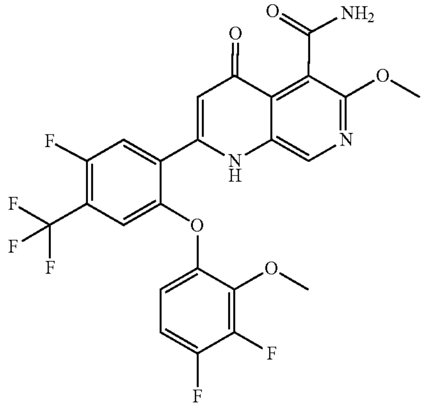 [SMILES: COc1ncc2[nH]c(-c3cc(F)c(C(F)(F)F)cc3Oc3ccc(F)c(F)c3OC)cc(=O)c2c1C(N)=O] |
| 2-[2-(3,4-difluoro-2-methoxy-phenoxy)-5-fluoro-4-(trifluoromethyl)phenyl]-6-methoxy-4-oxo-1H-1,7-naphthyridine-5-carboxamide |
| 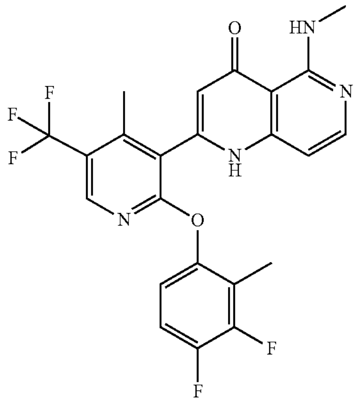 [SMILES: CNc1nccc2[nH]c(-c3c(Oc4ccc(F)c(F)c4C)ncc(C(F)(F)F)c3C)cc(=O)c12] |
| 2-[2-(3,4-difluoro-2-methyl-phenoxy)-4-methyl-5-(trifluoromethyl)-3-pyridyl]-5-(methylamino)-1H-1,6-naphthyridine-4-one |

TABLE A-continued

Compound Structures and Names.

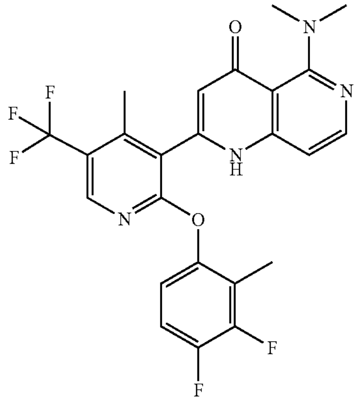 [SMILES: Cc1c(Oc2ncc(C(F)(F)F)c(C)c2-c2cc(=O)c3c(N(C)C)nccc3[nH]2)ccc(F)c1F]

2-[2-(3,4-difluoro-2-methyl-phenoxy)-4-methyl-5-(trifluoromethyl)-3-pyridyl]-5-(dimethylamino)-1H-1,6-naphthyridin-4-one

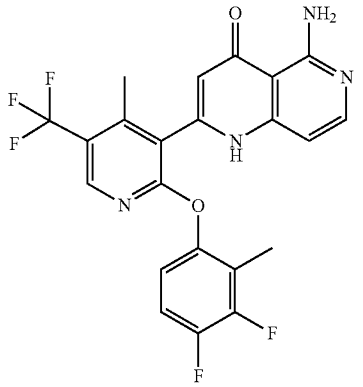 [SMILES: Cc1c(Oc2ncc(C(F)(F)F)c(C)c2-c2cc(=O)c3c(N)nccc3[nH]2)ccc(F)c1F]

5-amino-2-[2-(3,4-difluoro-2-methyl-phenoxy)-4-methyl-5-(trifluoromethyl)-3-pyridyl]-1H-1,6-naphthyridin-4-one

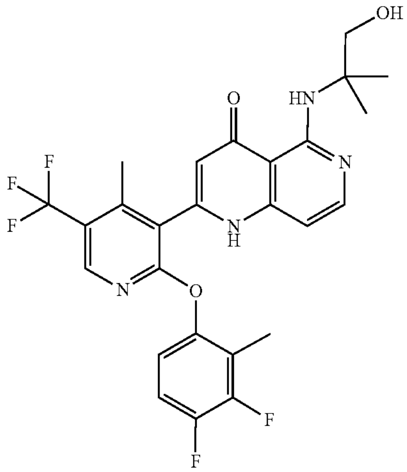 [SMILES: Cc1c(Oc2ncc(C(F)(F)F)c(C)c2-c2cc(=O)c3c(NC(C)(C)CO)nccc3[nH]2)ccc(F)c1F]

2-[2-(3,4-difluoro-2-methyl-phenoxy)-4-methyl-5-(trifluoromethyl)-3-pyridyl]-5-[(2-hydroxy-1,1-dimethyl-ethyl)amino]-1H-1,6-naphthyridin-4-one TABLE A-continued Compound Structures and Names.

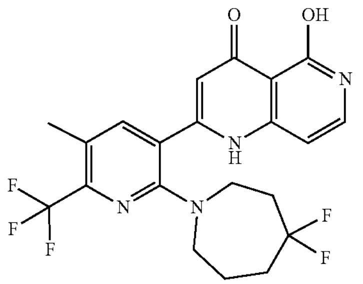 [SMILES: Cc1cc(-c2cc(=O)c3c(O)nccc3[nH]2)c(N2CCCC(F)(F)CC2)nc1C(F)(F)F]

2-[2-(4,4-difluoroazepan-1-yl)-5-methyl-6-(trifluoromethyl)-3-pyridyl]-5-hydroxy-1H-1,6-naphthyridin-4-one

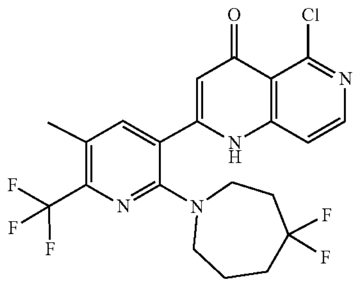 [SMILES: Cc1cc(-c2cc(=O)c3c(Cl)nccc3[nH]2)c(N2CCCC(F)(F)CC2)nc1C(F)(F)F]

5-chloro-2-[2-(4,4-difluoroazepan-1-yl)-5-methyl-6-(trifluoromethyl)-3-pyridyl]-1H-1,6-naphthyridin-4-one

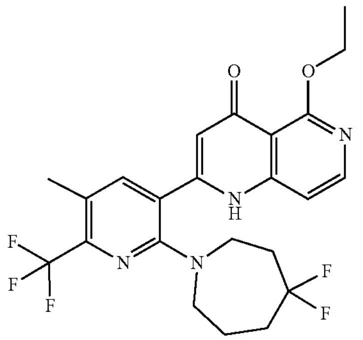 [SMILES: CCOc1nccc2[nH]c(-c3cc(C)c(C(F)(F)F)nc3N3CCCC(F)(F)CC3)cc(=O)c12]

2-[2-(4,4-difluoroazepan-1-yl)-5-methyl-6-(trifluoromethyl)-3-pyridyl]-5-ethoxy-1H-1,6-naphthyridin-4-one TABLE A-continued

| Compound Structures and Names. |
| --- |
| 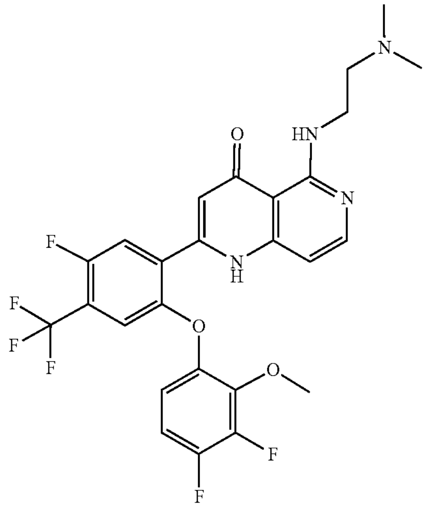 [SMILES: COc1c(Oc2cc(C(F)(F)F)c(F)cc2-c2cc(=O)c3c(NCCN(C)C)nccc3[nH]2)ccc(F)c1F] |
| 2-[2-(3,4-difluoro-2-methoxy-phenoxy)-5-fluoro-4-(trifluoromethyl)phenyl]-5-[2-(dimethylamino)ethylamino]-1H-1,6-naphthyridin-4-one |
| 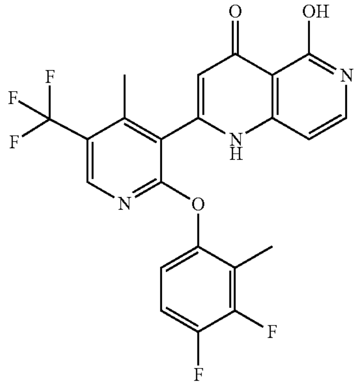 [SMILES: Cc1c(Oc2ncc(C(F)(F)F)c(C)c2-c2cc(=O)c3c(O)nccc3[nH]2)ccc(F)c1F] |
| 2-[2-(3,4-difluoro-2-methyl-phenoxy)-4-methyl-5-(trifluoromethyl)-3-pyridyl]-5-hydroxy-1H-1,6-naphthyridin-4-one |
| 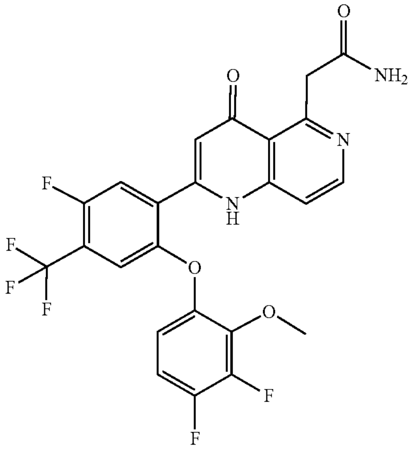 [SMILES: COc1c(Oc2cc(C(F)(F)F)c(F)cc2-c2cc(=O)c3c(CC(N)=O)nccc3[nH]2)ccc(F)c1F] |
| 2-[2-[2-(3,4-difluoro-2-methoxy-phenoxy)-5-fluoro-4-(trifluoromethyl)phenyl]-4-oxo-1H-1,6-naphthyridin-5-yl]acetamide |

TABLE A-continued

| Compound Structures and Names. |
| --- |
| 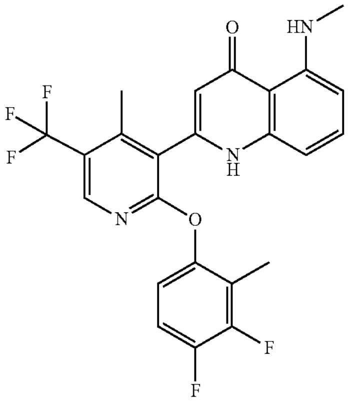 [SMILES: CNc1cccc2[nH]c(-c3c(Oc4ccc(F)c(F)c4C)ncc(C(F)(F)F)c3C)cc(=O)c12] |
| 2-[2-(3,4-difluoro-2-methyl-phenoxy)-4-methyl-5-(trifluoromethyl)-3-pyridyl]-5-(methylamino)-1H-quinolin-4-one |
| 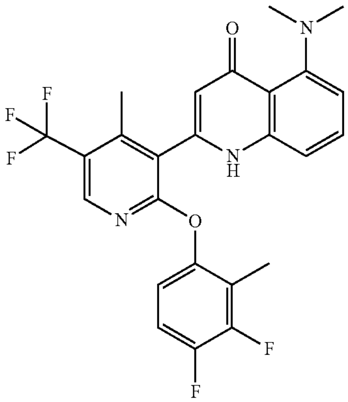 [SMILES: Cc1c(Oc2ncc(C(F)(F)F)c(C)c2-c2cc(=O)c3c(N(C)C)cccc3[nH]2)ccc(F)c1F] |
| 2-[2-(3,4-difluoro-2-methyl-phenoxy)-4-methyl-5-(trifluoromethyl)-3-pyridyl]-5-(dimethylamino)-1H-quinolin-4-one |
| 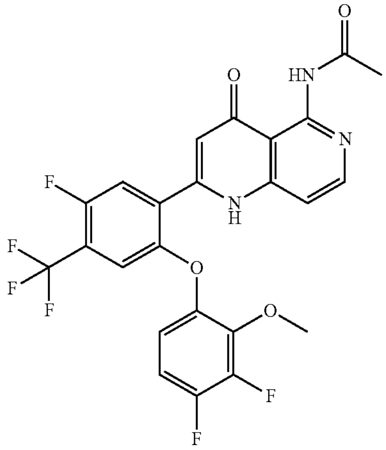 [SMILES: COc1c(Oc2cc(C(F)(F)F)c(F)cc2-c2cc(=O)c3c(NC(C)=O)nccc3[nH]2)ccc(F)c1F] |
| N-[2-[2-(3,4-difluoro-2-methoxy-phenoxy)-5-fluoro-4-(trifluoromethyl)phenyl]-4-oxo-1H-1,6-naphthyridin-5-yl]acetamide |

TABLE A-continued

| Compound Structures and Names. |
| --- |
| 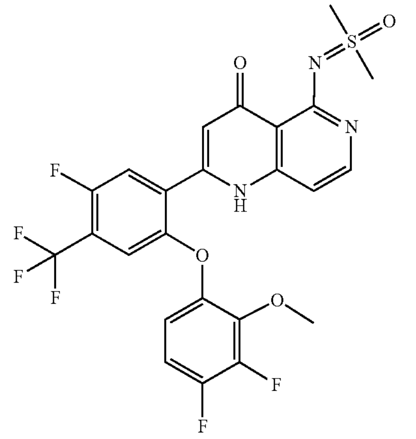 [SMILES: COc1c(Oc2cc(C(F)(F)F)c(F)cc2-c2cc(=O)c3c(N=S(C)(C)=O)nccc3[nH]2)ccc(F)c1F] |
| 2-[2-(3,4-difluoro-2-methoxy-phenoxy)-5-fluoro-4-(trifluoromethyl)phenyl]-5-[[dimethyl(oxo)-λ6-sulfanylidene]amino]-1H-1,6-naphthyridin-4-one |
| 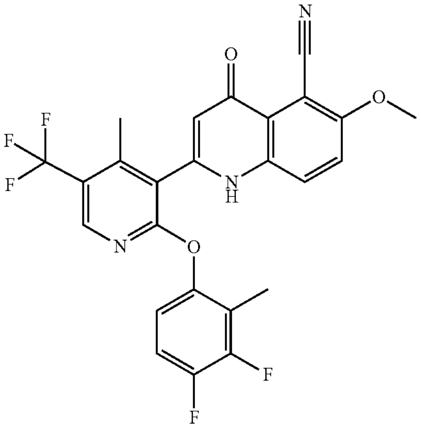 [SMILES: COc1ccc2[nH]c(-c3c(Oc4ccc(F)c(F)c4C)ncc(C(F)(F)F)c3C)cc(=O)c2c1C#N] |
| 2-[2-(3,4-difluoro-2-methyl-phenoxy)-4-methyl-5-(trifluoromethyl)-3-pyridyl]-6-methoxy-4-oxo-1H-quinoline-5-carbonitrile |
| 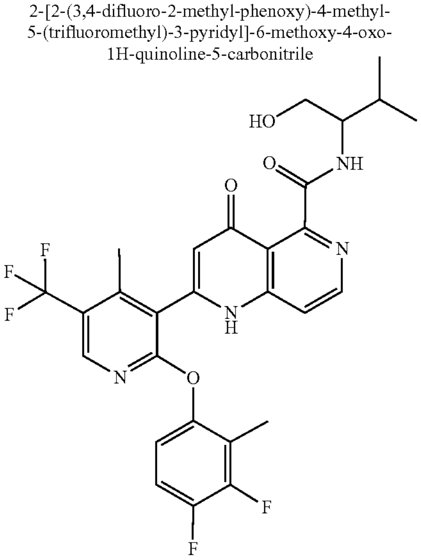 |
| 2-[2-(3,4-difluoro-2-methyl-phenoxy)-4-methyl-5-(trifluoromethyl)-3-pyridyl]-N-[1-(hydroxymethyl)-2-methyl-propyl]-4-oxo-1H-1,6-naphthyridine-5-carboxamide |

TABLE A-continued

| Compound Structures and Names. |
| --- |
| 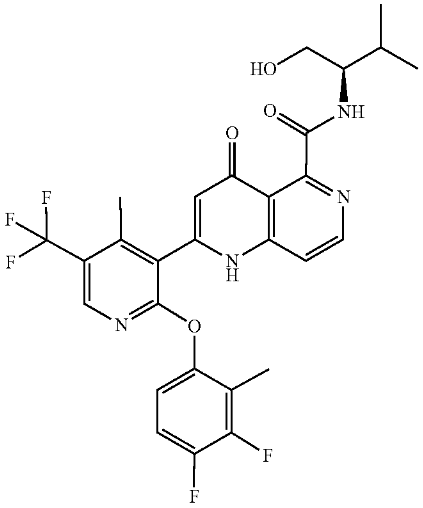 [SMILES: Cc1c(Oc2ncc(C(F)(F)F)c(C)c2-c2cc(=O)c3c(C(=O)N[C@@H](CO)C(C)C)nccc3[nH]2)ccc(F)c1F] |
| 2-[2-(3,4-difluoro-2-methyl-phenoxy)-4-methyl-5-(trifluoromethyl)-3-pyridyl]-N-[(1R)-1-(hydroxymethyl)-2-methyl-propyl]-4-oxo-1H-1,6-naphthyridine-5-carboxamide |
| 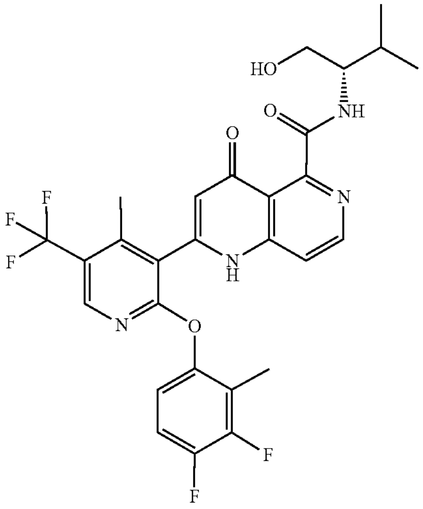 [SMILES: Cc1c(Oc2ncc(C(F)(F)F)c(C)c2-c2cc(=O)c3c(C(=O)N[C@H](CO)C(C)C)nccc3[nH]2)ccc(F)c1F] |
| 2-[2-(3,4-difluoro-2-methyl-phenoxy)-4-methyl-5-(trifluoromethyl)-3-pyridyl]-N-[(1S)-1-(hydroxymethyl)-2-methyl-propyl]-4-oxo-1H-1,6-naphthyridine-5-carboxamide |

TABLE A-continued

Compound Structures and Names.

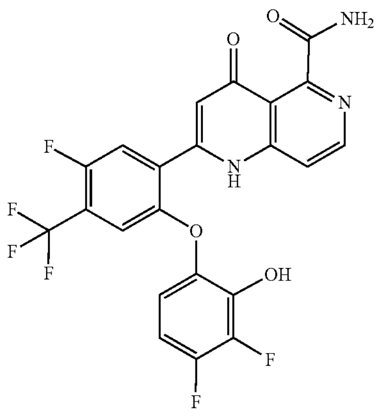 [SMILES: NC(=O)c1nccc2[nH]c(-c3cc(F)c(C(F)(F)F)cc3Oc3ccc(F)c(F)c3O)cc(=O)c12]

2-[2-(3,4-difluoro-2-hydroxy-phenoxy)-5-fluoro-4-(trifluoromethyl)phenyl]-4-oxo-1H-1,6-naphthyridine-5-carboxamide

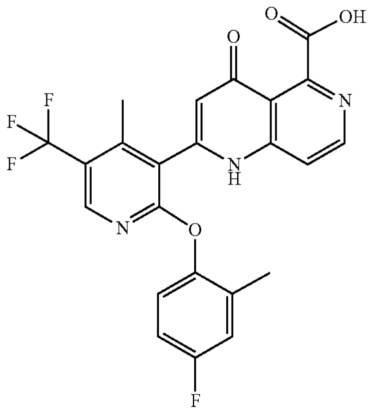 [SMILES: Cc1cc(F)ccc1Oc1ncc(C(F)(F)F)c(C)c1-c1cc(=O)c2c(C(=O)O)nccc2[nH]1]

2-[2-(4-fluoro-2-methyl-phenoxy)-4-methyl-5-(trifluoromethyl)-3-pyridyl]-4-oxo-1H-1,6-naphthyridine-5-carboxylic acid

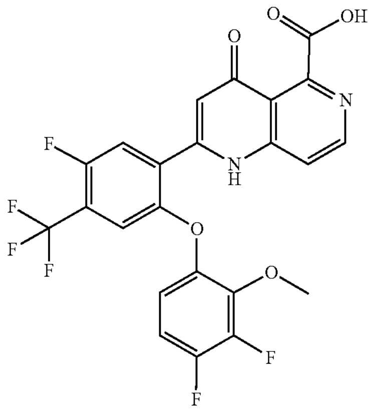 [SMILES: COc1c(Oc2cc(C(F)(F)F)c(F)cc2-c2cc(=O)c3c(C(=O)O)nccc3[nH]2)ccc(F)c1F]

2-[2-(3,4-difluoro-2-methoxy-phenoxy)-5-fluoro-4-(trifluoromethyl)phenyl]-4-oxo-1H-1,6-naphthyridine-5-carboxylic acid TABLE A-continued Compound Structures and Names.

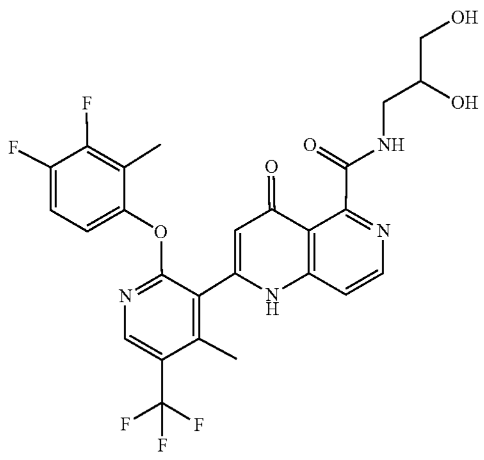 [SMILES: Cc1c(Oc2ncc(C(F)(F)F)c(C)c2-c2cc(=O)c3c(C(=O)NCC(O)CO)nccc3[nH]2)ccc(F)c1F]

2-[2-(3,4-difluoro-2-methyl-phenoxy)-4-methyl-5-(trifluoromethyl)-3-pyridyl]-N-[2,3-dihydroxypropyl]-4-oxo-1H-1,6-naphthyridine-5-carboxamide

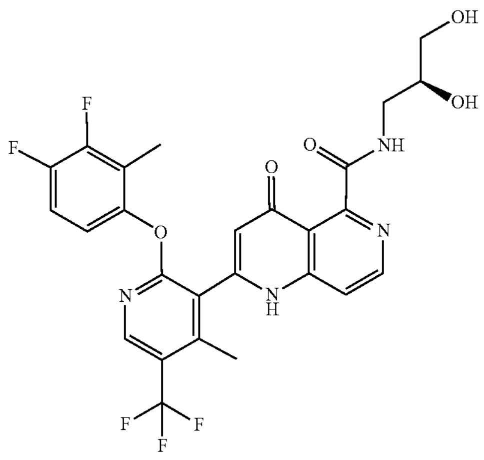 [SMILES: Cc1c(Oc2ncc(C(F)(F)F)c(C)c2-c2cc(=O)c3c(C(=O)NC[C@H](O)CO)nccc3[nH]2)ccc(F)c1F]

2-[2-(3,4-difluoro-2-methyl-phenoxy)-4-methyl-5-(trifluoromethyl)-3-pyridyl]-N-[(2S)-2,3-dihydroxypropyl]-4-oxo-1H-1,6-naphthyridine-5-carboxamide TABLE A-continued

| Compound Structures and Names. |
|---|
| 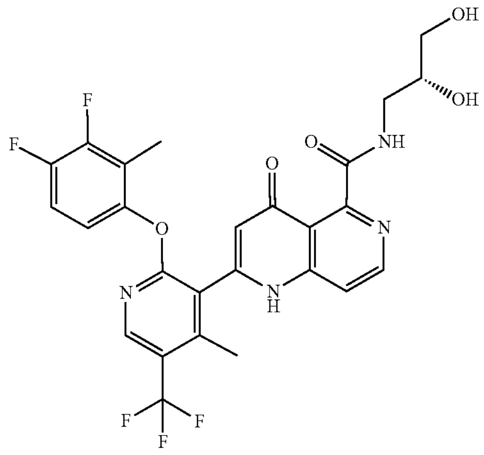 [SMILES: Cc1c(Oc2ncc(C(F)(F)F)c(C)c2-c2cc(=O)c3c(C(=O)NC[C@@H](O)CO)nccc3[nH]2)ccc(F)c1F] 2-[2-(3,4-difluoro-2-methyl-phenoxy)-4-methyl-5-(trifluoromethyl)-3-pyridyl]-N-[(2R)-2,3-dihydroxypropyl]-4-oxo-1H-1,6-naphthyridine-5-carboxamide |
| 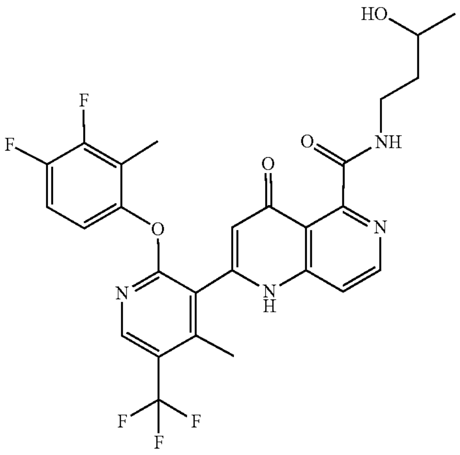 [SMILES: Cc1c(Oc2ncc(C(F)(F)F)c(C)c2-c2cc(=O)c3c(C(=O)NCCC(C)O)nccc3[nH]2)ccc(F)c1F] 2-[2-(3,4-difluoro-2-methyl-phenoxy)-4-methyl-5-(trifluoromethyl)-3-pyridyl]-N-(3-hydroxybutyl)-4-oxo-1H-1,6-naphthyridine-5-carboxamide |

TABLE A-continued

| Compound Structures and Names. |
|---|
| 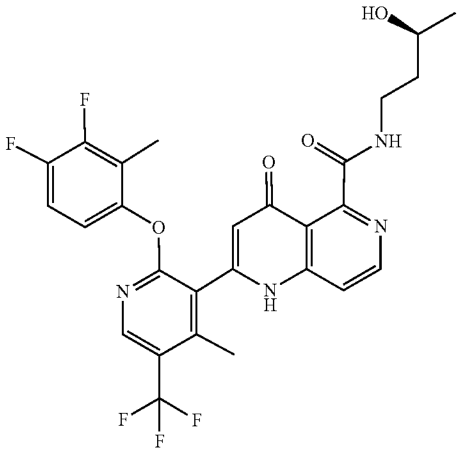 [SMILES: Cc1c(Oc2ncc(C(F)(F)F)c(C)c2-c2cc(=O)c3c(C(=O)NCC[C@H](C)O)nccc3[nH]2)ccc(F)c1F] (S)-2-[2-(3,4-difluoro-2-methyl-phenoxy)-4-methyl-5-(trifluoromethyl)-3-pyridyl]-N-(3-hydroxybutyl)-4-oxo-1H-1,6-naphthyridine-5-carboxamide |
| 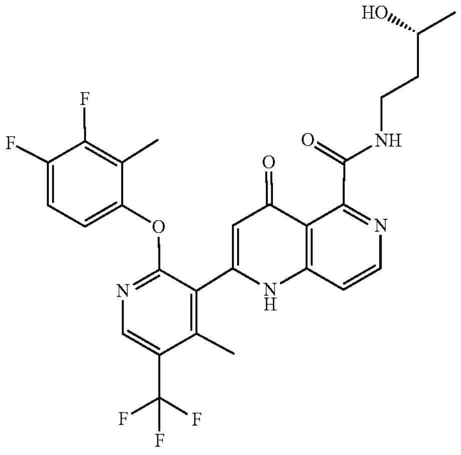 [SMILES: Cc1c(Oc2ncc(C(F)(F)F)c(C)c2-c2cc(=O)c3c(C(=O)NCC[C@@H](C)O)nccc3[nH]2)ccc(F)c1F] (R)-2-[2-(3,4-difluoro-2-methyl-phenoxy)-4-methyl-5-(trifluoromethyl)-3-pyridyl]-N-(3-hydroxybutyl)-4-oxo-1H-1,6-naphthyridine-5-carboxamide |
| 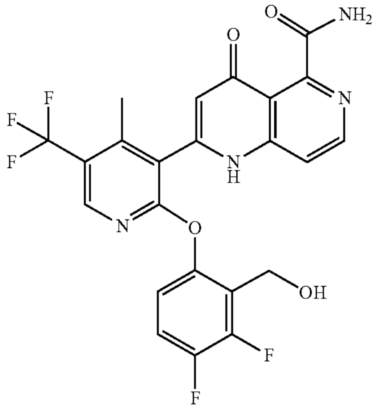 [SMILES: Cc1c(C(F)(F)F)cnc(Oc2ccc(F)c(F)c2CO)c1-c1cc(=O)c2c(C(N)=O)nccc2[nH]1] 2-[2-[3,4-difluoro-2-(hydroxymethyl)phenoxy]-4-methyl-5-(trifluoromethyl)-3-pyridyl]-4-oxo-1H-1,6-naphthyridine-5-carboxamide |

TABLE A-continued

| Compound Structures and Names. |
|---|
| 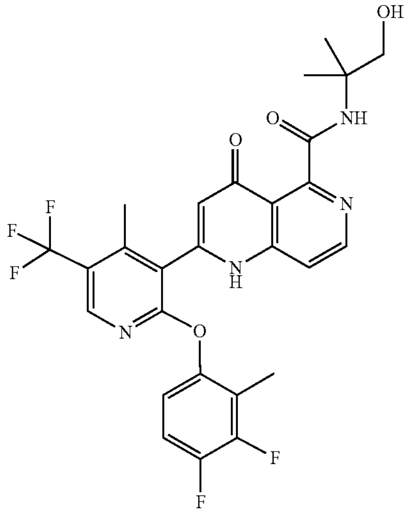 [SMILES: Cc1c(Oc2ncc(C(F)(F)F)c(C)c2-c2cc(=O)c3c(C(=O)NC(C)(C)CO)nccc3[nH]2)ccc(F)c1F] |
| 2-[2-(3,4-difluoro-2-methyl-phenoxy)-4-methyl-5-(trifluoromethyl)-3-pyridyl]-N-(2-hydroxy-1,1-dimethyl-ethyl)-4-oxo-1H-1,6-naphthyridine-5-carboxamide |
| 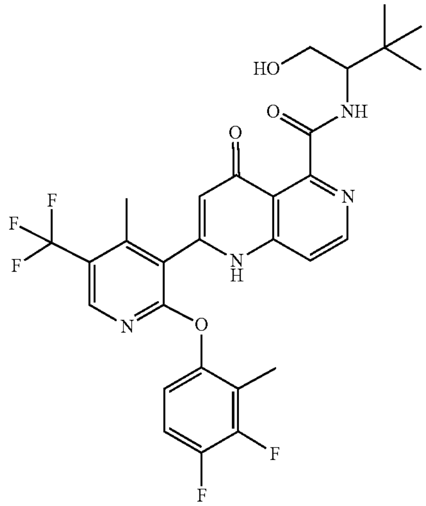 [SMILES: Cc1c(Oc2ncc(C(F)(F)F)c(C)c2-c2cc(=O)c3c(C(=O)NC(CO)C(C)(C)C)nccc3[nH]2)ccc(F)c1F] |
| 2-[2-(3,4-difluoro-2-methyl-phenoxy)-4-methyl-5-(trifluoromethyl)-3-pyridyl]-N-[1-(hydroxymethyl)-2,2-dimethyl-propyl]-4-oxo-1H-1,6-naphthyridine-5-carboxamide |

TABLE A-continued

| Compound Structures and Names. |
|---|
| 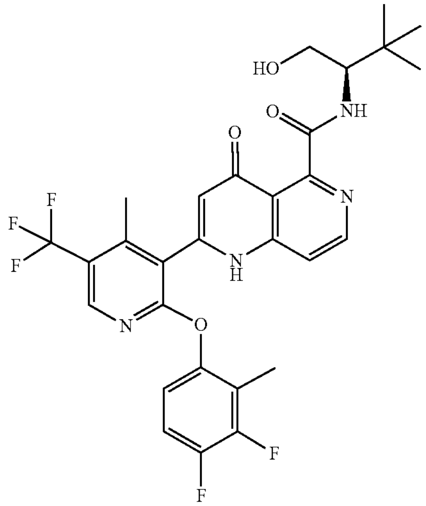 [SMILES: Cc1c(Oc2ncc(C(F)(F)F)c(C)c2-c2cc(=O)c3c(C(=O)N[C@@H](CO)C(C)(C)C)nccc3[nH]2)ccc(F)c1F] |
| (R)-2-[2-(3,4-difluoro-2-methyl-phenoxy)-4-methyl-5-(trifluoromethyl)-3-pyridyl]-N-[1-(hydroxymethyl)-2,2-dimethyl-propyl]-4-oxo-1H-1,6-naphthyridine-5-carboxamide |
| 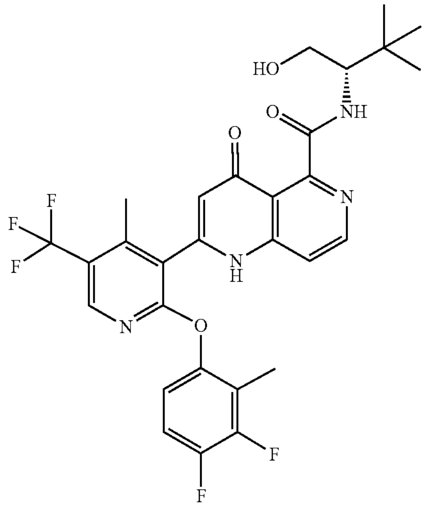 [SMILES: Cc1c(Oc2ncc(C(F)(F)F)c(C)c2-c2cc(=O)c3c(C(=O)N[C@H](CO)C(C)(C)C)nccc3[nH]2)ccc(F)c1F] |
| (S)-2-[2-(3,4-difluoro-2-methyl-phenoxy)-4-methyl-5-(trifluoromethyl)-3-pyridyl]-N-[1-(hydroxymethyl)-2,2-dimethyl-propyl]-4-oxo-1H-1,6-naphthyridine-5-carboxamide |

TABLE A-continued

| Compound Structures and Names. |
|---|
| 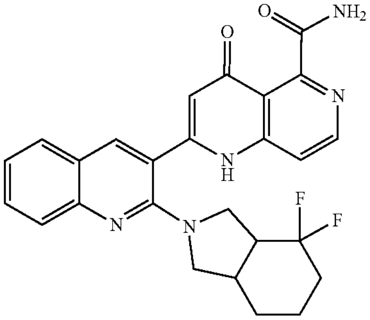 [SMILES: NC(=O)c1nccc2[nH]c(-c3cc4ccccc4nc3N3CC4CCCC(F)(F)C4C3)cc(=O)c12] |
| 2-[2-(7,7-difluoro-3,3a,4,5,6,7a-hexahydro-1H-isoindol-2-yl)-3-quinolyl]-4-oxo-1H-1,6-naphthyridine-5-carboxamide |
| 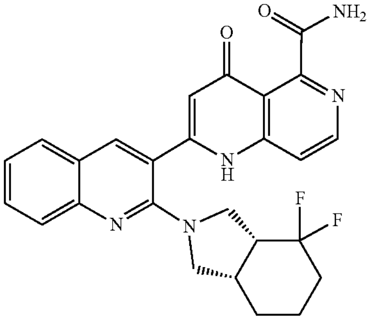 [SMILES: NC(=O)c1nccc2[nH]c(-c3cc4ccccc4nc3N3C[C@H]4CCCC(F)(F)[C@H]4C3)cc(=O)c12] |
| 2-[2-((3aR,7aS)-7,7-difluoro-3,3a,4,5,6,7a-hexahydro-1H-isoindol-2-yl)-3-quinolyl]-4-oxo-1H-1,6-naphthyridine-5-carboxamide |
| 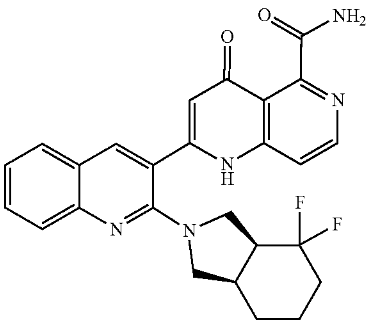 [SMILES: NC(=O)c1nccc2[nH]c(-c3cc4ccccc4nc3N3C[C@@H]4CCCC(F)(F)[C@@H]4C3)cc(=O)c12] |
| 2-[2-((3aS,7aR)-7,7-difluoro-3,3a,4,5,6,7a-hexahydro-1H-isoindol-2-yl)-3-quinolyl]-4-oxo-1H-1,6-naphthyridine-5-carboxamide |

TABLE A-continued

| Compound Structures and Names. |
|---|
| 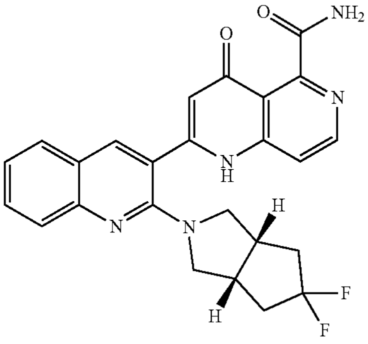 [SMILES: NC(=O)c1nccc2[nH]c(-c3cc4ccccc4nc3N3C[C@@H]4CC(F)(F)C[C@@H]4C3)cc(=O)c12] |
| 2-[2-[(3aR,6aS)-5,5-difluoro-1,3,3a,4,6,6a-hexahydrocyclopenta[c]pyrrol-2-yl]-3-quinolyl]-4-oxo-1H-1,6-naphthyridine-5-carboxamide |
| 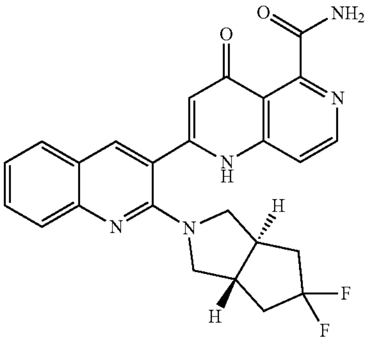 [SMILES: NC(=O)c1nccc2[nH]c(-c3cc4ccccc4nc3N3C[C@H]4CC(F)(F)C[C@@H]4C3)cc(=O)c12] |
| 2-[2-[(3aR,6aR)-5,5-difluoro-1,3,3a,4,6,6a-hexahydrocyclopenta[c]pyrrol-2-yl]-3-quinolyl]-4-oxo-1H-1,6-napthyridine-5-carboxamide |
| 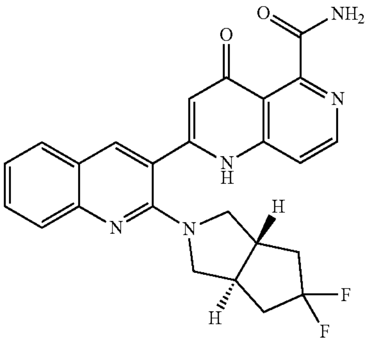 [SMILES: NC(=O)c1nccc2[nH]c(-c3cc4ccccc4nc3N3C[C@@H]4CC(F)(F)C[C@H]4C3)cc(=O)c12] |
| 2-[2-[(3aS,6aS)-5,5-difluoro-1,3,3a,4,6,6a-hexahydrocyclopenta[c]pyrrol-2-yl]-3-quinolyl]-4-oxo-1H-1,6-naphthyridine-5-carboxamide |

TABLE A-continued

| Compound Structures and Names. |
| --- |
| 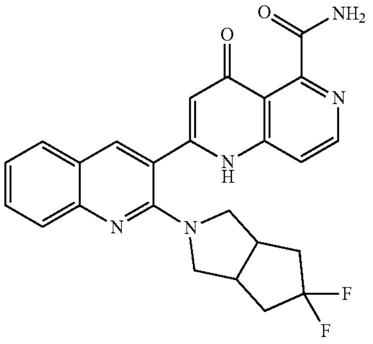 [SMILES: NC(=O)c1nccc2[nH]c(-c3cc4ccccc4nc3N3CC4CC(F)(F)CC4C3)cc(=O)c12] 2-[2-[5,5-difluoro-1,3,3a,4,6,6a-hexahydrocyclopenta[c]pyrrol-2-yl]-3-quinolyl]-4-oxo-1H-1,6-naphthyridine-5-carboxamide |
| 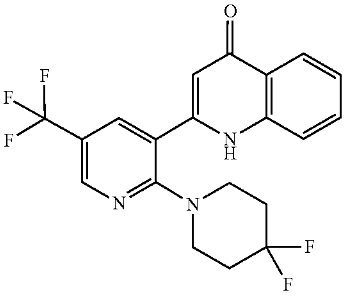 [SMILES: O=c1cc(-c2cc(C(F)(F)F)cnc2N2CCC(F)(F)CC2)[nH]c2ccccc12] 2-[2-(4,4-difluoro-1-piperidyl)-5-(trifluoromethyl)-3-pyridyl]-1H-quinolin-4-one |
| 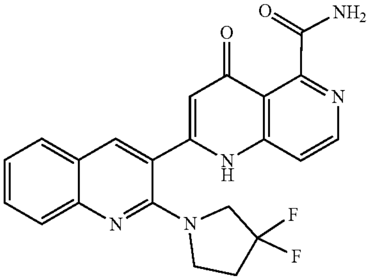 [SMILES: NC(=O)c1nccc2[nH]c(-c3cc4ccccc4nc3N3CCC(F)(F)C3)cc(=O)c12] 2-[2-(3,3-difluoropyrrolidin-1-yl)-3-quinolyl]-4-oxo-1H-1,6-naphthyridine-5-carboxamide |
| 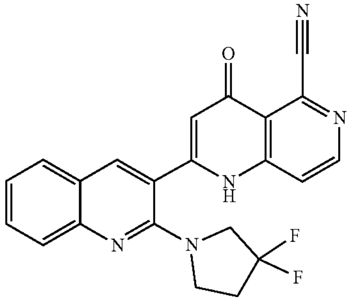 [SMILES: N#Cc1nccc2[nH]c(-c3cc4ccccc4nc3N3CCC(F)(F)C3)cc(=O)c12] 2-[2-(3,3-difluoropyrrolidin-1-yl)-3-quinolyl]-4-oxo-1H-1,6-naphthyridine-5-carbonitrile |

TABLE A-continued

| Compound Structures and Names. |
| --- |
| 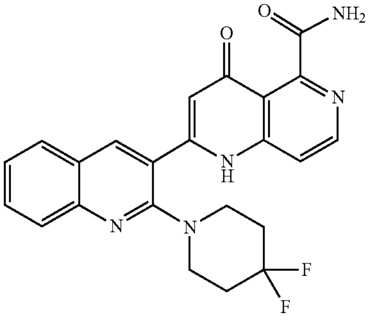 [SMILES: NC(=O)c1nccc2[nH]c(-c3cc4ccccc4nc3N3CCC(F)(F)CC3)cc(=O)c12] 2-[2-(4,4-difluoro-1-piperidyl)-3-quinolyl]-4-oxo-1H-1,6-naphthyridine-5-carboxamide |
| 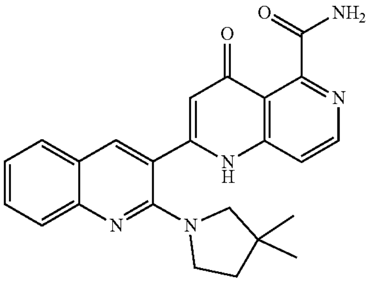 [SMILES: CC1(C)CCN(c2nc3ccccc3cc2-c2cc(=O)c3c(C(N)=O)nccc3[nH]2)C1] 2-[2-(3,3-dimethylpyrrolidin-1-yl)-3-quinolyl]-4-oxo-1H-1,6-naphthyridine-5-carboxamide |
| 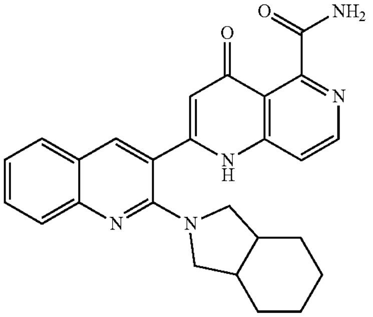 [SMILES: NC(=O)c1nccc2[nH]c(-c3cc4ccccc4nc3N3CC4CCCCC4C3)cc(=O)c12] 2-[2-(1,3,3a,4,5,6,7,7a-octahydroisoindol-2-yl)-3-quinolyl]-4-oxo-1H-1,6-naphthyridine-5-carboxamide |
| 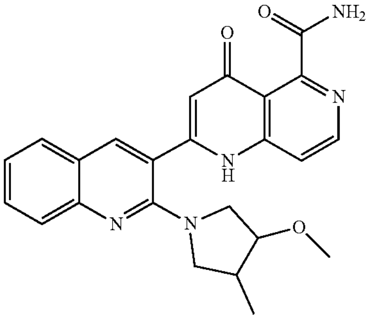 [SMILES: COC1CN(c2nc3ccccc3cc2-c2cc(=O)c3c(C(N)=O)nccc3[nH]2)CC1C] 2-[2-[3-methoxy-4-methyl-pyrrolidin-1-yl]-3-quinolyl]-4-oxo-1H-1,6-naphthyridine-5-carboxamide |

TABLE A-continued

| Compound Structures and Names. |
|---|
| 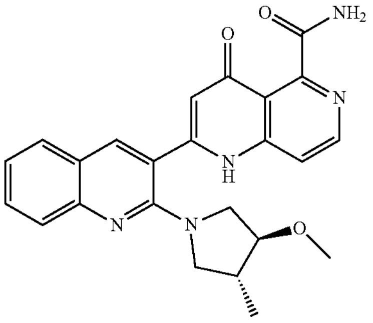 [SMILES: CO[C@@H]1CN(c2nc3ccccc3cc2-c2cc(=O)c3c(C(N)=O)nccc3[nH]2)C[C@H]1C] |
| 2-[2-[(3S,4R)-3-methoxy-4-methyl-pyrrolidin-1-yl]-3-quinolyl]-4-oxo-1H-1,6-naphthyridine-5-carboxamide |
| 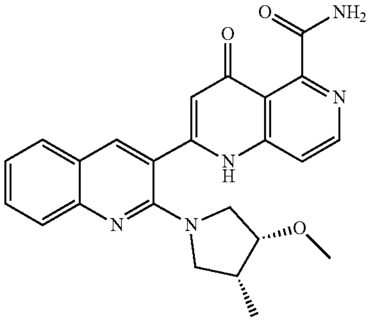 [SMILES: CO[C@H]1CN(c2nc3ccccc3cc2-c2cc(=O)c3c(C(N)=O)nccc3[nH]2)C[C@H]1C] |
| 2-[2-[(3S,4S)-3-methoxy-4-methyl-pyrrolidin-1-yl]-3-quinolyl]-4-oxo-1H-1,6-naphthyridine-5-carboxamide |
| 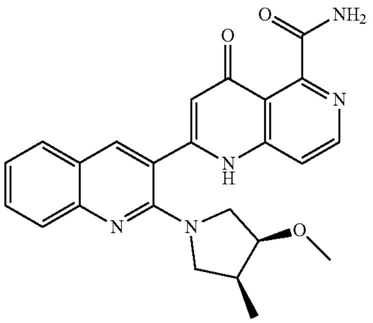 [SMILES: CO[C@@H]1CN(c2nc3ccccc3cc2-c2cc(=O)c3c(C(N)=O)nccc3[nH]2)C[C@@H]1C] |
| 2-[2-[(3R,4R)-3-methoxy-4-methyl-pyrrolidin-1-yl]-3-quinolyl]-4-oxo-1H-1,6-naphthyridine-5-carboxamide |

TABLE A-continued

| Compound Structures and Names. |
|---|
| 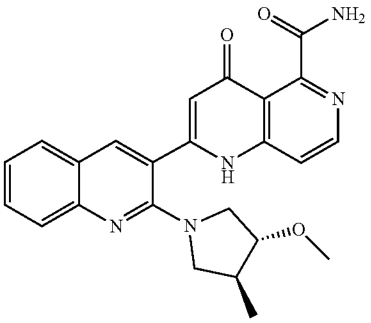 [SMILES: CO[C@H]1CN(c2nc3ccccc3cc2-c2cc(=O)c3c(C(N)=O)nccc3[nH]2)C[C@@H]1C] |
| 2-[2-[(3R,4S)-3-methoxy-4-methyl-pyrrolidin-1-yl]-3-quinolyl]-4-oxo-1H-1,6-naphthyridine-5-carboxamide |
| 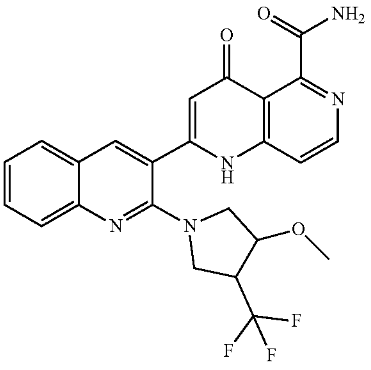 [SMILES: COC1CN(c2nc3ccccc3cc2-c2cc(=O)c3c(C(N)=O)nccc3[nH]2)CC1C(F)(F)F] |
| 2-[2-[3-methoxy-4-(trifluoromethyl)pyrrolidin-1-yl]-3-quinolyl]-4-oxo-1H-1,6-naphthyridine-5-carboxamide |
| 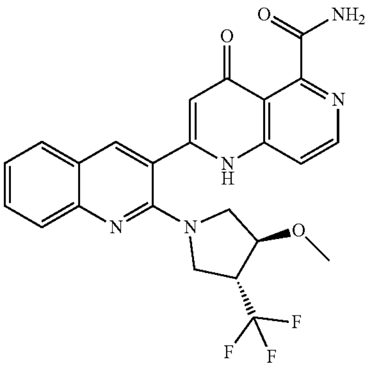 [SMILES: CO[C@@H]1CN(c2nc3ccccc3cc2-c2cc(=O)c3c(C(N)=O)nccc3[nH]2)C[C@H]1C(F)(F)F] |
| 2-[2-[(3S,4R)-3-methoxy-4-(trifluoromethyl)pyrrolidin-1-yl]-3-quinolyl]-4-oxo-1H-1,6-naphthyridine-5-carboxamide |

TABLE A-continued

Compound Structures and Names.

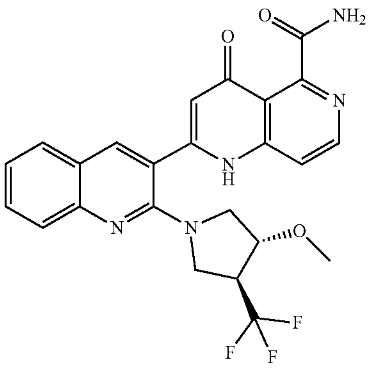 [SMILES: CO[C@H]1CN(c2nc3ccccc3cc2-c2cc(=O)c3c(C(N)=O)nccc3[nH]2)C[C@@H]1C(F)(F)F]

2-[2-[(3R,4S)-3-methoxy-4-(trifluoromethyl)pyrrolidin-1-yl]-3-quinolyl]-4-oxo-1H-1,6-naphthyridine-5-carboxamide

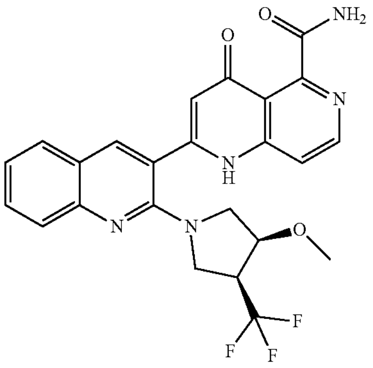 [SMILES: CO[C@@H]1CN(c2nc3ccccc3cc2-c2cc(=O)c3c(C(N)=O)nccc3[nH]2)C[C@@H]1C(F)(F)F]

2-[2-[(3S,4S)-3-methoxy-4-(trifluoromethyl)pyrrolidin-1-yl]-3-quinolyl]-4-oxo-1H-1,6-naphthyridine-5-carboxamide

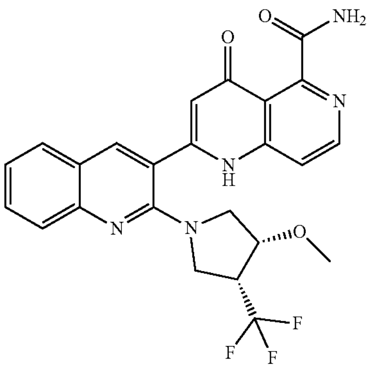 [SMILES: CO[C@H]1CN(c2nc3ccccc3cc2-c2cc(=O)c3c(C(N)=O)nccc3[nH]2)C[C@H]1C(F)(F)F]

2-[2-[(3R,4R)-3-methoxy-4-(trifluoromethyl)pyrrolidin-1-yl]-3-quinolyl]-4-oxo-1H-1,6-naphthyridine-5-carboxamide TABLE A-continued Compound Structures and Names.

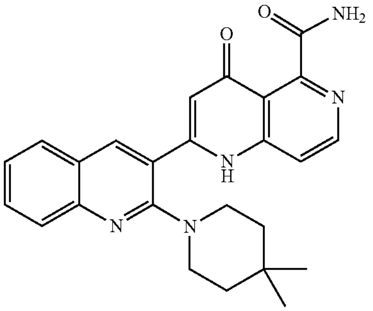 [SMILES: CC1(C)CCN(c2nc3ccccc3cc2-c2cc(=O)c3c(C(N)=O)nccc3[nH]2)CC1]

2-[2-(4,4-dimethyl-1-piperidyl)-3-quinolyl]-4-oxo-1H-1,6-naphthyridine-5-carboxamide

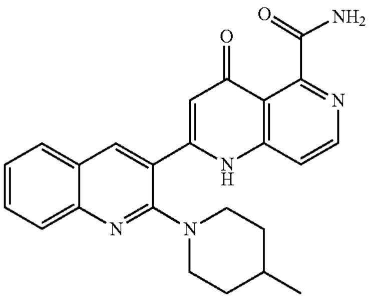 [SMILES: CC1CCN(c2nc3ccccc3cc2-c2cc(=O)c3c(C(N)=O)nccc3[nH]2)CC1]

2-[2-(4-methyl-1-piperidyl)-3-quinolyl]-4-oxo-1H-1,6-naphthyridine-5-carboxamide

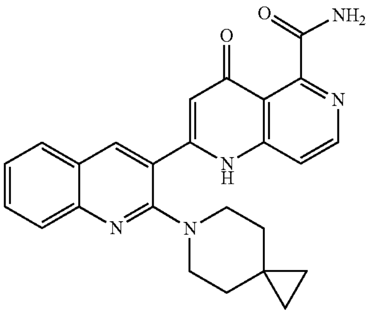 [SMILES: NC(=O)c1nccc2[nH]c(-c3cc4ccccc4nc3N3CCC4(CC3)CC4)cc(=O)c12]

2-[2-(6-azaspiro[2.5]octan-6-yl)-3-quinolyl]-4-oxo-1H-1,6-naphthyridine-5-carboxamide

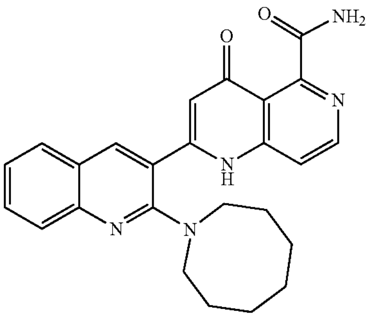 [SMILES: NC(=O)c1nccc2[nH]c(-c3cc4ccccc4nc3N3CCCCCCC3)cc(=O)c12]

2-[2-(azocan-1-yl)-3-quinolyl]-4-oxo-1H-1,6-naphthyridine-5-carboxamide

TABLE A-continued

| Compound Structures and Names. |
|---|
| 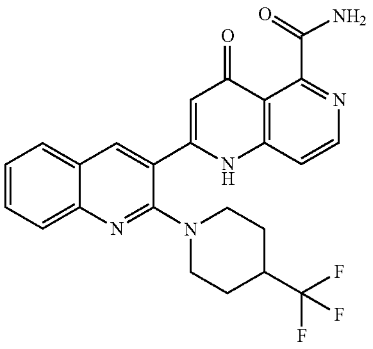 [SMILES: NC(=O)c1nccc2[nH]c(-c3cc4ccccc4nc3N3CCC(C(F)(F)F)CC3)cc(=O)c12] |
| 4-oxo-2-[2-[4-(trifluoromethyl)-1-piperidyl]-3-quinolyl]-1H-1,6-naphthyridine-5-carboxamide |
| 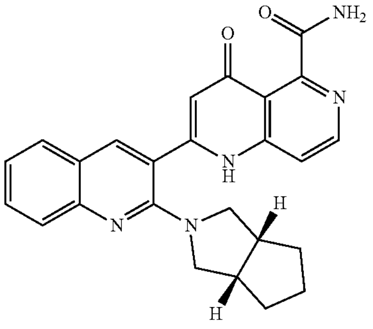 [SMILES: NC(=O)c1nccc2[nH]c(-c3cc4ccccc4nc3N3C[C@H]4CCC[C@H]4C3)cc(=O)c12] |
| 2-[2-[(3aR,6aS)-3,3a,4,5,6,6a-hexahydro-1H-cyclopenta[c]pyrrol-2-yl]-3-quinolyl]-4-oxo-1H-1,6-naphthyridine-5-carboxamide |
| 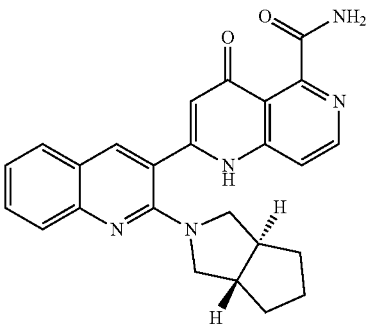 [SMILES: NC(=O)c1nccc2[nH]c(-c3cc4ccccc4nc3N3C[C@H]4CCC[C@@H]4C3)cc(=O)c12] |
| 2-[2-[(3aR,6aR)-3,3a,4,5,6,6a-hexahydro-1H-cyclopenta[c]pyrrol-2-yl]-3-quinolyl]-4-oxo-1H-1,6-naphthyridine-5-carboxamide |

TABLE A-continued

| Compound Structures and Names. |
|---|
| 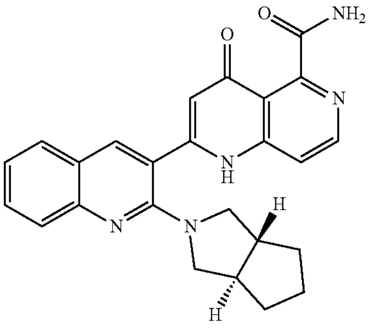 [SMILES: NC(=O)c1nccc2[nH]c(-c3cc4ccccc4nc3N3C[C@@H]4CCC[C@H]4C3)cc(=O)c12] |
| 2-[2-[(3aS,6aS)-3,3a,4,5,6,6a-hexahydro-1H-cyclopenta[c]pyrrol-2-yl]-3-quinolyl]-4-oxo-1H-1,6-naphthyridine-5-carboxamide |
| 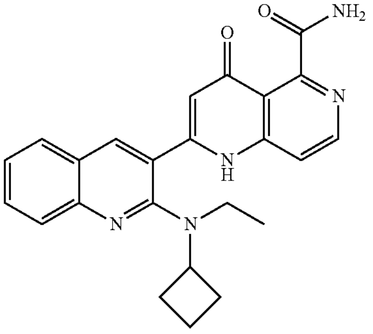 [SMILES: CCN(c1nc2ccccc2cc1-c1cc(=O)c2c(C(N)=O)nccc2[nH]1)C1CCC1] |
| 2-[2-[cyclobutyl(ethyl)amino]-3-quinolyl]-4-oxo-1H-1,6-naphthyridine-5-carboxamide |
| 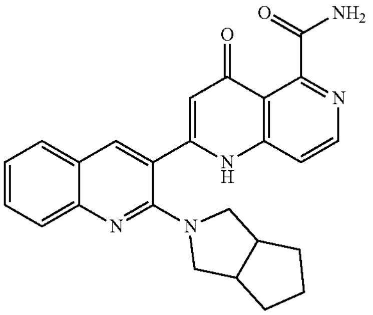 [SMILES: NC(=O)c1nccc2[nH]c(-c3cc4ccccc4nc3N3CC4CCCC4C3)cc(=O)c12] |
| 2-[2-[3,3a,4,5,6,6a-hexahydro-1H-cyclopenta[c]pyrrol-2-yl]-3-quinolyl]-4-oxo-1H-1,6-naphthyridine-5-carboxamide |
| 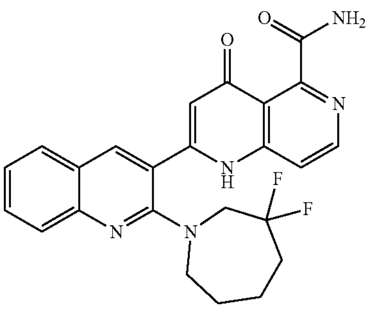 [SMILES: NC(=O)c1nccc2[nH]c(-c3cc4ccccc4nc3N3CCCCC(F)(F)C3)cc(=O)c12] |
| 2-[2-(3,3-difluoroazepan-1-yl)-3-quinolyl]-4-oxo-1H-1,6-naphthyridine-5-carboxamide |

TABLE A-continued

| Compound Structures and Names. |
|---|
| 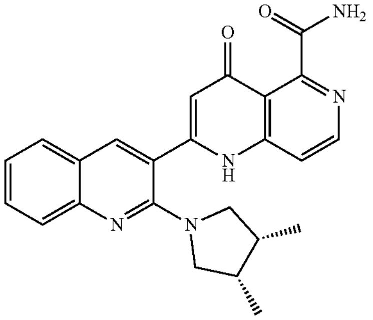 [SMILES: C[C@@H]1CN(c2nc3ccccc3cc2-c2cc(=O)c3c(C(N)=O)nccc3[nH]2)C[C@@H]1C]<br>2-[2-[(3R,4S)-3,4-dimethylpyrrolidin-1-yl]-3-quinolyl]-4-oxo-1H-1,6-naphthyridine-5-carboxamide |
| 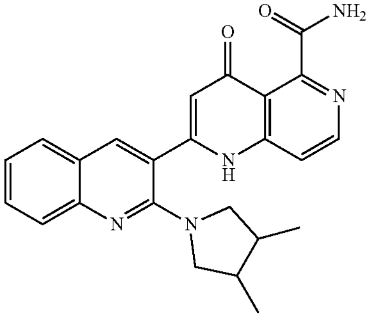 [SMILES: CC1CN(c2nc3ccccc3cc2-c2cc(=O)c3c(C(N)=O)nccc3[nH]2)CC1C]<br>2-[2-[3,4-dimethylpyrrolidin-1-yl]-3-quinolyl]-4-oxo-1H-1,6-naphthyridine-5-carboxamide |
| 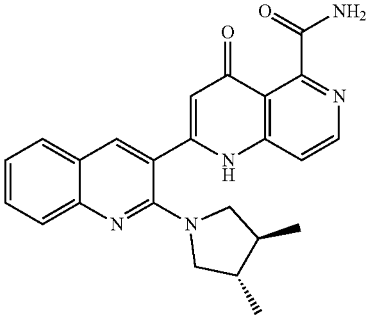 [SMILES: C[C@@H]1CN(c2nc3ccccc3cc2-c2cc(=O)c3c(C(N)=O)nccc3[nH]2)C[C@H]1C]<br>2-[2-[(3R,4R)-3,4-dimethylpyrrolidin-1-yl]-3-quinolyl]-4-oxo-1H-1,6-naphthyridine-5-carboxamide |
| 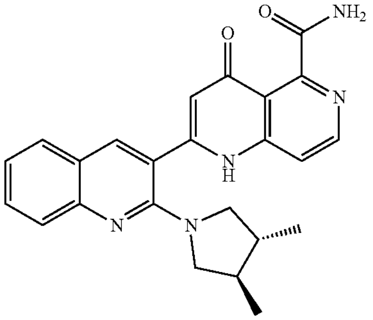 [SMILES: C[C@H]1CN(c2nc3ccccc3cc2-c2cc(=O)c3c(C(N)=O)nccc3[nH]2)C[C@@H]1C]<br>2-[2-[(3S,4S)-3,4-dimethylpyrrolidin-1-yl]-3-quinolyl]-4-oxo-1H-1,6-naphthyridine-5-carboxamide |

TABLE A-continued

| Compound Structures and Names. |
|---|
| 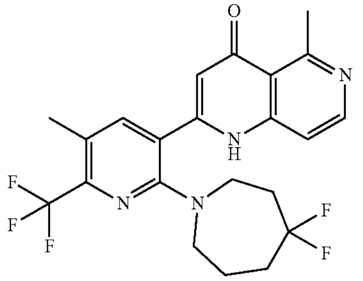 [SMILES: Cc1cc(-c2cc(=O)c3c(C)nccc3[nH]2)c(N2CCCC(F)(F)CC2)nc1C(F)(F)F]<br>2-[2-(4,4-difluoroazepan-1-yl)-5-methyl-6-(trifluoromethyl)-3-pyridyl]-5-methyl-1H-1,6-naphthyridin-4-one |
| 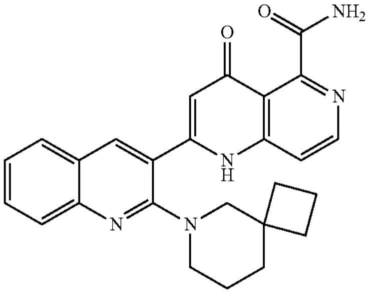 [SMILES: NC(=O)c1nccc2[nH]c(-c3cc4ccccc4nc3N3CCCC4(CCC4)C3)cc(=O)c12]<br>2-[2-(6-azaspiro[3.5]nonan-6-yl)-3-quinolyl]-4-oxo-1H-1,6-naphthyridine-5-carboxamide |
| 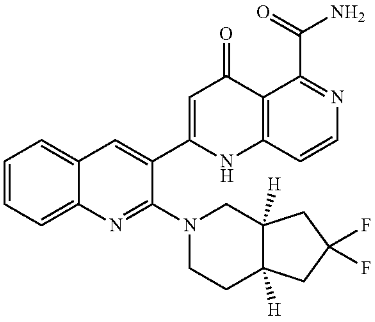 [SMILES: NC(=O)c1nccc2[nH]c(-c3cc4ccccc4nc3N3CC[C@@H]4CC(F)(F)C[C@@H]4C3)cc(=O)c12]<br>2-[2-[(4aS,7aR)-6,6-difluroo-3,4,4a,5,7,7a-hexahydro-1H-cyclopenta[c]pyridin-2-yl]-3-quinolyl]-4-oxo-1H-1,6-naphthyridine-5-carboxamide |
| 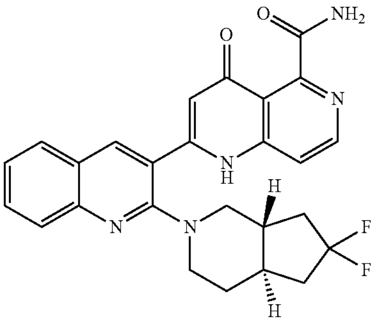 [SMILES: NC(=O)c1nccc2[nH]c(-c3cc4ccccc4nc3N3CC[C@@H]4CC(F)(F)C[C@H]4C3)cc(=O)c12]<br>2-[2-[(4aS,7aS)-6,6-difluoro-3,4,4a,5,7,7a-hexahydro-1H-cyclopenta[c]pyridin-2-yl]-3-quinolyl]-4-oxo-1H-1,6-naphthyridine-5-carboxamide |

TABLE A-continued

| Compound Structures and Names. |
| --- |
| 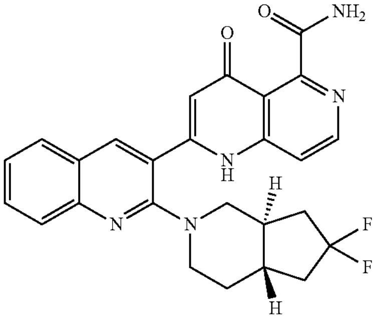 [SMILES: NC(=O)c1nccc2[nH]c(-c3cc4ccccc4nc3N3CC[C@H]4CC(F)(F)C[C@@H]4C3)cc(=O)c12] |
| 2-[2-[(4aR,7aR)-6,6-difluoro-3,4,4a,5,7,7a-hexahydro-1H-cyclopenta[c]prridin-2-yl]-3-quinolyl]-4-oxo-1H-1,6-naphthyridine-5-carboxamide |
| 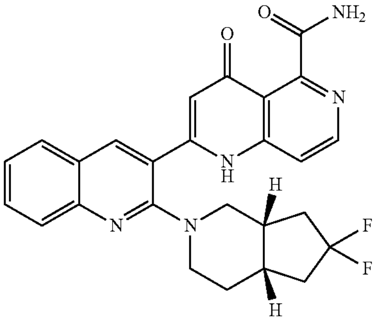 [SMILES: NC(=O)c1nccc2[nH]c(-c3cc4ccccc4nc3N3CC[C@H]4CC(F)(F)C[C@H]4C3)cc(=O)c12] |
| 2-[2-[(4aR,7aS)-6,6-difluoro-3,4,4a,5,7,7a-hexahydro-1H-cyclopenta[c]pyridin-2-yl]-3-quinolyl]-4-oxo-1H-1,6-naphthyridine-5-carboxamide |
| 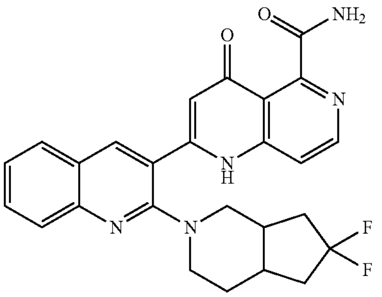 [SMILES: NC(=O)c1nccc2[nH]c(-c3cc4ccccc4nc3N3CCC4CC(F)(F)CC4C3)cc(=O)c12] |
| 2-[2-[6,6-difluoro-3,4,4a,5,7,7a-hexahydro-1H-cyclopenta[c]pyridin-2-yl]-3-quinolyl]-4-oxo-1H-1,6-naphthyridine-5-carboxamide |

TABLE A-continued

| Compound Structures and Names. |
| --- |
| 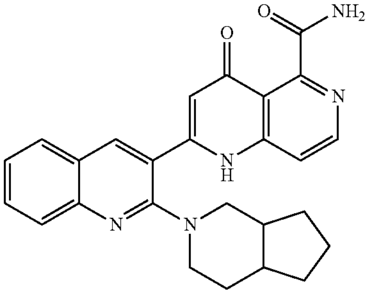 [SMILES: NC(=O)c1nccc2[nH]c(-c3cc4ccccc4nc3N3CCC4CCCC4C3)cc(=O)c12] |
| 2-[2-(1,3,4,4a,5,6,7,7a-octahydrocyclopenta[c]pyridin-2-yl)-3-quinolyl]-4-oxo-1H-1,6-naphthyridine-5-carboxamide |
| 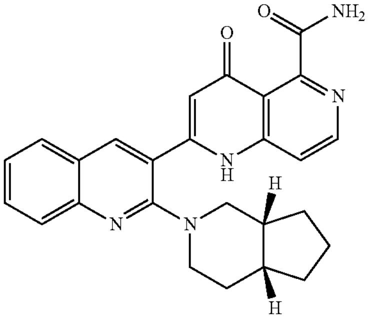 [SMILES: NC(=O)c1nccc2[nH]c(-c3cc4ccccc4nc3N3CC[C@H]4CCC[C@H]4C3)cc(=O)c12] |
| 2-[2-((4aR,7aR)-1,3,4,4a,5,6,7,7a-octahydrocyclopenta[c]pyridin-2-yl)-3-quinolyl]-4-oxo-1H-1,6-naphthyridine-5-carboxamide |
| 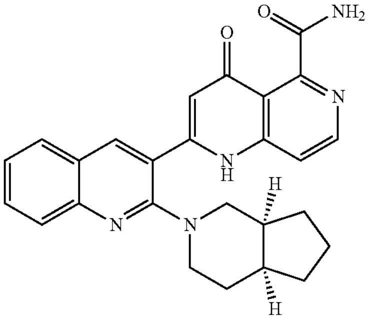 [SMILES: NC(=O)c1nccc2[nH]c(-c3cc4ccccc4nc3N3CC[C@@H]4CCC[C@@H]4C3)cc(=O)c12] |
| 2-[2-((4aS,7aS)-1,3,4,4a,5,6,7,7a-octahydrocyclopenta[c]pyridin-2-yl)-3-quinolyl]-4-oxo-1H-1,6-naphthyridine-5-carboxamide |
| 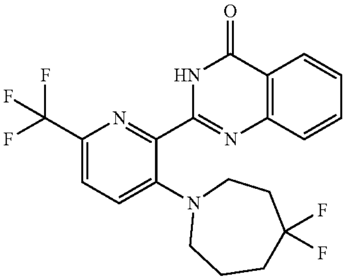 [SMILES: O=c1[nH]c(-c2nc(C(F)(F)F)ccc2N2CCCC(F)(F)CC2)nc2ccccc12] |
| 2-[3-(4,4-difluoroazepan-1-yl)-6-(trifluoromethyl)-2-pyridyl]-3H-quinolin-4-one |

TABLE A-continued

Compound Structures and Names.

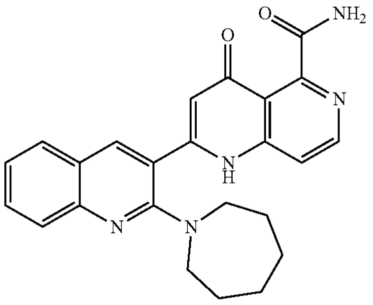 [SMILES: NC(=O)c1nccc2[nH]c(-c3cc4ccccc4nc3N3CCCCCC3)cc(=O)c12]

2-[2-(azepan-1-yl)-3-quinolyl]-4-oxo-1H-1,6-naphthyridine-5-carboxamide

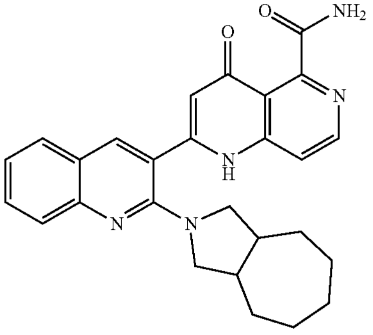 [SMILES: NC(=O)c1nccc2[nH]c(-c3cc4ccccc4nc3N3CC4CCCCCC4C3)cc(=O)c12]

2-[2-(3,3a,4,5,6,7,8,8a-octahydro-1H-cyclohepta[c]pyrrol-2-yl)-3-quinolyl]-4-oxo-1H-1,6-naphthyridine-5-carboxamide

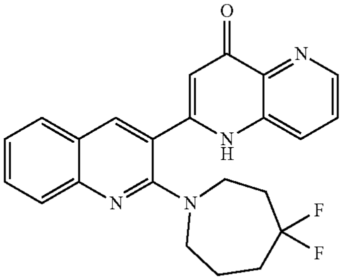 [SMILES: O=c1cc(-c2cc3ccccc3nc2N2CCCC(F)(F)CC2)[nH]c2cccnc12]

2-[2-(4,4-difluoroazepan-1-yl)-3-quinolyl]-1H-1,5-naphthyridin-4-one

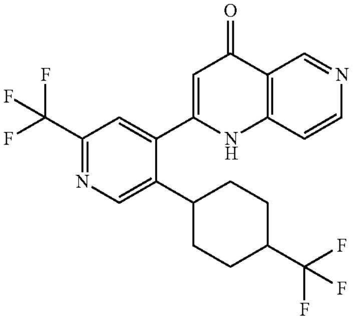 [SMILES: O=c1cc(-c2cc(C(F)(F)F)ncc2C2CCC(C(F)(F)F)CC2)[nH]c2ccncc12]

2-[2-(trifluromethyl)-5-[4-(trifluoromethyl)cyclohexyl]-4-pyridyl]-1H-1,6-naphthyridin-4-one TABLE A-continued Compound Structures and Names.

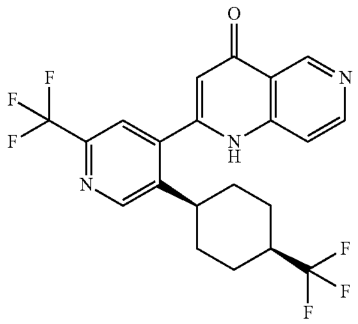 [SMILES: O=c1cc(-c2cc(C(F)(F)F)ncc2[C@H]2CC[C@@H](C(F)(F)F)CC2)[nH]c2ccncc12]

2-[2-(trifluoromethyl)-5-((1s,4s)-4-(trifluoromethyl)cyclohexyl)-4-pyridyl]-1H-1,6-naphthyridin-4-one

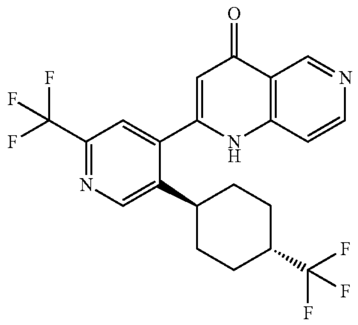 [SMILES: O=c1cc(-c2cc(C(F)(F)F)ncc2[C@H]2CC[C@H](C(F)(F)F)CC2)[nH]c2ccncc12]

2-[2-(trifluoromethyl)-5-((1r,4r)-4-(trifluoromethyl)cyclohexyl)-4-pyridyl]-1H-1,6-naphthyridin-4-one

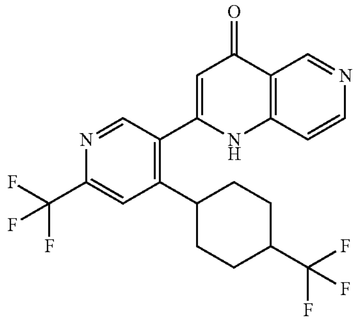 [SMILES: O=c1cc(-c2cnc(C(F)(F)F)cc2C2CCC(C(F)(F)F)CC2)[nH]c2ccncc12]

2-[6-(trifluoromethyl)-4-[4-(trifluoromethyl)cyclohexyl]-3-pyridyl]-1H-1,6-naphthyridin-4-one TABLE A-continued

| Compound Structures and Names. |
| --- |
| 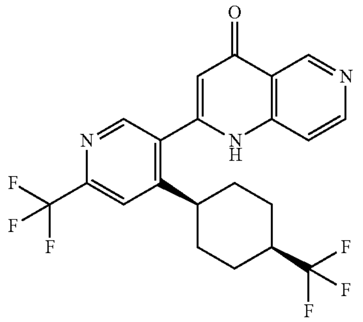 [SMILES: O=c1cc(-c2cnc(C(F)(F)F)cc2[C@H]2CC[C@@H](C(F)(F)F)CC2)[nH]c2ccncc12] |
| 2-[6-(trifluoromethyl)-4-((1r,4s)-4-(trifluoromethyl)cyclohexyl)-3-pyridyl]-1H-1,6-naphthyridin-4-one |
| 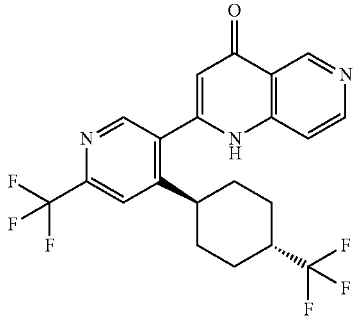 [SMILES: O=c1cc(-c2cnc(C(F)(F)F)cc2[C@H]2CC[C@H](C(F)(F)F)CC2)[nH]c2ccncc12] |
| 2-[6-(trifluoromethyl)-4-((1r,4r)-4-(trifluoromethyl)cyclohexyl)-3-pyridyl]-1H-1,6-naphthyridin-4-one |
| 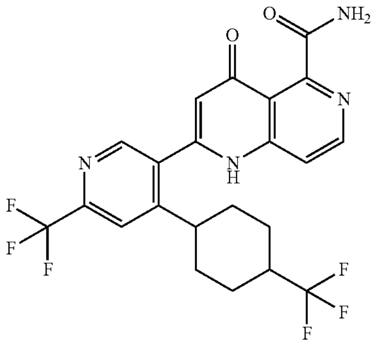 [SMILES: NC(=O)c1nccc2[nH]c(-c3cnc(C(F)(F)F)cc3C3CCC(C(F)(F)F)CC3)cc(=O)c12] |
| 2-[6-tert-butyl-4-[4-(trifluoromethyl)cyclohexyl]-3-pyridyl]-4-oxo-1H-1,6-naphthyridine-5-carboxamide |

TABLE A-continued

| Compound Structures and Names. |
| --- |
| 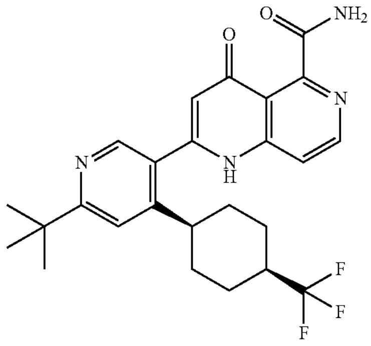 [SMILES: CC(C)(C)c1cc([C@H]2CC[C@@H](C(F)(F)F)CC2)c(-c2cc(=O)c3c(C(N)=O)nccc3[nH]2)cn1] |
| 2-[6-tert-butyl-4-((1S,4S)-4-(trifluoromethyl)cyclohexyl)-3-pyridyl]-4-oxo-1H-1,6-naphthyridine-5-carboxamide |
| 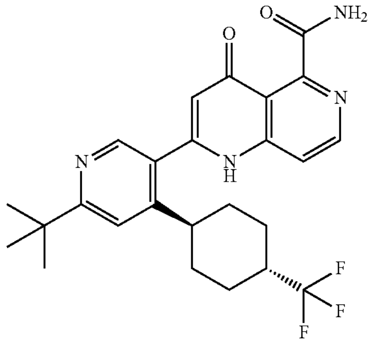 [SMILES: CC(C)(C)c1cc([C@H]2CC[C@H](C(F)(F)F)CC2)c(-c2cc(=O)c3c(C(N)=O)nccc3[nH]2)cn1] |
| 2-[6-tert-butyl-4-((1R,4R)-4-(trifluoromethyl)cyclohexyl)-3-pyridyl]-4-oxo-1H-1,6-naphthyridine-5-carboxamide |
| 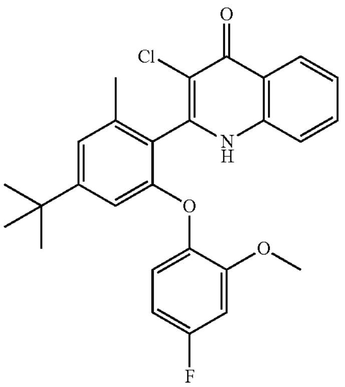 [SMILES: COc1cc(F)ccc1Oc1cc(C(C)(C)C)cc(C)c1-c1[nH]c2ccccc2c(=O)c1Cl] |
| 2-[4-tert-butyl-2-(4-fluoro-2-methoxy-phenoxy)-6-methyl-phenyl]-3-chloro-1H-quinolin-4-one |

TABLE A-continued

| Compound Structures and Names. |
|---|
| 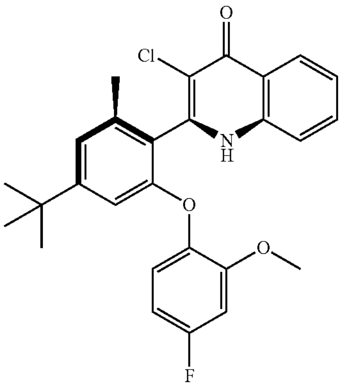 |
| 2-[4-tert-butyl-2-(4-fluoro-2-methoxy-phenoxy)-6-methyl-phenyl]-3-chloro-1H-quinolin-4-one |
| 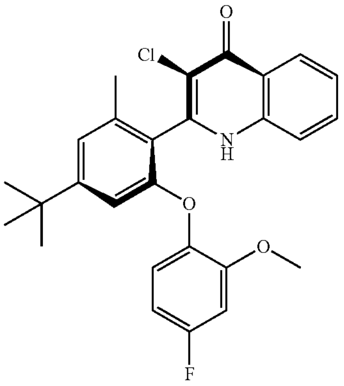 |
| 2-[4-tert-butyl-2-(4-fluoro-2-methoxy-phenoxy)-6-methyl-phenyl]-3-chloro-1H-quinolin-4-one |
| 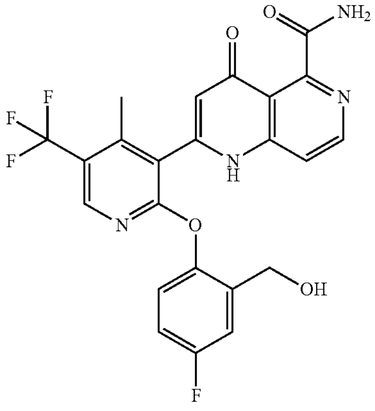 [SMILES: Cc1c(C(F)(F)F)cnc(Oc2ccc(F)cc2CO)c1-c1cc(=O)c2c(C(N)=O)nccc2[nH]1] |
| 2-[2-[4-fluoro-2-(hydroxymethyl)phenoxy]-4-methyl-5-(trifluoromethyl)-3-pyridyl]-4-oxo-1H-1,6-naphthyridine-5-carboxamide |

TABLE A-continued

| Compound Structures and Names. |
|---|
| 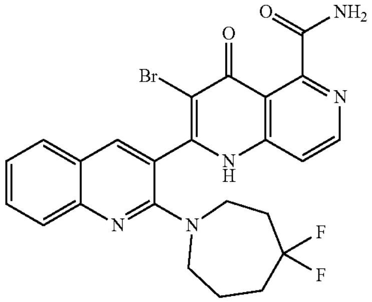 [SMILES: NC(=O)c1nccc2[nH]c(-c3cc4ccccc4nc3N3CCCC(F)(F)CC3)c(Br)c(=O)c12] |
| 3-bromo-2-[2-(4,4-difluoroazepan-1-yl)-3-quinolyl]-4-oxo-1H-1,6-naphthyridine-5-carboxamide |
| 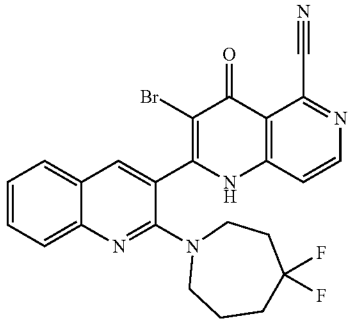 [SMILES: N#Cc1nccc2[nH]c(-c3cc4ccccc4nc3N3CCCC(F)(F)CC3)c(Br)c(=O)c12] |
| 3-bromo-2-[2-(4,4-difluoroazepan-1-yl)-3-quinolyl]-4-oxo-1H-1,6-naphthyridine-5-carbonitrile |
| 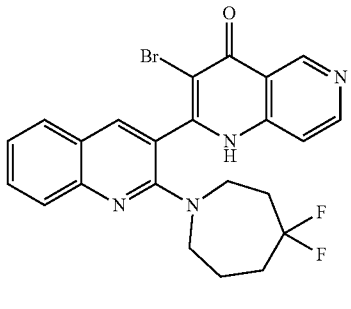 [SMILES: O=c1c(Br)c(-c2cc3ccccc3nc2N2CCCC(F)(F)CC2)[nH]c2ccncc12] |
| 3-bromo-2-[2-(4,4-difluoroazepan-1-yl)-3-quinolyl]-1H-1,6-naphthyridin-4-one |
| 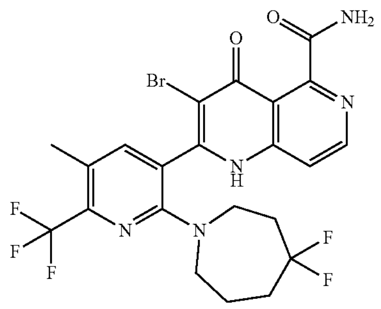 [SMILES: Cc1cc(-c2[nH]c3ccnc(C(N)=O)c3c(=O)c2Br)c(N2CCCC(F)(F)CC2)nc1C(F)(F)F] |
| 3-bromo-2-[2-(4,4-difluoroazepan-1-yl)-5-methyl-6-(trifluoromethyl)-3-pyridyl]-4-oxo-1H-1,6-naphthyridine-5-carboxamide |

TABLE A-continued

Compound Structures and Names.

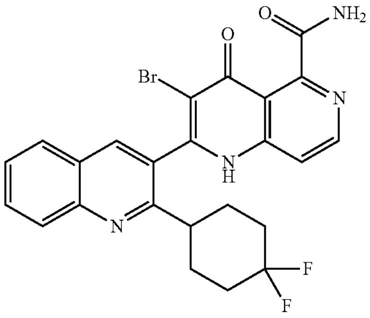 [SMILES: NC(=O)c1nccc2[nH]c(-c3cc4ccccc4nc3C3CCC(F)(F)CC3)c(Br)c(=O)c12]

3-bromo-2-[2-(4,4-difluorocyclohexyl)-3-quinolyl]-4-oxo-1H-1,6-naphthyridine-5-carboxamide

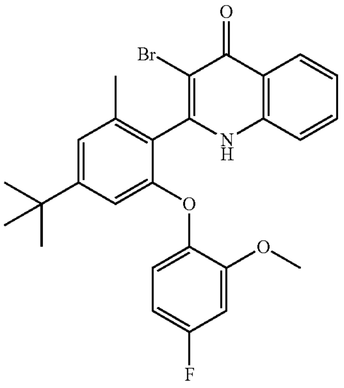 [SMILES: COc1cc(F)ccc1Oc1cc(C(C)(C)C)cc(C)c1-c1[nH]c2ccccc2c(=O)c1Br]

3-bromo-2-[4-tert-butyl-2-(4-fluoro-2-methoxy-phenoxy)-6-methyl-phenyl]-1H-quinolin-4-one

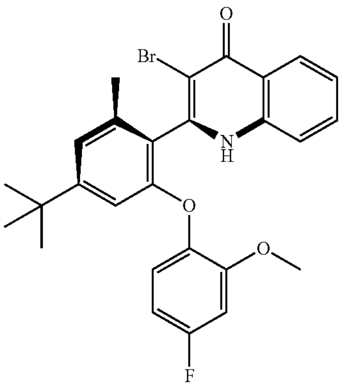

3-bromo-2-[4-tert-butyl-2-(4-fluoro-2-methoxy-phenoxy)-6-methyl-phenyl]-1H-quinolin-4-one TABLE A-continued Compound Structures and Names.

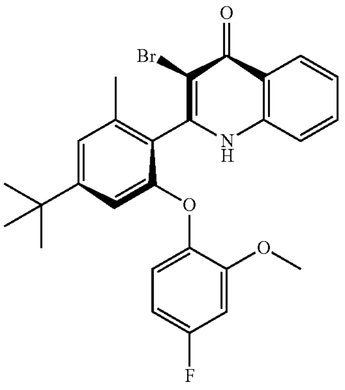

3-bromo-2-[4-tert-butyl-2-(4-fluoro-2-methoxy-phenoxy)-6-methyl-phenyl]-1H-quinolin-4-one

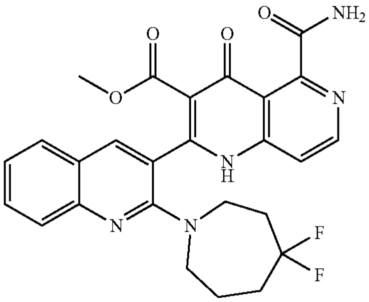 [SMILES: COC(=O)c1c(-c2cc3ccccc3nc2N2CCCC(F)(F)CC2)[nH]c2ccnc(C(N)=O)c2c1=O]

methyl 5-carbamoyl-2-[2-(4,4-difluoroazepan-1-yl)-3-quinolyl]-4-oxo-1H-1,6-naphthyridine-3-carboxylate

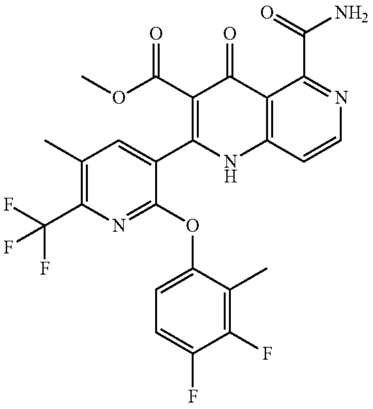 [SMILES: COC(=O)c1c(-c2cc(C)c(C(F)(F)F)nc2Oc2ccc(F)c(F)c2C)[nH]c2ccnc(C(N)=O)c2c1=O]

methyl 5-carbamoyl-2-[2-(3,4-difluoro-2-methyl-phenoxy)-5-methyl-6-(trifluoromethyl)-3-pyridyl]-4-oxo-1H-1,6-naphthyridine-3-carboxylate Compound Structures and Names.

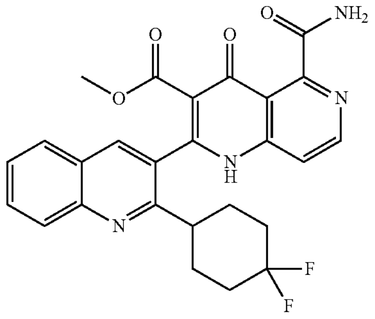 [SMILES: COC(=O)c1c(-c2cc3ccccc3nc2C2CCC(F)(F)CC2)[nH]c2ccnc(C(N)=O)c2c1=O]

methyl 5-carbamoyl-2-[2-(4,4-difluorocyclohexyl)-3-quinolyl]-4-oxo-1H-1,6-naphthyridine-3-carboxylate

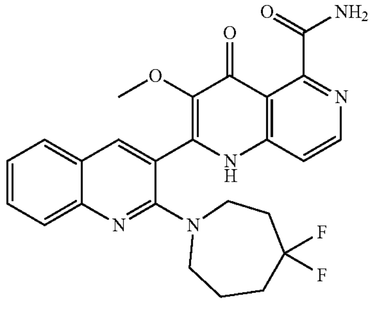 [SMILES: COc1c(-c2cc3ccccc3nc2N2CCCC(F)(F)CC2)[nH]c2ccnc(C(N)=O)c2c1=O]

2-[2-(4,4-difluoroazepan-1-yl)-3-quinolyl]-3-methoxy-4-oxo-1H-1,6-naphthyridine-5-carboxamide

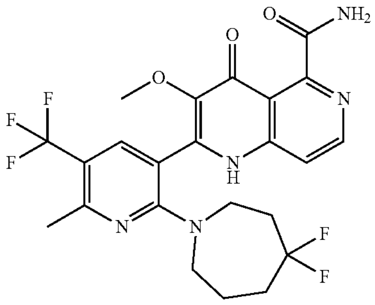 [SMILES: COc1c(-c2cc(C(F)(F)F)c(C)nc2N2CCCC(F)(F)CC2)[nH]c2ccnc(C(N)=O)c2c1=O]

2-[2-(4,4-difluoroazepan-1-yl)-6-methyl-5-(trifluoromethyl)-3-pyridyl]-3-methoxy-4-oxo-1H-1,6-naphthyridine-5-carboxamide

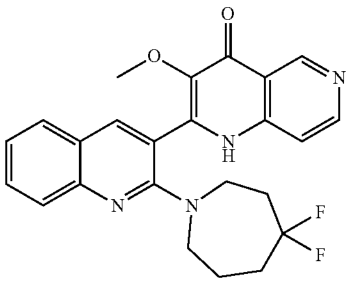 [SMILES: COc1c(-c2cc3ccccc3nc2N2CCCC(F)(F)CC2)[nH]c2ccncc2c1=O]

2-[2-(4,4-difluoroazepan-1-yl)-3-quinolyl]-3-methoxy-1H-1,6-naphthyridin-4-one

Compound Structures and Names.

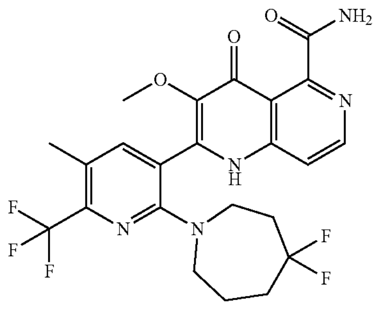 [SMILES: COc1c(-c2cc(C)c(C(F)(F)F)nc2N2CCCC(F)(F)CC2)[nH]c2ccnc(C(N)=O)c2c1=O]

2-[2-(4,4-difluoroazepan-1-yl)-5-methyl-6-(trifluoromethyl)-3-pyridyl]-3-methoxy-4-oxo-1H-1,6-naphthyridine-5-carboxamide

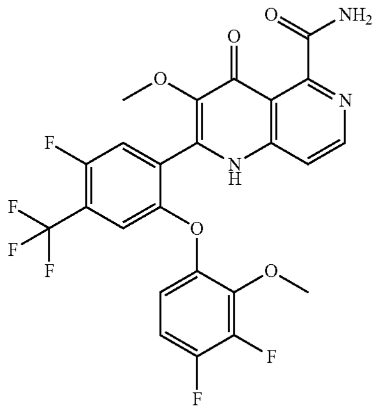 [SMILES: COc1c(Oc2cc(C(F)(F)F)c(F)cc2-c2[nH]c3ccnc(C(N)=O)c3c(=O)c2OC)ccc(F)c1F]

2-[2-(3,4-difluoro-2-methoxy-phenoxy)-5-fluoro-4-(trifluoromethyl)phenyl]-3-methoxy-4-oxo-1H-1,6-naphthyridine-5-carboxamide

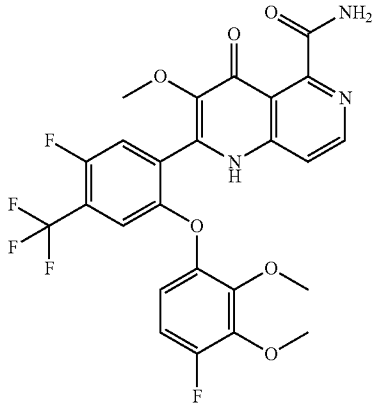 [SMILES: COc1c(F)ccc(Oc2cc(C(F)(F)F)c(F)cc2-c2[nH]c3ccnc(C(N)=O)c3c(=O)c2OC)c1OC]

2-[5-fluoro-2-(4-fluoro-2,3-dimethoxy-phenoxy)-4-(trifluoromethyl)phenyl]-3-methoxy-4-oxo-1H-1,6-naphthyridine-5-carboxamide TABLE A-continued

| Compound Structures and Names. |
| --- |
| 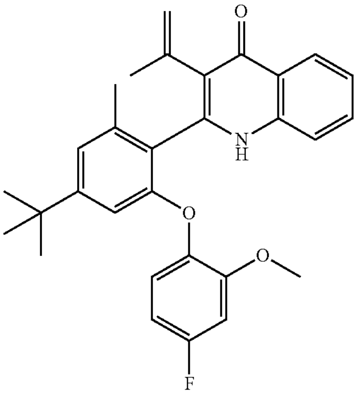 [SMILES: C=C(C)c1c(-c2c(C)cc(C(C)(C)C)cc2Oc2ccc(F)cc2OC)[nH]c2ccccc2c1=O] |
| 2-[4-tert-butyl-2-(4-fluoro-2-methoxy-phenoxy)-6-methyl-phenyl]-3-isopropenyl-1H-quinolin-4-one |
| 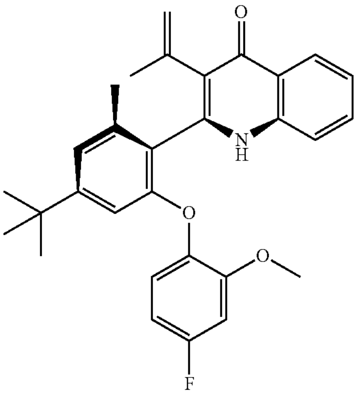 |
| 2-[4-tert-butyl-2-(4-fluoro-2-methoxy-phenoxy)-6-methyl-phenyl]-3-isopropenyl-1H-quinolin-4-one |
| 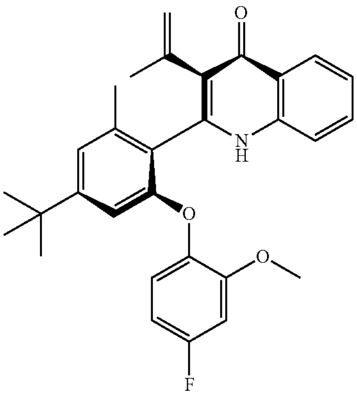 |
| 2-[4-tert-butyl-2-(4-fluoro-2-methoxy-phenoxy)-6-methyl-phenyl]-3-isopropenyl-1H-quinolin-4-one |

TABLE A-continued

| Compound Structures and Names. |
| --- |
| 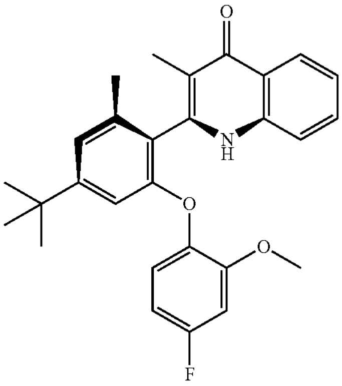 |
| 2-[4-tert-butyl-2-(4-fluoro-2-methoxy-phenoxy)-6-methyl-phenyl]-3-methyl-1H-quinolin-4-one |
| 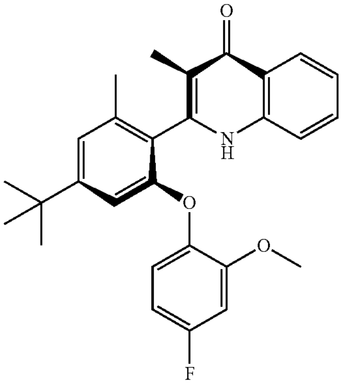 |
| 2-[4-tert-butyl-2-(4-fluoro-2-methoxy-phenoxy)-6-methyl-phenyl]-3-methyl-1H-quinolin-4-one |
| 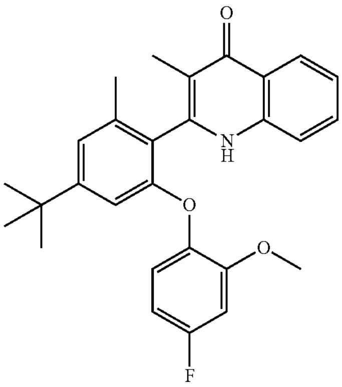 [SMILES: COc1cc(F)ccc1Oc1cc(C(C)(C)C)cc(C)c1-c1[nH]c2ccccc2c(=O)c1C] |
| 2-[4-tert-butyl-2-(4-fluoro-2-methoxy-phenoxy)-6-methyl-phenyl]-3-methyl-1H-quinolin-4-one |

TABLE A-continued

| Compound Structures and Names. |
|---|
| 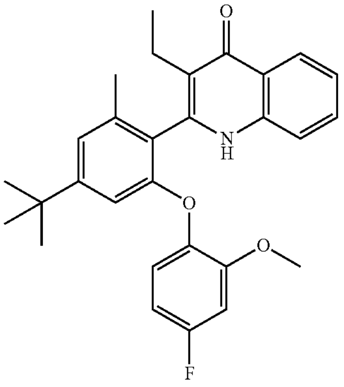 [SMILES: CCc1c(-c2c(C)cc(C(C)(C)C)cc2Oc2ccc(F)cc2OC)[nH]c2ccccc2c1=O] |
| 2-[4-tert-butyl-2-(4-fluoro-2-methoxy-phenoxy)-6-methyl-phenyl]-3-ethyl-1H-quinolin-4-one |
| 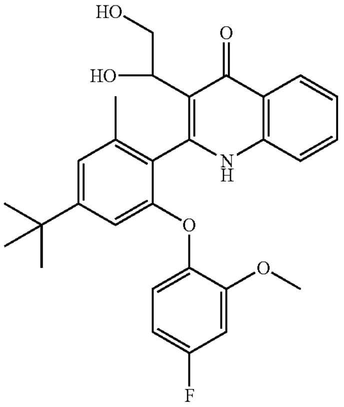 [SMILES: COc1cc(F)ccc1Oc1cc(C(C)(C)C)cc(C)c1-c1[nH]c2ccccc2c(=O)c1C(O)CO] |
| 2-[4-tert-butyl-2-(4-fluoro-2-methoxy-phenoxy)-6-methyl-phenyl]-3-(1,2-dihydroxyethyl)-1H-quinolin-4-one |
| 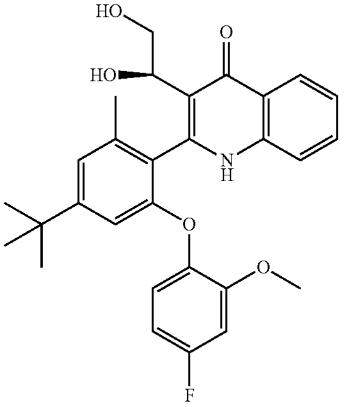 [SMILES: COc1cc(F)ccc1Oc1cc(C(C)(C)C)cc(C)c1-c1[nH]c2ccccc2c(=O)c1[C@@H](O)CO] |
| (R)-2-[4-tert-butyl-2-(4-fluoro-2-methoxy-phenoxy)-6-methyl-phenyl]-3-(1,2-dihydroxyethyl)-1H-quinolin-4-one |

TABLE A-continued

| Compound Structures and Names. |
|---|
| 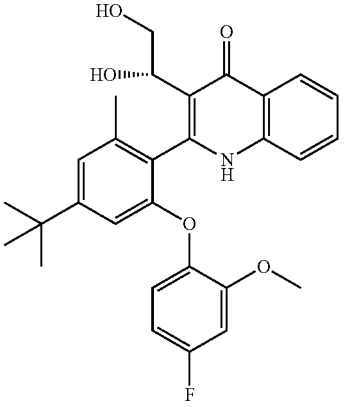 [SMILES: COc1cc(F)ccc1Oc1cc(C(C)(C)C)cc(C)c1-c1[nH]c2ccccc2c(=O)c1[C@H](O)CO] |
| (S)-2-[4-tert-butyl-2-(4-fluoro-2-methoxy-phenoxy)-6-methyl-phenyl]-3-(1,2-dihydroxyethyl)-1H-quinolin-4-one |
| 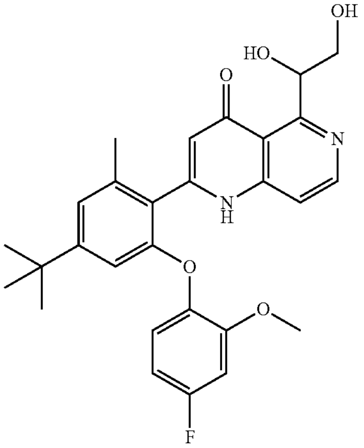 [SMILES: COc1cc(F)ccc1Oc1cc(C(C)(C)C)cc(C)c1-c1cc(=O)c2c(C(O)CO)nccc2[nH]1] |
| 2-[4-tert-butyl-2-(4-fluoro-2-methoxy-phenoxy)-6-methyl-phenyl]-5-(1,2-dihydroxyethyl)-1H-1,6-naphthyridin-4-one |
| 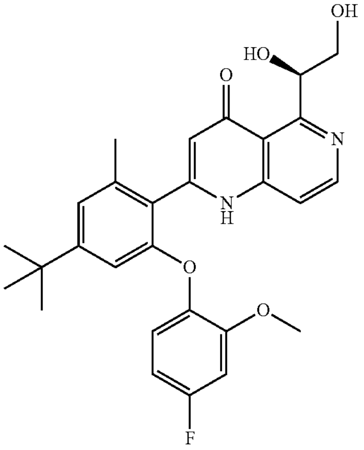 [SMILES: COc1cc(F)ccc1Oc1cc(C(C)(C)C)cc(C)c1-c1cc(=O)c2c([C@@H](O)CO)nccc2[nH]1] |
| (R)-2-[4-tert-butyl-2-(4-fluoro-2-methoxy-phenoxy)-6-methyl-phenyl]-5-(1,2-dihydroxyethyl)-1H-1,6-naphthyridin-4-one |

Compound Structures and Names.

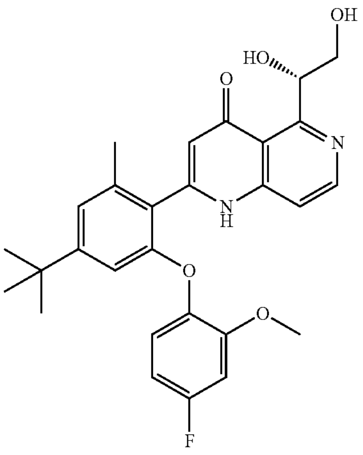 [SMILES: COc1cc(F)ccc1Oc1cc(C(C)(C)C)cc(C)c1-c1cc(=O)c2c([C@H](O)CO)nccc2[nH]1]

(S)-2-[4-tert-butyl-2-(4-fluoro-2-methoxy-phenoxy)-6-methyl-phenyl]-5-(1,2-dihydroxyethyl)-1H-1,6-naphthyridin-4-one

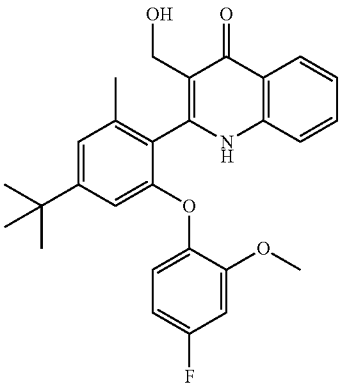 [SMILES: COc1cc(F)ccc1Oc1cc(C(C)(C)C)cc(C)c1-c1[nH]c2ccccc2c(=O)c1CO]

2-[4-tert-butyl-2-(4-fluoro-2-methoxy-phenoxy)-6-methyl-phenyl]-3-(hydroxymethyl)-1H-quinolin-4-one

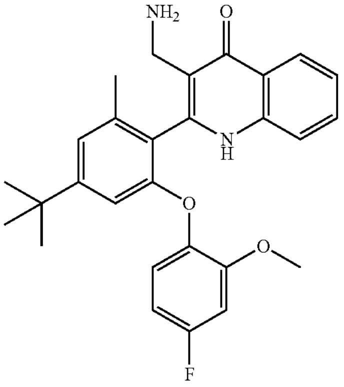 [SMILES: COc1cc(F)ccc1Oc1cc(C(C)(C)C)cc(C)c1-c1[nH]c2ccccc2c(=O)c1CN]

3-(aminomethyl)-2-[4-tert-butyl-2-(4-fluoro-2-methoxy-phenoxy)-6-methyl-phenyl]-1H-quinolin-4-one Compound Structures and Names.

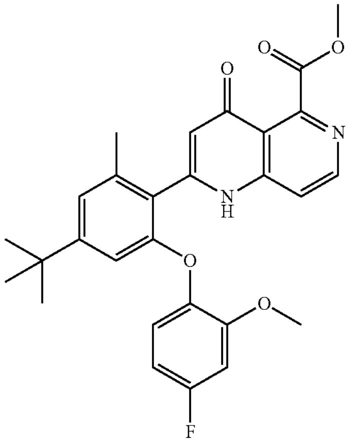 [SMILES: COC(=O)c1nccc2[nH]c(-c3c(C)cc(C(C)(C)C)cc3Oc3ccc(F)cc3OC)cc(=O)c12]

methyl 2-[4-tert-butyl-2-(4-fluoro-2-methoxy-phenoxy)-6-methyl-phenyl]-4-oxo-1H-1,6-naphthyridine-5-carboxylate

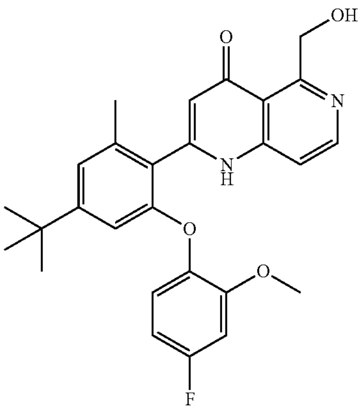 [SMILES: COc1cc(F)ccc1Oc1cc(C(C)(C)C)cc(C)c1-c1cc(=O)c2c(CO)nccc2[nH]1]

2-[4-tert-butyl-2-(4-fluoro-2-methoxy-phenoxy)-6-methyl-phenyl]-5-(hydroxymethyl)-1H-1,6-naphthyridin-4-one

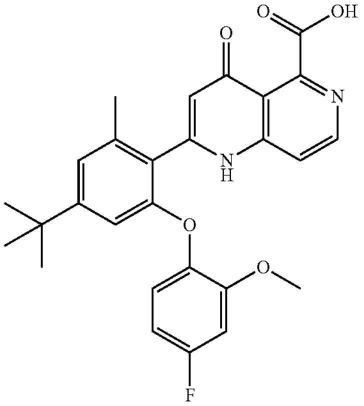 [SMILES: COc1cc(F)ccc1Oc1cc(C(C)(C)C)cc(C)c1-c1cc(=O)c2c(C(=O)O)nccc2[nH]1]

2-[4-tert-butyl-2-(4-fluoro-2-methoxy-phenoxy)-6-methyl-phenyl]-4-oxo-1H-1,6-naphthyridine-5-carboxylic acid TABLE A-continued

| Compound Structures and Names. |
| --- |
| 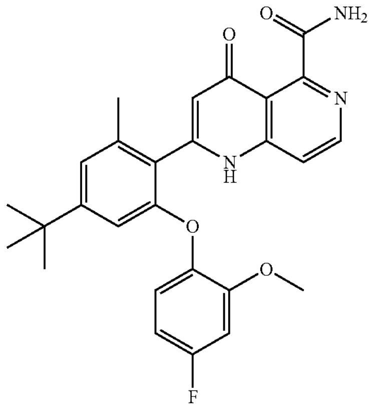 [SMILES: COc1cc(F)ccc1Oc1cc(C(C)(C)C)cc(C)c1-c1cc(=O)c2c(C(N)=O)nccc2[nH]1] |
| 2-[4-tert-butyl-2-(4-fluoro-2-methoxy-phenoxy)-6-methyl-phenyl]-4-oxo-1H-1,6-naphthyridine-5-carboxamide |
| 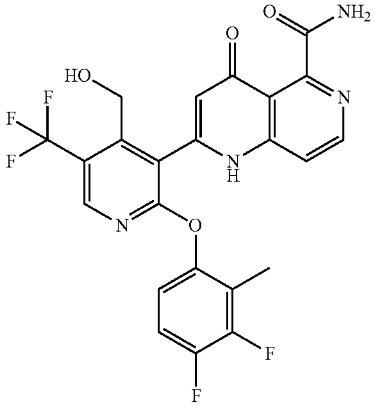 [SMILES: Cc1c(Oc2ncc(C(F)(F)F)c(CO)c2-c2cc(=O)c3c(C(N)=O)nccc3[nH]2)ccc(F)c1F] |
| 2-[2-(3,4-difluoro-2-methyl-phenoxy)-4-(hydroxymethyl)-5-(trifluoromethyl)-3-pyridyl]-4-oxo-1H-1,6-naphthyridine-5-carboxamide |
| 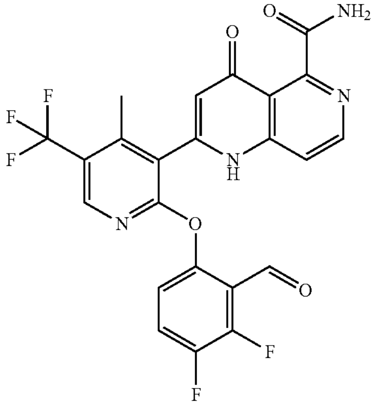 [SMILES: Cc1c(C(F)(F)F)cnc(Oc2ccc(F)c(F)c2C=O)c1-c1cc(=O)c2c(C(N)=O)nccc2[nH]1] |
| 2-[2-(3,4-difluoro-2-formyl-phenoxy)-4-methyl-5-(trifluoromethyl)-3-pyridyl]-4-oxo-1H-1,6-naphthyridine-5-carboxamide |

In some embodiments, the invention relates to a compound selected from Table B, or a pharmaceutically acceptable salt thereof. In other embodiments, the invention relates to a compound selected from Table B, i.e., the compound in non-salt form.

TABLE B

| Compound Structures and Names. |
| --- |
| 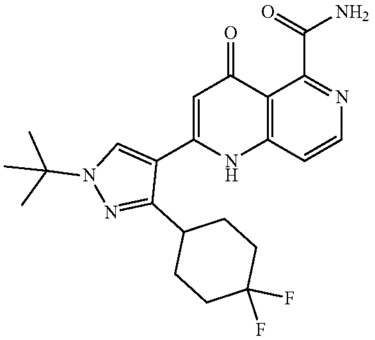 |
| 2-[1-tert-butyl-3-(4,4-difluorocyclohexyl)-pyrazol-4-yl]-4-oxo-1H-1,6-naphthyridine-5-carboxamide |
| 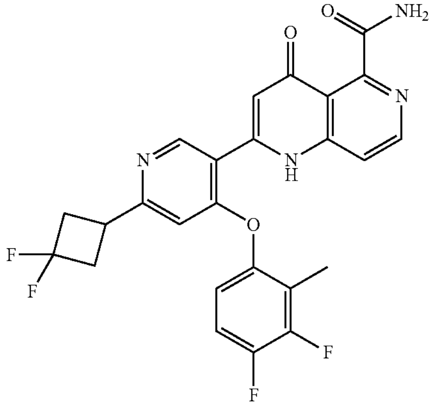 [SMILES: Cc1c(Oc2cc(C3CC(F)(F)C3)ncc2-c2cc(=O)c3c(C(N)=O)nccc3[nH]2)ccc(F)c1F] |
| 2-[6-(3,3-difluorocyclobutyl)-4-(3,4-difluoro-2-methyl-phenoxy)-3-pyridyl]-4-oxo-1H-1,6-naphthyridine-5-carboxamide |
| 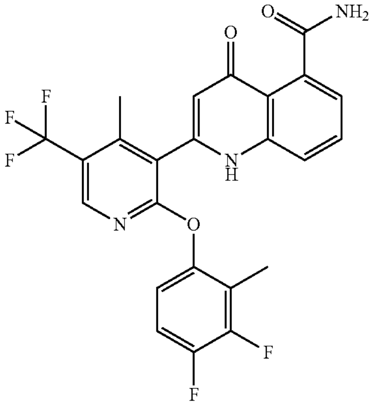 |
| 2-[2-(3,4-difluoro-2-methyl-phenoxy)-4-methyl-5-(trifluoromethyl)-3-pyridyl]-4-oxo-1H-quinoline-5-carboxamide |

TABLE B-continued

| Compound Structures and Names. |
| --- |
| 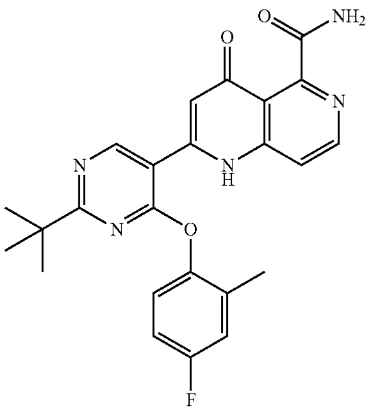 [SMILES: Cc1cc(F)ccc1Oc1nc(C(C)(C)C)ncc1-c1cc(=O)c2c(C(N)=O)nccc2[nH]1] |
| 2-[2-tert-butyl-4-(4-fluoro-2-methyl-phenoxy)pyrimidin-5-yl]-4-oxo-1H-1,6-naphthyridine-5-carboxamide |
| 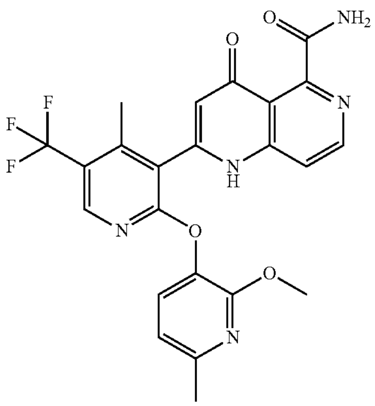 [SMILES: COc1nc(C)ccc1Oc1ncc(C(F)(F)F)c(C)c1-c1cc(=O)c2c(C(N)=O)nccc2[nH]1] |
| 2-[2-[(2-methoxy-6-methyl-3-pyridyl)oxy]-4-methyl-5-(trifluoromethyl)-3-pyridyl]-4-oxo-1H-1,6-naphthyridine-5-carboxamide |
| 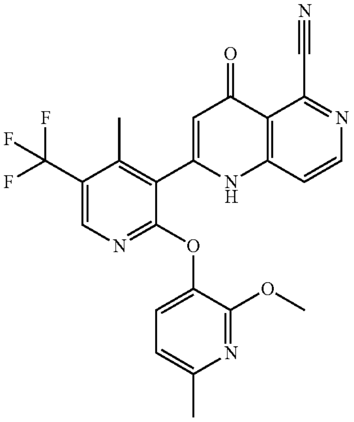 [SMILES: COc1nc(C)ccc1Oc1ncc(C(F)(F)F)c(C)c1-c1cc(=O)c2c(C#N)nccc2[nH]1] |
| 2-[2-[(2-methoxy-6-methyl-3-pyridyl)oxy]-4-methyl-5-(trifluoromethyl)-3-pyridyl]-4-oxo-1H-1,6-naphthyridine-5-carbonitrile |

TABLE B-continued

| Compound Structures and Names. |
| --- |
| 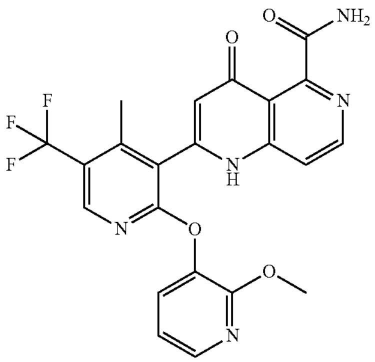 [SMILES: COc1ncccc1Oc1ncc(C(F)(F)F)c(C)c1-c1cc(=O)c2c(C(N)=O)nccc2[nH]1] |
| 2-[2-[(2-methoxy-3-pyridyl)oxy]-4-methyl-5-(trifluoromethyl)-3-pyridyl]-4-oxo-1H-1,6-naphthyridine-5-carboxamide |
| 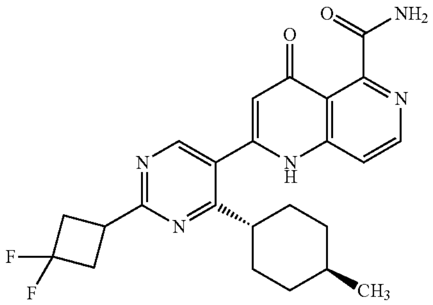 [SMILES: C[C@H]1CC[C@H](c2nc(C3CC(F)(F)C3)ncc2-c2cc(=O)c3c(C(N)=O)nccc3[nH]2)CC1] |
| 2-[2-(3,3-difluorocyclobutyl)-4-(4-methylcyclohexyl)pyrimidin-5-yl]-4-oxo-1H-1,6-naphthyridine-5-carboxamide (trans isomer) |
| 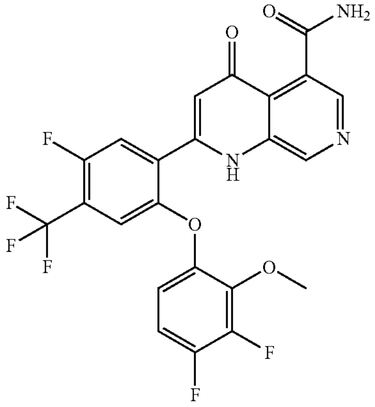 [SMILES: COc1c(Oc2cc(C(F)(F)F)c(F)cc2-c2cc(=O)c3c(C(N)=O)cncc3[nH]2)ccc(F)c1F] |
| 2-[2-(3,4-difluoro-2-methoxy-phenoxy)-5-fluoro-4-(trifluoromethyl)phenyl]-4-oxo-1H-1,7-naphthyridine-5-carboxamide |

TABLE B-continued

| Compound Structures and Names. |
| --- |
| 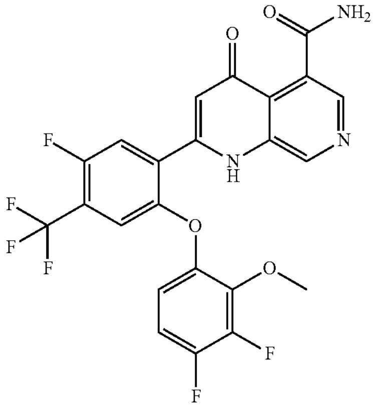 [SMILES: COc1c(Oc2cc(C(F)(F)F)c(F)cc2-c2cc(=O)c3c(C(N)=O)cncc3[nH]2)ccc(F)c1F] 2-[2-(3,4-difluoro-2-methoxy-phenoxy)-5-fluoro-4-(trifluoromethyl)phenyl]-5-(1H-tetrazol-5-yl)-1H-1,6-naphthyridin-4-one |
| 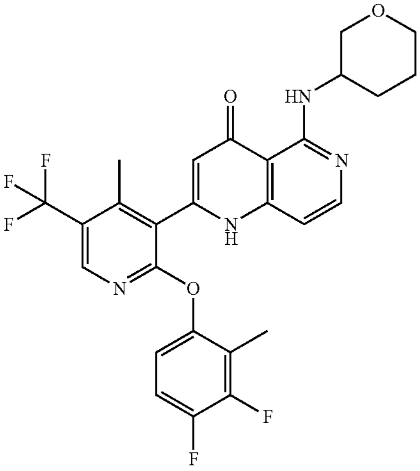 [SMILES: Cc1c(Oc2ncc(C(F)(F)F)c(C)c2-c2cc(=O)c3c(NC4CCCOC4)nccc3[nH]2)ccc(F)c1F] 2-[2-(3,4-difluoro-2-methyl-phenoxy)-4-methyl-5-(trifluoromethyl)-3-pyridyl]-5-(tetrahydro-pyran-3-ylamino)-1H-1,6-naphthyridin-4-one |
| 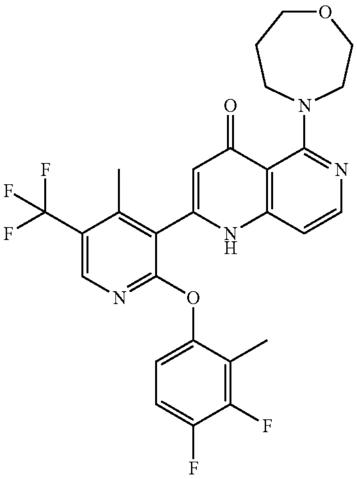 [SMILES: Cc1c(Oc2ncc(C(F)(F)F)c(C)c2-c2cc(=O)c3c(N4CCCOCC4)nccc3[nH]2)ccc(F)c1F] 2-[2-(3,4-difluoro-2-methyl-phenoxy)-4-methyl-5-(trifluoromethyl)-3-pyridyl]-5-(1,4-oxazepan-4-yl)-1H-1,6-naphthyridin-4-one |

TABLE B-continued

| Compound Structures and Names. |
| --- |
| 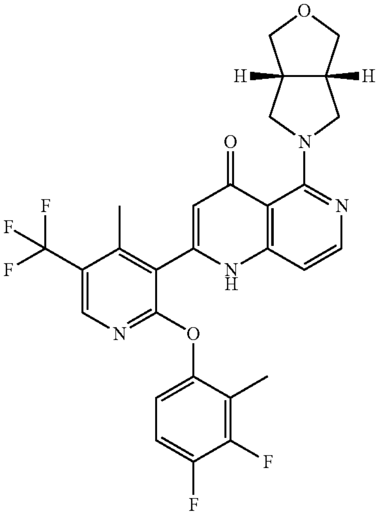 [SMILES: Cc1c(Oc2ncc(C(F)(F)F)c(C)c2-c2cc(=O)c3c(N4C[C@H]5COC[C@H]5C4)nccc3[nH]2)ccc(F)c1F] 5-[(3aS,6aR)-1,3,3a,4,6,6a-hexahydrofuro[3,4-c]pyrrol-5-yl]-2-[2-(3,4-difluoro-2-methyl-phenoxy)-4-methyl-5-(trifluoromethyl)-3-pyridyl]-1H-1,6-naphthyridin-4-one |
| 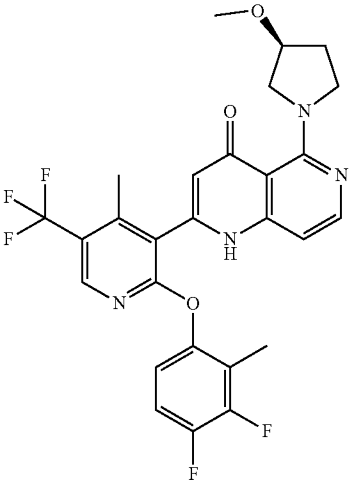 [SMILES: CO[C@H]1CCN(c2nccc3[nH]c(-c4c(Oc5ccc(F)c(F)c5C)ncc(C(F)(F)F)c4C)cc(=O)c23)C1] 2-[2-(3,4-difluoro-2-methyl-phenoxy)-4-methyl-5-(trifluoromethyl)-3-pyridyl]-5-[(3S)-3-methoxypyrrolidin-1-yl]-1H-1,6-naphthyridin-4-one |

TABLE B-continued

| Compound Structures and Names. |
| --- |
| 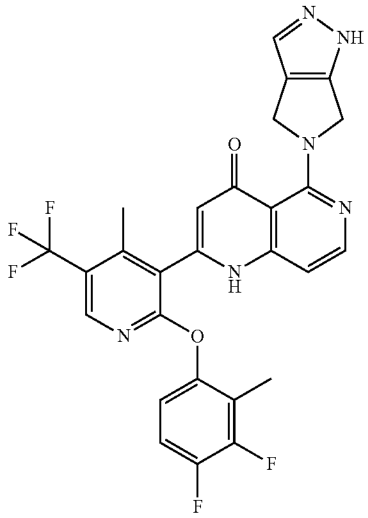 [SMILES: Cc1c(Oc2ncc(C(F)(F)F)c(C)c2-c2cc(=O)c3c(N4Cc5cn[nH]c5C4)nccc3[nH]2)ccc(F)c1F] |
| 2-[2-(3,4-difluoro-2-methyl-phenoxy)-4-methyl-5-(trifluoromethyl)-3-pyridyl]-5-(4,6-dihydro-1H-pyrrolo[3,4-c]pyrazol-5-yl)-1H-1,6-naphthyridin-4-one |
| 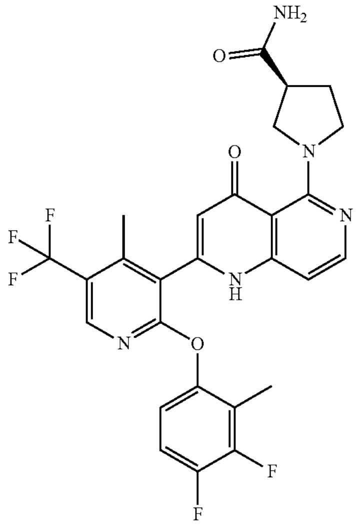 [SMILES: Cc1c(Oc2ncc(C(F)(F)F)c(C)c2-c2cc(=O)c3c(N4CC[C@H](C(N)=O)C4)nccc3[nH]2)ccc(F)c1F] |
| (3S)-1-[2-[2-(3,4-difluoro-2-methyl-phenoxy)-4-methyl-5-(trifluoromethyl)-3-pyridyl]-4-oxo-1H-1,6-naphthyridin-5-yl]pyrrolidine-3-carboxamide |

TABLE B-continued

| Compound Structures and Names. |
| --- |
| 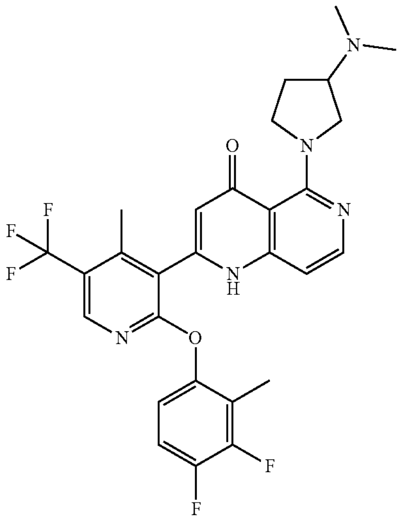 [SMILES: Cc1c(Oc2ncc(C(F)(F)F)c(C)c2-c2cc(=O)c3c(N4CCC(N(C)C)C4)nccc3[nH]2)ccc(F)c1F] |
| 2-[2-(3,4-difluoro-2-methyl-phenoxy)-4-methyl-5-(trifluoromethyl)-3-pyridyl]-5-[3-(dimethylamino)pyrrolidin-1-yl]-1H-1,6-naphthyridin-4-one |
| 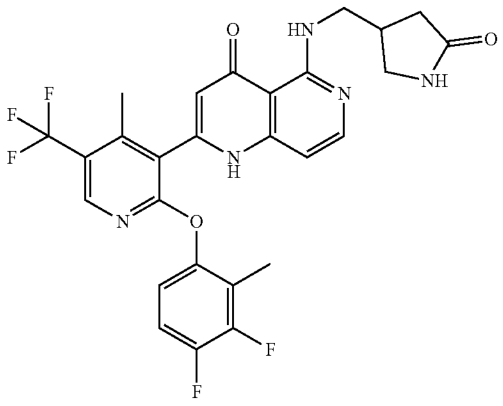 [SMILES: Cc1c(Oc2ncc(C(F)(F)F)c(C)c2-c2cc(=O)c3c(NCC4CNC(=O)C4)nccc3[nH]2)ccc(F)c1F] |
| 2-[2-(3,4-difluoro-2-methyl-phenoxy)-4-methyl-5-(trifluoromethyl)-3-pyridyl]-5-[(5-oxopyrrolidin-3-yl)methylamino]-1H-1,6-naphthyridin-4-one |

TABLE B-continued

| Compound Structures and Names. |
|---|
| 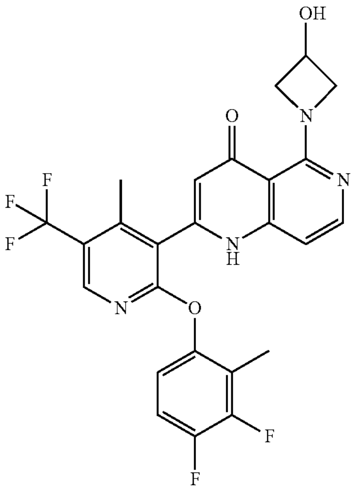 [SMILES: Cc1c(Oc2ncc(C(F)(F)F)c(C)c2-c2cc(=O)c3c(N4CC(O)C4)nccc3[nH]2)ccc(F)c1F] |
| 2-[2-(3,4-difluoro-2-methyl-phenoxy)-4-methyl-5-(trifluoromethyl)-3-pyridyl]-5-(3-hydroxyazetidin-1-yl)-1H-1,6-naphthyridin-4-one |
| 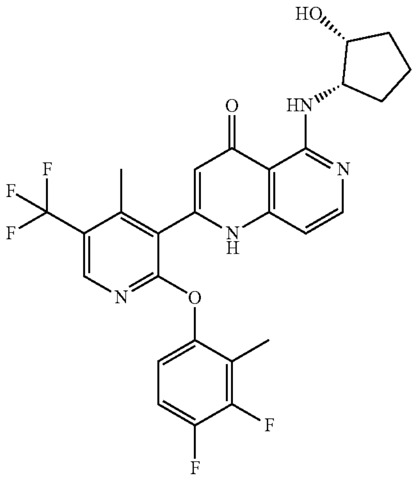 [SMILES: Cc1c(Oc2ncc(C(F)(F)F)c(C)c2-c2cc(=O)c3c(N[C@H]4CCC[C@H]4O)nccc3[nH]2)ccc(F)c1F] |
| 2-[2-(3,4-difluoro-2-methyl-phenoxy)-4-methyl-5-(trifluoromethyl)-3-pyridyl]-5-[[(1S,2R)-2-hydroxycyclopentyl]amino]-1H-1,6-naphthyridin-4-one |

TABLE B-continued

| Compound Structures and Names. |
|---|
| 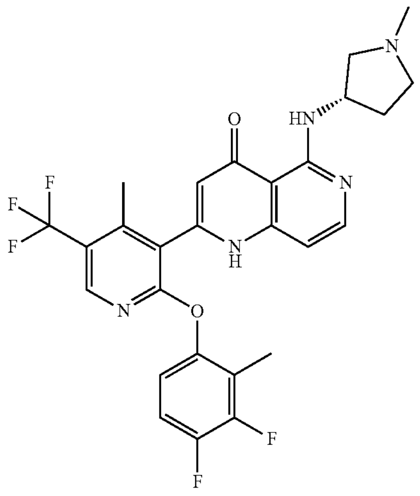 [SMILES: Cc1c(Oc2ncc(C(F)(F)F)c(C)c2-c2cc(=O)c3c(N[C@H]4CCN(C)C4)nccc3[nH]2)ccc(F)c1F] |
| 2-[2-(3,4-difluoro-2-methyl-phenoxy)-4-methyl-5-(trifluoromethyl)-3-pyridyl]-5-[[(3S)-1-methylpyrrolidin-3-yl]amino]-1H-1,6-naphthyridin-4-one |
| 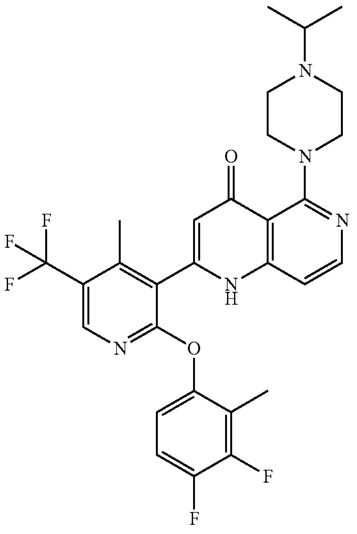 [SMILES: Cc1c(Oc2ncc(C(F)(F)F)c(C)c2-c2cc(=O)c3c(N4CCN(C(C)C)CC4)nccc3[nH]2)ccc(F)c1F] |
| 2-[2-(3,4-difluoro-2-methyl-phenoxy)-4-methyl-5-(trifluoromethyl)-3-pyridyl]-5-(4-isopropylpiperazin-1-yl)-1H-1,6-naphthyridin-4-one |

TABLE B-continued

Compound Structures and Names.

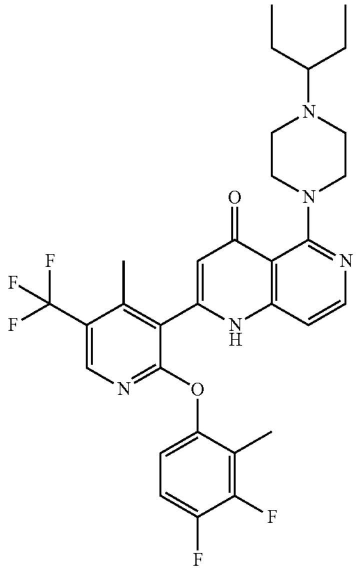 [SMILES: CCC(CC)N1CCN(c2nccc3[nH]c(-c4c(Oc5ccc(F)c(F)c5C)ncc(C(F)(F)F)c4C)cc(=O)c23)CC1]

2-[2-(3,4-difluoro-2-methyl-phenoxy)-4-methyl-5-(trifluoromethyl)-3-pyridyl]-5-[4-(1-ethylpropyl)piperazin-1-yl]-1H-1,6-naphthyridin-4-one

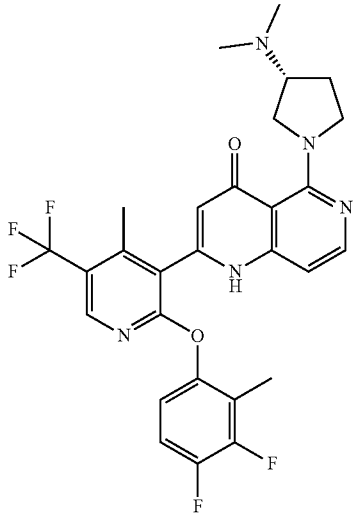 [SMILES: Cc1c(Oc2ncc(C(F)(F)F)c(C)c2-c2cc(=O)c3c(N4CC[C@@H](N(C)C)C4)nccc3[nH]2)ccc(F)c1F]

2-[2-(3,4-difluoro-2-methyl-phenoxy)-4-methyl-5-(trifluoromethyl)-3-pyridyl]-5-[(3R)-3-(dimethylamino)pyrrolidin-1-yl]-1H-1,6-naphthyridin-4-one TABLE B-continued Compound Structures and Names.

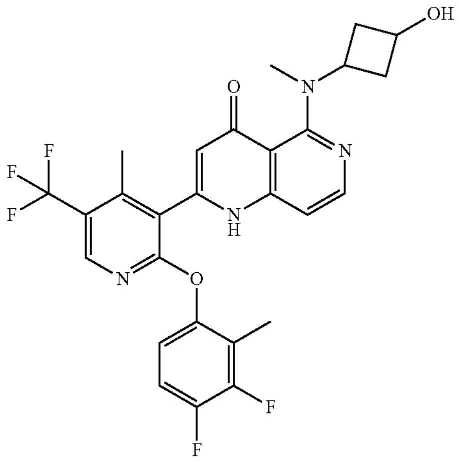 [SMILES: Cc1c(Oc2ncc(C(F)(F)F)c(C)c2-c2cc(=O)c3c(N(C)C4CC(O)C4)nccc3[nH]2)ccc(F)c1F]

2-[2-(3,4-difluoro-2-methyl-phenoxy)-4-methyl-5-(trifluoromethyl)-3-pyridyl]-5-[(3-hydroxycyclobutyl)-methyl-amino]-1H-1,6-naphthyridin-4-one

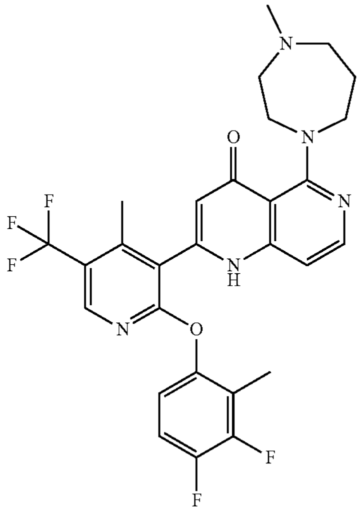 [SMILES: Cc1c(Oc2ncc(C(F)(F)F)c(C)c2-c2cc(=O)c3c(N4CCCN(C)CC4)nccc3[nH]2)ccc(F)c1F]

2-[2-(3,4-difluoro-2-methyl-phenoxy)-4-methyl-5-(trifluoromethyl)-3-pyridyl]-5-(4-methyl-1,4-diazepan-1-yl)-1H-1,6-naphthyridin-4-one TABLE B-continued

| Compound Structures and Names. |
|---|
| 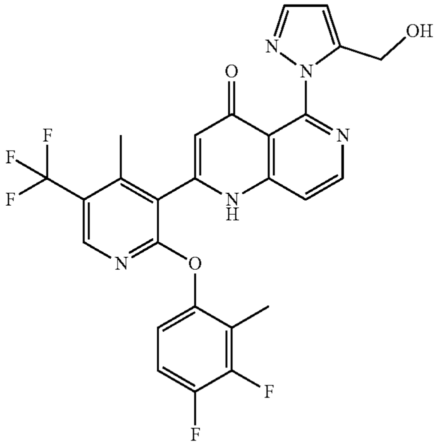 [SMILES: Cc1c(Oc2ncc(C(F)(F)F)c(C)c2-c2cc(=O)c3c(-n4nccc4CO)nccc3[nH]2)ccc(F)c1F] 2-[2-(3,4-difluoro-2-methyl-phenoxy)-4-methyl-5-(trifluoromethyl)-3-pyridyl]-5-[5-(hydroxymethyl)-pyrazol-1-yl]-1H-1,6-naphthyridin-4-one |
| 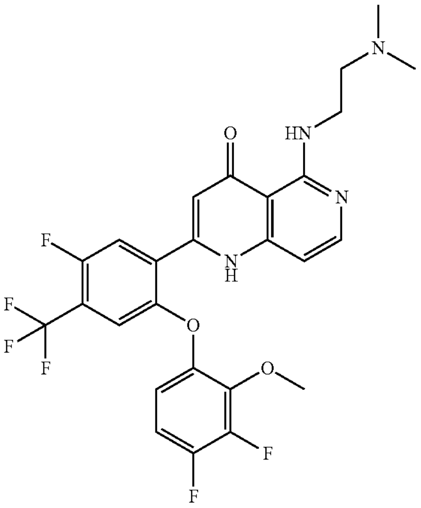 [SMILES: COc1c(Oc2cc(C(F)(F)F)c(F)cc2-c2cc(=O)c3c(NCCN(C)C)nccc3[nH]2)ccc(F)c1F] 2-[2-(3,4-difluoro-2-methoxy-phenoxy)-5-fluoro-4-(trifluoromethyl)phenyl]-5-[2-(dimethylamino)-ethylamino]-1H-1,6-naphthyridin-4-one |

TABLE B-continued

| Compound Structures and Names. |
|---|
| 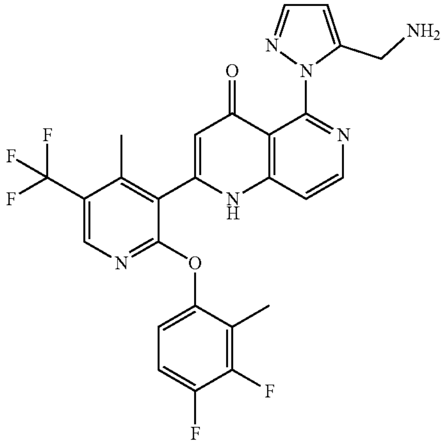 [SMILES: Cc1c(Oc2ncc(C(F)(F)F)c(C)c2-c2cc(=O)c3c(-n4nccc4CN)nccc3[nH]2)ccc(F)c1F] 5-[5-(aminomethyl)pyrazol-1-yl]-2-[2-(3,4-difluoro-2-methyl-phenoxy)-4-methyl-5-(trifluoromethyl)-3-pyridyl]-1H-1,6-naphthyridin-4-one |
| 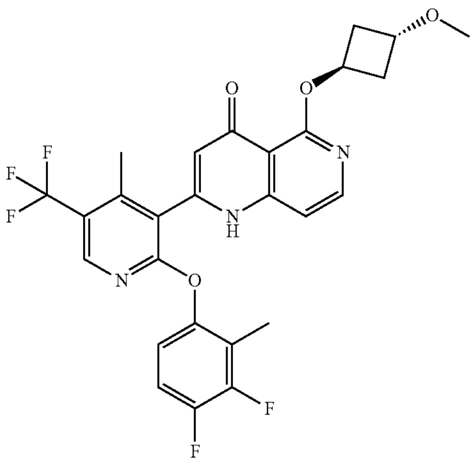 [SMILES: CO[C@H]1C[C@H](Oc2nccc3[nH]c(-c4c(Oc5ccc(F)c(F)c5C)ncc(C(F)(F)F)c4C)cc(=O)c23)C1] 2-[2-(3,4-difluoro-2-methyl-phenoxy)-4-methyl-5-(trifluoromethyl)-3-pyridyl]-5-(3-methoxycyclo-butoxy)-1H-1,6-naphthyridin-4-one |
| 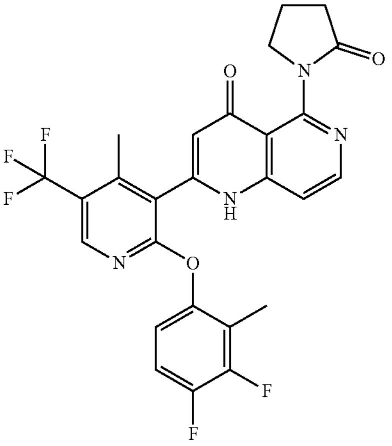 [SMILES: Cc1c(Oc2ncc(C(F)(F)F)c(C)c2-c2cc(=O)c3c(N4CCCC4=O)nccc3[nH]2)ccc(F)c1F] 2-[2-(3,4-difluoro-2-methyl-phenoxy)-4-methyl-5-(trifluoromethyl)-3-pyridyl]-5-(2-oxo-pyrrolidin-1-yl)-1H-1,6-naphthyridin-4-one |

TABLE B-continued

| Compound Structures and Names. |
| --- |
| 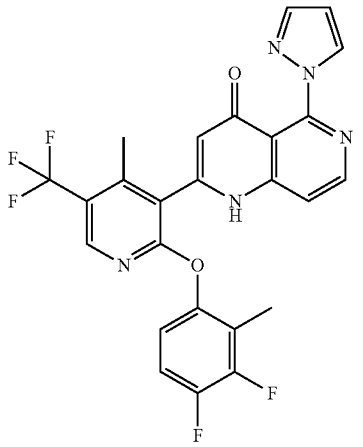 [SMILES: Cc1c(Oc2ncc(C(F)(F)F)c(C)c2-c2cc(=O)c3c(-n4cccn4)nccc3[nH]2)ccc(F)c1F] |
| 2-[2-(3,4-difluoro-2-methyl-phenoxy)-4-methyl-5-(trifluoromethyl)-3-pyridyl]-5-pyrazol-1-yl-1H-1,6-naphthyridin-4-one |
| 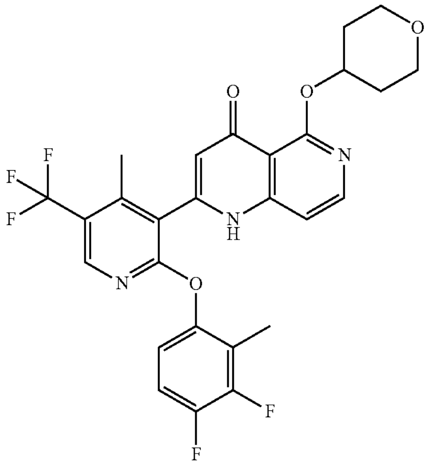 [SMILES: Cc1c(Oc2ncc(C(F)(F)F)c(C)c2-c2cc(=O)c3c(OC4CCOCC4)nccc3[nH]2)ccc(F)c1F] |
| 2-[2-(3,4-difluoro-2-methyl-phenoxy)-4-methyl-5-(trifluoromethyl)-3-pyridyl]-5-tetrahydropyran-4-yloxy-1H-1,6-naphthyridin-4-one |
| 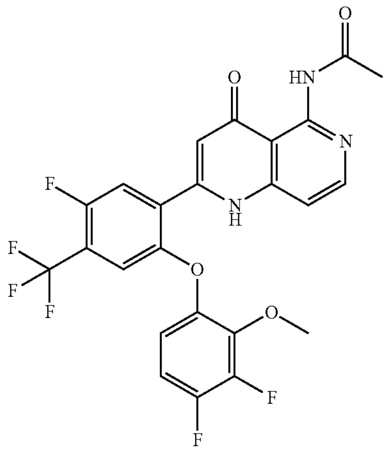 [SMILES: COc1c(Oc2cc(C(F)(F)F)c(F)cc2-c2cc(=O)c3c(NC(C)=O)nccc3[nH]2)ccc(F)c1F] |
| N-[2-[2-(3,4-difluoro-2-methoxy-phenoxy)-5-fluoro-4-(trifluoromethyl)phenyl]-4-oxo-1H-1,6-naphthyridin-5-yl]acetamide |

TABLE B-continued

| Compound Structures and Names. |
| --- |
| 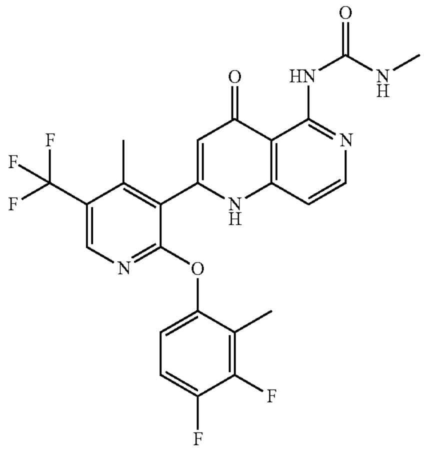 [SMILES: CNC(=O)Nc1nccc2[nH]c(-c3c(Oc4ccc(F)c(F)c4C)ncc(C(F)(F)F)c3C)cc(=O)c12] |
| 1-[2-[2-(3,4-difluoro-2-methyl-phenoxy)-4-methyl-5-(trifluoromethyl)-3-pyridyl]-4-oxo-1H-1,6-naphthyridin-5-yl]-3-methyl-urea |
| 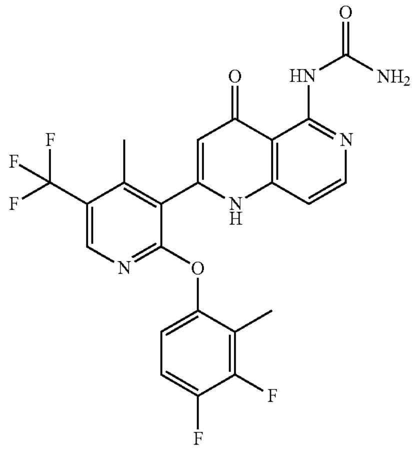 [SMILES: Cc1c(Oc2ncc(C(F)(F)F)c(C)c2-c2cc(=O)c3c(NC(N)=O)nccc3[nH]2)ccc(F)c1F] |
| [2-[2-(3,4-difluoro-2-methyl-phenoxy)-4-methyl-5-(trifluoromethyl)-3-pyridyl]-4-oxo-1H-1,6-naphthyridin-5-yl]urea |

TABLE B-continued

| Compound Structures and Names. |
|---|
| 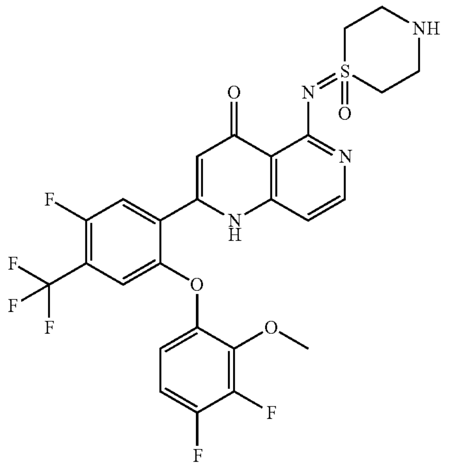 [SMILES: COc1c(Oc2cc(C(F)(F)F)c(F)cc2-c2cc(=O)c3c(N=S4(=O)CCNCC4)nccc3[nH]2)ccc(F)c1F] |
| 2-[2-(3,4-difluoro-2-methoxy-phenoxy)-5-fluoro-4-(trifluoromethyl)phenyl]-5-[(1-oxo-1,4-thiazinan-1-ylidene)amino]-1H-1,6-naphthyridin-4-one |
| 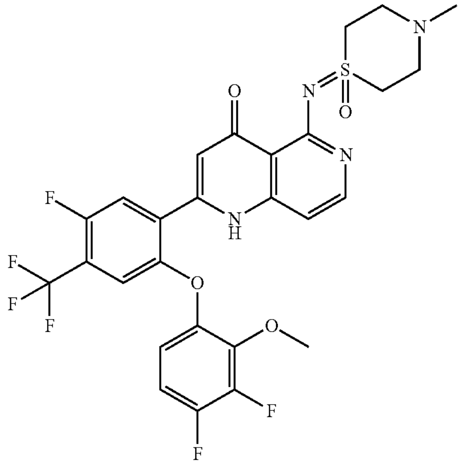 [SMILES: COc1c(Oc2cc(C(F)(F)F)c(F)cc2-c2cc(=O)c3c(N=S4(=O)CCN(C)CC4)nccc3[nH]2)ccc(F)c1F] |
| 2-[2-(3,4-difluoro-2-methoxy-phenoxy)-5-fluoro-4-(trifluoromethyl)phenyl]-5-[(4-methyl-1-oxo-1,4-thiazinan-1-ylidene)amino]-1H-1,6-naphthyridin-4-one |

TABLE B-continued

| Compound Structures and Names. |
|---|
| 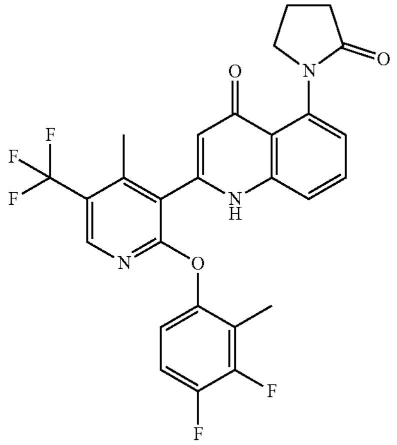 [SMILES: Cc1c(Oc2ncc(C(F)(F)F)c(C)c2-c2cc(=O)c3c(N4CCCC4=O)cccc3[nH]2)ccc(F)c1F] |
| 2-[2-(3,4-difluoro-2-methyl-phenoxy)-4-methyl-5-(trifluoromethyl)-3-pyridyl]-5-(2-oxopyrrolidin-1-yl)-1H-quinolin-4-one |
| 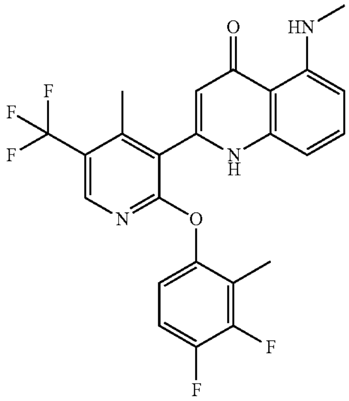 [SMILES: CNc1cccc2[nH]c(-c3c(Oc4ccc(F)c(F)c4C)ncc(C(F)(F)F)c3C)cc(=O)c12] |
| 2-[2-(3,4-difluoro-2-methyl-phenoxy)-4-methyl-5-(trifluoromethyl)-3-pyridyl]-5-(methylamino)-1H-quinolin-4-one |
| 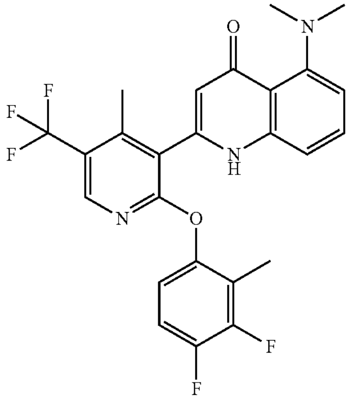 [SMILES: Cc1c(Oc2ncc(C(F)(F)F)c(C)c2-c2cc(=O)c3c(N(C)C)cccc3[nH]2)ccc(F)c1F] |
| 2-[2-(3,4-difluoro-2-methyl-phenoxy)-4-methyl-5-(trifluoromethyl)-3-pyridyl]-5-(dimethylamino)-1H-quinolin-4-one |

TABLE B-continued

| Compound Structures and Names. |
| --- |
| 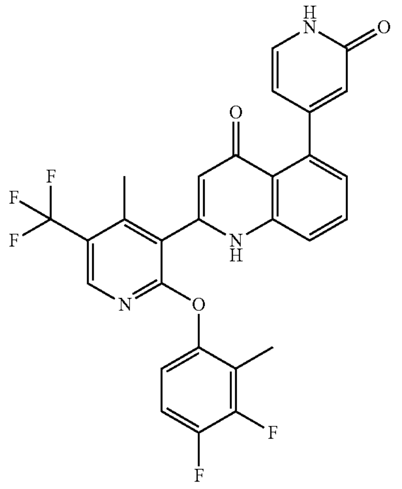 [SMILES: Cc1c(Oc2ncc(C(F)(F)F)c(C)c2-c2cc(=O)c3c(-c4cc[nH]c(=O)c4)cccc3[nH]2)ccc(F)c1F] |
| N-[2-[2-(3,4-difluoro-2-methoxy-phenoxy)-5-fluoro-4-(trifluoromethyl)phenyl]-4-oxo-1H-1,6-naphthyridin-5-yl]acetamide |
| 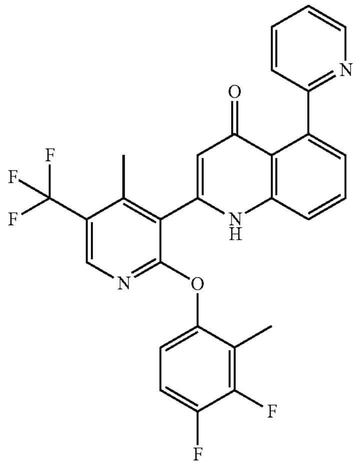 [SMILES: Cc1c(Oc2ncc(C(F)(F)F)c(C)c2-c2cc(=O)c3c(-c4ccccn4)cccc3[nH]2)ccc(F)c1F] |
| 2-[2-(3,4-difluoro-2-methyl-phenoxy)-4-methyl-5-(trifluoromethyl)-3-pyridyl]-5-(2-pyridyl)-1H-quinolin-4-one |

TABLE B-continued

| Compound Structures and Names. |
| --- |
| 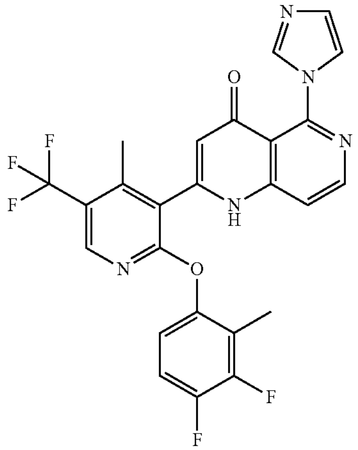 [SMILES: Cc1c(Oc2ncc(C(F)(F)F)c(C)c2-c2cc(=O)c3c(-n4ccnc4)nccc3[nH]2)ccc(F)c1F] |
| 2-[2-(3,4-difluoro-2-methyl-phenoxy)-4-methyl-5-(trifluoromethyl)-3-pyridyl]-5-imidazol-1-yl-1H-1,6-naphthyridin-4-one |
| 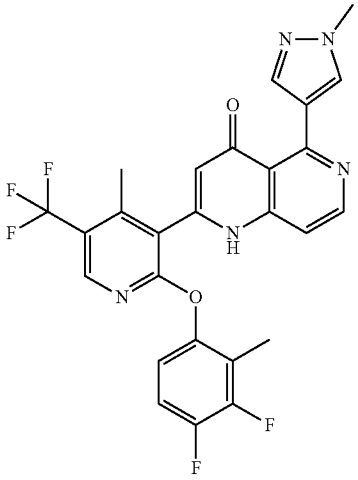 [SMILES: Cc1c(Oc2ncc(C(F)(F)F)c(C)c2-c2cc(=O)c3c(-c4cnn(C)c4)nccc3[nH]2)ccc(F)c1F] |
| 2-[2-(3,4-difluoro-2-methyl-phenoxy)-4-methyl-5-(trifluoromethyl)-3-pyridyl]-5-(1-methylpyrazol-4-yl)-1H-1,6-naphthyridin-4-one |

TABLE B-continued

| Compound Structures and Names. |
|---|
| 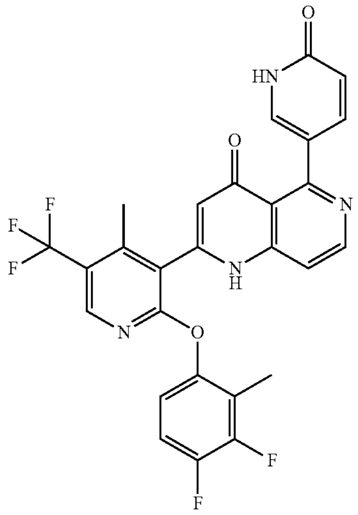 [SMILES: Cc1c(Oc2ncc(C(F)(F)F)c(C)c2-c2cc(=O)c3c(-c4ccc(=O)[nH]c4)nccc3[nH]2)ccc(F)c1F] |
| 2-[2-(3,4-difluoro-2-methyl-phenoxy)-4-methyl-5-(trifluoromethyl)-3-pyridyl]-5-(6-oxo-1H-pyridin-3-yl)-1H-1,6-naphthyridin-4-one |
| 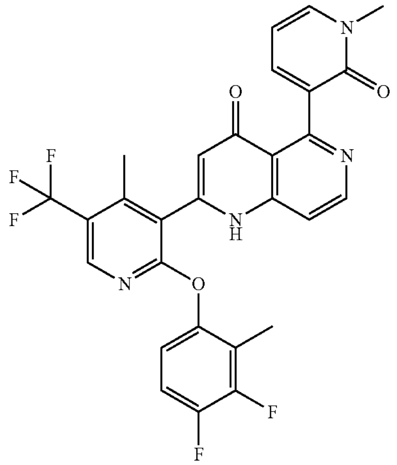 [SMILES: Cc1c(Oc2ncc(C(F)(F)F)c(C)c2-c2cc(=O)c3c(-c4cccn(C)c4=O)nccc3[nH]2)ccc(F)c1F] |
| 2-[2-(3,4-difluoro-2-methyl-phenoxy)-4-methyl-5-(trifluoromethyl)-3-pyridyl]-5-(1-methyl-2-oxo-3-pyridyl)-1H-1,6-naphthyridin-4-one |

TABLE B-continued

| Compound Structures and Names. |
|---|
| 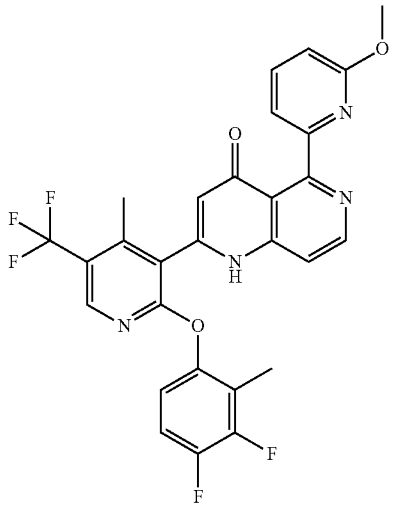 [SMILES: COc1cccc(-c2nccc3[nH]c(-c4c(Oc5ccc(F)c(F)c5C)ncc(C(F)(F)F)c4C)cc(=O)c23)n1] |
| 2-[2-(3,4-difluoro-2-methyl-phenoxy)-4-methyl-5-(trifluoromethyl)-3-pyridyl]-5-(6-methoxy-2-pyridyl)-1H-1,6-naphthyridin-4-one |
| 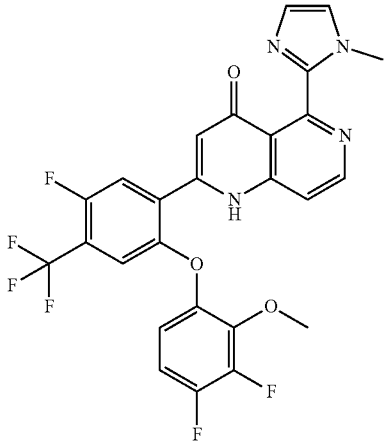 [SMILES: COc1c(Oc2cc(C(F)(F)F)c(F)cc2-c2cc(=O)c3c(-c4nccn4C)nccc3[nH]2)ccc(F)c1F] |
| 2-[2-(3,4-difluoro-2-methoxy-phenoxy)-5-fluoro-4-(trifluoromethyl)phenyl]-5-(1-methylimidazol-2-yl)-1H-1,6-naphthyridin-4- |

TABLE B-continued

| Compound Structures and Names. |
| --- |
| 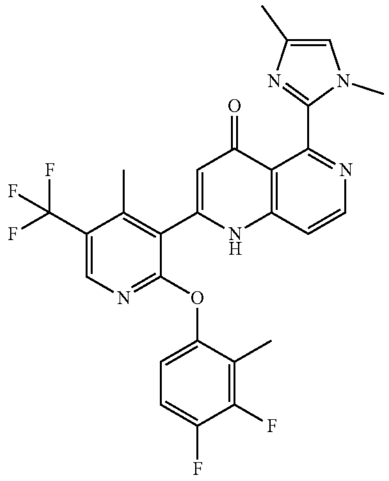 [SMILES: Cc1cn(C)c(-c2nccc3[nH]c(-c4c(Oc5ccc(F)c(F)c5C)ncc(C(F)(F)F)c4C)cc(=O)c23)n1] |
| 2-[2-(3,4-difluoro-2-methyl-phenoxy)-4-methyl-5-(trifluoromethyl)-3-pyridyl]-5-(1,4-dimethyl-imidazol-2-yl)-1H-1,6-naphthyridin-4-one |
| 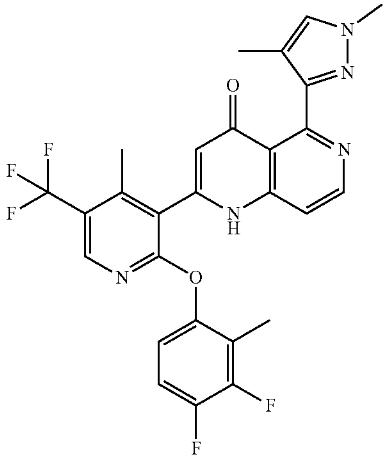 [SMILES: Cc1cn(C)nc1-c1nccc2[nH]c(-c3c(Oc4ccc(F)c(F)c4C)ncc(C(F)(F)F)c3C)cc(=O)c12] |
| 2-[2-(3,4-difluoro-2-methyl-phenoxy)-4-methyl-5-(trifluoromethyl)-3-pyridyl]-5-(1,4-dimethyl-pyrazol-3-yl)-1H-1,6-naphthyridin-4-one |

TABLE B-continued

| Compound Structures and Names. |
| --- |
| 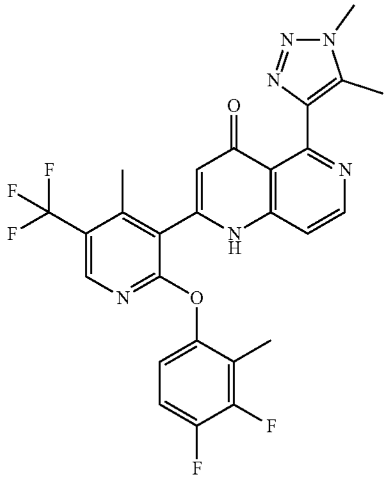 [SMILES: Cc1c(Oc2ncc(C(F)(F)F)c(C)c2-c2cc(=O)c3c(-c4nnn(C)c4C)nccc3[nH]2)ccc(F)c1F] |
| 2-[2-(3,4-difluoro-2-methyl-phenoxy)-4-methyl-5-(trifluoromethyl)-3-pyridyl]-5-(1,5-dimethyl-triazol-4-yl)-1H-1,6-naphthyridin-4-one |
| 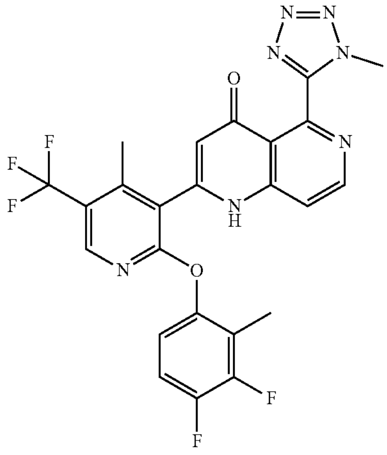 [SMILES: Cc1c(Oc2ncc(C(F)(F)F)c(C)c2-c2cc(=O)c3c(-c4nnnn4C)nccc3[nH]2)ccc(F)c1F] |
| 2-[2-(3,4-difluoro-2-methyl-phenoxy)-4-methyl-5-(trifluoromethyl)-3-pyridyl]-5-(1-methyl-tetrazol-5-yl)-1H-1,6-naphthyridin-4-one |

TABLE B-continued

| Compound Structures and Names. |
|---|
| 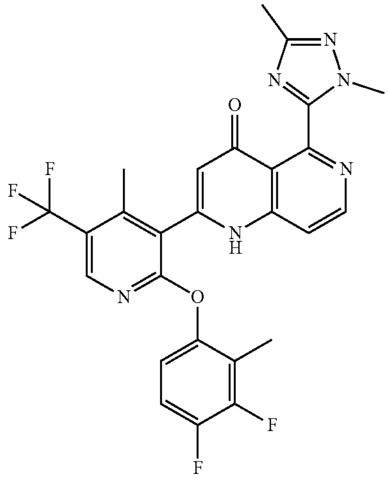 [SMILES: Cc1nc(-c2nccc3[nH]c(-c4c(Oc5ccc(F)c(F)c5C)ncc(C(F)(F)F)c4C)cc(=O)c23)n(C)n1] |
| 2-[2-(3,4-difluoro-2-methyl-phenoxy)-4-methyl-5-(trifluoromethyl)-3-pyridyl]-5-(2,5-dimethyl-1,2,4-triazol-3-yl)-1H-1,6-naphthyridin-4-one |
| 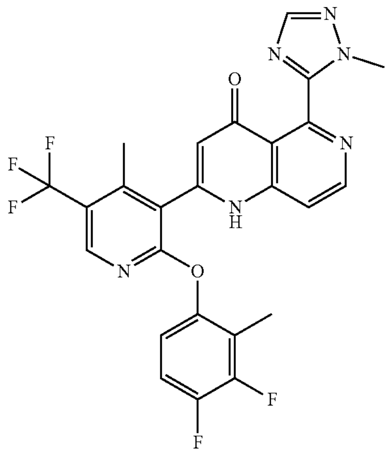 [SMILES: Cc1c(Oc2ncc(C(F)(F)F)c(C)c2-c2cc(=O)c3c(-c4ncnn4C)nccc3[nH]2)ccc(F)c1F] |
| 2-[2-(3,4-difluoro-2-methyl-phenoxy)-4-methyl-5-(trifluoromethyl)-3-pyridyl]-5-(2-methyl-1,2,4-triazol-3-yl)-1H-1,6-naphthyridin-4-one |

TABLE B-continued

| Compound Structures and Names. |
|---|
| 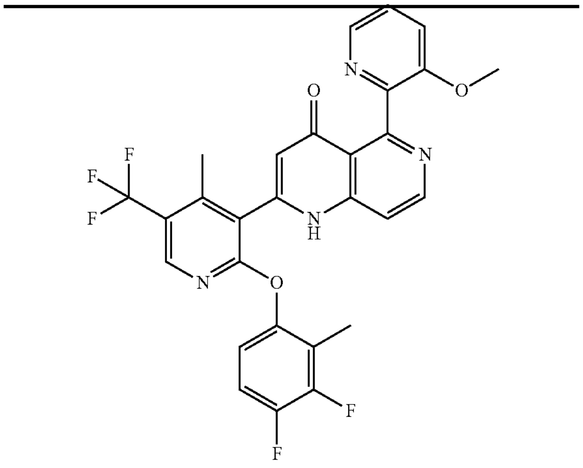 |
| 2-[2-(3,4-difluoro-2-methyl-phenoxy)-4-methyl-5-(trifluoromethyl)-3-pyridyl]-5-(3-methoxy-2-pyridyl)-1H-1,6-naphthyridin-4-one |
| 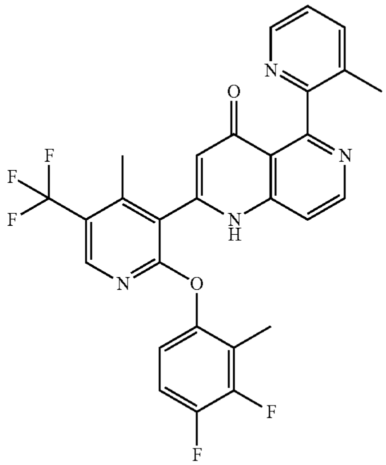 [SMILES: Cc1cccnc1-c1nccc2[nH]c(-c3c(Oc4ccc(F)c(F)c4C)ncc(C(F)(F)F)c3C)cc(=O)c12] |
| 2-[2-(3,4-difluoro-2-methyl-phenoxy)-4-methyl-5-(trifluoromethyl)-3-pyridyl]-5-(3-methyl-2-pyridyl)-1H-1,6-naphthyridin-4-one |
| 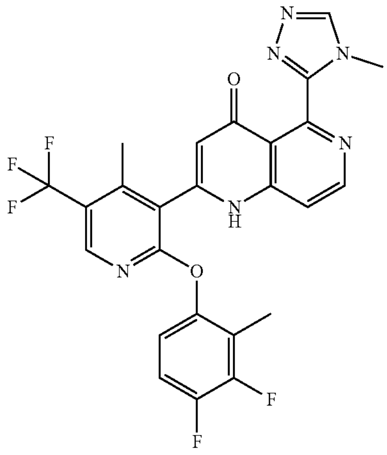 [SMILES: Cc1c(Oc2ncc(C(F)(F)F)c(C)c2-c2cc(=O)c3c(-c4nncn4C)nccc3[nH]2)ccc(F)c1F] |
| 2-[2-(3,4-difluoro-2-methyl-phenoxy)-4-methyl-5-(trifluoromethyl)-3-pyridyl]-5-(4-methyl-1,2,4-triazol-3-yl)-1H-1,6-naphthyridin-4-one |

TABLE B-continued

| Compound Structures and Names. |
| --- |
| 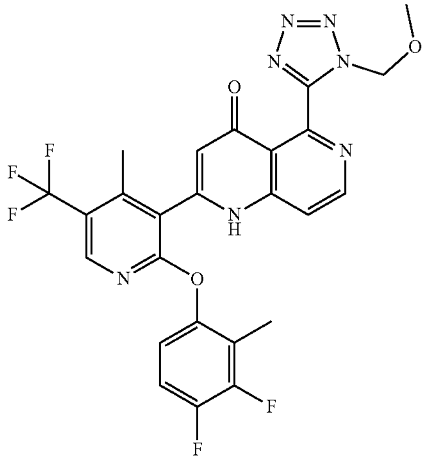 [SMILES: COCn1nnnc1-c1nccc2[nH]c(-c3c(Oc4ccc(F)c(F)c4C)ncc(C(F)(F)F)c3C)cc(=O)c12] |
| 2-[2-(3,4-difluoro-2-methyl-phenoxy)-4-methyl-5-(trifluoromethyl)-3-pyridyl]-5-[1-(methoxy-methyl)tetrazol-5-yl]-1H-1,6-naphthyridin-4-one |
| 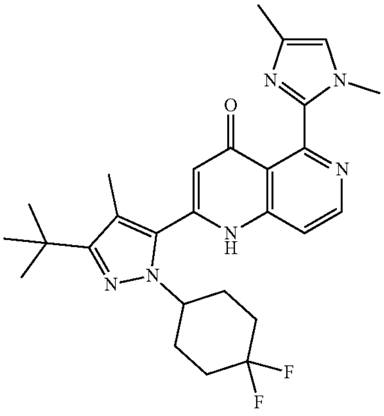 [SMILES: Cc1cn(C)c(-c2nccc3[nH]c(-c4c(C)c(C(C)(C)C)nn4C4CCC(F)(F)CC4)cc(=O)c23)n1] |
| 2-[5-tert-butyl-2-(4,4-difluorocyclohexyl)-4-methyl-pyrazol-3-yl]-5-(1,4-dimethylimidazol-2-yl)-1H-1,6-naphthyridin-4-one |
| 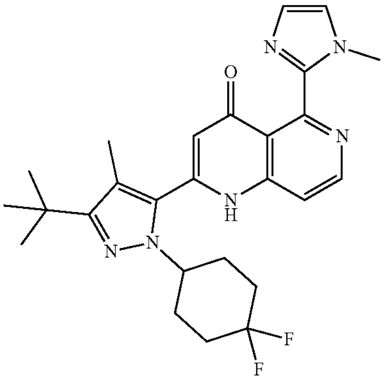 [SMILES: Cc1c(C(C)(C)C)nn(C2CCC(F)(F)CC2)c1-c1cc(=O)c2c(-c3nccn3C)nccc2[nH]1] |
| 2-[5-tert-butyl-2-(4,4-difluorocyclohexyl)-4-methyl-pyrazol-3-yl]-5-(1-methylimidazol-2-yl)-1H-1,6-naphthyridin-4-one |

TABLE B-continued

| Compound Structures and Names. |
| --- |
| 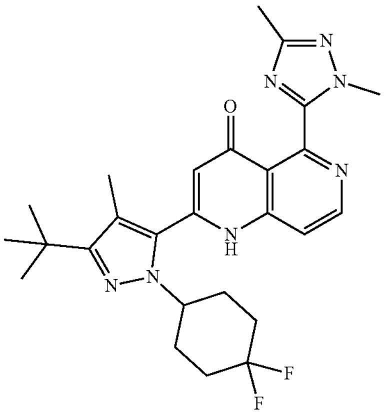 [SMILES: Cc1nc(-c2nccc3[nH]c(-c4c(C)c(C(C)(C)C)nn4C4CCC(F)(F)CC4)cc(=O)c23)n(C)n1] |
| 2-[5-tert-butyl-2-(4,4-difluorocyclohexyl)-4-methyl-pyrazol-3-yl]-5-(2,5-dimethyl-1,2,4-triazol-3-yl)-1H-1,6-naphthyridin-4-one |
| 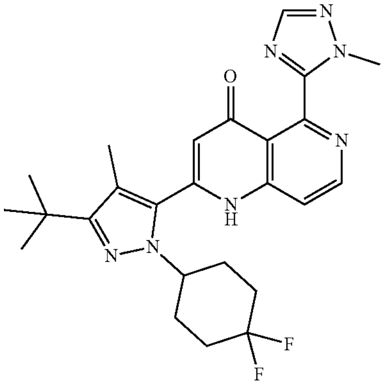 [SMILES: Cc1c(C(C)(C)C)nn(C2CCC(F)(F)CC2)c1-c1cc(=O)c2c(-c3ncnn3C)nccc2[nH]1] |
| 2-[5-tert-butyl-2-(4,4-difluorocyclohexyl)-4-methyl-pyrazol-3-yl]-5-(2-methyl-1,2,4-triazol-3-yl)-1H-1,6-naphthyridin-4-one |
| 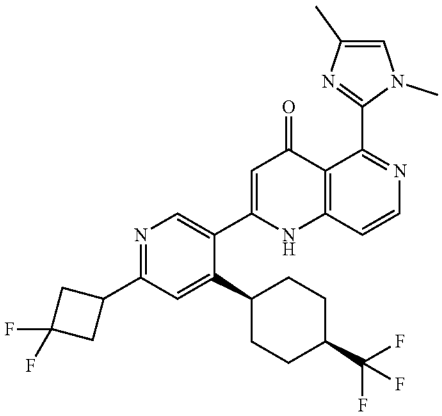 [SMILES: Cc1cn(C)c(-c2nccc3[nH]c(-c4cnc(C5CC(F)(F)C5)cc4[C@H]4CC[C@@H](C(F)(F)F)CC4)cc(=O)c23)n1] |
| 2-[6-(3,3-difluorocyclobutyl)-4-[4-(trifluoromethyl)-cyclohexyl]-3-pyridyl]-5-(1,4-dimethylimidazol-2-yl)-1H-1,6-naphthyridin-4-one (cis isomer) |

TABLE B-continued

| Compound Structures and Names. |
|---|
| 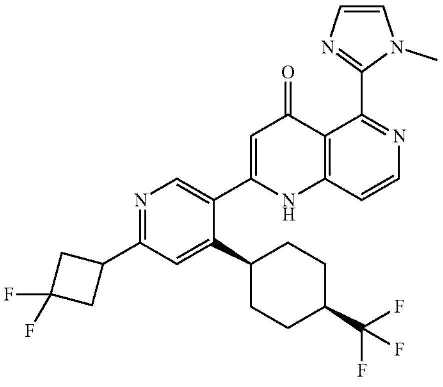 [SMILES: Cn1ccnc1-c1nccc2[nH]c(-c3cnc(C4CC(F)(F)C4)cc3[C@H]3CC[C@@H](C(F)(F)F)CC3)cc(=O)c12] 2-[6-(3,3-difluorocyclobutyl)-4-[4-(trifluoro-methyl)cyclohexyl]-3-pyridyl]-5-(1-methyl-imidazol-2-yl)-1H-1,6-naphthyridin-4-one (cis isomer) |
| 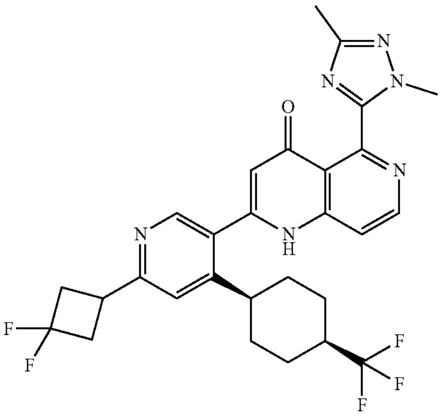 [SMILES: Cc1nc(-c2nccc3[nH]c(-c4cnc(C5CC(F)(F)C5)cc4[C@H]4CC[C@@H](C(F)(F)F)CC4)cc(=O)c23)n(C)n1] 2-[6-(3,3-difluorocyclobutyl)-4-[4-(trifluoro-methyl)cyclohexyl]-3-pyridyl]-5-(2,5-dimethyl-1,2,4-triazol-3-yl)-1H-1,6-naphthyridin-4-one (cis isomer) |
| 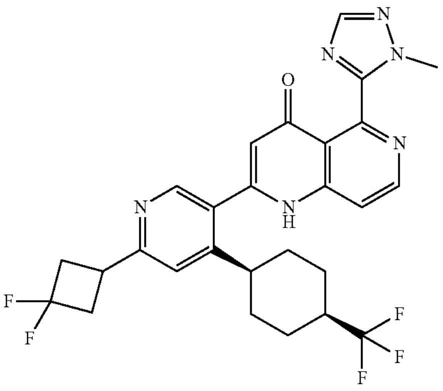 [SMILES: Cn1ncnc1-c1nccc2[nH]c(-c3cnc(C4CC(F)(F)C4)cc3[C@H]3CC[C@@H](C(F)(F)F)CC3)cc(=O)c12] 2-[6-(3,3-difluorocyclobutyl)-4-[4-(trifluoro-methyl)cyclohexyl]-3-pyridyl]-5-(2-methyl-1,2,4-triazol-3-yl)-1H-1,6-naphthyridin-4-one (cis isomer) |

TABLE B-continued

| Compound Structures and Names. |
|---|
| 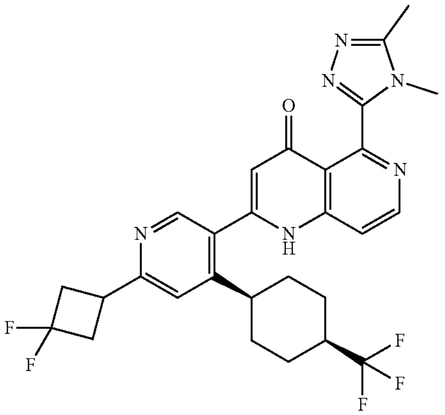 [SMILES: Cc1nnc(-c2nccc3[nH]c(-c4cnc(C5CC(F)(F)C5)cc4[C@H]4CC[C@@H](C(F)(F)F)CC4)cc(=O)c23)n1C] 2-[6-(3,3-difluorocyclobutyl)-4-[4-(trifluoromethyl)-cyclohexyl]-3-pyridyl]-5-(4,5dimethyl-1,2,4-triazol-3-yl)-1H-1,6-naphthyridin-4-one (cis isomer) |
| 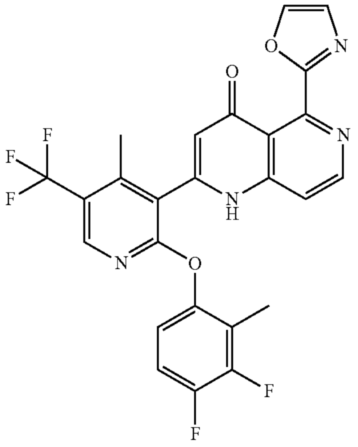 [SMILES: Cc1c(Oc2ncc(C(F)(F)F)c(C)c2-c2cc(=O)c3c(-c4ncco4)nccc3[nH]2)ccc(F)c1F] 2-[2-(3,4-difluoro-2-methyl-phenoxy)-4-methyl-5-(trifluoromethyl)-3-pyridyl]-5-oxazol-2-yl-1H-1,6-naphthyridin-4-one |
| 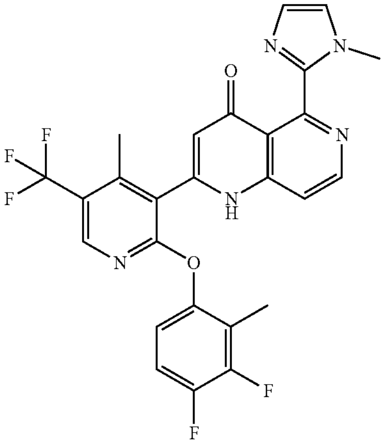 [SMILES: Cc1c(Oc2ncc(C(F)(F)F)c(C)c2-c2cc(=O)c3c(-c4nccn4C)nccc3[nH]2)ccc(F)c1F] 2-[2-(3,4-difluoro-2-methyl-phenoxy)-4-methyl-5-(trifluoromethyl)-3-pyridyl]-5-(1-methyl-imidazol-2-yl)-1H-1,6-naphthyridin-4-one |

Compound Structures and Names.

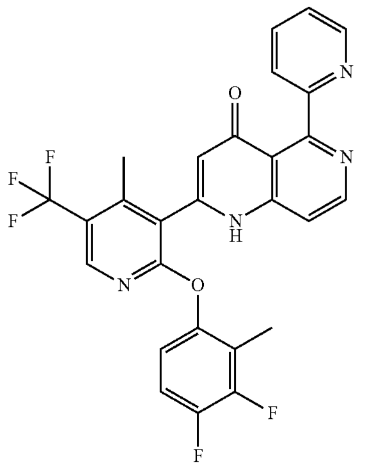 [SMILES: Cc1c(Oc2ncc(C(F)(F)F)c(C)c2-c2cc(=O)c3c(-c4ccccn4)nccc3[nH]2)ccc(F)c1F]

2-[2-(3,4-difluoro-2-methyl-phenoxy)-4-methyl-5-(trifluoromethyl)-3-pyridyl]-5-(2-pyridyl)-1H-1,6-naphthyridin-4-one

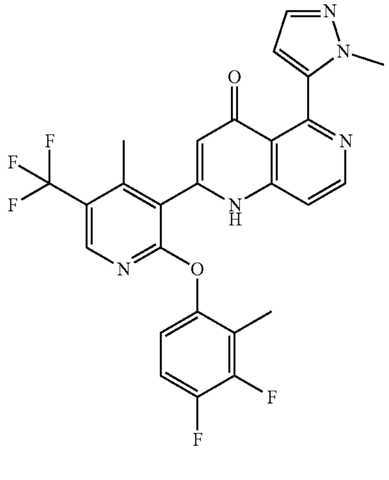 [SMILES: Cc1c(Oc2ncc(C(F)(F)F)c(C)c2-c2cc(=O)c3c(-c4ccnn4C)nccc3[nH]2)ccc(F)c1F]

2-[2-(3,4-difluoro-2-methyl-phenoxy)-4-methyl-5-(trifluoromethyl)-3-pyridyl]-5-(2-methyl-pyrazol-3-yl)-1H-1,6-naphthyridin-4-one Compound Structures and Names.

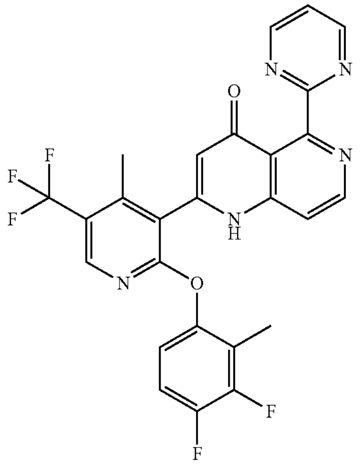 [SMILES: Cc1c(Oc2ncc(C(F)(F)F)c(C)c2-c2cc(=O)c3c(-c4ncccn4)nccc3[nH]2)ccc(F)c1F]

2-[2-(3,4-difluoro-2-methyl-phenoxy)-4-methyl-5-(trifluoromethyl)-3-pyridyl]-5-pyrimidin-2-yl-1H-1,6-naphthyridin-4-one

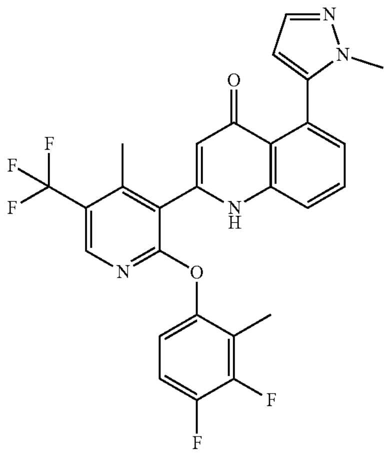 [SMILES: Cc1c(Oc2ncc(C(F)(F)F)c(C)c2-c2cc(=O)c3c(-c4ccnn4C)cccc3[nH]2)ccc(F)c1F]

2-[2-(3,4-difluoro-2-methyl-phenoxy)-4-methyl-5-(trifluoromethyl)-3-pyridyl]-5-(2-methyl-pyrazol-3-yl)-1H-quinolin-4-one

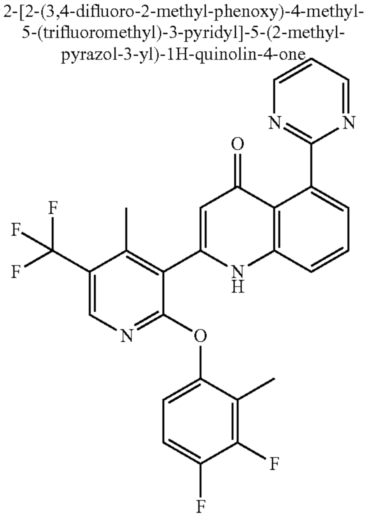

2-[2-(3,4-difluoro-2-methyl-phenoxy)-4-methyl-5-(trifluoromethyl)-3-pyridyl]-5-pyrimidin-2-yl-1H-quinolin-4-one TABLE B-continued

| Compound Structures and Names. |
|---|
| 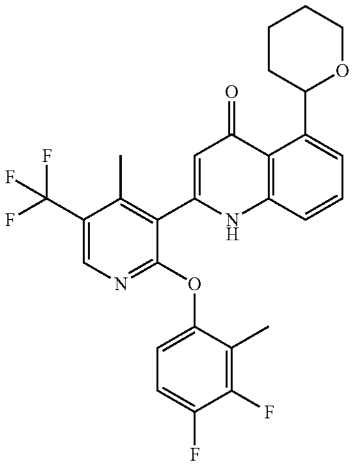 [SMILES: Cc1c(Oc2ncc(C(F)(F)F)c(C)c2-c2cc(=O)c3c(C4CCCCO4)cccc3[nH]2)ccc(F)c1F] |
| 2-[2-(3,4-difluoro-2-methyl-phenoxy)-4-methyl-5-(trifluoromethyl)-3-pyridyl]-5-tetrahydropyran-2-yl-1H-quinolin-4-one |
| 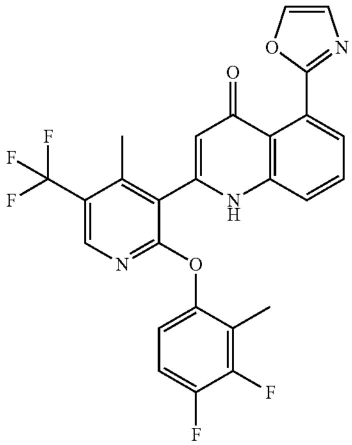 [SMILES: Cc1c(Oc2ncc(C(F)(F)F)c(C)c2-c2cc(=O)c3c(-c4ncco4)cccc3[nH]2)ccc(F)c1F] |
| 2-[2-(3,4-difluoro-2-methyl-phenoxy)-4-meth yl-5-(trifluoromethyl)-3-pyridyl]-5-oxazol-2-yl-1H-quinolin-4-one |

TABLE B-continued

| Compound Structures and Names. |
|---|
| 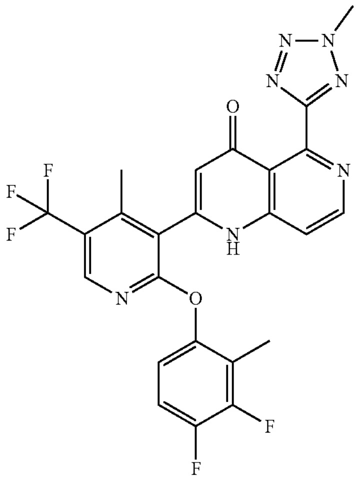 [SMILES: Cc1c(Oc2ncc(C(F)(F)F)c(C)c2-c2cc(=O)c3c(-c4nnn(C)n4)nccc3[nH]2)ccc(F)c1F] |
| 2-[2-(3,4-difluoro-2-methyl-phenoxy)-4-methyl-5-(trifluoromethyl)-3-pyridyl]-5-(2-methyl-tetrazol-5-yl)-1H-1,6-naphthyridin-4-one |
| 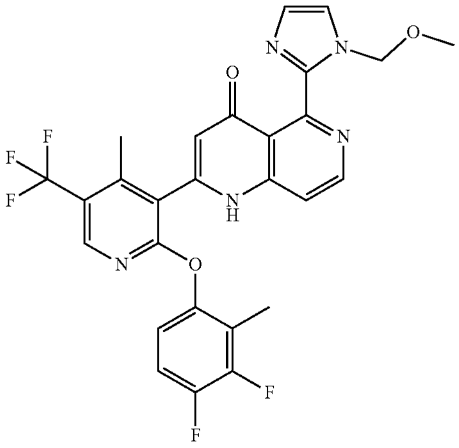 [SMILES: COCn1ccnc1-c1nccc2[nH]c(-c3c(Oc4ccc(F)c(F)c4C)ncc(C(F)(F)F)c3C)cc(=O)c12] |
| 2-[2-(3,4-difluoro-2-methyl-phenoxy)-4-methyl-5-(trifluoromethyl)-3-pyridyl]-5-[1-(methoxymethyl)imidazol-2-yl]-1H-1,6-naphthyridin-4-one |

TABLE B-continued

| Compound Structures and Names. |
| --- |
| 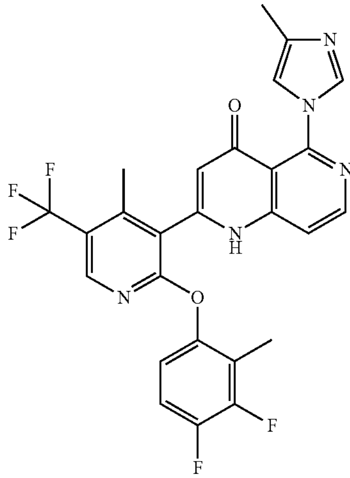 [SMILES: Cc1cn(-c2nccc3[nH]c(-c4c(Oc5ccc(F)c(F)c5C)ncc(C(F)(F)F)c4C)cc(=O)c23)cn1] |
| 2-[2-(3,4-difluoro-2-methyl-phenoxy)-4-methyl-5-(trifluoromethyl)-3-pyridyl]-5-(4-methyl-imidazol-1-yl)-1H-1,6-naphthyridin-4-one |
| 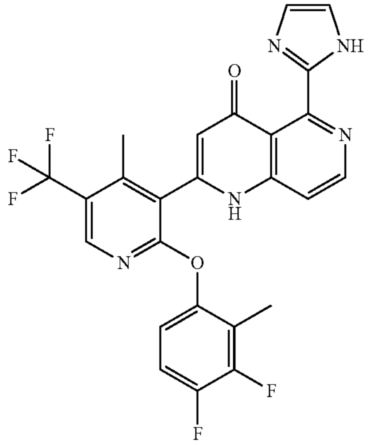 [SMILES: Cc1c(Oc2ncc(C(F)(F)F)c(C)c2-c2cc(=O)c3c(-c4ncc[nH]4)nccc3[nH]2)ccc(F)c1F] |
| 2-[2-(3,4-difluoro-2-methyl-phenoxy)-4-methyl-5-(trifluoromethyl)-3-pyridyl]-5-(1H-imidazol-2-yl)-1H-1,6-naphthyridin-4-one |
| 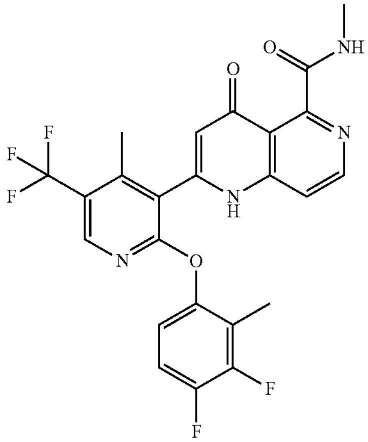 [SMILES: CNC(=O)c1nccc2[nH]c(-c3c(Oc4ccc(F)c(F)c4C)ncc(C(F)(F)F)c3C)cc(=O)c12] |
| 2-[2-(3,4-difluoro-2-methyl-phenoxy)-4-methyl-5-(trifluoromethyl)-3-pyridyl]-N-methyl-4-oxo-1H-1,6-naphthyridine-5-carboxamide |

TABLE B-continued

| Compound Structures and Names. |
| --- |
| 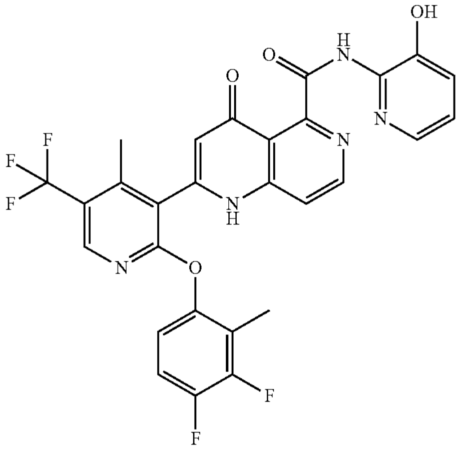 [SMILES: Cc1c(Oc2ncc(C(F)(F)F)c(C)c2-c2cc(=O)c3c(C(=O)Nc4ncccc4O)nccc3[nH]2)ccc(F)c1F] |
| 2-[2-(3,4-difluoro-2-methyl-phenoxy)-4-methyl-5-(trifluoromethyl)-3-pyridyl]-N-(3-hydroxy-2-pyridyl)-4-oxo-1H-1,6-naphthyridine-5-carboxamide |
| 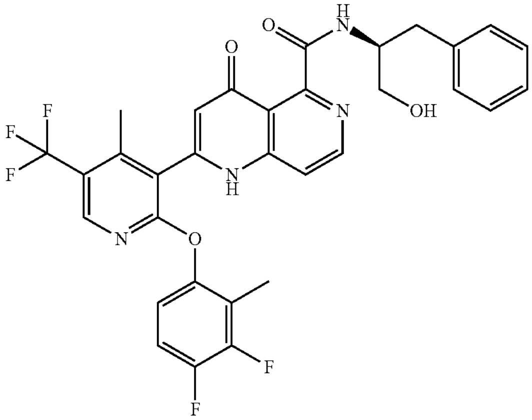 [SMILES: Cc1c(Oc2ncc(C(F)(F)F)c(C)c2-c2cc(=O)c3c(C(=O)N[C@H](CO)Cc4ccccc4)nccc3[nH]2)ccc(F)c1F] |
| N-[(1S)-1-benzyl-2-hydroxy-ethyl]-2-[2-(3,4-difluoro-2-methyl-phenoxy)-4-methyl-5-(trifluoromethyl)-3-pyridyl]-4-oxo-1H-1,6-naphthyridine-5-carboxamide |
| 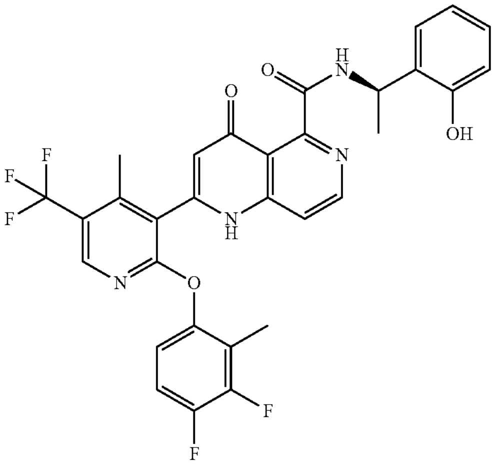 [SMILES: Cc1c(Oc2ncc(C(F)(F)F)c(C)c2-c2cc(=O)c3c(C(=O)N[C@H](C)c4ccccc4O)nccc3[nH]2)ccc(F)c1F] |
| 2-[2-(3,4-difluoro-2-methyl-phenoxy)-4-methyl-5-(trifluoromethyl)-3-pyridyl]-N-[(1R)-1-(2-hydroxyphenyl)ethyl]-4-oxo-1H-1,6-naphthyridine-5-carboxamide |

TABLE B-continued

| Compound Structures and Names. |
| --- |
| 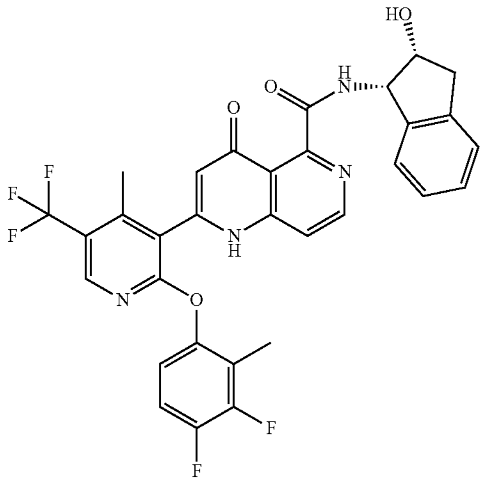 [SMILES: Cc1c(Oc2ncc(C(F)(F)F)c(C)c2-c2cc(=O)c3c(C(=O)N[C@H]4c5ccccc5C[C@H]4O)nccc3[nH]2)ccc(F)c1F] |
| 2-[2-(3,4-difluoro-2-methyl-phenoxy)-4-methyl-5-(trifluoro-methyl)-3-pyridyl]-N-[(1S,2R)-2-hydroxyindan-1-yl]-4-oxo-1H-1,6-naphthyridine-5-carboxamide |
| 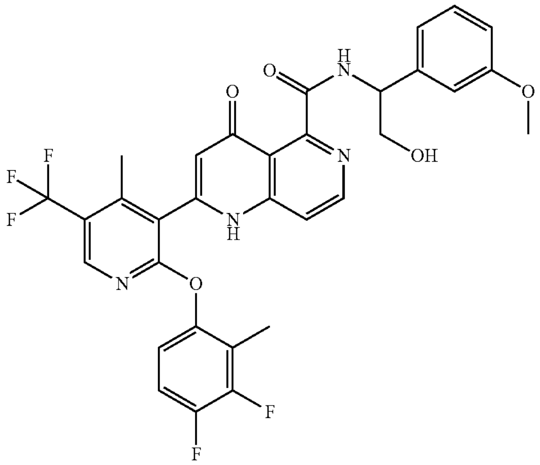 [SMILES: COc1cccc(C(CO)NC(=O)c2nccc3[nH]c(-c4c(Oc5ccc(F)c(F)c5C)ncc(C(F)(F)F)c4C)cc(=O)c23)c1] |
| 2-[2-(3,4-difluoro-2-methyl-phenoxy)-4-methyl-5-(trifluoro methyl)-3-pyridyl]-N-[2-hydroxy-1-(3-methoxyphenyl)-ethyl]-4-oxo-1H-1,6-naphthyridine-5-carboxamide |

TABLE B-continued

| Compound Structures and Names. |
| --- |
| 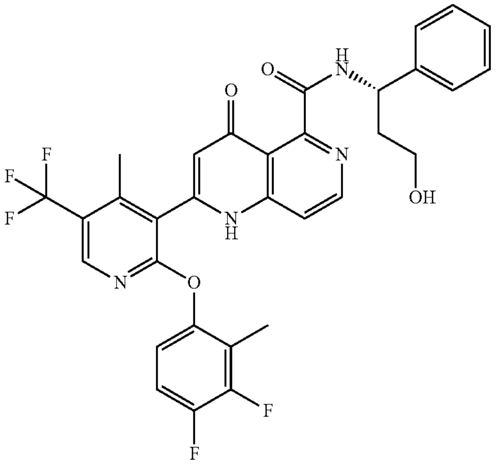 [SMILES: Cc1c(Oc2ncc(C(F)(F)F)c(C)c2-c2cc(=O)c3c(C(=O)N[C@@H](CCO)c4ccccc4)nccc3[nH]2)ccc(F)c1F] |
| 2-[2-(3,4-difluoro-2-methyl-phenoxy)-4-methyl-5-(trifluoro-methyl)-3-pyridyl]-N-[(1S)-3-hydroxy-1-phenyl-propyl]-4-oxo-1H-1,6-naphthyridine-5-carboxamide |
| 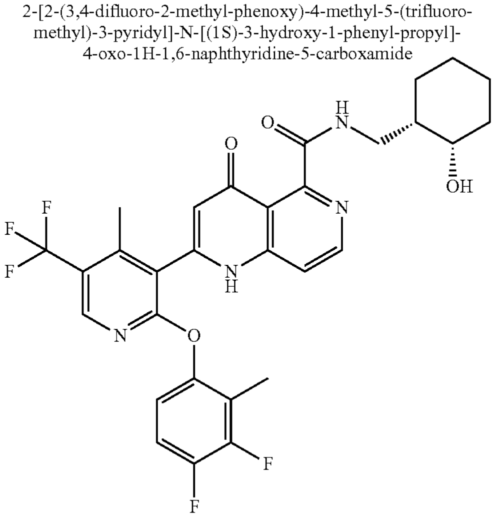 |
| 2-[2-(3,4-difluoro-2-methyl-phenoxy)-4-methyl-5-(trifluoro-methyl)-3-pyridyl]-N-[[(1S,2S)-2-hydroxycyclohexyl]-methyl]-4-oxo-1H-1,6-naphthyridine-5-carboxamide |
| 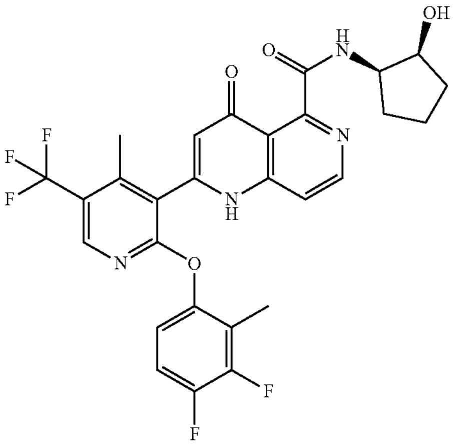 [SMILES: Cc1c(Oc2ncc(C(F)(F)F)c(C)c2-c2cc(=O)c3c(C(=O)N[C@@H]4CCC[C@@H]4O)nccc3[nH]2)ccc(F)c1F] |
| 2-[2-(3,4-difluoro-2-methyl-phenoxy)-4-methyl-5-(trifluoromethyl)-3-pyridyl]-N-[(1R,2S)-2-hydroxy-cyclopentyl]-4-oxo-1H-1,6-naphthyridine-5-carboxamide |

TABLE B-continued

| Compound Structures and Names. |
| --- |
| 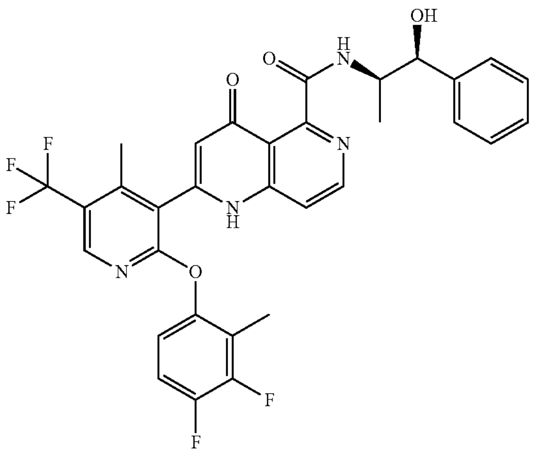 [SMILES: Cc1c(Oc2ncc(C(F)(F)F)c(C)c2-c2cc(=O)c3c(C(=O)N[C@H](C)[C@@H](O)c4ccccc4)nccc3[nH]2)ccc(F)c1F] |
| 2-[2-(3,4-difluoro-2-methyl-phenoxy)-4-methyl-5-(trifluoro-methyl)-3-pyridyl]-N-[(1R,2S)-2-hydroxy-1-methyl-2-phenyl-ethyl]-4-oxo-1H-1,6-naphthyridine-5-carboxamide |
| 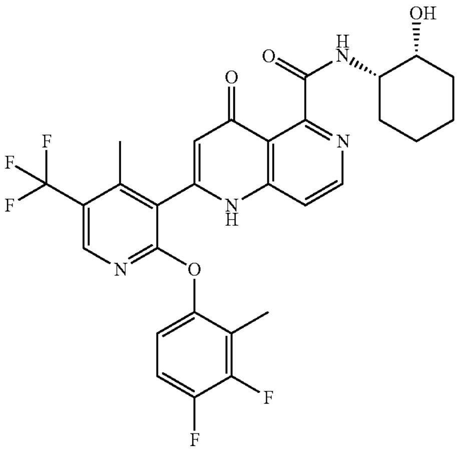 [SMILES: Cc1c(Oc2ncc(C(F)(F)F)c(C)c2-c2cc(=O)c3c(C(=O)N[C@H]4CCCC[C@H]4O)nccc3[nH]2)ccc(F)c1F] |
| 2-[2-(3,4-difluoro-2-methyl-phenoxy)-4-methyl-5-(trifluoromethyl)-3-pyridyl]-N-[(1S,2R)-2-hydroxy-cyclohexyl]-4-oxo-1H-1,6-naphthyridine-5-carboxamide |

TABLE B-continued

| Compound Structures and Names. |
| --- |
| 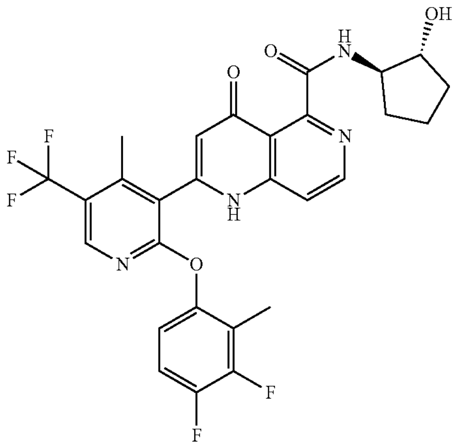 [SMILES: Cc1c(Oc2ncc(C(F)(F)F)c(C)c2-c2cc(=O)c3c(C(=O)N[C@@H]4CCC[C@H]4O)nccc3[nH]2)ccc(F)c1F] |
| 2-[2-(3,4-difluoro-2-methyl-phenoxy)-4-methyl-5-(trifluoromethyl)-3-pyridyl]-N-[(1R,2R)-2-hydroxy-cyclopentyl]-4-oxo-1H-1,6-naphthyridine-5-carboxamide |
| 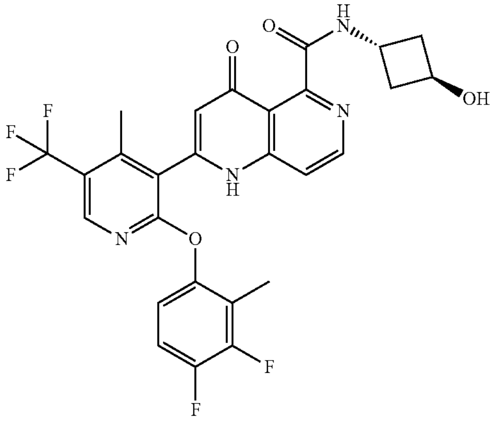 [SMILES: Cc1c(Oc2ncc(C(F)(F)F)c(C)c2-c2cc(=O)c3c(C(=O)N[C@H]4C[C@H](O)C4)nccc3[nH]2)ccc(F)c1F] |
| 2-[2-(3,4-difluoro-2-methyl-phenoxy)-4-methyl-5-(trifluoro-methyl)-3-pyridyl]-N-(3-hydroxycyclobutyl)-4-oxo-1H-1,6-naphthyridine-5-carboxamide (trans isomer) |
| 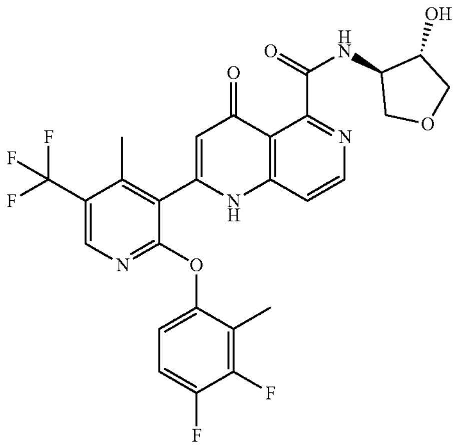 [SMILES: Cc1c(Oc2ncc(C(F)(F)F)c(C)c2-c2cc(=O)c3c(C(=O)N[C@@H]4COC[C@H]4O)nccc3[nH]2)ccc(F)c1F] |
| 2-[2-(3,4-difluoro-2-methyl-phenoxy)-4-methyl-5-(trifluoromethyl)-3-pyridyl]-N-[(3R,4S)-4-hydroxy-tetrahydrofuran-3-yl]-4-oxo-1H-1,6-naphthyridine-5-carboxamide |

TABLE B-continued

Compound Structures and Names.

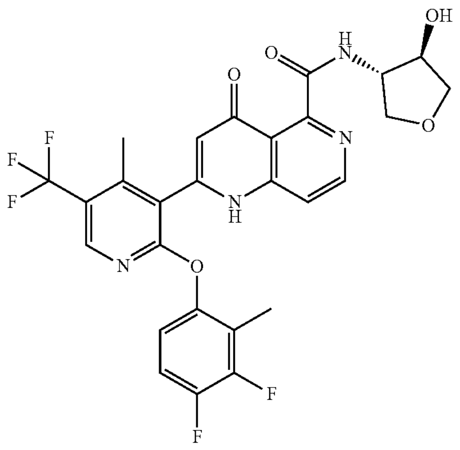 [SMILES: Cc1c(Oc2ncc(C(F)(F)F)c(C)c2-c2cc(=O)c3c(C(=O)N[C@H]4COC[C@@H]4O)nccc3[nH]2)ccc(F)c1F]

2-[2-(3,4-difluoro-2-methyl-phenoxy)-4-methyl-5-(trifluoromethyl)-3-pyridyl]-N-[(3S,4R)-4-hydroxy-tetrahydrofuran-3-yl]-4-oxo-1H-1,6-naphthyridine-5-carboxamide

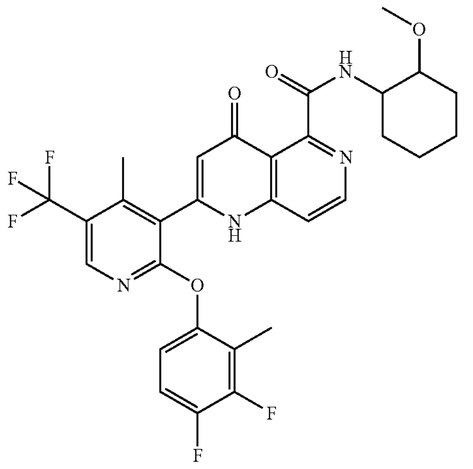 [SMILES: COC1CCCCC1NC(=O)c1nccc2[nH]c(-c3c(Oc4ccc(F)c(F)c4C)ncc(C(F)(F)F)c3C)cc(=O)c12]

2-[2-(3,4-difluoro-2-methyl-phenoxy)-4-methyl-5-(trifluoromethyl)-3-pyridyl]-N-(2-methoxycyclohexyl)-4-oxo-1H-1,6-naphthyridine-5-carboxamide TABLE B-continued Compound Structures and Names.

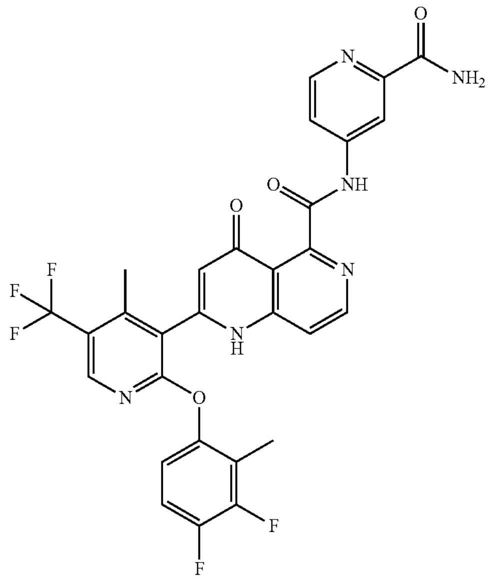 [SMILES: Cc1c(Oc2ncc(C(F)(F)F)c(C)c2-c2cc(=O)c3c(C(=O)Nc4ccnc(C(N)=O)c4)nccc3[nH]2)ccc(F)c1F]

N-(2-carbamoyl-4-pyridyl)-2-[2-(3,4-difluoro-2-methyl-phenoxy)-4-methyl-5-(trifluoromethyl)-3-pyridyl]-4-oxo-1H-1,6-naphthyridine-5-carboxamide

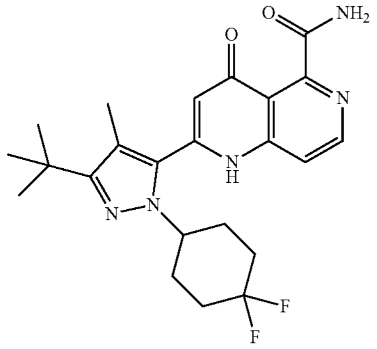 [SMILES: Cc1c(C(C)(C)C)nn(C2CCC(F)(F)CC2)c1-c1cc(=O)c2c(C(N)=O)nccc2[nH]1]

2-[5-tert-butyl-2-(4,4-difluorocyclohexyl)-4-methyl-pyrazol-3-yl]-4-oxo-1H-1,6-naphthyridine-5-carboxamide

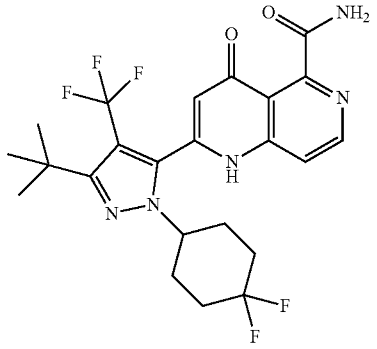 [SMILES: CC(C)(C)c1nn(C2CCC(F)(F)CC2)c(-c2cc(=O)c3c(C(N)=O)nccc3[nH]2)c1C(F)(F)F]

2-[5-tert-butyl-2-(4,4-difluorocyclohexyl)-4-(trifluoromethyl)pyrazol-3-yl]-4-oxo-1H-1,6-naphthyridine-5-carboxamide TABLE B-continued

| Compound Structures and Names. |
| --- |
| 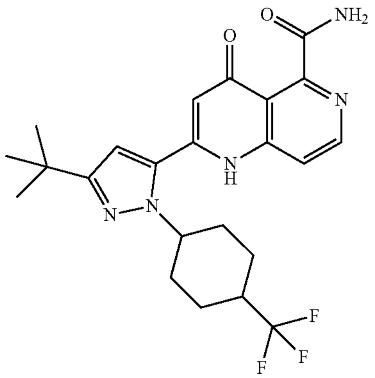 [SMILES: CC(C)(C)c1cc(-c2cc(=O)c3c(C(N)=O)nccc3[nH]2)n(C2CCC(C(F)(F)F)CC2)n1] |
| 2-[5-tert-butyl-2-[4-(trifluoromethyl)cyclohexyl]pyrazol-3-yl]-4-oxo-1H-1,6-naphthyridine-5-carboxamide |
| 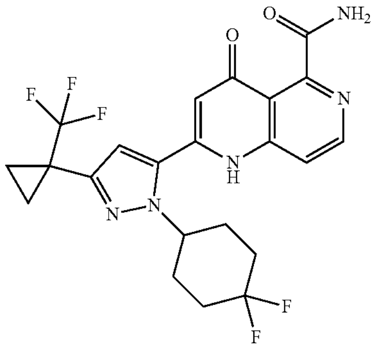 [SMILES: NC(=O)c1nccc2[nH]c(-c3cc(C4(C(F)(F)F)CC4)nn3C3CCC(F)(F)CC3)cc(=O)c12] |
| 2-[2-(4,4-difluorocyclohexyl)-5-[1-(trifluoromethyl)cyclopropyl]pyrazol-3-yl]-4-oxo-1H-1,6-naphthyridine-5-carboxamide |
| 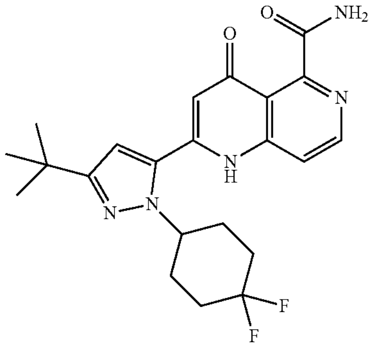 [SMILES: CC(C)(C)c1cc(-c2cc(=O)c3c(C(N)=O)nccc3[nH]2)n(C2CCC(F)(F)CC2)n1] |
| 2-[5-tert-butyl-2-(4,4-difluorocyclohexyl)-pyrazol-3-yl]-4-oxo-1H-1,6-naphthyridine-5-carboxamide |

TABLE B-continued

| Compound Structures and Names. |
| --- |
| 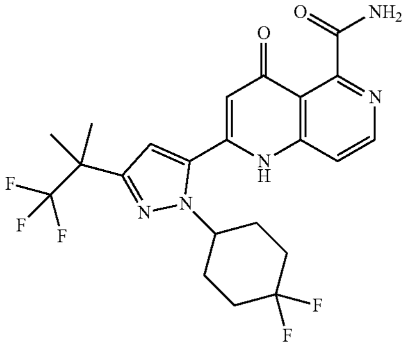 [SMILES: CC(C)(c1cc(-c2cc(=O)c3c(C(N)=O)nccc3[nH]2)n(C2CCC(F)(F)CC2)n1)C(F)(F)F] |
| 2-[2-(4,4-difluorocyclohexyl)-5-(2,2,2-trifluoro-1,1-dimethyl-ethyl)pyrazol-3-yl]-4-oxo-1H-1,6-naphthyridine-5-carboxamide |
| 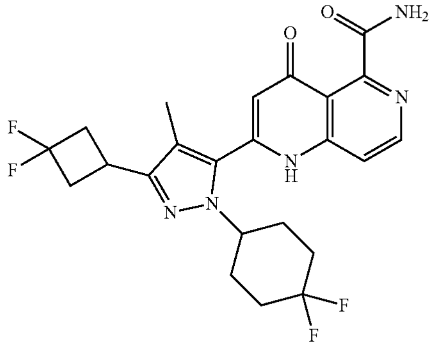 [SMILES: Cc1c(C2CC(F)(F)C2)nn(C2CCC(F)(F)CC2)c1-c1cc(=O)c2c(C(N)=O)nccc2[nH]1] |
| 2-[5-(3,3-difluorocyclobutyl)-2-(4,4-difluorocyclohexyl)-4-methyl-pyrazol-3-yl]-4-oxo-1H-1,6-naphthyridine-5-carboxamide |
| 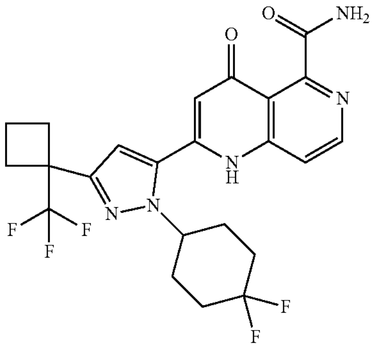 [SMILES: NC(=O)c1nccc2[nH]c(-c3cc(C4(C(F)(F)F)CCC4)nn3C3CCC(F)(F)CC3)cc(=O)c12] |
| 2-[2-(4,4-difluorocyclohexyl)-5-[1-(trifluoromethyl)cyclobutyl]pyrazol-3-yl]-4-oxo-1H-1,6-naphthyridine-5-carboxamide |

TABLE B-continued

Compound Structures and Names.

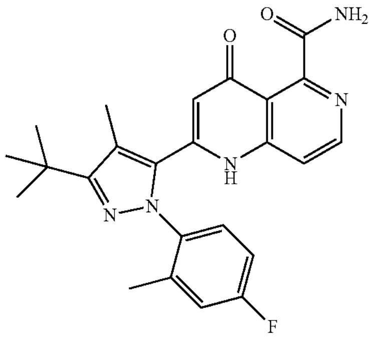 [SMILES: Cc1cc(F)ccc1-n1nc(C(C)(C)C)c(C)c1-c1cc(=O)c2c(C(N)=O)nccc2[nH]1]

2-[5-tert-butyl-2-(4-fluoro-2-methyl-phenyl)-4-methyl-pyrazol-3-yl]-4-oxo-1H-1,6-naphthyridine-5-carboxamide

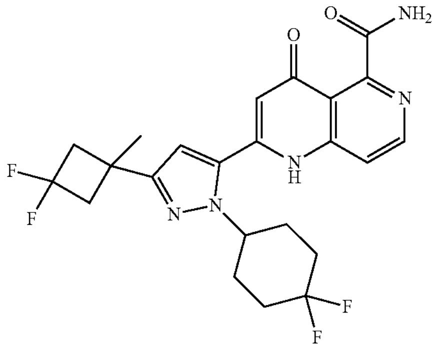 [SMILES: CC1(c2cc(-c3cc(=O)c4c(C(N)=O)nccc4[nH]3)n(C3CCC(F)(F)CC3)n2)CC(F)(F)C1]

2-[2-(4,4-difluorocyclohexyl)-5-(3,3-difluoro-1-methyl-cyclobutyl)pyrazol-3-yl]-4-oxo-1H-1,6-naphthyridine-5-carboxamide

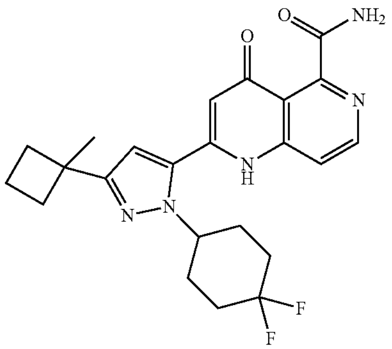 [SMILES: CC1(c2cc(-c3cc(=O)c4c(C(N)=O)nccc4[nH]3)n(C3CCC(F)(F)CC3)n2)CCC1]

2-[2-(4,4-difluorocyclohexyl)-5-(1-methylcyclobutyl)pyrazol-3-yl]-4-oxo-1H-1,6-naphthyridine-5-carboxamide TABLE B-continued Compound Structures and Names.

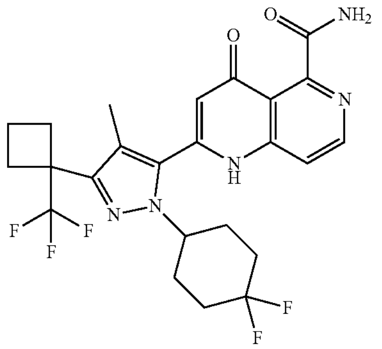 [SMILES: Cc1c(C2(C(F)(F)F)CCC2)nn(C2CCC(F)(F)CC2)c1-c1cc(=O)c2c(C(N)=O)nccc2[nH]1]

2-[2-(4,4-difluorocyclohexyl)-4-methyl-5-[1-(trifluoromethyl)cyclobutyl]pyrazol-3-yl]-4-oxo-1H-1,6-naphthyridine-5-carboxamide

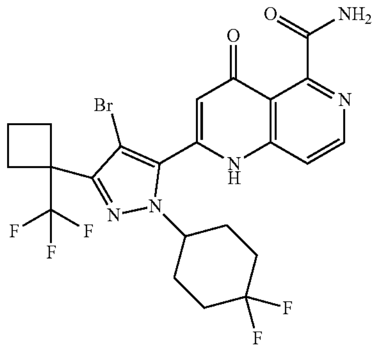 [SMILES: NC(=O)c1nccc2[nH]c(-c3c(Br)c(C4(C(F)(F)F)CCC4)nn3C3CCC(F)(F)CC3)cc(=O)c12]

2-[4-bromo-2-(4,4-difluorocyclohexyl)-5-[1-(trifluoromethyl)cyclobutyl]pyrazol-3-yl]-4-oxo-1H-1,6-naphthyridine-5-carboxamide

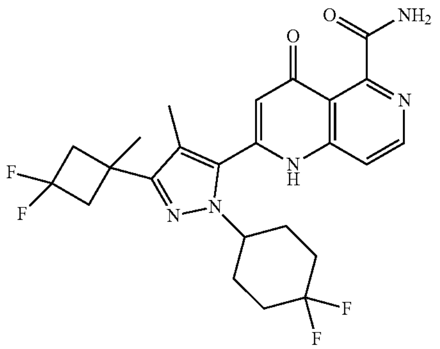 [SMILES: Cc1c(C2(C)CC(F)(F)C2)nn(C2CCC(F)(F)CC2)c1-c1cc(=O)c2c(C(N)=O)nccc2[nH]1]

2-[2-(4,4-difluorocyclohexyl)-5-(3,3-difluoro-1-methyl-cyclobutyl)-4-methyl-pyrazol-3-yl]-4-oxo-1H-1,6-naphthyridine-5-carboxamide TABLE B-continued

| Compound Structures and Names. |
|---|
| 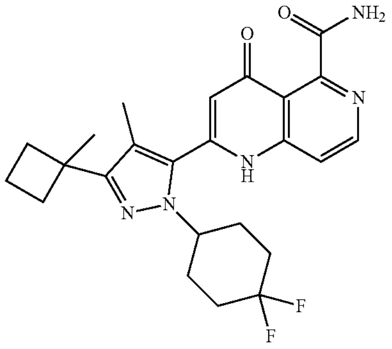 [SMILES: Cc1c(C2(C)CCC2)nn(C2CCC(F)(F)CC2)c1-c1cc(=O)c2c(C(N)=O)nccc2[nH]1] |
| 2-[2-(4,4-difluorocyclohexyl)-4-methyl-5-(1-methylcyclobutyl)pyrazol-3-yl]-4-oxo-1H-1,6-naphthyridine-5-carboxamide |
| 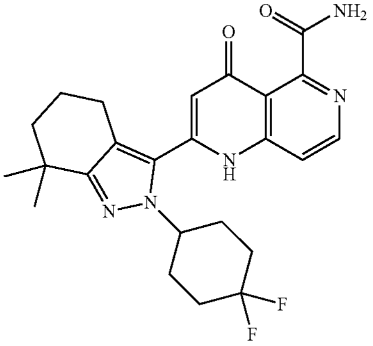 [SMILES: CC1(C)CCCc2c1nn(C1CCC(F)(F)CC1)c2-c1cc(=O)c2c(C(N)=O)nccc2[nH]1] |
| 2-[2-(4,4-difluorocyclohexyl)-7,7-dimethyl-5,6-dihydro-4H-indazol-3-yl]-4-oxo-1H-1,6-naphthyridine-5-carboxamide |
| 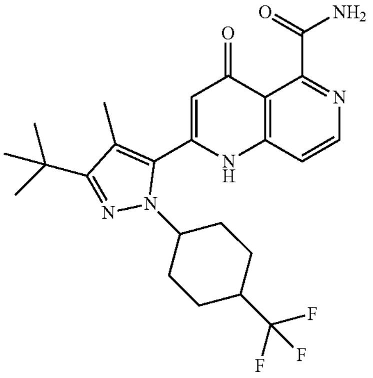 [SMILES: Cc1c(C(C)(C)C)nn(C2CCC(C(F)(F)F)CC2)c1-c1cc(=O)c2c(C(N)=O)nccc2[nH]1] |
| 2-[5-tert-butyl-4-methyl-2-[4-(trifluoro-methyl)cyclohexyl]pyrazol-3-yl]-4-oxo-1H-1,6-naphthyridine-5-carboxamide |

TABLE B-continued

| Compound Structures and Names. |
|---|
| 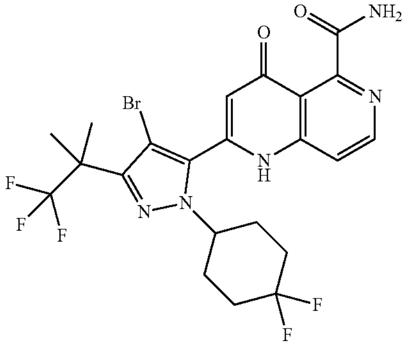 [SMILES: CC(C)(c1nn(C2CCC(F)(F)CC2)c(-c2cc(=O)c3c(C(N)=O)nccc3[nH]2)c1Br)C(F)(F)F] |
| 2-[4-bromo-2-(4,4-difluorocyclohexyl)-5-(2,2,2-trifluoro-1,1-dimethyl-ethyl)pyrazol-3-yl]-4-oxo-1H-1,6-naphthyridine-5-carboxamide |
| 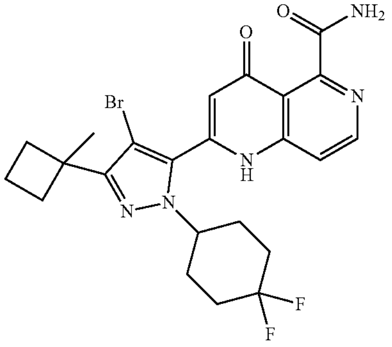 [SMILES: CC1(c2nn(C3CCC(F)(F)CC3)c(-c3cc(=O)c4c(C(N)=O)nccc4[nH]3)c2Br)CCC1] |
| 2-[4-bromo-2-(4,4-difluorocyclohexyl)-5-(1-methylcyclobutyl)pyrazol-3-yl]-4-oxo-1H-1,6-naphthyridine-5-carboxamide |
| 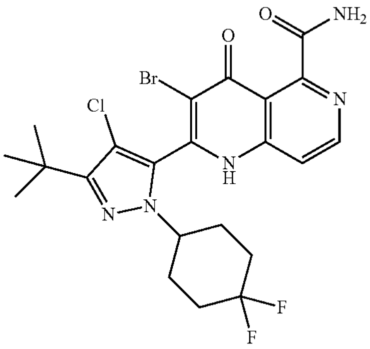 [SMILES: CC(C)(C)c1nn(C2CCC(F)(F)CC2)c(-c2[nH]c3ccnc(C(N)=O)c3c(=O)c2Br)c1Cl] |
| 3-bromo-2-[5-tert-butyl-4-chloro-2-(4,4-difluorocyclohexyl)pyrazol-3-yl]-4-oxo-1H-1,6-naphthyridine-5-carboxamide |

TABLE B-continued

Compound Structures and Names.

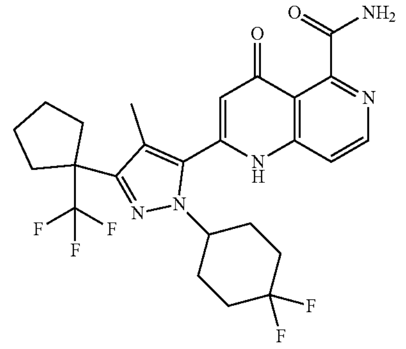 [SMILES: Cc1c(C2(C(F)(F)F)CCCC2)nn(C2CCC(F)(F)CC2)c1-c1cc(=O)c2c(C(N)=O)nccc2[nH]1]

2-[2-(4,4-difluorocyclohexyl)-4-methyl-5-[1-(trifluoromethyl)cyclopentyl]pyrazol-3-yl]-4-oxo-1H-1,6-naphthyridine-5-carboxamide

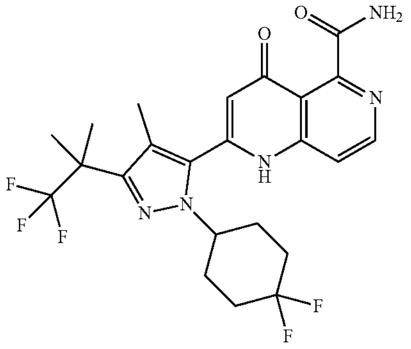 [SMILES: Cc1c(C(C)(C)C(F)(F)F)nn(C2CCC(F)(F)CC2)c1-c1cc(=O)c2c(C(N)=O)nccc2[nH]1]

2-[2-(4,4-difluorocyclohexyl)-4-methyl-5-(2,2,2-trifluoro-1,1-dimethyl-ethyl)pyrazol-3-yl]-4-oxo-1H-1,6-naphthyridine-5-carboxamide

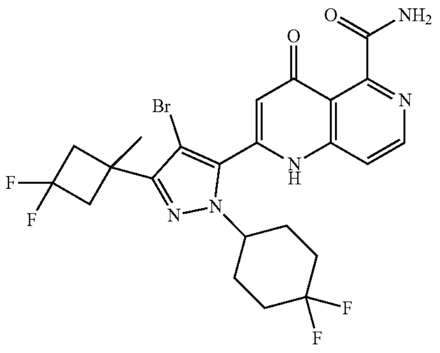 [SMILES: CC1(c2nn(C3CCC(F)(F)CC3)c(-c3cc(=O)c4c(C(N)=O)nccc4[nH]3)c2Br)CC(F)(F)C1]

2-[4-bromo-2-(4,4-difluorocyclohexyl)-5-(3,3-difluoro-1-methyl-cyclobutyl)pyrazol-3-yl]-4-oxo-1H-1,6-naphthyridine-5-carboxamide TABLE B-continued Compound Structures and Names.

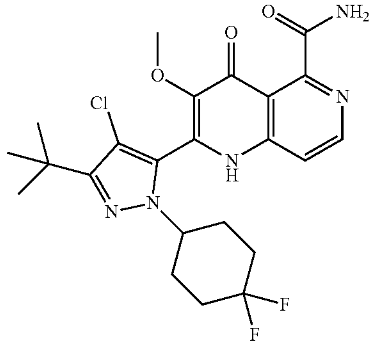 [SMILES: COc1c(-c2c(Cl)c(C(C)(C)C)nn2C2CCC(F)(F)CC2)[nH]c2ccnc(C(N)=O)c2c1=O]

2-[5-tert-butyl-4-chloro-2-(4,4-difluorocyclohexyl)pyrazol-3-yl]-3-methoxy-4-oxo-1H-1,6-naphthyridine-5-carboxamide

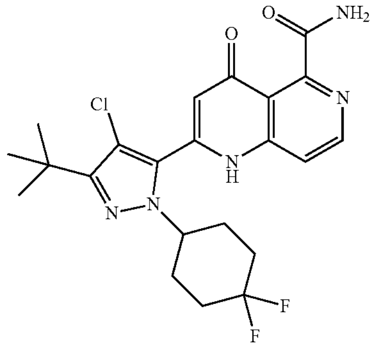

2-[5-tert-butyl-4-chloro-2-(4,4-difluorocyclohexyl)pyrazol-3-yl]-4-oxo-1H-1,6-naphthyridine-5-carboxamide

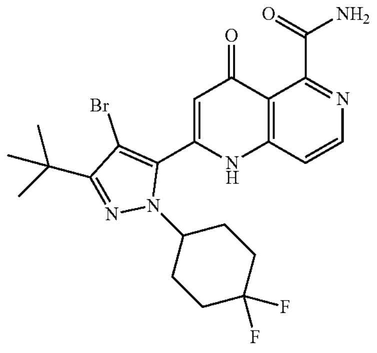 [SMILES: CC(C)(C)c1nn(C2CCC(F)(F)CC2)c(-c2cc(=O)c3c(C(N)=O)nccc3[nH]2)c1Br]

2-[4-bromo-5-tert-butyl-2-(4,4-difluorocyclohexyl)pyrazol-3-yl]-4-oxo-1H-1,6-naphthyridine-5-carboxamide TABLE B-continued

| Compound Structures and Names. |
| --- |
| 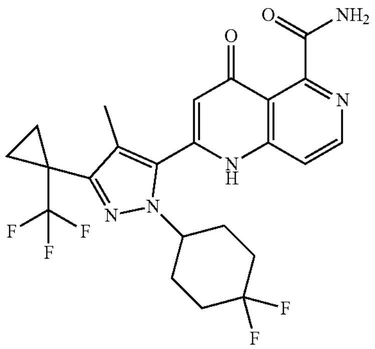 [SMILES: Cc1c(C2(C(F)(F)F)CC2)nn(C2CCC(F)(F)CC2)c1-c1cc(=O)c2c(C(N)=O)nccc2[nH]1] |
| 2-[2-(4,4-difluorocyclohexyl)-4-methyl-5-[1-(trifluoromethyl)cyclopropyl]pyrazol-3-yl]-4-oxo-1H-1,6-naphthyridine-5-carboxamide |
| 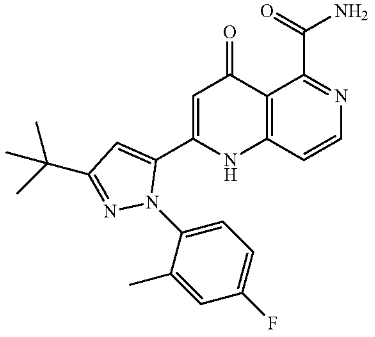 [SMILES: Cc1cc(F)ccc1-n1nc(C(C)(C)C)cc1-c1cc(=O)c2c(C(N)=O)nccc2[nH]1] |
| 2-[5-tert-butyl-2-(4-fluoro-2-methylphenyl)-pyrazol-3-yl]-4-oxo-1H-1,6-naphthyridine-5-carboxamide |
| 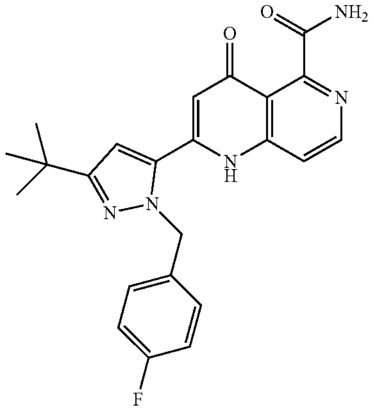 [SMILES: CC(C)(C)c1cc(-c2cc(=O)c3c(C(N)=O)nccc3[nH]2)n(Cc2ccc(F)cc2)n1] |
| 2-(3-(tert-butyl)-1-(4-fluorobenzyl)-1H-pyrazol-5-yl)-4-oxo-1,4-dihydro-1,6-naphthyridine-5-carboxamide |

TABLE B-continued

| Compound Structures and Names. |
| --- |
| 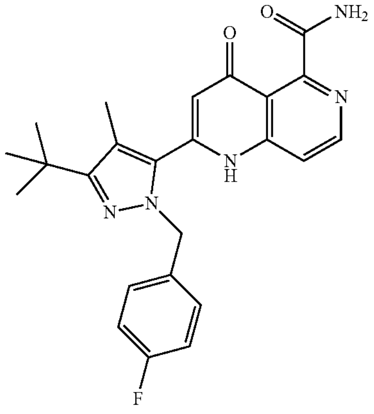 [SMILES: Cc1c(C(C)(C)C)nn(Cc2ccc(F)cc2)c1-c1cc(=O)c2c(C(N)=O)nccc2[nH]1] |
| 2-(3-(tert-butyl)-1-(4-fluorobenzyl)-4-methyl-1H-pyrazol-5-yl)-4-oxo-1,4-dihydro-1,6-naphthyridine-5-carboxamide |
| 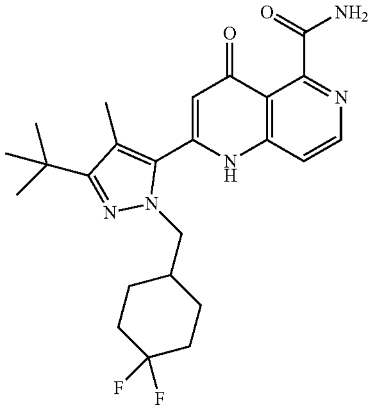 [SMILES: Cc1c(C(C)(C)C)nn(CC2CCC(F)(F)CC2)c1-c1cc(=O)c2c(C(N)=O)nccc2[nH]1] |
| 2-(3-(tert-butyl)-1-((4,4-difluorocyclohexyl)-methyl)-4-methyl-1H-pyrazol-5-yl)-4-oxo-1,4-dihydro-1,6-naphthyridine-5-carboxamide |
| 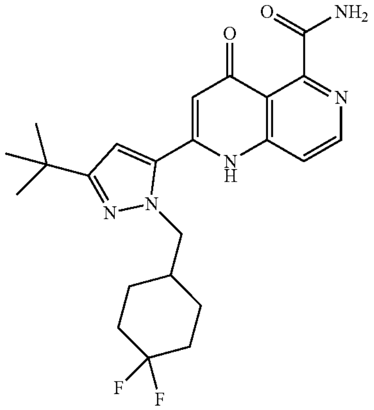 [SMILES: CC(C)(C)c1cc(-c2cc(=O)c3c(C(N)=O)nccc3[nH]2)n(CC2CCC(F)(F)CC2)n1] |
| 2-(3-(tert-butyl)-1-((4,4-difluorocyclohexyl)-methyl)-1H-pyrazol-5-yl)-4-oxo-1,4-dihydro-1,6-naphthyridine-5-carboxamide |

TABLE B-continued

| Compound Structures and Names. |
|---|
| 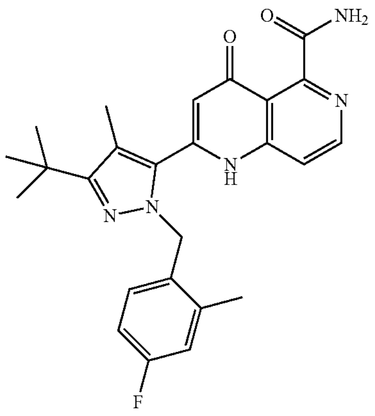 [SMILES: Cc1cc(F)ccc1Cn1nc(C(C)(C)C)c(C)c1-c1cc(=O)c2c(C(N)=O)nccc2[nH]1] |
| 2-(3-(tert-butyl)-1-(4-fluoro-2-methylbenzyl)-4-methyl-1H-pyrazol-5-yl)-4-oxo-1,4-dihydro-1,6-naphthyridine-5-carboxamide |
| 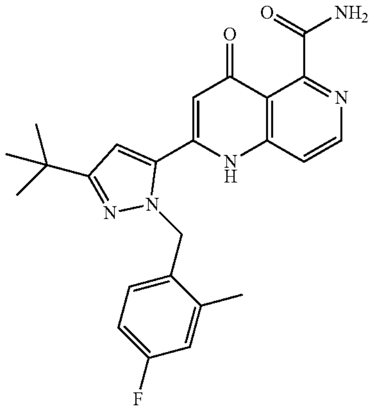 [SMILES: Cc1cc(F)ccc1Cn1nc(C(C)(C)C)cc1-c1cc(=O)c2c(C(N)=O)nccc2[nH]1] |
| 2-(3-(tert-butyl)-1-(4-fluoro-2-methylbenzyl)-1H-pyrazol-5-yl)-4-oxo-1,4-dihydro-1,6-naphthyridine-5-carboxamide |
| 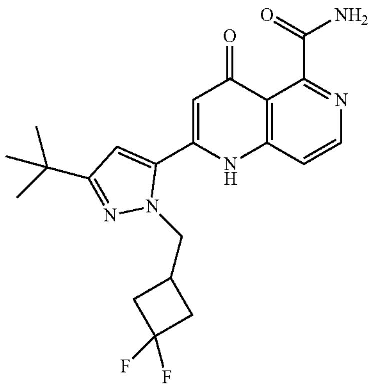 [SMILES: CC(C)(C)c1cc(-c2cc(=O)c3c(C(N)=O)nccc3[nH]2)n(CC2CC(F)(F)C2)n1] |
| 2-(3-(tert-butyl)-1-((3,3-difluorocyclobutyl)-methyl)-1H-pyrazol-5-yl)-4-oxo-1,4-dihydro-1,6-naphthyridine-5-carboxamide |

TABLE B-continued

| Compound Structures and Names. |
|---|
| 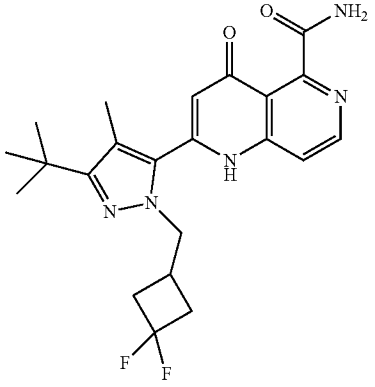 [SMILES: Cc1c(C(C)(C)C)nn(CC2CC(F)(F)C2)c1-c1cc(=O)c2c(C(N)=O)nccc2[nH]1] |
| 2-(3-(tert-butyl)-1-((3,3-difluorocyclo-butyl)methyl)-4-methyl-1H-pyrazol-5-yl)-4-oxo-1,4-dihydro-1,6-naphthyridine-5-carboxamide |
| 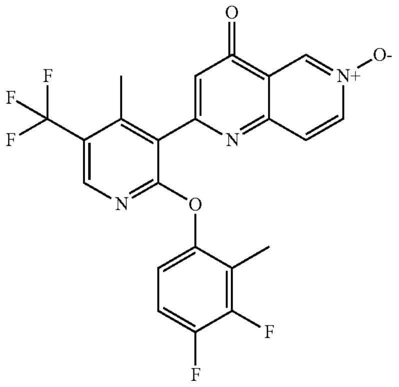 |
| 2-(2-(3,4-difluoro-2-methylphenoxy)-4-methyl-5-(trifluoromethyl)pyridin-3-yl)-4-oxo-4l5-1,6-naphthyridine 6-oxide |
| 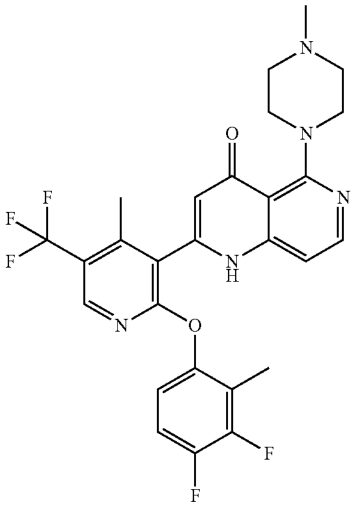 [SMILES: Cc1c(Oc2ncc(C(F)(F)F)c(C)c2-c2cc(=O)c3c(N4CCN(C)CC4)nccc3[nH]2)ccc(F)c1F] |
| 2-(2-(3,4-difluoro-2-methylphenoxy)-4-methyl-5-(trifluoromethyl)pyridin-3-yl)-5-(4-methylpiperazin-1-yl)-1,6-naphthyridin-4(1H)-one |

TABLE B-continued

| Compound Structures and Names. |
|---|
| 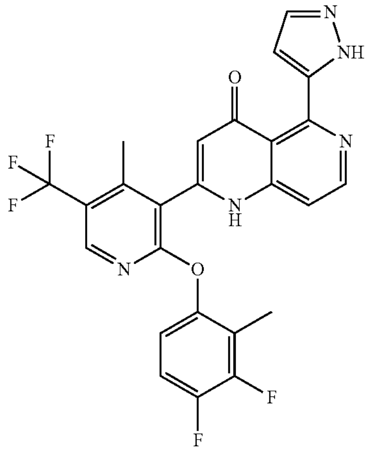 [SMILES: Cc1c(Oc2ncc(C(F)(F)F)c(C)c2-c2cc(=O)c3c(-c4ccn[nH]4)nccc3[nH]2)ccc(F)c1F] |
| 2-(2-(3,4-difluoro-2-methylphenoxy)-4-methyl-5-(trifluoromethyl)pyridin-3-yl)-5-(1H-pyrazol-5-yl)-1,6-naphthyridin-4(1H)-one |
| 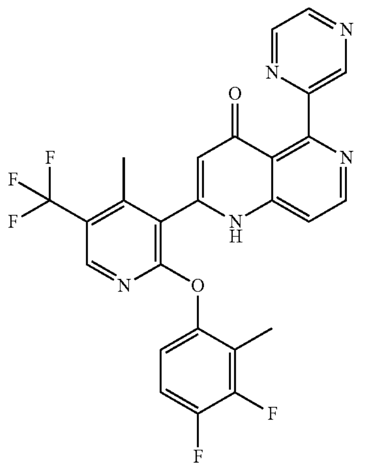 [SMILES: Cc1c(Oc2ncc(C(F)(F)F)c(C)c2-c2cc(=O)c3c(-c4cnccn4)nccc3[nH]2)ccc(F)c1F] |
| 2-(2-(3,4-difluoro-2-methylphenoxy)-4-methyl-5-(trifluoromethyl)pyridin-3-yl)-5-(pyrazin-2-yl)-1,6-naphthyridin-4(1H)-one |
| 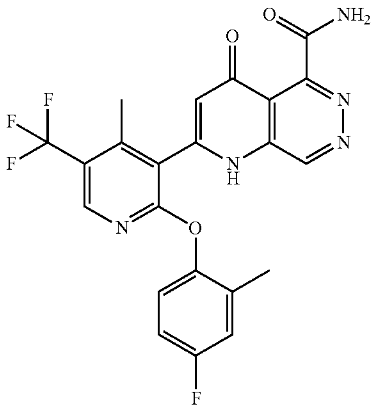 |
| 2-(2-(4-fluoro-2-methylphenoxy)-4-methyl-5-(trifluoromethyl)pyridin-3-yl)-4-oxo-1,4-dihydropyrido[2,3-d]pyridazine-5-carboxamide |

TABLE B-continued

| Compound Structures and Names. |
|---|
| 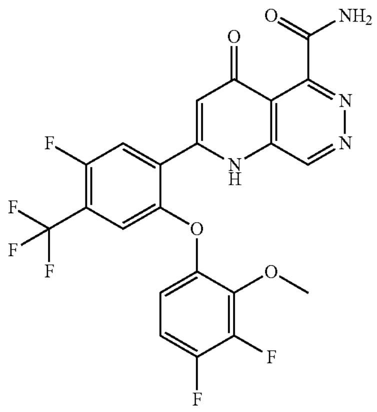 |
| 2-(2-(3,4-difluoro-2-methoxyphenoxy)-5-fluoro-4-(trifluoromethyl)phenyl)-4-oxo-1,4-dihydropyrido[2,3-d]pyridazine-5-carboxamide |
| 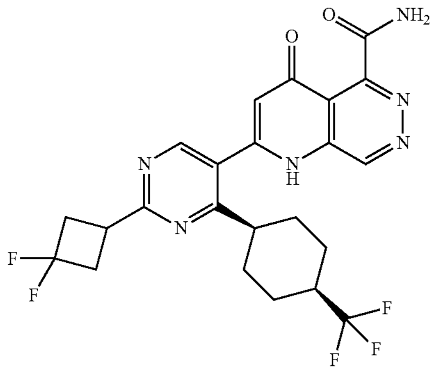 [SMILES: NC(=O)c1nncc2[nH]c(-c3cnc(C4CC(F)(F)C4)nc3[C@H]3CC[C@@H](C(F)(F)F)CC3)cc(=O)c12] |
| 2-(2-(3,3-difluorocyclobutyl)-4-((1s,4s)-4-(trifluoromethyl)cyclohexyl)pyrimidin-5-yl)-4-oxo-1,4-dihydropyrido[2,3-d]pyridazine-5-carboxamide |
| 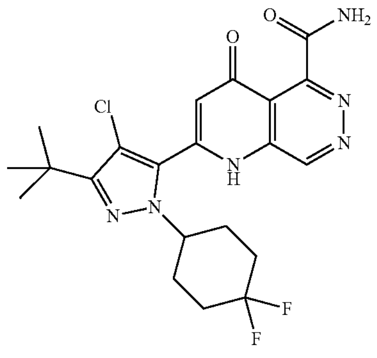 [SMILES: CC(C)(C)c1nn(C2CCC(F)(F)CC2)c(-c2cc(=O)c3c(C(N)=O)nncc3[nH]2)c1Cl] |
| 2-(3-(tert-butyl)-4-chloro-1-(4,4-difluorocyclohexyl)-1H-pyrazol-5-yl)-4-oxo-1,4-dihydropyrido[2,3-d]pyridazine-5-carboxamide |

TABLE B-continued

| Compound Structures and Names. |
|---|
| 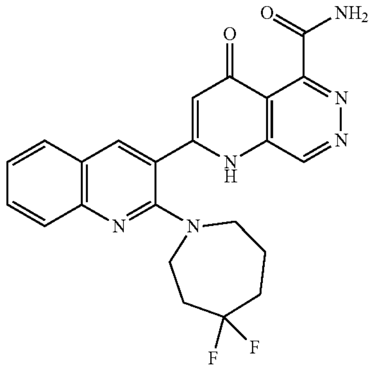 [SMILES: NC(=O)c1nncc2[nH]c(-c3cc4ccccc4nc3N3CCCC(F)(F)CC3)cc(=O)c12] |
| 2-(2-(4,4-difluoroazepan-1-yl)quinolin-3-yl)-4-oxo-1,4-dihydropyrido[2,3-d]pyridazine-5-carboxamide |
| 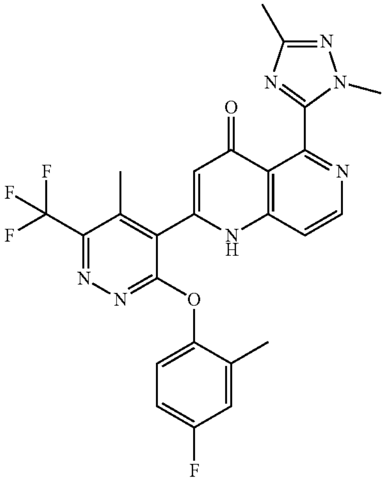 [SMILES: Cc1nc(-c2nccc3[nH]c(-c4c(Oc5ccc(F)cc5C)nnc(C(F)(F)F)c4C)cc(=O)c23)n(C)n1] |
| 5-(1,3-dimethyl-1H-1,2,4-triazol-5-yl)-2-(3-(4-fluoro-2-methylphenoxy)-5-methyl-6-(trifluoromethyl)pyridazin-4-yl)-1,6-naphthyridin-4(1H)-one |
| 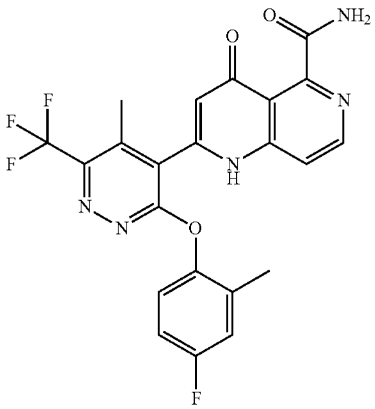 |
| 2-(3-(4-fluoro-2-methylphenoxy)-5-methyl-6-(trifluoromethyl)pyridazin-4-yl)-4-oxo-1,4-dihydro-1,6-naphthyridine-5-carboxamide |

TABLE B-continued

| Compound Structures and Names. |
|---|
| 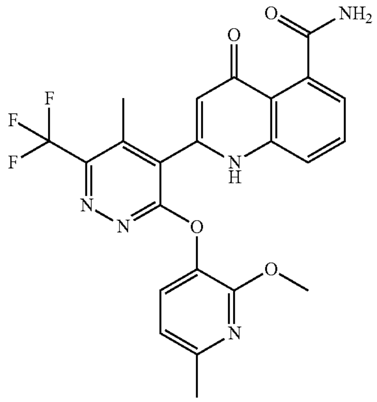 [SMILES: COc1nc(C)ccc1Oc1nnc(C(F)(F)F)c(C)c1-c1cc(=O)c2c(C(N)=O)cccc2[nH]1] |
| 2-(3-((2-methoxy-6-methylpyridin-3-yl)oxy)-5-methyl-6-(trifluoromethyl)pyridazin-4-yl)-4-oxo-1,4-dihydroquinoline-5-carboxamide |
| 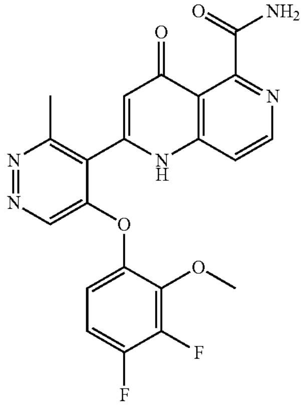 [SMILES: COc1c(Oc2cnnc(C)c2-c2cc(=O)c3c(C(N)=O)nccc3[nH]2)ccc(F)c1F] |
| 2-(5-(3,4-difluoro-2-methoxyphenoxy)-3-methylpyridazin-4-yl)-4-oxo-1,4-dihydro-1,6-naphthyridine-5-carboxamide |
| 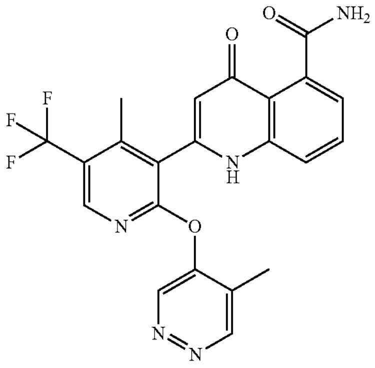 [SMILES: Cc1cnncc1Oc1ncc(C(F)(F)F)c(C)c1-c1cc(=O)c2c(C(N)=O)cccc2[nH]1] |
| 2-(4-methyl-2-((5-methylpyridazin-4-yl)oxy)-5-(trifluoromethyl)pyridin-3-yl)-4-oxo-1,4-dihydroquinoline-5-carboxamide |

TABLE B-continued

| Compound Structures and Names. |
| --- |
| 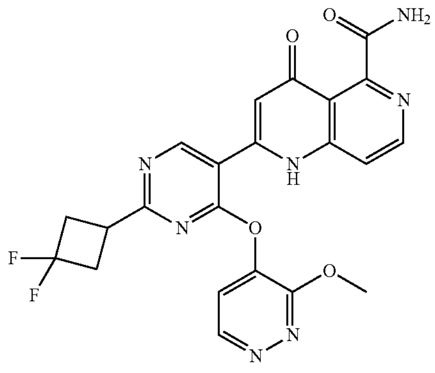 [SMILES: COc1nnccc1Oc1nc(C2CC(F)(F)C2)ncc1-c1cc(=O)c2c(C(N)=O)nccc2[nH]1] |
| 2-(2-(3,3-difluorocyclobutyl)-4-((3-methoxy-pyridazin-4-yl)oxy)pyrimidin-5-yl)-4-oxo-1,4-dihydro-1,6-naphthyridine-5-carboxamide |
| 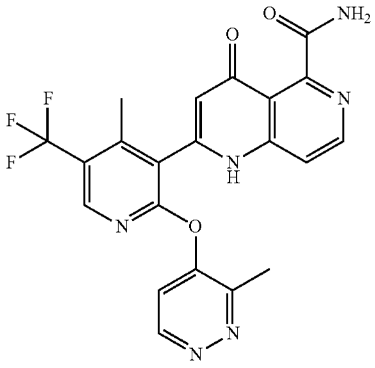 [SMILES: Cc1nnccc1Oc1ncc(C(F)(F)F)c(C)c1-c1cc(=O)c2c(C(N)=O)nccc2[nH]1] |
| 2-(4-methyl-2-((3-methylpyridazin-4-yl)oxy)-5-(trifluoromethyl)pyridin-3-yl)-4-oxo-1,4-dihydro-1,6-naphthyridine-5-carboxamide |
| 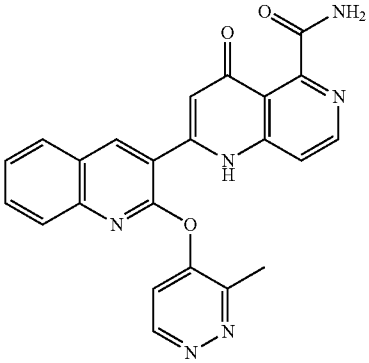 [SMILES: Cc1nnccc1Oc1nc2ccccc2cc1-c1cc(=O)c2c(C(N)=O)nccc2[nH]1] |
| 2-(2-((3-methylpyridazin-4-yl)oxy)quinolin-3-yl)-4-oxo-1,4-dihydro-1,6-naphthyridine-5-carboxamide |

TABLE B-continued

| Compound Structures and Names. |
| --- |
| 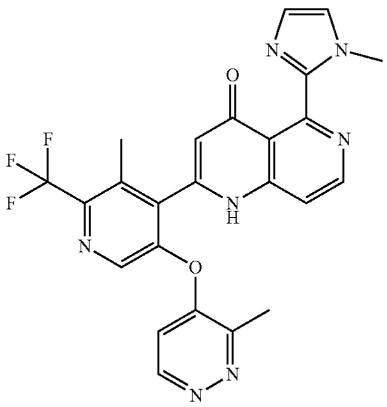 [SMILES: Cc1nnccc1Oc1cnc(C(F)(F)F)c(C)c1-c1cc(=O)c2c(-c3nccn3C)nccc2[nH]1] |
| 5-(1-methyl-1H-imidazol-2-yl)-2-(3-methyl-5-((3-methylpyridazin-4-yl)oxy)-2-(trifluoro-methyl)pyridin-4-yl)-1,6-naphthyridin-4(1H)-one |
| 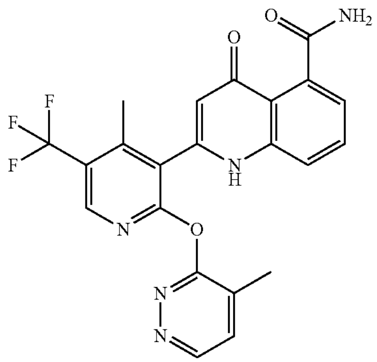 [SMILES: Cc1ccnnc1Oc1ncc(C(F)(F)F)c(C)c1-c1cc(=O)c2c(C(N)=O)cccc2[nH]1] |
| 2-(4-methyl-2-((4-methylpyridazin-3-yl)oxy)-5-(trifluoromethyl)pyridin-3-yl)-4-oxo-1,4-dihydroquinoline-5-carboxamide |
| 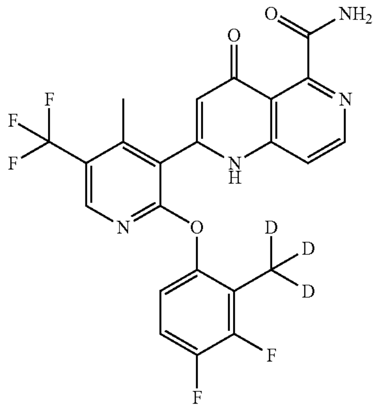 [SMILES: [2H]C([2H])([2H])c1c(Oc2ncc(C(F)(F)F)c(C)c2-c2cc(=O)c3c(C(N)=O)nccc3[nH]2)ccc(F)c1F] |
| 2-(2-(3,4-difluoro-2-(methyl-$d_3$)phenoxy)-4-methyl-5-(trifluoromethyl)pyridin-3-yl)-4-oxo-1,4-dihydro-1,6-naphthyridine-5-carboxamide |

TABLE B-continued

Compound Structures and Names.

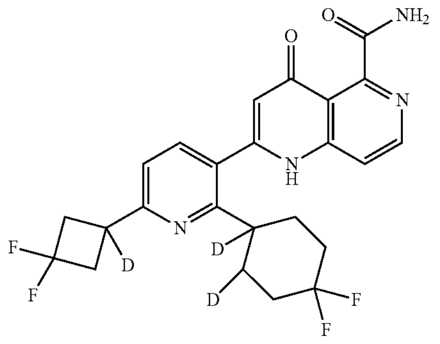 [SMILES: [2H]C1CC(F)(F)CCC1([2H])c1nc(C2([2H])CC(F)(F)C2)ccc1-c1cc(=O)c2c(C(N)=O)nccc2[nH]1]

2-(6-(3,3-difluorocyclobutyl-1-d)-2-(4,4-difluorocyclohexyl-1,2-$d_2$)pyridin-3-yl)-4-oxo-1,4-dihydro-1,6-naphthyridine-5-carboxamide

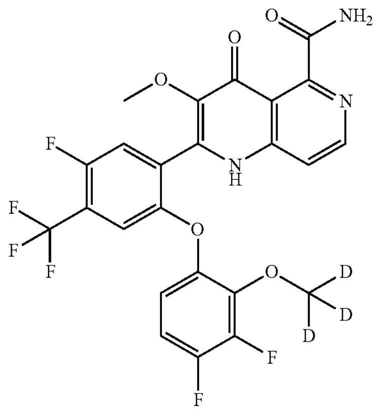 [SMILES: [2H]C([2H])([2H])Oc1c(Oc2cc(C(F)(F)F)c(F)cc2-c2[nH]c3ccnc(C(N)=O)c3c(=O)c2OC)ccc(F)c1F]

2-(2-(3,4-difluoro-2-(methoxy-$d_3$)phenoxy)-5-fluoro-4-(trifluoromethyl)phenyl)-3-methoxy-4-oxo-1,4-dihydro-1,6-naphthyridine-5-carboxamide

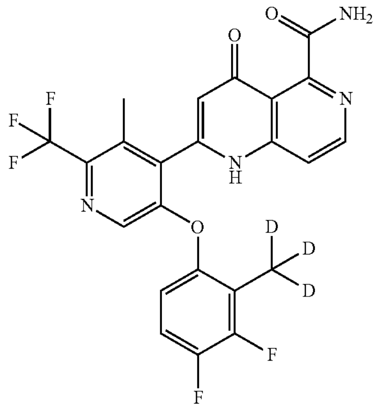 [SMILES: [2H]C([2H])([2H])c1c(Oc2cnc(C(F)(F)F)c(C)c2-c2cc(=O)c3c(C(N)=O)nccc3[nH]2)ccc(F)c1F]

2-(5-(3,4-difluoro-2-(methyl-$d_3$)phenoxy)-3-methyl-2-(trifluoromethyl)pyridin-4-yl)-4-oxo-1,4-dihydro-1,6-naphthyridine-5-carboxamide TABLE B-continued Compound Structures and Names.

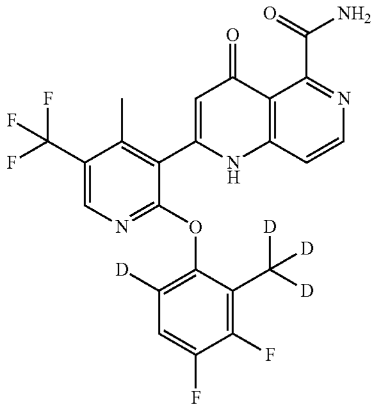 [SMILES: [2H]c1cc(F)c(F)c(C([2H])([2H])[2H])c1Oc1ncc(C(F)(F)F)c(C)c1-c1cc(=O)c2c(C(N)=O)nccc2[nH]1]

2-(2-(3,4-difluoro-2-(methyl-$d_3$)phenoxy-6-d)-4-methyl-5-(trifluoromethyl)pyridin-3-yl)-4-oxo-1,4-dihydro-1,6-naphthyridine-5-carboxamide In some embodiments, the invention relates to a compound of formula

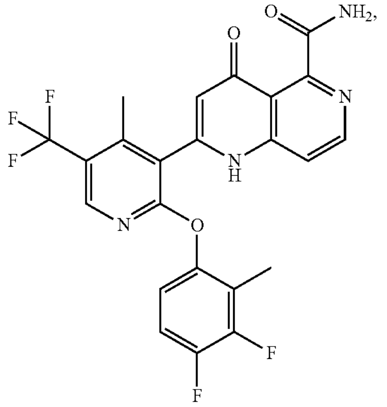 [SMILES: Cc1c(Oc2ncc(C(F)(F)F)c(C)c2-c2cc(=O)c3c(C(N)=O)nccc3[nH]2)ccc(F)c1F]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

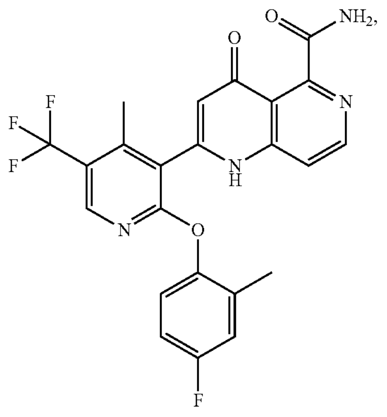

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

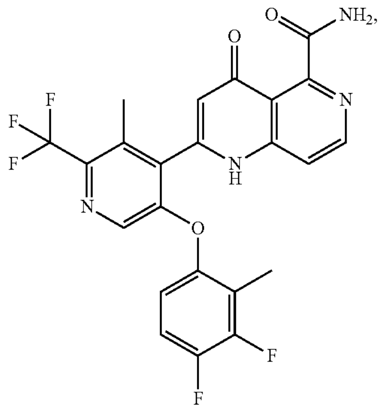 [SMILES: Cc1c(Oc2cnc(C(F)(F)F)c(C)c2-c2cc(=O)c3c(C(N)=O)nccc3[nH]2)ccc(F)c1F]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

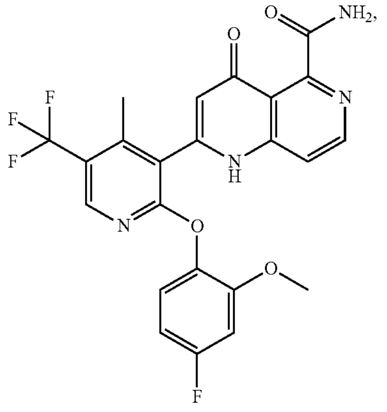 [SMILES: COc1cc(F)ccc1Oc1ncc(C(F)(F)F)c(C)c1-c1cc(=O)c2c(C(N)=O)nccc2[nH]1]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

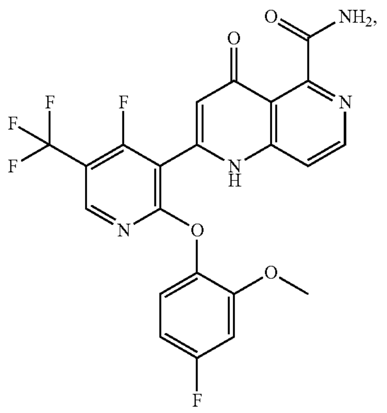 [SMILES: COc1cc(F)ccc1Oc1ncc(C(F)(F)F)c(F)c1-c1cc(=O)c2c(C(N)=O)nccc2[nH]1]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

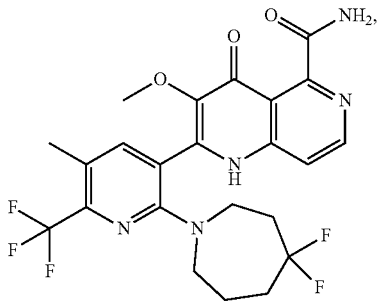 [SMILES: COc1c(-c2cc(C)c(C(F)(F)F)nc2N2CCCC(F)(F)CC2)[nH]c2ccnc(C(N)=O)c2c1=O]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

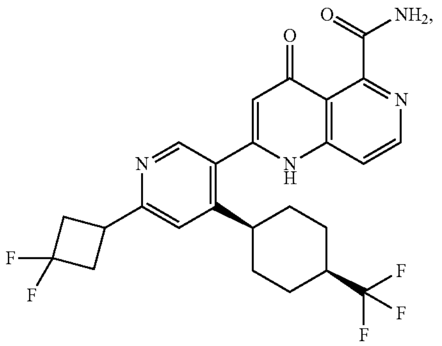 [SMILES: NC(=O)c1nccc2[nH]c(-c3cnc(C4CC(F)(F)C4)cc3[C@H]3CC[C@@H](C(F)(F)F)CC3)cc(=O)c12]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

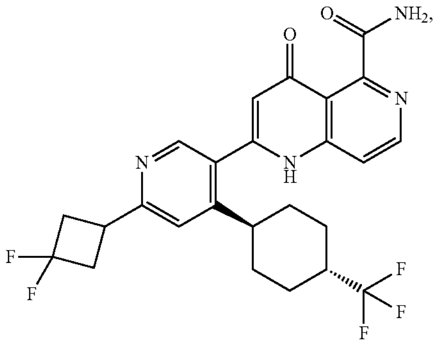 [SMILES: NC(=O)c1nccc2[nH]c(-c3cnc(C4CC(F)(F)C4)cc3[C@H]3CC[C@H](C(F)(F)F)CC3)cc(=O)c12]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

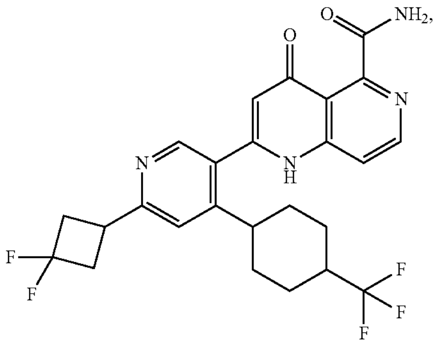 [SMILES: NC(=O)c1nccc2[nH]c(-c3cnc(C4CC(F)(F)C4)cc3C3CCC(C(F)(F)F)CC3)cc(=O)c12]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

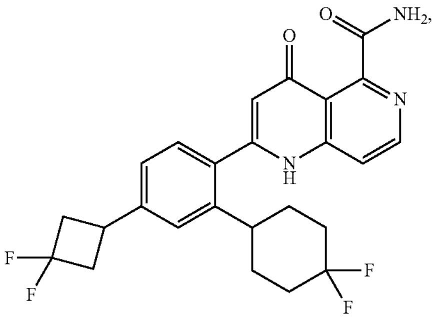 [SMILES: NC(=O)c1nccc2[nH]c(-c3ccc(C4CC(F)(F)C4)cc3C3CCC(F)(F)CC3)cc(=O)c12]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

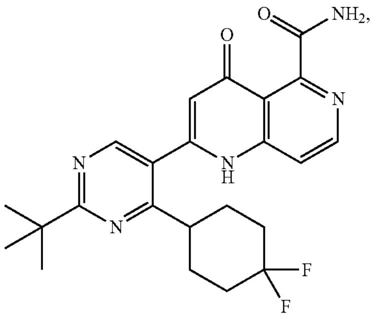 [SMILES: CC(C)(C)c1ncc(-c2cc(=O)c3c(C(N)=O)nccc3[nH]2)c(C2CCC(F)(F)CC2)n1]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

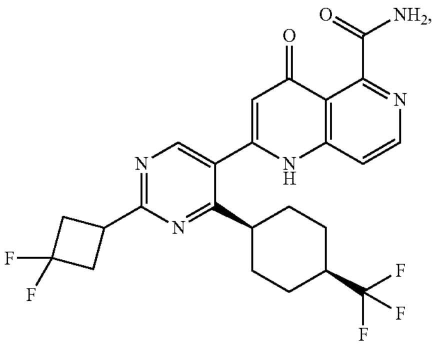 [SMILES: NC(=O)c1nccc2[nH]c(-c3cnc(C4CC(F)(F)C4)nc3[C@H]3CC[C@@H](C(F)(F)F)CC3)cc(=O)c12]

or a pharmaceutically acceptable salt thereof. In other embodiments, the invention relates to the foregoing compound in non-salt form. Such compound is considered to be a “compound of the invention,” as that term is used herein.

In some embodiments, the invention relates to a compound of formula

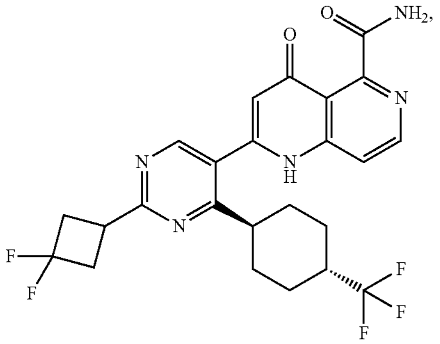 [SMILES: NC(=O)c1nccc2[nH]c(-c3cnc(C4CC(F)(F)C4)nc3[C@H]3CC[C@H](C(F)(F)F)CC3)cc(=O)c12]

or a pharmaceutically acceptable salt thereof. In other embodiments, the invention relates to the foregoing compound in non-salt form. Such compound is considered to be a “compound of the invention,” as that term is used herein.

In some embodiments, the invention relates to a compound of formula

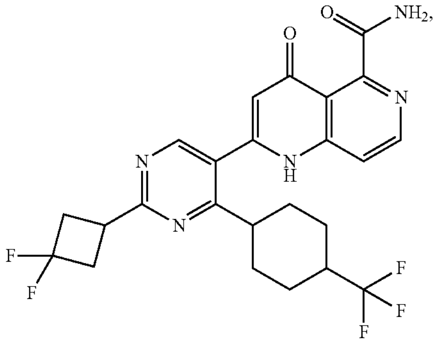 [SMILES: NC(=O)c1nccc2[nH]c(-c3cnc(C4CC(F)(F)C4)nc3C3CCC(C(F)(F)F)CC3)cc(=O)c12]

or a pharmaceutically acceptable salt thereof. In other embodiments, the invention relates to the foregoing compound in non-salt form. Such compound is considered to be a “compound of the invention,” as that term is used herein.

In some embodiments, the invention relates to a compound of formula

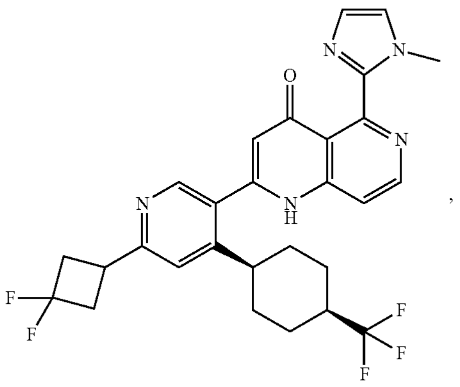 [SMILES: Cn1ccnc1-c1nccc2[nH]c(-c3cnc(C4CC(F)(F)C4)cc3[C@H]3CC[C@@H](C(F)(F)F)CC3)cc(=O)c12]

or a pharmaceutically acceptable salt thereof. In other embodiments, the invention relates to the foregoing compound in non-salt form. Such compound is considered to be a “compound of the invention,” as that term is used herein.

In some embodiments, the invention relates to a compound of formula

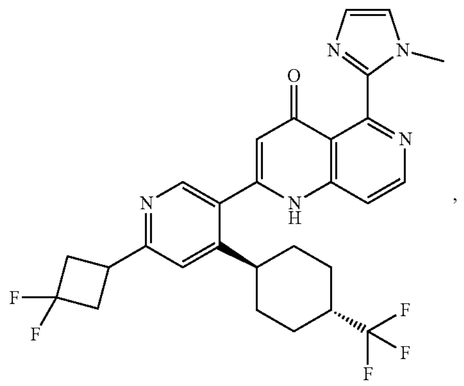 [SMILES: Cn1ccnc1-c1nccc2[nH]c(-c3cnc(C4CC(F)(F)C4)cc3[C@H]3CC[C@H](C(F)(F)F)CC3)cc(=O)c12]

or a pharmaceutically acceptable salt thereof. In other embodiments, the invention relates to the foregoing compound in non-salt form. Such compound is considered to be a “compound of the invention,” as that term is used herein.

In some embodiments, the invention relates to a compound of formula

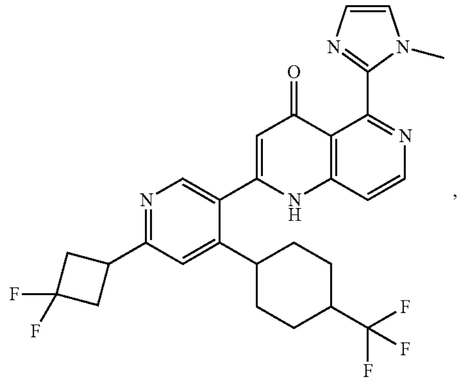 [SMILES: Cn1ccnc1-c1nccc2[nH]c(-c3cnc(C4CC(F)(F)C4)cc3C3CCC(C(F)(F)F)CC3)cc(=O)c12]

or a pharmaceutically acceptable salt thereof. In other embodiments, the invention relates to the foregoing compound in non-salt form. Such compound is considered to be a “compound of the invention,” as that term is used herein.

In some embodiments, the invention relates to a compound of formula

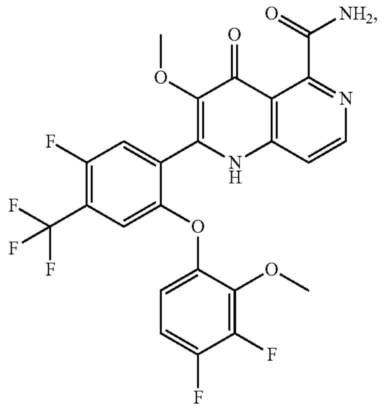 [SMILES: COc1c(Oc2cc(C(F)(F)F)c(F)cc2-c2[nH]c3ccnc(C(N)=O)c3c(=O)c2OC)ccc(F)c1F]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

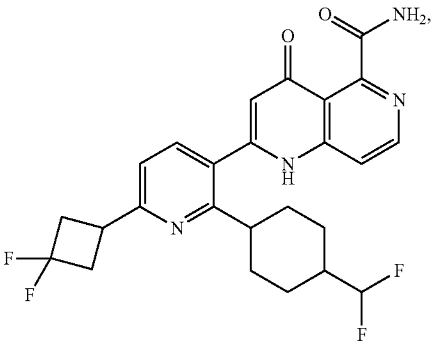 [SMILES: NC(=O)c1nccc2[nH]c(-c3ccc(C4CC(F)(F)C4)nc3C3CCC(C(F)F)CC3)cc(=O)c12]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

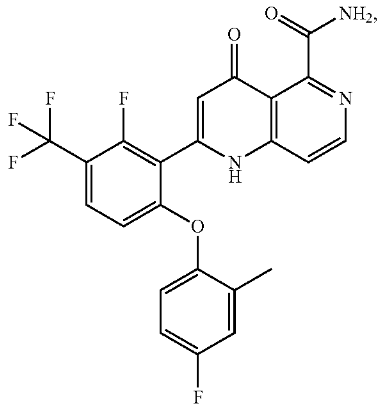 [SMILES: Cc1cc(F)ccc1Oc1ccc(C(F)(F)F)c(F)c1-c1cc(=O)c2c(C(N)=O)nccc2[nH]1]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

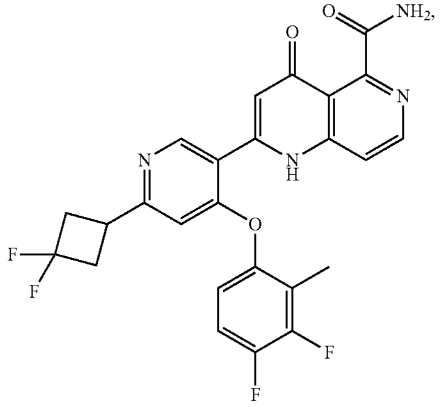 [SMILES: Cc1c(Oc2cc(C3CC(F)(F)C3)ncc2-c2cc(=O)c3c(C(N)=O)nccc3[nH]2)ccc(F)c1F]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

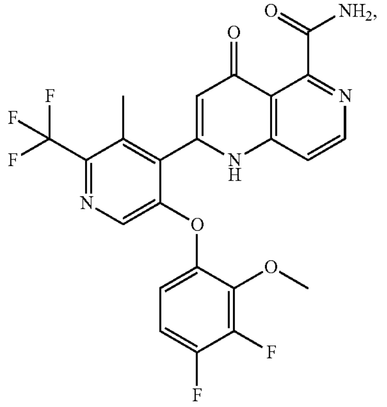 [SMILES: COc1c(Oc2cnc(C(F)(F)F)c(C)c2-c2cc(=O)c3c(C(N)=O)nccc3[nH]2)ccc(F)c1F]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

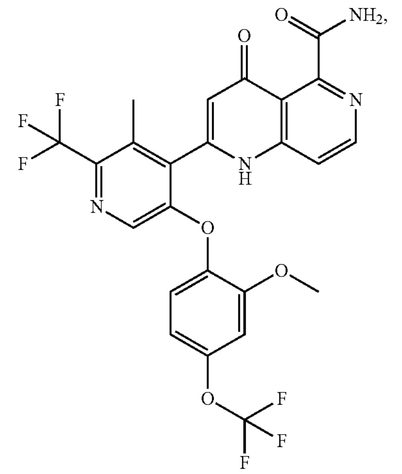 [SMILES: COc1cc(OC(F)(F)F)ccc1Oc1cnc(C(F)(F)F)c(C)c1-c1cc(=O)c2c(C(N)=O)nccc2[nH]1]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

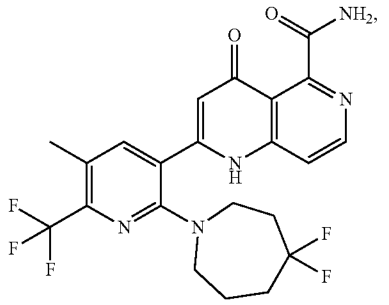 [SMILES: Cc1cc(-c2cc(=O)c3c(C(N)=O)nccc3[nH]2)c(N2CCCC(F)(F)CC2)nc1C(F)(F)F]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

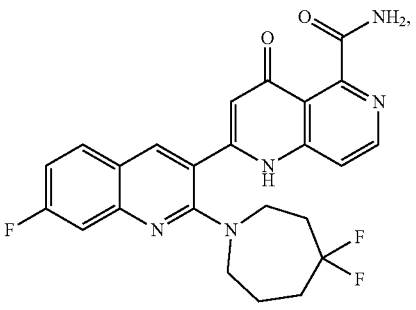 [SMILES: NC(=O)c1nccc2[nH]c(-c3cc4ccc(F)cc4nc3N3CCCC(F)(F)CC3)cc(=O)c12]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

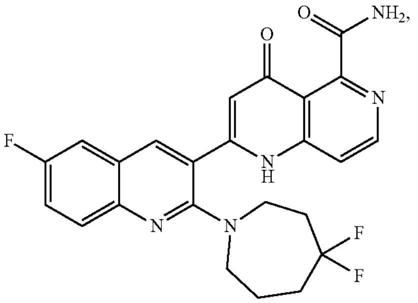 [SMILES: NC(=O)c1nccc2[nH]c(-c3cc4cc(F)ccc4nc3N3CCCC(F)(F)CC3)cc(=O)c12]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

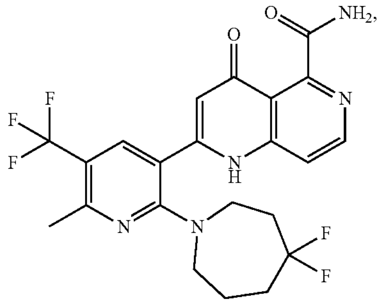 [SMILES: Cc1nc(N2CCCC(F)(F)CC2)c(-c2cc(=O)c3c(C(N)=O)nccc3[nH]2)cc1C(F)(F)F]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

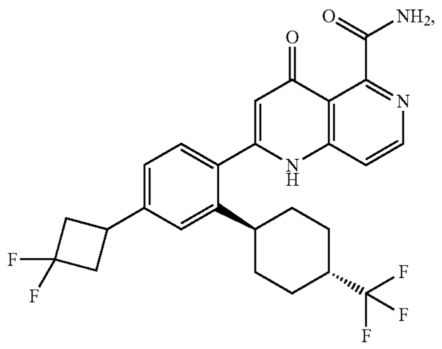 [SMILES: NC(=O)c1nccc2[nH]c(-c3ccc(C4CC(F)(F)C4)cc3[C@H]3CC[C@H](C(F)(F)F)CC3)cc(=O)c12]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

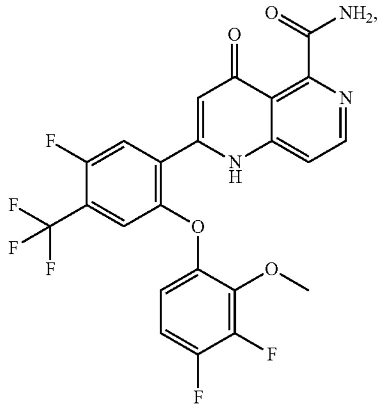 [SMILES: COc1c(Oc2cc(C(F)(F)F)c(F)cc2-c2cc(=O)c3c(C(N)=O)nccc3[nH]2)ccc(F)c1F]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

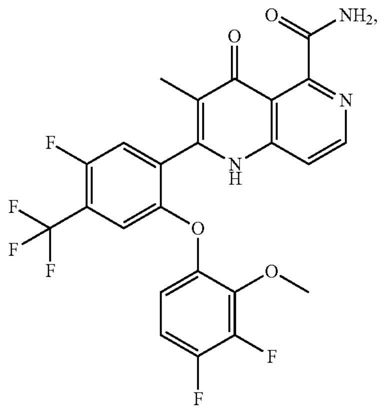 [SMILES: COc1c(Oc2cc(C(F)(F)F)c(F)cc2-c2[nH]c3ccnc(C(N)=O)c3c(=O)c2C)ccc(F)c1F]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

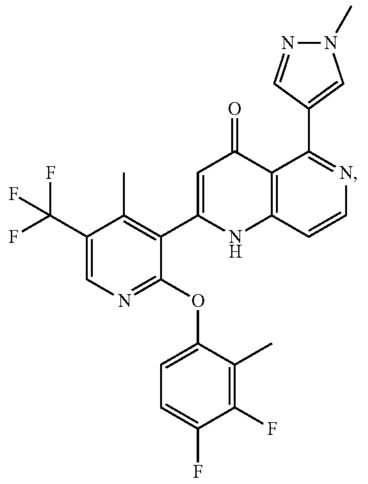 [SMILES: Cc1c(Oc2ncc(C(F)(F)F)c(C)c2-c2cc(=O)c3c(-c4cnn(C)c4)nccc3[nH]2)ccc(F)c1F]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

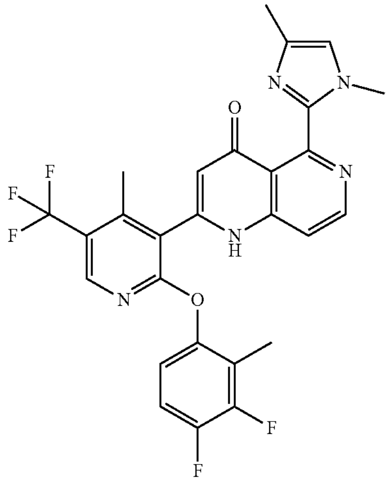

, or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

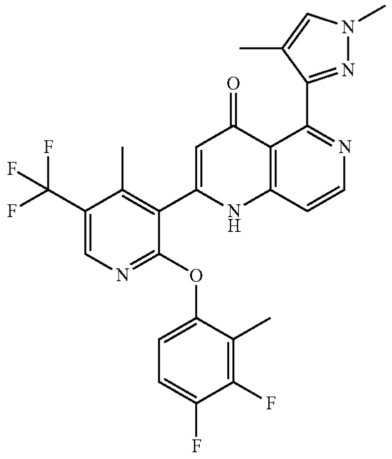

, or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

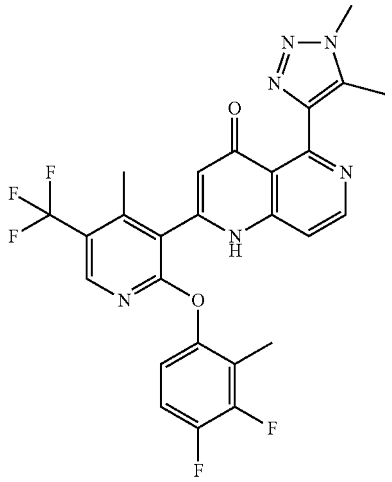

, or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

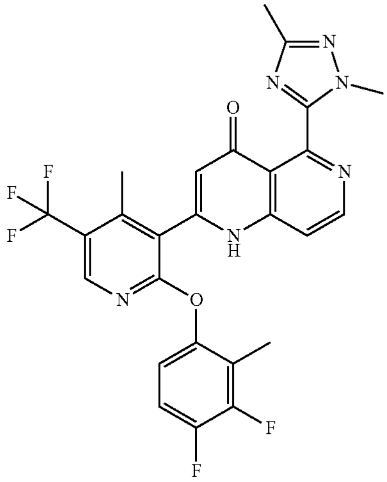

, or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

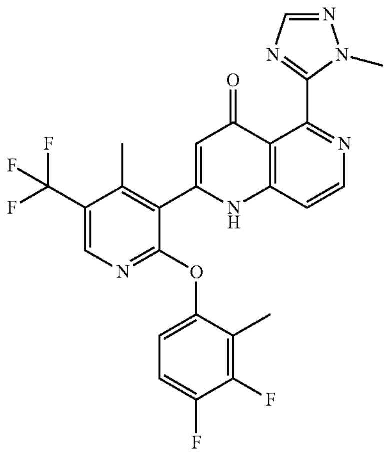

, or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

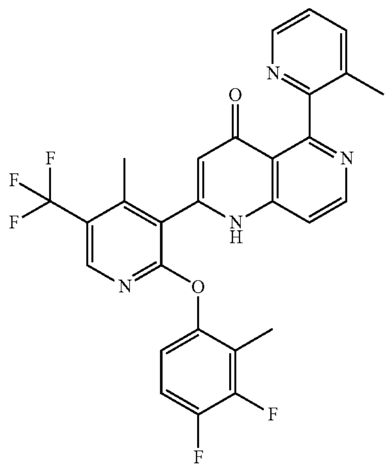

, or a pharmaceutically acceptable salt thereof. In other embodiments, the invention relates to the foregoing compound in non-salt form. Such compound is considered to be a “compound of the invention,” as that term is used herein.

In some embodiments, the invention relates to a compound of formula

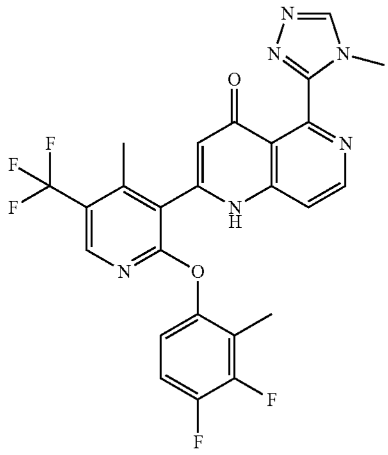

, or a pharmaceutically acceptable salt thereof. In other embodiments, the invention relates to the foregoing compound in non-salt form. Such compound is considered to be a “compound of the invention,” as that term is used herein.

In some embodiments, the invention relates to a compound of formula

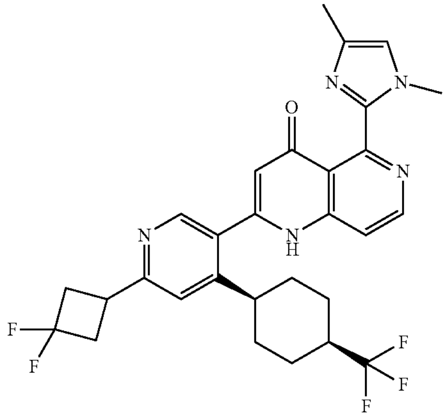

, or a pharmaceutically acceptable salt thereof. In other embodiments, the invention relates to the foregoing compound in non-salt form. Such compound is considered to be a “compound of the invention,” as that term is used herein.

In some embodiments, the invention relates to a compound of formula

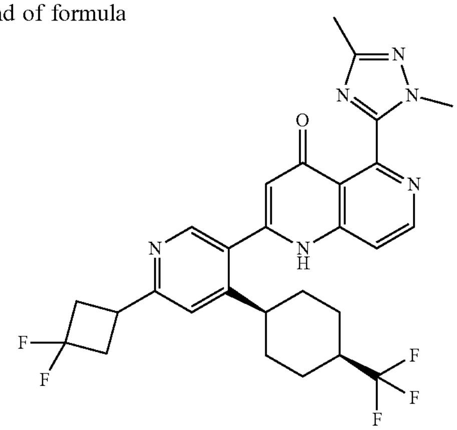

, or a pharmaceutically acceptable salt thereof. In other embodiments, the invention relates to the foregoing compound in non-salt form. Such compound is considered to be a “compound of the invention,” as that term is used herein.

In some embodiments, the invention relates to a compound of formula

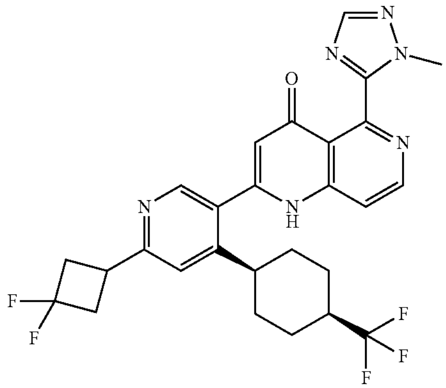

, or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

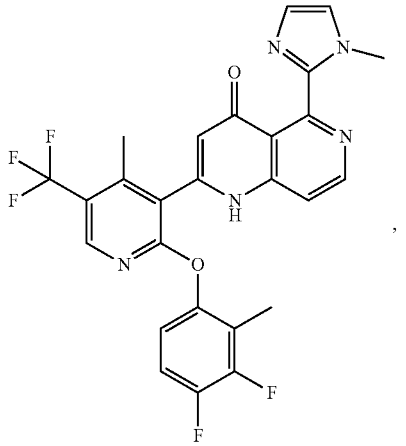 [SMILES: Cc1c(Oc2ncc(C(F)(F)F)c(C)c2-c2cc(=O)c3c(-c4nccn4C)nccc3[nH]2)ccc(F)c1F]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

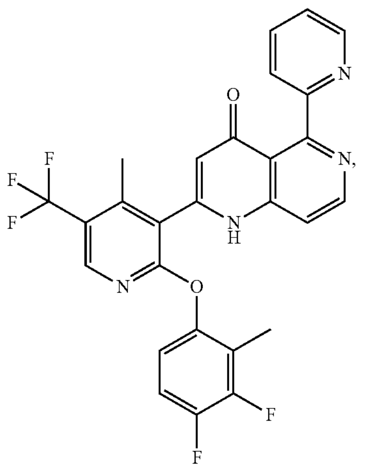 [SMILES: Cc1c(Oc2ncc(C(F)(F)F)c(C)c2-c2cc(=O)c3c(-c4ccccn4)nccc3[nH]2)ccc(F)c1F]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

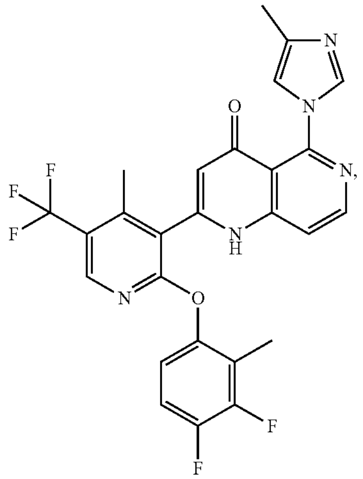 [SMILES: Cc1cn(-c2nccc3[nH]c(-c4c(Oc5ccc(F)c(F)c5C)ncc(C(F)(F)F)c4C)cc(=O)c23)cn1]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

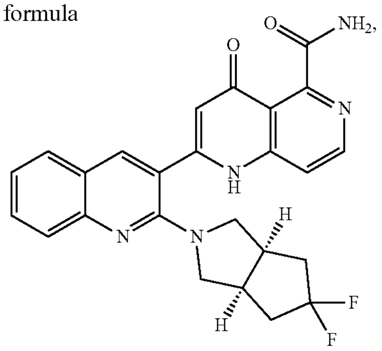

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

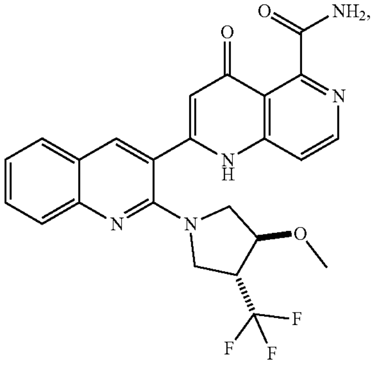 [SMILES: CO[C@@H]1CN(c2nc3ccccc3cc2-c2cc(=O)c3c(C(N)=O)nccc3[nH]2)C[C@H]1C(F)(F)F]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

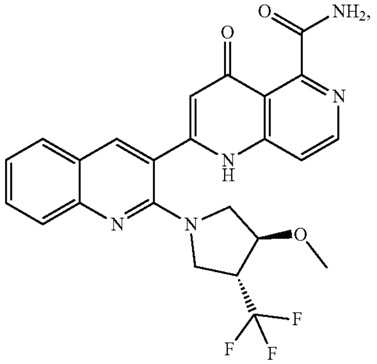 [SMILES: CO[C@@H]1CN(c2nc3ccccc3cc2-c2cc(=O)c3c(C(N)=O)nccc3[nH]2)C[C@H]1C(F)(F)F]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

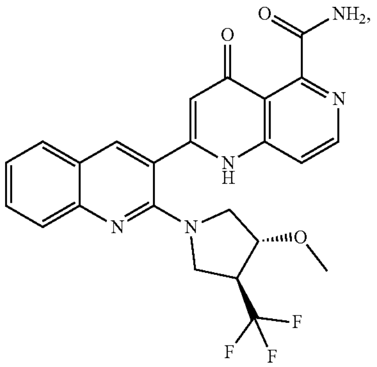 [SMILES: CO[C@H]1CN(c2nc3ccccc3cc2-c2cc(=O)c3c(C(N)=O)nccc3[nH]2)C[C@@H]1C(F)(F)F]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

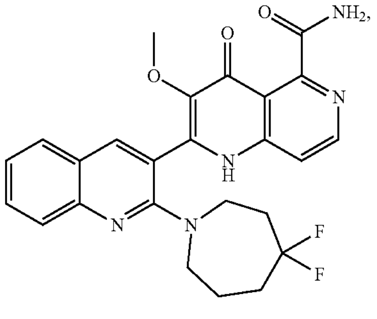 [SMILES: COc1c(-c2cc3ccccc3nc2N2CCCC(F)(F)CC2)[nH]c2ccnc(C(N)=O)c2c1=O]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

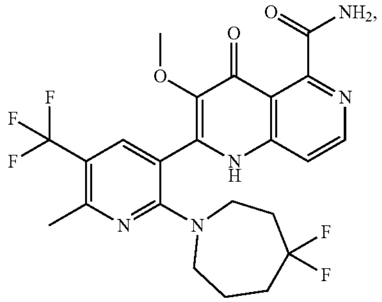 [SMILES: COc1c(-c2cc(C(F)(F)F)c(C)nc2N2CCCC(F)(F)CC2)[nH]c2ccnc(C(N)=O)c2c1=O]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

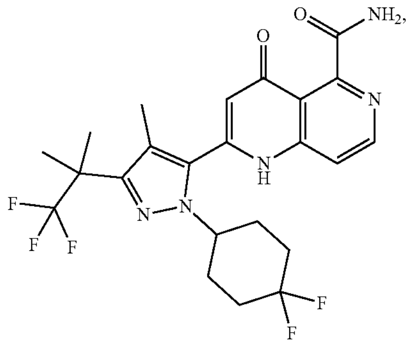 [SMILES: Cc1c(C(C)(C)C(F)(F)F)nn(C2CCC(F)(F)CC2)c1-c1cc(=O)c2c(C(N)=O)nccc2[nH]1]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

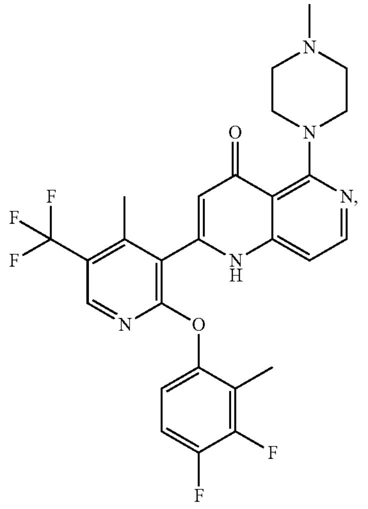 [SMILES: Cc1c(Oc2ncc(C(F)(F)F)c(C)c2-c2cc(=O)c3c(N4CCN(C)CC4)nccc3[nH]2)ccc(F)c1F]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

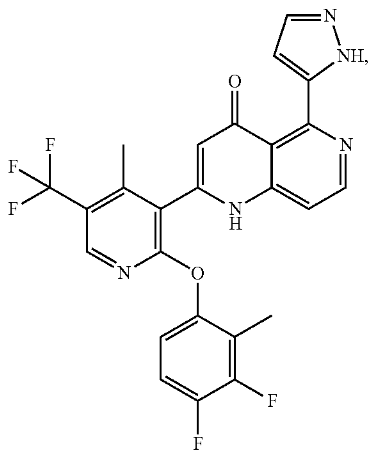 [SMILES: Cc1c(Oc2ncc(C(F)(F)F)c(C)c2-c2cc(=O)c3c(-c4ccn[nH]4)nccc3[nH]2)ccc(F)c1F]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

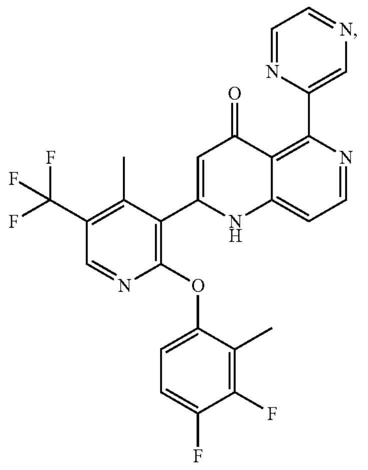 [SMILES: Cc1c(Oc2ncc(C(F)(F)F)c(C)c2-c2cc(=O)c3c(-c4cnccn4)nccc3[nH]2)ccc(F)c1F]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

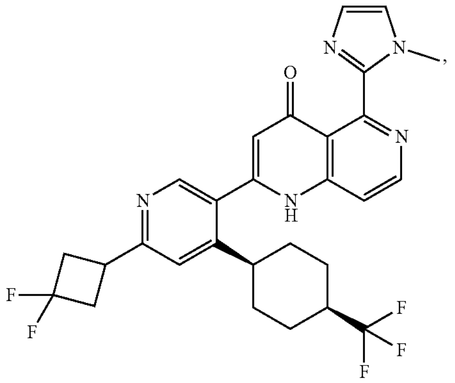 [SMILES: Cn1ccnc1-c1nccc2[nH]c(-c3cnc(C4CC(F)(F)C4)cc3[C@H]3CC[C@@H](C(F)(F)F)CC3)cc(=O)c12]

or a pharmaceutically acceptable salt thereof. In other embodiments, the invention relates to the foregoing compound in non-salt form. Such compound is considered to be a "compound of the invention," as that term is used herein.

Salts, Compositions, Uses, Formulation, Administration and Additional Agents

Pharmaceutically Acceptable Salts and Compositions

As discussed herein, the invention provides compounds, and pharmaceutically acceptable salts thereof, that are inhibitors of voltage-gated sodium channels, and thus the present compounds, and pharmaceutically acceptable salts thereof, are useful for the treatment of diseases, disorders, and conditions including, but not limited to chronic pain, gut pain, neuropathic pain, musculoskeletal pain, acute pain, inflammatory pain, cancer pain, idiopathic pain, postsurgical pain (e.g., bunionectomy pain, herniorrhaphy pain or abdominoplasty pain), visceral pain, multiple sclerosis, Charcot-Marie-Tooth syndrome, incontinence, pathological cough, or cardiac arrhythmia. Accordingly, in another aspect of the invention, pharmaceutical compositions are provided, wherein these compositions comprise a compound as described herein, or a pharmaceutically acceptable salt thereof, and optionally comprise a pharmaceutically acceptable carrier, adjuvant or vehicle. In certain embodiments, these compositions optionally further comprise one or more additional therapeutic agents. In some embodiments, the additional therapeutic agent is a sodium channel inhibitor.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" of a compound of this invention includes any non-toxic salt that, upon administration to a recipient, is capable of providing, either directly or indirectly, a compound of this invention or an inhibitorily active metabolite or residue thereof. The salt may be in pure form, in a mixture (e.g., solution, suspension, or colloid) with one or more other substances, or in the form of a hydrate, solvate, or co-crystal. As used herein, the term "inhibitorily active metabolite or residue thereof" means that a metabolite or residue thereof is also an inhibitor of a voltage-gated sodium channel.

Pharmaceutically acceptable salts are well known in the art. For example, S. M. Berge, et al. describe pharmaceutically acceptable salts in detail in *J Pharmaceutical Sciences,* 1977, 66, 1-19, incorporated herein by reference. Pharmaceutically acceptable salts of the compound of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As described herein, the pharmaceutically acceptable compositions of the invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In another aspect, the invention features a pharmaceutical composition comprising a compound of the invention, or a pharmaceutically acceptable salt thereof, and a pharmaceutically acceptable carrier.

In another aspect, the invention features a pharmaceutical composition comprising a therapeutically effective amount of a compound, or a pharmaceutically acceptable salt thereof, and one or more pharmaceutically acceptable carriers or vehicles.

Uses of Compounds and Pharmaceutically Acceptable Salts and Compositions

In another aspect, the invention features a method of inhibiting a voltage-gated sodium channel in a subject comprising administering to the subject a compound of the invention or a pharmaceutically acceptable salt thereof or a pharmaceutical composition thereof. In another aspect, the voltage-gated sodium channel is $Na_V1.8$.

In yet another aspect, the invention features a method of treating or lessening the severity in a subject of chronic pain, gut pain, neuropathic pain, musculoskeletal pain, acute pain, inflammatory pain, cancer pain, idiopathic pain, postsurgical pain (e.g., bunionectomy pain, herniorrhaphy pain or abdominoplasty pain), visceral pain, multiple sclerosis, Charcot-Marie-Tooth syndrome, incontinence, pathological cough, or cardiac arrhythmia comprising administering an effective amount of a compound of the invention, a pharmaceutically acceptable salt thereof or a pharmaceutical composition thereof.

In yet another aspect, the invention features a method of treating or lessening the severity in a subject of chronic pain, gut pain, neuropathic pain, musculoskeletal pain, acute pain, inflammatory pain, cancer pain, idiopathic pain, postsurgical pain, herniorrhaphy pain, bunionectomy pain, multiple sclerosis, Charcot-Marie-Tooth syndrome, incontinence, or cardiac arrhythmia comprising administering an effective amount of a compound of the invention, a pharmaceutically acceptable salt thereof or a pharmaceutical composition thereof.

In yet another aspect, the invention features a method of treating or lessening the severity in a subject of gut pain, wherein gut pain comprises inflammatory bowel disease pain, Crohn's disease pain, irritable bowel syndrome, endometriosis, polycystic ovarian disease, salpingitis, cervicitis or interstitial cystitis pain wherein said method comprises administering an effective amount of a compound of the invention, a pharmaceutically acceptable salt thereof or a pharmaceutical composition thereof.

In yet another aspect, the invention features a method of treating or lessening the severity in a subject of neuropathic pain comprising administering an effective amount of a compound of the invention, a pharmaceutically acceptable salt thereof or a pharmaceutical composition thereof. In some aspects, the neuropathic pain comprises post-herpetic neuralgia, small fiber neuropathy, diabetic neuropathy, or idiopathic small-fiber neuropathy. In some aspects, the neuropathic pain comprises diabetic neuropathy (e.g., diabetic peripheral neuropathy). As used herein, the phrase "idiopathic small-fiber neuropathy" shall be understood to include any small fiber neuropathy.

In yet another aspect, the invention features a method of treating or lessening the severity in a subject of neuropathic pain, wherein neuropathic pain comprises post-herpetic neuralgia, diabetic neuralgia, painful HIV-associated sensory neuropathy, trigeminal neuralgia, burning mouth syndrome, post-amputation pain, phantom pain, painful neuroma; traumatic neuroma; Morton's neuroma; nerve entrapment injury, spinal stenosis, carpal tunnel syndrome, radicular pain, sciatica pain; nerve avulsion injury, brachial plexus avulsion injury; complex regional pain syndrome, drug therapy induced neuralgia, cancer chemotherapy induced neuralgia, anti-retroviral therapy induced neuralgia, HIV-induced neuropathy; post spinal cord injury pain, spinal stenosis pain, small fiber neuropathy, idiopathic small-fiber neuropathy, idiopathic sensory neuropathy or trigeminal autonomic cephalalgia wherein said method comprises administering an effective amount of a compound of the invention, a pharmaceutically acceptable salt thereof or a pharmaceutical composition thereof.

In yet another aspect, the invention features a method of treating or lessening the severity in a subject of musculoskeletal pain comprising administering an effective amount of a compound of the invention, a pharmaceutically acceptable salt thereof or a pharmaceutical composition thereof. In some aspects, the musculoskeletal pain comprises osteoarthritis pain.

In yet another aspect, the invention features a method of treating or lessening the severity in a subject of musculoskeletal pain, wherein musculoskeletal pain comprises osteoarthritis pain, back pain, cold pain, burn pain or dental pain wherein said method comprises administering an effective amount of a compound of the invention, a pharmaceutically acceptable salt thereof or a pharmaceutical composition thereof.

In yet another aspect, the invention features a method of treating or lessening the severity in a subject of inflammatory pain, wherein inflammatory pain comprises rheumatoid arthritis pain, ankylosing spondylitis or vulvodynia wherein said method comprises administering an effective amount of a compound of the invention, a pharmaceutically acceptable salt thereof or a pharmaceutical composition thereof.

In yet another aspect, the invention features a method of treating or lessening the severity in a subject of inflammatory pain, wherein inflammatory pain comprises rheumatoid arthritis pain wherein said method comprises administering an effective amount of a compound of the invention, a pharmaceutically acceptable salt thereof or a pharmaceutical composition thereof.

In yet another aspect, the invention features a method of treating or lessening the severity in a subject of idiopathic pain, wherein idiopathic pain comprises fibromyalgia pain wherein said method comprises administering an effective amount of a compound of the invention, a pharmaceutically acceptable salt thereof or a pharmaceutical composition thereof.

In yet another aspect, the invention features a method of treating or lessening the severity in a subject of idiopathic pain, wherein idiopathic pain comprises reflex sympathetic dystrophy pain, wherein said method comprises administering an effective amount of a compound of the invention, a pharmaceutically acceptable salt thereof or a pharmaceutical composition thereof.

In yet another aspect, the invention features a method of treating or lessening the severity in a subject of pathological cough wherein said method comprises administering an effective amount of a compound of the invention, a pharmaceutically acceptable salt thereof or a pharmaceutical composition thereof.

In yet another aspect, the invention features a method of treating or lessening the severity in a subject of acute pain comprising administering an effective amount of a compound of the invention, a pharmaceutically acceptable salt thereof or a pharmaceutical composition thereof. In some aspects, the acute pain comprises acute post-operative pain.

In yet another aspect, the invention features a method of treating or lessening the severity in a subject of postsurgical pain (e.g., joint replacement pain, soft tissue surgery pain, post-thoracotomy pain, post-mastectomy pain, hemorrhoidectomy pain, heriorrhaphy pain, bunionectomy pain or abdominoplasty pain) comprising administering an effective amount of a compound of the invention, a pharmaceutically acceptable salt thereof or a pharmaceutical composition thereof.

In yet another aspect, the invention features a method of treating or lessening the severity in a subject of bunionectomy pain comprising administering an effective amount of a compound of the invention, a pharmaceutically acceptable salt thereof or a pharmaceutical composition thereof.

In yet another aspect, the invention features a method of treating or lessening the severity in a subject of shoulder arthroplasty pain or shoulder arthroscopy pain comprising administering an effective amount of a compound of the invention, a pharmaceutically acceptable salt thereof or a pharmaceutical composition thereof.

In yet another aspect, the invention features a method of treating or lessening the severity in a subject of herniorrhaphy pain comprising administering an effective amount of a compound of the invention, a pharmaceutically acceptable salt thereof or a pharmaceutical composition thereof.

In yet another aspect, the invention features a method of treating or lessening the severity in a subject of abdominoplasty pain comprising administering an effective amount of a compound of the invention, a pharmaceutically acceptable salt thereof or a pharmaceutical composition thereof.

In yet another aspect, the invention features a method of treating or lessening the severity in a subject of visceral pain comprising administering an effective amount of a compound of the invention, a pharmaceutically acceptable salt thereof or a pharmaceutical composition thereof. In some aspects, the visceral pain comprises visceral pain from abdominoplasty.

In yet another aspect, the invention features a method of treating or lessening the severity in a subject of a neurodegenerative disease comprising administering an effective amount of a compound of the invention, a pharmaceutically acceptable salt thereof or a pharmaceutical composition thereof. In some aspects, the neurodegenerative disease comprises multiple sclerosis. In some aspects, the neurodegenerative disease comprises Pitt Hopkins Syndrome (PTHS).

In yet another aspect, the invention features a method wherein the subject is treated with one or more additional therapeutic agents administered concurrently with, prior to, or subsequent to treatment with an effective amount of the compound, pharmaceutically acceptable salt or pharmaceutical composition. In some embodiments, the additional therapeutic agent is a sodium channel inhibitor.

In another aspect, the invention features a method of inhibiting a voltage-gated sodium channel in a biological sample comprising contacting the biological sample with an effective amount of a compound of the invention, a pharmaceutically acceptable salt thereof or a pharmaceutical composition thereof. In another aspect, the voltage-gated sodium channel is $Na_V1.8$.

In another aspect, the invention features a method of treating or lessening the severity in a subject of acute pain, sub-acute and chronic pain, nociceptive pain, neuropathic pain, inflammatory pain, nociplastic pain, arthritis, migraine, cluster headaches, tension headaches, and all other forms of headaches, trigeminal neuralgia, herpetic neuralgia, general neuralgias, epilepsy, epilepsy conditions, neurodegenerative disorders, psychiatric disorders, anxiety, depression, bipolar disorder, myotonia, arrhythmia, movement disorders, neuroendocrine disorders, ataxia, central neuropathic pain of multiple sclerosis and irritable bowel syndrome, incontinence, pathological cough, visceral pain, osteoarthritis pain, postherpetic neuralgia, diabetic neuropathy, radicular pain, sciatica, back pain, unspecific chronic back pain, head pain, neck pain, moderate pain, severe pain, intractable pain, nociceptive pain, breakthrough pain, postsurgical pain (e.g., joint replacement pain, soft tissue surgery pain, post-thoracotomy pain, post-mastectomy pain, heriorrhaphy pain, bunionectomy pain or abdominoplasty pain), cancer pain including chronic cancer pain and breakthrough cancer pain, stroke (e.g., post stroke central neuropathic pain), whiplash associated disorders, fragility fractures, spinal fractures, ankylosing spondylitis, pemphigus, Raynaud's Disease, scleroderma, systemic lupus erythematosus, Epidermolysis bullosa, gout, juvenile idiopathic arthritis, melorheostosis, polymyalgia reumatica, pyoderma gangrenosum, chronic widespread pain, diffuse idiopathic skeletal hyperostosis, disc degeneration/herniation pain, radiculopathy, facet joint syndrome, failed back surgery syndrome, burns, carpal tunnel syndrome, Paget's disease pain, spinal canal stenosis, spondylodyscitis, transverse myelitis, Ehlers-Danlos syndrome, Fabry's disease, mastocytocytosis, neurofibromatosis, ocular neuropathic pain, sarcoidosis, spondylolysis, spondylolisthesis, chemotherapy induced oral mucositis, Charcot neuropathic osteoarhropathy, temporo-mandibular joint disorder, painful joint arthroplasties, non-cardiac chest pain, pudendal neuralgia, renal colic, biliary tract diseases, vascular leg ulcers, pain in Parkinson's disease, pain in Alzheimer's disease, cerebral ischemia, traumatic brain injury, amyotrophic lateral sclerosis, stress induced angina, exercise induced angina, palpitations, hypertension, or abnormal gastro-intestinal motility, comprising administering an effective amount of a compound of the invention, a pharmaceutically acceptable salt thereof or a pharmaceutical composition thereof.

In another aspect, the invention features a method of treating or lessening the severity in a subject of femur cancer pain; non-malignant chronic bone pain; rheumatoid arthritis; osteoarthritis; spinal stenosis; neuropathic low back pain; myofascial pain syndrome; fibromyalgia; temporomandibular joint pain; chronic visceral pain, abdominal pain; pancreatic pain; IBS pain; chronic and acute headache pain; migraine; tension headache; cluster headaches; chronic and acute neuropathic pain, post-herpetic neuralgia; diabetic neuropathy; HIV-associated neuropathy; trigeminal neuralgia; Charcot-Marie-Tooth neuropathy; hereditary sensory neuropathy; peripheral nerve injury; painful neuromas; ectopic proximal and distal discharges; radiculopathy; chemotherapy induced neuropathic pain; radiotherapy-induced neuropathic pain; persistent/chronic post-surgical pain (e.g., post amputation, post-thoracotomy, post-cardiac surgery), post-mastectomy pain; central pain; spinal cord injury pain; post-stroke pain; thalamic pain; phantom pain (e.g., following removal of lower extremity, upper extremity, breast); intractable pain; acute pain, acute post-operative pain; acute musculoskeletal pain; joint pain; mechanical low back pain; neck pain; tendonitis; injury pain; exercise pain; acute visceral pain; pyelonephritis; appendicitis; cholecystitis; intestinal obstruction; hernias; chest pain, cardiac pain; pelvic pain, renal colic pain, acute obstetric pain, labor pain; cesarean section pain; acute inflammatory pain, burn pain, trauma pain; acute intermittent pain, endometriosis; acute herpes zoster pain; sickle cell anemia; acute pancreatitis; breakthrough pain; orofacial pain; sinusitis pain; dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; bladder and urogenital disease; urinary incontinence, pathological cough; hyperactive bladder; painful bladder syndrome; interstitial cystitis (IC); prostatitis; complex regional pain syndrome (CRPS), type I, complex regional pain syndrome (CRPS) type II; widespread pain, paroxysmal extreme pain, pruritus, tinnitus, or angina-induced pain, comprising administering an effective amount of a compound of the invention, a pharmaceutically acceptable salt thereof or a pharmaceutical composition thereof.

In another aspect, the invention features a method of treating or lessening the severity in a subject of trigeminal neuralgia, migraines treated with botox, cervical radiculopathy, occipital neuralgia, axillary neuropathy, radial neuropathy, ulnar neuropathy, brachial plexopathy, thoracic radiculopathy, intercostal neuralgia, lumbrosacral radiculopathy, iliolingual neuralgia, pudendal neuralgia, femoral neuropathy, meralgia paresthetica, saphenous neuropathy, sciatic neuropathy, peroneal neuropathy, tibial neuropathy, lumbosacral plexopathy, traumatic neuroma stump pain or postamputation pain, comprising administering an effective amount of a compound of the invention, a pharmaceutically acceptable salt thereof or a pharmaceutical composition thereof.

Compounds, Pharmaceutically Acceptable Salts, and Compositions for Use

In another aspect, the invention features a compound of the invention, or a pharmaceutically acceptable salt or pharmaceutical composition thereof, for use as a medicament.

In another aspect, the invention features a compound of the invention, or a pharmaceutically acceptable salt or pharmaceutical composition thereof, for use in a method of inhibiting a voltage-gated sodium channel in a subject. In another aspect, the voltage-gated sodium channel is $Na_V1.8$.

In another aspect, the invention features a compound of the invention, or a pharmaceutically acceptable salt or pharmaceutical composition thereof, for use in a method of treating or lessening the severity in a subject of chronic pain, gut pain, neuropathic pain, musculoskeletal pain, acute pain, inflammatory pain, cancer pain, idiopathic pain, postsurgical pain (e.g., heriorrhaphy pain, bunionectomy pain or abdominoplasty pain), visceral pain, multiple sclerosis, Charcot-Marie-Tooth syndrome, incontinence, pathological cough, or cardiac arrhythmia.

In another aspect, the invention features a compound of the invention, or a pharmaceutically acceptable salt or pharmaceutical composition thereof, for use in a method of treating or lessening the severity in a subject of gut pain, wherein gut pain comprises inflammatory bowel disease pain, Crohn's disease pain, irritable bowel syndrome, endometriosis, polycystic ovarian disease, salpingitis, cervicitis or interstitial cystitis pain.

In another aspect, the invention features a compound of the invention, or a pharmaceutically acceptable salt or pharmaceutical composition thereof, for use in a method of treating or lessening the severity in a subject of gut pain, wherein gut pain comprises inflammatory bowel disease pain, Crohn's disease pain, irritable bowel syndrome, endometriosis, polycyctic ovarian disease, salpingitis, cervicitis or interstitial cystitis pain.

In another aspect, the invention features a compound of the invention, or a pharmaceutically acceptable salt or pharmaceutical composition thereof, for use in a method of treating or lessening the severity in a subject of neuropathic pain. In some aspects, the neuropathic pain comprises post-herpetic neuralgia, small fiber neuropathy, diabetic neuropathy, or idiopathic small-fiber neuropathy. In some aspects, the neuropathic pain comprises diabetic neuropathy (e.g., diabetic peripheral neuropathy). As used herein, the phrase "idiopathic small-fiber neuropathy" shall be understood to include any small fiber neuropathy.

In another aspect, the invention features a compound of the invention, or a pharmaceutically acceptable salt or pharmaceutical composition thereof, for use in a method of treating or lessening the severity in a subject of neuropathic pain, wherein neuropathic pain comprises post-herpetic neuralgia, diabetic neuralgia, painful HIV-associated sensory neuropathy, trigeminal neuralgia, burning mouth syndrome, post-amputation pain, phantom pain, painful neuroma; traumatic neuroma; Morton's neuroma; nerve entrapment injury, spinal stenosis, carpal tunnel syndrome, radicular pain, sciatica pain; nerve avulsion injury, brachial plexus avulsion injury; complex regional pain syndrome, drug therapy induced neuralgia, cancer chemotherapy induced neuralgia, anti-retroviral therapy induced neuralgia, HIV-induced neuropathy; post spinal cord injury pain, spinal stenosis pain, small fiber neuropathy, idiopathic small-fiber neuropathy, idiopathic sensory neuropathy or trigeminal autonomic cephalalgia.

In another aspect, the invention features a compound of the invention, or a pharmaceutically acceptable salt or pharmaceutical composition thereof, for use in a method of treating or lessening the severity in a subject of musculoskeletal pain. In some aspects, the musculoskeletal pain comprises osteoarthritis pain.

In another aspect, the invention features a compound of the invention, or a pharmaceutically acceptable salt or pharmaceutical composition thereof, for use in a method of treating or lessening the severity in a subject of musculoskeletal pain, wherein musculoskeletal pain comprises osteoarthritis pain, back pain, cold pain, burn pain or dental pain.

In another aspect, the invention features a compound of the invention, or a pharmaceutically acceptable salt or pharmaceutical composition thereof, for use in a method of treating or lessening the severity in a subject of inflammatory pain, wherein inflammatory pain comprises rheumatoid arthritis pain, ankylosing spondylitis or vulvodynia.

In another aspect, the invention features a compound of the invention, or a pharmaceutically acceptable salt or pharmaceutical composition thereof, for use in a method of treating or lessening the severity in a subject of inflammatory pain, wherein inflammatory pain comprises rheumatoid arthritis pain.

In another aspect, the invention features a compound of the invention, or a pharmaceutically acceptable salt or pharmaceutical composition thereof, for use in a method of treating or lessening the severity in a subject of idiopathic pain, wherein idiopathic pain comprises fibromyalgia pain.

In yet another aspect, the invention features compound of the invention, or a pharmaceutically acceptable salt or pharmaceutical composition thereof, for use in a method of treating or lessening the severity in a subject of idiopathic pain, wherein idiopathic pain comprises reflex sympathetic dystrophy pain.

In another aspect, the invention features a compound of the invention, or a pharmaceutically acceptable salt or pharmaceutical composition thereof, for use in a method of treating or lessening the severity in a subject of pathological cough.

In another aspect, the invention features a compound of the invention, or a pharmaceutically acceptable salt or pharmaceutical composition thereof, for use in a method of treating or lessening the severity in a subject of acute pain. In some aspects, the acute pain comprises acute post-operative pain.

In another aspect, the invention features a compound of the invention, or a pharmaceutically acceptable salt or pharmaceutical composition thereof, for use in a method of treating or lessening the severity in a subject of postsurgical pain (e.g., joint replacement pain, soft tissue surgery pain, post-thoracotomy pain, post-mastectomy pain, hemorrhoidectomy pain, herniorrhaphy pain, bunionectomy pain or abdominoplasty pain).

In another aspect, the invention features a compound of the invention, or a pharmaceutically acceptable salt or pharmaceutical composition thereof, for use in a method of treating or lessening the severity in a subject of bunionectomy pain.

In yet another aspect, the invention features a compound of the invention, or a pharmaceutically acceptable salt or pharmaceutical composition thereof, for use in a method of treating or lessening the severity in a subject of shoulder arthroplasty pain or shoulder arthroscopy pain.

In another aspect, the invention features a compound of the invention, or a pharmaceutically acceptable salt or pharmaceutical composition thereof, for use in a method of treating or lessening the severity in a subject of herniorrhaphy pain.

In another aspect, the invention features a compound of the invention, or a pharmaceutically acceptable salt or pharmaceutical composition thereof, for use in a method of treating or lessening the severity in a subject of abdominoplasty pain.

In another aspect, the invention features a compound of the invention, or a pharmaceutically acceptable salt or pharmaceutical composition thereof, for use in a method of treating or lessening the severity in a subject of visceral pain. In some aspects, the visceral pain comprises visceral pain from abdominoplasty.

In another aspect, the invention features a compound of the invention, or a pharmaceutically acceptable salt or pharmaceutical composition thereof, for use in a method of treating or lessening the severity in a subject of a neurodegenerative disease. In some aspects, the neurodegenerative disease comprises multiple sclerosis. In some aspects, the neurodegenerative disease comprises Pitt Hopkins Syndrome (PTHS).

In another aspect, the invention features a compound of the invention, or a pharmaceutically acceptable salt or pharmaceutical composition thereof, for use in a method wherein the subject is treated with one or more additional therapeutic agents administered concurrently with, prior to, or subsequent to treatment with an effective amount of the compound, pharmaceutically acceptable salt or pharmaceutical composition. In some embodiments, the additional therapeutic agent is a sodium channel inhibitor.

In another aspect, the invention features a compound of the invention, or a pharmaceutically acceptable salt or pharmaceutical composition thereof, for use in a method of inhibiting a voltage-gated sodium channel in a biological sample comprising contacting the biological sample with an effective amount of a compound of the invention, a pharmaceutically acceptable salt thereof or a pharmaceutical composition thereof. In another aspect, the voltage-gated sodium channel is $Na_V1.8$.

In another aspect, the invention features a compound of the invention, or a pharmaceutically acceptable salt or pharmaceutical composition thereof, for use in a method of treating or lessening the severity in a subject of acute pain, sub-acute and chronic pain, nociceptive pain, neuropathic pain, inflammatory pain, nociplastic pain, arthritis, migraine, cluster headaches, tension headaches, and all other forms of headaches, trigeminal neuralgia, herpetic neuralgia, general neuralgias, epilepsy, epilepsy conditions, neurodegenerative disorders, psychiatric disorders, anxiety, depression, bipolar disorder, myotonia, arrhythmia, movement disorders, neuroendocrine disorders, ataxia, central neuropathic pain of multiple sclerosis and irritable bowel syndrome, incontinence, pathological cough, visceral pain, osteoarthritis pain, postherpetic neuralgia, diabetic neuropathy, radicular pain, sciatica, back pain, unspecific chronic back pain, head pain, neck pain, moderate pain, severe pain, intractable pain, nociceptive pain, breakthrough pain, postsurgical pain (e.g., joint replacement pain, soft tissue surgery pain, post-thoracotomy pain, post-mastectomy pain, herniorrhaphy pain, bunionectomy pain or abdominoplasty pain), cancer pain including chronic cancer pain and breakthrough cancer pain, stroke (e.g., post stroke central neuropathic pain), whiplash associated disorders, fragility fractures, spinal fractures, ankylosing spondylitis, pemphigus, Raynaud's Disease, scleroderma, systemic lupus erythematosus, Epidermolysis bullosa, gout, juvenile idiopathic arthritis, melorheostosis, polymyalgia reumatica, pyoderma gangrenosum, chronic widespread pain, diffuse idiopathic skeletal hyperostosis, disc degeneration/herniation pain, radiculopathy, facet joint syndrome, failed back surgery syndrome, burns, carpal tunnel syndrome, Paget's disease pain, spinal canal stenosis, spondylodyscitis, transverse myelitis, Ehlers-Danlos syndrome, Fabry's disease, mastocytocytosis, neurofibromatosis, ocular neuropathic pain, sarcoidosis, spondylolysis, spondylolisthesis, chemotherapy induced oral mucositis, Charcot neuropathic osteoarhropathy, temporo-mandibular joint disorder, painful joint arthroplasties, non-cardiac chest pain, pudendal, renal colic, biliary tract diseases, vascular leg ulcers, pain in Parkinson's disease, pain in Alzheimer's disease, cerebral ischemia, traumatic brain injury, amyotrophic lateral sclerosis, stress induced angina, exercise induced angina, palpitations, hypertension, or abnormal gastro-intestinal motility.

In another aspect, the invention features a compound of the invention, or a pharmaceutically acceptable salt or pharmaceutical composition thereof, for use in a method of treating or lessening the severity in a subject of femur cancer pain; non-malignant chronic bone pain; rheumatoid arthritis; osteoarthritis; spinal stenosis; neuropathic low back pain; myofascial pain syndrome; fibromyalgia; temporomandibular joint pain; chronic visceral pain, abdominal pain; pancreatic pain; IBS pain; chronic and acute headache pain; migraine; tension headache; cluster headaches; chronic and acute neuropathic pain, post-herpetic neuralgia; diabetic neuropathy; HIV-associated neuropathy; trigeminal neuralgia; Charcot-Marie-Tooth neuropathy; hereditary sensory neuropathy; peripheral nerve injury; painful neuromas; ectopic proximal and distal discharges; radiculopathy; chemotherapy induced neuropathic pain; radiotherapy-induced neuropathic pain; persistent/chronic post-surgical pain (e.g., post amputation, post-thoracotomy, post-cardiac surgery), post-mastectomy pain; central pain; spinal cord injury pain; post-stroke pain; thalamic pain; phantom pain (e.g., following removal of lower extremity, upper extremity, breast); intractable pain; acute pain, acute post-operative pain; acute musculoskeletal pain; joint pain; mechanical low back pain; neck pain; tendonitis; injury pain; exercise pain; acute visceral pain; pyelonephritis; appendicitis; cholecystitis; intestinal obstruction; hernias; chest pain, cardiac pain; pelvic pain, renal colic pain, acute obstetric pain, labor pain; cesarean section pain; acute inflammatory pain, burn pain, trauma pain; acute intermittent pain, endometriosis; acute herpes zoster pain; sickle cell anemia; acute pancreatitis; breakthrough pain; orofacial pain; sinusitis pain; dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; bladder and urogenital disease; urinary incontinence, pathological cough; hyperactive bladder; painful bladder syndrome; interstitial cystitis (IC); prostatitis; complex regional pain syndrome (CRPS), type I, complex regional pain syndrome (CRPS) type II; widespread pain, paroxysmal extreme pain, pruritus, tinnitus, or angina-induced pain.

In another aspect, the invention features a compound of the invention, or a pharmaceutically acceptable salt or pharmaceutical composition thereof, for use in a method of treating or lessening the severity in a subject of trigeminal neuralgia, migraines treated with botox, cervical radiculopathy, occipital neuralgia, axillary neuropathy, radial neuropathy, ulnar neuropathy, brachial plexopathy, thoracic radiculopathy, intercostal neuralgia, lumbrosacral radiculopathy, iliolingual neuralgia, pudendal neuralgia, femoral neuropathy, meralgia paresthetica, saphenous neuropathy, sciatic neuropathy, peroneal neuropathy, tibial neuropathy, lumbosacral plexopathy, traumatic neuroma stump pain or post-amputation pain.

Manufacture of Medicaments

In another aspect, the invention provides the use of a compound of the invention, or a pharmaceutically acceptable salt or pharmaceutical composition thereof, for the manufacture of a medicament.

In another aspect, the invention provides the use of a compound of the invention, a pharmaceutically acceptable salt thereof, or a pharmaceutical composition thereof for the manufacture of a medicament for use in inhibiting a voltage-gated sodium channel. In another aspect, the voltage-gated sodium channel is $Na_V1.8$.

In yet another aspect, the invention provides the use of a compound of the invention, a pharmaceutically acceptable salt thereof, or a pharmaceutical composition thereof for the manufacture of a medicament for use in treating or lessening the severity in a subject of chronic pain, gut pain, neuropathic pain, musculoskeletal pain, acute pain, inflammatory pain, cancer pain, idiopathic pain, postsurgical pain (e.g., herniorrhaphy pain, bunionectomy pain or abdominoplasty pain), visceral pain, multiple sclerosis, Charcot-Marie-Tooth syndrome, incontinence, pathological cough, or cardiac arrhythmia.

In yet another aspect, the invention provides the use of a compound of the invention, a pharmaceutically acceptable salt thereof, or a pharmaceutical composition thereof for the manufacture of a medicament for use in treating or lessening the severity in a subject of chronic pain, gut pain, neuropathic pain, musculoskeletal pain, acute pain, inflammatory pain, cancer pain, idiopathic pain, postsurgical pain, herniorrhaphy pain, bunionectomy pain, multiple sclerosis, Charcot-Marie-Tooth syndrome, incontinence, or cardiac arrhythmia.

In yet another aspect, the invention provides the use of the compound, pharmaceutically acceptable salt, or pharmaceutical composition described herein for the manufacture of a medicament for use in treating or lessening the severity in a subject of gut pain, wherein gut pain comprises inflammatory bowel disease pain, Crohn's disease pain, irritable bowel syndrome, endometriosis, polycystic ovarian disease, salpingitis, cervicitis or interstitial cystitis pain.

In yet another aspect, the invention provides a compound of the invention, a pharmaceutically acceptable salt thereof, or a pharmaceutical composition thereof for the manufacture of a medicament for use in treating or lessening the severity in a subject of neuropathic pain. In some aspects, the neuropathic pain comprises post-herpetic neuralgia, small fiber neuropathy, diabetic neuropathy, or idiopathic small-fiber neuropathy. In some aspects, the neuropathic pain comprises diabetic neuropathy (e.g., diabetic peripheral neuropathy).

In yet another aspect, the invention provides the use of a compound of the invention, a pharmaceutically acceptable salt thereof, or a pharmaceutical composition thereof for the manufacture of a medicament for use in a treating or lessening the severity in a subject of neuropathic pain, wherein neuropathic pain comprises post-herpetic neuralgia, diabetic neuralgia, painful HIV-associated sensory neuropathy, trigeminal neuralgia, burning mouth syndrome, post-amputation pain, phantom pain, painful neuroma; traumatic neuroma; Morton's neuroma; nerve entrapment injury, spinal stenosis, carpal tunnel syndrome, radicular pain, sciatica pain; nerve avulsion injury, brachial plexus avulsion injury; complex regional pain syndrome, drug therapy induced neuralgia, cancer chemotherapy induced neuralgia, anti-retroviral therapy induced neuralgia, HIV-induced neuropathy; post spinal cord injury pain, spinal stenosis pain, small fiber neuropathy, idiopathic small-fiber neuropathy, idiopathic sensory neuropathy or trigeminal autonomic neuropathy.

In yet another aspect, the invention provides the use of a compound of the invention, a pharmaceutically acceptable salt thereof, or a pharmaceutical composition thereof for the manufacture of a medicament for use in treating or lessening the severity in a subject of musculoskeletal pain. In some aspects the musculoskeletal pain comprises osteoarthritis pain.

In yet another aspect, the invention provides the use of a compound of the invention, a pharmaceutically acceptable salt thereof, or a pharmaceutical composition thereof for the manufacture of a medicament for use in treating or lessening the severity in a subject of musculoskeletal pain, wherein musculoskeletal pain comprises osteoarthritis pain, back pain, cold pain, burn pain or dental pain.

In yet another aspect, the invention provides the use of a compound of the invention, a pharmaceutically acceptable salt thereof, or a pharmaceutical composition thereof for the manufacture of a medicament for use in treating or lessening the severity in a subject of inflammatory pain, wherein inflammatory pain comprises rheumatoid arthritis pain, ankylosing spondylitis or vulvodynia.

In yet another aspect, the invention provides the use of a compound of the invention, a pharmaceutically acceptable salt thereof, or a pharmaceutical composition thereof for the manufacture of a medicament for use in treating or lessening the severity in a subject of inflammatory pain, wherein inflammatory pain comprises rheumatoid arthritis pain.

In yet another aspect, the invention provides the use of a compound of the invention, a pharmaceutically acceptable salt thereof, or a pharmaceutical composition thereof for the manufacture of a medicament for use in treating or lessening the severity in a subject of idiopathic pain, wherein idiopathic pain comprises fibromyalgia pain.

In yet another aspect, the invention provides for the use of a compound of the invention, a pharmaceutically acceptable salt thereof, or a pharmaceutical composition thereof for the manufacture of a medicament for use in treating or lessening the severity in a subject of idiopathic pain, wherein idiopathic pain comprises reflex sympathetic dystrophy pain.

In yet another aspect, the invention provides the use of a compound of the invention, a pharmaceutically acceptable salt thereof, or a pharmaceutical composition thereof for the manufacture of a medicament for use in treating or lessening the severity in a subject of pathological cough.

In yet another aspect, the invention provides the use of a compound of the invention, a pharmaceutically acceptable salt thereof, or a pharmaceutical composition thereof for the manufacture of a medicament for use in treating or lessening the severity in a subject of acute pain. In some aspects, the acute pain comprises acute post-operative pain.

In yet another aspect, the invention provides the use of a compound of the invention, a pharmaceutically acceptable salt thereof, or a pharmaceutical composition thereof for the manufacture of a medicament for use in treating or lessening the severity in a subject of postsurgical pain (e.g., joint replacement pain, soft tissue surgery pain, post-thoracotomy pain, post-mastectomy pain, hemorrhoidectomy pain, heriorrhaphy pain, bunionectomy pain or abdominoplasty pain).

In yet another aspect, the invention provides the use of a compound of the invention, a pharmaceutically acceptable salt thereof, or a pharmaceutical composition thereof for the manufacture of a medicament for use in treating or lessening the severity in a subject of herniorrhaphy pain.

In yet another aspect, the invention provides the use of a compound of the invention, a pharmaceutically acceptable salt thereof, or a pharmaceutical composition thereof for the manufacture of a medicament for use in treating or lessening the severity in a subject of bunionectomy pain.

In yet another aspect, the invention provides the use of a compound of the invention, a pharmaceutically acceptable salt thereof, or a pharmaceutical composition thereof for the manufacture of a medicament for use in treating or lessening the severity in a subject of shoulder arthroplasty pain or shoulder arthroscopy pain.

In yet another aspect, the invention provides the use of a compound of the invention, a pharmaceutically acceptable salt thereof, or a pharmaceutical composition thereof for the manufacture of a medicament for use in treating or lessening the severity in a subject of abdominoplasty pain.

In yet another aspect, the invention provides the use of a compound of the invention, a pharmaceutically acceptable salt thereof, or a pharmaceutical composition thereof for the manufacture of a medicament for use in treating or lessening the severity in a subject of visceral pain. In some aspects, the visceral pain comprises visceral pain from abdominoplasty.

In another aspect, the invention features a compound of the invention, or a pharmaceutically acceptable salt or pharmaceutical composition thereof, for the manufacture of a medicament for use in treating or lessening the severity in a subject of a neurodegenerative disease. In some aspects, the neurodegenerative disease comprises multiple sclerosis. In some aspects, the neurodegenerative disease comprises Pitt Hopkins Syndrome (PTHS).

In yet another aspect, the invention provides the use of a compound of the invention, a pharmaceutically acceptable salt thereof, or a pharmaceutical composition thereof for the manufacture of a medicament for use in combination with one or more additional therapeutic agents administered concurrently with, prior to, or subsequent to treatment with the compound or pharmaceutical composition.

In some embodiments, the additional therapeutic agent is a sodium channel inhibitor.

In another aspect, the invention provides the use of a compound of the invention, a pharmaceutically acceptable salt thereof, or a pharmaceutical composition thereof for the manufacture of a medicament for use in treating or lessening the severity of acute pain, sub-acute and chronic pain, nociceptive pain, neuropathic pain, inflammatory pain, nociplastic pain, arthritis, migraine, cluster headaches, tension headaches, and all other forms of headaches, trigeminal neuralgia, herpetic neuralgia, general neuralgias, epilepsy, epilepsy conditions, neurodegenerative disorders, psychiatric disorders, anxiety, depression, bipolar disorder, myotonia, arrhythmia, movement disorders, neuroendocrine disorders, ataxia, central neuropathic pain of multiple sclerosis and irritable bowel syndrome, incontinence, pathological cough, visceral pain, osteoarthritis pain, postherpetic neuralgia, diabetic neuropathy, radicular pain, sciatica, back pain, unspecific chronic back pain, head pain, neck pain, moderate pain, severe pain, intractable pain, nociceptive pain, breakthrough pain, postsurgical pain (e.g., joint replacement pain, soft tissue surgery pain, post-thoracotomy pain, post-mastectomy pain, herniorrhaphy pain, bunionectomy pain or abdominoplasty pain), cancer pain including chronic cancer pain and breakthrough cancer pain, stroke (e.g., post stroke central neuropathic pain), whiplash associated disorders, fragility fractures, spinal fractures, ankylosing spondylitis, pemphigus, Raynaud's Disease, scleroderma, systemic lupus erythematosus, Epidermolysis bullosa, gout, juvenile idiopathic arthritis, melorheostosis, polymyalgia reumatica, pyoderma gangrenosum, chronic widespread pain, diffuse idiopathic skeletal hyperostosis, disc degeneration/herniation pain, radiculopathy, facet joint syndrome, failed back surgery syndrome, burns, carpal tunnel syndrome, Paget's disease pain, spinal canal stenosis, spondylodyscitis, transverse myelitis, Ehlers-Danlos syndrome, Fabry's disease, mastocytocytosis, neurofibromatosis, ocular neuropathic pain, sarcoidosis, spondylolysis, spondylolisthesis, chemotherapy induced oral mucositis, Charcot neuropathic osteoarhropathy, temporo-mandibular joint disorder, painful joint arthroplasties, non-cardiac chest pain, pudendal, renal colic, biliary tract diseases, vascular leg ulcers, pain in Parkinson's disease, pain in Alzheimer's disease, cerebral ischemia, traumatic brain injury, amyotrophic lateral sclerosis, stress induced angina, exercise induced angina, palpitations, hypertension, or abnormal gastro-intestinal motility.

In another aspect, the invention provides the use of a compound of the invention, a pharmaceutically acceptable salt thereof, or a pharmaceutical composition thereof for the manufacture of a medicament for use in treating or lessening the severity of femur cancer pain; non-malignant chronic bone pain; rheumatoid arthritis; osteoarthritis; spinal stenosis; neuropathic low back pain; myofascial pain syndrome; fibromyalgia; temporomandibular joint pain; chronic visceral pain, abdominal pain; pancreatic pain; IBS pain; chronic and acute headache pain; migraine; tension headache; cluster headaches; chronic and acute neuropathic pain, post-herpetic neuralgia; diabetic neuropathy; HIV-associated neuropathy; trigeminal neuralgia; Charcot-Marie-Tooth neuropathy; hereditary sensory neuropathy; peripheral nerve injury; painful neuromas; ectopic proximal and distal discharges; radiculopathy; chemotherapy induced neuropathic pain; radiotherapy-induced neuropathic pain; persistent/chronic post-surgical pain (e.g., post amputation, post-thoracotomy, post-cardiac surgery), post-mastectomy pain; central pain; spinal cord injury pain; post-stroke pain; thalamic pain; phantom pain (e.g., following removal of lower extremity, upper extremity, breast); intractable pain; acute pain, acute post-operative pain; acute musculoskeletal pain; joint pain; mechanical low back pain; neck pain; tendonitis; injury pain; exercise pain; acute visceral pain; pyelonephritis; appendicitis; cholecystitis; intestinal obstruction; hernias; chest pain, cardiac pain; pelvic pain, renal colic pain, acute obstetric pain, labor pain; cesarean section pain; acute inflammatory pain, burn pain, trauma pain; acute intermittent pain, endometriosis; acute herpes zoster pain; sickle cell anemia; acute pancreatitis; breakthrough pain; orofacial pain; sinusitis pain; dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; bladder and urogenital disease; urinary incontinence, pathological cough; hyperactive bladder; painful bladder syndrome; interstitial cystitis (IC); prostatitis; complex regional pain syndrome (CRPS), type I, complex regional pain syndrome (CRPS) type II; widespread pain, paroxysmal extreme pain, pruritus, tinnitus, or angina-induced pain.

In another aspect, the invention provides the use of a compound of the invention, a pharmaceutically acceptable salt thereof, or a pharmaceutical composition thereof for the manufacture of a medicament for use in treating or lessening the severity of trigeminal neuralgia, migraines treated with botox, cervical radiculopathy, occipital neuralgia, axillary neuropathy, radial neuropathy, ulnar neuropathy, brachial plexopathy, thoracic radiculopathy, intercostal neuralgia, lumbrosacral radiculopathy, iliolingual neuralgia, pudendal neuralgia, femoral neuropathy, meralgia paresthetica, saphenous neuropathy, sciatic neuropathy, peroneal neuropathy, tibial neuropathy, lumbosacral plexopathy, traumatic neuroma stump pain or postamputation pain.

Administration of Compounds, Pharmaceutically Acceptable Salts, and Compositions In certain embodiments of the invention an "effective amount" of a compound of the invention, a pharmaceutically acceptable salt thereof, or a pharmaceutical composition thereof is that amount effective for treating or lessening the severity of one or more of the conditions recited above.

The compounds, salts, and compositions, according to the method of the invention, may be administered using any amount and any route of administration effective for treating or lessening the severity of one or more of the pain or non-pain diseases recited herein. The exact amount required will vary from subject to subject, depending on the species, age, and general condition of the subject, the severity of the condition, the particular agent, its mode of administration, and the like. The compounds, salts, and compositions of the invention are preferably formulated in dosage unit form for ease of administration and uniformity of dosage. The expression "dosage unit form" as used herein refers to a physically discrete unit of agent appropriate for the subject to be treated. It will be understood, however, that the total daily usage of the compounds, salts, and compositions of the invention will be decided by the attending physician within the scope of sound medical judgment. The specific effective dose level for any particular subject or organism will depend upon a variety of factors including the disorder being treated and the severity of the disorder; the activity of the specific compound or salt employed; the specific composition employed; the age, body weight, general health, sex and diet of the subject; the time of administration, route of administration, and rate of excretion of the specific compound or salt employed; the duration of the treatment; drugs used in combination or coincidental with the specific compound or salt employed, and like factors well known in the medical arts. The term "subject" or "patient," as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the condition being treated. In certain embodiments, the compound, salts, and compositions of the invention may be administered orally or parenterally at dosage levels of about 0.001 mg/kg to about 1000 mg/kg, one or more times a day, effective to obtain the desired therapeutic effect.

Liquid dosage forms for oral administration include, but are not limited to, pharmaceutically acceptable emulsions, microemulsions, solutions, suspensions, syrups and elixirs. In addition to the active compound or salt, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of the compounds of the invention, it is often desirable to slow the absorption of the compounds from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compound or salt of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound or salt is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compound or salt can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound or salt may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound or salt of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of voltage-gated sodium channels. In one embodiment, the compounds are inhibitors of $Na_V1.8$ and thus, without wishing to be bound by any particular theory, the compounds, salts, and compositions are particularly useful for treating or lessening the severity of a disease, condition, or disorder where activation or hyperactivity of $Na_V1.8$ is implicated in the disease, condition, or disorder. When activation or hyperactivity of $Na_V1.8$ is implicated in a particular disease, condition, or disorder, the disease, condition, or disorder may also be referred to as a "$Na_V1.8$-mediated disease, condition or disorder." Accordingly, in another aspect, the invention provides a method for treating or lessening the severity of a disease, condition, or disorder where activation or hyperactivity of $Na_V1.8$ is implicated in the disease state.

The activity of a compound utilized in this invention as an inhibitor of $Na_V1.8$ may be assayed according to methods described generally in International Publication No. WO 2014/120808 A9 and U.S. Publication No. 2014/0213616 A1, both of which are incorporated by reference in their entirety, methods described herein, and other methods known and available to one of ordinary skill in the art.

Additional Therapeutic Agents

It will also be appreciated that the compounds, salts, and pharmaceutically acceptable compositions of the invention can be employed in combination therapies, that is, the compounds, salts, and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated." For example, exemplary additional therapeutic agents include, but are not limited to: non-opioid analgesics (indoles such as Etodolac, Indomethacin, Sulindac, Tolmetin; naphthylalkanones such as Nabumetone; oxicams such as Piroxicam; para-aminophenol derivatives, such as Acetaminophen; propionic acids such as Fenoprofen, Flurbiprofen, Ibuprofen, Ketoprofen, Naproxen, Naproxen sodium, Oxaprozin; salicylates such as Aspirin, Choline magnesium trisalicylate, Diflunisal; fenamates such as meclofenamic acid, Mefenamic acid; and pyrazoles such as Phenylbutazone); or opioid (narcotic) agonists (such as Codeine, Fentanyl, Hydromorphone, Levorphanol, Meperidine, Methadone, Morphine, Oxycodone, Oxymorphone, Propoxyphene, Buprenorphine, Butorphanol, Dezocine, Nalbuphine, and Pentazocine). Additionally, nondrug analgesic approaches may be utilized in conjunction with administration of one or more compounds of the invention. For example, anesthesiologic (intraspinal infusion, neural blockade), neurosurgical (neurolysis of CNS pathways), neurostimulatory (transcutaneous electrical nerve stimulation, dorsal column stimulation), physiatric (physical therapy, orthotic devices, diathermy), or psychologic (cognitive methods-hypnosis, biofeedback, or behavioral methods) approaches may also be utilized. Additional appropriate therapeutic agents or approaches are described generally in The Merck Manual, Nineteenth Edition, Ed. Robert S. Porter and Justin L. Kaplan, Merck Sharp & Dohme Corp., a subsidiary of Merck & Co., Inc., 2011, and the Food and Drug Administration website, www.fda.gov, the entire contents of which are hereby incorporated by reference.

In another embodiment, additional appropriate therapeutic agents are selected from the following:

(1) an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine, pentazocine, or difelikefalin;

(2) a nonsteroidal antiinflammatory drug (NSAID), e.g. aspirin, diclofenac, diflunisal, etodolac, fenbufen, fenoprofen, flufenisal, flurbiprofen, ibuprofen (including without limitation intravenous ibuprofen (e.g., Caldolor®)), indomethacin, ketoprofen, ketorolac (including without limitation ketorolac tromethamine (e.g., Toradol®)), meclofenamic acid, mefenamic acid, meloxicam, IV meloxicam (e.g., Anjeso®), nabumetone, naproxen, nimesulide, nitroflurbiprofen, olsalazine, oxaprozin, phenylbutazone, piroxicam, sulfasalazine, sulindac, tolmetin or zomepirac;

(3) a barbiturate sedative, e.g. amobarbital, aprobarbital, butabarbital, butalbital, mephobarbital, metharbital, methohexital, pentobarbital, phenobarbital, secobarbital, talbutal, thiamylal or thiopental;

(4) a benzodiazepine having a sedative action, e.g. chlordiazepoxide, clorazepate, diazepam, flurazepam, lorazepam, oxazepam, temazepam or triazolam;

(5) a histamine ($H_1$) antagonist having a sedative action, e.g. diphenhydramine, pyrilamine, promethazine, chlorpheniramine or chlorcyclizine;

(6) a sedative such as glutethimide, meprobamate, methaqualone or dichloralphenazone;

(7) a skeletal muscle relaxant, e.g. baclofen, carisoprodol, chlorzoxazone, cyclobenzaprine, methocarbamol or orphenadrine;

(8) an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®), a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

(9) an alpha-adrenergic, e.g. doxazosin, tamsulosin, clonidine, guanfacine, dexmedetomidine, modafinil, or 4-amino-6,7-dimethoxy-2-(5-methane-sulfonamido-1,2,3,4-tetrahydroisoquinolin-2-yl)-5-(2-pyridyl) quinazoline;

(10) a tricyclic antidepressant, e.g. desipramine, imipramine, amitriptyline or nortriptyline;

(11) an anticonvulsant, e.g. carbamazepine (Tegretol®), lamotrigine, topiramate, lacosamide (Vimpat®) or valproate;

(12) a tachykinin (NK) antagonist, particularly an NK-3, NK-2 or NK-1 antagonist, e.g. (alphaR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

(13) a muscarinic antagonist, e.g oxybutynin, tolterodine, propiverine, tropsium chloride, darifenacin, solifenacin, temiverine and ipratropium;

(14) a COX-2 selective inhibitor, e.g. celecoxib, rofecoxib, parecoxib, valdecoxib, deracoxib, etoricoxib, or lumiracoxib;

(15) a coal-tar analgesic, in particular paracetamol;

(16) a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;

(17) a vanilloid receptor agonist (e.g. resinferatoxin or civamide) or antagonist (e.g. capsazepine, GRC-15300);

(18) a beta-adrenergic such as propranolol;

(19) a local anesthetic such as mexiletine;

(20) a corticosteroid such as dexamethasone;

(21) a 5-HT receptor agonist or antagonist, particularly a 5-$HT_{1B/1D}$ agonist such as eletriptan, sumatriptan, naratriptan, zolmitriptan or rizatriptan;

(22) a 5-$HT_{2A}$ receptor antagonist such as R(+)-alpha-(2,3-dimethoxy-phenyl)-1-[2-(4-fluorophenylethyl)]-4-piperidinemethanol (MDL-100907);

(23) a cholinergic (nicotinic) analgesic, such as ispronicline (TC-1734), (E)-N-methyl-4-(3-pyridinyl)-3-buten-1-amine (RJR-2403), (R)-5-(2-azetidinyl-methoxy)-2-chloropyridine (ABT-594) or nicotine;

(24) Tramadol®, Tramadol ER (Ultram ER®), IV Tramadol, Tapentadol ER (Nucynta®);

(25) a PDE5 inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

(26) an alpha-2-delta ligand such as gabapentin (Neurontin®), gabapentin GR (Gralise®), gabapentin, enacarbil (Horizant®), pregabalin (Lyrica®), 3-methyl gabapentin, (1[alpha],3[alpha],5[alpha])(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)

proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;

(27) a cannabinoid such as KHK-6188;

(28) metabotropic glutamate subtype 1 receptor (mGluRl) antagonist;

(29) a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

(30) a noradrenaline (norepinephrine) reuptake inhibitor, such as maprotiline, lofepramine, mirtazepine, oxaprotiline, fezolamine, tomoxetine, mianserin, bupropion, bupropion metabolite hydroxybupropion, nomifensine and viloxazine (Vivalan®), especially a selective noradrenaline reuptake inhibitor such as reboxetine, in particular (S,S)-reboxetine;

(31) a dual serotonin-noradrenaline reuptake inhibitor, such as venlafaxine, venlafaxine metabolite O-desmethylvenlafaxine, clomipramine, clomipramine metabolite desmethylclomipramine, duloxetine (Cymbalta®), milnacipran and imipramine;

(32) an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-S-chloro-S-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl)butyl]thio]-6-(trifluoromethyl)-3-pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, NXN-462, or guanidinoethyldisulfide;

(33) an acetylcholinesterase inhibitor such as donepezil;

(34) a prostaglandin E2 subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methylbenzenesulfonamide or 4-[(15)-1-({[5-chloro-2-(3-fluorophenoxy)pyridin-3-yl]carbonyl}amino)ethyl]benzoic acid;

(35) a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870;

(36) a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl)-1,4-benzoquinone (CV-6504);

(37) a sodium channel blocker, such as lidocaine, lidocaine plus tetracaine cream (ZRS-201) or eslicarbazepine acetate;

(38) a $Na_V1.7$ blocker, such as XEN-402, XEN403, TV-45070, PF-05089771, CNV1014802, GDC-0276, RG7893 BIIB-074 (Vixotrigine), BIIB-095, ASP-1807, DSP-3905, OLP-1002, RQ-00432979, FX-301, DWP-1706, DWP-17061, IMB-110, IMB-111, IMB-112 and such as those disclosed in WO2011/140425 (US2011/306607); WO2012/106499 (US2012196869); WO2012/112743 (US2012245136); WO2012/125613 (US2012264749), WO2012/116440 (US2014187533), WO2011026240 (US2012220605), U.S. Pat. Nos. 8,883,840, 8,466,188, WO2013/109521 (US2015005304), WO2020/117626, WO2021/252822, WO2021/252818, WO2021/252820, WO2014/201173, WO2012/125973, WO2013/086229, WO2013/134518, WO2014/201206, or WO2016/141035, and CN111217776, the entire contents of each application hereby incorporated by reference;

(38a) a $Na_V1.7$ blocker such as (2-benzylspiro[3,4-dihydropyrrolo[1,2-a]pyrazine-1,4'-piperidine]-1'-yl)-(4-isopropoxy-3-methyl-phenyl)methanone, 2,2,2-trifluoro-1-[1'-[3-methoxy-4-[2-(trifluoromethoxy)ethoxy]benzoyl]-2,4-dimethyl-spiro[3,4-dihydropyrrolo[1,2-a]pyrazine-1,4'-piperidine]-6-yl]ethanone, [8-fluoro-2-methyl-6-(trifluoromethyl)spiro[3,4-dihydropyrrolo[1,2-a]pyrazine-1,4'-piperidine]-1'-yl]-(4-isobutoxy-3-methoxy-phenyl)methanone, 1-(4-benzhydrylpiperazin-1-yl)-3-[2-(3,4-dimethylphenoxy)ethoxy]propan-2-ol, (4-butoxy-3-methoxy-phenyl)-[2-methyl-6-(trifluoromethyl)spiro[3,4-dihydropyrrolo[1,2-a]pyrazine-1,4'-piperidine]-1'-yl]methanone, [8-fluoro-2-methyl-6-(trifluoromethyl)spiro[3,4-dihydropyrrolo[1,2-a]pyrazine-1,4'-piperidine]-1'-yl]-(5-isopropoxy-6-methyl-2-pyridyl)methanone, (4-isopropoxy-3-methyl-phenyl)-[2-methyl-6-(1,1,2,2,2-pentafluoroethyl)spiro[3,4-dihydropyrrolo[1,2-a]pyrazine-1,4'-piperidine]-1'-yl]methanone, 5-[2-methyl-4-[2-methyl-6-(2,2,2-trifluoroacetyl)spiro[3,4-dihydropyrrolo[1,2-a]pyrazine-1,4'-piperidine]-1'-carbonyl]phenyl]pyridine-2-carbonitrile, (4-isopropoxy-3-methyl-phenyl)-[6-(trifluoromethyl)spiro[3,4-dihydro-2H-pyrrolo[1,2-a]pyrazine-1,4'-piperidine]-1'-yl]methanone, 2,2,2-trifluoro-1-[1'-[3-methoxy-4-[2-(trifluoromethoxy)ethoxy]benzoyl]-2-methyl-spiro[3,4-dihydropyrrolo[1,2-a]pyrazine-1,4'-piperidine]-6-yl]ethanone, 2,2,2-trifluoro-1-[1'-(5-isopropoxy-6-methyl-pyridine-2-carbonyl)-3,3-dimethyl-spiro[2,4-dihydropyrrolo[1,2-a]pyrazine-1,4'-piperidine]-6-yl]ethanone, 2,2,2-trifluoro-1-[1'-(5-isopentyloxypyridine-2-carbonyl)-2-methyl-spiro[3,4-dihydropyrrolo[1,2-a]pyrazine-1,4'-piperidine]-6-yl]ethanone, (4-isopropoxy-3-methoxy-phenyl)-[2-methyl-6-(trifluoromethyl)spiro[3,4-dihydropyrrolo[1,2-a]pyrazine-1,4'-piperidine]-1'-yl]methanone, 2,2,2-trifluoro-1-[1'-(5-isopentyloxypyridine-2-carbonyl)-2,4-dimethyl-spiro[3,4-dihydropyrrolo[1,2-a]pyrazine-1,4'-piperidine]-6-yl]ethanone, 1-[(3S)-2,3-dimethyl-1'-[4-(3,3,3-trifluoropropoxymethyl)benzoyl]spiro[3,4-dihydropyrrolo[1,2-a]pyrazine-1,4'-piperidine]-6-yl]-2,2,2-trifluoro-ethanone, [8-fluoro-2-methyl-6-(trifluoromethyl)spiro[3,4-dihydropyrrolo[1,2-a]

pyrazine-1,4'-piperidine]-1'-yl]-[3-methoxy-4-[(1R)-1-methylpropoxy]phenyl]methanone, 2,2,2-trifluoro-1-[1'-(5-isopropoxy-6-methyl-pyridine-2-carbonyl)-2,4-dimethyl-spiro[3,4-dihydropyrrolo[1,2-a]pyrazine-1,4'-piperidine]-6-yl]ethanone, 1-[1'-[4-methoxy-3-(trifluoromethyl)benzoyl]-2-methyl-spiro[3,4-dihydropyrrolo[1,2-a]pyrazine-1,4'-piperidine]-6-yl]-2,2-dimethyl-propan-1-one, (4-isopropoxy-3-methyl-phenyl)-[2-methyl-6-(trifluoromethyl)spiro[3,4-dihydropyrrolo[1,2-a]pyrazine-1,4'-piperidine]-1'-yl]methanone, [2-methyl-6-(1-methylcyclopropanecarbonyl)spiro[3,4-dihydropyrrolo[1,2-a]pyrazine-1,4'-piperidine]-1'-yl]-[4-(3,3,3-trifluoropropoxymethyl)phenyl]methanone, 4-bromo-N-(4-bromophenyl)-3-[(1-methyl-2-oxo-4-piperidyl)sulfamoyl]benzamide or (3-chloro-4-isopropoxy-phenyl)-[2-methyl-6-(1,1,2,2,2-pentafluoroethyl)spiro[3,4-dihydropyrrolo[1,2-a]pyrazine-1,4'-piperidine]-1'-yl]methanone.

(39) a $Na_V1.8$ blocker, such as PF-04531083, PF-06372865 and such as those disclosed in WO2008/135826 (US2009048306), WO2006/011050 (US2008312235), WO2013/061205 (US2014296313), US20130303535, WO2013131018, U.S. Pat. No. 8,466,188, WO2013114250 (US2013274243), WO2014/120808 (US2014213616), WO2014/120815 (US2014228371) WO2014/120820 (US2014221435), WO2015/010065 (US20160152561), WO2015/089361 (US20150166589), WO2019/014352 (US20190016671), WO2018/213426, WO2020/146682, WO2020/146612, WO2020/014243, WO2020/014246, WO2020/092187, WO2020/092667 (US2020140411), WO2020/261114, WO2020/140959, WO2020/144375, WO2020/151728, WO2021/032074, WO2021/257490, WO/2021/257420, WO2021/257418, WO2022/263498, WO2022/235558, WO2022/235859, CN112390745, CN111808019, CN112225695, CN112457294, CN112300051, CN112300069, CN112441969, CN112479996 (WO2021/047622), and CN114591293, the entire contents of each application hereby incorporated by reference;

(39a) a $Na_V1.8$ blocker such as 4,5-dichloro-2-(4-fluoro-2-methoxyphenoxy)-N-(2-oxo-1,2-dihydropyridin-4-yl)benzamide, 2-(4-fluoro-2-methoxyphenoxy)-N-(2-oxo-1,2-dihydropyridin-4-yl)-4-(perfluoroethyl)benzamide, 4,5-dichloro-2-(4-fluorophenoxy)-N-(2-oxo-1,2-dihydropyridin-4-yl)benzamide, 4,5-dichloro-2-(3-fluoro-4-methoxyphenoxy)-N-(2-oxo-1,2-dihydropyridin-4-yl)benzamide, 2-(4-fluoro-2-methoxyphenoxy)-N-(2-oxo-1,2-dihydropyridin-4-yl)-5-(trifluoromethyl)benzamide, N-(2-oxo-1,2-dihydropyridin-4-yl)-2-(4-(trifluoromethoxy)phenoxy)-4-(trifluoromethyl)benzamide, 2-(4-fluorophenoxy)-N-(2-oxo-1,2-dihydropyridin-4-yl)-4-(perfluoroethyl)benzamide, 5-chloro-2-(4-fluoro-2-methoxyphenoxy)-N-(2-oxo-1,2-dihydropyridin-4-yl)benzamide, N-(2-oxo-1,2-dihydropyridin-4-yl)-2-(4-(trifluoromethoxy)phenoxy)-5-(trifluoromethyl)benzamide, 2-(4-fluoro-2-methylphenoxy)-N-(2-oxo-1,2-dihydropyridin-4-yl)-5-(trifluoromethyl)benzamide, 2-(2-chloro-4-fluorophenoxy)-N-(2-oxo-1,2-dihydropyridin-4-yl)-5-(trifluoromethyl)benzamide, 5-chloro-2-(4-fluoro-2-methylphenoxy)-N-(2-oxo-1,2-dihydropyridin-4-yl)benzamide, 4-chloro-2-(4-fluoro-2-methylphenoxy)-N-(2-oxo-1,2-dihydropyridin-4-yl)benzamide, 5-chloro-2-(2-chloro-4-fluorophenoxy)-N-(2-oxo-1,2-dihydropyridin-4-yl)benzamide, 2-((5-fluoro-2-hydroxybenzyl)oxy)-N-(2-oxo-1,2-dihydropyridin-4-yl)-4-(trifluoromethyl)benzamide, N-(2-oxo-1,2-dihydropyridin-4-yl)-2-(o-tolyloxy)-5-(trifluoromethyl)benzamide, 2-(2,4-difluorophenoxy)-N-(2-oxo-1,2-dihydropyridin-4-yl)-4-(trifluoromethyl)benzamide, N-(2-oxo-1,2-dihydropyridin-4-yl)-2-(2-(trifluoromethoxy)phenoxy)-5-(trifluoromethyl)benzamide, 2-(4-fluorophenoxy)-N-(2-oxo-1,2-dihydropyridin-4-yl)-5-(trifluoromethyl)benzamide, 2-(4-fluoro-2-methyl-phenoxy)-N-(2-oxo-1H-pyridin-4-yl)-4-(trifluoromethyl)benzamide, [4-[[2-(4-fluoro-2-methyl-phenoxy)-4-(trifluoromethyl)benzoyl]amino]-2-oxo-1-pyridyl]methyl dihydrogen phosphate, 2-(4-fluoro-2-(methyl-$d_3$)phenoxy)-N-(2-oxo-1,2-dihydropyridin-4-yl)-4-(trifluoromethyl)benzamide, (4-(2-(4-fluoro-2-(methyl-$d_3$)phenoxy)-4-(trifluoromethyl)benzamido)-2-oxopyridin-1(2H)-yl)methyl dihydrogen phosphate, 3-(4-fluoro-2-methoxyphenoxy)-N-(3-(methylsulfonyl)phenyl)quinoxaline-2-carboxamide, 3-(2-chloro-4-fluorophenoxy)-N-(3-sulfamoylphenyl)quinoxaline-2-carboxamide, 3-(2-chloro-4-methoxyphenoxy)-N-(3-sulfamoylphenyl)quinoxaline-2-carboxamide, 3-(4-chloro-2-methoxyphenoxy)-N-(3-sulfamoylphenyl)quinoxaline-2-carboxamide, 4-(3-(4-(trifluoromethoxy)phenoxy)quinoxaline-2-carboxamido)picolinic acid, 2-(2,4-difluorophenoxy)-N-(3-sulfamoylphenyl)quinoline-3-carboxamide, 2-(4-fluoro-2-methoxyphenoxy)-N-(3-sulfamoylphenyl)quinoline-3-carboxamide, 3-(2,4-difluorophenoxy)-N-(3-sulfamoylphenyl)quinoxaline-2-carboxamide, N-(3-sulfamoylphenyl)-2-(4-(trifluoromethoxy)phenoxy)quinoline-3-carboxamide, N-(3-sulfamoylphenyl)-3-(4-(trifluoromethoxy)phenoxy)quinoxaline-2-carboxamide, 3-(4-chloro-2-methylphenoxy)-N-(3-sulfamoylphenyl)quinoxaline-2-carboxamide, 5-(3-(4-(trifluoromethoxy)phenoxy)quinoxaline-2-carboxamido)picolinic acid, 3-(4-fluoro-2-methoxyphenoxy)-N-(2-oxo-2,3-dihydro-1H-benzo[d]imidazol-5-yl)quinoxaline-2-carboxamide, 3-(4-fluoro-2-methoxyphenoxy)-N-(pyridin-4-yl)quinoxaline-2-carboxamide, 3-(4-fluorophenoxy)-N-(3-sulfamoylphenyl)quinoxaline-2-carboxamide, N-(3-cyanophenyl)-3-(4-fluoro-2-methoxyphenoxy)quinoxaline-2-carboxamide, N-(4-carbamoylphenyl)-3-(4-fluoro-2-methoxyphenoxy)quinoxaline-2-carboxamide, 4-(3-(4-(trifluoromethoxy)phenoxy)quinoxaline-2-carboxamido)benzoic acid, N-(4-cyanophenyl)-3-(4-fluoro-2-methoxyphenoxy)quinoxaline-2-carboxamide, 5-(4,5-dichloro-2-(4-fluoro-2-methoxyphenoxy)benzamido)picolinic acid, 5-(2-(2,4-dimethoxyphenoxy)-4,6-bis(trifluoromethyl)benzamido)picolinic acid, 4-(4,5-dichloro-2-(4-fluoro-2-methoxyphenoxy)benzamido)benzoic acid, 5-(2-(4-fluoro-2-methoxyphenoxy)-4,6-bis(trifluoromethyl)benzamido)picolinic acid, 4-(2-(4-fluoro-2-methoxyphenoxy)-4-(perfluoroethyl)benzamido)benzoic acid, 5-(2-(4-fluoro-2-methoxyphenoxy)-4-(perfluoroethyl)benzamido)picolinic acid, 4-(2-(4-fluoro-2-methylphenoxy)-4-(trifluoromethyl)benzamido)benzoic acid, 5-(4,5-dichloro-2-(4-fluoro-2-methoxyphenoxy)benzamido)picolinic acid, 4-(2-(2-chloro-4-fluorophenoxy)-4-(perfluoroethyl)benzamido)benzoic acid, 4-(2-(4-fluoro-2-methylphenoxy)-4-(perfluoroethyl)benzamido)benzoic acid, 4-(4,5-dichloro-2-(4-(trifluoromethoxy)phenoxy)benzamido)benzoic acid, 4-(4,5-dichloro-2-(4-chloro- 2-methylphenoxy)benzamido)benzoic acid, 5-(4-(tert-butyl)-2-(4-fluoro-2-methoxyphenoxy)benzamido)picolinic acid, 5-(4,5-dichloro-2-(4-(trifluoromethoxy)phenoxy)benzamido)picolinic acid, 4-(4,5-dichloro-2-(4-fluoro-2-methylphenoxy)benzamido)benzoic acid, 5-(4,5-dichloro-2-(2,4-dimethoxyphenoxy)benzamido)picolinic acid, 5-(4,5-dichloro-2-(2-chloro-4-fluoro-phenoxy)benzamido)picolinic acid, 5-(4,5-dichloro-2-(4-fluoro-2-methylphenoxy)benzamido)picolinic acid, 4-(4,5-dichloro-2-(4-chloro-2-methoxyphenoxy)benzamido)benzoic acid, 5-(4,5-dichloro-2-(2,4-difluoro-phenoxy)benzamido)picolinic acid, 2-(4-fluorophenoxy)-N-(3-sulfamoylphenyl)-5-(trifluoromethyl)benzamide, 2-(4-fluorophenoxy)-N-(3-sulfamoylphenyl)-4-(trifluoromethyl)benzamide, 2-(2-chloro-4-fluorophenoxy)-N-(3-sulfamoylphenyl)-5-(trifluoromethyl)benzamide, 2-(4-fluorophenoxy)-N-(3-sulfamoylphenyl)-4-(trifluoromethyl)benzamide, 2-(2-chloro-4-fluorophenoxy)-N-(3-sulfamoylphenyl)-6-(trifluoromethyl)benzamide, 2-(2-chloro-4-fluoro-phenoxy)-5-(difluoromethyl)-N-(3-sulfamoylphenyl)benzamide, 2-(4-fluorophenoxy)-4-(perfluoroethyl)-N-(3-sulfamoylphenyl)benzamide, 2-(4-chloro-2-methoxyphenoxy)-4-(perfluoroethyl)-N-(3-sulfamoylphenyl)benzamide, 2-(4-fluoro-2-methoxyphenoxy)-N-(3-sulfamoylphenyl)-5-(trifluoromethyl)benzamide, 5-chloro-2-(4-fluoro-2-methylphenoxy)-N-(3-sulfamoylphenyl)benzamide, 4,5-dichloro-2-(4-fluoro-2-methoxyphenoxy)-N-(3-sulfamoylphenyl)benzamide, 2,4-dichloro-6-(4-chloro-2-methoxyphenoxy)-N-(3-sulfamoylphenyl)benzamide, 2,4-dichloro-6-(4-fluoro-2-methylphenoxy)-N-(3-sulfamoylphenyl)benzamide, 2-(4-fluoro-2-methoxyphenoxy)-N-(3-sulfamoylphenyl)-4,6-bis(trifluoromethyl)benzamide, 2-(4-fluoro-2-methylphenoxy)-N-(3-sulfamoylphenyl)-4,6-bis(trifluoromethyl)benzamide, 5-chloro-2-(2-chloro-4-fluorophenoxy)-N-(3-sulfamoylphenyl)benzamide, 2-(4-fluoro-2-methoxyphenoxy)-N-(3-sulfamoylphenyl)-4-(trifluoromethoxy)benzamide, 2-(4-fluoro-2-methoxyphenoxy)-N-(3-sulfamoylphenyl)-4-(trifluoromethyl)benzamide, 4,5-dichloro-2-(4-fluorophenoxy)-N-(3-sulfamoylphenyl)benzamide, 2-(4-fluoro-2-methoxyphenoxy)-4-(perfluoroethyl)-N-(3-sulfamoylphenyl)benzamide, 5-fluoro-2-(4-fluoro-2-methylphenoxy)-N-(3-sulfamoylphenyl)benzamide, 2-(2-chloro-4-fluorophenoxy)-4-cyano-N-(3-sulfamoylphenyl)benzamide, N-(3-sulfamoylphenyl)-2-(4-(trifluoromethoxy)phenoxy)-4-(trifluoromethyl)benzamide, N-(3-carbamoyl-4-fluoro-phenyl)-2-fluoro-6-[2-(trideuteriomethoxy)-4-(trifluoromethoxy)phenoxy]-3-(trifluoromethyl)benzamide, N-(3-carbamoyl-4-fluoro-phenyl)-2-fluoro-6-[2-methoxy-4-(trifluoromethoxy)phenoxy]-3-(trifluoromethyl)benzamide, N-(3-carbamoyl-4-fluoro-phenyl)-2-fluoro-6-[2-(trideuteriomethoxy)-4-(trifluoromethoxy)phenoxy]-3-(trifluoromethoxy)benzamide, 4-[[2-fluoro-6-[2-methoxy-4-(trifluoromethoxy)phenoxy]-3-(trifluoromethyl)benzoyl]amino]pyridine-2-carboxamide, 4-[[3-chloro-2-fluoro-6-[2-methoxy-4-(trifluoromethoxy)phenoxy]benzoyl]amino]pyridine-2-carboxamide, 4-[[2-fluoro-6-[2-(trideuteriomethoxy)-4-(trifluoromethoxy)phenoxy]-3-(trifluoromethyl)benzoyl]amino]pyridine-2-carboxamide, N-(3-carbamoyl-4-fluoro-phenyl)-3-(difluoromethyl)-2-fluoro-6-[2-methoxy-4-(trifluoromethoxy)phenoxy]benzamide, 4-[[2-fluoro-6-[2-(trideuteriomethoxy)-4-(trifluoromethoxy)phenoxy]-3-(trifluoromethoxy)benzoyl]amino]pyridine-2-carboxamide, N-(3-carbamoyl-4-fluoro-phenyl)-6-[2-chloro-4-(trifluoromethoxy)phenoxy]-2-fluoro-3-(trifluoromethyl)benzamide, N-(3-carbamoyl-4-fluoro-phenyl)-2-fluoro-6-[2-methyl-4-(trifluoromethoxy)phenoxy]-3-(trifluoromethyl)benzamide, N-(3-carbamoyl-4-fluoro-phenyl)-2,3,4-trifluoro-6-[2-methoxy-4-(trifluoromethoxy)phenoxy]benzamide, N-(2-carbamoyl-4-pyridyl)-3-fluoro-5-[2-methoxy-4-(trifluoromethoxy)phenoxy]-2-(trifluoromethyl)pyridine-4-carboxamide, 4-[[6-[2-(difluoromethoxy)-4-(trifluoromethoxy)phenoxy]-2-fluoro-3-(trifluoromethyl)benzoyl]amino]pyridine-2-carboxamide, N-(3-carbamoyl-4-fluoro-phenyl)-6-[3-chloro-4-(trifluoromethoxy)phenoxy]-2-fluoro-3-(trifluoromethyl)benzamide, N-(3-carbamoyl-4-fluoro-phenyl)-2-fluoro-6-[4-(trifluoromethoxy)phenoxy]-3-(trifluoromethyl)benzamide, N-(4-carbamoyl-3-fluoro-phenyl)-2-fluoro-6-[2-methoxy-4-(trifluoromethoxy)phenoxy]-3-(trifluoromethyl)benzamide, 4-[[2-fluoro-6-[2-(trideuteriomethoxy)-4-(trifluoromethoxy)phenoxy]-4-(trifluoromethyl)benzoyl]amino]pyridine-2-carboxamide, N-(3-carbamoyl-4-fluoro-phenyl)-2-fluoro-6-[3-fluoro-4-(trifluoromethoxy)phenoxy]-3-(trifluoromethyl)benzamide, N-(3-carbamoyl-4-fluoro-phenyl)-2-[2-methoxy-4-(trifluoromethoxy)phenoxy]-5-(1,1,2,2,2-pentafluoroethyl)benzamide, 4-[[4-(difluoromethoxy)-2-fluoro-6-[2-methoxy-4-(trifluoromethoxy)phenoxy]benzoyl]amino]pyridine-2-carboxamide, N-(3-carbamoyl-4-fluoro-phenyl)-2-fluoro-6-[2-fluoro-4-(trifluoromethoxy)phenoxy]-3-(trifluoromethyl)benzamide, 4-[[4-cyclopropyl-2-fluoro-6-[2-methoxy-4-(trifluoromethoxy)phenoxy]benzoyl]amino]pyridine-2-carboxamide, N-(3-carbamoyl-4-fluoro-phenyl)-5-fluoro-2-[2-methoxy-4-(trifluoromethoxy)phenoxy]-4-(trifluoromethyl)benzamide, 5-[[2-fluoro-6-[2-(trideuteriomethoxy)-4-(trifluoromethoxy)phenoxy]-3-(trifluoromethyl)benzoyl]amino]pyridine-2-carboxamide, N-(3-carbamoyl-4-fluoro-phenyl)-2-fluoro-6-(4-fluorophenoxy)-3-(trifluoromethyl)benzamide, or 4-[[2-fluoro-6-[3-fluoro-2-methoxy-4-(trifluoromethoxy)phenoxy]-3-(trifluoromethyl)benzoyl]amino]pyridine-2-carboxamide;

(40) a combined $Na_V1.7$ and $Na_V1.8$ blocker, such as DSP-2230, Lohocla201 or BL-1021;

(41) a 5-HT3 antagonist, such as ondansetron;

(42) a TPRV 1 receptor agonist, such as capsaicin (NeurogesX®, Qutenza®); and the pharmaceutically acceptable salts and solvates thereof,

(43) a nicotinic receptor antagonist, such as varenicline;

(44) an N-type calcium channel antagonist, such as Z-160;

(45) a nerve growth factor antagonist, such as tanezumab;

(46) an endopeptidase stimulant, such as senrebotase;

(47) an angiotensin II antagonist, such as EMA-401;

(48) acetaminophen (including without limitation intravenous acetaminophen (e.g., Ofirmev®));

(49) bupivacaine (including without limitation bupivacaine liposome injectable suspension (e.g., Exparel®) bupivacaine ER (Posimir), bupivacaine collagen (Xaracoll) and transdermal bupivacaine (Eladur®)); and

(50) bupivacaine and meloxicam combination (e.g., HTX-011).

In one embodiment, the additional appropriate therapeutic agents are selected from V-116517, Pregabalin, controlled release Pregabalin, Ezogabine (Potiga®). Ketamine/amitriptyline topical cream (Amiket®), AVP-923, Perampanel (E-2007), Ralfinamide, transdermal bupivacaine (Eladur®), CNV1014802, JNJ-10234094 (Carisbamate), BMS-954561 or ARC-4558.

In another embodiment, the additional appropriate therapeutic agents are selected from N-(6-amino-5-(2,3,5-trichlorophenyl)pyridin-2-yl)acetamide; N-(6-amino-5-(2-chloro-5-methoxyphenyl)pyridin-2-yl)-1-methyl-1H-pyrazole-5-carboxamide; or 3-((4-(4-(trifluoromethoxy)phenyl)-1H-imidazol-2-yl)methyl)oxetan-3-amine.

In another embodiment, the additional therapeutic agent is selected from a GlyT2/5HT2 inhibitor, such as Operanserin (VVZ149), a TRPV modulator such as CA008, CMX-020, NE06860, FTABS, CNTX4975, MCP101, MDR16523, or MDR652, a EGR1 inhibitor such as Brivoglide (AYX1), an NGF inhibitor such as Tanezumab, Fasinumab, ASP6294, MEDI7352, a Mu opioid agonist such as Cebranopadol, NKTR181 (oxycodegol), a CB-1 agonist such as NEO1940 (AZN1940), an imidazoline 12 agonist such as CR4056 or a p75NTR-Fc modulator such as LEVI-04.

In another embodiment, the additional therapeutic agent is oliceridine or ropivacaine (TLC590).

In another embodiment, the additional therapeutic agent is a $Na_V1.7$ blocker such as ST-2427, ST-2578 and/or those disclosed in WO2010/129864, WO2015/157559, WO2017/059385, WO2018/183781, WO2018/183782, WO2020/072835, and WO2022/036297 the entire contents of each application hereby incorporated by reference.

In another embodiment, the additional therapeutic agent is ASP18071, CC-8464, ANP-230, ANP-231, NOC-100, NTX-1175, ASN008, NW3509, AM-6120, AM-8145, AM-0422, BL-017881, NTM-006, Opiranserin (Unafrar™), brivoligide, SR419, NRD.E1, LX9211, LY3016859, ISC-17536, NFX-88, LAT-8881, AP-235, NYX 2925, CNTX-6016, S-600918, S-637880, RQ-00434739, KLS-2031, MEDI 7352, or XT-150.

In another embodiment, the additional therapeutic agent is Olinvyk, Zynrelef, Seglentis, Neumentum, Nevakar, HTX-034, CPL-01, ACP-044, HRS-4800, Tarlige, BAY2395840, LY3526318, Eliapixant, TRV045, RTA901, NRD1355-E1, MT-8554, LY3556050, AP-325, tetrodotoxin, Otenaproxesul, CFTX-1554, Funapide, iN1011-N17, JMKX000623/ODM-111, ETX-801, OLP-1002, ANP-230/DSP-2230, iN1011-N17, DSP-3905 or ACD440.

In another embodiment, the additional therapeutic agent is a sodium channel inhibitor (also known as a sodium channel blocker), such as the $Na_V1.7$ and $Na_V1.8$ blockers identified above.

The amount of additional therapeutic agent present in the compositions of this invention may be no more than the amount that would normally be administered in a composition comprising that therapeutic agent as the only active agent. The amount of additional therapeutic agent in the presently disclosed compositions may range from about 10% to 100% of the amount normally present in a composition comprising that agent as the only therapeutically active agent.

The compounds and salts of this invention or pharmaceutically acceptable compositions thereof may also be incorporated into compositions for coating an implantable medical device, such as prostheses, artificial valves, vascular grafts, stents and catheters. Accordingly, the invention, in another aspect, includes a composition for coating an implantable device comprising a compound or salt of the invention as described generally above, and in classes and subclasses herein, and a carrier suitable for coating said implantable device. In still another aspect, the invention includes an implantable device coated with a composition comprising a compound or salt of the invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to inhibiting $Na_V1.8$ activity in a biological sample or a subject, which method comprises administering to the subject, or contacting said biological sample with a compound of the invention, a pharmaceutically acceptable salt thereof, or a pharmaceutical composition thereof. The term "biological sample," as used herein, includes, without limitation, cell cultures or extracts thereof, biopsied material obtained from a mammal or extracts thereof, and blood, saliva, urine, feces, semen, tears, or other body fluids or extracts thereof. Inhibition of $Na_V1.8$ activity in a biological sample is useful for a variety of purposes that are known to one of skill in the art. Examples of such purposes include, but are not limited to, the study of sodium channels in biological and pathological phenomena; and the comparative evaluation of new sodium channel inhibitors.

Synthesis of the Compounds of the Invention

The compounds of the invention can be prepared from known materials by the methods described in the Examples, other similar methods, and other methods known to one skilled in the art. As one skilled in the art would appreciate, the functional groups of the intermediate compounds in the methods described below may need to be protected by suitable protecting groups. Protecting groups may be added or removed in accordance with standard techniques, which are well-known to those skilled in the art. The use of protecting groups is described in detail in T. G. M. Wuts et al., *Greene's Protective Groups in Organic Synthesis* (4th ed. 2006).

Radiolabeled Analogs of the Compounds of the Invention

In another aspect, the invention relates to radiolabeled analogs of the compounds of the invention. As used herein, the term "radiolabeled analogs of the compounds of the invention" refers to compounds that are identical to the compounds of the invention, as described herein, including all embodiments thereof, except that one or more atoms has been replaced with a radioisotope of the atom present in the compounds of the invention.

As used herein, the term "radioisotope" refers to an isotope of an element that is known to undergo spontaneous radioactive decay. Examples of radioisotopes include $^{3}H$, $^{14}C$, $^{32}P$, $^{35}S$, $^{18}F$, $^{36}Cl$, and the like, as well as the isotopes for which a decay mode is identified in V. S. Shirley & C. M. Lederer, Isotopes Project, Nuclear Science Division, Lawrence Berkeley Laboratory, Table of Nuclides (January 1980).

The radiolabeled analogs can be used in a number of beneficial ways, including in various types of assays, such as substrate tissue distribution assays. For example, tritium ($^{3}H$)- and/or carbon-14 ($^{14}C$)-labeled compounds may be useful for various types of assays, such as substrate tissue distribution assays, due to relatively simple preparation and excellent detectability.

In another aspect, the invention relates to pharmaceutically acceptable salts of the radiolabeled analogs, in accordance with any of the embodiments described herein in connection with the compounds of the invention.

In another aspect, the invention relates to pharmaceutical compositions comprising the radiolabeled analogs, or pharmaceutically acceptable salts thereof, and a pharmaceutically acceptable carrier, adjuvant or vehicle, in accordance with any of the embodiments described herein in connection with the compounds of the invention.

In another aspect, the invention relates to methods of inhibiting voltage-gated sodium channels and methods of treating or lessening the severity of various diseases and disorders, including pain, in a subject comprising administering an effective amount of the radiolabeled analogs, pharmaceutically acceptable salts thereof, and pharmaceutical compositions thereof, in accordance with any of the embodiments described herein in connection with the compounds of the invention.

In another aspect, the invention relates to radiolabeled analogs, pharmaceutically acceptable salts thereof, and pharmaceutical compositions thereof, for use, in accordance with any of the embodiments described herein in connection with the compounds of the invention.

In another aspect, the invention relates to the use of the radiolabeled analogs, or pharmaceutically acceptable salts thereof, and pharmaceutical compositions thereof, for the manufacture of medicaments, in accordance with any of the embodiments described herein in connection with the compounds of the invention.

In another aspect, the radiolabeled analogs, pharmaceutically acceptable salts thereof, and pharmaceutical compositions thereof, can be employed in combination therapies, in accordance with any of the embodiments described herein in connection with the compounds of the invention.

EXAMPLES

General methods. $^{1}H$ NMR spectra were obtained as solutions in an appropriate deuterated solvent such as dimethyl sulfoxide-$d_6$ (DMSO-$d_6$).

Compound purity, retention time, and electrospray mass spectrometry (ESI-MS) data were determined by LC/MS analysis.

LC/MS Method: LC/MS determinations were carried out using one of the following chromatographic conditions: 1) Waters BEH C8 (1.7 μm, 2.1×50 mm) 2 to 98% acetonitrile in water (10 mM ammonium formate, pH 9), 45° C., flow rate 0.6 mL/min over 5.0 min; 2) Kinetex EVO C18 (2.6 μm, 2.1×50 mm) 2 to 98% acetonitrile in water (10 mM ammonium formate, pH 9), 45° C., flow rate 0.7 mL/min over 4.0 min; 3) Kinetex EVO C18 (2.6 m 2.1×50 mm) 2 to 98% acetonitrile in water (10 mM ammonium formate, pH 9), 45° C., flow rate 1.0 mL/min over 1.5 min; 4) Waters Acquity UPLC BEH C18 (1.7 μm, 30×2.1 mm) 1 to 99% acetonitrile (0.035% TFA) in water (0.05% TFA), 60° C., flow rate=1.5 mL/min over 3 min; 6) Kinetex Polar C18 (2.6 μm, 3.0×50 mm) 5 to 95% acetonitrile in water (0.1% formic acid), flow rate 1.2 mL/min over 6 min; 7) SunFire C18 (3.5 μm, 75×4.6 mm) initial 5 to 95% acetonitrile in water (0.1% formic acid) for 1 min then linear gradient to 95% acetonitrile for 5 min. 45° C., flow rate 1.5 mL/min over 6 min; 8) XBridge C18 (5 μm, 4.6×75 mm) initial gradient 5 to 95% acetonitrile ($NH_4HCO_3$), 6 min run with 1 min equilibration gradient 0 to 3 min at 95% acetonitrile and hold for 3 min, flow rate 1.5 mL/min; 9) Waters CSH C18 (1.7 μm, 2.1×50 mm) 2 to 98% acetonitrile in water (0.1% TFA, pH 2), 45° C., flow rate 0.6 mL/min over 5.0 min; 10) Waters CSH C18 (1.7 μm, 2.1×50 mm) 2 to 95% acetonitrile in water (0.1% formic acid), 40° C., flow rate 0.8 mL/min over 4.6 min; 11) Waters BEH C18 (2.5 μm, 2.1×50 mm) 2 to 95% acetonitrile in water (0.1% $NH_3$), 40° C., flow rate 0.8 mL/min over 4.6 min; 13) Waters BEH C18 (3.5 μm, 75×4.6 mm) initial gradient 5 to 95% acetonitrile in water (0.1% formic acid) then linear gradient to 95% acetonitrile for 4 min, hold for 2 min at 95% acetonitrile, 45° C., flow rate 1.5 mL/min over 6 min; 14) Waters BEH C18 (2.5 μm, 2.1×50 mm) 2 to 50% acetonitrile in water (0.1% $NH_3$), 40° C., flow rate 0.8 mL/min over 4.6 min; 15) Waters CSH C18 (1.7 μm, 2.1×50 mm) 2 to 98% acetonitrile in water (0.1% TFA), 45° C., flow rate 1.0 mL/min over 1.5 min; 16) Waters CSH C18 (1.7 μm, 2.1×50 mm) 2 to 95% acetonitrile in water (0.1% formic acid), 40° C., flow rate 0.8 mL/min over 1.4 min; 17) YMC Triart C18 (3 μm, 33×2.1 mm) 2 to 98% acetonitrile in water (5 mM $NH_4OAc$), flow rate 1.0 mL/min over 3 min; 18) Waters BEH C18 (2.5 μm, 2.1×50 mm) 2 to 95% acetonitrile in water (0.1% $NH_3$), 40° C., flow rate 0.8 mL/min over 1.4 min; 19) Waters Acquity UPLC BEH C18 (1.7 μm, 30×2.1 mm) 1 to 99% acetonitrile (0.035% TFA) in water (0.05% TFA), 60° C., flow rate=1.5 mL/min over 5 min; 20) Waters BEH C18 (2.5 μm, 2.1×50 mm) 20 to 70% acetonitrile in water (0.1% $NH_3$), 40° C., flow rate 0.8 mL/min over 4.60 min; 21) Kinetex Polar C18 (2.6 μm, 3.0×50 mm) 5 to 95% acetonitrile in water (0.1% formic acid), flow rate 1.2 mL/min over 3 min; 22) Waters Acquity UPLC BEH C18 column (1.7 μm, 30×2.1 mm) 1 to 99% acetonitrile (0.035% TFA) in water (0.05% TFA), 60° C., flow rate=1.5 mL/min over 1 min; 23) YMC Triart C18 (3 μm, 33×2.1 mm) 2 to 98% acetonitrile in water (0.05% formic acid), flow rate 1.0 mL/min over 3 min; 24) Waters Acquity UPLC BEH C18 (1.7 μm, 30×2.1 mm) 1 to 99% acetonitrile (0.05% ammonium formate) in water (0.05% ammonium formate), 60° C., flow rate=1.5 mL/min over 5 min; 25) Waters CSH C18 (1.7 m, 2.1×50 mm) 2 to 98% acetonitrile in water (0.1% TFA), 45° C., flow rate 0.6 mL/min over 4.0 min; 26) Acquity BEH C8 (1.7 μm, 50×2.1 mm) 2 to 98% 90:10 acetonitrile:water (0.05% formic acid), flow rate 0.8 mL/min over 3 min; 27) XBridge C18 (5 μm, 50×4.6 mm) 10 to 90% acetonitrile in water (10 mM $NH_4OAc$), flow rate 1.2 mL/min over 6 min; 28) YMC Triart C18 (3 μm, 33×2.1 mm) 5 to 95% acetonitrile in water (0.05% formic acid), flow rate 1.0 mL/min over 12 min; 29) Waters BEH C8 (1.7 m, 2.1×50 mm) 50 to 95% acetonitrile in water (0.1% $NH_3$), 40° C., flow rate 0.8 mL/min over 1.4 min.

Abbreviations

Unless otherwise noted, or where the context dictates otherwise, the following abbreviations shall be understood to have the following meanings:

| Abbreviation | Meaning |
|---|---|
| NMR | Nuclear magnetic resonance |
| ESI-MS | Electrospray mass spectrometry |
| LC/MS | Liquid chromatography-mass spectrometry |
| UPLC | Ultra performance liquid chromatography |
| HPLC/ MS/MS | High performance liquid chromatography/tandem mass spectrometry |
| IS | Internal standard |
| HPLC | High performance liquid chromatography |

-continued

| Abbreviation | Meaning |
|---|---|
| SFC | Supercritical fluid chromatography |
| ESI | Electrospray ionization |
| g | Grams |
| mg | Milligrams |
| kg | Kilograms |
| L | Liter(s) |
| mL | Milliliters |
| µL | Microliters |
| nL | Nanoliters |
| mol | Moles |
| mmol | Millimoles |
| hr, h | Hours |
| min | Minutes |
| ms | Millisecond |
| mm | Millimeters |
| µm | Micrometers |
| nm | Nanometer |
| MHz | Megahertz |
| Hz | Hertz |
| N | Normal (concentration) |
| M | Molar (concentration) |
| mM | Millimolar (concentration) |
| µM | Micromolar (concentration) |
| ppm | Parts per million |
| % w/v | Weight-volume concentration |
| % w/w | Weight-weight concentration |
| t-BuOH | Tert-butyl alcohol |
| CDI | 1,1'-Carbonyl diimidazole |
| DAST | Diethylaminosulfur trifluoride |
| DCM | Dichloromethane |
| DCE | Dichloroethane |
| DIEA, DIPEA | N, N-Diisopropyl ethyl amine |
| DMA | N,N-Dimethylacetamide |
| DMAP | N,N-Dimethylaminopyridine |
| DMF | N,N-Dimethylformamide |
| DMSO | Dimethyl sulfoxide |
| DRG | Dorsal root ganglia |
| EDC.HCl | Ethyl carbodiimide hydrochloride |
| EtOH | Ethanol |
| EtOAc | Ethyl acetate |
| HATU | 1-[Bis(dimethylamino)methylene]-1H-1,2,3-triazolo[4,5-b]pyridinium 3-Oxide hexafluorophosphate |
| HOBt | Hydroxybenzotriazole |
| EDCI | 1-Ethyl-3-(3-dimethylaminopropyl)carbodiimide |
| T3P | Propylphosphonic anhydride, i.e., 2,4,6-tripropyl-1,3,5,2,4,6-trioxatriphosphinane 2,4,6-trioxide |
| KOAc | Potassium acetate |
| m-CPBA | Meta-chloroperoxybenzoic acid |
| MeOH | Methanol |
| MTBE | Methyl tert-butyl ether |
| NaOH | Sodium hydroxide |
| NBS | N-Bromosuccinimide |
| NMP | N-Methylpyrrolidone |
| NMO | N-Methylmorpholine N-oxide |
| PPTS | Pyridinium para-toluene sulfonate |
| TBAB | Tetra-n-butylammonium bromide |
| TBAF | Tetra-n-butylammonium fluoride |
| TBSCl | Tert-butyldimethylsilyl chloride |
| TBSOTf | Tert-butyldimethylsilyl trifluoromethanesulfonate |
| THF | Tetrahydrofuran |
| TEA | Triethylamine |
| TFA | Trifluoroacetic acid |
| RB | Round bottom (flask) |
| RT | Room temperature |
| ca. | Circa (approximately) |
| E-VIPR | Electrical stimulation voltage ion probe reader |
| HEK | Human embryonic kidney |
| KIR2.1 | Inward-rectifier potassium ion channel 2.1 |
| DMEM | Dulbecco's Modified Eagle's Medium |
| FBS | Fetal bovine serum |
| NEAA | Non-essential amino acids |
| HEPES | 2-[4-(2-Hydroxyethyl)piperazin-1-yl]ethanesulfonic acid |
| $DiSBAC_6(3)$ | Bis-(1,3-dihexyl-thiobarbituric acid) trimethine oxonol |
| CC2-DMPE | Chlorocoumarin-2-dimyristoyl phosphatidylethanolamine |

-continued

| Abbreviation | Meaning |
|---|---|
| VABSC-1 | Voltage Assay Background Suppression Compound |
| HS | Human serum |
| BSA | Bovine Serum Albumin |

Example 1

Intermediate A-1

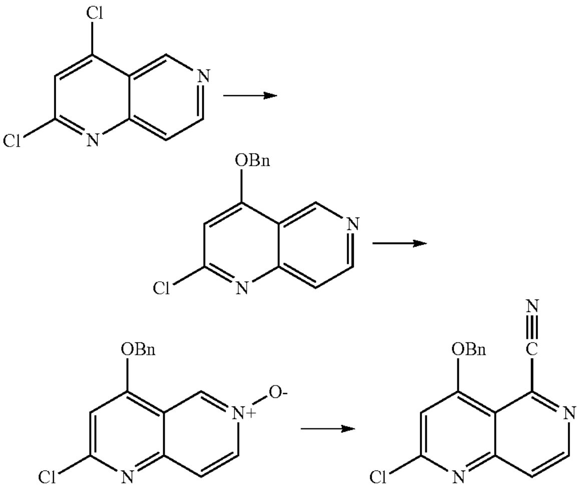

Step 1: 4-benzyloxy-2-chloro-1,6-naphthyridine

To a mixture of 2,4-dichloro-1,6-naphthyridine (1.0 g, 4.9 mmol) and benzyl alcohol (0.5 mL, 4.8 mmol) in DMF (10 mL) and 2-MeTHF (10 mL) at 0° C. was added sodium hydride (60% in mineral oil, 208 mg, 5.20 mmol) portion-wise. The reaction mixture was stirred at 0° C. for 1 h, followed gradual warming to room temperature and stirring for 2 h. The reaction mixture was poured into a stirring mixture of 0.1 M aqueous HCl (50 mL) and 2-MeTHF (50 mL). The layers were separated, and the aqueous layer extracted with 2-MeTHF (2×100 mL). The combined organic layers were washed with water (2×50 mL), 1:1 water/brine (50 mL) and brine (50 mL), dried over sodium sulfate, filtered and evaporated under reduced pressure. Purification by silica gel chromatography (0-35% ethyl acetate/heptanes) afforded 4-benzyloxy-2-chloro-1,6-naphthyridine (528 mg, 38%) as an off-white solid. ESI-MS m/z calc. 270.06, found 271.1 $(M+1)^+$. $^1H$ NMR (400 MHz, $CDCl_3$) δ 9.58 (s, 1H), 8.78 (d, J=5.9 Hz, 1H), 7.75 (dd, J=5.9, 0.6 Hz, 1H), 7.54-7.37 (m, 5H), 6.92 (s, 1H), 5.34 (s, 2H).

Step 2: 4-benzyloxy-2-chloro-6-oxido-1,6-naphthyridin-6-ium

To a solution of 4-benzyloxy-2-chloro-1,6-naphthyridine (1.75 g, 6.46 mmol) in DCM (14 mL) at 0° C. was added mCPBA (1.6 g, 7.14 mmol). The resulting mixture was stirred at room temperature for 18 h, then diluted with 2 M aqueous sodium carbonate (60 mL) and water (90 mL). The aqueous layer was extracted with additional DCM (3×100 mL), and the combined organic layers dried over sodium sulfate, filtered and concentrated under reduced pressure to give 4-benzyloxy-2-chloro-6-oxido-1,6-naphthyridin-6-ium (1.796 g, 97%) as an off-white solid. ESI-MS m/z calc. 286.05, found 287.1 $(M+1)^+$. $^1H$ NMR (400 MHz, $CDCl_3$) δ 9.02-8.94 (m, 1H), 8.30 (dd, J=7.3, 2.1 Hz, 1H), 7.79-7.72 (m, 1H), 7.44 (d, J=2.6 Hz, 5H), 6.93 (s, 1H), 5.29 (s, 2H).

Step 3: 4-benzyloxy-2-chloro-1,6-naphthyridine-5-carbonitrile

To a solution of 4-benzyloxy-2-chloro-6-oxido-1,6-naphthyridin-6-ium (1.0 g, 3.5 mmol) in DCM (10 mL) under an atmosphere of nitrogen was added trimethylsilylformonitrile (1.3 mL, 9.8 mmol), followed by the addition of TEA (1.25 mL, 8.97 mmol). The reaction mixture was stirred at room temperature for 20 h. The mixture was quenched with water and the aqueous layer was extracted with DCM (3×). The combined organic layers were dried over magnesium sulfate, filtered and concentrated. Purification by silica gel chromatography (0-30% ethyl acetate/DCM) provided 4-benzyloxy-2-chloro-1,6-naphthyridine-5-carbonitrile (840 mg, 81%). ESI-MS m/z calc. 295.05, found 296.1 $(M+1)^+$. $^1H$ NMR (400 MHz, DMSO-$d_6$) δ 8.91 (d, J=5.7 Hz, 1H), 8.12 (d, J=5.7 Hz, 1H), 7.67-7.58 (m, 3H), 7.50-7.34 (m, 3H), 5.61 (s, 2H).

Intermediate A-2

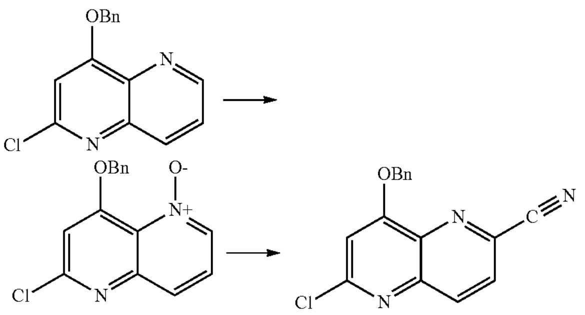

Step 1: 8-benzyloxy-6-chloro-1-oxido-1,5-naphthyridin-1-ium

8-Benzyloxy-6-chloro-1-oxido-1,5-naphthyridin-1-ium was prepared from 4-benzyloxy-2-chloro-1,5-naphthyridine (Intermediate A-31) using a procedure analogous to that found in Intermediate A-4, step 2. ESI-MS m/z calc. 286.05, found 287.1 $(M+1)^+$; Retention time: 1.62 minutes.

Step 2: 8-benzyloxy-6-chloro-1,5-naphthyridine-2-carbonitrile

8-Benzyloxy-6-chloro-1,5-naphthyridine-2-carbonitrile was prepared from 8-benzyloxy-6-chloro-1-oxido-1,5-naphthyridin-1-ium using a procedure analogous to that found in Intermediate A-4, step 3. $^1H$ NMR (400 MHz, DMSO-$d_6$) δ 8.55 (d, J=8.6 Hz, 1H), 8.34 (d, J=8.7 Hz, 1H), 7.63 (s, 1H), 7.60-7.53 (m, 2H), 7.51-7.39 (m, 3H), 5.50 (s, 2H). ESI-MS m/z calc. 295.05, found 296.1 $(M+1)^+$.

Intermediate A-3

Step 1: 4-benzyloxy-2-chloro-quinolin-5-ol

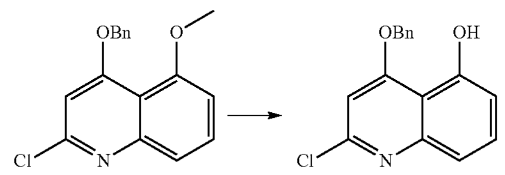 [SMILES: COc1cccc2nc(Cl)cc(OCc3ccccc3)c12 ; Oc1cccc2nc(Cl)cc(OCc3ccccc3)c12]

A mixture of 4-benzyloxy-2-chloro-5-methoxy-quinoline (100 mg, 0.334 mmol), hydrogen bromide (2.0 mL of 48% w/v, 11.7 mmol), sodium iodide (50 mg, 0.33 mmol) was heated to 90° C. for 18 h. Purification by reverse phase chromatography (1-100% $CH_3CN$/water) provided 4-benzyloxy-2-chloro-quinolin-5-ol (14 mg, 15%). ESI-MS m/z calc. 285.06, found 286.05 $(M+1)^+$.

Intermediate A-4

Step 1: 4-benzyloxy-2-chloro-quinoline

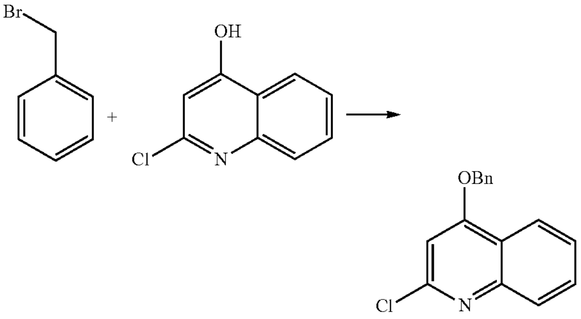

Sodium hydride (16 mg, 0.68 mmol) was added portion wise to 2-chloroquinolin-4-ol (102 mg, 0.570 mmol) in DMF (1 mL) at 0° C. under an atmosphere of nitrogen. The mixture was stirred for 10 min at room temperature and again cooled down at 0° C. and benzyl bromide (75 μL, 0.63 mmol) was added. The reaction mixture was stirred at room temperature for 3 h then partitioned between brine (20 mL) and ethyl acetate (30 mL). The layers were separated, and the organic layer was dried over sodium sulfate, filtered and concentrated under reduced pressure. Purification by silica gel chromatography (1-100% ethyl acetate/hexanes) provided 4-benzyloxy-2-chloro-quinoline (139 mg, 90%) as a white solid. ESI-MS m/z calc. 269.06, found 270.11 $(M+1)^+$.

Intermediate A-5

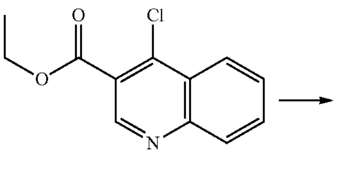

-continued

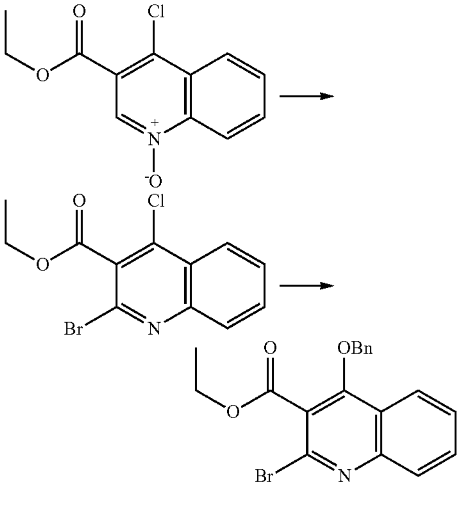

Step 1: Ethyl 4-chloro-1-oxido-quinolin-1-ium-3-carboxylate

Ethyl 4-chloro-1-oxido-quinolin-1-ium-3-carboxylate was prepared from ethyl 4-chloroquinoline-3-carboxylate using a procedure analogous to that found in Intermediate A-4, step 2 using chloroform as the solvent. $^1$H NMR (300 MHz, $CDCl_3$) δ 8.95 (s, 1H), 8.80 (d, J=8.5 Hz, 1H), 8.52-8.42 (m, 1H), 7.97-7.89 (m, 1H), 7.88-7.80 (m, 1H), 4.49 (q, J=7.1 Hz, 2H), 1.46 (t, J=7.2 Hz, 3H). ESI-MS m/z calc. 251.03, found 252.1 $(M+1)^+$.

Step 2: Ethyl 2-bromo-4-chloro-quinoline-3-carboxylate $POBr_3$ (1.20 g, 3.98 mmol) was added to a solution of ethyl 4-chloro-1-oxido-quinoline-3-carboxylate (1.0 g, 3.5 mmol) in chloroform (15 mL). The reaction mixture was stirred at room temperature for 2 h. Ice water (30 mL) was added to the reaction mixture and the layers were separated. The aqueous layer was extracted with DCM (2×25 mL), and the combined organic layers were washed with brine, dried over sodium sulfate, filtered and concentrated under reduced pressure to give 1.17 g of an orange solid. The crude product was adsorbed on silica gel under vacuum and purified by silica gel chromatography (0-10% ethyl acetate/heptanes) to provide ethyl 2-bromo-4-chloro-quinoline-3-carboxylate (771 mg, 69%) as a white solid. $^1$H NMR (300 MHz, $CDCl_3$) δ 8.24 (dd, J=8.4, 1.3 Hz, 1H), 8.08 (d, J=8.5 Hz, 1H), 7.90-7.80 (m, 1H), 7.76-7.68 (m, 1H), 4.55 (q, J=7.1 Hz, 2H), 1.48 (t, J=7.2 Hz, 3H). ESI-MS m/z calc. 312.95, found 314.0 $(M+1)^+$.

Step 3: Ethyl 4-benzyloxy-2-bromo-quinoline-3-carboxylate

Ethyl 4-benzyloxy-2-bromo-quinoline-3-carboxylate was prepared from ethyl 2-bromo-4-chloro-quinoline-3-carboxylate using a procedure analogous to that found in Intermediate A-1, step 1 using DMF as the solvent. ESI-MS m/z calc. 385.03, found 386.0 $(M+1)^+$.

Intermediate A-6

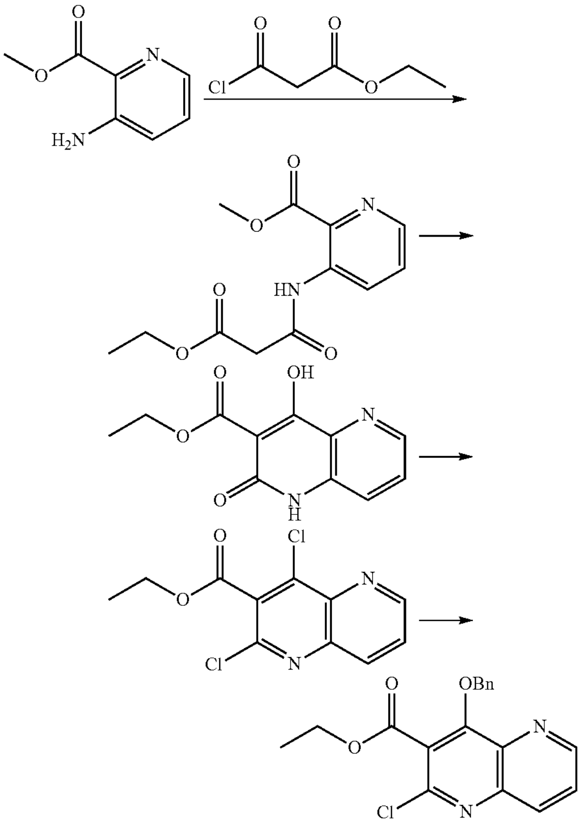

Step 1: Methyl 3-[(3-ethoxy-3-oxo-propanoyl)amino]pyridine-2-carboxylate

To methyl 3-aminopyridine-2-carboxylate (20.0 g, 132 mmol) in DCM (200 mL) was added ethyl 3-chloro-3-oxo-propanoate (19.8 g, 132 mmol). The reaction was stirred at reflux for 45 min then cooled to room temperature over 20 min. DCM (600 mL) was added and organic solution was washed with saturated aqueous sodium bicarbonate (600 mL) and brine (400 mL), dried over magnesium sulfate, filtered and concentrated to provide methyl 3-[(3-ethoxy-3-oxo-propanoyl)amino]pyridine-2-carboxylate (26.16 g, 72%) as a white solid. $^1$H NMR (400 MHz, $CDCl_3$) δ 11.53 (s, 1H), 9.11 (d, 1H, J=8.6 Hz), 8.46 (d, 1H, J=2.3 Hz), 7.52 (m, 1H), 4.32-4.27 (m, 2H), 4.06 (d, 3H, J=1.8 Hz), 3.57 (d, 2H, J=1.1 Hz), 1.33 (td, 3H, J=7.1, 1.8 Hz). ESI-MS m/z calc. 266.09, found 267.0 $(M+1)^+$.

Step 2: Ethyl 4-hydroxy-2-oxo-1H-1,5-naphthyridine-3-carboxylate

To methyl 3-[(3-ethoxy-3-oxo-propanoyl)amino]pyridine-2-carboxylate (24.16 g, 87.65 mmol) in ethanol (240 mL) under argon at 5° C. was added sodium ethoxide (12.9 g, 190 mmol) in ethanol (120 mL) over 5 min. The reaction was stirred at room temperature for 1 h, then cooled to 0° C. and adjusted to pH 7 using 4 M HCl. The solution was concentrated under reduced pressure to afford crude ethyl 4-hydroxy-2-oxo-1H-1,5-naphthyridine-3-carboxylate (30.15 g, 147%) as a pale yellow solid, $^1$H NMR (400 MHz, DMSO-$d_6$) δ 10.96 (s, 1H), 8.34 (d, 1H, J=3.4 Hz), 7.66-7.64 (m, 1H), 7.51 (dd, 1H, J=8.3, 4.4 Hz), 4.17 (q, 2H, J=7.1 Hz), 1.23 (t, 3H, J=7.1 Hz). ESI-MS m/z calc. 234.06, found 234.9 $(M+1)^+$.

Step 3: Ethyl 2,4-dichloro-1,5-naphthyridine-3-carboxylate

To phosphorus oxychloride (33.5 g, 17 mL, 218 mmol) was added ethyl 4-hydroxy-2-oxo-1H-1,5-naphthyridine-3-carboxylate (1.75 g, 7.47 mmol). The reaction was heated at 120° C. for 16 h. The reaction was cooled to room temperature over 1 h then concentrated under reduced pressure. Toluene (2×50 mL) was used to azeotrope the residue. The solid was added to ice water (100 mL) and neutralized with sodium carbonate. The aqueous mixture was extracted with DCM (2×50 mL). The organics were combined, washed with brine (30 mL), dried over sodium sulfate and concentrated under reduced pressure. Purification by silica gel chromatography (0-20% ethyl acetate/heptane) provided ethyl 2,4-dichloro-1,5-naphthyridine-3-carboxylate (1.05 g, 51%). $^1$H NMR (400 MHz, $CDCl_3$) δ 9.14 (dd, 1H, J=4.2, 1.6 Hz), 8.39 (dd, 1H, J=8.6, 1.6 Hz), 7.81 (dd, 1H, J=8.5, 4.2 Hz), 4.59 (q, 2H, J=7.1 Hz), 1.50 (t, 3H, J=7.2 Hz). ESI-MS m/z calc. 270.00, found 270.88 $(M+1)^+$.

Step 4: Ethyl 4-benzyloxy-2-chloro-1,5-naphthyridine-3-carboxylate

Ethyl 4-benzyloxy-2-chloro-1,5-naphthyridine-3-carboxylate was prepared from ethyl 2,4-dichloro-1,5-naphthyridine-3-carboxylate using a procedure analogous to that found in Intermediate A-1 step 1.] $^1$H NMR (400 MHz, CDCl3) δ 8.99 (dd, 1H, J=4.1, 1.7 Hz), 8.32 (dd, 1H, J=8.6, 1.7 Hz), 7.71 (dd, 1H, J=8.6, 4.0 Hz), 7.50-7.48 (m, 2H), 7.41-7.33 (m, 3H), 6.01 (s, 2H), 4.42 (q, 2H, J=7.2 Hz), 1.34 (t, 3H, J=7.1 Hz). ESI-MS m/z calc. 342.08, found 343.0 $(M+1)^+$.

Intermediate A-7

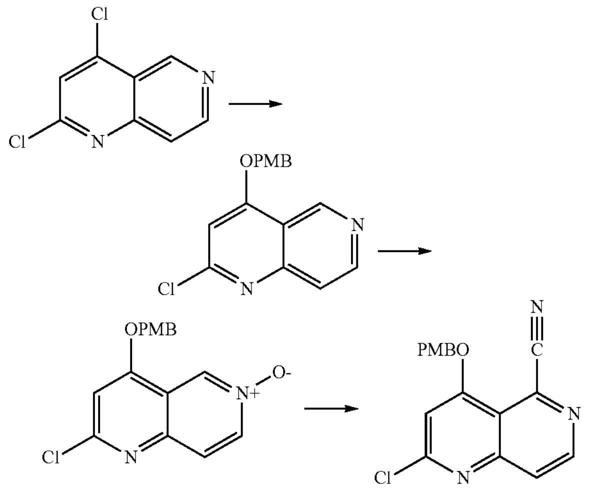

Step 1: 2-chloro-4-[(4-methoxyphenyl)methoxy]-1,6-naphthyridine

To a mixture at 0° C. of 2,4-dichloro-1,6-naphthyridine (3.29 g, 16.5 mmol) and (4-methoxyphenyl)methanol (2.28 g, 2.05 mL, 16.47 mmol) in DMF (33 mL) and 2-MeTHF (33 mL) was added sodium hydride (715 mg, 60% in mineral oil, 17.88 mmol) portionwise. The mixture was stirred at 0° C. for 1 h, then gradually warmed to room temperature and stirred for 19.5 h. The mixture was poured into a stirring mixture of 0.1 M aqueous HCl (100 mL) and 2-MeTHF (100 mL). The layers were separated and the aqueous layer extracted with additional 2-MeTHF (2×100 mL). The organic layers were combined and washed with water (2×50 mL), 1:1 water/brine (50 mL) and brine (50 mL). The solution was dried over sodium sulfate, filtered, and concentrated under reduced pressure. Purification by silica gel chromatography (5-100% ethyl acetate/heptanes) provided 2-chloro-4-[(4-methoxyphenoxy)methoxy]-1,6-naphthyridine (1.95 g, 39%) as a pale yellow solid. ESI-MS m/z calc. 300.06, found 301.2 $(M+1)^+$. $^1$H NMR (400 MHz, $CDCl_3$) δ 9.44 (s, 1H), 8.74 (d, J=5.9 Hz, 1H), 7.72-7.67 (m, 1H), 7.48-7.42 (m, 2H), 7.09 (s, 1H), 6.97-6.88 (m, 2H), 5.50 (s, 2H), 3.83 (s, 3H). ESI-MS m/z calc. 300.06, found 301.2 $(M+1)^+$.

Step 2: 2-chloro-4-[(4-methoxyphenyl)methoxy]-6-oxido-1,6-naphthyridin-6-ium

A solution of 2-chloro-4-[(4-methoxyphenoxy)methyl]-1,6-naphthyridine (5.0 g, 16.6 mmol) in DCM (100 mL) was cooled to 0° C. and treated with solid 3-chlorobenzenecarboperoxoic acid (4.7 g, 21 mmol). The reaction was warmed to room temperature and stirred for 4 h. The mixture was quenched with saturated aqueous sodium bicarbonate (100 mL) and the layers were separated. The aqueous layer was extracted with additional DCM (3×25 mL). The combined organic layers were washed with brine (20 mL×2), dried with anhydrous magnesium sulfate, filtered, and concentrated in vacuo to obtain 2-chloro-4-[(4-methoxyphenyl)methoxy]-6-oxido-1,6-naphthyridin-6-ium (5.1 g, 97%). ESI-MS m/z calc. 316.06, found 317.2 $(M+1)^+$. $^1$H NMR (400 MHz, DMSO-$d_6$) δ 8.66 (d, J=2.1 Hz, 1H), 8.40 (dd, J=7.3, 2.1 Hz, 1H), 7.86 (d, J=7.3 Hz, 1H), 7.53-7.47 (m, 2H), 7.41 (s, 1H), 7.05-6.95 (m, 2H), 5.39 (s, 2H), 3.78 (s, 3H).

Step 3: 2-chloro-4-[(4-methoxyphenyl)methoxy]-1,6-naphthyridine-5-carbonitrile

To a solution of 2-chloro-4-[(4-methoxyphenyl)methoxy]-6-oxido-1,6-naphthyridin-6-ium (6.1 g, 19.3 mmol) in DCM (50 mL) under an atmosphere of nitrogen was added trimethylsilyl cyanide (6.8 mL, 51 mmol), followed by the addition of TEA (8 mL, 57.4 mmol). The mixture was stirred for 20 h at room temperature. The reaction was quenched with water and the aqueous layer was extracted with DCM (3×). The combined organic layers were dried over magnesium sulfate, filtered and concentrated. Purification by silica gel chromatography (0-100% ethyl acetate/DCM) provided 2-chloro-4-[(4-methoxyphenyl)methoxy]-1,6-naphthyridine-5-carbonitrile (5.5 g, 88%). $^1$H NMR (400 MHz, DMSO-$d_6$) δ 8.90 (d, J=5.8 Hz, 1H), 8.11 (d, J=5.7 Hz, 1H), 7.61 (s, 1H), 7.60-7.52 (m, 2H), 7.03-6.95 (m, 2H), 5.52 (s, 2H), 3.77 (s, 3H).

Intermediate A-8

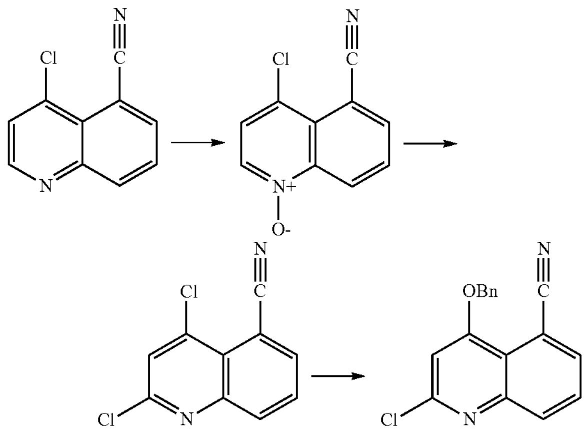

Step 1: 4-chloro-1-oxido-quinolin-1-ium-5-carbonitrile

A mixture of 4-chloroquinoline-5-carbonitrile (840 mg, 4.45 mmol) and m-CPBA (1.36 g, 5.52 mmol) in DCM (12 mL) was stirred for 2 hours at room temperature. The mixture was quenched with saturated sodium bicarbonate solution and extracted with DCM (3×). The combined organic layers were dried over magnesium sulfate, filtered and concentrated to provide 4-chloro-1-oxido-quinolin-1-ium-5-carbonitrile (910 mg, 100%). ESI-MS m/z calc. 204.01, found 205.0 $(M+1)^+$.

Step 2: 2,4-dichloroquinoline-5-carbonitrile

A vial charged with 4-chloro-1-oxido-quinolin-1-ium-5-carbonitrile (900 mg, 4.40 mmol) and $POCl_3$ (4.0 mL, 42.9 mmol) was heated at 50° C. for 4 h. The mixture was cooled to room temperature and poured on ice. The resulting precipitate was filtered and washed with water. The solid was dissolved in dichloromethane and washed with saturated sodium bicarbonate solution (2×). The organic layer was dried over magnesium sulfate, filtered and concentrated. Purification by silica gel chromatography (0-20% ethyl acetate/hexanes) provided 2,4-dichloroquinoline-5-carbonitrile (680 mg, 69%). ESI-MS m/z calc. 221.97, found 223.0 $(M+1)^+$.

Step 3: 4-benzyloxy-2-chloro-quinoline-5-carbonitrile

To a solution of benzyl alcohol (232 μL, 2.24 mmol) in DMF (10 mL) at 0° C. was added sodium hydride (98 mg of 60% w/w, 2.45 mmol) and the mixture warmed to room temperature and stirred for 30 min. The mixture was then cooled to −40° C. and 2,4-dichloroquinoline-5-carbonitrile (500 mg, 2.24 mmol) added. The mixture was allowed to warm to room temperature and stirred overnight. The mixture was cooled to 0° C., quenched with water and extracted with ethyl acetate (3×). The organic phase was washed with water and brine, dried over magnesium sulfate, filtered, and concentrated. Purification by silica gel chromatography (0-30% ethyl acetate/hexanes) provided 4-benzyloxy-2-chloro-quinoline-5-carbonitrile (410 mg, 62%) as an off-white white solid. ESI-MS m/z calc. 294.05, found 295.6 $(M+1)^+$. $^1H$ NMR (400 MHz, DMSO-$d_6$) δ (ppm) 8.23-8.15 (m, 2H), 7.92 (dd, J=8.5, 7.4 Hz, 1H), 7.67-7.57 (m, 2H), 7.48 (s, 1H), 7.46-7.32 (m, 3H), 5.56 (s, 2H). The regioisomer 2-benzyloxy-4-chloro-quinoline-5-carbonitrile was also isolated. ESI-MS m/z calc. 294.06 found 295.1 $(M+1)^+$. $^1H$ NMR (400 MHz, DMSO-$d_6$) δ 8.17 (m, 2H), 7.90 (dd, J=8.4, 7.4 Hz, 1H), 7.58 (s, 1H), 7.55-7.50 (m, 2H), 7.44-7.32 (m, 3H), 5.53 (s, 2H).

General Scheme for the Preparation of Intermediate A

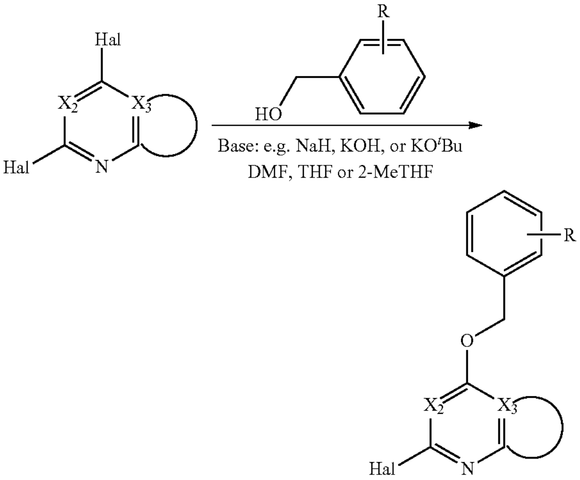

Hal = halogen

Intermediates in Table 1 were prepared using the corresponding dichloro-pyridine or -pyrimidines and a procedure analogous to that found in Intermediate A-1, step 1. Dichloro-pyridines or -pyrimidines were obtained from commercial sources. Benzyl alcohol or substituted benzyl alcohols, such as 2-methoxy benzyl alcohol, may be used. DMF, THF, 2-MeTHF, or mixtures of these solvents may be used as the reaction solvent.

TABLE 1

| Intermediate | Compound Name | MW & Found $[M + H]^+$ | NMR (shifts in ppm) |
|---|---|---|---|
| Intermediate A-9 | 4-benzyloxy-2-chloro-7-fluoro-3-methyl-quinoline | 301.07; 302.3 | $^1H$ NMR (400 MHz, DMSO-$d_6$) δ 8.08 (dd, J = 9.2, 6.1 Hz, 1H), 7.73 (dd, J = 10.2, 2.5 Hz, 1H), 7.55-7.50 (m, 3H), 7.47-7.39 (m, 3H), 5.18 (s, 2H), 2.38 (s, 3H). |
| Intermediate A-10 | 4-benzyloxy-2-chloro-6-fluoro-3-methyl-quinoline | 301.07 302.3 | NMR (400 MHz, DMSO-$d_6$) δ 8.01 (dd, J = 9.1, 5.2 Hz, 1H), 7.68 (m, 1H), 7.64 (m, 1H), 7.55-7.50 (m, 2H), 7.47-7.38 (m, 3H), 5.18 (s, 2H), 2.39 (s, 3H). |

TABLE 1-continued

| Intermediate | Compound Name | MW & Found [M + H]+ | NMR (shifts in ppm) |
|---|---|---|---|
| Intermediate A-11 | 4-benzyloxy-2-chloro-3-methyl-quinoline | 283.08 284.3 | $^1$H NMR (400 MHz, DMSO-$d_6$) δ 8.04 (dd, J = 8.4, 1.4 Hz, 1H), 7.94 (dd, J = 8.4, 1.7 Hz, 1H), 7.78 (ddd, J = 8.4, 6.9, 1.5 Hz, 1H), 7.63 (ddd, J = 8.2, 6.8, 1.2 Hz, 1H), 7.57-7.50 (m, 2H), 7.48-7.38 (m, 3H), 5.17 (s, 2H), 2.39 (s, 3H). |
| Intermediate A-12 | 4-benzyloxy-2-chloro-6-methyl-quinoline | 283.08 284.3 | $^1$H NMR (400 MHz, DMSO-$d_6$) δ 7.89 (s, 1H), 7.78 (d, J = 8.5 Hz, 1H), 7.63 (dd, J = 8.6, 2.0 Hz, 1H), 7.60-7.54 (m, 2H), 7.50-7.43 (m, 2H), 7.43-7.36 (m, 1H), 7.17 (s, 1H), 5.42 (s, 2H), 2.48 (s, 3H). |
| Intermediate A-13 | 2-chloro-4-[(4-methoxyphenyl) methoxy]-8-methyl-quinoline | 313.09; 314.3 | |
| Intermediate A-14 | 4-benzyloxy-2-chloro-6-methoxy-quinoline | 299.07; 300.3 | $^1$H NMR (400 MHz, DMSO-$d_6$) δ 7.81 (d, J = 9.1 Hz, 1H), 7.59-7.54 (m, 2H), 7.49-7.42 (m, 3H), 7.42-7.36 (m, 2H), 7.17 (s, 1H), 5.46 (s, 2H), 3.88 (s, 3H). |
| Intermediate A-15 | 4-benzyloxy-2-chloro-5-methoxy-quinoline | 299.07; 301.2 | $^1$H NMR (400 MHz, $CDCl_3$) δ 7.62-7.52 (m, 4H), 7.44 (t, J = 7.4 Hz, 2H), 7.38 (d, J = 7.5 Hz, 1H), 6.89 (dd, J = 7.7, 1.4 Hz, 1H), 6.79 (s, 1H), 5.27 (s, 2H), 1.56 (s, 3H). |
| Intermediate A-16 | 4-benzyloxy-2-chloro-8-fluoro-quinoline | 287.05; 288.1 | $^1$H NMR (400 MHz, $CDCl_3$) δ 8.04-7.91 (m, 1H), 7.55-7.36 (m, 7H), 6.88 (s, 1H), 5.29 (s, 2H). |
| Intermediate A-17 | 4-benzyloxy-2-chloro-7-fluoro-quinoline | 287.05; 288.1 | $^1$H NMR (400 MHz, $CDCl_3$) δ 8.20 (dd, J = 9.2, 6.0 Hz, 1H), 7.58 (dd, J = 9.9, 2.3 Hz, 1H), 7.52-7.39 (m, 5H), 7.30-7.23 (m, 1H), 6.81 (s, 1H), 5.28 (s, 2H). $^{19}$F NMR (377 MHz, $CDCl^3$) 8-107.64-108.00 (m, 1F). |
| Intermediate A-18 | 4-benzyloxy-2-chloro-6-fluoro-quinoline | 287.05; 288.1 | $^1$H NMR (400 MHz, $CDCl_3$) δ 7.94 (dd, J = 9.0, 5.1 Hz, 1H), 7.78 (dd, J = 9.2, 2.8 Hz, 1H), 7.53-7.38 (m, 6H), 6.83 (s, 1H), 5.27 (s, 2H). $^{19}$F NMR (377 MHz, $CDCl_3$) 8-112.82--113.06 (m, 1F). |
| Intermediate A-19 | 2-chloro-5-fluoro-4-[(4-methoxyphenyl) methoxy]quinoline | 317.06; 316.0 (M-1)$^-$ | $^1$H NMR (400 MHz, $CDCl_3$) δ 7.76 (d, 1H, J = 8.4 Hz), 7.63 (td, 1H, J = 8.2, 5.4 Hz), 7.47 (dd, 2H, J = 11.5, 2.8 Hz), 7.17 (ddd, 1H, J = 11.7, 7.9, 1.0 Hz), 7.00-6.97 (m, 2H), 6.86 (s, 1H), 5.23 (s, 2H), 3.86 (s, 3H). |
| Intermediate A-20 | 4-benzyloxy-2-chloro-1,5-naphthyridine | 270.06; 271.0 | $^1$H NMR (400 MHz, $CDCl_3$) δ 8.97 (dd, J = 4.2, 1.5 Hz, 1H), 8.26 (dd, J = 8.6, 1.5 Hz, 1H), 7.66 (dd, J = 8.6, 4.2 Hz, 1H), 7.55-7.48 (m, 2H), 7.45-7.33 (m, 3H), 6.98 (s, 1H), 5.44 (s, 2H) |
| Intermediate A-21 | 4-benzyloxy-2-chloro-1,8-naphthyridine | 270.06; 271.1 | $^1$H NMR (400 MHz, $CDCl_3$) δ 9.06 (dd, J = 4.4, 2.0 Hz, 1H), 8.55 (dd, J = 8.3, 2.0 Hz, 1H), 7.54-7.38 (m, 6H), 6.91 (s, 1H), 5.29 (s, 2H). |
| Intermediate A-22 | 4-benzyloxy-2-chloro-5-fluoro-quinazoline | 288.05; 289.1 | $^1$H NMR (400 MHz, DMSO-$d_6$) δ 7.99 (td, J = 8.3, 5.6 Hz, 1H), 7.71 (dd, J = 8.4, 1.0 Hz, 1H), 7.60-7.54 (m, 2H), 7.54-7.34 (m, 45.65 (s, 2H).H), |
| Intermediate A-23 | 4-benzyloxy-2-chloro-5,7-dimethoxy-quinoline | 329.08; 330.01 | $^1$H NMR (400 MHz, DMSO-$d_6$) δ 7.59-7.54 (m, 2H), 7.45 (dd, J = 8.4, 6.8 Hz, 2H), 7.38-7.32 (m, 1H), 6.95 (s, 1H), 6.87 (s, 1H), 6.64 (s, 1H), 5.35 (s, 2H), 3.88 (s, 6H). |
| Intermediate A-24 | 4-benzyloxy-2-chloro-6-methoxy-quinoline | 299.07; 300.0 | $^1$H NMR (400 MHz, $CDCl_3$) δ 7.86 (d, J = 9.1 Hz, 1H), 7.51-7.47 (m, 2H), 7.46-7.40 (m, 3H), 7.38-7.34 (m, 2H), 6.79 (s, 1H), 5.29 (s, 2H), 3.91 (s, 3H). |

Intermediate B-1

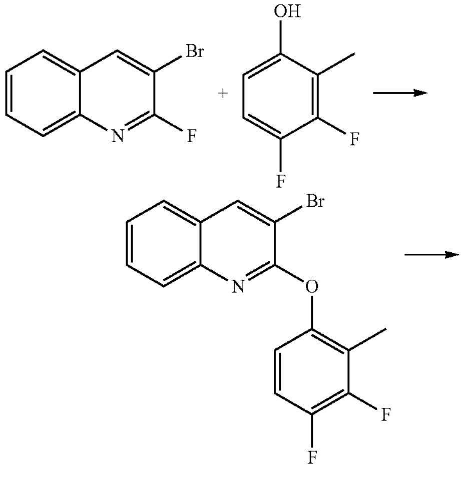

-continued

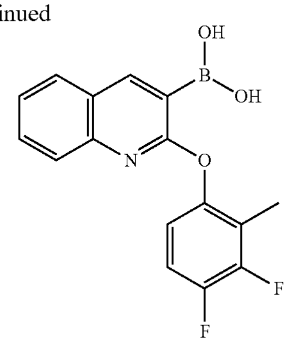

Step 1: 3-bromo-2-(3,4-difluoro-2-methyl-phenoxy)quinoline

To a mixture of 3-bromo-2-fluoro-quinoline (500 mg, 2.21 mmol) and 3,4-difluoro-2-methyl-phenol (478 mg, 3.32 mmol) in DMSO (12 mL) was added cesium carbonate (1.8 g, 5.5 mmol). The resulting mixture was stirred at 55° C. for 4 h. The reaction was cooled to room temperature, diluted with ethyl acetate, washed with water and brine. The organic layer was dried over sodium sulfate, filtered and concentrated under reduced pressure. Purification using silica gel chromatography (0-20% ethyl acetate/hexanes) provided 3-bromo-2-(3,4-difluoro-2-methyl-phenoxy)quinoline (596 mg, 77%). $^1$H NMR (400 MHz, DMSO-$d_6$) δ 8.89 (s, 1H), 7.95 (dd, J=8.1, 1.4 Hz, 1H), 7.69 (ddd, J=8.4, 6.9, 1.5 Hz, 1H), 7.60 (dd, J=8.1, 1.0 Hz, 1H), 7.54 (ddd, J=8.1, 6.8, 1.3 Hz, 1H), 7.40 (m, 1H), 7.17 (ddd, J=9.1, 4.4, 2.1 Hz, 1H), 2.07 (d, J=2.2 Hz, 3H). ESI-MS m/z calc. 348.99, found 350.0 $(M+1)^+$.

Step 2: [2-(3,4-difluoro-2-methyl-phenoxy)-3-quinolyl]boronic acid

A solution of 3-bromo-2-(3,4-difluoro-2-methyl-phenoxy)quinoline (600 mg, 1.71 mmol) in THF (4 mL) at −78° C. was treated dropwise with n-BuLi (750 µL of 2.5 M in hexanes, 1.9 mmol). The reaction mixture was stirred for 30 min then treated dropwise with triisopropyl borate (550 µL, 2.40 mmol). The mixture was stirred for 30 min at −78° C., then removed from the cooling bath and quenched with saturated aqueous $NH_4Cl$. The mixture was diluted with diethyl ether and the layers separated. The aqueous layer was extracted with additional diethyl ether (3×), and the combined organic layers dried over magnesium sulfate, filtered and concentrated to provide [2-(3,4-difluoro-2-methyl-phenoxy)-3-quinolyl]boronic acid (505 mg, 94%). ESI-MS m/z calc. 315.09, found 316.2 $(M+1)^+$. $^1$H NMR (400 MHz, DMSO-$d_6$) δ 8.51 (d, J=4.8 Hz, 1H), 8.36 (s, 2H), 7.94 (dd, J=8.1, 1.5 Hz, 1H), 7.66-7.57 (m, 1H), 7.54 (d, J=8.7 Hz, 1H), 7.46 (ddd, J=8.1, 6.8, 1.4 Hz, 1H), 7.41-7.28 (m, 1H), 7.13 (m, 1H), 2.06 (dd, J=5.4, 2.3 Hz, 3H).

Intermediate B-2

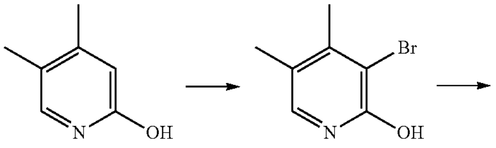

-continued

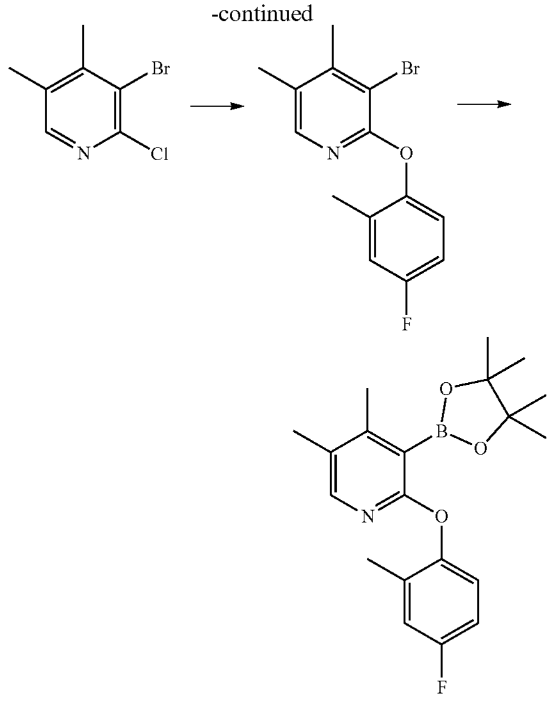

Step 1: 3-bromo-4,5-dimethyl-pyridin-2-ol

To a solution of 4,5-dimethylpyridin-2-ol (2.0 g, 16 mmol) in acetic acid (20 mL) was added bromine (2.8 g, 0.9 mL, 17.5 mmol). The reaction mixture was stirred at rt for 90 h. It was poured onto a stirred potassium carbonate 20% aqueous solution (250 mL) then diluted with water (50 mL). The crashed solid was recovered by Buchner filtration and dried in-vacuo to give 3-bromo-4,5-dimethyl-pyridin-2-ol (2.79 g, 82%) as a white solid. $^1$H NMR (400 MHz, $CDCl_3$) δ 13.45 (br. s, 1H), 7.21 (s, 1H), 2.36 (s, 3H), 2.10 (s, 3H). ESI-MS m/z calc. 200.98, found 202.1 $(M+1)^+$.

Step 2: 3-bromo-2-chloro-4,5-dimethyl-pyridine

A solution of 3-bromo-4,5-dimethyl-pyridin-2-ol (6.5 g, 29 mmol) in $POCl_3$ (52.6 g, 32 mL, 343 mmol) was stirred at 110° C. for 30 h. The phosphorus oxychloride was removed under reduced pressure. The residue was dissolved in DCM (100 mL) then poured into stirring saturated aqueous sodium bicarbonate (400 mL). The layers were separated and the aqueous layer was extracted with DCM (2×100 mL). The combined organic layers were dried over anhydrous sodium sulfate, filtered and concentrated under reduced pressure. The residue was adsorbed on silica gel under vacuum and purified by silica gel chromatography (120 g silica, 0-10% ethyl acetate/heptane) to give 3-bromo-2-chloro-4,5-dimethyl-pyridine (6.06 g, 94%) as a white solid. $^1$H NMR (400 MHz, $CDCl_3$) δ 8.05 (s, 1H), 2.43 (s, 3H), 2.29 (s, 3H). ESI-MS m/z calc. 218.95, found 220.0 $(M+1)^+$.

Step 3: 3-bromo-2-(4-fluoro-2-methyl-phenoxy)-4,5-dimethyl-pyridine

3-Bromo-2-(4-fluoro-2-methyl-phenoxy)-4,5-dimethyl-pyridine was prepared from 3-bromo-2-chloro-4,5-dimethyl-pyridine and 4-fluoro-2-methyl-phenol using a procedure analogous to that found in Intermediate B-1 step 1. $^{1}$H NMR (400 MHz, $CDCl_3$) δ 7.74 (s, 1H), 7.01 (dd, J=8.7, 5.0 Hz, 1H), 6.96 (dd, J=9.0, 2.9 Hz, 1H), 6.94-6.88 (m, 1H), 2.43 (s, 3H), 2.23 (s, 3H), 2.14 (s, 3H). ESI-MS m/z calc. 309.02, found 310.1 $(M+1)^+$.

Step 4: 2-(4-fluoro-2-methyl-phenoxy)-4,5-dimethyl-3-(4,4,5,5-tetramethyl-1,3,2-dioxaborolan-2-yl)pyridine A mixture of 3-bromo-2-(4-fluoro-2-methyl-phenoxy)-4,5-dimethyl-pyridine (2.05 g, 6.60 mmol), 4,4,5,5-tetramethyl-2-(4,4,5,5-tetramethyl-1,3,2-dioxaborolan-2-yl)-1,3,2-dioxaborolane (3.3 g, 13 mmol), potassium acetate (1.9 g, 19.4 mmol) and $Pd(dppf)Cl_2$·DCM (430 mg, 0.527 mmol) in DMSO (30 mL) was stirred for 4 h at 110° C. The reaction mixture was cooled to room temperature and partitioned between water (100 mL) and MTBE (500 mL). The biphasic mixture was filtered through Celite® and the layers were separated. The organic layer was washed with water (4×) and brine (100 mL), dried over anhydrous sodium sulfate, filtered and concentrated under reduced pressure. The residue was adsorbed on silica gel under vacuum and purified by silica chromatography (120 g silica, 0-10% ethyl acetate/heptane) to provide 1.4 g of material. The solid was triturated in pentane (5 mL), filtered and the solid dried in-vacuo to give 2-(4-fluoro-2-methyl-phenoxy)-4,5-dimethyl-3-(4,4,5,5-tetramethyl-1,3,2-dioxaborolan-2-yl)pyridine (749 mg, 31%) as a white solid. ESI-MS m/z calc. 357.19, found 358.2 $(M+1)^+$. $^{1}$H NMR (400 MHz, $CDCl_3$) δ 7.81 (s, 1H), 7.00 (dd, J=8.8, 5.1 Hz, 1H), 6.92 (dd, J=9.2, 2.8 Hz, 1H), 6.90-6.83 (m, 1H), 2.31 (s, 3H), 2.16 (s, 3H), 2.13 (s, 3H), 1.38 (s, 12H). $^{19}$F NMR (377 MHz, $CDCl_3$) δ −119.47--119.80 (m, 1F).

Intermediate B-3

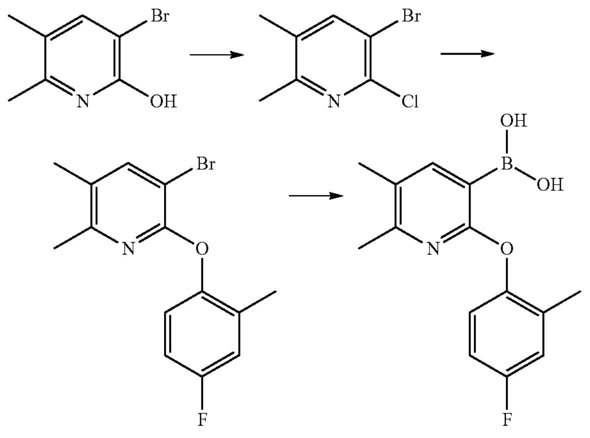

Step 1: 3-bromo-2-chloro-5,6-dimethyl-pyridine

A solution of 3-bromo-5,6-dimethyl-pyridin-2-ol (2.0 g, 9.9 mmol) in $POCl_3$ (17.2 g, 10.5 mL, 112 mmol) was purged with nitrogen for 10 min then heated at 110° C. for 30 h. The phosphorus oxychloride was removed under reduced pressure. The residue was dissolved in DCM (50 mL) then poured on to a stirring aqueous saturated solution of sodium bicarbonate (150 mL). The layers were separated and the aqueous layer was extracted with DCM (2×50 mL).

The combined organic layers were dried over anhydrous sodium sulfate, filtered and concentrated under reduced pressure to give a ash colored crude residue. The crude residue was purified by silica gel chromatography (40 g silica, 0-15% ethyl acetate/heptane) to obtain 3-bromo-2-chloro-5,6-dimethyl-pyridine (2.11 g, 97%) as a white solid. ESI-MS m/z calc. 218.95, found 220.0 $(M+1)^+$. $^{1}$H NMR (400 MHz, $CDCl_3$) δ 7.66 (s, 1H), 2.44 (s, 3H), 2.26 (s, 3H).

Step 2: 3-bromo-2-(4-fluoro-2-methyl-phenoxy)-5,6-dimethyl-pyridine

3-Bromo-2-(4-fluoro-2-methyl-phenoxy)-5,6-dimethyl-pyridine was prepared from 3-bromo-2-chloro-5,6-dimethyl-pyridine and 4-fluoro-2-methyl-phenol using a procedure analogous to that found in Intermediate B-1, step 1. ESI-MS m/z calc. 309.02, found 310.2 $(M+1)^+$. $^{1}$H NMR (400 MHz, $CDCl_3$) δ 7.64 (s, 1H), 6.99 (dd, J=8.9, 5.1 Hz, 1H), 6.95 (dd, J=9.0, 3.1 Hz, 1H), 6.91-6.85 (m, 1H), 2.23 (s, 3H), 2.21 (s, 3H), 2.18 (s, 3H).

Step 3: [2-(4-fluoro-2-methyl-phenoxy)-5,6-dimethyl-3-pyridyl]boronic acid

To a solution of 3-bromo-2-(4-fluoro-2-methyl-phenoxy)-5,6-dimethyl-pyridine (160 mg, 0.490 mmol) in diethyl ether (2.4 mL) at −78° C. was slowly added a solution of n-BuLi in hexanes (210 L of 2.5 M, 0.53 mmol) under nitrogen atmosphere. The mixture was then stirred at this temperature for 1 h after which, a solution of trimethyl borate (93 mg, 100 μL, 0.90 mmol) in diethyl ether (0.8 mL) was added dropwise. The resulting reaction mixture was allowed to warm to the room temperature (1.5 h) and stirred at room temperature for 2 h. The reaction was quenched with aqueous saturated solution of ammonium chloride (4 mL). The layers were separated, and the aqueous layer was extracted with ethyl acetate (3×8 mL). The combined organic layers were dried over anhydrous sodium sulfate, filtered and concentrated under reduced pressure to obtain the crude residue. Purification by reverse phase chromatography (C18, 5-100% $CH_3CN$/0.1% formic acid) provided [2-(4-fluoro-2-methyl-phenoxy)-5,6-dimethyl-3-pyridyl]boronic acid (98 mg, 72%) as white solid. ESI-MS m/z calc. 275.11, found 276.1 $(M+1)^+$. $^{1}$H NMR (400 MHz, $CD_3OD$) δ 7.54 (s, 1H), 6.99 (d, J=8.8 Hz, 1H), 6.89-6.86 (m, 2H), 2.28 (s, 3H), 2.24 (s, 3H), 2.16 (s, 3H).

Intermediate B-4

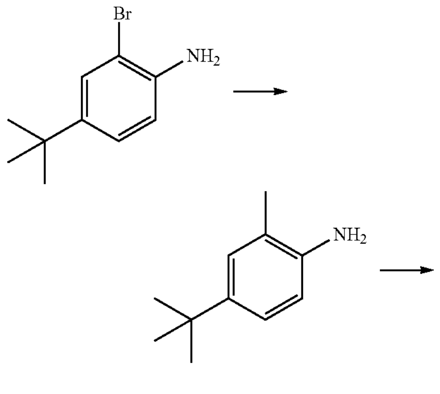

-continued

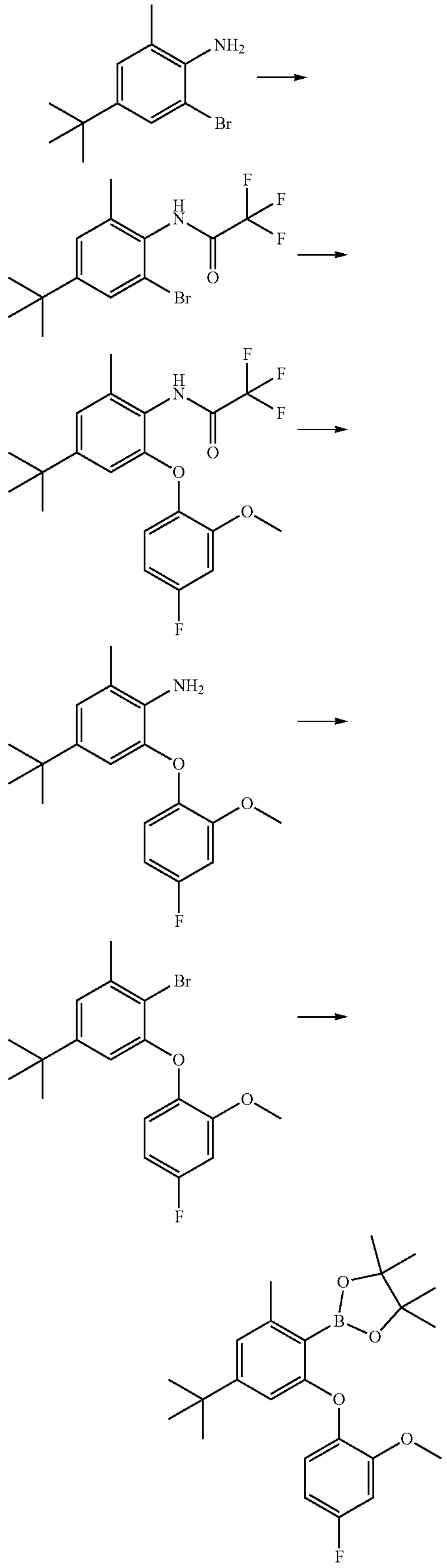

Step 1: 4-tert-butyl-2-methyl-aniline

To a solution of 2-bromo-4-tert-butyl-aniline (25 g, 110 mmol) in dioxane (750 mL) and water (85 mL) was added methylboronic acid (32.8 g, 548 mmol), tricyclohexylphosphine (6.3 g, 22.5 mmol) and potassium phosphate (70 g, 330 mmol). The mixture was bubbled with nitrogen for 5 min then palladium acetate (2.5 g, 11 mmol) was added. The mixture was heated at 110° C. for 18 h. The crude was filtered on Celite® and washed with dichloromethane (300 mL). The filtrate was washed with brine (2×200 mL), dried with anhydrous sodium sulfate, filtered and concentrated under reduced pressure. Purification by silica gel chromatography (330 g silica, 0-30% ethyl acetate/heptane) provided 4-tert-butyl-2-methyl-aniline (16.9 g, 94%) as a dark oil. ESI-MS m/z calc. 163.14, found 164.2 $(M+1)^+$. $^1H$ NMR (400 MHz, $CDCl_3$) δ 7.12-7.05 (m, 2H), 6.66 (d, J=7.8 Hz, 1H), 3.52 (br s, 2H), 2.21 (s, 3H), 1.31 (s, 9H).

Step 2: 2-bromo-4-tert-butyl-6-methyl-aniline

N-Bromosuccinimide (20.5 g, 115 mmol) was slowly added to a cold (−30° C.) solution of 4-tert-butyl-2-methyl-aniline (19.57 g, 119.9 mmol) in dichloromethane (1.2 L). The reaction mixture was stirred at −30° C. for 3 h then reaction was quenched with water (700 mL). Once warmed to room temperature, the organic layer was separated, dried over sodium sulfate and concentrated under reduced pressure to afford crude 2-bromo-4-tert-butyl-6-methyl-aniline (29.14 g, 96%) as a dark oil. The crude product was used for the next step without any further purification. ESI-MS m/z calc. 241.05, found 242.1 $(M+1)^+$. $^1H$ NMR (400 MHz, $CDCl_3$) δ 7.32 (d, J=2.2 Hz, 1H), 7.06-7.02 (m, 1H), 4.05-3.89 (m, 2H), 2.24 (s, 3H), 1.29 (s, 9H).

Step 3: N-(2-bromo-4-tert-butyl-6-methyl-phenyl)-2,2,2-trifluoro-acetamide

Trifluoroacetic anhydride (20 mL, 144 mmol) was added dropwise to a solution of 2-bromo-4-tert-butyl-6-methyl-aniline (29.14 g, 114.6 mmol) and triethylamine (24 mL, 172 mmol) in dichloromethane (300 mL) at 0° C. The reaction mixture was stirred at room temperature for 3 h, then water (200 mL) was added and mixture was extracted using dichloromethane (3×100 mL). Organic layer was washed with aqueous saturated sodium bicarbonate (2×150 mL), dried over sodium sulfate, filtered and concentrated under reduced pressure to afford N-(2-bromo-4-tert-butyl-6-methyl-phenyl)-2,2,2-trifluoro-acetamide (40.05 g, 100%) as brown solid. The crude material was used for the next step without any further purification. ESI-MS m/z calc. 337.03, found 338.0 $(M+1)^+$. $^1H$ NMR (400 MHz, $CDCl_3$) δ 7.64-7.56 (m, 1H), 7.51 (d, J=1.5 Hz, 1H), 7.26 (s, 1H), 2.32 (s, 3H), 1.33 (s, 9H).

Step 4: N-[4-tert-butyl-2-(4-fluoro-2-methoxy-phenoxy)-6-methyl-phenyl]-2,2,2-trifluoro-acetamide A mixture of N-(2-bromo-4-tert-butyl-6-methyl-phenyl)-2,2,2-trifluoro-acetamide (87.8 g, 235 mmol), 4-fluoro-2-methoxy-phenol (39.9 g, 32 mL, 281 mmol), cesium carbonate (230 g, 706 mmol) and N,N-dimethylglycine (24.2 g, 235 mmol) in dioxane (920 mL) was degassed with argon for 10 min, then copper (I) iodide (13.4 g, 70.4 mmol) added. The reaction was warmed to 60° C. under argon for 20 h, then allowed to cool. The reaction was filtered through Celite® and concentrated. The Celite® was washed with warm water (1.2 l) and ethyl acetate (600 mL), which were combined with the concentrate, and the phases separated. The aqueous was extracted with ethyl acetate (3×400 mL). The combined organics were washed with water (3×400 mL) then brine (400 mL), dried over sodium sulfate and silica gel, filtered and concentrated. The crude was boiled in heptane (200 mL), allowed to cool slowly to room temperature, then cooled to 0° C. The solid was collected by filtration to provide N-[4-tert-butyl-2-(4-fluoro-2-methoxy-phenoxy)-6-methyl-phenyl]-2,2,2-trifluoro-acetamide (70.3 g, 75%). ESI-MS m/z calc. 399.15, found 400.16 $(M+1)^+$. $^1$H NMR (301 MHz, $CDCl_3$) δ 7.91 (br s, 1H), 7.00 (d, J=1.4 Hz, 1H), 6.94 (dd, J=8.9, 5.4 Hz, 1H), 6.73-6.69 (m, 2H), 6.61 (td, J=8.4, 2.9 Hz, 1H), 3.80 (s, 3H), 2.27 (s, 3H), 1.21 (s, 9H).

Step 5: 4-tert-butyl-2-(4-fluoro-2-methoxy-phenoxy)-6-methyl-aniline

To a solution of N-[4-tert-butyl-2-(4-fluoro-2-methoxy-phenoxy)-6-methyl-phenyl]-2,2,2-trifluoro-acetamide (70 g, 175 mmol) in ethanol (875 mL) was added NaOH (350 mL of 2 M, 700 mmol), and the mixture was stirred under reflux for 3 h. The reaction was allowed to cool, then the ethanol removed under reduced pressure. The residue was diluted with water (300 mL) then extracted with CPME (3×250 mL). The combined organics were washed with 1 N NaOH (200 mL) then brine (200 mL), dried over sodium sulfate, filtered and concentrated to provide 4-tert-butyl-2-(4-fluoro-2-methoxy-phenoxy)-6-methyl-aniline (54.9 g, 100%). ESI-MS m/z calc. 303.16, found 304.14 $(M+1)^+$. $^1$H NMR (301 MHz, $CDCl_3$) δ 6.87 (d, J=1.7 Hz, 1H), 6.79-6.71 (m, 2H), 6.67 (d, J=2.1 Hz, 1H), 6.59-6.52 (m, 1H), 3.87 (s, 3H), 2.22 (s, 3H), 1.20 (s, 9H).

Step 6: 2-bromo-5-tert-butyl-1-(4-fluoro-2-methoxy-phenoxy)-3-methyl-benzene

To a slurry of copper (II) bromide (48.6 g, 218 mmol), lithium bromide (45.4 g, 523 mmol), and tert-butyl nitrite (19.7 g, 16 mL, 172 mmol) in $CH_3CN$ (700 mL) was added a solution of 4-tert-butyl-2-(4-fluoro-2-methoxy-phenoxy)-6-methyl-aniline (54.9 g, 174 mmol) in $CH_3CN$ (420 mL) at room temperature over 40 min. The reaction was warmed to 60° C. for 4 h then allowed to cool. The reaction was quenched with 1 N HCl (800 mL) and extracted with CPME (3×300 mL). The combined organics were washed with water (2×300 mL) and brine (300 mL), dried over sodium sulfate and concentrated. Purification by silica gel chromatography (0-2% ethyl acetate/heptane) provided 2-bromo-5-tert-butyl-1-(4-fluoro-2-methoxy-phenoxy)-3-methyl-benzene (41.3 g, 62%). $^1$H NMR (400 MHz, $CDCl_3$) δ 6.99 (d, J=2.3 Hz, 1H), 6.79-6.72 (m, 2H), 6.63 (d, J=2.3 Hz, 1H), 6.61-6.56 (m, 1H), 3.84 (s, 3H), 2.45 (s, 3H), 1.20 (s, 9H).

Step 7: 2-[4-tert-butyl-2-(4-fluoro-2-methoxy-phenoxy)-6-methyl-phenyl]-4,4,5,5-tetramethyl-1,3,2-dioxaborolane n-BuLi (1.2 mL of 2.5 M, 3.0 mmol) was slowly added to a solution of 2-bromo-5-tert-butyl-1-(4-fluoro-2-methoxy-phenoxy)-3-methyl-benzene (1.0 g, 2.7 mmol) in THF (20 mL) at −78° C. The reaction mixture was stirred for 15 min then a precooled solution of 2-isopropoxy-4,4,5,5-tetramethyl-1,3,2-dioxaborolane (684 mg, 0.75 mL, 3.68 mmol) in THF (5 mL) was slowly added. The reaction mixture was stirred for 1.5 h at −78° C., then warmed to 0° C. Reaction mixture was quenched with water (20 mL), poured into 1:1 saturated sodium chloride/water solution (50 mL) and extracted using ethyl acetate (3×50 mL). The organic layers were combined, dried over sodium sulfate, filtered and concentrated under reduced pressure. The residue was purified by silica gel chromatography (0-20% ethyl acetate/heptane) to afford 2-[4-tert-butyl-2-(4-fluoro-2-methoxy-phenoxy)-6-methyl-phenyl]-4,4,5,5-tetramethyl-1,3,2-dioxaborolane (890 mg, 79%) as clear oil. $^1$H NMR (400 MHz, $CDCl_3$) δ 6.96 (d, J=1.0 Hz, 1H), 6.76-6.62 (m, 3H), 6.59-6.47 (m, 1H), 3.89 (s, 3H), 2.45 (s, 3H), 1.24 (s, 9H), 1.24 (s, 12H).

Intermediate B-5

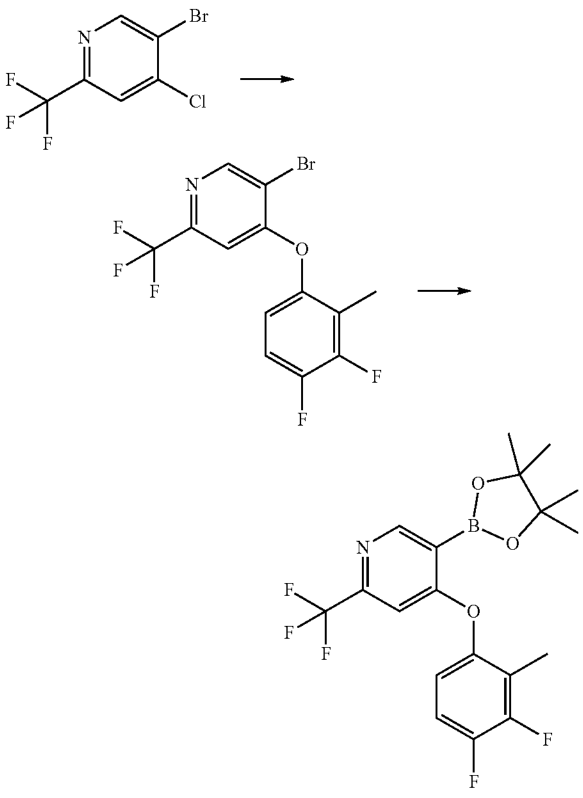

Step 1: 5-bromo-4-(3,4-difluoro-2-methyl-phenoxy)-2-(trifluoromethyl)pyridine

5-Bromo-4-(3,4-difluoro-2-methyl-phenoxy)-2-(trifluoromethyl)pyridine was prepared from 5-bromo-4-chloro-2-(trifluoromethyl)pyridine and 3,4-difluoro-2-methyl-phenol using a procedure analogous to that found in Intermediate B-1, step 1. ESI-MS m/z calc. 366.96, found 367.93 $(M+1)^+$.

Step 2: 4-(3,4-difluoro-2-methyl-phenoxy)-5-(4,4,5,5-tetramethyl-1,3,2-dioxaborolan-2-yl)-2-(trifluoromethyl)pyridine 4-(3,4-Difluoro-2-methyl-phenoxy)-5-(4,4,5,5-tetramethyl-1,3,2-dioxaborolan-2-yl)-2-(trifluoromethyl)pyridine was prepared using a procedure analogous to that found in Intermediate B-2, step 4. Purified by silica gel chromatography (40 g silica, 0-100% ethyl acetate/hexanes) to provide 4-(3,4-difluoro-2-methyl-phenoxy)-5-(4,4,5,5-tetramethyl-1,3,2-dioxaborolan-2-yl)-2-(trifluoromethyl)pyridine (402 mg, 54%) as a clear oil. ESI-MS m/z calc. 415.14, found 334.16 $(M+1)^+$. Product pinacol ester is believed to hydrolyze to the boronic acid under LC/MS conditions.

Intermediate B-6

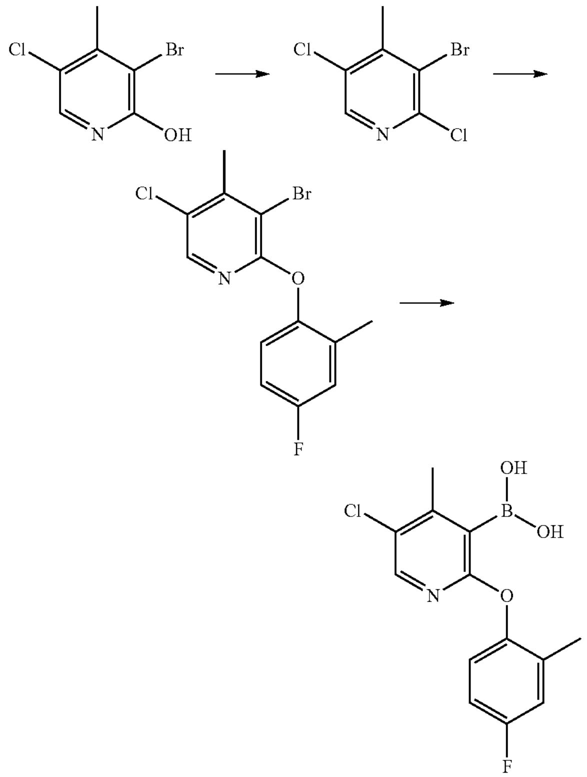

Step 1: 3-bromo-2,5-dichloro-4-methyl-pyridine

A mixture of 3-bromo-5-chloro-4-methyl-pyridin-2-ol (10 g, 45 mmol) and $POCl_3$ (65.8 g, 40 mL, 429 mmol) was heated at 90° C. for 24 h. The temperature was increased to 105° C. and the reaction was stirred for 18 h. It was then stirred at 120° C. for 3 h. It was cooled to room temperature and the $POCl_3$ was evaporated under reduced pressure. The residue was poured onto a stirring mixture of water (400 mL), ethyl acetate (200 mL) and sodium carbonate (80 g). After 30 min, the layers were separated. The aqueous layer was extracted with ethyl acetate (200 mL). The organic layers were combined and washed with water (100 mL) and brine (50 mL), dried over anhydrous sodium sulfate, filtered and evaporated under reduced pressure to give 3-bromo-2,5-dichloro-4-methyl-pyridine (9.38 g, 87%) as a brown oil. ESI-MS m/z calc. 238.89, found 240.0 $(M+1)^+$. $^1H$ NMR (400 MHz, $CDCl_3$) δ 8.26 (s, 1H), 2.59 (s, 3H).

Step 2: 3-bromo-5-chloro-2-(4-fluoro-2-methyl-phenoxy)-4-methyl-pyridine

3-Bromo-5-chloro-2-(4-fluoro-2-methyl-phenoxy)-4-methyl-pyridine was prepared from 3-bromo-2,5-dichloro-4-methyl-pyridine and 4-fluoro-2-methyl-phenol using a procedure analogous to that found in Intermediate B-1, step 1. ESI-MS m/z calc. 328.96, found 329.9 $(M+1)^+$. $^1H$ NMR (400 MHz, $CDCl_3$) δ 7.94 (s, 1H), 7.05-6.89 (m, 3H), 2.58 (s, 3H), 2.13 (s, 3H).

Step 3: [5-chloro-2-(4-fluoro-2-methyl-phenoxy)-4-methyl-3-pyridyl]boronic acid

5-Chloro-2-(4-fluoro-2-methyl-phenoxy)-4-methyl-3-pyridyl]boronic acid was prepared from 3-bromo-5-chloro-2-(4-fluoro-2-methyl-phenoxy)-4-methyl-pyridine using a procedure analogous to that found in Intermediate B-3, step 3. ESI-MS m/z calc. 295.06, found 296.2 $(M+1)^+$. $^1H$ NMR (400 MHz, $CDCl_3$) δ 8.04 (s, 1H), 7.05-6.86 (m, 3H), 5.69 (s, 2H), 2.67 (s, 3H), 2.13 (s, 3H).

Intermediate B-7

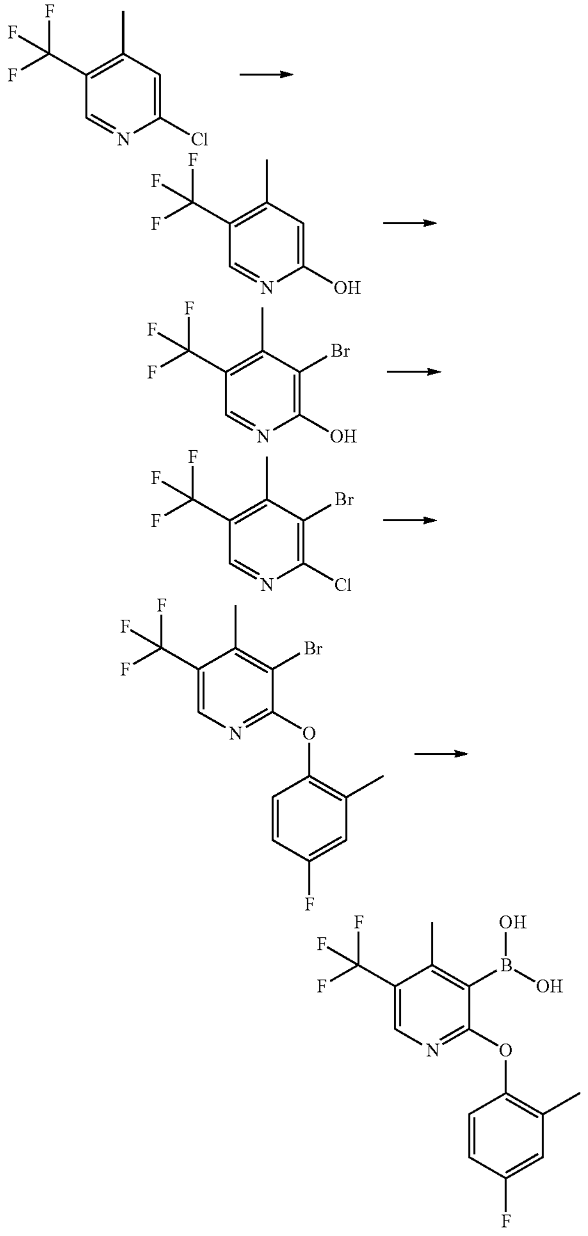

Step 1: 4-methyl-5-(trifluoromethyl)pyridin-2-ol

A mixture of 2-chloro-4-methyl-5-(trifluoromethyl)pyridine (5.0 g, 25.6 mmol), aqueous hydrochloric acid (20 mL of 37% w/v, 203 mmol), dioxane (40 mL) and water (20 mL) was stirred at 95° C. for 48 h, then stirred at 80° C. for an additional 24 h. The mixture was diluted with 2 M aqueous sodium hydroxide (100 mL) and saturated aqueous sodium bicarbonate (100 mL), then extracted with ethyl acetate (4×200 mL). The combined organic layers were washed with water (100 mL) and brine (100 mL), dried over sodium sulfate, filtered and evaporated under reduced pressure to give 4-methyl-5-(trifluoromethyl)pyridin-2-ol (4.82 g, 98%) as a white solid. ESI-MS m/z calc. 177.04, found 178.2 $(M+1)^+$. $^1H$ NMR (400 MHz, $CDCl_3$) δ 13.21 (br. s, 1H), 7.70 (s, 1H), 6.44 (s, 1H), 2.35 (s, 3H). $^{19}F$ NMR (377 MHz, $CDCl_3$) δ −61.29 (s, 3F).

Step 2: 3-bromo-4-methyl-5-(trifluoromethyl)pyridin-2-ol

To a solution of 4-methyl-5-(trifluoromethyl)pyridin-2-ol (4.8 g, 25 mmol) in acetic acid (65 mL) was added bromine (8.7 g, 2.8 mL, 54 mmol). The mixture was stirred at room temperature for 65 h, then poured onto a stirring mixture of sodium carbonate (90 g), water (400 mL) and sodium thiosulfate pentahydrate (17 g). The aqueous layer was extracted with ethyl acetate (3×250 mL). The combined organic extracts were washed with water (100 mL) and brine (100 mL), dried over sodium sulfate, filtered and evaporated under reduced pressure to provide a beige solid (6.05 g). The solid was triturated in 1:1 MTBE/heptane (30 mL) and filtered. The solid was washed with 1:1 MTBE/heptane (15 mL) and dried to provide 3-bromo-4-methyl-5-(trifluoromethyl)pyridin-2-ol (5.38 g, 84%) as a white solid. ESI-MS m/z calc. 254.95, found 256.0 $(M+1)^+$. $^1H$ NMR (400 MHz, $CDCl_3$) δ 13.23 (br. s, 1H), 7.83 (s, 1H), 2.53 (s, 3H). $^{19}F$ NMR (377 MHz, $CDCl_3$) δ −60.81 (s, 3F).

Step 3: 3-bromo-2-chloro-4-methyl-5-(trifluoromethyl)pyridine

A mixture of 3-bromo-4-methyl-5-(trifluoromethyl)pyridin-2-ol (4.09 g, 16.0 mmol) and $POCl_3$ (65.8 g, 40 mL, 429 mmol) was stirred at 80° C. for 23 h. The mixture was cooled and slowly poured into a stirring mixture of sodium carbonate (160 g), water (400 mL) and ethyl acetate (100 mL). Ice was added during the addition to control the exotherm. The mixture was stirred at room temperature for 30 min and the layers separated. The aqueous layer was extracted with additional ethyl acetate (3×100 mL). The combined extracts were washed with water (50 mL) and brine (50 mL), dried over sodium sulfate, filtered and evaporated under reduced pressure to provide 3-bromo-2-chloro-4-methyl-5-(trifluoromethyl)pyridine (3.87 g, 87%) as a light brown oil. ESI-MS m/z calc. 272.92, found 273.8 $(M+1)^+$. $^1H$ NMR (400 MHz, $CDCl_3$) δ 8.54 (s, 1H), 2.63 (s, 3H). 19F NMR (377 MHz, $CDCl_3$) δ −61.06 (s, 3F).

Step 4: 3-bromo-2-(4-fluoro-2-methyl-phenoxy)-4-methyl-5-(trifluoromethyl)pyridine A mixture of 3-bromo-2-chloro-4-methyl-5-(trifluoromethyl)pyridine (11.30 g, 41.17 mmol), 4-fluoro-2-methyl-phenol (5.710 g, 45.27 mmol) and cesium carbonate (26.83 g, 82.35 mmol) in DMSO (80 mL) was stirred at room temperature for 90 min. The mixture was partitioned between water and diethyl ether and the layers separated. The aqueous layer was extracted with additional diethyl ether and the combined organic layers washed with 1 N NaOH (2×) and brine, dried over MgSO4, filtered and concentrated. Purification by silica gel chromatography (220 g silica, 0-20% ethyl acetate/hexane) provided 3-bromo-2-(4-fluoro-2-methyl-phenoxy)-4-methyl-5-(trifluoromethyl)pyridine (14.22 g, 95%). ESI-MS m/z calc. 362.99, found 365.1 $(M+1)^+$. $^1H$ NMR (400 MHz, $CD_3OD$) δ 8.22 (s, 1H), 7.11-7.03 (m, 2H), 6.98 (td, J=8.5, 3.4 Hz, 1H), 2.63 (app d, J=1.4 Hz, 3H), 2.10 (s, 3H).

Step 5: [2-(4-fluoro-2-methyl-phenoxy)-4-methyl-5-(trifluoromethyl)-3-pyridyl]boronic acid A solution of n-BuLi (4.7 mL of 1.6 M in hexanes, 7.5 mmol) was added slowly to a stirring solution of 3-bromo-2-(4-fluoro-2-methyl-phenoxy)-4-methyl-5-(trifluoromethyl)pyridine (2.56 g, 6.82 mmol) in diethyl ether (30 mL) at −78° C. under argon. The mixture was stirred at −78° C. for 1 h. A solution of trimethylborate (1.2 g, 1.3 mL, 11.7 mmol) in diethyl ether (10 mL) was then added dropwise. The mixture was warmed to room temperature then quenched with saturated aqueous ammonium chloride (50 mL). The aqueous phase was extracted with additional diethyl ether (100 mL). The combined organic extracts were washed with brine (50 mL), dried over magnesium sulfate, filtered and concentrated. Trituration with hexane and filtration provided [2-(4-fluoro-2-methyl-phenoxy)-4-methyl-5-(trifluoromethyl)-3-pyridyl]boronic acid (1.91 g, 83%) as a pale cream solid. $^1H$ NMR (400 MHz, DMSO-$d_6$) δ 8.61 (m, 2H), 8.26 (s, 1H), 7.14-7.00 (m, 3H), 2.42 (s, 3H), 2.04 (s, 3H). $^{19}F$ NMR (376 MHz, DMSO-$d_6$) δ −59.3--58.9 (3F), −118.3--117.9 (1F). ESI-MS m/z calc. 329.09, found 329.99 $(M+1)^+$.

Intermediate B-8

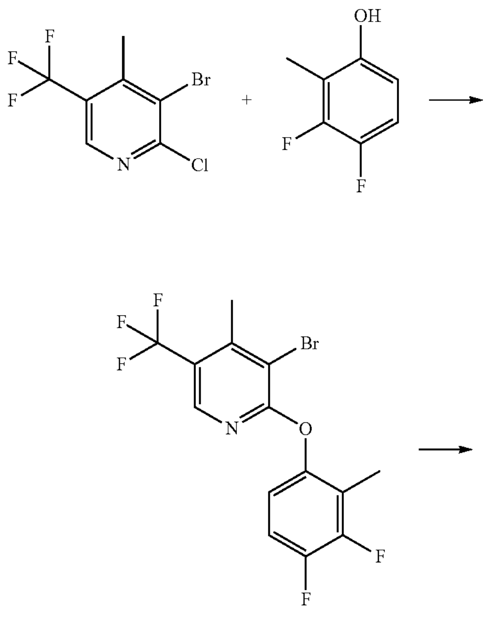

-continued

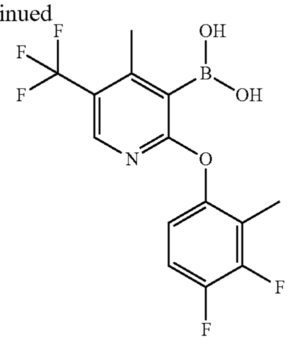

Step 1: 3-bromo-2-(3,4-difluoro-2-methyl-phenoxy)-4-methyl-5-(trifluoromethyl)pyridine A mixture of 3-bromo-2-chloro-4-methyl-5-(trifluoromethyl)pyridine (2.63 g, 9.58 mmol) and 3,4-difluoro-2-methyl-phenol (2.6 g, 18 mmol) was dissolved in DMSO (26 mL). To this solution was added cesium carbonate (7.73 g, 23.7 mmol) and the mixture stirred at 90° C. for 2.5 h. The mixture was allowed to cool to room temperature then diluted with ethyl acetate. The organic solution was washed with water and brine. dried over sodium sulfate, filtered and concentrated under reduced pressure. Purification using silica gel chromatography (120 g silica, 0-20% ethyl acetate/hexanes) provided 3-bromo-2-(3,4-difluoro-2-methyl-phenoxy)-4-methyl-5-(trifluoromethyl)pyridine (3.340 g, 91%) as light orange solid. ESI-MS m/z calc. 380.98, found 382.0 $(M+1)^+$. $^1H$ NMR (400 MHz, DMSO-$d_6$) δ 8.41 (s, 1H), 7.38 (q, J=9.4 Hz, 1H), 7.10 (ddd, J=9.2, 4.4, 2.1 Hz, 1H), 2.59 (d, J=1.4 Hz, 3H), 2.03 (d, J=2.2 Hz, 3H).

Step 2: [2-(3,4-difluoro-2-methyl-phenoxy)-4-methyl-5-(trifluoromethyl)-3-pyridyl]boronic acid To a stirring solution of 3-bromo-2-(3,4-difluoro-2-methyl-phenoxy)-4-methyl-5-(trifluoromethyl)pyridine (2.0 g, 5.2 mmol) in diethyl ether (20 mL) at −78° C. was slowly added a solution of n-BuLi (2.5 mL of 2.5 M in hexanes, 6.25 mmol) under nitrogen atmosphere. The mixture was stirred at this temperature for 20 min after which a solution of trimethyl borate (1 mL, 9 mmol) in diethyl ether (6 mL) was added dropwise. The resulting mixture was allowed to warm to room temperature and stirred for 90 min. The mixture was quenched with saturated aqueous ammonium chloride (150 mL) and extracted with ethyl acetate (3×100 mL). The combine extracts were washed with brine (100 mL), dried over sodium sulfate, filtered and concentrated under reduced pressure. The material was purified by reverse phase chromatography (C18, 5-95% acetonitrile/water containing 0.1% formic acid) and the product-containing fractions concentrated to remove the acetonitrile. The resulting aqueous solution was extracted with ethyl acetate (3×100 mL). The combined organic layers were dried over sodium sulfate, filtered and concentrated under reduced pressure to provide [2-(3,4-difluoro-2-methyl-phenoxy)-4-methyl-5-(trifluoromethyl)-3-pyridyl]boronic acid (1.64 g, 90%) as a white solid. $^1H$ NMR (400 MHz, $CDCl_3$) δ 8.32 (s, 1H), 7.06 (q, J=9.0 Hz, 1H), 6.85-6.80 (m, 1H), 5.45 (s, 2H), 2.71-2.67 (m, 3H), 2.10 (d, J=2.0 Hz, 3H). $^{19}F$ NMR (377 MHz, $CDCl_3$) δ −60.66 (s, 3F), −137.75-−137.88 (m, 1F), −140.42-−140.54 (m, 1F). ESI-MS m/z calc. 347.08, found 348.2 $(M+1)^+$.

Intermediate B-9

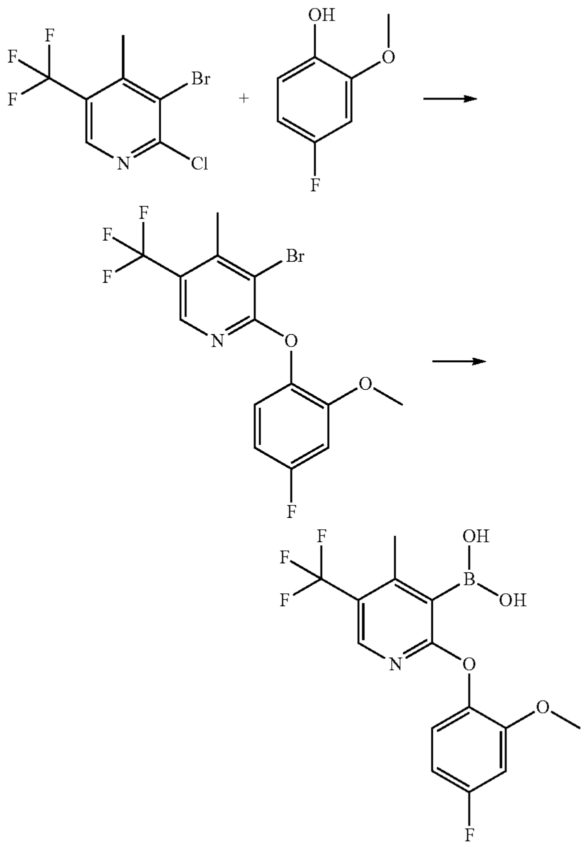

Step 1: 3-bromo-2-(4-fluoro-2-methoxy-phenoxy)-4-methyl-5-(trifluoromethyl)pyridine 3-Bromo-2-(4-fluoro-2-methoxy-phenoxy)-4-methyl-5-(trifluoromethyl)pyridine was prepared from 3-bromo-2-chloro-4-methyl-5-(trifluoromethyl)pyridine and 4-fluoro-2-methoxy-phenol using a procedure analogous to that found in Intermediate B-7, step 4. ESI-MS m/z calc. 378.98, found 380.15 $(M+1)^+$. $^1H$ NMR (400 MHz, $CD_3OD$) δ 8.18 (s, 1H), 7.12 (dd, J=8.8, 5.7 Hz, 1H), 6.92 (dd, J=10.4, 2.9 Hz, 1H), 6.72 (td, J=8.3, 2.9 Hz, 1H), 3.71 (s, 3H), 2.61 (d, J=1.2 Hz, 3H).

Step 2: [2-(4-fluoro-2-methoxy-phenoxy)-4-methyl-5-(trifluoromethyl)-3-pyridyl]boronic acid

[2-(4-Fluoro-2-methoxy-phenoxy)-4-methyl-5-(trifluoromethyl)-3-pyridyl]boronic acid was prepared from 3-bromo-2-(4-fluoro-2-methoxy-phenoxy)-4-methyl-5-(trifluoromethyl)pyridine using a procedure analogous to that found in Intermediate B-1, step 2 using diethyl ether as solvent. ESI-MS m/z calc. 345.08, found 346.1 $(M+1)^+$. H NMR (400 MHz, $CD_3OD$) δ 8.19 (s, 1H), 7.09 (dd, J=8.8, 5.7 Hz, 1H), 6.90 (dd, J=10.4, 2.9 Hz, 1H), 6.71 (td, J=8.4, 2.9 Hz, 1H), 3.70 (s, 3H), 2.44 (d, J=1.5 Hz, 3H).

Intermediate B-10

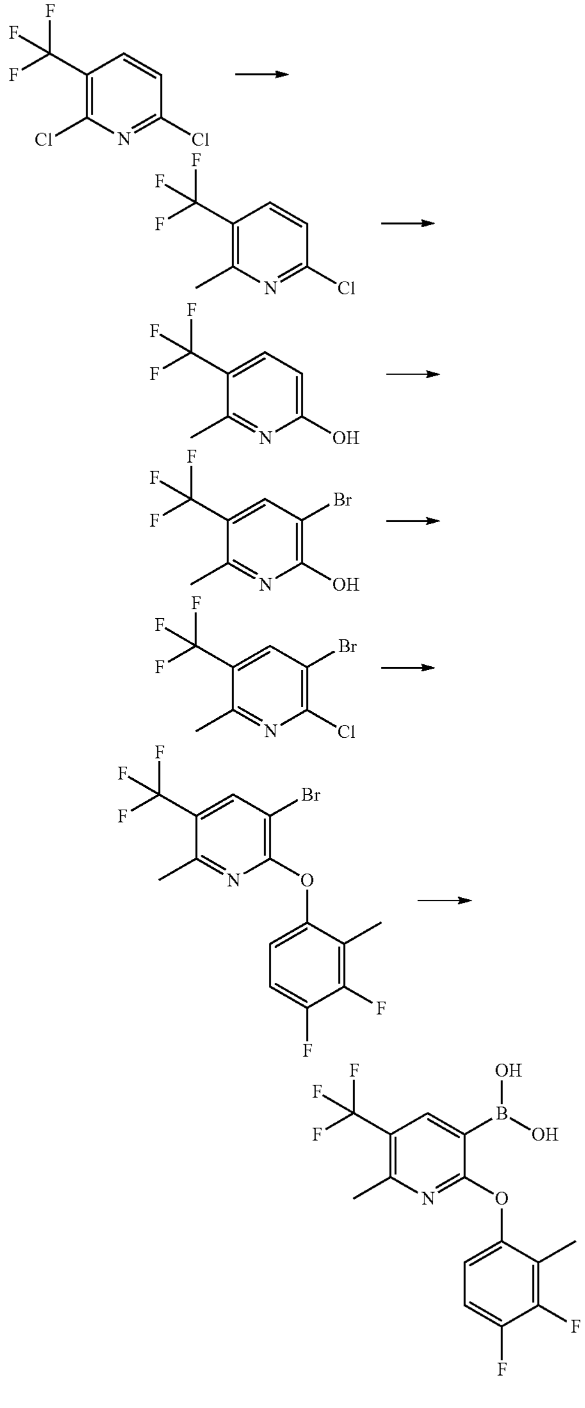

Step 1: 6-chloro-2-methyl-3-(trifluoromethyl)pyridine

A mixture of $Fe(acac)_3$ (140 mg, 0.394 mmol) and 2,6-dichloro-3-(trifluoromethyl)pyridine (2.0 g, 9.3 mmol) in a sealed flask was evacuated and place under nitrogen atmosphere. THF (40 mL) was added and the mixture cooled to 0° C. Methylmagnesium bromide (3.6 mL of 3 M in diethyl ether, 10.8 mmol) was added dropwise and the mixture stirred at 0° C. for 3 h. The mixture was quenched with water (50 mL) and extracted using ethyl acetate (3×80 mL). The organic layers were combined, dried over sodium sulfate and concentrated under reduced pressure to afford 6-chloro-2-methyl-3-(trifluoromethyl)pyridine (1.91 g, 95%) as a yellow oil. $^1$H NMR (400 MHz, $CDCl_3$) δ 7.90 (d, J=7.8 Hz, 1H), 7.22 (d, J=7.8 Hz, 1H), 2.63 (s, 3H).

Step 2: 6-methyl-5-(trifluoromethyl)pyridin-2-ol

6-Methyl-5-(trifluoromethyl)pyridin-2-ol was prepared from 6-chloro-2-methyl-3-(trifluoromethyl)pyridine using a procedure analogous to that found in Intermediate B-7, step 1. ESI-MS m/z calc. 177.04, found 178.0 $(M+1)^+$. $^1$H NMR (400 MHz, $CDCl_3$) δ 13.20 (s, 1H), 7.61 (d, J=9.6 Hz, 1H), 6.46 (d, J=9.5 Hz, 1H), 2.56-2.49 (m, 3H).

Step 3: 3-bromo-6-methyl-5-(trifluoromethyl)pyridin-2-ol

3-Bromo-6-methyl-5-(trifluoromethyl)pyridin-2-ol was prepared from 6-methyl-5-(trifluoromethyl)pyridin-2-ol using a procedure analogous to that found in Intermediate B-7, step 2. ESI-MS m/z calc. 254.95, found 255.79 $(M+1)^+$. $^1$H NMR (400 MHz, DMSO-$d_6$) δ 12.66 (s, 1H), 7.99 (s, 1H), 2.33-2.25 (m, 3H).

Step 4: 3-bromo-2-chloro-6-methyl-5-(trifluoromethyl)pyridine

3-Bromo-2-chloro-6-methyl-5-(trifluoromethyl)pyridine was prepared from 3-bromo-6-methyl-5-(trifluoromethyl)pyridin-2-ol and using a procedure analogous to that found in Intermediate B-6, step 1. $^1$H NMR (400 MHz, $CDCl_3$) δ 8.08 (s, 1H), 2.66-2.63 (m, 3H).

Step 5: 3-bromo-2-(3,4-difluoro-2-methyl-phenoxy)-6-methyl-5-(trifluoromethyl)pyridine 3-Bromo-2-(3,4-difluoro-2-methyl-phenoxy)-6-methyl-5-(trifluoromethyl)pyridine was prepared from 3-bromo-2-chloro-6-methyl-5-(trifluoromethyl)pyridine and 3,4-difluoro-2-methyl-phenol using a procedure analogous to that found in Intermediate B-1, step 1. ESI-MS m/z calc. 380.98, found 381.96 $(M+1)^+$. $^1$H NMR (400 MHz, $CDCl_3$) δ 8.08 (s, 1H), 7.02 (q, J=9.0 Hz, 1H), 6.83 (m, 1H), 2.40 (q, J=1.7 Hz, 3H), 2.09 (d, J=2.3 Hz, 3H).

Step 6: [2-(3,4-difluoro-2-methyl-phenoxy)-6-methyl-5-(trifluoromethyl)-3-pyridyl]boronic acid

[2-(3,4-Difluoro-2-methyl-phenoxy)-6-methyl-5-(trifluoromethyl)-3-pyridyl]boronic acid was prepared from 3-bromo-2-(3,4-difluoro-2-methyl-phenoxy)-6-methyl-5-(trifluoromethyl)pyridine using a procedure analogous to that found in Intermediate B-3, step 3 using trimethylborate. $^1$H NMR (400 MHz, $CD_3OD$) δ 8.04 (s, 1H), 7.10 (q, J=9.3 Hz, 1H), 6.87-6.84 (m, 1H), 2.39 (d, J=1.8 Hz, 3H), 2.06 (d, J=1.8 Hz, 3H).

Intermediate B-11

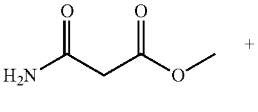

-continued

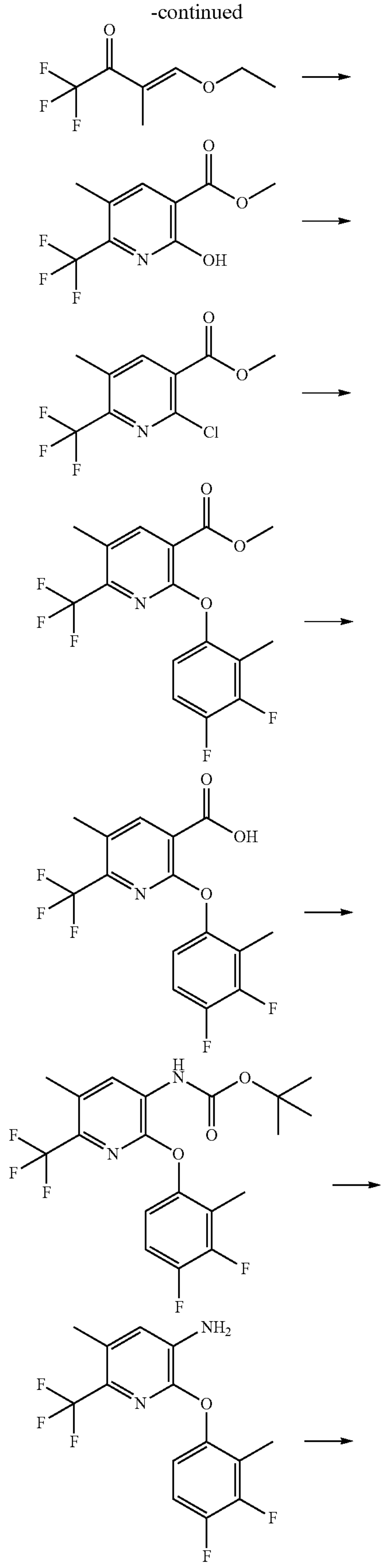

-continued

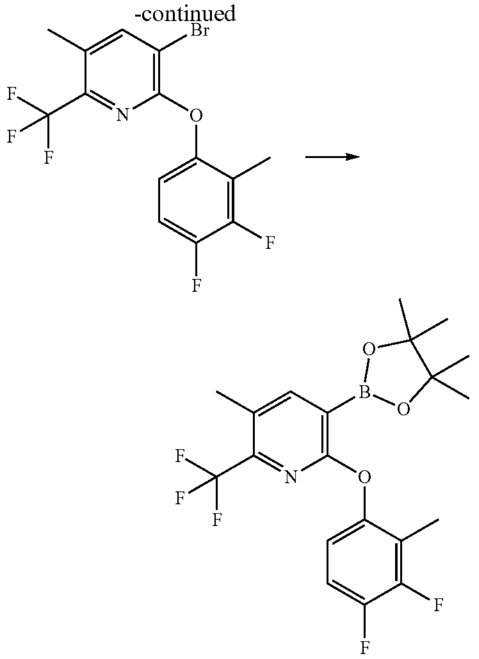

Step 1: Methyl 2-hydroxy-5-methyl-6-(trifluoromethyl)pyridine-3-carboxylat

To a solution of methyl 3-amino-3-oxo-propanoate (9.6 g, 82 mmol) and 4-ethoxy-1,1,1-trifluoro-3-methyl-but-3-en-2-one (15 g, 82 mmol) in methanol (120 mL) was added sodium methoxide in methanol (23 mL of 25% w/v, 106 mmol). The reaction mixture was heated at reflux for 1 h then allowed to cool to room temperature. The precipitate was removed by filtration and washed with methanol (2×250 mL). The resultant solid was suspended in ethyl acetate (500 mL) and 2 M hydrochloric acid (500 mL). The solid filtered off and the filtrate separated. The aqueous phase was re-extracted with ethyl acetate (500 mL). The combined organic extracts were washed with brine (500 mL), dried over magnesium sulfate and concentrated to give methyl 2-hydroxy-5-methyl-6-(trifluoromethyl)pyridine-3-carboxylate (11.4 g, 56%) as an off-white solid. ESI-MS m/z calc. 235.04, found 233.97 $(M-1)^-$. $^1H$ NMR (400 MHz, $CDCl_3$) δ 8.17 (s, 1H), 4.03 (s, 3H), 2.45 (m, 3H).

Step 2: Methyl 2-chloro-5-methyl-6-(trifluoromethyl)pyridine-3-carboxylate

A solution of methyl 2-hydroxy-5-methyl-6-(trifluoromethyl)pyridine-3-carboxylate (10 g, 40.5 mmol) in neat phenyl dichlorophosphate (56.5 g, 40 mL, 268 mmol) was heated to 155° C. for 6 h. The reaction mixture was cooled to room temperature then quenched into a vigorously stirred mixture of ethyl acetate (1000 mL), water (250 mL) and sodium carbonate (60 g) at a rate to keep the temperature below 45° C. The mixture was then stirred vigorously for 2 h. The layers were separated. The aqueous layer was extracted with ethyl acetate (200 mL). The combined organic layers were washed with water (500 mL), brine (500 mL), dried over magnesium sulfate and concentrated. Purification by silica gel chromatography (0-20% ethyl acetate/heptane) provided methyl 2-chloro-5-methyl-6-(trifluoromethyl)pyridine-3-carboxylate (6.15 g, 56%) as a white solid.

ESI-MS m/z calc. 253.01, found 253.96 $(M+1)^+$. $^1H$ NMR (400 MHz, $CDCl_3$) δ 8.11 (s, 1H), 3.99 (s, 3H), 2.53 (q, J=1.7 Hz, 3H).

Step 3: Methyl 2-(3,4-difluoro-2-methyl-phenoxy)-5-methyl-6-(trifluoromethyl)pyridine-3-carboxylate methyl 2-(3,4-difluoro-2-methyl-phenoxy)-5-methyl-6-(trifluoromethyl)pyridine-3-carboxylate was prepared from methyl 2-chloro-5-methyl-6-(trifluoromethyl)pyridine-3-carboxylate and 3,4-difluoro-2-methylphenol using a procedure analogous to that found in Intermediate B-1, step 1. ESI-MS m/z calc. 361.07, found 362.06 $(M+1)^+$. $^1H$ NMR (400 MHz, $CDCl_3$) δ 8.19 (s, 1H), 6.99 (q, J=9.2 Hz, 1H), 6.84 (m, 1H), 3.97 (s, 3H), 2.45 (q, J=1.8 Hz, 3H), 2.11 (d, J=2.3 Hz, 3H).

Step 4: 2-(3,4-difluoro-2-methyl-phenoxy)-5-methyl-6-(trifluoromethyl)pyridine-3-carboxylic acid To a mixture of methyl 2-(3,4-difluoro-2-methyl-phenoxy)-5-methyl-6-(trifluoromethyl)pyridine-3-carboxylate (30 g, 78.5 mmol) in methanol (60 mL), THF (120 mL), and water (60 mL) was added lithium hydroxide monohydrate (6.5 g, 155 mmol). The mixture was stirred at room temperature for 2 h and then the volatiles were removed under reduced pressure. The residue was acidified (~pH 6) using 2 M HCl. The resulting solid was collected by filtration and dried to provide 2-(3,4-difluoro-2-methyl-phenoxy)-5-methyl-6-(trifluoromethyl)pyridine-3-carboxylic acid (27 g, 97%). ESI-MS m/z calc. 347.06, found 346.0 $(M-1)^-$. $^1H$ NMR (400 MHz, $CDCl_3$) δ 8.39 (s, 1H), 7.07-6.99 (m, 1H), 6.86 (m, 1H), 2.48-2.44 (m, 3H), 2.15-2.08 (m, 3H).

Step 5: tert-butyl N-[2-(3,4-difluoro-2-methyl-phenoxy)-5-methyl-6-(trifluoromethyl)-3-pyridyl]carbamate To a solution of 2-(3,4-difluoro-2-methyl-phenoxy)-5-methyl-6-(trifluoromethyl)pyridine-3-carboxylic acid (27 g, 76 mmol) in toluene (240 mL) was added triethylamine (16 mL, 115 mmol) and DPPA (25.5 g, 20 mL, 93 mmol). The mixture was stirred at room temperature for 30 min and t-BuOH (45 mL) was added. The mixture was then heated at 110° C. for 2 h, cooled to room temperature and partitioned between ethyl acetate (400 mL) and water (200 mL). The aqueous layer was extracted with additional ethyl acetate (2×200 mL). The combined organics were washed with brine (200 mL), dried over sodium sulfate, filtered and concentrated under reduced pressure. Purification using silica gel chromatography (heptanes, followed by 10% ethyl acetate/heptanes) provided tert-butyl N-[2-(3,4-difluoro-2-methyl-phenoxy)-5-methyl-6-(trifluoromethyl)-3-pyridyl] carbamate (24 g, 74%). ESI-MS m/z calc. 418.13, found 417.05 $(M-1)^-$. $^1H$ NMR (400 MHz, $CDCl_3$) δ 8.43 (s, 1H), 7.18 (s, 1H), 7.00 (q, J=9.0 Hz, 1H), 6.81 (m, 1H), 2.40 (q, J=2.0 Hz, 3H), 2.09 (d, J=2.3 Hz, 3H), 1.56 (t, J=5.0 Hz, 9H).

Step 6: 2-(3,4-difluoro-2-methyl-phenoxy)-5-methyl-6-(trifluoromethyl)pyridin-3-amine A solution of tert-butyl N-[2-(3,4-difluoro-2-methyl-phenoxy)-5-methyl-6-(trifluoromethyl)-3-pyridyl]carbamate (24 g, 56 mmol) in HCl in dioxane (150 mL of 4 M, 600 mmol) was stirred at room temperature overnight. The mixture was concentrated in vacuo to provide 2-(3,4-difluoro-2-methyl-phenoxy)-5-methyl-6-(trifluoromethyl)pyridin-3-amine (21.5 g, 97%). ESI-MS m/z calc. 318.08, found 318.93 $(M+1)^+$. $^1H$ NMR (400 MHz, $CDCl_3$) δ 6.98 (q, J=9.2 Hz, 1H), 6.88 (s, 1H), 6.84 (m, 1H), 2.33 (q, J=2.0 Hz, 3H), 2.11 (d, J=2.3 Hz, 3H).

Step 7: 3-bromo-2-(3,4-difluoro-2-methyl-phenoxy)-5-methyl-6-(trifluoromethyl)pyridine tert-Butyl nitrite (208 mg, 0.24 mL, 2.02 mmol) was added dropwise to a stirring mixture of 2-(3,4-difluoro-2-methyl-phenoxy)-5-methyl-6-(trifluoromethyl)pyridin-3-amine (300 mg, 0.823 mmol) and copper (II) bromide (420 mg, 1.88 mmol) in anhydrous $CH_3CN$ (6 mL) under argon at 0° C. After stirring at 0° C. for 30 min, the mixture was allowed to warm to room temperature and stirred for 1 h. The mixture was diluted with water (20 mL) and extracted with ethyl acetate (3×30 mL). The combined organics were washed with brine, dried over anhydrous sodium sulfate and concentrated under reduced pressure. The crude was purified by flash chromatography on silica gel (0-10% ethyl acetate in heptanes) yielded 3-bromo-2-(3,4-difluoro-2-methyl-phenoxy)-5-methyl-6-(trifluoromethyl)pyridine (270 mg, 83%). $^1H$ NMR (400 MHz, $CDCl_3$) δ 7.92 (s, 1H), 7.07-6.98 (m, 1H), 6.91 (qd, J=4.4, 2.0 Hz, 1H), 2.44 (q, J=1.9 Hz, 3H), 2.15 (d, J=2.4 Hz, 3H).

Step 8: 2-(3,4-difluoro-2-methyl-phenoxy)-5-methyl-3-(4,4,5,5-tetramethyl-1,3,2-dioxaborolan-2-yl)-6-(trifluoromethyl)pyridine 2-(3,4-difluoro-2-methyl-phenoxy)-5-methyl-3-(4,4,5,5-tetramethyl-1,3,2-dioxaborolan-2-yl)-6-(trifluoromethyl) pyridine was prepared from 3-bromo-2-(3,4-difluoro-2-methyl-phenoxy)-5-methyl-6-(trifluoromethyl)pyridine using a procedure analogous to that found in Intermediate B-1, step 2 using 2-isopropoxy-4,4,5,5-tetramethyl-1,3,2-dioxaborolane. ESI-MS m/z calc. 429.15, found 346.0 (M-pinacol)-. $^1H$ NMR (400 MHz, $CDCl_3$) δ 8.01 (s, 1H), 6.94 (t, J=8.9 Hz, 1H), 6.87 (qd, J=4.4, 1.8 Hz, 1H), 2.40 (q, J=2.0 Hz, 3H), 2.16 (d, J=2.3 Hz, 3H), 1.34 (s, 12H).

Intermediate B-12

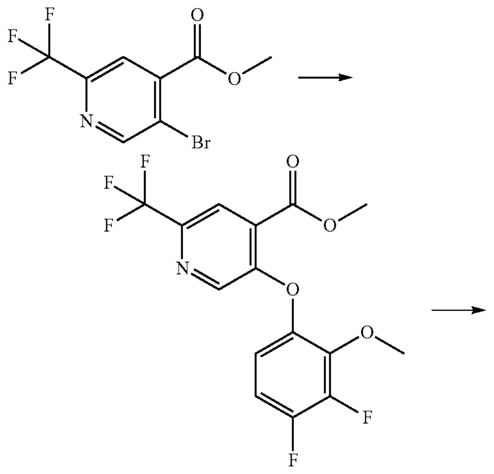

-continued

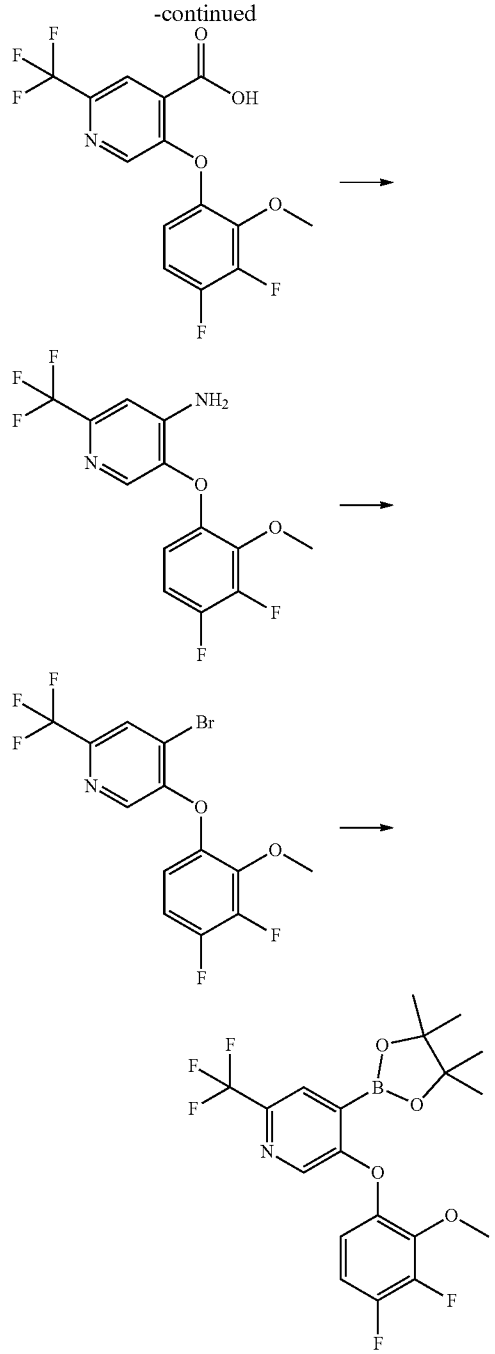

Step 1: methyl 5-(3,4-difluoro-2-methoxy-phenoxy)-2-(trifluoromethyl)pyridine-4-carboxylate Methyl 5-(3,4-difluoro-2-methoxy-phenoxy)-2-(trifluoromethyl)pyridine-4-carboxylate was prepared from methyl 5-bromo-2-(trifluoromethyl)pyridine-4-carboxylate and 3,4-difluoro-2-methoxy-phenol using a procedure analogous to that found in Intermediate B-4, step 4 but without N,N-dimethylglycine. ESI-MS m/z calc. 363.05, found 364.0 $(M+1)^+$. $^1$H NMR (500 MHz, $CDCl_3$) δ 8.24 (s, 1H), 8.12 (s, 1H), 6.95 (td, J=9.3, 7.9 Hz, 1H), 6.88 (ddd, J=9.3, 4.9, 2.2 Hz, 1H), 3.99 (s, 3H), 3.95 (d, J=1.8 Hz, 3H).

Step 2: 5-(3,4-difluoro-2-methoxy-phenoxy)-2-(trifluoromethyl)pyridine-4-carboxylic acid 5-(3,4-Difluoro-2-methoxy-phenoxy)-2-(trifluoromethyl) pyridine-4-carboxylic acid was prepared from methyl 5-(3,4-difluoro-2-methoxy-phenoxy)-2-(trifluoromethyl)pyridine-4-carboxylate using a procedure analogous to that found in Intermediate B-11, step 4. ESI-MS m/z calc. 349.04, found 350.0 $(M+1)^+$. $^1$H NMR (500 MHz, DMSO-$d_6$) δ 14.07 (s, 1H), 8.43 (s, 1H), 8.17 (s, 1H), 7.25 (td, J=9.7, 8.4 Hz, 1H), 7.12-7.08 (m, 1H), 3.88 (d, J=1.2 Hz, 3H).

Step 3: 5-(3,4-difluoro-2-methoxy-phenoxy)-2-(trifluoromethyl)pyridin-4-amine 5-(3,4-Difluoro-2-methoxy-phenoxy)-2-(trifluoromethyl) pyridin-4-amine was prepared from 5-(3,4-difluoro-2-methoxy-phenoxy)-2-(trifluoromethyl)pyridine-4-carboxylic acid using a procedure analogous to that found in Intermediate B-11, step 5 through step 7. ESI-MS m/z calc. 320.06, found 321.1 $(M+1)^+$; 319.0 $(M-1)^-$. $^1$H NMR (400 MHz, $CDCl_3$) δ 7.91 (s, 1H), 7.06 (s, 1H), 6.90 (td, J=9.3, 8.0 Hz, 1H), 6.80 (ddd, J=9.3, 4.9, 2.3 Hz, 1H), 4.72 (s, 2H), 3.97 (d, J=1.8 Hz, 3H).

Step 4: 4-bromo-5-(3,4-difluoro-2-methoxy-phenoxy)-2-(trifluoromethyl)pyridine

4-Bromo-5-(3,4-difluoro-2-methoxy-phenoxy)-2-(trifluoromethyl)pyridine was prepared from 5-(3,4-difluoro-2-methoxy-phenoxy)-2-(trifluoromethyl)pyridin-4-amine using a procedure analogous to that found in Intermediate B-4, step 6. ESI-MS m/z calc. 382.96, found 384.2 $(M+1)^+$. $^1$H NMR (400 MHz, $CDCl_3$) δ 8.02 (s, 1H), 7.97 (s, 1H), 7.02-6.84 (m, 2H), 3.97 (d, J=1.9 Hz, 3H).

Step 5: 5-(3,4-difluoro-2-methoxy-phenoxy)-4-(4,4,5,5-tetramethyl-1,3,2-dioxaborolan-2-yl)-2-(trifluoromethyl)pyridine 5-(3,4-Difluoro-2-methoxy-phenoxy)-4-(4,4,5,5-tetramethyl-1,3,2-dioxaborolan-2-yl)-2-(trifluoromethyl)pyridine was prepared using a procedure analogous to that found in Intermediate B-2, step 4 using $PdCl_2(PhP_3)_2$ catalyst. ESI-MS m/z calc. 431.13, found 350.1 (M-pinacol)+.

Intermediate B-13

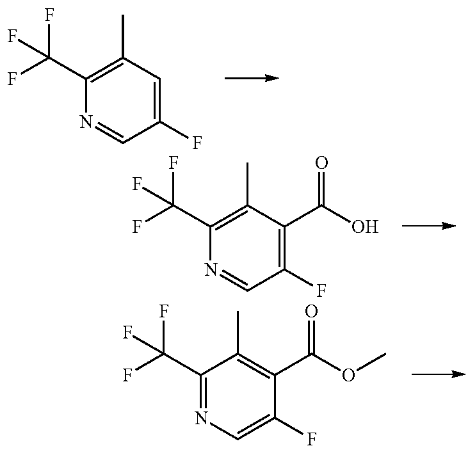

-continued

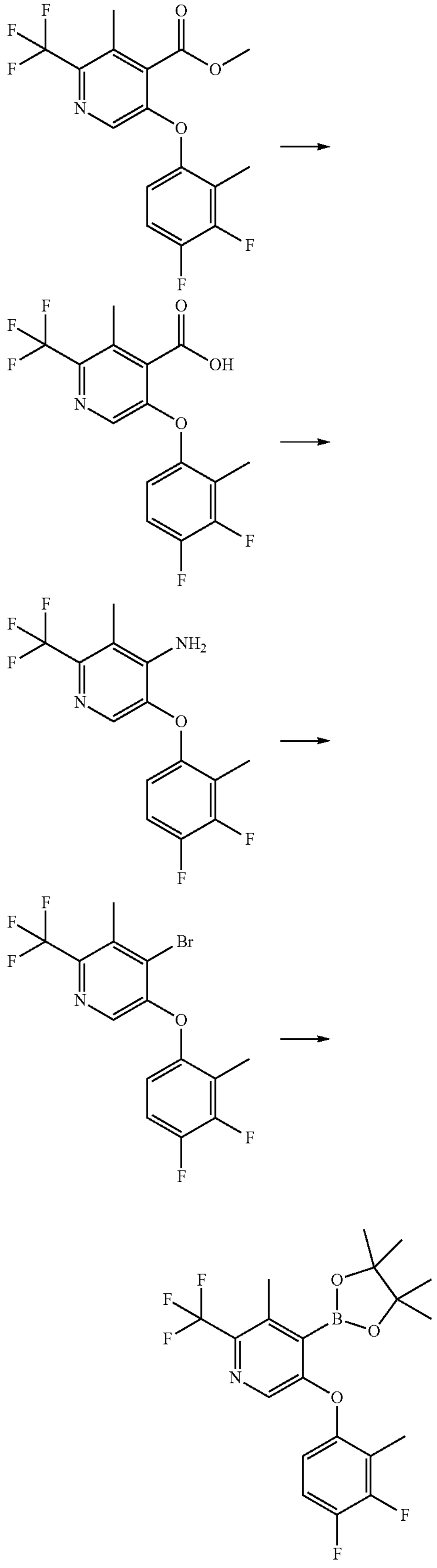

Step 1: 5-fluoro-3-methyl-2-(trifluoromethyl)pyridine-4-carboxylic acid

A solution of n-BuLi (62 mL of 2.5 M in hexanes, 155 mmol) was added dropwise to a solution of diisopropylamine (16.3 g, 22.5 mL, 161 mmol) in THF (190 mL) at −30° C. and the reaction mixture was slowly warmed up to 0° C. over 30 min. The reaction mixture was cooled down to −78° C. and a solution of 5-fluoro-3-methyl-2-(trifluoromethyl) pyridine (23.87 g, 122.6 mmol) in THF (50 mL) was added dropwise over 25 min. After 1 h, solid carbon dioxide (55 g, 1.2497 mol) was added in one portion (exotherm=−74 to −60° C.). After 10 min, the reaction mixture was slowly warmed up to room temperature. After 1.5 h, heptanes (75 mL), tert-butyl methyl ether (100 mL), a 1.5 M aqueous solution of sodium hydroxide (200 mL, 8.4 vol), and water (100 mL, 4.2 vol) were added and the biphasic mixture was filtered through Celite®. The organic layer was separated and extracted with water (150 mL). The aqueous layers were combined, washed with tert-butyl methyl ether (150 mL), acidified with a 3.0 M aqueous solution of hydrochloric acid (200 mL, 8.4 vol), and extracted with tert-butyl methyl ether (2×200 mL, 16.7 vol). The combined organic extracts were washed with a 15% aqueous solution of sodium chloride (100 mL), dried over anhydrous sodium sulfate, filtered, and concentrated under vacuum to a total weight of 42.6 g. This mixture was slowly cooled to 0° C. over 30 min then diluted with heptanes (50 mL) and the mixture was stirred at 0° C. for 15 min. The solids were filtered, rinsed with heptanes (50 mL) and dried under vacuum to provide 5-fluoro-3-methyl-2-(trifluoromethyl)pyridine-4-carboxylic acid (15.59 g). The mother liquor was concentrated to dryness under vacuum (9.04 g), then brought up in tert-Butyl methyl ether (9 mL) and the mixture heated at 55° C. After 10 min, heptanes (20 mL, 2.2 vol) was added over 25 min and the mixture was slowly cooled down to room temperature overnight. The resulting solid was filtered, rinsed with heptanes (25 mL), and dried under vacuum to provide a second crop of 5-fluoro-3-methyl-2-(trifluoromethyl)pyridine-4-carboxylic acid (3.97 g). Both crops were combined to provide 5-fluoro-3-methyl-2-(trifluoromethyl)pyridine-4-carboxylic acid (19.56 g, 70%). ESI-MS m/z calc. 223.03, found 222.1 $(M-1)^-$. $^1H$ NMR (400 MHz, DMSO-$d_6$) δ 14.74 (br s, 1H), 8.73 (s, 1H), 2.47-2.43 (m, 3H). $^{19}F$ NMR (377 MHz, DMSO-$d_6$) δ −62.99 (s, 1F), −125.50 (s, 1F).

Step 2: Bethyl 5-fluoro-3-methyl-2-(trifluoromethyl)pyridine-4-carboxylate

To a stirring mixture of 5-fluoro-3-methyl-2-(trifluoromethyl)pyridine-4-carboxylic acid (5.0 g, 22 mmol) in methanol (50.0 mL) was added $H_2SO_4$ (16 mL, 300 mmol) dropwise at room temperature. The reaction mixture was stirred at 80° C. for 48 h. After cooling to room temperature, the mixture was cooled to 0° C. and 2 M aqueous sodium hydroxide was added to adjust the solution to pH=9. The solution was diluted with ethyl acetate (50 mL) and the layers were separated. The aqueous layer was extracted with ethyl acetate (3×50 mL). The combined organic extracts were dried over magnesium sulfate, filtered and concentrated in vacuo to provide methyl 5-fluoro-3-methyl-2-(trifluoromethyl)pyridine-4-carboxylate (4.23 g, 80%). ESI-MS m/z calc. 237.04, found 238.0 $(M+1)^+$. $^1H$ NMR (500 MHz, $CDCl_3$) δ 8.45 (s, 1H), 4.01 (s, 3H), 2.50-2.48 (m, 3H).

Step 3: Methyl 5-(3,4-difluoro-2-methyl-phenoxy)-3-methyl-2-(trifluoromethyl)pyridine-4-carboxylate Methyl 5-(3,4-difluoro-2-methyl-phenoxy)-3-methyl-2-(trifluoromethyl)pyridine-4-carboxylate was prepared from methyl 5-fluoro-3-methyl-2-(trifluoromethyl)pyridine-4-carboxylate and 3,4-difluoro-2-methyl-phenol using a procedure analogous to that found in Intermediate B-1, step 1, using DMF as the solvent. ESI-MS m/z calc. 361.07, found 362.2 $(M+1)^+$. $^1H$ NMR (400 MHz, DMSO-$d_6$) δ 8.13 (s, 1H), 7.37 (q, J=9.4 Hz, 1H), 7.03 (ddd, J=9.2, 4.2, 2.0 Hz, 1H), 3.93 (s, 3H), 2.44-2.38 (m, 3H), 2.13 (d, J=2.2 Hz, 3H).

Step 4: 5-(3,4-difluoro-2-methyl-phenoxy)-3-methyl-2-(trifluoromethyl)pyridine-4-carboxylic acid A solution of methyl 5-(3,4-difluoro-2-methyl-phenoxy)-3-methyl-2-(trifluoromethyl)pyridine-4-carboxylate (407 mg, 1.13 mmol) in ethanol (3 mL) was treated with NaOH (3 mL of 2 M, 6 mmol) and stirred at 70° C. for 45 min. The reaction was cooled to room temperature and partitioned between 1 M HCl (10 mL) and ethyl acetate (20 mL). The organic layer was separated and washed with water, brine, dried with anhydrous sodium sulfate, filtered, and concentrated in vacuo to provide 5-(3,4-difluoro-2-methyl-phenoxy)-3-methyl-2-(trifluoromethyl)pyridine-4-carboxylic acid (400 mg, quantitative yield). $^1H$ NMR (400 MHz, DMSO-$d_6$) δ 8.09 (s, 1H), 7.36 (q, J=9.4 Hz, 1H), 6.99 (ddd, J=9.3, 4.2, 2.0 Hz, 1H), 2.46-2.41 (m, 3H), 2.15 (d, J=2.1 Hz, 3H).

Step 5: 5-(3,4-difluoro-2-methyl-phenoxy)-3-methyl-2-(trifluoromethyl)pyridin-4-amine A solution of DPPA (429 mg, 1.56 mmol) in 1,4-dioxane (1 mL) was added dropwise to a stirred mixture of 5-(3,4-difluoro-2-methyl-phenoxy)-3-methyl-2-(trifluoromethyl)pyridine-4-carboxylic acid (391 mg, 1.13 mmol) and DIPEA (300 μL, 1.72 mmol) in 1,4-dioxane (6 mL) and tert-butanol (2 mL). The reaction mixture was stirred at 70° C. for 21 h. After cooling to room temperature, the reaction mixture was partitioned between water (10 mL) and ethyl acetate (10 mL). The phases were separated and the aqueous phase was extracted with ethyl acetate (2×10 mL). The combined organic extracts were dried (sodium sulfate), filtered and concentrated under reduced pressure. The residue was dissolved in dichloromethane (5 mL) and trifluoroacetic acid (6 mL, 78 mmol) was added in one portion at room temperature and stirred overnight. The solvent was removed under reduced pressure and the residue was neutralized using 2 M sodium hydroxide. The aqueous layer was extracted with dichloromethane (3×) and the combined organic layers were dried over sodium sulfate, filtered and concentrated under reduced pressure. Purification by silica gel chromatography (0-20% ethyl acetate/heptane) provided 5-(3,4-difluoro-2-methyl-phenoxy)-3-methyl-2-(trifluoromethyl)pyridin-4-amine (327 mg, 91%). ESI-MS m/z calc. 318.08, found 319.2 $(M+1)^+$.

Step 6: 4-bromo-5-(3,4-difluoro-2-methyl-phenoxy)-3-methyl-2-(trifluoromethyl)pyridine 4-Bromo-5-(3,4-difluoro-2-methyl-phenoxy)-3-methyl-2-(trifluoromethyl)pyridine was prepared from 5-(3,4-difluoro-2-methyl-phenoxy)-3-methyl-2-(trifluoromethyl)pyridin-4-amine using a procedure analogous to that found in Intermediate B-11, step 7. ESI-MS m/z calc. 380.98, found 382.0 $(M+1)^+$. $^1H$ NMR (400 MHz, DMSO-$d_6$) δ 8.05 (s, 1H), 7.35 (q, J=9.4 Hz, 1H), 6.94 (ddd, J=9.2, 4.1, 2.0 Hz, 1H), 2.57 (d, J=1.8 Hz, 3H), 2.19 (d, J=2.2 Hz, 3H).

Step 7: 5-(3,4-difluoro-2-methyl-phenoxy)-3-methyl-4-(4,4,5,5-tetramethyl-1,3,2-dioxaborolan-2-yl)-2-(trifluoromethyl)pyridine To a solution of 4-bromo-5-(3,4-difluoro-2-methyl-phenoxy)-3-methyl-2-(trifluoromethyl)pyridine (125 mg, 0.3271 mmol) in 2-MeTHF (2 mL) under nitrogen was added isopropylmagnesium chloride lithium chloride complex (400 μL of 1.3 M in THF, 0.52 mmol) at 0° C. After 20 min at room temperature, the reaction mixture was cooled down to 0° C. and treated with a solution of 2-isopropoxy-4,4,5,5-tetramethyl-1,3,2-dioxaborolane (119 mg, 0.640 mmol) in 2-MeTHF (1.5 mL) under nitrogen at 0° C. After 2 h at room temperature, a saturated aqueous solution of ammonium chloride (10 mL) was added and the aqueous phase was separated and extracted with ethyl acetate (15 mL). The combined organic phases were dried over sodium sulfate, filtered and concentrated in vacuo. Purification by silica gel chromatography (0-50% ethyl acetate/hexanes) provided 5-(3,4-difluoro-2-methyl-phenoxy)-3-methyl-4-(4,4,5,5-tetramethyl-1,3,2-dioxaborolan-2-yl)-2-(trifluoromethyl)pyridine (29.9 mg, 21%). ESI-MS m/z calc. 429.15, found 430.1 $(M+1)^+$. $^1H$ NMR (400 MHz, DMSO-$d_6$) δ 8.03 (s, 1H), 7.30 (q, J=9.5 Hz, 1H), 6.85-6.77 (m, 1H), 2.48 (d, J=2.1 Hz, 3H), 2.18 (d, J=2.1 Hz, 3H), 1.27 (s, 12H).

Intermediate B-14

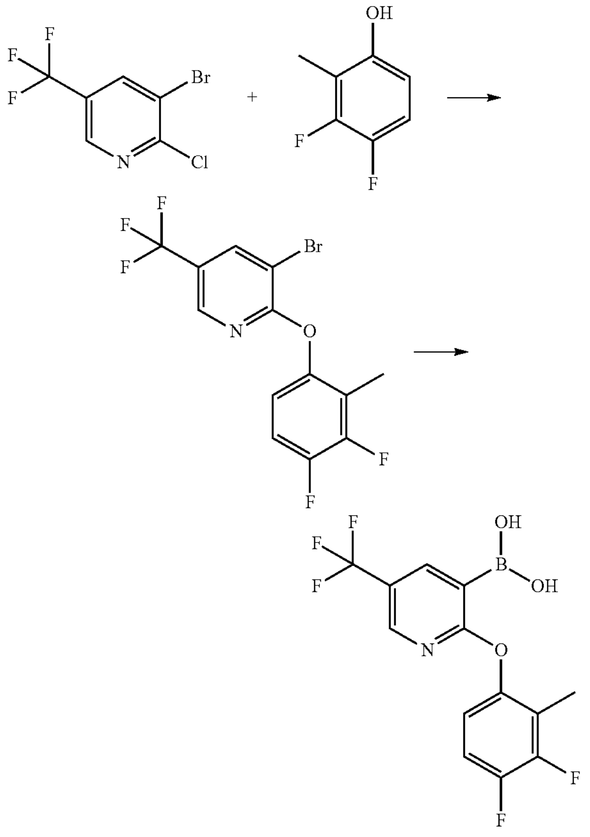

Step 1: 3-bromo-2-(3,4-difluoro-2-methyl-phenoxy)-5-(trifluoromethyl)pyridine

3-Bromo-2-(3,4-difluoro-2-methyl-phenoxy)-5-(trifluoromethyl)pyridine was prepared from 3-bromo-2-chloro-5-(trifluoromethyl)pyridine and 3,4-difluoro-2-methyl-phenol using a procedure analogous to that found in Intermediate B-1, step 1. ESI-MS m/z calc. 366.96, found 368.0 $(M+1)^+$. $^1H$ NMR (400 MHz, DMSO-$d_6$) δ 8.74-8.67 (m, 1H), 8.57-8.44 (m, 1H), 7.39 (q, J=9.4 Hz, 1H), 7.19-7.05 (m, 1H), 2.04 (d, J=2.1 Hz, 3H).

Step 2: [2-(3,4-difluoro-2-methyl-phenoxy)-5-(trifluoromethyl)-3-pyridyl]boronic acid

[2-(3,4-Difluoro-2-methyl-phenoxy)-5-(trifluoromethyl)-3-pyridyl]boronic acid was prepared from 3-bromo-2-(3,4-difluoro-2-methyl-phenoxy)-5-(trifluoromethyl)pyridine using a procedure analogous to that found in Intermediate B-3, step 3. ESI-MS m/z calc. 333.06, found 334.0 $(M+1)^+$. $^1H$ NMR (400 MHz, DMSO-$d_6$) δ 8.54 (s, 2H), 8.51-8.45 (m, 1H), 8.28-8.23 (m, 1H), 7.33 (q, J=9.4 Hz, 1H), 7.09-7.01 (m, 1H), 2.10-2.01 (m, 3H).

Intermediate B-15

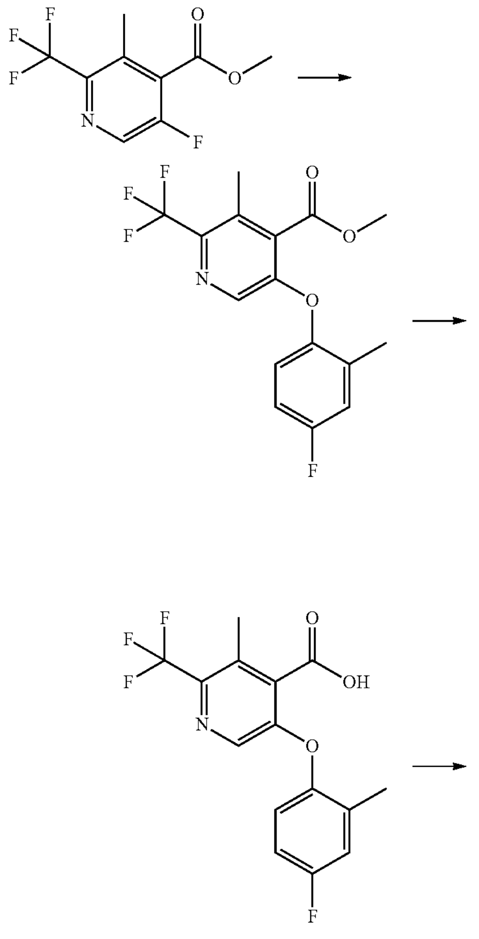

-continued

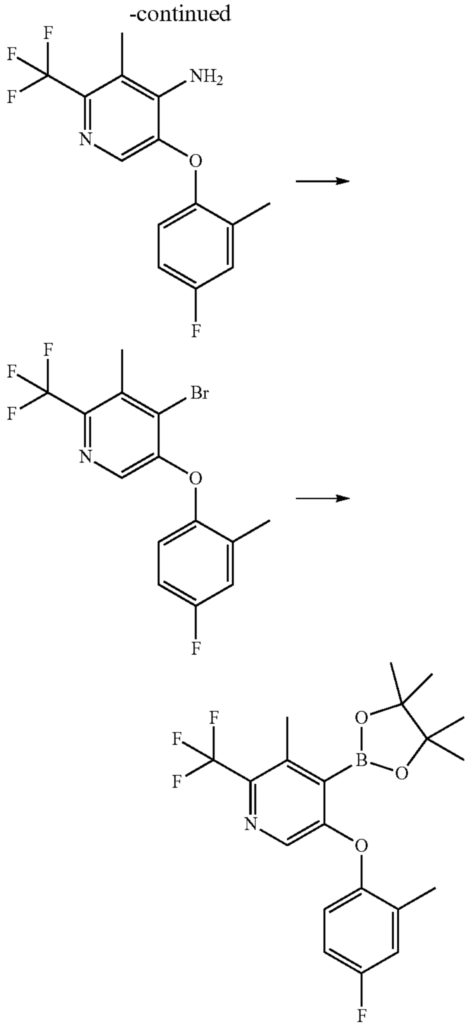

Step 1: Methyl 5-(4-fluoro-2-methyl-phenoxy)-3-methyl-2-(trifluoromethyl)pyridine-4-carboxylate Methyl 5-(4-fluoro-2-methyl-phenoxy)-3-methyl-2-(trifluoromethyl)pyridine-4-carboxylate was prepared from methyl 5-fluoro-3-methyl-2-(trifluoromethyl)pyridine-4-carboxylate (Intermediate B-13, step 2) and 4-fluoro-2-methyl-phenol using a procedure analogous to that found in Intermediate B-13, step 3. $^1H$ NMR (400 MHz, $CDCl_3$) δ 7.84 (s, 1H), 7.04-6.88 (m, 3H), 3.98 (s, 3H), 2.48-2.42 (m, 3H), 2.19 (s, 3H). ESI-MS m/z calc. 343.08, found 344.1 $(M+1)^+$.

Step 2: 5-(4-fluoro-2-methyl-phenoxy)-3-methyl-2-(trifluoromethyl)pyridine-4-carboxylic acid 5-(4-Fluoro-2-methyl-phenoxy)-3-methyl-2-(trifluoromethyl)pyridine-4-carboxylic acid was prepared from methyl 5-(4-fluoro-2-methyl-phenoxy)-3-methyl-2-(trifluoromethyl)pyridine-4-carboxylate using a procedure analogous to that found in Intermediate B-13, step 4. $^1H$ NMR (400 MHz, $CDCl_3$) δ 7.87 (s, 1H), 7.07-6.88 (m, 3H), 2.56-2.52 (m, 3H), 2.20 (s, 3H). ESI-MS m/z calc. 329.07, found 330.2 $(M+1)^+$.

Step 3: 5-(4-fluoro-2-methyl-phenoxy)-3-methyl-2-(trifluoromethyl)pyridin-4-amine 5-(4-Fluoro-2-methyl-phenoxy)-3-methyl-2-(trifluoromethyl)pyridin-4-amine was prepared from 5-(4-fluoro-2-methyl-phenoxy)-3-methyl-2-(trifluoromethyl)pyridine-4-carboxylic acid using a procedure analogous to that found in Intermediate B-13, step 5. $^1$H NMR (400 MHz, DMSO-$d_6$) δ 7.51 (s, 1H), 7.22 (dd, J=9.3, 3.2 Hz, 1H), 7.03 (td, J=8.6, 3.2 Hz, 1H), 6.88 (dd, J=8.9, 4.9 Hz, 1H), 6.29 (s, 2H), 2.24 (s, 3H), 2.22 (d, J=1.7 Hz, 3H). ESI-MS m/z calc. 300.09, found 301.2 $(M+1)^+$.

Step 4: 4-bromo-5-(4-fluoro-2-methyl-phenoxy)-3-methyl-2-(trifluoromethyl)pyridine 4-Bromo-5-(4-fluoro-2-methyl-phenoxy)-3-methyl-2-(trifluoromethyl)pyridine was prepared from 5-(4-fluoro-2-methyl-phenoxy)-3-methyl-2-(trifluoromethyl)pyridin-4-amine using a procedure analogous to that found in Intermediate B-11, step 7. $^1$H NMR (400 MHz, DMSO-$d_6$) δ 7.89 (s, 1H), 7.33-7.26 (m, 1H), 7.17-7.07 (m, 2H), 2.57 (d, J=1.7 Hz, 3H), 2.20 (s, 3H). ESI-MS m/z calc. 362.99, found 364.1 $(M+1)^+$.

Step 5: 5-(4-fluoro-2-methyl-phenoxy)-3-methyl-4-(4,4,5,5-tetramethyl-1,3,2-dioxaborolan-2-yl)-2-(trifluoromethyl)pyridine 5-(4-Fluoro-2-methyl-phenoxy)-3-methyl-4-(4,4,5,5-tetramethyl-1,3,2-dioxaborolan-2-yl)-2-(trifluoromethyl)pyridine was prepared from 4-bromo-5-(4-fluoro-2-methyl-phenoxy)-3-methyl-2-(trifluoromethyl)pyridine using a procedure analogous to that found in Intermediate B-13, step 7. $^1$H NMR (400 MHz, DMSO-$d_6$) δ 7.89 (s, 1H), 7.24 (dd, J=9.3, 3.1 Hz, 1H), 7.12-7.03 (m, 1H), 7.03-6.97 (m, 1H), 2.47 (d, J=2.0 Hz, 3H), 2.20 (s, 3H), 1.29 (s, 12H). ESI-MS m/z calc. 411.16, found 412.1 $(M+1)^+$.

Intermediate B-16

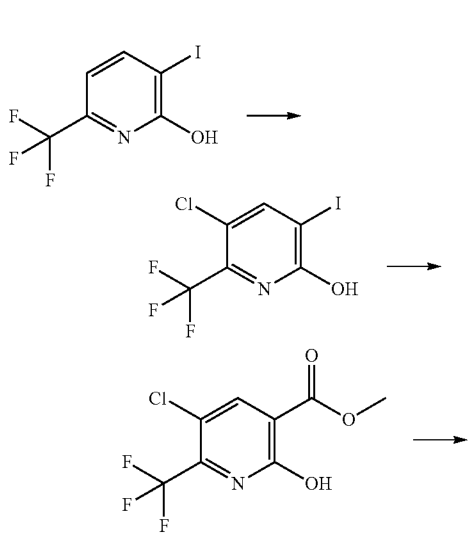

-continued

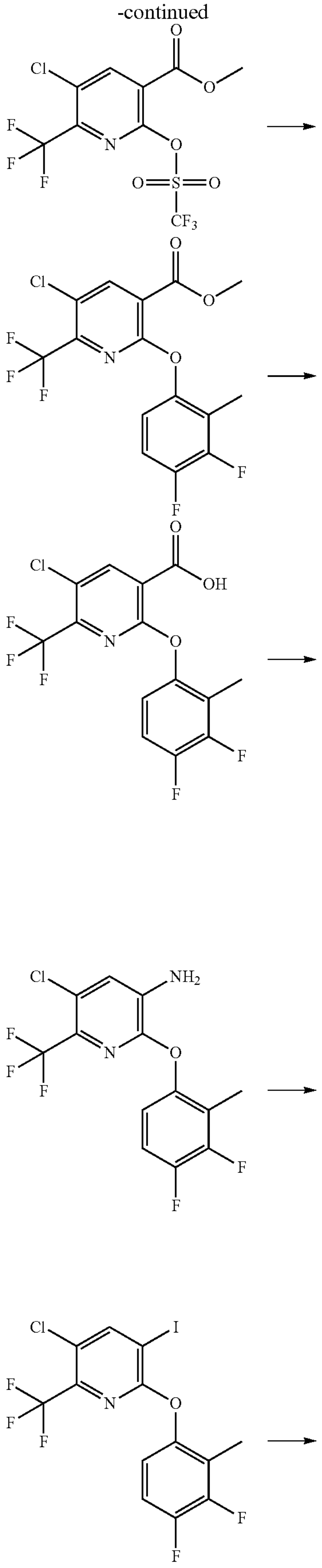

-continued

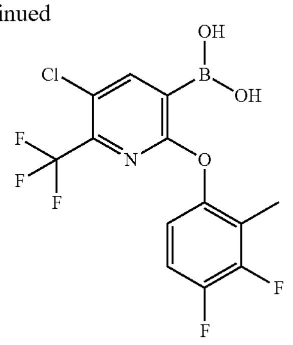

Step 1: 5-chloro-3-iodo-6-(trifluoromethyl)pyridin-2-ol

To a solution of 3-iodo-6-(trifluoromethyl)pyridin-2-ol (13.3 g, 45.2 mmol) in DMF (70 mL) was added 1,3-dichloro-5,5-dimethylhydantoin (15.960 g, 81.005 mmol). The reaction mixture was stirred 24 h at room temperature, then partitioned between ethyl acetate (500 mL) and water (200 mL). The biphasic mixture was cooled to 0-10° C., stirred vigorously and treated slowly with 10% aqueous sodium thiosulfate solution (200 mL). The layers were separated and the aqueous layer was extracted with ethyl acetate (2×100 mL). The pH of the aqueous layer was adjusted to 3 by addition of 3 M aqueous HCl (~10 mL) and was extracted with additional ethyl acetate (200 mL). The combined organic layers were washed with 50% saturated aqueous sodium chloride solution, dried over sodium sulfate, filtered and concentrated under reduced pressure. Purification by silica gel chromatography (0-5% methanol/dichloromethane) provided 5-chloro-3-iodo-6-(trifluoromethyl)pyridin-2-ol (8.68 g, 57%). ESI-MS m/z calc. 322.88, found 323.9 $(M+1)^+$. $^1$H NMR (400 MHz, $CDCl_3$) δ 9.45-8.67 (m, 1H), 8.22 (s, 1H). $^{19}$F NMR (377 MHz, $CDCl_3$) δ −65.53-−65.89 (m, 3F).

Step 2: Ethyl 5-chloro-2-hydroxy-6-(trifluoromethyl)pyridine-3-carboxylate

Palladium (II) acetate (250 mg, 1.11 mmol) was added to a solution of 5-chloro-3-iodo-6-(trifluoromethyl)pyridin-2-ol (7.08 g, 20.8 mmol), triethylamine (6.5 g, 9.0 mL, 64.6 mmol) and 1,1'-ferrocenediyl-bis(diphenylphosphine) (1.2 g, 2.2 mmol) in methanol (100 mL) in a sealed tube. Carbon monoxide was bubbled into the solution for 5 min, then the tube sealed and reaction mixture stirred at 60° C. for 5 h under CO atmosphere. Additional CO was bubbled into the solution and the reaction mixture was stirred at 60° C. overnight under CO atmosphere. The mixture was cooled to room temperature, filtered over Celite®, washed with methanol and the filtrate concentrated under reduced pressure. The residue was diluted with dichloromethane (150 mL) and washed with 1 M aqueous HCl (100 mL), water (50 mL) and brine (50 mL), dried over sodium sulfate and concentrated under reduced pressure. Purification by silica gel chromatography (0-5% methanol/dichloromethane) provided methyl 5-chloro-2-hydroxy-6-(trifluoromethyl)pyridine-3-carboxylate (4.99 g, 94%). $^1$H NMR (400 MHz, $CDCl_3$) δ 11.30 (br. s, 1H), 8.37 (s, 1H), 4.08 (s, 3H). $^{19}$F NMR (377 MHz, $CDCl_3$) δ −66.91 (s, 3F). ESI-MS m/z calc. 254.99, found 256.0 $(M+1)^+$.

Step 3: Methyl 5-chloro-6-(trifluoromethyl)-2-(trifluoromethylsulfonyloxy)pyridine-3-carboxylate To a solution of methyl 5-chloro-2-hydroxy-6-(trifluoromethyl)pyridine-3-carboxylate (4.59 g, 17.96 mmol) in DCM (100 mL) at 0° C. was added DIPEA (10.2 g, 13.8 mL, 79.2 mmol) and trifluoromethanesulfonic anhydride (15.4 g, 9.2 mL, 54.7 mmol). The resulting mixture was stirred for 3 h at room temperature, then diluted with saturated aqueous ammonium chloride (20 mL) and the layers separated. The aqueous layer was extracted with DCM (3×20 mL). The combined organic layers were dried over sodium sulfate, filtered and concentrated under reduced pressure. The residue was adsorbed on silica gel under vacuum and purified by silica gel chromatography (120 g silica, 0-20% ethyl acetate/heptane) to provide methyl 5-chloro-6-(trifluoromethyl)-2-(trifluoromethylsulfonyloxy)pyridine-3-carboxylate (6.36 g, 91%). $^1$H NMR (400 MHz, $CDCl_3$) δ 8.64 (s, 1H), 4.07 (s, 3H). $^{19}$F NMR (377 MHz, $CDCl_3$) δ −66.81 (s, 3F), −72.64 (s, 3F). ESI-MS m/z calc. 386.94, found 387.9 $(M+1)^+$.

Step 4: Methyl 5-chloro-2-(3,4-difluoro-2-methyl-phenoxy)-6-(trifluoromethyl)pyridine-3-carboxylate Methyl 5-chloro-2-(3,4-difluoro-2-methyl-phenoxy)-6-(trifluoromethyl)pyridine-3-carboxylate was prepared from methyl 5-chloro-6-(trifluoromethyl)-2-(trifluoromethylsulfonyloxy)pyridine-3-carboxylate and 3,4-difluoro-2-methyl-phenol using a procedure analogous to that found in Intermediate B-1, step 1, using DIPEA as base and DMF as solvent. $^1$H NMR (400 MHz, $CDCl_3$) δ 8.41 (s, 1H), 7.05 (dd, J=18.1, 10.0 Hz, 1H), 6.93-6.83 (m, 1H), 4.03 (s, 3H), 2.14 (d, J=2.0 Hz, 3H). $^{19}$F NMR (377 MHz, $CDCl_3$) δ −66.69 (s, 3F), −138.33 (d, J=20.4 Hz, 1F), −140.88 (d, J=21.8 Hz, 1F). ESI-MS m/z calc. 381.02, found 382.0 $(M+1)^+$.

Step 5: 5-chloro-2-(3,4-difluoro-2-methyl-phenoxy)-6-(trifluoromethyl)pyridine-3-carboxylic acid 5-Chloro-2-(3,4-difluoro-2-methyl-phenoxy)-6-(trifluoromethyl)pyridine-3-carboxylic acid was prepared from methyl 5-chloro-2-(3,4-difluoro-2-methyl-phenoxy)-6-(trifluoromethyl)pyridine-3-carboxylate using a procedure analogous to that found in Intermediate B-11, step 4. ESI-MS m/z calc. 367.00, found 367.9 $(M+1)^+$. $^1$H NMR (400 MHz, $CDCl_3$) δ 8.58 (s, 1H), 7.08 (dd, J=18.6, 9.3 Hz, 1H), 6.93-6.86 (m, 1H), 2.15 (d, J=2.0 Hz, 3H).

Step 6: tert-butyl N-[5-chloro-2-(3,4-difluoro-2-methyl-phenoxy)-6-(trifluoromethyl)-3-pyridyl]carbamate tert-Butyl N-[5-chloro-2-(3,4-difluoro-2-methyl-phenoxy)-6-(trifluoromethyl)-3-pyridyl]carbamate was prepared from 5-chloro-2-(3,4-difluoro-2-methyl-phenoxy)-6-(trifluoromethyl)pyridine-3-carboxylic acid using a procedure analogous to that found in Intermediate B-11, step 5, using tert-butanol as the solvent. ESI-MS m/z calc. 438.08, found 439.1 $(M+1)^+$.

Step 7: 5-chloro-2-(3,4-difluoro-2-methyl-phenoxy)-6-(trifluoromethyl)pyridin-3-amine 5-Chloro-2-(3,4-difluoro-2-methyl-phenoxy)-6-(trifluoromethyl)pyridin-3-amine was prepared from tert-butyl N-[5-chloro-2-(3,4-difluoro-2-methyl-phenoxy)-6-(trifluoromethyl)-3-pyridyl]carbamate using a procedure analogous to that found in Intermediate B-11, step 6. ESI-MS m/z calc. 338.02, found 339.0 $(M+1)^+$. $^1H$ NMR (400 MHz, $CDCl_3$) δ 7.07 (s, 1H), 7.06-6.98 (m, 1H), 6.93-6.84 (m, 1H), 4.42 (br. s, 2H), 2.13 (d, J=2.2 Hz, 3H). $^{19}F$ NMR (377 MHz, $CDCl_3$) δ −64.18 (s, 3F), −138.52 (d, J=20.4 Hz, 1F), −141.43 (d, J=20.4 Hz, 1F).

Step 8: 5-chloro-2-(3,4-difluoro-2-methyl-phenoxy)-3-iodo-6-(trifluoromethyl)pyridine To a suspension of 5-chloro-2-(3,4-difluoro-2-methyl-phenoxy)-6-(trifluoromethyl)pyridin-3-amine (683 mg, 1.88 mmol) and p-toluenesulfonic acid monohydrate (462 mg, 2.43 mmol) in acetonitrile (20 mL) cooled at 0° C. was slowly added isoamylnitrite (305 mg, 0.35 mL, 2.6 mmol) dropwise. The resulting mixture was stirred at 0° C. for 90 min. Potassium iodide (400 mg, 2.41 mmol) was added into the mixture at 0° C. and it was stirred at that temperature for 2 h. The mixture was allowed to warn to room temperature over 1 h and the resulting suspension concentrated under reduced pressure. The mixture was solubilized in ethyl acetate (50 mL) and an aqueous solution of sodium bicarbonate (25 mL) followed by water (25 mL) were added. The phases were separated and the organic layer was washed with an aqueous solution of sodium bicarbonate (25 mL) then by an aqueous solution of sodium thiosulfate (2×25) and brine (25 mL). The organic layer was dried over anhydrous sodium sulfate, filtered and concentrated under reduced pressure. Purification by silica gel chromatography (0-10% of ethyl acetate/heptane) provided 5-chloro-2-(3,4-difluoro-2-methyl-phenoxy)-3-iodo-6-(trifluoromethyl) pyridine (363 mg, 43%). ESI-MS m/z calc. 448.91, found 450.2 $(M+1)^+$. $^1H$ NMR (400 MHz, $CDCl_3$) δ 8.32 (s, 1H), 7.06 (dd, J=19.6, 9.2 Hz, 1H), 6.95-6.85 (m, 1H), 2.14 (d, J=2.0 Hz, 3H). $^{19}F$ NMR (377 MHz, $CDCl_3$) δ −66.31 (s, 3F), −138.21 (d, J=21.8 Hz, 1F), −140.67 (d, J=23.2 Hz, 1F).

Step 9: [5-chloro-2-(3,4-difluoro-2-methyl-phenoxy)-6-(trifluoromethyl)-3-pyridyl]boronic acid

[5-Chloro-2-(3,4-difluoro-2-methyl-phenoxy)-6-(trifluoromethyl)-3-pyridyl]boronic acid was prepared from 5-chloro-2-(3,4-difluoro-2-methyl-phenoxy)-3-iodo-6-(trifluoromethyl)pyridine using a procedure analogous to that found in Intermediate B-13, step 7. ESI-MS m/z calc. 367.02, found 368.1 $(M+1)^+$.

Intermediate B-17

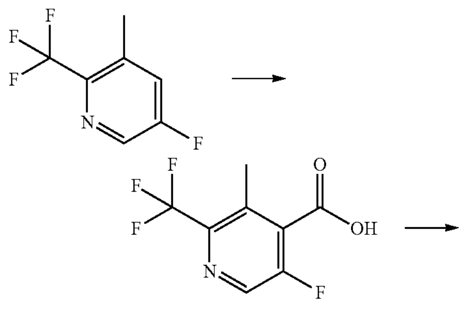

-continued

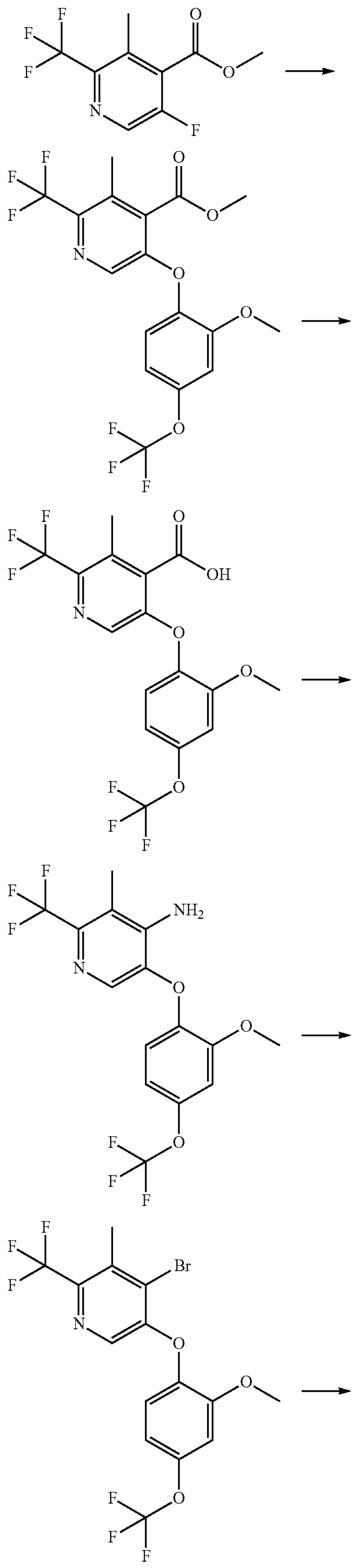

-continued

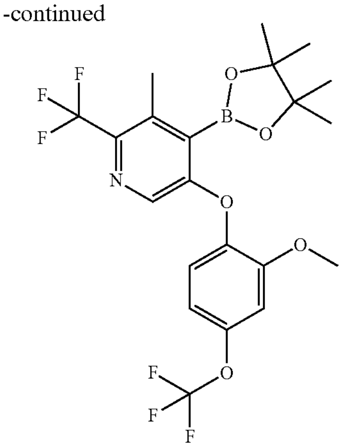

Step 1: 5-fluoro-3-methyl-2-(trifluoromethyl)pyridine-4-carboxylic acid

5-Fluoro-3-methyl-2-(trifluoromethyl)pyridine-4-carboxylic acid was prepared from 5-fluoro-3-methyl-2-(trifluoromethyl)pyridine using a procedure analogous to that found in Intermediate B-13, step 1. ESI-MS m/z calc. 223.03, found 222.1 $(M-1)^-$. $^1H$ NMR (400 MHz, DMSO-$d_6$) δ 14.74 (br s, 1H), 8.73 (s, 1H), 2.47-2.43 (m, 3H). $^{19}F$ NMR (377 MHz, DMSO-$d_6$) δ −62.99 (s, 1F), −125.50 (s, 1F).

Step 2: Methyl 5-fluoro-3-methyl-2-(trifluoromethyl)pyridine-4-carboxylate

To a stirring mixture of 5-fluoro-3-methyl-2-(trifluoromethyl)pyridine-4-carboxylic acid (8.20 g, 36.8 mmol) in methanol (75 mL) at 0° C. was added dropwise thionyl chloride (4.9 g, 3 mL, 41 mmol). The reaction mixture was heated to 70° C. and stirred for 24 h. The reaction mixture cooled to room temperature and partitioned between water and dichloromethane. The organic layer was washed with saturated aqueous sodium bicarbonate (2×) and brine, dried over sodium sulfate and then concentrated in vacuo. Purification by silica gel chromatography (0-20% ethyl acetate/heptane) provided methyl 5-fluoro-3-methyl-2-(trifluoromethyl)pyridine-4-carboxylate (1.085 g, 8%) as a clear, colorless oil. ESI-MS m/z calc. 237.04, found 238.03 $(M+1)^+$. $^1H$ NMR (400 MHz, $CDCl_3$) δ 8.45 (s, 1H), 4.00 (s, 3H), 2.50-2.48 (m, 3H). $^{19}F$ NMR (376 MHz, $CDCl_3$) δ −64.4 (s, 3F), −124.2 (s, 1F).

Step 3: Methyl 5-[2-methoxy-4-(trifluoromethoxy)phenoxy]-3-methyl-2-(trifluoromethyl)pyridine-4-carboxylate Methyl 5-[2-methoxy-4-(trifluoromethoxy)phenoxy]-3-methyl-2-(trifluoromethyl)pyridine-4-carboxylate was prepared from methyl 5-fluoro-3-methyl-2-(trifluoromethyl)pyridine-4-carboxylate and 2-methoxy-4-(trifluoromethoxy)phenol using a procedure analogous to that found in Intermediate B-1, step 1 and using toluene as the solvent. ESI-MS m/z calc. 425.07, found 426.04 $(M+1)^+$. $^1H$ NMR (400 MHz, $CDCl_3$) δ 7.86 (s, 1H), 7.13 (d, 1H), 6.87-6.83 (m, 2H), 3.97 (s, 3H), 3.79 (s, 3H), 2.44-2.44 (m, 3H). $^{19}F$ NMR (376 MHz, $CDCl_3$) δ −57.9-−58.0 (m, 3F), −64.0-−64.0 (m, 3F).

Step 4: 5-[2-methoxy-4-(trifluoromethoxy)phenoxy]-3-methyl-2-(trifluoromethyl)pyridine-4-carboxylic acid 5-[2-Methoxy-4-(trifluoromethoxy)phenoxy]-3-methyl-2-(trifluoromethyl)pyridine-4-carboxylic acid was prepared from methyl 5-[2-methoxy-4-(trifluoromethoxy)phenoxy]-3-methyl-2-(trifluoromethyl)pyridine-4-carboxylate using a procedure analogous to that found in Intermediate B-13, step 4. ESI-MS m/z calc. 411.05, found 411.98 $(M+1)^+$.

Step 5: 5-[2-methoxy-4-(trifluoromethoxy)phenoxy]-3-methyl-2-(trifluoromethyl)pyridin-4-amine 5-[2-Methoxy-4-(trifluoromethoxy)phenoxy]-3-methyl-2-(trifluoromethyl)pyridin-4-amine was prepared from 5-[2-methoxy-4-(trifluoromethoxy)phenoxy]-3-methyl-2-(trifluoromethyl)pyridine-4-carboxylic acid using a procedure analogous to that found in Intermediate B-13, step 5. ESI-MS m/z calc. 382.08, found 383.02 $(M+1)^+$. $^1H$ NMR (400 MHz, $CDCl_3$) δ 7.69 (s, 1H), 7.22 (dd, J=8.7, 7.3 Hz, 1H), 7.02-6.99 (m, 1H), 6.86-6.78 (m, 3H), 3.83 (s, 3H), 2.28 (d, J=1.4 Hz, 3H). $^{19}F$ NMR (376 MHz, $CDCl_3$) δ −57.9-−58.0 (m, 3F), −63.3 (d, J=18.8 Hz, 3F).

Step 6: 4-bromo-5-[2-methoxy-4-(trifluoromethoxy)phenoxy]-3-methyl-2-(trifluoromethyl)pyridine 4-Bromo-5-[2-methoxy-4-(trifluoromethoxy)phenoxy]-3-methyl-2-(trifluoromethyl)pyridine was prepared from 5-[2-methoxy-4-(trifluoromethoxy)phenoxy]-3-methyl-2-(trifluoromethyl)pyridin-4-amine using a procedure analogous to that found in Intermediate B-4, step 6. ESI-MS m/z calc. 444.98, found 445.89 $(M+1)^+$.

Step 7: 5-[2-methoxy-4-(trifluoromethoxy)phenoxy]-3-methyl-4-(4,4,5,5-tetramethyl-1,3,2-dioxaborolan-2-yl)-2-(trifluoromethyl)pyridine 5-[2-Methoxy-4-(trifluoromethoxy)phenoxy]-3-methyl-4-(4,4,5,5-tetramethyl-1,3,2-dioxaborolan-2-yl)-2-(trifluoromethyl)pyridine was prepared from 4-bromo-5-[2-methoxy-4-(trifluoromethoxy)phenoxy]-3-methyl-2-(trifluoromethyl)pyridine using a procedure analogous to that found in Intermediate B-13, step 7. ESI-MS m/z calc. 493.15, found 494.06 $(M+1)^+$. $^1H$ NMR (400 MHz, $CDCl_3$) δ 7.82 (s, 1H), 7.02 (d, J=8.2 Hz, 1H), 6.84-6.79 (m, 2H), 3.80 (s, 3H), 2.52 (d, J=1.8 Hz, 3H), 1.34 (s, 12H). $^{19}F$ NMR (376 MHz, $CDCl_3$) δ −58.0 (s, 3F), −64.0 (d, J=1.6 Hz, 3F).

Intermediate B-18

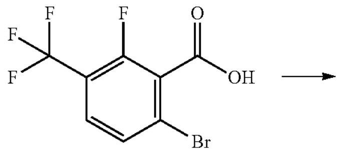

-continued

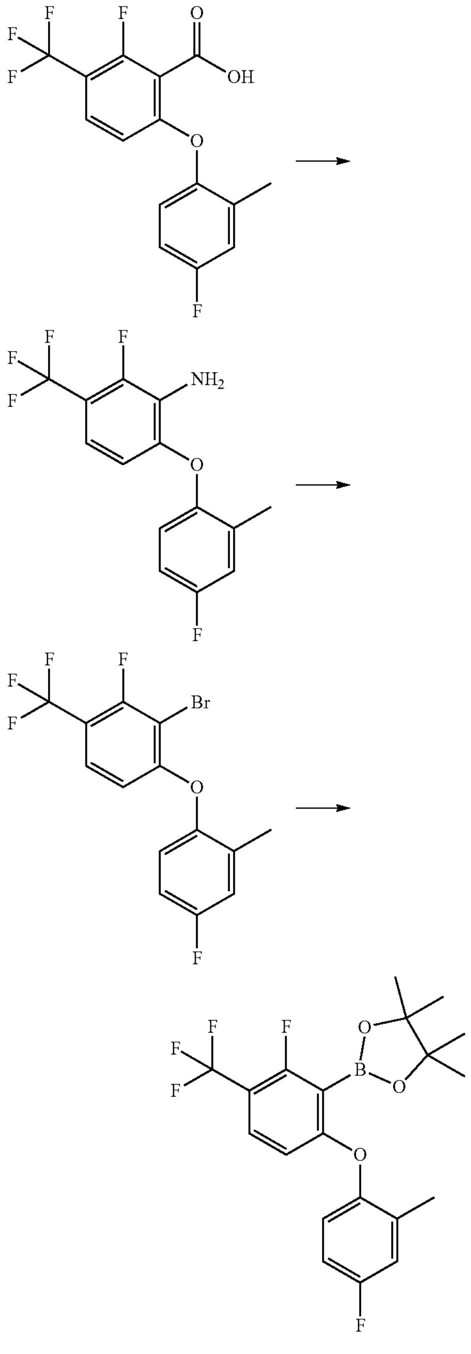

Step 1: 2-fluoro-6-(4-fluoro-2-methyl-phenoxy)-3-(trifluoromethyl)benzoic acid 2-fluoro-6-(4-fluoro-2-methyl-phenoxy)-3-(trifluoromethyl)benzoic acid was prepared using a procedure analogous to that found in Intermediate B-4, step 4 without N,N-dimethylglycine and using toluene as solvent. $^1$H NMR (400 MHz, $CDCl_3$) δ 9.40 (br. s, 1H), 7.54 (t, J=8.5 Hz, 1H), 7.04-6.99 (m, 2H), 6.98-6.92 (m, 1H), 6.45 (d, J=8.9 Hz, 1H), 2.19 (s, 3H). $^{19}$F NMR (376 MHz, $CDCl_3$) δ −60.8 (d, J=12.3 Hz, 3F), −112.1–−112.2 (m, 1F), −116.3 (s, 1F).

Step 2: 2-fluoro-6-(4-fluoro-2-methyl-phenoxy)-3-(trifluoromethyl)aniline

2-Fluoro-6-(4-fluoro-2-methyl-phenoxy)-3-(trifluoromethyl)aniline was prepared from 2-fluoro-6-(4-fluoro-2-methyl-phenoxy)-3-(trifluoromethyl)benzoic acid using a procedure analogous to that found in Intermediate B-13, step 5. ESI-MS m/z calc. 303.07, found 303.94 $(M+1)^+$. $^1$H NMR (400 MHz, $CDCl_3$) δ 7.23-7.18 (m, 1H), 6.93-6.89 (m, 2H), 6.83-6.76 (m, 1H), 6.31-6.26 (m, 1H), 2.19 (s, 3H). $^{19}$F NMR (376 MHz, $CDCl_3$) δ −60.6 (d, J=12.3 Hz, 3F), −117.7 (s, 1F), −135.6 (q, J=12.5 Hz, 1F).

Step 3: 2-bromo-3-fluoro-1-(4-fluoro-2-methyl-phenoxy)-4-(trifluoromethyl)benzene 2-Bromo-3-fluoro-1-(4-fluoro-2-methyl-phenoxy)-4-(trifluoromethyl)benzene was prepared from 2-fluoro-6-(4-fluoro-2-methyl-phenoxy)-3-(trifluoromethyl)aniline using a procedure analogous to that found in Intermediate B-4, step 6. $^1$H NMR (400 MHz, $CDCl_3$) δ 7.43-7.37 (m, 1H), 7.04-6.92 (m, 3H), 6.43-6.37 (m, 1H), 2.17 (s, 3H). $^{19}$F NMR (376 MHz, $CDCl_3$) δ −60.9 (d, J=12.3 Hz, 3F), −103.9–−104.0 (m, 1F), −116.6 (s, 1F).

Step 4: 2-[2-fluoro-6-(4-fluoro-2-methyl-phenoxy)-3-(trifluoromethyl)phenyl]-4,4,5,5-tetramethyl-1,3,2-dioxaborolane 2-[2-Fluoro-6-(4-fluoro-2-methyl-phenoxy)-3-(trifluoromethyl)phenyl]-4,4,5,5-tetramethyl-1,3,2-dioxaborolane was prepared from 2-bromo-3-fluoro-1-(4-fluoro-2-methyl-phenoxy)-4-(trifluoromethyl)benzene using a procedure analogous to that found in Intermediate B-13, step 7. $^1$H NMR (400 MHz, $CDCl_3$) δ 7.45 (t, J=8.5 Hz, 1H), 6.99-6.84 (m, 3H), 6.39 (d, J=8.8 Hz, 1H), 2.18 (s, 3H), 1.35 (s, 12H). $^{19}$F NMR (376 MHz, $CDCl_3$) δ −60.8 (d, J=12.2 Hz, 3F), −103.6–−103.8 (m, 1F), −118.0 (s, 1F).

Intermediate B-19

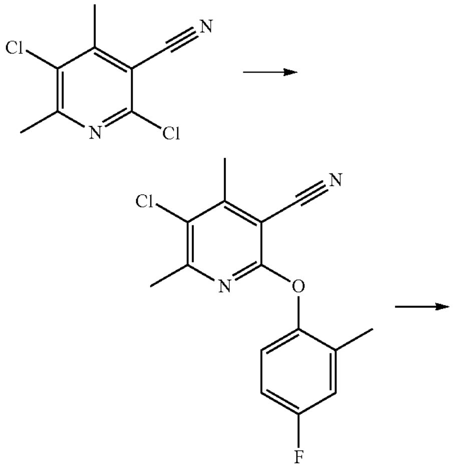

-continued

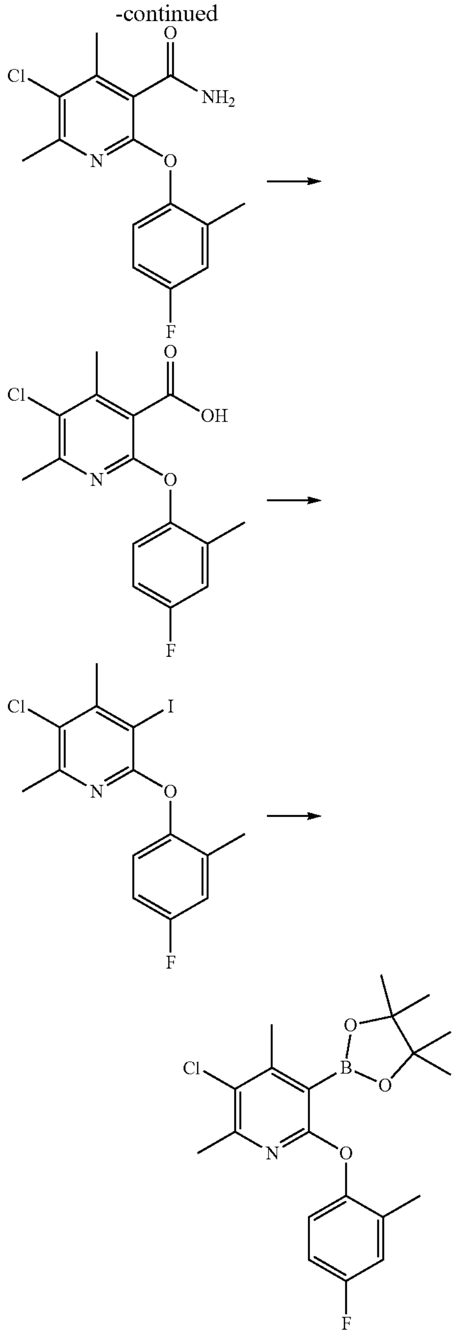

Step 1: 5-chloro-2-(4-fluoro-2-methyl-phenoxy)-4,6-dimethyl-pyridine-3-carbonitrile 5-Chloro-2-(4-fluoro-2-methyl-phenoxy)-4,6-dimethyl-pyridine-3-carbonitrile was prepared from 2,5-dichloro-4,6-dimethyl-pyridine-3-carbonitrile and 4-fluoro-2-methyl-phenol using a procedure analogous to that found in Intermediate B-1, step 1 using potassium carbonate as base and NMP as solvent. ESI-MS m/z calc. 290.06, found 291.2 $(M+1)^+$. $^1$H NMR (400 MHz, $CDCl_3$) δ 7.04 (dd, J=8.8, 4.9 Hz, 1H), 6.97 (dd, J=8.9, 2.8 Hz, 1H), 6.95-6.88 (m, 1H), 2.63 (s, 3H), 2.45 (s, 3H), 2.16 (s, 3H). $^{19}$F NMR (377 MHz, $CDCl_3$) δ −117.65 (s, 1F).

Step 2: 5-chloro-2-(4-fluoro-2-methyl-phenoxy)-4,6-dimethyl-pyridine-3-carbonitrile To a solution of 5-chloro-2-(4-fluoro-2-methyl-phenoxy)-4,6-dimethyl-pyridine-3-carbonitrile (1.09 g, 3.75 mmol) in DMSO (25 mL) at room temperature was added hydrogen peroxide (35% in water) (2.6 mL, 10.394 mmol) and NaOH (2.7 g, 67.5 mmol). The resulting mixture was stirred at 50° C. for 4 h. The mixture was cooled to 0° C., then a 10% aqueous solution of sodium thiosulfate (50 mL) and a 5% aqueous solution of citric acid (50 mL) were slowly added over 5 min. The resulting mixture was stirred for 10 min and then extracted with ethyl acetate (3×75 mL). The organic layers were combined, washed with brine (75 mL), dried over sodium sulfate, filtered and concentrated under reduced pressure. Purification by silica gel chromatography (10-80% ethyl acetate/heptanes) provided 5-chloro-2-(4-fluoro-2-methyl-phenoxy)-4,6-dimethyl-pyridine-3-carboxamide (952 mg, 82%) as a white solid. ESI-MS m/z calc. 308.07, found 309.2 $(M+1)^+$. $^1$H NMR (400 MHz, $CDCl_3$) δ 7.02-6.86 (m, 3H), 6.13-5.82 (m, 2H), 2.51 (s, 3H), 2.40 (s, 3H), 2.15 (s, 3H). $^{19}$F NMR (377 MHz, $CDCl_3$) δ −118.51 (s, 1F).

Step 3: 5-chloro-2-(4-fluoro-2-methyl-phenoxy)-4,6-dimethyl-pyridine-3-carboxylic acid Sulfuric acid (10 g, 5.5 mL, 103 mmol) and 5-chloro-2-(4-fluoro-2-methyl-phenoxy)-4,6-dimethyl-pyridine-3-carboxamide (900 mg, 2.91 mmol) were stirred until dissolution was complete. The solution was cooled to 0° C. and a solution of sodium nitrite (500 mg, 7.25 mmol) in water (2.5 mL) added dropwise over 5 min. The resulting mixture was allowed to reach room temperature and stirred for 5 h. An aqueous 1 M sodium hydroxide solution was added to the reaction mixture until pH 4-5 and the resulting suspension was extracted with ethyl acetate (2×100 mL). The combined organic layers were washed with brine (75 mL), dried over sodium sulfate, filtered and concentrated under reduced pressure. Purification by reverse-phase chromatography (5-80% acetonitrile/0.1% of formic acid) provided 5-chloro-2-(4-fluoro-2-methyl-phenoxy)-4,6-dimethyl-pyridine-3-carboxylic acid (792 mg, 79%) as a white solid. ESI-MS m/z calc. 309.06, found 310.2 $(M+1)^+$. $^1$H NMR (400 MHz, DMSO-$d_6$) δ 13.78 (br s, 1H), 7.16 (dd, J=9.4, 2.6 Hz, 1H), 7.11-7.00 (m, 2H), 2.36 (s, 3H), 2.32 (s, 3H), 2.07 (s, 3H). $^{19}$F NMR (377 MHz, DMSO-d6) δ −118.27-−118.47 (m, 1F).

Step 4: 5-chloro-2-(4-fluoro-2-methyl-phenoxy)-3-iodo-4,6-dimethyl-pyridine

5-Chloro-2-(4-fluoro-2-methyl-phenoxy)-3-iodo-4,6-dimethyl-pyridine was prepared from 5-chloro-2-(4-fluoro-2-methyl-phenoxy)-3-iodo-4,6-dimethyl-pyridine using a procedure analogous to that found in Intermediate B-26, step 2. ESI-MS m/z calc. 390.97, found 392.0 $(M+1)^+$. $^1$H NMR (400 MHz, $CDCl_3$) δ 7.02-6.97 (m, 1H), 6.95 (dd, J=9.2, 2.9 Hz, 1H), 6.93-6.86 (m, 1H), 2.67 (s, 3H), 2.36 (s, 3H), 2.15 (s, 3H). $^{19}$F NMR (377 MHz, $CDCl_3$) δ −118.77 (s, 1F).

Step 5: 5-chloro-2-(4-fluoro-2-methyl-phenoxy)-4,6-dimethyl-3-(4,4,5,5-tetramethyl-1,3,2-dioxaborolan-2-yl)pyridine 5-Chloro-2-(4-fluoro-2-methyl-phenoxy)-4,6-dimethyl-3-(4,4,5,5-tetramethyl-1,3,2-dioxaborolan-2-yl)pyridine was prepared from 5-chloro-2-(4-fluoro-2-methyl-phenoxy)-3-iodo-4,6-dimethyl-pyridine using a procedure analogous to that found in Intermediate B-2, step 4. ESI-MS m/z calc. 391.15, found 392.2 $(M+1)^+$. $^1H$ NMR (400 MHz, $CDCl_3$) δ 6.99-6.89 (m, 2H), 6.88-6.82 (m, 1H), 2.43 (s, 3H), 2.38 (s, 3H), 2.18 (s, 3H), 1.37 (s, 12H). $^{19}F$ NMR (377 MHz, $CDCl_3$) δ −119.98 (s, 3F).

Intermediate B-20

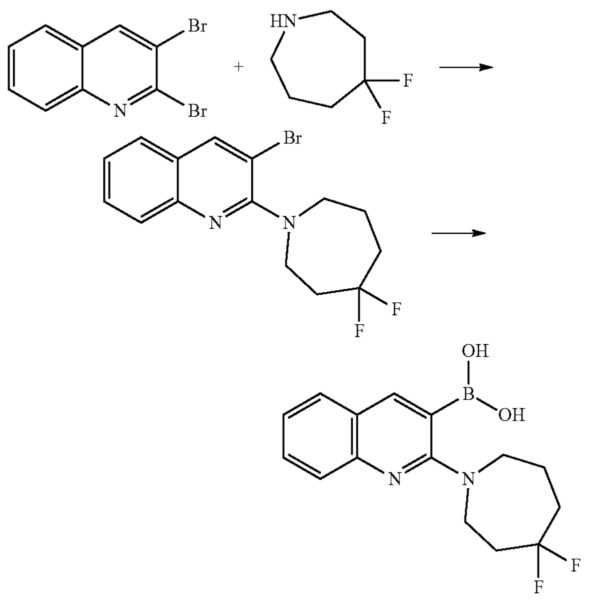

Step 1: 3-bromo-2-(4,4-difluoroazepane-1-yl)quinoline

A solution of 2,3-dibromoquinoline (8.16 g, 28.4 mmol) and 4,4-difluoroazepane hydrochloride (5.0 g, 29 mmol) in NMP (65 mL) was treated with $K_2CO_3$ (7.9 g, 57.16 mmol) and heated at 80-85° C. for 2 h. Additional 4,4-difluoroazepane hydrochloride (0.5 g, 2.9 mmol) was added and the mixture stirred for another 19 h at 80-85° C. Additional 4,4-difluoroazepane hydrochloride (0.5 g, 2.9 mmol) was added and the mixture stirred for another 6 h at 80-85° C. The mixture was extracted with MTBE (250 mL)/water (500 mL) and the organic phase was washed with water (500 mL) and brine (200 mL). The aqueous phases were extracted with additional MTBE (100 mL) and the combined organic phases were dried, filtered and evaporated to provide 3-bromo-2-(4,4-difluoroazepan-1-yl)quinoline (9.48 g, 94%). ESI-MS m/z calc. 340.04, found 341.0 $(M+1)^+$. $^1H$ NMR (400 MHz, $CDCl_3$) δ 8.26 (s, 1H), 7.84-7.70 (m, 1H), 7.66-7.52 (m, 2H), 7.34 (td, J=7.2, 1.2 Hz, 1H), 3.86-3.61 (m, 4H), 2.58-2.38 (m, 2H), 2.35-2.13 (m, 2H), 2.08-1.92 (m, 2H) ppm; $^{19}F$ NMR (376 MHz, $CDCl_3$) δ −88.51.

Step 2: [2-(4,4-difluoroazepan-1-yl)-3-quinolyl] boronic acid n-BuLi (16 mL of 1.6 M in hexanes, 25.6 mmol) was added slowly to a stirring solution of 3-bromo-2-(4,4-difluoroazepan-1-yl)quinoline (7.42 g, 20.95 mmol) in diethyl ether (95 mL) at −78° C. under argon. The mixture was stirred at −78° C. for 1 h, then treated dropwise with a solution of trimethylborate (3.3 g, 3.5 mL, 31 mmol) in diethyl ether (35 mL). The reaction was warmed to room temperature and stirred for 18 h. The mixture was diluted with saturated aqueous ammonium chloride (200 mL) and extracted with ethyl acetate (200 mL). The organic extract was washed with brine (200 mL), dried over magnesium sulfate, filtered and concentrated. The solid was triturated with 10% ethyl acetate in heptane (10 vol.), filtered and dried to provide [2-(4,4-difluoroazepan-1-yl)-3-quinolyl] boronic acid (2.6 g, 32%) as a white solid. ESI-MS m/z calc. 306.14, found 307.15 $(M+1)^+$. $^1H$ NMR (400 MHz, $CD_3OD$) δ 8.00 (s, 1H) 7.64 (t, J=7.1 Hz, 2H), 7.54-7.50 (m, 1H), 7.24-7.19 (m, 1H), 3.85-3.82 (m, 2H), 3.67 (t, J=5.5 Hz, 2H), 2.45-2.35 (m, 2H), 2.08-2.00 (m, 4H). $^{19}F$ NMR (376 MHz, $CD_3OD$) δ −92.0−−92.1 (m, 2F).

Intermediate B-21

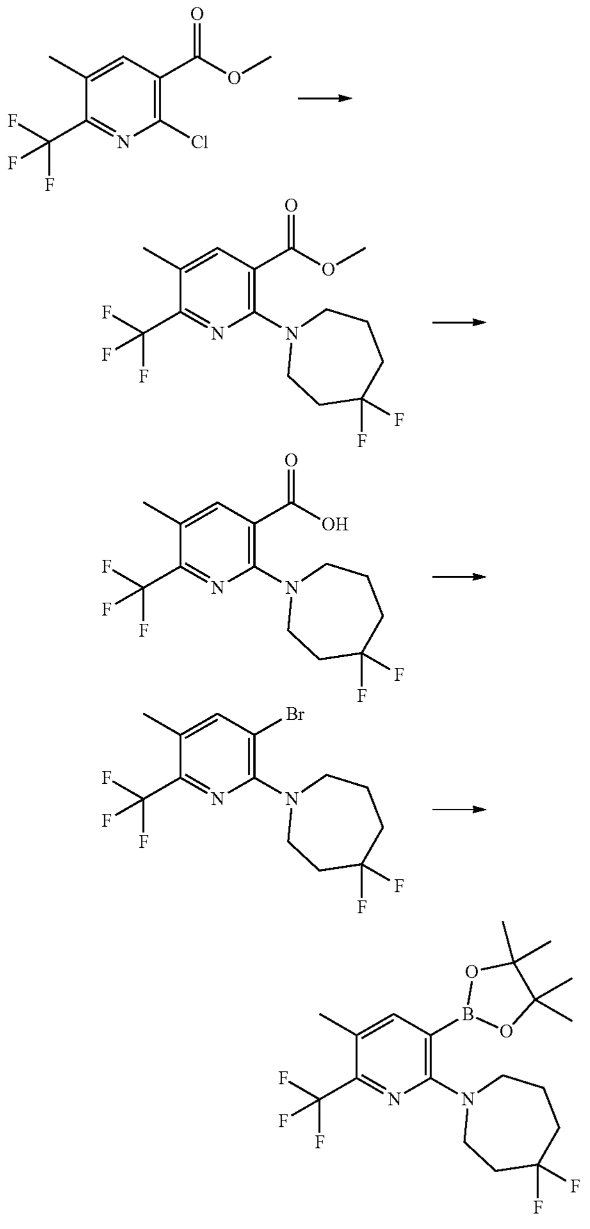

Step 1: methyl 2-(4,4-difluoroazepan-1-yl)-5-methyl-6-(trifluoromethyl)pyridine-3-carboxylate Methyl 2-(4,4-difluoroazepan-1-yl)-5-methyl-6-(trifluoromethyl)pyridine-3-carboxylate was prepared from methyl 2-chloro-5-methyl-6-(trifluoromethyl)pyridine-3-carboxylate (Intermediate B-11, step 2) and 4,4-difluoroazepane using a procedure analogous to that found in Intermediate B-20, step 1 using cesium carbonate as the base and DMF as solvent. ESI-MS m/z calc. 352.12, found 353.15 $(M+1)^+$. $^1H$ NMR (400 MHz, $CDCl_3$) δ 7.79 (s, 1H), 3.89 (s, 3H), 3.74-3.67 (m, 2H), 3.31-3.24 (m, 2H), 2.44-2.28 (m, 5H), 2.02-1.89 (m, 4H).

Step 2: 2-(4,4-difluoroazepan-1-yl)-5-methyl-6-(trifluoromethyl)pyridine-3-carboxylic acid 2-(4,4-Difluoroazepan-1-yl)-5-methyl-6-(trifluoromethyl)pyridine-3-carboxylic acid was prepared from methyl 2-(4,4-difluoroazepan-1-yl)-5-methyl-6-(trifluoromethyl) pyridine-3-carboxylate using a procedure analogous to that found in Intermediate B-11, step 4. ESI-MS m/z calc. 338.11, found 338.99 $(M+1)^+$. $^1H$ NMR (400 MHz, $CDCl_3$) δ 8.09 (s, 1H), 3.57-3.50 (m, 2H), 3.32 (t, J=6.0 Hz, 2H), 2.43-2.30 (m, 5H), 2.13-2.04 (m, 2H), 1.97-1.90 (m, 2H).

Step 3: 1-[3-bromo-5-methyl-6-(trifluoromethyl)-2-pyridyl]-4,4-difluoro-azepane

A vial was loaded with 2-(4,4-difluoroazepan-1-yl)-5-methyl-6-(trifluoromethyl)pyridine-3-carboxylic acid (1.5 g, 4.4 mmol), potassium phosphate (941 mg, 4.43 mmol), and tetrabutylammonium tribromide (3.2 g, 6.6 mmol). The vial was capped and purged with nitrogen. Acetonitrile (22 mL) was added via syringe and the reaction was stirred at 90° C. for 1.5 h. The reaction was cooled and concentrated under reduced pressure. Purification by reverse phase chromatography (C18, 1-99% acetonitrile/5 mM HCl) provided 1-[3-bromo-5-methyl-6-(trifluoromethyl)-2-pyridyl]-4,4-difluoro-azepane (1.3 g, 79%) as a yellow oil. ESI-MS m/z calc. 372.03, found 372.9 $(M+1)^+$. $^1H$ NMR (400 MHz, $CDCl_3$) δ 7.70 (s, 1H), 3.73-3.62 (m, 2H), 3.64-3.56 (m, 2H), 2.50-2.36 (m, 2H), 2.34 (s, 3H), 2.26-2.06 (m, 2H), 2.06-1.86 (m, 2H).

Step 4: 4,4-difluoro-1-[5-methyl-3-(4,4,5,5-tetramethyl-1,3,2-dioxaborolan-2-yl)-6-(trifluoromethyl)-2-pyridyl]azepane 4,4-Difluoro-1-[5-methyl-3-(4,4,5,5-tetramethyl-1,3,2-dioxaborolan-2-yl)-6-(trifluoromethyl)-2-pyridyl]azepane was prepared from 1-[3-bromo-5-methyl-6-(trifluoromethyl)-2-pyridyl]-4,4-difluoro-azepane using a procedure analogous to that found in Intermediate B-20, step 2 and 2-isopropoxy-4,4,5,5-tetramethyl-1,3,2-dioxaborolane. ESI-MS m/z calc. 420.21, found 339.12 (M-pinacol)+; Mass of the corresponding boronic acid observed by LC/MS. $^1H$ NMR (400 MHz, $CDCl_3$) δ 7.66 (s, 1H), 3.73-3.70 (m, 2H), 3.52 (t, J=5.5 Hz, 2H), 2.37-2.26 (m, 5H), 2.01-1.91 (m, 4H), 1.34 (s, 12H).

Intermediate B-22

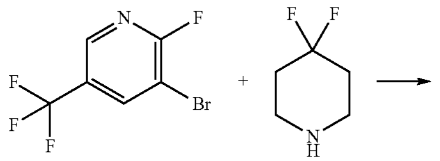

-continued

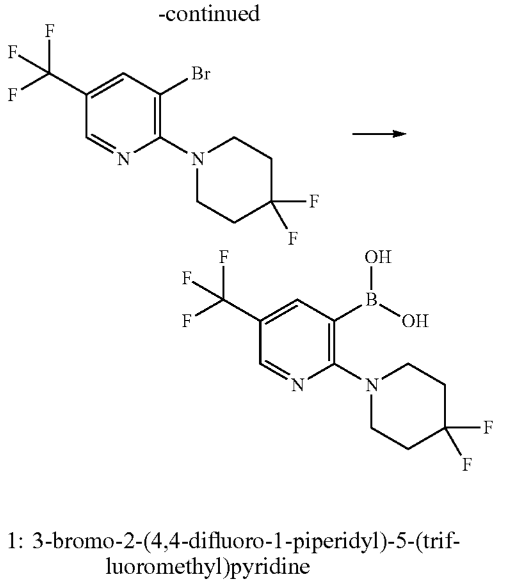

Step 1: 3-bromo-2-(4,4-difluoro-1-piperidyl)-5-(trifluoromethyl)pyridine

To a solution of 3-bromo-2-fluoro-5-(trifluoromethyl) pyridine (1.224 g, 5.017 mmol) in THF (6 mL) at 0° C. was added a solution of 4,4-difluoropiperidine (1.22 g, 10.1 mmol) in THF (2 mL) dropwise. The mixture was removed from the ice bath and allowed to come to room temperature over 1 h, then heated at 50° C. for 24 h. The mixture was partitioned between water and ethyl acetate. The organic layer was separated and washed with 50% saturated aqueous $NH_4Cl$, dried over sodium sulfate, filtered and concentrated in vacuo. Purification by silica gel chromatography (40 g silica, 10-100% ethyl acetate/hexane) provided 3-bromo-2-(4,4-difluoro-1-piperidyl)-5-(trifluoromethyl)pyridine (1.68 g, 97%). ESI-MS m/z calc. 343.99, found 345.0 $(M+1)^+$. $^1H$ NMR (400 MHz, DMSO-$d_6$) δ 8.62 (dd, J=2.2, 1.1 Hz, 1H), 8.40-8.35 (m, 1H), 3.58-3.51 (m, 4H), 2.19-2.06 (m, 4H).

Step 2: [2-(4,4-difluoro-1-piperidyl)-5-(trifluoromethyl)-3-pyridyl]boronic acid

[2-(4,4-Difluoro-1-piperidyl)-5-(trifluoromethyl)-3-pyridyl]boronic acid was prepared from 3-bromo-2-(4,4-difluoro-1-piperidyl)-5-(trifluoromethyl)pyridine using a procedure analogous to that found in Intermediate B-3, step 3 and triisopropyl borate. ESI-MS m/z calc. 310.09, found 311.0 $(M+1)^+$. $^1H$ NMR (400 MHz, DMSO-$d_6$) δ 8.42 (dd, J=2.6, 1.2 Hz, 1H), 7.79 (d, J=2.6 Hz, 1H), 3.66-3.55 (m, 4H), 2.16-1.98 (m, 4H).

Intermediate B-23

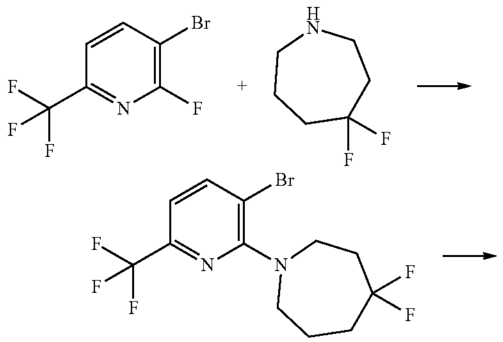

-continued

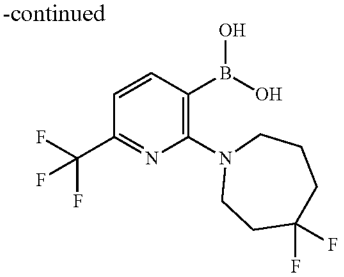

Step 1: 1-[3-bromo-6-(trifluoromethyl)-2-pyridyl]-4,4-difluoro-azepane

1-[3-Bromo-6-(trifluoromethyl)-2-pyridyl]-4,4-difluoro-azepane was prepared from 3-bromo-2-fluoro-6-(trifluoromethyl)pyridine using a procedure analogous to that found in Intermediate B-20, step 1, with DMSO as solvent and DIEA as the base. ESI-MS m/z calc. 358.01, found 359.0 $(M+1)^+$. $^1H$ NMR (400 MHz, $CDCl_3$) δ 7.87 (dd, J=7.8, 0.9 Hz, 1H), 6.97 (d, J=7.9 Hz, 1H), 3.77-3.65 (m, 4H), 2.49-2.34 (m, 2H), 2.23-2.08 (m, 2H), 2.03-1.92 (m, 2H).

Step 2: [2-(4,4-difluoroazepan-1-yl)-6-(trifluoromethyl)-3-pyridyl]boronic acid

[2-(4,4-Difluoroazepan-1-yl)-6-(trifluoromethyl)-3-pyridyl]boronic acid was prepared from 1-[3-bromo-6-(trifluoromethyl)-2-pyridyl]-4,4-difluoro-azepane using a procedure analogous to that found in Intermediate B-20, step 2 and triisopropyl borate. ESI-MS m/z calc. 324.11, found 325.2 $(M+1)^+$. $^1H$ NMR (400 MHz, DMSO-$d_6$) δ 7.72-7.62 (m, 1H), 7.00 (dd, J=7.3, 1.3 Hz, 1H), 3.71-3.60 (m, 2H), 3.54-3.46 (m, 3H), 2.39-2.18 (m, 2H), 2.13-1.83 (m, 5H).

Intermediate B-24

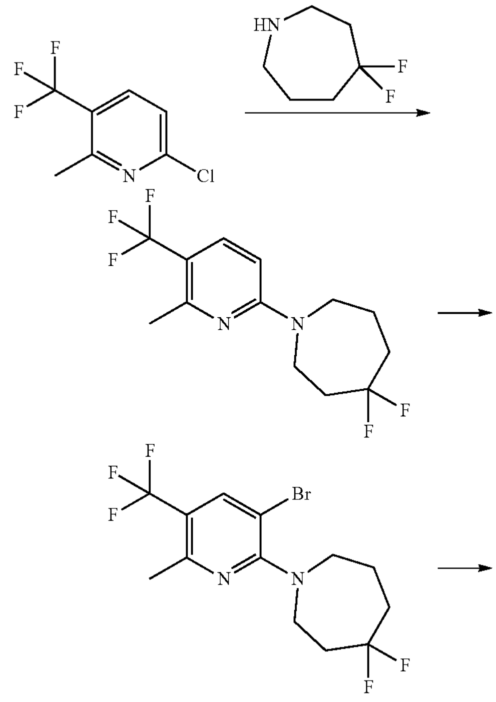

-continued

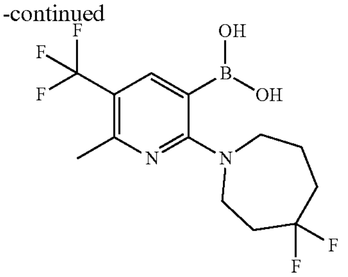

Step 1: 4,4-difluoro-1-[6-methyl-5-(trifluoromethyl)-2-pyridyl]azepane 4,4-Difluoro-1-[6-methyl-5-(trifluoromethyl)-2-pyridyl]azepane was prepared from 6-chloro-2-methyl-3-(trifluoromethyl)pyridine using a procedure analogous to that found in Intermediate B-20, step 1 with DMSO as solvent. ESI-MS m/z calc. 294.12, found 295.5 $(M+1)^+$. $^1H$ NMR (400 MHz, $CDCl_3$) δ 7.60 (d, J=8.9 Hz, 1H), 6.30 (d, J=8.9 Hz, 1H), 3.81-3.76 (m, 2H), 3.65 (t, J=6.1 Hz, 2H), 2.54-2.49 (m, 3H), 2.30-2.16 (m, 2H), 2.11-1.94 (m, 4H).

Step 2: 1-[3-bromo-6-methyl-5-(trifluoromethyl)-2-pyridyl]-4,4-difluoro-azepane 4,4-Difluoro-1-[6-methyl-5-(trifluoromethyl)-2-pyridyl]azepane (1.29 g, 4.38 mmol) and NBS (786 mg, 4.42 mmol) were combined in DCM (25 mL) and stirred at room temperature for 16 h. The reaction was evaporated and the resulting material purified by silica gel chromatography (0-20% ethyl acetate/hexanes) to provide 1-[3-bromo-6-methyl-5-(trifluoromethyl)-2-pyridyl]-4,4-difluoro-azepane (1.34 g, 82%) as a clear oil. ESI-MS m/z calc. 372.03, found 373.2 $(M+1)^+$. $^1H$ NMR (400 MHz, $CDCl_3$) δ 7.86 (s, 1H), 3.77 (t, J=6.3 Hz, 2H), 3.74-3.69 (m, 2H), 2.50-2.46 (m, 3H), 2.46-2.33 (m, 2H), 2.19-2.06 (m, 2H), 2.01-1.93 (m, 2H).

Step 3: [2-(4,4-difluoroazepan-1-yl)-6-methyl-5-(trifluoromethyl)-3-pyridyl]boronic acid

[2-(4,4-Difluoroazepan-1-yl)-6-methyl-5-(trifluoromethyl)-3-pyridyl]boronic acid was prepared from 1-[3-bromo-6-methyl-5-(trifluoromethyl)-2-pyridyl]-4,4-difluoro-azepane using a procedure analogous to that found in Intermediate B-20, step 2. ESI-MS m/z calc. 338.12, found 339.3 $(M+1)^+$. $^1H$ NMR (400 MHz, $CD_3OD$) δ 7.62 (s, 1H), 3.80-3.75 (m, 2H), 3.54-3.48 (m, 2H), 2.48 (s, 3H), 2.36-2.21 (m, 2H), 2.00-1.92 (m, 4H).

Intermediate B-25

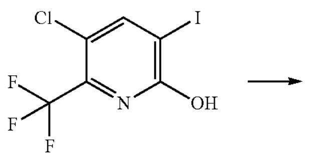

-continued

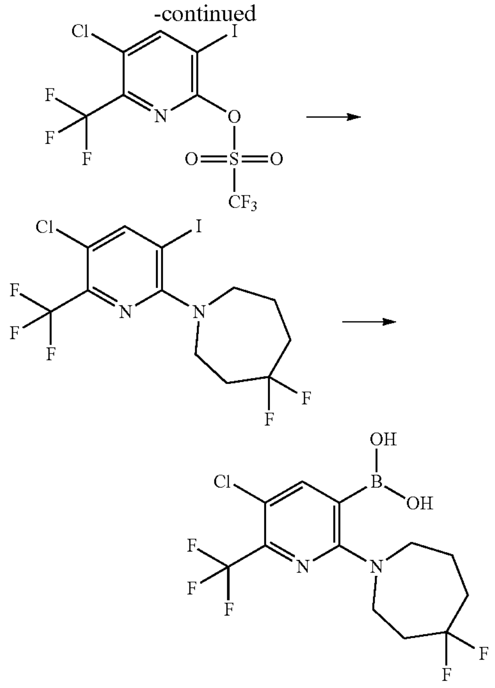

Step 1: [5-chloro-3-iodo-6-(trifluoromethyl)-2-pyridyl] trifluoromethanesulfonate

[5-Chloro-3-iodo-6-(trifluoromethyl)-2-pyridyl] trifluoromethanesulfonate was prepared from 5-chloro-3-iodo-6-(trifluoromethyl)pyridin-2-ol (Intermediate B-16, step 1) using a procedure analogous to that found in Intermediate B-16, step 3. ESI-MS m/z calc. 454.83, found 456.0 $(M+1)^+$. $^1H$ NMR (400 MHz, $CDCl_3$) δ 8.45 (s, 1H). $^{19}F$ NMR (377 MHz, $CDCl_3$) δ −66.56 (s, 3F), −71.85 (s, 3F).

Step 2: 1-[5-chloro-3-iodo-6-(trifluoromethyl)-2-pyridyl]-4,4-difluoro-azepane 1-[5-Chloro-3-iodo-6-(trifluoromethyl)-2-pyridyl]-4,4-difluoro-azepane was prepared from [5-chloro-3-iodo-6-(trifluoromethyl)-2-pyridyl] trifluoromethanesulfonate using a procedure analogous to that found in Intermediate B-20, step 1 with DIPEA as base and DMF as solvent. ESI-MS m/z calc. 439.96, found 441.2 $(M+1)^+$. $^1H$ NMR (400 MHz, $CDCl_3$) δ 8.17 (s, 1H), 3.71-3.57 (m, 4H), 2.47-2.33 (m, 2H), 2.24-2.09 (m, 2H), 2.02-1.92 (m, 2H). $^{19}F$ NMR (377 MHz, $CDCl_3$) δ −66.38 (s, 3F), −89.34 (quin, J=15.0 Hz, 2F).

Step 3: [5-chloro-2-(4,4-difluoroazepan-1-yl)-6-(trifluoromethyl)-3-pyridyl]boronic acid

[5-Chloro-2-(4,4-difluoroazepan-1-yl)-6-(trifluoromethyl)-3-pyridyl]boronic acid was prepared from 1-[5-chloro-3-iodo-6-(trifluoromethyl)-2-pyridyl]-4,4-difluoro-azepane using a procedure analogous to that found in Intermediate B-20, step 2 with triisopropyl borate and THF as the solvent. ESI-MS m/z calc. 358.07, found 359.1 $(M+1)^+$. $^1H$ NMR (400 MHz, $CDCl_3$) δ 7.14 (s, 1H), 5.35 (s, 2H), 3.80-3.72 (m, 2H), 3.66 (t, J=6.2 Hz, 2H), 2.31-2.17 (m, 2H), 2.12-1.94 (m, 4H). $^{19}F$ NMR (377 MHz, $CDCl_3$) δ −65.93 (s, 3F), −91.23 (quin, J=14.3 Hz, 2F).

Intermediate B-26

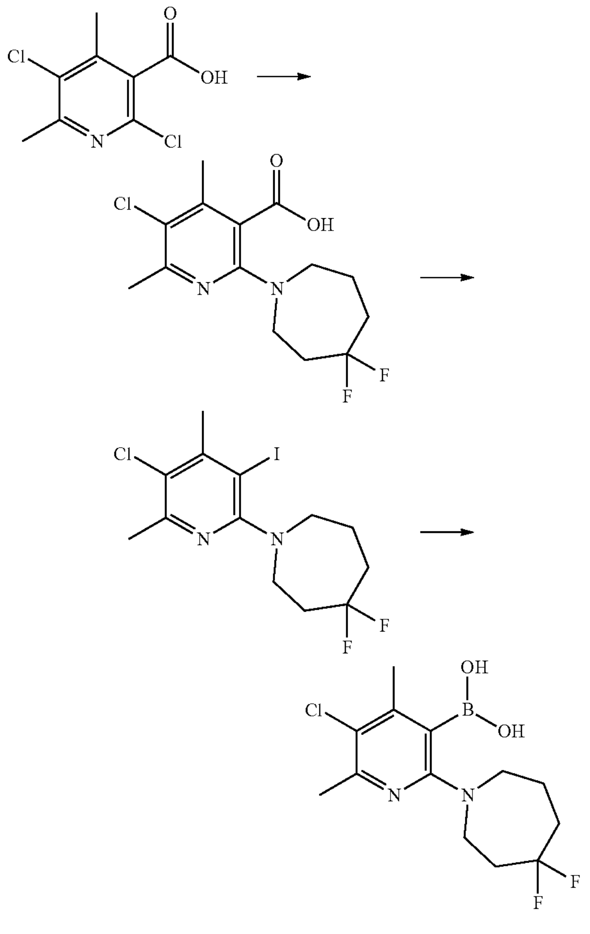

Step 1: 5-chloro-2-(4,4-difluoroazepan-1-yl)-4,6-dimethyl-pyridine-3-carboxylic acid 5-Chloro-2-(4,4-difluoroazepan-1-yl)-4,6-dimethyl-pyridine-3-carboxylic acid was prepared from 2,5-dichloro-4,6-dimethyl-pyridine-3-carboxylic acid and 4,4-difluoroazepane hydrochloride using a procedure analogous to that found in Intermediate B-20, step 1. ESI-MS m/z calc. 318.09, found 319.2 $(M+1)^+$. $^1H$ NMR (400 MHz, $CDCl_3$) δ 3.50-3.43 (m, 2H), 3.36 (t, J=6.0 Hz, 2H), 2.74 (s, 3H), 2.61 (s, 3H), 2.51-2.37 (m, 2H), 2.31-2.16 (m, 2H), 2.02 (dt, J=11.7, 6.0 Hz, 2H). $^{19}F$ NMR (377 MHz, $CDCl_3$) δ −88.93 (br s, 2F).

Step 2: 1-(5-chloro-3-iodo-4,6-dimethyl-2-pyridyl)-4,4-difluoro-azepane

A solution of 5-chloro-2-(4,4-difluoroazepan-1-yl)-4,6-dimethyl-pyridine-3-carboxylic acid (1.0 g, 3.1 mmol), potassium phosphate (670 mg, 3.16 mmol) and iodine (2.42 g, 9.54 mmol) in acetonitrile (15 mL) was purged with nitrogen for 5 min. The reaction vessel was sealed and the mixture stirred at 100° C. for 3 h. The reaction mixture was cooled to room temperature, diluted with 10% aqueous sodium thiosulfate (50 mL) and saturated aqueous sodium bicarbonate (50 mL), and extracted with dichloromethane (3×75 mL). The combined extracts were washed with 10% sodium thiosulfate (2×50 mL), dried over sodium sulfate, filtered and concentrated under reduced pressure. The crude product was adsorbed on silica gel under vacuum and purified by silica gel chromatography (0-10% ethyl acetate/heptanes) to provide 1-(5-chloro-3-iodo-4,6-dimethyl-2-pyridyl)-4,4-difluoro-azepane (1.03 g, 82%) as a light yellow oil. ESI-MS m/z calc. 400.00, found 401.0 $(M+1)^+$. $^1H$ NMR (400 MHz, $CDCl_3$) δ 3.42-3.33 (m, 4H), 2.63 (s, 3H), 2.50 (s, 3H), 2.42-2.24 (m, 4H), 1.98-1.91 (m, 2H). $^{19}F$ NMR (377 MHz, $CDCl_3$) δ −86.90 (quin, J=15.7 Hz, 2F).

Step 3: [5-chloro-2-(4,4-difluoroazepan-1-yl)-4,6-dimethyl-3-pyridyl]boronic acid

[5-Chloro-2-(4,4-difluoroazepan-1-yl)-4,6-dimethyl-3-pyridyl]boronic acid was prepared from 1-(5-chloro-3-iodo-4,6-dimethyl-2-pyridyl)-4,4-difluoro-azepane using a procedure analogous to that found in Intermediate B-20, step 2. ESI-MS m/z calc. 318.11, found 319.1 $(M+1)^+$. $^1H$ NMR (400 MHz, DMSO-$d_6$) δ 3.66-3.59 (m, 6H), 2.41 (s, 3H), 2.34-2.15 (m, 5H), 2.11-1.93 (m, 2H), 1.92-1.76 (m, 2H).

Intermediate B-27

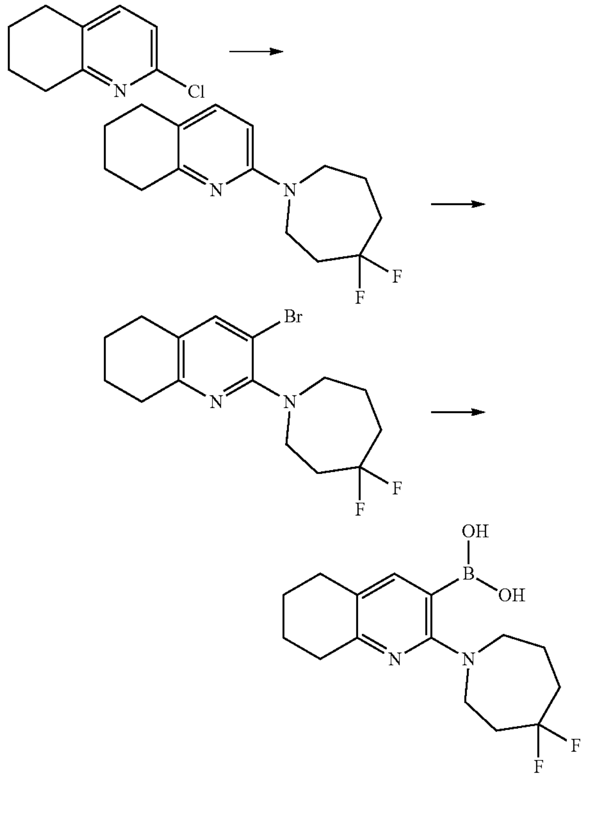

Step 1: 2-(4,4-difluoroazepan-1-yl)-5,6,7,8-tetrahydroquinoline

2-Chloro-5,6,7,8-tetrahydroquinoline (505 mg, 3.01 mmol), 4,4-difluoroazepane hydrochloride (535 mg, 3.12 mmol), potassium carbonate (1.321 g, 9.558 mmol), dicyclohexyl-[2-(2,6-diisopropoxyphenyl)phenyl]phosphane (88.6 mg, 0.190 mmol), and diacetoxypalladium (35 mg, 0.16 mmol) were combined in DMSO (2.5 mL). The reaction mixture was flushed with nitrogen and heated at 110° C. for 24 h. The reaction was cooled, diluted with DCM (2 mL) and purified by silica gel chromatography (0-10% methanol/dichloromethane) to provide 2-(4,4-difluoroazepan-1-yl)-5,6,7,8-tetrahydroquinoline (532 mg, 66%). ESI-MS m/z calc. 266.16, found 267.4 $(M+1)^+$. $^1H$ NMR (400 MHz, $CDCl_3$) δ 7.15 (d, J=8.5 Hz, 1H), 6.28 (d, J=8.5 Hz, 1H), 3.74-3.68 (m, 2H), 3.60 (t, J=6.2 Hz, 2H), 2.72 (t, J=6.4 Hz, 2H), 2.65-2.57 (m, 2H), 2.28-2.14 (m, 2H), 2.09-1.90 (m, 4H), 1.87-1.79 (m, 2H), 1.79-1.72 (m, 2H).

Step 2: 3-bromo-2-(4,4-difluoroazepan-1-yl)-5,6,7,8-tetrahydroquinoline

3-Bromo-2-(4,4-difluoroazepan-1-yl)-5,6,7,8-tetrahydroquinoline was prepared from 2-(4,4-difluoroazepan-1-yl)-5,6,7,8-tetrahydroquinoline using a procedure analogous to that found in Intermediate B-24, step 2. ESI-MS m/z calc. 344.07, found 345.2 $(M+1)^+$. $^1H$ NMR (400 MHz, $CDCl_3$) δ 7.46 (s, 1H), 3.56-3.47 (m, 4H), 2.71 (t, J=6.4 Hz, 2H), 2.64 (t, J=6.3 Hz, 2H), 2.44-2.29 (m, 2H), 2.27-2.13 (m, 2H), 1.97-1.88 (m, 2H), 1.88-1.79 (m, 2H), 1.79-1.71 (m, 2H).

Step 3: [2-(4,4-difluoroazepan-1-yl)-5,6,7,8-tetrahydroquinolin-3-yl]boronic acid

[2-(4,4-difluoroazepan-1-yl)-5,6,7,8-tetrahydroquinolin-3-yl]boronic acid was prepared from 3-Bromo-2-(4,4-difluoroazepan-1-yl)-5,6,7,8-tetrahydroquinoline using a procedure analogous to that found in Intermediate B-20, step 2. ESI-MS m/z calc. 310.17, found 311.2 $(M+1)^+$.

Intermediate B-28

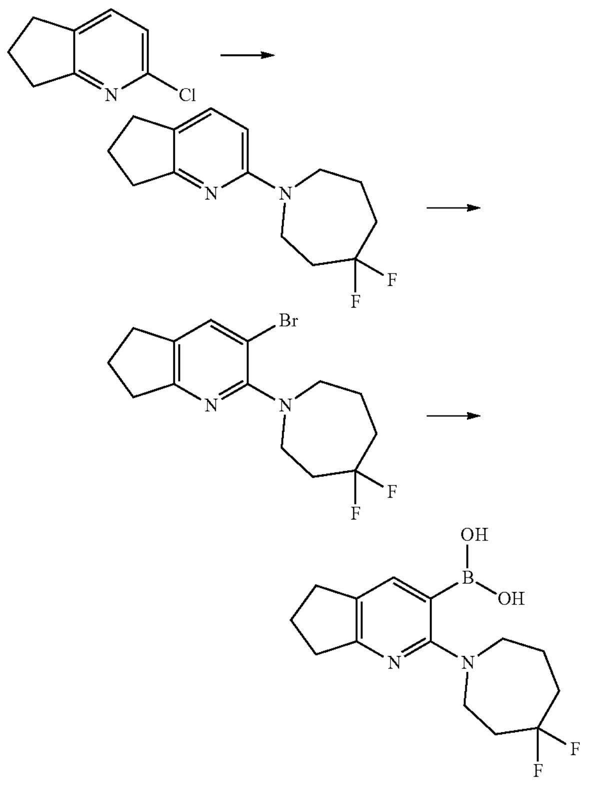

Step 1: 2-(4,4-difluoroazepan-1-yl)-6,7-dihydro-5H-cyclopenta[b]pyridine 2-(4,4-Difluoroazepan-1-yl)-6,7-dihydro-5H-cyclopenta[b]pyridine was prepared from 2-Chloro-6,7-dihydro-5H-cyclopenta[b]pyridine using a procedure analogous to that found in Intermediate B-27, step 1. ESI-MS m/z calc. 252.14, found 253.3 $(M+1)^+$. $^1$H NMR (400 MHz, $CDCl_3$) δ 7.30 (d, J=8.5 Hz, 1H), 6.24 (d, J=8.4 Hz, 1H), 3.75-3.69 (m, 2H), 3.62 (t, J=6.2 Hz, 2H), 2.85 (t, J=7.6 Hz, 2H), 2.79 (t, J=7.3 Hz, 2H), 2.29-2.17 (m, 2H), 2.11-1.92 (m, 6H).

Step 2: 3-bromo-2-(4,4-difluoroazepan-1-yl)-6,7-dihydro-5H-cyclopenta[b]pyridine 3-Bromo-2-(4,4-difluoroazepan-1-yl)-6,7-dihydro-5H-cyclopenta[b]pyridine was prepared from 2-(4,4-difluoroazepan-1-yl)-6,7-dihydro-5H-cyclopenta[b]pyridine using a procedure analogous to that found in Intermediate B-24, step 2. ESI-MS m/z calc. 330.05, found 331.2 $(M+1)^+$. $^1$H NMR (400 MHz, $CDCl_3$) δ 7.60 (s, 1H), 3.54-3.44 (m, 4H), 2.89-2.79 (m, 4H), 2.45-2.30 (m, 2H), 2.30-2.17 (m, 2H), 2.11 (p, J=7.6 Hz, 2H), 1.98-1.88 (m, 2H).

Step 3: [2-(4,4-difluoroazepan-1-yl)-6,7-dihydro-5H-cyclopenta[b]pyridin-3-yl]boronic acid

[2-(4,4-Difluoroazepan-1-yl)-6,7-dihydro-5H-cyclopenta[b]pyridin-3-yl]boronic acid was prepared from -bromo-2-(4,4-difluoroazepan-1-yl)-6,7-dihydro-5H-cyclopenta[b]pyridine using a procedure analogous to that found in Intermediate B-20, step 2. ESI-MS m/z calc. 296.15, found 297.1 $(M+1)^+$.

Intermediate B-29

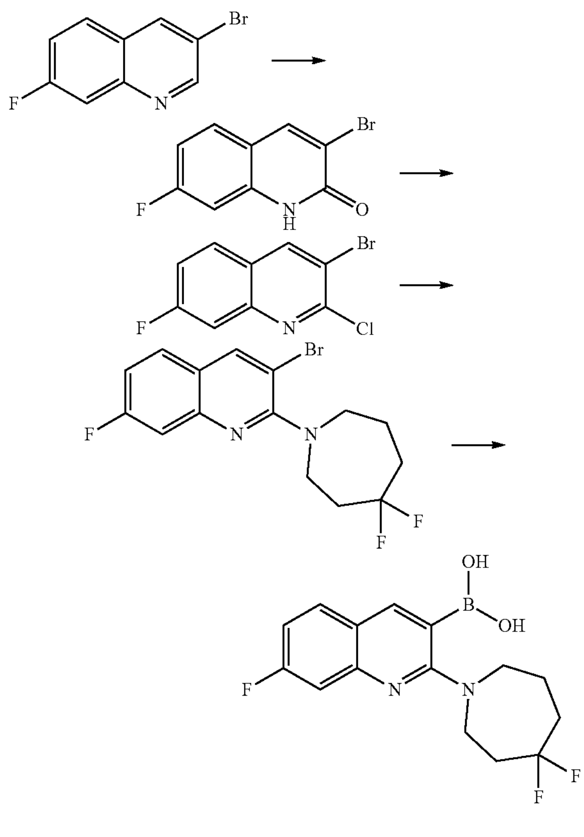

Step 1: 3-bromo-7-fluoro-1H-quinolin-2-one

Methyltrioxorhenium (70 mg, 0.20 mmol) was added to a solution of hydrogen peroxide (23 mL of 30% w/v in water, 202.85 mmol) in THF (18 mL) and the mixture was stirred for 15 min. 3-Bromo-7-fluoro-quinoline (4.5 g, 20 mmol) was added and the mixture stirred at room temperature for 20 h. The mixture was diluted with ethyl acetate (150 mL), cooled to 5° C. and quenched using aqueous 10% sodium thiosulfate (150 mL). The organic layer was separated and the aqueous layer was extracted with ethyl acetate (2×150 mL). The combined organic extracts were washed with saturated aqueous sodium bicarbonate (150 mL) and brine (150 mL), dried over sodium sulfate, filtered and concentrated under reduced pressure. The crude product was adsorbed on silica gel and purified by silica gel chromatography (120 g silica, 0-80% ethyl acetate/heptane) to afford 3-bromo-7-fluoro-1H-quinolin-2-one (4.19 g, 87%) as a tan solid. ESI-MS m/z calc. 240.95, found 242.0 $(M+1)^+$. $^1$H NMR (400 MHz, $CDCl_3$) δ 8.65 (s, 1H), 8.35 (dd, J=9.5, 2.2 Hz, 1H), 7.91 (s, 1H), 7.83 (dd, J=9.0, 5.4 Hz, 1H), 7.46 (d, J=1.2 Hz, 1H). $^{19}$F NMR (377 MHz, $CDCl_3$) δ −104.95--105.05 (m, 1F).

Step 2: 3-bromo-2-chloro-7-fluoro-quinoline

3-Bromo-2-chloro-7-fluoro-quinoline was prepared from 3-bromo-7-fluoro-1H-quinolin-2-one using a procedure analogous to that found in Intermediate B-6, step 1. ESI-MS m/z calc. 258.92, found 260.0 $(M+1)^+$. $^1$H NMR (400 MHz, $CDCl_3$) δ 8.44 (s, 1H), 7.80-7.75 (m, 1H), 7.66 (dd, J=9.7, 2.3 Hz, 1H), 7.39 (td, J=8.6, 2.4 Hz, 1H). $^{19}$F NMR (377 MHz, $CDCl_3$) δ −106.35--106.44 (m, 1F).

Step 3: 3-bromo-2-(4,4-difluoroazepan-1-yl)-7-fluoro-quinoline

A solution of 3-bromo-2-chloro-7-fluoro-quinoline (4.14 g, 15.5 mmol), 4,4-difluoroazepane hydrochloride (4.0 g, 23 mmol), cesium carbonate (12.7 g, 39.0 mmol), copper iodide (300 mg, 1.58 mmol) and N,N,N',N'-tetramethylethane-1,2-diamine (186 mg, 0.24 mL, 1.6 mmol) in NMP (50 mL) was stirred at 105° C. overnight. Once cooled to room temperature, the reaction mixture was diluted with water (50 mL) and extracted using ethyl acetate (3×20 mL). The organic layers were combined, washed with brine (20 mL), dried over sodium sulfate and concentrated under reduced pressure. The residue was purified by silica gel chromatography (0-10% of ethyl acetate/heptanes), followed by reverse phase chromatography (C18, 5-95% $CH_3CN$/0.1% formic acid) to provide 3-bromo-2-(4,4-difluoroazepan-1-yl)-7-fluoro-quinoline (2.3 g, 37%) as a light yellow oil. ESI-MS m/z calc. 358.03, found 359.0 $(M+1)^+$. $^1$H NMR (400 MHz, $CDCl_3$) δ 8.23 (s, 1H), 7.57 (dd, J=8.8, 6.1 Hz, 1H), 7.38 (dd, J=10.5, 2.4 Hz, 1H), 7.11 (td, J=8.6, 2.6 Hz, 1H), 3.80-3.68 (m, 4H), 2.55-2.42 (m, 2H), 2.29-2.17 (m, 2H), 2.05-1.98 (m, 2H). $^{19}$F NMR (377 MHz, $CDCl_3$) δ −88.99 (quin, J=15.0 Hz, 2F), −109.50--109.60 (m, 1F).

Step 4: [2-(4,4-difluoroazepan-1-yl)-7-fluoro-3-quinolyl]boronic acid

[2-(4,4-Difluoroazepan-1-yl)-7-fluoro-3-quinolyl]boronic acid was prepared from 3-bromo-2-(4,4-difluoroazepan-1-yl)-7-fluoro-quinoline using a procedure analogous to that found in Intermediate B-2, step 4 using 4,4,5,5-tetramethyl-2-(4,4,5,5-tetramethyl-1,3,2-dioxaborolan-2-yl)-1,3,2-dioxaborolane and dioxane as the organic solvent. ESI-MS m/z calc. 324.11, found 325.2 $(M+1)^+$.

Intermediate B-30

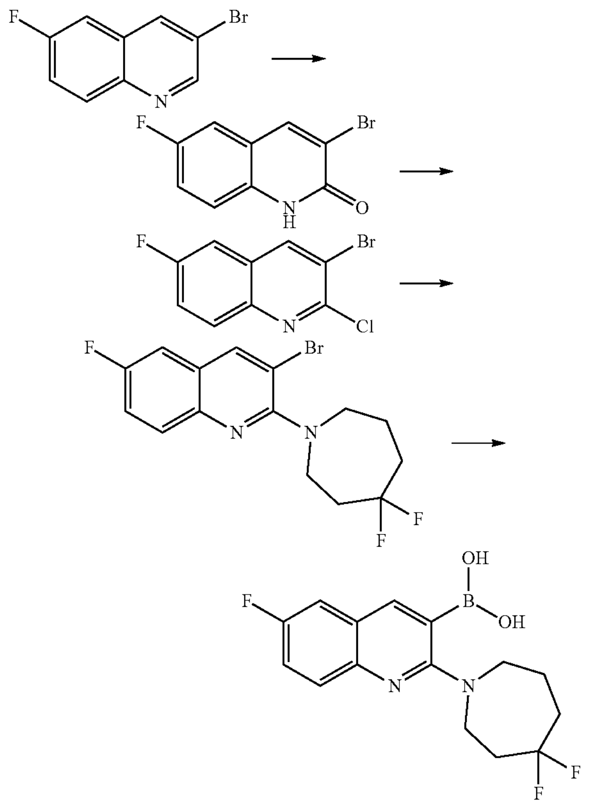

Step 1: 3-bromo-6-fluoro-1H-quinolin-2-one

3-Bromo-6-fluoro-1H-quinolin-2-one was prepared from 3-bromo-6-fluoro-quinoline using a procedure analogous to that found in Intermediate B-29, step 1. ESI-MS m/z calc. 240.95, found 242.0 $(M+1)^+$. $^1H$ NMR (400 MHz, DMSO-$d_6$) δ 8.87 (s, 1H), 8.53 (dd, J=9.4, 5.3 Hz, 1H), 8.26 (s, 1H), 7.89 (dd, J=9.2, 2.8 Hz, 1H), 7.80-7.70 (m, 1H). $^{19}F$ NMR (377 MHz, DMSO-$d_6$) δ −109.88 (s, 1F).

Step 2: 3-bromo-2-chloro-6-fluoro-quinoline

3-Bromo-2-chloro-6-fluoro-quinoline was prepared from 3-bromo-6-fluoro-1H-quinolin-2-one using a procedure analogous to that found in Intermediate B-6, step 1. ESI-MS m/z calc. 258.92, found 259.9 $(M+1)^+$. $^1H$ NMR (400 MHz, DMSO-$d_6$) δ 8.94 (s, 1H), 8.07 (dd, J=9.2, 5.3 Hz, 1H), 7.89-7.74 (m, 2H). $^{19}F$ NMR (377 MHz, DMSO-$d_6$) δ −110.94 (s, 1F).

Step 3: 3-bromo-2-(4,4-difluoroazepan-1-yl)-6-fluoro-quinoline

3-Bromo-2-(4,4-difluoroazepan-1-yl)-6-fluoro-quinoline was prepared from 3-bromo-2-(4,4-difluoroazepan-1-yl)-6-fluoro-quinoline and 4,4-difluoroazepane hydrochloride using a procedure analogous to that found in Intermediate B-29, step 3. ESI-MS m/z calc. 358.03, found 359.0 $(M+1)^+$. $^1H$ NMR (400 MHz, DMSO-$d_6$) δ 8.59 (s, 1H), 7.75 (dd, J=9.3, 5.4 Hz, 1H), 7.66-7.49 (m, 2H), 3.71-3.60 (m, 4H), 2.49-2.38 (m, 2H), 2.31-2.13 (m, 2H), 1.98-1.87 (m, 2H). $^{19}F$ NMR (377 MHz, DMSO-$d_6$) δ −86.16 (s, 2F), −116.86 (s, 1F).

Step 4: [2-(4,4-difluoroazepan-1-yl)-6-fluoro-3-quinolyl]boronic acid

[2-(4,4-Difluoroazepan-1-yl)-6-fluoro-3-quinolyl]boronic acid was prepared from 3-bromo-2-(4,4-difluoroazepan-1-yl)-6-fluoro-quinoline using a procedure analogous to that found in Intermediate B-2, step 4 using 4,4,5,5-tetramethyl-2-(4,4,5,5-tetramethyl-1,3,2-dioxaborolan-2-yl)-1,3,2-dioxaborolane and dioxane as the organic solvent. ESI-MS m/z calc. 324.11, found 325.1 $(M+1)^+$.

Intermediate B-31

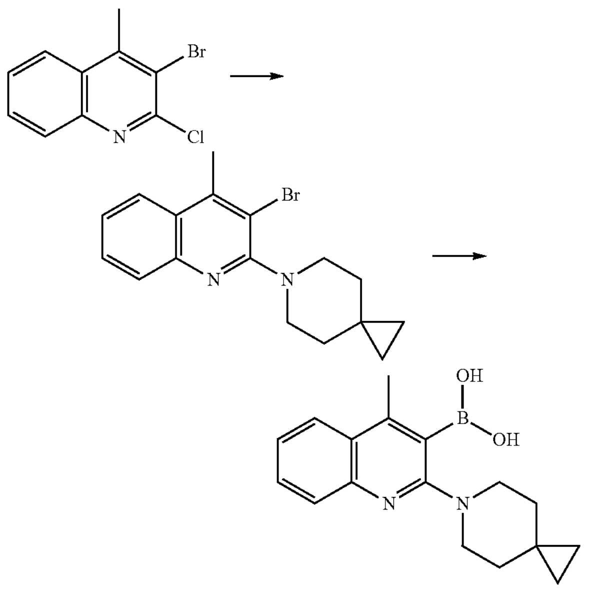

Step 1: 2-(6-azaspiro[2.5]octan-6-yl)-3-bromo-4-methyl-quinoline 2-(6-Azaspiro[2.5]octan-6-yl)-3-bromo-4-methyl-quinoline was prepared from 3-bromo-2-chloro-4-methyl-quinoline and 6-azaspiro[2.5]octane using a procedure analogous to that found in Intermediate B-29, step 3 using DMSO as the solvent. $^1H$ NMR (400 MHz, $CDCl_3$) δ 7.91-7.85 (m, 2H), 7.63-7.59 (m, 1H), 7.42-7.38 (m, 1H), 3.43 (t, J=5.3 Hz, 4H), 2.81 (s, 3H), 1.61 (br s, 4H), 0.38-0.34 (m, 4H).

Step 3: [2-(6-azaspiro[2.5]octan-6-yl)-4-methyl-3-quinolyl]boronic acid

[2-(6-Azaspiro[2.5]octan-6-yl)-4-methyl-3-quinolyl]boronic acid was prepared using a procedure analogous to that found in Intermediate B-20, step 2. ESI-MS m/z calc. 296.17, found 297.04 $(M+1)^+$. $^1H$ NMR (400 MHz, $CD_3OD$) δ 7.93 (dd, J=8.2, 0.9 Hz, 1H), 7.77-7.75 (m, 1H), 7.59-7.55 (m, 1H), 7.38-7.34 (m, 1H), 3.51 (m, 4H), 2.60 (s, 3H), 1.55-1.51 (m, 4H), 0.39 (s, 4H). Boronic acid protons not observed.

Intermediate B-32

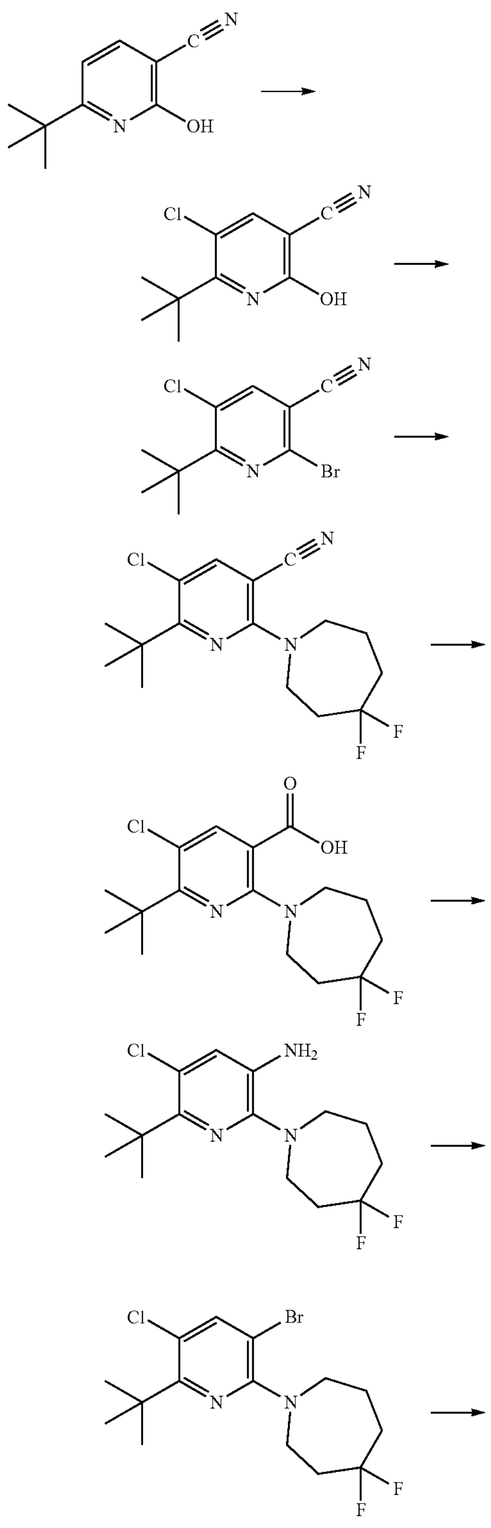

-continued

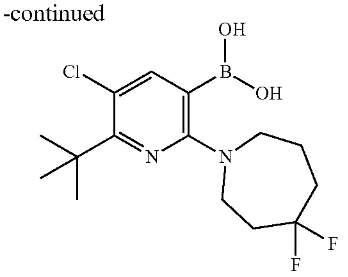

Step 1: 6-tert-butyl-5-chloro-2-hydroxy-pyridine-3-carbonitrile

A solution of 6-tert-butyl-2-hydroxy-pyridine-3-carbonitrile (5.0 g, 28 mmol) and NCS (4.7 g, 35 mmol) in anhydrous 1,2-dichloroethane (25 mL) was stirred at 80° C. for 4 h. The reaction was cooled to room temperature, diluted with saturated aqueous sodium bicarbonate (100 mL) and water (100 mL), and extracted with DCM (2×300 mL). The combined organic layers were washed with water (200 mL) and brine (200 mL), dried over sodium sulfate, filtered and concentrated under reduced pressure to provide 6-tert-butyl-5-chloro-2-hydroxy-pyridine-3-carbonitrile (5.99 g, 100%) as a beige solid. ESI-MS m/z calc. 210.06, found 211.2 $(M+1)^+$. $^1H$ NMR (400 MHz, $CDCl_3$) δ 9.94 (br s, 1H), 7.78 (s, 1H), 1.53 (s, 9H).

Step 2: 2-bromo-6-tert-butyl-5-chloro-pyridine-3-carbonitrile

To a stirring suspension of 6-tert-butyl-5-chloro-2-hydroxy-pyridine-3-carbonitrile (5.9 g, 28 mmol) in toluene (90 mL) was added $POBr_3$ (11 g, 38 mmol). The reaction mixture was stirred at 95° C. for 16 h. After the reaction mixture was cooled to room temperature, it was quenched by slow addition of sodium bicarbonate saturated aqueous solution (150 mL). The mixture was poured in a separatory funnel with water (200 mL) and extracted with ethyl acetate (2×200 mL). The combined organic layers were washed with brine (100 mL), dried over sodium sulfate, filtered and concentrated under reduced pressure. The residue was adsorbed on silica gel under vacuum and purified by silica gel chromatography (120 g silica, 0-10% ethyl acetate/heptane) to provide 2-bromo-6-tert-butyl-5-chloro-pyridine-3-carbonitrile (6.29 g, 82%). ESI-MS m/z calc. 271.97, found 273.0 $(M+1)^+$. $^1H$ NMR (400 MHz, $CDCl_3$) δ 7.81 (s, 1H), 1.48 (s, 9H).

Step 3: 6-tert-butyl-5-chloro-2-(4,4-difluoroazepan-1-yl)pyridine-3-carbonitrile 6-tert-Butyl-5-chloro-2-(4,4-difluoroazepan-1-yl)pyridine-3-carbonitrile was prepared from 2-bromo-6-tert-butyl-5-chloro-pyridine-3-carbonitrile using a procedure analogous to that found in Intermediate B-20, step 1 with DMF solvent and DIPEA. ESI-MS m/z calc. 327.13, found 328.2 $(M+1)^+$. $^1H$ NMR (400 MHz, $CDCl_3$) δ 7.64 (s, 1H), 3.89 (t, J=5.9 Hz, 2H), 3.87-3.83 (m, 2H), 2.39-2.27 (m, 2H), 2.14-2.02 (m, 4H), 1.44 (s, 9H). $^{19}F$ NMR (377 MHz, $CDCl_3$) δ −91.74 (s, 2F).

Step 4: 6-tert-butyl-5-chloro-2-(4,4-difluoroazepan-1-yl)pyridine-3-carboxylic acid A solution of 6-tert-butyl-5-chloro-2-(4,4-difluoroazepan-1-yl)pyridine-3-carbonitrile (3.8 g, 11 mmol) in ethanol (50 mL) and aqueous NaOH (11.2 mL of 10 M, 112 mmol) was stirred at 100° C. for 24 h. Additional aqueous NaOH (11.2 mL of 10 M, 112 mmol) was added and the mixture stirred at 115° C. for 24 h. The mixture was cooled to room temperature, ethanol was removed under reduced pressure and aqueous 6 M HCl added until pH 6 to 7. The mixture was diluted with water (400 mL) and ethyl acetate (300 mL) and the layers separated. The aqueous layer was extracted with additional ethyl acetate (3×200 mL). The combined organic layers were dried over sodium sulfate, filtered and concentrated under reduced pressure. Purification by reverse phase chromatography (C18, 0-35% $CH_3CN$/0.1% formic acid) provided 6-tert-butyl-5-chloro-2-(4,4-difluoroazepan-1-yl)pyridine-3-carboxylic acid (3.03 g, 75%) as a tan solid. ESI-MS m/z calc. 346.13, found 347.2 $(M+1)^+$. $^1H$ NMR (400 MHz, $CDCl_3$) δ 8.25 (s, 1H), 3.57-3.51 (m, 2H), 3.32 (t, J=5.7 Hz, 2H), 2.47-2.36 (m, 2H), 2.24-2.12 (m, 2H), 2.07-1.98 (m, 2H), 1.49 (s, 9H). $^{19}F$ NMR (377 MHz, $CDCl_3$) δ −89.67 (br s, 2F).

Step 5 & 6: 6-tert-butyl-5-chloro-2-(4,4-difluoro-azepan-1-yl)pyridin-3-amine 6-tert-Butyl-5-chloro-2-(4,4-difluoroazepan-1-yl)pyridin-3-amine was prepared from 6-tert-butyl-5-chloro-2-(4,4-difluoroazepan-1-yl)pyridine-3-carboxylic acid using a procedure analogous to that found in Intermediate B-11, step 5 and step 6. ESI-MS m/z calc. 317.15, found 318.2 $(M+1)^+$. $^1H$ NMR (400 MHz, $CDCl_3$) δ 7.15 (s, 1H), 3.92-3.73 (m, 4H), 2.39-2.21 (m, 4H), 1.70-1.47 (m, 2H), 1.44 (s, 9H). $^{19}F$ NMR (377 MHz, $CDCl_3$) δ −87.95−−89.92 (m, 1F), −92.01−−93.92 (m, 1F).

Step 7: 1-(3-bromo-6-tert-butyl-5-chloro-2-pyridyl)-4,4-difluoro-azepane 1-(3-Bromo-6-tert-butyl-5-chloro-2-pyridyl)-4,4-difluoro-azepane was prepared from 6-tert-butyl-5-chloro-2-(4,4-difluoroazepan-1-yl)pyridin-3-amine using a procedure analogous to that found in Intermediate B-4, step 6. ESI-MS m/z calc. 380.05, found 381.2 $(M+1)^+$. $^1H$ NMR (400 MHz, $CDCl_3$) δ 7.67 (s, 1H), 3.67 (t, J=6.2 Hz, 2H), 3.65-3.59 (m, 2H), 2.44-2.32 (m, 2H), 2.21-2.10 (m, 2H), 2.00-1.92 (m, 2H), 1.43 (s, 9H). $^{19}F$ NMR (377 MHz, $CDCl_3$) δ −89.67 (s, 2F).

Step 8: [6-tert-butyl-5-chloro-2-(4,4-difluoroazepan-1-yl)-3-pyridyl]boronic acid

[6-tert-butyl-5-chloro-2-(4,4-difluoroazepan-1-yl)-3-pyridyl]boronic acid was prepared from 1-(3-bromo-6-tert-butyl-5-chloro-2-pyridyl)-4,4-difluoro-azepane using a procedure analogous to that found in Intermediate B-1, step 2. ESI-MS m/z calc. 346.14, found 347.2 $(M+1)^+$.

Intermediate B-33

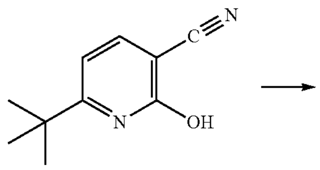

-continued

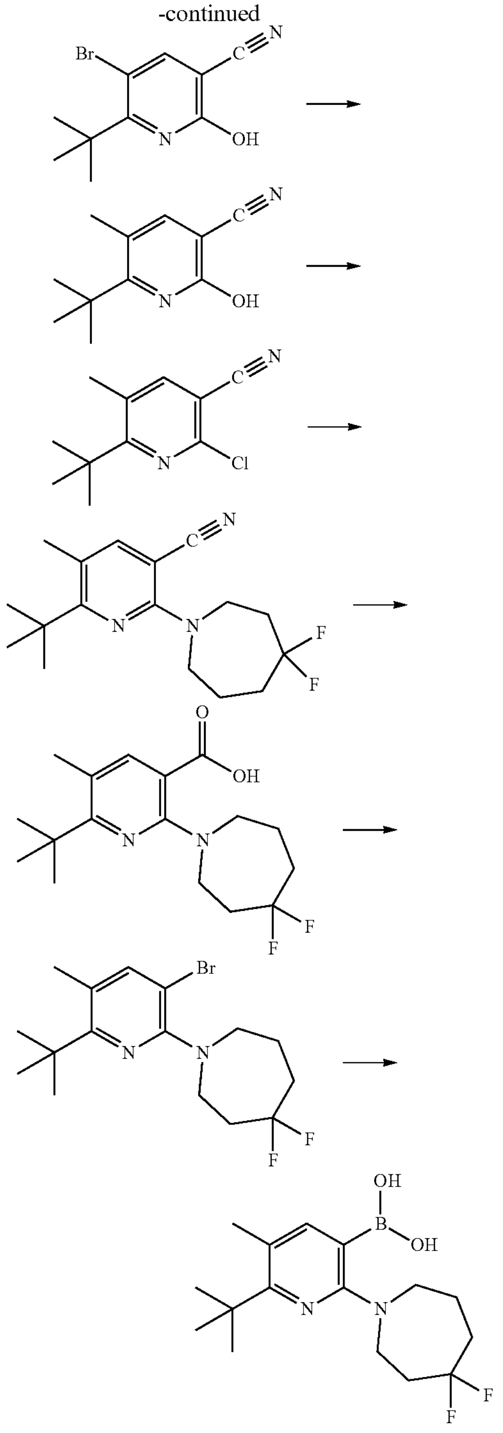

Step 1: 5-bromo-6-tert-butyl-2-hydroxy-pyridine-3-carbonitrile

A solution of 6-tert-butyl-2-hydroxy-pyridine-3-carbonitrile (10.9 g, 61.8 mmol) and NBS (16.5 g, 92.7 mmol) in anhydrous 1,2-dichloroethane (85 mL) was stirred at reflux for 2.5 h. The mixture was cooled to room temperature, diluted with water (300 mL) extracted with DCM (3×300 mL). The combined organic layers were washed with brine (150 mL), dried over sodium sulfate, filtered and concentrated under reduced pressure. Purification by silica gel chromatography (120 g silica, 0-10% methanol/DCM) provided 5-bromo-6-tert-butyl-2-hydroxy-pyridine-3-carbonitrile (16.11 g, 100%) as a yellow solid. ESI-MS m/z calc. 254.01, found 255.2 $(M+1)^+$. $^1$H NMR (400 MHz, DMSO-$d_6$) δ 8.37 (s, 1H), 1.45 (s, 9H).

Step 2: 6-tert-butyl-2-hydroxy-5-methyl-pyridine-3-carbonitrile

A mixture of 5-bromo-6-tert-butyl-2-hydroxy-pyridine-3-carbonitrile (1.0 g, 3.9 mmol), potassium carbonate (1.65 g, 11.9 mmol), Pd(dppf)$Cl_2$·DCM (700 mg, 0.857 mmol) and 2,4,6-trimethyl-1,3,5,2,4,6-trioxatriborinane (2.25 g, 2.5 mL, 17.9 mmol) in 1,4-dioxane (15 mL) was stirred at 120° C. for 8 h in a sealed vial. The mixture was cooled to room temperature and diluted with ethyl acetate (50 mL). The mixture was filtered through Celite®, rinsed with ethyl acetate (50 mL) and concentrated under reduced pressure. Purification by silica gel chromatography (40 g silica, 5-90% ethyl acetate/DCM) provided 6-tert-butyl-2-hydroxy-5-methyl-pyridine-3-carbonitrile (642 mg, 82%) as a yellow solid. ESI-MS m/z calc. 190.11, found 191.2 $(M+1)^+$. $^1$H NMR (400 MHz, $CDCl_3$) δ 9.34 (br s, 1H), 7.63 (s, 1H), 2.29 (s, 3H), 1.45 (s, 9H).

Step 3: 6-tert-butyl-2-chloro-5-methyl-pyridine-3-carbonitrile 6-tert-Butyl-2-chloro-5-methyl-pyridine-3-carbonitrile was prepared from 6-tert-butyl-2-hydroxy-5-methyl-pyridine-3-carbonitrile using a procedure analogous to that found in Intermediate B-6, step 1. ESI-MS m/z calc. 208.08, found 209.2 $(M+1)^+$. $^1$H NMR (400 MHz, $CDCl_3$) δ 7.64 (s, 1H), 2.52 (s, 3H), 1.42 (s, 9H).

Step 4: 6-tert-butyl-2-(4,4-difluoroazepan-1-yl)-5-methyl-pyridine-3-carbonitrile 6-tert-Butyl-2-(4,4-difluoroazepan-1-yl)-5-methyl-pyridine-3-carbonitrile was prepared from 6-tert-butyl-2-chloro-5-methyl-pyridine-3-carbonitrile and 4,4-difluoroazepane hydrochloride using a procedure analogous to that found in Intermediate B-20, step 1 and DIPEA as the base. ESI-MS m/z calc. 307.19, found 308.4 $(M+1)^+$. $^1$H NMR (400 MHz, $CDCl_3$) δ 7.45 (s, 1H), 3.90 (t, J=6.0 Hz, 2H), 3.85 (dt, J=5.4, 2.7 Hz, 2H), 2.38 (s, 3H), 2.43-2.28 (m, 2H), 2.17-1.99 (m, 4H), 1.39 (s, 9H). $^{19}$F NMR (377 MHz, $CDCl_3$) δ −91.53 (s, 2F).

Step 5: 6-tert-butyl-2-(4,4-difluoroazepan-1-yl)-5-methyl-pyridine-3-carboxylic acid 6-tert-Butyl-2-(4,4-difluoroazepan-1-yl)-5-methyl-pyridine-3-carboxylic acid was prepared from 6-tert-butyl-2-(4,4-difluoroazepan-1-yl)-5-methyl-pyridine-3-carbonitrile using a procedure analogous to that found in Intermediate B-32, step 4. ESI-MS m/z calc. 326.18, found 327.4 $(M+1)^+$. $^1$H NMR (400 MHz, $CDCl_3$) δ 8.20 (s, 1H), 3.41-3.33 (m, 2H), 3.33-3.25 (m, 2H), 2.57 (s, 3H), 2.54-2.42 (m, 2H), 2.40-2.26 (m, 2H), 2.10-2.01 (m, 2H), 1.45 (s, 9H). $^{19}$F NMR (377 MHz, $CDCl_3$) δ −87.53 (br s, 2F).

Step 6: 1-(3-bromo-6-tert-butyl-5-methyl-2-pyridyl)-4,4-difluoro-azepane

A solution of 6-tert-butyl-2-(4,4-difluoroazepan-1-yl)-5-methyl-pyridine-3-carboxylic acid (720 mg, 2.21 mmol) and sodium acetate (400 mg, 4.88 mmol) in acetic acid (10 mL) was stirred at room temperature for 30 min. A solution of bromine (47 mg, 0.15 mL, 2.9 mmol) in acetic acid (3 mL) was slowly added and reaction mixture was stirred at room temperature overnight. The reaction mixture was diluted with water (50 mL) and extracted using ethyl acetate (3×30 mL). The combined organic layers were dried over sodium sulfate, filtered and concentrated under reduced pressure. Purification by silica gel chromatography (0-10% ethyl acetate/heptane) provided 1-(3-bromo-6-tert-butyl-5-methyl-2-pyridyl)-4,4-difluoro-azepane (426 mg, 53%) as a clear oil. ESI-MS m/z calc. 360.10, found 361.2 $(M+1)^+$. $^1$H NMR (400 MHz, $CDCl_3$) δ 7.47 (s, 1H), 3.65 (t, J=6.4 Hz, 2H), 3.62-3.55 (m, 2H), 2.38 (s, 3H), 2.47-2.31 (m, 2H), 2.26-2.11 (m, 2H), 2.00-1.90 (m, 2H), 1.38 (s, 9H). $^{19}$F NMR (377 MHz, $CDCl_3$) δ −89.01 (s, 2F).

Step 7: [6-tert-butyl-2-(4,4-difluoroazepan-1-yl)-5-methyl-3-pyridyl]boronic acid A round-bottom flask was charged with 1-(3-bromo-6-tert-butyl-5-methyl-2-pyridyl)-4,4-difluoro-azepane (300 mg, 0.830 mmol), XPhos Pd G4 (60 mg, 0.070 mmol), XPhos (60 mg, 0.13 mmol), hypoboric acid (300 mg, 3.35 mmol) and potassium acetate (360 mg, 3.67 mmol) in ethanol (12 mL). The mixture was bubbled with nitrogen for 5 min and stirred at 85° C. for 1.5 h. Ethanol was removed by concentration under reduced pressure and the residue partitioned between water (20 mL) and ethyl acetate (30 mL). The aqueous phase was extracted with additional ethyl acetate (2×20 mL), and the combined organic layers dried over sodium sulfate, filtered and concentrated under reduced pressure to afford [6-tert-butyl-2-(4,4-difluoroazepan-1-yl)-5-methyl-3-pyridyl]boronic acid (389 mg, 76%). ESI-MS m/z calc. 326.20, found 327.2 $(M+1)^+$.

Intermediate B-34

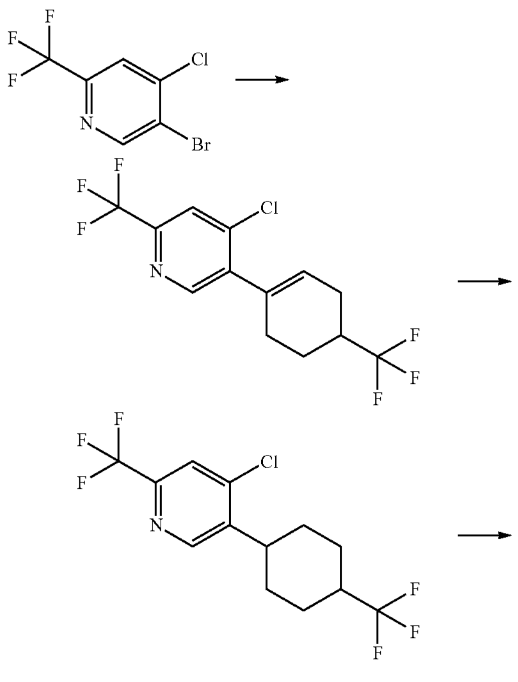

-continued

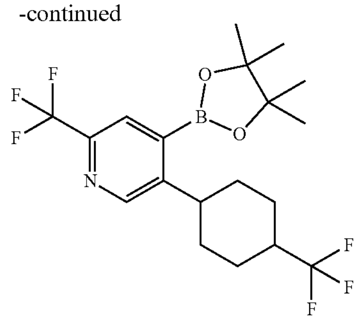

Step 1: 4-chloro-2-(trifluoromethyl)-5-[4-(trifluoromethyl)cyclohexen-1-yl]pyridine A vial was charged with 5-bromo-4-chloro-2-(trifluoromethyl)pyridine (617 mg, 2.37 mmol), 4,4,5,5-tetramethyl-2-[4-(trifluoromethyl)cyclohexen-1-yl]-1,3,2-dioxaborolane (654 mg, 2.37 mmol), Pd(dppf)$Cl_2$ (223 mg, 0.304 mmol) and potassium carbonate (1.11 g, 8.03 mmol). Dioxane (14 mL) and water (2 mL) were added and the mixture degassed for 5 min. The vial was sealed and mixture heated at 110° C. under nitrogen atmosphere for 4 h. The mixture was cooled to room temperature, diluted with dichloromethane (20 mL) and washed with saturated aqueous ammonium chloride and brine. The organic layer was dried over magnesium sulfate, filtered and concentrated under reduced pressure. Purification by silica gel chromatography (0-50% ethyl acetate/heptanes over 20 min) provided 4-chloro-2-(trifluoromethyl)-5-[4-(trifluoromethyl)cyclohexen-1-yl]pyridine (616 mg, 79%). ESI-MS m/z calc. 329.04, found 330.1 $(M+1)^+$. $^1$H NMR (400 MHz, DMSO-$d_6$) δ 8.61 (s, 1H), 8.14 (s, 1H), 5.93-5.88 (m, 1H), 2.75-2.59 (m, 1H), 2.58-2.43 (m, 2H), 2.43-2.30 (m, 1H), 2.30-2.18 (m, 1H), 2.11-2.03 (m, 1H), 1.70-1.55 (m, 1H). $^{19}$F NMR (376 MHz, DMSO-$d_6$) δ −66.35, −72.13.

Step 2: 4-chloro-2-(trifluoromethyl)-5-[4-(trifluoromethyl)cyclohexyl]pyridine

A mixture of 4-chloro-2-(trifluoromethyl)-5-[4-(trifluoromethyl)cyclohexen-1-yl]pyridine (300 mg, 0.910 mmol) and 5% rhodium on alumina (350 mg, 0.170 mmol) in isopropanol (12 mL) was stirred under hydrogen atmosphere for 3 h. The mixture was filtered and the solvent was removed under reduced pressure. Purification by silica gel chromatography (0-50% ethyl acetate/heptanes over 15 min) provided 4-chloro-2-(trifluoromethyl)-5-[4-(trifluoromethyl)cyclohexyl]pyridine (178.1 mg, 59%) as a mixture of cis- and trans-isomers. ESI-MS m/z calc. 331.06, found 332.1 $(M+1)^+$. $^1$H NMR (400 MHz, DMSO-$d_6$) δ 8.76 (s, 0.25H), 8.73 (s, 0.75H), 8.10 (s, 1H), 3.15-2.99 (m, 1H), 2.68-2.54 (m, 0.75H), 2.46-2.35 (m, 0.25H), 2.05-1.90 (m, 2.5H), 1.89-1.64 (m, 5H), 1.47 (qd, J=12.8, 3.4 Hz, 0.5H). $^{19}$F NMR (376 MHz, DMSO-$d_6$) δ −66.03 (major), −66.34 (minor) overlaps with −66.35 (major), −72.31 (minor).

Step 3: 4-(4,4,5,5-tetramethyl-1,3,2-dioxaborolan-2-yl)-2-(trifluoromethyl)-5-[4-(trifluoromethyl)cyclohexyl]pyridine 4-(4,4,5,5-Tetramethyl-1,3,2-dioxaborolan-2-yl)-2-(trifluoromethyl)-5-[4-(trifluoromethyl)cyclohexyl]pyridine was prepared from 4-chloro-2-(trifluoromethyl)-5-[4-(trifluoromethyl)cyclohexyl]pyridine using a procedure analogous to that found in Intermediate B-2, step 4 and dioxane as the organic solvent. The product was isolated as a mixture of cis- and trans-isomers. ESI-MS m/z calc. 423.18, found 424.153 $(M+1)^+$. $^1$H NMR (400 MHz, DMSO-$d_6$) δ 8.74 (s, 0.25H), 8.70 (s, 0.75H), 7.86 (s, 0.75H) overlaps with 7.85 (s, 0.25H), 3.31-3.11 (m, 1H), 2.65-2.54 (m, 1H), 2.07-1.87 (m, 2H), 1.75 (m, 5H), 1.45-1.36 (m, 1H), 1.17 (s, 12H). $^{19}$F NMR (376 MHz, DMSO-$d_6$) δ −65.92 (major), −66.28 (major minor), −72.34 (minor).

Intermediate B-35

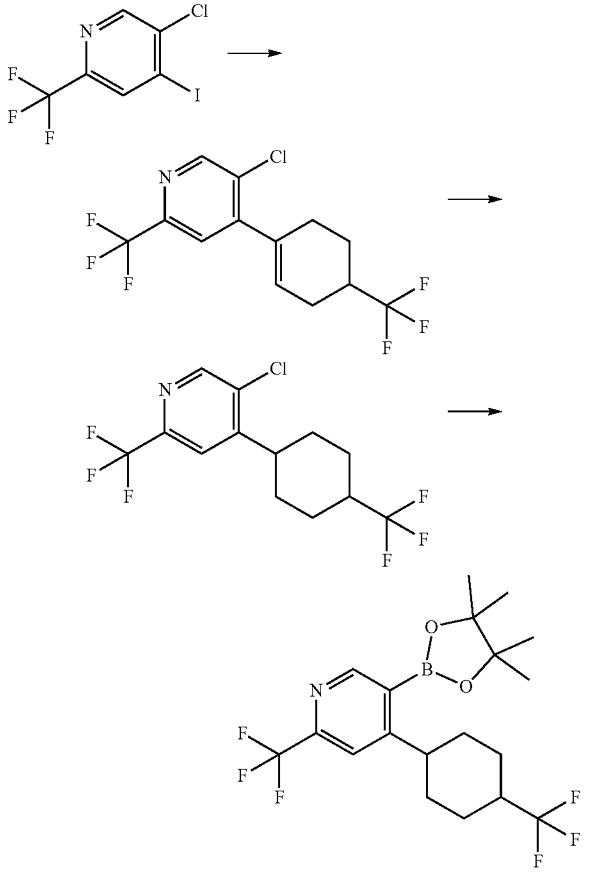

Step 1: 5-chloro-2-(trifluoromethyl)-4-[4-(trifluoromethyl)cyclohexen-1-yl]pyridine 5-Chloro-2-(trifluoromethyl)-4-[4-(trifluoromethyl)cyclohexen-1-yl]pyridine was prepared from 5-chloro-4-iodo-2-(trifluoromethyl)pyridine and using a procedure analogous to that found in Intermediate B-34, step 1. ESI-MS m/z calc. 329.04, found 330.1 $(M+1)^+$. $^1$H NMR (400 MHz, DMSO-$d_6$) δ 8.84 (s, 1H), 7.81 (s, 1H), 6.01-5.91 (m, 1H), 2.74-2.54 (m, 2H), 2.47-2.32 (m, 2H), 2.31-2.15 (m, 1H), 2.15-2.00 (m, 1H), 1.69-1.54 (m, 1H).

Step 2: 5-chloro-2-(trifluoromethyl)-4-[4-(trifluoromethyl)cyclohexyl]pyridine

5-Chloro-2-(trifluoromethyl)-4-[4-(trifluoromethyl)cyclohexyl]pyridine was prepared from 5-chloro-2-(trifluoromethyl)-4-[4-(trifluoromethyl)cyclohexen-1-yl]pyridine using a procedure analogous to that found in Intermediate B-34, step 2. The product was isolated as a 3:1 mixture of cis/trans isomers. ESI-MS m/z calc. 331.05, found 332.1 $(M+1)^+$.

Step 3: 5-(4,4,5,5-tetramethyl-1,3,2-dioxaborolan-2-yl)-2-(trifluoromethyl)-4-[4-(trifluoromethyl)cyclohexyl]pyridine 5-(4,4,5,5-tetramethyl-1,3,2-dioxaborolan-2-yl)-2-(trifluoromethyl)-4-[4-(trifluoromethyl)cyclohexyl]pyridine was prepared from 5-chloro-2-(trifluoromethyl)-4-[4-(trifluoromethyl)cyclohexyl]pyridine using a procedure analogous to that found in Intermediate B-2, step 4 using dioxane as the organic solvent. The product was isolated as a 3:1 mixture of cis/trans isomers. ESI-MS m/z calc. 423.18, found 424.1 $(M+1)^+$.

Intermediate B-36

Intermediate B-6, step 1 with a reaction time of 1.5 h. ESI-MS m/z calc. 241.09, found 241.5 $(M+1)^+$.

Step 2: Ethyl 6-tert-butyl-4-(4-methoxycyclohexen-1-yl)pyridine-3-carboxylate

Ethyl 6-tert-butyl-4-(4-methoxycyclohexen-1-yl)pyridine-3-carboxylate was prepared from ethyl 6-tert-butyl-4-chloro-pyridine-3-carboxylate and 2-(4-methoxycyclohexen-1-yl)-4,4,5,5-tetramethyl-1,3,2-dioxaborolane using a procedure analogous to that found in Intermediate B-34, step 1 and using $PdCl_2$(dtbpf) as the catalyst. ESI-MS m/z calc. 317.20, found 318.5 $(M+1)^+$. $^1H$ NMR (400 MHz, DMSO-$d_6$) δ 8.73 (s, 1H), 7.23 (s, 1H), 5.53-5.47 (m, 1H), 4.25 (q, J=7.1 Hz, 2H), 3.55-3.46 (m, 1H), 3.29 (s, 3H), 2.47-2.41 (m, 1H), 2.35-2.24 (m, 2H), 2.10-1.92 (m, 2H), 1.72-1.60 (m, 1H), 1.32 (s, 9H), 1.27 (t, J=7.1 Hz, 3H).

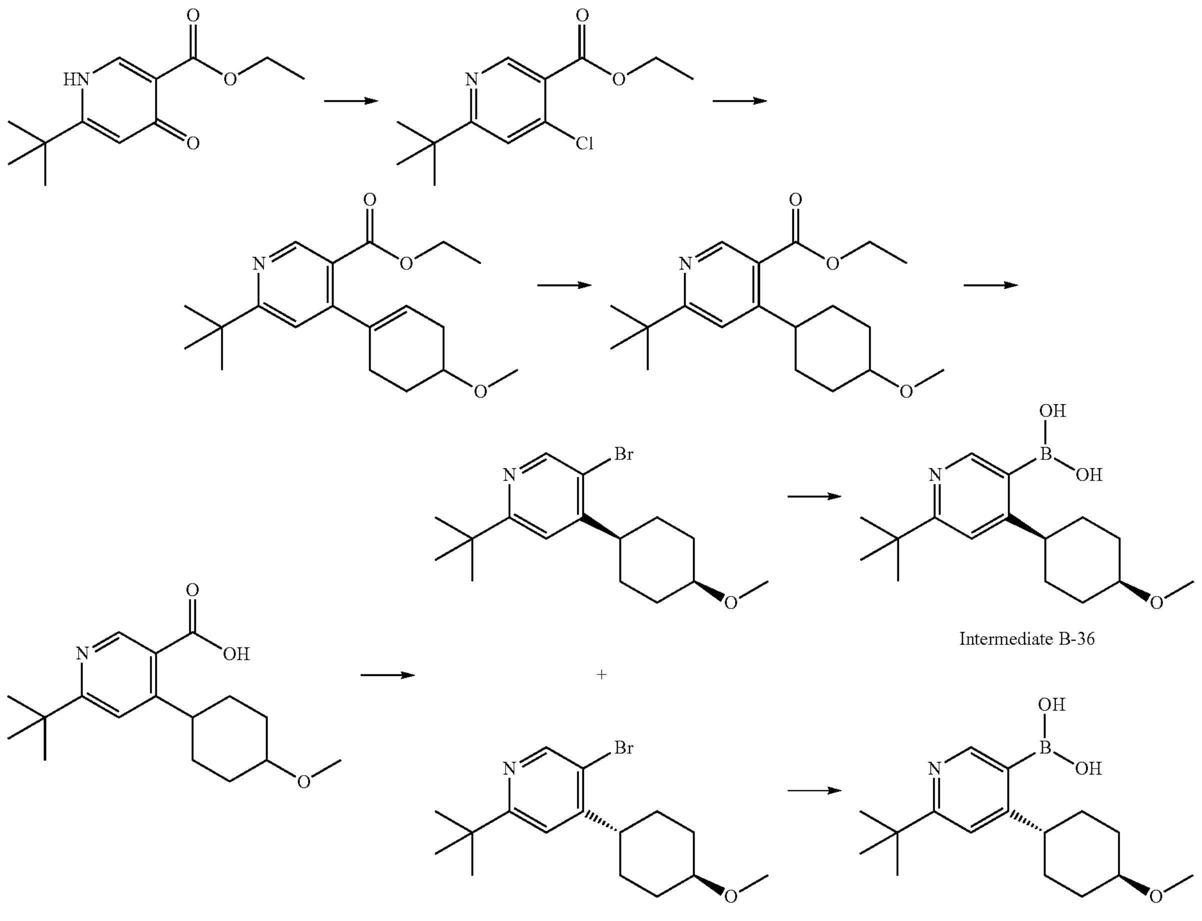

Intermediate B-36

Intermediate B-37

Step 1: Ethyl 6-tert-butyl-4-chloro-pyridine-3-carboxylate

Ethyl 6-tert-butyl-4-chloro-pyridine-3-carboxylate was prepared from ethyl 6-tert-butyl-4-oxo-1H-pyridine-3-carboxylate using a procedure analogous to that found in Step 3: Ethyl 6-tert-butyl-4-(4-methoxycyclohexyl) pyridine-3-carboxylate Ethyl 6-tert-butyl-4-(4-methoxycyclohexen-1-yl)pyridine-3-carboxylate was dissolved in methanol (9 mL) and stirred with 10% Pd/C (wet) (96 mg, 0.045 mmol) under hydrogen atmosphere for 30 min. The reaction was filtered and concentrated to provide ethyl 6-tert-butyl-4-(4-methoxycyclohexyl)pyridine-3-carboxylate. ESI-MS m/z calc. 319.22, found 320.6 $(M+1)^+$. $^1H$ NMR (400 MHz, DMSO-$d_6$) δ 8.77 (s, 1H), 7.32 (s, 1H), 4.32 (q, J=7.1 Hz, 2H), 3.51-3.45 (m, 1H), 3.25 (s, 3H), 2.17-1.94 (m, 2H), 1.84-1.61 (m, 2H), 1.60-1.42 (m, 4H), 1.37-1.28 (m, 12H), 1.26-1.09 (m, 1H).

Step 4: 6-tert-butyl-4-(4-methoxycyclohexyl)pyridine-3-carboxylic acid 6-tert-Butyl-4-(4-methoxycyclohexyl)pyridine-3-carboxylic acid was prepared from ethyl 6-tert-butyl-4-(4-methoxycyclohexyl)pyridine-3-carboxylate using a procedure analogous to that found in Intermediate B-13, step 4 with stirring for overnight at room temperature. ESI-MS m/z calc. 291.18, found 292.4 $(M+1)^+$. $^1H$ NMR (400 MHz, DMSO-$d_6$) δ 13.13 (br s, 1H), 8.77 (s, 1H), 7.30 (s, 1H), 3.51-3.42 (m, 1H), 3.25 (s, 3H), 2.19-1.93 (m, 2H), 1.82-1.60 (m, 2H), 1.59-1.41 (m, 4H), 1.34-1.29 (m, 9H), 1.26-1.11 (m, 1H).

Step 5: 5-bromo-2-tert-butyl-4-(4-methoxycyclohexyl)pyridine

A mixture of 6-tert-butyl-4-(4-methoxycyclohexyl)pyridine-3-carboxylic acid (345 mg, 1.13 mmol), tetrabutylammonium tribromide (1.09 g, 2.26 mmol) and potassium phosphate (238 mg, 1.12 mmol) in $CH_3CN$ (2.5 mL) and dioxane (0.5 mL) was degassed with nitrogen for 5 min then stirred at 100° C. for 24 h under nitrogen atmosphere in a sealed vial. The mixture was cooled, diluted with ethyl acetate and washed with a saturated aqueous ammonium chloride and brine. The organic layer was dried over magnesium sulfate, filtered, and concentrated under reduced pressure. Purification by silica gel chromatography (0-50% ethyl acetate/heptane over 20 min) provided the major cis isomer 5-bromo-2-tert-butyl-4-(4-methoxycyclohexyl)pyridine (50 mg, 13%). $^1H$ NMR (400 MHz, DMSO-$d_6$) δ 8.57 (s, 1H), 7.26 (s, 1H), 3.52-3.46 (m, 1H), 3.26 (s, 3H), 2.85 (tt, J=11.8, 3.3 Hz, 1H), 2.04-1.96 (m, 2H), 1.74-1.60 (m, 2H), 1.60-1.46 (m, 4H), 1.30 (s, 9H). ESI-MS m/z calc. 325.10, found 326.2 $(M+1)^+$; Retention time: 2.27 min. and minor trans isomer product 5-bromo-2-tert-butyl-4-(4-methoxycyclohexyl)pyridine (15 mg, 4%). $^1H$ NMR (400 MHz, DMSO-$d_6$) δ 8.56 (s, 1H), 7.35 (s, 1H), 3.27 (s, 3H), 3.25-3.19 (m, 1H), 2.86-2.75 (m, 1H), 2.17-2.10 (m, 2H), 1.84-1.77 (m, 2H), 1.62-1.49 (m, 2H), 1.29 (s, 9H), 1.27-1.17 (m, 2H). ESI-MS m/z calc. 325.10, found 326.2 $(M+1)^+$; Retention time: 2.19 min.

Retention times for the cis and trans isomers were determined by reversed phase UPLC using an Acquity UPLC BEH C18 column (50×2.1 mm, 1.7 m particle) made by Waters, and a dual gradient run from 1-99% mobile phase B over 4.5 min. Mobile phase A=water (0.05% TFA). Mobile phase B=$CH_3CN$ (0.035% TFA). Flow rate=1.2 mL/min, injection volume=1.5 μL, and column temperature=60° C.

Step 6: [6-tert-butyl-4-(4-methoxycyclohexyl)-3-pyridyl]boronic acid (cis isomer)

[6-tert-Butyl-4-(4-methoxycyclohexyl)-3-pyridyl]boronic acid was prepared from the 5-bromo-2-tert-butyl-4-(4-methoxycyclohexyl)pyridine (cis isomer) using a procedure analogous to that found in Intermediate B-2, step 4 using Pd(dppf)$Cl_2$ catalyst and dioxane as solvent. ESI-MS m/z calc. 291.19, found 292.2 $(M+1)^+$.

Intermediate B-37

Step 1: [6-tert-butyl-4-(4-methoxycyclohexyl)-3-pyridyl]boronic acid (trans isomer)

[6-tert-Butyl-4-(4-methoxycyclohexyl)-3-pyridyl]boronic acid was prepared from the 5-bromo-2-tert-butyl-4-(4-methoxycyclohexyl)pyridine (trans isomer isolated from Intermediate B-36, step 5) using a procedure analogous to that found in Intermediate B-2, step 4 using Pd(dppf)$Cl_2$ catalyst and dioxane as solvent. ESI-MS m/z calc. 291.19, found 292.3 $(M+1)^+$.

Intermediate B-38 (cis/trans Mixture)

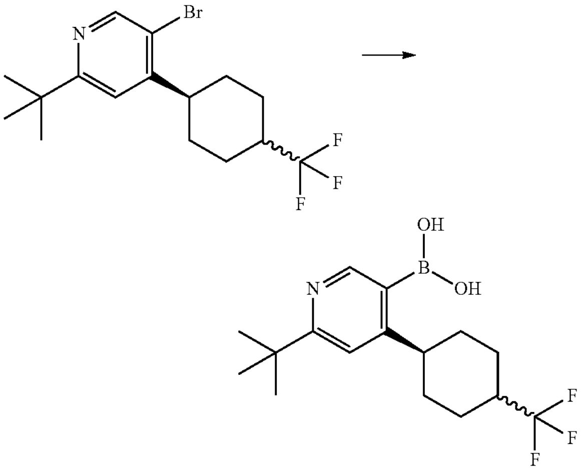

A vial was charged with 5-bromo-2-tert-butyl-4-[4-(trifluoromethyl)cyclohexyl]pyridine (3:1 mixture of cis/trans isomers, synthesized using a procedure analogous to Intermediate B-36 step 5) (140 mg, 0.384 mmol), bis(pinacol) diboron (151 mg, 0.595 mmol), potassium acetate (121 mg, 1.23 mmol) and CataCXium A Pd G3 (20 mg, 0.026 mmol). The vial was sealed and flushed with nitrogen. N,N-dimethylacetamide (1 mL) was then added under nitrogen atmosphere and the reaction was stirred at 80° C. for 4 h. The reaction was cooled to room temperature, filtered and purified by reverse phase HPLC (C18, 1-99% $CH_3CN$/5 mM HCl) to provide [6-tert-butyl-4-[4-(trifluoromethyl)cyclohexyl]-3-pyridyl]boronic acid as mixture of cis trans isomers. ESI-MS m/z calc. 329.18, found 330.1 $(M+1)^+$.

Intermediate B-39

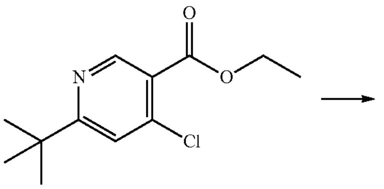

-continued

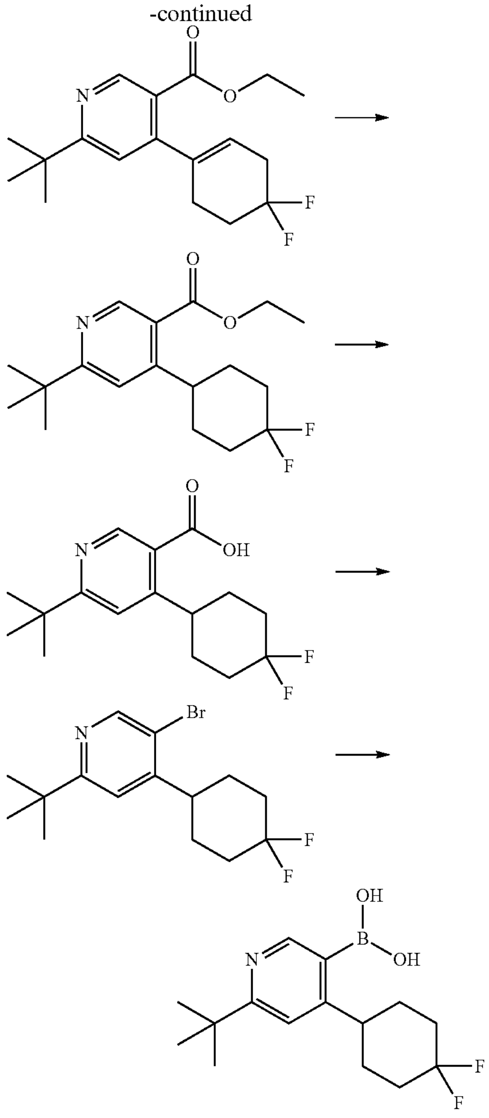

Step 1: Ethyl 6-tert-butyl-4-(4,4-difluorocyclohexen-1-yl)pyridine-3-carboxylate Ethyl 6-tert-butyl-4-(4,4-difluorocyclohexen-1-yl)pyridine-3-carboxylate was prepared from ethyl 6-tert-butyl-4-chloro-pyridine-3-carboxylate (Intermediate B-36, step 1) and 2-(4,4-difluorocyclohexen-1-yl)-4,4,5,5-tetramethyl-1,3,2-dioxaborolane using a procedure analogous to that found in Intermediate B-34, step 1 using $Pd(PPh_3)_4$ catalyst. ESI-MS m/z calc. 323.17, found 324.3 $(M+1)^+$; Retention time: 1.62 min. $^1H$ NMR (400 MHz, $CDCl_3$) δ 9.01 (s, 1H), 7.11 (s, 1H), 5.52-5.36 (m, 1H), 4.34 (q, J=7.1 Hz, 2H), 2.76-2.61 (m, 2H), 2.59-2.44 (m, 2H), 2.31-2.12 (m, 2H), 1.39-1.32 (m, 12H).

Step 2: Ethyl 6-tert-butyl-4-(4,4-difluorocyclohexyl)pyridine-3-carboxylate

Ethyl 6-tert-butyl-4-(4,4-difluorocyclohexyl)pyridine-3-carboxylate was prepared from ethyl 6-tert-butyl-4-(4,4-difluorocyclohexen-1-yl)pyridine-3-carboxylate using a procedure analogous to that found in Intermediate B-36, step 3. ESI-MS m/z calc. 325.19, found 326.3 $(M+1)^+$; Retention time: 1.57 min.

Step 3: 6-tert-butyl-4-(4,4-difluorocyclohexyl)pyridine-3-carboxylic acid 6-tert-Butyl-4-(4,4-difluorocyclohexyl)pyridine-3-carboxylic acid was prepared from ethyl 6-tert-butyl-4-(4,4-difluorocyclohexyl)pyridine-3-carboxylate using a procedure analogous to that found in Intermediate B-13, step 4 with stirring at room temperature for 16 h. ESI-MS m/z calc. 297.15, found 298.3 $(M+1)^+$.

Step 4: 5-bromo-2-tert-butyl-4-(4,4-difluorocyclohexyl)pyridine

5-Bromo-2-tert-butyl-4-(4,4-difluorocyclohexyl)pyridine was prepared from 6-tert-butyl-4-(4,4-difluorocyclohexyl)pyridine-3-carboxylic acid using a procedure analogous to that found in Intermediate B-36, step 5. ESI-MS m/z calc. 331.07, found 332.1 $(M+1)^+$; Retention time: 1.78 min. $^1H$ NMR (400 MHz, $CDCl_3$) δ 8.61 (s, 1H), 7.19 (s, 1H), 3.01 (t, J=12.4 Hz, 1H), 2.34-2.18 (m, 2H), 2.03-1.93 (m, 3H), 1.90-1.65 (m, 3H), 1.36 (s, 9H). $^{19}F$ NMR (376 MHz, $CDCl_3$) δ −91.74 (d, J=237.3 Hz), −102.22 (d, J=237.3 Hz).

Step 5: [6-tert-butyl-4-(4,4-difluorocyclohexyl)-3-pyridyl]boronic acid

[6-tert-Butyl-4-(4,4-difluorocyclohexyl)-3-pyridyl]boronic acid was prepared from 5-bromo-2-tert-butyl-4-(4,4-difluorocyclohexyl)pyridine using a procedure analogous to that found in Intermediate B-2, step 4 using CataCXium A Pd G3 catalyst and N,N-dimethylacetamide as solvent. ESI-MS m/z calc. 297.17, found 298.3 $(M+1)^+$.

Intermediate B-40

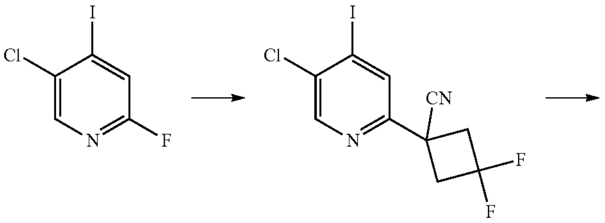

-continued

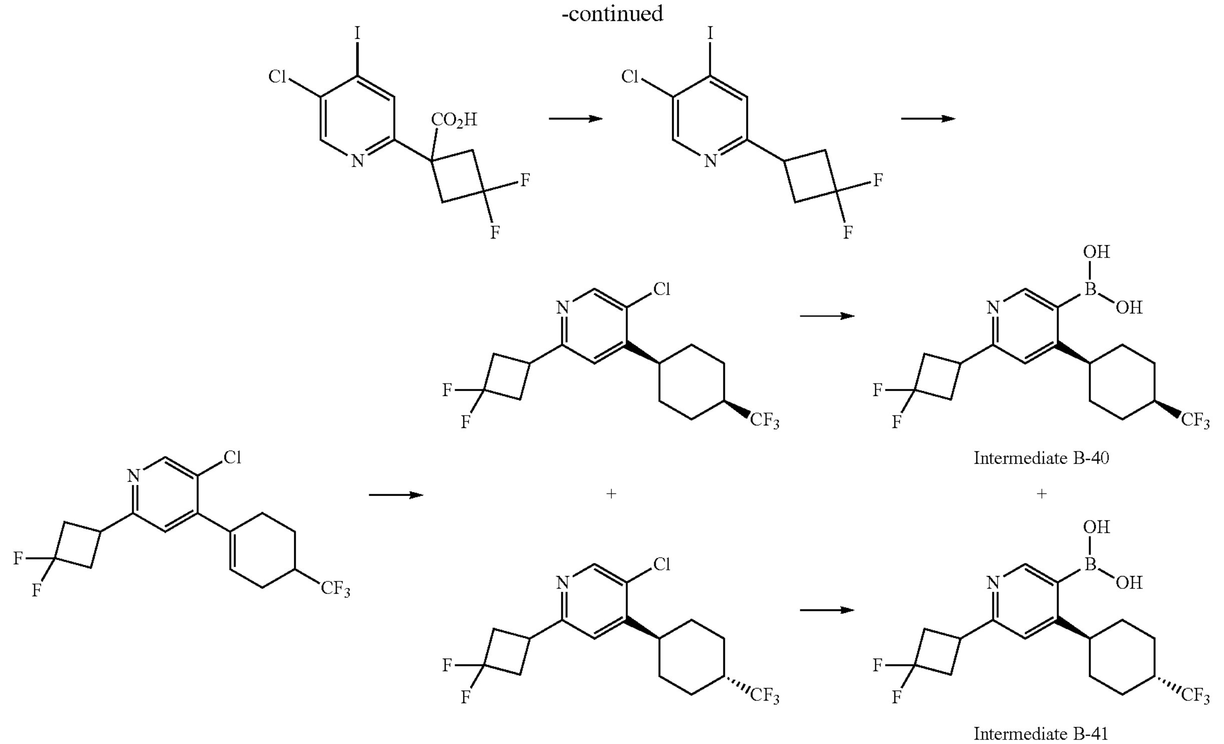

Intermediate B-40

Intermediate B-41

Step 1: Synthesis of 1-(5-chloro-4-iodopyridin-2-yl)-3,3-difluorocyclobutane-1-carbonitrile To a solution of 3,3-difluorocyclobutanecarbonitrile (5.0 g, 42.7 mmol) in toluene (200 mL) at 0° C. was added LiHMDS (50 mL of 1 M in toluene, 50 mmol) and the mixture stirred for 10 min. A solution of 5-chloro-2-fluoro-4-iodo-pyridine (11.37 g, 42.10 mmol) in toluene (50 mL) was added. The reaction mixture was allowed to warm to room temperature and stirred overnight. The reaction was quenched with saturated ammonium chloride solution (200 mL) and the mixture extracted with ethyl acetate (400 mL). The organic extract was washed with brine (150 mL), then dried over magnesium sulfate, filtered and concentrated. Purification on silica (0-2.9% ethyl acetate/heptane) provided 1-(5-chloro-4-iodo-2-pyridyl)-3,3-difluoro-cyclobutanecarbonitrile (19% yield) as a white solid. $^1$H NMR (400 MHz, $CDCl_3$) δ 8.55 (s, 1H), 8.14 (s, 1H), 3.54-3.42 (m, 2H), 3.36-3.26 (m, 2H).

Step 2: 1-(5-chloro-4-iodo-2-pyridyl)-3,3-difluoro-cyclobutanecarboxylic acid

To 1-(5-chloro-4-iodo-2-pyridyl)-3,3-difluoro-cyclobutanecarbonitrile (8.07 g, 22.3 mmol) in AcOH (90 mL) was added water (45 mL) and sulfuric acid (conc.) (45 mL of 95% w/v, 844 mmol). The resulting mixture was heated at 85° C. for 6 h. On cooling the reaction mixture was diluted with water (800 mL) and extracted with ethyl acetate (2×800 mL). The combined extracts were washed with brine (250 mL), dried over magnesium sulfate, filtered and concentrated under reduced pressure to give a brown gum 1-(5-chloro-4-iodo-2-pyridyl)-3,3-difluoro-cyclobutanecarboxylic acid (8.26 g, 97%). ESI-MS m/z calc. 372.92, found 327.86 $(M-45)^-$.

Step 3: 5-chloro-2-(3,3-difluorocyclobutyl)-4-iodopyridine

A solution of 1-(5-chloro-4-iodo-2-pyridyl)-3,3-difluoro-cyclobutanecarboxylic acid (8.26 g, 21.3 mmol) in toluene (100 mL) was heated at 100° C. overnight. The reaction mixture was concentrated under reduced pressure to provide 5-chloro-2-(3,3-difluorocyclobutyl)-4-iodopyridine (7 g, 98%) as a cream colored solid. $^1$H NMR (400 MHz, $CDCl_3$) δ 8.50 (s, 1H), 7.68 (s, 1H), 3.41-3.31 (m, 1H), 2.94-2.84 (m, 4H).

Step 4: 5-chloro-2-(3,3-difluorocyclobutyl)-4-(4-(trifluoromethyl)cyclohexen-1-yl)pyridine 5-Chloro-2-(3,3-difluorocyclobutyl)-4-[4-(trifluoromethyl)cyclohexen-1-yl]pyridine was prepared from 5-chloro-2-(3,3-difluorocyclobutyl)-4-iodo-pyridine using a procedure analogous to that found in Intermediate B-34, step 1. ESI-MS m/z calc. 351.08, found 352.09 $(M+1)^+$. $^1$H NMR (400 MHz, $CDCl_3$) δ 8.52 (s, 1H), 6.96 (s, 1H), 5.78 (s, 1H), 3.44-3.40 (m, 1H), 2.96-2.84 (m, 4H), 2.49-2.29 (m, 5H), 2.14 (d, J=12.8 Hz, 1H), 1.71 (qd, J=12.1, 5.4 Hz, 1H).

Step 5: 5-chloro-2-(3,3-difluorocyclobutyl)-4-((1S,4S)-4-(trifluoromethyl)cyclohexyl)pyridine and 5-chloro-2-(3,3-difluorocyclobutyl)-4-((1R,4R)-4-(trifluoromethyl)cyclohexyl)pyridine 5-Chloro-2-(3,3-difluorocyclobutyl)-4-(4-(trifluoromethyl)cyclohexyl)pyridine (cis and trans isomers) were prepared from 5-chloro-2-(3,3-difluorocyclobutyl)-4-[4-(trifluoromethyl)cyclohexen-1-yl]pyridine using a procedure analogous to that found in Intermediate B-34, step 2. Purification using silica gel chromatography (0-3.5% ethyl acetate/heptane over 41 min) provided product-containing fractions which were combined and the solvent removed under reduced pressure giving 5-chloro-2-(3,3-difluorocyclobutyl)-4-(4-(trifluoromethyl)cyclohexyl)pyridine (cis isomer, 1.12 g, 19%) as a white solid. $^1$H-NMR (400 MHz, $CDCl_3$) δ 8.49 (s, 1H), 7.02 (s, 1H), 3.44-3.35 (m, 1H), 3.47-3.30 (m, 1H), 2.95-2.86 (m, 4H), 2.48-2.32 (m, 1H), 2.20-2.03 (m, 2H), 1.80-1.65 (m, 6H). ESI-MS m/z calc. 353.10, found 354.16 $(M+1)^+$; Retention time: 3.23 min and 5-chloro-2-(3,3-difluorocyclobutyl)-4-(4-(trifluoromethyl) cyclohexyl)pyridine (trans isomer, 0.69 g, 11%) as a white solid. ESI-MS m/z calc. 353.10, found 354.14 $(M+1)^+$; Retention time: 3.2 min. $^1$H-NMR (400 MHz, $CDCl_3$) δ.

8.50-8.48 (m, 1H), 6.99 (s, 1H), 3.43-3.34 (m, 1H), 3.03-2.83 (m, 5H), 2.18-2.00 (m, 5H), 1.58-1.37 (m, 4H). Retention times for the cis and trans product isomers were determined using the following conditions: Waters UPLC, BEH C18 column, 2.1×50 mm, 2.5 m particle, 2-95% $CH_3CN$ in water (0.1% $NH_3$ modifier), 4.6 min run, 0.8 ml/min, 40° C.

Step 6: 2-(3,3-difluorocyclobutyl)-5-(4,4,5,5-tetramethyl-1,3,2-dioxaborolan-2-yl)-4-(4-(trifluoromethyl) cyclohexyl)pyridine (cis isomer)

2-(3,3-Difluorocyclobutyl)-5-(4,4,5,5-tetramethyl-1,3,2-dioxaborolan-2-yl)-4-(4-(trifluoromethyl)cyclohexyl)pyridine (cis isomer) was prepared from 5-chloro-2-(3,3-difluorocyclobutyl)-4-(4-(trifluoromethyl)cyclohexyl)pyridine (cis isomer) using a procedure analogous to that found in Intermediate B-2, step 4 using SPhos Pd G3 as catalyst. Product was isolated as a ~1:1 mixture of boronic acid and pinacol ester and used without further purification. ESI-MS m/z calc. 445.22, found 446.3 $(M+1)^+$; Retention time: 3.40 min (pinacol ester), and ESI-MS m/z calc. 363.14, found 364.2 $(M+1)^+$; Retention time: 2.03 min (boronic acid). $^1$H NMR of mixture (400 MHz, $CD_3OD$) δ 8.69 (s, 0.46H), 8.36 (s, 0.5H), 7.26-7.12 (m, 1H), 3.51-3.38 (m, 2H), 2.93-2.77 (m, 4H), 2.54-2.35 (m, 1H), 2.14-2.04 (m, 2H), 1.85-1.71 (m, 6H), 1.36 (s, 6H). $^{19}$F NMR (376 MHz, $CD_3OD$) δ −68.4–−68.5 (m, 3F), −83.0–−83.7 (m, 1F), −100.4–−101.1 (m, 1F). Retention times were determined using the following conditions: Waters UPLC, BEH C18 column, 2.1×50 mm, 2.5 m particle, 2-95% $CH_3CN$ in water (0.1% $NH_3$ modifier), 4.6 min run, 0.8 ml/min, 40° C.

Intermediate B-41

2-(3,3-Difluorocyclobutyl)-5-(4,4,5,5-tetramethyl-1,3,2-dioxaborolan-2-yl)-4-(4-(trifluoromethyl)cyclohexyl)pyridine (trans isomer) was prepared from 5-chloro-2-(3,3-difluorocyclobutyl)-4-(4-(trifluoromethyl)cyclohexyl) pyridine (trans isomer isolated from Intermediate B-40, step 6) using a procedure analogous to that found in Intermediate B-2, step 4 using SPhos Pd G3 as catalyst. Product was isolated as a ~2:3 mixture of boronic acid and pinacol ester and used without further purification. ESI-MS m/z calc. 445.22, found 364.14 $(M+1)^+$, only boronic acid observed by LC/MS. $^1$H NMR of mixture (400 MHz, $CD_3OD$) δ 8.69 (s, 0.55H), 8.35-8.41 (0.38H), 7.25-7.30 (m, 0.42H), 7.24 (s, 0.58H), 3.53-3.40 (m, 1H), 2.92-2.84 (m, 4H), 2.30-2.14 (m, 1H), 2.11-1.99 (m, 2H), 1.96-1.87 (m, 2H), 1.57-1.43 (m, 4H), 1.35 (s, 7H).

Intermediate B-42

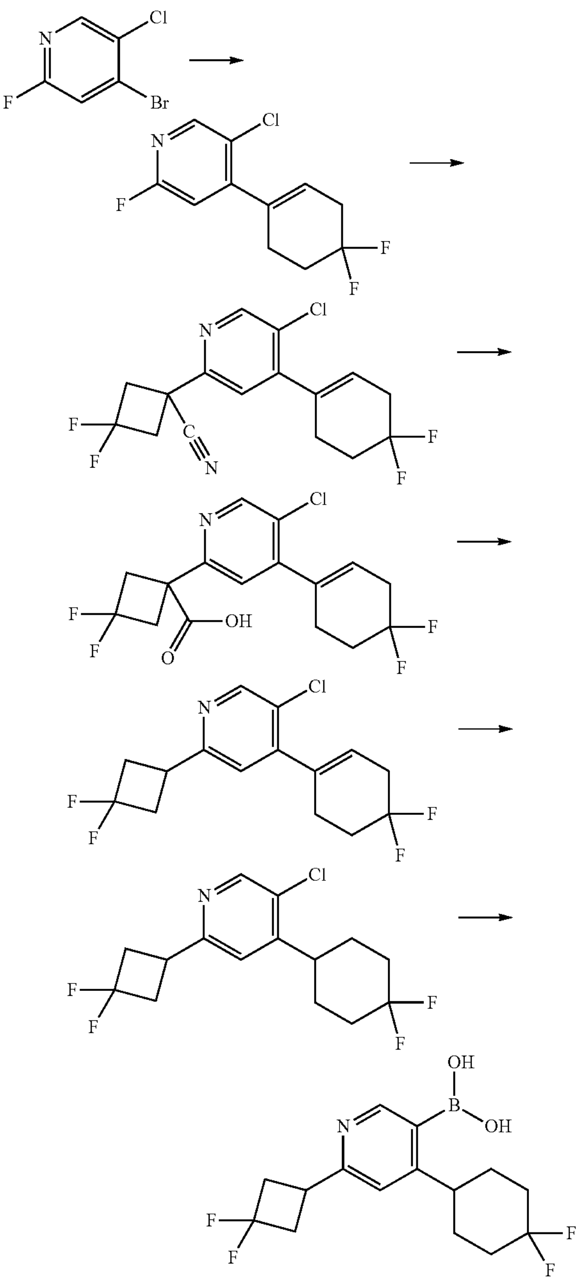

Step 1: 5-chloro-4-(4,4-difluorocyclohexen-1-yl)-2-fluoro-pyridine

5-Chloro-4-(4,4-difluorocyclohexen-1-yl)-2-fluoro-pyridine was prepared from 4-bromo-5-chloro-2-fluoro-pyridine and 2-(4,4-difluorocyclohexen-1-yl)-4,4,5,5-tetramethyl-1,3,2-dioxaborolane using a procedure analogous to that found in Intermediate B-2, step 4 with $PdCl_2$(dtbpf) as catalyst and dioxane as the organic solvent. ESI-MS m/z calc. 247.04, found 248.1 $(M+1)^+$. $^1$H NMR (400 MHz, DMSO-$d_6$) δ 8.34 (s, 1H), 7.23 (d, J=2.2 Hz, 1H), 5.86-5.78 (m, 1H), 2.83-2.70 (m, 2H), 2.61-2.53 (m, 2H), 2.25-2.10 (m, 2H). $^{19}$F NMR (376 MHz, DMSO-$d_6$) δ −71.53, −94.49.

Step 2: 1-[5-chloro-4-(4,4-difluorocyclohexen-1-yl)-2-pyridyl]-3,3-difluoro-cyclobutanecarbonitrile 1-[5-Chloro-4-(4,4-difluorocyclohexen-1-yl)-2-pyridyl]-3,3-difluoro-cyclobutanecarbonitrile was prepared from 5-chloro-4-(4,4-difluorocyclohexen-1-yl)-2-fluoro-pyridine and 3,3-difluorocyclobutanecarbonitrile using a procedure analogous to that found in Intermediate B-40, step 1. ESI-MS m/z calc. 344.07, found 345.3 $(M+1)^+$. $^1H$ NMR (400 MHz, DMSO-$d_6$) δ 8.73 (s, 1H), 7.59 (s, 1H), 5.82 (s, 1H), 3.57-3.44 (m, 4H), 2.85-2.72 (m, 2H), 2.64-2.56 (m, 2H), 2.27-2.13 (m, 2H). $^{19}F$ NMR (376 MHz, DMSO-$d_6$) δ −83.62 (d, J=194.9 Hz), −93.91 (d, J=194.9 Hz), −94.47.

Step 3: 1-[5-chloro-4-(4,4-difluorocyclohexen-1-yl)-2-pyridyl]-3,3-difluoro-cyclobutanecarboxylic acid 1-[5-Chloro-4-(4,4-difluorocyclohexen-1-yl)-2-pyridyl]-3,3-difluoro-cyclobutanecarboxylic acid was prepared from 1-[5-chloro-4-(4,4-difluorocyclohexen-1-yl)-2-pyridyl]-3,3-difluoro-cyclobutanecarbonitrile using a procedure analogous to that found in Intermediate B-40, step 2. ESI-MS m/z calc. 363.07, found 364.4 $(M+1)^+$.

Step 4: 5-chloro-2-(3,3-difluorocyclobutyl)-4-(4,4-difluorocyclohexen-1-yl)pyridine 5-Chloro-2-(3,3-difluorocyclobutyl)-4-(4,4-difluorocyclohexen-1-yl)pyridine was prepared from 1-[5-chloro-4-(4-fluorophenyl)-2-pyridyl]-3,3-difluoro-cyclobutanecarboxylic acid using a procedure analogous to that found in Intermediate B-40, step 3. ESI-MS m/z calc. 319.08, found 320.2 $(M+1)^+$. $^1H$ NMR (400 MHz, DMSO-$d_6$) δ 8.61 (s, 1H), 7.31 (s, 1H), 5.78-5.72 (m, 1H), 3.60-3.48 (m, 1H), 3.00-2.81 (m, 3H), 2.80-2.66 (m, 3H), 2.60-2.51 (m, 2H), 2.24-2.10 (m, 2H). Decoupled: $^{19}F$ NMR (376 MHz, DMSO-$d_6$) δ −79.87 (d, J=190.0 Hz), −94.52, −96.93 (d, J=190.0 Hz). Coupled: $^{19}F$ NMR (376 MHz, DMSO-$d_6$) δ −79.55 to −79.69 (m), −80.05 to −80.20 (m), −94.52 (app pd, J=14.5, 2.9 Hz), −96.68 (tt, J=19.2, 14.8 Hz), −97.18 (tt, J=19.4, 14.5 Hz).

Step 5: 5-chloro-2-(3,3-difluorocyclobutyl)-4-(4,4-difluorocyclohexyl)pyridine

5-Chloro-2-(3,3-difluorocyclobutyl)-4-(4,4-difluorocyclohexyl)pyridine was prepared from 5-chloro-2-(3,3-difluorocyclobutyl)-4-(4,4-difluorocyclohexen-1-yl)pyridine using a procedure analogous to that found in Intermediate B-34, step 2. ESI-MS m/z calc. 321.09, found 322.2 $(M+1)^+$. $^1H$ NMR (400 MHz, DMSO-$d_6$) δ 8.58 (s, 1H), 7.44 (s, 1H), 3.62-3.48 (m, 1H), 3.14-3.02 (m, 1H), 2.99-2.76 (m, 4H), 2.20-1.92 (m, 4H), 1.91-1.83 (m, 2H), 1.79-1.64 (m, 2H). Decoupled: $^{19}F$ NMR (376 MHz, DMSO-$d_6$) δ −79.80 (d, J=189.5 Hz), −89.42 (d, J=233.6 Hz), −97.13 (d, J=189.9 Hz), −99.83 (d, J=233.7 Hz).

Step 6: [6-(3,3-difluorocyclobutyl)-4-(4,4-difluorocyclohexyl)-3-pyridyl]boronic acid

[6-(3,3-difluorocyclobutyl)-4-(4,4-difluorocyclohexyl)-3-pyridyl]boronic acid was prepared using a procedure analogous to that found in Intermediate B-2, step 4 using SPhos Pd G3 catalyst and dioxane as the organic solvent. ESI-MS m/z calc. 331.14, found 332.2 $(M+1)^+$.

Intermediate B-43

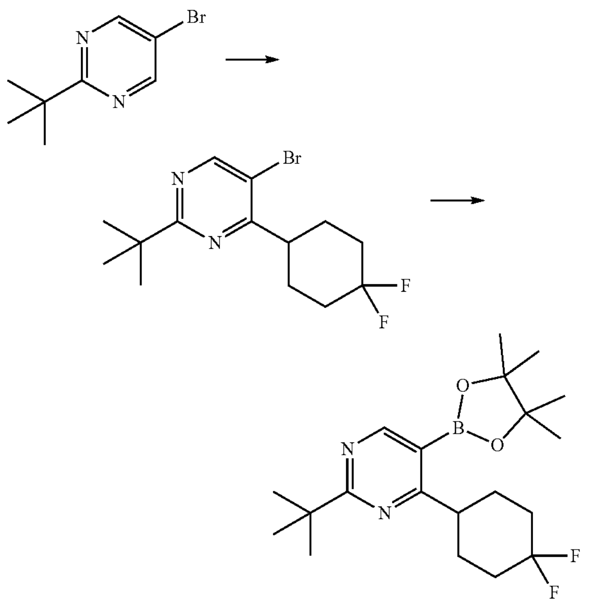

Step 1: 5-bromo-2-tert-butyl-4-(4,4-difluorocyclohexyl)pyrimidine

5-Bromo-2-tert-butyl-pyrimidine (2.48 g, 11.0 mmol), 4,4-difluorocyclohexanecarboxylic acid (2.762 g, 16.49 mmol), $AgNO_3$ (3.752 g, 22.08 mmol), and ammonium persulfate (6.39 g, 27.4 mmol) were combined in a flask, then dissolved in a mixture of acetonitrile (50 mL) and water (50 mL) and heated at 60° C. for 3.5 h. Additional 4,4-difluorocyclohexanecarboxylic acid (279 mg, 1.67 mmol), $AgNO_3$ (386 mg, 2.27 mmol) and ammonium persulfate (657 mg, 2.82 mmol) were added and stirring continued for 1 h. The reaction was cooled to room temperature and the acetonitrile removed under reduced pressure. The mixture was partitioned between brine and ethyl acetate and the layers separated. The organic phase was extracted with additional ethyl acetate (3×), then the combined organic phases were washed with brine, dried over magnesium sulfate, filtered, and concentrated under reduced pressure. Purification by silica gel chromatography (40 g, 0-50% ethyl acetate/hexanes) provided 5-bromo-2-tert-butyl-4-(4,4-difluorocyclohexyl)pyrimidine (3.44 g, 85%) as a clear, colorless oil. ESI-MS m/z calc. 332.07, found 333.1 $(M+1)^+$; Retention time: 2.27 min. $^1H$ NMR (400 MHz, DMSO-$d_6$) δ 8.84 (s, 1H), 3.28-3.19 (m, 1H), 2.18-2.02 (m, 2H), 1.98-1.79 (m, 6H), 1.33 (s, 9H). $^{19}F$ NMR (376 MHz, DMSO-$d_6$) δ −89.69, −90.31, −99.04, −99.66.

Step 2: 2-tert-butyl-4-(4,4-difluorocyclohexyl)-5-(4,4,5,5-tetramethyl-1,3,2-dioxaborolan-2-yl)pyrimidine 2-tert-Butyl-4-(4,4-difluorocyclohexyl)-5-(4,4,5,5-tetramethyl-1,3,2-dioxaborolan-2-yl)pyrimidine was prepared from 5-bromo-2-tert-butyl-4-(4,4-difluorocyclohexyl)pyrimidine and 2-isopropoxy-4,4,5,5-tetramethyl-1,3,2-dioxaborolane using a procedure analogous to that found in Intermediate B-1, step 2. ESI-MS m/z calc. 380.25, found 381.27 $(M+1)^+$.

Intermediate B-44

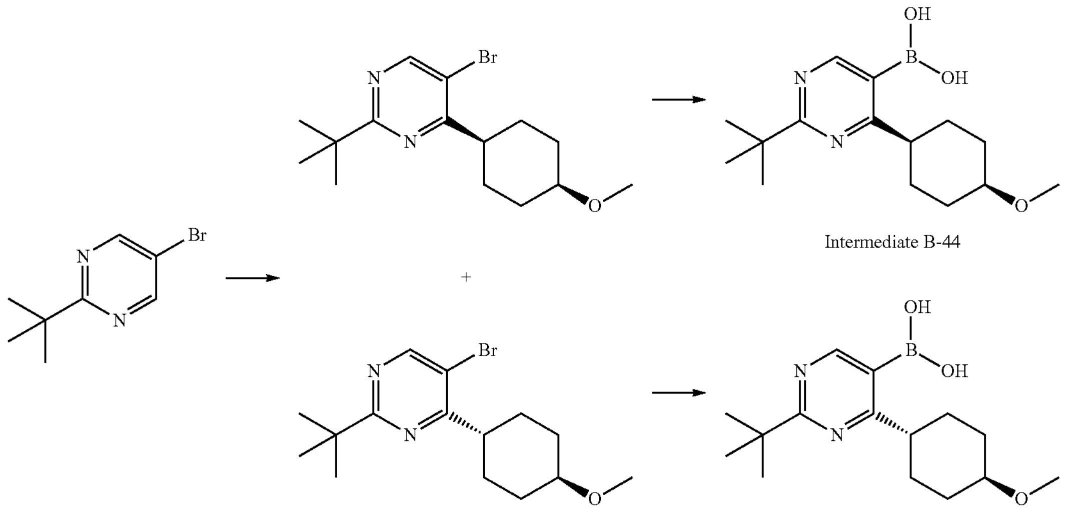

Intermediate B-44

Intermediate B-45

Step 1: 5-Bromo-2-tert-butyl-4-(4-methoxycyclohexyl)pyrimidine (cis and trans isomers)

5-Bromo-2-tert-butyl-4-(4-methoxycyclohexyl)pyrimidine (cis isomer) was prepared using 4-methoxycyclohexanecarboxylic acid and a procedure analogous to that found in Intermediate B-43, step 1. Purification by silica gel chromatography (120 g silica, 0-10% ethyl acetate/hexane) followed by reverse phase HPLC (C18, 10-99% $CH_3CN$/5 mM HCl) provided the separated cis- and trans-isomers Purification by silica gel chromatography (120 g silica, 0-10% ethyl acetate/hexane) followed by reverse phase HPLC (C18, 10-99% $CH_3CN$/5 mM HCl) provided the separated cis- and trans-isomers.

Peak 1 (elutes first during normal phase purification): 5-bromo-2-tert-butyl-4-(4-methoxycyclohexyl)pyrimidine (cis isomer) (165 mg, 23%). ESI-MS m/z calc. 326.10, found 327.2 $(M+1)^+$; Retention time: 0.75 minutes. $^1H$ NMR (400 MHz, $CD_3OD$) δ 8.64 (s, 1H), 3.56-3.52 (m, 1H), 3.35 (s, 3H), 3.23-3.11 (m, 1H), 2.12-2.04 (m, 2H), 2.04-1.91 (m, 2H), 1.67-1.54 (m, 4H), 1.37 (s, 9H).

Peak 2 (elutes second during normal phase purification): 5-bromo-2-tert-butyl-4-(4-methoxycyclohexyl)pyrimidine (trans isomer) (112 mg, 16%). ESI-MS m/z calc. 326.10, found 327.2 $(M+1)^+$; Retention time: 0.73 minutes. $^1H$ NMR (400 MHz, $CD_3OD$) δ 8.65 (s, 1H), 3.39 (s, 3H), 3.30-3.23 (m, 1H), 3.17-3.05 (m, 1H), 2.26-2.18 (m, 2H), 1.95-1.88 (m, 2H), 1.81-1.66 (m, 2H), 1.36 (s, 9H), 1.35-1.26 (m, 2H).

Reverse phase retention times were determined using a Acquity UPLC BEH C18 column (30×2.1 mm, 1.7 μm particle) made by Waters, and a dual gradient run from 1-99% mobile phase B over 1.0 min. Mobile phase A=water (0.05% TFA). Mobile phase B=$CH_3CN$ (0.035% TFA). Flow rate=1.5 mL/min, injection volume=1.5 μL, and column temperature=60° C.

Step 2: [2-tert-butyl-4-(4-methoxycyclohexyl)pyrimidin-5-yl]boronic acid (cis isomer)

[2-tert-Butyl-4-(4-methoxycyclohexyl)pyrimidin-5-yl] boronic acid (cis isomer) was prepared from 5-bromo-2-tert-butyl-4-(4-methoxycyclohexyl)pyrimidine (cis isomer) using a procedure analogous to that found in Intermediate B-2, step 4 using dioxane as the solvent. ESI-MS m/z calc. 292.20, found 293.25 $(M+1)^+$.

Intermediate B-45

[2-tert-Butyl-4-(4-methoxycyclohexyl)pyrimidin-5-yl] boronic acid (trans isomer) was prepared from -bromo-2-tert-butyl-4-(4-methoxycyclohexyl)pyrimidine (trans isomer isolated from Intermediate B-44, step 1) using a procedure analogous to that found in Intermediate B-2, step 4 using dioxane as the solvent. ESI-MS m/z calc. 292.20, found 293.20 $(M+1)^+$.

Intermediate B-46

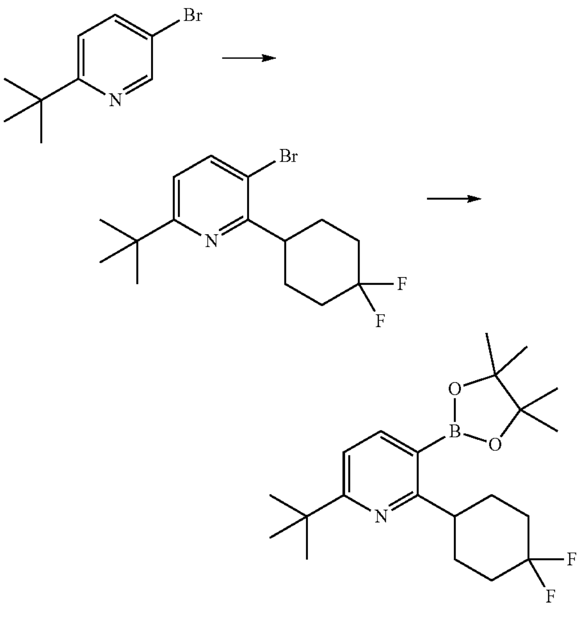

Step 1: 3-bromo-6-tert-butyl-2-(4,4-difluorocyclohexyl)pyridine

3-Bromo-6-tert-butyl-2-(4,4-difluorocyclohexyl)pyridine was prepared from 5-bromo-2-tert-butyl-pyridine and 4,4-difluorocyclohexanecarboxylic using a procedure analogous to that found in Intermediate B-43, step 1. Purification by reverse phase HPLC (C18, 10-99% $CH_3CN$/5 mM HCl) provided two regioisomeric products (Peak 1=0.75 min, Peak 2=0.95 min, 1 minute HPLC run, 1-99% $CH_3CN$/5 mM HCl). Peak 2 from the reverse phase purification was concentrated then partitioned between water and dichloromethane. The organic phase was separated, dried over magnesium sulfate, filtered and concentrated to provide 3-bromo-6-tert-butyl-2-(4,4-difluorocyclohexyl)pyridine (133 mg, 21%). ESI-MS m/z calc. 331.08, found 332.1 $(M+1)^+$. $^1$H NMR (400 MHz, $CDCl_3$) δ 7.68 (d, J=8.4 Hz, 1H), 7.02 (d, J=8.3 Hz, 1H), 3.27-3.17 (m, 1H), 2.35-2.16 (m, 2H), 2.10-1.77 (m, 6H), 1.32 (s, 9H).

Step 2: 6-tert-butyl-2-(4,4-difluorocyclohexyl)-3-(4,4,5,5-tetramethyl-1,3,2-dioxaborolan-2-yl)pyridine 6-tert-butyl-2-(4,4-difluorocyclohexyl)-3-(4,4,5,5-tetramethyl-1,3,2-dioxaborolan-2-yl)pyridine was prepared from 3-bromo-6-tert-butyl-2-(4,4-difluorocyclohexyl)pyridine using a procedure analogous to that found in Intermediate B-2 step 4 using $Pd(dppf)Cl_2$ as the catalyst and dioxane as solvent. ESI-MS m/z calc. 379.25, found 380.3 $(M+1)^+$.

Intermediate B-47

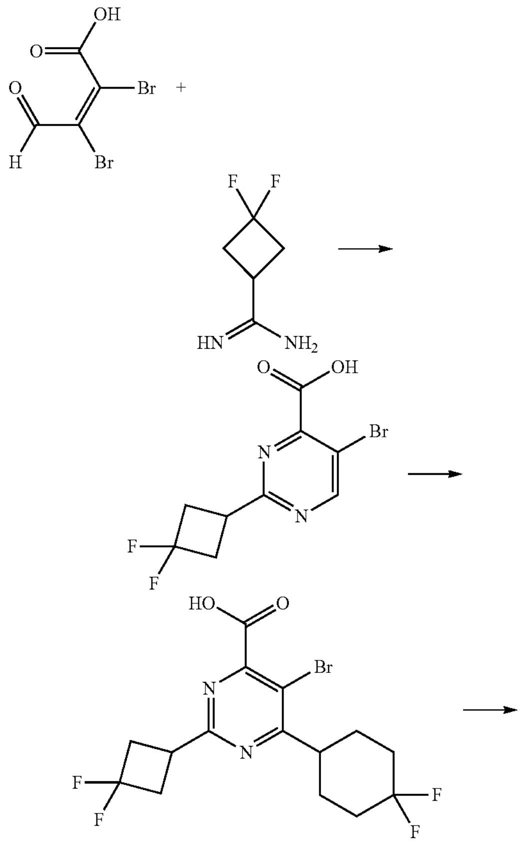

-continued

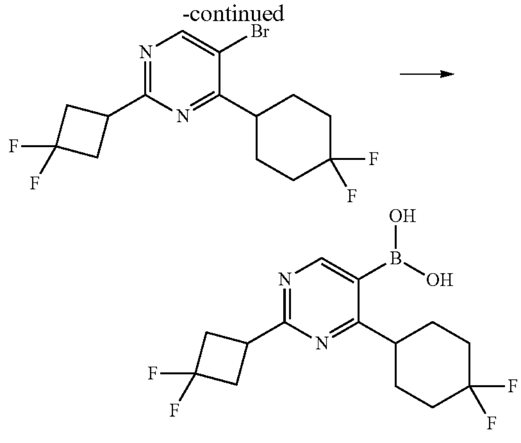

Step 1: 5-bromo-2-(3,3-difluorocyclobutyl)pyrimidine-4-carboxylic acid

Anhydrous ethanol (2.5 mL) was carefully added to NaH (60%, 128 mg, 3.20 mmol) at −78° C. under nitrogen. The resulting mixture was slowly warmed to ambient temperature and 3,3-difluorocyclobutanecarboxamidine hydrochloride (500 mg, 2.93 mmol) was added portionwise. The mixture was warmed to 55° C. and maintained at this temperature for 1 h followed by the portionwise addition of (Z)-2,3-dibromo-4-oxo-but-2-enoic acid (305 mg, 1.18 mmol) while keeping temperature at approximately 55° C. The mixture was cooled to room temperature and allowed to stir for additional 16 h. The mixture was diluted with ethyl acetate, acidified with 1 M HCl, then washed with a saturated aqueous ammonium chloride and brine. The organic layer was dried over magnesium sulfate, filtered, and concentrated under reduced pressure. The residue was triturated in dichloromethane/hexanes, filtered and dried to provide 5-bromo-2-(3,3-difluorocyclobutyl)pyrimidine-4-carboxylic acid (325 mg, 84%). ESI-MS m/z calc. 291.97, found 293.03 $(M+1)^+$. $^1$H NMR (400 MHz, DMSO-$d_6$) δ 14.55 (br s, 1H), 9.15 (s, 1H), 3.71-3.57 (m, 1H), 3.10-2.83 (m, 4H). Decoupled: $^{19}$F NMR (376 MHz, DMSO-$d_6$) δ −80.54 (d, J=188.7 Hz), −95.25 (d, J=90.1 Hz).

Step 2: 5-bromo-2-(3,3-difluorocyclobutyl)-6-(4,4-difluorocyclohexyl)pyrimidine-4-carboxylic acid 5-Bromo-2-(3,3-difluorocyclobutyl)-6-(4,4-difluorocyclohexyl)pyrimidine-4-carboxylic acid was prepared from 5-bromo-2-(3,3-difluorocyclobutyl)pyrimidine-4-carboxylic acid and 4,4-difluorocyclohexanecarboxylic acid using a procedure analogous to that found in Intermediate B-43, step 1. ESI-MS m/z calc. 410.03, found 411.13 $(M+1)^+$. $^1$H NMR (400 MHz, $CD_3OD$) δ 3.67-3.50 (m, 1H), 3.48-3.35 (m, 1H), 3.03-2.90 (m, 4H), 2.25-2.13 (m, 2H), 2.03-1.90 (m, 6H). Decoupled: $^{19}$F NMR (376 MHz, $CD_3OD$) δ −83.78 (d, J=193.5 Hz), −93.18 (d, J=237.5 Hz), −99.43 (d, J=193.5 Hz), −103.45 (d, J=237.5 Hz).

Step 3: 5-bromo-2-(3,3-difluorocyclobutyl)-4-(4,4-difluorocyclohexyl)pyrimidine

5-Bromo-2-(3,3-difluorocyclobutyl)-4-(4,4-difluorocyclohexyl)pyrimidine was prepared from 5-Bromo-2-(3,3-difluorocyclobutyl)-6-(4,4-difluorocyclohexyl)pyrimidine-4-carboxylic acid using a procedure analogous to that found in Intermediate B-40, step 3 with heating at 60° C. for 90 min. ESI-MS m/z calc. 366.04, found 367.16 $(M+1)^+$. $^1H$ NMR (400 MHz, $CD_3OD$) δ 8.76 (s, 1H), 3.63-3.50 (m, 1H), 3.34-3.25 (m, 1H) overlaps with $CHD_2OD$, 2.95 (dt, J=15.9, 8.6 Hz, 4H), 2.25-2.13 (m, 2H), 2.06-1.84 (m, 6H). Decoupled: $^{19}F$ NMR (376 MHz, $CD_3OD$) δ −83.78 (d, J=193.5 Hz), −93.16 (d, J=237.4 Hz), −99.63, −103.42 (d, J=237.4 Hz).

Step 4: [2-(3,3-difluorocyclobutyl)-4-(4,4-difluorocyclohexyl)pyrimidin-5-yl]boronic acid

[2-(3,3-Difluorocyclobutyl)-4-(4,4-difluorocyclohexyl)pyrimidin-5-yl]boronic acid was prepared from 5-bromo-2-(3,3-difluorocyclobutyl)-4-(4,4-difluorocyclohexyl)pyrimidine using a procedure analogous to that found in Intermediate B-2, step 4 using $Pd(dppf)Cl_2$ as catalyst and dioxane/water (5:1) as the solvent. ESI-MS m/z calc. 332.10, found 333.3 $(M+1)^+$.

Intermediate B-48

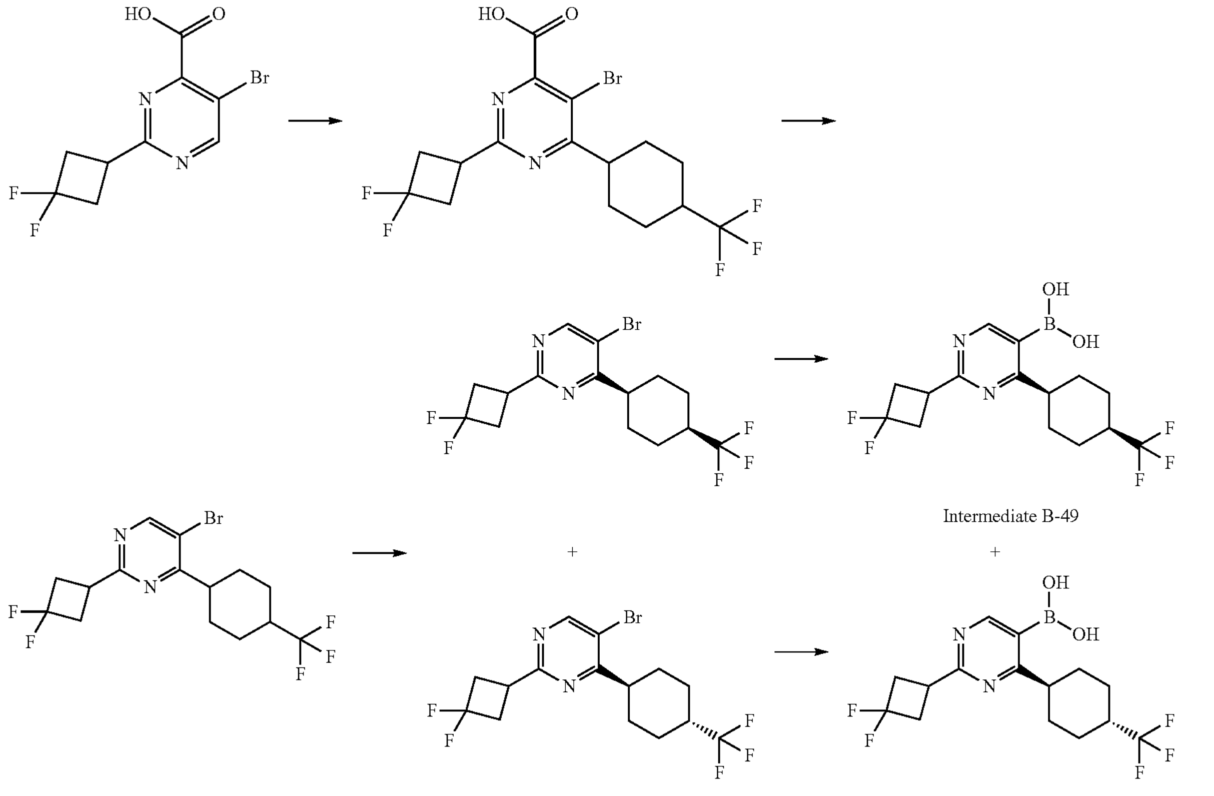

Intermediate B-49

+

Intermediate B-48

Step 1: 5-bromo-2-(3,3-difluorocyclobutyl)-6-[4-(trifluoromethyl)cyclohexyl]pyrimidine-4-carboxylic acid 5-Bromo-2-(3,3-difluorocyclobutyl)-6-[4-(trifluoromethyl)cyclohexyl]pyrimidine-4-carboxylic acid was prepared from 5-bromo-2-(3,3-difluorocyclobutyl)pyrimidine-4-carboxylic acid (Intermediate B-47 step 1) and 4-(trifluoromethyl)cyclohexanecarboxylic acid using a procedure analogous to that found in Intermediate B-43, step 1. ESI-MS m/z calc. 442.0, found 443.2 $(M+1)^+$.

Step 2: 5-bromo-2-(3,3-difluorocyclobutyl)-4-[4-(trifluoromethyl)cyclohexyl]pyrimidine (cis and trans isomers)

5-Bromo-2-(3,3-difluorocyclobutyl)-4-[4-(trifluoromethyl)cyclohexyl]pyrimidine (cis and trans isomers) were prepared from 5-bromo-2-(3,3-difluorocyclobutyl)-6-[4-(trifluoromethyl)cyclohexyl]pyrimidine-4-carboxylic acid using a procedure analogous to that found in Intermediate B-40, step 3 heating at 60° C. for 90 min. Purification by silica gel chromatography (0-100% ethyl acetate/hexanes over 15 min) afforded the major trans isomer product as a clear oil: 5-bromo-2-(3,3-difluorocyclobutyl)-4-[4-(trifluoromethyl)cyclohexyl]pyrimidine (trans isomer) (120 mg, 45%). $^1H$ NMR (400 MHz, $CD_3OD$) δ 8.75 (s, 1H), 3.62-3.50 (m, 1H), 3.17 (tt, J=12.0, 3.5 Hz, 1H), 3.05-2.86 (m, 4H), 2.34-2.17 (m, 1H), 2.15-2.03 (m, 2H), 2.03-1.96 (m, 2H), 1.74 (app qd, J=13.3, 3.4 Hz, 2H), 1.51 (app qd, J=13.1, 3.5 Hz, 2H). Decoupled: $^{19}F$ NMR (376 MHz, $CD_3OD$) δ −75.38, −83.72 (d, J=193.5 Hz), −99.54 (d, J=193.5 Hz). ESI-MS m/z calc. 398.04, found 399.25 $(M+1)^+$; Retention time: 3.25 min.

The minor cis isomer product was also isolated as a clear oil: 5-bromo-2-(3,3-difluorocyclobutyl)-4-[4-(trifluoromethyl)cyclohexyl]pyrimidine (cis isomer) (36 mg, 13%). $^1H$ NMR (400 MHz, $CD_3OD$) δ 8.73 (s, 1H), 3.63-3.51 (m, 1H), 3.45 (app p, J=5.2 Hz, 1H), 3.02-2.88 (m, 4H), 2.42-2.22 (m, 1H), 2.14-1.99 (m, 4H), 1.88-1.74 (m, 4H). Decoupled: $^{19}F$ NMR (376 MHz, $CD_3OD$) δ −72.70, −83.70 (d, J=193.1

Hz), −99.43 (d, J=193.0 Hz). ESI-MS m/z calc. 398.04, found 399.25 $(M+1)^+$; Retention time: 3.14 min. Reverse phase retention times were determined using a Acquity UPLC BEH C18 column (30×2.1 mm, 1.7 m particle) made by Waters, and a dual gradient run from 1-99% mobile phase B over 4.5 min. Mobile phase A=water (0.05% TFA). Mobile phase B=$CH_3CN$ (0.035% TFA). Flow rate=1.5 mL/min, injection volume=1.5 μL, and column temperature=60° C.

Step 2: [2-(3,3-difluorocyclobutyl)-4-[4-(trifluoromethyl)cyclohexyl]pyrimidin-5-yl]boronic acid (trans isomer)

[2-(3,3-difluorocyclobutyl)-4-[4-(trifluoromethyl)cyclohexyl]pyrimidin-5-yl]boronic acid (trans isomer) was prepared from 5-bromo-2-(3,3-difluorocyclobutyl)-4-[4-(trifluoromethyl)cyclohexyl]pyrimidine (trans isomer) using a procedure analogous to that found in Intermediate B-2, step 4 using Pd(dppf)$Cl_2$ as catalyst and dioxane/water (5:1) as the solvent. ESI-MS m/z calc. 364.12, found 365.2 $(M+1)^+$.

Intermediate B-49

[2-(3,3-difluorocyclobutyl)-4-[4-(trifluoromethyl)cyclohexyl]pyrimidin-5-yl]boronic acid (cis isomer) was prepared from 5-bromo-2-(3,3-difluorocyclobutyl)-4-[4-(trifluoromethyl)cyclohexyl]pyrimidine (cis isomer, Intermediate B-48 step 2) using a procedure analogous to that found in Intermediate B-2, step 4 using dioxane/water (5:1) as the solvent. ESI-MS m/z calc. 364.12, found 365.2 $(M+1)^+$.

Intermediate B-50

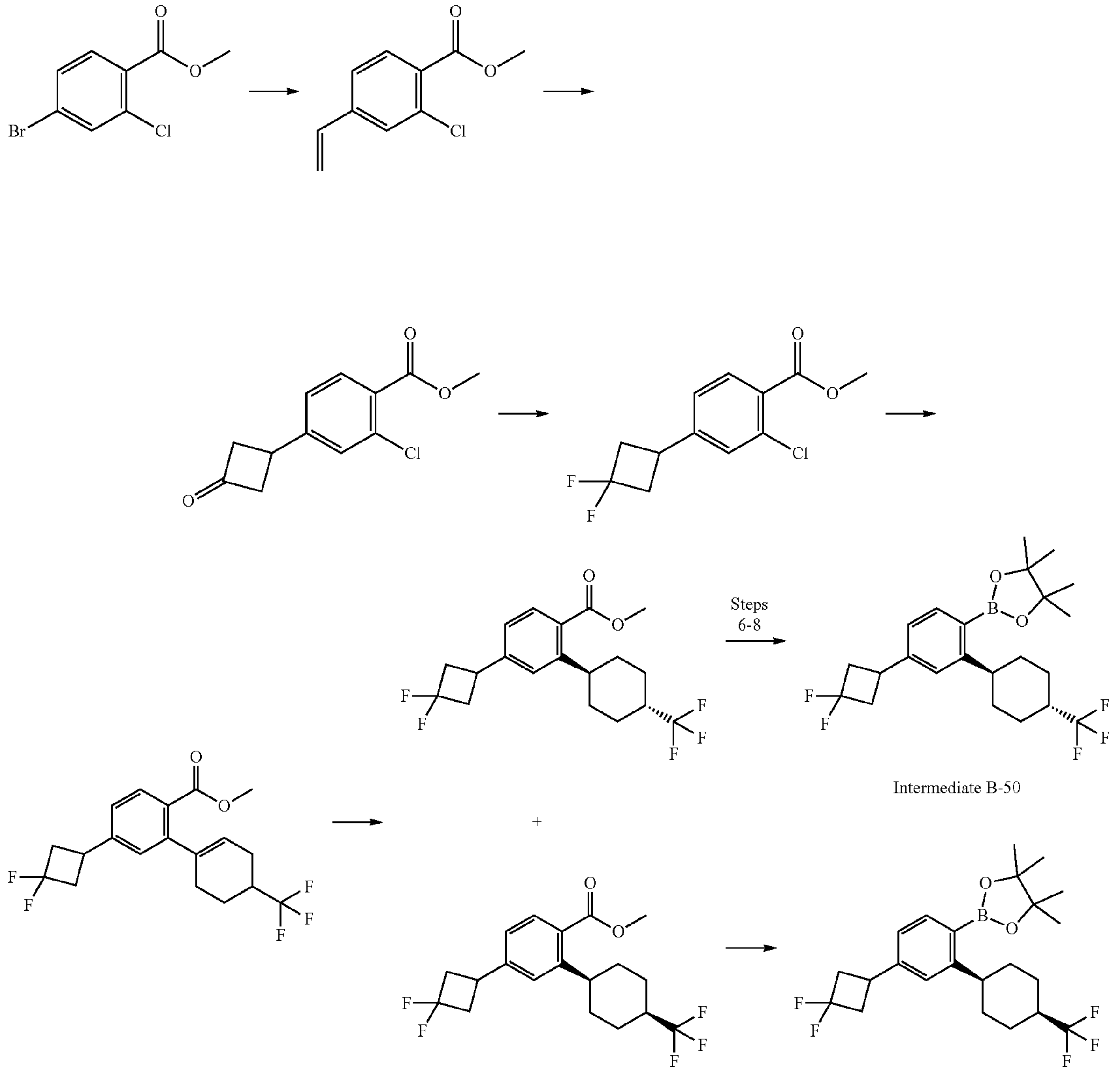

Intermediate B-50

Intermediate B-51

Step 1: Bethyl 2-chloro-4-vinyl-benzoate

A mixture of methyl 4-bromo-2-chlorobenzoate (2.0 g, 8.0 mmol), potassium vinyltrifluoroborate (1.3 g, 9.7 mmol), cesium carbonate (5.25 g, 16.1 mmol) in dioxane (40 mL) and water (6 mL) was degassed by nitrogen bubbling for 15 min and then Pd(dppf)$Cl_2$·DCM (197 mg, 0.241 mmol) was added. The mixture was heated at 100° C. and stirred at this temperature for 19 h. Once cooled to room temperature, the reaction mixture was filtered over Celite® and rinsed with ethyl acetate (50 mL). The filtrate was diluted with water (100 mL) and the layers were separated. The aqueous layer was extracted with ethyl acetate (2×50 mL), and the combined organic layers washed with brine (50 mL), dried over sodium sulfate, filtered and concentrated under reduced pressure. The resulting residue was adsorbed on silica gel under vacuum and purified by silica gel chromatography (0-10% ethyl acetate/heptanes) to provide methyl 2-chloro-4-vinyl-benzoate (1.14 g, 71%) as a colorless oil. ESI-MS m/z calc. 196.03, found 197.1 $(M+1)^+$. $^1$H NMR (400 MHz, $CDCl_3$) δ 7.83 (d, J=8.1 Hz, 1H), 7.48 (d, J=1.2 Hz, 1H), 7.33 (dd, J=8.1, 1.2 Hz, 1H), 6.68 (dd, J=17.6, 10.9 Hz, 1H), 5.87 (d, J=17.6 Hz, 1H), 5.43 (d, J=10.9 Hz, 1H), 3.94 (s, 3H).

Step 2: Methyl 2-chloro-4-(3-oxocyclobutyl)benzoate

To a solution of N,N-dimethylacetamide (1.3 g, 1.4 mL, 15 mmol) in 1,2-dichloroethane (4 mL) under nitrogen at −15° C. was added a solution of trifluoromethanesulfonic anhydride (4.2 g, 2.5 mL, 15 mmol) in 1,2-dichloroethane (9 mL) dropwise. The mixture was then stirred at −15° C. for 10 min. A separate vial was then charged with methyl 2-chloro-4-vinyl-benzoate (940 mg, 4.781 mmol) and 1,2-dichloroethane (9 mL) followed by a solution of 2,4,6-trimethylpyridine (917 mg, 1.0 mL, 7.6 mmol) in 1,2-dichloroethane (3 mL) was added dropwise under stirring at −15° C. The resulting mixture was added dropwise to the first solution and then the combined mixture heated at 80° C. for 65 h. After cooling to room temperature, the mixture was carefully quenched by water addition (50 mL) and extracted with ethyl acetate (2×100 mL). The combined organic layers were washed with brine (2×50 mL), dried over sodium sulfate, filtered and concentrated under reduced pressure to give 1.82 g of a brown oil. The crude product was adsorbed on silica gel under vacuum and purified by silica gel chromatography (0-30% ethyl acetate/heptanes) to provide methyl 2-chloro-4-(3-oxocyclobutyl)benzoate (271 mg, 22%) as a yellow oil (93% purity). ESI-MS m/z calc. 238.04, found 239.0 $(M+1)^+$. $^1$H NMR (400 MHz, $CDCl_3$) δ 7.86 (d, J=8.2 Hz, 1H), 7.40 (d, J=0.9 Hz, 1H), 7.25 (br d, J=1.1 Hz, 1H), 3.94 (s, 3H), 3.74-3.66 (m, 1H), 3.61-3.49 (m, 2H), 3.32-3.22 (m, 2H).

Step 3: Methyl 2-chloro-4-(3,3-difluorocyclobutyl)benzoate

To a solution of methyl 2-chloro-4-(3-oxocyclobutyl) benzoate (270 mg, 1.13 mmol) in dichloromethane (1 mL) was added Deoxo-Fluor® (2 mL of 50% w/v in THF, 4.5 mmol). The reaction mixture was stirred at room temperature for 40 h, then poured into stirring mixture of saturated aqueous sodium bicarbonate (25 mL) and dichloromethane (20 mL). The aqueous layer was extracted with additional dichloromethane (2×30 mL). The organic extracts were combined, dried over sodium sulfate, filtered and evaporated under reduced pressure. The crude product was adsorbed on silica gel under vacuum and purified by silica gel chromatography (0-10% ethyl acetate/heptane) to provide methyl 2-chloro-4-(3,3-difluorocyclobutyl)benzoate (235 mg, 78%) as a colorless oil. ESI-MS m/z calc. 260.04, found 261.0 $(M+1)^+$. $^1$H NMR (400 MHz, $CDCl_3$) δ 7.84 (d, J=8.1 Hz, 1H), 7.33 (d, J=0.9 Hz, 1H), 7.19 (dd, J=8.1, 1.1 Hz, 1H), 3.94 (s, 3H), 3.41 (quin, J=8.3 Hz, 1H), 3.12-2.97 (m, 2H), 2.77-2.61 (m, 2H). $^{19}$F NMR (377 MHz, $CDCl_3$) δ −81.94--82.83 (m, 1F), −98.38--99.29 (m, 1F).

Step 4: Methyl 4-(3,3-difluorocyclobutyl)-2-[4-(trifluoromethyl)cyclohexen-1-yl]benzoate Methyl 4-(3,3-difluorocyclobutyl)-2-[4-(trifluoromethyl) cyclohexen-1-yl]benzoate was prepared from methyl 2-chloro-4-(3,3-difluorocyclobutyl)benzoate and 4,4,5,5-tetramethyl-2-[4-(trifluoromethyl)cyclohexen-1-yl]-1,3,2-dioxaborolane using a procedure analogous to that found in Intermediate B-34, step 1 using potassium phosphate as base and XPhos Pd G2 catalyst. ESI-MS m/z calc. 374.13, found 375.1 $(M+1)^+$.

Step 5: Methyl 4-(3,3-difluorocyclobutyl)-2-[4-(trifluoromethyl)cyclohexyl]benzoate (trans isomer) and methyl 4-(3,3-difluorocyclobutyl)-2-[4-(trifluoromethyl)cyclohexyl]benzoate (cis isomer)

Methyl 4-(3,3-difluorocyclobutyl)-2-[4-(trifluoromethyl) cyclohexyl]benzoate (cis and trans isomers) were prepared from methyl 4-(3,3-difluorocyclobutyl)-2-[4-(trifluoromethyl)cyclohexen-1-yl]benzoate using a procedure analogous to that found in Intermediate B-36, step 3. Purification by silica gel chromatography (0-8% ethyl acetate/heptanes) provided the product as a 78/22 ratio of diastereoisomers: Methyl 4-(3,3-difluorocyclobutyl)-2-[4-(trifluoromethyl)cyclohexyl]benzoate (trans isomer) (225 mg, 20%). $^1$H NMR (400 MHz, $CDCl_3$) δ 7.83-7.78 (m, 1H), 7.19 (s, 1H), 7.14 (d, J=8.2 Hz, 1H), 3.91 (s, 3H), 3.50-3.35 (m, 2H), 3.03 (tdd, J=14.0, 9.0, 5.1 Hz, 2H), 2.76-2.60 (m, 2H), 2.18-2.11 (m, 1H), 2.11-1.99 (m, 4H), 1.62-1.43 (m, 4H). $^{19}$F NMR (377 MHz, $CDCl_3$) δ −73.73 (d, J=8.2 Hz, 3F), −81.72--82.65 (m, 1F), −98.51--99.35 (m, 1F). ESI-MS m/z calc. 376.15, found 377.2 $(M+1)^+$; Retention time: 2.43 min. and methyl 4-(3,3-difluorocyclobutyl)-2-[4-(trifluoromethyl)cyclohexyl]benzoate (cis isomer) (744 mg, 72%). $^1$H NMR (400 MHz, $CDCl_3$) δ 7.79 (d, J=8.1 Hz, 1H), 7.20 (s, 1H), 7.14 (dd, J=8.1, 1.2 Hz, 1H), 3.90 (s, 3H), 3.56-3.46 (m, 1H), 3.45-3.36 (m, 1H), 3.04 (tdd, J=14.0, 9.0, 5.1 Hz, 2H), 2.76-2.60 (m, 2H), 2.48-2.33 (m, 1H), 2.20-2.09 (m, 2H), 1.84-1.70 (m, 6H). $^{19}$F NMR (377 MHz, $CDCl_3$) δ −66.68 (br d, J=12.3 Hz, 3F), −81.94--82.62 (m, 1F), −98.59--99.32 (m, 1F). ESI-MS m/z calc. 376.15, found 377.2 $(M+1)^+$; Retention time: 2.41 min.

Reverse phase retention times were determined using a Kinetex Polar C18 (50×3.0 mm, 2.6 m particle), 5-95% $CH_3CN$/0.1% aqueous formic acid) over 3 min. Flow rate=1.2 mL/min.

Step 6: 4-(3,3-difluorocyclobutyl)-2-[4-(trifluoromethyl)cyclohexyl]benzoic acid (trans isomer)

4-(3,3-difluorocyclobutyl)-2-[4-(trifluoromethyl)cyclohexyl]benzoic acid (trans isomer) was prepared from methyl 4-(3,3-difluorocyclobutyl)-2-[4-(trifluoromethyl)cyclohexyl]benzoate (trans isomer) using a procedure analogous to that found in Intermediate B-11, step 4. $^1$H NMR (400

MHz, $CDCl_3$) δ 10.93 (br s, 1H), 7.99 (d, J=8.1 Hz, 1H), 7.23 (s, 1H), 7.19 (d, J=8.2 Hz, 1H), 3.65-3.55 (m, 1H), 3.49-3.38 (m, 1H), 3.05 (tdd, J=14.0, 9.0, 5.1 Hz, 2H), 2.79-2.63 (m, 2H), 2.22-2.00 (m, 5H), 1.63-1.44 (m, 4H). $^{19}F$ NMR (377 MHz, $CDCl_3$) δ −73.72 (d, J=8.2 Hz, 3F), −81.89−−82.59 (m, 1F), −98.49−−99.28 (m, 1F).

Step 7: 1-bromo-4-(3,3-difluorocyclobutyl)-2-[4-(trifluoromethyl)cyclohexyl]benzene (trans isomer)

1-Bromo-4-(3,3-difluorocyclobutyl)-2-[4-(trifluoromethyl)cyclohexyl]benzene (trans isomer) was prepared from 4-(3,3-difluorocyclobutyl)-2-[4-(trifluoromethyl)cyclohexyl]benzoic acid (trans isomer) using a procedure analogous to that found in Intermediate B-36, step 5. $^1H$ NMR (400 MHz, $CDCl_3$) δ 7.51 (d, J=8.2 Hz, 1H), 7.05 (d, J=2.3 Hz, 1H), 7.01-6.89 (m, 1H), 3.42-3.23 (m, 1H), 3.10-2.91 (m, 3H), 2.76-2.49 (m, 2H), 2.17-2.04 (m, 4H), 1.61-1.36 (m, 5H). $^{19}F$ NMR (376 MHz, $CDCl_3$) δ −73.74, −82.16 (d, J=194.1 Hz), −99.12 (d, J=194.2 Hz).

Step 8: 2-[4-(3,3-difluorocyclobutyl)-2-[4-(trifluoromethyl)cyclohexyl]phenyl]-4,4,5,5-tetramethyl-1,3,2-dioxaborolane (trans isomer)

2-[4-(3,3-Difluorocyclobutyl)-2-[4-(trifluoromethyl)cyclohexyl]phenyl]-4,4,5,5-tetramethyl-1,3,2-dioxaborolane (trans isomer) was prepared from 1-bromo-4-(3,3-difluorocyclobutyl)-2-[4-(trifluoromethyl)cyclohexyl]benzene (trans isomer) using a procedure analogous to that found in Intermediate B-2, step 4 using Pd(dppf)$Cl_2$ catalyst and dioxane as solvent. $^1H$ NMR (400 MHz, $CDCl_3$) δ 7.75 (d, J=8.2 Hz, 1H), 7.11-7.04 (m, 2H), 3.43-3.26 (m, 2H), 3.06-2.91 (m, 2H), 2.76-2.57 (m, 2H), 2.16-2.03 (m, 3H), 1.97 (s, 1H), 1.53-1.39 (m, 5H), 1.34 (s, 12H). $^{19}F$ NMR (376 MHz, $CDCl_3$) δ −73.70, −81.97 (d, J=193.5 Hz), −99.39 (d, J=192.8 Hz).

Intermediate B-51

Step 1: 4-(3,3-difluorocyclobutyl)-2-[4-(trifluoromethyl)cyclohexyl]benzoic acid (cis isomer)

4-(3,3-Difluorocyclobutyl)-2-[4-(trifluoromethyl)cyclohexyl]benzoic acid (cis isomer) was prepared from methyl 4-(3,3-difluorocyclobutyl)-2-[4-(trifluoromethyl)cyclohexyl]benzoate (cis isomer, from Intermediate B-50, step 5) using a procedure analogous to that found in Intermediate B-11, step 4. $^1H$ NMR (400 MHz, $CDCl_3$) δ 11.53-10.26 (m, 1H), 7.97 (d, J=8.1 Hz, 1H), 7.25 (s, 1H), 7.19 (d, J=8.2 Hz, 1H), 3.72-3.60 (m, 1H), 3.49-3.39 (m, 1H), 3.06 (tdd, J=14.0, 9.0, 5.3 Hz, 2H), 2.79-2.62 (m, 2H), 2.48-2.34 (m, 1H), 2.22-2.09 (m, 2H), 1.87-1.72 (m, 6H). $^{19}F$ NMR (377 MHz, $CDCl_3$) δ −66.67 (br d, J=12.3 Hz, 3F), −81.97−−82.67 (m, 1F), −98.45−−99.21 (m, 1F). ESI-MS m/z calc. 362.13, found 363.0 $(M+1)^+$; Retention time: 3.42 min.

Step 2: 1-bromo-4-(3,3-difluorocyclobutyl)-2-[4-(trifluoromethyl)cyclohexyl]benzene (cis isomer)

1-Bromo-4-(3,3-difluorocyclobutyl)-2-[4-(trifluoromethyl)cyclohexyl]benzene (cis isomer) was prepared from 4-(3,3-difluorocyclobutyl)-2-[4-(trifluoromethyl)cyclohexyl]benzoic acid (cis isomer) using a procedure analogous to that found in Intermediate B-36, step 5.

Step 3: 2-[4-(3,3-difluorocyclobutyl)-2-[4-(trifluoromethyl)cyclohexyl]phenyl]-4,4,5,5-tetramethyl-1,3,2-dioxaborolane 2-[4-(3,3-difluorocyclobutyl)-2-[4-(trifluoromethyl)cyclohexyl]phenyl]-4,4,5,5-tetramethyl-1,3,2-dioxaborolane (cis isomer) was prepared from 1-bromo-4-(3,3-difluorocyclobutyl)-2-[4-(trifluoromethyl)cyclohexyl]benzene (cis isomer) using a procedure analogous to that found in Intermediate B-50, step 8.

Intermediate B-52

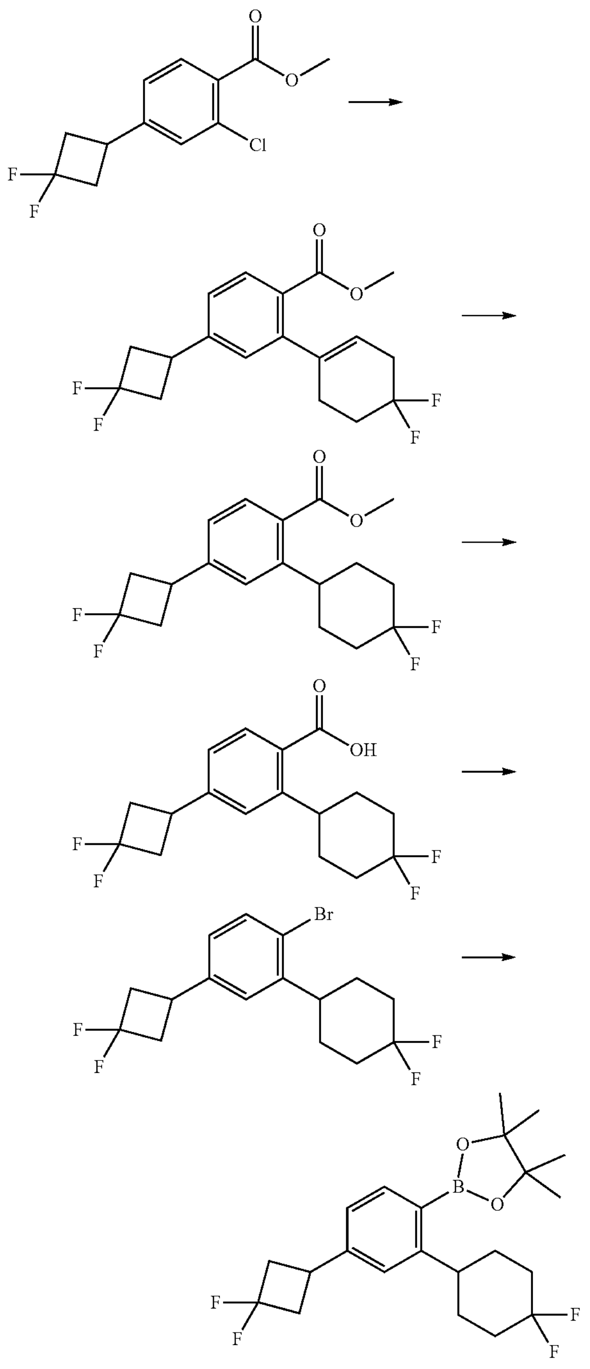

Step 1: Ethyl 4-(3,3-difluorocyclobutyl)-2-(4,4-difluorocyclohexen-1-yl)benzoate Methyl 4-(3,3-difluorocyclobutyl)-2-(4,4-difluorocyclohexen-1-yl)benzoate was prepared from methyl 2-chloro-4-(3,3-difluorocyclobutyl)benzoate and 4,4-difluoro-1-cyclohexene-1-boronic acid pinacol ester using a procedure analogous to that found in Intermediate B-34, step 1 using $Pd(PPh_3)_4$ as the catalyst. ESI-MS m/z calc. 342.12, found 343.0 $(M+1)^+$. $^1H$ NMR (400 MHz, $CDCl_3$) δ 7.87 (d, J=8.1 Hz, 1H), 7.22 (dd, J=8.1, 1.2 Hz, 1H), 7.04 (d, J=1.1 Hz, 1H), 5.38 (br s, 1H), 3.86 (s, 3H), 3.48-3.35 (m, 1H), 3.10-2.97 (m, 2H), 2.78-2.61 (m, 4H), 2.52 (brt, J=5.6 Hz, 2H), 2.21 (tt, J=13.7, 6.7 Hz, 2H). $^{19}F$ NMR (377 MHz, $CDCl_3$) δ −81.62-−82.46 (m, 1F), −95.90-−96.41 (m, 2F), −98.74-−99.64 (m, 1F).

Step 2: Methyl 4-(3,3-difluorocyclobutyl)-2-(4,4-difluorocyclohexyl)benzoate

Methyl 4-(3,3-difluorocyclobutyl)-2-(4,4-difluorocyclohexyl)benzoate was prepared from methyl 4-(3,3-difluorocyclobutyl)-2-(4,4-difluorocyclohexen-1-yl)benzoate using a procedure analogous to that found in Intermediate B-36, step 3. $^1H$ NMR (400 MHz, $CDCl_3$) δ 7.83 (d, J=8.1 Hz, 1H), 7.21 (s, 1H), 7.16 (dd, J=8.1, 1.2 Hz, 1H), 3.91 (s, 3H), 3.57 (brt, J=12.2 Hz, 1H), 3.48-3.35 (m, 1H), 3.11-2.97 (m, 2H), 2.77-2.61 (m, 2H), 2.29-2.17 (m, 2H), 1.95 (br d, J=13.2 Hz, 3H), 1.90-1.71 (m, 3H). $^{19}F$ NMR (377 MHz, $CDCl_3$) δ −81.72-−82.70 (m, 1F), −91.39 (br d, J=235.7 Hz, 1F), −98.52-−99.50 (m, 1F), −102.14 (dtt, J=235.7, 34.7, 10.9 Hz, 1F).

Step 3: 4-(3,3-difluorocyclobutyl)-2-(4,4-difluorocyclohexyl)benzoic acid 4-(3,3-Difluorocyclobutyl)-2-(4,4-difluorocyclohexyl)benzoic acid was prepared using a procedure analogous to that found in Intermediate B-13, step 4 with stirring at room temperature for 19 h. ESI-MS m/z calc. 330.12, found 311.0 (M−19)+. $^1H$ NMR (400 MHz, $CDCl_3$) δ 10.76 (br s, 1H), 8.01 (d, J=8.1 Hz, 1H), 7.25 (s, 1H), 7.21 (d, J=8.2 Hz, 1H), 3.77-3.66 (m, 1H), 3.50-3.38 (m, 1H), 3.06 (tdd, J=14.0, 9.0, 5.1 Hz, 2H), 2.79-2.62 (m, 2H), 2.30-2.19 (m, 2H), 1.97 (br d, J=11.2 Hz, 3H), 1.92-1.75 (m, 3H). $^{19}F$ NMR (377 MHz, $CDCl_3$) δ −81.84-−82.66 (m, 1F), −91.42 (br d, J=234.3 Hz, 1F), −98.43-−99.36 (m, 1F), −101.51-−102.66 (m, 1F).

Step 4: 1-bromo-4-(3,3-difluorocyclobutyl)-2-(4,4-difluorocyclohexyl)benzene

1-Bromo-4-(3,3-difluorocyclobutyl)-2-(4,4-difluorocyclohexyl)benzene was prepared from 4-(3,3-difluorocyclobutyl)-2-(4,4-difluorocyclohexyl)benzoic acid using a procedure analogous to that found in Intermediate B-36, step 5. $^1H$ NMR (500 MHz, DMSO-$d_6$) δ 7.56 (d, J=8.2 Hz, 1H), 7.29 (d, J=2.4 Hz, 1H), 7.13 (dd, J=8.2, 2.3 Hz, 1H), 3.51-3.35 (m, 1H), 3.12-2.91 (m, 3H), 2.79-2.60 (m, 2H), 2.24-2.09 (m, 2H), 2.09-1.91 (m, 2H), 1.91-1.80 (m, 2H), 1.81-1.63 (m, 2H).

Step 5: 2-[4-(3,3-difluorocyclobutyl)-2-(4,4-difluorocyclohexyl)phenyl]-4,4,5,5-tetramethyl-1,3,2-dioxaborolane 2-[4-(3,3-Difluorocyclobutyl)-2-(4,4-difluorocyclohexyl)phenyl]-4,4,5,5-tetramethyl-1,3,2-dioxaborolane was prepared from 1-bromo-4-(3,3-difluorocyclobutyl)-2-(4,4-difluorocyclohexyl)benzene and using a procedure analogous to that found in Intermediate B-2, step 4 using dioxane as solvent and $Pd(dppf)Cl_2$ as the catalyst. ESI-MS m/z calc. 412.22, found 413.6 $(M+1)^+$. $^1H$ NMR (400 MHz, $CD_3OD$) δ 7.70 (d, J=7.7 Hz, 1H), 7.18-7.14 (m, 1H), 7.14-7.08 (m, 1H), 3.52-3.33 (m, 2H), 3.06-2.87 (m, 2H), 2.75-2.54 (m, 2H), 2.22-2.09 (m, 2H), 1.96-1.82 (m, 4H), 1.81-1.71 (m, 2H), 1.35 (s, 12H). $^{19}F$ NMR (376 MHz, $CD_3OD$) δ −83.62 (dd, J=193.8, 2.7 Hz), −92.38 (dd, J=236.8, 2.7 Hz), −100.54 (d, J=193.6 Hz), −103.49 (dd, J=237.2, 2.7 Hz).

Intermediate B-53

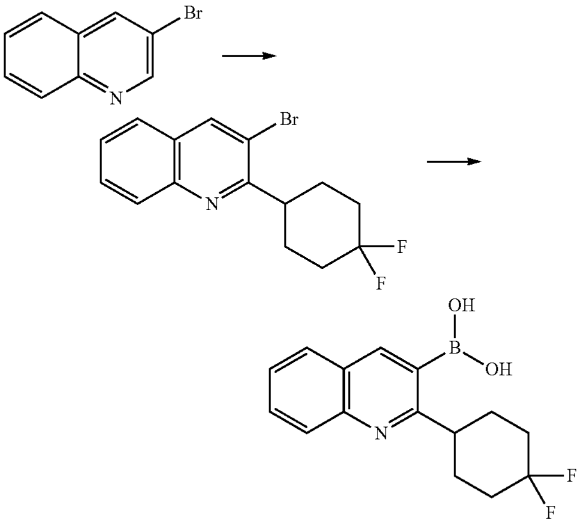

Step 1: 3-bromo-2-(4,4-difluorocyclohexyl)quinoline

3-Bromo-2-(4,4-difluorocyclohexyl)quinoline was prepared from 3-bromoquinoline and 4,4-difluorocyclohexanecarboxylic acid using a procedure analogous to that found in Intermediate B-43, step 1. The product was purified by silica gel chromatography (0-20% ethyl acetate/hexanes over 50 min) to remove the isomeric 3-bromo-4-(4,4-difluorocyclohexyl)quinoline, followed by reverse phase HPLC purification (10-99% acetonitrile/5 mM HCl over 20 min). ESI-MS m/z calc. 325.03, found 326.1 $(M+1)^+$; Retention time: 2.83 min. $^1H$ NMR (400 MHz, $CD_3OD$) δ 8.52 (br s, 1H), 8.06-7.94 (m, 1H), 7.88-7.79 (m, 1H), 7.79-7.67 (m, 1H), 7.62-7.49 (m, 1H), 3.62-3.45 (m, 1H), 2.31-2.17 (m, 2H), 2.13-1.86 (m, 6H).

Step 2: [2-(4,4-difluorocyclohexyl)-3-quinolyl]boronic acid

[2-(4,4-Difluorocyclohexyl)-3-quinolyl]boronic acid was prepared from 3-bromo-2-(4,4-difluorocyclohexyl)quinoline using a procedure analogous to that found in Intermediate B-2, step 4 using dioxane as the solvent. ESI-MS m/z calc. 291.12, found 292.2 $(M+1)^+$.

Intermediate B-54

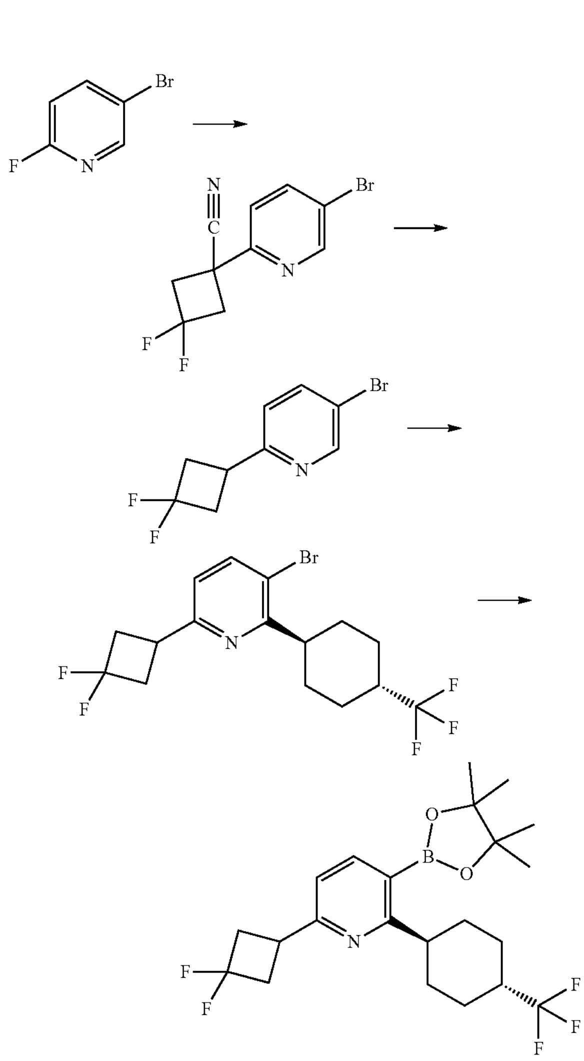

Step 1: 1-(5-bromo-2-pyridyl)-3,3-difluoro-cyclobutanecarbonitrile 1-(5-Bromo-2-pyridyl)-3,3-difluoro-cyclobutanecarbonitrile was prepared from 5-bromo-2-fluoro-pyridine using a procedure analogous to that found in Intermediate B-40, step 1. $^1$H NMR (400 MHz, $CDCl_3$) δ 8.72 (d, J=2.5 Hz, 1H), 7.89 (dd, J=8.4, 2.4 Hz, 1H), 7.57 (d, J=8.4 Hz, 1H), 3.58-3.43 (m, 2H), 3.38-3.26 (m, 2H). ESI-MS m/z calc. 271.98, found 273.1 $(M+1)^+$.

Step 2: 5-bromo-2-(3,3-difluorocyclobutyl)pyridine

5-Bromo-2-(3,3-difluorocyclobutyl)pyridine was prepared from 1-(5-bromo-2-pyridyl)-3,3-difluoro-cyclobutanecarbonitrile using a procedure analogous to that found in Intermediate B-40, step 2 and step 3. ESI-MS m/z calc. 246.98, found 248.0 $(M+1)^+$. $^1$H NMR (400 MHz, $CDCl_3$) δ 8.64 (d, J=3.1 Hz, 1H), 7.74 (dd, J=8.3, 2.4 Hz, 1H), 7.08 (d, J=8.3 Hz, 1H), 3.41 (pd, J=8.8, 3.2 Hz, 1H), 2.99-2.83 (m, 4H).

Step 3: 3-bromo-6-(3,3-difluorocyclobutyl)-2-[4-(trifluoromethyl)cyclohexyl]pyridine (trans isomer)

3-Bromo-6-(3,3-difluorocyclobutyl)-2-[4-(trifluoromethyl)cyclohexyl]pyridine was prepared from 5-bromo-2-(3,3-difluorocyclobutyl)pyridine and 4-(trifluoromethyl)cyclohexanecarboxylic acid using a procedure analogous to that found in Intermediate B-43, step 1. $^1$H NMR (400 MHz, $CDCl_3$) δ 7.71 (d, J=7.9 Hz, 1H), 6.87 (d, J=7.9 Hz, 1H), 3.36 (m, 1H), 3.17 (t, J=11.6 Hz, 1H), 3.00-2.80 (m, 4H), 2.18 (ddt, J=13.0, 8.4, 4.3 Hz, 1H), 2.10 (d, J=12.5 Hz, 2H), 1.98 (d, J=11.9 Hz, 2H), 1.72 (q, J=11.9 Hz, 2H), 1.51 (qd, J=13.0, 3.6 Hz, 2H). ESI-MS m/z calc. 397.05, found 398.0 $(M+1)^+$.

Step 4: 6-(3,3-difluorocyclobutyl)-3-(4,4,5,5-tetramethyl-1,3,2-dioxaborolan-2-yl)-2-[4-(trifluoromethyl)cyclohexyl]pyridine (trans isomer)

6-(3,3-Difluorocyclobutyl)-3-(4,4,5,5-tetramethyl-1,3,2-dioxaborolan-2-yl)-2-[4-(trifluoromethyl)cyclohexyl]pyridine was prepared using a procedure analogous to that found in Intermediate B-2, step 4. ESI-MS m/z calc. 445.22, found 446.2 $(M+1)^+$.

Intermediate B-55

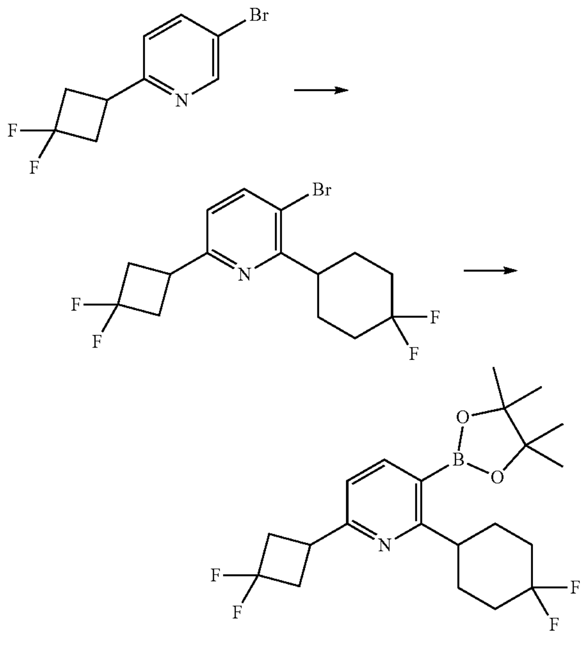

Step 1: 3-bromo-6-(3,3-difluorocyclobutyl)-2-(4,4-difluorocyclohexyl)pyridine 3-bromo-6-(3,3-difluorocyclobutyl)-2-(4,4-difluorocyclohexyl)pyridine was prepared from 5-bromo-2-(3,3-difluorocyclobutyl)pyridine (Intermediate 54, step 2) and 4,4-difluorocyclohexanecarboxylic acid using a procedure analogous to that found in Intermediate B-43, step 1. $^1$H NMR (400 MHz, $CDCl_3$) δ 7.72 (d, J=8.0 Hz, 1H), 6.89 (d, J=8.0 Hz, 1H), 3.37 (pd, J=8.6, 3.1 Hz, 1H), 3.29-3.17 (m, 1H), 3.03-2.77 (m, 4H), 2.32-2.19 (m, 2H), 2.10-1.78 (m, 6H).

Step 2: 6-(3,3-difluorocyclobutyl)-2-(4,4-difluorocyclohexyl)-3-(4,4,5,5-tetramethyl-1,3,2-dioxaborolan-2-yl)pyridine 6-(3,3-Difluorocyclobutyl)-2-(4,4-difluorocyclohexyl)-3-(4,4,5,5-tetramethyl-1,3,2-dioxaborolan-2-yl)pyridine was prepared using a procedure analogous to that found in Intermediate B-2, step 4 and Pd(dppf)$Cl_2$ as the catalyst. ESI-MS m/z calc. 413.22, found 414.2 $(M+1)^+$.

Intermediate B-56

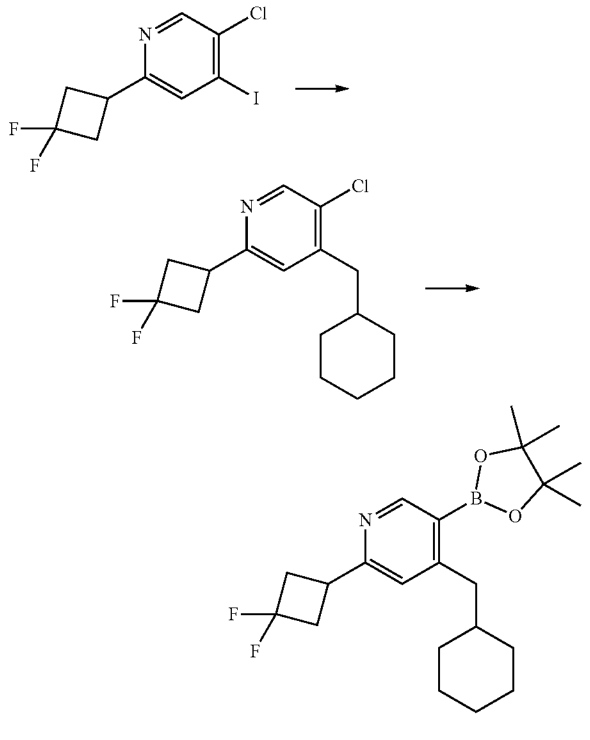

Step 1: 5-chloro-4-(cyclohexylmethyl)-2-(3,3-difluorocyclobutyl)pyridine

To a microwave vial charged with 5-chloro-2-(3,3-difluorocyclobutyl)-4-iodo-pyridine (Intermediate B-40 Step 3, 100 mg, 0.304 mmol), $Pd(^tBu_3P)_2$ (48 mg, 0.094 mmol) and THF (700 μL) under nitrogen atmosphere at 0° C. was slowly added bromo(cyclohexylmethyl)zinc in THF (620 μL of 0.5 M, 0.31 mmol). The reaction mixture was gradually warmed to room temperature and stirred at this temperature for 45 min then heated to 60° C. for 18 h. The mixture was filtered, concentrated and purified by reverse phase HPLC (C18, 10-99% $CH_3CN$/5 mM HCl) to provide 5-chloro-4-(cyclohexylmethyl)-2-(3,3-difluorocyclobutyl)pyridine (20 mg, 22%). ESI-MS m/z calc. 299.13, found 300.2 $(M+1)^+$. $^1H$ NMR (400 MHz, $CDCl_3$) δ 8.47 (s, 1H), 6.95 (s, 1H), 3.46-3.32 (m, 1H), 2.97-2.88 (m, 4H), 2.58 (d, J=6.7 Hz, 2H), 1.72-1.58 (m, 6H), 1.23-1.15 (m, 3H), 1.06-0.98 (m, 2H). $^{19}F$ NMR (376 MHz, $CDCl_3$) δ −81.76 (d, J=192.8 Hz), −99.46 (d, J=192.7 Hz).

Step 2: 4-(cyclohexylmethyl)-2-(3,3-difluorocyclobutyl)-5-(4,4,5,5-tetramethyl-1,3,2-dioxaborolan-2-yl)pyridine 4-(Cyclohexylmethyl)-2-(3,3-difluorocyclobutyl)-5-(4,4,5,5-tetramethyl-1,3,2-dioxaborolan-2-yl)pyridine was prepared using a procedure analogous to that found in Intermediate B-2, step 4. using dioxane as solvent and SPhos Pd G3 as catalyst. ESI-MS m/z calc. 391.25, found 392.2 $(M+1)^+$.

Intermediate B-57

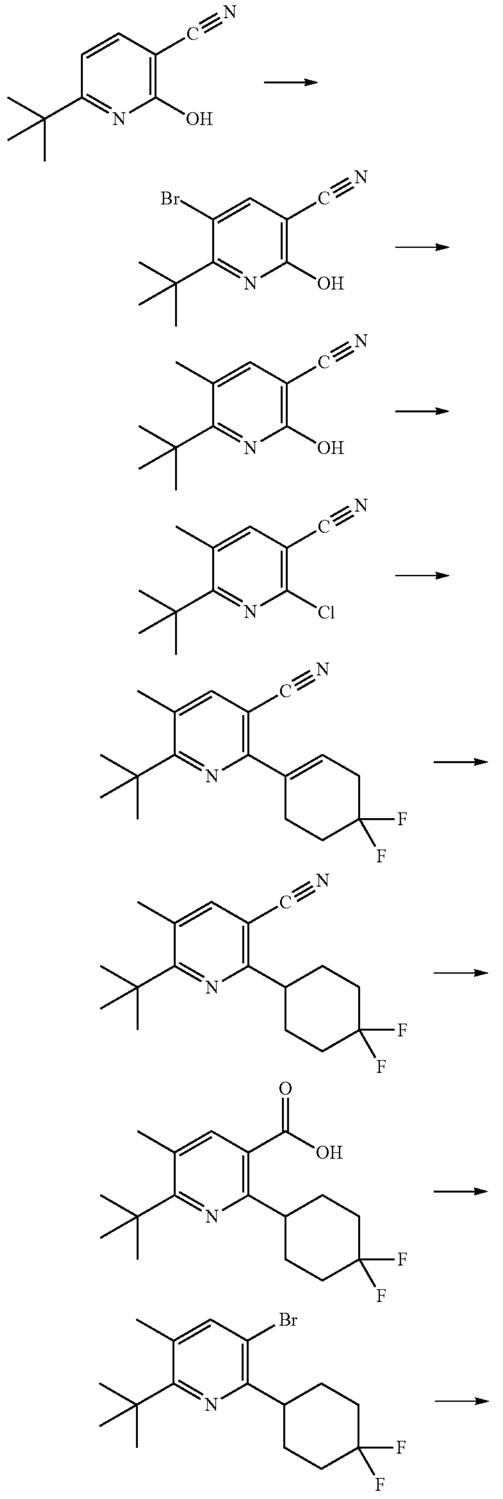

-continued

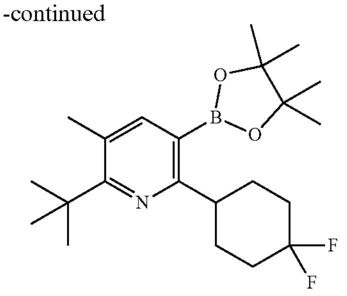

Step 1: 5-bromo-6-tert-butyl-2-hydroxy-pyridine-3-carbonitrile 5-bromo-6-tert-butyl-2-hydroxy-pyridine-3-carbonitrile was prepared from 6-tert-butyl-2-hydroxy-pyridine-3-carbonitrile using a procedure analogous to that found in Intermediate B-24, step 2. ESI-MS m/z calc. 254.01, found 255.2 $(M+1)^+$. $^1$H NMR (400 MHz, DMSO-$d_6$) δ 8.37 (s, 1H), 1.45 (s, 9H).

Step 2: 6-tert-butyl-2-hydroxy-5-methyl-pyridine-3-carbonitrile

A mixture of 5-bromo-6-tert-butyl-2-hydroxy-pyridine-3-carbonitrile (1.0 g, 3.9 mmol), potassium carbonate (1.65 g, 11.9 mmol), Pd(dppf)$Cl_2$·DCM (700 mg, 0.857 mmol) and 2,4,6-trimethyl-1,3,5,2,4,6-trioxatriborinane (2.25 g, 2.5 mL, 17.9 mmol) in nitrogen-degassed 1,4-dioxane (15 mL) was stirred at 120° C. for 8 h in a sealed vial. The mixture was diluted cooled to room temperature and diluted with ethyl acetate (50 mL). The mixture was filtered through Celite®, rinsed with ethyl acetate (50 mL) and concentrated under reduced pressure. The residue was adsorbed on silica gel under vacuum and purified by silica gel chromatography (40 g, 5-90% ethyl acetate/DCM) to provide 6-tert-butyl-2-hydroxy-5-methyl-pyridine-3-carbonitrile (642 mg, 82%). ESI-MS m/z calc. 190.11, found 191.2 $(M+1)^+$. $^1$H NMR (400 MHz, $CDCl_3$) δ 9.34 (br.s, 1H), 7.63 (s, 1H), 2.29 (s, 3H), 1.45 (s, 9H).

Step 3: 6-tert-butyl-2-chloro-5-methyl-pyridine-3-carbonitrile 6-tert-Butyl-2-chloro-5-methyl-pyridine-3-carbonitrile was prepared from 6-tert-butyl-2-hydroxy-5-methyl-pyridine-3-carbonitrile using a procedure analogous to that found in Intermediate B-6, step 1. $^1$H NMR (400 MHz, $CDCl_3$) δ 7.67 (s, 1H), 2.55 (s, 3H), 1.45 (s, 9H). ESI-MS m/z calc. 208.08, found 209.0 $(M+1)^+$.

Step 4: 6-tert-butyl-2-(4,4-difluorocyclohexen-1-yl)-5-methyl-pyridine-3-carbonitrile 6-tert-Butyl-2-(4,4-difluorocyclohexen-1-yl)-5-methyl-pyridine-3-carbonitrile was prepared from 6-tert-butyl-2-chloro-5-methyl-pyridine-3-carbonitrile and 2-(4,4-difluorocyclohexen-1-yl)-4,4,5,5-tetramethyl-1,3,2-dioxaborolane using a procedure analogous to that found in Intermediate B-b 34, step 1 and using cesium carbonate as the base. ESI-MS m/z calc. 290.16, found 291.2 $(M+1)^+$. $^1$H NMR (400 MHz, $CDCl_3$) δ 7.65 (s, 1H), 6.50 (br. s, 1H), 2.96-2.88 (m, 2H), 2.87-2.75 (m, 2H), 2.54 (s, 3H), 2.28-2.16 (m, 2H), 1.44 (s, 9H). $^{19}$F NMR (377 MHz, CDCl3) δ −96.15--96-51 (m, 2F).

Step 5: 6-tert-butyl-2-(4,4-difluorocyclohexyl)-5-methyl-pyridine-3-carbonitrile 6-tert-Butyl-2-(4,4-difluorocyclohexyl)-5-methyl-pyridine-3-carbonitrile was prepared from 6-tert-butyl-2-(4,4-difluorocyclohexen-1-yl)-5-methyl-pyridine-3-carbonitrile using a procedure analogous to that found in Intermediate B-34, step 2. ESI-MS m/z calc. 292.18, found 293.2 $(M+1)^+$; Retention time: 2.42 min. $^1$H NMR (400 MHz, $CDCl_3$) δ 7.48 (s, 1H), 3.16-3.01 (m, 1H), 2.42 (s, 3H), 2.23-2.10 (m, 2H), 2.06-1.73 (m, 6H), 1.34 (s, 9H).

Step 6: 6-tert-butyl-2-(4,4-difluorocyclohexyl)-5-methyl-pyridine-3-carboxylic acid 6-tert-butyl-2-(4,4-difluorocyclohexyl)-5-methyl-pyridine-3-carboxylic acid was prepared from 6-tert-butyl-2-(4,4-difluorocyclohexyl)-5-methyl-pyridine-3-carbonitrile using a procedure analogous to that found in Intermediate B-32, step 4. ESI-MS m/z calc. 311.17, found 312.2 $(M+1)^+$. $^1$H NMR (400 MHz, $CDCl_3$) δ 7.96 (s, 1H), 3.78-3.65 (m, 1H), 2.53 (s, 3H), 2.31-2.17 (m, 2H), 2.13-2.03 (m, 2H), 2.01-1.81 (m, 4H), 1.45 (s, 9H). $^{19}$F NMR (376 MHz, $CDCl_3$) δ −90.18--91.47 (m, 1F), −100.95--102.37 (m, 1F).

Step 7: 5-bromo-2-tert-butyl-6-(4,4-difluorocyclohexyl)-3-methyl-pyridine

5-Bromo-2-tert-butyl-6-(4,4-difluorocyclohexyl)-3-methyl-pyridine was prepared from 6-tert-butyl-2-(4,4-difluorocyclohexyl)-5-methyl-pyridine-3-carboxylic acid using a procedure analogous to that found in Intermediate B-36, step 5. ESI-MS m/z calc. 345.09, found 346.2 $(M+1)^+$. $^1$H NMR (400 MHz, $CDCl_3$) δ 7.50 (s, 1H), 3.23-3.12 (m, 1H), 2.45 (s, 3H), 2.32-2.16 (m, 2H), 2.10-1.78 (m, 6H), 1.41 (s, 9H). $^{19}$F NMR (377 MHz, $CDCl_3$) δ −91.35 (d, J=234.3 Hz, 1F), −101.48 (d, J=235.7 Hz, 1F).

Step 8: 2-tert-butyl-6-(4,4-difluorocyclohexyl)-3-methyl-5-(4,4,5,5-tetramethyl-1,3,2-dioxaborolan-2-yl)pyridine 2-tert-Butyl-6-(4,4-difluorocyclohexyl)-3-methyl-5-(4,4,5,5-tetramethyl-1,3,2-dioxaborolan-2-yl)pyridine was prepared from 5-bromo-2-tert-butyl-6-(4,4-difluorocyclohexyl)-3-methyl-pyridine using a procedure analogous to that found in Intermediate B-2, step 4 with 1,4-dioxane as the solvent. ESI-MS m/z calc. 393.27, found 394.4 $(M+1)^+$. $^1$H NMR (400 MHz, $CDCl_3$) δ 7.71 (s, 1H), 3.49-3.36 (m, 1H), 2.47 (s, 3H), 2.30-2.16 (m, 2H), 2.13-1.98 (m, 2H), 1.98-1.78 (m, 4H), 1.43 (s, 9H), 1.37 (s, 12H). $^{19}$F NMR (377 MHz, $CDCl_3$) δ −90.87 (d, J=234.3 Hz, 1F), −100.99 (d, J=233.0 Hz, 1F).

Intermediate B-58

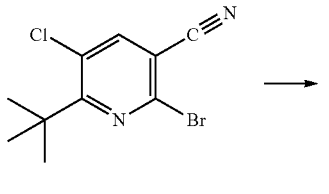

-continued

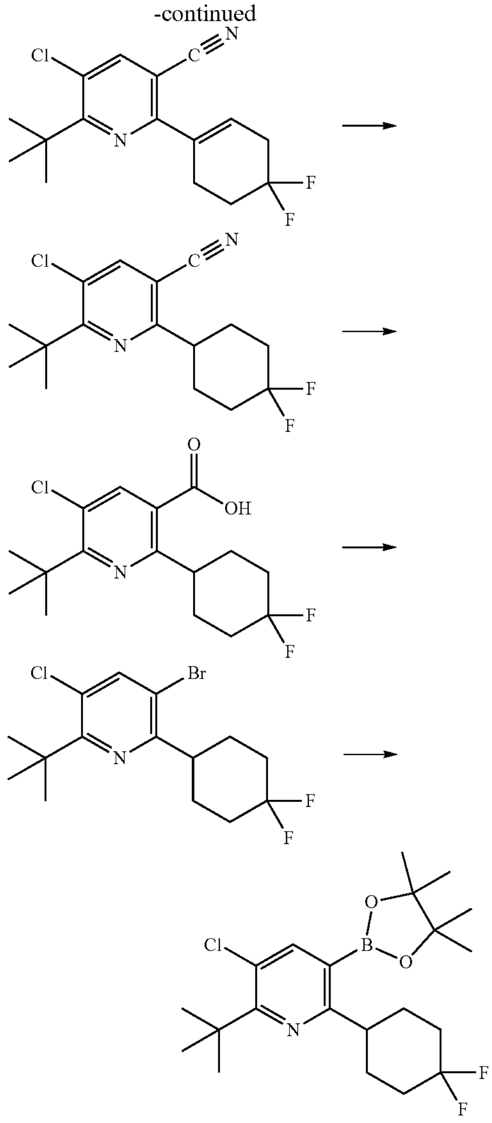

Step 1: 6-tert-butyl-5-chloro-2-(4,4-difluorocyclohexen-1-yl)pyridine-3-carbonitrile 6-tert-Butyl-5-chloro-2-(4,4-difluorocyclohexen-1-yl)pyridine-3-carbonitrile was prepared from 2-bromo-6-tert-butyl-5-chloro-pyridine-3-carbonitrile (Intermediate B-32, step 2) and 2-(4,4-difluorocyclohexen-1-yl)-4,4,5,5-tetramethyl-1,3,2-dioxaborolane using a procedure analogous to that found in Intermediate B-34, step 1 and using cesium carbonate as the base. ESI-MS m/z calc. 310.11, found 311.2 $(M+1)^+$. $^1H$ NMR (400 MHz, $CDCl_3$) δ 7.87 (s, 1H), 6.55 (br s, 1H), 2.92-2.86 (m, 2H), 2.86-2.77 (m, 2H), 2.28-2.14 (m, 2H), 1.50 (s, 9H). $^{19}F$ NMR (377 MHz, $CDCl_3$) δ −96.45 (s, 2F).

Step 2: 6-tert-butyl-5-chloro-2-(4,4-difluorocyclohexyl)pyridine-3-carbonitrile 6-tert-Butyl-5-chloro-2-(4,4-difluorocyclohexyl)pyridine-3-carbonitrile was prepared from 6-tert-butyl-5-chloro-2-(4,4-difluorocyclohexen-1-yl)pyridine-3-carbonitrile using a procedure analogous to that found in Intermediate B-34, step 2. ESI-MS m/z calc. 310.11, found 311.2 $(M+1)^+$. $^1H$ NMR (400 MHz, $CDCl_3$) δ 7.87 (s, 1H), 6.55 (br s, 1H), 2.93-2.78 (m, 4H), 2.21 (tt, J=13.8, 6.7 Hz, 2H), 1.50 (s, 9H). $^{19}F$ NMR (377 MHz, $CDCl_3$) δ −96.45 (s, 2F).

Step 3: 6-tert-butyl-5-chloro-2-(4,4-difluorocyclohexyl)pyridine-3-carboxylic acid 6-tert-Butyl-5-chloro-2-(4,4-difluorocyclohexyl)pyridine-3-carboxylic acid was prepared from 6-tert-butyl-5-chloro-2-(4,4-difluorocyclohexyl)pyridine-3-carbonitrile using a procedure analogous to that found in Intermediate B-32, step 4. ESI-MS m/z calc. 331.12, found 332.2 $(M+1)^+$. $^1H$ NMR (400 MHz, DMSO-$d_6$) δ 13.53 (br s, 1H), 8.05 (s, 1H), 3.71-3.61 (m, 1H), 2.18-2.05 (m, 2H), 1.98-1.83 (m, 6H), 1.45 (s, 9H).

Step 4: 5-bromo-2-tert-butyl-3-chloro-6-(4,4-difluorocyclohexyl)pyridine 5-bromo-2-tert-butyl-3-chloro-6-(4,4-difluorocyclohexyl)pyridine was prepared from 6-tert-butyl-5-chloro-2-(4,4-difluorocyclohexyl)pyridine-3-carboxylic acid using a procedure analogous to that found in Intermediate B-36, step 5. ESI-MS m/z calc. 365.04, found 366.2 $(M+1)^+$. 1H NMR (400 MHz, $CDCl_3$) δ 7.75 (s, 1H), 3.23-3.11 (m, 1H), 2.28-2.18 (m, 2H), 2.02-1.80 (m, 6H), 1.46 (s, 9H). $^{19}F$ NMR (377 MHz, CDCl3) δ −91.56 (d, J=235.7 Hz, 1F), −101.66 (d, J=234.3 Hz, 1F).

Step 5: 2-tert-butyl-3-chloro-6-(4,4-difluorocyclohexyl)-5-(4,4,5,5-tetramethyl-1,3,2-dioxaborolan-2-yl)pyridine 2-tert-Butyl-3-chloro-6-(4,4-difluorocyclohexyl)-5-(4,4,5,5-tetramethyl-1,3,2-dioxaborolan-2-yl)pyridine was prepared using a procedure analogous to that found in Intermediate B-2, step 4 using dioxane as the solvent. ESI-MS m/z calc. 413.21, found 414.3 $(M+1)^+$. $^1H$ NMR (400 MHz, $CDCl_3$) δ 7.91 (s, 1H), 3.45-3.35 (m, 1H), 2.28-2.15 (m, 2H), 2.03-1.78 (m, 6H), 1.47 (s, 9H), 1.35 (s, 12H). $^{19}F$ NMR (377 MHz, $CDCl_3$) δ −91.10 (d, J=234.3 Hz, 1F), −101.20 (d, J=235.7 Hz, 1F).

Intermediate B-59

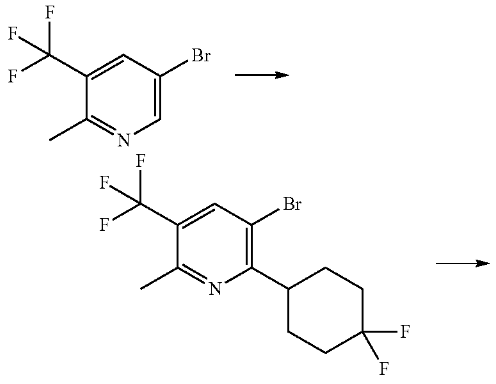

-continued

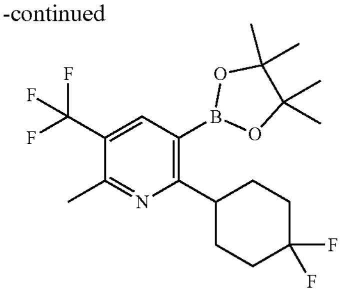

Step 1: 3-bromo-2-(4,4-difluorocyclohexyl)-6-methyl-5-(trifluoromethyl)pyridine

3-Bromo-2-(4,4-difluorocyclohexyl)-6-methyl-5-(trifluoromethyl)pyridine was prepared from 5-bromo-2-methyl-3-(trifluoromethyl)pyridine and 4,4-difluorocyclohexanecarboxylic acid using a procedure analogous to that found in Intermediate B-43, step 1. ESI-MS m/z calc. 357.02, found 357.93 $(M+1)^+$. $^1H$ NMR (400 MHz, $CDCl_3$) δ 7.97 (s, 1H), 3.28-3.22 (m, 1H), 2.62 (q, J=1.5 Hz, 3H), 2.28-2.20 (m, 2H), 2.07-1.79 (m, 6H).

Step 2: 2-(4,4-difluorocyclohexyl)-6-methyl-3-(4,4,5,5-tetramethyl-1,3,2-dioxaborolan-2-yl)-5-(trifluoromethyl)pyridine 2-(4,4-Difluorocyclohexyl)-6-methyl-3-(4,4,5,5-tetramethyl-1,3,2-dioxaborolan-2-yl)-5-(trifluoromethyl)pyridine was prepared from 3-bromo-2-(4,4-difluorocyclohexyl)-6-methyl-5-(trifluoromethyl)pyridine using a procedure analogous to that found in Intermediate B-2, step 4 using dioxane as solvent and $Pd(ddpf)_2Cl_2$ as catalyst. ESI-MS m/z calc. 405.19, found 406.15 $(M+1)^+$. $^1H$ NMR (400 MHz, $CDCl_3$) δ 8.21 (s, 1H), 7.28 (s, 2H), 3.54-3.49 (m, 1H), 2.71-2.65 (m, 3H), 2.29-2.21 (m, 2H), 2.11-2.02 (m, 2H), 1.96-1.79 (m, 4H), 1.38 (s, 12H).

Intermediate B-60

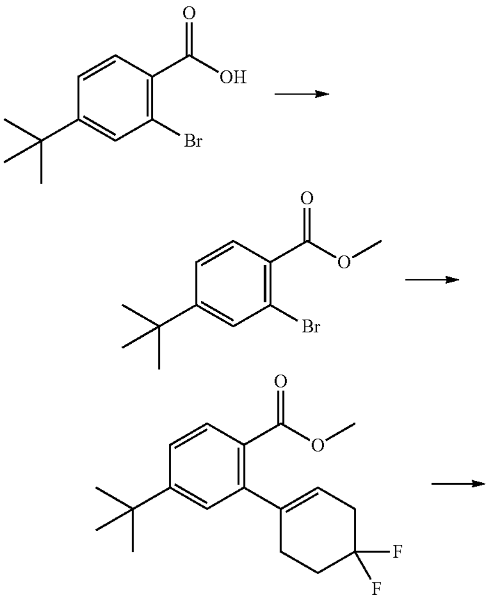

-continued

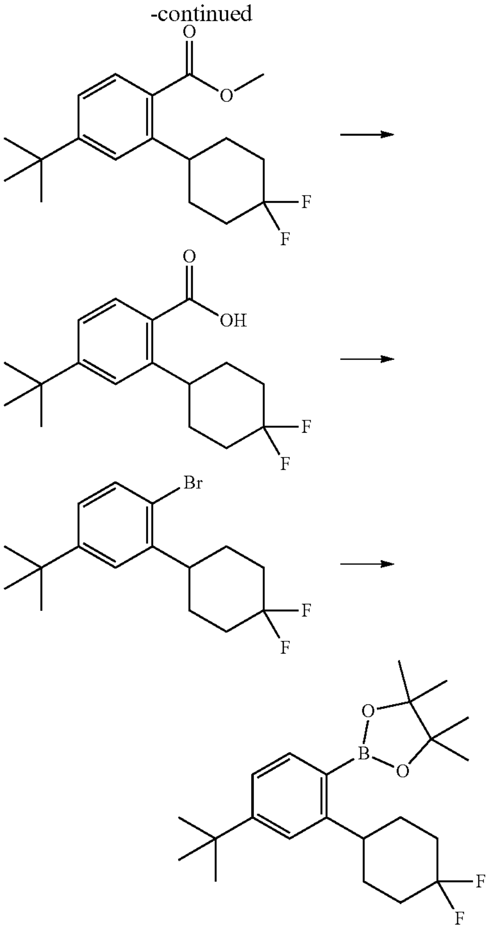

Step 1: Ethyl 2-bromo-4-tert-butyl-benzoate

To a solution of 2-bromo-4-tert-butyl-benzoic acid (0.95 g, 3.7 mmol) in DMF (8.5 mL) was added cesium carbonate (1.8 g, 5.5 mmol) followed by iodomethane (500 μL, 8.03 mmol). The mixture was stirred at room temperature for 16 h then partitioned between ethyl acetate and water. The organic layer was washed with brine (2×), dried over sodium sulfate, filtered and concentrated to provide methyl 2-bromo-4-tert-butyl-benzoate (935 mg, 93%). $^1H$ NMR (400 MHz, $CDCl_3$) δ 7.76 (d, J=8.2 Hz, 1H), 7.66 (d, J=1.9 Hz, 1H), 7.36 (dd, J=8.2, 1.9 Hz, 1H), 3.92 (s, 3H), 1.32 (s, 9H).

Step 2: Methyl 4-tert-butyl-2-(4,4-difluorocyclohexen-1-yl)benzoate

Methyl 4-tert-butyl-2-(4,4-difluorocyclohexen-1-yl)benzoate was prepared from methyl 2-bromo-4-tert-butyl-benzoate and 2-(4,4-difluorocyclohexen-1-yl)-4,4,5,5-tetramethyl-1,3,2-dioxaborolane using a procedure analogous to that found in Intermediate B-34, step 1 using $Pd(PPh_3)_4$ as the catalyst. ESI-MS m/z calc. 308.16, found 309.4 $(M+1)^+$. $^1H$ NMR (400 MHz, $CDCl_3$) δ 7.81 (d, J=8.3 Hz, 1H), 7.36 (dd, J=8.3, 2.0 Hz, 1H), 7.17 (d, J=2.1 Hz, 1H), 5.42-5.29 (m, 1H), 3.84 (s, 3H), 2.77-2.59 (m, 2H), 2.59-2.45 (m, 2H), 2.30-2.12 (m, 2H), 1.33 (s, 9H).

Step 3: Methyl 4-tert-butyl-2-(4,4-difluorocyclohexyl)benzoate

Methyl 4-tert-butyl-2-(4,4-difluorocyclohexyl)benzoate was prepared from the above intermediate methyl 4-tert-butyl-2-(4,4-difluorocyclohexen-1-yl)benzoate using a procedure analogous to that found in Intermediate B-36, step 3. ESI-MS m/z calc. 310.17, found 311.3 $(M+1)^+$. $^1$H NMR (400 MHz, Chloroform-d) δ 7.78 (d, J=8.3 Hz, 1H), 7.38 (d, J=2.0 Hz, 1H), 7.31-7.25 (m, 1H), 3.88 (s, 3H), 3.63-3.52 (m, 1H), 2.29-2.12 (m, 2H), 2.01-1.89 (m, 3H), 1.88-1.69 (m, 3H), 1.32 (s, 9H). $^{19}$F NMR (376 MHz, Chloroform-d) δ −91.19 (d, J=235.0 Hz), −102.04 (d, J=235.1 Hz).

Step 4: 4-tert-butyl-2-(4,4-difluorocyclohexyl)benzoic acid 4-tert-Butyl-2-(4,4-difluorocyclohexyl)benzoic acid was prepared from methyl 4-tert-butyl-2-(4,4-difluorocyclohexyl)benzoate using a procedure analogous to that found in Intermediate B-13, step 4 with stirring at room temperature for 16 hours. ESI-MS m/z calc. 296.16, found 295.2 $(M-1)^-$. $^1$H NMR (400 MHz, $CDCl_3$) δ 7.95 (d, J=8.3 Hz, 1H), 7.42 (d, J=1.9 Hz, 1H), 7.35-7.29 (m, 1H), 3.71 (t, J=12.0 Hz, 1H), 2.30-2.14 (m, 2H), 2.05-1.90 (m, 4H), 1.89-1.76 (m, 2H), 1.34 (s, 9H). $^{19}$F NMR (376 MHz, $CDCl_3$) δ −91.20 (d, J=235.2 Hz), −101.98 (d, J=235.2 Hz).

Step 5: 1-bromo-4-tert-butyl-2-(4,4-difluorocyclohexyl)benzene

1-Bromo-4-tert-butyl-2-(4,4-difluorocyclohexyl)benzene was prepared from 4-tert-butyl-2-(4,4-difluorocyclohexyl) benzoic acid using a procedure analogous to that found in Intermediate B-36, step 5. $^1$H NMR (400 MHz, $CDCl_3$) δ 7.46 (d, J=8.4 Hz, 1H), 7.24 (s, 1H), 7.10 (dd, J=8.4, 2.4 Hz, 1H), 3.11-3.01 (m, 1H), 2.29-2.18 (m, 2H), 2.01-1.93 (m, 3H), 1.92-1.68 (m, 3H), 1.30 (s, 9H). $^{19}$F NMR (376 MHz, $CDCl_3$) δ −91.37 (d, J=235.9 Hz), −102.08 (d, J=235.9 Hz).

Step 6: 2-[4-tert-butyl-2-(4,4-difluorocyclohexyl) phenyl]-4,4,5,5-tetramethyl-1,3,2-dioxaborolane 2-[4-tert-Butyl-2-(4,4-difluorocyclohexyl)phenyl]-4,4,5,5-tetramethyl-1,3,2-dioxaborolane was prepared from 1-bromo-4-tert-butyl-2-(4,4-difluorocyclohexyl)benzene using a procedure analogous to that found in Intermediate B-2, step 4. ESI-MS m/z calc. 378.25, found 379.4 $(M+1)^+$. $^1$H NMR (400 MHz, $CDCl_3$) δ 7.75 (d, J=7.8 Hz, 1H), 7.29 (d, J=1.9 Hz, 1H), 7.24 (dd, J=7.9, 1.9 Hz, 1H), 3.48-3.37 (m, 1H), 2.27-2.16 (m, 2H), 1.98-1.88 (m, 3H), 1.87-1.71 (m, 3H), 1.33 (s, 12H), 1.31 (s, 9H). $^{19}$F NMR (376 MHz, $CDCl_3$) δ −90.87 (d, J=234.7 Hz), −101.73 (d, J=234.8 Hz).

Intermediate B-61

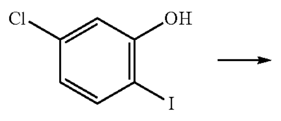

-continued

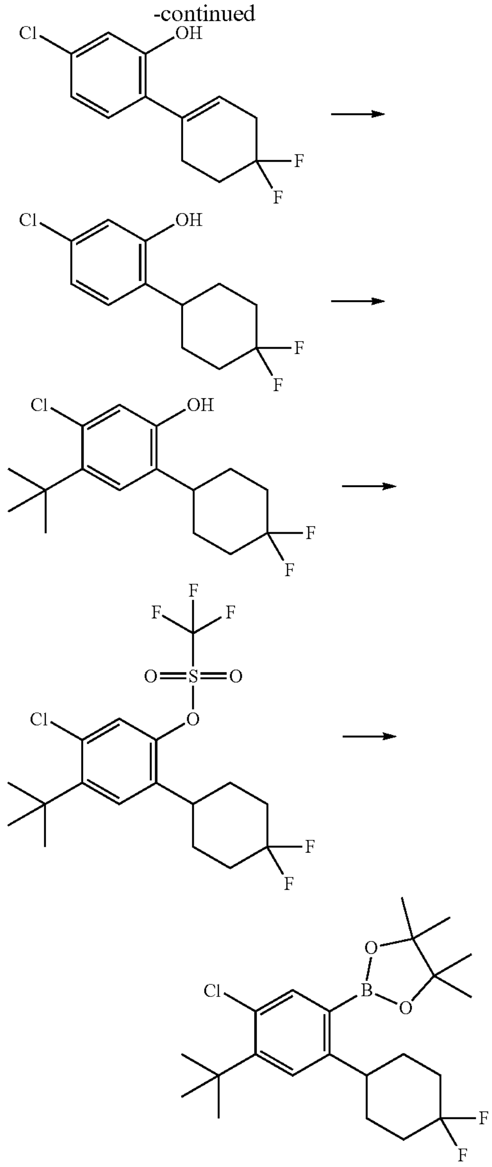

Step 1: 5-chloro-2-(4,4-difluorocyclohexen-1-yl)phenol

5-Chloro-2-(4,4-difluorocyclohexen-1-yl)phenol was prepared from 5-chloro-2-iodo-phenol and 2-(4,4-difluorocyclohexen-1-yl)-4,4,5,5-tetramethyl-1,3,2-dioxaborolane using a procedure analogous to that found in Intermediate B-34, step 1, using sodium carbonate as base and $Pd(PPh_3)_4$. ESI-MS m/z calc. 244.05, found 243.1 $(M-1)^-$. $^1$H NMR (400 MHz, $CDCl_3$) δ 7.02 (d, J=8.2 Hz, 1H), 6.96-6.86 (m, 2H), 5.72 (br. s, 1H), 5.38 (s, 1H), 2.80-2.66 (m, 2H), 2.63-2.54 (m, 2H), 2.52-2.29 (m, 2H). $^{19}$F NMR (377 MHz, $CDCl_3$) δ −97.01 (s, 2F).

Step 2: 5-chloro-2-(4,4-difluorocyclohexyl)phenol

5-Chloro-2-(4,4-difluorocyclohexyl)phenol was prepared from 5-chloro-2-(4,4-difluorocyclohexen-1-yl)phenol using a procedure analogous to that found in Intermediate B-36, step 3. ESI-MS m/z calc. 246.06, found 245.0 $(M-1)^-$. $^1$H NMR (400 MHz, $CDCl_3$) δ 7.09 (d, J=8.3 Hz, 1H), 6.90 (dd, J=8.2, 1.8 Hz, 1H), 6.77 (d, J=2.0 Hz, 1H), 5.14 (s, 1H), 3.00-2.88 (m, 1H), 2.28-2.16 (m, 2H), 1.99-1.69 (m, 6H). $^{19}F$ NMR (377 MHz, $CDCl_3$) δ −91.28 (d, J=235.7 Hz, 1F), −102.31 (d, J=234.3 Hz, 1F).

Step 3: 4-tert-butyl-5-chloro-2-(4,4-difluorocyclohexyl)phenol

5-Chloro-2-(4,4-difluorocyclohexyl)phenol (245 mg, 0.854 mmol) was added to a solution of heptane (2.5 mL) and 2-methylpropan-2-ol (0.35 mL, 3.66 mmol). The mixture was cooled to −10° C. and sulfuric acid (184 mg, 0.1 mL, 1.88 mmol) was added dropwise. The reaction mixture was stirred vigorously at room temperature for 18 h. Additional 2-methyl-2-propanol (0.35 mL, 3.66 mmol) and sulfuric acid (184 mg, 0.1 mL, 1.88 mmol) were added and the resulting mixture was stirred vigorously at room temperature for 72 h. The mixture was quenched with addition of saturated aqueous sodium bicarbonate until pH 8. The resulting mixture was extracted with dichloromethane (3×20 mL). The combined organic layers were dried over sodium sulfate, filtered and concentrated under reduced pressure. Purification by silica gel chromatography (0-15% ethyl acetate/heptanes), followed by reverse phase chromatography (5-90% CH3CN/0.1% aq. formic acid) provided 4-tert-butyl-5-chloro-2-(4,4-difluorocyclohexyl)phenol (112 mg, 43%). ESI-MS m/z calc. 302.12, found 301.1 $(M-1)^-$. $^1H$ NMR (400 MHz, $CDCl_3$) δ 7.18 (s, 1H), 6.77 (s, 1H), 4.66 (br. s, 1H), 2.96-2.85 (m, 1H), 2.28-2.17 (m, 2H), 1.99-1.73 (m, 6H), 1.45 (s, 9H). $^{19}F$ NMR (377 MHz, $CDCl_3$) δ −91.21 (d, J=235.7 Hz, 1F), −102.24 (d, J=235.7 Hz, 1F).

Step 4: [4-tert-butyl-5-chloro-2-(4,4-difluorocyclohexyl)phenyl]trifluoromethanesulfonate

[4-tert-Butyl-5-chloro-2-(4,4-difluorocyclohexyl)phenyl] trifluoromethanesulfonate was prepared from 4-tert-butyl-5-chloro-2-(4,4-difluorocyclohexyl)phenol using a procedure analogous to that found in Intermediate B-16, step 3 and pyridine as the base. $^1H$ NMR (400 MHz, $CDCl_3$) δ 7.39 (s, 1H), 7.26 (s, 1H), 2.97-2.86 (m, 1H), 2.31-2.19 (m, 2H), 2.00-1.71 (m, 6H), 1.49 (s, 9H). $^{19}F$ NMR (377 MHz, $CDCl_3$) δ −73.70 (s, 3F), −91.85 (d, J=237.1 Hz, 1F), −102.44 (d, J=237.1 Hz, 1F).

Step 5: 2-[4-tert-butyl-5-chloro-2-(4,4-difluorocyclohexyl)phenyl]-4,4,5,5-tetramethyl-1,3,2-dioxaborolane 2-[4-tert-Butyl-5-chloro-2-(4,4-difluorocyclohexyl)phenyl]-4,4,5,5-tetramethyl-1,3,2-dioxaborolane was prepared from [4-tert-butyl-5-chloro-2-(4,4-difluorocyclohexyl)phenyl]trifluoromethanesulfonate using a procedure analogous to that found in Intermediate B-2, step 4 using dioxane as the solvent. $^1H$ NMR (400 MHz, $CDCl_3$) δ 7.74 (s, 1H), 7.30 (s, 1H), 3.36 (t, J=12.2 Hz, 1H), 2.27-2.16 (m, 2H), 1.98-1.69 (m, 6H), 1.48 (s, 9H), 1.34 (s, 12H). $^{19}F$ NMR (377 MHz, $CDCl_3$) δ −91.12 (d, J=234.3 Hz, 1F), −101.84 (d, J=234.3 Hz, 1F).

Intermediate B-62

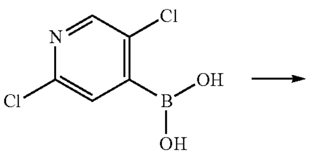

-continued

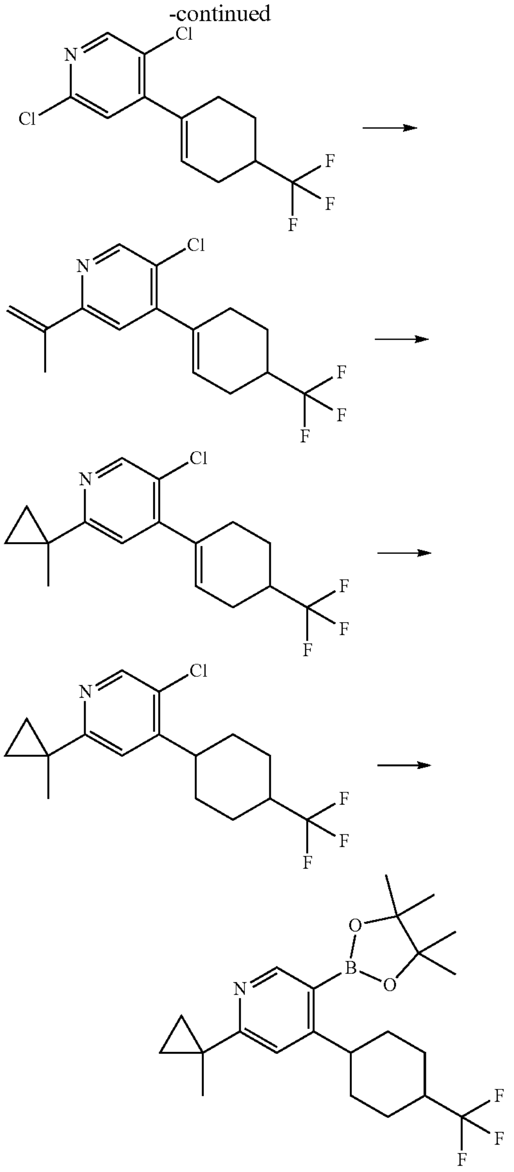

Step 1: 2,5-dichloro-4-[4-(trifluoromethyl)cyclohexen-1-yl]pyridine 2,5-Dichloro-4-[4-(trifluoromethyl)cyclohexen-1-yl] pyridine was prepared from (2,5-dichloro-4-pyridyl)boronic acid and [4-(trifluoromethyl)cyclohexen-1-yl] trifluoromethanesulfonate using a procedure analogous to that found in Intermediate B-34, step 1. ESI-MS m/z calc. 295.01, found 295.9 $(M+1)^+$. $^1H$ NMR (400 MHz, $CDCl_3$) δ 8.35 (s, 1H), 7.17 (s, 1H), 5.86 (d, 1H, J=2.6 Hz), 2.60-2.29 (m, 5H), 2.21-2.14 (m, 1H), 1.80-1.68 (m, 1H). $^{19}F$ NMR (376 MHz, $CDCl_3$) δ −73.7 (s, 3F).

Step 2: 5-chloro-2-isopropenyl-4-[4-(trifluoromethyl)cyclohexen-1-yl]pyridine

5-Chloro-2-isopropenyl-4-[4-(trifluoromethyl)cyclohexen-1-yl]pyridine was prepared from 2,5-dichloro-4-[4-(trifluoromethyl)cyclohexen-1-yl]pyridine and 2-isopropenyl-4,4,5,5-tetramethyl-1,3,2-dioxaborolane using a procedure analogous to that found in Intermediate B-34, step 1, using potassium phosphate as the base. ESI-MS m/z calc. 301.09, found 302.05 $(M+1)^+$. $^1H$ NMR (400 MHz, $CDCl_3$) δ 8.51 (s, 1H), 7.27 (s, 1H), 5.87 (d, 1H, J=0.6 Hz), 5.82 (s, 1H), 5.34 (t, 1H, J=1.5 Hz), 2.57-2.28 (m, 5H), 2.24-2.21 (m, 3H), 2.20-2.14 (m, 1H), 1.81-1.70 (m, 1H).

Step 3: 5-chloro-2-(1-methylcyclopropyl)-4-[4-(trifluoromethyl)cyclohexen-1-yl]pyridine Potassium tert-butoxide (3.3 g, 29.4 mmol) was added to trimethylsulfoxonium iodide (6.5 g, 29.5 mmol) in DMSO (22 mL) with THF (16.5 mL). The mixture was stirred for 30 min then 5-chloro-2-isopropenyl-4-[4-(trifluoromethyl)cyclohexen-1-yl]pyridine (3.0 g, 9.8 mmol) in THF (22 mL) was added. The reaction was stirred at room temperature for 2 h, then at 60° C. for 16 h. The reaction was cooled to room temperature, diluted with saturated aqueous sodium bicarbonate (40 mL) and extracted with ethyl acetate (500 mL). The organic layer was washed with water (3×500 mL), brine (500 mL), filtered through a silica plug and concentrated under reduced pressure. Purification by reverse phase chromatography (C8, 50-95% $CH_3CN$/aqueous 0.1% ammonia) provided 5-chloro-2-(1-methylcyclopropyl)-4-[4-(trifluoromethyl)cyclohexen-1-yl]pyridine (360 mg, 11%). $^1H$ NMR (400 MHz, $CDCl_3$) δ 8.39 (s, 1H), 7.06 (s, 1H), 5.79 (s, 1H), 2.55-2.29 (m, 5H), 2.19-2.14 (m, 1H), 1.81-1.69 (m, 1H), 1.51 (s, 3H), 1.26-1.23 (m, 2H), 0.84 (dd, 2H, J=6.3, 3.9 Hz). ESI-MS m/z calc. 315.10, found 316.08 $(M+1)^+$.

Step 4: 5-chloro-2-(1-methylcyclopropyl)-4-[4-(trifluoromethyl)cyclohexyl]pyridine (cis trans Mixture)

5-Chloro-2-(1-methylcyclopropyl)-4-[4-(trifluoromethyl)cyclohexyl]pyridine (cis trans mixture) was prepared from 5-chloro-2-(1-methylcyclopropyl)-4-[4-(trifluoromethyl)cyclohexen-1-yl]pyridine using a procedure analogous to that found in Intermediate B-34, step 2. ESI-MS m/z calc. 317.12, found 318.02 $(M+1)^+$. $^1H$ NMR (400 MHz, $CDCl_3$) δ 8.39-8.36 (m, 1H), 7.15 (d, 1H, J=17.6 Hz), 3.07-2.95 (m, 1H), 2.51-2.32 (m, 2H), 2.18-2.12 (m, 3H), 1.85-1.75 (m, 4H), 1.51 (s, 3H), 1.25-1.21 (m, 2H), 0.85-0.82 (m, 2H). $^{19}F$ NMR (376 MHz, $CDCl_3$) δ −67.23 (s, 3F).

Step 5: 2-(1-methylcyclopropyl)-5-(4,4,5,5-tetramethyl-1,3,2-dioxaborolan-2-yl)-4-[4-(trifluoromethyl)cyclohexyl]pyridine (cis trans Mixture)

2-(1-Methylcyclopropyl)-5-(4,4,5,5-tetramethyl-1,3,2-dioxaborolan-2-yl)-4-[4-(trifluoromethyl)cyclohexyl]pyridine (cis trans mixture) was prepared from 5-chloro-2-(1-methylcyclopropyl)-4-[4-(trifluoromethyl)cyclohexyl]pyridine (cis trans mixture) using a procedure analogous to that found in Intermediate B-2, step 4 using potassium phosphate as base and SPhos Pd G3 as catalyst. ESI-MS m/z calc. 409.24, found 410.23 $(M+1)^+$. $^1H$ NMR (400 MHz, $CDCl_3$) δ 8.73 (d, 1H, J=12.8 Hz), 7.15 (d, 1H, J=14.8 Hz), 2.44-2.37 (m, 1H), 2.14-2.10 (m, 2H), 1.80-1.73 (m, 4H), 1.49 (m, 5H), 1.39-1.27 (m, 12H), 1.27 (dd, 2H, J=5.7, 3.7 Hz), 1.25-1.19 (m, 1H), 0.87-0.76 (m, 2H). $^{19}F$ NMR (376 MHz, $CDCl_3$) δ −67.24–−67.31 (s, 3F).

Intermediate B-63

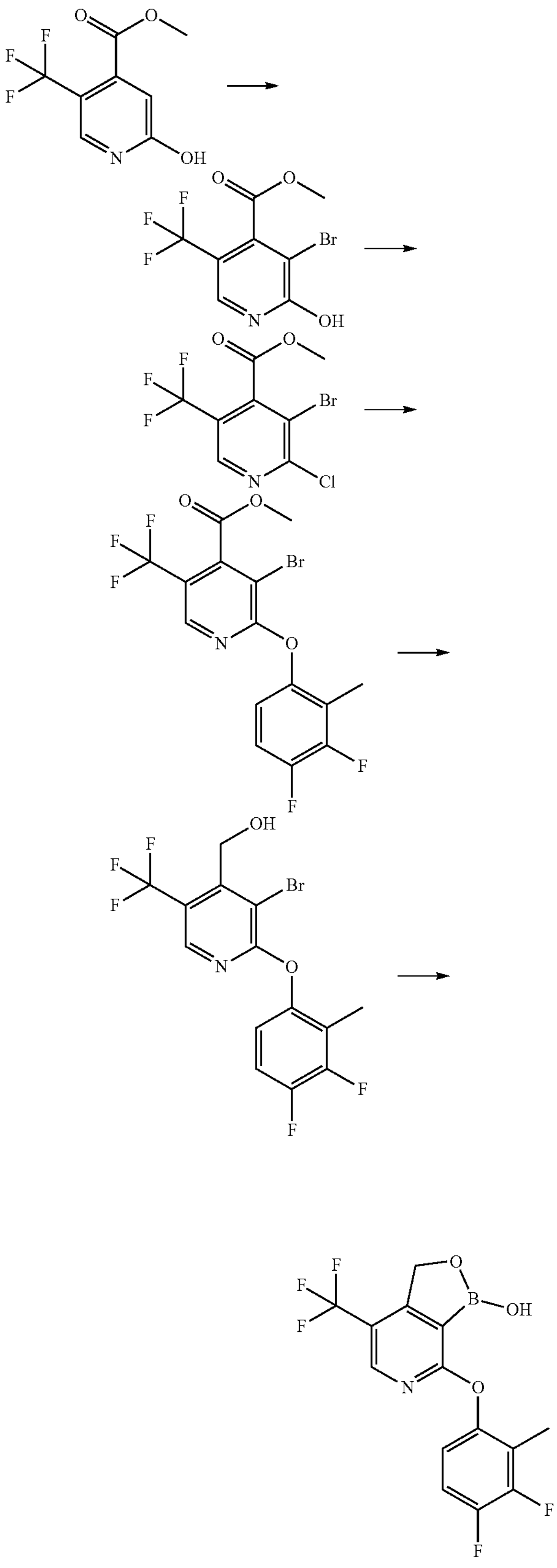

Step 1: Ethyl 3-bromo-2-hydroxy-5-(trifluoromethyl)pyridine-4-carboxylate

To a stirring suspension of methyl 2-hydroxy-5-(trifluoromethyl)pyridine-4-carboxylate (250 mg, 1.13 mmol) in acetic acid (4 mL) was added bromine (70 μL, 1.4 mmol) and the mixture was stirred at room temperature for 4 h. Additional bromine (100 μL, 1.94 mmol) was added and the mixture stirred at room temperature overnight. Additional bromine (100 μL, 1.94 mmol) was added and the mixture stirred for 72 h. The mixture was poured into a saturated solution of sodium thiosulfate pentahydrate (100 mL) and sodium hydrogen carbonate (100 mL) and extracted with ethyl acetate (2×300 mL). The combined organic extracts were washed with brine (100 mL), dried over magnesium sulfate, filtered and concentrated to provide methyl 3-bromo-2-hydroxy-5-(trifluoromethyl)pyridine-4-carboxylate (357 mg, 97%). $^{1}H$ NMR (400 MHz, $CDCl_3$) δ 12.60 (s, 1H), 7.87 (s, 1H), 3.99 (s, 3H). $^{19}F$ NMR (376 MHz, $CDCl_3$) δ −60.4−−60.0 (3F). ESI-MS m/z calc. 298.94, found 297.84 $(M-1)^-$.

Step 2: Methyl 3-bromo-2-chloro-5-(trifluoromethyl)pyridine-4-carboxylat

A mixture of methyl 3-bromo-2-hydroxy-5-(trifluoromethyl)pyridine-4-carboxylate (5.5 g, 18 mmol) in $POCl_3$ (74 g, 45 mL, 483 mmol) was heated at 110° C. overnight. The mixture was concentrated and partitioned between ethyl acetate (750 mL) and saturated sodium hydrogen carbonate (500 mL). The aqueous phase was extracted with additional ethyl acetate (500 mL). The combined organic phases were washed with brine (300 mL), dried over magnesium sulfate, filtered and concentrated to provide methyl 3-bromo-2-chloro-5-(trifluoromethyl)pyridine-4-carboxylate (5.58 g, 94%). $^{1}H$ NMR (400 MHz, $CDCl_3$) δ 8.65 (s, 1H), 4.01 (s, 3H). ESI-MS m/z calc. 316.91, found 317.75 $(M+1)^+$.

Step 3: Methyl 3-bromo-2-(3,4-difluoro-2-methyl-phenoxy)-5-(trifluoromethyl)pyridine-4-carboxylate A mixture of methyl 3-bromo-2-chloro-5-(trifluoromethyl)pyridine-4-carboxylate (2.79 g, 8.49 mmol), 3,4-difluoro-2-methyl-phenol (1.35 g, 9.37 mmol) and cesium carbonate (5.59 g, 17.2 mmol) in DMSO (25 mL) was heated at 90° C. for 2 h. The reaction was allowed to cool to room temperature and partitioned between water (500 mL) and ethyl acetate (500 mL). The organic phase was washed with brine (150 mL), dried over magnesium sulfate, filtered and concentrated. Purification by silica gel chromatography (0-10% ethyl acetate/heptane) provided methyl 3-bromo-2-(3,4-difluoro-2-methyl-phenoxy)-5-(trifluoromethyl)pyridine-4-carboxylate (1.9 g, 46%). $^{1}H$ NMR (400 MHz, $CDCl_3$) δ 8.31 (s, 1H), 7.07 (q, J=9.0 Hz, 1H), 6.84 (qd, J=4.4, 2.1 Hz, 1H) 4.03 (s, 3H), 2.09 (d, J=2.3 Hz, 3H). ESI-MS m/z calc. 424.97, found 425.98 $(M+1)^+$.

Step 4: [3-bromo-2-(3,4-difluoro-2-methyl-phenoxy)-5-(trifluoromethyl)-4-pyridyl]methanol To an ice cooled solution of methyl 3-bromo-2-(3,4-difluoro-2-methyl-phenoxy)-5-(trifluoromethyl)pyridine-4-carboxylate (1.9 g, 3.9 mmol) THF (120 mL) was added methanol (1.6 g, 2 mL, 49 mmol) followed by lithium borohydride (1.03 g, 47.3 mmol). After 3 h additional methanol (1.6 g, 2 mL, 49 mmol) and lithium borohydride (1.03 g, 47.3 mmol) was added. After 2 h additional methanol (790 mg, 1 mL, 25 mmol) and lithium borohydride (500 mg, 22.953 mmol) were added and the mixture allowed to come to room temperature overnight. The mixture was poured into 2 N aqueous hydrochloric acid (200 mL) then basified using saturated aqueous ammonium bicarbonate solution. The aqueous phase was extracted using ethyl acetate (2×500 mL), and the combined organic phases washed with brine (150 mL), dried over magnesium sulfate, filtered and concentrated. Purification by reverse phase chromatography (C18, 20-100% acetonitrile/water each with 0.1% formic acid) provided [3-bromo-2-(3,4-difluoro-2-methyl-phenoxy)-5-(trifluoromethyl)-4-pyridyl]methanol (425 mg, 27%) as a white solid. $^{1}H$ NMR (400 MHz, $CDCl_3$) δ 8.30 (s, 1H), 7.10-6.99 (m, 1H), 6.84 (qd, J=4.4, 2.1 Hz, 1H), 4.94 (d, J=11.9 Hz, 2H), 2.26 (s, 1H), 2.10 (d, J=2.3 Hz, 3H). ESI-MS m/z calc. 396.97, found 398.04 $(M+1)^+$.

Step 5: 7-(3,4-difluoro-2-methyl-phenoxy)-1-hydroxy-4-(trifluoromethyl)-3H-oxaborolo[3,4-c]pyridine To a mixture of [3-bromo-2-(3,4-difluoro-2-methyl-phenoxy)-5-(trifluoromethyl)-4-pyridyl]methanol (44 mg, 0.11 mmol) and trimethylborate (12 mg, 13 μL, 0.12 mmol) in anhydrous THF (1 mL) under argon was added a solution of nBuLi in hexanes (135 μL of 1.6 M in hexane, 0.22 mmol) dropwise over 5 min. The mixture was stirred for 1 h at −78° C. then allowed to warm to room temperature. The reaction mixture was quenched using saturated aqueous ammonium chloride solution (10 mL) and extracted with ethyl acetate (20 mL). The aqueous phase was extracted with additional ethyl acetate (20 mL), and the combined organic phases were dried over magnesium sulfate, filtered and concentrated to provide 7-(3,4-difluoro-2-methyl-phenoxy)-1-hydroxy-4-(trifluoromethyl)-3H-oxaborolo[3,4-c]pyridine (35 mg, 33%). ESI-MS m/z calc. 345.06, found 346.04 $(M+1)^+$.

Intermediate B-64

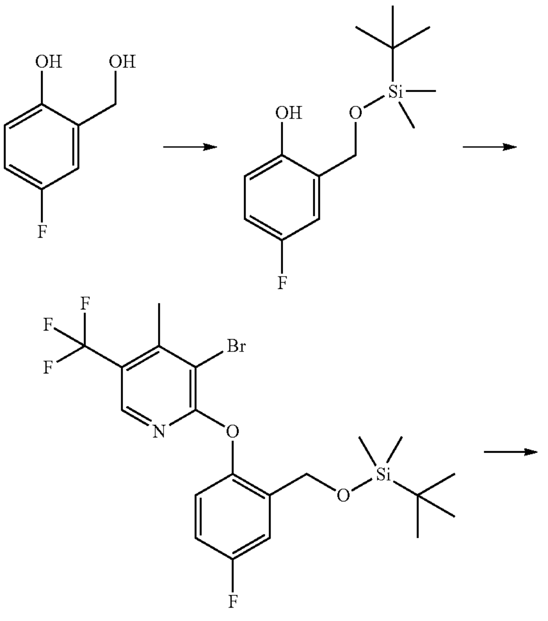

-continued

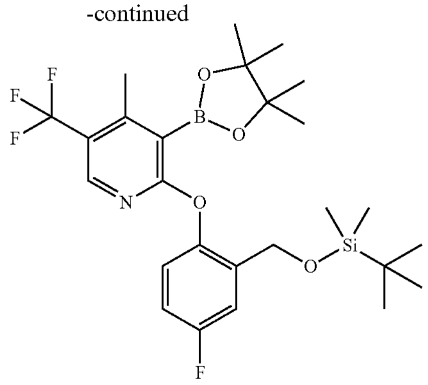

Step 1: 2-[[tert-butyl(dimethyl)silyl]oxymethyl]-4-fluoro-phenol

To a stirring mixture of 4-fluoro-2-(hydroxymethyl)phenol (2.2 g, 15.5 mmol) and imidazole (1.26 g, 18.5 mmol) in DCM (30 mL) at 0° C. was slowly added a solution of tert-butyl-chloro-dimethyl-silane (2.56 g, 17.0 mmol) in DCM (10 mL). The mixture was stirred at room temperature for 5 h and the resulting solid removed by filtration. The filtrate was concentrated and purified using silica gel chromatography (0-40% ethyl acetate/heptanes) to provide 2-[[tert-butyl(dimethyl)silyl]oxymethyl]-4-fluoro-phenol (3.2 g, 80%). $^1$H NMR (400 MHz, $CDCl_3$) δ 7.80 (s, 1H), 6.86 (td, J=8.5, 3.2 Hz, 1H), 6.78-6.78 (m, 1H), 6.66 (dd, J=8.7, 2.7 Hz, 1H), 4.84 (s, 2H), 0.92 (s, 9H), 0.13 (s, 6H). ESI-MS m/z calc. 256.13, found 255.04 $(M-1)^-$.

Step 2: [2-[[3-bromo-4-methyl-5-(trifluoromethyl)-2-pyridyl]oxy]-5-fluoro-phenyl]methoxy-tert-butyl-dimethyl-silane A mixture of 3-bromo-2-chloro-4-methyl-5-(trifluoromethyl)pyridine (3.2 g, 11 mmol) and 2-[[tert-butyl(dimethyl)silyl]oxymethyl]-4-fluoro-phenol (3.2 g, 12 mmol) in DMSO (40 mL) at ~0° C. was treated with cesium carbonate (5.41 g, 16.6 mmol) then stirred at room temperature for 1 h. The mixture was partitioned between water (40 mL) and ethyl acetate (100 mL). The organic layer was separated and washed with water (40 mL) and brine (40 mL), dried over sodium sulfate, filtered and concentrated. Purification by silica gel chromatography (0.2-5% ethyl acetate/heptane) provided [2-[[3-bromo-4-methyl-5-(trifluoromethyl)-2-pyridyl]oxy]-5-fluoro-phenyl]methoxy-tert-butyl-dimethyl-silane. $^1$H NMR (400 MHz, $CDCl_3$) δ 8.25 (s, 1H), 7.34 (dd, J=9.2, 2.8 Hz, 1H), 7.08-7.01 (m, 2H), 4.65 (s, 2H), 2.64 (d, J=1.0 Hz, 3H), 0.95-0.89 (m, 9H), 0.07 (t, J=3.1 Hz, 6H).

Step 3: tert-butyl-[[5-fluoro-2-[[4-methyl-3-(4,4,5,5-tetramethyl-1,3,2-dioxaborolan-2-yl)-5-(trifluoromethyl)-2-pyridyl]oxy]phenyl]methoxy]-dimethyl-silane To a solution of [2-[[3-bromo-4-methyl-5-(trifluoromethyl)-2-pyridyl]oxy]-5-fluoro-phenyl]methoxy-tert-butyl-dimethyl-silane (200 mg, 0.384 mmol) in toluene (8 mL) at −78° C. under argon was added n-BuLi in hexanes (0.5 mL of 2.5 M, 1.25 mmol). The resulting pale yellow solution was stirred at −78° C. for 20 min then at 0° C. for 30 min. The reaction mixture was cooled to −78° C. and 2-isopropoxy-4,4,5,5-tetramethyl-1,3,2-dioxaborolane (180 mg, 0.2 mL, 0.1 mmol) in toluene (1 mL) was added. Stirring was continued for 30 min at this temperature and then the mixture was placed in an ice-bath at 0° C. The reaction was quenched with saturated aqueous ammonium chloride (5 mL) and extracted with ethyl acetate (2×25 mL). The combined organic extracts were washed with water (20 mL) and brine (20 mL), dried over sodium sulfate and concentrated in vacuo to provide tert-butyl-[[5-fluoro-2-[[4-methyl-3-(4,4,5,5-tetramethyl-1,3,2-dioxaborolan-2-yl)-5-(trifluoromethyl)-2-pyridyl]oxy]phenyl]methoxy]-dimethyl-silane (180 mg, 78%). ESI-MS m/z calc. 541.24, found 542.17 $(M+1)^+$.

Intermediate B-65

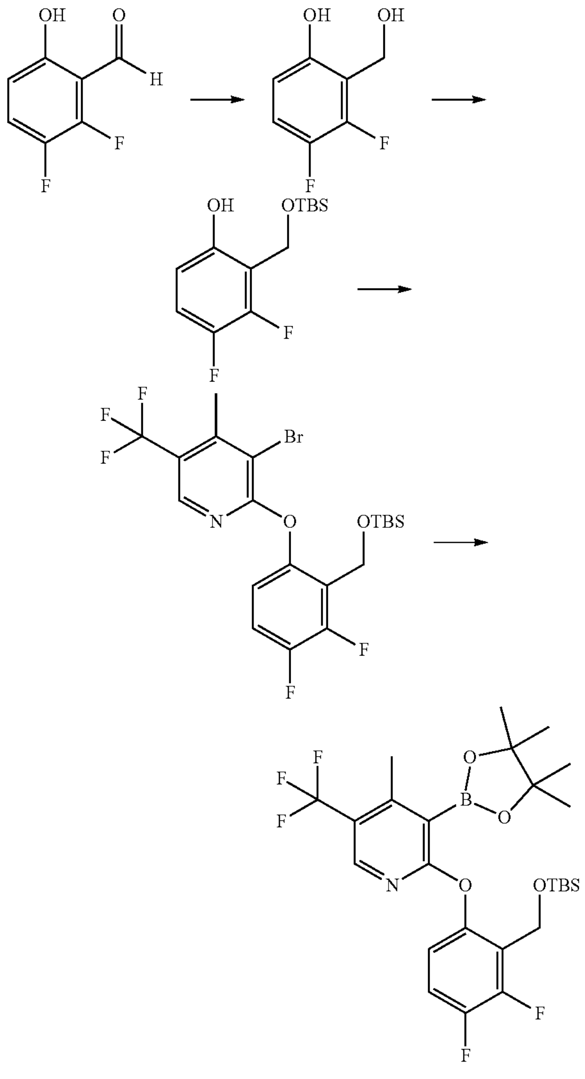

Step 1: 3,4-difluoro-2-(hydroxymethyl)phenol

A stirring solution of 2,3-difluoro-6-hydroxy-benzaldehyde (1.13 g, 7.15 mmol) in ethanol (20 mL) at ~ 0° C. was treated with $NaBH_4$ (135 mg, 3.57 mmol) and stirred at room temperature for 1 h. The reaction was quenched by the addition of ice under argon and was concentrated under vacuum. The residue was stirred in a mixture of 1 N HCl solution (20 mL) and ethyl acetate (40 mL) for 30 min. The layers were separated and the aqueous layer extracted with additional ethyl acetate (20 mL). The combined extracts were washed with brine (20 ml), dried over sodium sulfate, filtered and concentrated. The residue was recrystallized from DCM (5 mL) to provide 3,4-difluoro-2-(hydroxymethyl)phenol (520 mg, 42%). $^1$H NMR (400 MHz, $CDCl_3$) δ 7.54 (s, 1H), 7.01 (q, J=9.3 Hz, 1H), 6.62 (dq, J=9.0, 2.0 Hz, 1H), 5.04 (d, J=1.0 Hz, 2H), 2.36 (br s, 1H). ESI-MS m/z calc. 160.03, found 158.98 $(M-1)^-$.

Step 2: 2-[[tert-butyl(dimethyl)silyl]oxymethyl]-3,4-difluoro-phenol

2-[[tert-Butyl(dimethyl)silyl]oxymethyl]-3,4-difluoro-phenol was prepared from 3,4-difluoro-2-(hydroxymethyl) phenol using a procedure analogous to that found in Intermediate B-64, step 1. $^1$H NMR (400 MHz, $CDCl_3$) δ 8.33 (s, 1H), 6.98 (q, J=9.4 Hz, 1H), 6.59 (dq, J=9.1, 2.0 Hz, 1H), 5.04 (d, J=1.2 Hz, 2H), 0.93 (s, 9H), 0.19 (s, 6H). ESI-MS m/z calc. 274.12, found 273.03 $(M-1)^-$.

Step 3: [6-[[3-bromo-4-methyl-5-(trifluoromethyl)-2-pyridyl]oxy]-2,3-difluoro-phenyl]methoxy-tert-butyl-dimethyl-silane

[6-[[3-Bromo-4-methyl-5-(trifluoromethyl)-2-pyridyl] oxy]-2,3-difluoro-phenyl]methoxy-tert-butyl-dimethyl-silane was prepared from 2-[[tert-butyl(dimethyl)silyl]oxymethyl]-3,4-difluoro-phenol using a procedure analogous to that found in Intermediate B-64, step 2. $^1$H NMR (400 MHz, $CDCl_3$) δ 8.20 (s, 1H), 7.17 (q, J=9.0 Hz, 1H), 6.91-6.87 (m, 1H), 4.67 (d, J=1.8 Hz, 2H), 2.60 (d, J=0.9 Hz, 3H), 0.72 (s, 9H), −0.06 (s, 6H). ESI-MS m/z calc. 511.06, found 510.1 $(M-1)^-$.

Step 4: tert-butyl-[[2,3-difluoro-6-[[4-methyl-3-(4,4,5,5-tetramethyl-1,3,2-dioxaborolan-2-yl)-5-(trifluoromethyl)-2-pyridyl]oxy]phenyl]methoxy]-dimethyl-silane tert-Butyl-[[2,3-difluoro-6-[[4-methyl-3-(4,4,5,5-tetramethyl-1,3,2-dioxaborolan-2-yl)-5-(trifluoromethyl)-2-pyridyl]oxy]phenyl]methoxy]-dimethyl-silane was prepared from [6-[[3-bromo-4-methyl-5-(trifluoromethyl)-2-pyridyl] oxy]-2,3-difluoro-phenyl]methoxy-tert-butyl-dimethyl-silane using a procedure analogous to that found in Intermediate B-64, step 3. $^1$H NMR (400 MHz, $CDCl_3$) δ 8.25 (s, 1H), 7.12 (q, J=9.2 Hz, 1H), 6.85 (qd, J=4.4, 2.2 Hz, 1H), 4.68 (d, J=1.8 Hz, 2H), 2.50 (dd, J=5.0, 1.4 Hz, 3H), 1.38 (s, 12H), 0.76 (s, 9H), −0.04 (s, 6H). ESI-MS m/z calc. 559.24, found 560.15 $(M+1)^+$.

Intermediate B-66

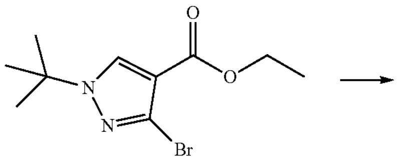

-continued

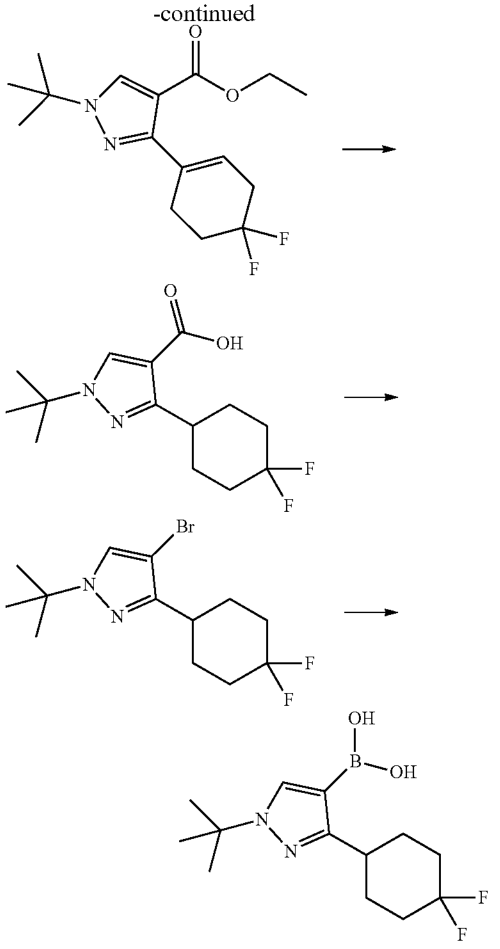

Step 1: ethyl 1-tert-butyl-3-(4,4-difluorocyclohexen-1-yl)pyrazole-4-carboxylate To a mixture of ethyl 3-bromo-1-tert-butyl-pyrazole-4-carboxylate (730 mg, 2.65 mmol), 2-(4,4-difluorocyclohexen-1-yl)-4,4,5,5-tetramethyl-1,3,2-dioxaborolane (782 mg, 3.20 mmol) and $Pd(PPh_3)_4$ (200 mg, 0.173 mmol) in dioxane (7 mL) was added potassium carbonate (3 mL of 2 M, 6 mmol). The mixture was sparged with nitrogen then heated (microwave irradiation) at 100° C. for 45 min. The mixture was cooled, diluted with ethyl acetate and the layers separated. The organic layer was dried over sodium sulfate, filtered and concentrated. Purification by silica gel chromatography (40 g silica, 0-50% ethyl acetate/hexanes) provided ethyl 1-tert-butyl-3-(4,4-difluorocyclohexen-1-yl)pyrazole-4-carboxylate (562 mg, 68%). ESI-MS m/z calc. 312.17, found 313.3 $(M+1)^+$.

Step 2: 1-tert-butyl-3-(4,4-difluorocyclohexyl)pyrazole-4-carboxylic acid

Ethyl 1-tert-Butyl-3-(4,4-difluorocyclohexyl)pyrazole-4-carboxylate was prepared from ethyl 1-tert-butyl-3-(4,4-difluorocyclohexen-1-yl)pyrazole-4-carboxylate using a hydrogenation procedure analogous to that found in Intermediate B-36, step 3. ESI-MS m/z calc. 314.18, found 315.3 $(M+1)^+$. The ester was hydrolyzed using a procedure analogous to that found in Intermediate B-11, step 4 to provide 1-tert-butyl-3-(4,4-difluorocyclohexyl)pyrazole-4-carboxylic acid. $^{1}H$ NMR (400 MHz, DMSO-$d_6$) δ 12.11 (s, 1H), 8.12 (s, 1H), 3.30-3.22 (m, 1H), 2.15-2.03 (m, 2H), 1.99-1.87 (m, 3H), 1.87-1.69 (m, 3H), 1.50 (s, 9H). ESI-MS m/z calc. 286.15, found 287.4 $(M+1)^+$ Step 3: 4-bromo-1-tert-butyl-3-(4,4-difluorocyclohexyl)pyrazole 4-Bromo-1-tert-butyl-3-(4,4-difluorocyclohexyl)pyrazole was prepared from 1-tert-butyl-3-(4,4-difluorocyclohexyl) pyrazole-4-carboxylic acid using a procedure analogous to that found in Intermediate B-21, step 3. $^{1}H$ NMR (400 MHz, $CDCl_3$) δ 7.44 (s, 1H), 2.99-2.74 (m, 1H), 2.28-2.13 (m, 2H), 2.05-1.94 (m, 4H), 1.91-1.76 (m, 2H), 1.54 (s, 9H). $^{19}F$ NMR (376 MHz, $CDCl_3$) δ −92.85 (d, J=234.0 Hz), −99.84 (d, J=234.2 Hz). ESI-MS m/z calc. 320.07, found 321.1 $(M+1)^+$.

Step 4: [1-tert-butyl-3-(4,4-difluorocyclohexyl)pyrazol-4-yl]boronic acid

[1-tert-Butyl-3-(4,4-difluorocyclohexyl)pyrazol-4-yl]boronic acid was prepared from 4-bromo-1-tert-butyl-3-(4,4-difluorocyclohexyl)pyrazole using a procedure analogous to that found in B-3, step 3. ESI-MS m/z calc. 286.17, found 287.2 $(M+1)^+$.

Intermediate B-67

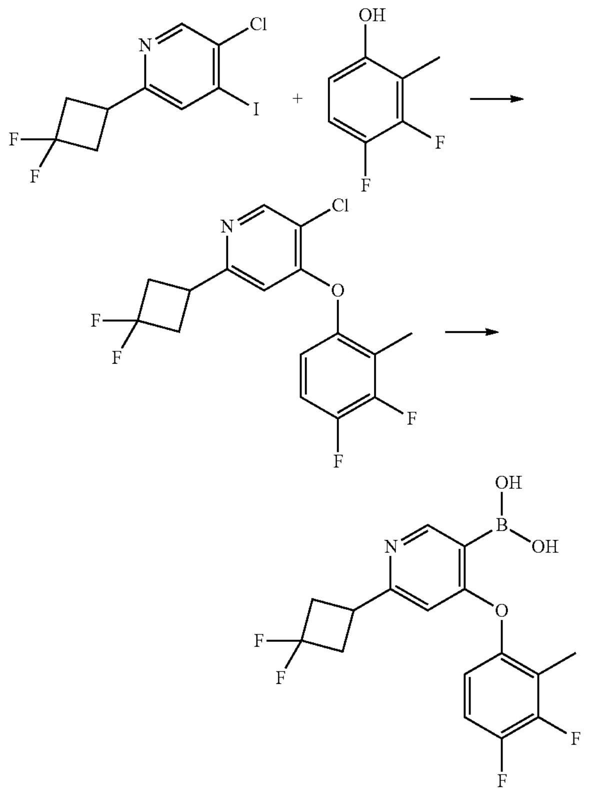

Step 1: 5-chloro-2-(3,3-difluorocyclobutyl)-4-(3,4-difluoro-2-methyl-phenoxy)pyridine A mixture of 5-chloro-2-(3,3-difluorocyclobutyl)-4-iodopyridine (Intermediate B-40 Step 3, 250 mg, 0.76 mmol), 3,4-difluoro-2-methyl-phenol (142 mg, 0.985 mmol), 2-(2-methylpropanoyl)cyclohexanone (50 µL, 0.30 mmol), potassium carbonate (500 mg, 3.62 mmol) and CuI (90 mg, 0.47 mmol) in DMSO (1.5 mL) was degassed with nitrogen for 2 min then stirred at 80° C. for 3 h. The reaction mixture was cooled to room temperature and diluted with ethyl acetate. The organic phase was washed with water and brine, dried over sodium sulfate, filtered and concentrated. Purification by silica gel chromatography (24 g silica, 0-100% ethyl acetate/hexanes) provided 5-chloro-2-(3,3-difluorocyclobutyl)-4-(3,4-difluoro-2-methyl-phenoxy)pyridine (51.4 mg, 20%). $^{1}H$ NMR (400 MHz, $CD_3OD$) δ 8.54 (s, 1H), 7.22 (app q, J=9.3 Hz, 1H), 7.02-6.76 (m, 1H), 6.57 (s, 1H), 2.91-2.71 (m, 5H), 2.16-2.05 (m, 3H). ESI-MS m/z calc. 345.05, found 346.2 $(M+1)^+$.

Step 2: [6-(3,3-difluorocyclobutyl)-4-(3,4-difluoro-2-methyl-phenoxy)-3-pyridyl]boronic acid A mixture of 5-chloro-2-(3,3-difluorocyclobutyl)-4-(3,4-difluoro-2-methyl-phenoxy)pyridine (24.5 mg, 0.07 mmol), bis(pinacol)diboron (22 mg, 0.087 mmol), potassium 2-ethylhexanoate (30 mg, 0.16 mmol) and X-Phos (2 mg, 0.004 mmol) was suspended in isopropyl acetate (500 µL) under nitrogen atmosphere. The mixture was heated to 35° C. then XPhos Pd G3 (3 mg, 0.0035 mmol) was added under nitrogen. The resulting mixture was stirred at 35° C. for 1 h. The temperature was raised to 50° C. and the mixture stirred for 18 h. The mixture was cooled to room temperature and partitioned between ethyl acetate and water. The organic layer was dried over sodium sulfate, filtered and concentrated to provide [6-(3,3-difluorocyclobutyl)-4-(3,4-difluoro-2-methyl-phenoxy)-3-pyridyl]boronic acid. ESI-MS m/z calc. 355.10, found 356.2 $(M+1)^+$.

Intermediate B-68

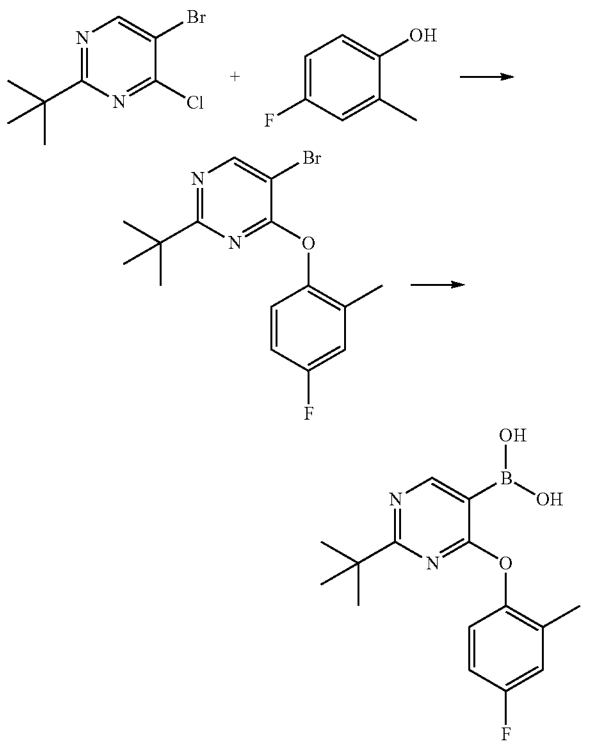

Step 1: 5-bromo-2-tert-butyl-4-(4-fluoro-2-methyl-phenoxy)pyrimidine

5-Bromo-2-tert-butyl-4-(4-fluoro-2-methyl-phenoxy)pyrimidine was prepared from 5-bromo-2-tert-butyl-4-chloro-pyrimidine and 4-fluoro-2-methyl-phenol using a procedure analogous to that found in Intermediate B-1, step 1. $^1$H NMR (400 MHz, DMSO-$d_6$) δ 8.85 (s, 1H), 7.29-7.21 (m, 2H), 7.12 (td, J=8.6, 3.1 Hz, 1H), 2.06 (s, 3H), 1.13 (s, 9H). ESI-MS m/z calc. 338.04, found 339.2 $(M+1)^+$.

Step 2: [2-tert-butyl-4-(4-fluoro-2-methyl-phenoxy)pyrimidin-5-yl]boronic acid

[2-tert-Butyl-4-(4-fluoro-2-methyl-phenoxy)pyrimidin-5-yl]boronic acid was prepared from 5-bromo-2-tert-butyl-4-(4-fluoro-2-methyl-phenoxy)pyrimidine using a procedure analogous to that found in Intermediate B-3, step 3. The isolated solid was used directly for Suzuki coupling to Intermediate A.

Intermediate B-69

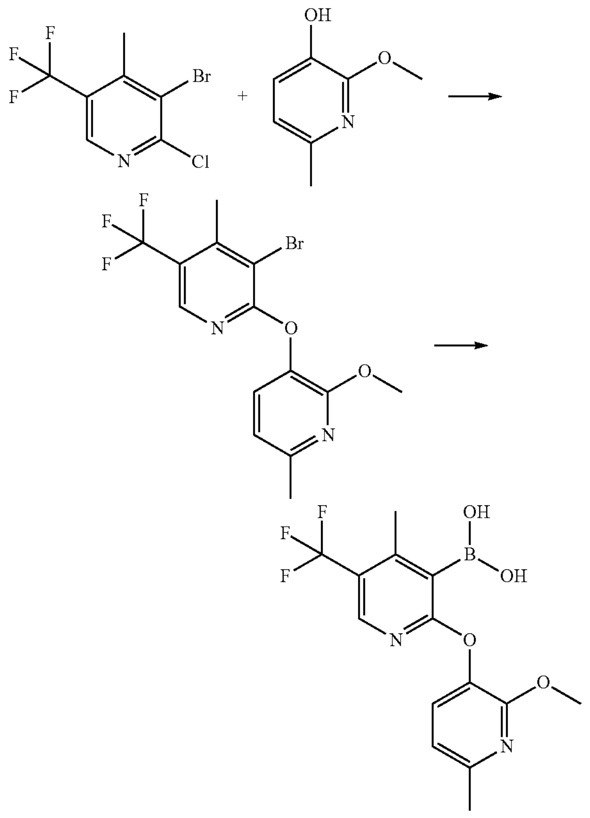

Step 1: 3-bromo-2-[(2-methoxy-6-methyl-3-pyridyl)oxy]-4-methyl-5-(trifluoromethyl)pyridine 3-Bromo-2-[(2-methoxy-6-methyl-3-pyridyl)oxy]-4-methyl-5-(trifluoromethyl)pyridine was prepared from 3-bromo-2-chloro-4-methyl-5-(trifluoromethyl)pyridine and 2-methoxy-6-methyl-pyridin-3-ol using a procedure analogous to that found for Intermediate B-1, Step 1. ESI-MS m/z calc. 376.00, found 377.1 $(M+1)^+$. $^1$H NMR (400 MHz, $CDCl_3$) δ 8.20 (s, 1H), 7.29 (d, J=7.7 Hz, 1H), 6.77 (d, J=7.7 Hz, 1H), 3.87 (s, 3H), 2.61 (m, 3H), 2.48 (s, 3H). $^{19}$F NMR (376 MHz, $CDCl_3$) δ −60.51.

Step 2: [2-[(2-methoxy-6-methyl-3-pyridyl)oxy]-4-methyl-5-(trifluoromethyl)-3-pyridyl]boronic acid

[2-[(2-Methoxy-6-methyl-3-pyridyl)oxy]-4-methyl-5-(trifluoromethyl)-3-pyridyl]boronic acid was synthesized from 3-bromo-2-[(2-methoxy-6-methyl-3-pyridyl)oxy]-4-methyl-5-(trifluoromethyl)pyridine using a procedure analogous to that found for Intermediate B-1, Step 2. ESI-MS m/z calc. 342.09, found 343.1 $(M+1)^+$.

Intermediate B-70

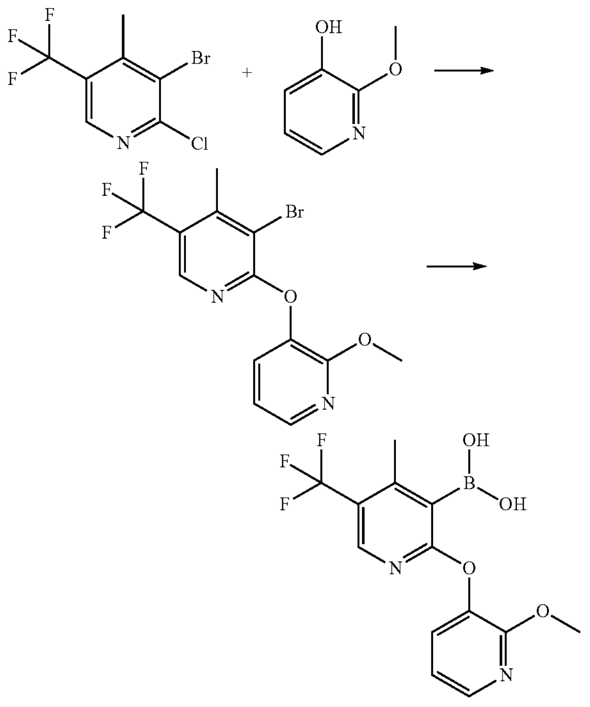

Step 1: 3-bromo-2-[(2-methoxy-3-pyridyl)oxy]-4-methyl-5-(trifluoromethyl)pyridine 3-Bromo-2-[(2-methoxy-3-pyridyl)oxy]-4-methyl-5-(trifluoromethyl)pyridine was synthesized from 3-bromo-2-chloro-4-methyl-5-(trifluoromethyl)pyridine (125 mg, 0.455 mmol) and 2-methoxypyridin-3-ol using a procedure analogous to that found for Intermediate B-1, Step 1. ESI-MS m/z calc. 361.99, found 363.1 $(M+1)^+$. $^1$H NMR (400 MHz, $CDCl_3$) δ 8.20 (s, 1H), 8.09 (dd, J=5.0, 1.7 Hz, 1H), 7.43 (dd, J=7.6, 1.7 Hz, 1H), 6.97 (dd, J=7.6, 5.0 Hz, 1H), 3.89 (s, 3H), 2.62 (q, J=1.3 Hz, 3H). $^{19}$F NMR (376 MHz, $CDCl_3$) δ −60.54.

Step 2: [2-[(2-methoxy-3-pyridyl)oxy]-4-methyl-5-(trifluoromethyl)-3-pyridyl]boronic acid

[2-[(2-Methoxy-3-pyridyl)oxy]-4-methyl-5-(trifluoromethyl)-3-pyridyl]boronic acid was synthesized from 3-bromo-2-[(2-methoxy-3-pyridyl)oxy]-4-methyl-5-(trifluoromethyl)pyridine using a procedure analogous to that found for Intermediate B-1, Step 2. ESI-MS m/z calc. 328.08, found 329.0 $(M+1)^+$.

Example 2

Methods for the Synthesis of Compounds of Formula (I) Using Intermediates A and Intermediates B Method A

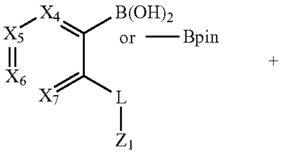

Intermediate B

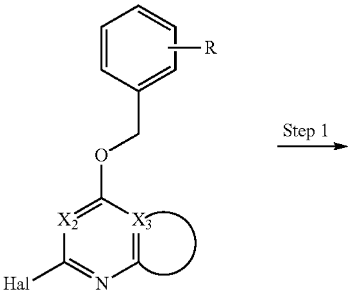

Intermediate A
Hal = halogen

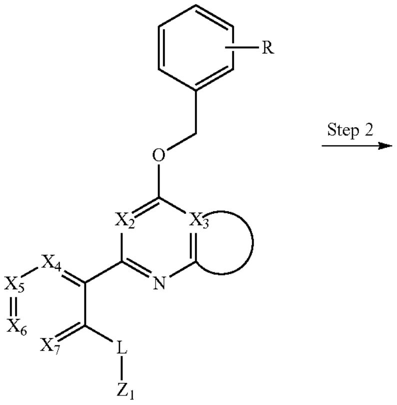

I
Protected Intermediate

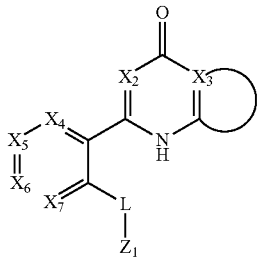

I

Step 1

A mixture of Intermediate A (1 eq), Intermediate B (1-2 eq, custom or commercial boronic acid or boronic ester), palladium catalyst (1-5 mol %), e.g. $PdCl_2$(dppf) or $PdCl_2$(dtbpf), base (2-3 eq, eg. potassium phosphate) in organic solvent (e.g. dioxane, DMSO, toluene) and water is degassed with nitrogen bubbling and stirred under inert atmosphere at a temperature ranging from room temperature to 120° C. The reaction mixture is filtered and purified via silica gel column chromatography or reverse phase HPLC to obtain protected Intermediate I.

Step 2

A mixture of the protected intermediate I and Pd/C is stirred in the appropriate solvent (e.g. methanol, ethanol, or ethyl acetate) under an atmosphere of hydrogen. The reaction mixture is filtered, concentrated, and purified via silica gel column chromatography or reverse phase column chromatography to provide the desired product I.

Alternatively, a solution of protected intermediate I in the appropriate solvent (DCM, dioxane or toluene) is treated with acid (e.g. HCl or TFA) and stirred at room temperature or 60-70° C. The mixture is neutralized and purified via silica gel column chromatography or reverse phase column chromatography to provide the desired product I.

Method B

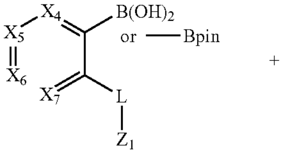

Intermediate B

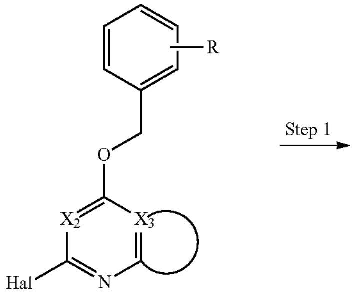

Intermediate A
Hal = halogen

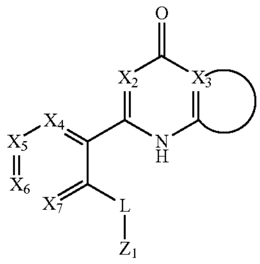

I

A mixture of Intermediate A (1 eq), Intermediate B (1-2 eq, custom or commercial boronic acid or boronic ester), palladium catalyst (e.g. XPhos Pd G3, SPhos Pd G3, $PdCl_2$(dppf), with or without additional ligand (1-10 mol %, e.g X-Phos), base (2-3 eq, e.g. potassium carbonate or phosphate) in organic solvent (e.g. dioxane, DMSO, toluene) and water is degassed with nitrogen bubbling, sealed and heated under inert atmosphere at 60-120° C. overnight or subjected to microwave irradiation at 100-120° C. for 30-60 min. The reaction mixture is filtered, concentrated, and purified via silica gel column chromatography or reverse phase column chromatography to provide the desired product I.

Method C

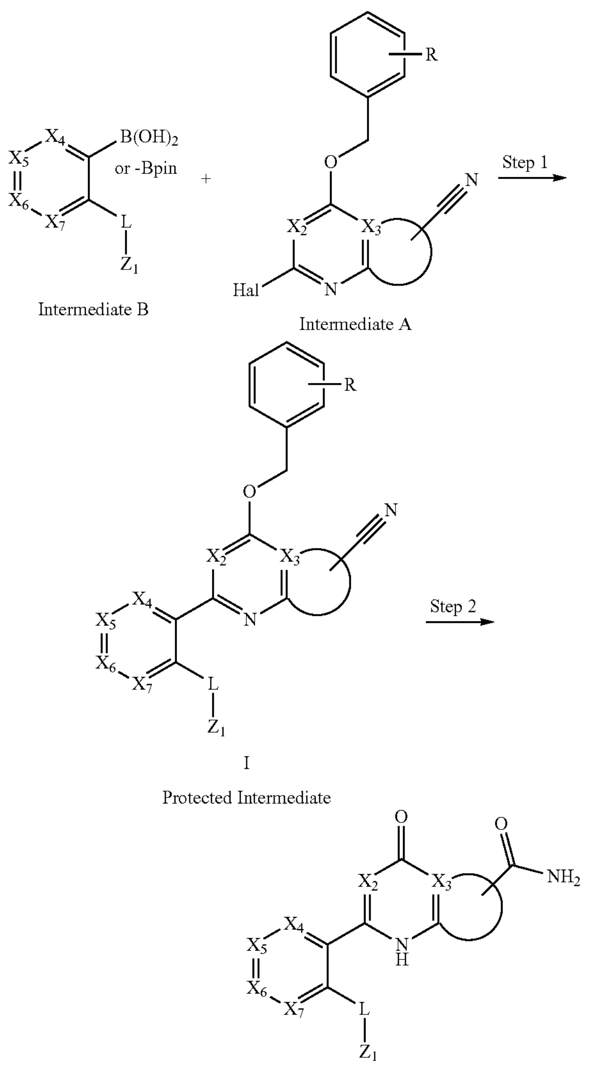

Intermediate B

Intermediate A

I

Protected Intermediate

I

Step 1

A mixture of Intermediate A (1 eq), Intermediate B (1-2 eq, custom or commercial boronic acid or boronic ester), palladium catalyst (1-5 mol %), e.g. $PdCl_2$(dppf) or $PdCl_2$(dtbpf), base (2-3 eq, eg. potassium phosphate) in organic solvent (e.g. dioxane, DMSO, toluene) and water is degassed with nitrogen bubbling and stirred under inert atmosphere at a temperature ranging from room temperature to 120° C. The reaction mixture is filtered and purified via silica gel column chromatography or reverse phase HPLC to obtain protected Intermediate I.

Step 2

A solution of the protected intermediate I in the appropriate solvent (e.g. toluene, dioxane) is treated with acid (TFA or HCl) and stirred at either room temperature or elevated temperature (e.g. 70° C.) to convert the nitrile functionality to the carboxamide. The reaction mixture is neutralized and purified via silica gel column chromatography or reverse phase column chromatography to provide the desired product I.

Method D

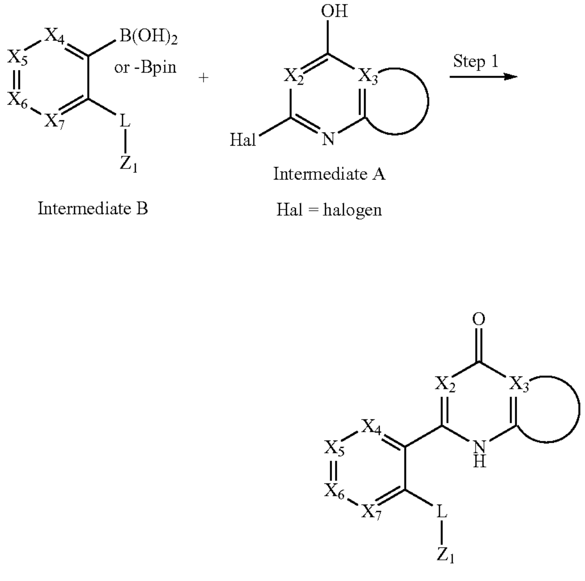

Intermediate B

Intermediate A

Hal = halogen

I

A mixture of Intermediate A (1 eq), Intermediate B (1-2 eq, custom or commercial boronic acid or boronic ester), palladium catalyst (e.g. XPhos Pd G3, SPhos Pd G3, $PdCl_2$(dppf), with or without additional ligand (1-10 mol %), e.g X-Phos), base (2-3 eq, e.g. potassium carbonate or phosphate) in organic solvent (e.g. dioxane, DMSO, toluene) and water is degassed with nitrogen bubbling, sealed and heated under inert atmosphere at 60-120° C. overnight or subjected to microwave irradiation at 100-120° C. for 30-60 min. The reaction mixture is filtered, concentrated, and purified via silica gel column chromatography or reverse phase column chromatography to provide the desired product I.

The following compounds were synthesized using the corresponding Intermediates A and Intermediates B boronic acid/esters using conditions described above in Method A, Method B, or Method C.

Compounds were also synthesized from the appropriate Intermediate A using the following commercially available boronic acids or esters: (2-cyclopropylphenyl)boronic acid, [2-(cyclopropylmethoxy)phenyl]boronic acid, (2-benzyloxyphenyl)boronic acid, [2-[(3-fluorophenyl)methoxy]phenyl]boronic acid, [2-benzyloxy-5-(trifluoromethyl)phenyl]boronic acid, [2-[(4-fluorophenyl)methoxy]phenyl]boronic acid and (2-benzyloxy-4-methyl-phenyl)boronic acid.

TABLE 2

| Cmpd No. | Compound Name | Method | MW & Found [M + H]$^+$ | NMR (shifts in ppm) |
|---|---|---|---|---|
| 1 | 2-(2-cyclopropylphenyl)-1H-quinolin-4-one | D | 261.32; 262.2 | $^1$H NMR (400 MHz, DMSO-$d_6$) δ 12.85 (s, 1H), 8.22 (d, 1H), 7.86-7.74 (m, 2H), 7.55-7.43 (m, 3H), 7.36 (td, J = 7.5, 1.2 Hz, 1H), 7.18-7.11 (m, 1H), 6.51 (s, 1H), 1.98-1.87 (m, 1H), 0.90-0.81 (m, 2H), 0.75-0.67 (m, 2H). |
| 2 | 2-[2-(cyclopropylmethoxy)phenyl]-1H-quinolin-4-one | D | 291.34; 292.2 | |
| 3 | 2-(2-benzyloxyphenyl)-1H-quinolin-4-one | D | 327.38; 328.2 | $^1$H NMR (400 MHz, DMSO-$d_6$) δ 11.75 (s, 1H), 8.10 (d, 1H), 7.69-7.59 (m, 2H), 7.56-7.48 (m, 2H), 7.45-7.36 (m, 2H), 7.35-7.29 (m, 2H), 7.29-7.19 (m, 3H), 7.14 (td, J = 7.5, 1.0 Hz, 1H), 6.15 (s, 1H), 5.19 (s, 2H). |
| 4 | 2-[2-[(3-fluorophenyl)methoxy]phenyl]-1H-quinolin-4-one | D | 345.37; 346.2 | $^1$H NMR (400 MHz, DMSO-$d_6$) δ 11.95 (s, 1H), 8.12 (d, 1H), 7.67 (d, J = 3.7, 3.0 Hz, 2H), 7.60-7.47 (m, 2H), 7.38-7.28 (m, 3H), 7.28-7.20 (m, 2H), 7.16 (td, J = 7.5, 1.0 Hz, 1H), 7.11-7.01 (m, 1H), 6.22 (s, 1H), 5.22 (s, 2H). |
| 5 | 2-[2-benzyloxy-5-(trifluoromethyl)phenyl]-1H-quinolin-4-one | D | 395.37; 396.3 | $^1$H NMR (400 MHz, DMSO-$d_6$) δ 13.65 (s, 1H), 8.25 (d, 1H), 7.97 (d, 3H), 7.90 (t, J = 7.7 Hz, 1H), 7.60 (t, J = 7.6 Hz, 1H), 7.55 (d, 1H), 7.44 (d, J = 7.3 Hz, 2H), 7.37-7.20 (m, 3H), 6.95 (s, 1H), 5.32 (s, 2H). |
| 6 | 2-[2-[(4-fluorophenyl)methoxy]phenyl]-1H-quinolin-4-one | D | 345.37; 346.2 | $^1$H NMR (400 MHz, DMSO-$d_6$) δ 10.16 (s, 1H), 8.31-7.99 (m, 1H), 7.61-7.50 (m, 1H), 7.39-7.15 (m, 3H), 7.09-6.93 (m, 4H), 6.88-6.71 (m, 1H), 6.05-5.82 (m, 1H), 5.62-5.37 (m, 1H), 5.20-4.94 (m, 1H), 3.29 (s, 2H). |
| 7 | 2-(2-benzyloxy-4-methyl-phenyl)-1H-quinolin-4-one | D | 341.4; 342.3 | |
| 8 | 2-(2-benzyloxy-4-methyl-phenyl)-1H-1,6-naphthyridin-4-one | B | 342.39; 343.2 | |
| 9 | 2-[2-(3,4-difluoro-2-methyl-phenoxy)-3-quinolyl]-1H-1,5-naphthyridin-4-one | A | 415.39; 416.3 | $^1$H NMR (400 MHz, DMSO-$d_6$) δ 8.88-8.81 (m, 2H), 8.33 (d, J = 8.5 Hz, 1H), 8.14-8.08 (m, 1H), 7.84 (dd, J = 8.5, 4.3 Hz, 1H), 7.76 (ddd, J = 8.4, 6.8, 1.5 Hz, 1H), 7.68 (d, J = 8.4 Hz, 1H), 7.59 (t, J = 7.5 Hz, 1H), 7.39 (q, J = 9.4 Hz, 1H), 7.29-7.25 (m, 1H), 7.24 (t, J = 2.9 Hz, 1H), 2.07 (d, J = 2.0 Hz, 3H). |
| 10 | 2-[2-(3,4-difluoro-2-methyl-phenoxy)-3-quinolyl]-1H-1,6-naphthyridin-4-one | B | 415.39; 416.2 | $^1$H NMR (400 MHz, DMSO-$d_6$) δ 12.85 (s, 1H), 9.37 (s, 1H), 8.82 (s, 1H), 8.71 (d, J = 6.3 Hz, 1H), 8.10 (dd, J = 8.1, 1.4 Hz, 1H), 7.83-7.74 (m, 2H), 7.69 (d, J = 8.3 Hz, 1H), 7.61 (t, J = 7.3 Hz, 1H), 7.40 (q, J = 9.4 Hz, 1H), 7.29 (m, 1H), 6.73 (s, 1H), 2.10-2.02 (m, 3H). |
| 11 | 2-[2-(3,4-difluoro-2-methyl-phenoxy)-3-quinolyl]-3-methyl-1H-quinolin-4-one | A | 428.43; 429.3 | |
| 12 | 2-[2-(3,4-difluoro-2-methyl-phenoxy)-3-quinolyl]-6-methyl-1H-quinolin-4-one | A | 428.43; 429.3 | |
| 13 | 2-[2-(3,4-difluoro-2-methyl-phenoxy)-3-quinolyl]-5-methyl-1H-1,6-naphthyridin-4-one | A | 429.42; 430.01 | $^1$H NMR (400 MHz, DMSO-$d_6$) δ 13.50 (s, 1H), 8.83 (s, 1H), 8.55 (d, J = 6.8 Hz, 1H), 8.09 (d, J = 8.0 Hz, 1H), 7.98 (d, J = 6.8 Hz, 1H), 7.80-7.74 (m, 1H), 7.68 (d, J = 8.4 Hz, 1H), 7.60 (t, J = 7.5 Hz, 1H), 7.41-7.36 (m, 2H), 6.77 (s, 1H), 3.15 (s, 3H), 2.04 (s, 3H). |
| 14 | 2-[2-(3,4-difluoro-2-methyl-phenoxy)-3-quinolyl]-5-hydroxy-1H-quinolin-4-one | A | 430.4; 431.38 | |
| 15 | 2-[2-(3,4-difluoro-2-methyl-phenoxy)-3-quinolyl]-5-fluoro-1H-quinolin-4-one | B | 432.39; 433.2 | $^1$H NMR (400 MHz, DMSO-$d_6$) δ 12.18 (s, 1H), 8.78 (s, 1H), 8.08 (dd, J = 8.1, 1.4 Hz, 1H), 7.76 (ddd, J = 8.4, 6.8, 1.5 Hz, 1H), 7.71-7.62 (m, 2H), 7.59 (ddd, J = 8.2, 6.8, 1.3 Hz, 1H), 7.47 (d, J = 8.3 Hz, 1H), 7.38 (q, J = 9.4 Hz, 1H), 7.29-7.21 (m, 1H), 7.06 (dd, J = 11.9, 7.9 Hz, 1H), 6.41 (s, 1H), 2.05 (d, J = 2.1 Hz, 3H). |

TABLE 2-continued

| Cmpd No. | Compound Name | Method | MW & Found [M + H]+ | NMR (shifts in ppm) |
|---|---|---|---|---|
| 16 | 2-[2-(3,4-difluoro-2-methyl-phenoxy)-3-quinolyl]-6-fluoro-1H-quinolin-4-one | A | 432.39; 433.18 | $^1$H NMR (400 MHz, DMSO-$d_6$) δ 12.28 (s, 1H), 8.79 (s, 1H), 8.09 (dd, J = 8.2, 1.5 Hz, 1H), 7.83-7.71 (m, 3H), 7.71-7.54 (m, 3H), 7.43-7.31 (m, 1H), 7.31-7.20 (m, 1H), 6.46 (s, 1H), 2.05 (d, J = 2.1 Hz, 3H). |
| 17 | 2-[2-(3,4-difluoro-2-methyl-phenoxy)-3-quinolyl]-7-fluoro-1H-quinolin-4-one | B | 432.39; 433.2 | $^1$H NMR (400 MHz, DMSO-$d_6$) δ 12.24 (s, 1H), 8.79 (s, 1H), 8.21 (dd, J = 9.0, 6.4 Hz, 1H), 8.09 (dd, J = 8.1, 1.4 Hz, 1H), 7.81-7.73 (m, 1H), 7.68 (d, J = 8.2 Hz, 1H), 7.65-7.54 (m, 1H), 7.45-7.33 (m, 2H), 7.30-7.18 (m, 2H), 6.49 (s, 1H), 2.05 (d, J = 2.1 Hz, 3H). |
| 18 | 2-[2-(3,4-difluoro-2-methyl-phenoxy)-3-quinolyl]-8-fluoro-1H-quinolin-4-one | A | 432.39; 433.2 | $^1$H NMR (400 MHz, $CD_3OD$) δ 8.64 (s, 1H), 8.11 (dt, J = 8.3, 1.1 Hz, 1H), 8.07-7.97 (m, 1H), 7.79-7.67 (m, 2H), 7.63-7.51 (m, 2H), 7.43 (td, J = 8.1, 4.9 Hz, 1H), 7.22-7.13 (m, 1H), 7.13-7.08 (m, 1H), 6.69 (s, 1H), 2.10 (d, J = 2.2 Hz, 3H). |
| 19 | 2-[2-(3,4-difluoro-2-methyl-phenoxy)-3-quinolyl]-4-oxo-1H-1,6-naphthyridine-5-carbonitrile | B | 440.4; 441.2 | $^1$H NMR (400 MHz, $CD_3OD$) δ 8.74 (d, J = 5.8 Hz, 1H), 8.69 (s, 1H), 8.05-7.98 (m, 1H), 7.79-7.74 (m, 2H), 7.73-7.69 (m, 1H), 7.61-7.52 (m, 1H), 7.19 (q, J = 9.2 Hz, 1H), 7.13-7.06 (m, 1H), 6.82 (s, 1H), 2.08 (d, J = 2.1 Hz, 3H). |
| 20 | 2-[2-(3,4-difluoro-2-methyl-phenoxy)-3-quinolyl]-5-methoxy-1H-quinolin-4-one | B | 444.43; 445.42 | |
| 21 | 2-[2-(3,4-difluoro-2-methyl-phenoxy)-3-quinolyl]-6-methoxy-1H-quinolin-4-one | A | 444.43; 445.0 | |
| 22 | 2-[2-(3,4-difluoro-2-methyl-phenoxy)-3-quinolyl]-7-methoxy-1H-quinolin-4-one | B | 444.43; 445.42 | |
| 23 | 2-[2-(3,4-difluoro-2-methyl-phenoxy)-3-quinolyl]-6-fluoro-3-methyl-1H-quinolin-4-one | A | 446.42; 447.3 | |
| 24 | 2-[2-(3,4-difluoro-2-methyl-phenoxy)-3-quinolyl]-7-fluoro-3-methyl-1H-quinolin-4-one | A | 446.42; 447.2 | |
| 25 | 2-[2-(4-fluoro-2-methyl-phenoxy)-4,5-dimethyl-3-pyridyl]-4-oxo-1H-1,6-naphthyridine-5-carboxamide | C | 418.42; 419.4 | $^1$H NMR (400 MHz, $CD_3OD$) δ 8.55 (d, J = 5.9 Hz, 1H), 7.93 (s, 1H), 7.51 (d, J = 6.0 Hz, 1H), 7.02-6.95 (m, 2H), 6.90 (td, J = 8.4, 3.1 Hz, 1H), 6.40 (s, 1H), 2.29 (s, 3H), 2.27 (s, 3H), 2.05 (s, 3H). |
| 26 | 2-[2-(4-fluoro-2-methyl-phenoxy)-5,6-dimethyl-3-pyridyl]-4-oxo-1H-1,6-naphthyridine-5-carboxamide | C | 418.42; 419.3 | $^1$H NMR (400 MHz, $CD_3OD$) δ 8.54 (d, J = 5.9 Hz, 1H), 7.84 (s, 1H), 7.59 (d, J = 5.8 Hz, 1H), 7.03 (dd, J = 8.9, 5.0 Hz, 1H), 6.97 (dd, J = 9.3, 3.1 Hz, 1H), 6.90 (td, J = 8.5, 3.1 Hz, 1H), 6.63 (s, 1H), 2.34 (s, 3H), 2.33 (s, 3H), 2.09 (s, 3H). |
| 27 | 2-[4-tert-butyl-2-(4-fluoro-2-methoxy-phenoxy)-6-methyl-phenyl]-1H-quinolin-4-one | A | 431.5; 432.2 | $^1$H NMR (400 MHz, DMSO-$d_6$) δ 11.84 (s, 1H), 8.10 (dd, J = 8.1, 1.0 Hz, 1H), 7.69-7.60 (m, 1H), 7.60-7.55 (m, 1H), 7.36-7.28 (m, 1H), 7.14 (d, J = 1.0 Hz, 1H), 7.10-7.01 (m, 2H), 6.77 (td, J = 8.4, 2.9 Hz, 1H), 6.53 (d, J = 1.2 Hz, 1H), 6.01 (d, J = 1.2 Hz, 1H), 3.69 (s, 3H), 2.24 (s, 3H), 1.20 (s, 9H). |
| 28 | 2-[4-tert-butyl-2-(4-fluoro-2-methoxy-phenoxy)-6-methyl-phenyl]-1H-quinazolin-4-one | A | 432.49; 433.5 | $^1$H NMR (400 MHz, DMSO-$d_6$) δ 12.36 (s, 1H), 8.13 (dd, J = 8.0, 1.5 Hz, 1H), 7.82 (td, J = 8.4, 7.1, 1.6 Hz, 1H), 7.64 (d, 1H), 7.53 (t, J = 8.1, 7.1, 1.2 Hz, 1H), 7.13 (dd, J = 8.9, 5.9 Hz, 1H), 7.08 (s, 1H), 7.00 (dd, J = 10.7, 3.0 Hz, 1H), 6.77 (td, J = 8.5, 3.0 Hz, 1H), 5.75 (s, 1H), 3.68 (s, 3H), 2.23 (s, 3H), 1.19 (s, 9H). |
| 29 | 2-[4-tert-butyl-2-(4-fluoro-2-methoxy-phenoxy)-6-methyl-phenyl]-1H-1,5-naphthyridin-4-one | A | 432.49; 433.2 | $^1$H NMR (400 MHz, DMSO-$d_6$) δ 11.93 (s, 1H), 8.65 (d, J = 3.2 Hz, 1H), 7.97 (d, J = 7.6 Hz, 1H), 7.65 (dd, J = 8.4, 4.0 Hz, 1H), 7.14 (s, 1H), 7.09-6.99 (m, 2H), 6.76 (td, J = 8.4, 2.9 Hz, 1H), 6.55 (s, 1H), 6.17 (d, J = 1.5 Hz, 1H), 3.68 (s, 3H), 2.24 (s, 3H), 1.20 (s, 9H). |

TABLE 2-continued

| Cmpd No. | Compound Name | Method | MW & Found [M + H]+ | NMR (shifts in ppm) |
|---|---|---|---|---|
| 30 | 2-[4-tert-butyl-2-(4-fluoro-2-methoxy-phenoxy)-6-methyl-phenyl]-1H-1,8-naphthyridin-4-one | A | 432.49; 433.3 | $^1$H NMR (400 MHz, $CDCl_3$) δ 10.95 (br s, 1H), 8.67 (d, J = 7.1 Hz, 1H), 7.91 (br s, 1H), 7.16 (dd, J = 7.8, 4.6 Hz, 1H), 7.06 (s, 1H), 6.92 (dd, J = 8.6, 5.9 Hz, 1H), 6.71-6.52 (m, 3H), 6.40 (s, 1H), 3.67 (s, 3H), 2.35 (s, 3H), 1.26 (s, 9H). |
| 31 | 2-[4-tert-butyl-2-(4-fluoro-2-methoxy-phenoxy)-6-methyl-phenyl]-1H-1,6-naphthyridin-4-one | A | 432.49; 433.3 | $^1$H NMR (400 MHz, DMSO-$d_6$) δ 12.08 (s, 1H), 9.20 (s, 1H), 8.59 (d, J = 5.6 Hz, 1H), 7.45-7.40 (m, 1H), 7.14 (d, J = 1.0 Hz, 1H), 7.09-7.00 (m, 2H), 6.76 (td, J = 8.4, 2.9 Hz, 1H), 6.54 (d, J = 1.2 Hz, 1H), 6.15 (d, J = 1.5 Hz, 1H), 3.68 (s, 3H), 2.24 (s, 3H), 1.19 (s, 9H). |
| 32 | 2-[4-tert-butyl-2-(4-fluoro-2-methoxy-phenoxy)-6-methyl-phenyl]-8-methyl-1H-quinolin-4-one | B | 445.53; 446.5 | |
| 33 | 2-[4-tert-butyl-2-(4-fluoro-2-methoxy-phenoxy)-6-methyl-phenyl]-6-oxido-1H-1,6-naphthyridin-6-ium-4-one | B | 448.49; 449.2 | $^1$H NMR (400 MHz, DMSO-$d_6$) δ 12.35 (s, 1H), 8.53 (d, J = 1.7 Hz, 1H), 8.31 (dd, J = 7.3, 2.0 Hz, 1H), 7.52 (d, J = 7.3 Hz, 1H), 7.14 (s, 1H), 7.10-7.01 (m, 2H), 6.76 (td, J = 8.6, 2.9 Hz, 1H), 6.55 (s, 1H), 6.12 (s, 1H), 3.69 (s, 3H), 2.23 (s, 3H), 1.19 (s, 9H). |
| 34 | 2-[4-tert-butyl-2-(4-fluoro-2-methoxy-phenoxy)-6-methyl-phenyl]-6-fluoro-1H-quinolin-4-one | A | 449.49; 450.2 | $^1$H NMR (400 MHz, $CDCl_3$) δ 9.17 (br s, 1H), 8.03 (dd, J = 9.0, 2.9 Hz, 1H), 7.36-7.29 (m, 1H), 7.21 (dd, J = 8.9, 4.3 Hz, 1H), 7.04 (d, J = 1.0 Hz, 1H), 7.00 (dd, J = 8.7, 5.7 Hz, 1H), 6.72 (dd, J = 9.9, 2.8 Hz, 1H), 6.69-6.61 (m, 2H), 6.31 (d, J = 1.7 Hz, 1H), 3.80 (s, 3H), 2.38 (s, 3H), 1.22 (s, 9H). |
| 35 | 2-[4-tert-butyl-2-(4-fluoro-2-methoxy-phenoxy)-6-methyl-phenyl]-8-fluoro-1H-quinolin-4-one | A | 449.49; 450.4 | $^1$H NMR (500 MHz, DMSO-$d_6$) δ 11.93 (s, 1H), 7.93 (dd, J = 8.2, 1.4 Hz, 1H), 7.56 (ddd, J = 11.3, 7.9, 1.5 Hz, 1H), 7.33 (td, J = 7.9, 4.6 Hz, 1H), 7.12 (d, J = 1.8 Hz, 1H), 7.08 (dd, J = 8.9, 5.8 Hz, 1H), 7.01 (dd, J = 10.7, 2.9 Hz, 1H), 6.75 (td, J = 8.5, 2.9 Hz, 1H), 6.54 (d, J = 1.9 Hz, 1H), 6.08 (s, 1H), 3.69 (s, 3H), 2.23 (s, 3H), 1.21 (s, 9H). |
| 36 | ethyl 2-[4-tert-butyl-2-(4-fluoro-2-methoxy-phenoxy)-6-methyl-phenyl]-4-oxo-1H-quinoline-3-carboxylate | A | 503.56; 504.4 | $^1$H NMR (400 MHz, $CD_3OD$) δ 8.31 (dd, J = 8.2, 1.4 Hz, 1H), 7.71 (td, J = 8.5, 7.0, 1.5 Hz, 1H), 7.57 (d, 1H), 7.44 (td, J = 8.2, 7.0, 1.1 Hz, 1H), 7.07 (s, 1H), 7.03 (dd, J = 8.8, 5.8 Hz, 1H), 6.86 (dd, J = 10.4, 2.9 Hz, 1H), 6.65 (td, J = 8.9, 8.0, 2.9 Hz, 1H), 6.51 (d, J = 1.7 Hz, 1H), 4.14-3.95 (m, 2H), 3.71 (s, 3H), 2.25 (s, 3H), 1.20 (s, 9H), 0.86 (t, J = 7.1 Hz, 3H). |
| 37 | 2-[4-tert-butyl-2-(4-fluoro-2-methoxy-phenoxy)-6-methyl-phenyl]pyrido[1,2-a]pyrimidin-4-one | D | 432.49; 433.6 | $^1$H NMR (400 MHz, DMSO-$d_6$) δ 9.03 (d, J = 7.1 Hz, 1H), 8.14-7.97 (m, 1H), 7.72 (d, J = 8.9 Hz, 1H), 7.45 (t, J = 6.9 Hz, 1H), 7.10-6.98 (m, 3H), 6.74 (td, J = 8.5, 3.0 Hz, 1H), 6.54-6.49 (m, 2H), 3.70 (s, 3H), 2.22 (s, 3H), 1.19 (s, 9H). |
| 38 | 2-[4-tert-butyl-2-(4-fluoro-2-methoxy-phenoxy)-6-methyl-phenyl]-5-fluoro-3H-quinazolin-4-one | A | 450.48; 451.3 | $^1$H NMR (400 MHz, DMSO-$d_6$) δ 12.41 (s, 1H), 7.79 (td, J = 8.2, 5.4 Hz, 1H), 7.46 (d, J = 8.2 Hz, 1H), 7.27 (dd, J = 11.0, 8.1 Hz, 1H), 7.14 (dd, J = 8.9, 5.9 Hz, 1H), 7.10-7.06 (m, 1H), 7.02 (dd, J = 10.7, 2.9 Hz, 1H), 6.77 (td, J = 8.5, 2.9 Hz, 1H), 6.51 (d, J = 1.7 Hz, 1H), 3.70 (s, 3H), 2.24 (s, 3H), 1.19 (s, 9H). |

TABLE 2-continued

| Cmpd No. | Compound Name | Method | MW & Found [M + H]+ | NMR (shifts in ppm) |
|---|---|---|---|---|
| 39 | 2-[4-(3,4-difluoro-2-methyl-phenoxy)-6-(trifluoromethyl)-3-pyridyl]-1H-1,6-naphthyridin-4-one | A | 433.33; 434.26 | |
| 40 | 2-[5-chloro-2-(4-fluoro-2-methyl-phenoxy)-4-methyl-3-pyridyl]-4-oxo-1H-1,6-naphthyridine-5-carboxamide | C | 438.84; 439.4 | $^1H$ NMR (400 MHz, $CD_3OD$) δ 8.57 (d, J = 5.9 Hz, 1H), 8.16 (s, 1H), 7.52 (d, J = 5.8 Hz, 1H), 7.03 (dd, J = 8.9, 5.0 Hz, 1H), 6.98 (dd, J = 9.2, 3.1 Hz, 1H), 6.92 (td, J = 8.4, 3.1 Hz, 1H), 6.45 (s, 1H), 2.39 (s, 3H), 2.06 (s, 3H). |
| 41 | 2-[2-(4-fluoro-2-methyl-phenoxy)-4-methyl-5-(trifluoromethyl)-3-pyridyl]-4-oxo-1H-1,6-naphthyridine-5-carboxamide | C | 472.39; 473.4 | $^1H$ NMR (400 MHz, DMSO-$d_6$) δ 12.27 (s, 1H), 8.59 (s, 1H), 8.53 (d, J = 5.8 Hz, 1H), 7.52 (br s, 1H), 7.42 (d, J = 5.8 Hz, 1H), 7.31 (br s, 1H), 7.21-7.13 (m, 2H), 7.07 (td, J = 8.5, 3.1 Hz, 1H), 6.38 (s, 1H), 2.41 (s, 3H), 2.04 (s, 3H). |
| 42 | 2-[2-(3,4-difluoro-2-methyl-phenoxy)-4-methyl-5-(trifluoromethyl)-3-pyridyl]-4-oxo-1H-1,6-naphthyridine-5-carboxamide | C | 490.38; 491.2 | $^1H$ NMR (400 MHz, DMSO-$d_6$) δ 12.28 (s, 1H), 8.60 (s, 1H), 8.53 (d, J = 5.7 Hz, 1H), 7.53 (s, 1H), 7.45-7.29 (m, 3H), 7.06 (ddd, J = 8.9, 5.1, 2.9 Hz, 1H), 6.40 (s, 1H), 2.41 (s, 3H), 2.02 (d, J = 2.0 Hz, 3H). |
| 43 | 2-[2-(4-fluoro-2-methoxy-phenoxy)-4-methyl-5-(trifluoromethyl)-3-pyridyl]-4-oxo-1H-1,6-naphthyridine-5-carboxamide | C | 488.39; 489.25 | $^1H$ NMR (400 MHz, DMSO-$d_6$) δ 12.25 (s, 1H), 8.58 (s, 1H), 8.52 (d, J = 5.8 Hz, 1H), 7.51 (s, 1H), 7.43 (d, J = 5.8 Hz, 1H), 7.30 (s, 1H), 7.21 (dd, J = 8.8, 5.8 Hz, 1H), 7.06 (dd, J = 10.7, 2.9 Hz, 1H), 6.79 (td, J = 8.5, 2.9 Hz, 1H), 6.32 (s, 1H), 3.70 (s, 3H), 2.40 (s, 3H). |
| 44 | ethyl 2-[2-(3,4-difluoro-2-methyl-phenoxy)-6-methyl-5-(trifluoromethyl)-3-pyridyl]-4-oxo-1H-1,5-naphthyridine-3-carboxylate | A | 519.42; 520.6 | $^1H$ NMR (400 MHz, DMSO-$d_6$) δ 12.58 (br s, 1H), 8.88-8.68 (m, 1H), 8.39 (s, 1H), 8.12-7.99 (m, 1H), 7.81-7.74 (m, 1H), 7.37 (app q, J = 9.4 Hz, 1H), 7.05-6.97 (m, 1H), 4.05 (q, J = 7.1 Hz, 2H), 2.51-2.47 (m, 3H) overlaps with DMSO, 2.02 (d, J = 2.1 Hz, 3H), 0.91 (t, J = 7.1 Hz, 3H). |

TABLE 2-continued

| Cmpd No. | Compound Name | Method | MW & Found [M + H]+ | NMR (shifts in ppm) |
|---|---|---|---|---|
| 45 | 2-[2-(3,4-difluoro-2-methyl-phenoxy)-6-methyl-5-(trifluoromethyl)-3-pyridyl]-4-oxo-1H-1,6-naphthyridine-5-carboxamide | C | 490.38; 491.2 | $^1H$ NMR (400 MHz, DMSO-$d_6$) δ 8.58 (d, J = 5.9 Hz, 1H), 8.49 (s, 1H), 7.81 (s, 1H), 7.69 (d, J = 5.9 Hz, 1H), 7.60 (s, 1H), 7.37 (q, J = 9.4 Hz, 1H), 7.28-7.17 (m, 1H), 6.67 (s, 1H), 2.48 (s, 3H), 2.04 (d, J = 2.0 Hz, 3H). |
| 46 | 2-[2-(3,4-difluoro-2-methyl-phenoxy)-5-methyl-6-(trifluoromethyl)-3-pyridyl]-4-oxo-1H-1,6-naphthyridine-5-carboxamide | C | 490.38; 491.3 | $^1H$ NMR (400 MHz, $CD_3OD$) δ 8.73 (d, J = 6.1 Hz, 1H), 8.26 (s, 1H), 7.84 (d, J = 6.1 Hz, 1H), 7.15 (q, J = 9.3 Hz, 1H), 7.06-6.99 (m, 2H), 2.54 (app q, J = 2.1 Hz, 3H), 2.06 (d, J = 2.2 Hz, 3H). |
| 47 | 2-[5-(3,4-difluoro-2-methoxy-phenoxy)-2-(trifluoromethyl)-4-pyridyl]-4-oxo-1H-1,6-naphthyridine-5-carboxamide | C | 492.36; 493.2 | $^1H$ NMR (400 MHz, DMSO-$d_6$) δ 12.23 (s, 1H), 8.54 (d, J = 5.5 Hz, 1H), 8.43 (s, 1H), 8.31 (s, 1H), 7.50 (s, 2H), 7.33-7.19 (m, 3H), 6.50 (s, 1H), 3.81 (s, 3H). |
| 48 | 2-[5-(4-fluoro-2-methyl-phenoxy)-3-methyl-2-(trifluoromethyl)-4-pyridyl]-4-oxo-1H-1,6-naphthyridine-5-carboxamide | A | 472.39; 473.4 | $^1H$ NMR (400 MHz, DMSO-$d_6$) δ 12.48 (s, 1H), 8.55 (d, J = 5.9 Hz, 1H), 8.02 (s, 1H), 7.64 (s, 1H), 7.57-7.33 (m, 2H), 7.25-7.17 (m, 2H), 7.16-7.07 (m, 1H), 6.41 (s, 1H), 2.39 (d, J = 2.0 Hz, 3H), 2.13 (s, 3H). |
| 49 | 2-[5-(3,4-difluoro-2-methyl-phenoxy)-3-methyl-2-(trifluoromethyl)-4-pyridyl]-4-oxo-1H-1,6-naphthyridine-5-carboxamide | C | 490.38; 491.4 | $^1H$ NMR (400 MHz, DMSO-$d_6$) δ 12.28 (s, 1H), 8.52 (d, J = 5.8 Hz, 1H), 8.14 (s, 1H), 7.53 (s, 1H), 7.43-7.38 (m, 1H), 7.38-7.28 (m, 2H), 7.08-7.00 (m, 1H), 6.35 (s, 1H), 2.39 (s, 3H), 2.13-2.06 (m, 3H). |
| 50 | 2-[5-(3,4-difluoro-2-methoxy-phenoxy)-3-methyl-2-(trifluoromethyl)-4-pyridyl]-4-oxo-1H-1,6-naphthyridine-5-carboxamide | C | 506.38; 507.0 | $^1H$ NMR (400 MHz, DMSO-$d_6$) δ 12.28 (s, 1H), 8.53 (d, J = 5.7 Hz, 1H), 8.20 (s, 1H), 7.53-7.12 (m, 5H), 6.34 (s, 1H), 3.80 (d, J = 0.9 Hz, 3H), 2.39 (s, 3H). |
| 51 | 2-[5-chloro-2-(3,4-difluoro-2-methyl-phenoxy)-6-(trifluoromethyl)-3-pyridyl]-8-fluoro-1H-quinolin-4-one | A | 484.78; 485.1 | $^1H$ NMR (400 MHz, $CDCl_3$) δ 9.66 (br. s, 1H), 8.29 (s, 1H), 8.17 (d, J = 8.1 Hz, 1H), 7.50-7.41 (m, 1H), 7.40-7.32 (m, 1H), 7.12 (dd, J = 17.9, 9.2 Hz, 1H), 6.97-6.89 (m, |

TABLE 2-continued

| Cmpd No. | Compound Name | Method | MW & Found [M + H]$^+$ | NMR (shifts in ppm) |
|---|---|---|---|---|
| | | | | 1H), 6.73 (d, J = 2.0 Hz, 1H), 2.18 (d, J = 1.7 Hz, 3H). |
| 52 | 2-[5-chloro-2-(3,4-difluoro-2-methyl-phenoxy)-6-(trifluoromethyl)-3-pyridyl]-1H-quinolin-4-one | A | 466.79; 467.1 | $^1$H NMR (400 MHz, $CDCl_3$) δ 9.61 (br. s, 1H), 8.39 (d, J = 7.6 Hz, 1H), 8.23 (s, 1H), 7.70 (t, J = 7.0 Hz, 1H), 7.48-7.40 (m, 2H), 7.10 (dd, J = 18.6, 9.1 Hz, 1H), 6.99-6.90 (m, 1H), 6.67 (s, 1H), 2.13 (d, J = 1.5 Hz, 3H). |
| 53 | 2-[2-(3,4-difluoro-2-methyl-phenoxy)-5-(trifluoromethyl)-3-pyridyl]-4-oxo-1H-1,6-naphthyridine-5-carboxamide | C | 476.36; 477.2 | $^1$H NMR (400 MHz, $CD_3OD$) δ 8.72 (d, J = 6.0 Hz, 1H), 8.63-8.54 (m, 2H), 7.82 (d, J = 6.0 Hz, 1H), 7.18 (q, J = 9.3 Hz, 1H), 7.07-7.01 (m, 2H), 2.07 (d, J = 2.1 Hz, 3H). |
| 54 | 2-[5-[2-methoxy-4-(trifluoromethoxy) phenoxy]-3-methyl-2-(trifluoromethyl)-4-pyridyl]-4-oxo-1H-1,6-naphthyridine-5-carboxamide | C | 554.4; 555.0 | $^1$H NMR (400 MHz, $CDCl_3$) δ 8.93 (s, 1H), 8.69 (d, J = 5.5 Hz, 1H), 8.32 (s, 1H), 7.98 (s, 1H), 7.20 (s, 1H), 7.11 (d, J = 9.2 Hz, 1H), 6.77-6.75 (m, 2H), 6.15 (s, 1H), 3.77 (s, 3H), 2.33 (d, J = 1.4 Hz, 3H). |
| 55 | 2-[2-fluoro-6-(4-fluoro-2-methyl-phenoxy)-3-(trifluoromethyl)phenyl]-4-oxo-1H-1,6-naphthyridine-5-carboxamide | C | 475.37; 476.09 | $^1$H NMR (400 MHz, $CDCl_3$) δ 15.60 (s, 1H), 8.97 (s, 1H), 8.67 (d, J = 5.6 Hz, 1H), 8.16 (s, 1H), 7.53 (t, J = 7.5 Hz, 1H), 7.28 (s, 1H), 7.03-6.85 (m, 3H), 6.51 (d, J = 8.8 Hz, 1H), 6.19-6.11 (m, 1H), 2.15 (s, 3H) |
| 56 | 2-[5-chloro-2-(4-fluoro-2-methyl-phenoxy)-4,6-dimethyl-3-pyridyl]-4-oxo-1H-1,6-naphthyridine-5-carboxamide | C | 452.87; 453.1 | $^1$H NMR (400 MHz, $CDCl_3$) δ 15.56 (s, 1H), 9.03-8.92 (m, 1H), 8.66 (d, J = 5.6 Hz, 1H), 8.13 (d, J = 5.6 Hz, 1H), 7.21 (s, 1H), 6.97 (dd, J = 8.7, 5.0 Hz, 1H), 6.90-6.77 (m, 2H), 6.21-6.09 (m, 1H), 2.46 (s, 3H), 2.27 (s, 3H), 2.09 (s, 3H). |
| 57 | 2-[2-(3,4-difluoro-2-methoxy-phenoxy)-5-fluoro-4-(trifluoromethyl) phenyl]-6-methyl-1H-1,6-naphthyridine-4,5-dione | A | 496.36; 497.11 | $^1$H NMR (400 MHz, $CDCl_3$) δ 7.87 (d, J = 10.5 Hz, 1H), 7.49 (s, 1H), 7.29 (d, J = 7.3 Hz, 1H), 7.01 (d, J = 6.0 Hz, 1H), 6.87-6.81 (m, 2H), |

TABLE 2-continued

| Cmpd No. | Compound Name | Method | MW & Found [M + H]$^+$ | NMR (shifts in ppm) |
|---|---|---|---|---|
| | | | | 6.69 (m, 1H), 3.90 (d, J = 1.8 Hz, 3H), 3.62 (s, 3H). |
| 58 | 2-[2-(4,4-difluoroazepan-1-yl)-3-quinolyl]-1H-1,6-naphthyridin-4-one | A | 406.43; 407.3 | |
| 59 | 2-[2-(4,4-difluoroazepan-1-yl)-3-quinolyl]-4-oxo-1H-1,6-naphthyridine-5-carboxamide | C | 449.45; 450.2 | $^1$H NMR (400 MHz, DMSO-$d_6$) & 12.10 (s, 1H), 8.52 (d, J = 5.8 Hz, 1H), 8.34 (s, 1H), 7.87 (d, J = 8.1 Hz, 1H), 7.77-7.62 (m, 2H), 7.55 (s, 1H), 7.46 (d, J = 5.8 Hz, 1H), 7.40-7.34 (m, 1H), 7.31 (s, 1H), 6.39 (s, 1H), 3.73-3.61 (m, 2H), 3.46 (t, J = 5.9 Hz, 2H), 2.39-2.25 (m, 2H), 2.12-1.93 (m, 2H), 1.82-1.69 (m, 2H). |
| 60 | 2-[2-(4,4-difluoroazepan-1-yl)-3-quinolyl]-4-oxo-1H-1,6-naphthyridine-5-carbonitrile | A | 431.44; 432.3 | $^1$H NMR (400 MHz, $CD_3OD$) δ 8.80 (s, 1H), 8.77 (d, J = 5.9 Hz, 1H), 8.11 (d, J = 8.5 Hz, 1H), 8.07-8.00 (m, 1H), 8.01-7.93 (m, 1H), 7.76 (d, J = 5.8 Hz, 1H), 7.72-7.62 (m, 1H), 6.69 (s, 1H), 3.94-3.86 (m, 2H), 3.80-3.71 (m, 2H), 2.51-2.34 (m, 2H), 2.22-2.06 (m, 2H), 2.02-1.90 (m, 2H). |
| 61 | 6-[2-(4,4-difluoroazepan-1-yl)-3-quinolyl]-8-oxo-5H-1,5-naphthyridine-2-carbonitrile | A | 431.44; 432.2 | $^1$H NMR (400 MHz, $CD_3OD$) δ 8.79 (s, 1H), 8.41 (d, J = 8.7 Hz, 1H), 8.19 (d, J = 8.7 Hz, 1H), 8.12 (d, J = 8.5 Hz, 1H), 8.05 (d, J = 8.0 Hz, 1H), 8.02-7.91 (m, 1H), 7.66 (t, J = 7.5 Hz, 1H), 7.15 (s, 1H), 3.91-3.81 (m, 2H), 3.74-3.65 (m, 2H), 2.45-2.30 (m, 2H), 2.20-2.06 (m, 2H), 1.99-1.87 (m, 2H). |
| 62 | 6-[2-(4,4-difluoroazepan-1-yl)-3-quinolyl]-8-oxo-5H-1,5-naphthyridine-2-carboxamide | C | 449.45; 450.2 | $^1$H NMR (400 MHz, $CD_3OD$) δ 8.70 (s, 1H), 8.51 (d, J = 8.8 Hz, 1H), 8.32 (d, J = 8.8 Hz, 1H), 8.03 (d, J = 8.4 Hz, 1H), 8.00 (d, J = 8.0 Hz, 1H), 7.90 (t, J = 7.8 Hz, 1H), 7.60 (t, J = 7.5 Hz, 1H), 7.04 (s, 1H), 3.93-3.79 (m, 2H), 3.73-3.59 (m, 2H), 2.50-2.28 (m, 2H), |

TABLE 2-continued

| Cmpd No. | Compound Name | Method | MW & Found [M + H]+ | NMR (shifts in ppm) |
|---|---|---|---|---|
| | | | | 2.23-2.04 (m, 2H), 1.98-1.83 (m, 2H). |
| 63 | ethyl 2-[2-(4,4-difluoroazepan-1-yl)-3-quinolyl]-4-oxo-1H-1,5-naphthyridine-3-carboxylate | A | 478.49; 479.5 | $^1$H NMR (400 MHz, DMSO-$d_6$) δ 12.69 (br s, 1H), 8.81 (d, J = 4.4 Hz, 1H), 8.25 (s, 1H), 8.21 (d, J = 8.5 Hz, 1H), 7.89-7.82 (m, 2H), 7.77-7.65 (m, 2H), 7.41-7.33 (m, 1H), 3.99 (q, J = 7.1 Hz, 2H), 3.69-3.61 (m, 2H), 3.61-3.52 (m, 1H), 3.45-3.33 (m, 1H), 2.40-2.22 (m, 2H), 2.08-1.92 (m, 2H), 1.81-1.71 (m, 2H), 0.85 (t, J = 7.1 Hz, 3H). |
| 64 | ethyl 2-[2-(4,4-difluoroazepan-1-yl)-5-methyl-6-(trifluoromethyl)-3-pyridyl]-4-oxo-1H-1,5-naphthyridine-3-carboxylate | A | 510.46; 511.6 | $^1$H NMR (400 MHz, DMSO-$d_6$) δ 12.39 (br s, 1H), 8.76 (d, J = 4.3 Hz, 1H), 8.05 (d, J = 8.4 Hz, 1H), 7.77 (dd, J = 8.5, 4.3 Hz, 1H), 7.73 (s, 1H), 4.02 (q, J = 7.1 Hz, 2H), 3.55-3.48 (m, 2H), 3.48-3.37 (m, 1H), 3.29-3.15 (m, 1H), 2.34 (q, J = 2.3 Hz, 3H), 2.31-2.15 (m, 2H), 2.04-1.84 (m, 2H), 1.78-1.67 (m, 2H), 0.93 (t, J = 7.1 Hz, 3H). |
| 65 | 2-[2-(4,4-difluoroazepan-1-yl)-5-methyl-6-(trifluoromethyl)-3-pyridyl]-1H-1,6-naphthyridin-4-one | A | 438.39; 439.14 | $^1$H NMR (400 MHz, $CD_3OD$) δ 9.45 (s, 1H), 8.72 (d, J = 6.9, 1.1 Hz, 1H), 7.93 (d, J = 6.8 Hz, 1H), 7.83 (s, 1H), 6.64 (s, 1H), 3.70-3.61 (m, 2H), 3.36 (d, J = 6.0 Hz, 2H), 2.45 (s, 3H), 2.33 (tt, J = 10.5, 6.3 Hz, 2H), 1.94 (d, J = 13.7 Hz, 2H), 1.87-1.78 (m, 2H). |
| 66 | 2-[2-(4,4-difluoroazepan-1-yl)-5-methyl-6-(trifluoromethyl)-3-pyridyl]-1H-quinolin-4-one | A | 437.41; 438.14 | $^1$H NMR (400 MHz, DMSO-$d_6$) δ 8.17 (d, J = 8.1Hz, 1H), 7.82 (s, 1H), 7.72 (dd, J = 8.3, 6.8 Hz, 1H), 7.64 (d, J = 8.2 Hz, 1H), 7.41 (t, J = 7.5 Hz, 1H), 6.31 (s, 1H), 3.61-3.51 (m, 2H), 3.30 (d, J = 12.2 Hz, 2H), 2.38 (s, 3H), 2.32-2.21 (m, 2H), 2.02-1.89 (m, 2H), 1.72 (m, 2H). |
| 67 | 2-[2-(4,4-difluoroazepan-1-yl)-5-methyl-6-(trifluoromethyl)-3-pyridyl]-8-fluoro-1H-quinolin-4-one | A | 455.4; 456.14 | $^1$H NMR (400 MHz, $CD_3OD$) δ 8.29 (dt, J = 8.4, 1.1 Hz, 1H), 8.00-7.90 (m, 2H), 7.83 (td, J = 8.2, 4.9 Hz, 1H), 7.25 (s, 1H), 3.69-3.58 (m, 2H), 3.16 (t, J = 6.0 Hz, 2H), 2.45 (s, 3H), 2.42-2.27 (m, 2H), 2.02-1.89 (m, 2H), 1.80 (p, J = 6.1 Hz, 2H). |
| 68 | 2-[2-(4,4-difluoroazepan-1-yl)-5-methyl-6-(trifluoromethyl)-3-pyridyl]-6-oxido-1H-1,6-naphthyridin-6-ium-4-one | B | 454.39; 455.2 | $^1$H NMR (400 MHz, $CD_3OD$) δ 9.16 (s, 1H), 8.57 (d, J = 7.2 Hz, 1H), 7.78 (d, J = 11.5 Hz, 2H), 6.53 (s, 1H), 3.67-3.60 (m, 2H), 3.33 (d, J = 3.0 Hz, 2H), 2.41 (q, J = 2.1 Hz, 3H), 2.31 (td, J = 16.2, 15.3, 10.5 Hz, 1H), 2.03-1.88 (m, 2H), 1.82 (q, J = 5.5, 5.0 Hz, 2H). |
| 69 | 2-[2-(4,4-difluoroazepan-1-yl)-5-methyl-6-(trifluoromethyl)-3-pyridyl]-5-methoxy-1H-quinolin-4-one | B | 467.43; 468.6 | |
| 70 | 2-[2-(4,4-difluoroazepan-1-yl)-5-methyl-6-(trifluoromethyl)-3-pyridyl]-6-fluoro-1H-quinolin-4-one | B | 455.4; 456.14 | $^1$H NMR (400 MHz, DMSO-$d_6$) δ 12.01 (s, 1H), 7.84 (s, 1H), 7.75 (d, J = 9.3 Hz, 1H), 7.61 (qd, J = 9.6, 9.1, 3.9 Hz, 2H), 6.20 (s, 1H), 3.51 (d, J = 6.3 Hz, 2H), 3.29 (m, 2H), 2.36 (s, 3H), 2.23 (m, 2H), 1.98 (m, 2H), 1.69 (m, 2H) |
| 71 | 2-[2-(4,4-difluoroazepan-1-yl)-5-methyl-6-(trifluoromethyl)-3-pyridyl]-7-fluoro-1H-quinolin-4-one | B | 455.4; 456.4 | $^1$H NMR (400 MHz, DMSO-$d_6$) δ 11.90 (s, 1H), 8.15 (dd, J = 9.0, 6.3 Hz, 1H), 7.84 (s, 1H), 7.28 (dd, J = 10.1, 2.5 Hz, 1H), 7.21 (td, J = 8.8, 2.5 Hz, 1H), 6.19 (d, J = 1.7 Hz, 1H), 3.56-3.49 (m, 2H), 2.36 (q, J = 2.2 Hz, 3H), 3.3 (m, 2H, obscured by water peak), 2.31-2.16 (m, 2H), 2.03-1.87 (m, 2H), 1.79-1.63 (m, 2H). |
| 72 | 2-[2-(4,4-difluoroazepan-1-yl)-5-methyl-6-(trifluoromethyl)-3-pyridyl]-5-hydroxy-1H-quinolin-4-one | A | 453.41; 454.49 | |
| 73 | 2-[2-(4,4-difluoroazepan-1-yl)-5-methyl-6-(trifluoromethyl)-3-pyridyl]-5,7-dimethoxy-1H-quinolin-4-one | B | 497.46; 498.79 | $^1$H NMR (400 MHz, $CDCl_3$) δ 8.17 (s, 1H), 8.04 (s, 1H), 6.72 (s, 1H), 6.65 (s, 1H), 4.15 (s, 3H), 4.03 (s, 3H), 3.69-3.64 (m, 2H), 3.08 (t, J = 6.0 Hz, 2H), 2.43 (s, 3H), 2.41- |

TABLE 2-continued

| Cmpd No. | Compound Name | Method | MW & Found [M + H]+ | NMR (shifts in ppm) |
|---|---|---|---|---|
| | | | | 2.29 (m, 2H), 1.96 (qd, J = 13.7, 12.1, 3.9 Hz, 2H), 1.79 (t, J = 5.7 Hz, 2H). |
| 74 | 2-[2-(4,4-difluoroazepan-1-yl)-5-methyl-6-(trifluoromethyl)-3-pyridyl]-5-fluoro-1H-quinolin-4-one | B | 455.4; 456.2 | $^1$H NMR (400 MHz, DMSO-d$_6$) δ 11.86 (s, 1H), 7.83 (s, 1H), 7.61 (td, J = 8.2, 5.2 Hz, 1H), 7.35 (d, J = 8.4 Hz, 1H), 7.01 (dd, J = 11.8, 7.9 Hz, 1H), 6.11 (d, J = 1.7 Hz, 1H), 3.56-3.49 (m, 2H), 3.30 (s, 2H), 2.36 (d, J = 2.4 Hz, 3H), 2.24 (s, 2H), 1.95 (s, 2H), 1.71 (s, 2H). |
| 75 | 2-[2-(4,4-difluoroazepan-1-yl)-5-methyl-6-(trifluoromethyl)-3-pyridyl]-6-methyl-1H-quinolin-4-one | A | 451.43; 452.4 | $^1$H NMR (400 MHz, DMSO-d$_6$) δ 11.94 (s, 1H), 7.92 (s, 1H), 7.81 (s, 1H), 7.58-7.48 (m, 2H), 6.23 (s, 1H), 3.54-3.49 (m, 2H), 3.30 (t, 2H), 2.43 (s, 3H), 2.39-2.33 (m, 3H), 2.28-2.14 (m, 2H), 2.01-1.88 (m, 2H), 1.74-1.63 (m, 2H). |
| 76 | 2-[2-(4,4-difluoroazepan-1-yl)-5-methyl-6-(trifluoromethyl)-3-pyridyl]-3-methyl-1H-quinolin-4-one | A | 451.43; 452.4 | $^1$H NMR (400 MHz, DMSO-d$_6$) δ 11.70 (s, 1H), 8.14 (d, J = 8.2 Hz, 1H), 7.75 (s, 1H), 7.63 (t, J = 7.7 Hz, 1H), 7.55 (d, J = 8.4 Hz, 1H), 7.32 (t, J = 7.8 Hz, 1H), 3.66-3.40 (m, 4H), 2.38 (s, 3H), 2.25-2.11 (m, 2H), 2.04-1.93 (m, 2H), 1.83 (s, 3H), 1.76-1.57 (m, 2H). |
| 77 | 2-[2-(4,4-difluoroazepan-1-yl)-5-methyl-6-(trifluoromethyl)-3-pyridyl]-6-fluoro-3-methyl-1H-quinolin-4-one | A | 469.42; 470.3 | $^1$H NMR (400 MHz, DMSO-d$_6$) δ 11.86 (s, 1H), 7.78 (s, 1H), 7.75 (s, 1H), 7.67-7.59 (m, 1H), 7.59-7.50 (m, 1H), 3.63-3.40 (m, 4H), 2.37 (s, 3H), 2.25-2.11 (m, 2H), 2.03-1.89 (m, 2H), 1.83 (s, 3H), 1.76-1.59 (m, 2H). |
| 78 | 2-[2-(4,4-difluoroazepan-1-yl)-5-methyl-6-(trifluoromethyl)-3-pyridyl]-6-methoxy-1H-quinolin-4-one | A | 467.43; 468.3 | $^1$H NMR (400 MHz, DMSO-d$_6$) δ 12.13 (s, 1H), 7.82 (s, 1H), 7.63 (d, 1H), 7.54 (d, J = 2.9 Hz, 1H), 7.36 (dd, 1H), 6.28 (s, 1H), 3.88 (s, 3H), 3.54-3.50 (m, 2H), 3.32 (s, 2H), 2.37 (s, 3H), 2.29-2.15 (m, 2H), 2.04-1.89 (m, 2H), 1.75-1.64 (m, 2H). |
| 79 | 2-[2-(4,4-difluoroazepan-1-yl)-5-methyl-6-(trifluoromethyl)-3-pyridyl]-7-fluoro-3-methyl-1H-quinolin-4-one | A | 469.42; 470.3 | $^1$H NMR (400 MHz, DMSO-d$_6$) & 11.71 (s, 1H), 8.17 (t, 1H), 7.74 (s, 1H), 7.23 (dd, 1H), 7.15 (td, 1H), 3.57-3.41 (m, 2H), 3.36-3.24 (m, 2H), 2.36 (s, 3H), 2.25-2.11 (m, 2H), 2.03-1.88 (m, 2H), 1.80 (s, 3H), 1.74-1.56 (m, 2H). |
| 80 | 2-[2-(4,4-difluoroazepan-1-yl)-5-methyl-6-(trifluoromethyl)-3-pyridyl]-1H-1,5-naphthyridin-4-one | A | 438.39; 439.25 | $^1$H NMR (400 MHz, DMSO-d$_6$) δ 8.79 (d, J = 4.2 Hz, 1H), 8.21 (d, J = 8.6 Hz, 1H), 7.87 (s, 1H), 7.81 (dd, J = 8.6, 4.3 Hz, 1H), 6.65 (s, 1H), 3.59-3.43 (m, 2H), 3.24 (s, 2H), 2.37 (q, J = 2.3 Hz, 3H), 2.24 (s, 2H), 2.05-1.85 (m, 2H), 1.70 (d, J = 7.1 Hz, 2H). |
| 81 | 2-[2-(4,4-difluoroazepan-1-yl)-5-methyl-6-(trifluoromethyl)-3-pyridyl]-4-oxo-1H-1,6-naphthyridine-5-carboxamide | C | 481.42; 482.45 | $^1$H NMR (400 MHz, DMSO-d$_6$) δ 12.03 (s, 1H), 8.51 (d, J = 5.8 Hz, 1H), 7.85 (s, 1H), 7.54 (s, 1H), 7.43 (d, J = 5.8 Hz, 1H), 7.32 (s, 1H), 6.29 (s, 1H), 3.59-3.52 (m, 2H), 3.32-3.28 (m, 2H, obscured by water peak), 2.37 (q, J = 2.2 Hz, 3H), 2.28-2.19 (m, 2H), 2.04-1.86 (m, 2H), 1.79-1.69 (m, 2H). |
| 82 | 2-[2-(4,4-difluoro-1-piperidyl)-5-methyl-6-(trifluoromethyl)-3-pyridyl]-4-oxo-1H-1,6-naphthyridine-5-carboxamide | C | 467.39; 468.4 | $^1$H NMR (400 MHz, CD$_3$OD) δ 8.57 (d, J = 5.9 Hz, 1H), 7.89 (s, 1H), 7.56 (br s, 1H), 6.61 (br s, 1H), 3.43-3.34 (m, 4H), 2.45 (q, J = 2.1 Hz, 3H), 2.04-1.87 (m, 4H). |
| 83 | 2-[2-(4,4-difluoro-1-piperidyl)-5-(trifluoromethyl)-3-pyridyl]-1H-quinolin-4-one | A | 409.35; 410.1 | $^1$H NMR (400 MHz, DMSO-d$_6$) δ 11.98 (s, 1H), 8.68 (dd, J = 2.4, 1.1 Hz, 1H), 8.15-8.08 (m, 2H), 7.70 (ddd, J = 8.4, 6.8, 1.5 Hz, 1H), 7.63 (d, J = 8.4 Hz, 1H), 7.38 (t, J = 7.5 Hz, 1H), 6.36 (s, 1H), 3.49-3.41 (m, 4H), 2.02-1.88 (m, 4H). |
| 84 | 2-[2-(4,4-difluoroazepan-1-yl)-6-(trifluoromethyl)-3-pyridyl]-1H-1,6-naphthyridin-4-one | A | 424.37; 425.3 | $^1$H NMR (400 MHz, DMSO-d$_6$) δ 12.98 (s, 1H), 9.35 (s, 1H), 8.71 (d, J = 6.5 Hz, 1H), 8.00 (d, J = 7.6 Hz, 1H), 7.87 (d, J = 6.5 Hz, 1H), |

TABLE 2-continued

| Cmpd No. | Compound Name | Method | MW & Found [M + H]+ | NMR (shifts in ppm) |
|---|---|---|---|---|
| | | | | 7.32 (d, J = 7.7 Hz, 1H), 6.50 (s, 1H), 3.67-3.53 (m, 2H), 3.32 (t, J = 6.0 Hz, 2H), 2.41-2.19 (m, 2H), 2.11-1.84 (m, 2H), 1.85-1.65 (m, 2H). |
| 85 | 2-[5-chloro-2-(4,4-difluoroazepan-1-yl)-6-(trifluoromethyl)-3-pyridyl]-1H-quinolin-4-one | A | 457.82; 458.1 | $^1$H NMR (400 MHz, DMSO-$d_6$) δ 12.02 (s, 1H), 8.13 (dd, J = 8.2, 1.3 Hz, 1H), 7.73-7.66 (m, 1H), 7.58 (d, J = 8.1 Hz, 1H), 7.41-7.34 (m, 1H), 7.29 (s, 1H), 6.12 (d, J = 1.7 Hz, 1H), 3.80-3.74 (m, 2H), 3.70 (br t, J = 5.9 Hz, 2H), 2.32-2.20 (m, 2H), 2.16-2.02 (m, 2H), 1.93-1.83 (m, 2H). |
| 86 | 2-[5-chloro-2-(4,4-difluoroazepan-1-yl)-4,6-dimethyl-3-pyridyl]-4-oxo-1H-1,6-naphthyridine-5-carbonitrile | A | 443.88; 444.2 | $^1$H NMR (400 MHz, DMSO-$d_6$) δ 12.48 (s, 1H), 8.73 (d, J = 5.8 Hz, 1H), 7.71 (d, J = 5.8 Hz, 1H), 6.33 (s, 1H), 3.51-3.38 (m, 2H), 3.36-3.25 (m, 1H), 3.26-3.05 (m, 1H), 2.21 (s, 3H), 2.20-2.07 (m, 2H), 2.02-1.81 (m, 2H), 1.72-1.55 (m, 2H).-CH3 overlapping with DMSO peak |
| 87 | 2-[2-(4,4-difluoroazepan-1-yl)-5,6,7,8-tetrahydroquinolin-3-yl]-4-oxo-1H-1,6-naphthyridine-5-carbonitrile | A | 435.47; 436.4 | $^1$H NMR (400 MHz, $CD_3OD$) δ 8.67 (d, J = 5.9 Hz, 1H), 7.69 (d, J = 5.9 Hz, 1H), 7.44 (s, 1H), 6.45 (s, 1H), 3.60-3.52 (m, 2H), 3.26 (app t, J = 6.1 Hz, 2H) overlaps with CD2HOD, 2.80 (app t, J = 6.4 Hz, 2H), 2.73 (app t, J = 6.2 Hz, 2H), 2.34-2.19 (m, 2H), 2.02-1.86 (m, 4H), 1.86-1.78 (m, 2H), 1.78-1.69 (m, 2H). |
| 88 | 2-[2-(4,4-difluoroazepan-1-yl)-6,7-dihydro-5H-cyclopenta[b]pyridin-3-yl]-4-oxo-1H-1,6-naphthyridine-5-carboxamide | C | 439.46; 440.4 | $^1$H NMR (400 MHz, $CDCl_3$) δ 15.32 (s, 1H), 8.97 (s, 1H), 8.67-8.57 (m, 1H), 8.20-8.03 (m, 1H), 7.74 (s, 1H), 7.20 (s, 1H), 6.15 (s, 1H), 3.62-3.53 (m, 2H), 3.17 (t, J = 6.1 Hz, 2H), 2.98-2.84 (m, 4H), 2.40-2.23 (m, 2H), 2.13 (p, J = 7.5 Hz, 2H), 2.06-1.88 (m, 2H), 1.79-1.67 (m, 2H). |
| 89 | 2-[2-(4,4-difluoroazepan-1-yl)-7-fluoro-3-quinolyl]-4-oxo-1H-1,6-naphthyridine-5-carboxamide | C | 467.44; 468.1 | $^1$H NMR (400 MHz, $CD_3OD$) δ 8.56 (d, J = 5.9 Hz, 1H), 8.28 (s, 1H), 7.86 (dd, J = 8.9, 6.2 Hz, 1H), 7.54 (d, J = 5.1 Hz, 1H), 7.39 (dd, J = 10.8, 2.4 Hz, 1H), 7.16 (td, J = 8.7, 2.6 Hz, 1H), 6.57 (br. s, 1H), 3.74 (dt, J = 5.5, 2.6 Hz, 2H), 3.49 (t, J = 6.0 Hz, 2H), 2.43-2.30 (m, 2H), 2.07-1.94 (m, 2H), 1.86-1.77 (m, 2H). |
| 90 | 2-[2-(6-azaspiro[2.5]octan-6-yl)-4-methyl-3-quinolyl]-4-oxo-1H-1,6-naphthyridine-5-carboxamide | C | 439.51; 440.3 | $^1$H NMR (400 MHz, $CD_3OD$) δ 8.57 (d, J = 5.9 Hz, 1H), 8.07 (d, J = 8.4 Hz, 1H), 7.86 (d, J = 8.4 Hz, 1H), 7.74-7.66 (m, 1H), 7.54 (d, J = 5.9 Hz, 1H), 7.51-7.44 (m, 1H), 6.49 (s, 1H), 3.35-3.31 (m, 4H), 2.62 (s, 3H), 1.34-1.20 (m, 4H), 0.26 (s, 4H). |
| 91 | 2-[6-tert-butyl-5-chloro-2-(4,4-difluoroazepan-1-yl)-3-pyridyl]-4-oxo-1H-1,6-naphthyridine-5-carboxamide | C | 489.95; 490.1 | $^1$H NMR (400 MHz, DMSO-$d_6$) δ 11.95 (s, 1H), 8.49 (d, J = 5.9 Hz, 1H), 7.70 (s, 1H), 7.52 (br s, 1H), 7.42 (d, J = 5.9 Hz, 1H), 7.30 (br s, 1H), 6.23 (s, 1H), 3.61-3.54 (m, 2H), 3.31-3.28 (m, 2H, overlapped with water), 2.31-2.19 (m, 2H), 2.03-1.90 (m, 2H), 1.78-1.69 (m, 2H), 1.46 (s, 9H). |
| 92 | 2-[6-tert-butyl-2-(4,4-difluoroazepan-1-yl)-5-methyl-3-pyridyl]-4-oxo-1H-1,6-naphthyridine-5-carboxamide | C | 469.53; 470.3 | $^1$H NMR (400 MHz, $CDCl_3$) δ 15.34 (s, 1H), 8.99 (br. s, 1H), 8.63 (d, J = 5.6 Hz, 1H), 8.12 (d, J = 5.6 Hz, 1H), 7.59 (s, 1H), 7.22 (s, 1H), 6.13 (br. s, 1H), 3.73-3.61 (m, 2H), 3.14 (t, J = 6.2 Hz, 2H), 2.46 (s, 3H), 2.42-2.27 (m, 2H), 2.02-1.89 (m, 2H), 1.78-1.68 (m, 2H), 1.45 (s, 9H). |

TABLE 2-continued

| Cmpd No. | Compound Name | Method | MW & Found [M + H]+ | NMR (shifts in ppm) |
|---|---|---|---|---|
| 93 | 2-[2-(4,4-difluoroazepan-1-yl)-5-(trifluoromethyl)-3-pyridyl]-1H-quinolin-4-one | A | 423.38; 424.1 | $^1$H NMR (400 MHz, DMSO-$d_6$) δ 12.27 (s, 1H), 8.64-8.59 (m, 1H), 8.13 (dd, J = 8.1, 1.5 Hz, 1H), 8.03 (d, J = 2.5 Hz, 1H), 7.73 (ddd, J = 8.4, 6.8, 1.5 Hz, 1H), 7.65 (d, J = 8.3 Hz, 1H), 7.41 (ddd, J = 8.1, 6.9, 1.2 Hz, 1H), 6.29 (s, 1H), 3.6 (m, 2H, obscured by water peak), 3.32 (t, J = 6.0 Hz, 2H), 2.33-2.21 (m, 2H), 2.04-1.89 (m, 2H), 1.74 (m, 2H). |
| 94 | 2-[2-(6-azaspiro[2.5]octan-6-yl)-6-methyl-5-(trifluoromethyl)-3-pyridyl]-4-oxo-1H-1,6-naphthyridine-5-carboxamide | C | 457.45; 458.25 | $^1$H NMR (400 MHz, $CD_3OD$) δ 8.55 (d, J = 5.9 Hz, 1H), 7.91 (s, 1H), 7.65-7.44 (m, 1H), 6.52 (s, 1H), 3.49-3.40 (m, 4H), 2.59 (d, J = 1.7 Hz, 3H), 1.41-1.31 (m, 4H), 0.31 (s, 4H). |
| 95 | 2-[5-chloro-2-(4,4-difluoroazepan-1-yl)-6-(trifluoromethyl)-3-pyridyl]-8-fluoro-1H-quinolin-4-one | A | 475.81; 476.1 | $^1$H NMR (400 MHz, DMSO-$d_6$) δ 12.08 (br s, 1H), 7.96 (d, J = 8.1 Hz, 1H), 7.68-7.58 (m, 1H), 7.39 (br s, 1H), 7.25 (br s, 1H), 6.17 (br s, 1H), 3.81-3.72 (m, 2H), 3.72-3.63 (m, 2H), 2.32-2.18 (m, 2H), 2.16-2.02 (m, 2H), 1.94-1.82 (m, 2H). |
| 96 | 2-[5-chloro-2-(4,4-difluoroazepan-1-yl)-4,6-dimethyl-3-pyridyl]-4-oxo-1H-1,6-naphthyridine-5-carboxamide | C | 461.89; 462.2 | $^1$H NMR (400 MHz, $CD_3OD$) δ 8.89 (d, J = 6.0 Hz, 1H), 7.98 (d, J = 6.1 Hz, 1H), 7.07 (s, 1H), 3.54-3.46 (m, 2H), 3.20-3.11 (m, 2H), 2.58 (s, 3H), 2.29 (s, 3H), 2.26-2.16 (m, 2H), 2.01-1.88 (m, 2H), 1.72-1.63 (m, 2H). |
| 97 | 2-[2-(4,4-difluoroazepan-1-yl)-5,6,7,8-tetrahydroquinolin-3-yl]-4-oxo-1H-1,6-naphthyridine-5-carboxamide | C | 453.48; 454.5 | $^1$H NMR (400 MHz, DMSO-$d_6$) δ 11.88 (br s, 1H), 8.49 (d, J = 5.8 Hz, 1H), 7.52 (br s, 1H), 7.47-7.41 (m, 2H), 7.29 (br s, 1H), 6.18 (s, 1H), 3.54-3.47 (m, 2H), 3.27 (app t, J = 6.1 Hz, 2H), 2.74 (app t, J = 6.3 Hz, 2H), 2.68 (app t, J = 6.2 Hz, 2H), 2.32-2.17 (m, 2H), 2.02-1.88 (m, 2H), 1.88-1.80 (m, 2H), 1.79-1.72 (m, 2H), 1.72-1.63 (m, 2H). |
| 98 | 2-[2-(4,4-difluoroazepan-1-yl)-6-fluoro-3-quinolyl]-4-oxo-1H-1,6-naphthyridine-5-carboxamide | C | 467.44; 468.2 | $^1$H NMR (400 MHz, $CDCl_3$) δ 15.56 (s, 1H), 9.01 (br. s, 1H), 8.70 (d, J = 5.6 Hz, 1H), 8.22 (s, 1H), 8.18 (d, J = 5.6 Hz, 1H), 7.79 (dd, J = 9.0, 5.4 Hz, 1H), 7.45-7.34 (m, 2H), 7.30 (s, 1H), 6.18 (br. s, 1H), 3.75-3.67 (m, 2H), 3.31 (t, J = 6.1 Hz, 2H), 2.50-2.32 (m, 2H), 2.11-1.93 (m, 2H), 1.83-1.71 (m, 2H). |
| 99 | 2-[2-(6-azaspiro[2.5]octan-6-yl)-4-methyl-3-quinolyl]-4-oxo-1H-1,6-naphthyridine-5-carbonitrile | A | 421.49; 422.3 | $^1$H NMR (400 MHz, $CD_3OD$) δ 8.79 (d, J = 5.8 Hz, 1H), 8.28 (d, J = 8.3 Hz, 1H), 8.06 (d, J = 8.4 Hz, 1H), 8.03-7.92 (m, 1H), 7.80-7.65 (m, 2H), 6.64 (s, 1H), 3.63 (br s, 4H), 2.73 (s, 3H), 1.42 (br s, 4H), 0.39 (s, 4H) |
| 100 | 2-[2-(4,4-difluoroazepan-1-yl)-5-(trifluoromethyl)-3-pyridyl]-4-oxo-1H-1,6-naphthyridine-5-carboxamide | C | 467.39; 468.2 | $^1$H NMR (400 MHz, $CD_3OD$) δ 8.93 (d, J = 5.7 Hz, 1H), 8.64 (d, J = 2.2 Hz, 1H), 8.18 (d, J = 2.3 Hz, 1H), 8.13-8.00 (m, 1H), 7.10 (s, 1H), 3.83-3.64 (m, 2H), 3.28-3.18 (m, 2H), 2.47-2.26 (m, 2H), 2.05-1.77 (m, 4H). |
| 101 | 2-[2-(4,4-difluoroazepan-1-yl)-6-methyl-5-(trifluoromethyl)-3-pyridyl]-4-oxo-1H-1,6-naphthyridine-5-carboxamide | C | 481.42; 482.4 | $^1$H NMR (400 MHz, $CDCl_3$) δ 15.57 (s, 1H), 9.09-8.88 (m, 1H), 8.65 (d, J = 5.6 Hz, 1H), 8.16-8.05 (m, 1H), 8.00 (s, 1H), 7.06 (s, 1H), 6.21-6.09 (m, 1H), 3.76-3.69 (m, 2H), 3.11 (t, J = 6.2 Hz, 2H), 2.63-2.55 (m, 3H), 2.43-2.29 (m, 2H), 1.96-1.85 (m, 2H), 1.79-1.69 (m, 2H). |
| 102 | 2-[5-chloro-2-(4,4-difluoroazepan-1-yl)-6-(trifluoromethyl)-3-pyridyl]-1H-1,6-naphthyridin-4-one | B | 458.81; 459.1 | $^1$H NMR (400 MHz, DMSO-$d_6$) δ 12.35 (br. s, 1H), 9.25 (br. s, 1H), 8.70-8.58 (m, 1H), 7.46 (d, J = 5.9 Hz, 1H), 7.31 (s, 1H), 6.30 (s, 1H), 3.81-3.73 (m, 2H), 3.73-3.64 (m, 2H), 2.34-2.19 (m, 2H), 2.15-2.02 (m, 2H), 1.92-1.83 (m, 2H). |

TABLE 2-continued

| Cmpd No. | Compound Name | Method | MW & Found [M + H]+ | NMR (shifts in ppm) |
|---|---|---|---|---|
| 103 | ethyl 2-[2-(4,4-difluoroazepan-1-yl)-5-methyl-6-(trifluoromethyl)-3-pyridyl]-4-oxo-1H-quinoline-3-carboxylate | A | 509.47; 510.3 | $^1$H NMR (400 MHz, $CD_3OD$) δ 8.30 (dd, J = 8.3, 1.5 Hz, 1H), 7.76 (td, J = 8.5, 7.0, 1.5 Hz, 1H), 7.64-7.57 (m, 2H), 7.48 (td, J = 8.2, 7.0, 1.1 Hz, 1H), 4.58 (s, 2H), 4.09 (q, J = 7.1 Hz, 2H), 3.67-3.58 (m, 2H), 2.38 (q, J = 2.1 Hz, 3H), 2.33-2.13 (m, 2H), 1.97 (q, J = 14.2, 13.1 Hz, 2H), 1.78 (p, J = 6.1 Hz, 2H), 1.01 (t, J = 7.1 Hz, 3H). |
| 104 | 2-[6-(3,3-difluorocyclobutyl)-4-[4-(trifluoromethyl) cyclohexyl]-3-pyridyl]-4-oxo-1H-1,6-naphthyridine-5-carboxamide (cis isomer) | C | 506.47; 507.3 | $^1$H NMR (400 MHz, DMSO-$d_6$) δ 12.12 (s, 1H), 8.60 (s, 1H), 8.52 (d, J = 5.8 Hz, 1H), 7.55 (s, 1H), 7.43 (d, J = 5.3 Hz, 2H), 7.35 (s, 1H), 6.16 (s, 1H), 3.75-3.61 (m, 1H), 3.06-2.81 (m, 4H), 2.80-2.68 (m, 1H), 2.47-2.37 (m, 1H), 2.08 (s, 0H), 1.96-1.82 (m, 2H), 1.77-1.50 (m, 6H). |
| 105 | 2-[2-tert-butyl-4-(4,4-difluorocyclohexyl) pyrimidin-5-yl]-4-oxo-1H-1,6-naphthyridine-5-carboxamide | C | 441.47; 442.4 | $^1$H NMR (400 MHz, $CD_3OD$) δ 8.83 (d, J = 6.1 Hz, 1H), 8.79 (s, 1H), 7.91 (d, J = 6.1 Hz, 1H), 6.92 (s, 1H), 3.06-2.92 (m, 1H), 2.20-2.04 (m, 4H), 1.96-1.69 (m, 4H), 1.45 (s, 9H) |
| 106 | 2-[6-tert-butyl-2-(4,4-difluorocyclohexyl)-3-pyridyl]-4-oxo-1H-1,6-naphthyridine-5-carboxamide | C | 440.49; 441.4 | $^1$H NMR (400 MHz, $CD_3OD$) δ 8.83 (d, J = 6.0 Hz, 1H), 7.91 (d, J = 6.0 Hz, 1H), 7.81 (d, J = 8.2 Hz, 1H), 7.48 (d, J = 8.2 Hz, 1H), 6.88 (s, 1H), 2.98-2.88 (m, 1H), 2.23-2.05 (m, 4H), 1.90-1.77 (m, 3H), 1.77-1.66 (m, 1H), 1.41 (s, 9H). |
| 107 | 2-[2-(3,3-difluorocyclobutyl)-4-(4,4-difluorocyclohexyl) pyrimidin-5-yl]-4-oxo-1H-1,6-naphthyridine-5-carboxamide | C | 475.44; 476.4 | $^1$H NMR (400 MHz, $CD_3OD$) δ 8.90 (d, J = 6.2 Hz, 1H), 8.85 (s, 1H), 8.04 (d, J = 6.2 Hz, 1H), 7.04 (s, 1H), 3.79-3.67 (m, 1H), 3.11-2.96 (m, 5H), 2.18-2.05 (m, 4H), 1.96-1.69 (m, 4H). |
| 108 | 2-[4-tert-butyl-2-(4,4-difluorocyclohexen-1-yl)phenyl]-4-oxo-1H-1,6-naphthyridine-5-carboxamide | C | 437.48; 438.3 | $^1$H NMR (400 MHz, $CD_3OD$) δ 8.82 (d, J = 6.0 Hz, 1H), 7.91 (d, J = 6.0 Hz, 1H), 7.65-7.53 (m, 2H), 7.49 (d, J = 1.7 Hz, 1H), 6.91 (s, 1H), 5.67-5.52 (m, 1H), 2.56 (t, J = 14.4 Hz, 2H), 2.49-2.37 (m, 2H), 2.12-1.92 (m, 2H), 1.39 (s, 9H). |
| 109 | 2-[4-tert-butyl-2-(cyclohexylmethyl) phenyl]-4-oxo-1H-1,6-naphthyridine-5-carboxamide | C | 417.54; 418.4 | $^1$H NMR (400 MHz, $CD_3OD$) δ 8.76 (s, 1H), 7.84 (s, 1H), 7.49-7.43 (m, 2H), 7.39 (d, J = 7.9 Hz, 1H), 6.75 (s, 1H), 2.64 (d, J = 7.1 Hz, 2H), 1.67-1.49 (m, 5H), 1.43-1.31 (m, 10H), 1.16-1.00 (m, 3H), 0.92-0.72 (m, 2H). |
| 110 | 2-[4-(3,3-difluorocyclobutyl)-2-(4,4-difluorocyclohexyl) phenyl]-4-oxo-1H-1,6-naphthyridine-5-carboxamide | C | 473.46; 474.3 | $^1$H NMR (400 MHz, DMSO-$d_6$) δ 12.14 (s, 1H), 8.53 (d, J = 5.8 Hz, 1H), 7.58 (s, 1H), 7.50 (d, J = 5.8 Hz, 1H), 7.44 (s, 1H), 7.40-7.33 (m, 2H), 7.32-7.27 (m, 1H), 6.09 (s, 1H), 3.56-3.48 (m, 1H), 3.13-2.97 (m, 2H), 2.84-2.63 (m, 3H), 2.12-1.97 (m, 2H), 1.93 -1.64 (m, 6H). |
| 111 | 2-[2-(4,4-difluorocyclohexyl)-3-quinolyl]-4-oxo-1H-1,6-naphthyridine-5-carboxamide | C | 434.44; 435.3 | $^1$H NMR (400 MHz, $CD_3OD$) δ 8.59 (d, J = 5.9 Hz, 1H), 8.41 (s, 1H), 8.17-8.05 (m, 1H), 8.05-7.90 (m, 1H), 7.90-7.73 (m, 1H), 7.71-7.60 (m, 1H), 7.55 (d, J = 5.9 Hz, 1H), 6.44 (s, 1H), 3.21-2.93 (m, 1H), 2.28-2.05 (m, 4H), 2.05-1.90 (m, 2H), 1.90-1.54 (m, 2H) |
| 112 | 2-[6-(3,3-difluorocyclobutyl)-2-(4,4-difluorocyclohexyl)-3-pyridyl]-4-oxo-1H-1,6-naphthyridine-5-carboxamide | C | 474.45; 475.1 | $^1$H NMR (400 MHz, $CD_3OD$) δ 8.88 (d, J = 6.1 Hz, 1H), 7.97 (d, J = 6.0 Hz, 1H), 7.84 (d, J = 7.9 Hz, 1H), 7.39 (d, J = 8.0 Hz, 1H), 6.95 (s, 1H), 3.65-3.56 (m, 1H), 3.04-2.91 (m, 5H), 2.24-2.06 (m, 4H), 1.94-1.67 (m, 4H). |
| 113 | 2-[4-(cyclohexylmethyl)-6-(3,3-difluorocyclobutyl)-3-pyridyl]-4-oxo-1H-1,6-naphthyridine-5-carboxamide | C | 452.5; 453.3 | $^1$H NMR (400 MHz, $CD_3OD$) δ 8.98-8.90 (m, 1H), 8.85 (d, J = 6.3 Hz, 1H), 8.16-8.07 (m, 1H), 8.03 (d, J = 5.7 Hz, 1H), 6.93 (s, 1H), 3.95-3.78 (m, 1H), 3.28-2.99 (m, 4H), 2.86 (d, J = 7.0 Hz, 2H), 1.74-1.51 (m, 6H), 1.33-1.23 |

TABLE 2-continued

| Cmpd No. | Compound Name | Method | MW & Found [M + H]+ | NMR (shifts in ppm) |
|---|---|---|---|---|
| | | | | (m, 2H), 1.20-1.15 (m, 1H), 1.00-0.84 (m, 2H). |
| 114 | 2-[6-tert-butyl-2-(4,4-difluorocyclohexyl)-5-methyl-3-pyridyl]-4-oxo-1H-1,6-naphthyridine-5-carboxamide | C | 454.51; 455.2 | $^1$H NMR (400 MHz, $CD_3OD$) δ 8.46 (d, J = 4.6 Hz, 1H), 7.42 (s, 2H), 6.22 (br. s, 1H), 2.86-2.75 (m, 1H), 2.46 (s, 3H), 2.11-1.92 (m, 4H), 1.79-1.51 (m, 4H), 1.37 (s, 9H). |
| 115 | 2-[6-tert-butyl-5-chloro-2-(4,4-difluorocyclohexyl)-3-pyridyl]-4-oxo-1H-1,6-naphthyridine-5-carboxamide | C | 474.93; 475.1 | $^1$H NMR (400 MHz, DMSO-$d_6$) δ 12.08 (br s, 1H), 8.51 (d, J = 5.4 Hz, 1H), 7.96 (s, 1H), 7.52 (br s, 1H), 7.40 (d, J = 5.6 Hz, 1H), 7.34 (brs, 1H), 6.21 (s, 1H), 3.01-2.88 (m, 1H), 2.10-1.98 (m, 2H, overlapped with acetonitrile), 1.97-1.75 (m, 6H), 1.50 (s, 9H). |
| 116 | 2-[2-(4,4-difluorocyclohexyl)-6-methyl-5-(trifluoromethyl)-3-pyridyl]-4-oxo-1H-1,6-naphthyridine-5-carboxamide | C | 466.4; 467.04 | $^1$H NMR (400 MHz, DMSO-$d_6$) δ 12.05 (s, 1H), 8.49 (d, J = 6.1 Hz, 1H), 8.13 (d, J = 22.1 Hz, 1H), 7.61-7.31 (m, 3H), 6.18 (s, 1H), 2.97 (s, 1H), 2.65 (s, 3H), 2.03-1.75 (m, 8H) |
| 117 | 2-[6-(3,3-difluorocyclobutyl)-4-(4,4-difluorocyclohexyl)-3-pyridyl]-4-oxo-1H-1,6-naphthyridine-5-carbonitrile | A | 456.44; 457.4 | $^1$H NMR (400 MHz, $CD_3OD$) δ 8.84 (s, 1H), 8.76 (d, J = 5.8 Hz, 1H), 7.89 (s, 1H), 7.72 (d, J = 5.8 Hz, 1H), 6.46 (s, 1H), 3.86-3.73 (m, 1H), 3.15-2.96 (m, 5H), 2.17-2.05 (m, 2H), 2.00-1.75 (m, 6H). |
| 118 | 2-[2-tert-butyl-4-(4-methoxycyclohexyl) pyrimidin-5-yl]-4-oxo-1H-1,6-naphthyridine-5-carboxamide (cis isomer) | C | 435.52; 436.5 | $^1$H NMR (400 MHz, $CD_3OD$) δ 8.87 (d, J = 6.1 Hz, 1H), 8.76 (s, 1H), 7.98 (d, J = 6.1 Hz, 1H), 6.99 (s, 1H), 3.49-3.44 (m, 1H), 3.34 (s, 3H), 2.90 (tt, J = 11.3, 3.5 Hz, 1H), 2.20-2.06 (m, 2H), 2.06-1.98 (m, 2H), 1.64-1.53 (m, 2H), 1.46 (s, 9H), 1.48-1.38 (m, 2H). |
| 119 | 2-[2-(3,3-difluorocyclobutyl)-4-[4-(trifluoromethyl) cyclohexyl] pyrimidin-5-yl]-4-oxo-1H-1,6-naphthyridine-5-carboxamide (trans isomer) | C | 507.46; 508.5 | $^1$H NMR (400 MHz, $CD_3OD$) δ 8.83 (d, J = 6.2 Hz, 1H) overlaps with 8.82 (s, 1H), 7.92 (d, J = 6.1 Hz, 1H), 6.89 (s, 1H), 3.78-3.65 (m, 1H), 3.10-2.97 (m, 4H), 2.87 (tt, J = 11.1, 3.9 Hz, 1H), 2.30-2.16 (m, 1H), 2.06-1.82 (m, 6H), 1.41-1.26 (m, 2H). |
| 120 | 2-[4-(3,3-difluorocyclobutyl)-2-[4-(trifluoromethyl) cyclohexyl] phenyl]-4-oxo-1H-1,6-naphthyridine-5-carboxamide (cis isomer) | C | 505.48; 506.3 | $^1$H NMR (400 MHz, $CD_3OD$) δ 8.72 (d, J = 6.0 Hz, 1H), 7.76 (d, J = 6.0 Hz, 1H), 7.43 (d, J = 8.4 Hz, 1H), 7.39-7.34 (m, 2H), 6.61 (s, 1H), 3.58-3.44 (m, 1H), 3.16-3.00 (m, 2H), 2.81-2.59 (m, 3H), 2.44-2.30 (m, 1H), 2.11-2.03 (m, 2H), 1.91-1.76 (m, 2H), 1.76-1.67 (m, 2H), 1.63 (d, J = 13.9 Hz, 2H). |
| 121 | 2-[6-(3,3-difluorocyclobutyl)-2-[4-(trifluoromethyl) cyclohexyl]-3-pyridyl]-4-oxo-1H-1,6-naphthyridine-5-carboxamide | C | 506.47; 507.1 | $^1$H NMR (400 MHz, $CD_3OD$) δ 8.88 (d, J = 6.0 Hz, 1H), 7.99 (d, J = 6.1 Hz, 1H), 7.84 (d, J = 8.0 Hz, 1H), 7.38 (d, J = 8.0 Hz, 1H), 6.94 (s, 1H), 3.61 (pd, J = 8.5, 3.1 Hz, 1H), 3.09-2.89 (m, 4H), 2.88-2.75 (m, 1H), 2.30-2.15 (m, 1H), 2.07-1.88 (m, 6H), 1.40-1.24 (m, 2H). |
| 122 | 2-[6-tert-butyl-4-(4,4-difluorocyclohexyl)-3-pyridyl]-4-oxo-1H-1,6-naphthyridine-5-carboxamide | C | 440.49; 441.3 | $^1$H NMR (400 MHz, $CD_3OD$) δ 8.80 (s, 1H), 8.76 (d, J = 6.1 Hz, 1H), 7.91 (s, 1H), 7.87 (d, J = 6.0 Hz, 1H), 6.84 (s, 1H), 3.16-2.95 (m, 1H), 2.20-2.08 (m, 2H), 2.02-1.92 (m, 4H), 1.89-1.72 (m, 2H), 1.54 (s, 9H). |
| 123 | 2-[6-(3,3-difluorocyclobutyl)-4-(4,4-difluorocyclohexyl)-3-pyridyl]-4-oxo-1H-1,6-naphthyridine-5-carboxamide | C | 474.45; 475.5 | $^1$H NMR (400 MHz, $CD_3OD$) δ 8.88 (d, J = 6.1 Hz, 1H), 8.80 (s, 1H), 8.05 (d, J = 6.1 Hz, 1H), 7.80 (s, 1H), 6.98 (s, 1H), 3.83-3.70 (m, 1H), 3.11-2.99 (m, 4H), 2.98-2.88 (m, 1H), 2.18-2.06 (m, 2H), 2.01-1.91 (m, 4H), 1.91-1.69 (m, 2H). |
| 124 | 2-[2-tert-butyl-4-(4-methoxycyclohexyl) pyrimidin-5-yl]-4-oxo-1H-1,6-naphthyridine-5-carboxamide (trans isomer) | C | 435.52; 436.5 | $^1$H NMR (400 MHz, $CD_3OD$) δ 8.69 (s, 1H), 8.58 (d, J = 5.9 Hz, 1H), 7.52 (br s, 1H), 6.37 (br s, 1H), 3.33 (s, 3H), 3.28-3.19 (m, 1H), 2.88-2.72 (m, 1H), 2.20-2.09 (m, |

TABLE 2-continued

| Cmpd No. | Compound Name | Method | MW & Found [M + H]+ | NMR (shifts in ppm) |
|---|---|---|---|---|
| | | | | 2H), 1.92-1.84 (m, 4H), 1.43 (s, 9H), 1.21-1.06 (m, 2H). |
| 125 | 2-[2-(3,3-difluorocyclobutyl)-4-[4-(trifluoromethyl)cyclohexyl]pyrimidin-5-yl]-4-oxo-1H-1,6-naphthyridine-5-carboxamide (cis isomer) | C | 507.46; 508.4 | $^1$H NMR (400 MHz, $CD_3OD$) δ 8.88 (d, J = 6.1 Hz, 1H), 8.81 (s, 1H), 8.00 (d, J = 6.2 Hz, 1H), 7.01 (s, 1H), 3.73 (app pd, J = 8.6, 3.1 Hz, 1H), 3.22 (app p, J = 5.3 Hz, 1H), 3.11-2.98 (m, 4H), 2.36-2.21 (m, 1H), 2.16-2.00 (m, 4H), 1.82-1.66 (m, 4H). |
| 126 | 2-[4-tert-butyl-2-(4,4-difluorocyclohexyl)phenyl]-4-oxo-1H-1,6-naphthyridine-5-carboxamide | C | 439.5; 440.5 | $^1$H NMR (400 MHz, $CD_3OD$) δ 8.60 (d, J = 5.9 Hz, 1H), 7.64-7.55 (m, 1H), 7.50 (d, J = 1.9 Hz, 1H), 7.49-7.39 (m, 1H), 7.36 (d, J = 8.1 Hz, 1H), 6.40 (s, 1H), 2.84-2.72 (m, 1H), 2.18-1.97 (m, 2H), 1.91-1.85 (m, 4H), 1.81-1.61 (m, 2H), 1.37 (s, 9H). |
| 127 | 2-[4-(3,3-difluorocyclobutyl)-2-[4-(trifluoromethyl)cyclohexyl]phenyl]-4-oxo-1H-1,6-naphthyridine-5-carboxamide (trans isomer) | C | 505.48; 506.3 | $^1$H NMR (400 MHz, $CD_3OD$) δ 8.75 (d, J = 6.0 Hz, 1H), 7.80 (d, J = 6.0 Hz, 1H), 7.48-7.44 (m, 1H), 7.43 (s, 1H), 7.39-7.33 (m, 1H), 6.66 (s, 1H), 3.57-3.45 (m, 1H), 3.16-2.96 (m, 2H), 2.83-2.52 (m, 3H), 2.32-2.18 (m, 1H), 2.02-1.99 (m, 1H), 1.99-1.88 (m, 3H), 1.78-1.62 (m, 2H), 1.35-1.20 (m, 2H). |
| 128 | 2-[6-tert-butyl-4-(4-methoxycyclohexyl)-3-pyridyl]-4-oxo-1H-1,6-naphthyridine-5-carbonitrile (cis isomer) | A | 416.52; 417.5 | $^1$H NMR (400 MHz, $CD_3OD$) δ 8.84 (s, 1H), 8.76 (d, J = 5.8 Hz, 1H), 8.02 (s, 1H), 7.71 (d, J = 5.8 Hz, 1H), 6.48 (s, 1H), 3.53-3.47 (m, 1H), 3.36 (s, 3H), 2.99-2.88 (m, 1H), 2.09-2.00 (m, 2H), 1.99-1.84 (m, 2H), 1.71-1.62 (m, 2H), 1.56 (s, 9H), 1.51-1.41 (m, 2H). |
| 129 | 2-[6-(3,3-difluorocyclobutyl)-4-[4-(trifluoromethyl)cyclohexyl]-3-pyridyl]-1H-1,6-naphthyridin-4-one (cis isomer) | A | 463.44; 464.3 | |
| 130 | 2-[6-tert-butyl-4-(4-methoxycyclohexyl)-3-pyridyl]-4-oxo-1H-1,6-naphthyridine-5-carboxamide (cis isomer) | C | 434.53; 435.6 | $^1$H NMR (400 MHz, DMSO-$d_6$) δ 12.65 (br s, 1H), 8.63 (s, 1H), 8.60 (d, J = 6.0 Hz, 1H), 7.89 (br s, 1H), 7.74 (br s, 1H), 7.66 (d, J = 6.1 Hz, 1H), 7.52 (s, 1H), 6.34 (s, 1H), 3.43-3.36 (m, 1H), 3.24 (s, 3H), 2.80-2.69 (m, 1H), 1.97-1.88 (m, 2H), 1.84-1.69 (m, 2H), 1.61-1.53 (m, 2H), 1.42 (s, 9H), 1.39-1.27 (m, 2H). |
| 131 | 2-[6-(3,3-difluorocyclobutyl)-4-[4-(trifluoromethyl)cyclohexyl]-3-pyridyl]-5-hydroxy-1H-1,6-naphthyridin-4-one | A | 479.44; 480.3 | $^1$H NMR (400 MHz, $CD_3OD$) δ 8.73 (s, 1H), 7.88 (d, J = 7.5 Hz, 1H), 7.65 (s, 1H), 7.29 (s, 1H), 6.85 (d, J = 7.5 Hz, 1H), 3.84-3.67 (m, 1H), 3.15-2.95 (m, 4H), 2.95-2.82 (m, 1H), 2.51-2.33 (m, 1H), 2.14-1.94 (m, 2H), 1.95-1.58 (m, 6H). |
| 132 | 2-[6-tert-butyl-4-(4-methoxycyclohexyl)-3-pyridyl]-4-oxo-1H-1,6-naphthyridine-5-carbonitrile (trans isomer) | | 416.52; 417.4 | $^1$H NMR (400 MHz, $CD_3OD$) δ 8.86 (s, 1H), 8.76 (d, J = 5.9 Hz, 1H), 8.05 (s, 1H), 7.71 (d, J = 5.8 Hz, 1H), 6.48 (s, 1H), 3.37-3.34 (m, 1H) overlaps with 3.33 (s, 3H), 2.94-2.83 (m, 1H), 2.20-2.13 (m, 2H), 2.00-1.93 (m, 2H), 1.85-1.71 (m, 2H), 1.56 (s, 9H), 1.28-1.13 (m, 2H). |
| 133 | 2-[6-tert-butyl-4-(4-methoxycyclohexyl)-3-pyridyl]-4-oxo-1H-1,6-naphthyridine-5-carboxamide (trans isomer) | C | 434.53; 435.6 | $^1$H NMR (400 MHz, $CD_3OD$) δ 8.94 (s, 1H), 8.85 (d, J = 6.3 Hz, 1H), 8.17-8.06 (m, 2H), 6.90 (s, 1H), 3.38-3.34 (m, 1H) overlaps with 3.34 (s, 3H), 2.94-2.82 (m, 1H), 2.22-2.13 (m, 2H), 2.04-1.97 (m, 2H), 1.88-1.73 (m, 2H), 1.60 (s, 9H), 1.25-1.10 (m, 2H). |
| 134 | 2-[6-(3,3-difluorocyclobutyl)-4-[4-(trifluoromethyl)cyclohexyl]-3-pyridyl]-4-oxo-1H-1,6-naphthyridine-5-carboxamide (trans isomer) | C | 506.47; 507.4 | $^1$H NMR (400 MHz, DMSO-$d_6$) δ 12.09 (s, 1H), 8.59 (s, 1H), 8.52 (d, J = 5.8 Hz, 1H), 7.56-7.48 (m, 2H), 7.43 (d, J = 5.8 Hz, 1H), 7.33 (s, 1H), 6.14 (s, 1H), 3.65-3.56 (m, 1H), 3.08-2.80 (m, 4H), 2.71-2.58 (m, 1H), 2.41- |

TABLE 2-continued

| Cmpd No. | Compound Name | Method | MW & Found [M + H]+ | NMR (shifts in ppm) |
|---|---|---|---|---|
| | | | | 2.24 (m, 1H), 1.99-1.80 (m, 4H), 1.74-1.57 (m, 2H), 1.30-1.12 (m, 2H). |
| 135 | 2-[4-tert-butyl-5-chloro-2-(4,4-difluorocyclohexyl) phenyl]-4-oxo-1H-1,6-naphthyridine-5-carboxamide | C | 473.94; 474.2 | $^1$H NMR (400 MHz, $CD_3OD$) δ 8.56 (d, J = 5.9 Hz, 1H), 7.56-7.49 (m, 2H), 7.47 (s, 1H), 6.29 (br. s, 1H), 2.85-2.73 (m, 1H), 2.15-2.03 (m, 2H), 1.94-1.66 (m, 6H), 1.53 (s, 9H). |
| 136 | 2-[6-(1-methylcyclopropyl)-4-[4-(trifluoromethyl) cyclohexyl]-3-pyridyl]-4-oxo-1H-1,6-naphthyridine-5-carboxamide (cis isomer) | C | 470.49; 471.3 | $^1$H NMR (400 MHz, $CD_3OD$) δ 8.82 (d, J = 6.2 Hz, 1H), 8.79 (s, 1H), 8.00 (d, J = 6.1 Hz, 1H), 7.78 (s, 1H), 6.88 (s, 1H), 3.09-2.97 (m, 1H), 2.52-2.33 (m, 1H), 2.13-2.00 (m, 2H), 1.90-1.79 (m, 4H), 1.76-1.66 (m, 2H), 1.63 (s, 3H), 1.43-1.35 (m, 2H), 1.27-1.17 (m, 2H). |
| 137 | 2-[6-(1-methylcyclopropyl)-4-[4-(trifluoromethyl) cyclohexyl]-3-pyridyl]-4-oxo-1H-1,6-naphthyridine-5-carboxamide (trans isomer) | C | 470.49; 471.3 | |
| 138 | 2-[1-tert-butyl-3-(4,4-difluorocyclohexyl) pyrazol-4-yl]-4-oxo-1H-1,6-naphthyridine-5-carboxamide | C | 429.20; 430.3 | $^1$H NMR (400 MHz, $CD_3OD$) δ 8.88 (d, J = 5.9 Hz, 1H), 8.46 (s, 1H), 8.09 (d, J = 5.9 Hz, 1H), 7.07 (s, 1H), 3.27-3.15 (m, 1H), 2.27-2.10 (m, 2H), 2.10-1.82 (m, 6H), 1.65 (s, 9H) |
| 139 | 2-[6-(3,3-difluorocyclobutyl)-4-(3,4-difluoro-2-methyl-phenoxy)-3-pyridyl]-4-oxo-1H-1,6-naphthyridine-5-carboxamide | C | 498.13; 499.3 | $^1$H NMR (400 MHz, $CD_3OD$) δ 8.86 (s, 1H), 8.76 (d, J = 6.0 Hz, 1H), 7.90 (d, J = 6.0 Hz, 1H), 7.25 (q, J = 9.2 Hz, 1H), 7.08 (s, 1H), 7.06-7.01 (m, 1H), 6.78 (s, 1H), 3.54-3.44 (m, 1H), 2.99-2.81 (m, 4H), 2.11 (d, J = 2.1 Hz, 3H). |
| 140 | 2-[2-(3,4-difluoro-2-methyl-phenoxy)-4-methyl-5-(trifluoromethyl)-3-pyridyl]-4-oxo-1H-quinoline-5-carboxamide | C | 489.11; 490.0 | $^1$H NMR (400 MHz, DMSO-$d_6$) δ 12.03 (s, 1H), 8.60 (s, 1H), 7.64 (dd, J = 8.4, 7.1 Hz, 1H), 7.53 (dd, J = 8.4, 1.2 Hz, 1H), 7.44-7.28 (m, 2H), 7.16 (br s, 1H), 7.12 (dd, J = 7.2, 1.1 Hz, 1H), 7.05 (ddd, J = 9.2, 4.3, 1.9 Hz, 1H), 6.23 (d, J = 1.5 Hz, 1H), 2.41 (s, 3H), 2.02 (d, J = 2.0 Hz, 3H) |
| 141 | 2-[2-tert-butyl-4-(4-fluoro-2-methyl-phenoxy)pyrimidin-5-yl]-4-oxo-1H-1,6-naphthyridine-5-carboxamide | C | 447.17; 448.5 | $^1$H NMR (400 MHz, DMSO-$d_6$) δ 12.15 (s, 1H), 8.92 (s, 1H), 8.52 (d, J = 5.7 Hz, 1H), 7.51 (s, 1H), 7.47 (d, J = 5.8 Hz, 1H), 7.35 (dd, J = 8.9, 5.1 Hz, 1H), 7.31 (s, 1H), 7.21 (dd, J = 9.4, 3.2 Hz, 1H), 7.13 (td, J = 8.6, 3.1 Hz, 1H), 6.50 (s, 1H), 2.06 (s, 3H), 1.20 (s, 9H). |
| 142 | 2-[2-[(2-methoxy-6-methyl-3-pyridyl)oxy]-4-methyl-5-(trifluoromethyl)-3-pyridyl]-4-oxo-1H-1,6-naphthyridine-5-carboxamide | C | 485.13; 486.4 | $^1$H NMR (400 MHz, $CD_3OD$) δ 8.85 (d, J = 6.2 Hz, 1H), 8.51 (s, 1H), 7.98 (d, J = 6.2 Hz, 1H), 7.38 (d, J = 7.8 Hz, 1H), 7.04 (s, 1H), 6.82 (dd, J = 7.8, 0.7 Hz, 1H), 3.82 (s, 3H), 2.48 (m, 3H), 2.42 (s, 3H) |
| 143 | 2-[2-[(2-methoxy-6-methyl-3-pyridyl)oxy]-4-methyl-5-(trifluoromethyl)-3-pyridyl]-4-oxo-1H-1,6-naphthyridine-5-carbonitrile | A | 467.12; 468.4 | $^1$H NMR (400 MHz, $CD_3OD$) δ 8.73 (d, J = 5.9 Hz, 1H), 8.45 (s, 1H), 7.69 (d, J = 5.8 Hz, 1H), 7.35 (d, J = 7.8 Hz, 1H), 6.81 (d, J = 7.7 Hz, 1H), 6.53 (s, 1H), 3.82 (s, 3H), 2.46 (m, 3H), 2.42 (s, 3H) |
| 144 | 2-[2-[(2-methoxy-3-pyridyl)oxy]-4-methyl-5-(trifluoromethyl)-3-pyridyl]-4-oxo-1H-1,6-naphthyridine-5-carboxamide | C | 471.12; 472.3 | $^1$H NMR (400 MHz, $CDCl_3$) δ 15.62 (s, 1H), 8.96 (d, J = 5.6 Hz, 1H), 8.68 (d, J = 5.6 Hz, 1H), 8.37 (s, 1H), 8.15 (d, J = 5.6 Hz, 1H), 8.02 (dd, J = 5.0, 1.6 Hz, 1H), 7.34 (d, J = 7.6 Hz, 1H), 7.30 (s, 1H), 6.89 (dd, J = 7.6, 5.0 Hz, 1H), 6.15 (s, 1H), 3.91 (s, 3H), 2.37-2.33 (m, 3H). |
| 145 | 6-[2-(3,4-difluoro-2-methyl-phenoxy)-4-methyl-5-(trifluoromethyl)-3-pyridyl]-1-imino-1-oxo-2,3,4,5-tetrahydrothiopyrano[3,2-b]pyridin-8-one | A | 499.5; 500.1 | $^1$H NMR (400 MHz, $CD_3OD$) δ 8.47 (s, 1H), 7.15 (q, J = 9.3 Hz, 1H), 6.92 (ddd, J = 9.1, 4.1, 2.1 Hz, 1H), 6.71 (s, 1H), 4.13-3.99 (m, 2H), 3.25-3.07 (m, 2H), 2.71-2.55 (m, 2H), 2.51-2.45 (m,3H), 2.05 (d, J = 2.1 Hz, 3H). |

TABLE 2-continued

| Cmpd No. | Compound Name | Method | MW & Found [M + H]+ | NMR (shifts in ppm) |
|---|---|---|---|---|
| 146 | 2-[2-(3,4-difluoro-2-methyl-phenoxy)-4-(hydroxymethyl)-5-(trifluoromethyl)-3-pyridyl]-4-oxo-1H-1,6-naphthyridine-5-carboxamide | C | 506.10; 507.1 | $^1$H NMR (400 MHz, DMSO-$d_6$) δ 8.62 (s, 1H), 8.46 (d, J = 5.3 Hz, 1H), 7.48-7.25 (m, 4H), 7.03 (m, 1H), 6.36 (s, 1H), 5.35-5.90 (m, 1H), 4.57 (d, J = 35.9 Hz, 2H), 1.98 (s, 3H). |
| 147 | 2-[2-(3,3-difluorocyclobutyl)-4-(4-methylcyclohexyl) pyrimid in-5-yl]-4-oxo-1H-1,6-naphthyridine-5-carboxamide (trans isomer) | C | 453.20; 454.1 | $^1$H NMR (400 MHz, DMSO-$d_6$) δ 12.14 (br s, 1H), 8.82 (s, 1H), 8.53 (d, J = 5.9 Hz, 1H), 7.55 (br s, 1H), 7.42 (d, J = 5.9 Hz, 1H), 7.35 (br s, 1H), 6.22 (s, 1H), 3.73-3.63 (m, 1H), 3.15-3.03 (m, 2H), 3.02-2.88 (m, 2H), 2.77-2.68 (m, 1H), 1.84-1.62 (m, 6H), 1.44-1.31 (m, 1H), 0.95-0.85 (m, 2H), 0.83 (d, J = 6.4 Hz, 3H). |

2-[2-(4-fluoro-2-methyl-phenoxy)-4-methyl-5-(trifluoromethyl)-3-pyridyl]-4-oxo-1H-1,6-naphthyridine-5-carboxamide (41)

A mixture of 4-benzyloxy-2-chloro-1,6-naphthyridine-5-carbonitrile (630 mg, 2.13 mmol) and [2-(4-fluoro-2-methyl-phenoxy)-4-methyl-5-(trifluoromethyl)-3-pyridyl] boronic acid (702 mg, 2.13 mmol) in dioxane (15 mL) and aqueous potassium phosphate (5 mL of 1 M, 5 mmol) was bubbled with nitrogen for 10 min. $PdCl_2$(dtbpf) (137 mg, 0.210 mmol) was added and the mixture bubbled again with nitrogen for 5 min. The reaction vessel was sealed and the mixture stirred at room temperature under nitrogen for 10 min. The mixture was partitioned between ethyl acetate and brine and the layers separated. The aqueous layer was extracted with additional ethyl acetate, and the combined organic layers dried over magnesium sulfate, filtered and concentrated. Purification by silica gel chromatography (12 g silica, 0-50% ethyl acetate/hexane) provided 4-benzyloxy-2-[2-(4-fluoro-2-methyl-phenoxy)-4-methyl-5-(trifluoromethyl)-3-pyridyl]-1,6-naphthyridine-5-carbonitrile. ESI-MS m/z calc. 544.15, found 545.4 $(M+1)^+$. The intermediate was dissolved in toluene (10 mL) and TFA (8 mL) and the mixture heated at 75° C. for 16 h. The mixture was concentrated and evaporated with additional toluene (3×) to remove residual TFA. Purification was performed using silica gel chromatography (40 g silica, 0-10% methanol/dichloromethane) followed by an additional silica gel chromatography purification (20-100% ethyl acetate/dichloromethane). Product fractions were concentrated, redissolved in dichloromethane and washed with saturated sodium bicarbonate and brine. The solution was dried over sodium sulfate, filtered and concentrated to provide 2-[2-(4-fluoro-2-methyl-phenoxy)-4-methyl-5-(trifluoromethyl)-3-pyridyl]-4-oxo-1H-1,6-naphthyridine-5-carboxamide (41, 585 mg, 61%). ESI-MS m/z calc. 472.11, found 473.5 $(M+1)^+$. $^1$H NMR (400 MHz, $CD_3OD$) δ 8.57 (d, J=6.0 Hz, 1H), 8.46 (s, 1H), 7.52 (d, J=5.8 Hz, 1H), 7.06 (dd, J=8.9, 4.9 Hz, 1H), 7.01 (dd, J=9.2, 3.1 Hz, 1H), 6.94 (td, J=8.4, 3.1 Hz, 1H), 6.48 (s, 1H), 2.47 (s, 3H), 2.07 (s, 3H).

2-[2-(3,4-difluoro-2-methyl-phenoxy)-4-methyl-5-(trifluoromethyl)-3-pyridyl]-4-oxo-1H-1,6-naphthyridine-5-carboxamide (42)

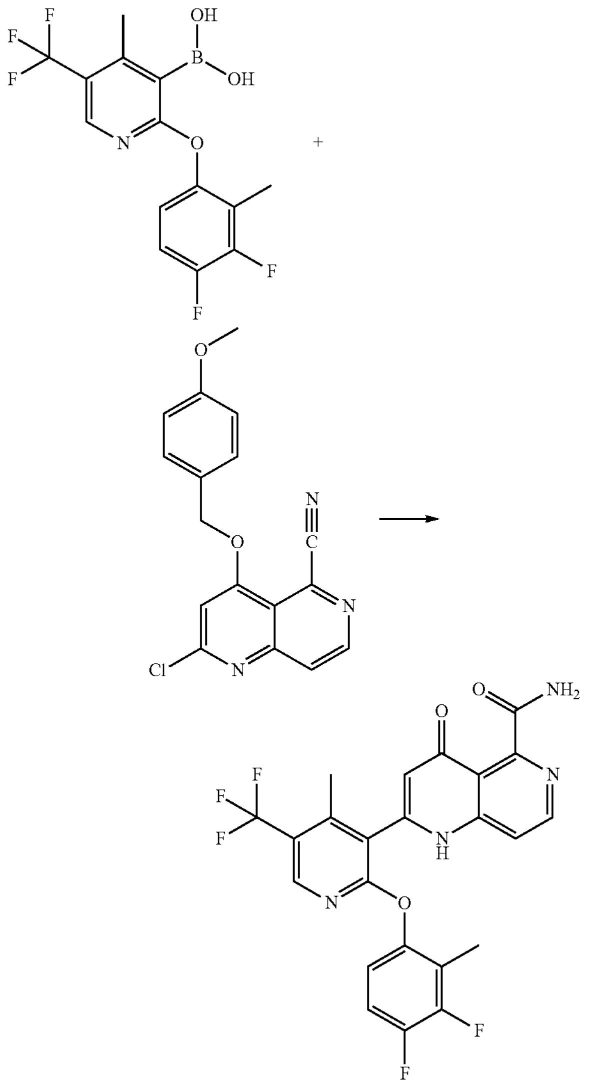

A mixture of [2-(3,4-difluoro-2-methyl-phenoxy)-4-methyl-5-(trifluoromethyl)-3-pyridyl]boronic acid (35 mg, 0.10 mmol), 2-chloro-4-[(4-methoxyphenyl)methoxy]-1,6-naphthyridine-5-carbonitrile (35 mg, 0.11 mmol) and potassium phosphate (41 mg, 0.19 mmol) in dioxane (720 μL) and water (240 μL) was flushed with nitrogen for 30 seconds then SPhos Pd G3 (11 mg, 0.014 mmol) added. The resulting mixture was flushed with nitrogen for 30 seconds, capped and stirred at room temperature for 16 h. The mixture was concentrated under reduced pressure and purified by silica gel chromatography (4 g silica, 0-70% ethyl acetate/hexanes to provide 2-[2-(3,4-difluoro-2-methyl-phenoxy)-4-methyl-5-(trifluoromethyl)-3-pyridyl]-4-[(4-methoxyphenyl) methoxy]-1,6-naphthyridine-5-carbonitrile. ESI-MS m/z calc. 592.15, found 593.3 $(M+1)^+$. The PMB-protected intermediate was dissolved in toluene (1 mL) and treated with TFA (500 µL, 6.49 mmol). The reaction mixture was stirred at 60° C. for 3 days. The mixture was concentrated under reduced pressure and purified by reverse phase HPLC (C18 column, 1-99% acetonitrile/5 mM HCl) to provide 2-[2-(3,4-difluoro-2-methyl-phenoxy)-4-methyl-5-(trifluoromethyl)-3-pyridyl]-4-oxo-1H-1,6-naphthyridine-5-carboxamide (42, 21.9 mg, 44%) as an off-white solid. ESI-MS m/z calc. 490.11, found 491.2 $(M+1)^+$. $^1H$ NMR (400 MHz, DMSO-$d_6$) δ 12.48 (s, 1H), 8.61 (s, 1H), 8.55 (d, J=5.8 Hz, 1H), 7.63 (s, 1H), 7.50 (d, J=5.9 Hz, 1H), 7.44 (s, 1H), 7.35 (q, J=9.4 Hz, 1H), 7.12-7.03 (m, 1H), 6.45 (s, 1H), 2.42 (s, 3H), 2.02 (d, J=2.0 Hz, 3H). $^{19}F$ NMR (376 MHz, DMSO-$d_6$) δ −59.29, −139.15 (d, J=22.4 Hz), −141.51 (d, J=22.2 Hz).

2-[4-tert-butyl-2-(4,4-difluorocyclohexen-1-yl)phenyl]-4-oxo-1H-1,6-naphthyridine-5-carboxamide (108)

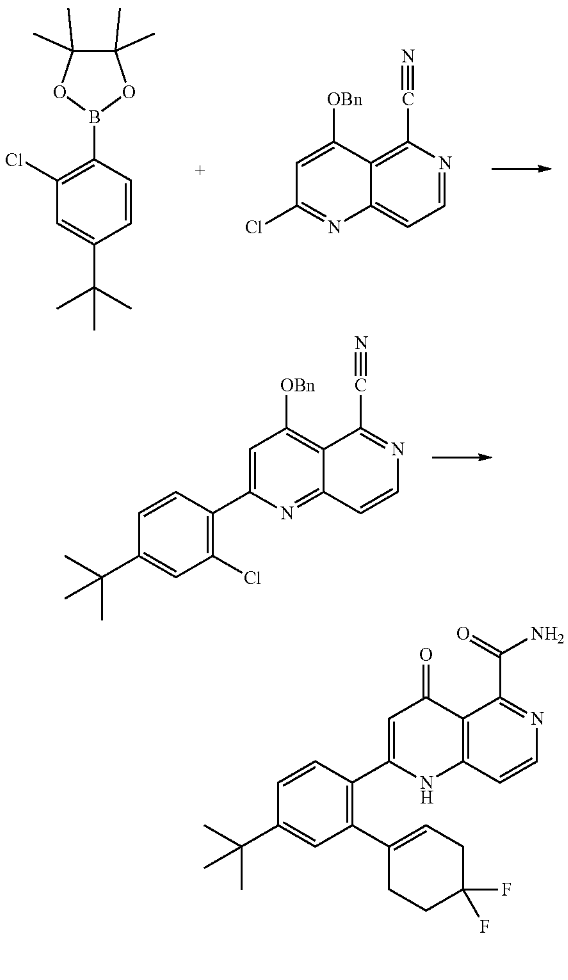

Step 1: 4-benzyloxy-2-(4-tert-butyl-2-chloro-phenyl)-1,6-naphthyridine-5-carbonitrile 4-Benzyloxy-2-(4-tert-butyl-2-chloro-phenyl)-1,6-naphthyridine-5-carbonitrile was prepared from 4-benzyloxy-2-chloro-1,6-naphthyridine-5-carbonitrile and 2-(4-tert-butyl-2-chloro-phenyl)-4,4,5,5-tetramethyl-1,3,2-dioxaborolane using a procedure analogous to that found in Intermediate B-34, step 1 using Pd(dtbpf)$Cl_2$ as the catalyst. ESI-MS m/z calc. 427.15, found 428.2 $(M+1)^+$. $^1H$ NMR (400 MHz, DMSO-$d_6$) δ 8.90 (d, J=5.7 Hz, 1H), 8.19 (d, J=5.7 Hz, 1H), 7.70 (s, 1H), 7.64 (dd, J=8.3, 2.2 Hz, 3H), 7.60-7.54 (m, 2H), 7.43 (dd, J=8.1, 6.5 Hz, 2H), 7.39-7.34 (m, 1H), 5.64 (s, 2H), 1.35 (s, 9H).

Step 2: 2-[4-tert-butyl-2-(4,4-difluorocyclohexen-1-yl)phenyl]-4-oxo-1H-1,6-naphthyridine-5-carboxamide (108)

4-Benzyloxy-2-[4-tert-butyl-2-(4,4-difluorocyclohexen-1-yl)phenyl]-1,6-naphthyridine-5-carbonitrile was prepared from 4-benzyloxy-2-(4-tert-butyl-2-chloro-phenyl)-1,6-naphthyridine-5-carbonitrile and 2-(4,4-difluorocyclohexen-1-yl)-4,4,5,5-tetramethyl-1,3,2-dioxaborolane using a procedure analogous to that found in Intermediate B-34, step 1 using Pd(dtbpf)$Cl_2$ as the catalyst. ESI-MS m/z calc. 509.23, found 510.4 $(M+1)^+$. The benzyl-protected intermediate was dissolved in toluene (2 mL) and TFA (1.6 mL) and stirred at 60° C. for 16 h with a needle air vent. The mixture was concentrated to dryness and the residue was purified by silica gel chromatography (0-20% methanol/DCM) to provide 2-[4-tert-butyl-2-(4,4-difluorocyclohexen-1-yl)phenyl]-4-oxo-1H-1,6-naphthyridine-5-carboxamide (108, 83.9 mg, 71%). ESI-MS m/z calc. 437.19, found 438.3 $(M+1)^+$. $^1H$ NMR (400 MHz, $CD_3OD$) δ 8.82 (d, J=6.0 Hz, 1H), 7.91 (d, J=6.0 Hz, 1H), 7.65-7.53 (m, 2H), 7.49 (d, J=1.7 Hz, 1H), 6.91 (s, 1H), 5.67-5.52 (m, 1H), 2.56 (t, J=14.4 Hz, 2H), 2.49-2.37 (m, 2H), 2.12-1.92 (m, 2H), 1.39 (s, 9H).

2-[4-tert-butyl-2-(cyclohexylmethyl)phenyl]-4-oxo-1H-1,6-naphthyridine-5-carboxamide (109)

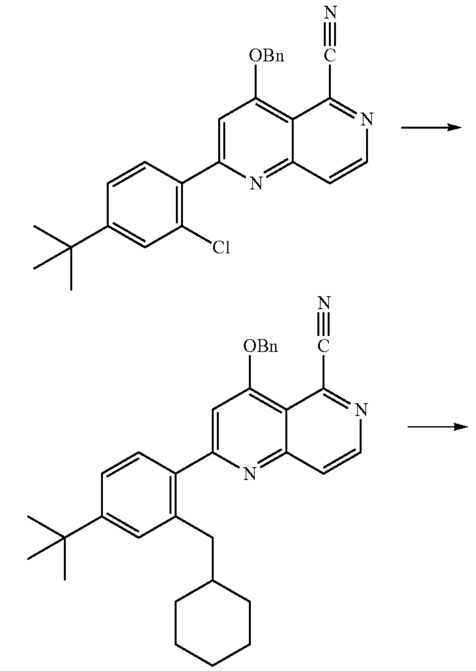

-continued

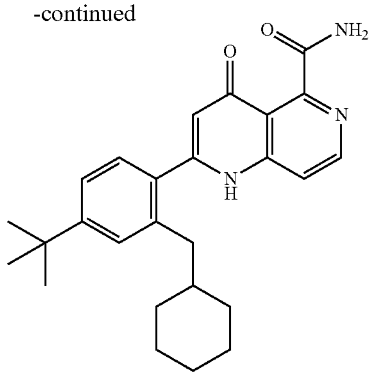

To a microwave vial charged with 4-benzyloxy-2-(4-tert-butyl-2-chloro-phenyl)-1,6-naphthyridine-5-carbonitrile (108, step 1, 30 mg, 0.070 mmol), $Pd(^tBu_3P)_2$ (11 mg, 0.022 mmol) and THF (200 μL) under nitrogen atmosphere at 0° C. was slowly added bromo(cyclohexylmethyl)zinc in THF (210 μL of 0.5 M, 0.105 mmol). The reaction mixture was gradually warmed to room temperature and stirred at this temperature for 45 min then heated to 60° C. for 3 h. The reaction mixture was quenched with 1 M HCl and the aqueous layer was extracted with ethyl acetate. The organic layer was dried over sodium sulfate, filtered and concentrated. Purification by reverse phase HPLC (C18, 30-99% $CH_3CN$/5 mM HCl) provided 4-benzyloxy-2-[4-tert-butyl-2-(cyclohexylmethyl)phenyl]-1,6-naphthyridine-5-carbonitrile (6 mg, 17%). ESI-MS m/z calc. 489.3, found 490.4 $(M+1)^+$. The benzyl-protected intermediate was dissolved in toluene (300 μL) and TFA (300 μL) and the mixture stirred at 70° C. for 16 h. The mixture was concentrated and purified by reverse phase HPLC (C18, 1-99% $CH_3CN$/5 mM HCl) to provide 2-[4-tert-butyl-2-(cyclohexylmethyl)phenyl]-4-oxo-1H-1,6-naphthyridine-5-carboxamide (109, 3.7 mg, 12%). ESI-MS m/z calc. 417.24, found 418.4 $(M+1)^+$. $^1H$ NMR (400 MHz, $CD_3OD$) δ 8.76 (s, 1H), 7.84 (s, 1H), 7.49-7.43 (m, 2H), 7.39 (d, J=7.9 Hz, 1H), 6.75 (s, 1H), 2.64 (d, J=7.1 Hz, 2H), 1.67-1.49 (m, 5H), 1.43-1.31 (m, 10H), 1.16-1.00 (m, 3H), 0.92-0.72 (m, 2H).

Example 3

2-[2-(3,4-difluoro-2-methyl-phenoxy)-3-quinolyl]-1H-quinolin-4-one (148)

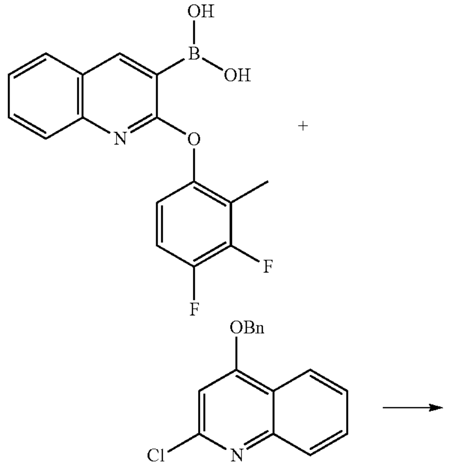

-continued

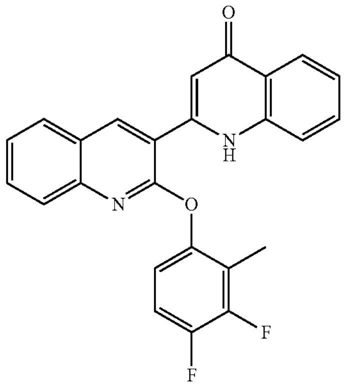

A mixture of [2-(3,4-difluoro-2-methyl-phenoxy)-3-quinolyl]boronic acid (50 mg, 0.16 mmol), 4-benzyloxy-2-chloro-quinoline (43 mg, 0.16 mmol), potassium carbonate (44 mg, 0.32 mmol), XPhos Pd G3 (4 mg, 0.005 mmol) and XPhos (2.3 mg, 0.0048 mmol) in dioxane (500.0 μL)/ethanol (500.0 μL)/water (100.0 μL) was degassed with nitrogen for 2 min. The reaction mixture was stirred for 30 min at 120° C. under microwave irradiation. The mixture was filtered and purified by reverse phase HPLC (10-99% acetonitrile/5 mM HCl over 15 min) to provide 2-[2-(3,4-difluoro-2-methyl-phenoxy)-3-quinolyl]-1H-quinolin-4-one (27.4 mg, 42%). ESI-MS m/z calc. 414.12, found 415.2 $(M+1)^+$. $^1H$ NMR (400 MHz, DMSO-$d_6$) δ 12.19 (s, 1H), 8.79 (s, 1H), 8.16 (dd, J=8.1, 1.4 Hz, 1H), 8.09 (dd, J=8.1, 1.4 Hz, 1H), 7.79-7.64 (m, 4H), 7.62-7.56 (m, 1H), 7.47-7.33 (m, 2H), 7.33-7.16 (m, 1H), 6.47 (s, 1H), 2.05 (d, J=2.1 Hz, 3H).

2-[2-(3,4-difluoro-2-methyl-phenoxy)-3-quinolyl]-4-oxo-1H-1,6-naphthyridine-5-carboxamide (149)

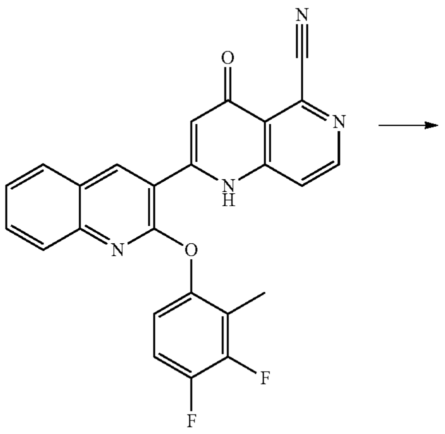

-continued

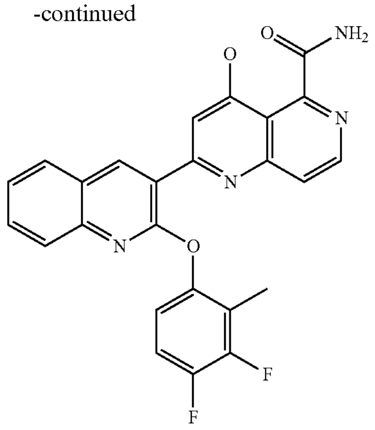

2-[2-(3,4-Difluoro-2-methyl-phenoxy)-3-quinolyl]-4-oxo-1H-1,6-naphthyridine-5-carbonitrile (19, 45.9 mg) and ethanol (2.5 mL) was added to a pressure vial. KOH (775 μL of 10% w/v, 1.381 mmol) and $H_2O_2$ (315 μL of 30% w/v, 2.78 mmol) were added to the reaction suspension. The reaction was stirred at 40° C. for 18 h, then cooled to room temperature and concentrated. Purification by reverse phase HPLC (10-99% acetonitrile/5 mM HCl over 25 min) provided 2-[2-(3,4-difluoro-2-methyl-phenoxy)-3-quinolyl]-4-oxo-1H-1,6-naphthyridine-5-carboxamide (149, 24.5 mg, 17%) as a yellow solid. $^1$H NMR (400 MHz, $CD_3OD$) δ 8.68 (s, 1H), 8.60 (d, J=6.0 Hz, 1H), 8.05-7.97 (m, 1H), 7.79-7.68 (m, 2H), 7.65 (d, J=5.9 Hz, 1H), 7.60-7.52 (m, 1H), 7.19 (q, J=9.3 Hz, 1H), 7.13-7.05 (m, 1H), 6.80 (s, 1H), 2.08 (d, J=2.2 Hz, 3H). ESI-MS m/z calc. 458.12, found 459.2 $(M+1)^+$.

2-[2-(3,4-difluoro-2-methyl-phenoxy)-3-quinolyl]-5-methyl-1H-1,6-naphthyridin-4-one (13)

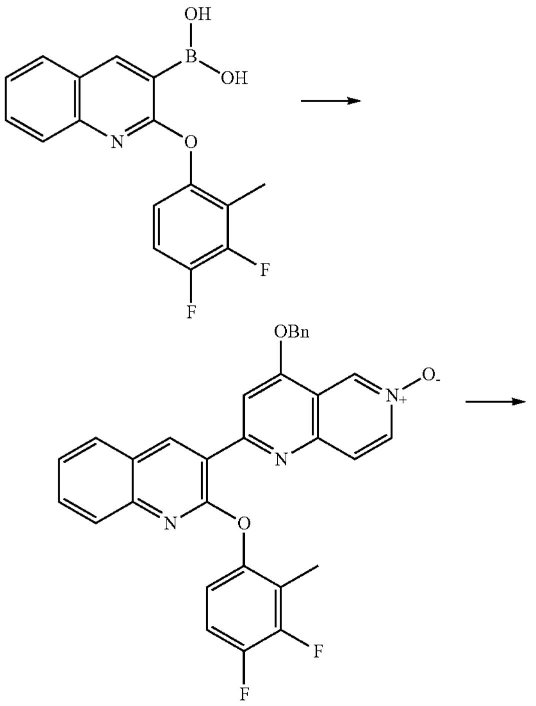

-continued

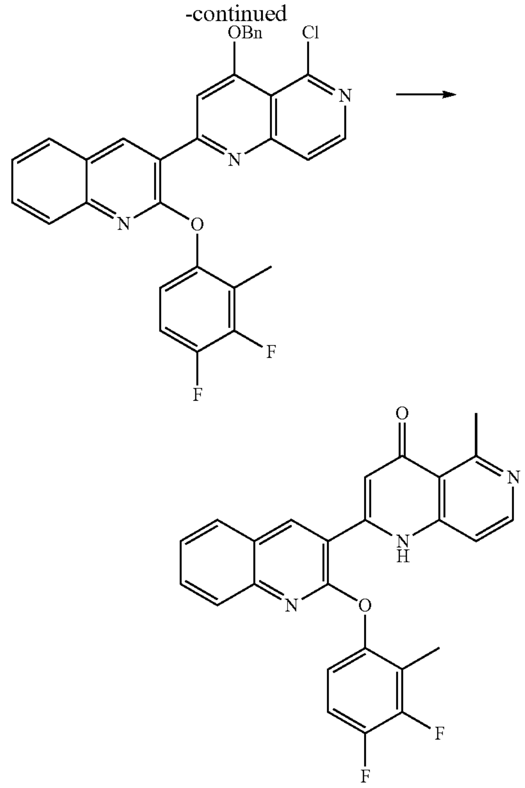

Step 1: 4-benzyloxy-2-[2-(3,4-difluoro-2-methyl-phenoxy)-3-quinolyl]-6-oxido-1,6-naphthyridin-6-ium A dioxane (5 mL) mixture of [2-(3,4-difluoro-2-methyl-phenoxy)-3-quinolyl]boronic acid (105 mg, 0.333 mmol), 4-benzyloxy-2-chloro-6-oxido-1,6-naphthyridin-6-ium (95 mg, 0.33 mmol), sodium bicarbonate (123 mg, 1.46 mmol), and water (0.5 mL) was treated with $Pd(PPh_3)_4$ (59 mg, 0.051 mmol) and the mixture was sparged with nitrogen for 3 min and then microwaved at 65° C. for 105 min. The reaction was filtered over a bed of Celite® and the filtrate was diluted with ethyl acetate (15 mL) and washed with water (2×10 mL), brine (5 mL), dried with sodium sulfate, filtered, and concentrated in vacuo. Purification by silica gel chromatography (12 g silica, 0-5% methanol/DCM gradient over 25 min) provided 4-benzyloxy-2-[2-(3,4-difluoro-2-methyl-phenoxy)-3-quinolyl]-6-oxido-1,6-naphthyridin-6-ium (100 mg, 55%). $^1$H NMR (400 MHz, $CD_3OD$) δ 9.17 (d, J=2.1 Hz, 1H), 8.91 (s, 1H), 8.48 (dd, J=7.3, 2.2 Hz, 1H), 8.12 (d, J=7.3 Hz, 1H), 8.01 (d, J=8.1 Hz, 1H), 7.94 (s, 1H), 7.75-7.64 (m, 2H), 7.53 (ddd, 1H), 7.46 (dd, J=6.5, 2.9 Hz, 2H), 7.27-7.15 (m, 4H), 7.02 (ddd, J=9.1, 4.2, 2.0 Hz, 1H), 5.56 (s, 2H), 1.99 (d, J=2.2 Hz, 3H). ESI-MS m/z calc. 521.16, found 522.2 $(M+1)^+$.

Step 2: 4-benzyloxy-5-chloro-2-[2-(3,4-difluoro-2-methyl-phenoxy)-3-quinolyl]-1,6-naphthyridine 4-Benzyloxy-2-[2-(3,4-difluoro-2-methyl-phenoxy)-3-quinolyl]-6-oxido-1,6-naphthyridin-6-ium (100 mg, 0.192 mmol) was treated with $POCl_3$ (400 μL, 4.29 mmol) and stirred at 50° C. for 2 h and then concentrated in vacuo. The crude residue was taken up in DCM (20 mL) and washed with saturated aqueous sodium bicarbonate (2×20 mL), water (10 mL), dried over sodium sulfate, filtered, and concentrated in vacuo. Purification by silica gel chromatography (0-5% methanol/DCM) provided 4-benzyloxy-5-chloro-2-[2-(3,4-difluoro-2-methyl-phenoxy)-3-quinolyl]-1,6-naphthyridine (85.9 mg, 83%). $^1$H NMR (400 MHz, $CDCl_3$) δ 9.06 (s, 1H), 8.54 (d, J=5.8 Hz, 1H), 7.96 (d, J=8.1 Hz, 1H), 7.86 (s, 1H), 7.73-7.63 (m, 2H), 7.53-7.42 (m, 3H), 7.31-7.27 (m, 3H), 7.10 (q, J=9.1 Hz, 1H), 6.93-6.85 (m, 1H), 5.47 (s, 2H), 2.05 (d, J=2.3 Hz, 3H).

Step 3: 4-benzyloxy-2-[2-(3,4-difluoro-2-methyl-phenoxy)-3-quinolyl]-5-methyl-1,6-naphthyridine and 2-[2-(3,4-difluoro-2-methyl-phenoxy)-3-quinolyl]-5-methyl-1H-1,6-naphthyridin-4-one (13)

A mixture of 4-benzyloxy-5-chloro-2-[2-(3,4-difluoro-2-methyl-phenoxy)-3-quinolyl]-1,6-naphthyridine (25 mg, 0.046 mmol), trimethylalumane (9 μL, 0.09 mmol) and $Pd(PPh_3)_4$ (10.8 mg, 0.0094 mmol) was dissolved in dry 1,4-dioxane (0.5 mL) and refluxed for 2 h under nitrogen atmosphere. The mixture was cooled to room temperature, diluted with ethyl acetate and washed with brine, dried over sodium sulfate, filtered and concentrated. Purification by HPLC (C18, 1-99% $CH_3CN$/5 mM HCl) afforded 4-benzyloxy-2-[2-(3,4-difluoro-2-methyl-phenoxy)-3-quinolyl]-5-methyl-1,6-naphthyridine. The protected intermediate was combined with Pd/C (0.5 mg, 0.005 mmol) in a septa-capped vial and purged with nitrogen followed by the addition of ethyl acetate (0.5 mL) by syringe. The reaction mixture was then purged with hydrogen gas and stirred at room temperature for 30 min. The reaction was filtered and concentrated to provide 2-[2-(3,4-difluoro-2-methyl-phenoxy)-3-quinolyl]-5-methyl-1H-1,6-naphthyridin-4-one (13, 18.2 mg, 92%) as a white solid. ESI-MS m/z calc. 429.42, found 430.01 $(M+1)^+$. $^1$H NMR (400 MHz, DMSO-$d_6$) δ 13.50 (s, 1H), 8.83 (s, 1H), 8.55 (d, J=6.8 Hz, 1H), 8.09 (d, J=8.0 Hz, 1H), 7.98 (d, J=6.8 Hz, 1H), 7.80-7.74 (m, 1H), 7.68 (d, J=8.4 Hz, 1H), 7.60 (t, J=7.5 Hz, 1H), 7.41-7.36 (m, 2H), 6.77 (s, 1H), 3.15 (s, 3H), 2.04 (s, 3H).

methyl 2-[2-(3,4-difluoro-2-methyl-phenoxy)-3-quinolyl]-4-oxo-1H-1,6-naphthyridine-5-carboxylate (150)

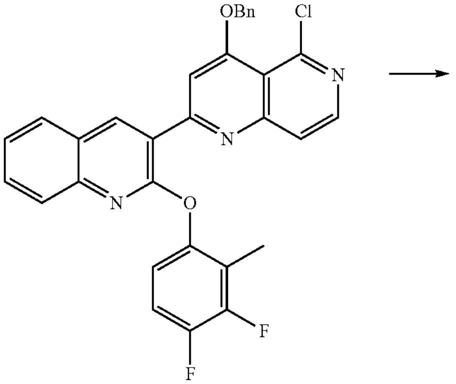

-continued

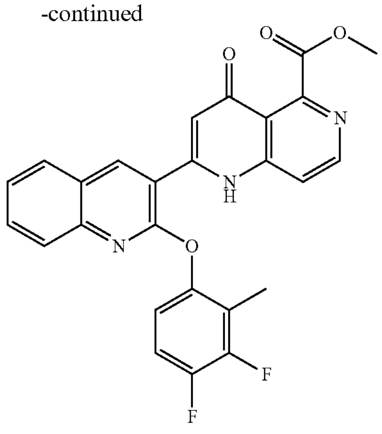

A mixture of 4-benzyloxy-5-chloro-2-[2-(3,4-difluoro-2-methyl-phenoxy)-3-quinolyl]-1,6-naphthyridine (synthesis of compound 13, step 2, 10 mg, 0.019 mmol), Pd(dppf)$Cl_2$·DCM (3.2 mg, 0.0039 mmol) and DIPEA (20 μL, 0.12 mmol) in methanol (3 mL) was directly added to a stainless steel high pressure reaction vessel and the system was evacuated (vacuum) then pressurized with carbon monoxide gas. This was repeated twice more. The sealed vessel was heated to 90° C. at 100 psi carbon monoxide for 16 h. The reaction was filtered over a Celite® bed and concentrated in vacuo to provide methyl 2-[2-(3,4-difluoro-2-methyl-phenoxy)-3-quinolyl]-4-oxo-1H-1,6-naphthyridine-5-carboxylate (150) (3.6 mg, 41%). ESI-MS m/z calc. 473.12, found 474.2 $(M+1)^+$.

Example 4

Pyridone Synthesis Through Amide Ring Closure

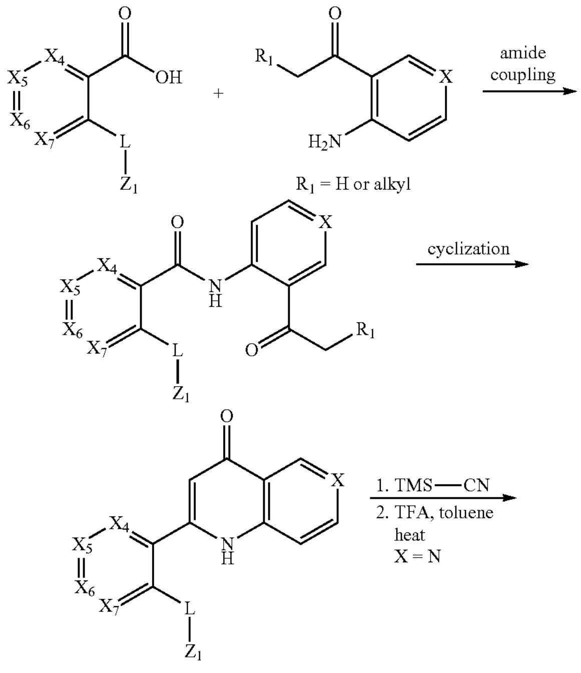

-continued

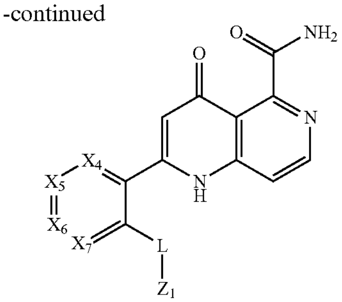

2-[2-(3,4-difluoro-2-methoxy-phenoxy)-5-fluoro-4-(trifluoromethyl)phenyl]-1H-1,6-naphthyridin-4-one (151)

Step 1: tert-butyl 2,5-difluoro-4-(trifluoromethyl)benzoate

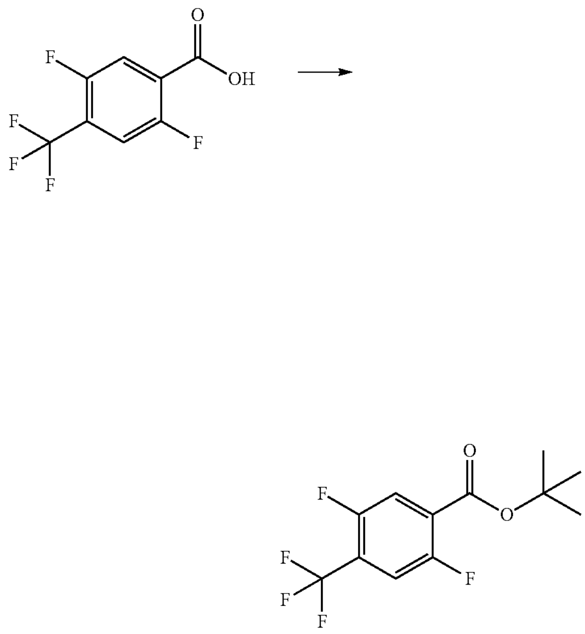

A solution of DMAP (3.0 g, 24.6 mmol), 2,5-difluoro-4-(trifluoromethyl)benzoic acid (56 g, 248 mmol) and $Boc_2O$ (90 mL, 392 mmol) were dissolved in DCM (300 mL)/tBuOH (150 mL) and the mixture was stirred at ambient temperature for 1 h then heated to 40° C. for 72 h. The mixture was concentrated in vacuo and the residue was partitioned between ethyl acetate (300 mL), water (300 mL) and saturated aqueous sodium bicarbonate (100 mL). The organic layer was separated and washed with citric acid (0.5 M, 100 mL), dried and filtered using Whatman 1PS hydrophobic phase separator filter paper. The filtrate was concentrated in vacuo to give tert-butyl 2,5-difluoro-4-(trifluoromethyl)benzoate (69.8 g, 100%). $^1$H NMR (400 MHz, DMSO-$d_6$) δ 7.91 (ddd, J=10.9, 5.7, 3.5 Hz, 2H), 1.55 (s, 9H). $^{19}$F NMR (376 MHz, DMSO-$d_6$) δ −58.91--63.69 (m), −114.33 (d, J=19.5 Hz), −120.29 (dq, J=20.2, 13.4 Hz). $^{19}$F NMR (376 MHz, DMSO-$d_6$) δ −58.91--63.69 (m), −114.33 (d, J=19.5 Hz), −120.29 (dq, J=20.2, 13.4 Hz).

Step 2: tert-butyl 2-(3,4-difluoro-2-methoxy-phenoxy)-5-fluoro-4-(trifluoromethyl)benzoate

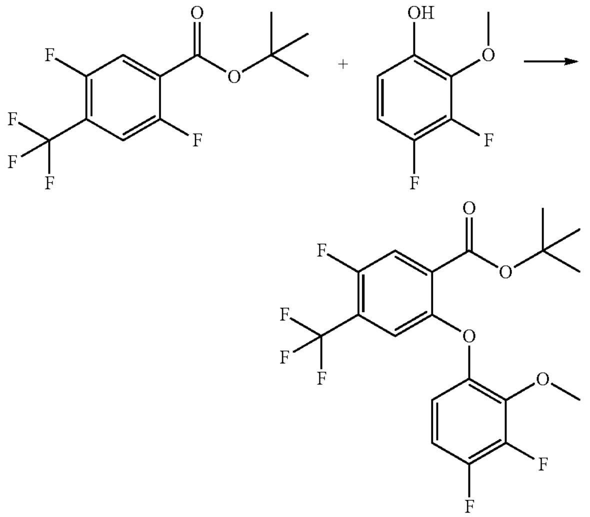

tert-Butyl 2,5-difluoro-4-(trifluoromethyl)benzoate (69.8 g, 247 mmol), 3,4-difluoro-2-methoxy-phenol (55 g, 344 mmol) and cesium carbonate (140 g, 430 mmol) in 2-MeTHF (500 mL) were heated at 100° C. for 66 h. The reaction mixture was cooled and then concentrated in vacuo and the residue was partitioned between TBME (300 mL) and water (200 mL). The phases were separated and the organic phase was washed twice with 1 M aqueous NaOH (200 mL) and brine (200 mL), dried and filtered using Whatman 1PS hydrophobic phase separator filter paper. The filtrate was concentrated in vacuo to give tert-butyl 2-(3,4-difluoro-2-methoxy-phenoxy)-5-fluoro-4-(trifluoromethyl)benzoate (80.7 g, 63%). $^1$H NMR (400 MHz, DMSO-$d_6$) δ 7.89 (d, J=10.3 Hz, 1H), 7.41 (d, J=5.8 Hz, 1H), 7.20-7.08 (m, 1H), 6.77 (ddd, J=9.4, 5.0, 2.4 Hz, 1H), 3.91 (d, J=1.0 Hz, 3H), 1.42 (s, 9H). δ $^{19}$F NMR (376 MHz, DMSO-$d_6$) δ −57.94--64.66 (m), −118.84--122.58 (m), −141.71 (d, J=21.9 Hz), −152.92 (d, J=21.9 Hz). δ $^{19}$F NMR (376 MHz, DMSO-$d_6$) δ −57.94--64.66 (m), −118.84--122.58 (m), −141.71 (d, J=21.9 Hz), −152.92 (d, J=21.9 Hz).

Step 3: 2-(3,4-difluoro-2-methoxy-phenoxy)-5-fluoro-4-(trifluoromethyl)benzoic acid

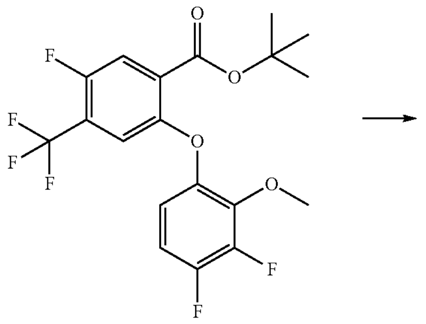

-continued

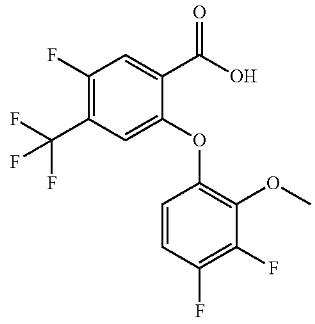

To a solution of tert-butyl 2-(3,4-difluoro-2-methoxy-phenoxy)-5-fluoro-4-(trifluoromethyl)benzoate (80.70 g, 154.8 mmol) in DCM (400 mL) was added TFA (120 mL, 1.56 mol) slowly and the reaction mixture was stirred at ambient temperature overnight, then concentrated in vacuo. The residue was partitioned between MTBE (200 mL) and water (100 mL). The phases were separated and the organic phase was washed with water (2×100 mL). The organic phase was dried and filtered using Whatman 1PS hydrophobic phase separator filter paper and filtrate concentrated in vacuo yielding a red oil. The oil was re-dissolved in 1:3 TBME/heptane (200 mL), stirred for 30 min and filtered. The solid was washed with heptane and dried at 40° C. in vacuo overnight to provide 2-(3,4-difluoro-2-methoxy-phenoxy)-5-fluoro-4-(trifluoromethyl)benzoic acid (43.7241 g, 77%). 6 $^1$H NMR (400 MHz, DMSO-$d_6$) δ 13.77 (s, 1H), 7.92 (d, J=10.5 Hz, 1H), 7.35 (d, J=5.8 Hz, 1H), 7.17 (td, J=9.8, 8.5 Hz, 1H), 6.83 (ddd, J=9.4, 5.0, 2.4 Hz, 1H), 3.90 (d, J=1.0 Hz, 3H). δ $^{19}$F NMR (376 MHz, DMSO-$d_6$) δ −60.49 (d, J=13.4 Hz), −121.36 (q, J=13.5 Hz), −141.37 (d, J=22.8 Hz), −152.76 (d, J=22.1 Hz). $^{19}$F NMR (376 MHz, DMSO-$d_6$) δ −60.49 (d, J=13.4 Hz), −121.36 (q, J=13.5 Hz), −141.37 (d, J=22.8 Hz), −152.76 (d, J=22.1 Hz). ESI-MS m/z calc. 366.03, found 365.0 $(M-1)^-$.

Step 4: N-(3-acetyl-4-pyridyl)-2-(3,4-difluoro-2-methoxy-phenoxy)-5-fluoro-4-(trifluoromethyl)benzamide

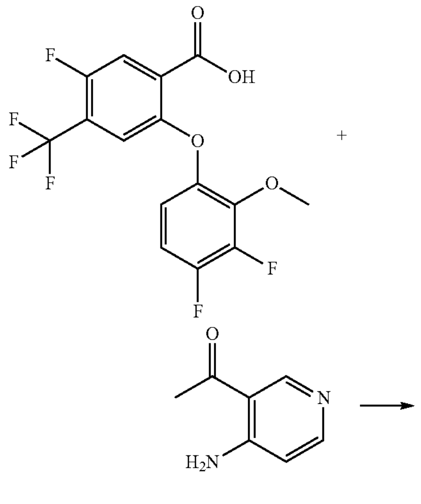

-continued

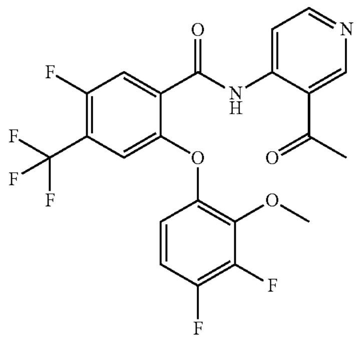

To a solution of 2-(3,4-difluoro-2-methoxy-phenoxy)-5-fluoro-4-(trifluoromethyl)benzoic acid (50 g, 131 mmol) in dichloromethane (500 mL) was added DMF (667 mg, 0.707 mL, 9.13 mmol). Oxalyl chloride (33 g, 22.7 mL, 260 mmol) was added drop-wise and the reaction mixture stirred at room temperature for 2 h. The resultant solution was concentrated, treated with toluene (500 mL) and concentrated further. The resultant oil was dissolved in dichloromethane (500 mL) and added portionwise to a mixture of 1-(4-amino-3-pyridyl)ethanone (18.6 g, 136.6 mmol) and triethylamine (22 g, 30.3 mL, 217 mmol) in dichloromethane (750 mL). After stirring for 2 h the mixture was washed with 1 M aqueous citric acid solution (300 mL) and saturated aqueous sodium bicarbonate (500 mL). The organic layer was separated, dried over sodium sulfate, concentrated to 500 mL and treated with heptane (1 L). The mixture was concentrated to 500 mL and the solid filtered, washed with heptane (250 mL) and air dried to give N-(3-acetyl-4-pyridyl)-2-(3,4-difluoro-2-methoxy-phenoxy)-5-fluoro-4-(trifluoromethyl)benzamide (51.2 g, 78%) as a light brown solid. ESI-MS m/z calc. 484.09, found 483.13 $(M-1)^-$. $^1$H NMR (400 MHz, $CDCl_3$) δ 9.11 (s, 1H), 8.86 (d, J=6.0 Hz, 1H), 8.73-8.68 (m, 1H), 7.97 (d, J=10.5 Hz, 1H), 7.25 (s, 1H), 7.12-6.87 (m, 3H), 3.94-3.86 (m, 3H), 2.65-2.62 (m, 3H).

Step 5: 2-[2-(3,4-difluoro-2-methoxy-phenoxy)-5-fluoro-4-(trifluoromethyl)phenyl]-1H-1,6-naphthyridin-4-one (151)

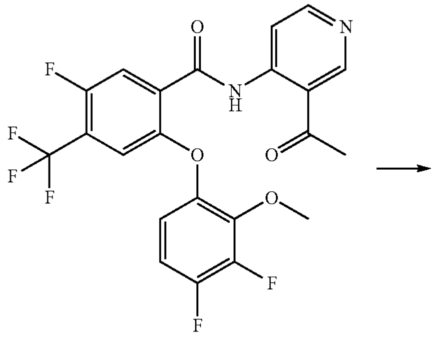

-continued

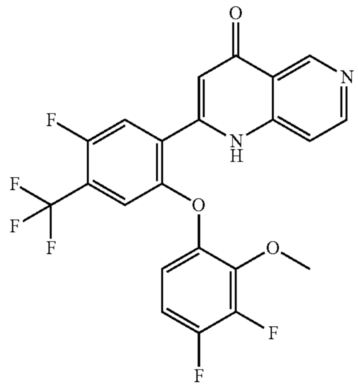

N-(3-Acetyl-4-pyridyl)-2-(3,4-difluoro-2-methoxy-phenoxy)-5-fluoro-4-(trifluoromethyl)benzamide (5.0 g, 9.1 mmol) was dissolved in 2-MeTHF (45 mL) and NMP (5 mL). This solution was heated at 40° C. and potassium 2-methylpropan-2-olate (2.0341 g, 2.2551 mL, 18.127 mmol) was added portionwise (4 additions over 15 min). The reaction was stirred at 40° C. for 1 h. The reaction was cooled back to room temperature before adding saturated aqueous $NH_4Cl$ (50 mL). The layers were separated and the aqueous phase was back extracted using 2-MeTHF. The combined organic extracts were washed with water (2×50 mL), brine (50 mL), dried over sodium sulfate, filtered and evaporated under reduce pressure. The residue was treated with MTBE (50 mL) and heated at reflux for 15 min. The resulting suspension was cooled back to room temperature and filtered. The filter cake was rinsed with MTBE (10 mL) to yield 2-[2-(3,4-difluoro-2-methoxy-phenoxy)-5-fluoro-4-(trifluoromethyl)phenyl]-1H-1,6-naphthyridin-4-one (151) (3.01 g, 70%) as a beige solid $^1$H NMR (400 MHz, DMSO-$d_6$) δ 12.28 (br s, 1H), 9.21 (s, 1H), 8.63 (d, J=5.9 Hz, 1H), 8.02 (d, J=10.5 Hz, 1H), 7.50 (d, J=5.9 Hz, 1H), 7.34 (d, J=5.9 Hz, 1H), 7.19 (q, J=9.3 Hz, 1H), 7.03 (ddd, J=7.0, 5.0, 2.4 Hz, 1H), 6.43 (br s, 1H), 3.77 (s, 3H). ESI-MS m/z calc. 466.08, found 467.0 $(M+1)^+$.

2-[2-(3,4-difluoro-2-methoxy-phenoxy)-5-fluoro-4-(trifluoromethyl)phenyl]-4-oxo-1H-1,6-naphthyridine-5-carboxamide (152)

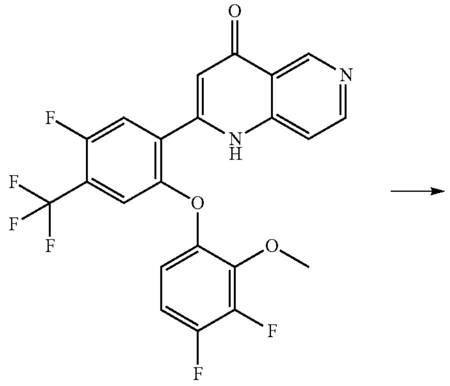

-continued

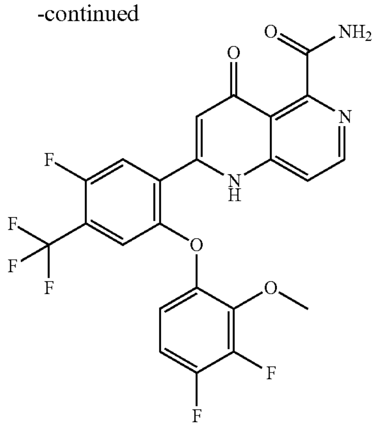

To a solution of 2-[2-(3,4-difluoro-2-methoxy-phenoxy)-5-fluoro-4-(trifluoromethyl)phenyl]-1H-1,6-naphthyridin-4-one (151, 3.0 g, 5.6 mmol) in formamide (30 mL) was added potassium persulfate (3.5 g, 12.9 mmol) and the mixture was heated to 70° C. After 24 h, the reaction mixture was quenched in an aqueous sodium bisulfite solution (10% w/w, 100 mL). The mixture was then filtered and the solid recovered in MTBE (50 mL), filtered on silica (10 g) and washed with MTBE (50 mL). Evaporation afforded 2-[2-(3,4-difluoro-2-methoxy-phenoxy)-5-fluoro-4-(trifluoromethyl)phenyl]-4-oxo-1H-1,6-naphthyridine-5-carboxamide (142, 2.05 g, 60%) as a beige solid. $^1$H NMR (400 MHz, DMSO-$d_6$) δ 12.21 (br s, 1H), 8.52 (br d, J=5.4 Hz, 1H), 8.03 (br d, J=10.0 Hz, 1H), 7.58-7.45 (m, 2H), 7.31 (br d, J=5.9 Hz, 2H), 7.25-7.16 (m, 1H), 7.08-7.00 (m, 1H), 6.38 (s, 1H), 3.78 (s, 3H). ESI-MS m/z calc. 509.08, found 510.0 $(M+1)^+$.

Example 5

2-[3-(4,4-difluoroazepan-1-yl)-6-(trifluoromethyl)-2-pyridyl]-3H-quinazolin-4-one (153)

Step 1: 3-bromo-N-(2-carbamoylphenyl)-6-(trifluoromethyl)pyridine-2-carboxamide

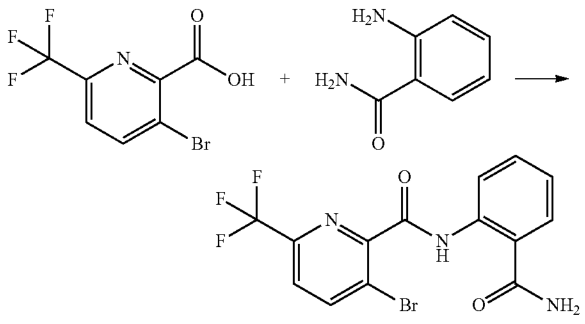

To a mixture of 3-bromo-6-(trifluoromethyl)pyridine-2-carboxylic acid (345 mg, 1.28 mmol), 2-aminobenzamide (183 mg, 1.34 mmol) and DIPEA (0.65 mL, 3.7 mmol) in DMF (3 mL) was added BOP (623 mg, 1.41 mmol) and the reaction was stirred at 70° C. for 4 h. The mixture was partitioned between water (30 mL) and ethyl acetate (30 mL) and the layers separated. The aqueous phase was extracted with additional ethyl acetate (2×30 mL) and the combined layers dried over sodium sulfate, filtered and concentrated under reduced pressure. Purification using silica gel chromatography (80 g silica, 0-50% ethyl acetate/heptanes) provided 3-bromo-N-(2-carbamoylphenyl)-6-(trifluoromethyl)pyridine-2-carboxamide (213 mg, 39%) as a white solid. ESI-MS m/z calc. 386.98, found 388.1 $(M+1)^+$. $^1H$ NMR (400 MHz, DMSO-$d_6$): 13.09 (s, 1H), 8.68 (d, J=8.2 Hz, 1H), 8.61 (d, J=8.4 Hz, 1H), 8.31 (br. s, 1H), 8.04 (d, J=8.2 Hz, 1H), 7.88 (d, J=8.1 Hz, 1H), 7.83 (br. s, 1H), 7.60 (t, J=7.5 Hz, 1H), 7.23 (t, J=7.5 Hz, 1H).

Step 2: 2-[3-bromo-6-(trifluoromethyl)-2-pyridyl]-3H-quinazolin-4-one

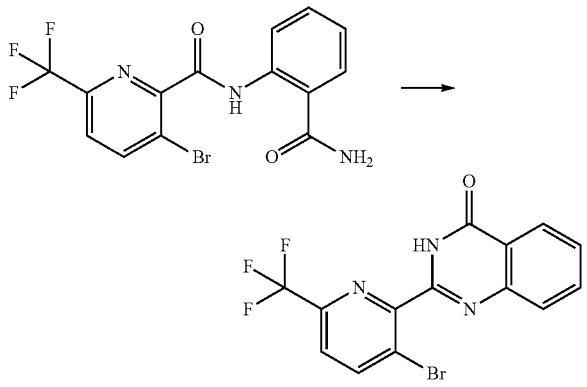

To a solution of 3-bromo-N-(2-carbamoylphenyl)-6-(trifluoromethyl)pyridine-2-carboxamide (244 mg, 0.592 mmol) in THF (11 mL) was added NaOH (15 mL of 1 M, 15 mmol) and the reaction was stirred at room temperature for 7 h. The mixture was diluted with water (50 mL) and extracted with ethyl acetate (3×20 mL). The combined organic layers were washed with brine, dried over sodium sulfate, filtered and concentrated under reduced pressure. The crude was adsorbed on silica gel and purified using silica gel chromatography (40 g silica, 0-30% ethyl acetate/heptanes) to afford 2-[3-bromo-6-(trifluoromethyl)-2-pyridyl]-3H-quinazolin-4-one (120 mg, 52%) as a white solid. ESI-MS m/z calc. 368.97, found 370.0 $(M+1)^+$. $^1H$ NMR (400 MHz, DMSO-$d_6$): 12.83 (s, 1H), 8.65 (d, J=8.3 Hz, 1H), 8.22 (d, J=8.3 Hz, 1H), 8.09 (d, J=8.8 Hz, 1H), 7.95-7.88 (m, 1H), 7.80-7.74 (m, 1H), 7.67-7.60 (m, 1H).

Step 3: 2-[3-(4,4-difluoroazepan-1-yl)-6-(trifluoromethyl)-2-pyridyl]-3H-quinazolin-4-one

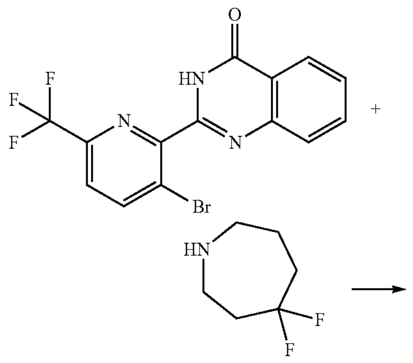

-continued

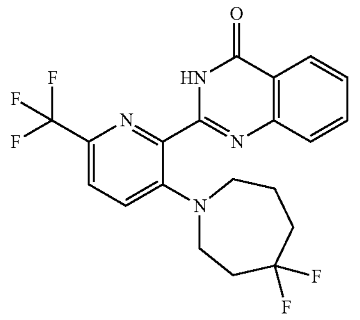

A solution of 2-[3-bromo-6-(trifluoromethyl)-2-pyridyl]-3H-quinazolin-4-one (120 mg, 0.308 mmol), 4,4-difluoroazepane hydrochloride (70 mg, 0.41 mmol), cesium carbonate (230 mg, 0.706 mmol) in toluene (5 mL) was bubbled with nitrogen for 5 min then rac-BINAP (32 mg, 0.05 mmol) and tris(dibenzylideneacetone)dipalladium (0) (36 mg, 0.039 mmol) added. The mixture was bubbled with nitrogen for another 5 min then stirred at 100° C. for 18 h. The crude was adsorbed on silica gel and purified using silica gel chromatography (40 g silica, 0-30% ethyl acetate/heptanes) to afford 2-[3-(4,4-difluoroazepan-1-yl)-6-(trifluoromethyl)-2-pyridyl]-3H-quinazolin-4-one (37.14 mg, 28%) as a light yellow solid. ESI-MS m/z calc. 424.13, found 425.2 $(M+1)^+$. $^1H$ NMR (400 MHz, $CDCl_3$) δ 10.49 (br s, 1H), 8.39 (d, J=7.8 Hz, 1H), 7.88-7.74 (m, 2H), 7.66 (d, J=8.8 Hz, 1H), 7.60-7.50 (m, 2H), 3.69-3.59 (m, 2H), 3.55-3.46 (m, 2H), 2.47-2.30 (m, 2H), 2.25-2.10 (m, 2H), 2.01-1.93 (m, 2H).

The following examples were synthesized in an analogous fashion as Compound 151 and Compound 152, wherein the appropriately substituted phenol and appropriately substituted benzoic ester were reacted as shown in Compound 151, step 2. Subsequent conversion of the ester to the carboxylic acid and amide formation with appropriately substituted 1-(4-amino-3-pyridyl)ethenone, 1-(4-amino-3-pyridyl)propan-1-one or the appropriately substituted 1-(2-amino-phenyl)ethenone provided the key amide intermediate. Cyclization as shown in Compound 151, Step 5 and optional installation of the carboxamide as shown in Compound 152 provided the compounds below.

TABLE 3

| Compound No. | Compound Name | MW & Found [M + H]$^+$ | NMR (shifts in ppm) |
|---|---|---|---|
| 154 | 2-[2-fluoro-6-(4-fluoro-2-methoxy-phenoxy)-3-(trifluoromethyl)phenyl]-4-oxo-1H-1,6-naphthyridine-5-carboxamide | 491.37; 492.08 | $^1H$ NMR (400 MHz, $CDCl_3$) δ 8.96 (br s, 1H), 8.64 (d, J = 6.0 Hz, 1H), 8.17 (d, J = 5.5 Hz, 1H), 7.49 (t, J = 8.2 Hz, 1H), 7.35 (s, 1H), 7.02 (dd, J = 8.8, 6.0 Hz, 1H), 6.70 (dd, J = 9.8, 3.0 Hz, 1H), 6.63 (td, J = 8.2, 2.7 Hz, 1H), 6.50 (d, J = 8.7 Hz, 1H), 6.16 (br s, 1H), 3.77 (s, 3H). |

TABLE 3-continued

| Compound No. | Compound Name | MW & Found [M + H]+ | NMR (shifts in ppm) |
|---|---|---|---|
| 155 | 2-[5-chloro-2-(4-fluoro-2-methyl-phenoxy)-4-(trifluoromethyl)phenyl]-4-oxo-1H-1,6-naphthyridine-5-carboxamide | 491.82; 492.2 | $^1$H NMR (500 MHz, DMSO-$d_6$) δ 12.16 (s, 1H), 8.51 (s, 1H), 8.13 (s, 1H), 7.47 (d, J = 6.2 Hz, 2H), 7.27 (s, 1H), 7.24-7.18 (m, 1H), 7.13 (s, 1H), 7.11 (d, J = 6.9 Hz, 1H), 7.08 (d, J = 2.9 Hz, 1H), 6.39 (s, 1H), 2.14 (s, 3H). |
| 156 | 2-[2-(3,4-difluoro-2-methyl-phenoxy)-5-fluoro-4-(trifluoromethyl)phenyl]-4-oxo-1H-1,6-naphthyridine-5-carboxamide | 493.36; 494.2 | $^1$H NMR (400 MHz, DMSO-$d_6$) δ 12.18 (s, 1H), 8.51 (d, J = 5.8 Hz, 1H), 8.02 (d, J = 10.5 Hz, 1H), 7.50 (s, 1H), 7.46 (d, J = 5.9 Hz, 1H), 7.39 (d, J = 5.9 Hz, 1H), 7.32-7.19 (m, 2H), 6.81 (d, J = 9.7 Hz, 1H), 6.33 (s, 1H), 2.13 (d, J = 2.0 Hz, 3H). |
| 157 | 2-[2-(3,4-difluoro-2-methoxy-phenoxy)-5-fluoro-4-(trifluoromethyl)phenyl]-3-methyl-1H-1,6-naphthyridin-4-one | 480.36; 481.6 | $^1$H NMR (500 MHz, DMSO-$d_6$) δ 9.22 (d, J = 0.8 Hz, 1H), 8.57-8.45 (m, 1H), 7.91 (d, J = 10.3 Hz, 1H), 7.36 (d, J = 5.9 Hz, 1H), 7.34 (d, J = 5.9 Hz, 1H), 7.14 (td, J = 9.8, 8.5 Hz, 1H), 6.93 (ddd, J = 9.4, 5.0, 2.2 Hz, 1H), 3.72 (d, J = 1.2 Hz, 3H), 1.86 (s, 3H). |
| 158 | 2-[2-(3,4-difluoro-2-methoxy-phenoxy)-5-fluoro-4-(trifluoromethyl)phenyl]-3-methyl-4-oxo-1H-1,6-naphthyridine-5-carboxamide | 523.38; 524.6 | $^1$H NMR (500 MHz, DMSO-$d_6$) δ 12.04 (s, 1H), 8.46 (d, J = 5.8 Hz, 1H), 7.96 (d, J = 10.2 Hz, 1H), 7.47 (s, 1H), 7.39 (d, J = 5.8 Hz, 1H), 7.30 (d, J = 5.8 Hz, 1H), 7.24 (s, 1H), 7.18 (td, J = 9.8, 8.5 Hz, 1H), 6.96 (ddd, J = 9.4, 5.0, 2.2 Hz, 1H), 3.74 (d, J = 1.2 Hz, 3H), 1.84 (s, 3H). |
| 159 | 2-[2-(3,4-difluoro-2-methoxy-phenoxy)-5-fluoro-4-(trifluoromethyl)phenyl]-6-methoxy-1H-quinolin-4-one | 495.37; 496.4 | $^1$H NMR (500 MHz, DMSO-$d_6$) δ 11.97 (s, 1H), 8.00 (d, J = 10.4 Hz, 1H), 7.59 (d, J = 9.1 Hz, 1H), 7.50 (d, J = 3.0 Hz, 1H), 7.39-7.28 (m, 2H), 7.18 (q, J = 9.3 Hz, 1H), 7.04-6.96 (m, 1H), 6.23 (s, 1H), 3.85 (s, 3H), 3.80-3.74 (m, 3H). |
| 160 | 2-[2-(3,4-difluoro-2-methoxy-phenoxy)-5-fluoro-4-(trifluoromethyl)phenyl]-5-methyl-1H-1,6-naphthyridin-4-one | 480.36; 481.1 | $^1$H NMR (500 MHz, DMSO-$d_6$) δ 12.01 (s, 1H), 8.38 (d, J = 5.8 Hz, 1H), 8.00 (d, J = 10.5 Hz, 1H), 7.32 (d, J = 5.8 Hz, 2H), 7.19 (td, J = 9.7, 8.4 Hz, 1H), 7.02 (ddd, J = 9.5, 5.0, 2.2 Hz, 1H), 6.36 (s, 1H), 3.79 (d, J = 1.2 Hz, 3H), 2.93 (s, 3H). |
| 161 | 2-[2-(3,4-difluoro-2-methoxy-phenoxy)-5-fluoro-4-(trifluoromethyl)phenyl]-7-methyl-1H-1,6-naphthyridin-4-one | 480.36; 481.3 | $^1$H NMR (500 MHz, DMSO-$d_6$) δ 9.00 (s, 1H), 7.90 (d, J = 11.6 Hz, 1H), 7.23 (d, J = 6.1 Hz, 1H), 7.14-7.07 (m, 2H), 6.78 (ddd, J = 9.5, 5.0, 2.2 Hz, 1H), 6.43 (s, 1H), 3.86 (s, 3H), 2.43 (s, 3H). |
| 162 | 2-[2-(3,4-difluoro-2-methoxy-phenoxy)-5-fluoro-4-(trifluoromethyl)phenyl]-7-methyl-4-oxo-1H-1,6-naphthyridine-5-carboxamide | 523.38; 524.3 | $^1$H NMR (500 MHz, DMSO-$d_6$) δ 12.07 (s, 1H), 8.00 (d, J = 10.4 Hz, 1H), 7.48 (s, 1H), 7.32-7.24 (m, 2H), 7.24-7.15 (m, 1H), 7.04 (ddd, J = 9.7, 5.2, 2.2 Hz, 1H), 6.31 (s, 1H), 3.81-3.74 (m, 3H), 2.53 (s, 3H). |

2-[2-(3,4-difluoro-2-methoxy-phenoxy)-5-fluoro-4-(trifluoromethyl)phenyl]-6-methoxy-4-oxo-1H-quinoline-5-carboxamide (163)

Step 1: 1-(2-amino-5-methoxy-phenyl)ethanone

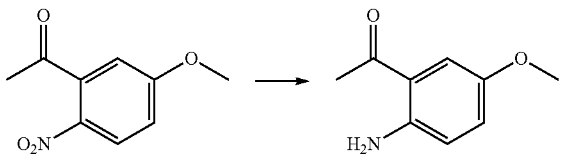

A solution of 1-(5-methoxy-2-nitro-phenyl)ethanone (6.5 g, 33.3 mmol) in ethanol (45 mL) was stirred with Pd/C under hydrogen atmosphere for 12 h. The mixture was filtered through Celite® and the pad washed with methanol. The filtrate was concentrated under reduced pressure and purified by silica gel chromatography (0-20% ethyl acetate/hexanes) to afford 1-(2-amino-5-methoxy-phenyl)ethanone (5.5 g, 94%). ESI-MS m/z calc. 165.08, found 166.0 $(M+1)^+$.

Step 2: N-(2-acetyl-4-methoxy-phenyl)-2-(3,4-difluoro-2-methoxy-phenoxy)-5-fluoro-4-(trifluoromethyl)benzamide

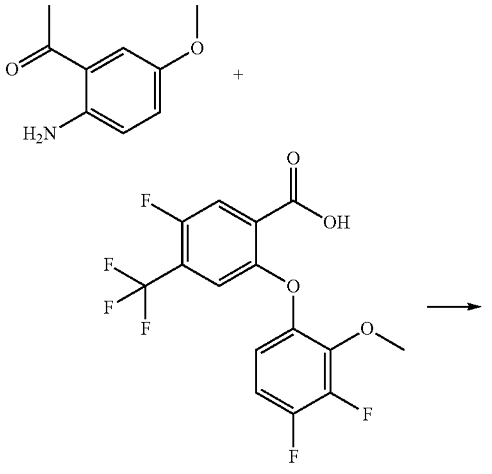

-continued

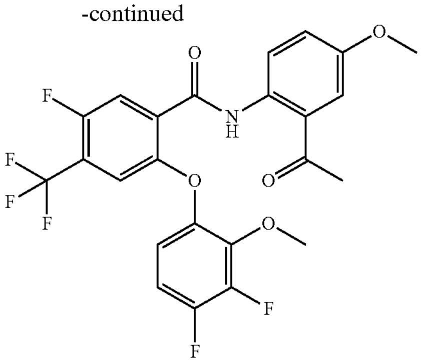

2-(3,4-Difluoro-2-methoxy-phenoxy)-5-fluoro-4-(trifluoromethyl)benzoic acid (2.0 g, 5.3 mmol) in DCM (40 mL) was treated with DMF followed by oxalyl chloride (1.5 mL, 17 mmol). The mixture was stirred for 30 min then the mixture concentrated. The residue was redissolved in DCM (40 mL) and treated with 1-(2-amino-5-methoxy-phenyl) ethanone (948 mg, 5.74 mmol) and triethylamine (1.5 mL, 10.8 mmol). The mixture was stirred for 2 h then concentrated. Purification by silica gel chromatography (40 g silica, 0-20% ethyl acetate/heptane) provided N-(2-acetyl-4-methoxy-phenyl)-2-(3,4-difluoro-2-methoxy-phenoxy)-5-fluoro-4-(trifluoromethyl)benzamide (2.75 g, 101%). ESI-MS m/z calc. 513.10, found 514.3 $(M+1)^+$.

Step 3: N-(2-acetyl-3-bromo-4-methoxy-phenyl)-2-(3,4-difluoro-2-methoxy-phenoxy)-5-fluoro-4-(trifluoromethyl)benzamide

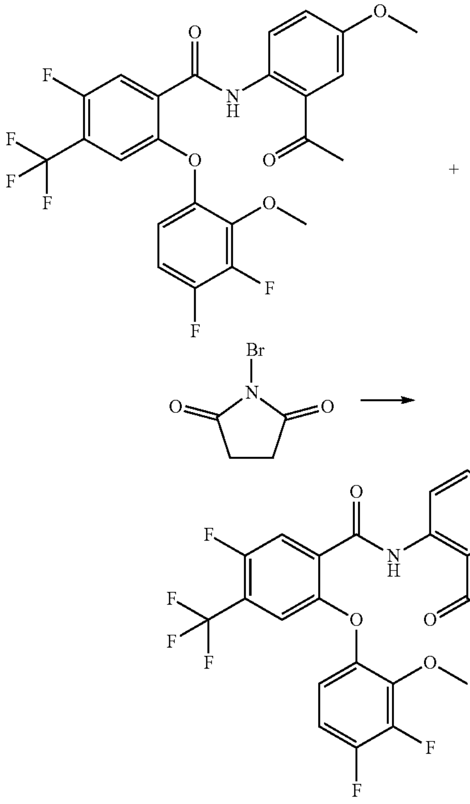

N-(2-Acetyl-4-methoxy-phenyl)-2-(3,4-difluoro-2-methoxy-phenoxy)-5-fluoro-4-(trifluoromethyl)benzamide (638 mg, 1.24 mmol) in acetonitrile (8 mL) was treated with $FeCl_3$ (205 mg, 1.27 mmol) followed by NBS (453 mg, 2.54 mmol). The mixture was stirred at room temperature under nitrogen for 1 h. The mixture was then treated with methanol (5 mL) concentrating. Purification over silica (12 g silica, 0-20% ethyl acetate/heptane) provided N-(2-acetyl-3-bromo-4-methoxy-phenyl)-2-(3,4-difluoro-2-methoxy-phenoxy)-5-fluoro-4-(trifluoromethyl)benzamide (548 mg, 74%). ESI-MS m/z calc. 591.01, found 592.2 $(M+1)^+$. $^1H$ NMR (500 MHz, DMSO-$d_6$) δ 10.19 (s, 1H), 7.80 (d, J=10.0 Hz, 1H), 7.44 (d, J=8.9 Hz, 1H), 7.28-7.20 (m, 2H), 7.17 (d, J=5.5 Hz, 1H), 7.00 (ddd, J=9.4, 5.1, 2.3 Hz, 1H), 3.89 (s, 3H), 3.88 (d, J=1.0 Hz, 3H), 2.42 (s, 3H).

Step 4: 5-bromo-2-[2-(3,4-difluoro-2-methoxy-phenoxy)-5-fluoro-4-(trifluoromethyl)phenyl]-6-methoxy-1H-quinolin-4-one

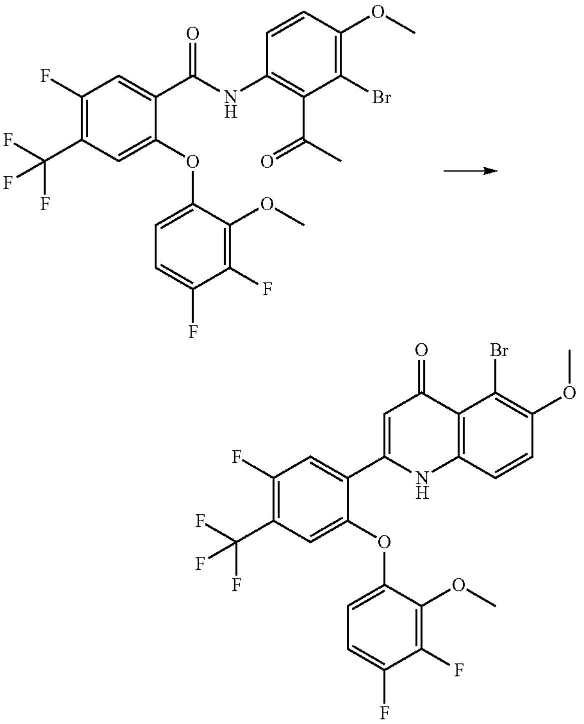

N-(2-Acetyl-3-bromo-4-methoxy-phenyl)-2-(3,4-difluoro-2-methoxy-phenoxy)-5-fluoro-4-(trifluoromethyl) benzamide (90 mg, 0.15 mmol) in dioxane (10 mL) was treated with potassium tert-butoxide (46 mg, 0.41 mmol) and heated at 120° C. under nitrogen for 27 h. The reaction mixture was cooled, diluted with ethyl acetate and washed with brine. The organic layer was separated, dried over magnesium sulfate, filtered and concentrated in vacuo. Purification over silica (12 g silica, 25-50% ethyl acetate/heptane) provided 5-bromo-2-[2-(3,4-difluoro-2-methoxy-phenoxy)-5-fluoro-4-(trifluoromethyl)phenyl]-6-methoxy-1H-quinolin-4-one (66 mg, 76%). ESI-MS m/z calc. 573.00, found 574.2 $(M+1)^+$.

Step 5: 2-[2-(3,4-difluoro-2-methoxy-phenoxy)-5-fluoro-4-(trifluoromethyl)phenyl]-6-methoxy-4-oxo-1H-quinoline-5-carbonitrile

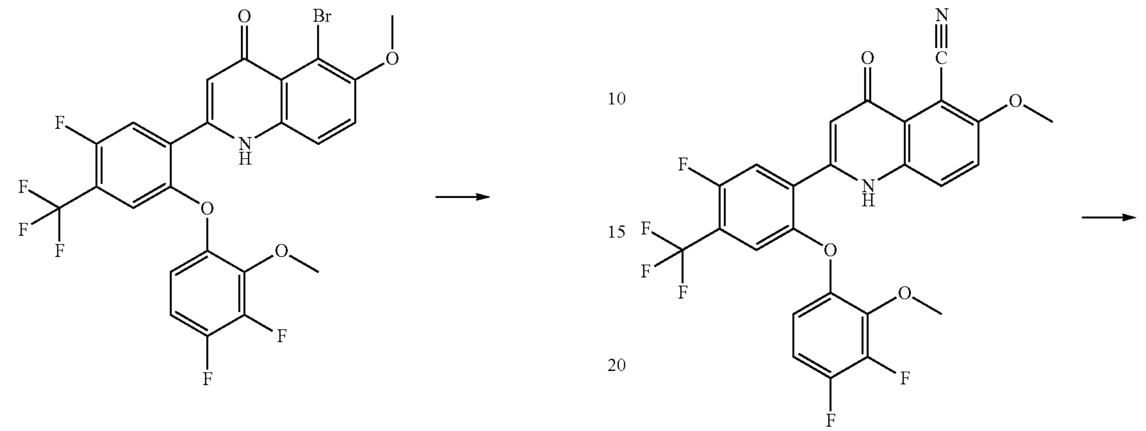

Step 6: 2-[2-(3,4-difluoro-2-methoxy-phenoxy)-5-fluoro-4-(trifluoromethyl)phenyl]-6-methoxy-4-oxo-1H-quinoline-5-carboxamide (163)

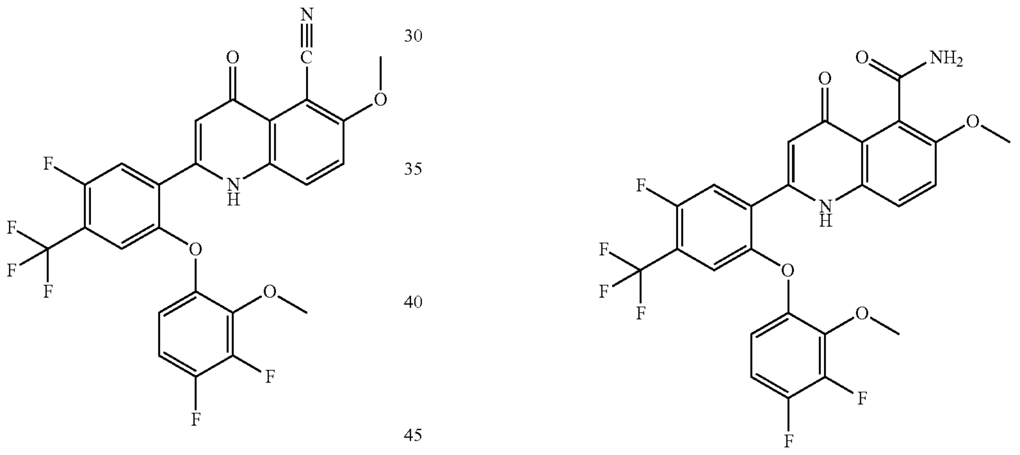

A solution of 5-bromo-2-[2-(3,4-difluoro-2-methoxy-phenoxy)-5-fluoro-4-(trifluoromethyl)phenyl]-6-methoxy-1H-quinolin-4-one (250 mg, 0.435 mmol) in NMP (3 mL) was degassed with nitrogen/vacuum cycles before the addition of dicyanozinc (130 mg, 1.11 mmol) and $Pd(PPh_3)_4$ (75 mg, 0.065 mmol). The mixture was stirred at 140° C. under nitrogen for 3 h. The mixture was diluted with ethyl acetate and washed with saturated aqueous sodium bicarbonate (2×), dried over magnesium sulfate, filtered and concentrated. Purification by HPLC (C18, $CH_3CN$/0.1% ammonium hydroxide gradient) provided 2-[2-(3,4-difluoro-2-methoxy-phenoxy)-5-fluoro-4-(trifluoromethyl)phenyl]-6-methoxy-4-oxo-1H-quinoline-5-carbonitrile (156.5 mg, 69%). ESI-MS m/z calc. 520.09, found 521.1 $(M+1)^+$.

2-[2-(3,4-Difluoro-2-methoxy-phenoxy)-5-fluoro-4-(trifluoromethyl)phenyl]-6-methoxy-4-oxo-1H-quinoline-5-carbonitrile (156.5 mg, 0.3007 mmol) in toluene (3.5 mL) was treated with TFA (2 mL, 26 mmol) and heated at 80° C. (exposed to air) for 3 h before concentrating and purifying by HPLC (C18, $CH_3CN$/0.1% ammonium hydroxide gradient) to provide 2-[2-(3,4-difluoro-2-methoxy-phenoxy)-5-fluoro-4-(trifluoromethyl)phenyl]-6-methoxy-4-oxo-1H-quinoline-5-carboxamide (Trifluoroacetate salt) (23.5 mg, 12%). $^1H$ NMR (500 MHz, DMSO-$d_6$) δ 8.01 (d, J=10.5 Hz, 1H), 7.71 (d, J=9.1 Hz, 1H), 7.59 (d, J=9.3 Hz, 1H), 7.31 (d, J=5.9 Hz, 1H), 7.20 (td, J=9.8, 8.4 Hz, 1H), 7.02 (ddd, J=9.4, 5.0, 2.2 Hz, 1H), 6.40 (s, 1H), 3.84 (s, 3H), 3.79 (d, J=1.2 Hz, 3H). ESI-MS m/z calc. 538.10, found 539.2 $(M+1)^+$.

2-[2-(3,4-difluoro-2-methoxy-phenoxy)-5-fluoro-4-(trifluoromethyl)phenyl]-6-methoxy-4-oxo-1H-1,7-naphthyridine-5-carboxamide (164)

Step 1: 1-(3,5-dibromo-2-methoxy-4-pyridyl)ethanol

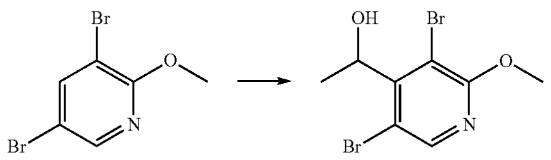

n-BuLi (4 mL of 2.5 M in hexanes, 10 mmol) was added to a solution of diisopropylamine (1.08 g, 1.5 mL, 10.7 mmol) in THF (15 mL) at −78° C. The reaction was stirred for 30 min, then 3,5-dibromo-2-methoxy-pyridine (2.0 g, 7.5 mmol) in THF (20 mL) was added slowly. After 30 min, acetaldehyde (1.2 g, 1.5 mL, 26.8 mmol) was added. The mixture was stirred at −78° C. for 30 min and allowed to warm up to room temperature over 1 h. The reaction mixture was partitioned between ethyl acetate and water. The organic layer was separated, dried over sodium sulfate, filtered and concentrated to provide 1-(3,5-dibromo-2-methoxy-4-pyridyl)ethanol (2.05 g, 62%) as a yellow oil. $^1$H NMR (400 MHz, $CDCl_3$) δ 8.14 (s, 1H), 5.49 (t, J=6.2 Hz, 1H), 3.97 (s, 3H), 3.08 (d, J=8.2 Hz, 1H), 1.59 (d, J=6.9 Hz, 3H).

Step 2: 1-(3,5-dibromo-2-methoxy-4-pyridyl)ethanone

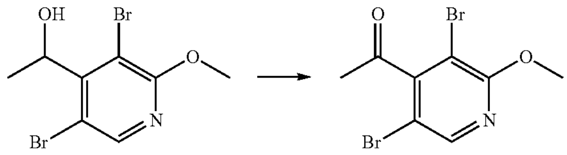

To a solution of 1-(3,5-dibromo-2-methoxy-4-pyridyl) ethanol (2.0 g, 4.5 mmol) and 1-(3,5-dibromo-2-methoxy-4-pyridyl)ethanol (405 mg, 0.912 mmol) in DCM (80 mL) at 0° C. was added Dess Martin periodinane (3.5 g, 8.3 mmol) portionwise. The reaction was stirred at ambient temperature for 2 h. The reaction mixture was passed through a pad of silica gel, eluting with DCM to give 1-(3,5-dibromo-2-methoxy-4-pyridyl)ethanone as a colorless oil which solidified on standing. $^1$H NMR (400 MHz, $CDCl_3$) δ 8.18 (s, 1H), 3.99 (s, 3H), 2.55 (s, 3H). ESI-MS m/z calc. 306.88, found 307.85 $(M+1)^+$.

Step 3: 2-(3,4-difluoro-2-methoxy-phenoxy)-5-fluoro-4-(trifluoromethyl)benzamide

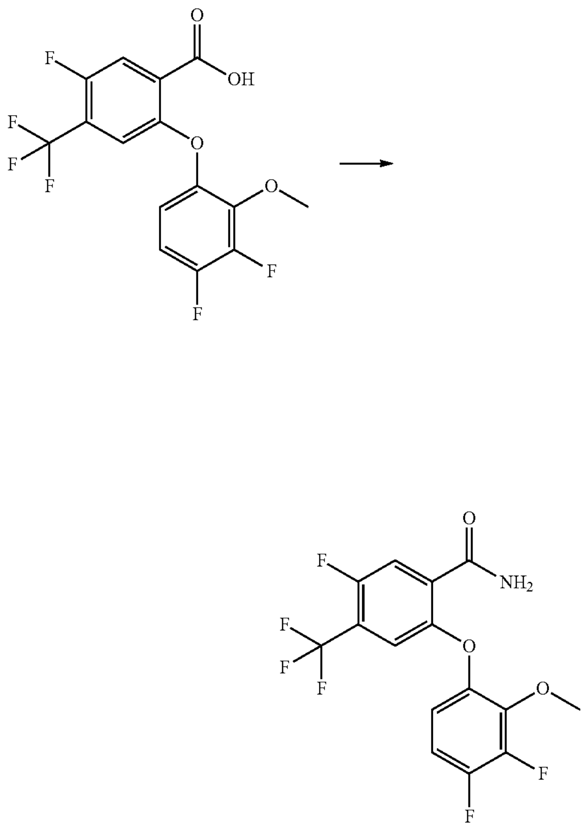

To a solution of 2-(3,4-difluoro-2-methoxy-phenoxy)-5-fluoro-4-(trifluoromethyl)benzoic acid (601 mg, 1.64 mmol) in 2-MeTHF (10 mL) and DMF (5 μL, 0.065 mmol) was added oxalyl dichloride (280 μL, 3.21 mmol) at 0° C. and the reaction mixture was warmed to room temperature and stirred for 30 min. The mixture was concentrated in vacuo. The crude residue was dissolved in 2-MeTHF (5 mL) and added to a solution of ammonium hydroxide (2 mL of 28% w/v, 16 mmol) in 2-MeTHF (5 mL) at 0° C. and the reaction mixture was warmed to room temperature and stirred for 1 h. The reaction mixture was diluted with ethyl acetate (30 mL), washed with water (30 mL), and the aqueous layer back-extracted with additional ethyl acetate (2×30 mL). The combined organic extracts were dried over magnesium sulfate, filtered and concentrated in vacuo to provide 2-(3,4-difluoro-2-methoxy-phenoxy)-5-fluoro-4-(trifluoromethyl)benzamide (545 mg, 91%). ESI-MS m/z calc. 365.05, found 366.4 $(M+1)^+$; 364.4 $(M-1)^-$. $^1$H NMR (500 MHz, DMSO-$d_6$) δ 7.92 (s, 1H), 7.85 (s, 1H), 7.76 (d, J=10.4 Hz, 1H), 7.25-7.15 (m, 2H), 6.98-6.91 (m, 1H), 3.88 (d, J=1.0 Hz, 3H).

Step 4: N-(4-acetyl-5-bromo-6-methoxy-3-pyridyl)-2-(3,4-difluoro-2-methoxy-phenoxy)-5-fluoro-4-(trifluoromethyl)benzamide 5-bromo-2-[2-(3,4-difluoro-2-methoxy-phenoxy)-5-fluoro-4-(trifluoromethyl)phenyl]-6-methoxy-1H-1,7-naphthyridin-4-one

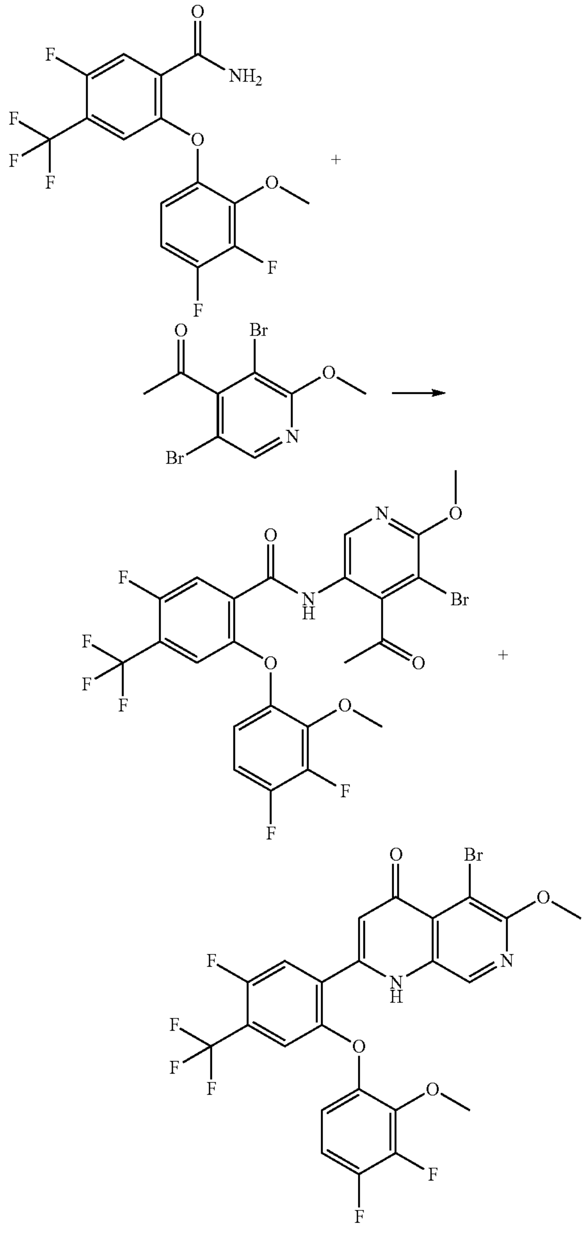

A solution of 2-(3,4-difluoro-2-methoxy-phenoxy)-5-fluoro-4-(trifluoromethyl)benzamide (200 mg, 0.547 mmol), 1-(3,5-dibromo-2-methoxy-4-pyridyl)ethanone (260 mg, 0.589 mmol), cesium carbonate (400 mg, 1.23 mmol) in toluene (5 mL) was degassed for 5 min. A pre-mixed solution of $Pd_2dba_3$ (5 mg, 0.02 mmol) and XantPhos (11 mg, 0.019 mmol) in degassed toluene (0.5 mL) was added and the reaction mixture was then stirred at 100° C. for 24 h. The reaction mixture was partitioned between ethyl acetate and water. The organic layer was dried over sodium sulfate and concentrated. Purification by reverse phase chromatography (C18, 10-60% $CH_3CN$/water each with 0.1% ammonium hydroxide) provided the cyclized product 5-bromo-2-[2-(3,4-difluoro-2-methoxy-phenoxy)-5-fluoro-4-(trifluoromethyl)phenyl]-6-methoxy-1H-1,7-naphthyridin-4-one. ESI-MS m/z calc. 574.00, found 574.91 $(M+1)^+$. $^1H$ NMR (400 MHz, $CDCl_3$) δ 9.85 (br s, 1H), 8.02 (s, 1H), 7.52-7.47 (m, 1H), 6.98-6.85 (m, 3H), 6.54 (s, 1H), 3.97 (s, 3H), 3.82 (s, 3H).

Step 5: 2-[2-(3,4-difluoro-2-methoxy-phenoxy)-5-fluoro-4-(trifluoromethyl)phenyl]-6-methoxy-4-oxo-1H-1,7-naphthyridine-5-carbonitrile

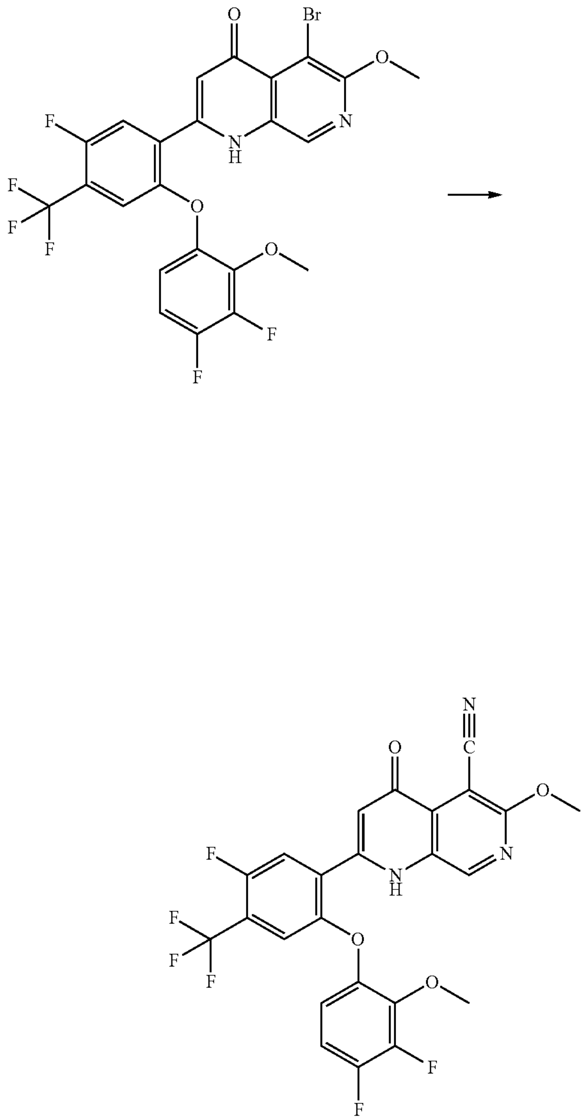

2-[2-(3,4-Difluoro-2-methoxy-phenoxy)-5-fluoro-4-(trifluoromethyl)phenyl]-6-methoxy-4-oxo-1H-1,7-naphthyridine-5-carbonitrile was prepared from 5-bromo-2-[2-(3,4-difluoro-2-methoxy-phenoxy)-5-fluoro-4-(trifluoromethyl)phenyl]-6-methoxy-1H-1,7-naphthyridin-4-one using a procedure analogous to that found in Compound 163, step 5. ESI-MS m/z calc. 521.08, found 521.99 $(M+1)^+$.

Step 6: 2-[2-(3,4-difluoro-2-methoxy-phenoxy)-5-fluoro-4-(trifluoromethyl)phenyl]-6-methoxy-4-oxo-1H-1,7-naphthyridine-5-carboxamide (164)

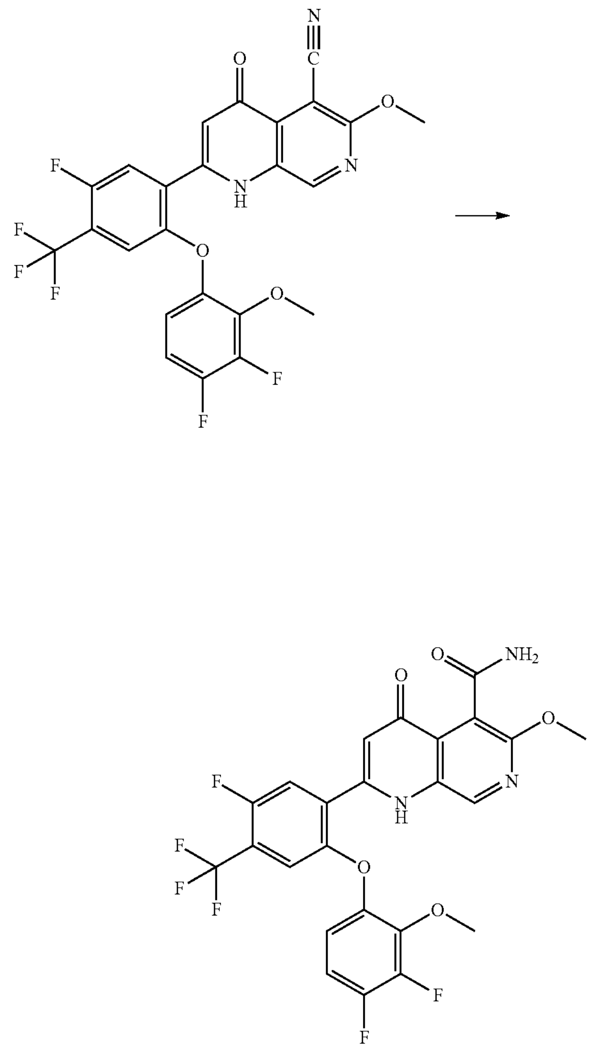

To a solution of 2-[2-(3,4-difluoro-2-methoxy-phenoxy)-5-fluoro-4-(trifluoromethyl)phenyl]-6-methoxy-4-oxo-1H-1,7-naphthyridine-5-carbonitrile (47 mg, 0.062 mmol) and potassium carbonate (30 mg, 0.22 mmol) in DMSO (1 mL) was slowly added aqueous hydrogen peroxide (150 μL of 35% w/w, 0.600 mmol) at 10° C. The mixture was stirred at room temperature for 15 h then partitioned between ethyl acetate and water. The organic layer was dried over sodium sulfate, filtered and concentrated. Purification by reverse phase chromatography (C18, 5-60% acetonitrile/water, both 0.1% containing 0.1% ammonium hydroxide) provided 2-[2-(3,4-difluoro-2-methoxy-phenoxy)-5-fluoro-4-(trifluoromethyl)phenyl]-6-methoxy-4-oxo-1H-1,7-naphthyridine-5-carboxamide (164, 10.2 mg, 30%) as a white solid. ESI-MS m/z calc. 539.09, found 539.99 $(M+1)^+$. $^1H$ NMR (400 MHz, $CD_3OD$) δ 8.01 (s, 1H), 7.73 (d, J=10.5 Hz, 1H), 7.10 (d, J=5.5 Hz, 1H), 6.99 (d, J=8.2 Hz, 1H), 6.68-6.93 (m, 2H), 4.14 (s, 3H), 3.82 (d, J=1.4 Hz, 3H). $^{19}F$ NMR (376 MHz, $CD_3OD$) δ −63.0 (d, J=12.9 Hz, 3F), −123.0 (s, 1F), −141.6 (s, 1F), −153.8 (s, 1F).

2-[2-(3,4-difluoro-2-methoxy-phenoxy)-5-fluoro-4-(trifluoromethyl)phenyl]-4-oxo-1H-1,7-naphthyridine-5-carboxamide (165)

Step 1: 2-(3,4-difluoro-2-methoxy-phenoxy)-5-fluoro-4-(trifluoromethyl)benzamide

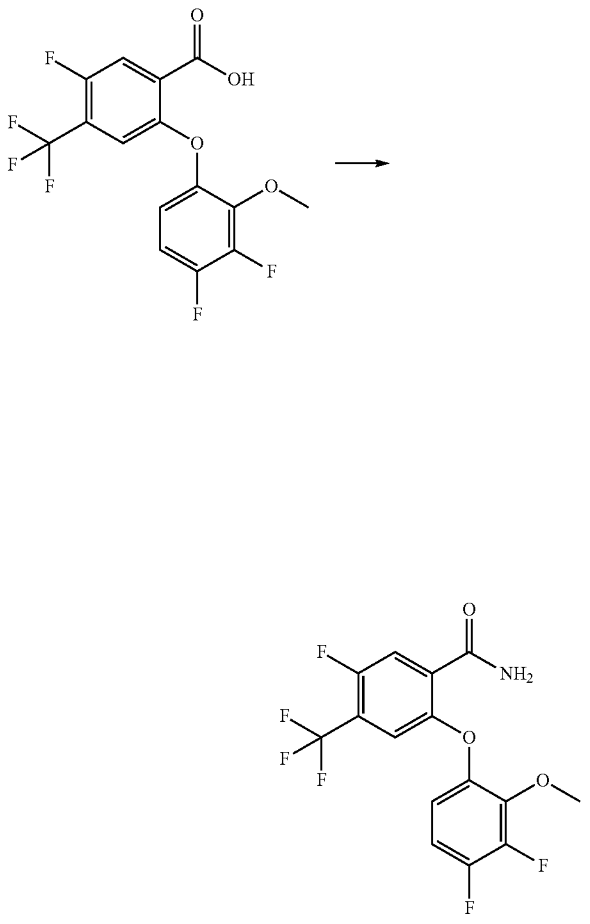

To a solution of 2-(3,4-difluoro-2-methoxy-phenoxy)-5-fluoro-4-(trifluoromethyl)benzoic acid (601 mg, 1.64 mmol) in 2-MeTHF (10 mL) and DMF (5 μL, 0.06 mmol) at 0° C. was added oxalyl dichloride (280 μL, 3.21 mmol). The mixture was warmed to room temperature, stirred for 30 min and then concentrated. The residue was dissolved in 2-MeTHF (5 mL) and added to a solution of ammonium hydroxide (2 mL of 28% w/v, 15.98 mmol) in 2-MeTHF (5 mL) at 0° C. The mixture was warmed to room temperature and stirred for 1 h. The mixture was diluted with ethyl acetate (30 mL) and washed with water (30 mL). The aqueous layer was extracted with additional ethyl acetate (2×30 mL) and the combined organic extracts were dried over magnesium sulfate, filtered and concentrated to provide 2-(3,4-difluoro-2-methoxy-phenoxy)-5-fluoro-4-(trifluoromethyl)benzamide (545 mg, 91%). $^1H$ NMR (500 MHz, DMSO-$d_6$) δ 7.92 (s, 1H), 7.85 (s, 1H), 7.76 (d, J=10.4 Hz, 1H), 7.25-7.15 (m, 2H), 6.98-6.91 (m, 1H), 3.88 (d, J=1.0 Hz, 3H). ESI-MS m/z calc. 365.05, found 366.4 $(M+1)^+$; 364.4 $(M-1)^-$.

Step 2: 5-bromo-2-[2-(3,4-difluoro-2-methoxy-phenoxy)-5-fluoro-4-(trifluoromethyl)phenyl]-1H-1,7-naphthyridin-4-one

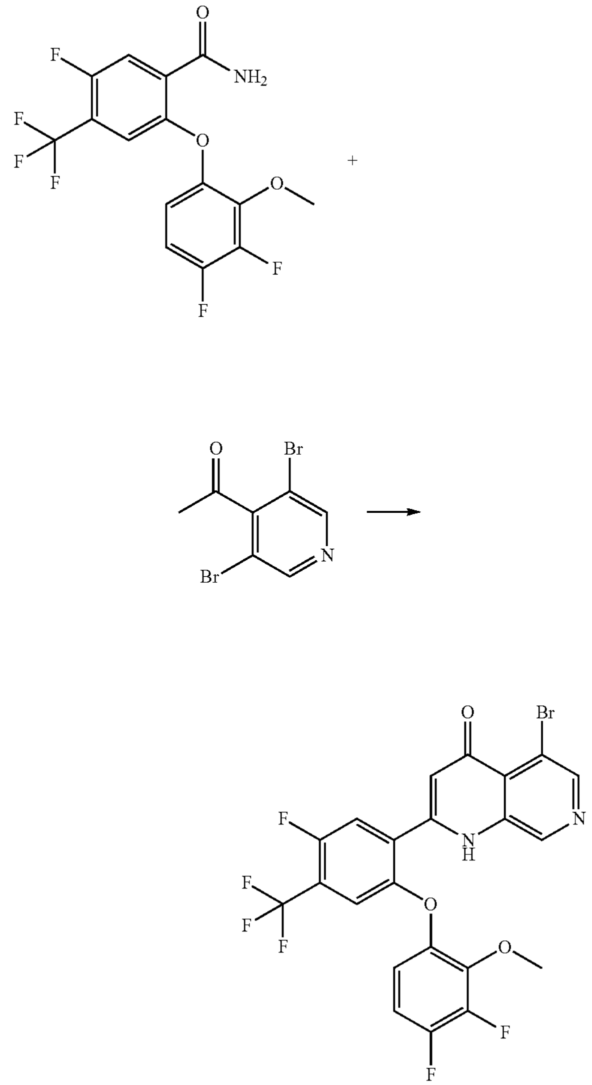

A suspension of 2-(3,4-difluoro-2-methoxy-phenoxy)-5-fluoro-4-(trifluoromethyl)benzamide (632 mg, 1.65 mmol) in toluene (5 mL) was degassed with argon for 10 min and then 1-(3,5-dibromo-4-pyridyl)ethanone (307 mg, 1.10 mmol), $Pd_2dba_3$ (101 mg, 0.110 mmol), Xantphos (127 mg, 0.220 mmol) and cesium carbonate (1.08 g, 3.31 mmol) were added. The mixture was heated to 100° C. under argon for 3 h, then stirred at room temperature under argon for 4 days. The mixture was filtered through Celite and washed with ethyl acetate. The filtrate was concentrated and purified by reverse phase chromatography (C18, 5-80% acetonitrile/water each containing 0.1% ammonium hydroxide) to provide 5-bromo-2-[2-(3,4-difluoro-2-methoxy-phenoxy)-5-fluoro-4-(trifluoromethyl)phenyl]-1H-1,7-naphthyridin-4-one (74 mg, 12%). $^1H$ NMR (400 MHz, $CDCl_3$) δ 10.03 (s, 1H), 8.68 (s, 1H), 8.61 (s, 1H), 7.52 (d, J=9.2 Hz, 1H), 7.08 (d, J=6.4 Hz, 1H), 7.01 (d, J=4.1 Hz, 2H), 6.57 (s, 1H), 3.94 (s, 3H). ESI-MS m/z calc. 543.99, found 543.0 $(M-1)^-$.

Step 3: 2-[2-(3,4-difluoro-2-methoxy-phenoxy)-5-fluoro-4-(trifluoromethyl)phenyl]-4-oxo-1H-1,7-naphthyridine-5-carbonitrile

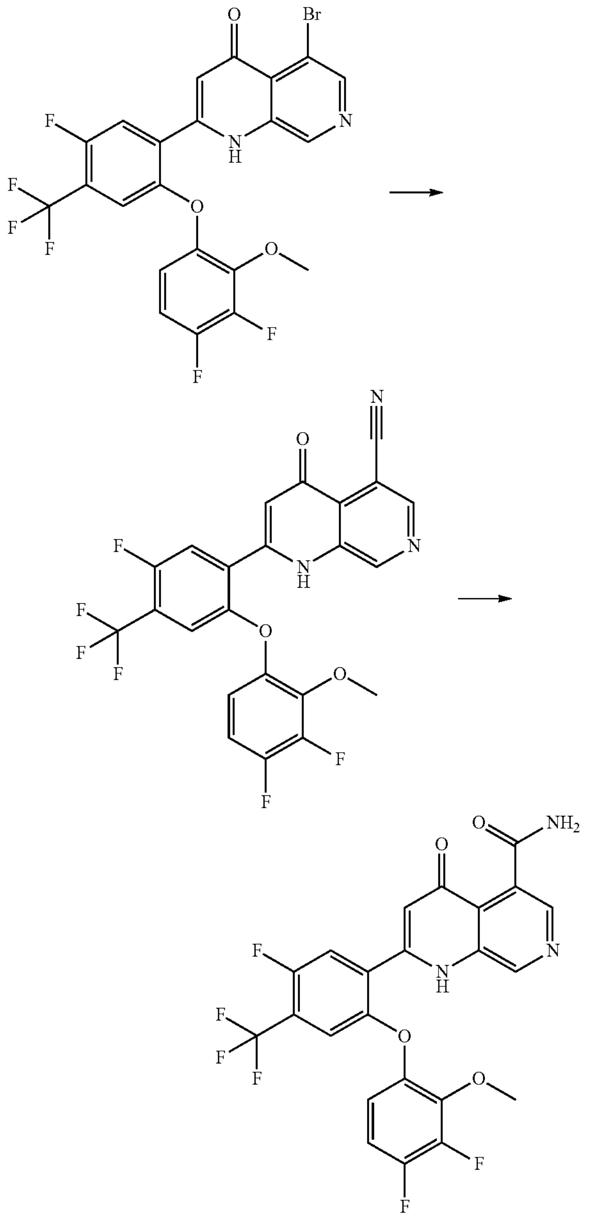

5-Bromo-2-[2-(3,4-difluoro-2-methoxy-phenoxy)-5-fluoro-4-(trifluoromethyl)phenyl]-1H-1,7-naphthyridin-4-one (74 mg, 0.1289 mmol) was dissolved in degassed DMF (1.5 mL). Zinc cyanide (20 mg, 0.17 mmol) and $Pd(PPh_3)_4$ (15 mg, 0.013 mmol) were added and the mixture was stirred under microwave irradiation at 110° C. for 90 min. The mixture was partitioned between ethyl acetate and water and the layers separated. The aqueous layer was extracted with additional ethyl acetate, and the combined layers were washed with brine, dried over magnesium sulfate, filtered and concentrated. Purification by silica gel (0-100% ethyl acetate/heptane) provided 2-[2-(3,4-difluoro-2-methoxy-phenoxy)-5-fluoro-4-(trifluoromethyl)phenyl]-4-oxo-1H-1,7-naphthyridine-5-carbonitrile (30 mg, 47%). $^1H$ NMR (400

MHz, $CDCl_3$) δ 9.07 (s, 1H), 8.83 (s, 1H), 7.56 (d, J=10.1 Hz, 1H), 7.09 (d, J=5.5 Hz, 1H), 7.01 (m, 2H), 6.73 (s, 1H), 3.93 (d, J=2.3 Hz, 3H). ESI-MS m/z calc. 491.07, found 492.08 $(M+1)^+$. The product was converted to 2-[2-(3,4-difluoro-2-methoxy-phenoxy)-5-fluoro-4-(trifluoromethyl)phenyl]-4-oxo-1H-1,7-naphthyridine-5-carboxamide using the conditions found in Example 2-[2-(3,4-difluoro-2-methyl-phenoxy)-3-quinolyl]-4-oxo-1H-1,6-naphthyridine-5-carboxamide (149). $^1H$ NMR (400 MHz, $CD_3OD$) δ 9.13 (s, 1H), 8.44 (s, 1H), 7.82 (d, J=10.1 Hz, 1H), 7.17 (d, J=6.0 Hz, 1H), 7.01-6.61 (m, 3H), 3.80 (d, J=1.4 Hz, 3H). ESI-MS m/z calc. 509.08, found 510.06 $(M+1)^+$.

2-[2-(3,4-difluoro-2-methoxy-phenoxy)-5-fluoro-4-(trifluoromethyl)phenyl]-5-(1H-tetrazol-5-yl)-1H-1,6-naphthyridin-4-one (166)

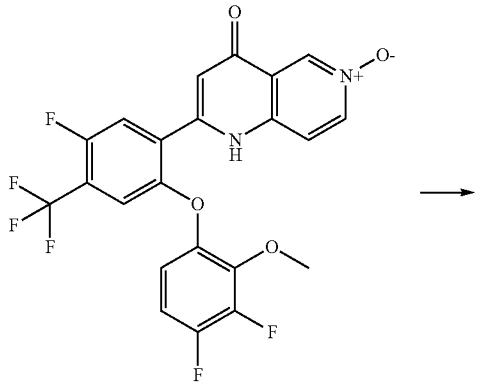

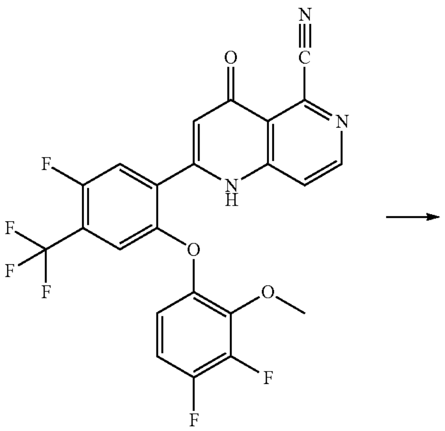

-continued

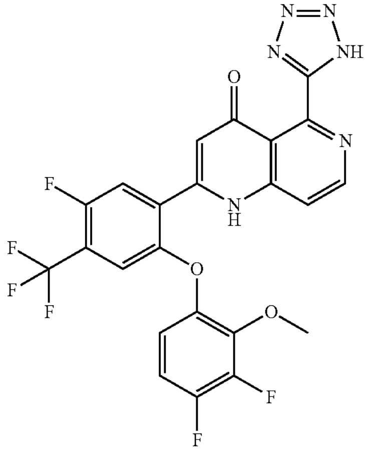

Step 1: 2-[2-(3,4-difluoro-2-methoxy-phenoxy)-5-fluoro-4-(trifluoromethyl)phenyl]-4-oxo-1H-1,6-naphthyridine-5-carbonitrile To a stirring solution of 2-[2-(3,4-difluoro-2-methoxy-phenoxy)-5-fluoro-4-(trifluoromethyl)phenyl]-6-oxido-1H-1,6-naphthyridin-6-ium-4-one (975 mg, 2.021 mmol) in DCM (25 mL) at ambient temperature and under nitrogen atmosphere, trimethylsilylformonitrile (2 mL, 15 mmol) was added followed by TEA (3 mL, 22 mmol). The mixture was stirred at the same temperature for 60 min before being quenched by the addition of 10 mL of saturated aqueous sodium bicarbonate. The mixture was extracted with DCM (2×10 mL) and the combined organic layers dried over magnesium sulfate, filtered and concentrated in vacuo. Purification by silica gel chromatography (24 g silica, 0-100% 3:1 ethyl acetate/ethanol gradient in heptane) afforded 2-[2-(3,4-difluoro-2-methoxy-phenoxy)-5-fluoro-4-(trifluoromethyl)phenyl]-4-oxo-1H-1,6-naphthyridine-5-carbonitrile (650 mg, 65%). ESI-MS m/z calc. 491.07, found 492.2 $(M+1)^+$; 490.2 (M−1).

Step 2: 2-[2-(3,4-difluoro-2-methoxy-phenoxy)-5-fluoro-4-(trifluoromethyl)phenyl]-5-(1H-tetrazol-5-yl)-1H-1,6-naphthyridin-4-one A degassed solution of 2-[2-(3,4-difluoro-2-methoxy-phenoxy)-5-fluoro-4-(trifluoromethyl)phenyl]-4-oxo-1H-1,6-naphthyridine-5-carbonitrile (50 mg, 0.10 mmol), $NaN_3$ (10 mg, 0.15 mmol) and $ZnCl_2$ (15 mg, 0.11 mmol) in n-propanol (600 μL) was stirred at 100° C. for 80 min. The mixture was purified directly using silica gel chromatography (12 g silica, 0-100% 3:1 ethyl acetate/ethanol gradient in heptane) to afford 2-[2-(3,4-difluoro-2-methoxy-phenoxy)-5-fluoro-4-(trifluoromethyl)phenyl]-5-(1H-tetrazol-5-yl)-1H-1,6-naphthyridin-4-one (7.7 mg, 14%). ESI-MS m/z calc. 534.09, found 535.2 $(M+1)^+$; 533.2 $(M-1)^-$.

Example 6
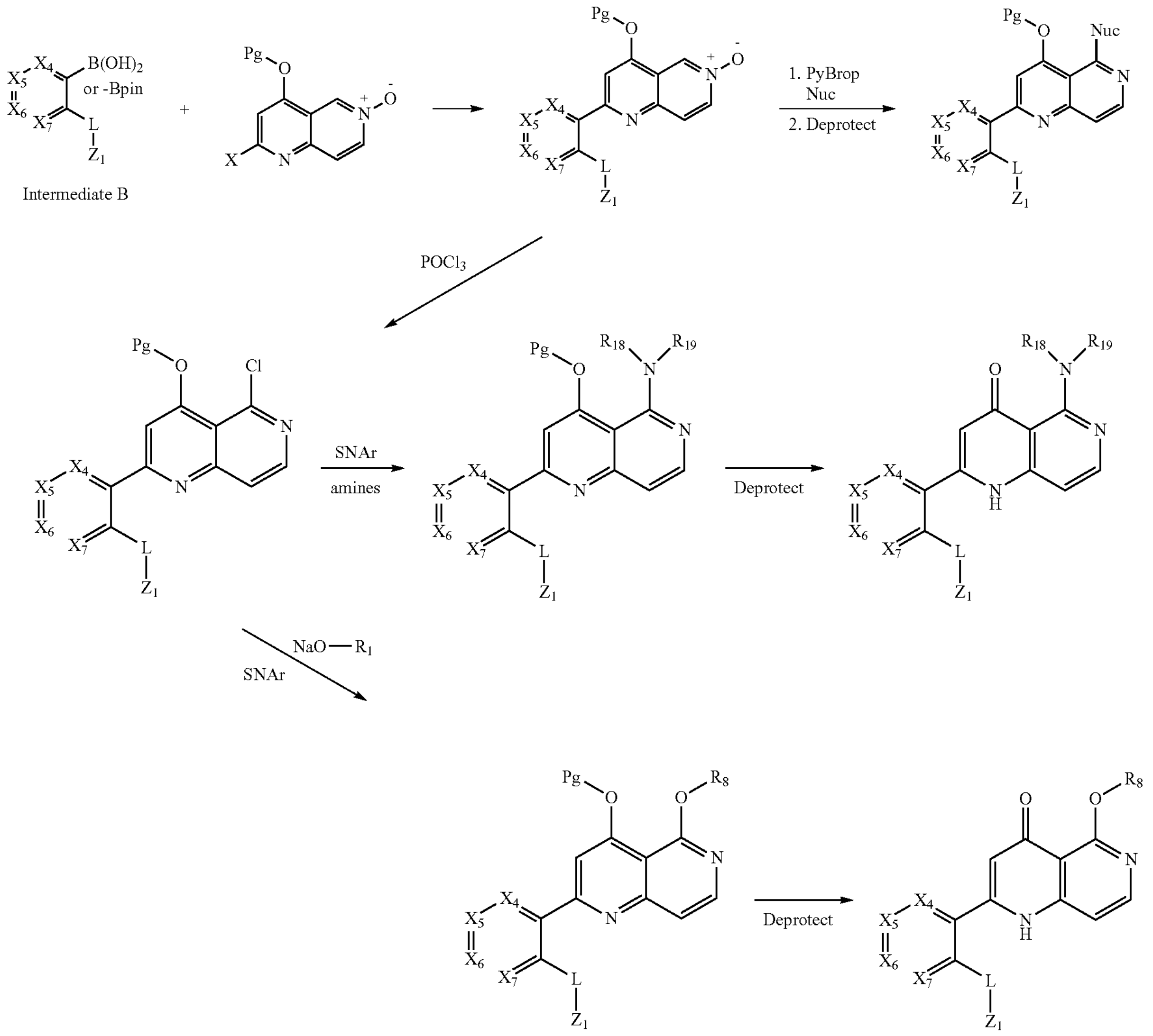
2-[2-(3,4-difluoro-2-methyl-phenoxy)-4-methyl-5-(trifluoromethyl)-3-pyridyl]-5-(methylamino)-1H-1,6-naphthyridin-4-one (167)
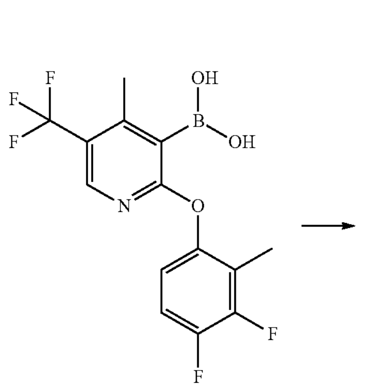
-continued
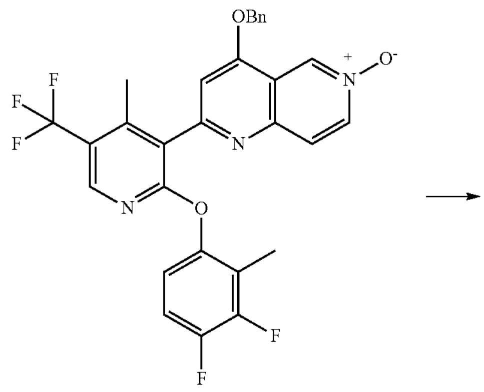

-continued

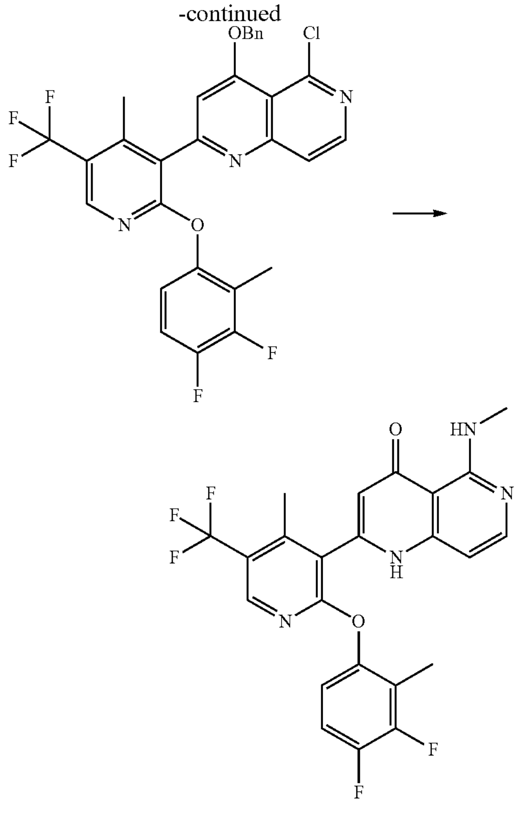

Step 1: 4-benzyloxy-2-[2-(3,4-difluoro-2-methyl-phenoxy)-4-methyl-5-(trifluoromethyl)-3-pyridyl]-6-oxido-1,6-naphthyridin-6-ium A mixture of [2-(3,4-difluoro-2-methyl-phenoxy)-4-methyl-5-(trifluoromethyl)-3-pyridyl]boronic acid (6.66 g, 16.7 mmol), 4-benzyloxy-2-chloro-6-oxido-1,6-naphthyridin-6-ium (5.4 g, 18.5 mmol), SPhos Pd G3 (1.5 g, 1.9 mmol) and potassium phosphate (15 g, 71 mmol) in dioxane (90 mL) and water (9 mL) was degassed for 5 min and stirred under nitrogen atmosphere at 75° C. for 1.5 h. The mixture was cooled to room temperature, diluted with ethyl acetate (300 mL) and washed with saturated aqueous ammonium chloride (150 mL) and brine (150 mL). The organic layer was dried over sodium sulfate, filtered and concentrated under reduced pressure. Purification by silica gel chromatography (0-100% ethyl acetate/heptanes) afforded 4-benzyloxy-2-[2-(3,4-difluoro-2-methyl-phenoxy)-4-methyl-5-(trifluoromethyl)-3-pyridyl]-6-oxido-1,6-naphthyridin-6-ium (7.35 g, 80%) as a beige solid. $^1$H NMR (400 MHz, $CDCl_3$) δ 9.16 (d, J=1.5 Hz, 1H), 8.42 (s, 1H), 8.38 (dd, J=7.5, 2.1 Hz, 1H), 7.90 (d, J=7.3 Hz, 1H), 7.50-7.37 (m, 5H), 7.09-6.96 (m, 2H), 6.78-6.69 (m, 1H), 5.37 (s, 2H), 2.33 (s, 3H), 2.01 (d, J=1.5 Hz, 3H). $^{19}$F NMR (377 MHz, $CDCl_3$) δ −60.71 (s, 3F), −137.95 (d, J=21.8 Hz, 1F), −140.67 (d, J=21.8 Hz, 1F). ESI-MS m/z calc. 553.14, found 554.2 $(M+1)^+$.

Step 2: 4-benzyloxy-5-chloro-2-[2-(3,4-difluoro-2-methyl-phenoxy)-4-methyl-5-(trifluoromethyl)-3-pyridyl]-1,6-naphthyridine A solution of 4-benzyloxy-2-[2-(3,4-difluoro-2-methyl-phenoxy)-4-methyl-5-(trifluoromethyl)-3-pyridyl]-6-oxido-1,6-naphthyridin-6-ium (4.9 g, 8.8 mmol) and triethylamine (2.5 mL, 18 mmol) in dichloromethane (40 mL) was cooled to −78° C. To the reaction mixture was added dropwise oxalyl chloride (2.2 g, 1.5 mL, 17.2 mmol) and the reaction was stirred at −78° C. for 90 min. The reaction mixture was concentrated under reduced pressure and co-evaporated twice with DCM (100 mL). Purification by reverse phase chromatography (C18, 5-100% $CH_3CN$/water with 0.1% formic acid) provided 4-benzyloxy-5-chloro-2-[2-(3,4-difluoro-2-methyl-phenoxy)-4-methyl-5-(trifluoromethyl)-3-pyridyl]-1,6-naphthyridine (3.02 g, 60%) as a white solid. ESI-MS m/z calc. 571.11, found 572.2 $(M+1)^+$.

Step 3: 2-[2-(3,4-difluoro-2-methyl-phenoxy)-4-methyl-5-(trifluoromethyl)-3-pyridyl]-5-(methylamino)-1H-1,6-naphthyridin-4-one (167)

A mixture of 4-benzyloxy-5-chloro-2-[2-(3,4-difluoro-2-methyl-phenoxy)-4-methyl-5-(trifluoromethyl)-3-pyridyl]-1,6-naphthyridine (50 mg, 0.087 mmol) and methanamine in ethanol (165 mg, 1.75 mmol) was heated at 60° C. for 1 hour in a sealed vial. The mixture was cooled to room temperature, diluted with DMSO (500 uL), filtered, and purified by reverse phase chromatography (C18, 1-99% acetonitrile/5 mM HCl) to provide 4-benzyloxy-2-[2-(3,4-difluoro-2-methyl-phenoxy)-4-methyl-5-(trifluoromethyl)-3-pyridyl]-N-methyl-1,6-naphthyridin-5-amine. The benzyl-protected intermediate and 10% Pd/C (19 mg, 0.018 mmol) were stirred in ethanol (1 mL) under an atmosphere of hydrogen for 1 h. The mixture was filtered and purified by reverse phase chromatography (C18, 1-99% acetonitrile/5 mM HCl) to provide 2-[2-(3,4-difluoro-2-methyl-phenoxy)-4-methyl-5-(trifluoromethyl)-3-pyridyl]-5-(methylamino)-1H-1,6-naphthyridin-4-one (167, 5.1 mg, 12) as a white solid. ESI-MS m calc. 476.13, found 477.1 $(M+1)^+$. $^1$H NMR (400 MHz, $CD_3OD$) δ 8.49 (s, 1H), 7.82 (d, J=7.3 Hz, 1H), 7.23-7.04 (m, 1H), 6.97-6.87 (m, 1H), 6.79 (dd, J=7.3, 1.9 Hz, 1H), 6.67 (s, 1H), 3.21 (s, 3H), 2.48 (s, 3H), 2.04 (s, 3H).

The following examples were synthesized in an analogous fashion as Compound 167 using the appropriate amine nucleophile and Intermediate B.

TABLE 4

| Compound Number | Compound Name | MW & Found [M + H]$^+$ | NMR (shifts in ppm) |
|---|---|---|---|
| 168 | 2-[2-(3,4-difluoro-2-methyl-phenoxy)-4-methyl-5-(trifluoromethyl)-3-pyridyl]-5-(dimethylamino)-1H-1,6-naphthyridin-4-one | 490.43; 491.1 | $^1$H NMR (400 MHz, DMSO-$d_6$) δ 13.17 (s, 1H), 8.60 (s, 1H), 7.95 (d, J = 6.9 Hz, 1H), 7.46-7.28 (m, 1H), 7.24-7.11 (m, 1H), 7.11-6.97 (m, 1H), 6.55 (s, 1H), 3.18 (s, 6H), 2.43 (s, 3H), 2.02 (s, 3H). |
| 169 | 5-amino-2-[2-(3,4-difluoro-2-methyl-phenoxy)-4-methyl-5-(trifluoromethyl)-3-pyridyl]-1H-1,6-naphthyridin-4-one | 462.37; 463.1 | $^1$H NMR (400 MHz, DMSO-$d_6$) δ 13.36 (s, 1H), 10.41 (s, 1H), 8.78 (s, 1H), 8.62 (s, 1H), 7.91 (d, J = 7.2 Hz, 1H), 7.47-7.27 (m, 1H), 7.17-7.08 (m, 1H), 6.87 (d, J = 7.4, 1.8 Hz, 1H), 6.67 (s, 1H), 2.42 (s, 3H), 2.02 (s, 3H). |

TABLE 4-continued

| Compound Number | Compound Name | MW & Found [M + H]+ | NMR (shifts in ppm) |
|---|---|---|---|
| 170 | 2-[2-(3,4-difluoro-2-methyl-phenoxy)-4-methyl-5-(trifluoromethyl)-3-pyridyl]-5-[(2-hydroxy-1,1-dimethyl-ethyl)amino]-1H-1,6-naphthyridin-4-one | 534.48; 535.1 | $^1$H NMR (400 MHz, $CD_3OD$) δ 8.49 (s, 1H), 7.93 (d, J = 7.3 Hz, 1H), 7.27-7.06 (m, 1H), 7.04-6.87 (m, 1H), 6.86-6.74 (m, 1H), 6.69 (s, 1H), 3.79 (s, 2H), 2.48 (d, J = 1.3 Hz, 3H), 2.04 (d, J = 2.2 Hz, 3H), 1.52 (s, 6H). |
| 171 | 2-[2-(3,4-difluoro-2-methyl-phenoxy)-4-methyl-5-(trifluoromethyl)-3-pyridyl]-5-(tetrahydropyran-3-ylamino)-1H-1,6-naphthyridin-4-one | 546.49; 547.3 | |
| 172 | 2-[2-(3,4-difluoro-2-methyl-phenoxy)-4-methyl-5-(trifluoromethyl)-3-pyridyl]-5-(1,4-oxazepan-4-yl)-1H-1,6-naphthyridin-4-one | 546.49; 547.3 | |
| 173 | 5-[(3aS,6aR)-1,3,3a,4,6,6a-hexahydrofuro[3,4-c]pyrrol-5-yl]-2-[2-(3,4-difluoro-2-methyl-phenoxy)-4-methyl-5-(trifluoromethyl)-3-pyridyl]-1H-1,6-naphthyridin-4-one | 558.5; 559.3 | |
| 174 | 2-[2-(3,4-difluoro-2-methyl-phenoxy)-4-methyl-5-(trifluoromethyl)-3-pyridyl]-5-[(3S)-3-methoxypyrrolidin-1-yl]-1H-1,6-naphthyridin-4-one | 546.49; 547.3 | |
| 175 | 2-[2-(3,4-difluoro-2-methyl-phenoxy)-4-methyl-5-(trifluoromethyl)-3-pyridyl]-5-(4,6-dihydro-1H-pyrrolo[3,4-c]pyrazol-5-yl)-1H-1,6-naphthyridin-4-one | 554.47; 555.3 | |
| 176 | (3S)-1-[2-[2-(3,4-difluoro-2-methyl-phenoxy)-4-methyl-5-(trifluoromethyl)-3-pyridyl]-4-oxo-1H-1,6-naphthyridin-5-yl]pyrrolidine-3-carboxamide | 559.49; 560.3 | |
| 177 | 2-[2-(3,4-difluoro-2-methyl-phenoxy)-4-methyl-5-(trifluoromethyl)-3-pyridyl]-5-[3-(dimethylamino)pyrrolidin-1-yl]-1H-1,6-naphthyridin-4-one | 559.53; 560.3 | |
| 178 | 2-[2-(3,4-difluoro-2-methyl-phenoxy)-4-methyl-5-(trifluoromethyl)-3-pyridyl]-5-[(5-oxopyrrolidin-3-yl)methylamino]-1H-1,6-naphthyridin-4-one | 559.49; 560 | |
| 179 | 2-[2-(3,4-difluoro-2-methyl-phenoxy)-4-methyl-5-(trifluoromethyl)-3-pyridyl]-5-(3-hydroxyazetidin-1-yl)-1H-1,6-naphthyridin-4-one | 518.44; 519.3 | |
| 180 | 2-[2-(3,4-difluoro-2-methyl-phenoxy)-4-methyl-5-(trifluoromethyl)-3-pyridyl]-5-[[(1S,2R)-2-hydroxycyclopentyl]amino]-1H-1,6-naphthyridin-4-one | 546.49; 547.3 | |
| 181 | 2-[2-(3,4-difluoro-2-methyl-phenoxy)-4-methyl-5-(trifluoromethyl)-3-pyridyl]-5-[[(3S)-1-methylpyrrolidin-3-yl]amino]-1H-1,6-naphthyridin-4-one | 545.5; 546.3 | |
| 182 | 2-[2-(3,4-difluoro-2-methyl-phenoxy)-4-methyl-5-(trifluoromethyl)-3-pyridyl]-5-(4-isopropylpiperazin-1-yl)-1H-1,6-naphthyridin-4-one | 573.56; 574.4 | |
| 183 | 2-[2-(3,4-difluoro-2-methyl-phenoxy)-4-methyl-5-(trifluoromethyl)-3-pyridyl]-5-[4-(1-ethylpropyl)piperazin-1-yl]-1H-1,6-naphthyridin-4-one | 601.61; 602.4 | |
| 184 | 2-[2-(3,4-difluoro-2-methyl-phenoxy)-4-methyl-5-(trifluoromethyl)-3-pyridyl]-5-[(3R)-3-(dimethylamino)pyrrolidin-1-yl]-1H-1,6-naphthyridin-4-one | 559.53; 560.3 | |
| 185 | 2-[2-(3,4-difluoro-2-methyl-phenoxy)-4-methyl-5-(trifluoromethyl)-3-pyridyl]-5-[(3-hydroxycyclobutyl)-methyl-amino]-1H-1,6-naphthyridin-4-one | 546.49; 547.3 | |
| 186 | 2-[2-(3,4-difluoro-2-methyl-phenoxy)-4-methyl-5-(trifluoromethyl)-3-pyridyl]-5-(4-methyl-1,4-diazepan-1-yl)-1H-1,6-naphthyridin-4-one | 559.53; 560.3 | |
| 187 | 2-[2-(3,4-difluoro-2-methyl-phenoxy)-4-methyl-5-(trifluoromethyl)-3-pyridyl]-5-[5-(hydroxymethyl)pyrazol-1-yl]-1H-1,6-naphthyridin-4-one | 543.13; 544.4 | $^1$H NMR (400 MHz, $CD_3OD$) δ 8.85-8.33 (m, 3H), 7.70 (s, 1H), 7.14 (app q, J = 9.3 Hz, 1H), 6.99-6.90 (m, 2H), 6.81-6.61 (m, 1H), 4.77 (s, 2H), 2.50 (m, 3H), 2.05 (d, J = 2.1 Hz, 3H) |
| 188 | 2-[2-(3,4-difluoro-2-methoxy-phenoxy)-5-fluoro-4-(trifluoromethyl)phenyl]-5-[2-(dimethylamino)ethylamino]-1H-1,6-naphthyridin-4-one | 552.16; 551.3 (M-1)$^-$ | $^1$H NMR (500 MHz, DMSO-$d_6$) δ 11.94 (s, 1H), 9.99 (s, 1H), 7.99 (d, J = 10.5 Hz, 1H), 7.93 (s, 1H), 7.32 (d, J = 5.9 Hz, 1H), 7.20 (q, J = 9.4 Hz, 1H), 7.00 (s, 1H), 6.48 (d, J = 5.9 Hz, 1H), 6.30 (s, 1H), 3.79 (d, J = 1.1 Hz, 3H), 3.51 (q, J = 6.1 Hz, 2H), 2.45 (t, J = 6.3 Hz, 2H), 2.19 (s, 6H) |

5-[5-(aminomethyl)pyrazol-1-yl]-2-[2-(3,4-difluoro-2-methyl-phenoxy)-4-methyl-5-(trifluoromethyl)-3-pyridyl]-1H-1,6-naphthyridin-4-one (189)

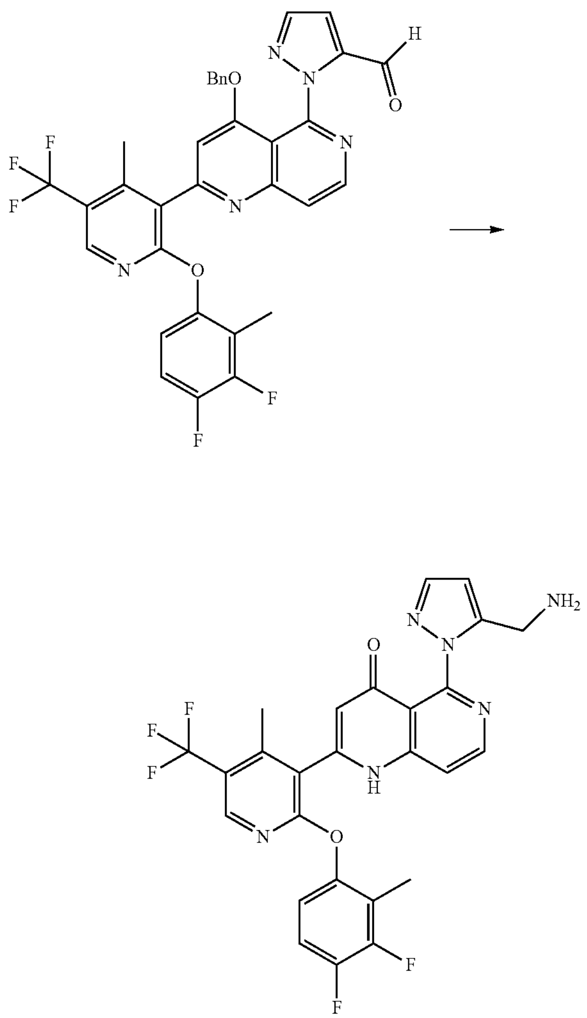 [SMILES: Cc1c(Oc2ncc(C(F)(F)F)c(C)c2-c2cc(OCc3ccccc3)c3c(-n4nccc4C=O)nccc3n2)ccc(F)c1F ; Cc1c(Oc2ncc(C(F)(F)F)c(C)c2-c2cc(=O)c3c(-n4nccc4CN)nccc3[nH]2)ccc(F)c1F]

A methanol (0.5 mL) solution of 2-[4-benzyloxy-2-[2-(3,4-difluoro-2-methyl-phenoxy)-4-methyl-5-(trifluoromethyl)-3-pyridyl]-1,6-naphthyridin-5-yl]pyrazole-3-carbaldehyde (9.2 mg, 0.015 mmol) was treated with ammonium acetate (47 mg, 0.61 mmol) and sodium cyanoborohydride (1.1 mg, 0.018 mmol) and the reaction was stirred at 50° C. for 3 h. The reaction was diluted with methanol (0.5 mL), filtered, and purified by HPLC (1-99% $CH_3CN$/5 mM HCl). The resulting benzyl-protected intermediate was dissolved in ethanol (0.5 mL) and stirred with Pd/C (3 mg) under hydrogen atmosphere for 30 min. The mixture was filtered and purified by HPLC (C18, 1-99% $CH_3CN$/5 mM ammonium formate) to provide 5-[5-(aminomethyl)pyrazol-1-yl]-2-[2-(3,4-difluoro-2-methyl-phenoxy)-4-methyl-5-(trifluoromethyl)-3-pyridyl]-1H-1,6-naphthyridin-4-one formate salt (1.9 mg, 22%). $^1H$ NMR (400 MHz, $CD_3OD$) δ 8.46 (s, 2H), 8.08 (d, J=2.5 Hz, 1H), 7.61 (d, J=5.9 Hz, 1H), 7.13 (app q, J=9.3 Hz, 1H), 6.97-6.88 (m, 1H), 6.59 (d, J=2.6 Hz, 1H), 6.50 (s, 1H), 4.21 (s, 2H), 2.48 (m, 3H), 2.05 (d, J=2.1 Hz, 3H). ESI-MS m/z calc. 542.15, found 543.4 $(M+1)^+$.

2-[2-(4,4-difluoroazepan-1-yl)-5-methyl-6-(trifluoromethyl)-3-pyridyl]-5-hydroxy-1H-1,6-naphthyridin-4-one (190)

5-chloro-2-[2-(4,4-difluoroazepan-1-yl)-5-methyl-6-(trifluoromethyl)-3-pyridyl]-1H-1,6-naphthyridin-4-one (191)

Step 1: 4-benzyloxy-2-[2-(4,4-difluoroazepan-1-yl)-5-methyl-6-(trifluoromethyl)-3-pyridyl]-6-oxido-1,6-naphthyridin-6-ium

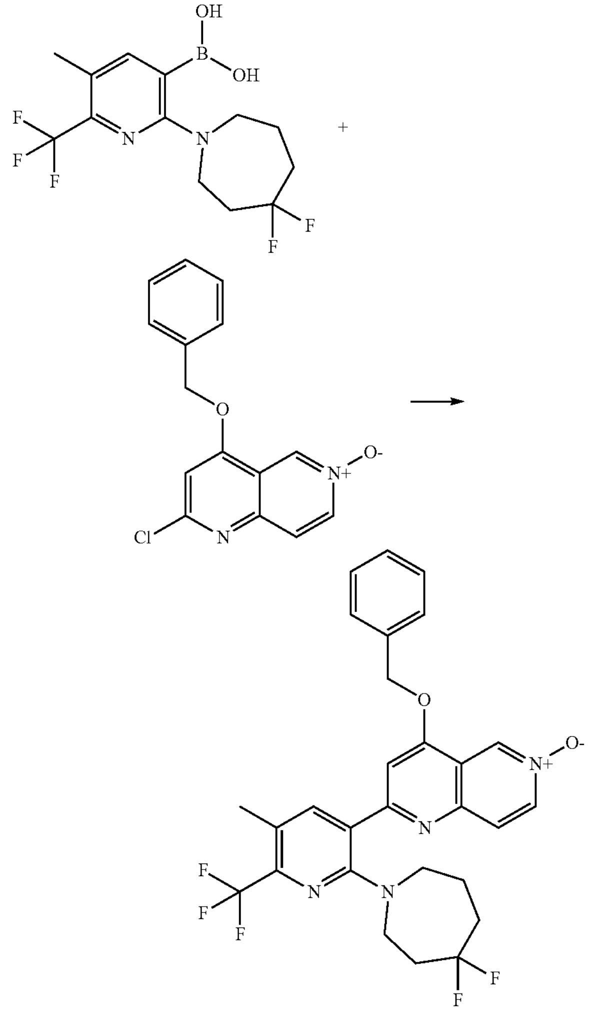

4-Benzyloxy-2-[2-(4,4-difluoroazepan-1-yl)-5-methyl-6-(trifluoromethyl)-3-pyridyl]-6-oxido-1,6-naphthyridin-6-ium was prepared using suitable intermediates in a procedure analogous to that used in the synthesis of compound 167. ESI-MS m/z calc. 544.19, found 545.3 $(M+1)^+$. $^1H$ NMR (400 MHz, DMSO-$d_6$) δ 8.85 (d, J=2.1 Hz, 1H), 8.39 (dd, J=7.3, 2.1 Hz, 1H), 7.93 (d, J=7.3 Hz, 1H), 7.84 (s 1H), 7.62-7.54 (m, 2H), 7.51-7.33 (m, 3H), 7.29 (s, 1H), 5.52 (s, 2H), 2.76 (t, J=6.1 Hz, 2H), 2.53 (s OH), 2.36 (q, J=2.2 Hz, 3H), 2.22 (s, 4H), 1.83 (q, J=14.4, 10.1 Hz, 2H), 1.60-1.40 (m, 2H) ppm.

Step 2: 4-benzyloxy-5-chloro-2-[2-(4,4-difluoroazepan-1-yl)-5-methyl-6-(trifluoromethyl)-3-pyridyl]-1,6-naphthyridine

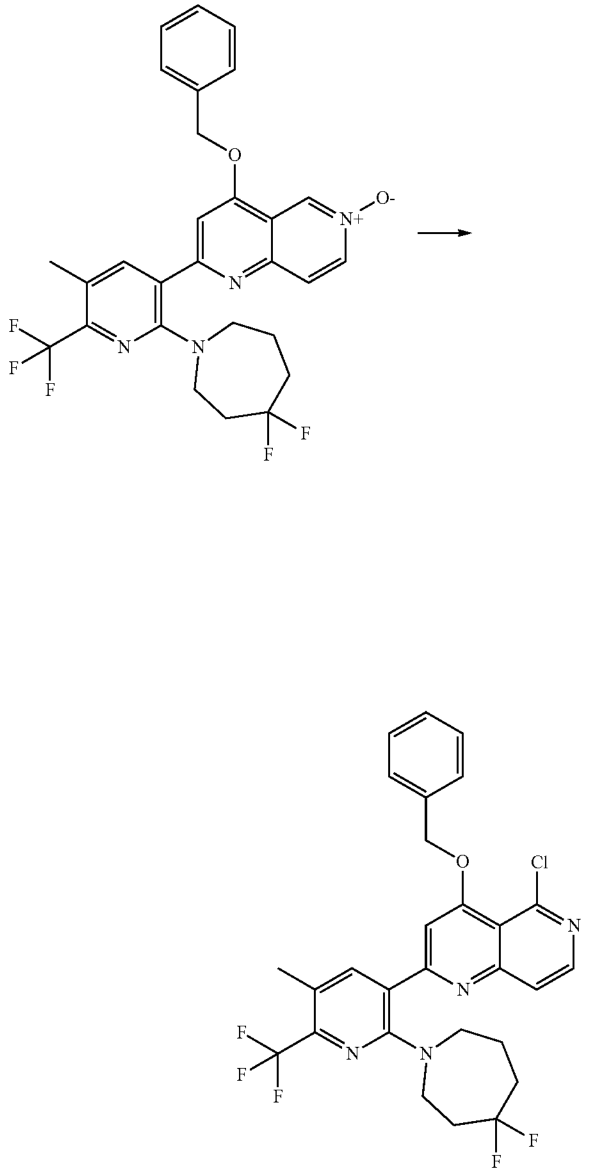

4-Benzyloxy-5-chloro-2-[2-(4,4-difluoroazepan-1-yl)-5-methyl-6-(trifluoromethyl)-3-pyridyl]-1,6-naphthyridine was prepared from 4-benzyloxy-2-[2-(4,4-difluoroazepan-1-yl)-5-methyl-6-(trifluoromethyl)-3-pyridyl]-6-oxido-1,6-naphthyridin-6-ium using a procedure analogous to that found in Compound 13, step 2. ESI-MS m/z calc. 562.16, found 563.2 $(M+1)^+$; Retention time: 2.32 min.

Step 3: 5-chloro-2-[2-(4,4-difluoroazepan-1-yl)-5-methyl-6-(trifluoromethyl)-3-pyridyl]-1H-1,6-naphthyridin-4-one (Compound 191) and 2-[2-(4,4-difluoroazepan-1-yl)-5-methyl-6-(trifluoromethyl)-3-pyridyl]-5-hydroxy-1H-1,6-naphthyridin-4-one (Compound 159)

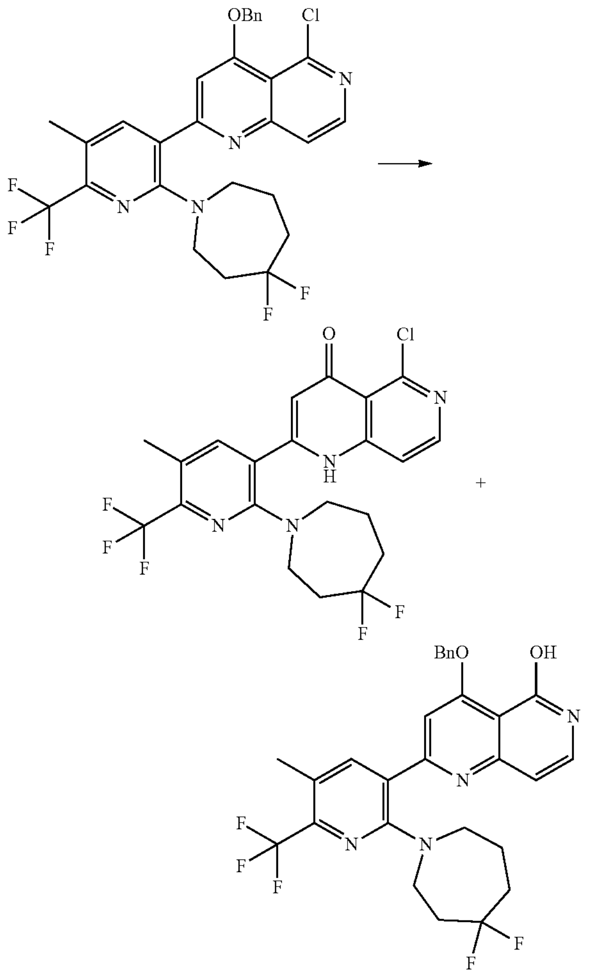

To a mixture of 4-benzyloxy-5-chloro-2-[2-(4,4-difluoroazepan-1-yl)-5-methyl-6-(trifluoromethyl)-3-pyridyl]-1,6-naphthyridine (25 mg, 0.036 mmol), potassium carbonate (15 mg, 0.11 mmol) and ethanol (400 μL) was added 4-benzyloxy-5-chloro-2-[2-(4,4-difluoroazepan-1-yl)-5-methyl-6-(trifluoromethyl)-3-pyridyl]-1,6-naphthyridine (25 mg, 0.0355 mmol). The resulting mixture was heated at 100° C. for 30 min. The mixture was filtered and purified by reverse phase HPLC (C18, 1-99% $CH_3CN$/5 mM HCl) to provide 5-chloro-2-[2-(4,4-difluoroazepan-1-yl)-5-methyl-6-(trifluoromethyl)-3-pyridyl]-1H-1,6-naphthyridin-4-one (191, 2.1 mg, 13%), ESI-MS m/z calc. 472.11, found 473.2 $(M+1)^+$; Retention time: 2.3 min. $^1H$ NMR (400 MHz, $CD_3OD$) δ 8.32 (d, J=5.9 Hz, 1H), 7.76 (s, 1H), 7.41 (d, J=5.9 Hz, 1H), 6.44 (s, 1H), 3.63 (dd, J=5.4, 2.8 Hz, 2H), 3.34 (d, J=6.1 Hz, 2H), 2.40 (q, J=2.1 Hz, 4H), 2.37-2.22 (m, 2H), 2.05-1.94 (m, 2H), 1.83-1.77 (m, 2H). 4-Benzyloxy-2-[2-(4,4-difluoroazepan-1-yl)-5-methyl-6-(trifluoromethyl)-3-pyridyl]-1,6-naphthyridin-5-ol was also isolated (4 mg, 21%). ESI-MS m/z calc. 544.19, found 545.3 $(M+1)^+$.

The benzyl-protected intermediate and Pd/C (1 mg) were stirred in methanol (2 mL) for 16 h under an atmosphere of hydrogen. The mixture was filtered and purified by HPLC (C18, 15-60% acetonitrile/5 mM HCl) to provide 2-[2-(4,4-difluoroazepan-1-yl)-5-methyl-6-(trifluoromethyl)-3-pyridyl]-5-hydroxy-1H-1,6-naphthyridin-4-one (159). ESI-MS m/z calc. 454.14, found 455.2 $(M+1)^+$; Retention time: 2.31 min. $^1H$ NMR (400 MHz, $CD_3OD$) δ 7.80 (s, 1H), 7.71 (d, J=7.4 Hz, 1H), 7.09 (s, 1H), 6.76 (d, J=7.4 Hz, 1H), 3.65-3.58 (m, 2H), 3.17 (t, J=6.0 Hz, 2H), 2.41 (q, J=2.1 Hz, 3H), 2.32 (td, J=15.3, 7.6 Hz, 1H), 2.04-1.88 (m, 3H), 1.80 (p, J=6.1 Hz, 2H).

2-[2-(4,4-difluoroazepan-1-yl)-5-methyl-6-(trifluoromethyl)-3-pyridyl]-5-ethoxy-1H-1,6-naphthyridin-4-one (192)

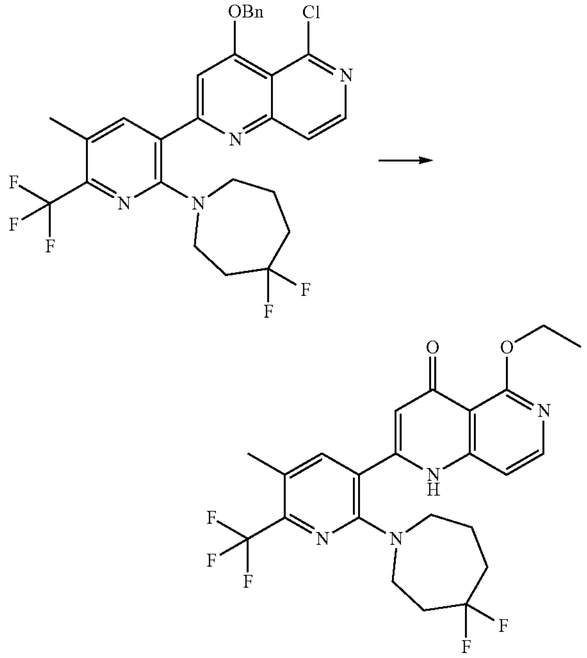

To a solution of ethanol (50 μL, 0.8563 mmol) in THF (360 μL) in ice bath was added NaH (25 mg, 0.63 mmol). The mixture was removed from ice bath and allowed to stir at room temperature. After stirring for 15 min, a solution of 4-benzyloxy-5-chloro-2-[2-(4,4-difluoroazepan-1-yl)-5-methyl-6-(trifluoromethyl)-3-pyridyl]-1,6-naphthyridine (30 mg, 0.043 mmol) in THF (240 μL) was added. The reaction was stirred at 40° C. for 16 h. Purification by reverse phase HPLC (C18, 10-99% $CH_3CN$/5 mM HCl) provided 4-benzyloxy-2-[2-(4,4-difluoroazepan-1-yl)-5-methyl-6-(trifluoromethyl)-3-pyridyl]-5-ethoxy-1,6-naphthyridine (3.6 mg, 15%). ESI-MS m/z calc. 572.22, found 573.3 $(M+1)^+$. The benzyl protected intermediate was dissolved in methanol (400 μL) and stirred with Pd/C (5 mg) under hydrogen atmosphere for 30 min. Filtration and purification by reverse phase HPLC (C18, 1-99% $CH_3CN$/5 mM HCl) provided 2-[2-(4,4-difluoroazepan-1-yl)-5-methyl-6-(trifluoromethyl)-3-pyridyl]-5-ethoxy-1H-1,6-naphthyridin-4-one (1.9 mg, 62%). ESI-MS m/z calc. 482.17, found 483.3 $(M+1)^+$. $^1H$ NMR (400 MHz, $CD_3OD$) δ 8.11 (d, J=6.0 Hz, 1H), 7.73 (s, 1H), 6.97 (d, J=6.0 Hz, 1H), 6.39 (s, 1H), 4.56 (q, J=7.0, 6.1 Hz, 4H), 3.66-3.57 (m, 2H), 2.40 (q, J=2.2 Hz, 3H), 2.35-2.23 (m, 2H), 2.01-1.90 (m, 2H), 1.80 (q, J=6.0 Hz, 2H), 1.45 (t, J=7.0 Hz, 3H).

2-[2-(4,4-difluoroazepan-1-yl)-5-methyl-6-(trifluoromethyl)-3-pyridyl]-5-methyl-1H-1,6-naphthyridin-4-one (193)

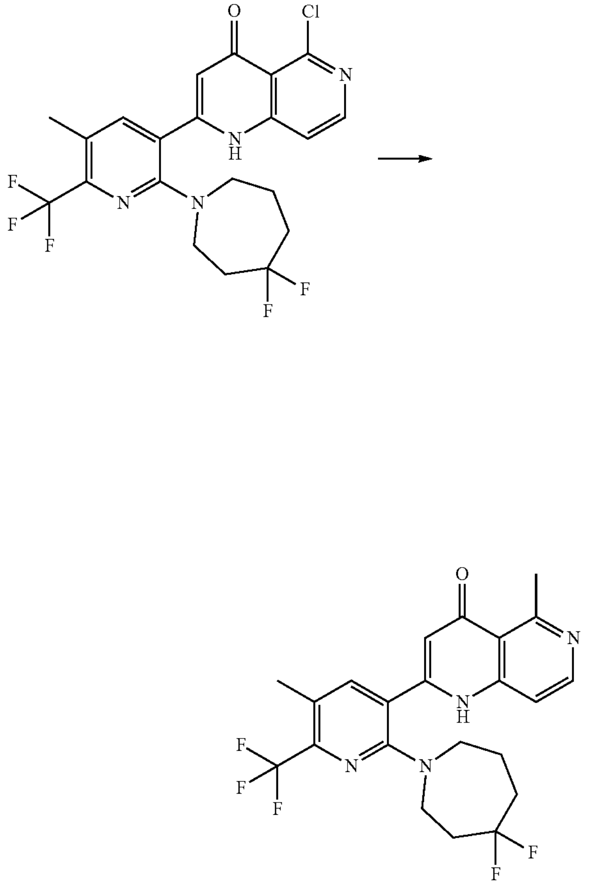

A mixture of 5-chloro-2-[2-(4,4-difluoroazepan-1-yl)-5-methyl-6-(trifluoromethyl)-3-pyridyl]-1H-1,6-naphthyridin-4-one (191, step 2), trimethylalumane (2.5 μL, 0.026 mmol) and $Pd(PPh_3)_4$ (5.5 mg, 0.0048 mmol) was dissolved in dry dioxane (0.5 mL) was gently refluxed for 2 h under nitrogen atmosphere. The mixture was cooled to room temperature and partitioned between ethyl acetate and brine. The organic layer was dried over sodium sulfate, filtered and concentrated. Purification by reverse phase chromatography (C18, 1-99% $CH_3CN$/5 mM HCl) provided 2-[2-(4,4-difluoroazepan-1-yl)-5-methyl-6-(trifluoromethyl)-3-pyridyl]-5-methyl-1H-1,6-naphthyridin-4-one (2.2 mg, 19%) as a yellow solid. ESI-MS m/z calc. 452.16, found 453.19 $(M+1)^+$. $^1H$ NMR (400 MHz, $CD_3OD$) δ 7.88 (s, 1H), 7.71 (d, J=7.3 Hz, 1H), 7.67 (s, 1H), 6.74 (d, J=7.3 Hz, 1H), 3.67-3.59 (m, 2H), 3.07 (m, 5H), 2.43 (s, 3H), 2.32 (qd, J=10.2, 5.1 Hz, 2H), 1.92 (t, J=12.4 Hz, 2H), 1.80 (p, J=6.1 Hz, 2H).

2-[2-(3,4-difluoro-2-methoxy-phenoxy)-5-fluoro-4-(trifluoromethyl)phenyl]-5-[2-(dimethylamino)ethyl-amino]-1H-1,6-naphthyridin-4-one (188)

Step 1: 4-chloro-2-[2-(3,4-difluoro-2-methoxy-phenoxy)-5-fluoro-4-(trifluoromethyl)phenyl]-1,6-naphthyridine

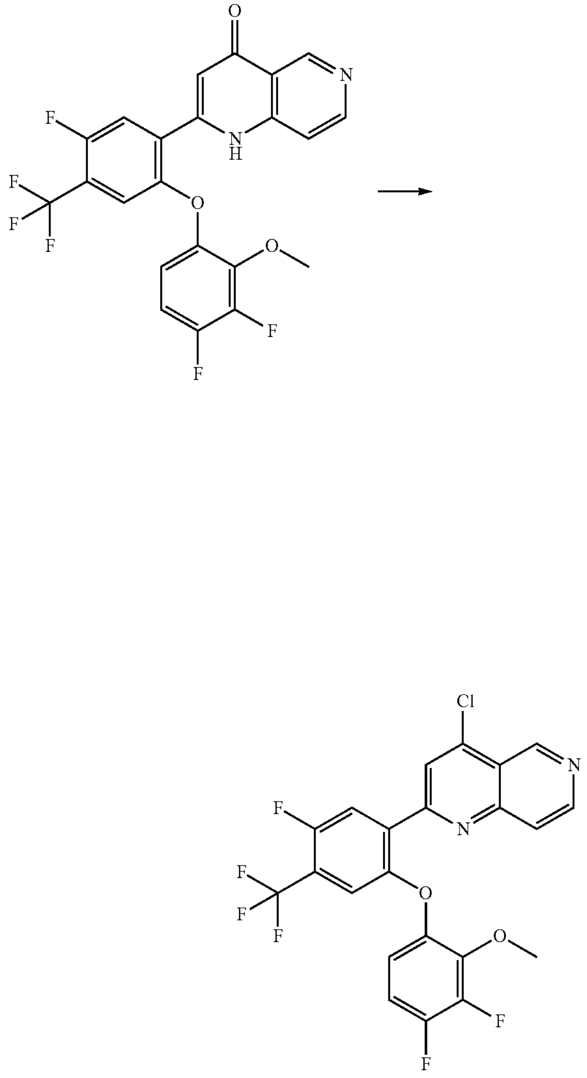

4-Chloro-2-[2-(3,4-difluoro-2-methoxy-phenoxy)-5-fluoro-4-(trifluoromethyl)phenyl]-1,6-naphthyridine was prepared from 2-[2-(3,4-difluoro-2-methoxy-phenoxy)-5-fluoro-4-(trifluoromethyl)phenyl]-1H-1,6-naphthyridin-4-one (141) using a procedure analogous to that found in Intermediate B-6, step 1. $^{1}$H NMR (500 MHz, DMSO-$d_6$) δ 9.65 (d, J=0.9 Hz, 1H), 8.93 (d, J=5.9 Hz, 1H), 8.37 (s, 1H), 8.09 (d, J=10.8 Hz, 1H), 8.05 (dd, J=5.8, 0.9 Hz, 1H), 7.33 (d, J=5.8 Hz, 1H), 7.20 (td, J=9.8, 8.4 Hz, 1H), 7.10 (ddd, J=9.4, 5.1, 2.2 Hz, 1H), 3.83 (d, J=1.4 Hz, 3H) ppm. ESI-MS m/z calc. 484.04, found 485.0 $(M+1)^+$.

Step 2: 4-benzyloxy-2-[2-(3,4-difluoro-2-methoxy-phenoxy)-5-fluoro-4-(trifluoromethyl)phenyl]-1,6-naphthyridine

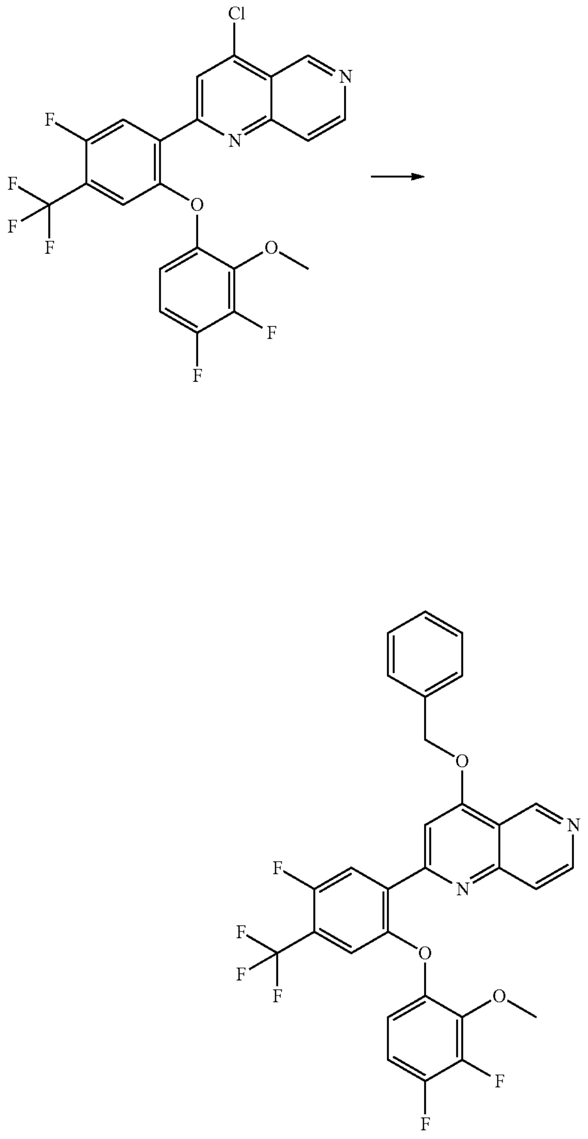

4-Benzyloxy-2-[2-(3,4-difluoro-2-methoxy-phenoxy)-5-fluoro-4-(trifluoromethyl)phenyl]-1,6-naphthyridine was prepared from 4-chloro-2-[2-(3,4-difluoro-2-methoxy-phenoxy)-5-fluoro-4-(trifluoromethyl)phenyl]-1,6-naphthyridine and benzyl alcohol using a procedure analogous to that found in Intermediate A-4 step 1 using THF as the solvent. $^{1}$H NMR (400 MHz, DMSO-$d_6$) δ 9.60 (d, J=0.9 Hz, 1H), 8.81 (d, J=5.9 Hz, 1H), 8.05 (d, J=10.9 Hz, 1H), 7.89 (dd, J=5.9, 0.9 Hz, 1H), 7.78 (s, 1H), 7.58-7.50 (m, 2H), 7.39-7.28 (m, 4H), 7.21 (td, J=9.7, 8.5 Hz, 1H), 7.04 (ddd, J=9.3, 5.1, 2.3 Hz, 1H), 5.52 (s, 2H), 3.76 (d, J=1.4 Hz, 3H) ppm. ESI-MS m/z calc. 556.12, found 557.2 $(M+1)^+$.

Step 3: 4-benzyloxy-2-[2-(3,4-difluoro-2-methoxy-phenoxy)-5-fluoro-4-(trifluoromethyl)phenyl]-6-oxido-1,6-naphthyridin-6-ium

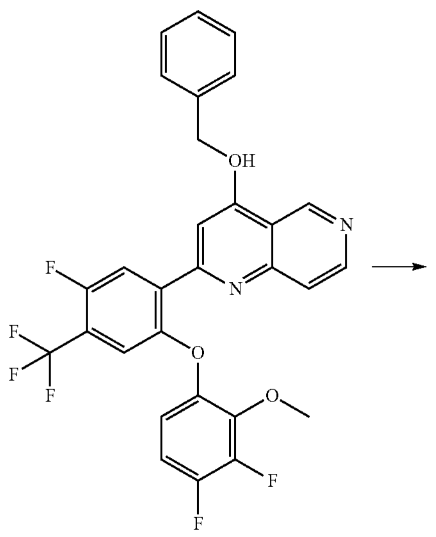

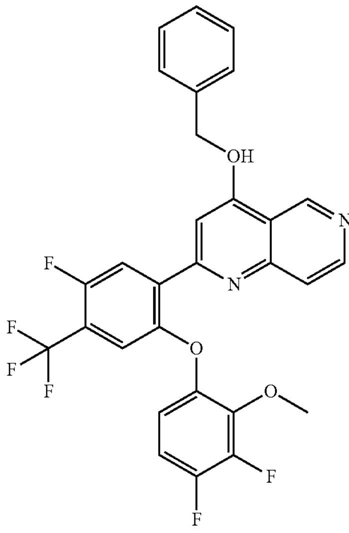

4-Benzyloxy-2-[2-(3,4-difluoro-2-methoxy-phenoxy)-5-fluoro-4-(trifluoromethyl)phenyl]-6-oxido-1,6-naphthyridin-6-ium was prepared from 4-benzyloxy-2-[2-(3,4-difluoro-2-methoxy-phenoxy)-5-fluoro-4-(trifluoromethyl)phenyl]-1,6-naphthyridine using a procedure analogous to that found in Intermediate A-4, step 2. $^1$H NMR (500 MHz, DMSO-$d_6$) δ 8.82 (dd, J=2.2, 0.6 Hz, 1H), 8.41 (dd, J=7.3, 2.1 Hz, 1H), 8.03 (d, J=10.9 Hz, 1H), 7.94 (dd, J=7.3, 0.6 Hz, 1H), 7.75 (s, 1H), 7.52-7.46 (m, 2H), 7.34-7.28 (m, 3H), 7.27 (d, J=5.9 Hz, 1H), 7.24-7.17 (m, 1H), 7.03 (ddd, J=9.3, 5.1, 2.2 Hz, 1H), 5.47 (s, 2H), 3.74 (d, J=1.3 Hz, 3H) ppm. ESI-MS m/z calc. 572.12, found 573.1 $(M+1)^+$.

Step 4: 4-benzyloxy-5-chloro-2-[2-(3,4-difluoro-2-methoxy-phenoxy)-5-fluoro-4-(trifluoromethyl)phenyl]-1,6-naphthyridine

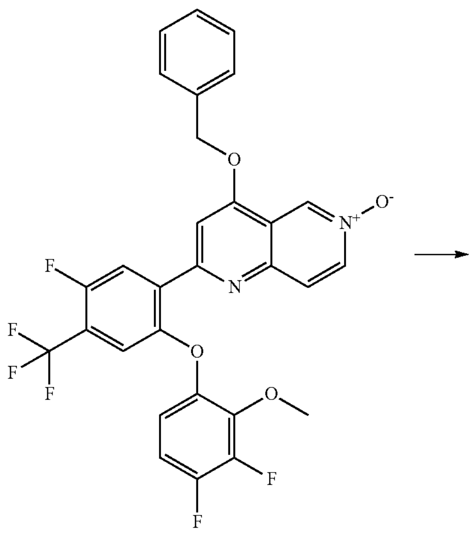

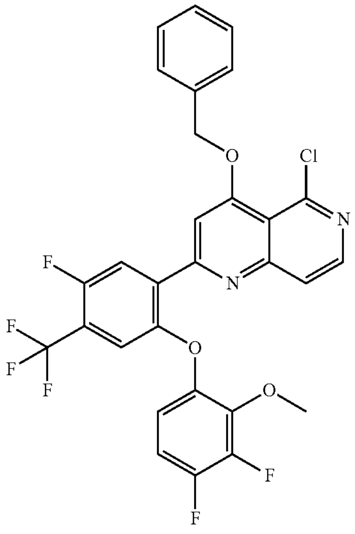

4-Benzyloxy-5-chloro-2-[2-(3,4-difluoro-2-methoxy-phenoxy)-5-fluoro-4-(trifluoromethyl)phenyl]-1,6-naphthyridine was prepared from 4-benzyloxy-2-[2-(3,4-difluoro-2-methoxy-phenoxy)-5-fluoro-4-(trifluoromethyl)phenyl]-6-oxido-1,6-naphthyridin-6-ium using a procedure analogous to that found in Compound 13, step 2. $^1$H NMR (500 MHz, DMSO-$d_6$) δ 8.51 (d, J=5.7 Hz, 1H), 8.07 (d, J=10.8 Hz, 1H), 7.88-7.84 (m, 2H), 7.55-7.49 (m, 2H), 7.38-7.29 (m, 4H), 7.25-7.16 (m, 1H), 7.04 (ddd, J=9.3, 5.0, 2.2 Hz, 1H), 5.50 (s, 2H), 3.75 (d, J=1.3 Hz, 3H) ppm. ESI-MS m/z calc. 590.08, found 591.2 $(M+1)^+$.

Step 5: N-[4-benzyloxy-2-[2-(3,4-difluoro-2-methoxy-phenoxy)-5-fluoro-4-(trifluoromethyl)phenyl]-1,6-naphthyridin-5-yl]-N,N-dimethyl-ethane-1,2-diamine

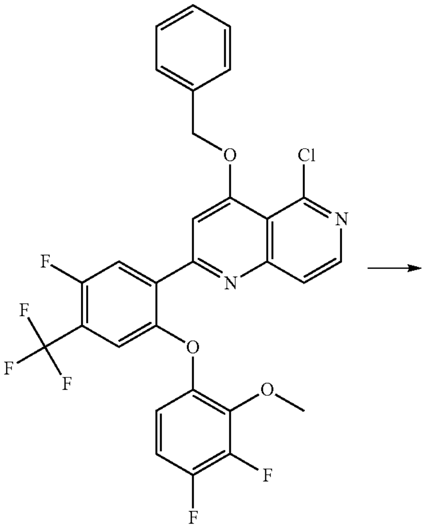

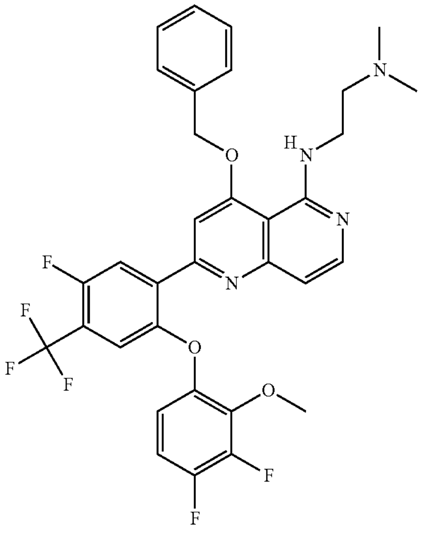

N',N'-Dimethylethane-1,2-diamine (28 μL, 0.26 mmol) was added to a solution of 4-benzyloxy-5-chloro-2-[2-(3,4-difluoro-2-methoxy-phenoxy)-5-fluoro-4-(trifluoromethyl)phenyl]-1,6-naphthyridine (30 mg, 0.051 mmol) in NMP (0.7 mL) and the mixture stirred in a sealed vial at 100° C. for 40 min. The mixture was cooled to room temperature, diluted with ethyl acetate (10 mL) and washed with saturated sodium bicarbonate (5 mL), water (5 mL) and brine. The organic layer was dried over magnesium sulfate, filtered concentrated in vacuo to afford N-[4-benzyloxy-2-[2-(3,4-difluoro-2-methoxy-phenoxy)-5-fluoro-4-(trifluoromethyl)phenyl]-1,6-naphthyridin-5-yl]-N,N-dimethyl-ethane-1,2-diamine (35 mg, 107%) as a yellow oil. ESI-MS m/z calc. 642.21, found 643.2 $(M+1)^+$.

Step 6: 2-[2-(3,4-difluoro-2-methoxy-phenoxy)-5-fluoro-4-(trifluoromethyl)phenyl]-5-[2-(dimethylamino)ethylamino]-1H-1,6-naphthyridin-4-one (188)

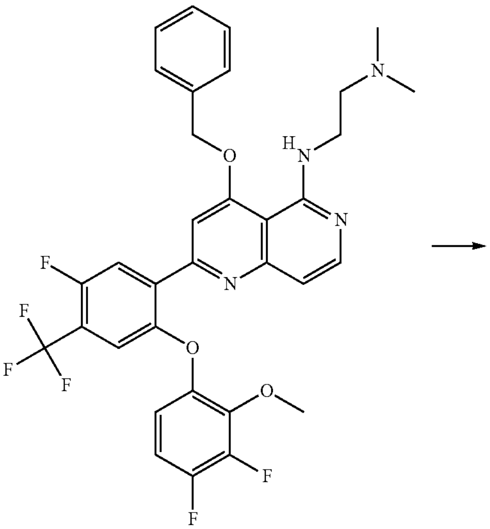

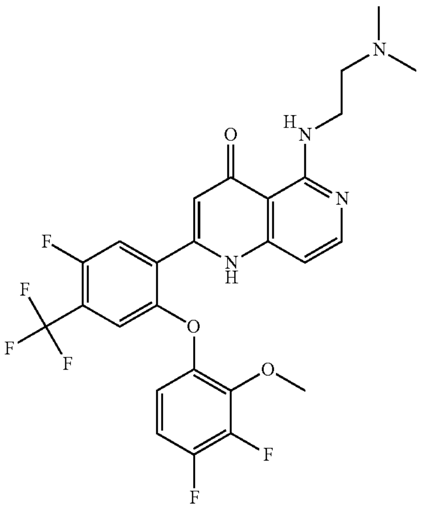

A mixture of N-[4-benzyloxy-2-[2-(3,4-difluoro-2-methoxy-phenoxy)-5-fluoro-4-(trifluoromethyl)phenyl]-1,6-naphthyridin-5-yl]-N,N-dimethyl-ethane-1,2-diamine (35 mg, 0.055 mmol) and 5% Pd/C (23 mg, 0.011 mmol) was stirred for 2 min under hydrogen atmosphere. Filtration and HPLC purification provided 2-[2-(3,4-difluoro-2-methoxy-phenoxy)-5-fluoro-4-(trifluoromethyl)phenyl]-5-[2-(dimethylamino)ethylamino]-1H-1,6-naphthyridin-4-one (188, 12 mg, 40%). $^1H$ NMR (500 MHz, DMSO-$d_6$) δ 11.94 (s, 1H), 9.99 (s, 1H), 7.99 (d, J=10.5 Hz, 1H), 7.93 (s, 1H), 7.32 (d, J=5.9 Hz, 1H), 7.20 (q, J=9.4 Hz, 1H), 7.00 (s, 1H), 6.48 (d, J=5.9 Hz, 1H), 6.30 (s, 1H), 3.79 (d, J=1.1 Hz, 3H), 3.51 (q, J=6.1 Hz, 2H), 2.45 (t, J=6.3 Hz, 2H), 2.19 (s, 6H) ppm. ESI-MS m/z calc. 552.16, found 551.3 $(M-1)^-$.

Example 7

2-[2-(3,4-difluoro-2-methyl-phenoxy)-4-methyl-5-(trifluoromethyl)-3-pyridyl]-5-hydroxy-1H-1,6-naphthyridin-4-one (194)

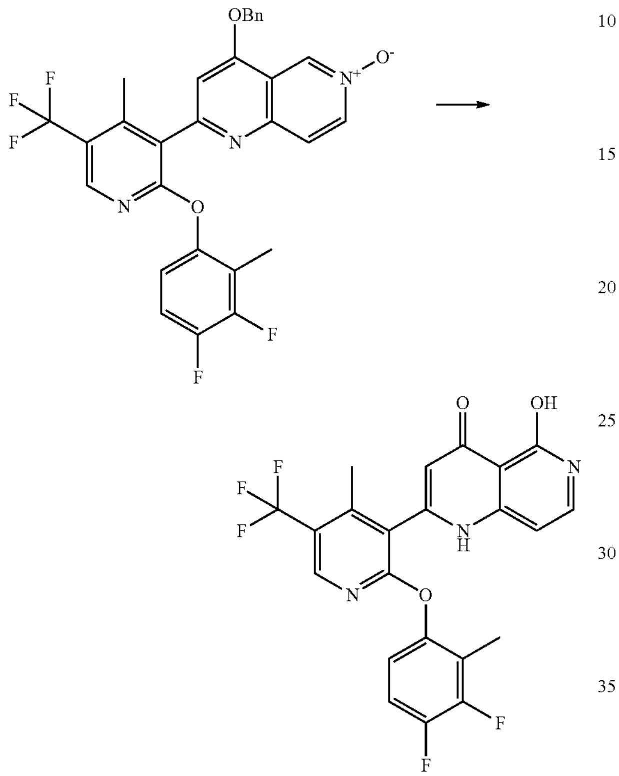

A mixture of 4-benzyloxy-2-[2-(3,4-difluoro-2-methyl-phenoxy)-4-methyl-5-(trifluoromethyl)-3-pyridyl]-6-oxido-1,6-naphthyridin-6-ium (100 mg, 0.181 mmol), ammonia in dioxane (542 μL of 0.5 M, 0.27 mmol), DIPEA (118 μL, 0.678 mmol) and bromo(tripyrrolidin-1-yl)phosphonium hexafluorophosphate (110 mg, 0.236 mmol) in dichloromethane (1 mL) was stirred in a sealed microwave vial at room temperature under an atmosphere of nitrogen for 17 h. The mixture was diluted with methanol (2 mL), filtered and purified by reverse phase chromatography (C18, 1-99% acetonitrile/5 mM HCl) to provide 4-benzyloxy-2-[2-(3,4-difluoro-2-methyl-phenoxy)-4-methyl-5-(trifluoromethyl)-3-pyridyl]-1,6-naphthyridin-5-ol. ESI-MS m/z calc. 553.14, found 554.0 $(M+1)^+$. The benzyl-protected intermediate was dissolved in ethanol (2 mL) and stirred with 10% Pd/C (39 mg, 0.037 mmol) under an atmosphere of hydrogen for 1 h. The mixture was filtered and purified by reverse phase chromatography (C18, 1-99% acetonitrile/5 mM HCl) to provide 2-[2-(3,4-difluoro-2-methyl-phenoxy)-4-methyl-5-(trifluoromethyl)-3-pyridyl]-5-hydroxy-1H-1,6-naphthyridin-4-one hydrochloride (13 mg, 14%) as a white solid. ESI-MS m/z calc. 463.10, found 464.1 $(M+1)^+$. $^1H$ NMR (400 MHz, $CD_3OD$) δ 8.49 (s, 1H), 7.75 (d, J=7.4 Hz, 1H), 7.30 (s, 1H), 7.13 (q, J=9.3 Hz, 1H), 7.00-6.87 (m, 1H), 6.79 (d, J=7.5 Hz, 1H), 2.41 (d, J=1.5 Hz, 3H), 2.03 (d, J=2.2 Hz, 3H).

2-[2-(3,4-difluoro-2-methyl-phenoxy)-4-methyl-5-(trifluoromethyl)-3-pyridyl]-5-(3-methoxycyclobutoxy)-1H-1,6-naphthyridin-4-one (trans isomer) (195)

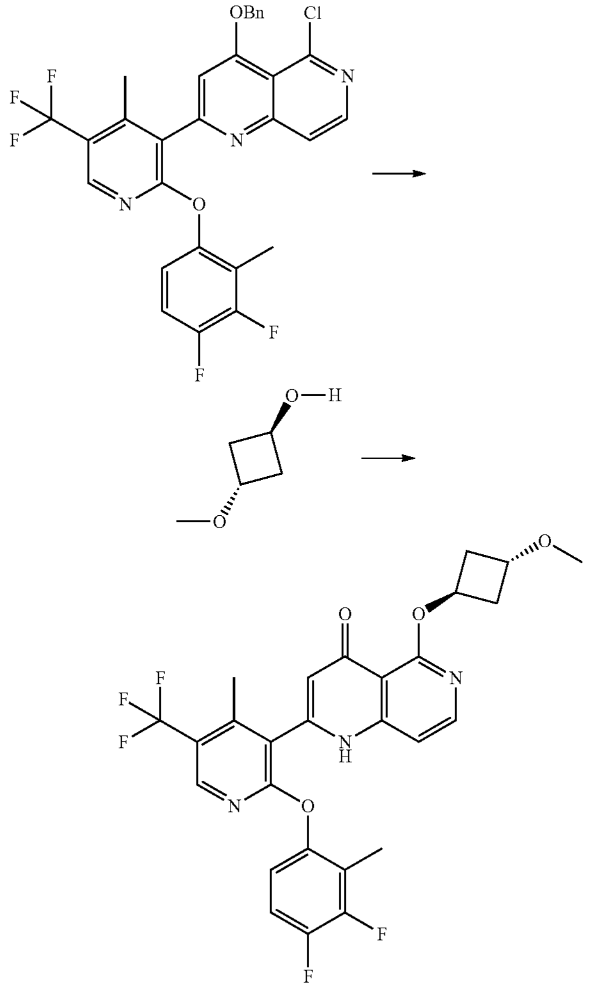

To a stirring solution of 3-methoxycyclobutanol (trans isomer, 9 mg, 0.09 mmol) in THF at 0° C. under nitrogen was added sodium hydride (0.7 mg, 0.03 mmol). The mixture was stirred at 0° C. for 30 min and then treated slowly with a solution of 4-benzyloxy-5-chloro-2-[2-(3,4-difluoro-2-methyl-phenoxy)-4-methyl-5-(trifluoromethyl)-3-pyridyl]-1,6-naphthyridine (20 mg, 0.029 mmol) in THF (1 mL). The resulting mixture was stirred at 50° C. for 16 h and then quenched with water. The mixture was filtered and purified by HPLC (C18, 30-99% $CH_3CN$/5 mM HCl) to provide 2-[2-(3,4-difluoro-2-methyl-phenoxy)-4-methyl-5-(trifluoromethyl)-3-pyridyl]-5-(3-methoxycyclobutoxy)-1H-1,6-naphthyridin-4-one (1.2 mg, 8%). The intermediate was dissolved in methanol (2 mL) and stirred with 10% Pd/C (8 mg) under an atmosphere of hydrogen for 2 h. The mixture was filtered and purified by HPLC (C18, 30-70% $CH_3CN$/5 mM HCl) to provide 2-[2-(3,4-difluoro-2-methyl-phenoxy)-4-methyl-5-(trifluoromethyl)-3-pyridyl]-5-(3-methoxycyclobutoxy)-1H-1,6-naphthyridin-4-one (trans isomer). ESI-MS m/z calc. 547.15, found 548.0 $(M+1)^+$.

2-[2-(3,4-difluoro-2-methyl-phenoxy)-4-methyl-5-(trifluoromethyl)-3-pyridyl]-5-(2-oxopyrrolidin-1-yl)-1H-1,6-naphthyridin-4-one (196)

Step 1: 1-[4-benzyloxy-2-[2-(3,4-difluoro-2-methyl-phenoxy)-4-methyl-5-(trifluoromethyl)-3-pyridyl]-6-oxido-1,6-naphthyridin-6-ium-5-yl]pyrrolidin-2-one

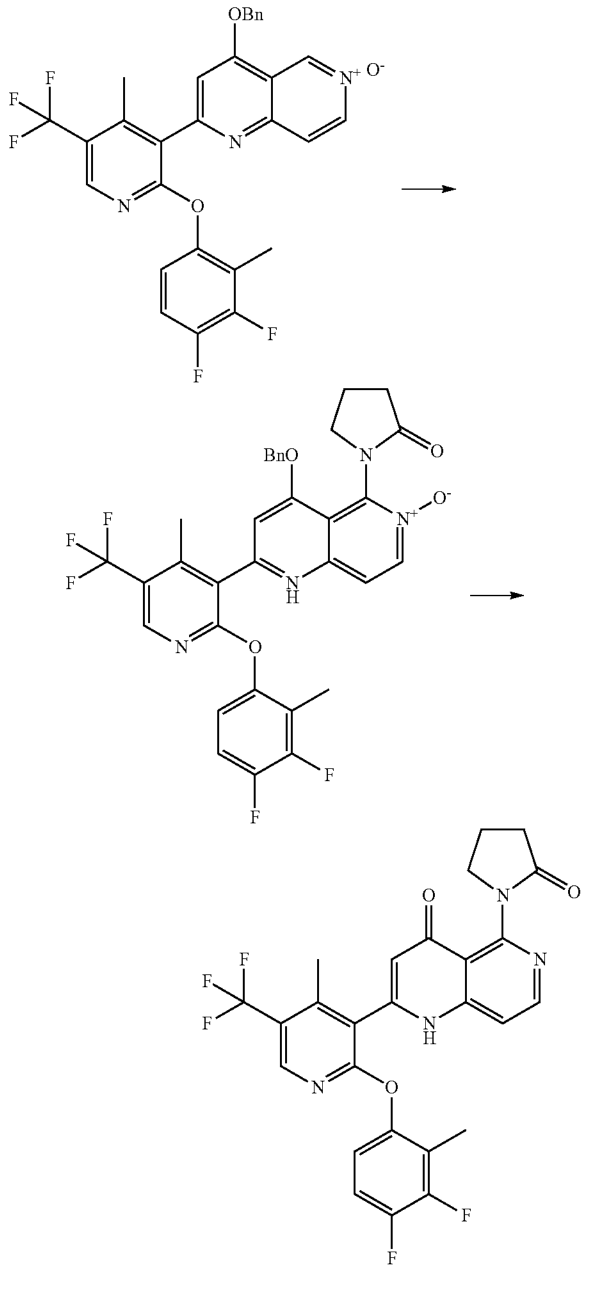

A vial was charged with 4-benzyloxy-2-[2-(3,4-difluoro-2-methyl-phenoxy)-4-methyl-5-(trifluoromethyl)-3-pyridyl]-6-oxido-1,6-naphthyridin-6-ium (100 mg, 0.181 mmol), pyrrolidin-2-one (41 μL, 0.54 mmol), copper (II) acetate (4 mg, 0.02 mmol), silver(I) carbonate (100 mg, 0.363 mmol) and toluene (1 mL). The vial was capped, purged with nitrogen and the mixture heated at 120° C. for 12 h. The cooled mixture was diluted with methanol (2 mL), filtered, and purified by HPLC (1-99% acetonitrile/5 mM HCl) to provide 1-[4-benzyloxy-2-[2-(3,4-difluoro-2-methyl-phenoxy)-4-methyl-5-(trifluoromethyl)-3-pyridyl]-6-oxido-1,6-naphthyridin-6-ium-5-yl]pyrrolidin-2-one (35 mg, 30%) as a white solid. ESI-MS m/z calc. 636.18, found 637.1 $(M+1)^+$.

Step 2: 2-[2-(3,4-difluoro-2-methyl-phenoxy)-4-methyl-5-(trifluoromethyl)-3-pyridyl]-5-(2-oxopyrrolidin-1-yl)-1H-1,6-naphthyridin-4-one A mixture of 1-[4-benzyloxy-2-[2-(3,4-difluoro-2-methyl-phenoxy)-4-methyl-5-(trifluoromethyl)-3-pyridyl]-6-oxido-1,6-naphthyridin-6-ium-5-yl]pyrrolidin-2-one (30 mg, 0.047 mmol), $NH_4Cl$ (4 mg, 0.075 mmol) and zinc (16 mg, 0.25 mmol) in THF (300 μL) and water (30 μL) was stirred at room temperature for 1 h. The mixture was filtered through a short bed of silica gel eluting with ethyl acetate (200 mL). The filtrate was concentrated to provide 1-[4-benzyloxy-2-[2-(3,4-difluoro-2-methyl-phenoxy)-4-methyl-5-(trifluoromethyl)-3-pyridyl]-1,6-naphthyridin-5-yl]pyrrolidin-2-one. The benzyl-protected intermediate was dissolved in ethanol (600 μL) and stirred with 10% Pd/C (1 mg, 0.009 mmol) under hydrogen atmosphere for 30 min. Filtration and purification by reverse phase chromatography (C18, 0-1-99% $CH_3CN$/5 mM HCl) provided 2-[2-(3,4-difluoro-2-methyl-phenoxy)-4-methyl-5-(trifluoromethyl)-3-pyridyl]-5-(2-oxopyrrolidin-1-yl)-1H-1,6-naphthyridin-4-one hydrochloride (10 mg, 37%) as a white solid. ESI-MS m/z calc. 530.14, found 531.0 $(M+1)^+$. $^1H$ NMR (400 MHz, DMSO-$d_6$) δ 12.45 (s, 1H), 8.61 (s, 1H), 8.47 (d, J=5.8 Hz, 1H), 7.55-7.41 (m, 1H), 7.35 (q, J=9.4 Hz, 1H), 7.15-7.00 (m, 1H), 6.36 (s, 1H), 3.92-3.73 (m, 2H), 2.46-2.36 (m, 5H), 2.27-2.09 (m, 2H), 2.02 (d, J=2.0 Hz, 3H).

2-[2-(3,4-difluoro-2-methyl-phenoxy)-4-methyl-5-(trifluoromethyl)-3-pyridyl]-5-pyrazol-1-yl-1H-1,6-naphthyridin-4-one (197)

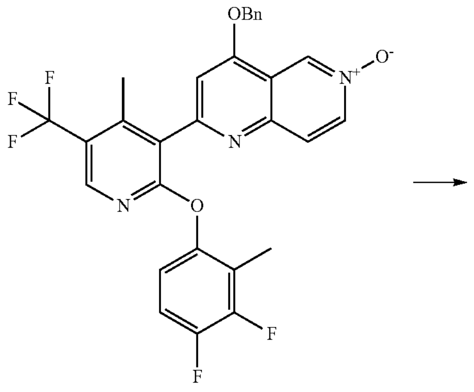

-continued

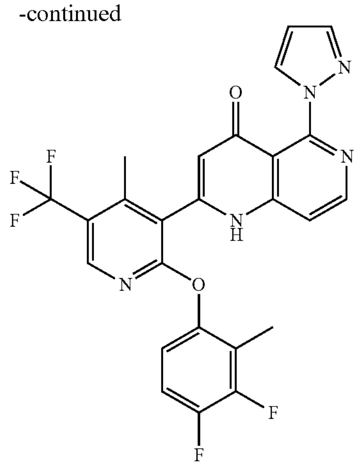

A mixture of 4-benzyloxy-2-[2-(3,4-difluoro-2-methyl-phenoxy)-4-methyl-5-(trifluoromethyl)-3-pyridyl]-6-oxido-1,6-naphthyridin-6-ium (100 mg, 0.181 mmol), 1H-pyrazole (19 mg, 0.281 mmol), DIPEA (118 μL, 0.678 mmol) and bromo(tripyrrolidin-1-yl)phosphonium (phosphorus hexafluoride) (110 mg, 0.236 mmol) in dichloromethane (1 mL) was stirred in a sealed vial under nitrogen at room temperature for 17 h. The mixture was diluted with methanol (2 mL), filtered, and purified by reverse phase chromatography (C18, 1-99% $CH_3CN$/5 mM HCl) to provide 4-benzyloxy-2-[2-(3,4-difluoro-2-methyl-phenoxy)-4-methyl-5-(trifluoromethyl)-3-pyridyl]-5-pyrazol-1-yl-1,6-naphthyridine (61 mg, 56%). The benzyl-protected intermediate was dissolved in ethanol (2 mL) and stirred with 10% Pd/C (4 mg, 0.04 mmol) under hydrogen atmosphere for 2 h. Filtration and purification by reverse phase chromatography (C18, 1-99% $CH_3CN$/5 mM HCl) provided 2-[2-(3,4-difluoro-2-methyl-phenoxy)-4-methyl-5-(trifluoromethyl)-3-pyridyl]-5-pyrazol-1-yl-1H-1,6-naphthyridin-4-one (19 mg, 20%). ESI-MS m/z calc. 513.12, found 514.1 $(M+1)^+$. $^1H$ NMR (400 MHz, DMSO-$d_6$) δ 12.53 (s, 1H), 8.61 (s, 1H), 8.50 (d, J=5.8 Hz, 1H), 8.07 (d, J=2.5 Hz, 1H), 7.66 (d, J=1.7 Hz, 1H), 7.61-7.47 (m, 1H), 7.36 (q, J=9.4 Hz, 1H), 7.18-7.00 (m, 1H), 6.44 (s, 1H), 6.39 (s, 1H), 2.44 (s, 3H), 2.03 (d, J=2.1 Hz, 3H).

2-[2-(3,4-difluoro-2-methyl-phenoxy)-4-methyl-5-(trifluoromethyl)-3-pyridyl]-5-tetrahydropyran-4-yloxy-1H-1,6-naphthyridin-4-one (198)

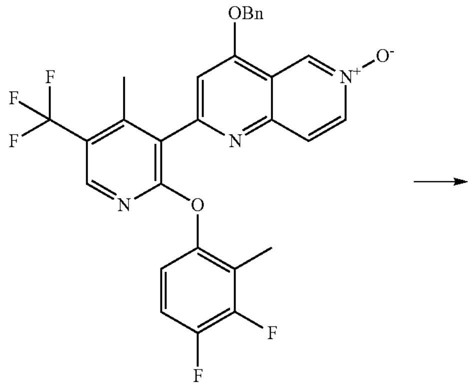

-continued

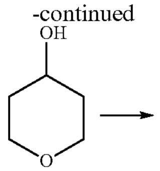

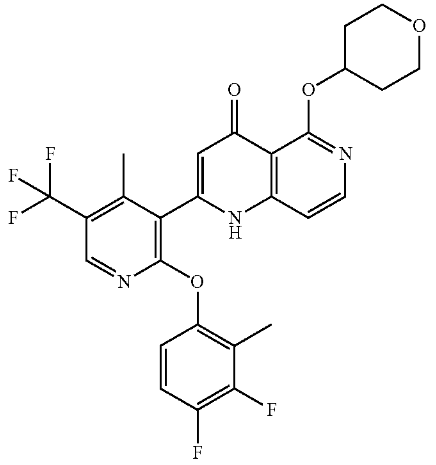

To a solution of 4-benzyloxy-2-[2-(3,4-difluoro-2-methyl-phenoxy)-4-methyl-5-(trifluoromethyl)-3-pyridyl]-6-oxido-1,6-naphthyridin-6-ium (50 mg, 0.090 mmol) in DCM (0.5 mL) were added tetrahydropyran-4-ol (28 mg, 0.27 mmol), sodium carbonate (30 mg, 0.28 mmol), 3 Å molecular sieves and bromo(tripyrrolidin-1-yl)phosphonium (phosphorus hexafluoride) (60 mg, 0.13 mmol). The mixture was stirred at room temperature for 48 h. Additional sodium carbonate (30 mg, 0.28 mmol) and bromo(tripyrrolidin-1-yl)phosphonium (phosphorus hexafluoride Ion) (60 mg, 0.13 mmol) were added and stirring continued for 24 h at room temperature. The mixture was concentrated, dissolved in DMSO and filtered. Purification by HPLC (C18, 30-99% $CH_3CN$/5 mM HCl) provided 4-benzyloxy-2-[2-(3,4-difluoro-2-methyl-phenoxy)-4-methyl-5-(trifluoromethyl)-3-pyridyl]-5-tetrahydropyran-4-yloxy-1,6-naphthyridine (5.5 mg, 9%). ESI-MS m/z calc. 637.2, found 368.0 $(M+1)^+$. The benzyl-protected intermediate was stirred with 10% Pd/C (5 mg) in methanol (2 mL) under hydrogen atmosphere for 2 h. Filtration and purification by HPLC (C18, 30-70% $CH_3CN$/5 mM HCl) provided 2-[2-(3,4-difluoro-2-methyl-phenoxy)-4-methyl-5-(trifluoromethyl)-3-pyridyl]-5-tetrahydropyran-4-yloxy-1H-1,6-naphthyridin-4-one (1.7 mg, 3%). ESI-MS m/z calc. 547.15, found 548.0 $(M+1)^+$.

Example 8

2-[2-[2-(3,4-difluoro-2-methoxy-phenoxy)-5-fluoro-4-(trifluoromethyl)phenyl]-4-oxo-1H-1,6-naphthyridin-5-yl]acetamide (199)

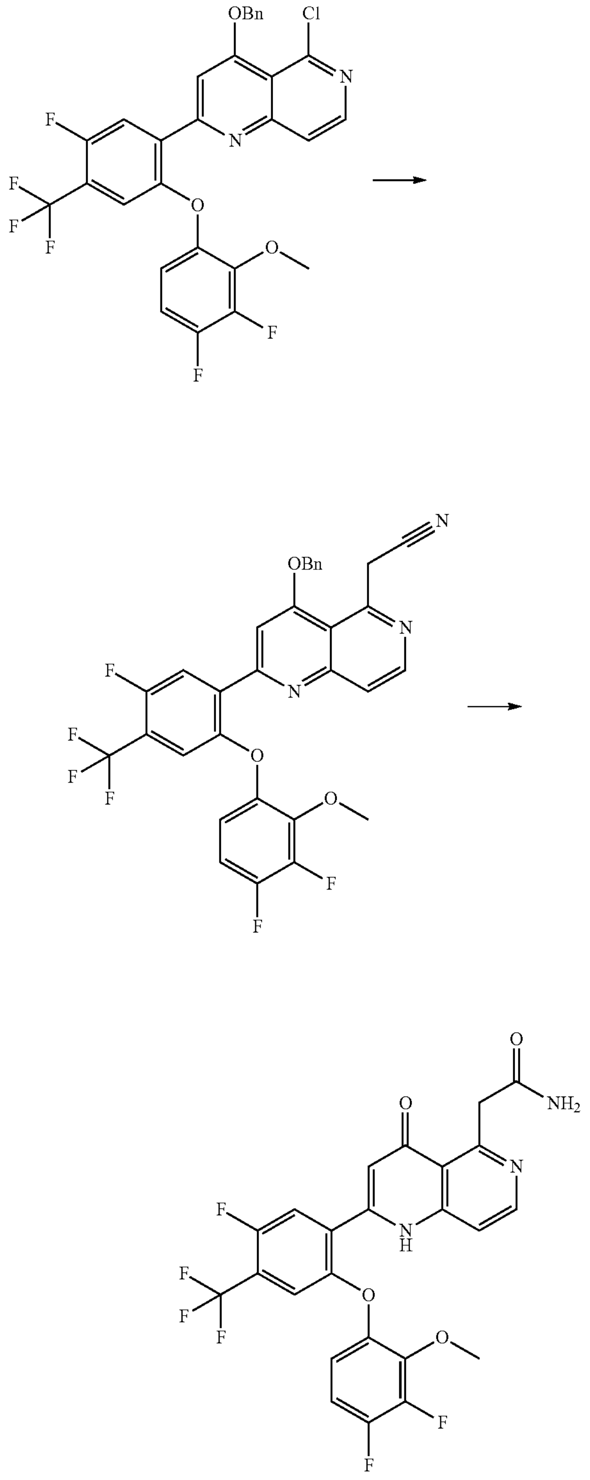

Step 1: 2-[4-benzyloxy-2-[2-(3,4-difluoro-2-methoxy-phenoxy)-5-fluoro-4-(trifluoromethyl)phenyl]-1,6-naphthyridin-5-yl]acetonitrile n-BuLi (70 μL of 2.5 M, 0.1750 mmol) was added to a solution of anhydrous acetonitrile (10 μL, 0.19 mmol) in THF (0.5 mL) cooled to −78° C. and the mixture stirred at this temperature. After 10 min, this solution was added dropwise to a solution of 4-benzyloxy-5-chloro-2-[2-(3,4-difluoro-2-methoxy-phenoxy)-5-fluoro-4-(trifluoromethyl)phenyl]-1,6-naphthyridine (188, step 4, 50 mg, 0.085 mmol) in THF (1 mL), cooled to −78° C. and the resulting solution stirred at this temperature. After 2 h, in a separate flask, n-BuLi (70 μL of 2.5 M, 0.18 mmol) was added to a solution of acetonitrile (10 μL, 0.19 mmol) in THF (1 mL) cooled to −78° C. and the mixture stirred for 15 min at this temperature. The mixture was added dropwise to the reaction mixture at −78° C. and stirred at this temperature. After 20 min, the reaction was quenched with saturated aqueous $NH_4Cl$ (2 mL), followed by the addition of water (5 mL). The suspension allowed to warm to room temperature and diluted with ethyl acetate. The organic layer was separated, washed with brine, dried over magnesium sulfate, filtered and concentrated in vacuo to provide crude 2-[4-benzyloxy-2-[2-(3,4-difluoro-2-methoxy-phenoxy)-5-fluoro-4-(trifluoromethyl)phenyl]-1,6-naphthyridin-5-yl]acetonitrile (53.00 mg, 105%) as a yellow sticky foam. ESI-MS m/z calc. 595.49, found 596.2 $(M+1)^+$.

Step 2: 2-[2-[2-(3,4-difluoro-2-methoxy-phenoxy)-5-fluoro-4-(trifluoromethyl)phenyl]-4-oxo-1H-1,6-naphthyridin-5-yl]acetamide (199)

Ghaffar-Parkins catalyst (2.7 mg, 0.0063 mmol) was added to a solution of 2-[4-benzyloxy-2-[2-(3,4-difluoro-2-methoxy-phenoxy)-5-fluoro-4-(trifluoromethyl)phenyl]-1,6-naphthyridin-5-yl]acetonitrile (38 mg, 0.064 mmol) in ethanol (1.6 mL) and water (0.4 mL). The mixture was stirred at 90° C. for 130 min, then allowed to cool to room temperature and concentrated in vacuo. The mixture was dissolved in ethanol (1.5 mL) and stirred with 5% Pd/C (27 mg) under hydrogen atmosphere for 20 min. The mixture was filtered, concentrated, and resuspended in ethanol (1.5 mL) and ethyl acetate (1 mL). 5% Pd/C was added (31 mg) and the mixture stirred under hydrogen atmosphere for 45 min. The mixture was filtered, the filter washed with ethyl acetate, and concentrated. HPLC purification provided 2-[2-[2-(3,4-difluoro-2-methoxy-phenoxy)-5-fluoro-4-(trifluoromethyl)phenyl]-4-oxo-1H-1,6-naphthyridin-5-yl]acetamide (199, 12 mg, 35%) as light-yellow solid. $^1H$ NMR (500 MHz, DMSO-$d_6$) δ 12.08 (s, 1H), 8.44 (d, J=5.8 Hz, 1H), 8.01 (d, J=10.5 Hz, 1H), 7.39 (d, J=5.9 Hz, 1H), 7.30 (d, J=5.9 Hz, 2H), 7.20 (td, J=9.7, 8.4 Hz, 1H), 7.07-6.98 (m, 1H), 6.69 (s, 1H), 6.37 (s, 1H), 4.28 (s, 2H), 3.79 (d, J=1.2 Hz, 3H). $^{19}F$ NMR (471 MHz, DMSO-$d_6$) δ −60.23 (d, J=12.7 Hz), −121.90 (d, J=13.4 Hz), −139.87, −152.09 (d, J=21.3 Hz). ESI-MS m/z calc. 523.10, found 524.0 $(M+1)^+$.

Example 9

2-[2-(3,4-difluoro-2-methyl-phenoxy)-4-methyl-5-(trifluoromethyl)-3-pyridyl]-5-(dimethylamino)-1H-quinolin-4-one (200)

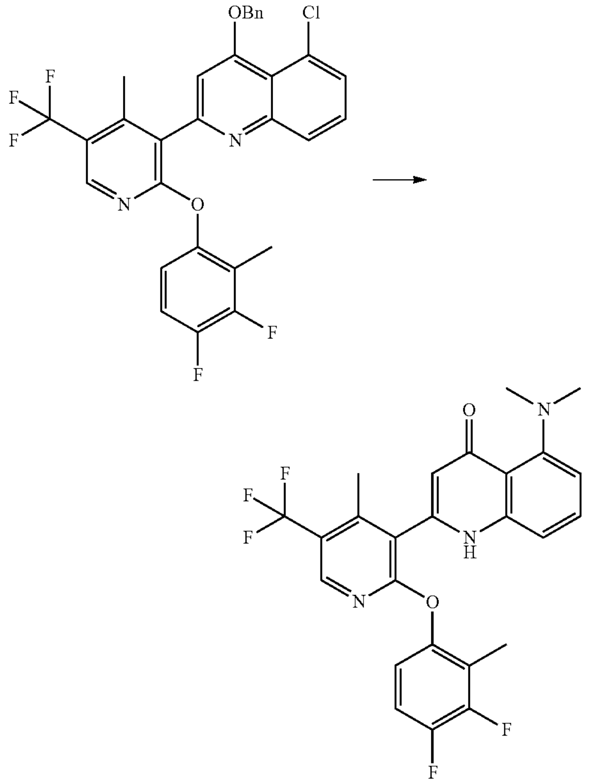

A mixture of 4-benzyloxy-5-chloro-2-[2-(3,4-difluoro-2-methyl-phenoxy)-4-methyl-5-(trifluoromethyl)-3-pyridyl] quinoline (35 mg, 0.061 mmol), N-methylmethanamine (100 μL of 2 M, 0.2 mmol), Xantphos (5 mg, 0.009 mmol), $Pd_2(dba)_3$ (4.8 mg, 0.0052 mmol) was stirred at 100° C. under nitrogen for 2 h. The mixture was filtered and purified by reverse phase HPLC (10-60% acetonitrile/5 mM HCl)) to afford 4-benzyloxy-2-[2-(3,4-difluoro-2-methyl-phenoxy)-4-methyl-5-(trifluoromethyl)-3-pyridyl]-N,N-dimethyl-quinolin-5-amine. The benzyl-protected intermediate was stirred with Pd/C (5 mg) in methanol (2 mL) under an atmosphere of hydrogen for 2 h. Filtration and purification by reverse phase chromatography (C18, 5-50% acetonitrile/5 mM HCl) provided 2-[2-(3,4-difluoro-2-methyl-phenoxy)-4-methyl-5-(trifluoromethyl)-3-pyridyl]-5-(dimethylamino)-1H-quinolin-4-one (200, 1.3 mg, 4%). $^1H$ NMR (400 MHz, DMSO-$d_6$) δ 13.68 (s, 1H), 8.62 (s, 1H), 8.13-7.80 (m, 3H), 7.42-7.29 (m, 1H), 7.11 (s, 1H), 6.77 (s, 1H), 3.32 (s, 6H), 2.38 (s, 3H), 2.02 (s, 3H). $^{19}F$ NMR (376 MHz, DMSO-$d_6$) δ −59.25, −139.10, −141.37. ESI-MS m/z calc. 489.15, found 490.3 $(M+1)^+$.

The following compounds were synthesized using a similar method to that described in the synthesis of Compound 200 using the appropriate amine. Compounds 202, 203 and 204 were synthesized using the appropriate urea or acetamide and cesium carbonate as the base.

TABLE 5

| Compound Number | Compound Name | MW & Found $[M+H]^+$ | NMR (shifts in ppm) |
|---|---|---|---|
| 201 | 2-[2-(3,4-difluoro-2-methyl-phenoxy)-4-methyl-5-(trifluoromethyl)-3-pyridyl]-5-(methylamino)-1H-quinolin-4-one | 475.41; 476.3 | $^1H$ NMR (400 MHz, DMSO-$d_6$) δ 11.84 (s, 1H), 8.57 (s, 1H), 7.43-7.27 (m, 2H), 7.12-7.00 (m, 1H), 6.56 (d, J = 8.1 Hz, 1H), 6.23 (d, J = 8.2 Hz, 1H), 6.09 (s, 1H), 2.82 (s, 3H), 2.39 (s, 3H), 2.02 (s, 3H). |
| 202 | N-[2-[2-(3,4-difluoro-2-methoxy-phenoxy)-5-fluoro-4-(trifluoromethyl) phenyl]-4-oxo-1H-1,6-naphthyridin-5-yl]acetamide | 523.38; 524.3 | $^1H$ NMR (500 MHz, DMSO-$d_6$) δ 12.87 (s, 1H), 12.51 (s, 1H), 8.26 (s, 1H), 8.03 (d, J = 10.5 Hz, 1H), 7.34 (d, J = 5.8 Hz, 1H), 7.24-7.17 (m, 1H), 7.13 (d, J = 6.0 Hz, 1H), 7.04 (s, 1H), 6.52 (s, 1H), 3.79 (d, J = 1.1 Hz, 3H), 2.45 (s, 3H). |
| 203 | 1-[2-[2-(3,4-difluoro-2-methyl-phenoxy)-4-methyl-5-(trifluoromethyl)-3-pyridyl]-4-oxo-1H-1,6-naphthyridin-5-yl]-3-methyl-urea | 519.133; 520.4 | $^1H$ NMR (500 MHz, DMSO-$d_6$) δ 12.56 (s, 1H), 12.18 (s, 1H), 9.45 (q, J = 4.6 Hz, 1H), 8.61 (s, 1H), 8.18 (d, J = 6.0 Hz, 1H), 7.35 (q, J = 9.4 Hz, 1H), 7.12-7.02 (m, 1H), 6.95 (d, J = 6.0 Hz, 1H), 6.55 (s, 1H), 2.82 (d, J = 4.6 Hz, 3H), 2.41 (s, 3H), 2.02 (d, J = 2.0 Hz, 3H). |
| 204 | [2-[2-(3,4-difluoro-2-methyl-phenoxy)-4-methyl-5-(trifluoromethyl)-3-pyridyl]-4-oxo-1H-1,6-naphthyridin-5-yl]urea | 505.12; 506.25 | $^1H$ NMR (400 MHz, DMSO-$d_6$) δ 12.55 (s, 1H), 12.09 (s, 1H), 8.99 (s, 1H), 8.61 (s, 1H), 8.18 (d, J = 6.0 Hz, 1H), 7.35 (q, J = 9.4 Hz, 1H), 7.23 (s, 1H), 7.11-7.03 (m, 1H), 6.94 (d, J = 6.0 Hz, 1H), 6.54 (s, 1H), 2.41 (s, 3H), 2.02 (d, J = 2.0 Hz, 3H). |

Example 10

2-[2-(3,4-difluoro-2-methoxy-phenoxy)-5-fluoro-4-(trifluoromethyl)phenyl]-5-[[dimethyl(oxo)-λ6-sulfanylidene]amino]-1H-1,6-naphthyridin-4-one (205)

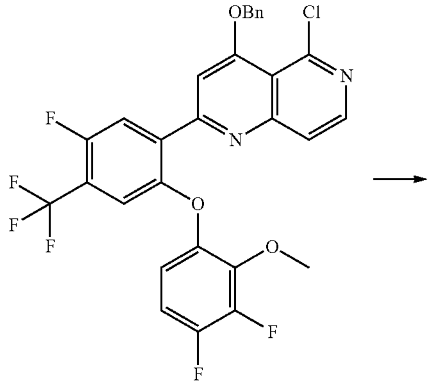

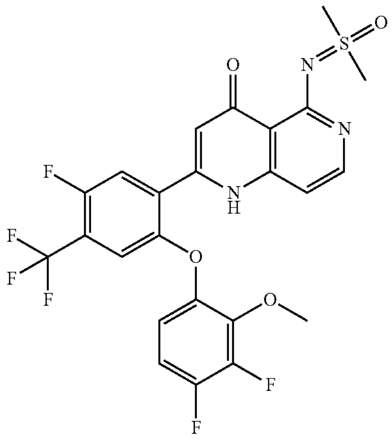

4-Benzyloxy-5-chloro-2-[2-(3,4-difluoro-2-methoxy-phenoxy)-5-fluoro-4-(trifluoromethyl)phenyl]-1,6-naphthyridine (52 mg, 0.088 mmol), dimethyl sulfoximide (17 mg, 0.18 mmol) and tButylXPhos Pd G3 (7 mg, 0.009 mmol) were added to a screw-top vial and the vessel purged with nitrogen. Nitrogen-sparged THF (550 μL) and phosphazene base $P_2$-Et (Aldrich #79417, 88 μL, 0.27 mmol) were added and the mixture sparged for 1 min with nitrogen. The vial was sealed and the mixture stirred at 50° C. for 50 min under nitrogen atmosphere. The mixture was allowed to cool to room temperature, diluted with ethyl acetate (10 mL) and washed with 50% saturated aqueous ammonium chloride (5 mL) and brine. The organic layer was dried over magnesium sulfate, filtered and concentrated in vacuo. Purification by silica gel chromatography (12 g silica, 0-100% ethyl acetate/heptane) provided [4-benzyloxy-2-[2-(3,4-difluoro-2-methoxy-phenoxy)-5-fluoro-4-(trifluoromethyl)phenyl]-1,6-naphthyridin-5-yl]imino-dimethyl-oxo-λ6-sulfane (45 mg, 79%). $^1$H NMR (500 MHz, DMSO-$d_6$) δ 8.14 (d, J=5.9 Hz, 1H), 8.05 (d, J=10.9 Hz, 1H), 7.66-7.61 (m, 2H), 7.59 (s, 1H), 7.42-7.37 (m, 3H), 7.35-7.31 (m, 1H), 7.20-7.13 (m, 2H), 6.94 (ddd, J=9.4, 5.0, 2.2 Hz, 1H), 5.30 (s, 2H), 3.83 (d, J=1.2 Hz, 3H), 3.37 (s, 6H). ESI-MS m/z calc. 647.13, found 648.4 $(M+1)^+$. The benzyl-protected intermediate was stirred with 5% Pd/C (29 mg, 0.014 mmol) in hydrogen-sparged ethanol under hydrogen atmosphere for 20 min at room temperature. The mixture was filtered and purified by reverse phase chromatography (C18, 47-95% acetonitrile/water containing 0.1% ammonium hydroxide) to provide 2-[2-(3,4-difluoro-2-methoxy-phenoxy)-5-fluoro-4-(trifluoromethyl)phenyl]-5-[[dimethyl(oxo)-6-sulfanylidene]amino]-1H-1,6-naphthyridin-4-one (205, 39 mg, 79%). ESI-MS m/z calc. 557.08, found 558.3 $(M+1)^+$. $^1$H NMR (500 MHz, $CD_3OD$) δ 8.15 (d, J=6.1 Hz, 1H), 7.82 (d, J=10.7 Hz, 1H), 7.35 (s, 1H), 7.28 (s, 1H), 7.17 (d, J=5.8 Hz, 1H), 7.00 (td, J=9.6, 8.2 Hz, 1H), 6.87 (ddd, J=9.3, 4.9, 2.3 Hz, 1H), 3.86 (d, J=1.4 Hz, 3H), 3.65 (s, 6H). $^{19}$F NMR (471 MHz, $CD_3OD$) δ −63.08, −123.29, −142.01, −153.91.

The following compounds were synthesized using a similar method to that described in the synthesis of Compound 205 using tert-butyl 1-imino-1-oxo-1,4-thiazinane-4-carboxylate. Boc-deprotection followed by reductive amination provided 2-[12-(3,4-difluoro-2-methoxy-phenoxy)-5-fluoro-4-(trifluoromethyl)phenyl]-5-[(4-methyl-1-oxo-1,4-thiazinan-1l-ylidene)amino]-1H-1,6-naphthyridin-4-one.

TABLE 6

| Example No. | Compound Name | MW & Found $[M + H]^+$ | NMR (shifts in ppm) |
|---|---|---|---|
| 206 | 2-[2-(3,4-difluoro-2-methoxy-phenoxy)-5-fluoro-4-(trifluoromethyl) phenyl]-5-[(1-oxo-1,4-thiazinan-1-ylidene)amino]-1H-1,6-naphthyridin-4-one | 598.11; 599.1 | |
| 207 | 2-[2-(3,4-difluoro-2-methoxy-phenoxy)-5-fluoro-4-(trifluoromethyl) phenyl]-5-[(4-methyl-1-oxo-1,4-thiazinan-1-ylidene)amino]-1H-1,6-naphthyridin-4-one | 612.13; 613.1 | $^1$H NMR (500 MHz, DMSO-$d_6$) δ 12.62 (s, 1H), 8.11 (d, J = 6.1 Hz, 1H), 8.02 (d, J = 11.0 Hz, 1H), 7.35 (s, 1H), 7.32 (d, J = 5.9 Hz, 1H), 7.24 (d, J = 6.0 Hz, 1H), 7.17 (td, J = 9.8, 8.6 Hz, 1H), 6.97 (ddd, J = 9.4, 5.0, 2.2 Hz, 1H), 4.10 (s, 2H), 3.85 (d, J = 1.1 Hz, 3H), 3.75 (s, 2H), 3.00 (s, 2H), 2.79 (t, J = 11.0 Hz, 2H), 2.30 (s, 3H) |

Buchwald Cross Coupling

2-[2-(3,4-difluoro-2-methyl-phenoxy)-4-methyl-5-(trifluoromethyl)-3-pyridyl]-5-(2-oxopyrrolidin-1-yl)-1H-quinolin-4-one (208)

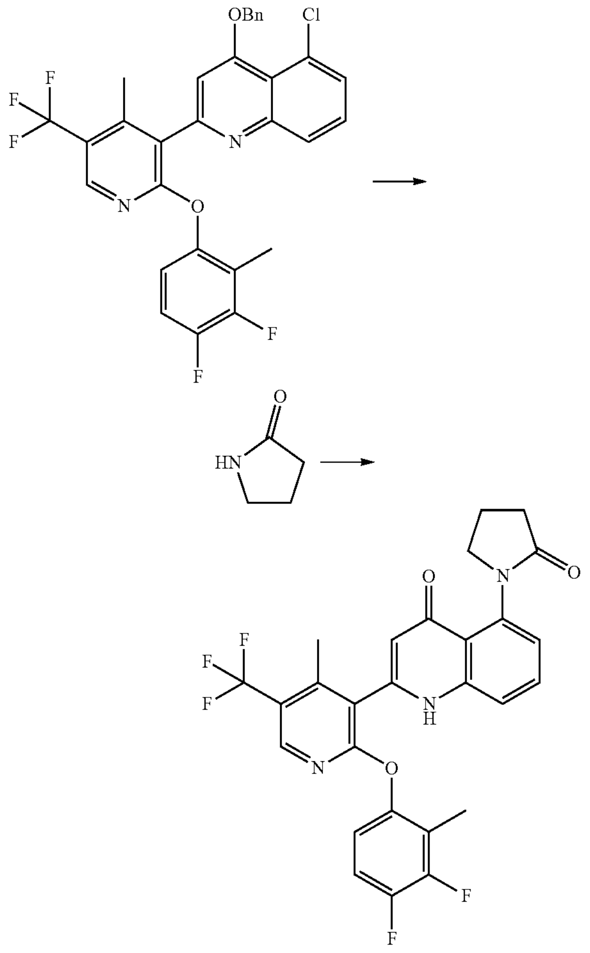

A mixture of 4-benzyloxy-5-chloro-2-[2-(3,4-difluoro-2-methyl-phenoxy)-4-methyl-5-(trifluoromethyl)-3-pyridyl] quinoline (50 mg, 0.088 mmol), pyrrolidin-2-one (15 mg, 0.18 mmol), Xantphos (10 mg, 0.017 mmol), $Pd_2(dba)_3$ (8 mg, 0.009 mmol) and sodium tert-butoxide (25 mg, 0.26 mmol) in microwave vial was purged with nitrogen. Toluene (1.0 mL) was added and the mixture was stirred at 110° C. for 16 h. The mixture was filtered and purified by HPLC (C18, 40-80% $CH_3CN$/5 mM HCl) to afford 1-[4-benzyloxy-2-[2-(3,4-difluoro-2-methyl-phenoxy)-4-methyl-5-(trifluoromethyl)-3-pyridyl]-5-quinolyl]pyrrolidin-2-one. The benzyl-protected intermediate was dissolved in methanol (2 mL) and stirred with 10% Pd/C (5 mg) under hydrogen atmosphere for 2 h. The reaction mixture was concentrated, diluted with DMSO (1 mL), filtered and purified by HPLC (C18 column, 30-70% $CH_3CN$/5 mM HCl) to provide 2-[2-(3,4-difluoro-2-methyl-phenoxy)-4-methyl-5-(trifluoromethyl)-3-pyridyl]-5-(2-oxopyrrolidin-1-yl)-1H-quinolin-4-one (5.4 mg, 6%). $^1H$ NMR (400 MHz, DMSO-$d_6$) δ 12.17 (s, 1H), 8.60 (s, 1H), 7.69 (t, J=8.0 Hz, 1H), 7.61-7.52 (m, 1H), 7.39-7.28 (m, 1H), 7.12 (d, J=7.4 Hz, 1H), 7.09-7.01 (m, 1H), 6.21 (s, 1H), 3.73 (s, 2H), 2.41 (s, 3H), 2.38-2.26 (m, 2H), 2.20-2.08 (m, 2H), 2.02 (s, 3H). $^{19}F$ NMR (376 MHz, DMSO-$d_6$) δ −59.30, −139.24, −141.60. ESI-MS m/z calc. 529.14, found 530.0 $(M+1)^+$.

The following compounds were synthesized using a similar method to that described in 208 using the appropriate amine. Compound 202 was synthesized using analogous conditions from 4-benzyloxy-5-chloro-2-[2-(3,4-difluoro-2-methoxy-phenoxy)-5-fluoro-4-(trifluoromethyl)phenyl]-1,6-naphthyridine (188 step 4) and acetamide but using cesium carbonate as base.

TABLE 7

| Example No. | Compound Name | MW & Found $[M + H]^+$ | NMR (shifts in ppm) |
|---|---|---|---|
| 202 | N-[2-[2-(3,4-difluoro-2-methoxy-phenoxy)-5-fluoro-4-(trifluoromethyl) phenyl]-4-oxo-1H-1,6-naphthyridin-5-yl]acetamide | 523.38; 524.3 | $^1H$ NMR (500 MHz, DMSO-$d_6$) δ 12.87 (s, 1H), 12.51 (s, 1H), 8.26 (s, 1H), 8.03 (d, J = 10.5 Hz, 1H), 7.34 (d, J = 5.8 Hz, 1H), 7.24-7.17 (m, 1H), 7.13 (d, J = 6.0 Hz, 1H), 7.04 (s, 1H), 6.52 (s, 1H), 3.79 (d, J = 1.1 Hz, 3H), 2.45 (s, 3H). |

General Scheme for Metal Catalyzed Cross-Coupling Reaction

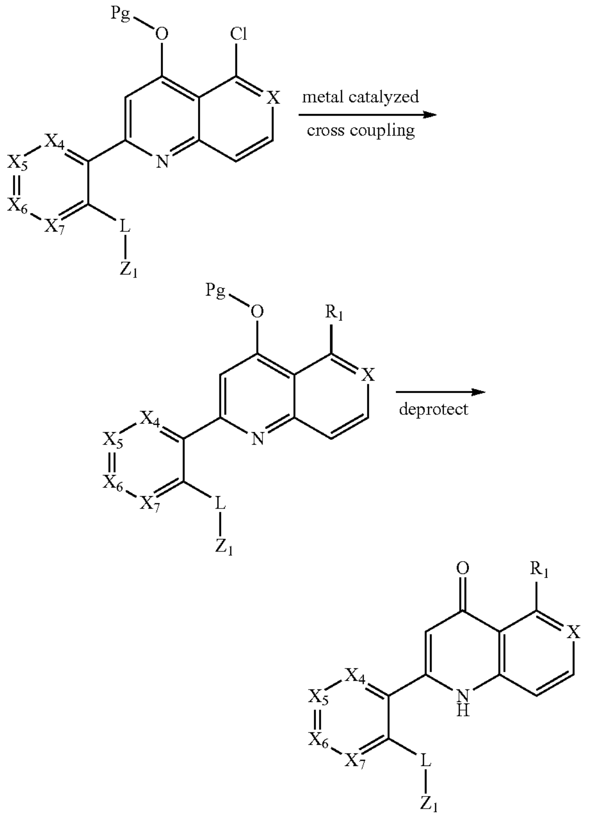

2-[2-(3,4-difluoro-2-methyl-phenoxy)-4-methyl-5-(trifluoromethyl)-3-pyridyl]-5-(2-oxo-1H-pyridin-4-yl)-1H-1,6-naphthyridin-4-one (211)

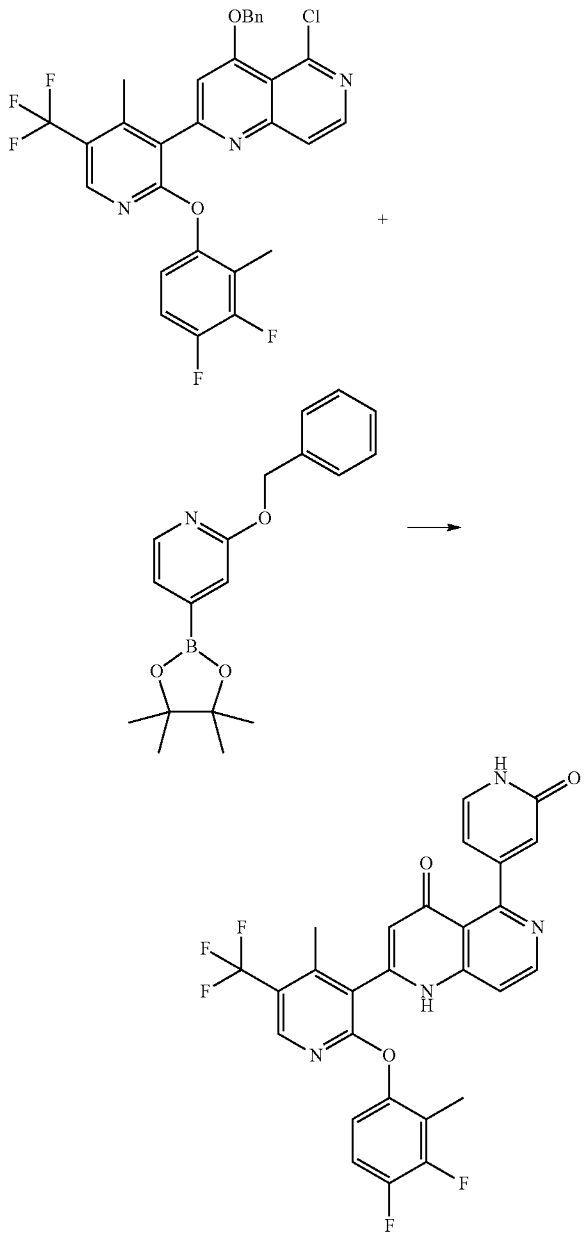

A mixture of 4-benzyloxy-5-chloro-2-[2-(3,4-difluoro-2-methyl-phenoxy)-4-methyl-5-(trifluoromethyl)-3-pyridyl]-1,6-naphthyridine (50 mg, 0.087 mmol), 2-benzyloxy-4-(4,4,5,5-tetramethyl-1,3,2-dioxaborolan-2-yl)pyridine (35 mg, 0.11 mmol), $PdCl_2$(dtbpf) (11 mg, 0.017 mmol) and potassium phosphate (56 mg, 0.26 mmol) in dioxane (1 mL) and water (250 μL) was sparged with nitrogen for 10 min. The mixture was stirred under nitrogen at room temperature for 2 h, then directly purified by silica gel column chromatography (1-100% ethyl acetate/hexanes) to provide 4-benzyloxy-5-(2-benzyloxy-4-pyridyl)-2-[2-(3,4-difluoro-2-methyl-phenoxy)-4-methyl-5-(trifluoromethyl)-3-pyridyl]-1,6-naphthyridine. The benzyl-protected intermediate was dissolved in ethanol and stirred with 10% Pd/C (19 mg, 0.018 mmol) under hydrogen atmosphere for 1 h. Filtration and purification by reverse phase chromatography (C18, 1-99% $CH_3CN$/5 mM HCl) provided 2-[2-(3,4-difluoro-2-methyl-phenoxy)-4-methyl-5-(trifluoromethyl)-3-pyridyl]-5-(2-oxo-1H-pyridin-4-yl)-1H-1,6-naphthyridin-4-one (21 mg, 44%). ESI-MS m/z calc. 540.44, found 541 $(M+1)^+$. $^1H$ NMR (400 MHz, DMSO-$d_6$) δ 13.26 (s, 1H), 8.65 (d, J=6.2 Hz, 1H), 8.61 (s, 1H), 7.97-7.72 (m, 1H), 7.58-7.43 (m, 1H), 7.43-7.27 (m, 1H), 7.21-7.10 (m, 1H), 6.48 (s, 2H), 6.42-6.22 (m, 1H), 2.44 (s, 3H), 2.03 (s, 3H).

2-[2-(3,4-difluoro-2-methyl-phenoxy)-4-methyl-5-(trifluoromethyl)-3-pyridyl]-5-(2-pyridyl)-1H-quinolin-4-one (212)

Step 1: 4,5-dichloro-2-[2-(3,4-difluoro-2-methyl-phenoxy)-4-methyl-5-(trifluoromethyl)-3-pyridyl]quinoline

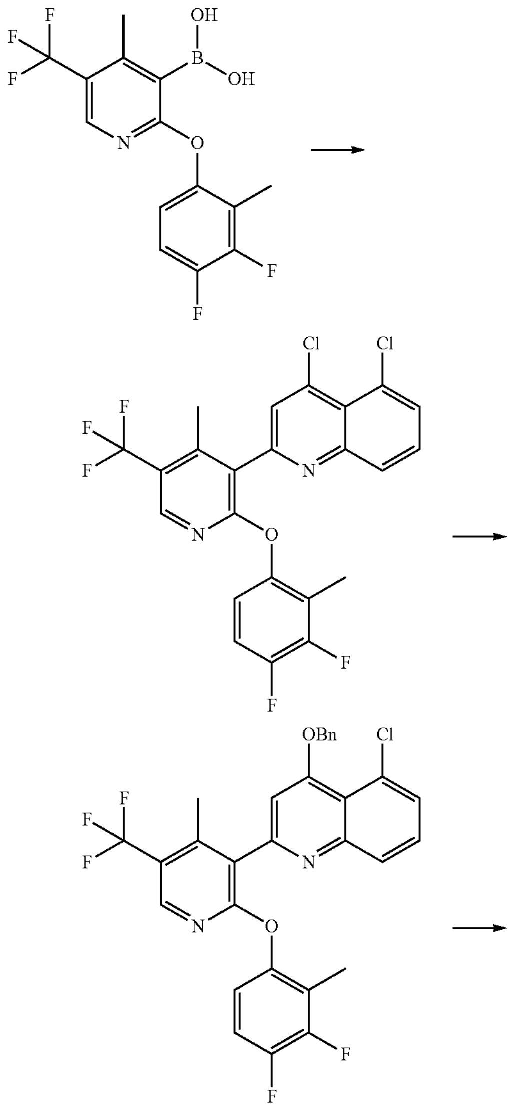

-continued

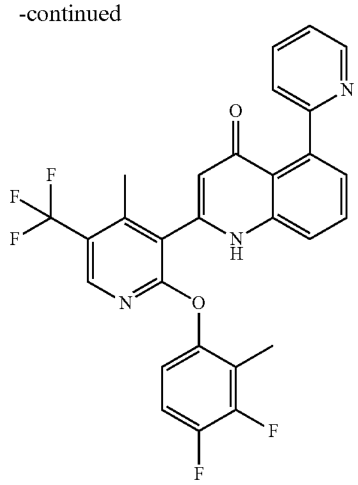

A mixture of 2,4,5-trichloroquinoline (100 mg, 0.430 mmol), [2-(3,4-difluoro-2-methyl-phenoxy)-4-methyl-5-(trifluoromethyl)-3-pyridyl]boronic acid (150 mg, 0.428 mmol), potassium carbonate (148 mg, 1.07 mmol) and $Pd(PPh_3)_4$ (30 mg, 0.026 mmol) in THF (2.5 mL) and water (0.5 mL) was degassed for 2 min then sealed and stirred under nitrogen at 80° C. for 3 h. The mixture was concentrated to remove organic solvent then extracted with ethyl acetate (3×5 mL). The combined organic layers were dried over sodium sulfate, filtered and concentrated. Purification by silica gel chromatography using a gradient of ethyl acetate in hexanes provided 4,5-dichloro-2-[2-(3,4-difluoro-2-methyl-phenoxy)-4-methyl-5-(trifluoromethyl)-3-pyridyl] quinoline (115 mg, 54%). $^1H$ NMR (400 MHz, $CDCl_3$) δ 8.41 (s, 1H), 8.15-8.06 (m, 1H), 7.75 (dt, J=8.1, 2.0 Hz, 1H), 7.72-7.58 (m, 2H), 7.08-6.93 (m, 1H), 6.85-6.70 (m, 1H), 2.35 (s, 3H), 2.06 (t, J=2.4 Hz, 3H). $^{19}F$ NMR (376 MHz, $CDCl_3$) δ −60.69, −138.06 (dd, J=21.0, 8.4 Hz), −140.78 (ddd, J=21.3, 9.7, 4.2 Hz). ESI-MS m/z calc. 498.03, found 499.0 $(M+1)^+$.

Step 2: 4-benzyloxy-5-chloro-2-[2-(3,4-difluoro-2-methyl-phenoxy)-4-methyl-5-(trifluoromethyl)-3-pyridyl]quinoline Sodium hydride (114 mg, 4.75 mmol) was added to benzyl alcohol (400 μL, 3.87 mmol) in THF (5 mL) at 0° C. The mixture was stirred at 0° C. for 15 min then at room temperature for 20 min. The resulting mixture was added slowly to a stirring solution of 4,5-dichloro-2-[2-(3,4-difluoro-2-methyl-phenoxy)-4-methyl-5-(trifluoromethyl)-3-pyridyl]quinoline (1.45 g, 2.90 mmol) in THF (10 mL). The reaction was heated at 60° C. for 2 h then partitioned between ethyl acetate and water. The organic layer was dried over sodium sulfate, filtered and concentrated. Purification by silica gel chromatography (0-25% ethyl acetate/hexanes) provided 4-benzyloxy-5-chloro-2-[2-(3,4-difluoro-2-methyl-phenoxy)-4-methyl-5-(trifluoromethyl)-3-pyridyl] quinoline (614 mg, 33%). ESI-MS m/z calc. 570.11, found 571.0 $(M+1)^+$. $^1H$ NMR (400 MHz, DMSO-$d_6$) δ 8.55 (s, 1H), 7.99 (d, J=7.6 Hz, 1H), 7.72 (q, J=7.6 Hz, 2H), 7.58 (s, 1H), 7.56 (s, 2H), 7.39 (t, J=7.1 Hz, 2H), 7.36-7.28 (m, 2H), 7.04-6.96 (m, 1H), 5.46 (s, 2H), 2.25 (s, 3H), 1.96 (s, 3H). $^{19}F$ NMR (376 MHz, DMSO-$d_6$) δ −59.18, −139.46 (dd, J=22.5, 8.9 Hz), −141.88 (ddd, J=22.0, 10.1, 4.0 Hz).

Step 3: 2-[2-(3,4-difluoro-2-methyl-phenoxy)-4-methyl-5-(trifluoromethyl)-3-pyridyl]-5-(2-pyridyl)-1H-quinolin-4-one A mixture of 4-benzyloxy-5-chloro-2-[2-(3,4-difluoro-2-methyl-phenoxy)-4-methyl-5-(trifluoromethyl)-3-pyridyl] quinoline (40 mg, 0.07 mmol), tributyl(2-pyridyl)stannane (39 mg, 0.11 mmol), $Pd(PPh_3)_4$ (8 mg, 0.007 mmol) in toluene (1 mL) was purged with nitrogen for 1 min, capped, and stirred at 110° C. for 16 h. Purification by reverse phase chromatography (C18, 40-80% acetonitrile/5 mM HCl over 15 min) provided the benzyl-protected intermediate. The intermediate was dissolved in methanol (2 mL) and stirred with 10% Pd/C (5 mg) under hydrogen atmosphere for 2 h. The mixture was concentrated and purified by HPLC (C18, 20-80% $CH_3CN$/5 mM HCl) to provide 2-[2-(3,4-difluoro-2-methyl-phenoxy)-4-methyl-5-(trifluoromethyl)-3-pyridyl]-5-(2-pyridyl)-1H-quinolin-4-one (22 mg, 60%). ESI-MS m/z calc. 523.13, found 524.0 $(M+1)^+$. $^1H$ NMR (400 MHz, DMSO-$d_6$) δ 12.67 (s, 1H), 8.81 (d, J=5.6 Hz, 1H), 8.61 (s, 1H), 8.45 (s, 1H), 8.00-7.89 (m, 2H), 7.87 (d, J=7.4 Hz, 2H), 7.40 (d, J=7.1 Hz, 1H), 7.38-7.27 (m, 1H), 7.14-7.02 (m, 1H), 6.27 (s, 1H), 2.41 (s, 3H), 2.02 (s, 3H).

2-[2-(3,4-difluoro-2-methyl-phenoxy)-4-methyl-5-(trifluoromethyl)-3-pyridyl]-5-imidazol-1-yl-1H-1,6-naphthyridin-4-one (213)

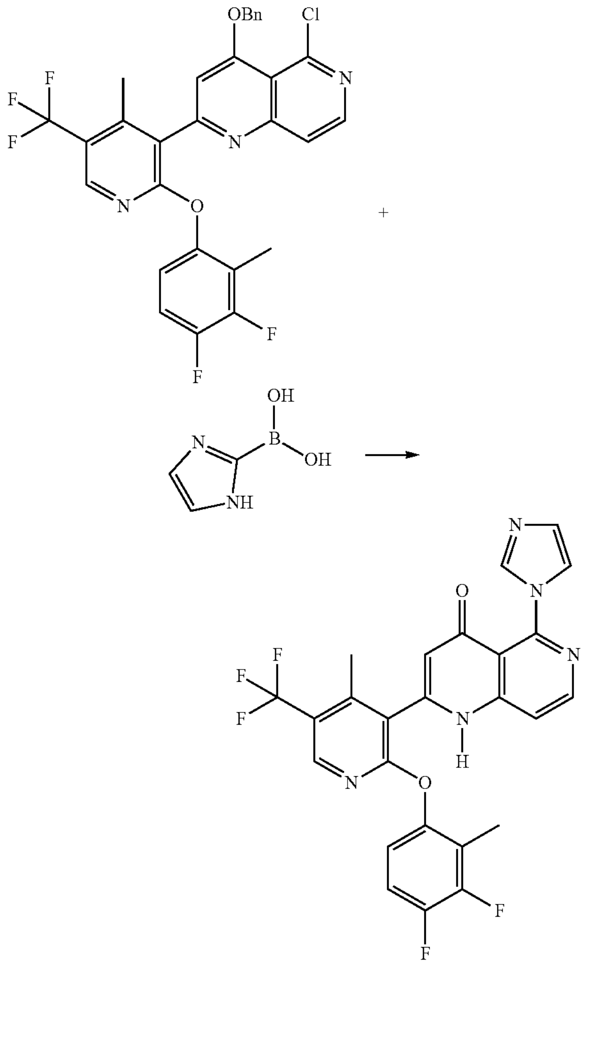

A vial containing 4-benzyloxy-5-chloro-2-[2-(3,4-difluoro-2-methyl-phenoxy)-4-methyl-5-(trifluoromethyl)-3-pyridyl]-1,6-naphthyridine (100 mg, 0.175 mmol), 1H-imidazol-2-ylboronic acid hydrochloride (55 mg, 0.37 mmol), XPhos Pd G3 (45 mg, 0.053 mmol) and potassium carbonate (75 mg, 0.54 mmol) was sealed and flushed with nitrogen for 2 min. Ethanol (900 μL) was added and the mixture heated for 1 h at 100° C. Purification using reverse phase chromatography (C18, 1-100% $CH_3CN$/5 mM HCl over 20 min) provided 2-[2-(3,4-difluoro-2-methyl-phenoxy)-4-methyl-5-(trifluoromethyl)-3-pyridyl]-5-imidazol-1-yl-1H-1,6-naphthyridin-4-one hydrochloride (4.6 mg, 5%). ESI-MS m/z calc. 513.12, found 514.6 $(M+1)^+$. $^1H$ NMR (400 MHz, $CD_3OD$) δ 9.40 (t, J=1.4 Hz, 1H), 8.66 (d, J=5.9 Hz, 1H), 8.50 (s, 1H), 7.97 (t, J=1.8 Hz, 1H), 7.74 (d, J=5.9 Hz, 1H), 7.72 (dd, J=2.1, 1.4 Hz, 1H), 7.14 (q, J=9.2 Hz, 1H), 6.92 (m, 1H), 6.55 (s, 1H), 2.50 (d, J=1.4 Hz, 3H), 2.04 (d, J=2.2 Hz, 3H).

The following compounds were synthesized using methods analogous to that described for 212 or 211 using the appropriate aryl or heteroaryl chloride and the appropriately protected organostannanes or boronic acid.

TABLE 8

| Example No. | Compound Name | MW & Found $[M + H]^+$ | NMR (shifts in ppm) |
|---|---|---|---|
| 214 | 2-[2-(3,4-difluoro-2-methyl-phenoxy)-4-methyl-5-(trifluoromethyl)-3-pyridyl]-5-(1-methylpyrazol-4-yl)-1H-1,6-naphthyridin-4-one | 527.45; 528.0 | $^1H$ NMR (400 MHz, $CD_3OD$) δ 8.54-8.41 (m, 3H), 8.08 (s, 1H), 7.73 (d, J = 6.9 Hz, 1H), 7.15 (q, J = 9.2 Hz, 1H), 7.01-6.87 (m, 1H), 6.65 (s, 1H), 4.04 (s, 3H), 2.53 (s, 3H), 2.05 (d, J = 2.1 Hz, 3H). |
| 215 | 2-[2-(3,4-difluoro-2-methyl-phenoxy)-4-methyl-5-(trifluoromethyl)-3-pyridyl]-5-(6-oxo-1H-pyridin-3-yl)-1H-1,6-naphthyridin-4-one | 540.44; 541.0 | $^1H$ NMR (400 MHz, $CD_3OD$) δ 8.63 (d, J = 6.9 Hz, 1H), 8.51 (s, 1H), 7.96 (d, J = 2.6 Hz, 1H), 7.88 (d, J = 6.8 Hz, 1H), 7.80 (dd, J = 9.6, 2.7 Hz, 1H), 7.15 (q, J = 9.3 Hz, 1H), 6.99-6.91 (m, 1H), 6.64 (d, J = 9.3 Hz, 2H), 2.66 (s, 1H), 2.53 (s, 3H), 2.05 (d, J = 2.3 Hz, 3H). |
| 216 | 2-[2-(3,4-difluoro-2-methyl-phenoxy)-4-methyl-5-(trifluoromethyl)-3-pyridyl]-5-(1-methyl-2-oxo-3-pyridyl)-1H-1,6-naphthyridin-4-one | 554.47; 555.3 | $^1H$ NMR (400 MHz, $CD_3OD$) δ 8.68 (d, J = 6.9 Hz, 1H), 8.50 (s, 1H), 7.93 (dd, J = 6.8, 2.0 Hz, 1H), 7.89 (d, J = 6.8 Hz, 1H), 7.76 (dd, J = 7.0, 2.0 Hz, 1H), 7.15 (q, J = 9.1 Hz, 1H), 6.94 (ddd, J = 9.1, 4.3, 2.1 Hz, 1H), 6.60 (s, 1H), 6.57 (t, J = 6.9 Hz, 1H), 3.66 (s, 3H), 2.53 (d, J = 1.4 Hz, 3H), 2.05 (d, J = 2.3 Hz, 3H). |
| 217 | 2-[2-(3,4-difluoro-2-methyl-phenoxy)-4-methyl-5-(trifluoromethyl)-3-pyridyl]-5-(6-methoxy-2-pyridyl)-1H-1,6-naphthyridin-4-one | 554.47; 555.7 | |
| 218 | 2-[2-(3,4-difluoro-2-methoxy-phenoxy)-5-fluoro-4-(trifluoromethyl)phenyl]-5-(1-methylimidazol-2-yl)-1H-1,6-naphthyridin-4-one | 546.42; 547.3 | $^1H$ NMR (400 MHz, $CD_3OD$) δ 8.87 (d, J = 5.9 Hz, 1H), 7.86 (d, J = 5.9 Hz, 1H), 7.78 (d, J = 10.1 Hz, 1H), 7.67 (d, J = 2.0 Hz, 1H), 7.63 (d, J = 2.0 Hz, 1H), 7.26 (d, J = 5.8 Hz, 1H), 7.07-6.96 (m, 1H), 6.96-6.87 (m, 1H), 6.60 (s, 1H), 3.83 (d, J = 1.7 Hz, 3H), 3.66 (s, 3H). |
| 219 | 2-[2-(3,4-difluoro-2-methyl-phenoxy)-4-methyl-5-(trifluoromethyl)-3-pyridyl]-5-(1,4-dimethylimidazol-2-yl)-1H-1,6-naphthyridin-4-one | 541.47; 542.4 | $^1H$ NMR (400 MHz, $CD_3OD$) δ 8.87 (d, J = 5.9 Hz, 1H), 8.50 (s, 1H), 7.80 (d, J = 5.9 Hz, 1H), 7.39 (s, 1H), 7.20-7.09 (m, 1H), 6.97-6.88 (m, 1H), 6.57 (s, 1H), 3.66 (s, 3H), 2.50 (d, J = 1.6 Hz, 3H), 2.41 (s, 3H), 2.04 (d, J = 2.1 Hz, 3H). |
| 220 | 2-[2-(3,4-difluoro-2-methyl-phenoxy)-4-methyl-5-(trifluoromethyl)-3-pyridyl]-5-(1,4-dimethylpyrazol-3-yl)-1H-1,6-naphthyridin-4-one | 541.47; 542.84 | |
| 221 | 2-[2-(3,4-difluoro-2-methyl-phenoxy)-4-methyl-5-(trifluoromethyl)-3-pyridyl]-5-(1,5-dimethyltriazol-4-yl)-1H-1,6-naphthyridin-4-one | 542.46; 543.83 | |
| 222 | 2-[2-(3,4-difluoro-2-methyl-phenoxy)-4-methyl-5-(trifluoromethyl)-3-pyridyl]-5-(1-methyltetrazol-5-yl)-1H-1,6-naphthyridin-4-one | 529.42; 530.35 | |
| 223 | 2-[2-(3,4-difluoro-2-methyl-phenoxy)-4-methyl-5-(trifluoromethyl)-3-pyridyl]-5-(2,5-dimethyl-1,2,4-triazol-3-yl)-1H-1,6-naphthyridin-4-one | 542.46; 543.2 | $^1H$ NMR (400 MHz, $CD_3OD$) δ 8.87 (d, J = 5.9 Hz, 1H), 8.50 (s, 1H), 7.80 (d, J = 5.9 Hz, 1H), 7.20-7.09 (m, 1H), 6.96-6.87 (m, 1H), 6.57 (s, 1H), 3.82 (s, 3H), 2.57 (s, 3H), 2.50 (d, J = 1.6 Hz, 3H), 2.04 (d, J = 2.1 Hz, 3H). |

TABLE 8-continued

| Example No. | Compound Name | MW & Found $[M + H]^+$ | NMR (shifts in ppm) |
|---|---|---|---|
| 224 | 2-[2-(3,4-difluoro-2-methyl-phenoxy)-4-methyl-5-(trifluoromethyl)-3-pyridyl]-5-(2-methyl-1,2,4-triazol-3-yl)-1H-1,6-naphthyridin-4-one | 528.43; 529.55 | $^1H$ NMR (400 MHz, $CD_3OD$) δ 8.85 (d, J = 5.9 Hz, 1H), 8.49 (app s, 2H), 7.78 (d, J = 5.9 Hz, 1H), 7.20-7.08 (m, 1H), 6.97-6.89 (m, 1H), 6.54 (s, 1H), 3.84 (s, 3H), 2.52-2.47 (m, 3H), 2.04 (d, J = 2.1 Hz, 3H). |
| 225 | 2-[2-(3,4-difluoro-2-methyl-phenoxy)-4-methyl-5-(trifluoromethyl)-3-pyridyl]-5-(3-methoxy-2-pyridyl)-1H-1,6-naphthyridin-4-one | 554.47; 555.3 | $^1H$ NMR (400 MHz, $CD_3OD$) δ 8.83 (d, J = 6.0 Hz, 1H), 8.50 (s, 1H), 8.44 (d, J = 5.6, 1.0 Hz, 1H), 8.24 (d, 1H), 8.09-8.01 (m, 1H), 7.81 (d, J = 6.1 Hz, 1H), 7.20-7.09 (m, 1H), 6.99-6.91 (m, 1H), 6.52 (s, 1H), 3.94 (s, 3H), 2.50 (s, 3H), 2.05 (d, J = 2.1 Hz, 3H). |
| 226 | 2-[2-(3,4-difluoro-2-methyl-phenoxy)-4-methyl-5-(trifluoromethyl)-3-pyridyl]-5-(3-methyl-2-pyridyl)-1H-1,6-naphthyridin-4-one | 538.47; 539.3 | $^1H$ NMR (400 MHz, $CD_3OD$) δ 8.87 (d, J = 5.9 Hz, 1H), 8.70 (d, J = 5.8 Hz, 1H), 8.56 (d, J = 8.0 Hz, 1H), 8.50 (s, 1H), 8.08-8.00 (m, 1H), 7.78 (d, J = 5.9 Hz, 1H), 7.20-7.09 (m, 1H), 6.97-6.89 (m, 1H), 6.51 (s, 1H), 2.50 (d, J = 1.4 Hz, 3H), 2.30 (s, 3H), 2.04 (d, J = 2.1 Hz, 3H). |
| 227 | 2-[2-(3,4-difluoro-2-methyl-phenoxy)-4-methyl-5-(trifluoromethyl)-3-pyridyl]-5-(4-methyl-1,2,4-triazol-3-yl)-1H-1,6-naphthyridin-4-one | 528.43; 529.42 | |
| 228 | 2-[2-(3,4-difluoro-2-methyl-phenoxy)-4-methyl-5-(trifluoromethyl)-3-pyridyl]-5-[1-(methoxymethyl)tetrazol-5-yl]-1H-1,6-naphthyridin-4-one | 559.45; 560.2 | $^1H$ NMR (400 MHz, $CD_3OD$) δ 8.69 (d, J = 5.9 Hz, 1H), 8.46 (s, 1H), 7.69 (d, J = 5.9 Hz, 1H), 7.18-7.07 (m, 1H), 6.97-6.88 (m, 1H), 6.42 (s, 1H), 6.01 (s, 2H), 3.52 (s, 3H), 2.47 (s, 3H), 2.04 (d, J = 2.1 Hz, 3H). |
| 229 | 2-[5-tert-butyl-2-(4,4-difluorocyclohexyl)-4-methyl-pyrazol-3-yl]-5-(1,4-dimethylimidazol-2-yl)-1H-1,6-naphthyridin-4-one | 494.58; 495.52 | |
| 230 | 2-[5-tert-butyl-2-(4,4-difluorocyclohexyl)-4-methyl-pyrazol-3-yl]-5-(1-methylimidazol-2-yl)-1H-1,6-naphthyridin-4-one | 480.55; 481.88 | |
| 231 | 2-[5-tert-butyl-2-(4,4-difluorocyclohexyl)-4-methyl-pyrazol-3-yl]-5-(2,5-dimethyl-1,2,4-triazol-3-yl)-1H-1,6-naphthyridin-4-one | 495.57; 496.51 | |
| 232 | 2-[5-tert-butyl-2-(4,4-difluorocyclohexyl)-4-methyl-pyrazol-3-yl]-5-(2-methyl-1,2,4-triazol-3-yl)-1H-1,6-naphthyridin-4-one | 481.54; 482.48 | |
| 233 | 2-[6-(3,3-difluorocyclobutyl)-4-[4-(trifluoromethyl)cyclohexyl]-3-pyridyl]-5-(1,4-dimethylimidazol-2-yl)-1H-1,6-naphthyridin-4-one (cis isomer) | 557.56; 558.74 | |
| 234 | 2-[6-(3,3-difluorocyclobutyl)-4-[4-(trifluoromethyl)cyclohexyl]-3-pyridyl]-5-(1-methylimidazol-2-yl)-1H-1,6-naphthyridin-4-one (cis isomer) | 543.53; 544.60 | |
| 235 | 2-[6-(3,3-difluorocyclobutyl)-4-[4-(trifluoromethyl)cyclohexyl]-3-pyridyl]-5-(2,5-dimethyl-1,2,4-triazol-3-yl)-1H-1,6-naphthyridin-4-one (cis isomer) | 558.55; 559.68 | |
| 236 | 2-[6-(3,3-difluorocyclobutyl)-4-[4-(trifluoromethyl)cyclohexyl]-3-pyridyl]-5-(2-methyl-1,2,4-triazol-3-yl)-1H-1,6-naphthyridin-4-one (cis isomer) | 544.52; 545.76 | |
| 237 | 2-[6-(3,3-difluorocyclobutyl)-4-[4-(trifluoromethyl)cyclohexyl]-3-pyridyl]-5-(4,5-dimethyl-1,2,4-triazol-3-yl)-1H-1,6-naphthyridin-4-one (cis isomer) | 558.55; 559.79 | |

TABLE 8-continued

| Example No. | Compound Name | MW & Found $[M + H]^+$ | NMR (shifts in ppm) |
|---|---|---|---|
| 238 | 2-[2-(3,4-difluoro-2-methyl-phenoxy)-4-methyl-5-(trifluoromethyl)-3-pyridyl]-5-oxazol-2-yl-1H-1,6-naphthyridin-4-one | 514.4; 515.2 | $^1$H NMR (400 MHz, $CD_3OD$) δ 8.78 (br d, J = 6.4 Hz, 1H), 8.50 (s, 1H), 8.16 (s, 1H), 7.76 (d, J = 6.0 Hz, 1H), 7.47 (s, 1H), 7.14 (q, J = 8.9 Hz, 1H), 6.97-6.91 (m, 1H), 6.63 (s, 1H), 2.50 (s, 3H), 2.05 (d, J = 2.1 Hz, 3H). |
| 239 | 2-[2-(3,4-difluoro-2-methyl-phenoxy)-4-methyl-5-(trifluoromethyl)-3-pyridyl]-5-(1-methylimidazol-2-yl)-1H-1,6-naphthyridin-4-one | 527.45; 528.2 | $^1$H NMR (400 MHz, $CD_3OD$) δ 8.90 (d, J = 5.9 Hz, 1H), 8.51 (s, 1H), 7.84 (d, J = 5.9 Hz, 1H), 7.74 (d, J = 2.0 Hz, 1H), 7.70 (d, J = 2.0 Hz, 1H), 7.15 (q, J = 9.1 Hz, 1H), 6.98-6.90 (m, 1H), 6.57 (s, 1H), 3.74 (s, 3H), 2.51 (s, 3H), 2.04 (d, J = 2.3 Hz, 3H). |
| 240 | 2-[2-(3,4-difluoro-2-methyl-phenoxy)-4-methyl-5-(trifluoromethyl)-3-pyridyl]-5-(2-pyridyl)-1H-1,6-naphthyridin-4-one | 524.44; 525.2 | $^1$H NMR (400 MHz, $CD_3OD$) δ 8.89 (d, J = 8.3 Hz, 1H), 8.86 (d, J = 5.9 Hz, 1H), 8.68 (td, J = 7.9, 1.5 Hz, 1H), 8.50 (s, 1H), 8.33 (d, J = 8.0 Hz, 1H), 8.18-8.10 (m, 1H), 7.81 (d, J = 5.9 Hz, 1H), 7.15 (q, J = 9.1 Hz, 1H), 6.94 (ddd, J = 9.1, 4.1, 2.1 Hz, 1H), 6.59 (s, 1H), 2.51 (d, J = 1.4 Hz, 3H), 2.05 (d, J = 2.3 Hz, 3H). |
| 241 | 2-[2-(3,4-difluoro-2-methyl-phenoxy)-4-methyl-5-(trifluoromethyl)-3-pyridyl]-5-(2-methylpyrazol-3-yl)-1H-1,6-naphthyridin-4-one | 527.45; 528.2 | $^1$H NMR (400 MHz, $CD_3OD$) δ 8.72 (d, J = 6.5 Hz, 1H), 8.50 (s, 1H), 7.83 (d, J = 6.4 Hz, 1H), 7.66 (d, J = 2.1 Hz, 1H), 7.14 (q, J = 9.3 Hz, 1H), 6.94 (ddd, J = 9.1, 4.1, 2.1 Hz, 1H), 6.57 (s, 1H), 6.55 (d, J = 2.1 Hz, 1H), 3.73 (s, 3H), 2.52 (d, J = 1.4 Hz, 3H), 2.05 (d, J = 2.3 Hz, 3H). |
| 242 | 2-[2-(3,4-difluoro-2-methyl-phenoxy)-4-methyl-5-(trifluoromethyl)-3-pyridyl]-5-pyrimidin-2-yl-1H-1,6-naphthyridin-4-one | 525.43; 526.2 | $^1$H NMR (400 MHz, $CD_3OD$) δ 8.90 (d, J = 5.1 Hz, 2H), 8.67 (d, J = 5.9 Hz, 1H), 8.47 (s, 1H), 7.67-7.55 (m, 2H), 7.13 (q, J = 9.2 Hz, 1H), 6.93 (ddd, J = 9.1, 4.3, 2.2 Hz, 1H), 6.39 (s, 1H), 2.49 (d, J = 1.4 Hz, 3H), 2.04 (d, J = 2.3 Hz, 3H). |
| 243 | 2-[2-(3,4-difluoro-2-methyl-phenoxy)-4-methyl-5-(trifluoromethyl)-3-pyridyl]-5-(2-methylpyrazol-3-yl)-1H-quinolin-4-one | 526.46; 527.4 | $^1$H NMR (400 MHz, DMSO-$d_6$) δ 12.28 (s, 1H), 8.60 (s, 1H), 7.77-7.67 (m, 2H), 7.38 (d, J = 1.8 Hz, 1H), 7.37-7.29 (m, 1H), 7.15 (dd, J = 6.4, 2.0 Hz, 1H), 7.08 (t, J = 5.9 Hz, 1H), 6.24 (s, 1H), 6.11 (d, J = 1.9 Hz, 1H), 3.46 (s, 3H), 2.42 (s, 3H), 2.02 (d, J = 2.1 Hz, 3H). |
| 244 | 2-[2-(3,4-difluoro-2-methyl-phenoxy)-4-methyl-5-(trifluoromethyl)-3-pyridyl]-5-pyrimidin-2-yl-1H-quinolin-4-one | 524.44; 525.3 | $^1$H NMR (400 MHz, DMSO-$d_6$) δ 12.46 (s, 1H), 8.80 (d, J = 4.9 Hz, 2H), 8.60 (s, 1H), 7.81-7.66 (m, 2H), 7.47 (t, J = 5.0 Hz, 1H), 7.41-7.29 (m, 1H), 7.27 (dd, J = 6.9, 1.4 Hz, 1H), 7.12-7.01 (m, 1H), 6.20 (s, 1H), 2.42 (d, J = 1.8 Hz, 3H), 2.02 (d, J = 2.0 Hz, 3H). |
| 245 | 2-[2-(3,4-difluoro-2-methyl-phenoxy)-4-methyl-5-(trifluoromethyl)-3-pyridyl]-5-tetrahydropyran-2-yl-1H-quinolin-4-one | 530.49; 531.3 | $^1$H NMR (400 MHz, DMSO-$d_6$) δ 12.07 (s, 1H), 8.59 (s, 1H), 7.62 (t, J = 7.9 Hz, 1H), 7.54 (d, J = 7.6 Hz, 1H), 7.49-7.40 (m, 1H), 7.40-7.27 (m, 1H), 7.07 (t, J = 6.2 Hz, 1H), 6.21 (s, 1H), 5.90-5.79 (m, 1H), 4.13-4.02 (m, 1H), 3.57 (s, 1H), 2.40 (s, 3H), 2.15-2.03 (m, 1H), 2.02 (s, 3H), 1.82 (s, 1H), 1.76-1.66 (m, 1H), 1.58 (s, 2H), 1.20-1.02 (m, 1H). |
| 246 | 2-[2-(3,4-difluoro-2-methyl-phenoxy)-4-methyl-5-(trifluoromethyl)-3-pyridyl]-5-oxazol-2-yl-1H-quinolin-4-one | 513.42; 514.3 | $^1$H NMR (400 MHz, DMSO-$d_6$) δ 12.40 (s, 1H), 8.60 (s, 1H), 8.11 (d, J = 0.9 Hz, 1H), 7.85-7.69 (m, 2H), 7.38 (d, J = 4.7 Hz, 1H), 7.36-7.29 (m, 1H), 7.28 (d, J = 0.9 Hz, 1H), 7.12-7.05 (m, 1H), 6.23 (s, 1H), 2.42 (s, 3H), 2.02 (d, J = 2.0 Hz, 3H). |
| 247 | 2-[2-(3,4-difluoro-2-methyl-phenoxy)-4-methyl-5-(trifluoromethyl)-3-pyridyl]-5-(2-methyltetrazol-5-yl)-1H-1,6-naphthyridin-4-one | 529.42; 530.2 | $^1$H NMR (400 MHz, $CD_3OD$) δ 8.75 (d, J = 6.1 Hz, 1H), 8.49 (s, 1H), 7.76 (d, J = 6.1 Hz, 1H), 7.14 (q, J = 9.2 Hz, 1H), 6.94 (ddd, J = 9.1, 4.1, 2.1 Hz, 1H), 6.49 (s, 1H), 4.51 (s, 3H), 2.51 (s, 3H), 2.05 (d, J = 2.3 Hz, 3H). |
| 248 | 2-[2-(3,4-difluoro-2-methyl-phenoxy)-4-methyl-5-(trifluoromethyl)-3-pyridyl]-5-[1-(methoxymethyl)imidazol-2-yl]-1H-1,6-naphthyridin-4-one | 557.47; 558.2 | $^1$H NMR (400 MHz, $CD_3OD$) δ 8.88 (d, J = 5.9 Hz, 1H), 8.49 (s, 1H), 7.91 (d, J = 2.0 Hz, 1H), 7.88 (d, J = 5.9 Hz, 1H), 7.78 (d, J = 2.0 Hz, 1H), 7.14 (q, J = 9.2 Hz, 1H), 6.96 (ddd, J = 9.1, 4.3, 2.1 Hz, 1H), 6.55 (s, 1H), 5.45 (s, 2H), 3.28 (s, 3H), 2.50 (s, 3H), 2.04 (d, J = 2.3 Hz, 3H). |

TABLE 8-continued

| Example No. | Compound Name | MW & Found $[M + H]^+$ | NMR (shifts in ppm) |
|---|---|---|---|
| 249 | 2-[2-(3,4-difluoro-2-methyl-phenoxy)-4-methyl-5-(trifluoromethyl)-3-pyridyl]-5-(4-methylimidazol-1-yl)-1H-1,6-naphthyridin-4-one | 527.14; 528.2 | $^1H$ NMR (400 MHz, $CD_3OD$) δ 8.68 (d, J = 5.9 Hz, 1H), 8.46 (s, 1H), 7.64 (d, J = 5.9 Hz, 1H), 7.21 (d, J = 1.3 Hz, 1H), 7.19-7.05 (m, 2H), 6.96-6.88 (m, 1H), 6.46 (s, 1H), 3.53 (s, 3H), 2.47 (d, J = 1.5 Hz, 3H), 2.04 (d, J = 2.1 Hz, 3H) |

2-[2-(3,4-difluoro-2-methyl-phenoxy)-4-methyl-5-(trifluoromethyl)-3-pyridyl]-5-(1H-imidazol-2-yl)-1H-1,6-naphthyridin-4-one (250)

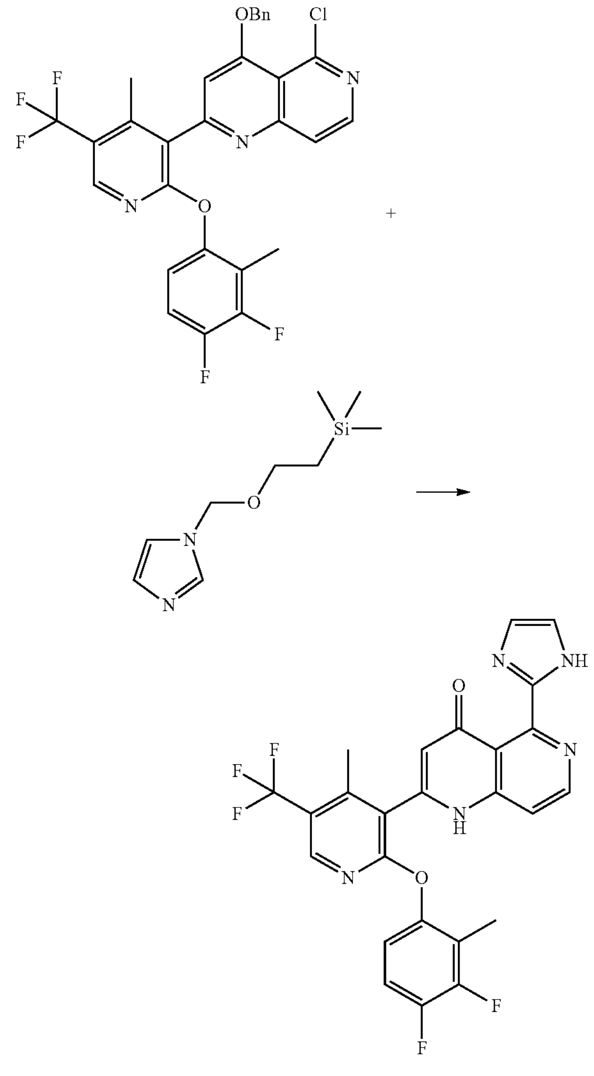

A solution of 2-(imidazol-1-ylmethoxy)ethyl-trimethyl-silane (102 mg, 0.514 mmol) in THF (6 mL) at −78° C. under nitrogen atmosphere was treated with n-BuLi (240 μL of 2.5 M in hexanes, 0.60 mmol) and stirred at −78° C. for 30 min. The solution was then treated dropwise with a solution of zinc chloride (3.0 mL of 0.5 M, 1.5 mmol) in THF. A separate capped vial containing 4-benzyloxy-5-chloro-2-[2-(3,4-difluoro-2-methyl-phenoxy)-4-methyl-5-(trifluoromethyl)-3-pyridyl]-1,6-naphthyridine (100 mg, 0.175 mmol), $Pd_2(dba)_3$ (16 mg, 0.018 mmol) and XPhos (16 mg, 0.034 mmol) was purged with nitrogen. THF (1.5 mL) was added via syringe and the reaction mixture was sparged with nitrogen for 10 min. To the mixture was added the above zincate solution (2 mL, 0.33 eq) via syringe in a single portion. The mixture was stirred vigorously at 60° C. for 18 h. The reaction was diluted with DMSO (500 uL), filtered, and purified by reverse phase chromatography (C18, 1-99% acetonitrile/5 mM HCl) to provide 2-[[2-[4-benzyloxy-2-[2-(3,4-difluoro-2-methyl-phenoxy)-4-methyl-5-(trifluoromethyl)-3-pyridyl]-1,6-naphthyridin-5-yl]imidazol-1-yl]methoxy]ethyl-trimethyl-silane (20 mg, 5%). The solid was dissolved in ethanol (10 mL), treated with 4 M aqueous HCl (10 mL) and stirred at 70° C. for 18 h. The mixture was concentrated and purified by reverse phase chromatography (C18, 1-100% $CH_3CN$/5 mM HCl over 20 min) to provide 2-[2-(3,4-difluoro-2-methyl-phenoxy)-4-methyl-5-(trifluoromethyl)-3-pyridyl]-5-(1H-imidazol-2-yl)-1H-1,6-naphthyridin-4-one hydrochloride (4.5 mg, 2%). ESI-MS m/z calc. 513.12, found 514.4 $(M+1)^+$. $^1H$ NMR (400 MHz, $CD_3OD$) δ 8.88 (d, J=5.7 Hz, 1H), 8.52 (s, 1H), 7.74 (d, J=5.7 Hz, 1H), 7.73 (s, 2H), 7.14 (q, J=9.2 Hz, 1H), 6.94 (ddd, J=9.1, 4.2, 2.1 Hz, 1H), 6.84 (s, 1H), 2.50 (q, J=1.4 Hz, 3H), 2.05 (d, J=2.2 Hz, 3H).

Example 11

A-Ring Bromination and Coupling Reaction

2-[2-(3,4-difluoro-2-methyl-phenoxy)-4-methyl-5-(trifluoromethyl)-3-pyridyl]-6-methoxy-4-oxo-1H-quinoline-5-carbonitrile (251)

Step 1: 4-benzyloxy-2-[2-(3,4-difluoro-2-methyl-phenoxy)-4-methyl-5-(trifluoromethyl)-3-pyridyl]-6-methoxy-quinoline

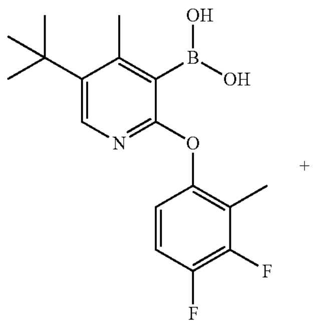

-continued

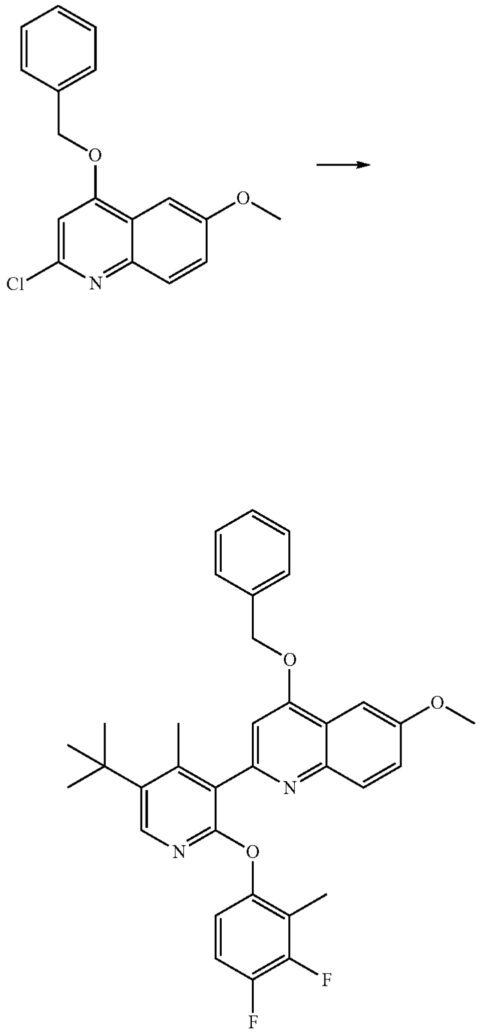

A glass vial was charged with 4-benzyloxy-2-chloro-6-methoxy-quinoline (200 mg, 0.561 mmol), [2-(3,4-difluoro-2-methyl-phenoxy)-4-methyl-5-(trifluoromethyl)-3-pyridyl]boronic acid (230 mg, 0.663 mmol), $PdCl_2$(dtbpf) (55 mg, 0.084 mmol), and potassium phosphate (360 mg, 1.70 mmol). Dioxane (5 mL) and water (3 mL) were then added and the reaction mixture was degassed for 5 min with nitrogen. The vial was sealed and the mixture stirred under nitrogen at 60° C. for 1 h. At room temperature, additional [2-(3,4-difluoro-2-methyl-phenoxy)-4-methyl-5-(trifluoromethyl)-3-pyridyl]boronic acid (230 mg, 0.663 mmol), $PdCl_2$(dtbpf) (55 mg, 0.084 mmol), and potassium phosphate (360 mg, 1.70 mmol) was added and the reaction mixture was heated for 1 h at 90° C. The mixture was concentrated and purified by silica gel column chromatography (0-50% ethyl acetate/hexanes over 30 min) to afford 4-benzyloxy-2-[2-(3,4-difluoro-2-methyl-phenoxy)-4-methyl-5-(trifluoromethyl)-3-pyridyl]-6-methoxy-quinoline (181 mg, 57%); ESI-MS m/z calc. 566.16, found 567.0 $(M+1)^+$.

Step 2: 4-benzyloxy-5-bromo-2-[2-(3,4-difluoro-2-methyl-phenoxy)-4-methyl-5-(trifluoromethyl)-3-pyridyl]-6-methoxy-quinoline

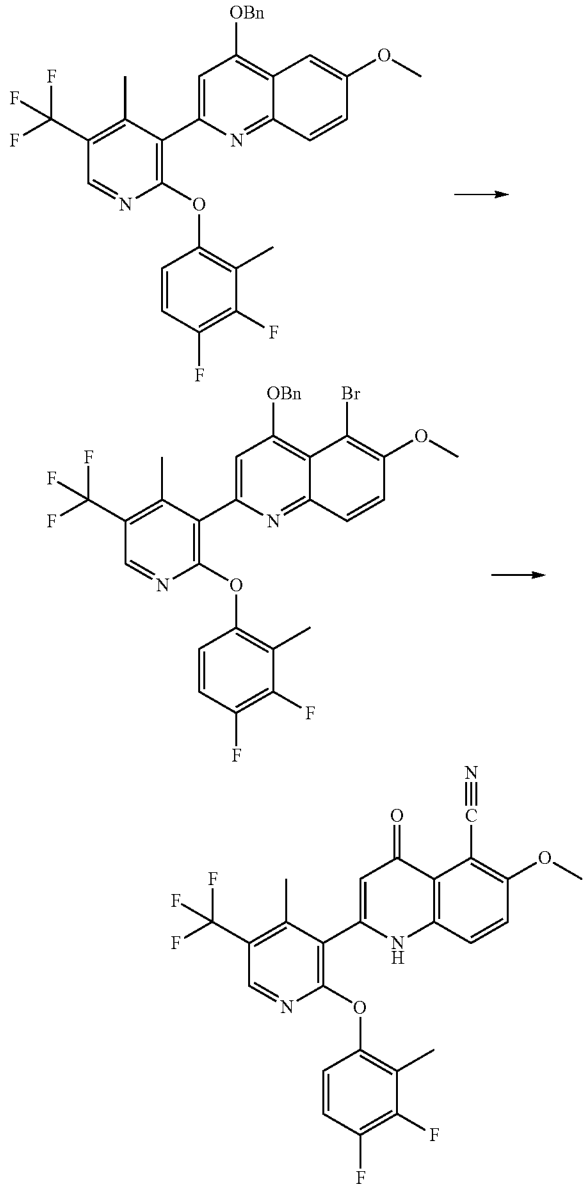

N-bromo-succinimide (115 mg, 0.646 mmol) was added to a solution of 4-benzyloxy-2-[2-(3,4-difluoro-2-methyl-phenoxy)-4-methyl-5-(trifluoromethyl)-3-pyridyl]-6-methoxy-quinoline (180 mg, 0.318 mmol) in DMF (4 mL) in one portion. The reaction mixture was heated to 50° C. for 1 h. The mixture was cooled to room temperature, filtered and purified by HPLC (C18, 10-99% $CH_3CN$/5 mM HCl over 25 min) to afford 4-benzyloxy-5-bromo-2-[2-(3,4-difluoro-2-methyl-phenoxy)-4-methyl-5-(trifluoromethyl)-3-pyridyl]-6-methoxy-quinoline (Hydrochloride salt) (105 mg, 48%) as a light yellow oil. ESI-MS m/z calc. 644.07, found 645.0 $(M+1)^+$; Retention time: 0.87 min.

Step 3: 4-benzyloxy-2-[2-(3,4-difluoro-2-methyl-phenoxy)-4-methyl-5-(trifluoromethyl)-3-pyridyl]-6-methoxy-quinoline-5-carbonitrile 2-[2-(3,4-difluoro-2-methyl-phenoxy)-4-methyl-5-(trifluoromethyl)-3-pyridyl]-6-methoxy-4-oxo-1H-quinoline-5-carbonitrile (251)

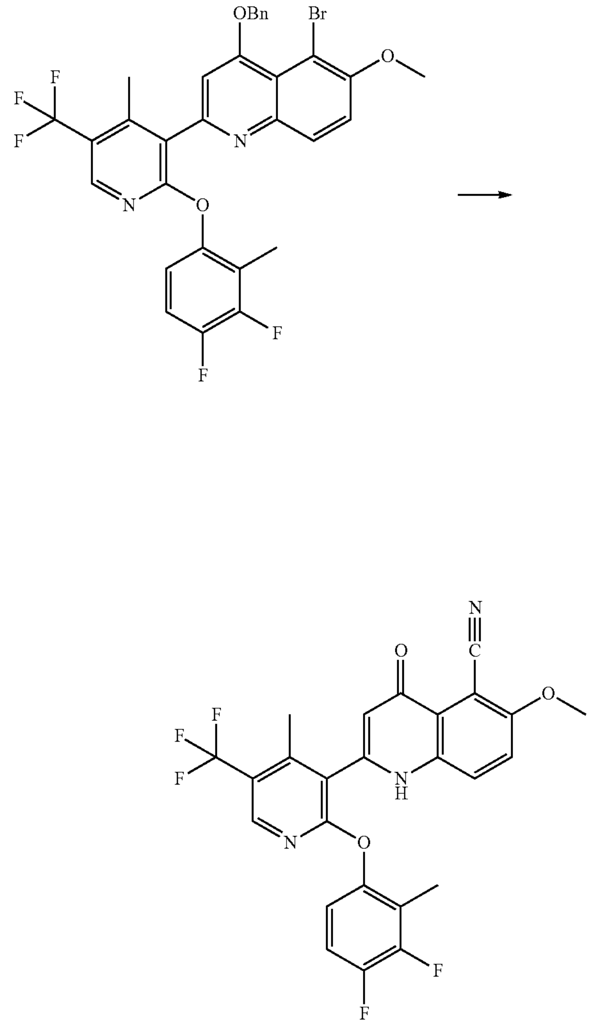

A mixture of 4-benzyloxy-5-bromo-2-[2-(3,4-difluoro-2-methyl-phenoxy)-4-methyl-5-(trifluoromethyl)-3-pyridyl]-6-methoxy-quinoline (Hydrochloride salt) (100 mg, 0.147 mmol) and copper (I) cyanide (30 mg, 0.34 mmol) in DMF (2.5 mL) was heated at 150° C. for 16 h. The mixture was cooled to room temperature, filtered and purified by reverse phase HPLC (C18, 1-99% $CH_3CN$/5 mM HCl over 30 min) to afford 2-[2-(3,4-difluoro-2-methyl-phenoxy)-4-methyl-5-(trifluoromethyl)-3-pyridyl]-6-methoxy-4-oxo-1H-quinoline-5-carbonitrile hydrochloride (251, 11.2 mg, 14%). ESI-MS m/z calc. 501.11, found 502.0 $(M+1)^+$. $^1H$ NMR (400 MHz, $CD_3OD$) δ 8.49 (s, 1H), 7.99 (d, J=9.4 Hz, 1H), 7.83 (d, J=9.5 Hz, 1H), 7.12 (q, J=9.2 Hz, 1H), 6.92 (d, J=7.6 Hz, 1H), 6.64 (s, 1H), 4.11 (s, 3H), 2.44 (s, 3H), 2.03 (s, 3H). $^{19}F$ NMR (376 MHz, $CD_3OD$) δ −62.13, −141.29 (d, J=20.8 Hz), −143.50 (d, J=20.1 Hz).

Example 12

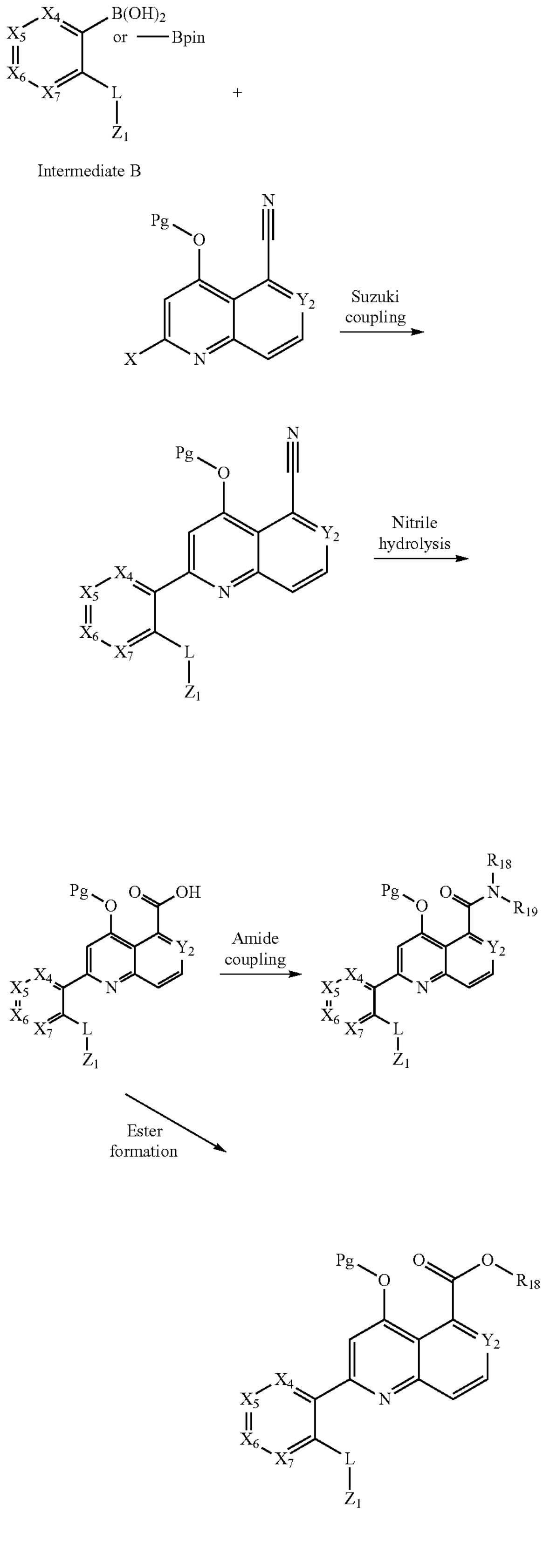

2-[2-(3,4-difluoro-2-methyl-phenoxy)-4-methyl-5-(trifluoromethyl)-3-pyridyl]-N-[(1S)-1-(hydroxymethyl)-2-methyl-propyl]-4-oxo-1H-1,6-naphthyridine-5-carboxamide (252)

Step 1: 4-benzyloxy-2-[2-(3,4-difluoro-2-methyl-phenoxy)-4-methyl-5-(trifluoromethyl)-3-pyridyl]-1,6-naphthyridine-5-carbonitrile

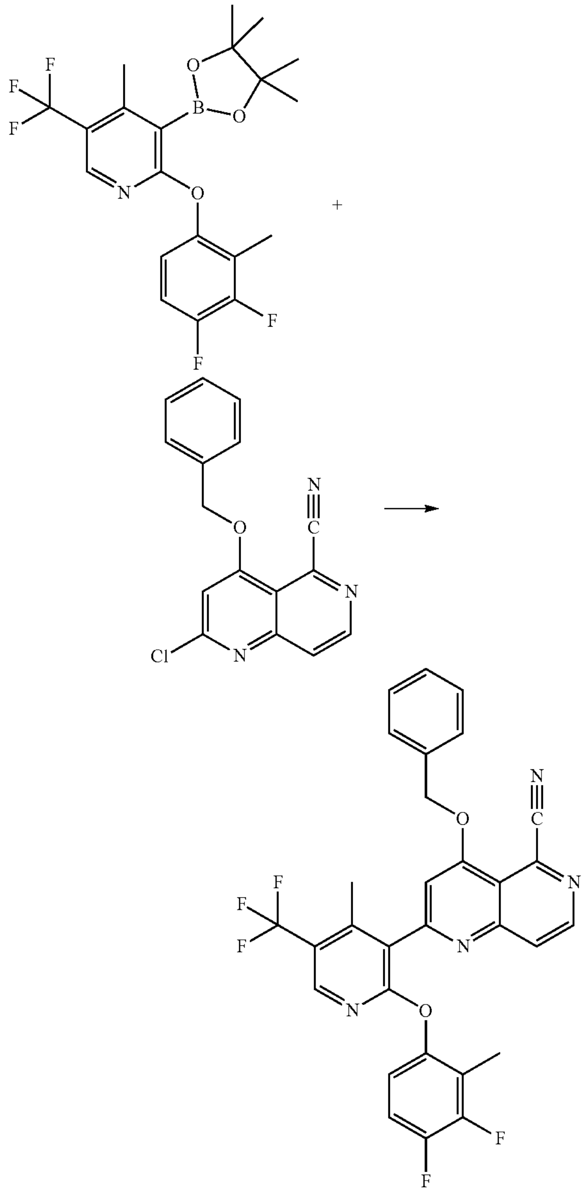

A mixture of [2-(3,4-difluoro-2-methyl-phenoxy)-4-methyl-5-(trifluoromethyl)-3-pyridyl]boronic acid (1.2 g, 3.5 mmol), 4-benzyloxy-2-chloro-1,6-naphthyridine-5-carbonitrile (1.217 g, 4.115 mmol) and potassium phosphate (1.957 g, 9.220 mmol) in dioxane (18 mL) was flushed with nitrogen for 2 min. To this mixture was added Pd(dtbpf)$Cl_2$ (230 mg, 0.353 mmol) followed by degassed water (3.6 mL). The resulting mixture was flushed with nitrogen for 30 seconds, capped and stirred at room temperature for 3 h. The mixture was diluted with water and extracted with ethyl acetate (3×). The combined organic layers were washed with brine, dried over sodium sulfate, filtered and concentrated under reduced pressure. Purification by silica gel chromatography (20 g silica, 0-30% ethyl acetate/hexanes) provided 4-benzyloxy-2-[2-(3,4-difluoro-2-methyl-phenoxy)-4-methyl-5-(trifluoromethyl)-3-pyridyl]-1,6-naphthyridine-5-carbonitrile (1.642 g, 84%). $^1$H NMR (400 MHz, DMSO-$d_6$) δ 8.93 (dd, J=5.8, 1.8 Hz, 1H), 8.58 (s, 1H), 8.24 (dd, J=5.7, 1.8 Hz, 1H), 7.87 (d, J=1.8 Hz, 1H), 7.67-7.58 (m, 2H), 7.43-7.26 (m, 4H), 7.05-6.93 (m, 1H), 5.63 (s, 2H), 2.25 (s, 3H), 1.94 (d, J=2.0 Hz, 3H) ppm. ESI-MS m/z calc. 562.14, found 563.0 $(M+1)^+$.

Step 2: 2-[2-(3,4-difluoro-2-methyl-phenoxy)-4-methyl-5-(trifluoromethyl)-3-pyridyl]-4-oxo-1H-1,6-naphthyridine-5-carboxylic acid

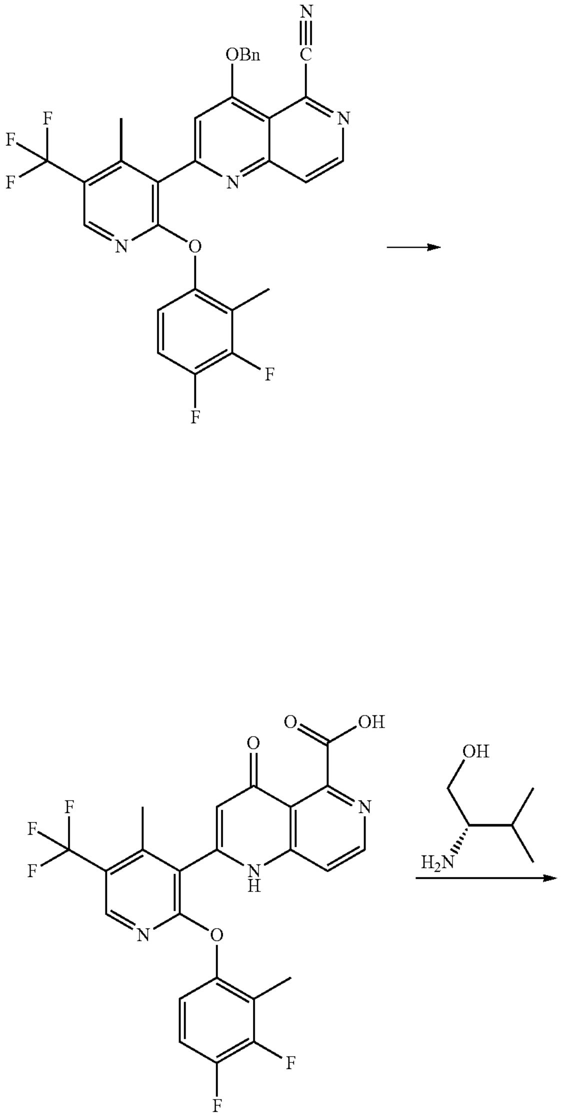

-continued

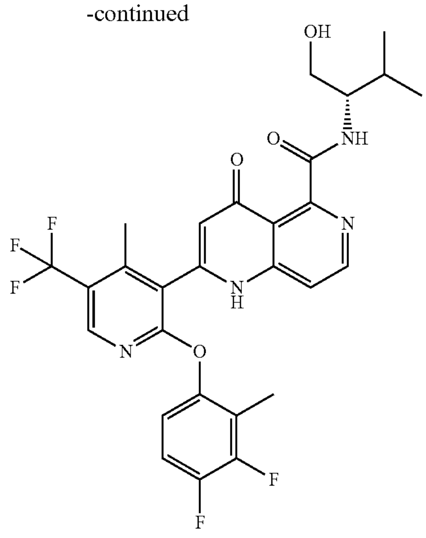

A solution of 4-benzyloxy-2-[2-(3,4-difluoro-2-methyl-phenoxy)-4-methyl-5-(trifluoromethyl)-3-pyridyl]-1,6-naphthyridine-5-carbonitrile (3.2 g, 5.7 mmol) in ethanol (64 mL) and KOH (36 mL of 10% w/v, 64 mmol) was heated at 70° C. for 18 h. The reaction mixture was cooled to room temperature and the solvent was evaporated. The crude material was taken up in water and was slowly treated with 1 M HCl until acidic. The aqueous layer was extracted with ethyl acetate (3×) and DCM (2×). The combined organic layers were dried over magnesium sulfate, filtered and concentrated. Purification by silica gel chromatography (1-100% ethyl acetate/hexane) followed by purification by HPLC (1-50% $CH_3CN$/5 mM HCl) provided 2-[2-(3,4-difluoro-2-methyl-phenoxy)-4-methyl-5-(trifluoromethyl)-3-pyridyl]-4-oxo-1H-1,6-naphthyridine-5-carboxylic acid (1.2 g, 43%). $^1H$ NMR (400 MHz, DMSO-$d_6$) δ 12.56 (s, 1H), 8.62 (s, 1H), 8.58 (d, J=5.8 Hz, 1H), 7.52 (d, J=5.9 Hz, 1H), 7.41-7.28 (m, 1H), 7.12-7.02 (m, 1H), 6.47 (s, 1H), 2.43 (s, 3H), 2.02 (s, 3H). ESI-MS m/z calc. 491.09, found 492.0 $(M+1)^+$.

Step 3: 2-[2-(3,4-difluoro-2-methyl-phenoxy)-4-methyl-5-(trifluoromethyl)-3-pyridyl]-N-[(1S)-1-(hydroxymethyl)-2-methyl-propyl]-4-oxo-1H-1,6-naphthyridine-5-carboxamide (252)

A mixture of 2-[2-(3,4-difluoro-2-methyl-phenoxy)-4-methyl-5-(trifluoromethyl)-3-pyridyl]-4-oxo-1H-1,6-naphthyridine-5-carboxylic acid (20 mg, 0.041 mmol), (2S)-2-amino-3-methyl-butan-1-ol (5.0 mg, 5.4 μL, 0.049 mmol), HATU (23 mg, 0.061 mmol) and DIEA (21 μL, 0.12 mmol) in NMP (0.5 mL) was stirred at 50° C. for 1 h. The mixture was filtered and purified by reverse phase chromatography (C18, 10-70% $CH_3CN$/5 mM HCl) to provide 2-[2-(3,4-difluoro-2-methyl-phenoxy)-4-methyl-5-(trifluoromethyl)-3-pyridyl]-N-[(1S)-1-(hydroxymethyl)-2-methyl-propyl]-4-oxo-1H-1,6-naphthyridine-5-carboxamide (252, 8.8 mg, 37%). ESI-MS m/z calc. 576.18, found 577.0 $(M+1)^+$. $^1H$ NMR (400 MHz, DMSO-$d_6$) δ 12.62 (s, 1H), 8.60 (s, 1H), 8.58 (d, J=1.9 Hz, 1H), 7.95-7.80 (m, 1H), 7.57 (d, J=5.9 Hz, 1H), 7.39-7.27 (m, 1H), 7.13-7.03 (m, 1H), 6.49 (s, 1H), 3.87-3.83 (m, 1H), 3.60-3.51 (m, 3H), 2.43 (s, 3H), 2.03 (s, 3H), 1.94-1.82 (m, 1H), 0.97 (d, J=6.8 Hz, 3H), 0.93 (d, J=6.8 Hz, 3H).

2-[2-(4-fluoro-2-methyl-phenoxy)-4-methyl-5-(trifluoromethyl)-3-pyridyl]-4-oxo-1H-1,6-naphthyridine-5-carboxylic acid (253)

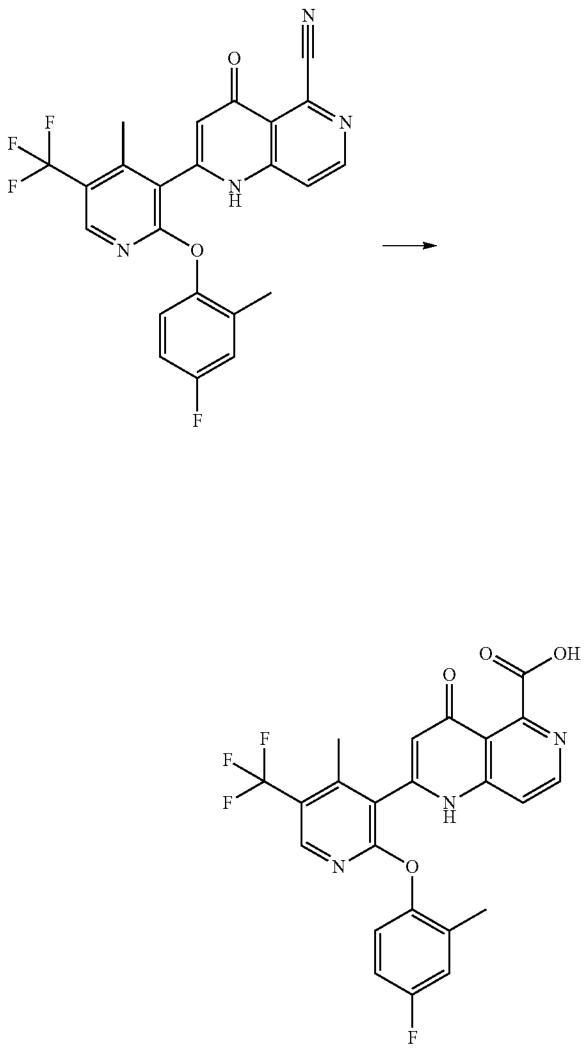

2-[2-(4-Fluoro-2-methyl-phenoxy)-4-methyl-5-(trifluoromethyl)-3-pyridyl]-4-oxo-1H-1,6-naphthyridine-5-carboxylic acid (253) (Hydrochloride salt) can be prepared from 2-(2-(4-fluoro-2-methylphenoxy)-4-methyl-5-(trifluoromethyl)pyridin-3-yl)-4-oxo-1,4-dihydro-1,6-naphthyridine-5-carbonitrile in an analogous procedure as found in Compound 252, step 2. ESI-MS m/z calc. 473.10, found 474.0 $(M+1)^+$; $^1H$ NMR (400 MHz, DMSO-$d_6$) δ 12.52 (s, 1H), 8.60 (s, 1H), 8.57 (d, J=5.9 Hz, 1H), 7.51 (d, J=5.9 Hz, 1H), 7.17 (td, J=9.1, 4.1 Hz, 2H), 7.08 (td, J=8.5, 3.2 Hz, 1H), 6.45 (s, 1H), 2.42 (s, 3H), 2.04 (s, 3H). $^{19}F$ NMR (376 MHz, DMSO-$d_6$) δ −59.28, −117.52.

2-[2-(3,4-difluoro-2-methoxy-phenoxy)-5-fluoro-4-(trifluoromethyl)phenyl]-4-oxo-1H-1,6-naphthyridine-5-carboxylic acid (254)

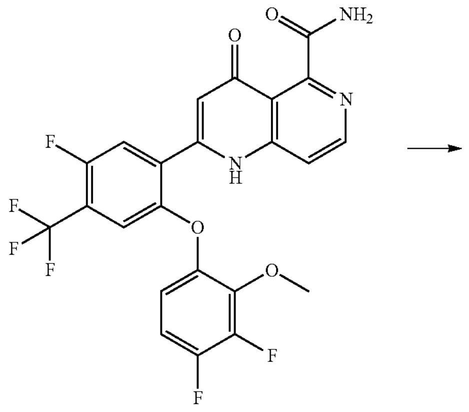

-continued

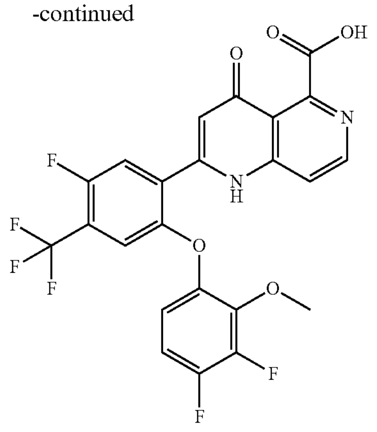

2-[2-(3,4-Difluoro-2-methoxy-phenoxy)-5-fluoro-4-(trifluoromethyl)phenyl]-4-oxo-1H-1,6-naphthyridine-5-carboxamide (12 mg, 0.018 mmol) in dioxane (1 mL) and water (1 mL) was treated with LiOH (22 mg, 0.92 mmol) and heated at 110° C. in a sealed tube for 30 min. The mixture was purified directly by reversed-phase HPLC ($CH_3CN$/0.1% ammonium hydroxide) and product fractions lyophilized to provide 2-[2-(3,4-difluoro-2-methoxy-phenoxy)-5-fluoro-4-(trifluoromethyl)phenyl]-4-oxo-1H-1,6-naphthyridine-5-carboxylic acid (254) (Ammonia salt) (5.8 mg, 60%). ESI-MS m/z calc. 510.07, found 509.1 $(M-1)^-$. $^1H$ NMR (500 MHz, DMSO-$d_6$) δ 8.59 (d, J=5.7 Hz, 1H), 8.05 (d, J=11.1 Hz, 1H), 7.76 (d, J=5.6 Hz, 1H), 7.29 (d, J=5.9 Hz, 1H), 7.17 (q, J=9.4 Hz, 3H), 6.97 (ddd, J=9.5, 5.0, 2.2 Hz, 1H), 3.83 (s, 3H).

The following examples were synthesized in an analogous fashion as Compound 252 using the appropriate amine for amide bond formation, or from the carboxylate Compound 253 using the appropriate amine for amide bond formation.

TABLE 9

| Compound Number | Compound Name | MW & Found $[M + H]^+$ | NMR (shifts in ppm) |
|---|---|---|---|
| 255 | 2-[2-(3,4-difluoro-2-methyl-phenoxy)-4-methyl-5-(trifluoromethyl)-3-pyridyl]-N-[(2S)-2,3-dihydroxypropyl]-4-oxo-1H-1,6-naphthyridine-5-carboxamide | 564.46; 565.3 | $^1H$ NMR (400 MHz, DMSO-$d_6$) δ 12.54 (s, 1H), 8.60 (s, 1H), 8.57 (d, J = 5.8 Hz, 1H), 8.08 (s, 1H), 7.55 (d, J = 5.9 Hz, 1H), 7.38-7.27 (m, 1H), 7.12-7.04 (m, 1H), 6.47 (s, 1H), 3.78-3.74 (m, 3H), 3.45 (d, J = 5.5 Hz, 3H), 3.26 (s, 1H), 2.43 (s, 3H), 2.03 (d, J = 2.0 Hz, 3H). |
| 256 | 2-[2-(3,4-difluoro-2-methyl-phenoxy)-4-methyl-5-(trifluoromethyl)-3-pyridyl]-N-(3-hydroxybutyl)-4-oxo-1H-1,6-naphthyridine-5-carboxamide | 562.49; 563.3 | $^1H$ NMR (400 MHz, DMSO-$d_6$) δ 12.41 (s, 1H), 8.59 (s, 1H), 8.55 (d, J = 5.9 Hz, 1H), 8.02 (s, 1H), 7.53 (d, J = 5.9 Hz, 1H), 7.38-7.27 (m, 1H), 7.12-7.04 (m, 1H), 6.44 (s, 1H), 3.85-3.75 (m, 1H), 3.37-3.29 (m, 2H), 2.43 (s, 3H), 2.03 (d, J = 2.0 Hz, 3H), 1.71-1.55 (m, 2H), 1.11 (d, J = 6.2 Hz, 3H). |
| 257 | 2-[2-(3,4-difluoro-2-methyl-phenoxy)-4-methyl-5-(trifluoromethyl)-3-pyridyl]-N-[(2R)-2,3-dihydroxypropyl]-4-oxo-1H-1,6-naphthyridine-5-carboxamide | 564.46; 565.3 | $^1H$ NMR (400 MHz, DMSO-$d_6$) δ 12.52 (s, 1H), 8.70-8.44 (m, 2H), 8.08 (s, 1H), 7.54 (d, J = 5.6 Hz, 1H), 7.39-7.24 (m, 1H), 7.13-7.00 (m, 1H), 6.46 (s, 1H), 3.83-3.70 (m, 2H), 3.58 (s, 1H), 3.26 (s, 2H), 2.42 (s, 3H), 2.03 (s, 3H). |
| 258 | 2-[2-(3,4-difluoro-2-methyl-phenoxy)-4-methyl-5-(trifluoromethyl)-3-pyridyl]-N-(2-hydroxy-1,1-dimethyl-ethyl)-4-oxo-1H-1,6-naphthyridine-5-carboxamide | 562.49; 563.3 | |

TABLE 9-continued

| Compound Number | Compound Name | MW & Found $[M + H]^+$ | NMR (shifts in ppm) |
|---|---|---|---|
| 259 | 2-[2-(3,4-difluoro-2-methyl-phenoxy)-4-methyl-5-(trifluoromethyl)-3-pyridyl]-N-[(1R)-1-(hydroxymethyl)-2,2-dimethyl-propyl]-4-oxo-1H-1,6-naphthyridine-5-carboxamide | 590.54; 591.4 | |
| 260 | 2-[2-(3,4-difluoro-2-methyl-phenoxy)-4-methyl-5-(trifluoromethyl)-3-pyridyl]-N-methyl-4-oxo-1H-1,6-naphthyridine-5-carboxamide | 504.12; 505.8 | $^1$H NMR (400 MHz, $CD_3OD$) δ 8.58 (d, J = 5.9 Hz, 1H), 8.48 (s, 1H), 7.54 (d, J = 5.9 Hz, 1H ), 7.13 (q, J = 9.3 Hz, 1H), 6.92 (ddd, J = 9.1, 4.2, 2.0 Hz, 1H), 6.51 (s, 1H), 2.99 (s, 3H), 2.47 (d, J = 1.5 Hz, 3H), 2.03 (d, J = 2.1 Hz, 3H) |
| 261 | 2-[2-(3,4-difluoro-2-methyl-phenoxy)-4-methyl-5-(trifluoromethyl)-3-pyridyl]-N-(3-hydroxy-2-pyridyl)-4-oxo-1H-1,6-naphthyridine-5-carboxamide | 583.47; 584.2 | |
| 262 | N-[(1S)-1-benzyl-2-hydroxy-ethyl]-2-[2-(3,4-difluoro-2-methyl-phenoxy)-4-methyl-5-(trifluoromethyl)-3-pyridyl]-4-oxo-1H-1,6-naphthyridine-5-carboxamide | 624.56; 625.4 | |
| 263 | 2-[2-(3,4-difluoro-2-methyl-phenoxy)-4-methyl-5-(trifluoromethyl)-3-pyridyl]-N-[(1R)-1-(2-hydroxyphenyl)ethyl]-4-oxo-1H-1,6-naphthyridine-5-carboxamide | 610.53; 611.4 | |
| 264 | 2-[2-(3,4-difluoro-2-methyl-phenoxy)-4-methyl-5-(trifluoromethyl)-3-pyridyl]-N-[(1S,2R)-2-hydroxyindan-1-yl]-4-oxo-1H-1,6-naphthyridine-5-carboxamide | 622.54; 623.3 | |
| 265 | 2-[2-(3,4-difluoro-2-methyl-phenoxy)-4-methyl-5-(trifluoromethyl)-3-pyridyl]-N-[2-hydroxy-1-(3-methoxyphenyl)ethyl]-4-oxo-1H-1,6-naphthyridine-5-carboxamide | 640.56; 641.4 | |
| 266 | 2-[2-(3,4-difluoro-2-methyl-phenoxy)-4-methyl-5-(trifluoromethyl)-3-pyridyl]-N-[(1S)-3-hydroxy-1-phenyl-propyl]-4-oxo-1H-1,6-naphthyridine-5-carboxamide | 624.56; 625.3 | |
| 267 | 2-[2-(3,4-difluoro-2-methyl-phenoxy)-4-methyl-5-(trifluoromethyl)-3-pyridyl]-N-[[(1S,2S)-2-hydroxycyclohexyl]methyl]-4-oxo-1H-1,6-naphthyridine-5-carboxamide | 602.55; 603.4 | $^1$H NMR (400 MHz, DMSO-$d_6$) δ 12.38 (s, 1H), 8.58 (s, 1H), 8.54 (d, J = 5.8 Hz, 1H), 8.03 (s, 1H), 7.51 (d, J = 5.9 Hz, 1H), 7.37-7.25 (m, 1H), 7.10-7.01 (m, 1H), 6.43 (s, 1H), 3.93 (dt, J = 5.1, 2.7 Hz, 1H), 3.35-3.21 (m, 1H), 3.19-3.04 (m, 1H), 2.41 (s, 3H), 2.02 (s, 3H), 1.76-1.50 (m, 4H), 1.50-1.28 (m, 4H), 1.27-1.13 (m, 1H). |
| 268 | 2-[2-(3,4-difluoro-2-methyl-phenoxy)-4-methyl-5-(trifluoromethyl)-3-pyridyl]-N-[(1R,2S)-2-hydroxycyclopentyl]-4-oxo-1H-1,6-naphthyridine-5-carboxamide | 574.5; 575.3 | |
| 269 | 2-[2-(3,4-difluoro-2-methyl-phenoxy)-4-methyl-5-(trifluoromethyl)-3-pyridyl]-N-[(1R,2S)-2-hydroxy-1-methyl-2-phenyl-ethyl]-4-oxo-1H-1,6-naphthyridine-5-carboxamide | 624.56; 625.3 | |

TABLE 9-continued

| Compound Number | Compound Name | MW & Found [M + H]+ | NMR (shifts in ppm) |
|---|---|---|---|
| 270 | 2-[2-(3,4-difluoro-2-methylphenoxy)-4-methyl-5-(trifluoromethyl)-3-pyridyl]-N-[(1S,2R)-2-hydroxycyclohexyl]-4-oxo-1H-1,6-naphthyridine-5-carboxamide | 588.53; 589.3 | |
| 271 | 2-[2-(3,4-difluoro-2-methylphenoxy)-4-methyl-5-(trifluoromethyl)-3-pyridyl]-N-[(1R,2R)-2-hydroxycyclopentyl]-4-oxo-1H-1,6-naphthyridine-5-carboxamide | 574.5; 575.3 | |
| 272 | 2-[2-(3,4-difluoro-2-methylphenoxy)-4-methyl-5-(trifluoromethyl)-3-pyridyl]-N-(3-hydroxycyclobutyl)-4-oxo-1H-1,6-naphthyridine-5-carboxamide (trans isomer) | 560.47; 561.3 | |
| 273 | 2-[2-(3,4-difluoro-2-methylphenoxy)-4-methyl-5-(trifluoromethyl)-3-pyridyl]-N-[(3R,4S)-4-hydroxytetrahydrofuran-3-yl]-4-oxo-1H-1,6-naphthyridine-5-carboxamide | 576.47; 577.3 | |
| 274 | 2-[2-(3,4-difluoro-2-methylphenoxy)-4-methyl-5-(trifluoromethyl)-3-pyridyl]-N-[(3S,4R)-4-hydroxytetrahydrofuran-3-yl]-4-oxo-1H-1,6-naphthyridine-5-carboxamide | 576.47; 577.3 | |
| 275 | 2-[2-(3,4-difluoro-2-methylphenoxy)-4-methyl-5-(trifluoromethyl)-3-pyridyl]-N-(2-methoxycyclohexyl)-4-oxo-1H-1,6-naphthyridine-5-carboxamide | 602.55; 603.4 | |
| 276 | N-(2-carbamoyl-4-pyridyl)-2-[2-(3,4-difluoro-2-methylphenoxy)-4-methyl-5-(trifluoromethyl)-3-pyridyl]-4-oxo-1H-1,6-naphthyridine-5-carboxamide | 610.49; 610.9 | $^1H$ NMR (400 MHz, $CD_3OD$) δ 8.78 (d, J = 2.2 Hz, 1H), 8.72 (dd, J = 13.1, 6.4 Hz, 2H), 8.50 (d, J = 1.0 Hz, 1H), 8.22 (dd, J = 6.6, 2.2 Hz, 1H), 7.71 (d, J = 6.0 Hz, 1H), 7.14 (q, J = 9.3 Hz, 1H), 6.94 (ddd, J = 9.1, 4.1, 2.0 Hz, 1H), 6.58 (s, 1H), 2.50 (d, J = 1.4 Hz, 3H), 2.04 (d, J = 2.1 Hz, 3H) |

Example 13

-continued

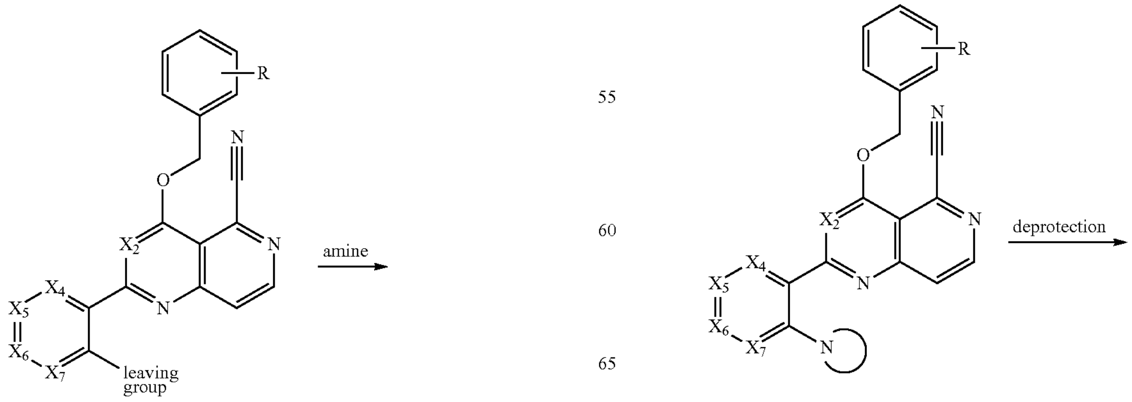

-continued

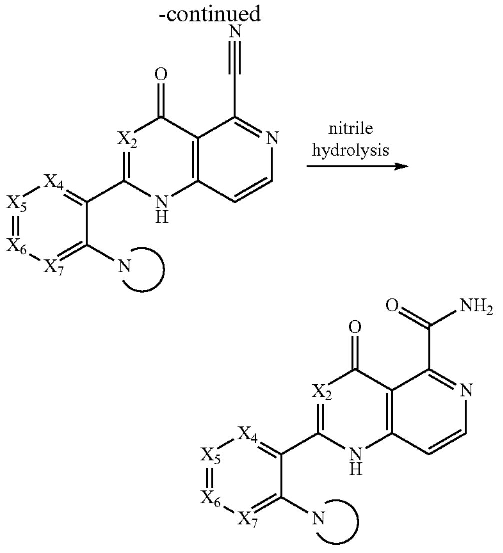

Preparation of Amines

Amine 1: (3S,4S)-3-methoxy-4-methyl-pyrrolidine

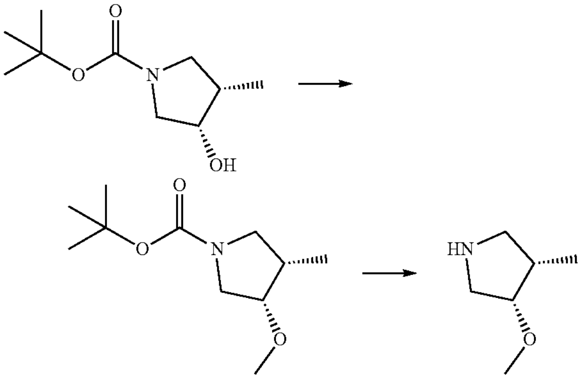

Step 1: tert-butyl (3S,4S)-3-methoxy-4-methyl-pyrrolidine-1-carboxylate

To solution of tert-butyl (3S,4S)-3-hydroxy-4-methyl-pyrrolidine-1-carboxylate (3.0 g, 14.9 mmol) in THF (6 mL) cooled on an ice-bath was added sodium hydride (720 mg, 30.0 mmol) and the mixture stirred for 20 min followed by the addition of iodomethane (1.8 mL, 29 mmol). The temperature was allowed to rise to room temperature and the mixture stirred for a further 30 min. The reaction mixture was partitioned between ethyl acetate (10 mL) and water (10 mL). The aqueous layer was further extracted with ethyl acetate (10 mL). The organic extracts were washed with brine (20 mL), dried over magnesium sulfate, filtered and concentrated. Purification using silica gel chromatography (0-100% ethyl acetate/petroleum ether) provided tert-butyl (3S,4S)-3-methoxy-4-methyl-pyrrolidine-1-carboxylate (2.3 g, 72%). ESI-MS m/z calc. 215.15, found 216.4 $(M+1)^+$. $^1H$ NMR (400 MHz, $CDCl_3$) δ 3.67 (td, J=4.5, 2.2 Hz, 1H), 3.49 (td, J=10.3, 9.8, 4.8 Hz, 2H), 3.34 (s, 4H), 3.02 (t, J=9.9 Hz, 1H), 2.39-2.11 (m, 1H), 1.40 (s, 9H), 1.05 (d, J=6.9 Hz, 3H).

Step 2: (3S,4S)-3-methoxy-4-methyl-pyrrolidine

To a solution of tert-butyl (3S,4S)-3-methoxy-4-methyl-pyrrolidine-1-carboxylate (3.0 g, 13.9 mmol) in dioxane (4 mL) was added hydrogen chloride (10.4 mL of 4 M, 42 mmol) and the mixture stirred at room temperature for 2 h. The solution was concentrated in vacuo to provide (3S,4S)-3-methoxy-4-methyl-pyrrolidine hydrochloride hydrate (2.1 g, 89%). $^1H$ NMR (400 MHz, $CDCl_3$) δ 3.78 (ddd, J=4.9, 3.9, 1.2 Hz, 1H), 3.59-3.38 (m, 2H), 3.36 (s, 4H), 3.01 (tt, J=11.2, 7.1 Hz, 1H), 2.36 (dtd, J=11.5, 7.1, 4.3 Hz, 1H), 1.11 (d, J=6.8 Hz, 3H).

Amine 2: 7,7-difluoro-1,2,3,3a,4,5,6,7a-octahydroisoindole

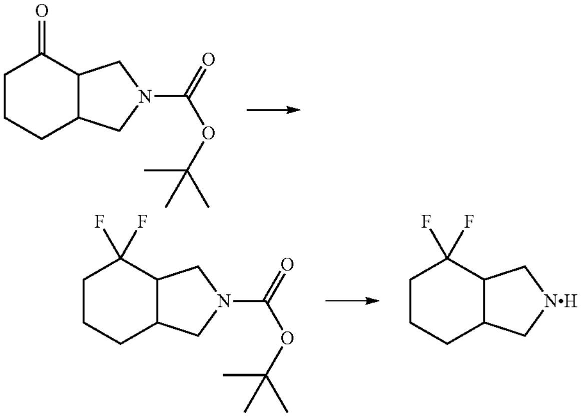

Step 1: tert-butyl 7,7-difluoro-3,3a,4,5,6,7a-hexahydro-1H-isoindole-2-carboxylate A solution of tert-butyl 7-oxo-3,3a,4,5,6,7a-hexahydro-1H-isoindole-2-carboxylate (300 mg, 1.25 mmol) in DCE (4.0 mL) was slowly added to a solution of Deoxo-Fluor® (411 mg, 1.86 mmol) in DCE (4.0 mL) and the mixture stirred overnight at 80° C. The mixture was cooled to 0° C. and saturated aqueous sodium bicarbonate was slowly added. After stirring for 20 min, the reaction was extracted with DCM (3×). The combined extracts were dried over sodium sulfate, filtered and concentrated. Purification by silica gel chromatography (24 g silica, 0-100% ethyl acetate/hexanes) provided tert-butyl 7,7-difluoro-3,3a,4,5,6,7a-hexahydro-1H-isoindole-2-carboxylate. ESI-MS m/z calc. 261.15, found 261.962 $(M+1)^+$.

Step 2: 7,7-difluoro-1,2,3,3a,4,5,6,7a-octahydroisoindole tert-Butyl 7,7-difluoro-3,3a,4,5,6,7a-hexahydro-1H-isoindole-2-carboxylate (1.25 g, 3.83 mmol) was dissolved in a solution of HCl in dioxane (10 mL of 4 M, 40 mmol) at room temperature and stirred for 64 h. The reaction was concentrated to provide 7,7-difluoro-1,2,3,3a,4,5,6,7a-octahydroisoindole hydrochloride (1.08 g, 100%) as a yellow solid. $^1H$ NMR (301 MHz, $CDCl_3$) δ 9.92 (br s, 2H), 3.50-3.05 (m, 4H), 2.83-2.64 (m, 2H), 1.96-1.85 (m, 2H), 1.81-1.63 (m, 4H). $^{19}F$ NMR (283 MHz, $CDCl_3$) δ −90.8−−91.9 (m, 1F), −96.4−−97.3 (m, 1F).

2-[2-(7,7-difluoro-3,3a,4,5,6,7a-hexahydro-1H-isoindol-2-yl)-3-quinolyl]-4-oxo-1H-1,6-naphthyridine-5-carboxamide (277)

Step 1: 4-benzyloxy-2-(2-fluoro-3-quinolyl)-1,6-naphthyridine-5-carbonitrile

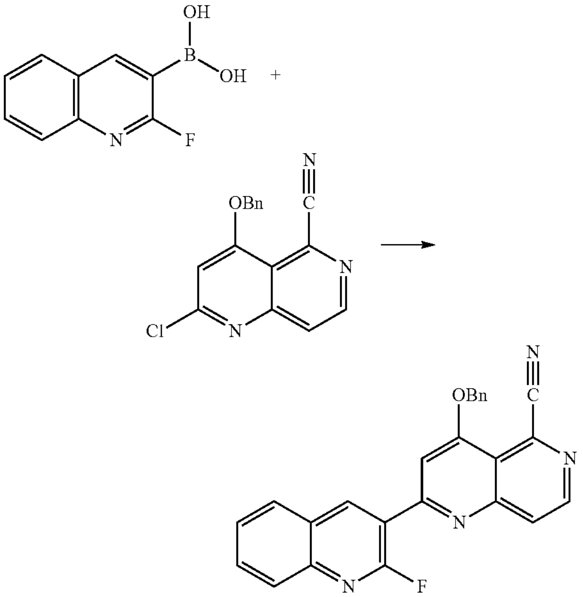

4-Benzyloxy-2-(2-fluoro-3-quinolyl)-1,6-naphthyridine-5-carbonitrile was prepared from 4-benzyloxy-2-chloro-1,6-naphthyridine-5-carbonitrile and (2-fluoro-3-quinolyl)boronic acid using a procedure analogous to that found in Intermediate B-34, step 1 using $PdCl_2$(dtbpf) as the catalyst. ESI-MS m/z calc. 406.12, found 407.2 $(M+1)^+$. $^1H$ NMR (400 MHz, DMSO-$d_6$) δ 9.20 (d, J=9.9 Hz, 1H), 8.94 (d, J=5.7 Hz, 1H), 8.32-8.25 (m, 2H), 8.04-7.98 (m, 2H), 7.98-7.90 (m, 1H), 7.78-7.66 (m, 3H), 7.51-7.44 (m, 2H), 7.44-7.35 (m, 1H), 5.68 (s, 2H).

Step 2: 4-benzyloxy-2-[2-(7,7-difluoro-3,3a,4,5,6,7a-hexahydro-1H-isoindol-2-yl)-3-quinolyl]-1,6-naphthyridine-5-carbonitrile

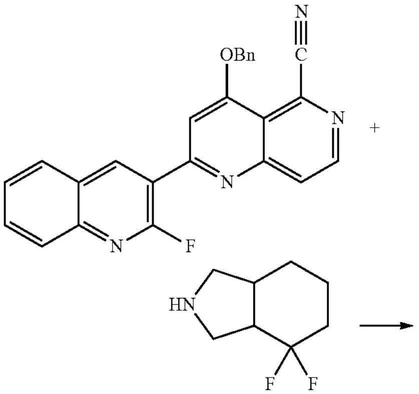

-continued

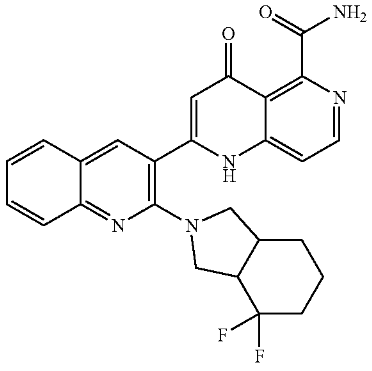

4-Benzyloxy-2-[2-(7,7-difluoro-3,3a,4,5,6,7a-hexahydro-1H-isoindol-2-yl)-3-quinolyl]-1,6-naphthyridine-5-carbonitrile was prepared from 4-benzyloxy-2-(2-fluoro-3-quinolyl)-1,6-naphthyridine-5-carbonitrile and 7,7-difluoro-1,2,3,3a,4,5,6,7a-octahydroisoindole (Amine 2) using a procedure analogous to that found in Intermediate B-20, step 1 using cesium carbonate as base and DMF as solvent. ESI-MS m/z calc. 547.21, found 548.4 $(M+1)^+$. The benzyl-protected intermediate was heated in toluene (5 mL) and TFA (5 mL) at 70° C. for 15 h. The mixture was concentrated, dissolved in ethyl acetate and washed with a saturated aqueous sodium bicarbonate (3×). The combined organic layers were dried over sodium sulfate, filtered and concentrated. Purification by reverse phase HPLC (1-99% acetonitrile/5 mM HCl over 15 min) provided racemic 2-[2-(7,7-difluoro-3,3a,4,5,6,7a-hexahydro-1H-isoindol-2-yl)-3-quinolyl]-4-oxo-1H-1,6-naphthyridine-5-carboxamide hydrochloride (277). ESI-MS m/z calc. 475.18, found 476.3 $(M+1)^+$. $^1H$ NMR (400 MHz, $CD_3OD$) δ 8.78 (d, J=6.0 Hz, 1H), 8.76 (s, 1H), 8.12 (d, J=8.5 Hz, 1H), 8.04 (d, J=8.0 Hz, 1H), 8.01-7.94 (m, 1H), 7.91 (d, J=6.1 Hz, 1H), 7.65 (t, J=7.5 Hz, 1H), 6.94 (s, 1H), 4.01-3.79 (m, 2H), 3.79-3.65 (m, 1H), 3.57-3.36 (m, 1H), 3.06-2.85 (m, 1H), 2.81-2.66 (m, 1H), 2.06-1.82 (m, 2H), 1.76-1.40 (m, 4H).

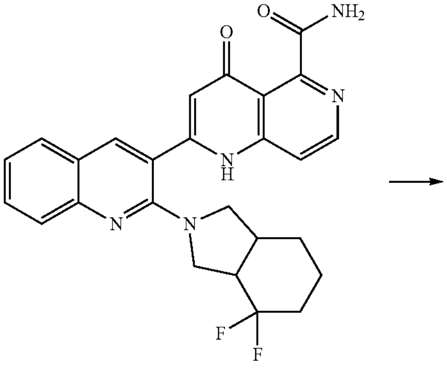

-continued

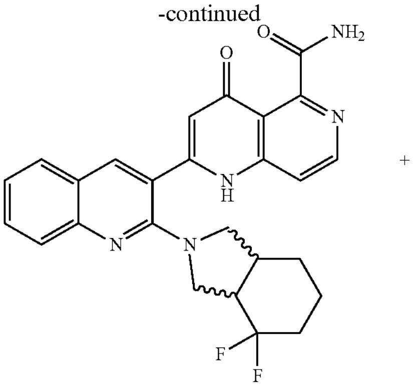

stereoisomer 1

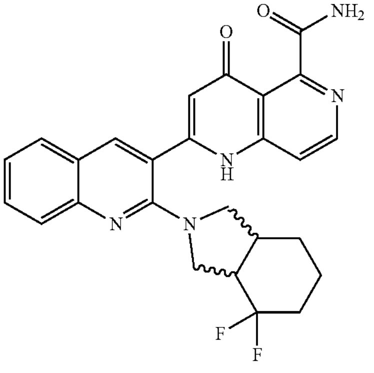

stereoisomer 2

The racemic 2-[2-(7,7-difluoro-3,3a,4,5,6,7a-hexahydro-1H-isoindol-2-yl)-3-quinolyl]-4-oxo-1H-1,6-naphthyridine-5-carboxamide 277 hydrochloride (50 mg, 0.10 mmol) was purified by SFC [ChiralPak IG (21.2×250 mm, 5 um), temperature=40° C., isocractic mode, mobile phase: 40% methanol+20 mM $NH_3$, flow=70 mL/min] to provide the separated stereoisomers.

Compound 278 Stereoisomer 1: 2-[2-(7,7-difluoro-3,3a,4,5,6,7a-hexahydro-1H-isoindol-2-yl)-3-quinolyl]-4-oxo-1H-1,6-naphthyridine-5-carboxamide (14.6 mg, 31%). $^1H$ NMR (400 MHz, $CD_3OD$) δ 8.57 (d, J=5.9 Hz, 1H), 8.24 (s, 1H), 7.81-7.74 (m, 2H), 7.69-7.61 (m, 1H), 7.56 (d, J=5.7 Hz, 1H), 7.31 (t, J=7.5 Hz, 1H), 6.51 (s, 1H), 3.81-3.70 (m, 1H), 3.69-3.58 (m, 1H), 3.57-3.49 (m, 1H), 3.28-3.23 (m, 1H), 2.80-2.64 (m, 1H), 2.49-2.37 (m, 1H), 1.95-1.78 (m, 2H), 1.77-1.65 (m, 1H), 1.65-1.47 (m, 2H), 1.40-1.24 (m, 1H). ESI-MS m/z calc. 475.18, found 476.3 $(M+1)^+$, SFC retention time 9.66 min.

Compound 279 Stereoisomer 2: 2-[2-(7,7-difluoro-3,3a,4,5,6,7a-hexahydro-1H-isoindol-2-yl)-3-quinolyl]-4-oxo-1H-1,6-naphthyridine-5-carboxamide (14.3 mg, 29%). $^1H$ NMR (400 MHz, $CD_3OD$) δ 8.57 (d, J=5.9 Hz, 1H), 8.24 (s, 1H), 7.83-7.71 (m, 2H), 7.70-7.61 (m, 1H), 7.61-7.51 (m, 1H), 7.31 (t, J=7.4 Hz, 1H), 6.51 (s, 1H), 3.82-3.71 (m, 1H), 3.71-3.61 (m, 1H), 3.58-3.49 (m, 1H), 3.28-3.23 (m, 1H), 2.80-2.65 (m, 1H), 2.51-2.36 (m, 1H), 1.97-1.78 (m, 2H), 1.78-1.65 (m, 1H), 1.65-1.49 (m, 2H), 1.44-1.15 (m, 1H). ESI-MS m/z calc. 475.18, found 476.3 $(M+1)^+$; SFC retention time 10.86 min.

UPLC retention times for both stereoisomers were determined using the following conditions: Waters Acquity UPC2 SFC, ChiralPak IG column (4.6×250 mm, 5 um), Temperature: 55° C., Mobile Phase: 36% methanol+20 mM $NH_3$ (isocratic), Flow: 2.25 mL/min.

The following compounds were synthesized using the conditions analogous to those described in Compound 277, step 2 using either commercially available amines or the amines described above. Deprotection and conversion of the nitrile to carboxamide was performed using conditions as show in Compound 277, step 3.

TABLE 10

| Compound Number | Compound Name | MW & Found $[M + H]^+$ | NMR (shifts in ppm) |
|---|---|---|---|
| 278 | 2-[2-(7,7-difluoro-3,3a,4,5,6,7a-hexahydro-1H-isoindol-2-yl)-3-quinolyl]-4-oxo-1H-1,6-naphthyridine-5-carboxamide | 475.49; 476.3 | $^1H$ NMR (400 MHz, $CD_3OD$) δ 8.57 (d, J = 5.9 Hz, 1H), 8.24 (s, 1H), 7.81-7.74 (m, 2H), 7.69-7.61 (m, 1H), 7.56 (d, J = 5.7 Hz, 1H), 7.31 (t, J = 7.5 Hz, 1H), 6.51 (s, 1H), 3.81-3.70 (m, 1H), 3.69-3.58 (m, 1H), 3.57-3.49 (m, 1H), 3.28-3.23 (m, 1H), 2.80-2.64 (m, 1H), 2.49-2.37 (m, 1H), 1.95-1.78 (m, 2H), 1.77-1.65 (m, 1H), 1.65-1.47 (m, 2H), 1.40-1.24 (m, 1H). |
| 279 | 2-[2-(7,7-difluoro-3,3a,4,5,6,7a-hexahydro-1H-isoindol-2-yl)-3-quinolyl]-4-oxo-1H-1,6-naphthyridine-5-carboxamide | 475.49; 476.3 | $^1H$ NMR (400 MHz, $CD_3OD$) δ 8.57 (d, J = 5.9 Hz, 1H), 8.24 (s, 1H), 7.83-7.71 (m, 2H), 7.70-7.61 (m, 1H), 7.61-7.51 (m, 1H), 7.31 (t, J = 7.4 Hz, 1H), 6.51 (s, 1H), 3.82-3.71 (m, 1H), 3.71-3.61 (m, 1H), 3.58-3.49 (m, 1H), 3.28-3.23 (m, 1H), 2.80-2.65 (m, 1H), 2.51-2.36 (m, 1H), 1.97-1.78 (m, 2H), 1.78-1.65 (m, 1H), 1.65-1.49 (m, 2H), 1.44-1.15 (m, 1H) |
| 280 | 2-[2-[(3aR,6aS)-5,5-difluoro-1,3,3a,4,6,6a-hexahydrocyclopenta[c]pyrrol-2-yl]-3-quinolyl]-4-oxo-1H-1,6-naphthyridine-5-carboxamide | 461.46; 462.3 | |

TABLE 10-continued

| Compound Number | Compound Name | MW & Found [M + H]+ | NMR (shifts in ppm) |
|---|---|---|---|
| 281 | 2-[2-(3,3-difluoropyrrolidin-1-yl)-3-quinolyl]-4-oxo-1H-1,6-naphthyridine-5-carboxamide | 421.4; 422.2 | $^1$H NMR (400 MHz, $CD_3OD$) δ 8.81 (d, J = 6.0 Hz, 1H), 8.71 (s, 1H), 8.07 (d, J = 8.5 Hz, 1H), 8.04-8.00 (m, 1H), 7.97-7.91 (m, 2H), 7.62 (t, J = 7.6 Hz, 1H), 7.03 (s, 1H), 4.03 (t, J = 12.1 Hz, 2H), 3.85 (t, J = 7.3 Hz, 2H), 2.60-2.31 (m, 2H). |
| 282 | 2-[2-(3,3-difluoropyrrolidin-1-yl)-3-quinolyl]-4-oxo-1H-1,6-naphthyridine-5-carbonitrile | 403.38; 404.2 | $^1$H NMR (400 MHz, $CD_3OD$) δ 8.77 (d, J = 5.8 Hz, 1H), 8.64 (s, 1H), 8.02 (d, J = 8.6 Hz, 1H), 7.98 (d, J = 8.0 Hz, 1H), 7.90 (t, J = 7.9 Hz, 1H), 7.73 (d, J = 5.9 Hz, 1H), 7.58 (t, J = 7.5 Hz, 1H), 6.64 (s, 1H), 4.05 (t, J = 12.2 Hz, 2H), 3.85 (t, J = 7.4 Hz, 2H), 2.61-2.39 (m, 2H). |
| 283 | 2-[2-(4,4-difluoro-1-piperidyl)-3-quinolyl]-4-oxo-1H-1,6-naphthyridine-5-carboxamide | 435.43; 436.2 | $^1$H NMR (400 MHz, $CD_3OD$) δ 8.89 (d, J = 6.2 Hz, 1H), 8.85 (s, 1H), 8.20 (d, J = 6.2 Hz, 1H), 8.12-8.04 (m, 2H), 8.00-7.94 (m, 1H), 7.67 (t, J = 7.6 Hz, 1H), 7.27 (s, 1H), 3.76-3.64 (m, 4H), 2.24-2.06 (m, 4H). |
| 284 | 2-[2-(3,3-dimethylpyrrolidin-1-yl)-3-quinolyl]-4-oxo-1H-1,6-naphthyridine-5-carboxamide | 413.47; 414.3 | $^1$H NMR (400 MHz, $CD_3OD$) δ 8.81 (d, J = 6.1 Hz, 1H), 8.73 (s, 1H), 8.11 (d, J = 8.5 Hz, 1H), 8.04-7.99 (m, 2H), 7.99-7.93 (m, 1H), 7.63 (t, J = 7.6 Hz, 1H), 6.99 (s, 1H), 3.99-3.39 (m, 4H), 1.95-1.78 (m, 2H), 1.16 (s, 6H). |
| 285 | 2-[2-(1,3,3a,4,5,6,7,7a-octahydroisoindol-2-yl)-3-quinolyl]-4-oxo-1H-1,6-naphthyridine-5-carboxamide | 439.51; 440.3 | |
| 286 | 2-[2-[(3S,4S)-3-methoxy-4-methyl-pyrrolidin-1-yl]-3-quinolyl]-4-oxo-1H-1,6-naphthyridine-5-carboxamide | 429.47; 430.3 | $^1$H NMR (400 MHz, $CD_3OD$) δ 8.85 (d, J = 6.3 Hz, 1H), 8.76 (s, 1H), 8.17-8.07 (m, 2H), 8.07-8.01 (m, 1H), 8.01-7.91 (m, 1H), 7.64 (t, J = 7.6 Hz, 1H), 7.06 (s, 1H), 4.03-3.57 (m, 4H), 3.51-3.39 (m, 1H), 3.33 (s, 3H), 2.62-2.42 (m, 1H), 1.21-1.00 (m, 3H). |
| 287 | 2-[2-[3-methoxy-4-(trifluoromethyl)pyrrolidin-1-yl]-3-quinolyl]-4-oxo-1H-1,6-naphthyridine-5-carboxamide (trans isomer, racemic) | 483.44; 484.2 | $^1$H NMR (400 MHz, $CD_3OD$) δ 8.78 (d, J = 6.0 Hz, 1H), 8.76 (s, 1H), 8.11 (d, J = 8.5 Hz, 1H), 8.07-8.02 (m, 1H), 8.00- 7.93 (m, 1H), 7.91 (d, J = 6.0 Hz, 1H), 7.65 (t, J = 7.6 Hz, 1H), 6.98 (s, 1H), 4.27-4.18 (m, 1H), 4.14-4.02 (m, 2H), 3.70 (s, 2H), 3.53-3.40 (m, 1H), 3.32 (s, 3H). |
| 288 | 2-[2-(4,4-dimethyl-1-piperidyl)-3-quinolyl]-4-oxo-1H-1,6-naphthyridine-5-carboxamide | 427.5; 428.3 | $^1$H NMR (400 MHz, $CD_3OD$) δ 8.89 (s, 1H), 8.87 (d, J = 6.3 Hz, 1H), 8.22 (d, J = 6.2 Hz, 1H), 8.14 (d, J = 8.5 Hz, 1H), 8.09 (dd, J = 8.1, 1.3 Hz, 1H), 8.05-7.97 (m, 1H), 7.70 (t, J = 7.6 Hz, 1H), 7.15 (s, 1H), 3.71-3.60 (m, 4H), 1.61-1.49 (m, 4H), 1.03 (s, 6H). |
| 289 | 2-[2-(4-methyl-1-piperidyl)-3-quinolyl]-4-oxo-1H-1,6-naphthyridine-5-carboxamide | 413.47; 414.3 | $^1$H NMR (400 MHz, $CD_3OD$) δ 8.87 (s, 1H), 8.85 (d, J = 6.1 Hz, 1H), 8.15-8.05 (m, 3H), 8.05-7.96 (m, 1H), 7.69 (t, J = 7.6 Hz, 1H), 7.11 (s, 1H), 3.99-3.89 (m, 2H), 3.40-3.32 (m, 2H), 1.82-1.65 (m, 3H), 1.42-1.26 (m, 2H), 0.98 (d, J = 6.1 Hz, 3H). |
| 290 | 2-[2-(6-azaspiro[2.5]octan-6-yl)-3-quinolyl]-4-oxo-1H-1,6-naphthyridine-5-carboxamide | 425.48; 426.3 | $^1$H NMR (400 MHz, $CD_3OD$) δ 8.92 (s, 1H), 8.88 (d, J = 6.3 Hz, 1H), 8.25 (d, J = 6.3 Hz, 1H), 8.16 (d, J = 8.5 Hz, 1H), 8.14-8.07 (m, 1H), 8.06-7.97 (m, 1H), 7.70 (t, J = 7.6 Hz, 1H), 7.18 (s, 1H), 3.77-3.68 (m, 4H), 1.62-1.52 (m, 4H), 0.44 (s, 4H). |
| 291 | 2-[2-(azocan-1-yl)-3-quinolyl]-4-oxo-1H-1,6-naphthyridine-5-carboxamide | 427.5; 428.3 | |
| 292 | 4-oxo-2-[2-[4-(trifluoromethyl)-1-piperidyl]-3-quinolyl]-1H-1,6-naphthyridine-5-carboxamide | 467.44; 468.2 | |

TABLE 10-continued

| Compound Number | Compound Name | MW & Found [M + H]+ | NMR (shifts in ppm) |
|---|---|---|---|
| 293 | 2-[2-[(3aR,6aS)-3,3a,4,5,6,6a-hexahydro-1H-cyclopenta[c]pyrrol-2-yl]-3-quinolyl]-4-oxo-1H-1,6-naphthyridine-5-carboxamide | 425.48; 426.3 | |
| 294 | 2-[2-(3,3-difluoroazepan-1-yl)-3-quinolyl]-4-oxo-1H-1,6-naphthyridine-5-carboxamide | 449.45; 450.2 | |
| 295 | 2-[2-[(3R,4S)-3,4-dimethylpyrrolidin-1-yl]-3-quinolyl]-4-oxo-1H-1,6-naphthyridine-5-carboxamide | 413.47; 414.3 | |
| 296 | 2-[2-(6-azaspiro[3.5]nonan-6-yl)-3-quinolyl]-4-oxo-1H-1,6-naphthyridine-5-carboxamide | 439.51; 440.3 | |
| 297 | 2-[2-[(4aS,7aR)-6,6-difluoro-3,4,4a,5,7,7a-hexahydro-1H-cyclopenta[c]pyridin-2-yl]-3-quinolyl]-4-oxo-1H-1,6-naphthyridine-5-carboxamide | 475.49; 476.307 | |
| 298 | 2-[2-(1,3,4,4a,5,6,7,7a-octahydrocyclopenta[c]pyridin-2-yl)-3-quinolyl]-4-oxo-1H-1,6-naphthyridine-5-carboxamide | 439.51; 440.3 | |
| 299 | 2-[2-(azepan-1-yl)-3-quinolyl]-4-oxo-1H-1,6-naphthyridine-5-carboxamide | 413.47; 414.3 | |
| 300 | 2-[2-[3-methoxy-4-(trifluoromethyl)pyrrolidin-1-yl]-3-quinolyl]-4-oxo-1H-1,6-naphthyridine-5-carboxamide (trans isomer, peak 1 by chiral SFC) | 483.44; 484.2 | |
| 301 | 2-[2-[3-methoxy-4-(trifluoromethyl)pyrrolidin-1-yl]-3-quinolyl]-4-oxo-1H-1,6-naphthyridine-5-carboxamide (trans isomer, peak 2 by chiral SFC) | 483.44; 484.2 | |
| 302 | 2-[2-(3,3a,4,5,6,7,8,8a-octahydro-1H-cyclohepta[c]pyrrol-2-yl)-3-quinolyl]-4-oxo-1H-1,6-naphthyridine-5-carboxamide | 453.54; 454.3 | |
| 303 | 2-[2-[cyclobutyl(ethyl)amino]-3-quinolyl]-4-oxo-1H-1,6-naphthyridine-5-carboxamide | 413.47; 414.3 | $^1$H NMR (400 MHz, $CD_3OD$) δ 8.97 (s, 1H), 8.85 (d, J = 6.1 Hz, 1H), 8.16-8.00 (m, 4H), 7.80-7.67 (m, 1H), 7.10 (s, 1H), 4.58-4.43 (m, 1H), 3.52 (q, J = 7.1 Hz, 2H), 2.51-2.35 (m, 2H), 2.35-2.17 (m, 2H), 1.94-1.73 (m, 2H), 1.20 (t, J = 7.1 Hz, 3H). |

2-[2-(4,4-difluoroazepan-1-yl)-3-quinolyl]-1H-1,5-naphthyridin-4-one (304)

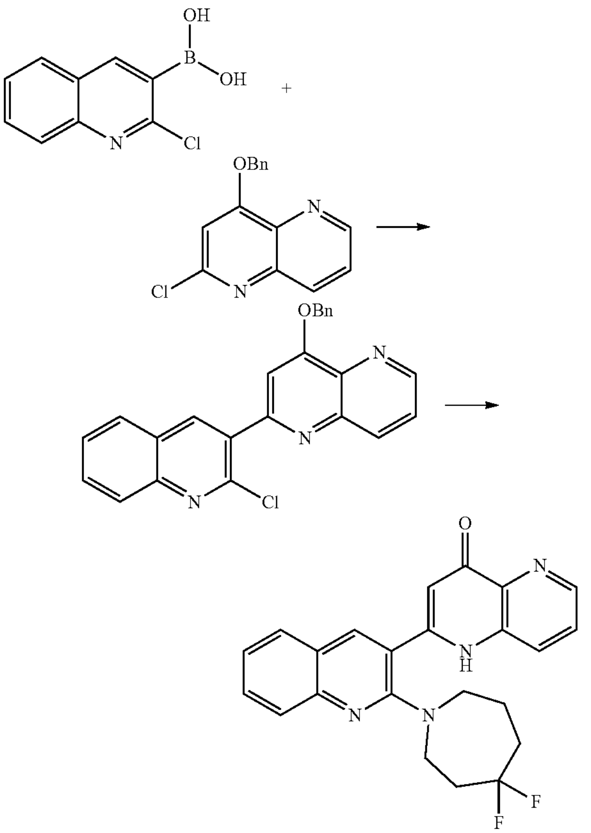

Step 1: 4-benzyloxy-2-(2-chloro-3-quinolyl)-1,5-naphthyridine

4-Benzyloxy-2-(2-chloro-3-quinolyl)-1,5-naphthyridine was prepared from (2-chloro-3-quinolyl)boronic acid and 4-benzyloxy-2-chloro-1,5-naphthyridine using a procedure analogous to that found in Intermediate B-34, step 1 with $Pd(PPh_3)_4$ as catalyst. ESI-MS m/z calc. 397.10, found 398.2 $(M+1)^+$. $^1H$ NMR (400 MHz, DMSO-$d_6$) δ 9.00 (dd, J=4.2, 1.6 Hz, 1H), 8.77 (s, 1H), 8.47 (dd, J=8.6, 1.6 Hz, 1H), 8.19 (d, J=7.7 Hz, 1H), 8.08 (d, J=8.2 Hz, 1H), 7.97-7.91 (m, 1H), 7.88 (dd, J=8.5, 4.1 Hz, 1H), 7.82-7.72 (m, 2H), 7.62-7.56 (m, 2H), 7.46 (t, J=7.3 Hz, 2H), 7.44-7.37 (m, 1H), 5.50 (s, 2H).

Step 2: 2-[2-(4,4-difluoroazepan-1-yl)-3-quinolyl]-1H-1,5-naphthyridin-4-one (303)

4-Benzyloxy-2-[2-(4,4-difluoroazepan-1-yl)-3-quinolyl]-1,5-naphthyridine was prepared from 4-benzyloxy-2-(2-chloro-3-quinolyl)-1,5-naphthyridine and 4,4-difluoroazepane using a procedure analogous to that found in Intermediate B-20, step 1 and cesium carbonate as the base. ESI-MS m/z calc. 496.21, found 497.3. The benzyl-protected intermediate was stirred in 1:1 MeOH/ethyl acetate with 10% Pd/C under hydrogen atmosphere for 1 h. Filtration and purification by reverse phase HPLC (1-99% $CH_3CN$/5 mM HCl provided 2-[2-(4,4-difluoroazepan-1-yl)-3-quinolyl]-1H-1,5-naphthyridin-4-one (304, 13.0 mg, 26%). ESI-MS m/z calc. 406.16, found 407.3 $(M+1)^+$. $^1H$ NMR (400 MHz, DMSO-$d_6$) δ 8.96-8.84 (m, 1H), 8.54 (s, 1H), 8.47 (s, 1H), 8.04 (s, 1H), 7.91 (d, J=7.9 Hz, 1H), 7.85-7.67 (m, 2H), 7.40 (t, J=7.4 Hz, 1H), 6.98 (s, 1H), 3.67 (dd, J=6.1, 3.2 Hz, 2H), 3.40 (t, J=5.9 Hz, 2H), 2.34 (s, 2H), 1.99 (q, J=14.3, 10.5 Hz, 2H), 1.74 (d, J=5.6 Hz, 2H). $^{19}F$ NMR (376 MHz, DMSO-$d_6$) δ −88.20.

Example 14

Post Suzuki Cis-Trans Separation

2-[2-(trifluoromethyl)-5-[4-(trifluoromethyl)cyclohexyl]-4-pyridyl]-1H-1,6-naphthyridin-4-one (trans) (305)

2-[2-(trifluoromethyl)-5-[4-(trifluoromethyl)cyclohexyl]-4-pyridyl]-1H-1,6-naphthyridin-4-one (cis) (306)

Step 1: 4-benzyloxy-2-[2-(trifluoromethyl)-5-[4-(trifluoromethyl)cyclohexyl]-4-pyridyl]-1,6-naphthyridine

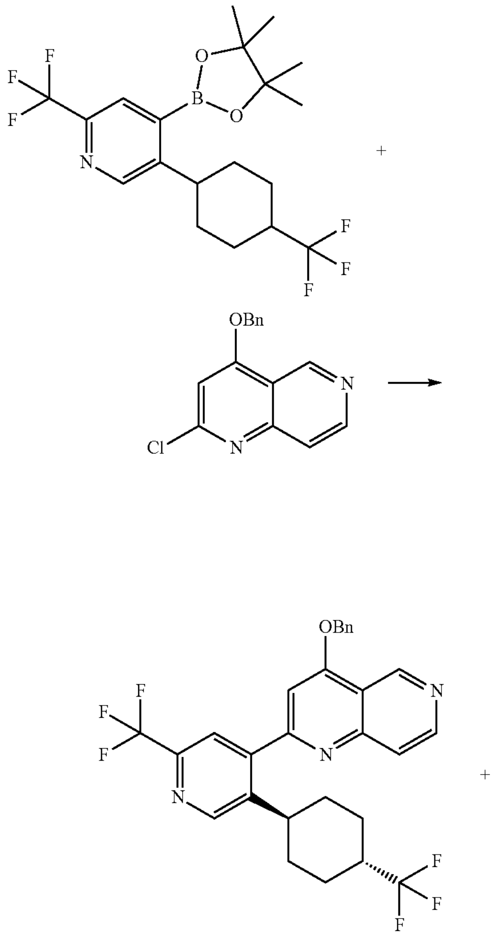

-continued

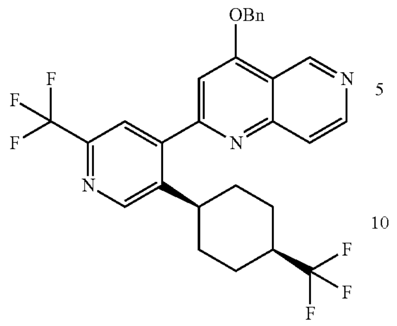

4-Benzyloxy-2-[2-(trifluoromethyl)-5-[4-(trifluoromethyl)cyclohexyl]-4-pyridyl]-1,6-naphthyridine (mixture of cis and trans isomers) was prepared from 4-(4,4,5,5-tetramethyl-1,3,2-dioxaborolan-2-yl)-2-(trifluoromethyl)-5-[4-(trifluoromethyl)cyclohexyl]pyridine (Intermediate B-34, mixture of cis- and trans-isomers) and 4-benzyloxy-2-chloro-1,6-naphthyridine using a procedure analogous to that found in Intermediate B-34, step 1. Purification by silica gel chromatography (0-50% ethyl acetate/heptanes over 20 min) afforded the minor trans product 4-benzyloxy-2-[2-(trifluoromethyl)-5-[4-(trifluoromethyl)cyclohexyl]-4-pyridyl]-1,6-naphthyridine ESI-MS m/z calc. 531.18, found 532.3 $(M+1)^+$; Retention time: 2.55 min, and the major cis product 4-benzyloxy-2-[2-(trifluoromethyl)-5-[4-(trifluoromethyl)cyclohexyl]-4-pyridyl]-1,6-naphthyridine ESI-MS m/z calc. 531.18, found 532.5 $(M+1)^+$; Retention time: 2.58 min. Retention times for the separated stereoisomers were determined using reverse phase UPLC using an Acquity UPLC BEH C18 column (50×2.1 mm, 1.7 m particle) made by Waters, and a dual gradient run from 1-99% mobile phase B over 4.5 min. Mobile phase A=water (0.05% TFA). Mobile phase B=$CH_3CN$ (0.035% TFA). Flow rate=1.2 mL/min, injection volume=1.5 μL, and column temperature=60° C.

Step 2a: 2-[2-(trifluoromethyl)-5-[4-(trifluoromethyl)cyclohexyl]-4-pyridyl]-1H-1,6-naphthyridin-4-one (305)

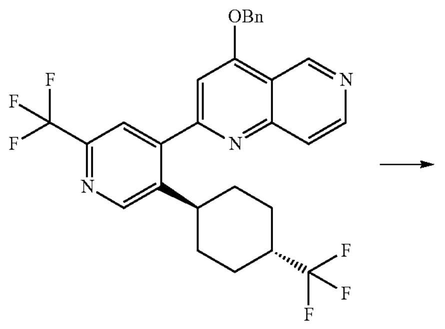

-continued

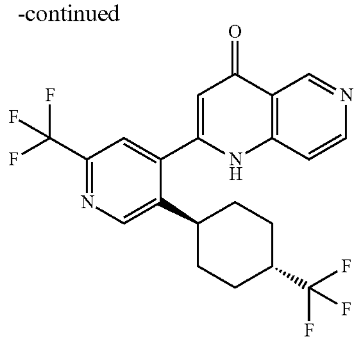

Trans Isomer 4-Benzyloxy-2-[2-(trifluoromethyl)-5-[4-(trifluoromethyl)cyclohexyl]-4-pyridyl]-1,6-naphthyridine was stirred with 10% Pd/C in methanol, then filtered and purified twice by reverse phase HPLC (10-99% acetonitrile/5 mM HCl over 15 min) to provide (trans isomer) 2-[2-(trifluoromethyl)-5-[4-(trifluoromethyl)cyclohexyl]-4-pyridyl]-1H-1,6-naphthyridin-4-one hydrochloride (305, 1.8 mg, 7%). $^1H$ NMR (400 MHz, $CD_3OD$) δ 9.51 (s, 1H), 8.97 (s, 1H), 8.75 (dd, J=6.9, 1.0 Hz, 1H), 7.97 (s, 1H), 7.91 (d, J=6.8 Hz, 1H), 6.56 (s, 1H), 2.88-2.76 (m, 1H), 2.37-2.25 (m, 1H), 2.08-1.96 (m, 4H), 1.90-1.75 (m, 2H), 1.44-1.29 (m, 2H). $^{19}F$ NMR (376 MHz, $CD_3OD$) δ −69.27, −75.41. ESI-MS m/z calc. 441.13, found 442.2 $(M+1)^+$; Retention time: 1.62 min. as a white solid.

Step 2b: 2-[2-(trifluoromethyl)-5-[4-(trifluoromethyl)cyclohexyl]-4-pyridyl]-1H-1,6-naphthyridin-4-one (306)

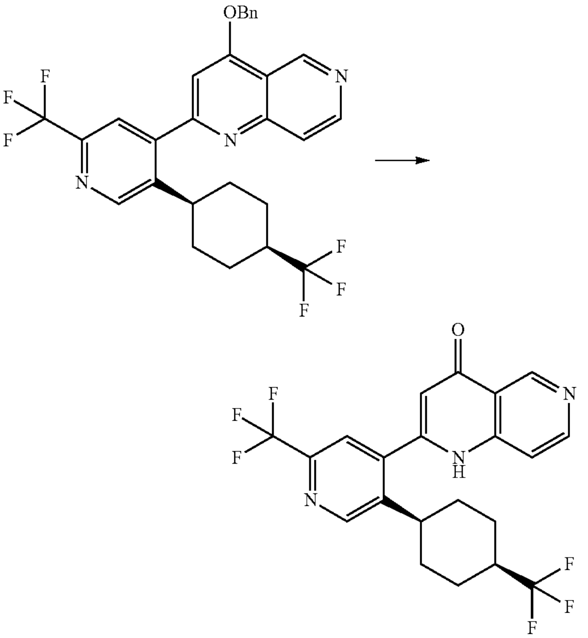

cis 4-Benzyloxy-2-[2-(trifluoromethyl)-5-[4-(trifluoromethyl)cyclohexyl]-4-pyridyl]-1,6-naphthyridine was stirred with 10% Pd/C in methanol, then filtered and purified twice by reverse phase HPLC (10-99% acetonitrile/5 mM HCl over 15 min) to provide (cis isomer) 2-[2-(trifluoromethyl)-5-[4-(trifluoromethyl)cyclohexyl]-4-pyridyl]-1H-1,6-naphthyridin-4-one hydrochloride (306, 15 mg, 58%). $^1$H NMR (400 MHz, $CD_3OD$) δ 9.51 (s, 1H), 8.88 (s, 1H), 8.76 (app dd, J=6.8, 1.1 Hz, 1H), 7.97 (s, 1H), 7.92 (app d, J=6.9 Hz, 1H), 6.58 (s, 1H), 2.99-2.89 (m, 1H), 2.53-2.32 (m, 1H), 2.13-2.05 (m, 2H), 2.01-1.86 (m, 2H), 1.84-1.77 (m, 2H), 1.77-1.64 (m, 2H). $^{19}$F NMR (376 MHz, $CD_3OD$) δ −68.19, −69.27. ESI-MS m/z calc. 441.13, found 442.3 $(M+1)^+$; Retention time: 1.68 min.

2-[6-(trifluoromethyl)-4-[4-(trifluoromethyl)cyclohexyl]-3-pyridyl]-1H-1,6-naphthyridin-4-one (307) (cis isomer)

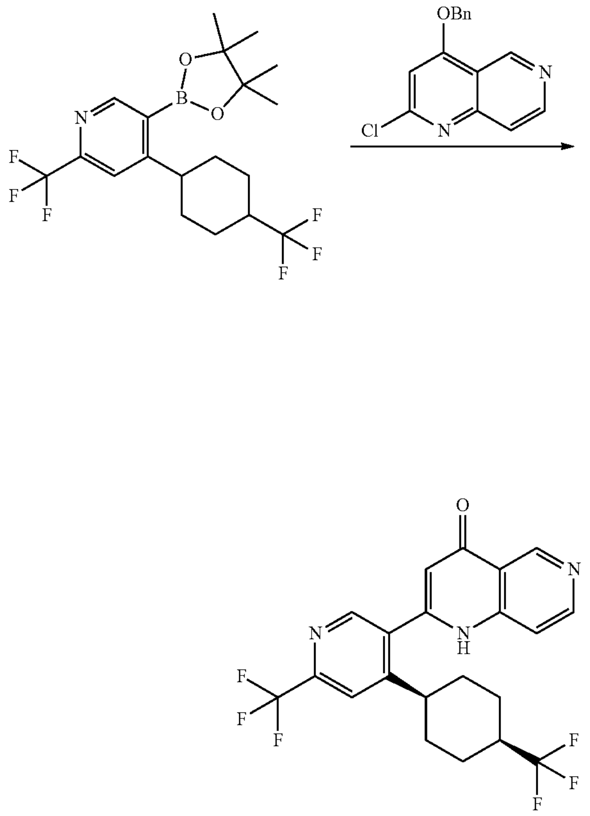

4-Benzyloxy-2-[6-(trifluoromethyl)-4-[4-(trifluoromethyl)cyclohexyl]-3-pyridyl]-1,6-naphthyridine (mixture of cis trans) was prepared from Intermediate B-35 (3:1 cis trans) and 4-benzyloxy-2-chloro-1,6-naphthyridine using a procedure analogous to that found in Intermediate B-34, step 1. ESI-MS m/z calc. 531.18, found 532.2 $(M+1)^+$. The benzyl-protected intermediate dissolved in ethanol (1 mL) and stirred with 10% Pd/C (5.3 mg) and stirred under an atmosphere of hydrogen for 30 min. Filtration and purification by reverse phase chromatography (C18, 1-99% $CH_3CN$/HCl over 15 min) provided 2-[6-(trifluoromethyl)-4-[4-(trifluoromethyl)cyclohexyl]-3-pyridyl]-1H-1,6-naphthyridin-4-one (cis isomer) (307, 1.4 mg, 6%) ESI-MS m/z calc. 441.13, found 442.1 $(M+1)^+$. $^1$H NMR (400 MHz, $CD_3OD$) δ 9.50 (s, 1H), 8.79 (s, 1H), 8.74 (dd, J=6.7, 0.9 Hz, 1H), 7.85 (d, J=6.7 Hz, 1H), 7.82 (s, 1H), 6.59 (s, 1H), 3.00-2.91 (m, 1H), 2.47-2.37 (m, 1H), 2.08 (d, J=14.3 Hz, 2H), 1.91-1.60 (m, 6H).

2-[6-tert-butyl-4-[4-(trifluoromethyl)cyclohexyl]-3-pyridyl]-4-oxo-1H-1,6-naphthyridine-5-carboxamide (cis) (308)

And

2-[6-tert-butyl-4-[4-(trifluoromethyl)cyclohexyl]-3-pyridyl]-4-oxo-1H-1,6-naphthyridine-5-carboxamide (trans) (309)

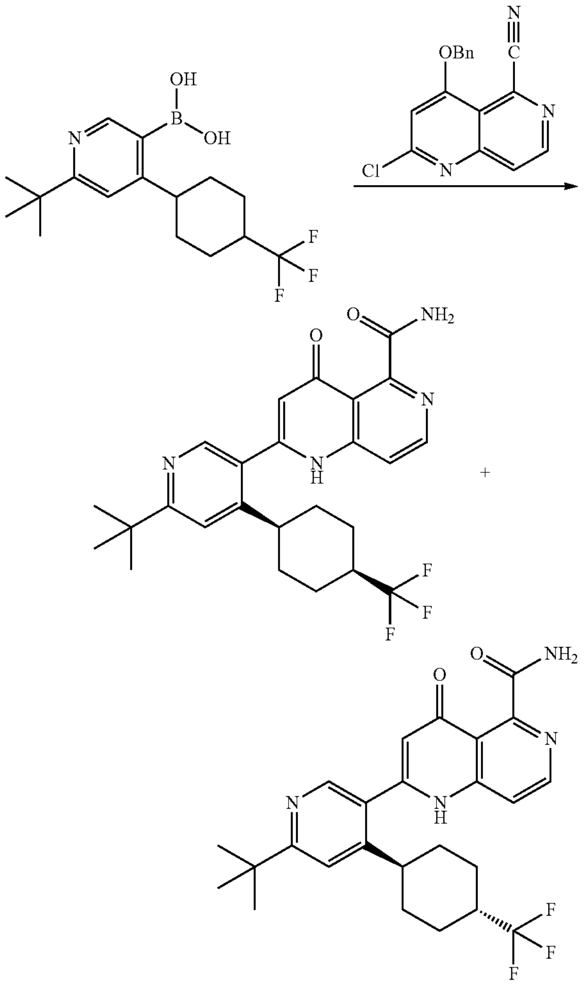

4-Benzyloxy-2-[6-tert-butyl-4-[4-(trifluoromethyl)cyclohexyl]-3-pyridyl]-1,6-naphthyridine-5-carbonitrile was synthesized using from [6-tert-butyl-4-[4-(trifluoromethyl)cyclohexyl]-3-pyridyl]boronic acid (Intermediate B-38, cis/trans mixture, 110 mg, 0.287 mmol) and 4-benzyloxy-2-chloro-1,6-naphthyridine-5-carbonitrile using condition analogous to those found in Intermediate B-34, step 1 using $PdCl_2$(dtbpf) as the catalyst. ESI-MS m/z calc. 544.25, found 545.4 $(M+1)^+$. The benzyl-protected intermediate was dissolved in toluene (1.5 mL) and TFA (1 mL) and stirred at 60° C. for 16 h. The mixture was concentrated under reduced pressure and purified by reverse phase HPLC (C18, 1-99% $CH_3CN$/5 mM HCl over 30 min) to provide the separated cis and trans product isomers. Retention times for the separated isomer were determined using reverse phase UPLC under the following conditions: Acquity UPLC BEH C18 column (30×2.1 mm, 1.7 m particle) made by Waters and a dual gradient run from 1-99% mobile phase B over 1.0 min. Mobile phase A=water (0.05% TFA). Mobile phase B=$CH_3CN$ (0.035% TFA). Flow rate=1.5 mL/min, injection volume=1.5 μL, and column temperature=60° C.

Peak 1 (309, trans isomer): 2-[6-tert-butyl-4-[4-(trifluoromethyl)cyclohexyl]-3-pyridyl]-4-oxo-1H-1,6-naphthyridine-5-carboxamide hydrochloride. ESI-MS m/z calc. 472.21, found 473.3 $(M+1)^+$; Retention time: 1.47 min. $^1H$ NMR (400 MHz, $CD_3OD$) δ 8.89 (s, 1H), 8.79 (d, J=6.2 Hz, 1H), 8.09 (s, 1H), 7.98 (d, J=6.2 Hz, 1H), 6.83 (s, 1H), 3.03-2.83 (m, 1H), 2.44-2.23 (m, 1H), 2.08-2.01 (m, 4H), 1.91-1.70 (m, 2H), 1.58 (s, 9H), 1.44-1.21 (m, 2H).

Peak 2 (308, cis isomer): 2-[6-tert-butyl-4-[4-(trifluoromethyl)cyclohexyl]-3-pyridyl]-4-oxo-1H-1,6-naphthyridine-5-carboxamide hydrochloride. ESI-MS m/z calc. 472.21, found 473.3 $(M+1)^+$; Retention time: 1.54 min., $^1H$ NMR (400 MHz, $CD_3OD$) δ 8.90 (s, 1H), 8.82 (d, J=6.2 Hz, 1H), 8.01 (d, J=6.2 Hz, 1H), 7.91 (s, 1H), 6.90 (s, 1H), 3.16-2.98 (m, 1H), 2.44 (s, 1H), 2.08 (d, J=14.6 Hz, 2H), 1.87 (s, 4H), 1.72 (dd, J=14.7, 7.6 Hz, 2H), 1.57 (s, 9H).

Example 15

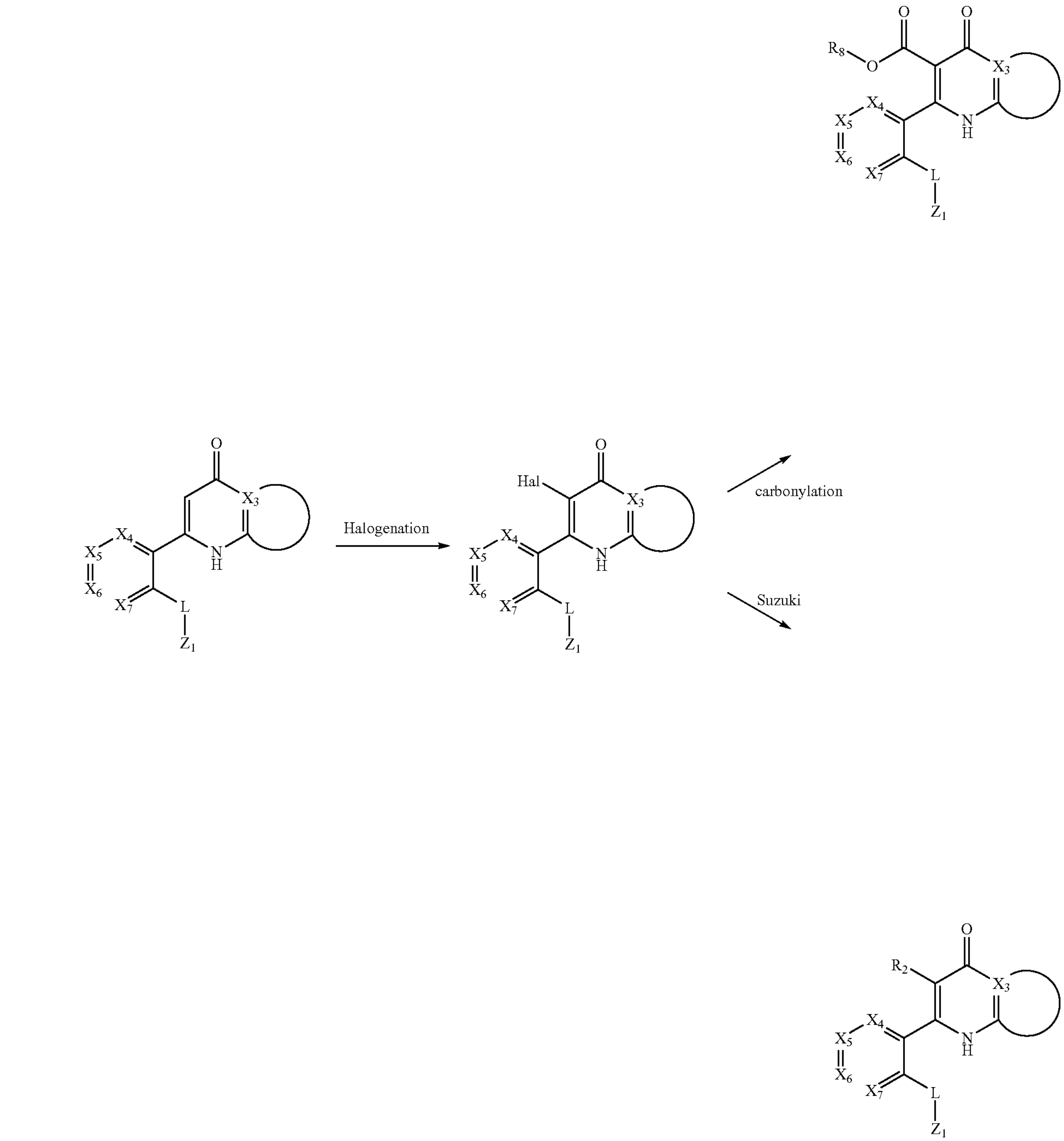

2-[4-tert-butyl-2-(4-fluoro-2-methoxy-phenoxy)-6-methyl-phenyl]-3-chloro-1H-quinolin-4-one (310)

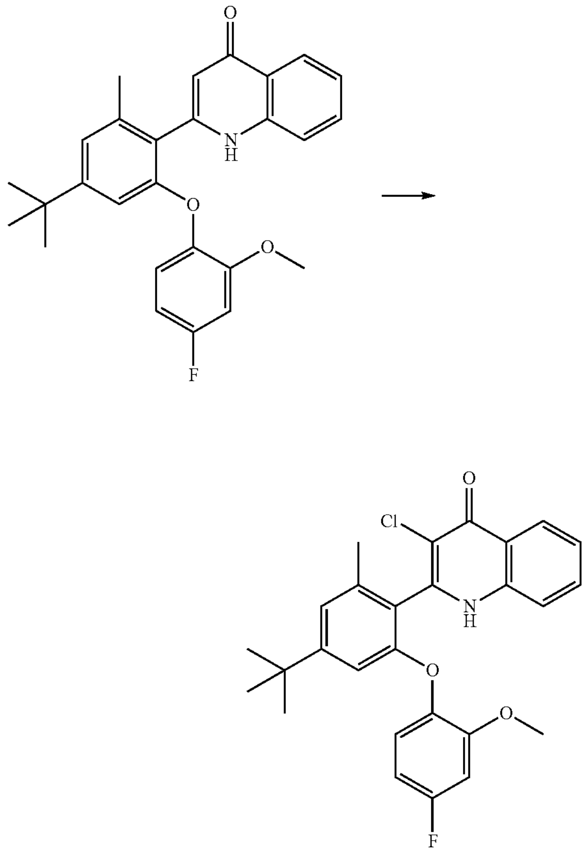

2-[4-tert-Butyl-2-(4-fluoro-2-methoxy-phenoxy)-6-methyl-phenyl]-1H-quinolin-4-one (15 mg, 0.035 mmol) was dissolved in DCM (350 μL) and NCS (6 mg, 0.045 mmol) added in a single portion. The reaction was stirred for 3 h, then treated with additional 1-chloropyrrolidine-2,5-dione (6 mg, 0.045 mmol) and allowed to stir overnight. The mixture was then concentrated and then purified by silica gel chromatography (4 g silica, 0-100% ethyl acetate/hexanes) to afford 2-[4-tert-butyl-2-(4-fluoro-2-methoxy-phenoxy)-6-methyl-phenyl]-3-chloro-1H-quinolin-4-one (7 mg, 43%) as a white solid. ESI-MS m/z calc. 465.15, found 466.0 $(M+1)^+$. The resulting mixture of atropisomers were separated by chiral SFC using a Phenomenex LUX-4 column (250×10 mm; 5 μm) at 50° C. Mobile phase was 28% methanol (w/20 mM $NH_3$), 72% $CO_2$ at a 10 mL/min flow.

Peak 1 (310): 2-[4-tert-butyl-2-(4-fluoro-2-methoxy-phenoxy)-6-methyl-phenyl]-3-chloro-1H-quinolin-4-one. ESI-MS m/z calc. 465.15, found 466.30 $(M+1)^+$; Retention time: 2.36 min (Phenomenex Lux-4 (150×2.1 mm), 3 m; 55° C., 18% methanol (20 mM $NH_3$), 82% $CO_2$, 1.8 mL/min, 5 min run)

Peak 2 (312): 2-[4-tert-butyl-2-(4-fluoro-2-methoxy-phenoxy)-6-methyl-phenyl]-3-chloro-1H-quinolin-4-one. ESI-MS m/z calc. 466.3, found 468.0 $(M+1)^+$; Retention time: 3.26 min (Phenomenex Lux-4 (150×2.1 mm), 3 μm; 55° C., 18% methanol (20 mM $NH_3$), 82% $CO_2$, 1.8 mL/min, 5 min run)

3-bromo-2-[2-(4,4-difluoroazepan-1-yl)-3-quinolyl]-4-oxo-1H-1,6-naphthyridine-5-carboxamide (313)

Step 1: 3-bromo-2-[2-(4,4-difluoroazepan-1-yl)-3-quinolyl]-4-oxo-1H-1,6-naphthyridine-5-carboxamide (313)

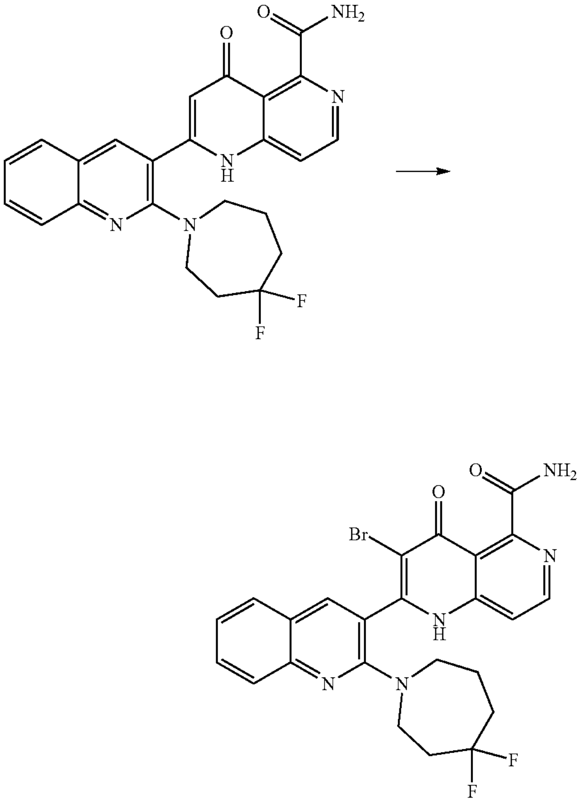 [SMILES: NC(=O)c1nccc2[nH]c(-c3cc4ccccc4nc3N3CCCC(F)(F)CC3)cc(=O)c12 ; NC(=O)c1nccc2[nH]c(-c3cc4ccccc4nc3N3CCCC(F)(F)CC3)c(Br)c(=O)c12]

To a solution of 2-[2-(4,4-difluoroazepan-1-yl)-3-quinolyl]-4-oxo-1H-1,6-naphthyridine-5-carboxamide (82 mg, 0.18 mmol) in DCM (1.5 mL) and acetic acid (676 μL) was added NBS (46 mg, 0.26 mmol) in a single portion. The mixture was stirred at room temperature for 1 h, then partitioned between DCM and a solution of saturated aqueous sodium thiosulfate. The two layers were separated and the aqueous layer was extracted with ethyl acetate (3×). The combined organic layers were washed with saturated aqueous sodium bicarbonate, dried over sodium sulfate, filtered and concentrated under reduced pressure. Purification by silica gel chromatography (0-10% methanol/DCM) provided 3-bromo-2-[2-(4,4-difluoroazepan-1-yl)-3-quinolyl]-4-oxo-1H-1,6-naphthyridine-5-carboxamide (313, 30 mg, 29%). ESI-MS m/z calc. 527.08, found 528.23 $(M+1)^+$. $^1H$ NMR (400 MHz, $CD_3OD$) δ 8.59 (d, J=5.9 Hz, 1H), 8.24 (s, 1H), 7.83-7.73 (m, 2H), 7.71-7.63 (m, 1H), 7.54 (d, J=6.0 Hz, 1H), 7.39-7.32 (m, 1H), 3.87-3.56 (m, 2H), 3.52-3.34 (m, 2H), 2.45-2.19 (m, 2H), 2.08-1.93 (m, 2H), 1.91-1.68 (m, 2H).

The following compounds were synthesized in an analogous fashion as Compound 313 using NBS and starting from Compound 111, Compound 81, Compound 58, and Compound 60, respectively.

TABLE 11

| Compound Number | Compound Name | MW & Found [M + H]+ | NMR (shifts in ppm) |
|---|---|---|---|
| 314 | 3-bromo-2-[2-(4,4-difluoroazepan-1-yl)-3-quinolyl]-4-oxo-1H-1,6-naphthyridine-5-carbonitrile | 509.07; 510.1 | $^1$H NMR (400 MHz, $CD_3OD$) δ 8.81 (d, J = 5.9 Hz, 1H), 8.72 (s, 1H), 8.07 (d, J = 8.5 Hz, 1H), 8.00 (d, J = 8.2 Hz, 1H), 7.99-7.90 (m, 1H), 7.77 (d, J = 5.8 Hz, 1H), 7.63 (t, J = 7.6 Hz, 1H), 3.97-3.78 (m, 2H), 3.75-3.57 (m, 2H), 2.50-2.33 (m, 2H), 2.21-2.04 (m, 2H), 2.03-1.83 (m, 2H). |
| 315 | 3-bromo-2-[2-(4,4-difluoroazepan-1-yl)-3-quinolyl]-1H-1,6-naphthyridin-4-one | 484.07; 485.16 | $^1$H NMR (400 MHz, $CD_3OD$) δ 9.61 (s, 1H), 8.83 (s, 1H), 8.81 (dd, J = 6.8, 1.1 Hz, 1H), 8.30-8.08 (m, 2H), 8.08-8.04 (m, 1H), 8.04-7.98 (m, 1H), 7.87-7.53 (m, 1H), 4.01-3.80 (m, 2H), 3.75 (t, J = 5.5 Hz, 2H), 2.51-2.23 (m, 2H), 2.23-2.08 (m, 2H), 2.08-1.78 (m, 2H). |
| 316 | 3-bromo-2-[2-(4,4-difluoroazepan-1-yl)-5-methyl-6-(trifluoromethyl)-3-pyridyl]-4-oxo-1H-1,6-naphthyridine-5-carboxamide | 559.06; 560.3 | $^1$H NMR (400 MHz, DMSO-$d_6$) δ 12.67 (s, 1H), 8.58 (d, J = 5.8 Hz, 1H), 7.85 (s, 1H), 7.60 (br s, 1H), 7.47 (d, J = 5.8 Hz, 1H), 7.40 (br s, 1H), 3.66-3.55 (m, 1H), 3.55-3.44 (m, 1H), 3.32-3.25 (m, 1H, obscured by water peak), 3.25-3.14 (m, 1H), 2.37 (q, J = 2.2 Hz, 3H), 2.31-2.19 (m, 2H), 2.05-1.88 (m, 2H), 1.83-1.66 (m, 2H). |
| 317 | 3-bromo-2-[2-(4,4-difluorocyclohexyl)-3-quinolyl]-4-oxo-1H-1,6-naphthyridine-5-carboxamide | 512.07; 513.2 | $^1$H NMR (400 MHz, $CD_3OD$) δ 8.60 (d, J = 5.9 Hz, 1H), 8.37 (s, 1H), 8.14 (d, J = 8.5 Hz, 1H), 7.99 (dd, J = 8.2, 1.4 Hz, 1H), 7.94-7.79 (m, 1H), 7.74-7.59 (m, 1H), 7.53 (d, J = 6.0 Hz, 1H), 2.98-2.82 (m, 1H), 2.47-2.25 (m, 1H), 2.25-2.03 (m, 4H), 2.00-1.86 (m, 1H), 1.86-1.54 (m, 2H). |

3-bromo-2-[4-tert-butyl-2-(4-fluoro-2-methoxy-phenoxy)-6-methyl-phenyl]-1H-quinolin-4-one (317) and Separated Atropisomers (319) & (320)

3-Bromo-2-[4-tert-butyl-2-(4-fluoro-2-methoxy-phenoxy)-6-methyl-phenyl]-1H-quinolin-4-one (317) was prepared from Compound 27 using a NBS bromination procedure analogous to that found in Compound 313. ESI-MS m/z calc. 509.10, found 510.2 $(M+1)^+$. $^1$H NMR (400 MHz, DMSO-$d_6$) δ 12.41 (s, 1H), 8.16 (d, J=8.1 Hz, 1H), 7.67 (dd, J=23.1, 7.8 Hz, 2H), 7.41 (t, J=7.5 Hz, 1H), 7.15 (s, 1H), 7.10-6.99 (m, 2H), 6.77 (td, J=8.5, 2.9 Hz, 1H), 6.53 (s, 1H), 3.68 (s, 3H), 2.17 (s, 3H), 1.21 (s, 9H). The resulting mixture of atropisomers were separated by chiral SFC using a Phenomenex LUX-4 column (250×10 mm; 5 m) at 50° C. Mobile phase was 20-45% methanol (w/20 mM $NH_3$), 72% $CO_2$ at a 10 mL/min flow over 15 min.

Peak 1 (319): 3-bromo-2-[4-tert-butyl-2-(4-fluoro-2-methoxy-phenoxy)-6-methyl-phenyl]-1H-quinolin-4-one. ESI-MS m/z calc. 509.10, found 510.3 $(M+1)^+$; Retention time: 7.03 min under preparative SFC separation conditions.

Peak 2 (320): 3-bromo-2-[4-tert-butyl-2-(4-fluoro-2-methoxy-phenoxy)-6-methyl-phenyl]-1H-quinolin-4-one (5.2 mg, 59%). ESI-MS m/z calc. 509.10, found 510.3 $(M+1)^+$; Retention time: 8.36 min under preparative SFC separation conditions.

Example 16

Methyl 5-carbamoyl-2-[2-(4,4-difluoroazepan-1-yl)-3-quinolyl]-4-oxo-1H-1,6-naphthyridine-3-carboxylate (321)

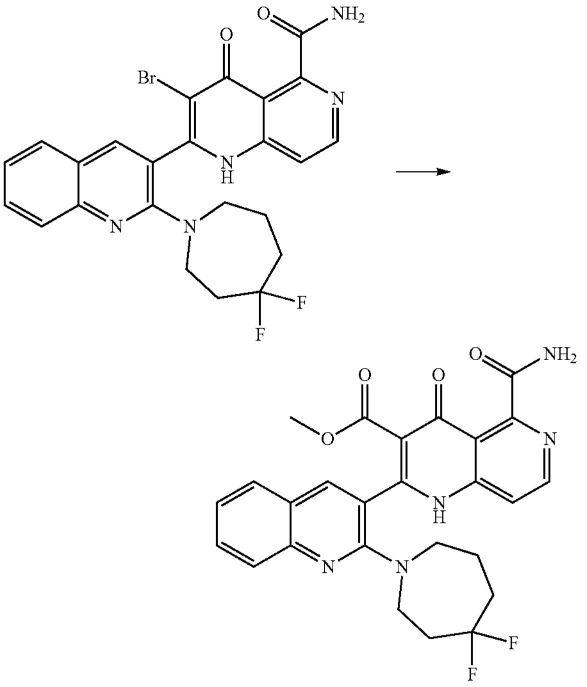

A flask was charged with 3-bromo-2-[2-(4,4-difluoroazepan-1-yl)-3-quinolyl]-4-oxo-1H-1,6-naphthyridine-5-carboxamide (313, 20 mg, 0.038 mmol), $Pd(dppf)Cl_2 \cdot DCM$ (10 mg, 0.012 mmol), methanol (3 mL) and $Et_3N$ (16 μL, 0.12 mmol). The reaction was sparged with CO for 5 min at room temperature, then stirred under CO atmosphere at 65° C. for 17 h. The reaction was filtered and purified by reverse phase HPLC (10-99% acetonitrile/5 mM HCl over 25 min) to provide methyl 5-carbamoyl-2-[2-(4,4-difluoroazepan-1-yl)-3-quinolyl]-4-oxo-1H-1,6-naphthyridine-3-carboxylate (Hydrochloride salt) (321, 13.7 mg, 67%). ESI-MS m/z calc. 507.17, found 508.3 $(M+1)^+$. $^1$H NMR (400 MHz, $CD_3OD$) δ 8.70 (d, J=5.9 Hz, 1H), 8.58 (s, 1H), 8.04 (d, J=8.6 Hz, 1H), 7.97 (d, J=8.0 Hz, 1H), 7.95-7.89 (m, 1H), 7.67 (d, J=5.9 Hz, 1H), 7.61 (t, J=7.5 Hz, 1H), 3.90-3.83 (m, 2H), 3.83-3.71 (m, 2H), 3.69 (s, 3H), 2.45-2.30 (m, 2H), 2.20-2.05 (m, 2H), 2.00-1.89 (m, 2H).

methyl 5-carbamoyl-2-[2-(3,4-difluoro-2-methyl-phenoxy)-5-methyl-6-(trifluoromethyl)-3-pyridyl]-4-oxo-1H-1,6-naphthyridine-3-carboxylate (322)

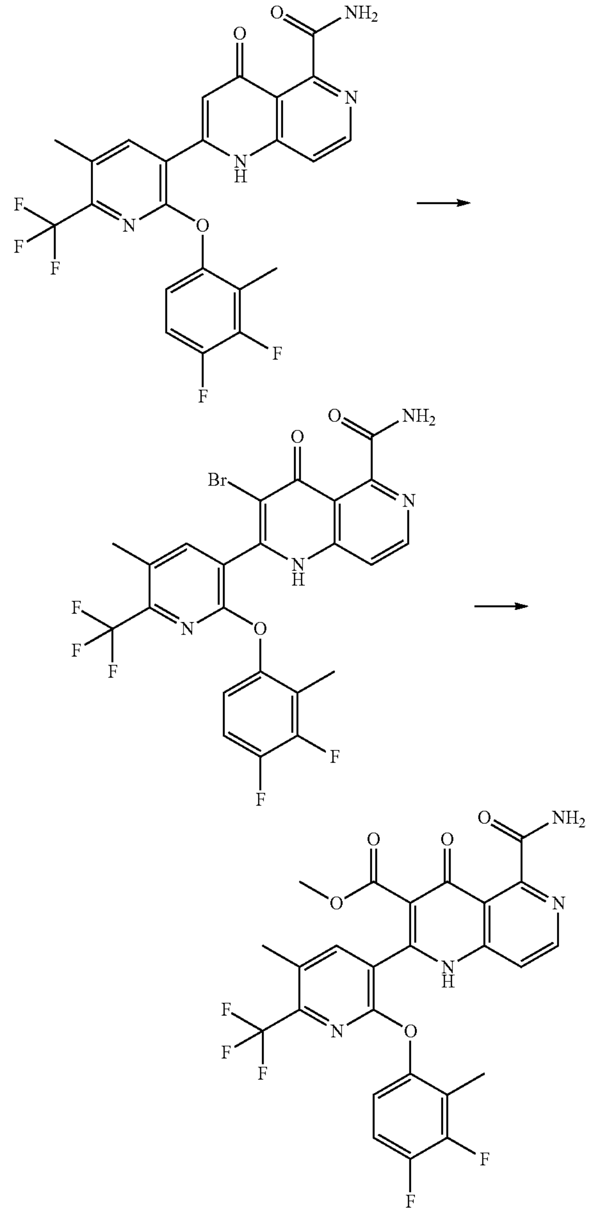

Step 1: 3-bromo-2-[2-(3,4-difluoro-2-methyl-phenoxy)-5-methyl-6-(trifluoromethyl)-3-pyridyl]-4-oxo-1H-1,6-naphthyridine-5-carboxamide 3-Bromo-2-[2-(3,4-difluoro-2-methyl-phenoxy)-5-methyl-6-(trifluoromethyl)-3-pyridyl]-4-oxo-1H-1,6-naphthyridine-5-carboxamide was prepared from 46 using an NBS bromination procedure analogous to that found in 313. ESI-MS m/z calc. 568.02, found 569.2 $(M+1)^+$. $^1H$ NMR (400 MHz, $CD_3OD$) δ 8.60 (d, J=6.0 Hz, 1H), 8.12 (s, 1H), 7.54 (d, J=5.9 Hz, 1H), 7.12 (app q, J=9.3 Hz, 1H), 6.98-6.91 (m, 1H), 2.53 (q, J=2.2 Hz, 3H), 2.06 (d, J=2.2 Hz, 3H).

Step 2: Methyl 5-carbamoyl-2-[2-(3,4-difluoro-2-methyl-phenoxy)-5-methyl-6-(trifluoromethyl)-3-pyridyl]-4-oxo-1H-1,6-naphthyridine-3-carboxylate (322)

Methyl 5-carbamoyl-2-[2-(3,4-difluoro-2-methyl-phenoxy)-5-methyl-6-(trifluoromethyl)-3-pyridyl]-4-oxo-1H-1,6-naphthyridine-3-carboxylate (322) was prepared from 3-bromo-2-[2-(3,4-difluoro-2-methyl-phenoxy)-5-methyl-6-(trifluoromethyl)-3-pyridyl]-4-oxo-1H-1,6-naphthyridine-5-carboxamide using a procedure analogous to that found in Compound 321. ESI-MS m/z calc. 548.11, found 549.4 $(M+1)^+$.

Methyl 5-carbamoyl-2-[2-(4,4-difluorocyclohexyl)-3-quinolyl]-4-oxo-1H-1,6-naphthyridine-3-carboxylate (323)

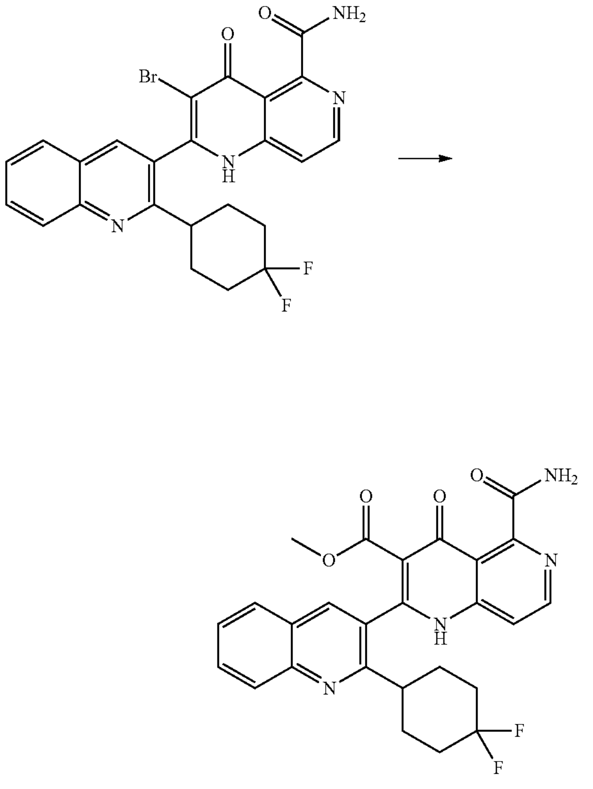

Methyl 5-carbamoyl-2-[2-(4,4-difluorocyclohexyl)-3-quinolyl]-4-oxo-1H-1,6-naphthyridine-3-carboxylate (323) was prepared from Compound 317 using a procedure analogous to that found in Compound 321. ESI-MS m/z calc. 492.16, found 493.3 $(M+1)^+$. $^1H$ NMR (400 MHz, $CD_3OD$) δ 8.61 (d, J=5.9 Hz, 1H), 8.32 (s, 1H), 8.11 (d, J=8.5 Hz, 1H), 7.96 (dd, J=8.2, 1.5 Hz, 1H), 7.88-7.79 (m, 1H), 7.66-7.57 (m, 1H), 7.51 (d, J=5.9 Hz, 1H), 3.48 (s, 3H), 3.04-2.89 (m, 1H), 2.34-2.07 (m, 4H), 2.07-1.90 (m, 2H), 1.89-1.58 (m, 2H).

Example 17
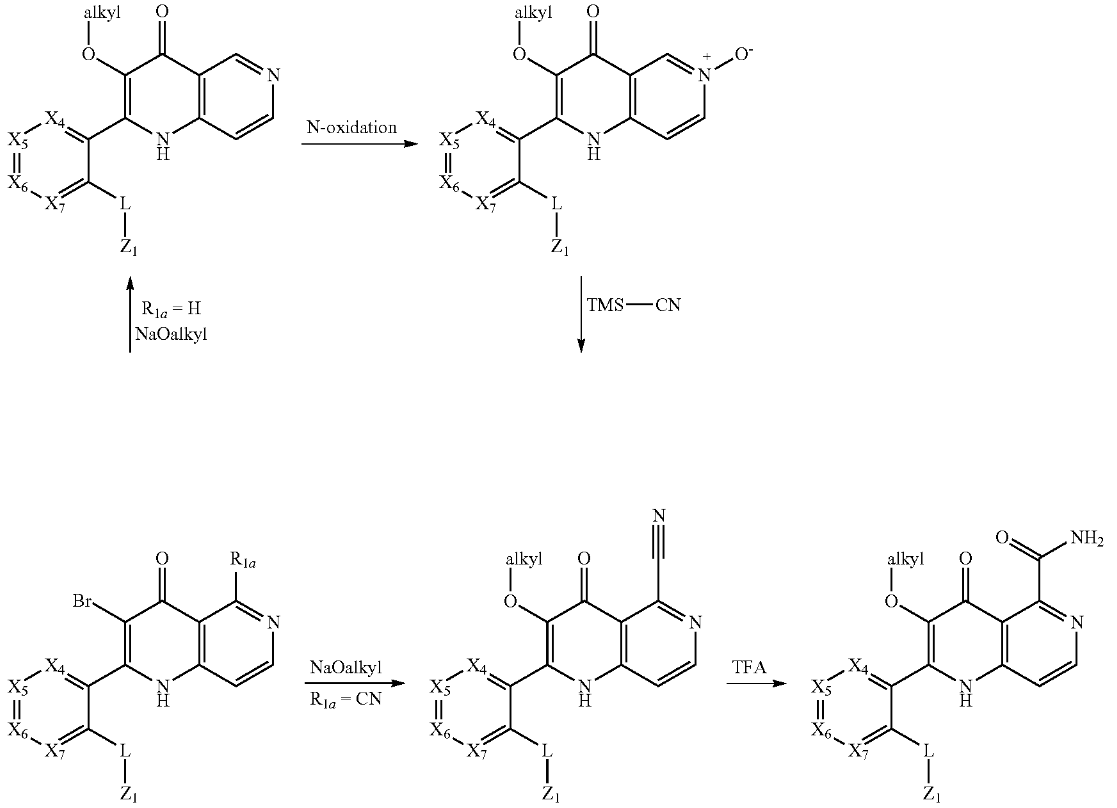
2-[2-(4,4-difluoroazepan-1-yl)-3-quinolyl]-3-methoxy-4-oxo-1H-1,6-naphthyridine-5-carboxamide (324)
Step 1: 3-bromo-2-[2-(4,4-difluoroazepan-1-yl)-3-quinolyl]-4-oxo-1H-1,6-naphthyridine-5-carbonitrile (314)
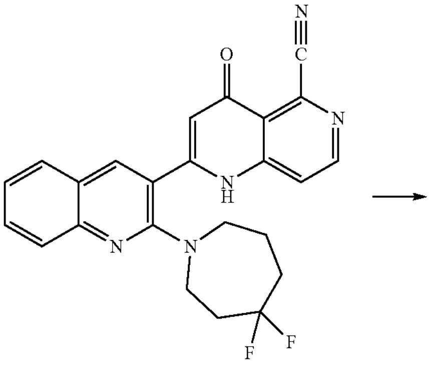
-continued
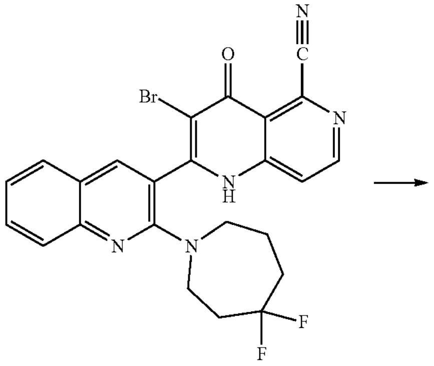
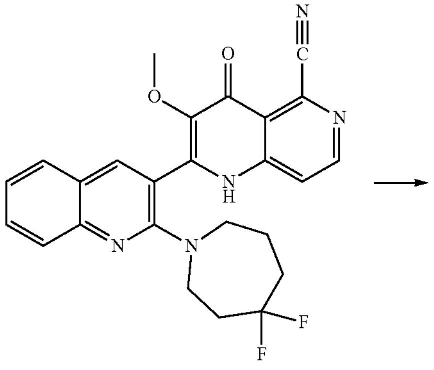

-continued

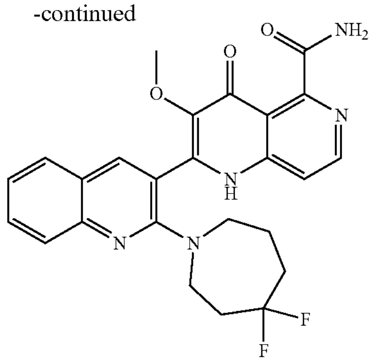

3-Bromo-2-[2-(4,4-difluoroazepan-1-yl)-3-quinolyl]-4-oxo-1H-1,6-naphthyridine-5-carbonitrile (314) was prepared from 2-[2-(4,4-difluoroazepan-1-yl)-3-quinolyl]-4-oxo-1H-1,6-naphthyridine-5-carbonitrile (Compound 60) using an NBS bromination procedure analogous to that found in Compound 313. ESI-MS m/z calc. 509.07, found 510.1 $(M+1)^+$.

Step 2 and 3: 2-[2-(4,4-difluoroazepan-1-yl)-3-quinolyl]-3-methoxy-4-oxo-1H-1,6-naphthyridine-5-carboxamide (324)

3-Bromo-2-[2-(4,4-difluoroazepan-1-yl)-3-quinolyl]-4-oxo-1H-1,6-naphthyridine-5-carbonitrile (314, 250 mg, 0.490 mmol) and iodocopper (127 mg, 0.668 mmol) were suspended in cyclopentyl methyl ether (2.0 mL). The solution was purged with nitrogen for 5 min and sodium methoxide solution (350 μL of 25 wt. % in methanol) was then added. The reaction mixture was stirred at 70° C. for 65 h. The mixture was cooled to room temperature, diluted with ethyl acetate, filtered through a plug of Celite® and concentrated in vacuo to provide 2-[2-(4,4-difluoroazepan-1-yl)-3-quinolyl]-3-methoxy-4-oxo-1H-1,6-naphthyridine-5-carbonitrile. ESI-MS m/z calc. 461.17, found 462.3 $(M+1)^+$. The residue was dissolved in toluene (24 mL) and TFA (24 mL) and stirred at 65° C. for 4 h. The mixture was concentrated and purified by reverse phase HPLC (10-99% acetonitrile/5 mM HCl over 15 min) to provide 2-[2-(4,4-difluoroazepan-1-yl)-3-quinolyl]-3-methoxy-4-oxo-1H-1,6-naphthyridine-5-carboxamide (Hydrochloride salt) as a yellow solid (324, 83.5 mg, 33%). ESI-MS m/z calc. 479.18, found 480.3 $(M+1)^+$. $^1H$ NMR (400 MHz, $CD_3OD$) δ 8.83 (s, 1H), 8.68 (s, 1H), 8.15 (d, J=8.5 Hz, 1H), 8.07 (d, J=8.0 Hz, 1H), 8.04-7.96 (m, 2H), 7.68 (t, J=7.6 Hz, 1H), 3.88-3.84 (m, 5H), 3.77-3.69 (m, 2H), 2.42-2.30 (m, 2H), 2.22-2.08 (m, 2H), 2.02-1.92 (m, 2H).

The following compounds were synthesized in an analogous fashion as Compound 324 starting from Compound 101, Compound 58, and Compound 315, respectively.

TABLE 12

| Compound Number | Compound Name | MW & Found $[M + H]^+$ | NMR (shifts in ppm) |
|---|---|---|---|
| 325 | 2-[2-(4,4-difluoroazepan-1-yl)-6-methyl-5-(trifluoromethyl)-3-pyridyl]-3-methoxy-4-oxo-1H-1,6-naphthyridine-5-carboxamide | 511.44; 512.3 | $^1H$ NMR (400 MHz, $CD_3OD$) δ 8.48 (d, J = 6.2 Hz, 1H), 7.86 (s, 1H), 7.60-7.35 (m, 1H), 3.75-3.59 (m, 5H), 3.24-3.16 (m, 2H), 2.66-2.46 (m, 3H), 2.39-2.17 (m, 2H), 2.00-1.84 (m, 2H), 1.84-1.58 (m, 2H). |
| 326 | 2-[2-(4,4-difluoroazepan-1-yl)-3-quinolyl]-3-methoxy-1H-1,6-naphthyridin-4-one | 436.45; 437.3 | $^1H$ NMR (400 MHz, DMSO-$d_6$) δ 13.38 (s, 1H), 9.50 (s, 1H), 8.69 (d, J = 6.8 Hz, 1H), 8.39 (s, 1H), 7.96 (d, J = 6.7 Hz, 1H), 7.89 (d, J = 8.0 Hz, 1H), 7.79 (d, J = 8.5 Hz, 1H), 7.76-7.69 (m, 1H), 7.40 (t, J = 7.5 Hz, 1H), 3.84 (s, 3H), 3.72-3.62 (m, 2H), 3.46-3.37 (m, 2H), 2.40-2.24 (m, 2H), 2.06-1.86 (m, 2H), 1.86-1.68 (m, 2H). |
| 327 | 2-[2-(4,4-difluoroazepan-1-yl)-5-methyl-6-(trifluoromethyl)-3-pyridyl]-3-methoxy-4-oxo-1H-1,6-naphthyridine-5-carboxamide | 511.44; 512.3 | $^1H$ NMR (400 MHz, DMSO-$d_6$) δ 12.03 (s, 1H), 8.46 (d, J = 5.9 Hz, 1H), 7.77 (s, 1H), 7.56 (br s, 1H), 7.40 (d, J = 5.9 Hz, 1H), 7.32 (br s, 1H), 3.74 (s, 3H), 3.56-3.47 (m, 2H), 3.30-3.21 (m, 2H), 2.40-2.33 (m, 3H), 2.30-2.15 (m, 2H), 2.03-1.86 (m, 2H), 1.78-1.65 (m, 2H). |

2-[2-(3,4-difluoro-2-methoxy-phenoxy)-5-fluoro-4-(trifluoromethyl)phenyl]-3-methoxy-4-oxo-1H-1,6-naphthyridine-5-carboxamide (328)

2-[5-fluoro-2-(4-fluoro-2,3-dimethoxy-phenoxy)-4-(trifluoromethyl)phenyl]-3-methoxy-4-oxo-1H-1,6-naphthyridine-5-carboxamide (329)

Step 1: 3-bromo-2-[2-(3,4-difluoro-2-methoxy-phenoxy)-5-fluoro-4-(trifluoromethyl)phenyl]-1H-1,6-naphthyridin-4-one

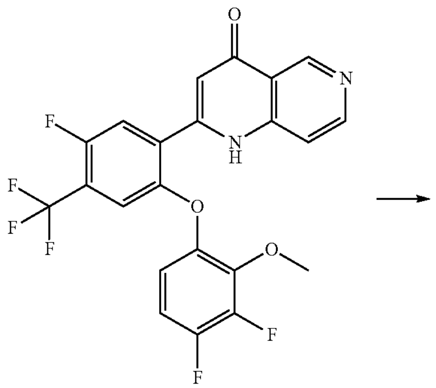

-continued

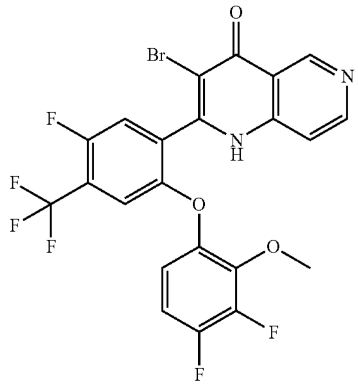

3-Bromo-2-[2-(3,4-difluoro-2-methoxy-phenoxy)-5-fluoro-4-(trifluoromethyl)phenyl]-1H-1,6-naphthyridin-4-one was prepared from 2-[2-(3,4-difluoro-2-methoxy-phenoxy)-5-fluoro-4-(trifluoromethyl)phenyl]-1H-1,6-naphthyridin-4-one using a procedure analogous to that found in Compound 313. ESI-MS m/z calc. 543.99, found 545.0 $(M+1)^+$. $^1H$ NMR (500 MHz, DMSO-$d_6$) δ 12.85 (s, 1H), 9.31 (d, J=0.7 Hz, 1H), 8.70 (d, J=5.9 Hz, 1H), 8.06 (d, J=10.1 Hz, 1H), 7.49 (d, J=5.9 Hz, 1H), 7.35 (d, J=5.7 Hz, 1H), 7.18 (td, J=9.7, 8.4 Hz, 1H), 6.97 (ddd, J=9.4, 5.0, 2.2 Hz, 1H), 3.76 (d, J=1.1 Hz, 3H).

Step 2: 2-[2-(3,4-difluoro-2-methoxy-phenoxy)-5-fluoro-4-(trifluoromethyl)phenyl]-3-methoxy-1H-1,6-naphthyridin-4-one

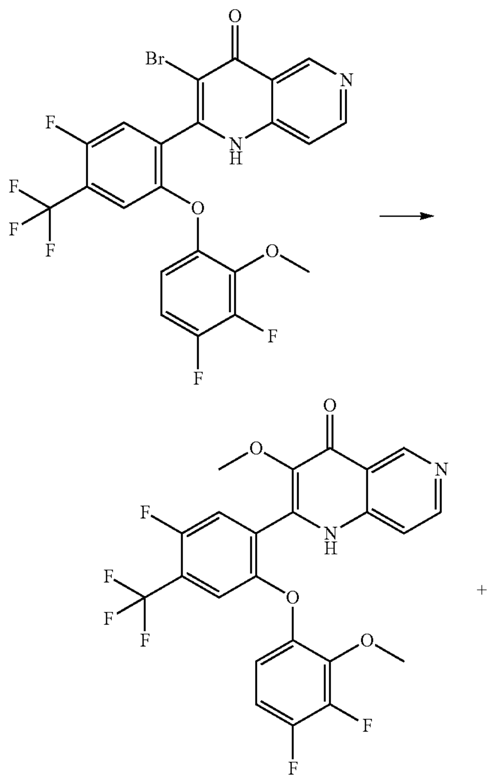

+

-continued

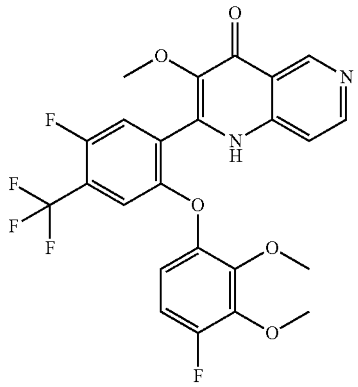

2-[2-(3,4-Difluoro-2-methoxy-phenoxy)-5-fluoro-4-(trifluoromethyl)phenyl]-3-methoxy-1H-1,6-naphthyridin-4-one was prepared from 3-bromo-2-[2-(3,4-difluoro-2-methoxy-phenoxy)-5-fluoro-4-(trifluoromethyl)phenyl]-1H-1,6-naphthyridin-4-one using a procedure analogous to that found in Compound 324, step 2. Purification by silica gel chromatography (24 g silica, 0-100% ethyl acetate/heptane) provided an inseparable 1:1 mixture of 2-[2-(3,4-difluoro-2-methoxy-phenoxy)-5-fluoro-4-(trifluoromethyl)phenyl]-3-methoxy-1H-1,6-naphthyridin-4-one (172 mg, 29%) ESI-MS m/z calc. 496.09, found 495.1 $(M-1)^-$ and 2-[5-fluoro-2-(4-fluoro-2,3-dimethoxy-phenoxy)-4-(trifluoromethyl)phenyl]-3-methoxy-1H-1,6-naphthyridin-4-one (172 mg, 28%). ESI-MS m/z calc. 508.11, found 507.1 $(M-1)^-$. The mixture was taken to the next step without further purification.

Step 3: 2-[2-(3,4-difluoro-2-methoxy-phenoxy)-5-fluoro-4-(trifluoromethyl)phenyl]-3-methoxy-6-oxido-1H-1,6-naphthyridin-6-ium-4-one and 2-[5-fluoro-2-(4-fluoro-2,3-dimethoxy-phenoxy)-4-(trifluoromethyl)phenyl]-3-methoxy-6-oxido-1H-1,6-naphthyridin-6-ium-4-one

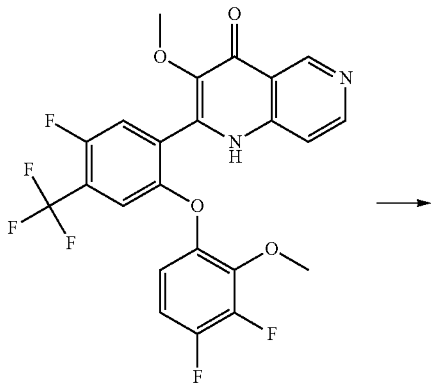

-continued

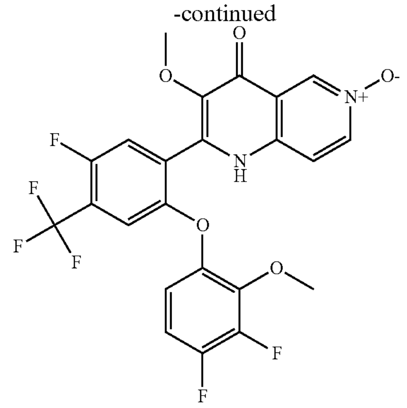

+

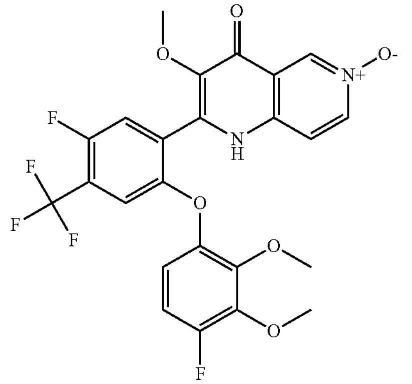

To a stirring solution of the product mixture from step 2 above (220 mg, approximately 0.44 mmol) in DCM (5 mL) at ambient temperature was added 3-chlorobenzenecarbop-eroxoic acid (180 mg, 1.043 mmol). The mixture was stirred for 30 min, then diluted with saturated sodium bicarbonate solution (10 mL) and extracted with 10:1 ethyl acetate/methanol (2×10 mL). The organic layer was dried over magnesium sulfate, filtered and concentrated in vacuo to afford an inseparable 1:1 mixture of 2-[2-(3,4-difluoro-2-methoxy-phenoxy)-5-fluoro-4-(trifluoromethyl)phenyl]-3-methoxy-6-oxido-1H-1,6-naphthyridin-6-ium-4-one (110 mg, 97%). ESI-MS m/z calc. 512.08, found 515.1 $(M+1)^+$ and 2-[5-fluoro-2-(4-fluoro-2,3-dimethoxy-phenoxy)-4-(trifluoromethyl)phenyl]-3-methoxy-6-oxido-1H-1,6-naphthyridin-6-ium-4-one (110 mg, 95%). ESI-MS m/z calc. 524.10, found 525.1 $(M+1)^+$. The mixture was taken to the next step without further purification.

Step 4: 2-[2-(3,4-difluoro-2-methoxy-phenoxy)-5-fluoro-4-(trifluoromethyl)phenyl]-3-methoxy-4-oxo-1H-1,6-naphthyridine-5-carboxamide (328) and 2-[5-fluoro-2-(4-fluoro-2,3-dimethoxy-phenoxy)-4-(trifluoromethyl)phenyl]-3-methoxy-4-oxo-1H-1,6-naphthyridine-5-carboxamide (329)

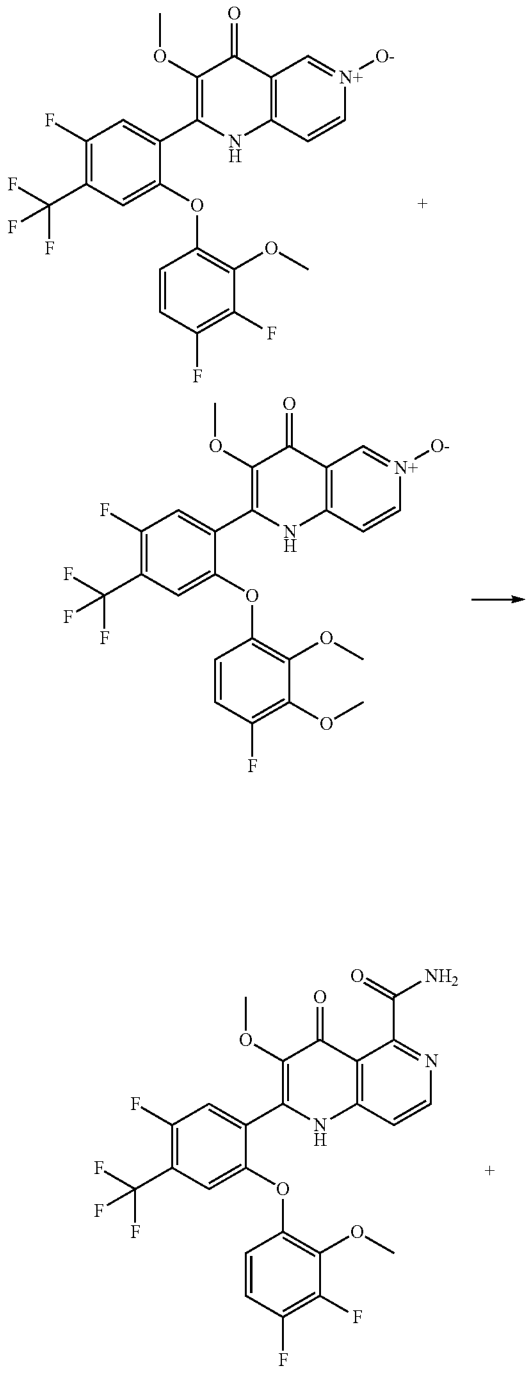

-continued

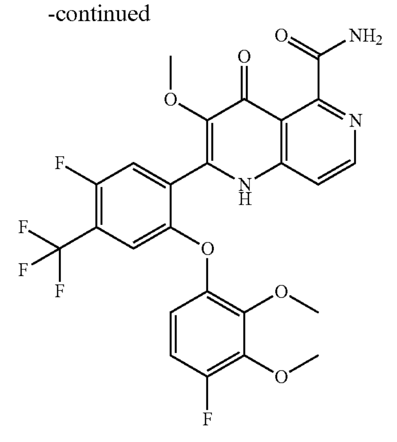

To a stirring solution of the 2-[2-(3,4-difluoro-2-methoxy-phenoxy)-5-fluoro-4-(trifluoromethyl)phenyl]-3-methoxy-6-oxido-1H-1,6-naphthyridin-6-ium-4-one (220 mg, 0.429 mmol) and 2-[5-fluoro-2-(4-fluoro-2,3-dimethoxy-phenoxy)-4-(trifluoromethyl)phenyl]-3-methoxy-6-oxido-1H-1,6-naphthyridin-6-ium-4-one (220 mg, 0.420 mmol) mixture in DCM (6 mL) at ambient temperature and under nitrogen atmosphere was added trimethylsilylformonitrile (400 μL, 3.00 mmol) followed by TEA (600 μL, 4.31 mmol). The mixture was stirred at 80° C. for 150 min, then diluted with of sodium bicarbonate saturated solution (20 mL) and extracted with DCM (2×10 mL). The organic layer was dried over magnesium sulfate, filtered and concentrated in vacuo. The residue was dissolved in toluene (2.2 mL) and TFA (2 mL) and heated to 70° C. in a sealed vial. Upon completion the mixture was neutralized by the addition of saturated solution of sodium bicarbonate and extracted with ethyl acetate/methanol, 10:1 (3×10 mL). The combined extracts were dried over magnesium sulfate, filtered and concentrated under reduced pressure. Purification by silica gel chromatography (12 g silica, 0-100% ethyl acetate:ethanol, 3:1 in heptane) afforded 2-[2-(3,4-difluoro-2-methoxy-phenoxy)-5-fluoro-4-(trifluoromethyl)phenyl]-3-methoxy-4-oxo-1H-1,6-naphthyridine-5-carboxamide (328, 8 mg, 3%). ESI-MS m/z calc. 539.09, found 540.1 $(M+1)^+$. $^1H$ NMR (500 MHz, DMSO-$d_6$) δ 11.38 (s, 1H), 7.65 (d, J=5.9 Hz, 1H), 7.17 (d, J=10.3 Hz, 1H), 6.72 (s, 1H), 6.60 (d, J=5.9 Hz, 1H), 6.47 (d, J=5.8 Hz, 2H), 6.42-6.33 (m, 1H), 6.13 (ddd, J=9.3, 5.0, 2.1 Hz, 1H), 2.94 (d, J=1.2 Hz, 3H), 2.92 (s, 3H). $^{19}F$ NMR (471 MHz, DMSO-$d_6$) δ −60.22 (d, J=13.8 Hz), −122.34−−122.53 (m), −139.78 (d, J=32.4 Hz), −151.96−−152.21 (m) ppm; and 2-[5-fluoro-2-(4-fluoro-2,3-dimethoxy-phenoxy)-4-(trifluoromethyl)phenyl]-3-methoxy-4-oxo-1H-1,6-naphthyridine-5-carboxamide (329, 7 mg, 3%). ESI-MS m/z calc. 551.11, found 552.1 $(M+1)^+$. $^1H$ NMR (500 MHz, DMSO-$d_6$) δ 12.19 (s, 1H), 8.46 (d, J=5.9 Hz, 1H), 7.96 (d, J=10.2 Hz, 1H), 7.53 (s, 1H), 7.42 (d, J=5.9 Hz, 1H), 7.29 (s, 1H), 7.18 (d, J=5.8 Hz, 1H), 7.05 (dd, J=10.6, 9.3 Hz, 1H), 6.85 (dd, J=9.2, 5.1 Hz, 1H), 3.83 (d, J=0.9 Hz, 3H), 3.74 (s, 3H), 3.66 (s, 3H). $^{19}F$ NMR (471 MHz, DMSO-$d_6$) δ −60.34 (d, J=14.1 Hz), −122.84−−123.15 (m), −132.22−−132.53 (m).

2-[4-tert-butyl-2-(4-fluoro-2-methoxy-phenoxy)-6-methyl-phenyl]-3-isopropenyl-1H-quinolin-4-one (330)

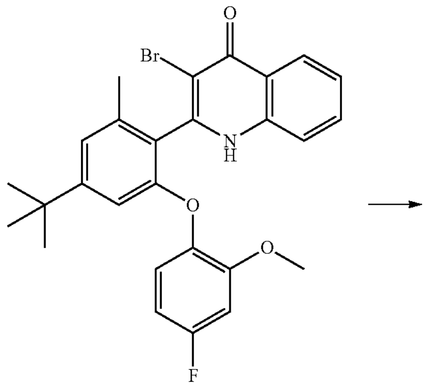

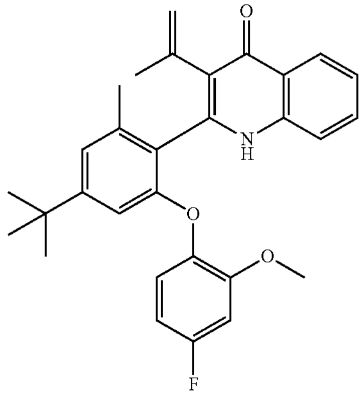

A mixture of $Pd(PPh_3)_4$ (8 mg, 0.007 mmol), 3-bromo-2-[4-tert-butyl-2-(4-fluoro-2-methoxy-phenoxy)-6-methyl-phenyl]-1H-quinolin-4-one (Compound 318, 25 mg, 0.044 mmol, mixture of atropisomers) and isopropenylboronic acid (7 mg, 0.08 mmol) in dioxane (300 μL) and aqueous potassium phosphate (110 μL of 1.0 M, 0.11 mmol) was heated under nitrogen at 110° C. for 1 h. The mixture was purified by silica gel chromatography (8 g silica, 0-60% ethyl acetate/hexanes) to afford 2-[4-tert-butyl-2-(4-fluoro-2-methoxy-phenoxy)-6-methyl-phenyl]-3-isopropenyl-1H-quinolin-4-one (330, 7.2 mg, 34%) as a white powder. ESI-MS m/z calc. 471.22, found 472.4 $(M+1)^+$. The mixture of atropisomers was separated by chiral SFC using a ChiralPak IG column (250×10 mm), 5 m; 50° C., Mobile phase was 16% methanol (20 mM $NH_3$), 84% $CO_2$, 10.0 mL/min Peak 1 (331): 2-[4-tert-butyl-2-(4-fluoro-2-methoxy-phenoxy)-6-methyl-phenyl]-3-isopropenyl-1H-quinolin-4-one. ESI-MS m/z calc. 471.22, found 472.4 $(M+1)^+$; Retention time: 4.49 min under the following analytical SFC conditions: ChiralPak IG (150×2.1 mm), 3 m; 55° C., 8% methanol (20 mM $NH_3$), 92% $CO_2$, 1.8 mL/min, 8 minute run.

Peak 2 (332): 2-[4-tert-butyl-2-(4-fluoro-2-methoxy-phenoxy)-6-methyl-phenyl]-3-isopropenyl-1H-quinolin-4-one. ESI-MS m/z calc. 471.22, found 472.4 $(M+1)^+$; Retention time: 5.61 min under the following analytical SFC conditions: ChiralPak IG (150×2.1 mm), 3 μm; 55° C., 8% methanol (20 mM $NH_3$), 92% $CO_2$, 1.8 mL/min, 8 minute run.

2-[4-tert-butyl-2-(4-fluoro-2-methoxy-phenoxy)-6-methyl-phenyl]-3-methyl-1H-quinolin-4-one (333 and 334)

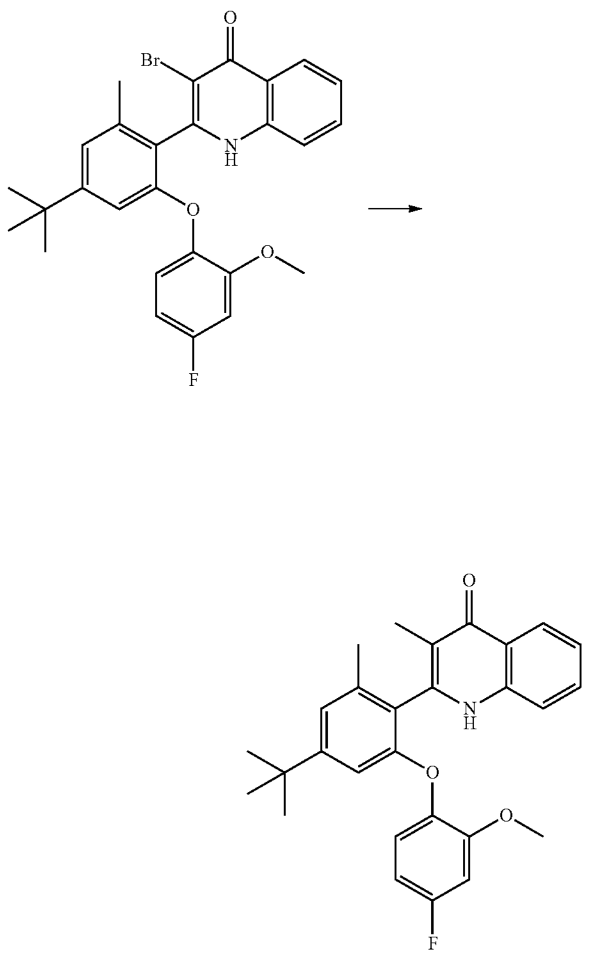

2-[4-tert-Butyl-2-(4-fluoro-2-methoxy-phenoxy)-6-methyl-phenyl]-3-methyl-1H-quinolin-4-one was prepared from 3-bromo-2-[4-tert-butyl-2-(4-fluoro-2-methoxy-phenoxy)-6-methyl-phenyl]-1H-quinolin-4-one (318) and 2,4,6-trimethyl-1,3,5,2,4,6-trioxatriborinane using a procedure analogous to that found in Compound 330. ESI-MS m/z calc. 445.1, found 446.0 $(M+1)^+$. The mixture of atropisomers was separated by chiral SFC using a Phenomenex LUX-4 column (250×10 mm; 5 μm) at 55° C. Mobile phase was 24% MeOH (w/20 mM $NH_3$), 76% $CO_2$ at a 10 mL/min flow rate.

Peak 1 (333): 2-[4-tert-butyl-2-(4-fluoro-2-methoxy-phenoxy)-6-methyl-phenyl]-3-methyl-1H-quinolin-4-one (1.8 mg, 65%) ESI-MS m/z calc. 445.21, found 446.0 $(M+1)^+$; Retention time: 3.32 minutes.

Peak 2 (334): 2-[4-tert-butyl-2-(4-fluoro-2-methoxy-phenoxy)-6-methyl-phenyl]-3-methyl-1H-quinolin-4-one (2.2 mg, 79%) ESI-MS m/z calc. 445.1, found 446.0 $(M+1)^+$; Retention time: 4.33 minutes. Retention times were determined using the following analytical SFC conditions: Phenomenex LUX-4 column (150×2.1 mm; 3 μm) at 55° C. Mobile phase was 15% MeOH (w/20 mM $NH_3$), 85% $CO_2$ at a 1.8 mL/min flow rate.

2-[4-tert-butyl-2-(4-fluoro-2-methoxy-phenoxy)-6-methyl-phenyl]-3-ethyl-1H-quinolin-4-one (335)

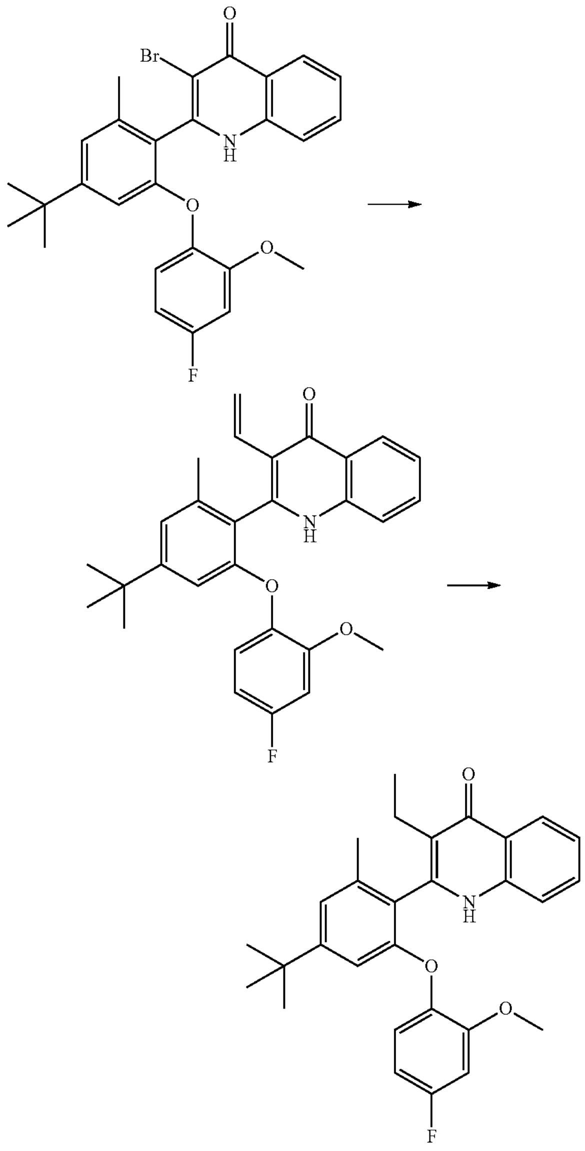

Step 1: 2-[4-tert-butyl-2-(4-fluoro-2-methoxy-phenoxy)-6-methyl-phenyl]-3-vinyl-1H-quinolin-4-one 2-[4-tert-Butyl-2-(4-fluoro-2-methoxy-phenoxy)-6-methyl-phenyl]-3-vinyl-1H-quinolin-4-one was prepared from 3-bromo-2-[4-tert-butyl-2-(4-fluoro-2-methoxy-phenoxy)-6-methyl-phenyl]-1H-quinolin-4-one (318) using a procedure analogous to that found in Compound 330 and vinylboronic acid. ESI-MS m/z calc. 457.21, found 458.0 $(M+1)^+$; Retention time: 0.71 min.

Step 2: 2-[4-tert-butyl-2-(4-fluoro-2-methoxy-phenoxy)-6-methyl-phenyl]-3-ethyl-1H-quinolin-4-one (335)

A solution of 2-[4-tert-butyl-2-(4-fluoro-2-methoxy-phenoxy)-6-methyl-phenyl]-3-vinyl-1H-quinolin-4-one (7 mg, 0.015 mmol) in methanol (400 µL) was stirred with 10% Pd/C (1 mg) under hydrogen atmosphere for 12 h. The reaction solution was filtered through Celite®, concentrated, then dissolved in 10% methanol in DCM and filtered through a silica plug. The filtrate was concentrated to provide 2-[4-tert-butyl-2-(4-fluoro-2-methoxy-phenoxy)-6-methyl-phenyl]-3-ethyl-1H-quinolin-4-one (335, 5.0 mg, 70%) as a mixture of atropisomers. ESI-MS m/z calc. 459.22, found 460.0 $(M+H)^+$.

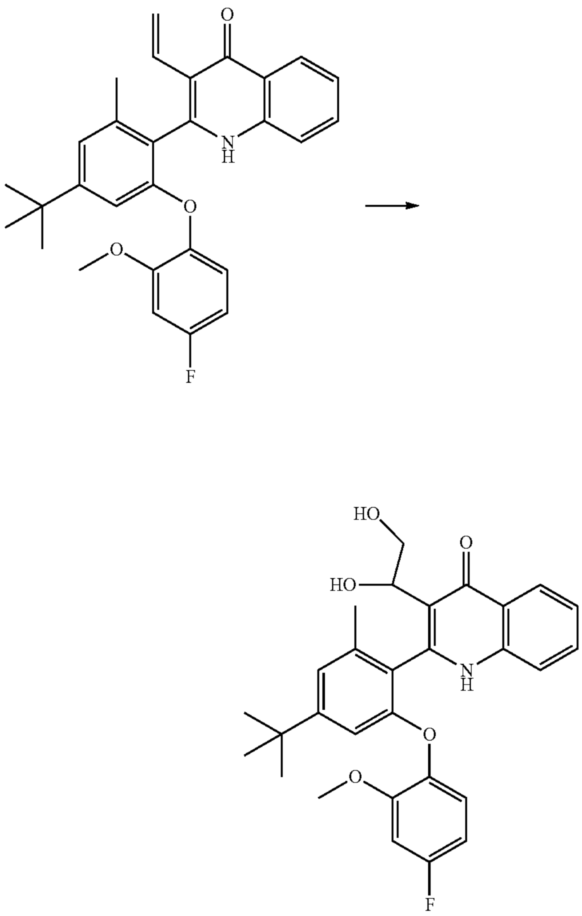

2-[4-tert-Butyl-2-(4-fluoro-2-methoxy-phenoxy)-6-methyl-phenyl]-3-vinyl-1H-quinolin-4-one (335, step 1, 11.2 mg, 0.0245 mmol) was dissolved in acetone (120 µL) and water (250 µL) and treated with 4-methyl-4-oxido-morpholin-4-ium (8 µL of 4.8 M, 0.04 mmol) and $OsO_4$ (25 µL of 2.5% w/v in $^t$BuOH, 0.0025 mmol). The mixture was stirred at room temperature for 20 min, then partitioned between 10% aqueous sodium bisulfite and ethyl acetate. The organic layer was separated, dried over sodium sulfate, filtered and concentrated in vacuo. Purification by reverse phase HPLC (C18, 1-99% $CH_3CN$/5 mM HCl) provided 2-[4-tert-butyl-2-(4-fluoro-2-methoxy-phenoxy)-6-methyl-phenyl]-3-(1,2-dihydroxyethyl)-1H-quinolin-4-one (336, 0.9 mg, 4%) as a mixture of stereoisomers. ESI-MS m/z calc. 491.21, found 492.4 $(M+1)^+$; Retention time: 2.21 min. $^1H$ NMR (400 MHz, DMSO-$d_6$) δ 12.09 (s, 1H), 8.15 (d, J=8.2 Hz, 1H), 7.68-7.59 (m, 4H), 7.37 (t, J=7.3 Hz, 2H), 7.16 (d, J=2.1 Hz, 1H), 7.12-7.04 (m, 2H), 6.82-6.77 (m, 1H), 6.44 (s, 1H), 3.82-3.64 (m, 5H), 2.18 (d, J=14.5 Hz, 3H), 1.15 (d, J=1.6 Hz, 9H).

2-[4-tert-butyl-2-(4-fluoro-2-methoxy-phenoxy)-6-methyl-phenyl]-5-(1,2-dihydroxyethyl)-1H-1,6-naphthyridin-4-one (337)

Step 1: 4-benzyloxy-2-[4-tert-butyl-2-(4-fluoro-2-methoxy-phenoxy)-6-methyl-phenyl]-6-oxido-1,6-naphthyridin-6-ium

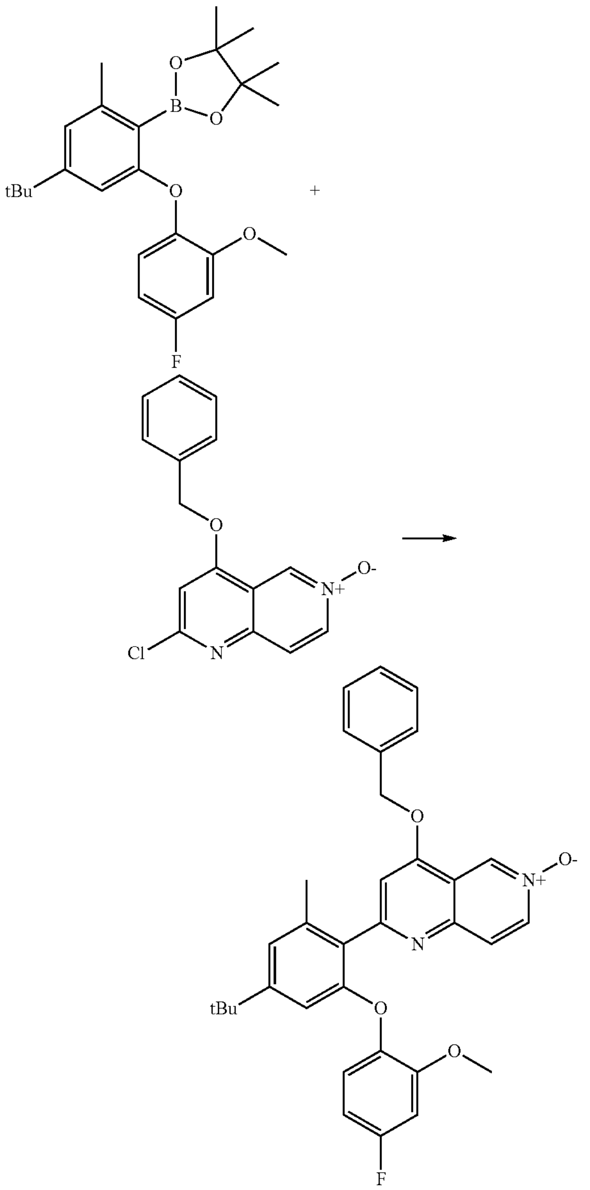

4-Benzyloxy-2-[4-tert-butyl-2-(4-fluoro-2-methoxy-phenoxy)-6-methyl-phenyl]-6-oxido-1,6-naphthyridin-6-ium was prepared from Intermediate A-4, step 2 and Intermediate B-4 using a procedure analogous to that found in Intermediate B-34, step 1 and sodium bicarbonate as base. ESI-MS m/z calc. 538.23, found 539.2 $(M+1)^+$. $^1H$ NMR (400 MHz, $CDCl_3$) δ 9.08 (s, 1H), 8.29 (d, J=7.1 Hz, 1H), 7.83 (d, J=7.1 Hz, 1H), 7.45-7.35 (m, 5H), 7.23 (s, 1H), 7.08 (s, 1H), 6.81 (dd, J=8.8, 5.6 Hz, 1H), 6.71 (s, 1H), 6.60 (dd, J=9.9, 2.6 Hz, 1H), 6.57-6.50 (m, 1H), 5.23 (s, 2H), 3.71 (s, 3H), 2.25 (s, 3H), 1.25 (s, 9H) ppm; $^{19}F$ NMR (377 MHz, $CDCl_3$) δ −115.99--116.17 (m, 1F) ppm.

Step 2: 4-benzyloxy-2-[4-tert-butyl-2-(4-fluoro-2-methoxy-phenoxy)-6-methyl-phenyl]-5-chloro-1,6-naphthyridine

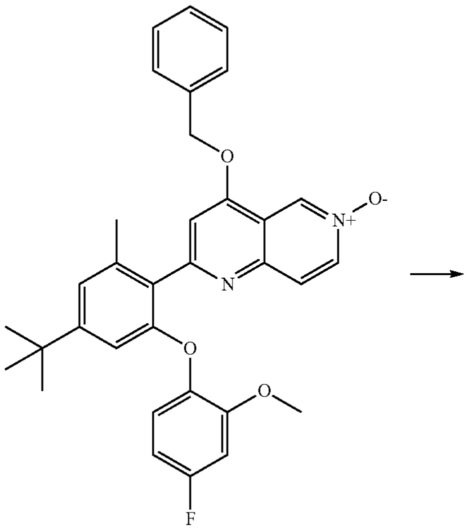

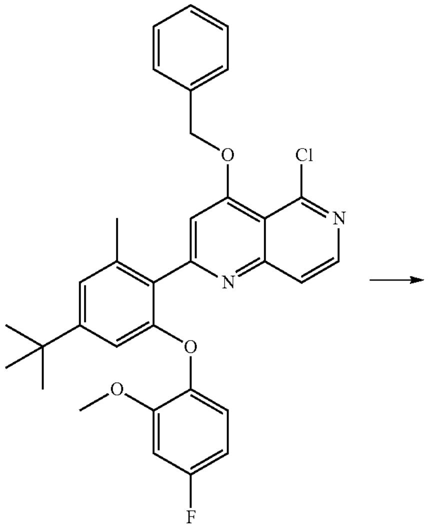

-continued

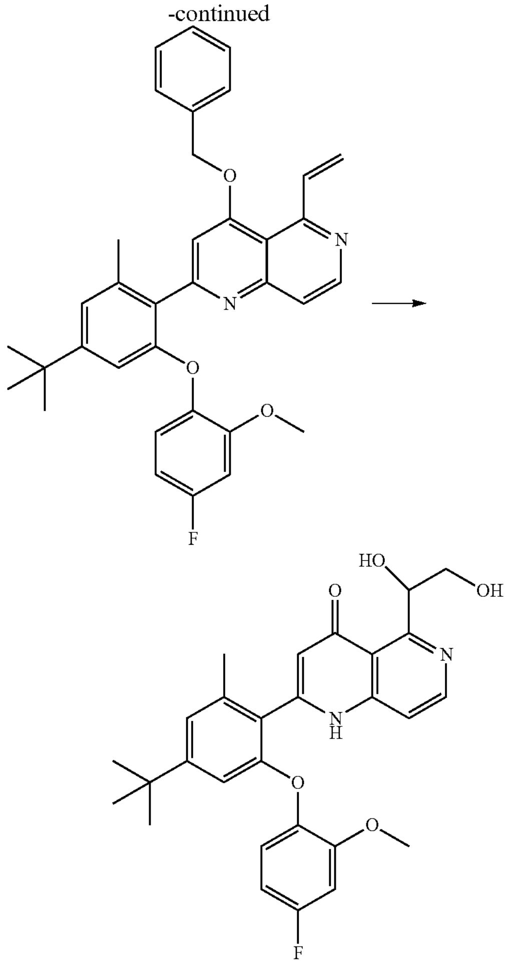

4-benzyloxy-2-[4-tert-butyl-2-(4-fluoro-2-methoxy-phenoxy)-6-methyl-phenyl]-5-chloro-1,6-naphthyridine was prepared from 4-benzyloxy-2-[4-tert-butyl-2-(4-fluoro-2-methoxy-phenoxy)-6-methyl-phenyl]-6-oxido-1,6-naphthyridin-6-ium using a procedure analogous to that found in Compound 13, step 2. ESI-MS m/z calc. 556.19, found 557.3 $(M+1)^+$; Retention time: 2.51 min.

Step 3: 4-benzyloxy-2-[4-tert-butyl-2-(4-fluoro-2-methoxy-phenoxy)-6-methyl-phenyl]-5-vinyl-1,6-naphthyridine A mixture of 4-benzyloxy-2-[4-tert-butyl-2-(4-fluoro-2-methoxy-phenoxy)-6-methyl-phenyl]-5-chloro-1,6-naphthyridine (43 mg, 0.073 mmol), potassium vinyltrifluoroborate (15 mg, 0.11 mmol), Pd(dppf)$Cl_2$·DCM (3 mg, 0.004 mmol) and DIPEA (15 mg, 20 μL, 0.11 mmol) in nitrogen degassed ethanol (0.5 mL) was stirred at 100° C. overnight in a sealed tube. The solvent was removed under reduced pressure. The residue was adsorbed on silica gel under vacuum and purified by silica gel chromatography (12 g silica, 5-60% ethyl acetate/heptane) to provide 4-benzyloxy-2-[4-tert-butyl-2-(4-fluoro-2-methoxy-phenoxy)-6-methyl-phenyl]-5-vinyl-1,6-naphthyridine (14 mg, 33%). $^1H$ NMR (400 MHz, $CDCl_3$) δ 8.65 (d, J=5.9 Hz, 1H), 7.96 (dd, J=17.0, 10.6 Hz, 1H), 7.74 (d, J=5.6 Hz, 1H), 7.51-7.45 (m, 2H), 7.44-7.34 (m, 3H), 7.20 (s, 1H), 7.08 (s, 1H), 6.82 (dd, J=8.8, 5.6 Hz, 1H), 6.72 (s, 1H), 6.62-6.50 (m, 2H), 6.28 (dd, J=16.9, 2.2 Hz, 1H), 5.44 (dd, J=10.8, 2.2 Hz, 1H), 5.25 (s, 2H), 3.68 (s, 3H), 2.25 (s, 3H), 1.25 (s, 9H). $^{19}F$ NMR (377 MHz, $CDCl_3$) δ −116.43-−116.70 (m, 1F). ESI-MS m/z calc. 548.25, found 549.3 $(M+1)^+$.

Step 4: 1-[4-benzyloxy-2-[4-tert-butyl-2-(4-fluoro-2-methoxy-phenoxy)-6-methyl-phenyl]-1,6-naphthyridin-5-yl]ethane-1,2-diol 1-[4-Benzyloxy-2-[4-tert-butyl-2-(4-fluoro-2-methoxy-phenoxy)-6-methyl-phenyl]-1,6-naphthyridin-5-yl]ethane-1,2-diol was prepared from 4-benzyloxy-2-[4-tert-butyl-2-(4-fluoro-2-methoxy-phenoxy)-6-methyl-phenyl]-5-vinyl-1,6-naphthyridine using a procedure analogous to that found in Compound 336. ESI-MS m/z calc. 582.25, found 583.4 $(M+1)^+$.

Step 5: 2-[4-tert-butyl-2-(4-fluoro-2-methoxy-phenoxy)-6-methyl-phenyl]-5-(1,2-dihydroxyethyl)-1H-1,6-naphthyridin-4-one (337)

A solution of 1-[4-benzyloxy-2-[4-tert-butyl-2-(4-fluoro-2-methoxy-phenoxy)-6-methyl-phenyl]-1,6-naphthyridin-5-yl]ethane-1,2-diol (49 mg, 0.08 mmol) and 10% Pd/C (20 mg, 50% wet, 0.0094 mmol) in methanol (1 mL) was stirred under hydrogen atmosphere for 4 h. Filtration and purification by reverse phase chromatography (C18, 2-60% $CH_3CN$ (0.1% formic acid)/0.1% aqueous formic acid), followed by purified preparative TLC purification (2×) using 12% methanol in ethyl acetate as eluent provided 2-[4-tert-butyl-2-(4-fluoro-2-methoxy-phenoxy)-6-methyl-phenyl]-5-(1,2-dihydroxyethyl)-1H-1,6-naphthyridin-4-one (337, 6 mg, 14%) as a white solid. $^1H$ NMR (400 MHz, DMSO-$d_6$) δ 12.28 (br s, 1H), 8.49 (br s, 1H), 7.43 (d, J=5.6 Hz, 1H), 7.14 (s, 1H), 7.10-7.05 (m, 1H), 7.02 (dd, J=10.8, 2.9 Hz, 1H), 6.76 (td, J=8.4, 2.9 Hz, 1H), 6.53 (s, 1H), 6.24 (s, 1H), 5.85 (br s, 1H), 5.50 (br s, 1H), 4.48 (br s, 1H), 3.79-3.71 (m, 1H), 3.68 (s, 3H), 3.65-3.57 (m, 1H), 2.23 (s, 3H), 1.19 (s, 9H). $^{19}F$ NMR (377 MHz, DMSO-$d_6$) δ −114.78 (s, 1F). ESI-MS m/z calc. 492.21, found 493.2 $(M+1)^+$.

2-[4-tert-butyl-2-(4-fluoro-2-methoxy-phenoxy)-6-methyl-phenyl]-3-(hydroxymethyl)-1H-quinolin-4-one (338)

Step 1: 2-[4-tert-butyl-2-(4-fluoro-2-methoxy-phenoxy)-6-methyl-phenyl]-3-(hydroxymethyl)-1H-quinolin-4-one

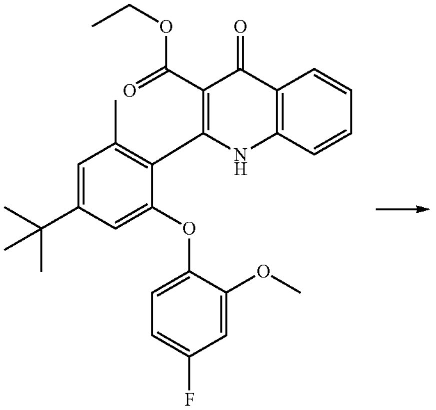

-continued

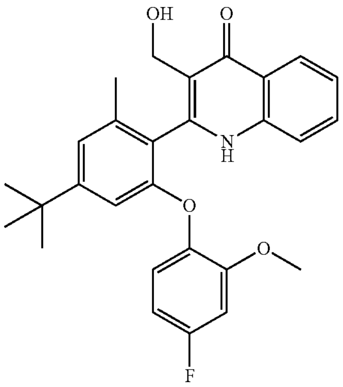

A solution of ethyl 2-[4-tert-butyl-2-(4-fluoro-2-methoxy-phenoxy)-6-methyl-phenyl]-4-oxo-1H-quinoline-3-carboxylate (36, 57 mg, 0.11 mmol) in DCM (1.2 mL) was treated with LiBH4 (225 μL of 0.5 M, 0.1125 mmol) and stirred for 2 h at room temperature. The mixture was quenched by adding saturated $NH_4Cl$ and extracted with ethyl acetate. The organic layer was dried, filtered and concentrated to provide 2-[4-tert-butyl-2-(4-fluoro-2-methoxy-phenoxy)-6-methyl-phenyl]-3-(hydroxymethyl)-1H-quinolin-4-one (338, 43 mg, 82%). ESI-MS m/z calc. 461.20, found 462.3 $(M+1)^+$.

3-(aminomethyl)-2-[4-tert-butyl-2-(4-fluoro-2-methoxy-phenoxy)-6-methyl-phenyl]-1H-quinolin-4-one (339)

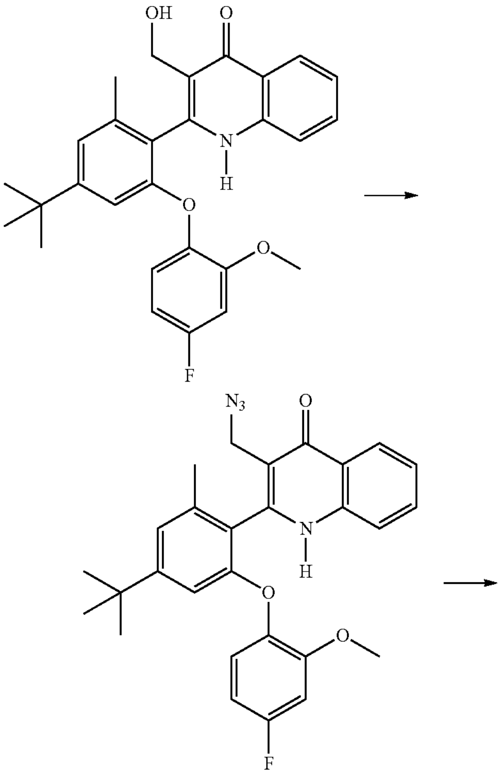

-continued

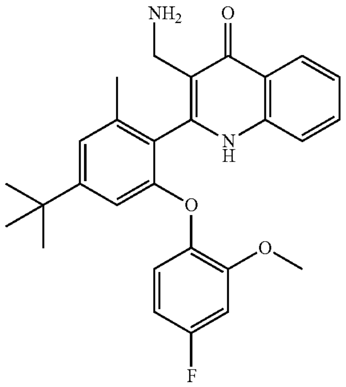

Step 1: 3-(azidomethyl)-2-[4-tert-butyl-2-(4-fluoro-2-methoxy-phenoxy)-6-methyl-phenyl]-1H-quinolin-4-one A solution of 2-[4-tert-butyl-2-(4-fluoro-2-methoxy-phenoxy)-6-methyl-phenyl]-3-(hydroxymethyl)-1H-quinolin-4-one (338, 117 mg, 0.254 mmol) in THF (940 μL) at 0° C. was treated with DBU (95 μL, 0.64 mmol) and stirred for 5 min. DPPA (140 mg, 110 μL, 0.509 mmol) was added dropwise and the mixture allowed to gradually warm to room temperature over 2 h. The mixture was diluted with saturated sodium bicarbonate, extracted using ethyl acetate, and concentrated. Purification by silica gel chromatography provided 3-(azidomethyl)-2-[4-tert-butyl-2-(4-fluoro-2-methoxy-phenoxy)-6-methyl-phenyl]-1H-quinolin-4-one (47.5 mg, 38%) as a white solid. ESI-MS m/z calc. 486.21, found 487.4 $(M+1)^+$.

Step 2: 3-(aminomethyl)-2-[4-tert-butyl-2-(4-fluoro-2-methoxy-phenoxy)-6-methyl-phenyl]-1H-quinolin-4-one (339)

A mixture of 3-(azidomethyl)-2-[4-tert-butyl-2-(4-fluoro-2-methoxy-phenoxy)-6-methyl-phenyl]-1H-quinolin-4-one (27 mg, 0.056 mmol) and 10% Pd/C (6.5 mg) in methanol (1 mL) was stirred under hydrogen atmosphere at 40° C. for 30 min. The mixture was filtered through a pad of Celite®, concentrated and purified using the reverse phase HPLC (C18, 1-99% $CH_3CN$/5 mM HCl) to provide 3-(aminomethyl)-2-[4-tert-butyl-2-(4-fluoro-2-methoxy-phenoxy)-6-methyl-phenyl]-1H-quinolin-4-one (339, 12.4 mg, 49%) as a white solid. ESI-MS m/z calc. 460.22, found 461.3 $(M+1)^+$. $^1H$ NMR (400 MHz, $CD_3OD$) δ 8.32 (dd, J=8.2, 1.4 Hz, 1H), 7.77 (td, J=8.4, 7.0, 1.5 Hz, 1H), 7.59 (d, J=8.4 Hz, 1H), 7.50 (td, J=8.1, 7.0, 1.1 Hz, 1H), 7.25 (s, 1H), 6.97 (dd, J=8.8, 5.6 Hz, 1H), 6.87 (dd, J=10.3, 2.9 Hz, 1H), 6.73-6.63 (m, 2H), 4.05 (d, J=13.5 Hz, 1H), 3.91 (d, J=13.6 Hz, 1H), 3.75 (s, 3H), 2.27 (s, 3H), 1.26 (s, 9H).

Methyl 2-[4-tert-butyl-2-(4-fluoro-2-methoxy-phenoxy)-6-methyl-phenyl]-4-oxo-1H-1,6-naphthyridine-5-carboxylate (340)

Step 1: Methyl 4-benzyloxy-2-[4-tert-butyl-2-(4-fluoro-2-methoxy-phenoxy)-6-methyl-phenyl]-1,6-naphthyridine-5-carboxylate and methyl 2-[4-tert-butyl-2-(4-fluoro-2-methoxy-phenoxy)-6-methyl-phenyl]-4-oxo-1H-1,6-naphthyridine-5-carboxylate (340)

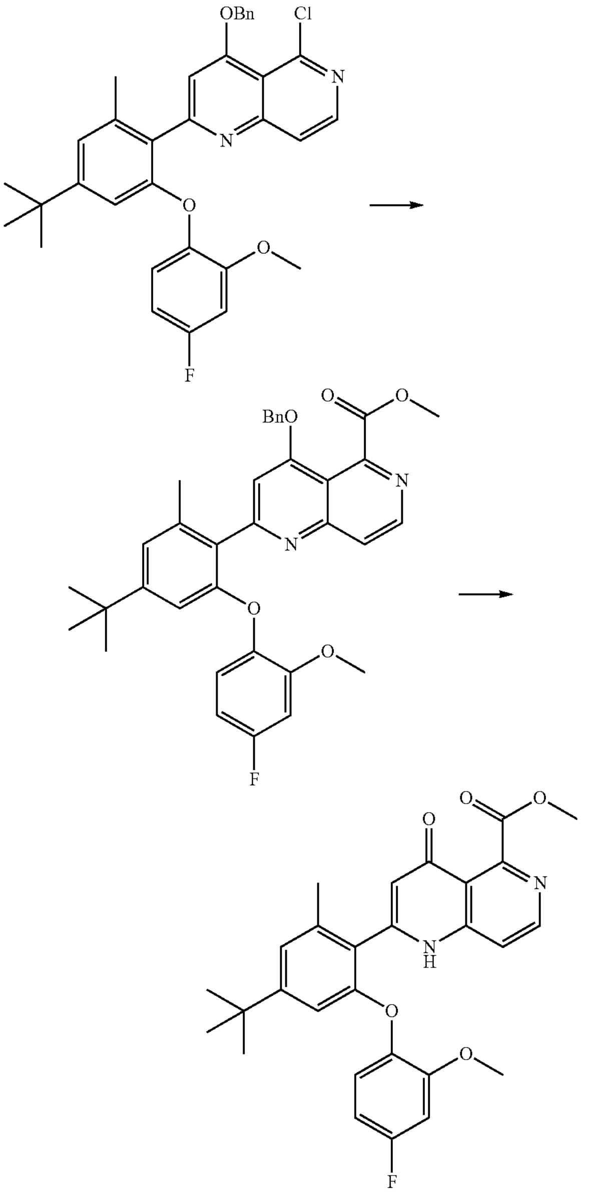

A pressure glass-tube mounted with a pressure gauge was charged with 4-benzyloxy-2-[4-tert-butyl-2-(4-fluoro-2-methoxy-phenoxy)-6-methyl-phenyl]-5-chloro-1,6-naphthyridine (337, step 1, 388 mg, 0.697 mmol), Pd(dppf) $Cl_2$·DCM (20 mg, 0.025 mmol), nitrogen degassed methanol (8 mL) and DIPEA (103.88 mg, 0.14 mL, 0.8038 mmol). The reactor was purged with nitrogen then with carbon monoxide. The reaction mixture was stirred at 80° C. for 20 h under carbon monoxide 70 psi pressure. Once cooled to room temperature, it was concentrated under reduced pressure. The residue was adsorbed on silica gel under vacuum and purified by silica gel chromatography (40 g silica, 30-100% ethyl acetate/heptane) to provide the benzyl-protected product methyl 4-benzyloxy-2-[4-tert-butyl-2-(4-fluoro-2-methoxy-phenoxy)-6-methyl-phenyl]-1,6-naphthyridine-5-carboxylate (141 mg, 35%) as a white solid, ESI-MS m/z calc. 580.24, found 581.3 $(M+1)^+$; Retention time: 2.37 min, and the deprotected product methyl 2-[4-tert-butyl-2-(4-fluoro-2-methoxy-phenoxy)-6-methyl-phenyl]-4-oxo-1H-1,6-naphthyridine-5-carboxylate (340, 147 mg, 43%) as a white solid, $^1H$ NMR (400 MHz, DMSO-$d_6$) δ 12.33 (s, 1H), 8.55 (d, J=5.6 Hz, 1H), 7.52 (d, J=5.6 Hz, 1H), 7.15 (s, 1H), 7.07 (dd, J=9.0, 5.9 Hz, 1H), 7.03 (dd, J=10.8, 2.9 Hz, 1H), 6.76 (td, J=8.5, 2.8 Hz, 1H), 6.55 (s, 1H), 6.16 (d, J=1.0 Hz, 1H), 3.84 (s, 3H), 3.68 (s, 3H), 2.25 (s, 3H), 1.19 (s, 9H). $^{19}F$ NMR (377 MHz, DMSO-$d_6$) δ −114.71-−115.04 (m, 1F). ESI-MS m/z calc. 490.19, found 491.3 $(M+1)^+$.

2-[4-tert-butyl-2-(4-fluoro-2-methoxy-phenoxy)-6-methyl-phenyl]-5-(hydroxymethyl)-1H-1,6-naphthyridin-4-one (341)

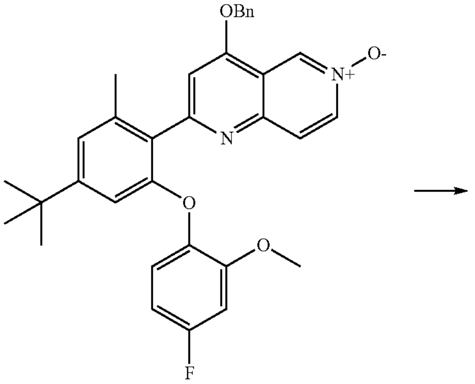

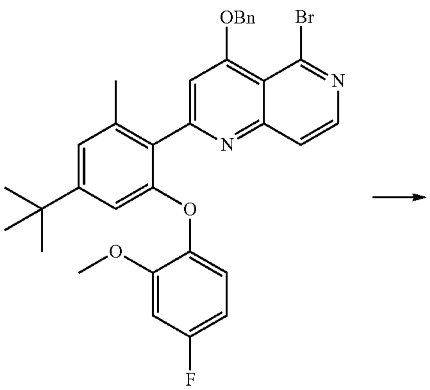

-continued

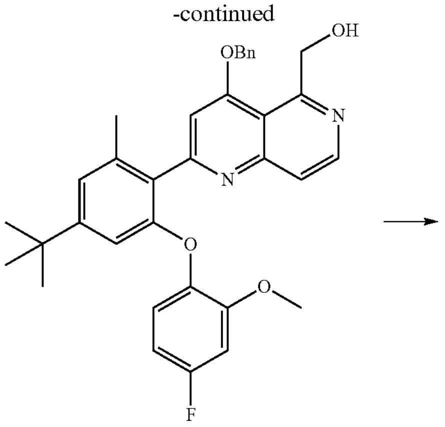

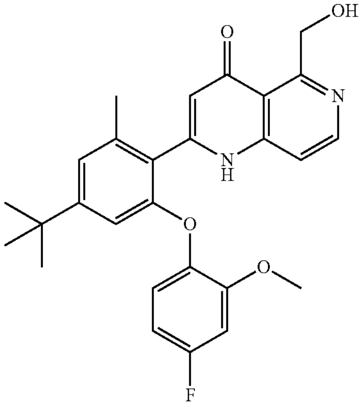

Step 1: 4-benzyloxy-5-bromo-2-[4-tert-butyl-2-(4-fluoro-2-methoxy-phenoxy)-6-methyl-phenyl]-1,6-naphthyridine 4-Benzyloxy-5-bromo-2-[4-tert-butyl-2-(4-fluoro-2-methoxy-phenoxy)-6-methyl-phenyl]-1,6-naphthyridine was prepared from 4-benzyloxy-2-[4-tert-butyl-2-(4-fluoro-2-methoxy-phenoxy)-6-methyl-phenyl]-6-oxido-1,6-naphthyridin-6-ium (337, step 1) using a procedure analogous to that found in Compound 337, step 2 and using $POBr_3$. ESI-MS m/z calc. 600.14, found 601.2 $(M+1)^+$; Retention time: 2.73 min.

Step 2: [4-benzyloxy-2-[4-tert-butyl-2-(4-fluoro-2-methoxy-phenoxy)-6-methyl-phenyl]-1,6-naphthyridin-5-yl]methanol A mixture of 4-benzyloxy-5-bromo-2-[4-tert-butyl-2-(4-fluoro-2-methoxy-phenoxy)-6-methyl-phenyl]-1,6-naphthyridine (100 mg, 0.150 mmol), tributylstannylmethanol (90 mg, 0.28 mmol) and $Pd(Ph_3)_4$ (17 mg, 0.015 mmol) in toluene (1.5 mL) was stirred at 80° C. for 12 h. The mixture was cooled to room temperature and the solvent was removed under a stream of nitrogen. The residue was dissolved in acetonitrile (2 mL) and washed with heptane (2×4 mL). The acetonitrile layer was concentrated under reduced pressure. Purification by silica gel chromatography (12 g silica, 10-80% ethyl acetate/heptane) provided [4-benzyloxy-2-[4-tert-butyl-2-(4-fluoro-2-methoxy-phenoxy)-6-methyl-phenyl]-1,6-naphthyridin-5-yl]methanol (52 mg, 63%) as a pale yellow solid. $^1H$ NMR (400 MHz, $CDCl_3$) δ 8.58 (d, J=5.9 Hz, 1H), 7.77 (d, J=5.9 Hz, 1H), 7.48-7.36 (m, 5H), 7.24 (s, 1H), 7.08 (d, J=1.0 Hz, 1H), 6.83 (dd, J=8.8, 5.6 Hz, 1H), 6.71 (d, J=1.5 Hz, 1H), 6.59 (dd, J=10.0, 2.9 Hz, 1H), 6.54 (ddd, J=8.7, 7.9, 2.9 Hz, 1H), 5.55 (br s, 1H), 5.21 (s, 2H), 5.19 (s, 2H), 3.69 (s, 3H), 2.25 (s, 3H), 1.25 (s, 9H). $^{19}F$ NMR (377 MHz, $CDCl_3$) δ −116.17−−116.40 (m, 1F). ESI-MS m/z calc. 552.24, found 553.4 $(M+1)^+$.

Step 3: 2-[4-tert-butyl-2-(4-fluoro-2-methoxy-phenoxy)-6-methyl-phenyl]-5-(hydroxymethyl)-1H-1,6-naphthyridin-4-one (341)

To a solution of [4-benzyloxy-2-[4-tert-butyl-2-(4-fluoro-2-methoxy-phenoxy)-6-methyl-phenyl]-1,6-naphthyridin-5-yl]methanol (50 mg, 0.091 mmol) in ethyl acetate (1 mL) and methanol (0.6 mL) was added 10% Pd/C (wet, 14 mg, 0.0066 mmol) and the mixture stirred under hydrogen atmosphere for 4 h. Three additional portions of 10% Pd/C (wet, 14 mg, 0.0066 mmol) were added incrementally over the following 40 h of stirring under hydrogen. The reaction mixture was then diluted with DCM (6 mL), filtered and concentrated under reduced pressure. Purification by reverse phase chromatography (C18, 2-70% $CH_3CN$ (0.1% formic acid)/water (0.1% formic acid) provided 2-[4-tert-butyl-2-(4-fluoro-2-methoxy-phenoxy)-6-methyl-phenyl]-5-(hydroxymethyl)-1H-1,6-naphthyridin-4-one (341, 20 mg, 47%) as a white solid. $^1H$ NMR (400 MHz, DMSO-$d_6$) δ 12.27 (br s, 1H), 8.49 (d, J=5.9 Hz, 1H), 7.43 (d, J=5.9 Hz, 1H), 7.15 (s, 1H), 7.11-6.99 (m, 2H), 6.76 (td, J=8.5, 2.8 Hz, 1H), 6.54 (s, 1H), 6.23 (s, 1H), 5.59-5.51 (m, 1H), 5.02-4.90 (m, 2H), 3.68 (s, 3H), 2.24 (s, 3H), 1.19 (s, 9H). $^{19}F$ NMR (377 MHz, DMSO-$d_6$) δ −114.83 (br s, 1F). ESI-MS m/z calc. 462.20, found 463.2 $(M+1)^+$.

2-[4-tert-butyl-2-(4-fluoro-2-methoxy-phenoxy)-6-methyl-phenyl]-4-oxo-1H-1,6-naphthyridine-5-carboxylic acid (342)

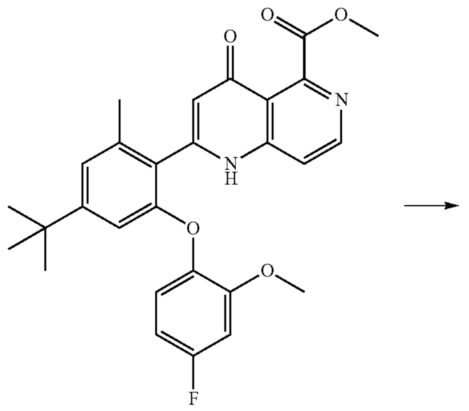

-continued

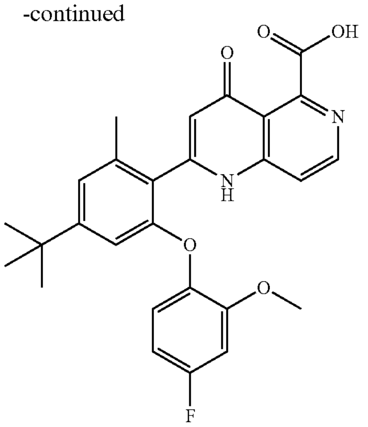

2-[4-tert-Butyl-2-(4-fluoro-2-methoxy-phenoxy)-6-methyl-phenyl]-4-oxo-1H-1,6-naphthyridine-5-carboxylic acid (342) was prepared from Compound 340 using an ester hydrolysis procedure analogous to that found in Intermediate B-11, step 4. ESI-MS m/z calc. 476.17, found 477.3 $(M+1)^+$. $^1H$ NMR (400 MHz, DMSO-$d_6$) δ 13.15 (br s, 1H), 12.24 (br s, 1H), 8.52 (d, J=5.9 Hz, 1H), 7.48 (d, J=5.6 Hz, 1H), 7.15 (s, 1H), 7.10-6.99 (m, 2H), 6.76 (td, J=8.5, 2.8 Hz, 1H), 6.54 (s, 1H), 6.17 (br s, 1H), 3.69 (s, 3H), 2.25 (s, 3H), 1.19 (s, 9H). $^{19}F$ NMR (377 MHz, DMSO-$d_6$) δ −114.88 (br s, 1F).

2-[4-tert-butyl-2-(4-fluoro-2-methoxy-phenoxy)-6-methyl-phenyl]-4-oxo-1H-1,6-naphthyridine-5-carboxamide (343)

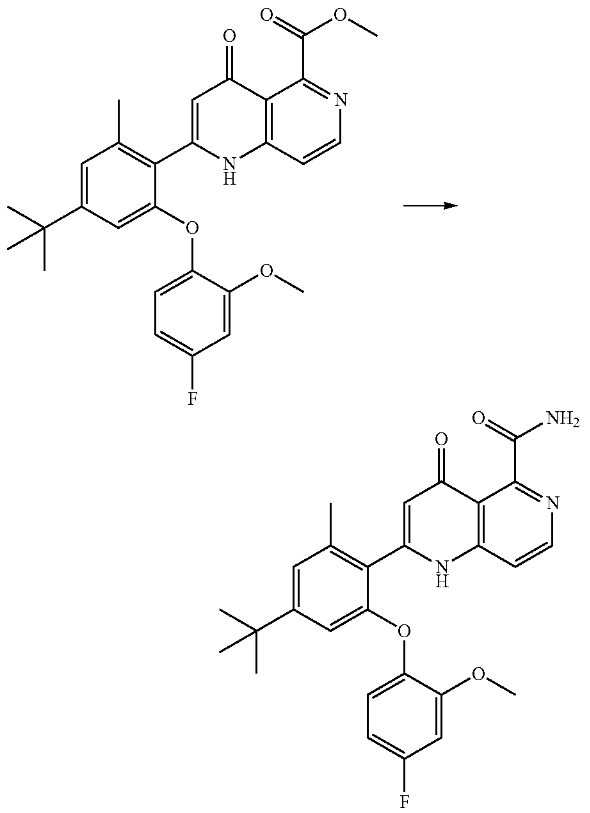

A solution of methyl 2-[4-tert-butyl-2-(4-fluoro-2-methoxy-phenoxy)-6-methyl-phenyl]-4-oxo-1H-1,6-naphthyridine-5-carboxylate (340, 40 mg, 0.082 mmol) in ammonia (7 M in methanol) (1.5 mL of 7 M, 10.5 mmol) was stirred for 60 h at room temperature followed by 8 h at 40° C. Additional ammonia (7 M in methanol) (1 mL of 7 M, 7 mmol) was added and the mixture stirred overnight at 40° C. The mixture was concentrated and again treated with ammonia (7 N in methanol) (1.5 mL of 7 M, 10.5 mmol) and heated overnight a 60° C. in a sealed tube. The mixture was concentrated with a nitrogen stream and purified by reverse phase chromatography (C18, 2-20% $CH_3CN$ (0.1% formic acid)/0.1% aqueous formic acid to provide 2-[4-tert-butyl-2-(4-fluoro-2-methoxy-phenoxy)-6-methyl-phenyl]-4-oxo-1H-1,6-naphthyridine-5-carboxamide (343, 32 mg, 82%) as a white solid. $^1H$ NMR (400 MHz, DMSO-$d_6$) δ 12.05 (br s, 1H), 8.47 (d, J=5.9 Hz, 1H), 7.49 (br s, 1H), 7.42 (d, J=5.9 Hz, 1H), 7.27 (br s, 1H), 7.14 (s, 1H), 7.11-7.01 (m, 2H), 6.77 (td, J=8.5, 3.1 Hz, 1H), 6.52 (s, 1H), 6.12 (s, 1H), 3.70 (s, 3H), 2.25 (s, 3H), 1.19 (s, 9H). $^{19}F$ NMR (377 MHz, DMSO-$d_6$) δ −114.73--115.00 (m, 1F). ESI-MS m/z calc. 475.19, found 476.3 $(M+1)^+$.

2-[2-(3,4-difluoro-2-formyl-phenoxy)-4-methyl-5-(trifluoromethyl)-3-pyridyl]-4-oxo-1H-1,6-naphthyridine-5-carboxamide (344)

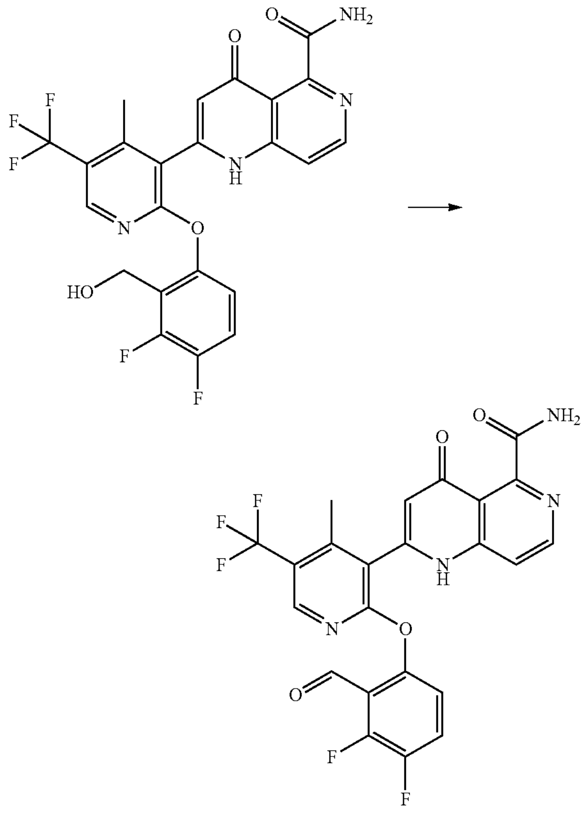

To a solution of 2-[2-[3,4-difluoro-2-(hydroxymethyl)phenoxy]-4-methyl-5-(trifluoromethyl)-3-pyridyl]-4-oxo-1H-1,6-naphthyridine-5-carboxamide (48 mg, 0.088 mmol) in DCM (5 mL) was added Dess-Martin periodinane (56 mg, 0.13 mmol). The mixture was stirred at room temperature for 3 h, then diluted with additional DCM (20 mL) and washed with saturated aqueous sodium bicarbonate (5 mL). The organic layer was separated and concentrated. The residue was purified by reverse phase chromatography (C18, 0-40% acetonitrile/water, each containing 0.1% ammonium hydroxide) and the product-containing fractions freeze dried. The resulting solid was further purified by reverse phase chromatography (C18, 0-40% acetonitrile/water, each containing 0.1% formic acid) to provide 2-[2-(3,4-difluoro-2-formyl-phenoxy)-4-methyl-5-(trifluoromethyl)-3-pyridyl]-4-oxo-1H-1,6-naphthyridine-5-carboxamide (344, 15 mg, 34%). $^1H$ NMR (400 MHz, DMSO-$d_6$) δ 10.03 (s, 1H), 8.54 (s, 1H), 8.48 (d, J=6.0 Hz, 1H), 7.84 (dd, J=9.5 Hz, 1H), 7.49 (br s, 1H), 7.40 (d, J=5.0 Hz, 1H), 7.27-7.22 (m, 2H), 6.39 (br s, 1H), 2.39 (s, 3H). $^{19}F$ NMR (376 MHz, DMSO-$d_6$) δ −59.2 (d, J=29.4 Hz, 3F), −139.8--139.8 (m, 1F), −141.7 (dd, J=21.3, 8.7 Hz, 1F). ESI-MS m/z calc. 504.09, found 505.12 $(M+1)^+$.

2-[2-[4-fluoro-2-(hydroxymethyl)phenoxy]-4-methyl-5-(trifluoromethyl)-3-pyridyl]-4-oxo-1H-1,6-naphthyridine-5-carboxamide (345)

Step 1: 4-benzyloxy-2-[2-[2-[[tert-butyl(dimethyl)silyl]oxymethyl]-4-fluoro-phenoxy]-4-methyl-5-(trifluoromethyl)-3-pyridyl]-1,6-naphthyridine-5-carbonitrile

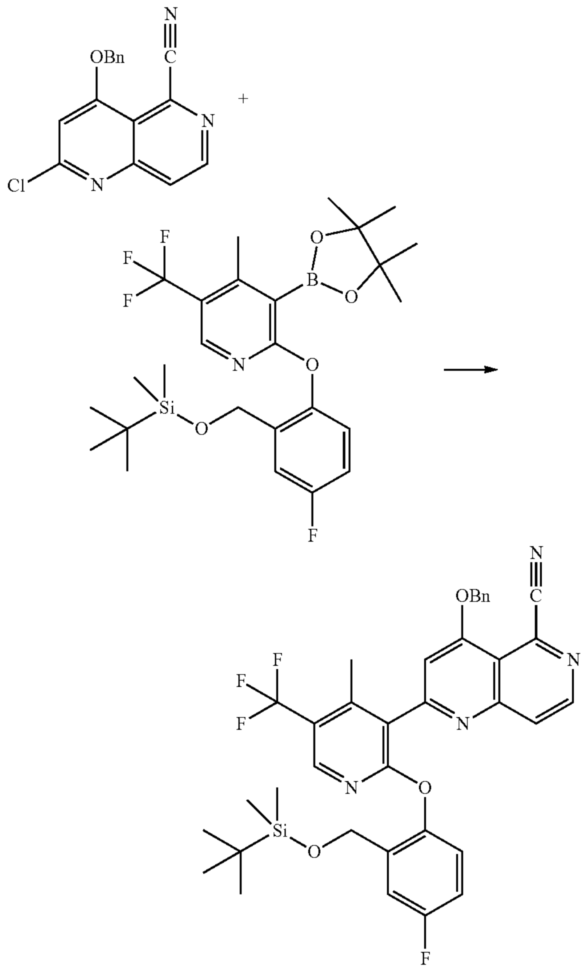

A mixture of 4-benzyloxy-2-chloro-1,6-naphthyridine-5-carbonitrile (225 mg, 0.723 mmol), tert-butyl-[[5-fluoro-2-[[4-methyl-3-(4,4,5,5-tetramethyl-1,3,2-dioxaborolan-2-yl)-5-(trifluoromethyl)-2-pyridyl]oxy]phenyl]methoxy]-dimethyl-silane (420 mg, 0.737 mmol) and potassium carbonate (300 mg, 2.17 mmol) in dioxane (8 mL) and water (2 mL) was degassed with argon for 10 min. Pd(dppf)$Cl_2$ (53 mg, 0.072 mmol) was added and the mixture was stirred under microwave irradiation at 120° C. for 45 min. The reaction mixture was partitioned between ethyl acetate (50 mL) and water (30 mL). The organic layer was washed with brine (20 mL), dried over sodium sulfate and concentrated. Purification by silica gel chromatography (0.5-10% EtOAc/heptanes) provided 4-benzyloxy-2-[2-[2-[[tert-butyl(dimethyl)silyl]oxymethyl]-4-fluoro-phenoxy]-4-methyl-5-(trifluoromethyl)-3-pyridyl]-1,6-naphthyridine-5-carbonitrile (330 mg, 67%). ESI-MS m/z calc. 674.23, found 675.22 $(M+1)^+$. $^1H$ NMR (400 MHz, $CDCl_3$) δ 8.92 (d, 1H, J=5.7 Hz), 8.44 (s, 1H), 8.11 (d, 1H, J=5.7 Hz), 7.58-7.54 (m, 2H), 7.41-7.33 (m, 3H), 7.25 (dd, 1H, J=9.2, 2.6 Hz), 7.18 (s, 1H), 6.99-6.91 (m, 2H), 5.54 (s, 2H), 4.45 (s, 2H), 2.28 (s, 3H), 0.85 (s, 9H), −0.03 (t, 6H, J=3.0 Hz). $^{19}F$ NMR (376 MHz, $CDCl_3$) δ −60.42-−61.15 (m, 3F), −115.95.0-−116.24 (m, 1F).

Step 2: 2-[2-[4-fluoro-2-(hydroxymethyl)phenoxy]-4-methyl-5-(trifluoromethyl)-3-pyridyl]-4-oxo-1H-1,6-naphthyridine-5-carboxamide (345)

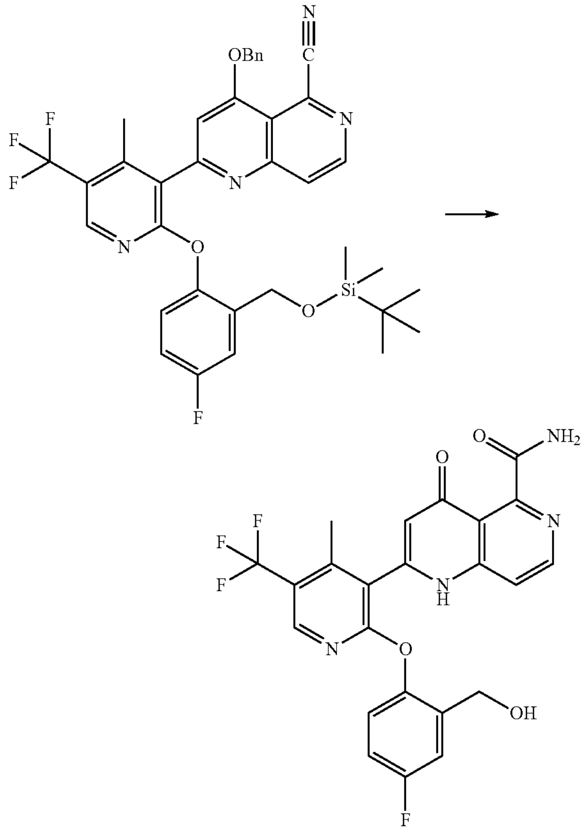

A solution of 4-benzyloxy-2-[2-[2-[[tert-butyl(dimethyl)silyl]oxymethyl]-4-fluoro-phenoxy]-4-methyl-5-(trifluoromethyl)-3-pyridyl]-1,6-naphthyridine-5-carbonitrile (310 mg, 0.4575 mmol) in toluene (4.5 mL) and TFA (3 mL) was stirred at 70° C. for 16 h. The mixture was cooled to room temperature, then concentrated under reduced pressure and azeotroped with toluene (3×25 mL) and DCM (3×25 mL). Purification by reverse phase chromatography (0-40% acetonitrile/water with 0.1% v/v ammonia) provided 2-[2-[4-fluoro-2-(hydroxymethyl)phenoxy]-4-methyl-5-(trifluoromethyl)-3-pyridyl]-4-oxo-1H-1,6-naphthyridine-5-carboxamide (345, 47 mg, 20%). $^1H$ NMR (400 MHz, DMSO-$d_6$) δ 12.27 (s, 1H), 8.59 (s, 1H), 8.54 (s, 1H), 7.54 (s, 1H), 7.43 (d, 1H, J=5.3 Hz), 7.33 (s, 1H), 7.27 (dd, 1H, J=9.5, 2.9 Hz), 7.23-7.10 (m, 2H), 6.39 (s, 1H), 5.33 (s, 1H), 4.37-4.28 (m, 1H), 2.55 (s, 1H), 2.41 (s, 3H). $^{19}F$ NMR (376 MHz, DMSO-$d_6$) δ −59.2 (s, 3F), −116.7 (s, 1F). ESI-MS m/z calc. 488.11, found 489.0 $(M+1)^+$.

2-[2-[3,4-difluoro-2-(hydroxymethyl)phenoxy]-4-methyl-5-(trifluoromethyl)-3-pyridyl]-4-oxo-1H-1,6-naphthyridine-5-carboxamide (346)

Step 1: 4-benzyloxy-2-[2-[2-[[tert-butyl(dimethyl)silyl]oxymethyl]-3,4-difluoro-phenoxy]-4-methyl-5-(trifluoromethyl)-3-pyridyl]-1,6-naphthyridine-5-carbonitrile

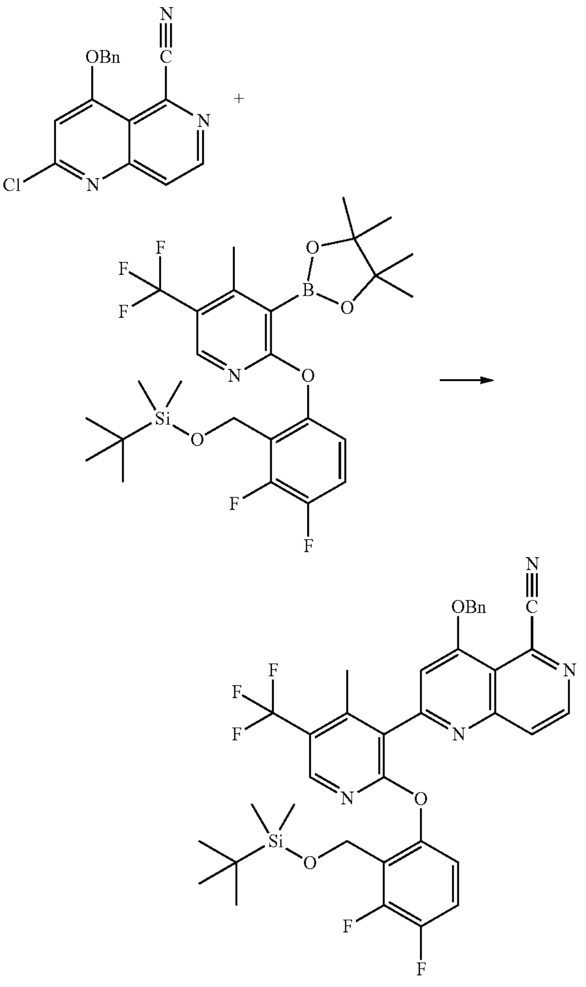

4-Benzyloxy-2-[2-[2-[[tert-butyl(dimethyl)silyl]oxymethyl]-3,4-difluoro-phenoxy]-4-methyl-5-(trifluoromethyl)-

3-pyridyl]-1,6-naphthyridine-5-carbonitrile was prepared from 4-benzyloxy-2-chloro-1,6-naphthyridine-5-carbonitrile and tert-butyl-[[2,3-difluoro-6-[[4-methyl-3-(4,4,5,5-tetramethyl-1,3,2-dioxaborolan-2-yl)-5-(trifluoromethyl)-2-pyridyl]oxy]phenyl]methoxy]-dimethyl-silane using a procedure analogous to that found in Compound 345, step 1. $^{1}$H NMR (400 MHz, $CDCl_3$) δ 8.88 (d, J=5.5 Hz, 1H), 8.39 (s, 1H), 8.08 (d, J=6.0 Hz, 1H), 7.55 (d, J=6.4 Hz, 2H), 7.41-7.32 (m, 3H), 7.26 (s, 1H), 7.12 (dd, J=9.0 Hz, 1H), 6.79 (qd, J=4.4, 1.9 Hz, 1H), 5.49 (s, 2H), 4.56 (d, J=1.4 Hz, 2H), 2.24 (s, 3H), 0.64 (s, 9H), −0.14 (s, 6H). $^{19}$F NMR (376 MHz, $CDCl_3$) δ −60.6 (s, 3F), −139.0 (dd, J=21.0, 8.4 Hz, 1F), −139.9 (ddd, J=21.4, 9.5, 3.8 Hz, 1F). ESI-MS m/z calc. 692.22, found 693.17 (M+1)$^+$.

Step 2: 4-benzyloxy-2-[2-[2-[[tert-butyl(dimethyl)silyl]oxymethyl]-3,4-difluoro-phenoxy]-4-methyl-5-(trifluoromethyl)-3-pyridyl]-1,6-naphthyridine-5-carboxamide

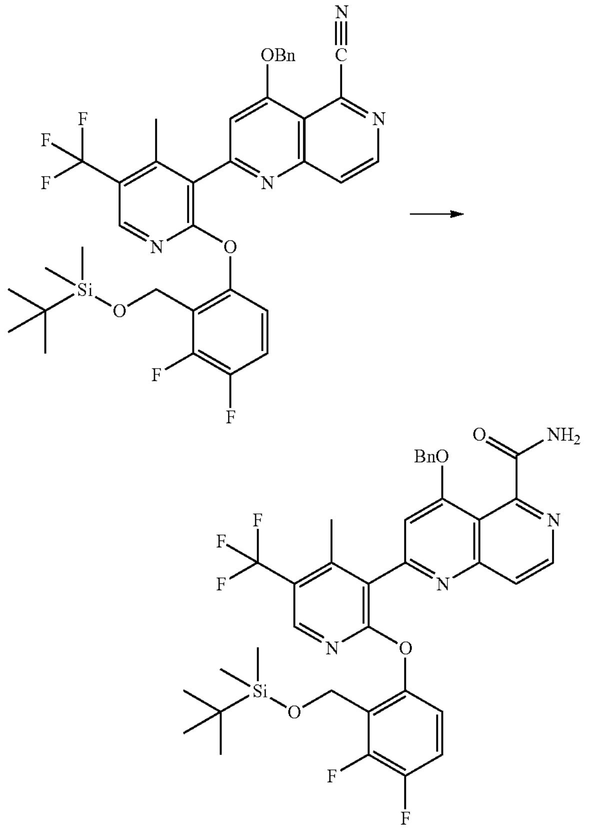

A mixture of 4-benzyloxy-2-[2-[2-[[tert-butyl(dimethyl)silyl]oxymethyl]-3,4-difluoro-phenoxy]-4-methyl-5-(trifluoromethyl)-3-pyridyl]-1,6-naphthyridine-5-carbonitrile (20 mg, 0.029 mmol) and potassium carbonate (12 mg, 0.087 mmol) in DMSO (2 mL) was treated with $H_2O_2$ (50 μL of 35% w/w, 0.20 mmol) dropwise while maintaining the solution temperature<20° C. The mixture was stirred at room temperature for 3 h then diluted with DCM (30 mL). The solution was washed with water (20 mL) and brine (20 mL), dried over sodium sulfate, filtered and concentrated to provide 4-benzyloxy-2-[2-[2-[[tert-butyl(dimethyl)silyl]oxymethyl]-3,4-difluoro-phenoxy]-4-methyl-5-(trifluoromethyl)-3-pyridyl]-1,6-naphthyridine-5-carboxamide (20 mg, 95%). ESI-MS m/z calc. 710.24, found 711.2 (M+1)$^+$.

Step 3: 2-[2-[3,4-difluoro-2-(hydroxymethyl)phenoxy]-4-methyl-5-(trifluoromethyl)-3-pyridyl]-4-oxo-1H-1,6-naphthyridine-5-carboxamide (346)

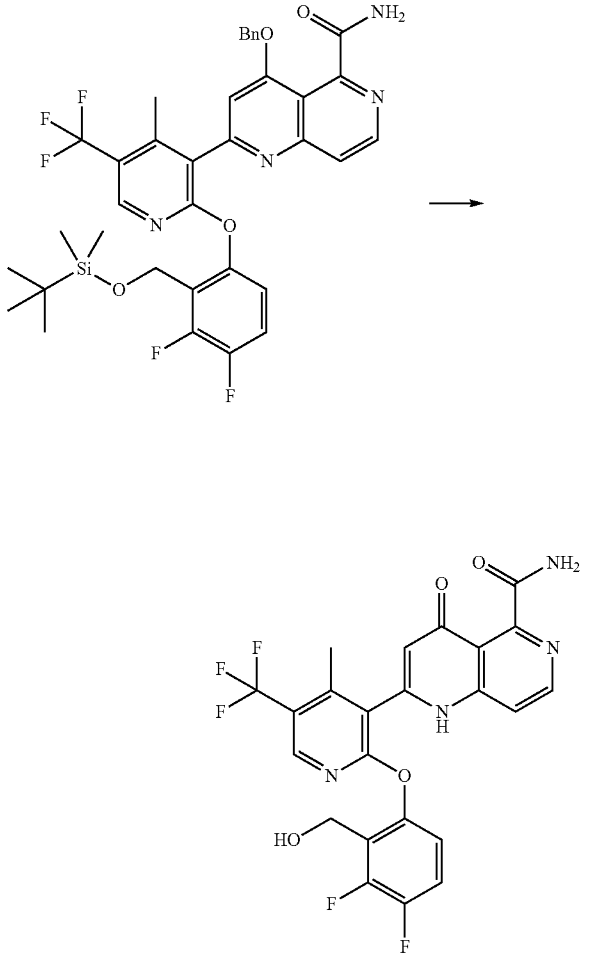

To a solution of 4-benzyloxy-2-[2-[2-[[tert-butyl(dimethyl)silyl]oxymethyl]-3,4-difluoro-phenoxy]-4-methyl-5-(trifluoromethyl)-3-pyridyl]-1,6-naphthyridine-5-carboxamide (160 mg, 0.225 mmol) in ethyl acetate (30 mL) was added 10% Pd/C (24 mg, 0.023 mmol) and the mixture stirred under an atmosphere of hydrogen for 8 h. The mixture was filtered through Celite®, rinsed with ethyl acetate and concentrated in vacuo. The residue was loaded onto a ISOLUTE SCX-2 cartridge (5 g, 25 mL) and allowed to sit for 10 min. Elution with methanol followed by 10% ammonia in methanol provided 2-[2-[3,4-difluoro-2-(hydroxymethyl)phenoxy]-4-methyl-5-(trifluoromethyl)-3-pyridyl]-4-oxo-1H-1,6-naphthyridine-5-carboxamide (346, 83 mg, 69%). $^{1}$H NMR (400 MHz, $CD_3OD$) δ 8.53 (d, J=6.0 Hz, 1H), 8.44 (s, 1H), 7.53 (d, J=5.5 Hz, 1H), 7.26 (dd, J=9.3 Hz, 1H), 6.99-6.97 (m, 1H), 6.51 (s, 1H), 4.49 (d, J=1.1 Hz, 2H), 2.45 (s, 3H). $^{19}$F NMR (376 MHz, $CD_3OD$) δ −62.1 (d, J=35.2 Hz, 3F), −142.5 (dd, J=20.5, 8.2 Hz, 1F), −143.0 (td, J=10.1, 6.9 Hz, 1F). ESI-MS m/z calc. 506.10, found 507.14 (M+1)$^+$.

2-[2-(3,4-difluoro-2-hydroxy-phenoxy)-5-fluoro-4-(trifluoromethyl)phenyl]-4-oxo-1H-1,6-naphthyridine-5-carboxamide (347)

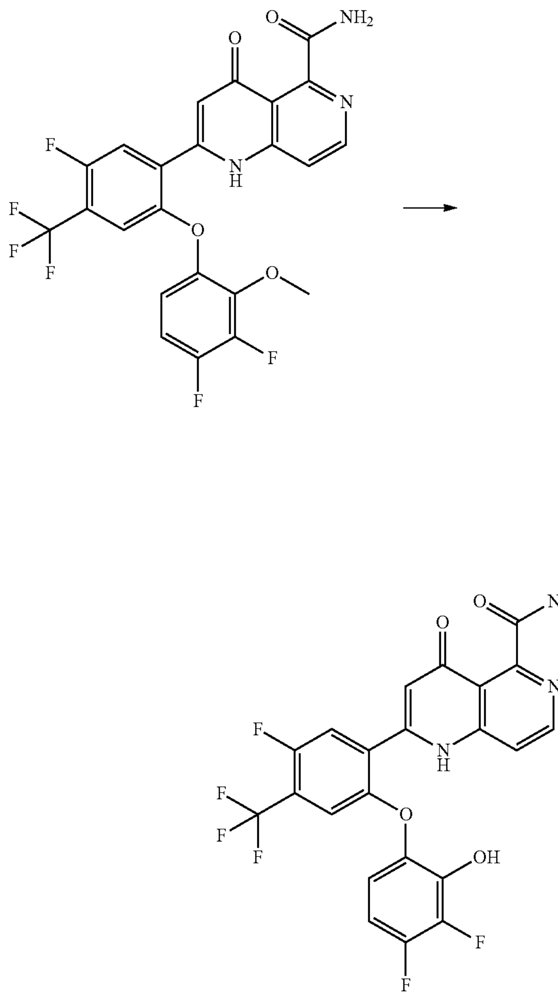

To a solution of 2-[2-(3,4-difluoro-2-methoxy-phenoxy)-5-fluoro-4-(trifluoromethyl)phenyl]-4-oxo-1H-1,6-naphthyridine-5-carboxamide (152, 20 mg, 0.040 mmol) in DCM (1 mL) at −0° C. was added a solution of $BBr_3$ (120 μL of 1.0 M in DCM, 0.12 mmol). After 1.5 h additional $BBr_3$ (120 μL of 1.0 M in DCM, 0.12 mmol) was added followed by DCM (1 mL) and the mixture stirred overnight. Additional $BBr_3$ (120 μL of 1.0 M in DCM, 0.12 mmol) and DCM (1 mL) were then added and the mixture stirred for 30 min. The mixture was diluted with methanol (1 mL) and aqueous NaOH (120 μL of 1.0 M, 0.12 mmol) then stirred for 10 min. The mixture was concentrated and purified by reverse phase HPLC (C18, acetonitrile/water containing 0.1% ammonium hydroxide gradient) to provide 2-[2-(3,4-difluoro-2-hydroxy-phenoxy)-5-fluoro-4-(trifluoromethyl)phenyl]-4-oxo-1H-1,6-naphthyridine-5-carboxamide bis-ammonium salt (347, 10.3 mg, 49%). $^1H$ NMR (500 MHz, $CD_3OD$) δ 8.57 (d, J=5.9 Hz, 1H), 7.73 (d, J=10.2 Hz, 1H), 7.66 (s, 1H), 7.11 (d, J=5.7 Hz, 1H), 6.89 (ddd, J=9.2, 5.0, 2.3 Hz, 1H), 6.70 (q, J=9.1 Hz, 1H). ESI-MS m/z calc. 495.07, found 496.3 $(M+1)^+$.

3-bromo-2-[5-chloro-2-(4,4-difluoroazepan-1-yl)-4,6-dimethyl-3-pyridyl]-4-oxo-1H-1,6-naphthyridine-5-carboxamide (348)

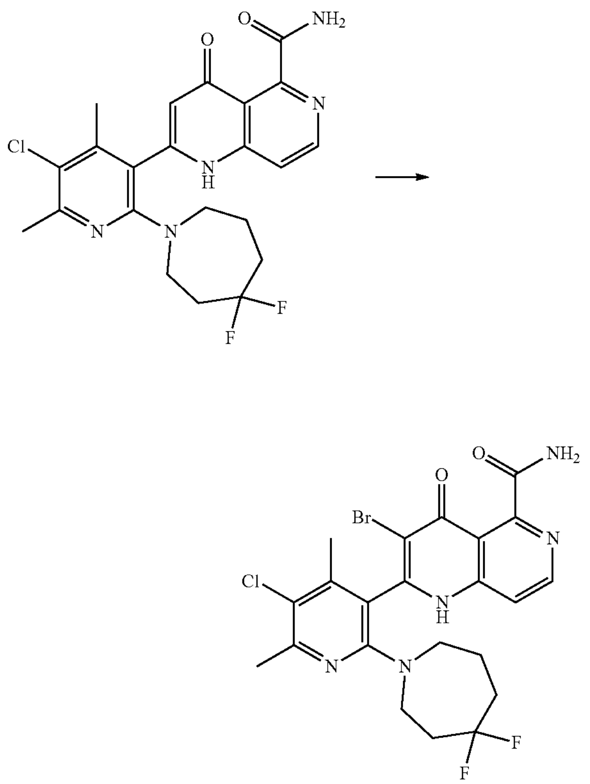

To a solution of 2-[5-chloro-2-(4,4-difluoroazepan-1-yl)-4,6-dimethyl-3-pyridyl]-4-oxo-1H-1,6-naphthyridine-5-carboxamide (HCl salt) (8 mg, 0.016 mmol) in DCM (300 μL) and acetic acid (150 μL) was added NBS (4 mg, 0.02 mmol) in a single portion. The mixture was stirred at room temperature for 16 h. The mixture was concentrated, dissolved in DMSO, filtered and purified by reverse phase HPLC (C18, 1-99% acetonitrile/5 mM HCl over 15 min) to provide 3-bromo-2-[5-chloro-2-(4,4-difluoroazepan-1-yl)-4,6-dimethyl-3-pyridyl]-4-oxo-1H-1,6-naphthyridine-5-carboxamide (348, 1.3 mg, 15%). ESI-MS m/z calc. 539.05, found 540.2 $(M+1)^+$. $^1H$ NMR (400 MHz, $CD_3OD$) δ 8.66 (d, J=6.2 Hz, 1H), 7.69 (d, J=6.3 Hz, 1H), 3.74-3.41 (m, 2H), 3.29-3.10 (m, 2H), 2.65 (s, 1H), 2.58 (s, 2H), 2.22 (s, 5H), 1.97 (m, 2H), 1.83-1.55 (m, 2H).

Representative Scheme

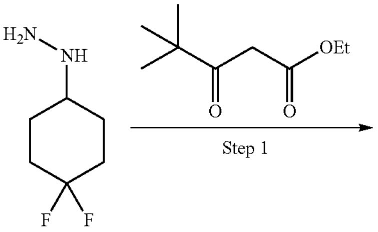

-continued

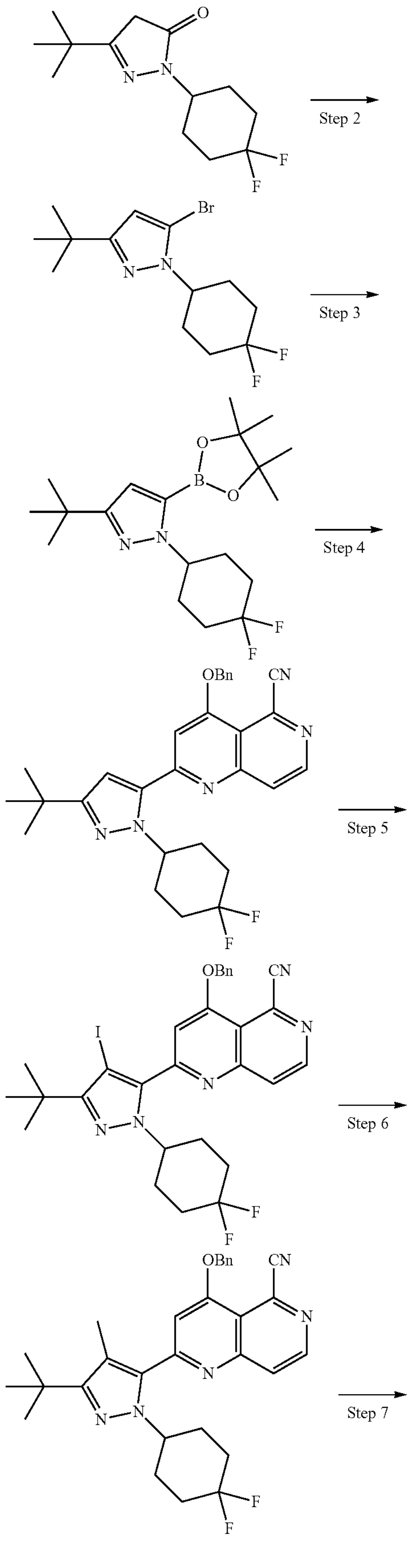

-continued

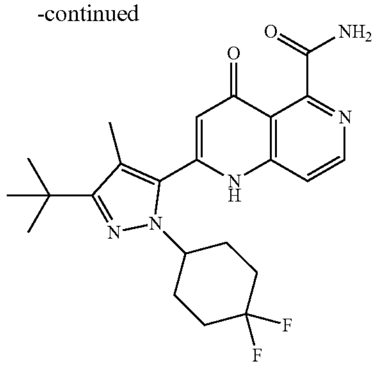

2-[5-tert-butyl-2-(4,4-difluorocyclohexyl)-4-methyl-pyrazol-3-yl]-4-oxo-1H-1,6-naphthyridine-5-carboxamide (349)

Step 1: 5-tert-butyl-2-(4,4-difluorocyclohexyl)-4H-pyrazol-3-one

To a suspension of (4,4-difluorocyclohexyl)hydrazine 2HCl (3.0 g, 12.8 mmol) in ethanol (60 mL) was added triethylamine (12.5 mL, 89.7 mmol) and a solution of ethyl 4,4-dimethyl-3-oxo-pentanoate (2.64 g, 15.3 mmol) in ethanol (10 mL). The resulting mixture was heated at reflux for 3 days. On cooling, volatiles were removed under reduced pressure. The residue was co-evaporated with heptane (2×20 mL) and methanol (2×30 mL). The resulting solid was dissolved in ethyl acetate (100 mL) and washed with water and brine. The phases were separated and the organic phase was dried over sodium sulfate, filtered and concentrated to afford 5-tert-butyl-2-(4,4-difluorocyclohexyl)-4H-pyrazol-3-one (3.61 g, 98%) as a light brown solid. $^1$H NMR (400 MHz, $CDCl_3$) δ 4.16-4.10 (m, 1H), 3.22 (s, 2H), 2.27-2.17 (m, 2H), 2.14-2.04 (m, 2H), 1.98-1.79 (m, 4H), 1.19 (s, 9H). $^{19}$F NMR (377 MHz, $CDCl_3$) δ −94.26 (br d, J=237.1 Hz, 1F), −101.04 (br d, J=237.1 Hz, 1F). ESI-MS m/z calc. 258.15, found 259.2 $(M+1)^+$.

Step 2: 5-bromo-3-tert-butyl-1-(4,4-difluorocyclohexyl)pyrazole

To a stirring suspension of 5-tert-butyl-2-(4,4-difluorocyclohexyl)-4H-pyrazol-3-one (210 mg, 0.488 mmol) in acetonitrile (3 mL) was added phosphorus oxybromide (160 mg, 0.558 mmol). The mixture was stirred at 100° C. for 16 h. After cooling to room temperature, the mixture was poured into water (10 mL) and extracted with MTBE (2×20 mL). The combined organic layers were washed with water and brine, dried over sodium sulfate, filtered and concentrated. Purification using silica gel chromatography (0-5% ethyl acetate/heptane) provided 5-bromo-3-tert-butyl-1-(4,4-difluorocyclohexyl)pyrazole (160 mg, 99%) as a yellow oil. $^1$H NMR (400 MHz, $CDCl_3$) δ 6.12 (s, 1H), 4.39-4.30 (m, 1H), 2.40-2.21 (m, 4H), 2.04-1.84 (m, 4H), 1.26 (s, 9H). $^{19}$F NMR (377 MHz, $CDCl_3$) δ −95.37 (br. d, J=235.7 Hz, 1F), −99.38 (br. d, J=234.3 Hz, 1F). ESI-MS m/z calc. 320.07, found 321.1 $(M+1)^+$.

Step 3: 3-tert-butyl-1-(4,4-difluorocyclohexyl)-5-(4,4,5,5-tetramethyl-1,3,2-dioxaborolan-2-yl)pyrazole To a solution of 5-bromo-3-tert-butyl-1-(4,4-difluorocyclohexyl)pyrazole (738 mg, 2.16 mmol) in THF (20.5 mL)

at −78° C. under argon was added n-BuLi in hexanes (1.5 mL of 1.6 M, 2.4 mmol) dropwise and the mixture stirred at this temperature for 30 min. A solution of 2-isopropoxy-4,4,5,5-tetramethyl-1,3,2-dioxaborolane (502 mg, 0.550 mL, 2.70 mmol) in THF (2 mL) was added and stirring continued at −78° C. for 2 h. The mixture was allowed to warm to room temperature then quenched with saturated aqueous ammonium chloride (25 mL). The mixture was diluted with water (25 mL) and extracted with ethyl acetate (2×50 mL). The combined extracts were washed with water and brine, dried over sodium sulfate, filtered and concentrated to provide 3-tert-butyl-1-(4,4-difluorocyclohexyl)-5-(4,4,5,5-tetramethyl-1,3,2-dioxaborolan-2-yl)pyrazole (812 mg, 60%). ESI-MS m/z calc. 368.24, found 369.27 $(M+1)^+$. $^1H$ NMR (400 MHz, $CDCl_3$) δ 6.56 (s, 1H), 4.78-4.69 (m, 1H), 2.36-2.23 (m, 4H), 2.03-1.81 (m, 4H), 1.32 (s, 12H), 1.27 (s, 9H).

Step 4: 4-benzyloxy-2-[5-tert-butyl-2-(4,4-difluorocyclohexyl)pyrazol-3-yl]-1,6-naphthyridine-5-carbonitrile To a solution of 3-tert-butyl-1-(4,4-difluorocyclohexyl)-5-(4,4,5,5-tetramethyl-1,3,2-dioxaborolan-2-yl)pyrazole (1.05 g, 2.00 mmol) and 4-benzyloxy-2-chloro-1,6-naphthyridine-5-carbonitrile (590 mg, 2.00 mmol) in dioxane (16 mL) was added potassium carbonate (552 mg, 3.99 mmol) and water (4 mL), followed by $Pd(PPh_3)_4$ (231 mg, 0.200 mmol). The resulting mixture was heated for 1 h at 120° C. (microwave irradiation). The mixture was cooled, diluted with ethyl acetate (50 mL) and washed with water (25 mL) and brine (25 mL). The organic phase was dried over sodium sulfate, filtered and concentrated. Purification by silica gel chromatography (5-50% ethyl acetate/heptane) provided 4-benzyloxy-2-[5-tert-butyl-2-(4,4-difluorocyclohexyl) pyrazol-3-yl]-1,6-naphthyridine-5-carbonitrile (685 mg, 56%). $^1H$ NMR (400 MHz, $CDCl_3$) δ 8.80 (d, J=5.5 Hz, 1H), 7.91 (d, J=6.0 Hz, 1H), 7.62 (d, J=7.3 Hz, 2H), 7.47-7.32 (m, 3H), 7.23 (s, 1H), 6.48 (s, 1H), 5.53 (d, J=6.0 Hz, 2H), 5.47-5.38 (m, 1H), 2.43-2.28 (m, 4H), 2.17-2.08 (m, 2H), 1.99-1.83 (m, 2H), 1.34 (s, 9H). ESI-MS m/z calc. 501.23, found 502.3 $(M+1)^+$.

Step 5: 4-benzyloxy-2-[5-tert-butyl-2-(4,4-difluorocyclohexyl)-4-iodo-pyrazol-3-yl]-1,6-naphthyridine-5-carbonitrile To a suspension of 4-benzyloxy-2-[5-tert-butyl-2-(4,4-difluorocyclohexyl)pyrazol-3-yl]-1,6-naphthyridine-5-carbonitrile (1.62 g, 3.13 mmol) in acetonitrile (60 mL) was added NIS (845 mg, 3.76 mmol) and the mixture heated for 16 h at 90° C. Additional NIS (845 mg, 3.76 mmol) was added and heating continued for 6 h. A further portion of NIS (1.06 g, 4.71 mmol) was added and heating continued for another 16 h. The mixture was cooled, diluted with water (120 mL), and the resulting solid was collected by filtration. The solid was washed with water (2×20 mL) and dried to provide 4-benzyloxy-2-[5-tert-butyl-2-(4,4-difluorocyclohexyl)-4-iodo-pyrazol-3-yl]-1,6-naphthyridine-5-carbonitrile (1.82 g, 86%). $^1H$ NMR (400 MHz, $CDCl_3$) δ 8.86 (d, J=6.0 Hz, 1H), 8.01 (d, J=5.5 Hz, 1H), 7.60 (d, J=7.3 Hz, 2H), 7.47-7.34 (m, 4H), 5.58 (s, 2H), 4.51-4.42 (m, 1H), 2.34-2.20 (m, 4H), 2.04-1.94 (m, 2H), 1.83-1.65 (m, 2H), 1.46 (s, 9H). ESI-MS m/z calc. 627.13, found 628.25 $(M+1)^+$.

Alternatively, the pyrazole ring can be chlorinated using NCS under analogous conditions to provide the intermediate 4-benzyloxy-2-[5-tert-butyl-4-chloro-2-(4,4-difluorocyclohexyl)pyrazol-3-yl]-1,6-naphthyridine-5-carbonitrile (36 mg, 77%). ESI-MS m/z calc. 535.20, found 536.5 $(M+1)^+$. $^1H$ NMR (400 MHz, $CDCl_3$) δ 8.85 (d, J=5.7 Hz, 1H), 7.97 (d, J=5.7 Hz, 1H), 7.64-7.58 (m, 2H), 7.50 (s, 1H), 7.48-7.34 (m, 3H), 5.56 (s, 2H), 4.89-4.80 (m, 1H), 2.40-2.22 (m, 4H), 2.10-2.02 (m, 2H), 1.91-1.71 (m, 2H), 1.42 (s, 9H).

Alternatively, the pyrazole ring can be brominated using NBS under analogous conditions to provide the intermediate 4-benzyloxy-2-[4-bromo-5-tert-butyl-2-(4,4-difluorocyclohexyl)pyrazol-3-yl]-1,6-naphthyridine-5-carbonitrile (1.943 g, 93%). $^1H$ NMR (400 MHz, $CDCl_3$) δ 8.85 (d, J=6.0 Hz, 1H), 7.99 (d, J=6.0 Hz, 1H), 7.61-7.59 (m, 2H), 7.47 (s, 1H), 7.45-7.35 (m, 3H), 5.56 (s, 2H), 4.73-4.64 (m, 1H), 2.36-2.23 (m, 4H), 2.08-2.01 (m, 2H), 1.87-1.69 (m, 2H), 1.43 (s, 9H). ESI-MS m/z calc. 579.15, found 580.2 $(M+1)^+$.

Step 6: 4-benzyloxy-2-[5-tert-butyl-2-(4,4-difluorocyclohexyl)-4-methyl-pyrazol-3-yl]-1,6-naphthyridine-5-carbonitrile To a solution of 4-benzyloxy-2-[5-tert-butyl-2-(4,4-difluorocyclohexyl)-4-iodo-pyrazol-3-yl]-1,6-naphthyridine-5-carbonitrile (129 mg, 0.191 mmol) and trimethylboroxine (48 mg, 0.38 mmol) in DMF (5 mL) was added potassium carbonate (80 mg, 0.58 mmol) followed by $Pd(dppf)Cl_2$ (14 mg, 0.019 mmol). The resulting mixture was heated at 120° C. for 1 h (microwave irradiation). The mixture was diluted with water (20 mL) and extracted with ethyl acetate (2×25 mL). The combined extracts were washed with water and brine, dried over sodium sulfate, filtered and concentrated to provide 4-benzyloxy-2-[5-tert-butyl-2-(4,4-difluorocyclohexyl)-4-methyl-pyrazol-3-yl]-1,6-naphthyridine-5-carbonitrile (134 mg, 87%). ESI-MS m/z calc. 515.25, found 516.3 $(M+1)^+$.

Step 7: 2-[5-tert-butyl-2-(4,4-difluorocyclohexyl)-4-methyl-pyrazol-3-yl]-4-oxo-1H-1,6-naphthyridine-5-carboxamide A mixture 4-benzyloxy-2-[5-tert-butyl-2-(4,4-difluorocyclohexyl)-4-methyl-pyrazol-3-yl]-1,6-naphthyridine-5-carbonitrile (215 mg, 0.380 mmol) in toluene (5 mL) and TFA (5 mL, 65 mmol) was heated at 70° C. for 10 h. The mixture was cooled, concentrated and purified by reverse phase chromatography (C18, 20-100% acetonitrile/water containing 0.1% formic acid) to provide 2-[5-tert-butyl-2-(4,4-difluorocyclohexyl)-4-methyl-pyrazol-3-yl]-4-oxo-1H-1,6-naphthyridine-5-carboxamide (167 mg, 99%). $^1H$ NMR (400 MHz, $CD_3OD$) δ 8.54 (d, J=6.0 Hz, 1H), 7.49 (d, J=5.0 Hz, 1H), 6.31 (s, 1H), 4.20 (s, 1H), 2.27-2.11 (m, 4H). 2.11 (s, 3H), 1.94-1.78 (m, 4H), 1.35 (s, 9H). ESI-MS m/z calc. 443.21, found 444.22 $(M+1)^+$.

2-[5-tert-butyl-2-(4,4-difluorocyclohexyl)-4-(trifluoromethyl)pyrazol-3-yl]-4-oxo-1H-1,6-naphthyridine-5-carboxamide (350)

Step 1: 4-benzyloxy-2-[5-tert-butyl-2-(4,4-difluorocyclohexyl)-4-(trifluoromethyl)pyrazol-3-yl]-1,6-naphthyridine-5-carbonitrile

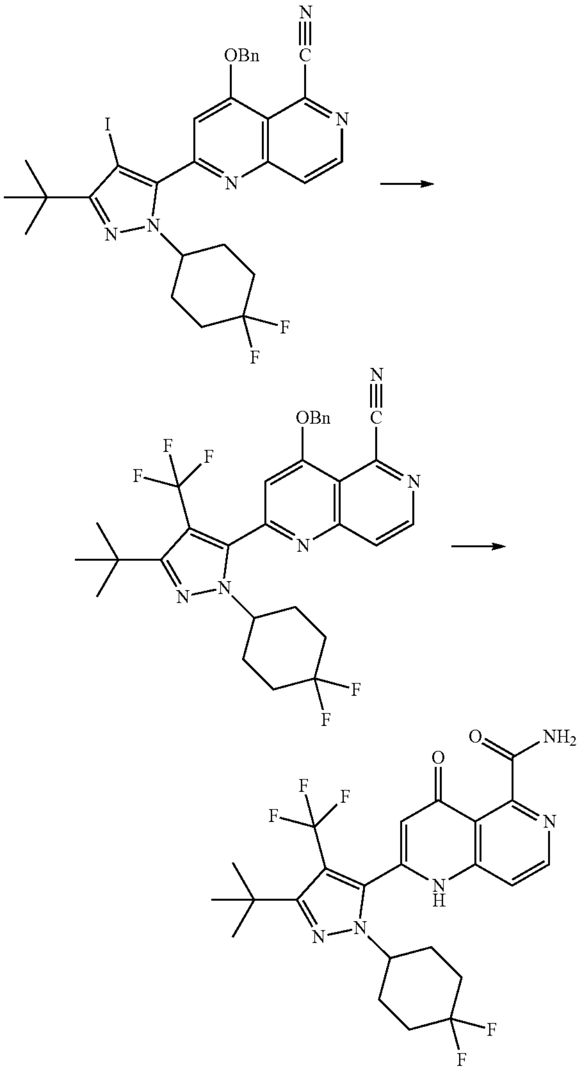

A solution of 4-benzyloxy-2-[5-tert-butyl-2-(4,4-difluorocyclohexyl)-4-iodo-pyrazol-3-yl]-1,6-naphthyridine-5-carbonitrile (89 mg, 0.14 mmol), methyl 2,2-difluoro-2-(fluorosulfonyl)acetate (136 mg, 90 μL, 0.71 mmol), HMPA (124 mg, 120 μL, 0.690 mmol) and copper iodide (31 mg, 0.16 mmol) in DMF (2.6 mL) was stirred at 70° C. for 20 h. On cooling, the mixture was diluted with ethyl acetate (20 mL) and washed with water (2×10 mL) and brine (10 mL). The organic phase was dried over sodium sulfate and concentrated to provide 4-benzyloxy-2-[5-tert-butyl-2-(4,4-difluorocyclohexyl)-4-(trifluoromethyl)pyrazol-3-yl]-1,6-naphthyridine-5-carbonitrile (112 mg, 133%). ESI-MS m/z calc. 569.22, found 570.32 $(M+1)^+$. $^1$H NMR (400 MHz, $CDCl_3$) δ 8.90 (d, J=5.5 Hz, 1H), 8.05 (d, J=5.5 Hz, 1H), 7.58-7.55 (m, 2H), 7.45-7.36 (m, 3H), 7.11 (s, 1H), 5.51 (s, 2H), 4.01-3.93 (m, 1H), 2.31-2.18 (m, 4H), 1.94-1.86 (m, 2H), 1.72-1.55 (m, 2H), 1.39 (s, 9H). 2H protons at 1.72-1.55 obscured by water peak.

Step 2: 2-[5-tert-butyl-2-(4,4-difluorocyclohexyl)-4-(trifluoromethyl)pyrazol-3-yl]-4-oxo-1H-1,6-naphthyridine-5-carboxamide A solution of 4-benzyloxy-2-[5-tert-butyl-2-(4,4-difluorocyclohexyl)-4-(trifluoromethyl)pyrazol-3-yl]-1,6-naphthyridine-5-carbonitrile (252 mg, 0.423 mmol) in toluene (5 mL) and TFA (5 mL, 65 mmol) was heated at 70° C. for 6 h. The mixture was cooled, concentrated and purified by reverse phase chromatography (40-100% acetonitrile/water containing 0.1% formic acid) to provide 2-[5-tert-butyl-2-(4,4-difluorocyclohexyl)-4-(trifluoromethyl)pyrazol-3-yl]-4-oxo-1H-1,6-naphthyridine-5-carboxamide (135 mg, 63%). $^1$H NMR (400 MHz, DMSO-$d_6$) δ 12.35 (s, 1H), 8.50 (d, J=6.1 Hz, 1H), 7.52 (s, 1H), 7.38 (d, J=6.1 Hz, 1H), 7.33 (s, 1H), 6.29 (s, 1H), 4.32-4.22 (m, 1H), 2.16-1.87 (m, 8H), 1.34 (s, 9H). ESI-MS m/z calc. 497.19, found 498.19 $(M+1)^+$.

Representative Keto Ester Building Block Synthesis

Step 1: 5-(3,3-difluorocyclobutanecarbonyl)-2,2-dimethyl-1,3-dioxane-4,6-dione

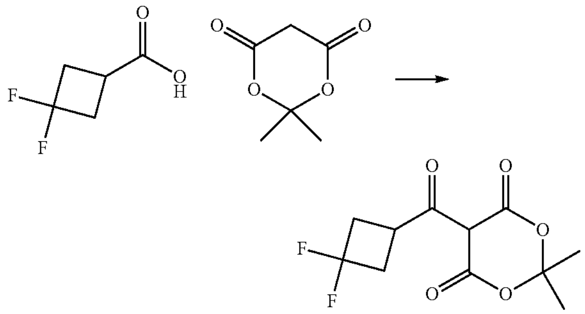

To a stirring solution of 3,3-difluorocyclobutanecarboxylic acid (10.0 g, 73.5 mmol) in dichloromethane (200 mL) at 0° C. were added DMAP (9.0 g, 73.7 mmol), 2,2-dimethyl-1,3-dioxane-4,6-dione (10.6 g, 73.5 mmol) and EDCI (HCl) (16.8 g, 73.6 mmol). The mixture was allowed to warm to room temperature and stirred for 16 h. The mixture was then quenched with water (200 mL) and the layers separated. The organic layer was washed with 2 N HCl (2×100 mL) and brine, dried over sodium sulfate, filtered and concentrated to provide 5-(3,3-difluorocyclobutanecarbonyl)-2,2-dimethyl-1,3-dioxane-4,6-dione (17.1 g, 84%). $^1$H NMR (400 MHz, $CDCl_3$) δ 4.32-4.27 (m, 1H), 3.00-2.86 (m, 4H), 1.74 (s, 6H).

Step 2: Ethyl 3-(3,3-difluorocyclobutyl)-3-oxo-propanoate

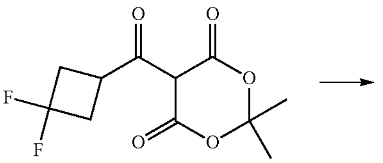

-continued

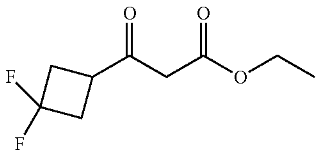

A solution of 5-(3,3-difluorocyclobutanecarbonyl)-2,2-dimethyl-1,3-dioxane-4,6-dione (10 g, 36.231 mmol) in IMS (Industrial Methylated Spirits, 70 mL) was heated at 90° C. for 16 h. The mixture was cooled and concentrated under vacuum to provide ethyl 3-(3,3-difluorocyclobutyl)-3-oxo-propanoate (7.5 g, 95%). $^1$H NMR (400 MHz, $CDCl_3$) δ 4.28-4.17 (m, 2H), 3.47 (s, 2H), 3.30-3.19 (m, 1H), 2.89-2.67 (m, 4H), 1.33-1.26 (m, 3H). ESI-MS m/z calc. 206.08, found 205.1 $(M-1)^-$.

The following compounds are synthesized using the general route shown for compound 349. Pyrazole boronates are synthesized from the appropriate alkyl or aryl hydrazine and the appropriate beta-keto ester. Suzuki coupling followed by the appropriate deprotection/nitrile hydrolysis provides the following compounds.

TABLE 13

| Compound No. | Compound Name | MW & Found [M + H] | NMR (shifts in ppm) |
|---|---|---|---|
| 351 | 2-[5-tert-butyl-2-[4-(trifluoromethyl)cyclohexyl]pyrazol-3-yl]-4-oxo-1H-1,6-naphthyridine-5-carboxamide (mixture of cis and trans isomers) | 461.48; 462.3 | |
| 352 | 2-[2-(4,4-difluorocyclohexyl)-5-[1-(trifluoromethyl)cyclopropyl] pyrazol-3-yl]-4-oxo-1H-1,6-naphthyridine-5-carboxamide | 481.42; 482.15 | $^1$H NMR (400 MHz, $CDCl_3$) δ 15.46 (s, 1H), 8.94 (s, 1H), 8.63 (d, J = 6.1 Hz, 1H), 7.98 (d, J = 5.3 Hz, 1H), 7.33 (s, 1H), 6.84 (s, 1H), 6.14 (s, 1H), 5.57-5.45 (m, 1H), 2.42-2.23 (m, 4H), 2.20-2.10 (m, 2H), 2.00-1.84 (m, 2H), 1.37-1.30 (m, 4H). |
| 353 | 2-[5-tert-butyl-2-(4,4-difluorocyclohexyl)pyrazol-3-yl]-4-oxo-1H-1,6-naphthyridine-5-carboxamide | 429.46; 430.5 | $^1$H NMR (400 MHz, $CD_3OD$) δ 8.58 (d, J = 5.9 Hz, 1H), 7.63 (s, 1H), 6.59 (s, 1H), 6.45 (s, 1H), 4.53 (s, 1H), 2.39-2.17 (m, 4H), 2.11-1.78 (m, 4H), 1.34 (s, 9H). |
| 354 | 2-[2-(4,4-difluorocyclohexyl)-5-(2,2,2-trifluoro-1,1-dimethyl-ethyl)pyrazol-3-yl]-4-oxo-1H-1,6-naphthyridine-5-carboxamide | 483.43; 484.19 | |
| 355 | 2-[5-(3,3-difluorocyclobutyl)-2-(4,4-difluorocyclohexyl)-4-methyl-pyrazol-3-yl]-4-oxo-1H-1,6-naphthyridine-5-carboxamide | 477.45; 478.21 | $^1$H NMR (400 MHz, $CD_3OD$) δ 8.56 (d, J = 5.5 Hz, 1H), 7.50 (br s, 1H), 6.30 (br s, 1H), 4.29 (br s, IH), 3.41-3.34 (m, 1H), 2.98-2.79 (m, 4H), 2.30-2.13 (m, 4H), 1.99-1.80 (m, 7H). |
| 356 | 2-[2-(4,4-difluorocyclohexyl)-5-[1-(trifluoromethyl)cyclobutyl]pyrazol-3-yl]-4-oxo-1H-1,6-naphthyridine-5-carboxamide | 495.45; 496.19 | $^1$H NMR (400 MHz, $CDCl_3$) δ 15.46 (s, 1H), 8.97 (s, 1H), 8.65 (d, J = 6.1 Hz, 1H), 8.01 (d, J = 5.3 Hz, 1H), 7.33 (s, 1H), 6.73 (s, 1H), 6.21 (s, 1H), 5.60-5.55 (m, 1H), 2.71-2.59 (m, 4H), 2.48-1.89 (m, 10H). |
| 357 | 2-[5-tert-butyl-2-(4-fluoro-2-methyl-phenyl)-4-methyl-pyrazol-3-yl]-4-oxo-1H-1,6-naphthyridine-5-carboxamide | 433.48; 434.21 | $^1$H NMR (400 MHz, $CD_3OD$) δ 8.50 (d, J = 6.0 Hz, 1H), 7.46 (d, J = 5.0 Hz, 1H), 7.32-7.22 (m, 1H), 7.06-6.98 (m, 1H), 6.92 (td, J = 8.4, 2.9 Hz, 1H), 6.07 (br s, 1H), 2.28 (s, 3H), 2.04 (s, 3H), 1.41 (s, 9H). |
| 358 | 2-[2-(4,4-difluorocyclohexyl)-5-(3,3-difluoro-1-methyl-cyclobutyl)pyrazol-3-yl]-4-oxo-1H-1,6-naphthyridine-5-carboxamide | 477.45; 478.23 | |
| 359 | 2-[2-(4,4-difluorocyclohexyl)-5-(1-methylcyclobutyl)pyrazol-3-yl]-4-oxo-1H-1,6-naphthyridine-5-carboxamide | 441.47; 442.2 | $^1$H NMR (400 MHz, $CDCl_3$) δ 15.39 (s, 1H), 8.96 (s, 1H), 8.63 (d, J = 5.3 Hz, 1H), 8.00 (d, J = 5.3 Hz, 1H), 7.34 (s, 1H), 6.62 (s, 1H), 6.15 (s, 1H), 5.55-5.50 (m, 1H), 2.53-1.88 (m, 14H), 1.54 (s, 3H). |

TABLE 13-continued

| Compound No. | Compound Name | MW & Found [M + H] | NMR (shifts in ppm) |
|---|---|---|---|
| 360 | 2-[2-(4,4-difluorocyclohexyl)-4-methyl-5-[1-(trifluoromethyl)cyclobutyl]pyrazol-3-yl]-4-oxo-1H-1,6-naphthyridine-5-carboxamide | 509.47; 510.21 | $^1$H NMR (400 MHz, $CDCl_3$) δ 15.65 (s, 1H), 8.98 (s, 1H), 8.67 (d, J = 5.3 Hz, 1H), 8.07 (d, J = 6.1 Hz, 1H), 7.17 (s, 1H), 6.24 (s, 1H), 4.74-4.70 (m, 1H), 2.81-2.67 (m, 4H), 2.41-1.75 (m, 13H). |
| 361 | 2-[4-bromo-2-(4,4-difluorocyclohexyl)-5-[1-(trifluoromethyl)cyclobutyl]pyrazol-3-yl]-4-oxo-1H-1,6-naphthyridine-5-carboxamide | 574.34; 574.13 | $^1$H NMR (400 MHz, $CDCl_3$) δ 15.71 (s, 1H), 8.97 (s, 1H), 8.68 (d, J = 6.1 Hz, 1H), 8.07 (d, J = 6.1 Hz, 1H), 7.49 (s, 1H), 6.22 (s, 1H), 4.79 (t, J = 9.9 Hz, 1H), 2.90-2.83 (m, 2H), 2.78-2.71 (m, 2H), 2.41-1.72 (m, 10H). |
| 362 | 2-[2-(4,4-difluorocyclohexyl)-5-(3,3-difluoro-1-methyl-cyclobutyl)-4-methyl-pyrazol-3-yl]-4-oxo-1H-1,6-naphthyridine-5-carboxamide | 491.48; 492.1 | $^1$H NMR (400 MHz, $CD_3OD$) δ 8.56 (d, J = 5.9 Hz, 1H), 7.51 (s, 1H), 6.35 (s, 1H), 4.28 (br s, 1H), 3.14 (q, J = 14.2 Hz, 2H), 2.75-2.62 (m, 2H), 2.34-2.10 (m, 4H), 2.02 (s, 3H), 2.00-1.76 (m, 4H), 1.55 (s, 3H). |
| 363 | 2-[2-(4,4-difluorocyclohexyl)-4-methyl-5-(1-methylcyclobutyl)pyrazol-3-yl]-4-oxo-1H-1,6-naphthyridine-5-carboxamide | 455.5; 456.23 | $^1$H NMR (400 MHz, $CD_3OD$) δ 8.57 (d, J = 6.1 Hz, 1H), 7.51 (s, 1H), 6.33 (s, 1H), 4.58 (s, 1H), 4.25 (s, 1H), 2.63-2.57 (m, 2H), 2.32-1.81 (m, 16H), 1.49 (s, 3H). |
| 364 | 2-[2-(4,4-difluorocyclohexyl)-7,7-dimethyl-5,6-dihydro-4H-indazol-3-yl]-4-oxo-1H-1,6-naphthyridine-5-carboxamide | 455.5; 456.23 | $^1$H NMR (400 MHz, $CD_3OD$) δ 8.54 (d, J = 6.0 Hz, 1H), 7.52 (br d, J = 4.6 Hz, 1H), 6.35 (br s, 1H), 4.37 (s, 1H), 2.49 (t, J = 6.2 Hz, 2H), 2.32-2.09 (m, 4H), 2.00-1.64 (m, 6H), 1.68-1.63 (m, 2H), 1.29 (s, 6H). |
| 365 | 2-[5-tert-butyl-4-methyl-2-[4-(trifluoromethyl)cyclohexyl]pyrazol-3-yl]-4-oxo-1H-1,6-naphthyridine-5-carboxamide (mixture of cis and trans isomers) | 475.51; 476.4 | |
| 366 | 2-[4-bromo-2-(4,4-difluorocyclohexyl)-5-(2,2,2-trifluoro-1,1-dimethyl-ethyl)pyrazol-3-yl]-4-oxo-1H-1,6-naphthyridine-5-carboxamide | 561.08; 562.13 | $^1$H NMR (400 MHz, $CD_3OD$) δ 8.58 (d, J = 6.0 Hz, 1H), 7.53 (br s, 1H), 6.44 (br s, 1H), 4.44-4.34 (s, 1H), 2.30-2.11 (m, 4H), 2.05-1.80 (m, 4H), 1.70 (s, 6H). |
| 367 | 2-[4-bromo-2-(4,4-difluorocyclohexyl)-5-(1-methylcyclobutyl)pyrazol-3-yl]-4-oxo-1H-1,6-naphthyridine-5-carboxamide | 519.11; 520.13 | $^1$H NMR (400 MHz, $CDCl_3$) δ 15.62 (s, 1H), 8.95 (d, J = 3.8 Hz, 1H), 8.65 (d, J = 6.1 Hz, 1H), 8.05 (d, J = 6.1 Hz, 1H), 7.46 (s, 1H), 6.17 (d, J = 3.8 Hz, 1H), 4.76-4.71 (m, 1H), 2.70-2.61 (m, 2H), 2.40-2.23 (m, 4H), 2.12-2.03 (m, 5H), 1.90-1.71 (m, 3H), 1.55 (s, 3H). |
| 368 | 3-bromo-2-[5-tert-butyl-4-chloro-2-(4,4-difluorocyclohexyl)pyrazol-3-yl]-4-oxo-1H-1,6-naphthyridine-5-carboxamide | 541.07; 542.24 | $^1$H NMR (400 MHz, DMSO-$d_6$) δ 12.93 (s, 1H), 8.59 (d, J = 5.9 Hz, 1H), 7.60 (s, 1H), 7.49 (d, J = 5.9 Hz, 1H), 7.43 (s, 1H), 4.32-4.13 (m, 1H), 2.19-1.85 (m, 8H), 1.39 (s, 9H). |
| 369 | 2-[2-(4,4-difluorocyclohexyl)-4-methyl-5-[1-(trifluoromethyl)cyclopentyl]pyrazol-3-yl]-4-oxo-1H-1,6-naphthyridine-5-carboxamide | 523.5; 524.2 | $^1$H NMR (400 MHz, $CDCl_3$) δ 15.63 (s, 1H), 8.96 (d, J = 4.6 Hz, 1H), 8.65 (d, J = 5.3 Hz, 1H), 8.06 (d, J = 5.3 Hz, 1H), 7.14 (s, 1H), 6.26 (d, J = 4.6 Hz, 1H), 4.64-4.60 (m, 1H), 2.59 (td, J = 12.6, 6.1 Hz, 2H), 2.35-2.21 (m, 6H), 2.15 (d, J = 13.7 Hz, 3H), 2.05-2.02 (m, 2H), 1.86-1.70 (m, 4H), 1.68-1.63 (m, 2H). |

TABLE 13-continued

| Compound No. | Compound Name | MW & Found [M + H] | NMR (shifts in ppm) |
|---|---|---|---|
| 370 | 2-[2-(4,4-difluorocyclohexyl)-4-methyl-5-(2,2,2-trifluoro-1,1-dimethyl-ethyl)pyrazol-3-yl]-4-oxo-1H-1,6-naphthyridine-5-carboxamide | 497.46; 498.21 | $^1$H NMR (400 MHz, $CD_3OD$) δ 8.55 (d, J = 6.0 Hz, 1H), 7.49 (br s, 1H), 6.34 (br s, 1H), 4.32-4.22 (m, 1H), 2.29-2.11 (m, 4H), 2.11 (s, 3H), 2.00-1.78 (m, 4H), 1.62 (s, 6H). |
| 371 | 2-[4-bromo-2-(4,4-difluorocyclohexyl)-5-(3,3-difluoro-1-methyl-cyclobutyl)pyrazol-3-yl]-4-oxo-1H-1,6-naphthyridine-5-carboxamide | 556.35; 557.2 | $^1$H NMR (400 MHz, $CD_3OD$) δ 8.56 (d, J = 5.5 Hz, 1H), 7.57 (d, J = 6.0 Hz, 1H), 6.53 (br s, 1H), 4.56 (br s, 1H), 4.40 (t, J = 10.3 Hz, 1H), 3.20 (q, J = 14.0 Hz, 2H), 2.75-2.64 (m, 2H), 2.29-2.13 (m, 4H), 2.02-1.80 (m, 4H), 1.60 (s, 3H). |
| 372 | 2-[5-tert-butyl-4-chloro-2-(4,4-difluorocyclohexyl)pyrazol-3-yl]-3-methoxy-4-oxo-1H-1,6-naphthyridine-5-carboxamide | 493.93; 494.3 | $^1$H NMR (400 MHz, $CD_3OD$) δ 8.58 (d, J = 6.4 Hz, 1H), 7.70 (d, J = 6.4 Hz, 1H), 4.20-4.03 (m, 1H), 3.79 (s, 3H), 2.39-2.01 (m, 5H), 1.99-1.74 (m, 3H), 1.44 (s, 9H). |
| 373 | 2-[5-tert-butyl-4-chloro-2-(4,4-difluorocyclohexyl)pyrazol-3-yl]-4-oxo-1H-1,6-naphthyridine-5-carboxamide | 463.91; 464.4 | $^1$H NMR (400 MHz, $CD_3OD$) δ 8.58 (d, J = 5.9 Hz, 1H), 7.55 (br s, 1H), 6.41 (br s, 1H), 4.35 (br s, 1H), 2.40-2.10 (m, 4H), 2.06-1.81 (m, 4H), 1.42 (s, 9H). |
| 374 | 2-[4-bromo-5-tert-butyl-2-(4,4-difluorocyclohexyl)pyrazol-3-yl]-4-oxo-1H-1,6-naphthyridine-5-carboxamide | 508.36; 509.2 | $^1$H NMR (400 MHz, $CD_3OD$) δ 8.56 (d, J = 6.0 Hz, 1H), 7.53 (s, 1H), 6.40 (br s, 1H), 4.31 (s, 1H), 2.31-2.21 (m, 4H), 2.02-1.79 (m, 4H), 1.42 (s, 9H). |
| 375 | 2-[2-(4,4-difluorocyclohexyl)-4-methyl-5-[1-(trifluoromethyl) cyclopropyl]pyrazol-3-yl]-4-oxo-1H-1,6-naphthyridine-5-carboxamide | 495.45; 496.18 | $^1$H NMR (400 MHz, $CDCl_3$) δ 15.64 (s, 1H), 8.96 (s, 1H), 8.65 (d, J = 6.1 Hz, 1H), 8.04 (d, J = 5.3 Hz, 1H), 7.16 (s, 1H), 6.16 (s, 1H), 4.77-4.67 (m, 1H), 2.38-2.17 (m, 7H), 2.11-2.01 (m, 2H), 1.86-1.67 (m, 2H), 1.38 (q, J = 3.8 Hz, 2H), 1.13-1.07 (m, 2H). |
| 376 | 2-[5-tert-butyl-2-(4-fluoro-2-methyl-phenyl)pyrazol-3-yl]-4-oxo-1H-1,6-naphthyridine-5-carboxamide | 419.45; 420.22 | $^1$H NMR (400 MHz, $CDCl_3$) δ 15.32 (s, 1H), 8.88 (br s, 1H), 8.50 (d, J = 5.3 Hz, 1H), 7.68 (d, J = 6.1 Hz, 1H), 7.27 (dd, J = 9.2, 6.1 Hz, 1H), 6.99-6.89 (m, 4H), 6.10 (s, 1H), 2.00 (s, 3H), 1.41 (s, 9H). |
| 377 | 2-(3-(tert-butyl)-1-(4-fluorobenzyl)-1H-pyrazol-5-yl)-4-oxo-1,4-dihydro-1,6-naphthyridine-5-carboxamide | 419.45; 420.21 | $^1$H NMR (400 MHz, $CDCl_3$) δ 15.35 (s, 1H), 8.94 (s, 1H), 8.60 (d, J = 5.3 Hz, 1H), 7.98 (d, J = 5.3 Hz, 1H), 7.31 (s, 1H), 7.16-7.12 (m, 2H), 6.93-6.87 (m, 2H), 6.71 (s, 1H), 6.12 (s, 1H), 6.05 (s, 2H), 1.39 (s, 9H). |
| 378 | 2-(3-(tert-butyl)-1-(4-fluorobenzyl)-4-methyl-1H-pyrazol-5-yl)-4-oxo-1,4-dihydro-1,6-naphthyridine-5-carboxamide | 433.49; 434.21 | $^1$H NMR (400 MHz, $CDCl_3$) δ 15.51 (s, 1H), 8.96 (s, 1H), 8.64 (d, J = 5.3 Hz, 1H), 8.04-8.02 (m, 1H), 7.03 (d, J = 16.0 Hz, 1H), 6.97 (td, J = 6.1, 2.5 Hz, 2H), 6.88-6.83 (m, 2H), 6.14 (s, 1H), 5.54 (s, 2H), 2.27 (s, 3H), 1.43 (s, 9H). |
| 379 | 2-(3-(tert-butyl)-1-((4,4-difluorocyclohexyl)methyl)-4-methyl-1H-pyrazol-5-yl)-4-oxo-1,4-dihydro-1,6-naphthyridine-5-carboxamide | | |
| 380 | 2-(3-(tert-butyl)-1-((4,4-difluorocyclohexyl)methyl)-1H-pyrazol-5-yl)-4-oxo-1,4-dihydro-1,6-naphthyridine-5-carboxamide | | |
| 381 | 2-(3-(tert-butyl)-1-(4-fluoro-2-methylbenzyl)-4-methyl-1H-pyrazol-5-yl)-4-oxo-1,4-dihydro-1,6-naphthyridine-5-carboxamide | | |

TABLE 13-continued

| Compound No. | Compound Name | MW & Found [M + H] | NMR (shifts in ppm) |
|---|---|---|---|
| 382 | 2-(3-(tert-butyl)-1-(4-fluoro-2-methylbenzyl)-1H-pyrazol-5-yl)-4-oxo-1,4-dihydro-1,6-naphthyridine-5-carboxamide | | |
| 383 | 2-(3-(tert-butyl)-1-((3,3-difluorocyclobutyl)methyl)-1H-pyrazol-5-yl)-4-oxo-1,4-dihydro-1,6-naphthyridine-5-carboxamide | | |
| 384 | 2-(3-(tert-butyl)-1-((3,3-difluorocyclobutyl)methyl)-4-methyl-1H-pyrazol-5-yl)-4-oxo-1,4-dihydro-1,6-naphthyridine-5-carboxamide | | |

Example 18

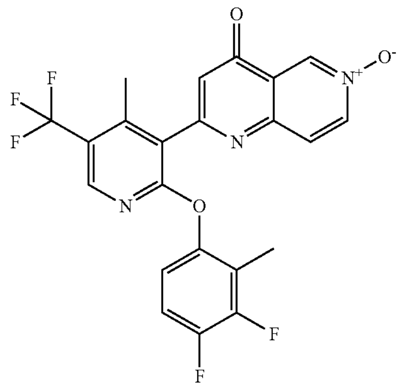

2-(2-(3,4-difluoro-2-methylphenoxy)-4-methyl-5-(trifluoromethyl)pyridin-3-yl)-4-oxo-415-1,6-naphthyridine 6-oxide (385) is prepared via a process analogous to the methods disclosed herein.

Example 19

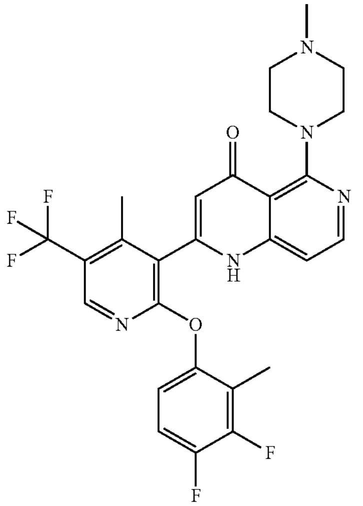 [SMILES: Cc1c(Oc2ncc(C(F)(F)F)c(C)c2-c2cc(=O)c3c(N4CCN(C)CC4)nccc3[nH]2)ccc(F)c1F]

2-(2-(3,4-difluoro-2-methylphenoxy)-4-methyl-5-(trifluoromethyl)pyridin-3-yl)-5-(4-methylpiperazin-1-yl)-1,6-naphthyridin-4(1H)-one (386) was prepared via a process analogous to the methods disclosed herein for compound 188. ESI-MS m/z calc. 545.185, found 546.3 $(M+1)^+$.

Example 20

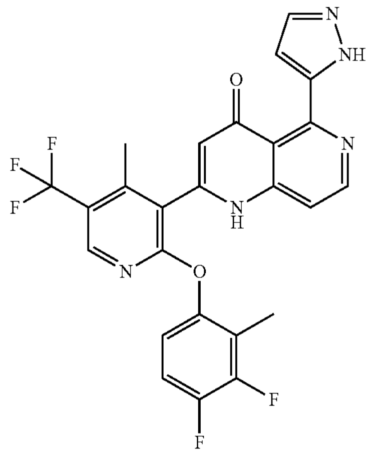 [SMILES: Cc1c(Oc2ncc(C(F)(F)F)c(C)c2-c2cc(=O)c3c(-c4ccn[nH]4)nccc3[nH]2)ccc(F)c1F]

2-(2-(3,4-difluoro-2-methylphenoxy)-4-methyl-5-(trifluoromethyl)pyridin-3-yl)-5-(1H-pyrazol-5-yl)-1,6-naphthyridin-4(1H)-one (387) was prepared via a process analogous to the methods disclosed herein for compound 212. ESI-MS m/z calc. 513.12, found 514.0 $(M+1)^+$. $^1H$ NMR (400 MHz, DMSO-$d_6$) δ 14.43 (br s, 1H), 12.58 (br s, 1H), 8.65 (br s, 1H), 8.62 (s, 1H), 7.57 (br s, 1H), 7.45 (br s, 1H), 7.35 (q, J=9.4 Hz, 1H), 7.12-7.04 (m, 1H), 6.96 (br s, 1H), 6.61 (br s, 1H), 2.43 (s, 3H), 2.03 (d, J=2.3 Hz, 3H).

Example 21

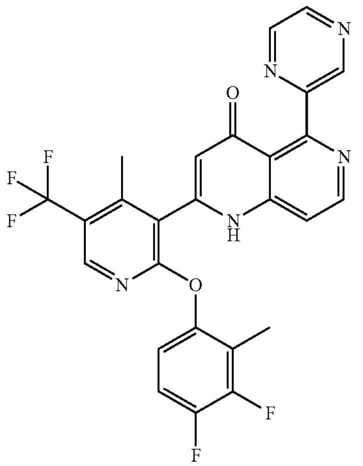 [SMILES: Cc1c(Oc2ncc(C(F)(F)F)c(C)c2-c2cc(=O)c3c(-c4cnccn4)nccc3[nH]2)ccc(F)c1F]

2-(2-(3,4-difluoro-2-methylphenoxy)-4-methyl-5-(trifluoromethyl)pyridin-3-yl)-5-(pyrazin-2-yl)-1,6-naphthyridin-4(1H)-one (388) was prepared via a process analogous to the methods disclosed herein for compound 212. ESI-MS m/z calc. 525.12, found 526.2 $(M+1)^+$. $^1H$ NMR (400 MHz, $CD_3OD$) δ 8.98 (d, J=1.0 Hz, 1H), 8.81-8.73 (m, 3H), 8.50 (s, 1H), 7.88 (d, J=6.5 Hz, 1H), 7.15 (q, J=9.2 Hz, 1H), 6.99-6.90 (m, 1H), 6.58 (s, 1H), 2.53 (d, J=1.6 Hz, 3H), 2.05 (d, J=2.1 Hz, 3H).

Example 22

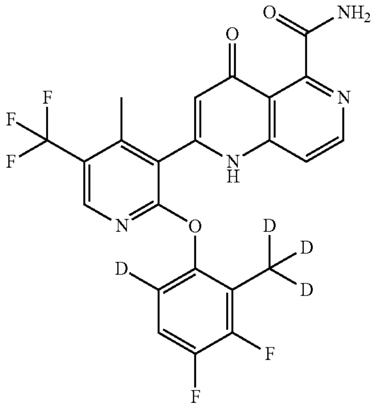 [SMILES: [2H]c1cc(F)c(F)c(C([2H])([2H])[2H])c1Oc1ncc(C(F)(F)F)c(C)c1-c1cc(=O)c2c(C(N)=O)nccc2[nH]1]

2-(2-(3,4-difluoro-2-(methyl-$d_3$)phenoxy-6-d)-4-methyl-5-(trifluoromethyl)pyridin-3-yl)-4-oxo-1,4-dihydro-1,6-naphthyridine-5-carboxamide (389) is prepared via a process analogous to the methods disclosed herein.

Example 23

E-VIPR Assay Detecting and Measuring $Na_V$ Inhibition Properties

Sodium ion channels are voltage-dependent proteins that can be activated by inducing membrane voltage changes by applying electric fields. The electrical stimulation instrument and methods of use, referred to as E-VIPR, are described in International Publication No. WO 2002/008748 A3 and C.-J. Huang et al. *Characterization of voltage-gated sodium channel blockers by electrical stimulation and fluorescence detection of membrane potential,* 24 Nature Biotech. 439-46 (2006), both of which are incorporated by reference in their entirety. The instrument comprises a microtiter plate handler, an optical system for exciting the coumarin dye while simultaneously recording the coumarin and oxonol emissions, a waveform generator, a current- or voltage-controlled amplifier, and parallel electrode pairs that are inserted into assay plate wells. Under integrated computer control, this instrument passes user-programmed electrical stimulus protocols to cells within the wells of the microtiter plate.

16-20 hours prior to running the assay on E-VIPR, HEK cells expressing a truncated form of human $Na_V$ 1.8 with full channel activity were seeded into microtiter 384-well plates, pre-coated with matrigel, at a density of 25,000 cells per well. 2.5-5% KIR2.1 BacMam virus was added to the final cell suspension before seeding into cell plates. HEK cells were grown in Dulbecco's Modified Eagle's Medium (DMEM) supplemented with 10% FBS (Fetal Bovine Serum, qualified; Sigma #F4135), 1% NEAA (Non-Essential Amino Acids, Gibco #11140), 1% HEPES (Gibco #15630), 1% Pen-Strep (Penicillin-Streptomycin; Gibco #15140) and 5 μg/ml Blasticidin (Gibco #R210-01). Cells were expanded in 5-layer CellSTACK culture chambers or cell culture flasks with vented caps, with 90-95% humidity and 5% $CO_2$.

Reagents and Stock Solutions:

100 mg/mL Pluronic F-127 (Sigma #P2443), in dry DMSO

Compound Plates: Corning 384-well Polypropylene Round Bottom #3656

Cell Plates: 384-well tissue culture treated plates (Greiner #781091-2B)

2.5-5% KIR 2.1 Bacmam virus (produced in-house), prepared as described in Section 3.3 of J. A. Fornwald et al., *Gene Expression in Mammalian Cells Using BacMam, a Modified Baculovirus System,* 1350 Methods in Molecular Biology 95-116 (2016), the entire contents of which are incorporated by reference. The concentration used can be dependent on viral titer of each batch.

5 mM $DiSBAC_6(3)$, a voltage sensitive oxonol acceptor (CAS number 169211-44-3; 5-[3-(1,3-dihexylhexahydro-4,6-dioxo-2-thioxo-5-pyrimidinyl)-2-propen-1-ylidene]-1,3-dihexyldihydro-2-thioxo-4,6(1H,5H)-pyrimidinedione), in dry DMSO. The preparation of $DiSBAC_6(3)$ is analogous to that of $DiSBAC_4(3)$ as described in *Voltage Sensing by Fluorescence Resonance Energy Transfer in Single Cells*, Gonzalez, J. E. and Tsien, R. Y. (1995) Biophys. J. 69, 1272-1280.

5 mM CC2-DMPE, a commercially available membrane-bound coumarin phospholipid FRET donor (ThermoFisher Scientific catalog number K1017, CAS number 393782-57-5; tetradecanoic acid, 1,1'-[(1R)-1-[8-(6-chloro-7-hydroxy-2-oxo-2H-1-benzopyran-3-yl)-3-hydroxy-3-oxido-8-oxo-2,4-dioxa-7-aza-3-phosphaoct-1-yl]-1,2-ethanediyl] ester) was prepared in dry DMSO. See also, *Improved indicators of cell membrane potential that use fluorescence resonance energy transfer*, Gonzalez, J. E. and Tsien, R. Y. (1997) *Chem. Biol.* 4, 269-277.

Voltage Assay Background Suppression Compound (VABSC-1) is prepared in $H_2O$ (89-363 mM, range used to maintain solubility)

Human Serum (HS, Millipore #S1P1-01KL, or Sigma SLBR5469V and SLBR5470V as a 50%/50% mixture, for 25% assay final concentration)

Bath 1 Buffer:

Sodium Chloride 160 mM (9.35 g/L), Potassium Chloride, 4.5 mM (0.335 g/L), Glucose 10 mM (1.8 g/L), Magnesium Chloride (Anhydrous) 1 mM (0.095 g/L), Calcium Chloride 2 mM (0.222 g/L), HEPES 10 mM (2.38 g/L) in water.

Na/TMA Cl Bath 1 Buffer:

Sodium Chloride 96 mM (5.61 g/L), Potassium Chloride 4.5 mM (0.335 g/L), Tetramethylammonium (TMA)-Cl 64 mM (7.01 g/L), Glucose 10 mM (1.8 g/L), Magnesium Chloride (Anhydrous) 1 mM (0.095 g/L), Calcium Chloride 2 mM (0.222 g/L) HEPES 10 mM (2.38 g/L) in water.

Hexyl Dye Solution (2× Concentration):

Bath 1 Buffer containing 0.5% β-cyclodextrin (made fresh prior to each use, Sigma #C4767), 8 μM CC2-DMPE and 2 μM $DiSBAC_6(3)$. The solution was made by adding 10% Pluronic F127 stock equal to combined volumes of CC2-DMPE and $DiSBAC_6(3)$. The order of preparation was first mix Pluronic and CC2-DMPE, then add $DiSBAC_6(3)$, then while vortexing add Bath 1/β-Cyclodextrin.

Compound Loading Buffer (2× concentration): Na/TMA Cl Bath1 Buffer containing HS (omitted in experiments run in the absence of human serum (HS)) 50%, VABSC-1 1 mM, BSA 0.2 mg/ml (in Bath-1), KCl 9 mM, DMSO 0.625%.

Assay Protocol (7 Key Steps):

1) To reach the final concentration in each well, 375 nL of each compound was pre-spotted (in neat DMSO) into polypropylene compound plates at 240× desired final concentration from an intermediate stock concentration of 0.075 mM, in an 11-point dose response, 3-fold dilution, resulting in a top dose of 300 nM final concentration in the cell plate. Vehicle control (neat DMSO), and positive control (an established $Na_V1.8$ inhibitor, 25 μM final in assay in DMSO) were added manually to the outermost columns of each plate respectively. The compound plate was backfilled with 45 μL per well of Compound Loading Buffer resulting in a 240-fold dilution of compound following a 1:1 transfer of compound into the cell plate (see Step 6). Final DMSO concentration for all wells in the assay was 0.625% (0.75% DMSO was supplemented to the Compound Loading Buffer for a final DMSO concentration of 0.625%). This assay dilution protocol was adjusted to enable a higher dose range to be tested in the presence of HS or if the final assay volume was altered.
2) Hexyl Dye Solution was prepared.
3) Cell plates were prepared. On the day of the assay, the media was aspirated, and the cells were washed three times with 80 μL of Bath-1 buffer, maintaining 25 μL residual volume in each well.
4) 25 μL per well of Hexyl Dye Solution was dispensed into the cell plates. The cells were incubated for 20 minutes at room temperature or ambient conditions in darkness.
5) 45 μL per well of Compound Loading Buffer was dispensed into compound plates.
6) The cell plates were washed three times with 80 μL per well of Bath-1 Buffer, leaving L of residual volume. Then 25 μL per well from compound plate was transferred to each cell plate. The mixture was incubated for 30 minutes at room temperature/ambient conditions.
7) The cell plate containing compound was read on E-VIPR using the current-controlled amplifier to deliver stimulation wave pulses using a symmetrical biphasic waveform. The user-programmed electrical stimulus protocols were 1.25-4 Amps and 4 millisecond pulse width (dependent on electrode composition) were delivered at 10 Hz for 10 seconds. A pre-stimulus recording was performed for each well for 0.5 seconds to obtain the un-stimulated intensities baseline. The stimulatory waveform was followed by 0.5 seconds of post-stimulation recording to examine the relaxation to the resting state. All E-VIPR responses were measured at 200 Hz acquisition rate.

Data Analysis:

Data were analyzed and reported as normalized ratios of emission intensities measured in the 460 nm and 580 nm channels. The response as a function of time was reported as the ratios obtained using the following formula:

$$R(t) = \frac{(\text{intensity}_{460\,nm})}{(\text{intensity}_{580\,nm})}$$

The data were normalized by calculating the initial ($R_i$) and final ($R_f$) ratios. These were the average ratio values during part or all of the pre-stimulation period and during sample points during the stimulation period. The fluorescence ratio ($R_f/R_i$) was then calculated and reported as a function of time.

Control responses were obtained by performing assays in the presence of the positive control, and in the absence of pharmacological agents (DMSO vehicle negative control). Responses to the negative (N) and positive (P) controls were calculated as above. The compound antagonist % activity A was then defined as:

$$A = \frac{X - N}{P - N} \times 100$$

where X is the maximum amplitude of the ratio response or number of action potential peaks, at the beginning of the pulse train in the presence of test compound. Using this analysis protocol, dose response curves were plotted and $IC_{50}$ values were generated for various compounds of the present invention.

Compounds having a measured $IC_{50}$ value less than 0.5 μM in the E-VIPR Assay described above include: 5, 7-27, 29-31, 33-36, 39-71, 73-82, 84-94, 96-132, 134-137, 139-152, 154-156, 158-169, 171-174, 176-178. 180-192, 194-280, 283-302, 304, 306-311, 313-319, 321-330, 332, 333, 335-345, 349-378, and 386-388.

Compounds having a measured $IC_{50}$ value less than 2 μM and greater than or equal to 0.5 μM in the E-VIPR Assay described above include: 3, 4, 28, 32, 38, 95, 133, 138, 170, 175, 179, 281, 282, 312, 320, 331, 346, and 347.

Compounds having a measured $IC_{50}$ value less than 5 μM and greater than or equal to 2 μM in the E-VIPR Assay described above include: 6 and 334.

Compounds having a measured $IC_{50}$ value greater than or equal to 5 μM in the E-VIPR Assay described above include: 1, 2, 37, 153, 193, 303, and 305.

An $IC_{50}$ value was not determined in the E-VIPR Assay described for Compounds 72, 83, 157, 348, 379-385, and 389.

Many modifications and variations of the embodiments described herein may be made without departing from the scope, as is apparent to those skilled in the art. The specific embodiments described herein are offered by way of example only.

What is claimed is:

1. A compound of formula (I):

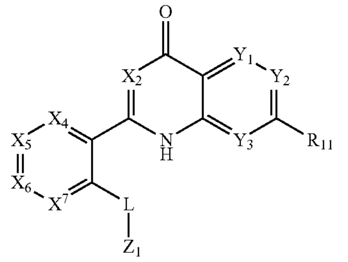

or a pharmaceutically acceptable salt thereof, wherein:

L is —O—, a single bond, —O—C(R)$_2$—, —C(R)$_2$—, —C(R)$_2$—O—, or —N(R)—;

each R is independently H, halo, or $C_1$-$C_6$ alkyl;

$X_2$, $Y_1$, $Y_2$, and $Y_3$ are defined as follows:

(i) $X_2$ is $CR_2$, $Y_1$ is $CR_{1a}$, $Y_2$ is $CR_{2a}$, and $Y_3$ is $CR_{3a}$; or (ii) $X_2$ is N, $Y_1$ is $CR_{1a}$, $Y_2$ is $CR_{2a}$, and $Y_3$ is $CR_{3a}$; or (iii) $X_2$ is $CR_2$, $Y_1$ is N, $Y_2$ is $CR_{2a}$, and $Y_3$ is $CR_{3a}$; or (iv) $X_2$ is $CR_2$, $Y_1$ is $CR_{1a}$, $Y_2$ is N, and $Y_3$ is $CR_{3a}$; or (v) $X_2$ is $CR_2$, $Y_1$ is $CR_{1a}$, $Y_2$ is $^+N$—$O^-$, and $Y_3$ is $CR_{3a}$; or (vi) $X_2$ is $CR_2$, $Y_1$ is $CR_{1a}$, $Y_2$ is $CR_{2a}$, and $Y_3$ is N;

$X_4$, $X_5$, $X_6$, and $X_7$ are defined as follows:

(i) $X_4$ is $CR_4$, $X_5$ is $CR_5$, $X_6$ is $CR_6$, and $X_7$ is $CR_7$; or (ii) $X_4$ is N, $X_5$ is $CR_5$, $X_6$ is $CR_6$, and $X_7$ is $CR_7$; or (iii) $X_4$ is $CR_4$, $X_5$ is N, $X_6$ is $CR_6$, and $X_7$ is $CR_7$; or (iv) $X_4$ is $CR_4$, $X_5$ is $CR_5$, $X_6$ is N, and $X_7$ is $CR_7$; or (v) $X_4$ is $CR_4$, $X_5$ is $CR_5$, $X_6$ is $CR_6$, and $X_7$ is N; or (vi) $X_4$ is $CR_4$, $X_5$ is N, $X_6$ is $CR_6$, and $X_7$ is N; or (vii) $X_4$ is $CR_4$, $X_5$ is N, $X_6$ is N, and $X_7$ is $CR_7$; or (viii) $X_4$ is $CR_4$, $X_5$ is $CR_5$, $X_6$ is N, and $X_7$ is N;

$R_2$ is H, halo, $C_1$-$C_6$ alkyl, ($C_1$-$C_6$ alkylene)-$NR_8R_9$, $C_2$-$C_6$ alkenyl, $C_1$-$C_6$ alkoxy, ($C_1$-$C_6$ alkylene)-OH, C(O)$OR_8$, or CH(OH)$(CH_2)_m$(CHOH)$_n$$(CH_2)_p$H;

$R_4$, $R_5$, $R_6$, and $R_7$ are defined as follows:

(i) $R_4$, $R_5$, $R_6$, and $R_7$ are each independently H, halo, $C_1$-$C_6$ alkyl, $C_1$-$C_6$ haloalkyl, or $C_3$-$C_6$ cycloalkyl optionally substituted with one or more alkyl, halo, or OH;

(ii) $R_4$ and $R_7$ are each independently H, halo, $C_1$-$C_6$ alkyl, $C_1$-$C_6$ haloalkyl, or $C_3$-$C_6$ cycloalkyl optionally substituted with one or more halo; and $R_5$ and $R_6$, together with the carbon atoms to which they are attached, form a ring of formula:

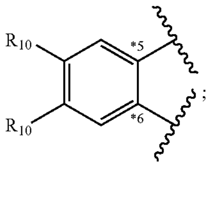

or (iii) $R_4$ and $R_7$ are each independently H, halo, $C_1$-$C_6$ alkyl, $C_1$-$C_6$ haloalkyl, $C_3$-$C_6$ cycloalkyl, or $C_3$-$C_6$ cycloalkyl substituted with one or more halo; and $R_5$ and $R_6$, together with the carbon atoms to which they are attached, form a ring of formula:

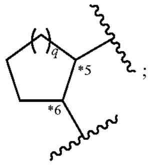

$R_8$ and $R_9$ are each independently H or $C_1$-$C_6$ alkyl;

each $R_{10}$ is independently H or halo;

$R_{1a}$ is H, halo, CN, $C_1$-$C_6$ alkyl, OH, C(O)$NR_{12}R_{13}$, $C_1$-$C_6$ alkoxy, $NR_{12}R_{13}$, $NR_8$C(O)$NR_8R_9$, ($C_1$-$C_6$ alkylene)-C(O)$NR_8R_9$, ($C_1$-$C_6$ alkylene)-OH, C(O)$OR_{12}$, $OR_{12}$, CH(OH)$(CH_2)_m$(CHOH)$_n$$(CH_2)_p$H, N═S(═O)$(CH_3)_2$, N═S(═O)R'R", 5-10 membered heteroaryl, or 4-10 membered heterocyclyl, wherein the heterocyclyl or heteroaryl in said 5-10 membered heteroaryl or 4-10 membered heterocyclyl is optionally substituted with 1-4 substituents selected from OH, halo, oxo, C(O)$NR_8R_9$, $NR_8R_9$, $C_1$-$C_6$ alkyl, $C_1$-$C_6$ alkoxy, ($C_1$-$C_6$ alkylene)-OH, ($C_1$-$C_6$ alkylene)-O—($C_1C_6$ alkyl), and ($C_1$-$C_6$ alkylene)-$NR_8R_9$;

R' and R", together with the S atom to which they are attached, form a 4-7 membered heterocyclyl;

$R_{11}$, $R_{2a}$, and $R_{3a}$ are each independently H, halo, CN, $C_1$-$C_6$ alkyl, C(O)$NR_8R_9$, or $C_1$-$C_6$ alkoxy;

$R_{12}$ and $R_{13}$ are each independently H, C(O)($C_1$-$C_6$ alkyl), ($C_1$-$C_6$ alkylene)-$NR_8R_9$, $CH_2$CH(OH)$(CH_2)_m$(CHOH)$_n$$(CH_2)_p$H, $C_1$-$C_6$ alkyl optionally substituted with one or more OH, indanyl, ($C_1$-$C_6$ alkylene)-($C_3$-$C_6$ cycloalkyl), ($C_1$-$C_6$ alkylene)-phenyl, ($C_1$-$C_6$ alkylene)-(5-membered heterocyclyl), $C_4$-$C_7$ cycloalkyl, $C_6$-$C_{10}$ aryl, 5-6 membered heteroaryl, or 4-7 membered heterocyclyl, wherein the indanyl, ($C_1$-$C_6$ alkylene)-($C_3$-$C_6$ cycloalkyl), ($C_1$-$C_6$ alkylene)-phenyl, ($C_1$-$C_6$ alkylene)-(5 membered heterocyclyl), $C_4$-$C_7$ cycloalkyl, $C_6$-$C_{10}$ aryl, 5-6 membered heteroaryl, or 4-7 membered heterocyclyl is optionally substituted with 1-4 substituents selected from OH, oxo, $C_1$-$C_6$ alkyl, ($C_1$-$C_6$ alkylene)-OH, and $C_1$-$C_6$ alkoxy;

$Z_1$ is, 3-7 membered cycloalkenyl, phenyl, 4-10 membered heterocyclyl, or 5-6 membered heteroaryl, wherein said 3-7 membered cycloalkenyl, phenyl, 4-10 membered heterocyclyl, or 5-6 membered heteroaryl may be unsubstituted or may be substituted with 1-4 substituents selected from halo, OH, $CD_3$, $C_1$-$C_6$ alkyl, $C_1$-$C_6$ alkoxy, $C_1$-$C_6$ haloalkyl, $CH_2OH$, C(O)H, and $C_1$-$C_6$ haloalkoxy;

m, n, and p are each independently 0 or 1; and q is 1, 2, or 3, wherein when $X_2$ is N, then:

(i) L is O, and $Z_1$ is phenyl, wherein said phenyl is substituted with 2-4 substituents selected from halo, OH, $C_1$-$C_6$ alkyl, $C_1$-$C_6$ alkoxy, $C_1$-$C_6$ haloalkyl, and $C_1$-$C_6$ haloalkoxy; or (ii) L is a single bond, and $Z_1$ is 4-10 membered heterocyclyl, wherein said 4-10 membered heterocyclyl is substituted with 2-4 substituents selected from halo, OH, $C_1$-$C_6$ alkyl, $C_1$-$C_6$ alkoxy, $C_1$-$C_6$ haloalkyl, and $C_1$-$C_6$ haloalkoxy; and wherein when $X_2$, $X_4$, $X_5$, $X_6$ and $X_7$ are each CH, L is a single bond, and $Z_1$ is phenyl, then said phenyl is substituted with 1-4 substituents selected from halo, OH, $C_1$-$C_6$ alkyl, $C_1$-$C_6$ alkoxy, $C_1$-$C_6$ haloalkyl, and $C_1$-$C_6$ haloalkoxy.

2. The compound of claim 1, or a pharmaceutically acceptable salt thereof, wherein:

$R_{1a}$ is H, halo, CN, $C_1$-$C_6$ alkyl, OH, $C(O)NR_{12}R_{13}$, $C_1$-$C_6$ alkoxy, $NR_{12}R_{13}$, ($C_1$-$C_6$ alkylene)-$C(O)NR_8R_9$, ($C_1$-$C_6$ alkylene)-OH, $C(O)OR_{12}$, $CH(OH)(CH_2)_m(CHOH)_n(CH_2)_pH$, or $N{=}S({=}O)(CH_3)$ 2; and $R_{12}$ and $R_{13}$ are each independently H, $C(O)(C_1$-$C_6$ alkyl), ($C_1$-$C_6$ alkylene)-$NR_8R_9$, $CH_2CH(OH)(CH_2)_m(CHOH)_n(CH_2)_pH$, or $C_1$-$C_6$ alkyl optionally substituted with one or more OH.

3. The compound of claim 1, or a pharmaceutically acceptable salt thereof, wherein $R_4$, $R_5$, $R_6$, and $R_7$ are each independently H, halo, $C_1$-$C_6$ alkyl, $C_1$-$C_6$ haloalkyl, or $C_3$-$C_6$ cycloalkyl optionally substituted with one or more alkyl, halo, or OH.

4. The compound of claim 1, wherein the compound is selected from:

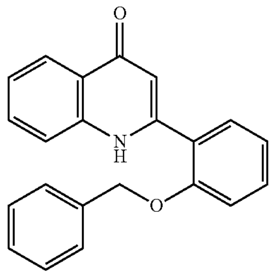
, 2-(2-benzyloxyphenyl)-1H-quinolin-4-one

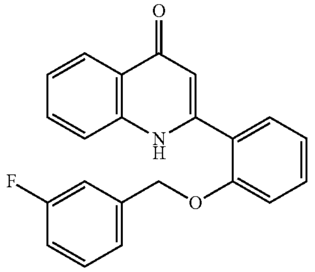
,

2-[2-[(3-fluorophenyl)methoxy]phenyl]-1H-quinolin-4-one

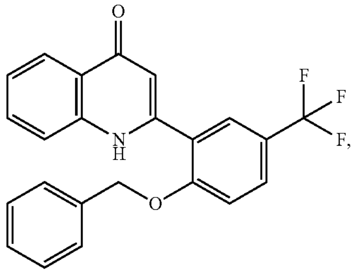
,

2-[2-benzyloxy-5-(trifluoromethyl)phenyl]-1H-quinolin-4-one

-continued

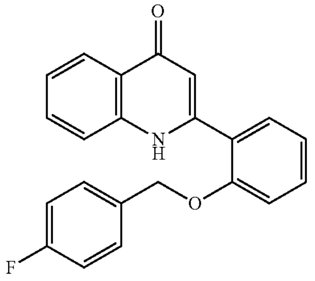
,

2-[2-[(4-fluorophenyl)methoxy]phenyl]-1H-quinolin-4-one

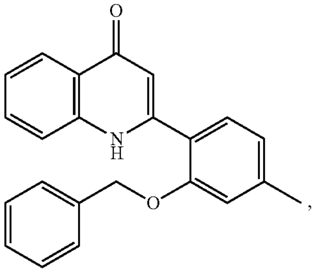
, 2-(2-benzyloxy-4-methyl-phenyl)-1H-quinolin-4-one

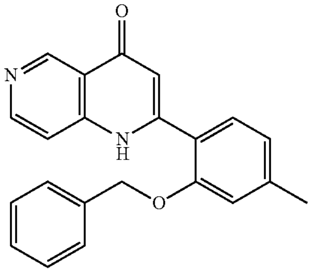
, 2-(2-benzyloxy-4-methyl-phenyl)-1H-1,6-naphthyridin-4-one

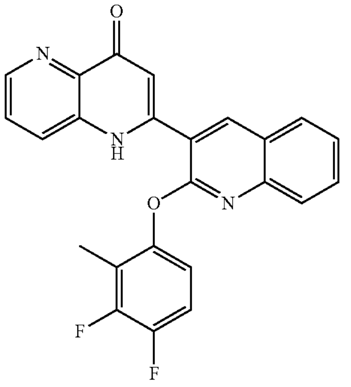
,

2-[2-(3,4-difluoro-2-methyl-phenoxxy)-3-quinolyl]-1H-1,5-naphthyridin-4-one

-continued
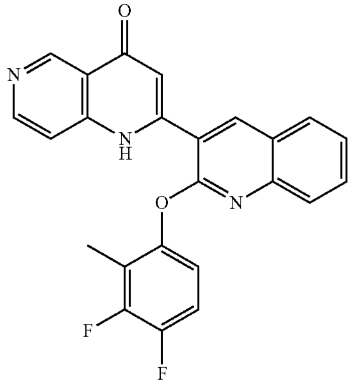
,
2-[2-(3-,4-difluoro-2-methyl-phenoxy)-3-quinolyl]-1H-1,6-naphthyridin-4-one
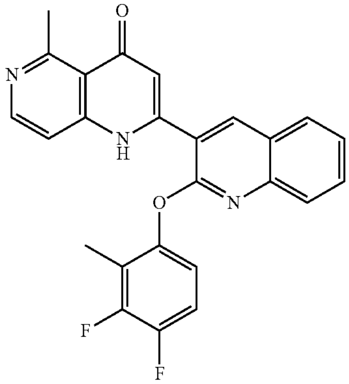
,
2-[2-(3,4-difluoro-2-methyl-phenoxy)-3-quinolyl]-5-methyl-1H-1,6-naphthyridin-4-one
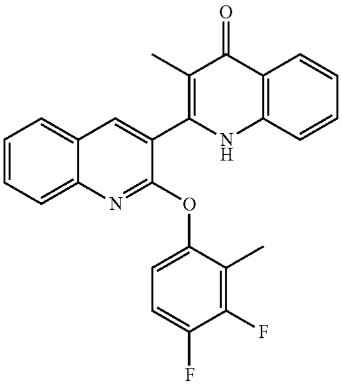
,
2-[2-(3,4-difluoro-2-methyl-phenoxy)-3-quinolyl]-3-methyl-1H-quinolin-4-one
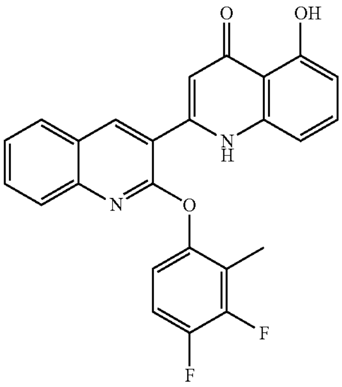
,
2-[2-(3,4-diflouro-2-methyl-phenoxy)-3-quinolyl]-5-hydroxy-1H-quinolin-4-one
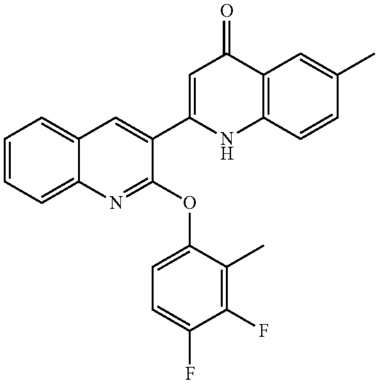
,
2-[2-(3,4-difluoro-2-methyl-phenoxy)-3-quinolyl]-6-methyl-1H-quinolin-4-one
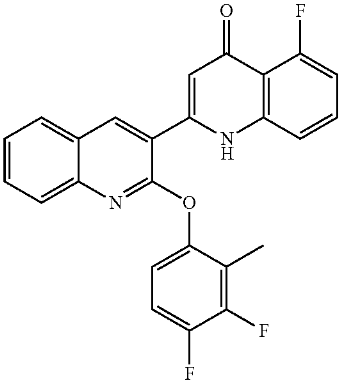
,
2-[2-(3,4-diflouro-2-methyl-phenoxy)-3-quinolyl]-5-fluoro-1H-quinolin-4-one -continued

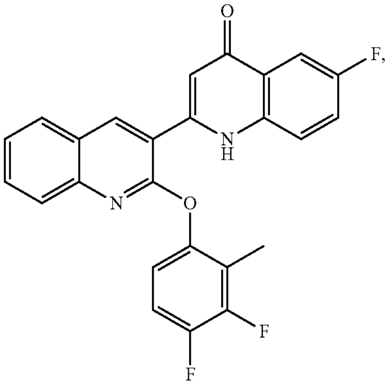

2-[2-(3,4-difluoro-2-methyl-phenoxy)-3-quinolyl]-6-fluoro-1H-quinolin-4-one

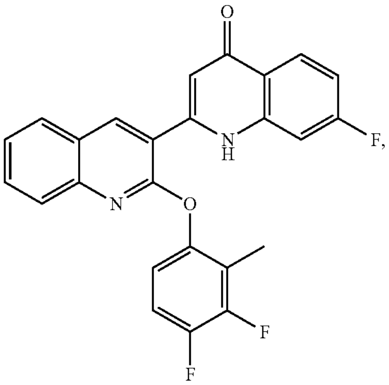

2-[2-(3,4-difluoro-2-methyl-phenoxy)-3-quinolyl]-7-fluoro-1H-quinolin-4-one

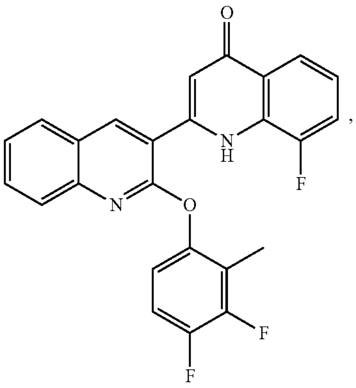

2-[2-(3,4-difluoro-2-methyl-phenoxy)-3-quinolyl]-8-fluoro-1H-quinolin-4-one

-continued

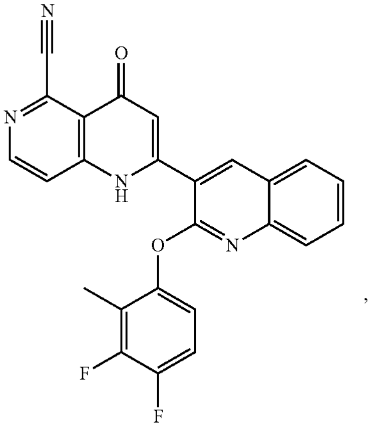

2-[2-(3,4-difluoro-2-methyl-phenoxy)-3-quinolyl]-4-oxo-1H-1,6-naphthyridine-5-carbonitrile

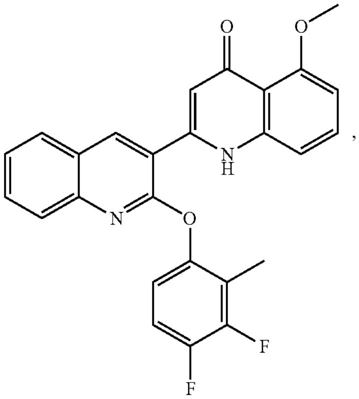

2-[2-(3,4-difluoro-2-methyl-phenoxy)-3-quinolyl]-5-methoxy-1H-quinolyl-4-one

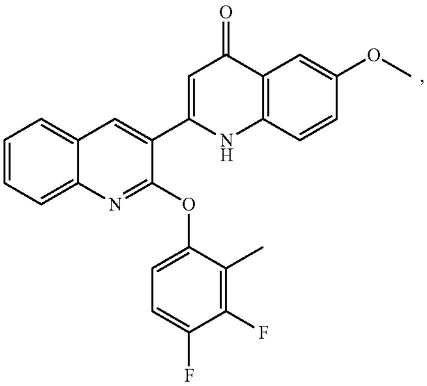

2-[2-(3,4-difluoro-2-methyl-phenoxy)-3-quinolyl]-6-methoxy-1H-quinolin-4-one

-continued

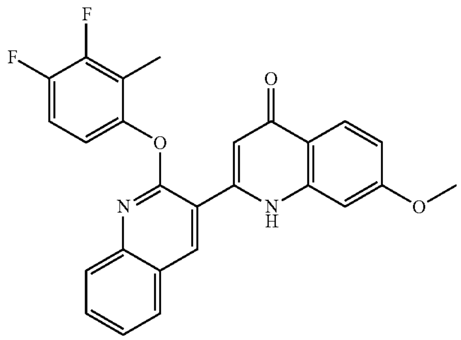

,

2-[2-(3,4-difluoro-2-methyl-phenoxy)-3-quinolyl]-7-methoxy-1H-quinolin-4-one

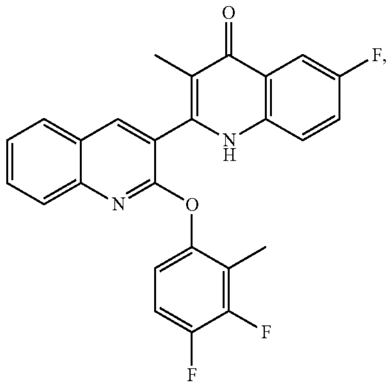

2-[2-(3,4-difluoro-2-methyl-phenoxy)-3-quinolyl]-6-fluoro-3-methyl-1H-quinolin-4-one

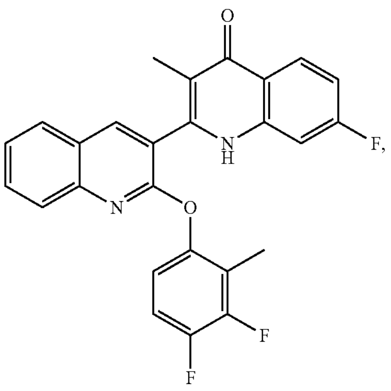

2-[2-(3,4-difluoro-2-methyl-phenoxy)-3-quinolyl]-7-fluoro-3-methyl-1H-quinolin-4-one -continued

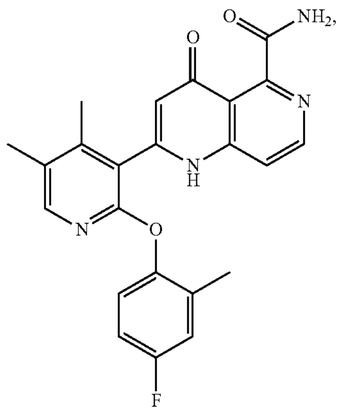

2-[2-(4-fluoro-2-methyl-phenoxy)-4,5-dimethyl-3-pyridyl]-4-oxo-1H-1,6-naphthyridine-5-carboxamide

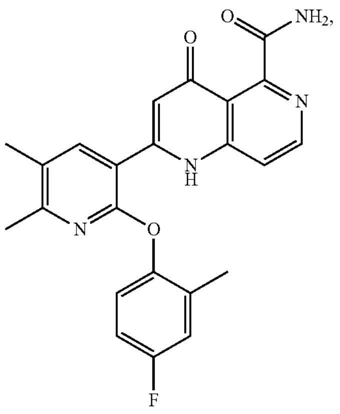

2-[2-(4-fluoro-methyl-phenoxxy)-5,6-dimethyl-3-pyridyl]-4-oxo-1H-1,6-naphthyridine-5-carboxamide

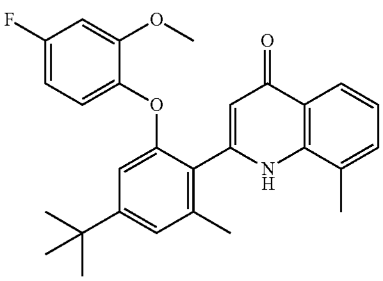

,

2-[4-tert-butyl-2-(4-fluoro-2-methoxy-phenoxy)-6-methyl-phenyl]-8-methyl-1H-quinolin-4-one -continued

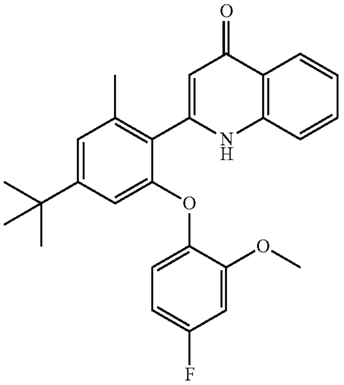

,

2-[4-tert-butyl-2-(4-fluoro-2-methoxy-phenoxy)-6-methyl-phenyl]-1H-quinolin-4-one

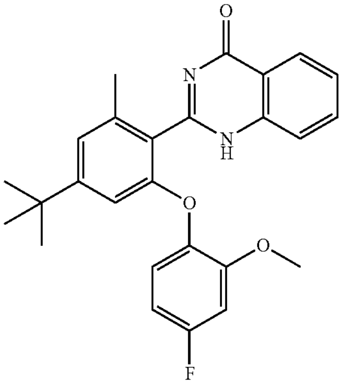

,

2-[4-tert-butyl-2-(4-fluoro-2-methoxy-phenoxy)-6-methyl-phenyl]-1H-quinazolin-4-one

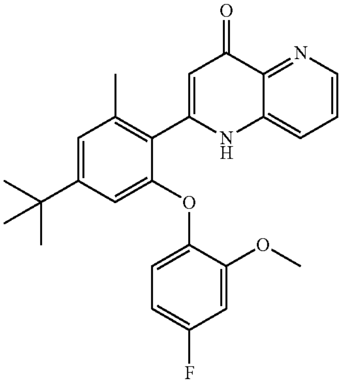

,

2-[4-tert-butyl-2-(4-fluoro-2-methoxy-phenoxy)-6-methyl-phenyl]-1H-1,5-naphthyridin-4-one -continued

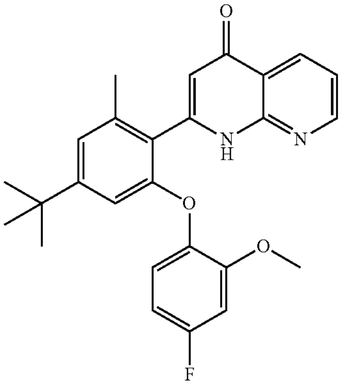

,

2-[4-tert-butyl-2-(4-fluoro-2-methoxy-phenoxy)-6-methyl-phenyl]-1H-1,8-naphthyridin-4-one

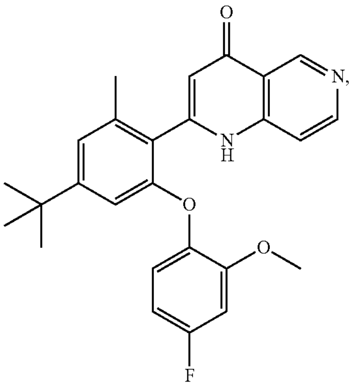

2-[4-tert-butyl-2-(4-fluoro-2-methoxy-phenoxy)-6-methyl-phenyl]-1H-1,6-naphthyridin-4-one

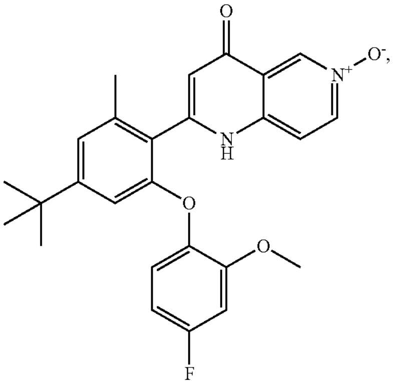

2-[4-tert-butyl-2-(4-fluoro-2-methoxy-phenoxy)-6-methyl-phenyl]-6-oxido-1H-1,6-naphthyridin-6-ium-4-one -continued

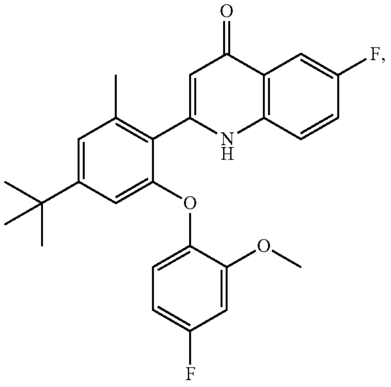

2-[4-tert-butyl-2-(4-fluoro-2-methoxy-phenoxy)-6-methyl-phenyl]-6-fluoro-1H-quinolin-4-one

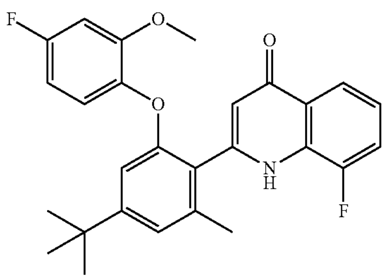

,

2-[4-tert-butyl-2-(4-fluoro-2-methoxy-phenoxy)-6-methyl-phenyl]-8-fluoro-1H-quinolin-4-one

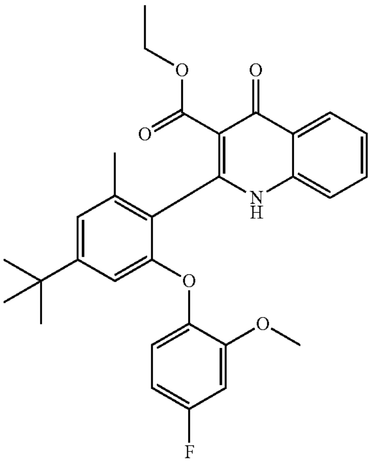

, ethyl 2-[4-tert-butyl-2-(4-fluoro-2-methoxy-phenoxy)-6-methyl-phenyl]-4-oxo-1H-quinoline-3-carboxylate -continued

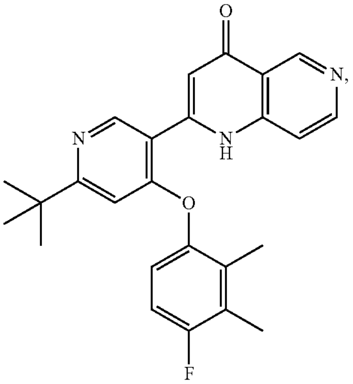

2-[4-(3,4-difluoro-2-methyl-phenoxy)-6-(trifluoromethyl)-3-pyridyl]-1H-1,6-naphthyridin-4-one

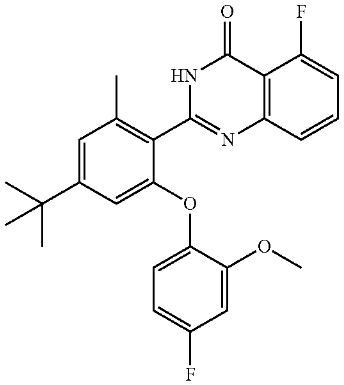

,

2-[4-tert-butyl-2-(4-fluoro-2-methoxy-phenoxy)-6-methyl-phenyl]-5-fluoro-3H-quinazolin-4-one

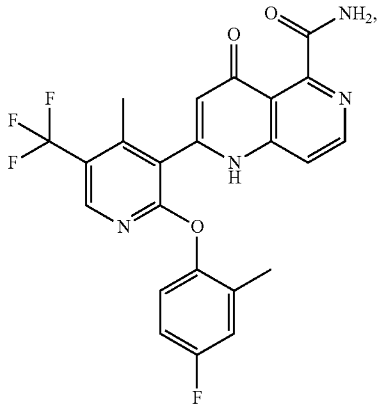

2-[2-(4-fluoro-2-methyl-phenoxy)-4-methyl-5-(trifluoromethyl)-3-pyridyl]-4-oxo-1H-1,6-naphthyridine-5-carboxamide -continued

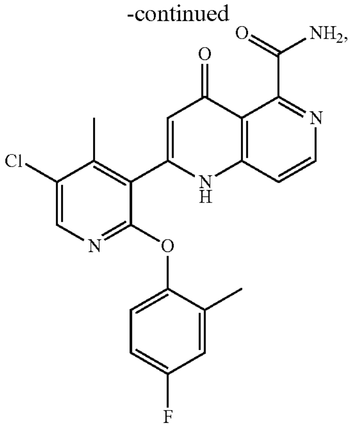

2-[5-chloro-2-(4-fluoro-2-methyl-phenoxy)-4-methyl-3-pyridyl]-4-oxo-1H-1,6-naphthyridine-5-carboxamide

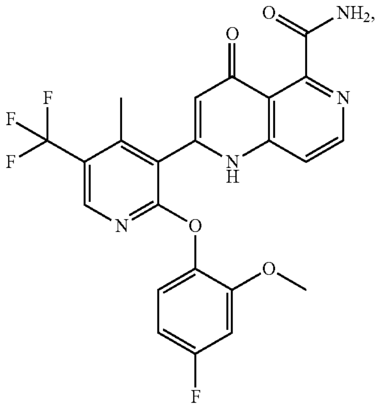

2-[2-(4-fluoro-2-methoxy-phenoxy)-4-methyl-5-(trifluoromethyl)-3-pyridyl]-4-oxo-1H-1,6-naphthyridine-5-carboxamide

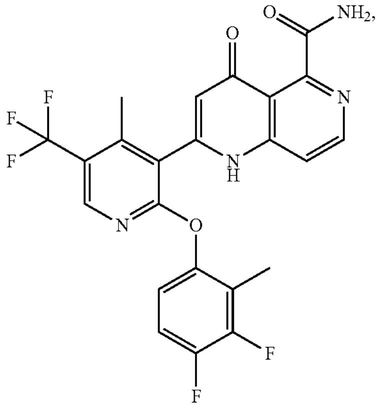

2-[2-(3,4-difluoro-2-methyl-phenoxy)-4-methyl-5-(trifluoromethyl)-3-pyridyl)-4-oxo-1H-1,6-naphthyridine-5-carboxamide

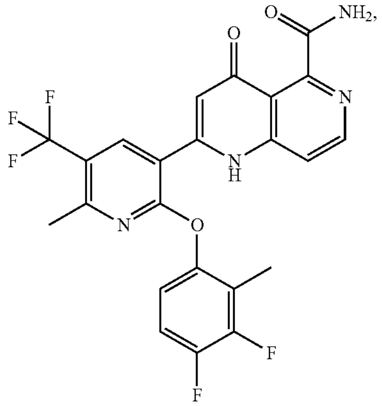

2-[2-(3,4-difluoro-2-methyl-phenoxy)-6-methyl-5-(trifluoromethyl)-3 -pyridyl]-4-oxo-1H-1,6-naphthyridine-5-carboxamide

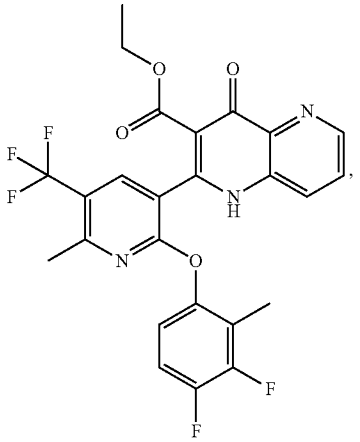

ethyl 2-[2-(3,4-difluoro-2-methyl-phenoxy)-6-methyl-5-(trifluoromethyl)-3-pyridyl]-4-oxo-1H-1,5-naphthyridine-3-carboxylate

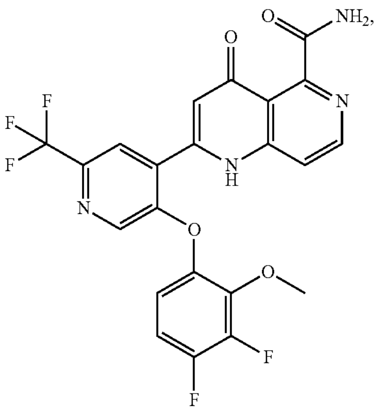

2-[5-(3,4-difluoro-2-methoxy-phenoxy)-2-(trifluoromethyl)-4-pyridyl]-4-oxo-1H-1,6-naphthyridine-5-carboxamide -continued

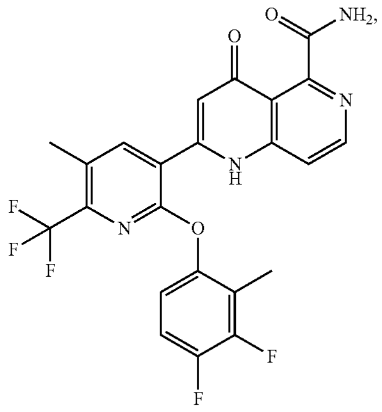

2-[2-(3,4-difluoro-2-methyl-phenoxy)-5-methyl-6-(trifluoromethyl)-3-pyridyl]-4-oxo-1H-1,6-naphthyridine-5-carboxamide

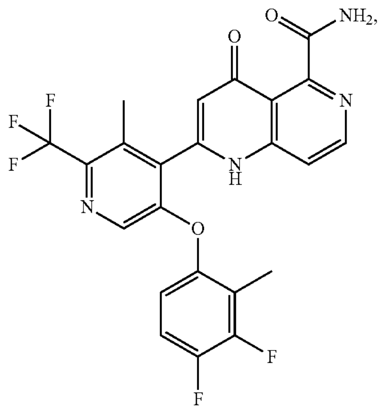 [SMILES: Cc1c(Oc2cnc(C(F)(F)F)c(C)c2-c2cc(=O)c3c(C(N)=O)nccc3[nH]2)ccc(F)c1F]

2-[5-(3,4-difluoro-2-methyl-phenoxy)-3-methyl-2-(trifluoromethyl)-4-pyridyl]-4-oxo-1H-1,6-naphthyridine-5-carboxamide

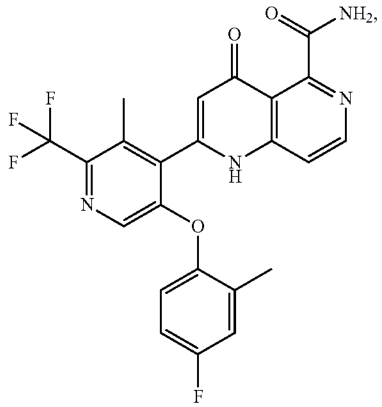

2-[5-(4-fluoro-2-methyl-phenoxy)-3-methyl-2-(trifluoromethyl)-4-pyridyl]-4-oxo-1H-1,6-naphthyridine-5-carboxamide -continued

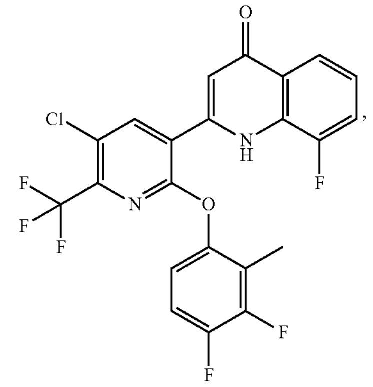

2-[5-chloro-2-(3,4-difluoro-2-methyl-phenoxy)-6-(trifluoromethyl)-3-pyridyl]-8-fluoro-1H-quinolin-4-one

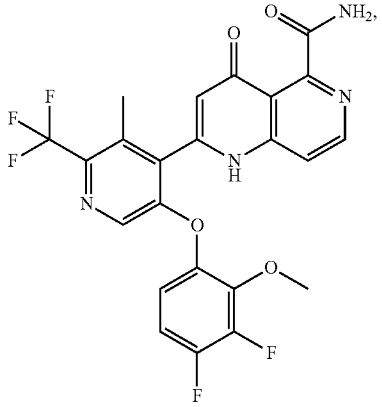

2-[5-(3,4-difluoro-2-methoxy-phenoxy)-3-methyl-2-(trifluoromethyl)-4-pyridyl]-4-oxo-1H-1,6-naphthyridine-5-carboxamide

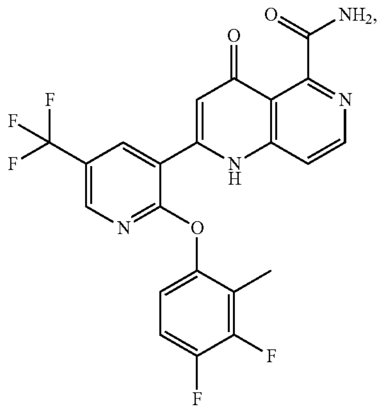

2-[2-(3,4-difluoro-2-methyl-phenoxy)-5-(trifluoromethyl)-3-pyridyl]-4-oxo-1H-1,6-naphthyridine-5-carboxamide -continued

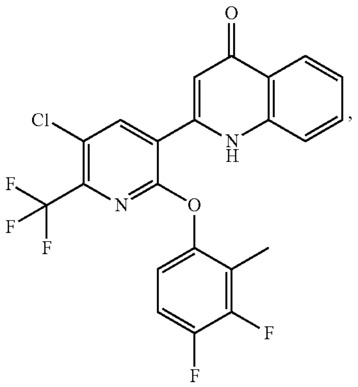

2-[5-chloro-2-(3,4-difluoro-2-methyl-phenoxy)-6-(trifluoromethyl)-3-pyridyl]-1H-quinolin-4-one

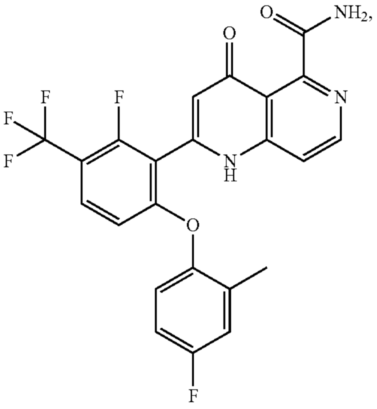

2-[2-fluoro-6-(4-fluoro-2-methyl-phenoxy)-3-(trifluoromethyl)phenyl]-4-oxo-1H-1,6-naphthyridine-5-carboxamide,

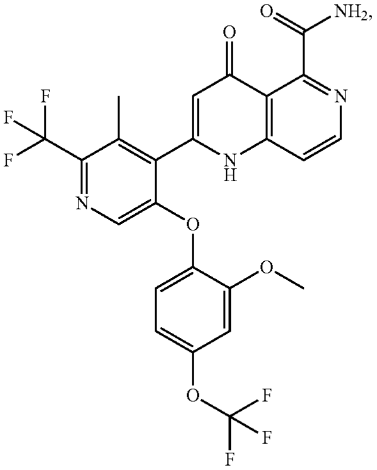

2-[5-[2-methoxy-4-(trifluoromethoxy)phenoxy]-3-methyl-2-(trifluoromethyl)-4-pyridyl]-4-oxo-1H-1,6-naphthyridine-5-carboxamide -continued

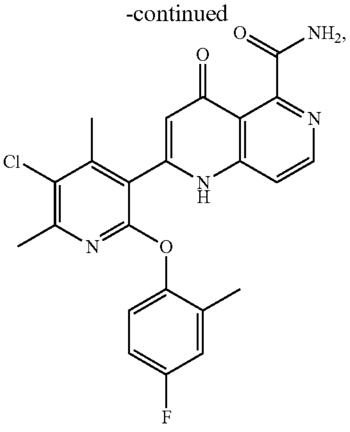

2-[5-chloro-2-(4-fluoro-2-methyl-phenoxy)-4,6-dimethyl-3-pyridyl]-4-oxo-1H-1,6-naphthyridine-5-carboxamide

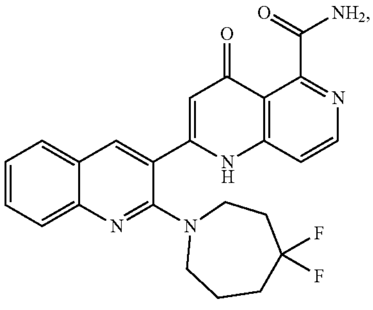

2-[2-(4,4-difluoroazepan-1-yl)-3-quinolyl]-4-oxo-1H-1,6-naphthyridine-5-carboxamide

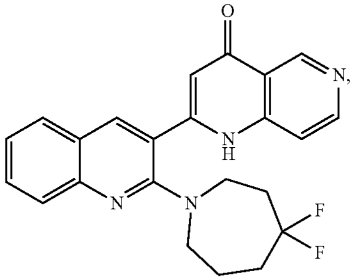

2-[2-(4,4-difluoroazepan-1-yl)-3-quinolyl]-1H-1,6-naphthyridin-4-one

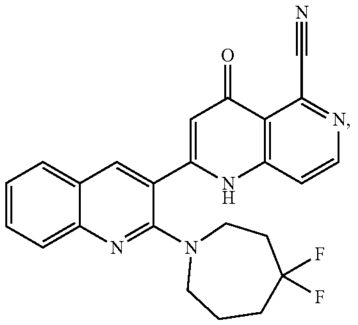

2-[2-(4,4-difluoroazepan-1-yl)-3-quinolyl]-4-oxo-1H-1,6-naphthyridine-5-carbonitrile -continued

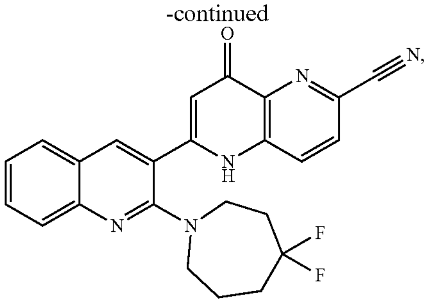

6-[2-(4,4-difluoroazepan-1-yl)-3-quinolyl]-8-oxo-5H-1,5-naphthyridine-2-carbonitrile

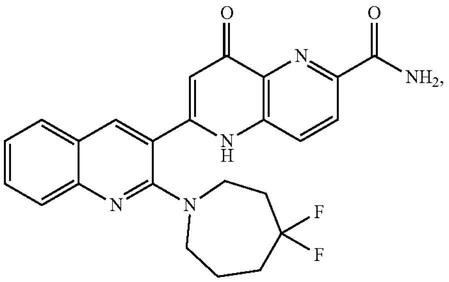

6-[2-(4,4-difluoroazepan-1-yl)-3-quinolyl]-8-oxo-5H-1,5-naphthyridine-2-carboxamide

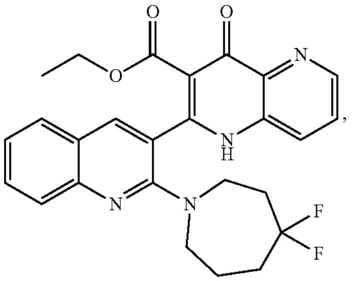

ethyl 2-[2-(4,4-difluoroazepan-1-yl)-3-quinolyl]-4-oxo-1H-1,5-naphthyridine-3-carboxylate

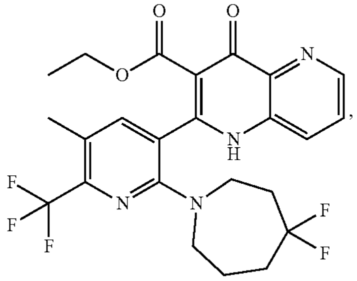

ethyl 2-[2-(4,4-difluoroazepan-1-yl)-5-methyl-6-(trifluoromethyl)-3-pyridyl]-4-oxo-1H-1,5-naphthyridine-3-carboxylate

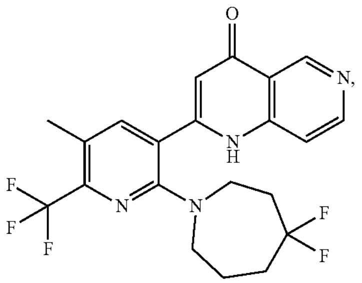

2-[2-(4,4-difluoroazepan-1-yl)-5-methyl-6-(trifluoromethyl)-3-pyridyl]-1H-1,6-naphthyridin-4-one -continued

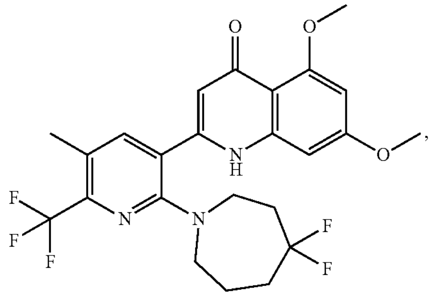

2-[2-(4,4-difluoroazepan-1-yl)-5-methyl-6-(trifluoromethyl)-3-pyridyl]-5,7-dimethoxy-1H-quinolin-4-one

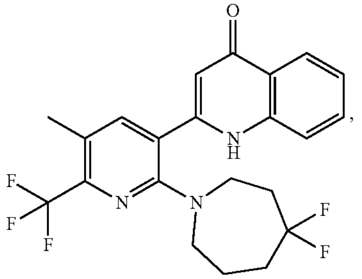

2-[2-(4,4-difluoroazepan-1-yl)-5-methyl-6-(trifluoromethyl)-3-pyridyl]-1H-quinolin-4-one

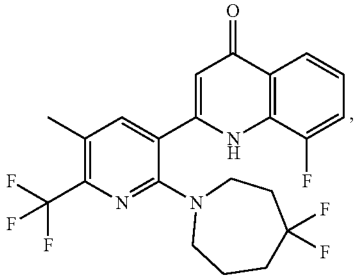

2-[2-(4,4-difluoroazepan-1-yl)-5-methyl-6-(trifluoromethyl)-3-pyridyl]-8-fluoro-1H-quinolin-4-one

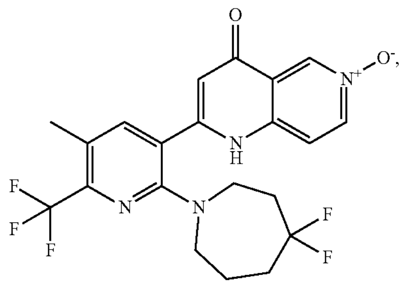

2-[2-(4,4-difluoroazepan-1-yl)-5-methyl-6-(trifluoromethyl)-3-pyridyl]-6-oxido-1H-1,6-naphthyridin-6-ium-4-one -continued

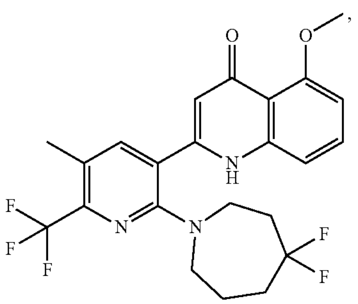

2-[2-(4,4-difluoroazepan-1-yl)-5-methyl-6-(trifluoromethyl)-3-pyridyl]-5-methoxy-1H-quinolin-4-one

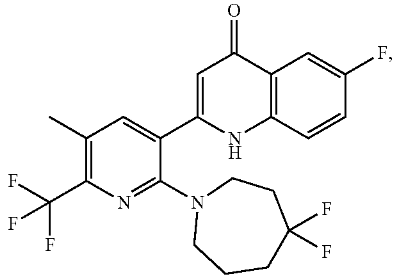

2-[2-(4,4-difluoroazepan-1-yl)-5-methyl-6-(trifluoromethyl)-3-pyridyl]-6-fluoro-1H-quinolin-4-one

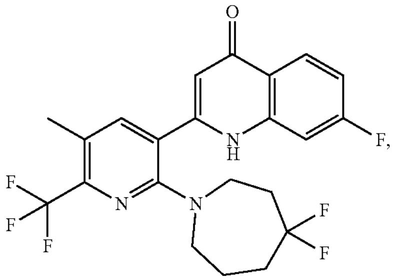

2-[2-(4,4-difluoroazepan-1-yl)-5-methyl-6-(trifluoromethyl)-3-pyridyl]-7-fluoro-1H-quinolin-4-one

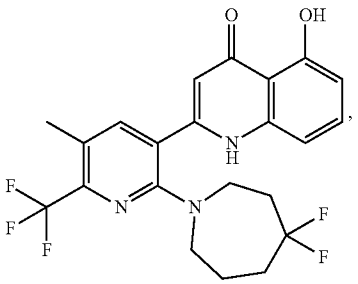

2-[2-(4,4-difluoroazepan-1-yl)-5-methyl-6-(trifluoromethyl)-3-pyridyl]-5-hydroxy-1H-quinolin-4-one -continued

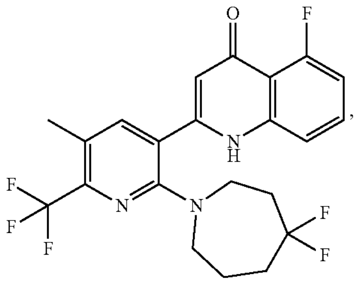

2-[2-(4,4-difluoroazepan-1-yl)-5-methyl-6-(trifluoromethyl)-3-pyridyl]-5-fluoro-1H-quinolin-4-one

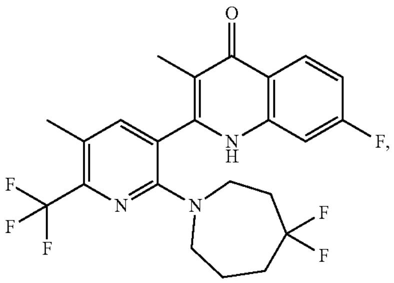

2-[2-(4,4-difluoroazepan-1-yl)-5-methyl-6-(trifluoromethyl)-3-pyridyl]-7-fluoro-3-methyl-1H-quinolin-4-one

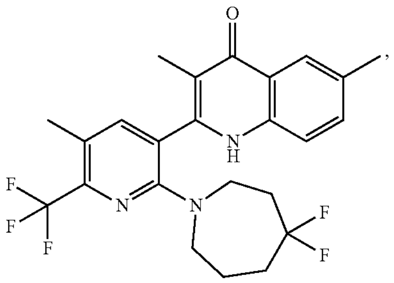

2-[2-(4,4-difluoroazepan-1-yl)-5-methyl-6-(trifluoromethyl)-3-pyridyl]-6-methyl-1H-quinolin-4-one

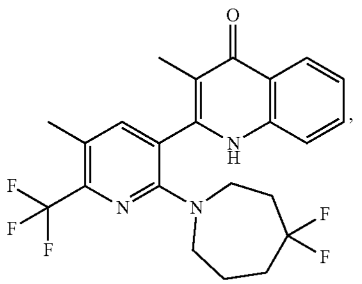

2-[2-(4,4-difluoroazepan-1-yl)-5-methyl-6-(trifluoromethyl)-3-pyridyl]-3-methyl-1H-quinolin-4-one -continued

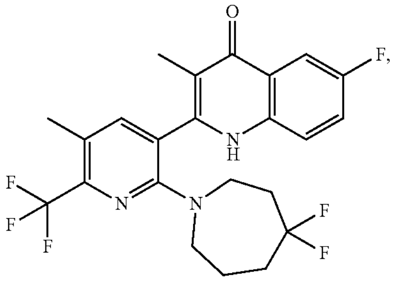

2-[2-(4,4-difluoroazepan-1-yl)-5-methyl-6-(trifluoromethyl)-3-pyridyl]-6-fluoro-3-methyl-1H-quinolin-4-one

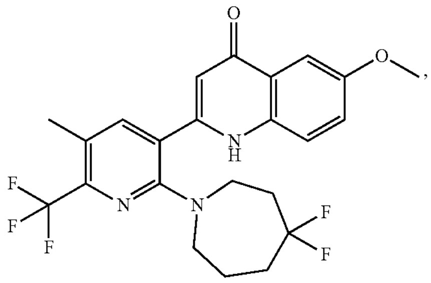

2-[2-(4,4-difluoroazepan-1-yl)-5-methyl-6-(trifluoromethyl)-3-pyridyl]-6-methoxy-1H-quinolin-4-one

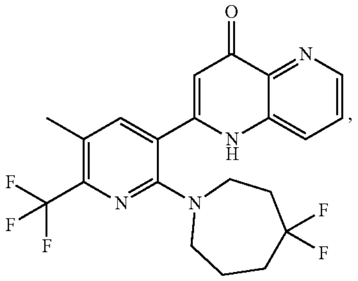

2-[2-(4,4-difluoroazepan-1-yl)-5-methyl-6-(trifluoromethyl)-3-pyridyl]-1H-1,5-naphthyridin-4-one

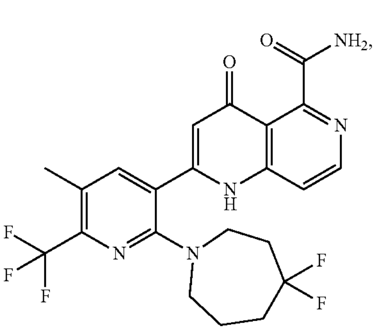

2-[2-(4,4-difluoroazepan-1-yl)-5-methyl-6-(trifluoromethyl)-3-pyridyl]-4-oxo-1H-1,6-naphthyridine-5-carboxamide -continued

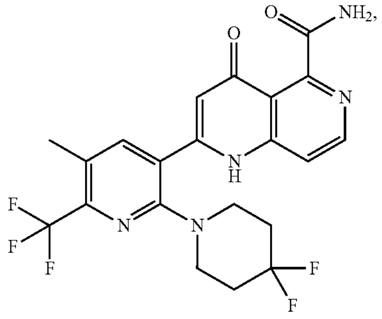

2-[2-(4,4-difluoroazepan-1-yl)-5-methyl-6-(trifluoromethyl)-3-pyridyl]-4-oxo-1H-1,6-naphthyridine-5-carboxamide

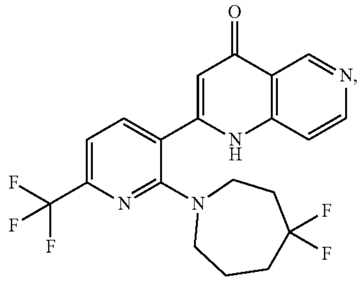

2-[2-(4,4-difluoroazepan-1-yl)-6-(trifluoromethyl)-3-pyridyl]-1H-1,6-naphthyridin-4-one

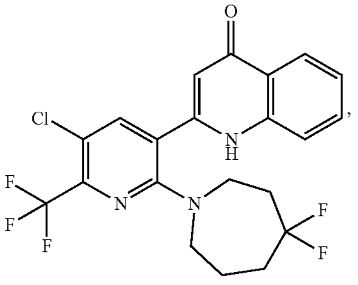

2-[5-chloro-2-(4,4-difluoroazepan-1-yl)-6-(trifluoromethyl)-3-pyridyl]-1H-quinolin-4-one

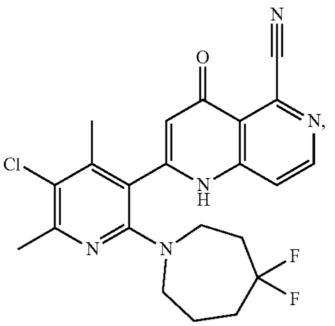

2-[5-chloro-2-(4,4-difluoroazepan-1-yl)-4,6-dimethyl-3-pyridyl]-4-oxo-1H-1,6-naphthyridine-5-carbonitrile -continued

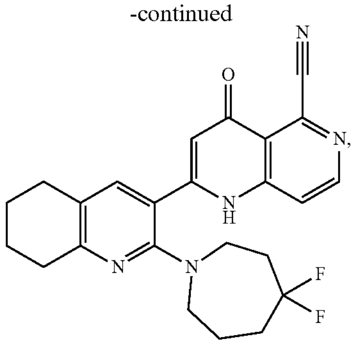

2-[2-(4,4-difluoroazepan-1-yl)-5,6,7,8-tetrahydroquinolin-3-yl]-4-oxo-1H-1,6-naphthyridine-5-carbonitrile,

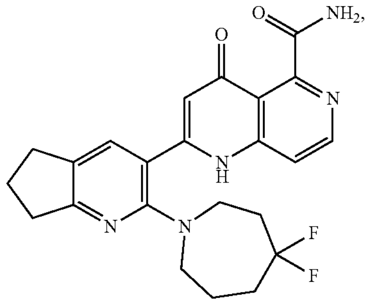

2-[2-(4,4-difluoroazepan-1-yl)-6,7-dihydro-5H- cyclopenta[b]pyridin-3-yl]-4-oxo-1H-1,6-naphthyridine-5-carboxamide,

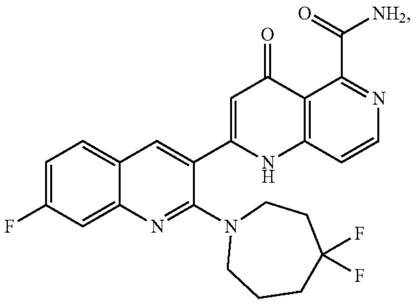

2-[2-(4,4-difluoroazepan-1-yl)-7-fluoro-3-quinolyl]-4-oxo-1H-1,6-naphthyridine-5-carboxamide

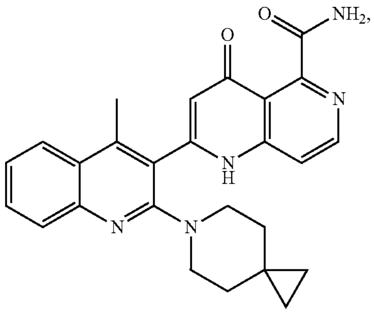

2-[2-(6-azaspiro[2.5]octan-6-yl)-4-methyl-3-quinolyl]-4-oxo-1H-1,6-naphthyridine-5-carboxamide -continued

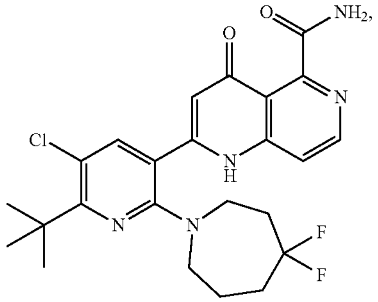

2-[6-tert-butyl-5-chloro-2-(4,4-difluoroazepan-1-yl)-3 -pyridyl]-4-oxo-1H-1,6-naphthyridine-5-carboxamide

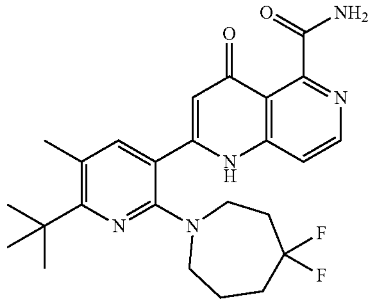

2-[6-*tert*-butyl-2-(4, 4-difluoroazepan-1-yl)-5-methyl-3-pyridy1]-4-oxo-1H -1, 6-naphthyridine-5-carboxamide,

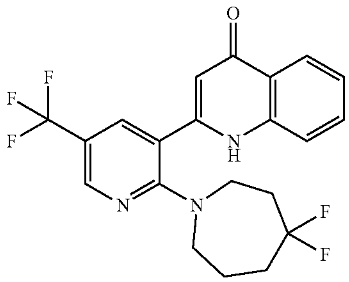

2- [2-(4, 4-difluoroazepan-1-y1)-5-(trifluoromethyl)-3-pyridy1]-1H-quinolin-4-one,

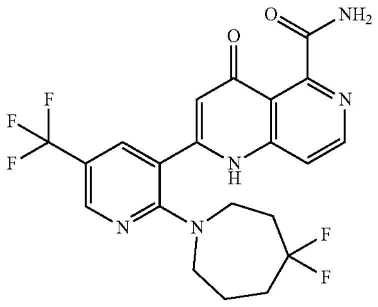

2-[2-(4, 4-difluuoroazepan-1-y1)-5-(trifluoromethyl)-3-pyridy1]-4-oxo-1*H*-1, 6-naphthyridine-5-carboxamide, -continued

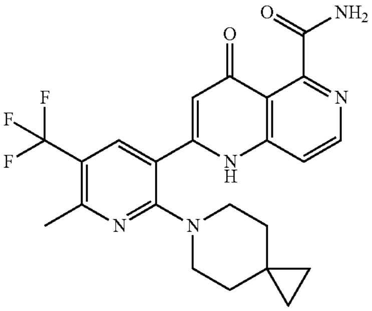

2-[2-(6-azaspiro[2.5]octan-6-y1)-6-methyl-5-(trifluoromethyl)-3-pyridy1]-4-oxo-1*H*-1, 6-naphthyridine-S-carboxamide,

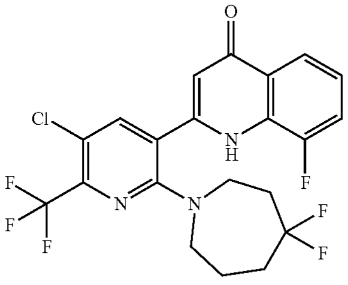

2-[5-chloro-2-(4, 4-difluoroazepan-1-yl)-6-(trifluoromethyl)-3-pyridyl]-8-fluoro-1*H*-quinolin-4-one,

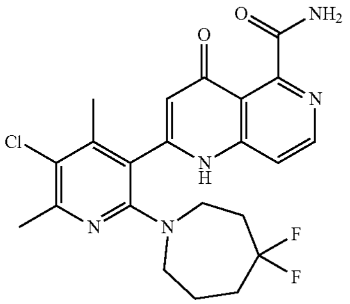

2-[5-chloro-2-(4, 4-difluoroazepan-1-y1)-4, 6-dimethyl-3-pyridyl]-4-oxo-1*H*-1, 6-naphthyridine-S-carboxamide,

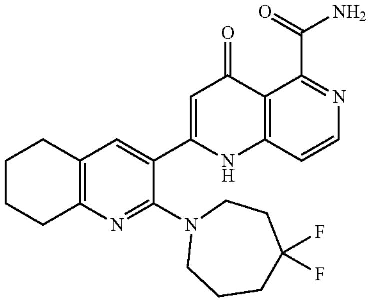

2-[2-(4, 4-difluuoroazep2m-1-y1)-5, 6, 7, 8-tetrahydroquinolin-3-y1]-4-oxo-1*H*-1, 6-naphthyridine-S-carboxamide, -continued

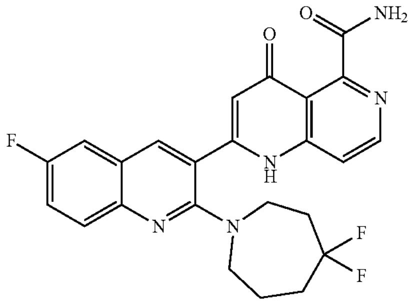

2-[2-(4, 4-difluoroazepan-1-yl)-6-fluoro-3-quinolyl]-4-oxo-1*H*-1, 6-naphthyridine-5-carboxamide,

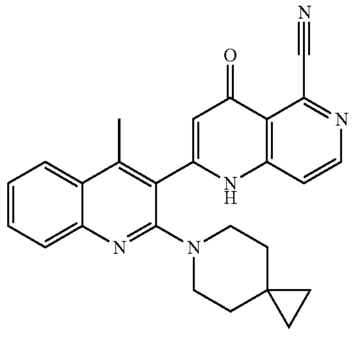

2-[2-(6-azaspiro[2.5]octan-6-y1)-4-methyl-3-quinolyl]-4-oxo-1*H*-1, 6-naphthyridine-5-carbonitrile,

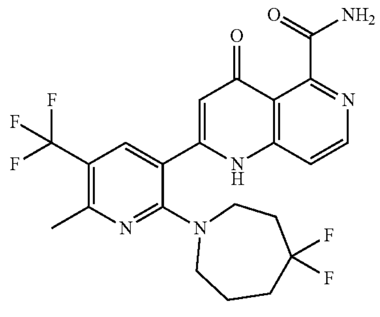

2-[2-(4, 4-difluoroazepan-1-yl)-6-methy1-5-(trifluoromethyl)-3-pyridy1]-4-oxo-1*H*-1, 6-naphthyridine-5-carboxamide,

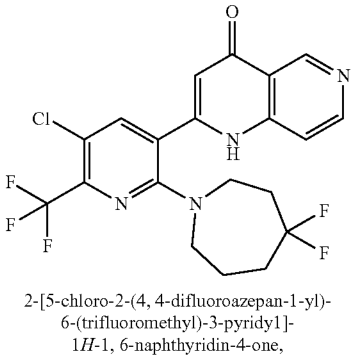

2-[5-chloro-2-(4, 4-difluoroazepan-1-yl)-6-(trifluoromethyl)-3-pyridy1]-1*H*-1, 6-naphthyridin-4-one, -continued

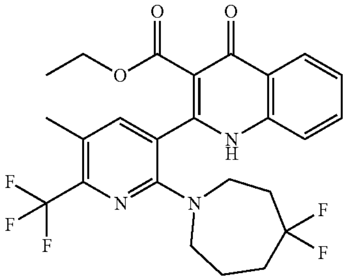

ethyl 2-[2-(4, 4-difluoroazepan-1-yl)-5-methyl-6-(trifluoromethyl)-3-pyridyl]-4-oxo-1*H*-quinoline-3-carboxylate,

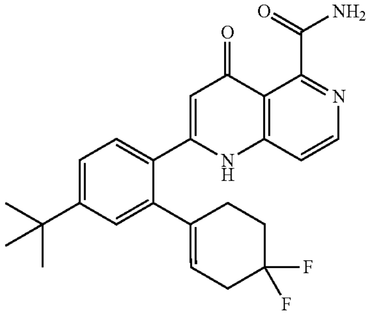

2-[4-tert-butyl-Z-(4, 4-difluorocyclohexen-1-yl)phenyl]-4-oxo-1*H*-1, 6-naphthyridine-5-carboxamide,

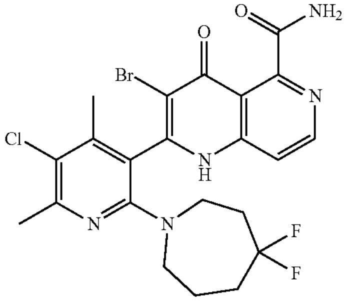

3-bromo-2-[5-chloro-2-(4, 4-difluoroazepan-1-yl)-4, 6-dimethyl-3-pyridyl]-4-oxo-1*H*-1, 6-naphthyridine-S-carboxamide,

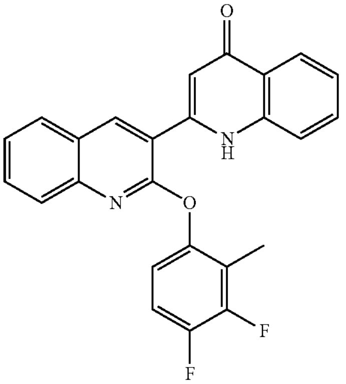

2-[2-(3, 4-difluoro-2-methyl-phenoxy)-3-quinolyl]-1*H*-quinolin-4-one,

-continued

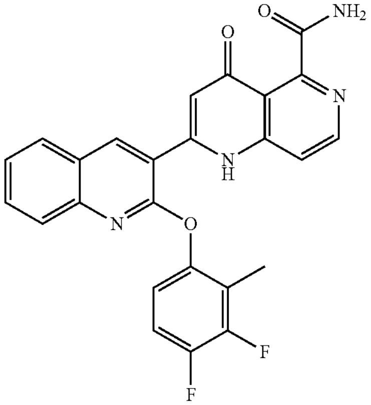

2- [2-(3, 4-difluoro-2-methyl-phenoxy)-3-quinolyl]-4-oxo-1*H*-1, 6-naphthyridine-5-carboxamide,

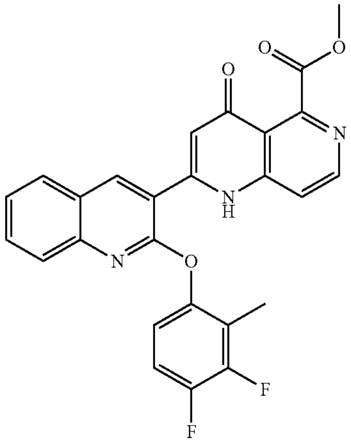

methyl 2-[2-(3, 4-difluoro-2-methyl-phenoxy)-3- quinolyl]-4-oxo-1*H*-1, 6-naphthyridine-5-carboxylate ,

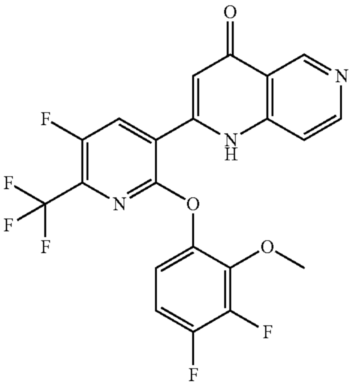

2-[2-(3, 4-difluoro-2-methoxy-phenoxy)-5-fluoro-4-(trifluoromethyl)phenyl]-1*H*-1 ,6-naphthyridin-4-one, -continued

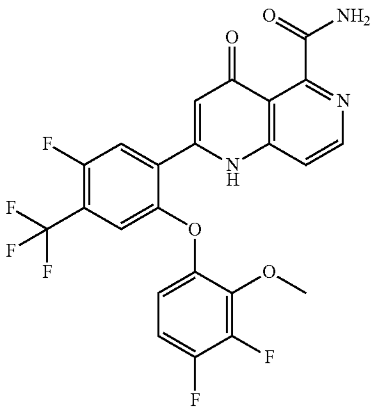

2-[2-(3, 4-difluoro-2-methoxy-phenoxy)-5-fluoro-4-(trifluoromethyl)phenyl]-4-oxo-1*H*-1, 6-naphthyridine-S-carboxamide,

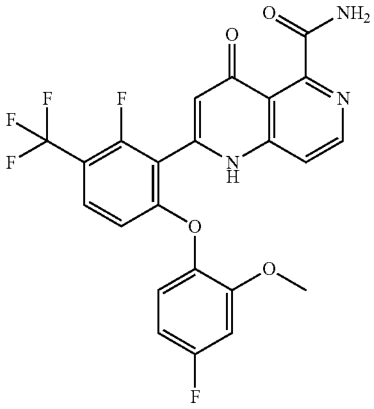

2-[2-fluoro-6-(4-fluoro-2-methoxy-phenoxy)-3- (trifluoromethyl)phenyl]-4-oxo-1*H*-1, 6-naphthyridine-S-carboxamide,

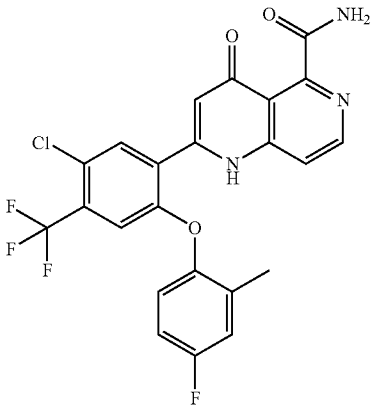

2-[5-chloro-2-(4-fluoro-2-methy1-phenoxy)-4-(trifluoromethyl)phenyl]-4-oxo-1*H*-1 ,6-naphthyridine-S-carboxamide, -continued

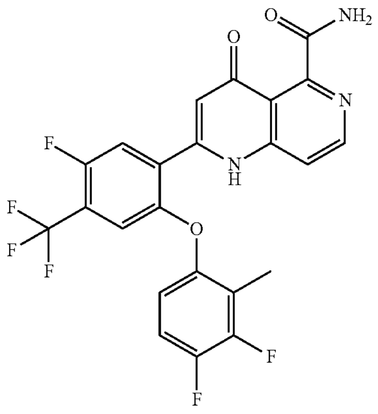

2-[2-(3, 4-difluoro-2-methy1-phenoxy)-5-fluoro-4-(trifluoromethyl)phenyl]-4-oxo-1*H*-1, 6-naphthyridine-S-carboxamide,

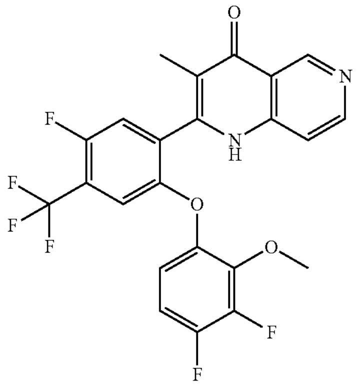

2-[2-(3, 4-difluoro-2-methoxy-phenoxy)-5-fluoro-4-(trifluoromethyl)phenyl]-3-methyl-1*H*-1, 6-naphthyridin-4-one,

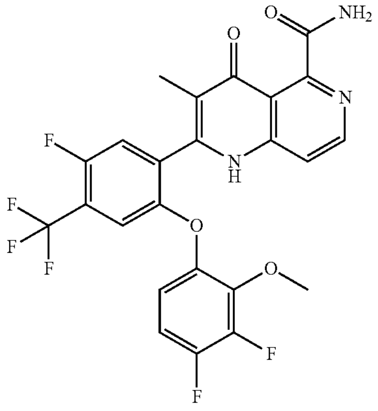

2-[2-(3, 4-difluoro-2-methoxy-phenoxy)-5-fluoro-4-(trifluoromethyl)phenyl]-3-methyl-4-oxo-1*H*-1, 6-naphthyridine-5-carboxamide,

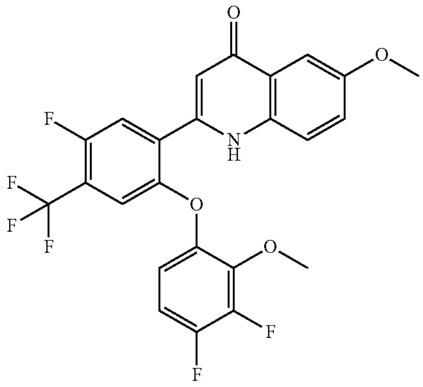

2-[2-(3, 4-difluoro-2-methoxy-phenoxy)-5-fluoro-4-(trifluoromethyl)phenyl]-6-methoxy-1*H*-quinolin-4-one,

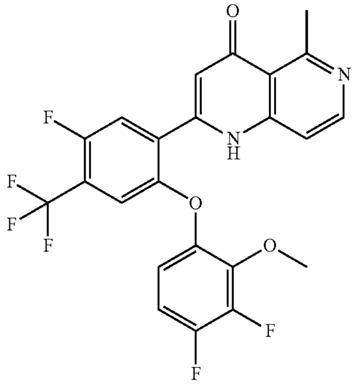

2-[2-(3, 4-difluoro-2-methoxy-phenoxy)-5-fluoro-4-(trifluoromethyl)phenyl]-5-methyl-1*H*-1, 6-naphthyridin-4-one,

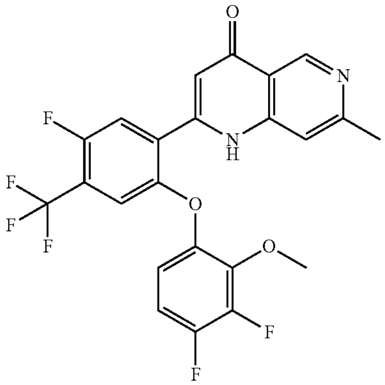

2-[2-(3, 4-difluoro-2-methloxy-phenoxy)-5-fluoro-4-(trifluoromethyl)phenyl]-7-methyl-1*H*-1, 6-naphthyridin-4-one,

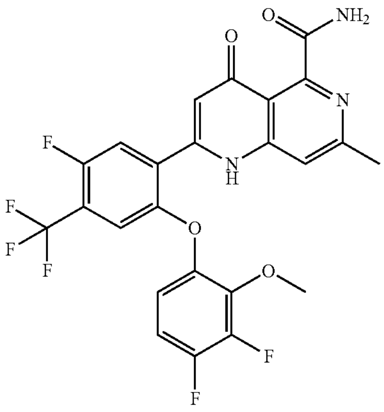

2-[2-(3, 4-difluoro-2-methoxy-phenoxy)-5-fluoro-4-(trifluoromethyl)phenyl]-7-methyl-4-oxo-1*H*-1, 6-naphthyridine-5-carboxamide,

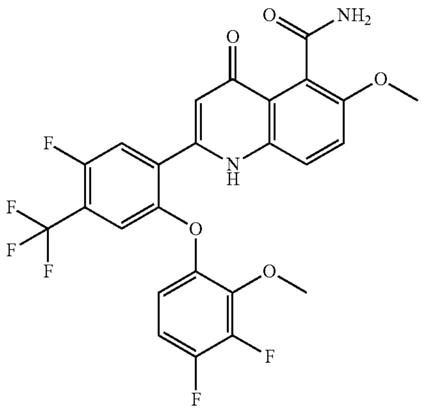

2-[2-(3, 4-difluoro-2-methoxy-phenoxy)-5-fluoro-4-(trifluoromethyl)phenyl]-6-methoxy-4-oxo-1*H*-quinoline-5-carboxamide,

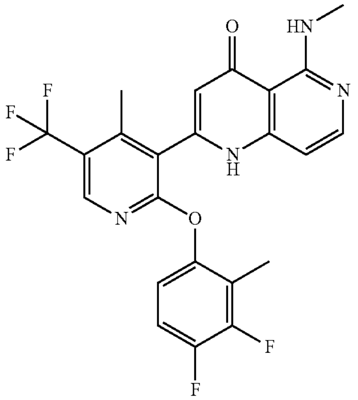

2-[2-(3, 4-difluoro-2-methyl-phenoxy)-4-methyl-5-(trifluoromethyl)-3-pyridy1]-5-(methylamino)-1*H*-1 ,6-naphthyridin-4-one, -continued

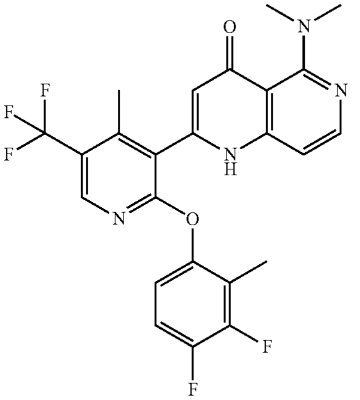

2-[2-(3, 4-difluoro-2-methyl-phenoxy)-4-methyl-5-(trifluoromethyl)-3-pyridy1]-5-(dimethylamino)-1*H*-1, 6-naphthyridin-4-one,

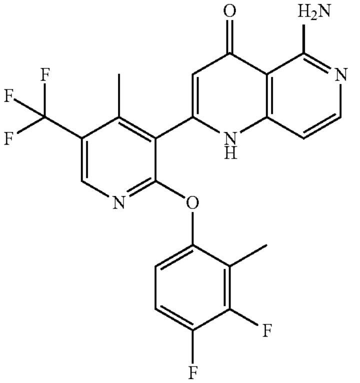

5-amino-2-[2-(3, 4-difluoro-2-methyl-phenoxy)-4-methyl-5-(trifluoromethyl)-3-pyridy1]-1*H*-1, 6-naphthyridin-4-one,

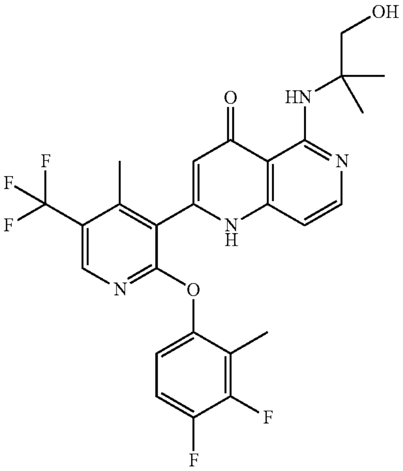

2-[2-(3, 4-difluoro-2-methyl-phenoxy)-4-methyl-5-(trifluoromethyl)-3-pyridy1]-5-[(2-hydroxy-1, 1-dimethyl-ethyl)amino]-1H-1, 6-naphthyridin-4-one, -continued

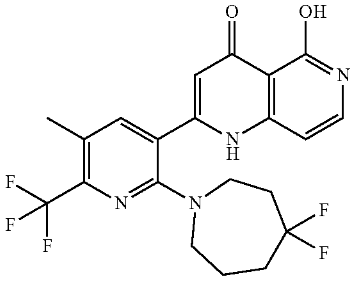

2-[2-(4, 4-difluoroazepan-1-y1)-5-methyl-6-(trifluoromethyl)-3-pyridy1]-5-hydroxy-1*H*-1, 6-naphthyridin-4-one,

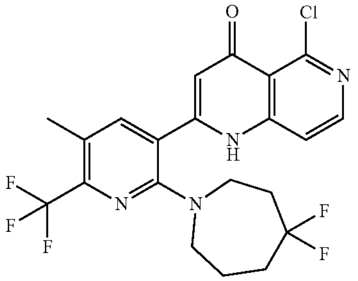

5-chloro-2-[2-(4, 4-difluoroazepan-1-y1)-5-methyl-6-(trifluoromethy1)-3-pyridy1]-1*H*-1, 6-naphthyridin-4-one,

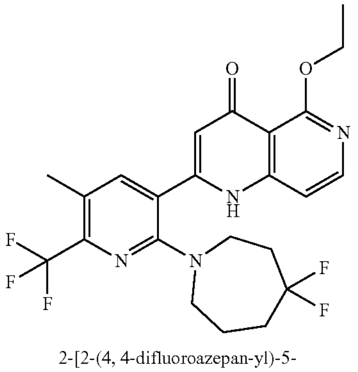

2-[2-(4, 4-difluoroazepan-yl)-5-methyl-6-(trifluoromethyl)-3-pyridyl]-5-ethoxy-1*H*-1, 6-naphthyridin-4-one, -continued

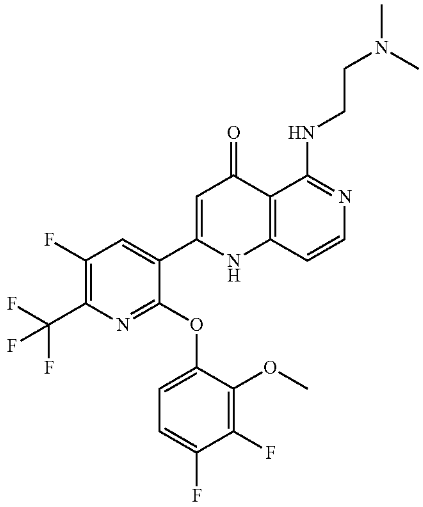

2-[2-(3, 4-difluoro-2-methoxy-phenoxy)-5-fluoro-4-(trifluoromethyl)phenyl]-5-[2-(dimethylamino)ethylamino]-1*H*-1, 6-naphthyridin-4-one,

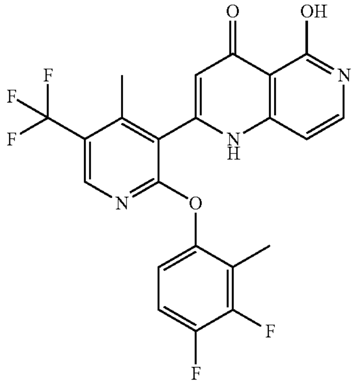

2-[2-(3, 4-difluoro-2-methyl-phenoxy)-4-methyl-5-(trifluoromethy1)-3-pyridy1]-5-hydroxy-1*H*-1, 6-naphthyridin-4-one,

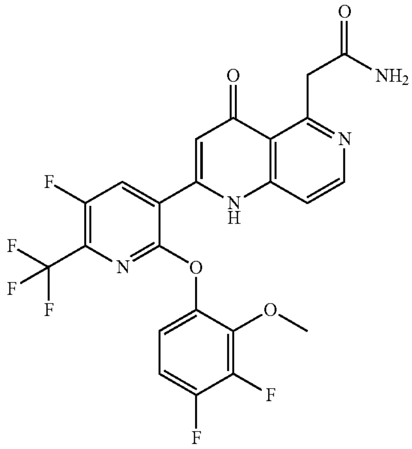

2-[2-[2-(3, 4-difluoro-methoxy-phenoxy)-5-fluoro-4-(trifluoromethyl)phenyl]-4-oxo-1H-1 ,6-naphthyridin-S-y1]acetamide, -continued

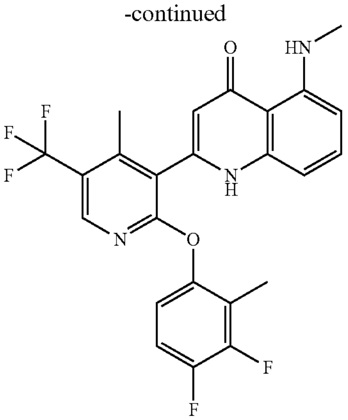

2-[2-(3, 4-difluoro-2-methyl-phenoxy)-4-methyl-5-(trifluoromethyl)-3-pyridy1]-5-(methylamino)-1*H*-quinolin-4-one,

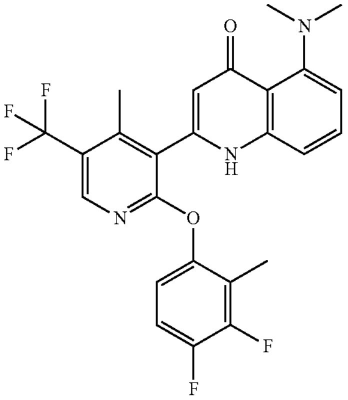

2-[2-(3, 4-difluoro-2-methyl-phenoxy)-4-methyl-5-(trifluoromethyl)-3-pyridy1]-5-(dimethylamino)-1*H*-quinolin-4-one,

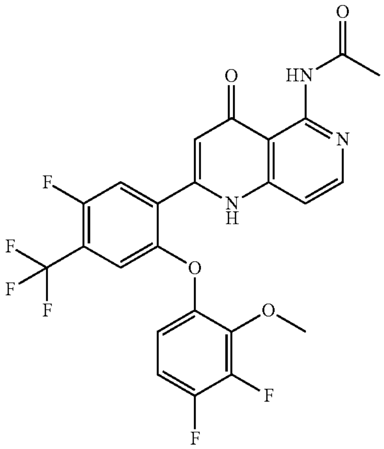

N-[2-[2-(3, 4-difluoro-2-methoxy-phenoxy)-5-fluoro-4-(trifluoromethyl)phenyl]-4-oxo-1*H*-1, 6-naphthyridin-S-y1]acetamide,

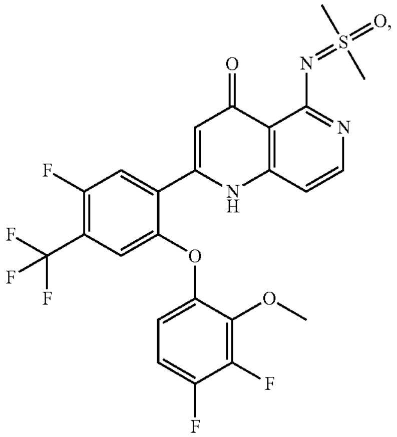

2-[2-(3,4-difluoro-2-methoxy-phenoxy)-5-fluoro-4-(trifluoromethyl)phenyl]-5-[[dimethyl(oxo)-λ6-sulfanylidene]amino]-1H-1,6-naphthyridin-4-one

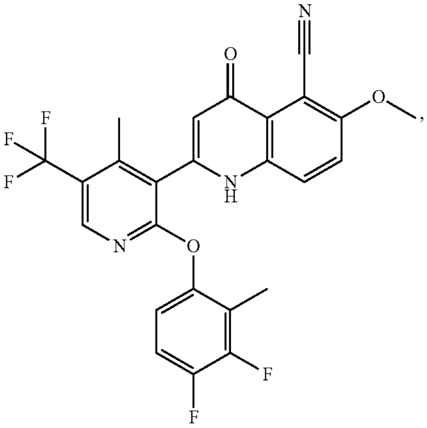

2-[2-(3,4-difluoro-2-methyl-phenoxy)-4-methyl-5-(trifluoromethyl)-3-pyridyl]-6-methoxy-4-oxo-1H-quinoline-5-carbonitrile

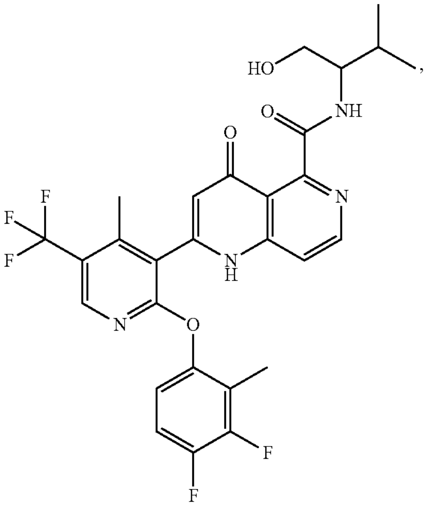

2-[2-(3,4-difluoro-2-methyl-phenoxy)-4-methyl-5-(trifluoromethyl)-3-pyridyl]-N-[1-(hydroxymethyl)-2-methyl-propyl]-4-oxo-1H-1,6-naphthyridine-5-carboxamide -continued

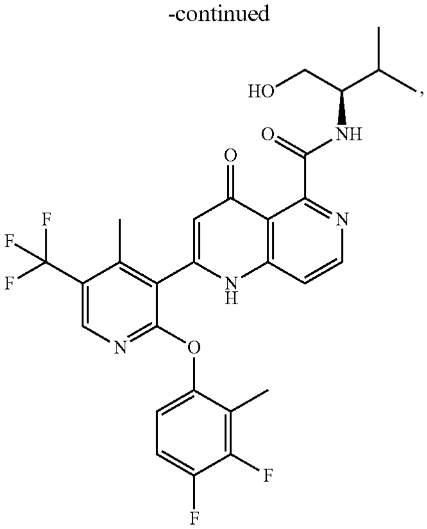

2-[2-(3,4-difluoro-2-methyl-phenoxy)-4-methyl-5-(trifluoromethyl)-3-pyridyl]-N-[(1R)-1-(hydroxymethyl)-2-methyl-propyl]-4-oxo-1H-1,6-naphthyridine-5-carboxamide

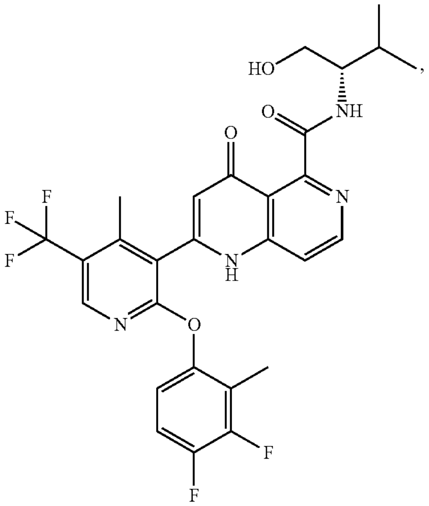

2-[2-(3,4-difluoro-2-methyl-phenoxy)-4-methyl-5-(trifluoromethyl)-3-pyridyl]-N-[(1S)-1-(hydroxymethyl)-2-methyl-propyl]-4-oxo-1H-1,6-naphthyridine-5-carboxamide

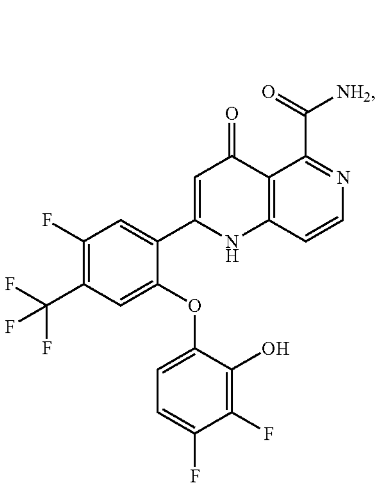

2-[2-(3,4-difluoro-2-hydroxy-phenoxy)-5-fluoro-4-(trifluoromethyl)phenyl]-4-oxo-1H-1,6-naphthyridine-5-carboxamide -continued

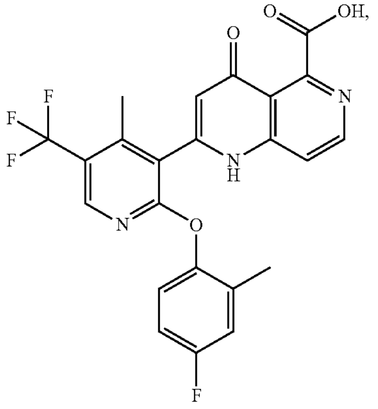

2-[2-(4-fluoro-2-methyl-phenoxy)-4-methyl-5-(trifluoromethyl)-3-pyridyl]-4-oxo-1H-1,6-naphthyridine-5-carboxylic acid

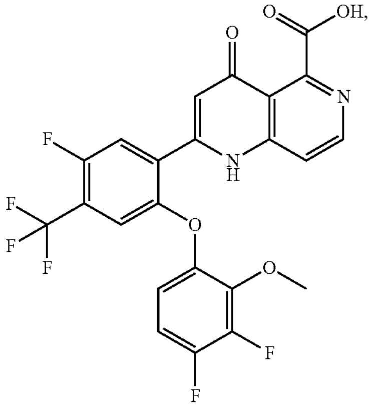

2-[2-(3,4-difluoro-2-methoxy-phenoxy)-5-fluoro-4-(trifluoromethyl)phenyl]-4-oxo-1H-1,6-naphthyridine-5-carboxylic acid

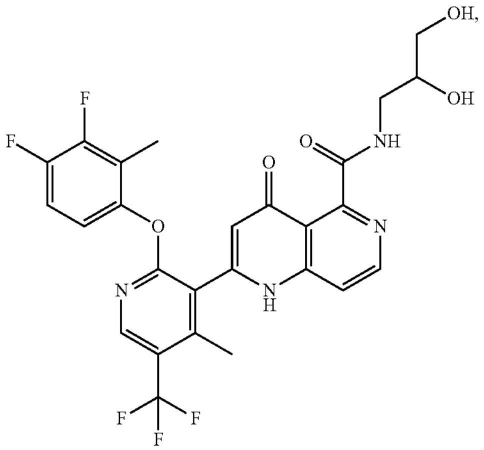

2-[2-(3,4-difluoro-2-methyl-phenoxy)-4-methyl-5-(trifluoromethyl)-3-pyridyl]-N-[2,3-dihydroxypropyl]-4-oxo-1H-1,6-naphthyridine-5-carboxamide -continued

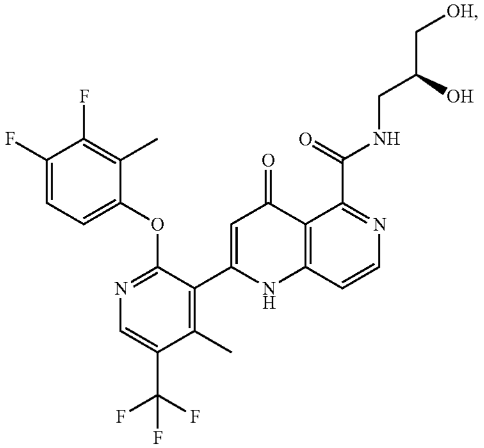

2-[2-(3,4-difluoro-2-methyl-phenoxy)-4-methyl-5-(trifluoromethyl)-3-pyridyl]-N-[(2S)-2,3-dihydroxypropyl]-4-oxo-1H-1,6-naphthyridine-5-carboxamide

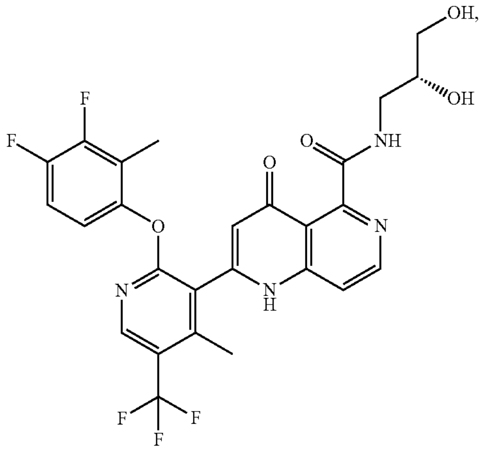

2-[2-(3,4-difluoro-2-methyl-phenoxy)-4-methyl-5-(trifluoromethyl)-3-pyridyl]-N-[(2R)-2,3-dihydroxypropyl]-4-oxo-1H-1,6-naphthyridine-5-carboxamide

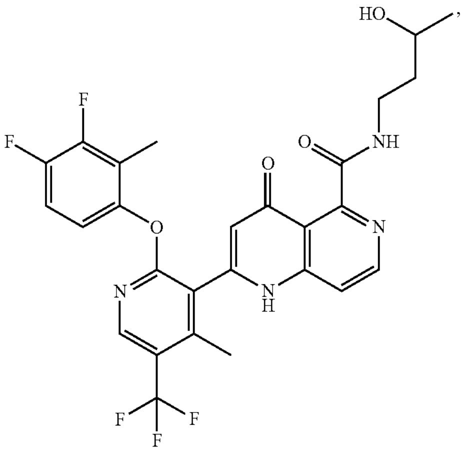

2-[2-(3,4-difluoro-2-methyl-phenoxy)-4-methyl-5-(trifluoromethyl)-3-pyridyl]-N-(3-hydroxybutyl)-4-oxo-1H-1,6-naphthyridine-5-carboxamide -continued

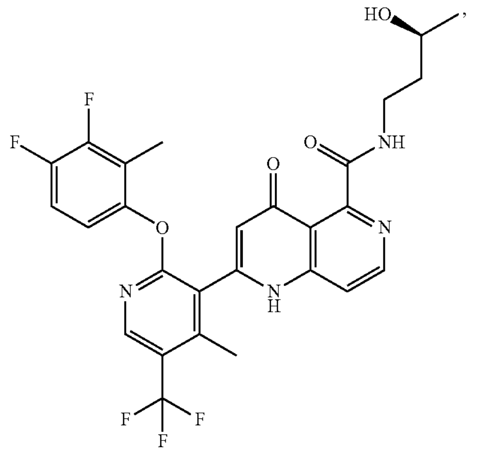

(S)-2-[2-(3,4-difluoro-2-methyl-phenoxy)-4-methyl-5-(trifluoromethyl)-3-pyridyl]-N-(3-hydroxybutyl)-4-oxo-1H-1,6-naphthyridine-5-carboxamide

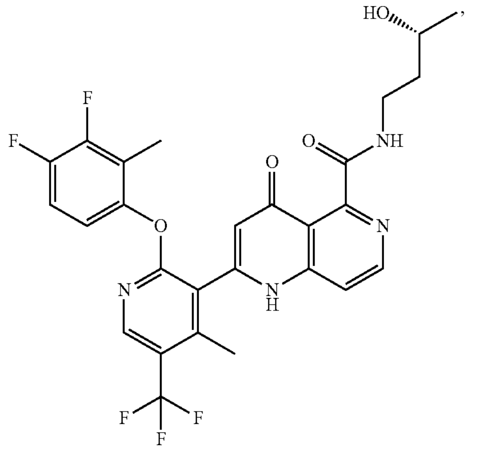

(R)-2-[2-(3,4-difluoro-2-methyl-phenoxy)-4-methyl-5-(trifluoromethyl)-3-pyridyl]-N-(3-hydroxybutyl)-4-oxo-1H-1,6-naphthyridine-5-carboxamide

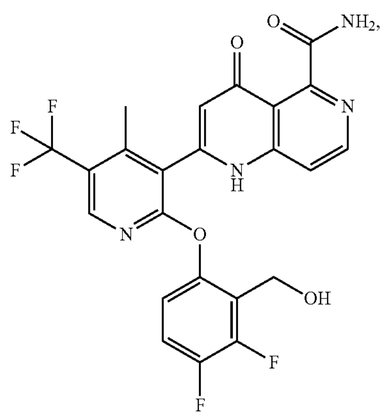

2-[2-[3,4-difluoro-2-(hydroxymethyl)phenoxy]-4-methyl-5-(trifluoromethyl)-3-pyridyl]-4-oxo-1H-1,6-naphthyridine-5-carboxamuide -continued

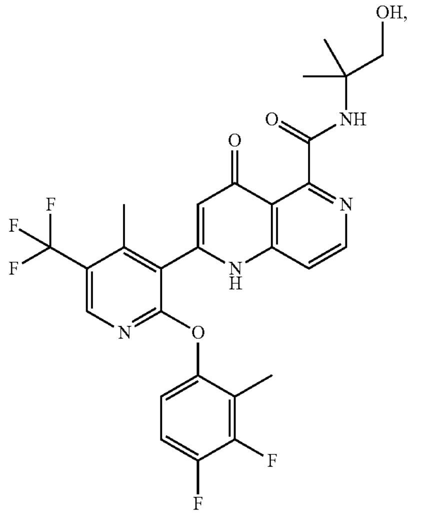

2-[2-(3,4-difluoro-2-methyl-phenoxy)-4-methyl-5-(trifluoromethyl)-3-pyridyl]-N-(2-hydroxy-1,1-dimethyl-ethyl)-4-oxo-1H-1,6-naphthyridine-5-carboxamide

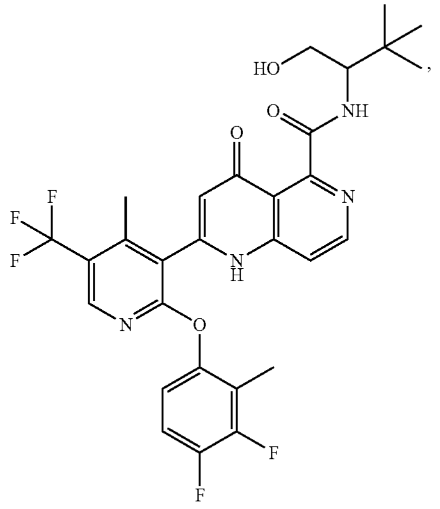

2-[2-(3,4-difluoro-2-methyl-phenoxy)-4-methyl-5-(trifluoromethyl)-3-pyridyl]-N-[1-(hydroxymethyl)-2,2-dimethyl-propyl]-4-oxo-1H-1,6-naphthyridine-5-carboxamide -continued

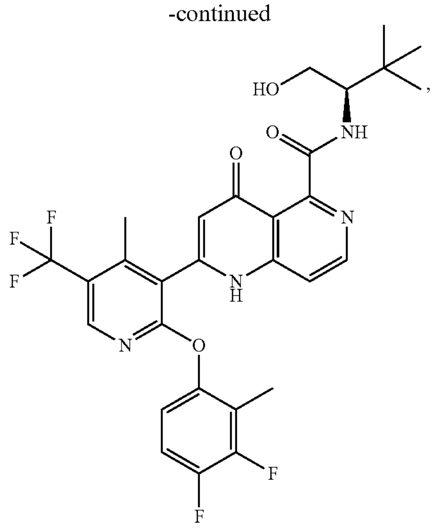

(R)-2-[2-(3,4-difluoro-2-methyl-phenoxy)-4-methyl-5-(trifluoromethyl)-3-pyridyl]-N-[1-(hydroxymethyl)-2,2-dimethyl-propyl]-4-oxo-1H-1,6-naphthyridine-5-carboxamide

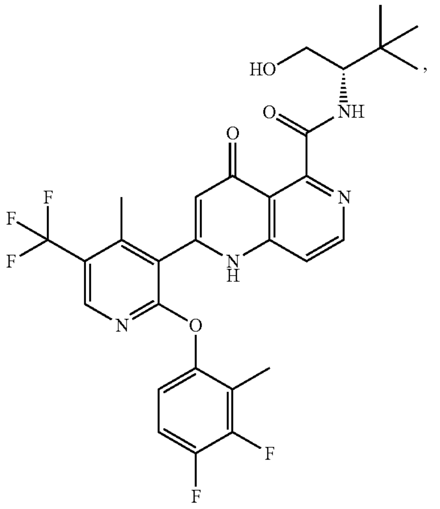

(S)-2-[2-(3,4-difluoro-2-methyl-phenoxy)-4-methyl-5-(trifluoromethyl)-3-pyridyl]-N-[1-(hydroxymethyl)-2,2-dimethyl-propyl]-4-oxo-1H-1,6-naphthyridine-5-carboxamide

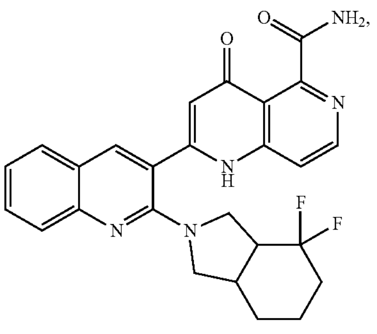

2-[2-(7,7-difluoro-3,3a,4,5,6,7a-hexahydro-1H-isoindol-2-yl)-3-quinolyl]-4-oxo-1H-1,6-naphthyridine-5-carboxamide -continued

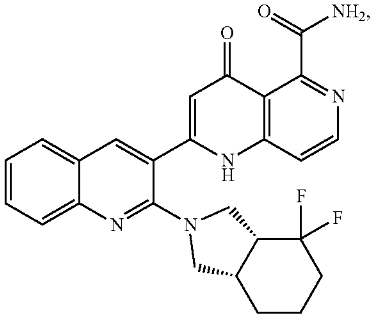

2-[2-((3aR,7aS)-7,7-difluoro-3,3a,4,5,6,7a-hexahydro-1H-isoindol-2-yl)-3-quinolyl]-4-1H-1,6-naphthyridine-5-carboxamide

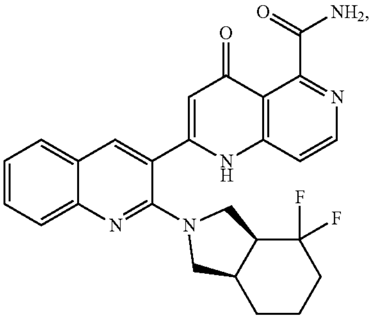

2-[2-((3aS,7aR)-7,7-difluoro-3,3a,4,5,6,7a-hexahydro-1H-isoindol-2-yl)-3-quinolyl]-4-oxo-1H-1,6-naphthyridine-5-carboxamide

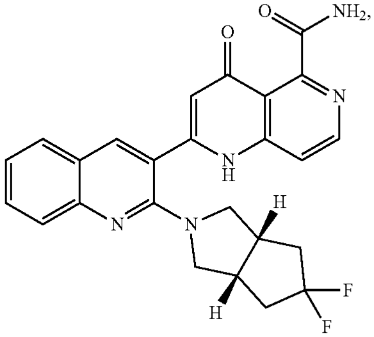

2-[2-[(3aR,6aS)-5,5-difluoro-1,3,3a,4,6,6a-hexahydrocyclopenta[c]pyrrol-2-yl]-3-quinolyl]-4-oxo-1H-1,6-naphthyridine-5-carboxamide

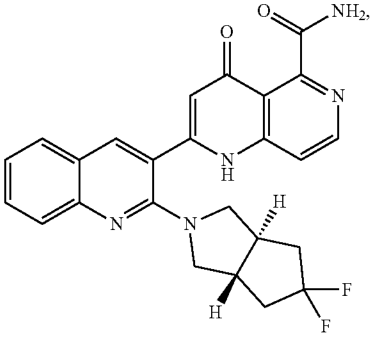

2-[2-[(3aR,6aR)-5,5-difluoro-1,3,3a,4,6,6a-hexahydrocyclopenta[c]pyrrol-2-yl]-3-quinolyl]-4-oxo-1H-1,6-naphthyridine-5-carboxamide -continued

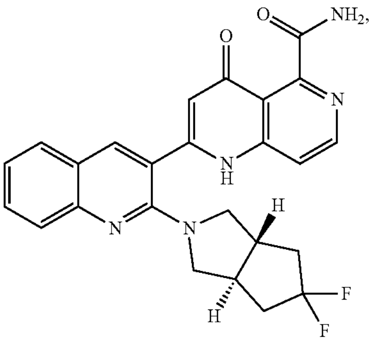

2-[2-[(3aS,6aS)-5,5-difluoro-1,3,3a,4,6,6a-hexahydrocyclopenta[c]pyrrol-2-yl]-3-quinolyl]-4-oxo-1H-1,6-naphthyridine-5-carboxamide

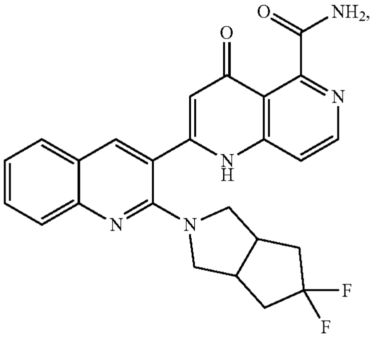

2-[2-[5,5-difluoro-1,3,3a,4,6,6a-hexahydrocyclopenta[c]pyrrol-2-yl]-3-quinolyl]-4-oxo-1H-1,6-naphthyridine-5-carboxamide

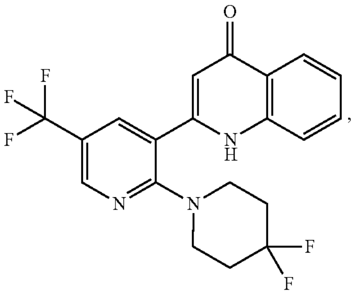

2-[2-(4,4-difluoro-1-piperidyl)-5-(trifluoromethyl)-3-pyridyl]-1H-quinolin-4-one

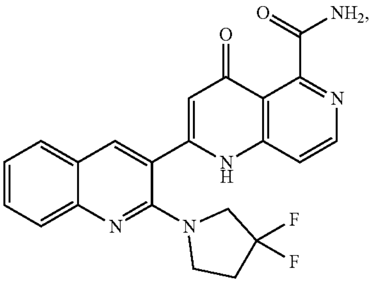

2-[2-(3,3-difluoropyrrolidin-1-piperidyl)-3-quinolyl]-4-oxo-1H-1,6-naphthyridine-5-carboxamide -continued

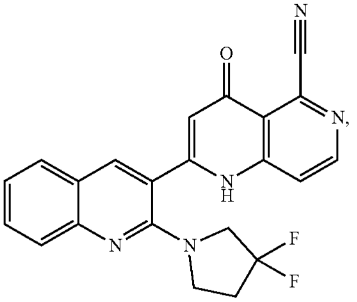

2-[2-(3,3-difluoropyrrolidin-1-yl)-3-quinolyl]-4-oxo-1H-1,6-naphthyridine-5-carbonitrile

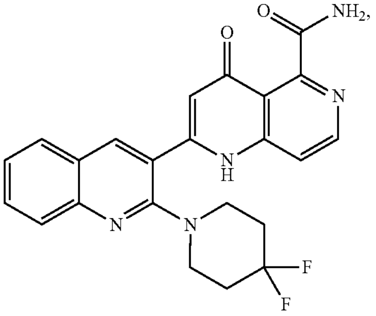

2-[2-(4,4-difluoro-1-piperidyl)-3-quinolyl]-4-oxo-1H-1,6-naphthyridine-5-carboxamide

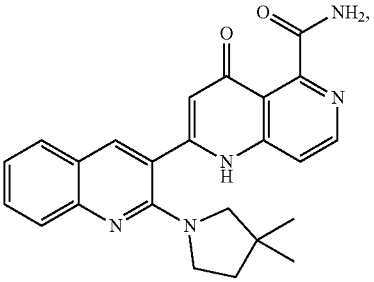

2-[2-(3,3-dimethylpyrrolidin-1-yl)-3-quinolyl]-4-oxo-1H-1,6-naphthyridine-5-carboxamide

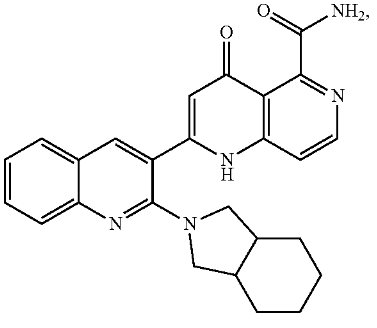

2-[2-(1,3,3a,4,5,6,7,7a-octahydroisoindol-2-yl)-3-quinolyl]-4-oxo-1H-1,6-naphthyridine-5-carboxamide

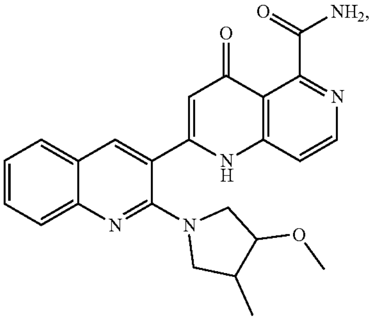

2-[2-[3-methoxy-4-methyl-pyrrolidin-1-yl]-3-quinolyl]-4-oxo-1H-1,6-naphthyridine-5-carboxamide

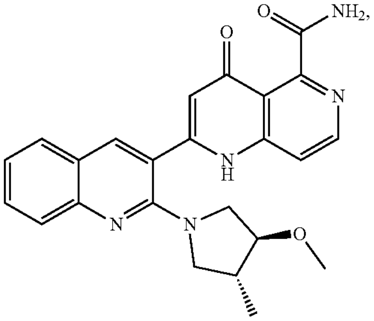

2-[2-[(3S,4R)-3-methoxy-4-methyl-pyrrolidin-1-yl]-3-quinolyl]-4-oxo-1H-1,6-naphthyridine-5-carboxamide

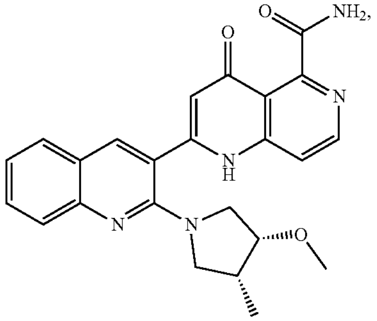

2-[2-[(3S,4S)-3-methoxy-4-methyl-pyrrolidin-1-yl]-3-quinolyl]-4-oxo-1H-1,6-naphthyridine-5-carboxamide

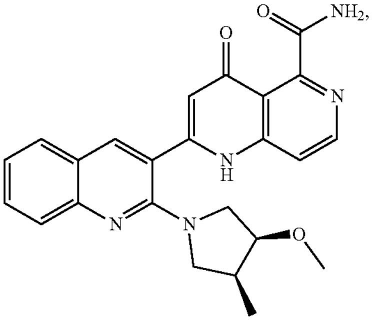

2-[2-[(3R,4R)-3-methoxy-4-methyl-pyrrolidin-1-yl]-3-quinolyl]-4-oxo-1H-1,6-naphthyridine-5-carboxamide

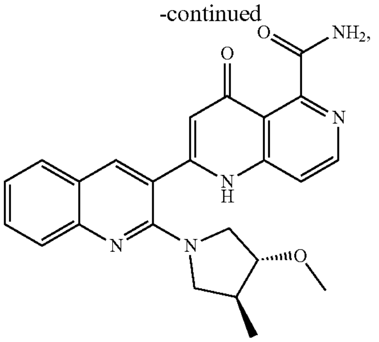

2-[2-[(3R,4S)-3-methoxy-4-methyl-pyrrolidin-1-yl]-3-quinolyl]-4-oxo-1H-1,6-naphthyridine-5-carboxamide

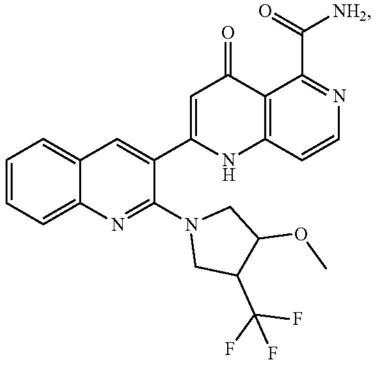

2-[2-[3-methoxy-4-(trifluoromethyl)pyrrolidin-1-yl]-3-quinoloyl]-4-oxo-1H-1,6-naphthyridine-5-carboxamide

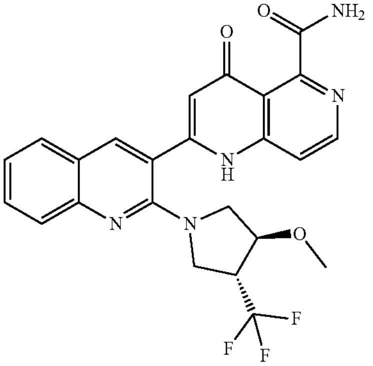

,

2-[2-[(3S,4R)-3-methoxy-4-(trifluoromethyl)pyrrolidin-1-yl]-3-quinolyl]-4-oxo-1H-1,6-naphthyridine-5-carboxamide -continued

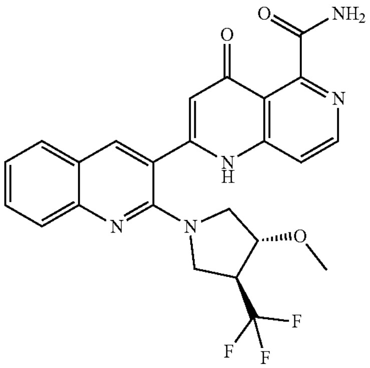

,

2-[2-[(3R,4S)-3-methoxy-4-(trifluoromethyl)pyrrolidin-1-yl]-3-quinolyl]-4-oxo-1H-1,6-naphthyridine-5-carboxamide

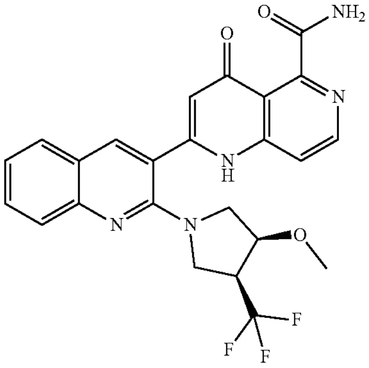

,

2-[2-[(3S,4S)-3-methoxy-4-(trifluoromethyl)pyrrolidin-1-yl]-3-quinolyl]-4-oxo-1H-1,6-naphthyridine-5-carboxamide

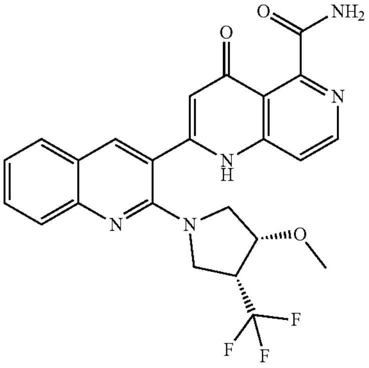

,

2-[2-[(3R,4R)-3-methoxy-4-(trifluoromethyl)pyrrolidin-1-yl]-3-quinolyl]-4-oxo-1H-1,6-naphthyridine-5-carboxamide

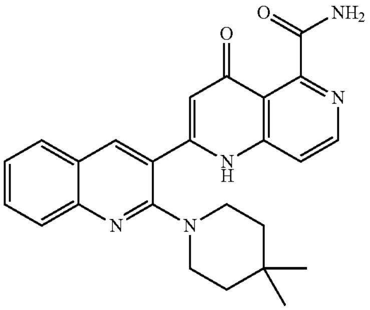

,

2-[2-(4,4-dimethyl-1-piperidyl)-3-quinolyl]-4-oxo-1H-1,6-naphthyridine-5-carboxamide -continued

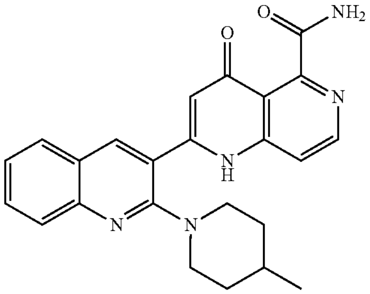

,

2-[2-(4-methyl-1-piperidyl)-3-quinolyl]-4-oxo-1H-1,6-naphthyridine-5-carboxamide

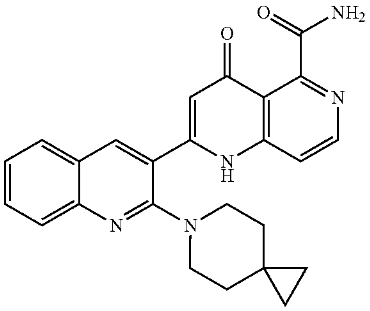

,

2-[2-(6-azaspiro[2.5]octan-6-yl)-3-quinolyl]-4-oxo-1H-1,6-naphthyridine-5-carboxamide

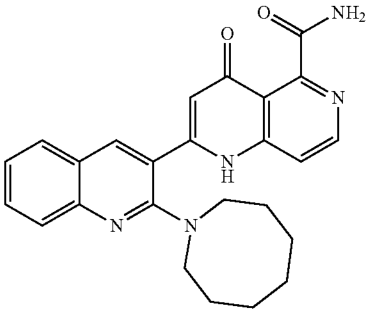

,

2-[2-(azocan-1-yl)-3-quinolyl]-4-oxo-1H-1,6-naphthyridine-5-carboxamide

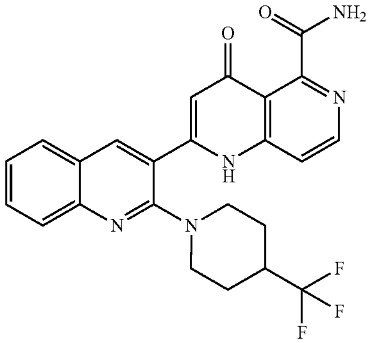

, 4-oxo-2-[2-[4-(trifluoromethyl)-1-piperidyl]-3-quinolyl]-1H-1,6-naphthyridine-5-carboxamide

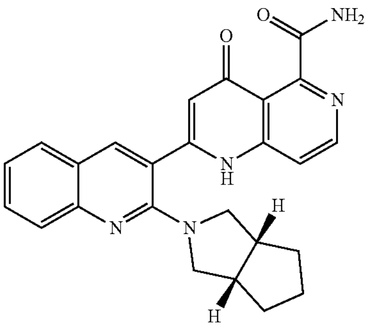

,

2-[2-[(3aR,6aS)-3,3a,4,5,6,6a-hexahydro-1H-cyclopenta[c]pyrrol-2-yl]-3-quinolyl]-4-oxo-1H-1,6-naphthyridine-5-carboxamide

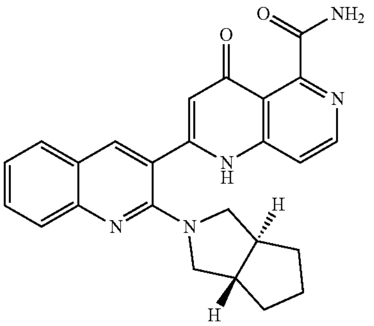

,

2-[2-[(3aR,6aR)-3,3a,4,5,6,6a-hexahydro-1H-cyclopenta[c]pyrrol-2-yl]-3-quinolyl]-4-oxo-1H-1,6-naphthyridine-5-carboxamide

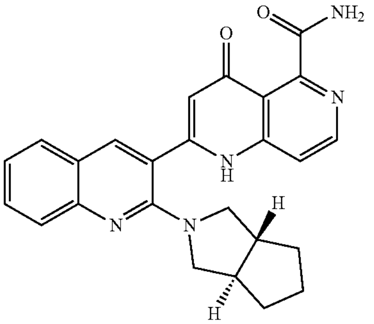

,

2-[2-[(3aS,6aS)-3,3a,4,5,6,6a-hexahydro-1H-cyclopenta[c]pyrrol-2-yl]-3-quinolyl]-4-oxo-1H-1,6-naphthyridine-5-carboxamide

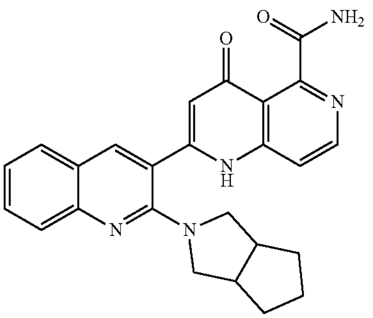

,

2-[2-[3,3a,4,5,6,6a-hexahydro-1H-cyclopenta[c]pyrrol-2-yl]-3-quinolyl]-4-oxo-1H-1,6-naphthyridine-5-carboxamide

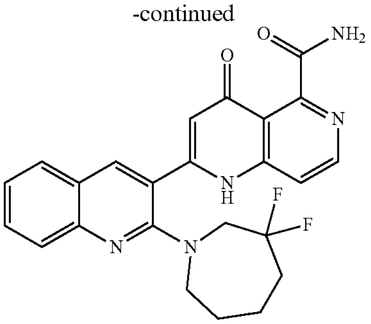

,

2-[2-(3,3-difluoroazepan-1-yl)-3-quinolyl]-4-oxo-1H-1,6-naphthyridine-5-carboxamide

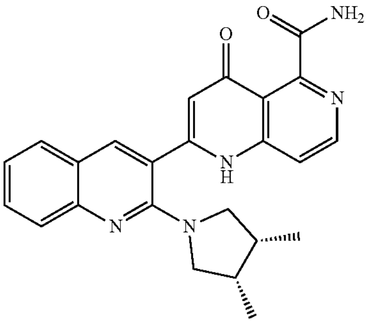

,

2-[2-[(3R,4S)-3,4-dimethylpyrrolidin-1-yl]-3-quinolyl]-4-oxo-1H-1,6-naphthyridine-5-carboxamide

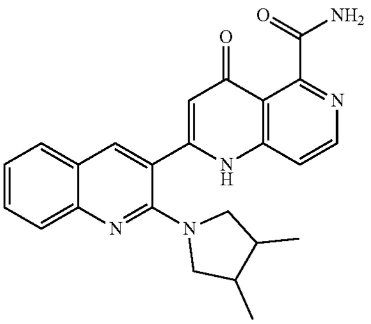

,

2-[2-[3,4-dimethylpyrrolidin-1-yl]-3-quinolyl]-4-oxo-1H-1,6-naphthyridine-5-carboxamide

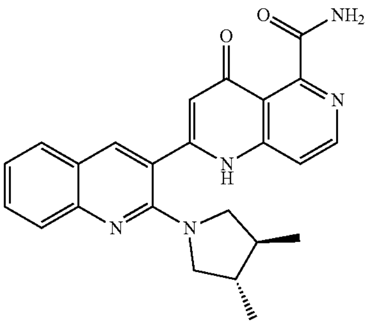

,

2-[2-[(3R,4R)-3,4-dimethylpyrrolidin-1-yl]-3-quinolyl]-4-oxo-1H-1,6-naphthyridine-5-carboxamide -continued

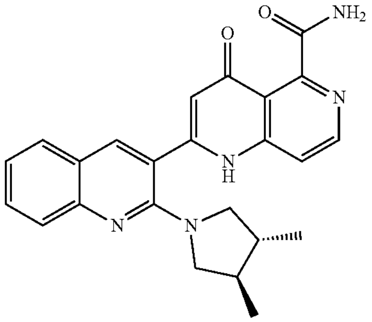

,

2-[2-[(3S,4S)-3,4-dimethylpyrrolidin-1-yl]-3-quinolyl]-4-oxo-1H-1,6-naphthyridine-5-carboxamide

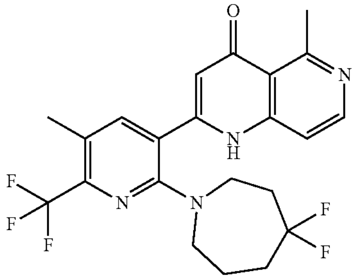

,

2-[2-(4,4-difluoroazepan-1-yl)-5-methyl-6-(trifluoromethyl)-3-pyridyl]-5-methyl-1H-1,6-naphthyridin-4-one

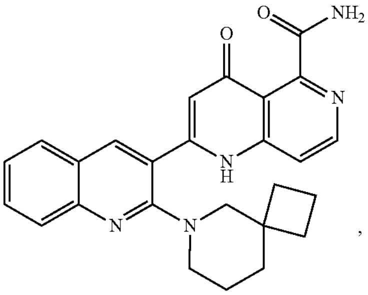

,

2-[2-(6-azaspiro[3.5]nonan-6-yl)-3-quinolyl]-4-oxo-1H-1,6-naphthyridine-5-carboxamide

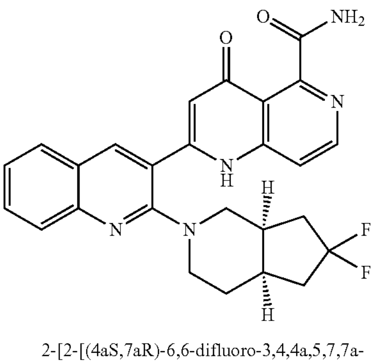

,

2-[2-[(4aS,7aR)-6,6-difluoro-3,4,4a,5,7,7a-hexahydro-1H-cyclopenta[c]pyridin-2-yl]-3-quinolyl]-4-oxo-1H-1,6-naphthyridine-5-caboxamide -continued

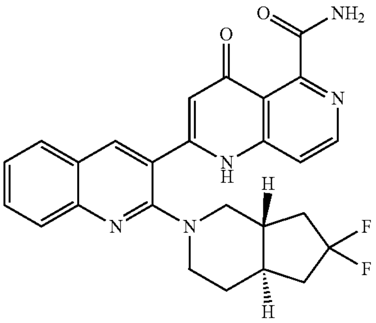

,

2-[2-[(4aS,7aS)-6,6-difluoro-3,4,4a,5,7,7a-hexahydro-1H-cyclopenta[c]pyridin-2-yl]-3-quinolyl]-4-oxo-1H-1,6-naphthyridine-5-caboxamide

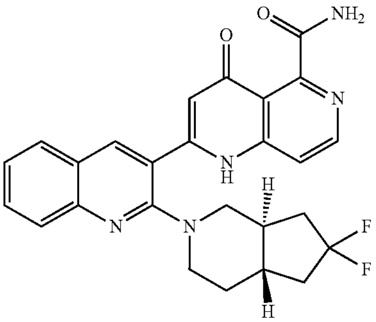

,

2-[2-[(4aR,7aR)-6,6-difluoro-3,4,4a,5,7,7a-hexahydro-1H-cyclopenta[c]pyridin-2-yl]-3-quinolyl]-4-oxo-1H-1,6-naphthyridine-5-caboxamide

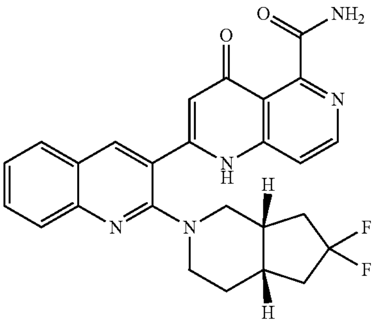

,

2-[2-[(4aR,7aS)-6,6-difluoro-3,4,4a,5,7,7a-hexahydro-1H-cyclopenta[c]pyridin-2-yl]-3-quinolyl]-4-oxo-1H-1,6-naphthyridine-5-caboxamide

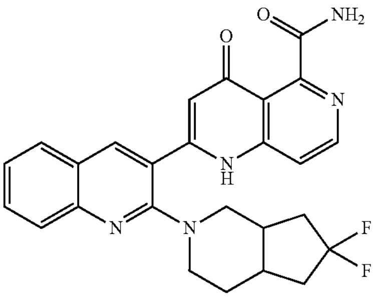

,

2-[2-[6,6-difluoro-3,4,4a,5,7,7a-hexahydro-1H-cyclopenta[c]pyridin-2-yl]-3-quinolyl]-4-oxo-1H-1,6-naphthyridine-5-carboxamide -continued

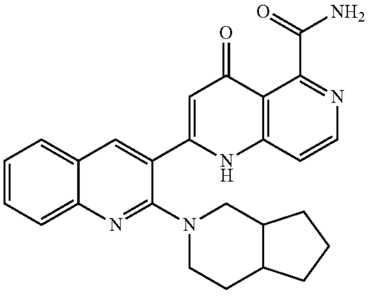

,

2-[2-(1,3,4,4a,5,6,7,7a-cyclopenta[c]pyridin-2-yl]-3-quinolyl]-4-oxo-1H-1,6-naphthyridine-5-carboxamide

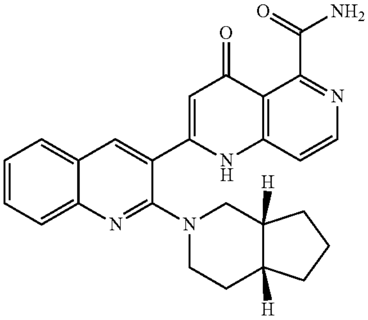

,

2-[2-((4aR,7aR)-1,3,4,4a,5,6,7,7a-cyclopenta[c]pyridin-2-yl]-3-quinolyl]-4-oxo-1H-1,6-naphthyridine-5-carboxamide

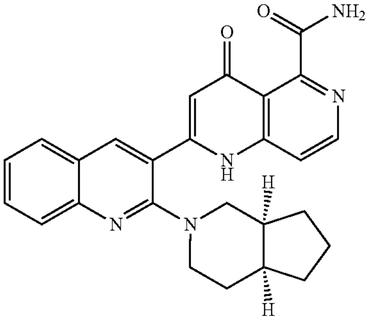

,

2-[2-((4aS,7aS)-1,3,4,4a,5,6,7,7a-octahydropenta[c]pyridin-2-yl]-3-quinolyl]-4-oxo-1H-1,6-naphthyridine-5-carboxamide

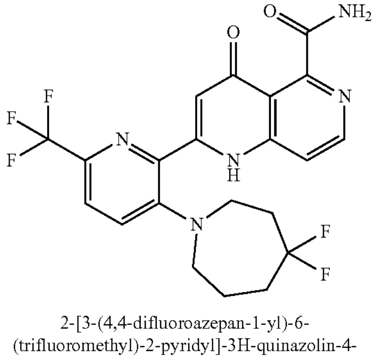

,

2-[3-(4,4-difluoroazepan-1-yl)-6-(trifluoromethyl)-2-pyridyl]-3H-quinazolin-4-one -continued

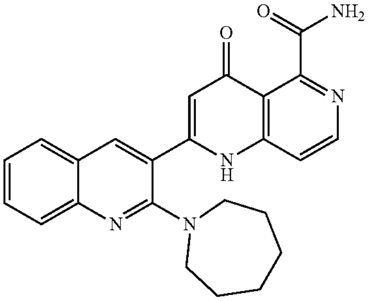

,

2-[2-(azepan-1-yl)-3-quinolyl]-4-oxo-1H-1,6-naphthyridine-5-carboxamide

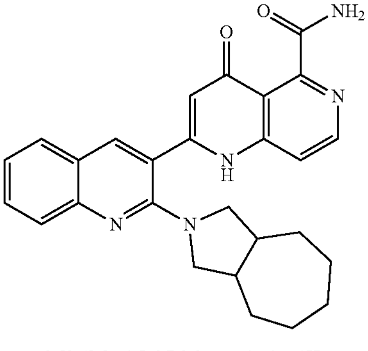

,

2-[2-(3,3a,4,5,6,7,8,8s-octahydro-1H-cyclohepta[c]pyrrol-2-yl)-3-quinolyl]-4-oxo-1H-1,6-naphthyridine-5-carboxamide

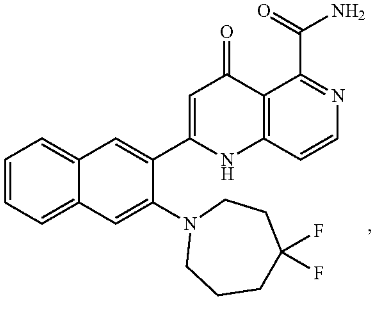

,

2-[2-(4,4-difluoroazepan-1-yl)-3-quinolyl]-1H-1,5-naphthyridin-4-one

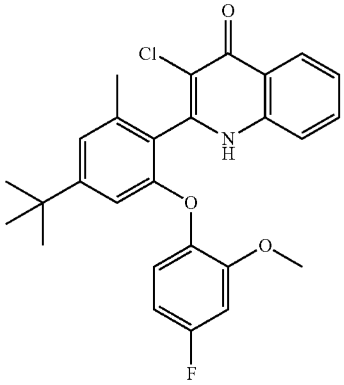

,

2-[4-tert-butyl-2-(4-fluoro-2-methoxy-phenoxy)-6-methyl-phenyl]-3-chloro-1H-quinolin-4-one -continued

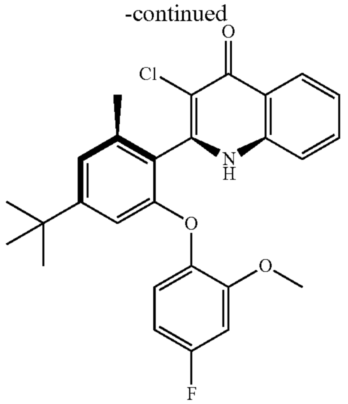

,

2-[4-tert-butyl-2-(4-fluoro-2-methoxy-phenoxy)-6-methyl-phenyl]-3-chloro-1H-quinolin-4-one

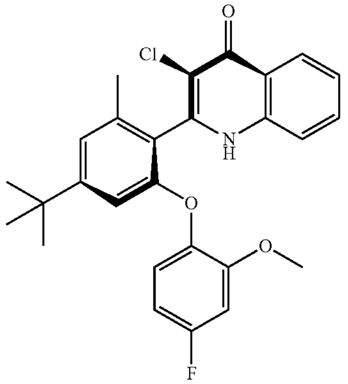

,

2-[4-tert-butyl-2-(4-fluoro-2-methoxy-phenoxy)-6-methyl-phenyl]-3-chloro-1H-quinolin-4-one

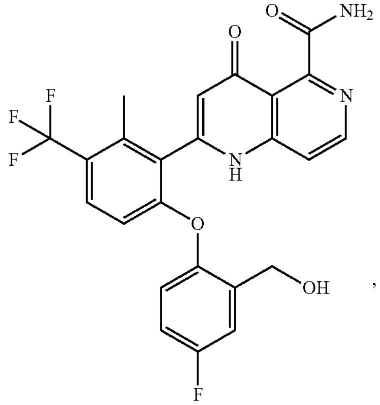

,

2-[2-[4-fluoro-2-(hydroxymethyl)phenoxy]-4-methyl-5-(trifluoromethyl)-3-pyridyl]-4-oxo-1H-1,6-naphthyridine-5-carboxamide

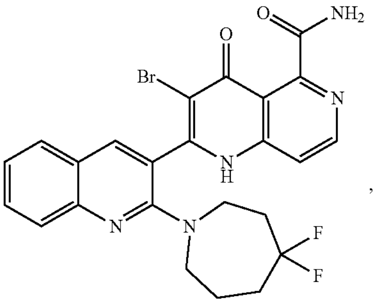

, 3-bromo-2-[2-(4,4-difluoroazepan-1-yl)-3-quinolyl]-4-oxo-1H-1,6-naphthyridine-5-carboxamide -continued

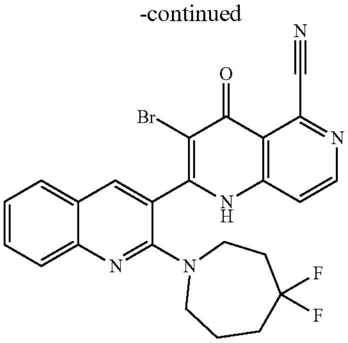

, 3-bromo-2-[2-(4,4-difluoroazepan-1-yl)-3-quinolyl]-4-oxo-1H-1,6-naphthyridine-5-carbonitrile

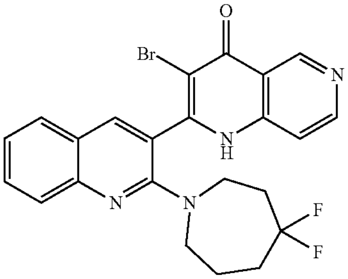

, 3-bromo-2-[2-(4,4-difluoroazepan-1-yl)-3-quinolyl]-1H-1,6-naphthyridin-4-one

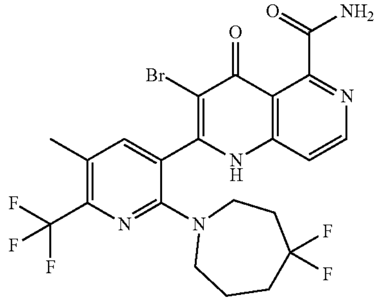

, 3-bromo-2-[2-(4,4-difluoroazepan-1-yl)-5-methyl-6-(trifluoromethyl)-3-pyridyl]-4-oxo-1H-1,6-naphthyridine-5-carboxamide

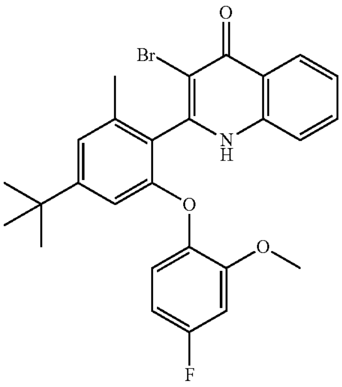

, 3-bromo-2-[4-tert-butyl-2-(4-fluoro-2-methoxy-phenoxy)-6-methyl-phenyl]-1H-quinolin-4-one -continued

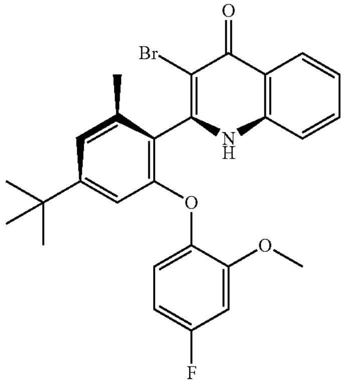

, 3-bromo-2-[4-tert-butyl-2-(4-fluoro-2-methoxy-phenoxy)-6-methyl-phenyl]-1H-quinolin-4-one

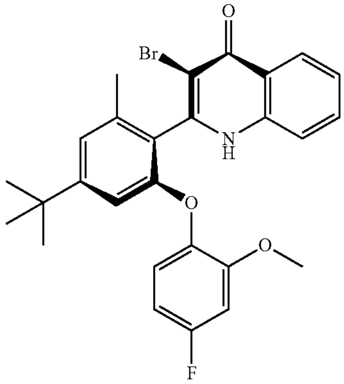

, 3-bromo-2-[4-tert-butyl-2-(4-fluoro-2-methoxy-phenoxy)-6-methyl-phenyl]-1H-quinolin-4-one

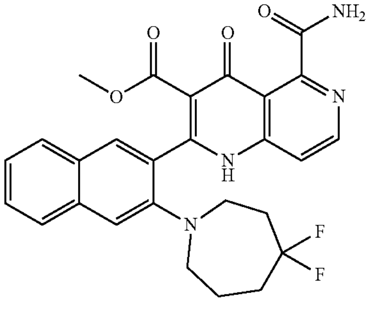

, methyl 5-carbamoyl-2-[2-(4,4-difluoroazepan-1-yl)-3-quinolyl]-4-oxo-1H-1,6-naphthyridine-3-carboxylate, -continued

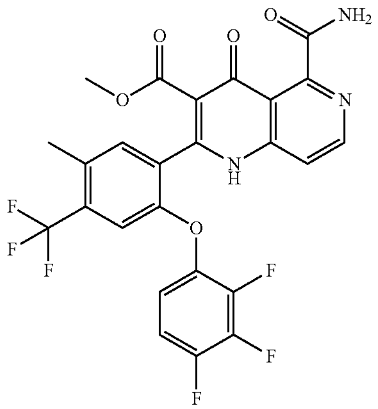

, methyl-5-carbamoyl-2-[2-(3,4-difluoro-2-methyl-phenoxy)-5-methyl-6-(trifluoromethyl)-3-pyridyl]-4-oxo-1H-1,6-naphthyridine-3-carboxylate

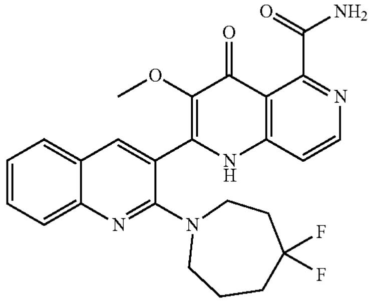

,

2-[2-(4,4-difluoroazepan-1-yl)-3-quinolyl]-3-methoxy-4-oxo-1H-1,6-naphthyridine-5-carboxamide

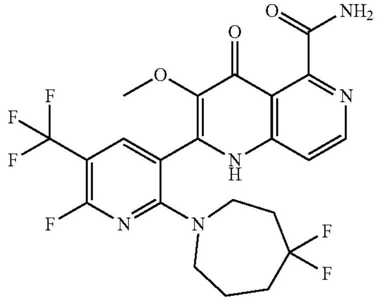

,

2-[2-(4,4-difluoroazepan-1-yl)-6-methyl-5-(trifluoromethyl)-3-pyridyl]-3-methoxy-3-oxo-1H-1,6-naphthyridine-5-carboxamide

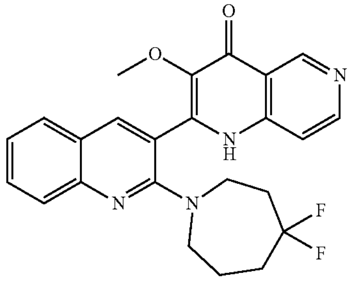

,

2-[2-(4,4-difluoroazepan-1-yl)-3-quinolyl]-3-methoxy-1H-1,6-naphthyridin-4-one

-continued

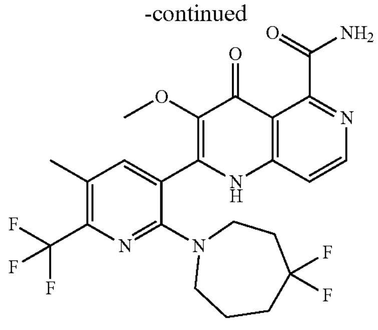

,

2-[2-(4,4-difluoroazepan-1-yl)-5-methyl-6-(trifluoromethyl)-3-pyridyl]-3-methoxy-4-oxo-1H-1,6-naphthyridine-5-carboxamide

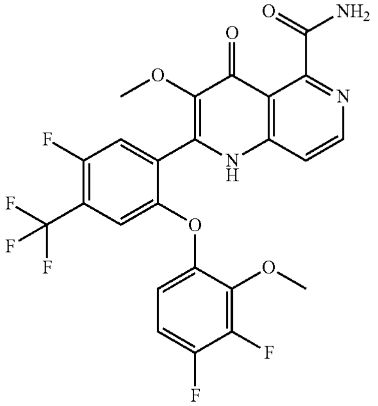

,

2-[2-(3,4-difluoro-2-methoxy-phenoxy)-5-fluoro-4-(trifluoromethyl)phenyl]-3-methoxy-4-oxo-1H-1,6-naphthyridine-5-carboxamide

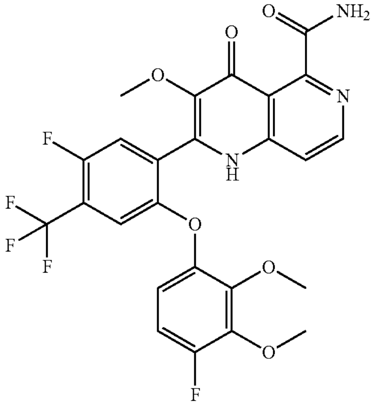

,

2-[5-fluoro-2-(4-fluoro-2,3-dimethoxy-phenoxy)-4-(trifluoromethyl)phenyl]-3-methoxy-4-oxo-1H-1,6-naphthyridine-5-carboxamide -continued

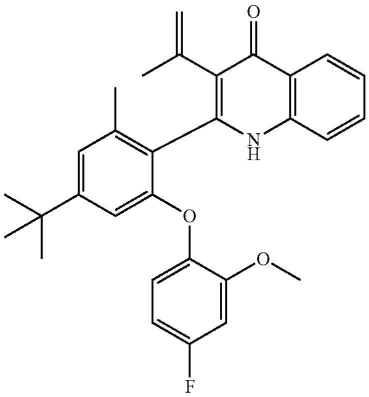

,

2-[4-tert-butyl-2-(4-fluoro-2-methoxy-phenoxy)-6-methyl-phenyl]-3-isopropenyl-1H-quinolin-4-one

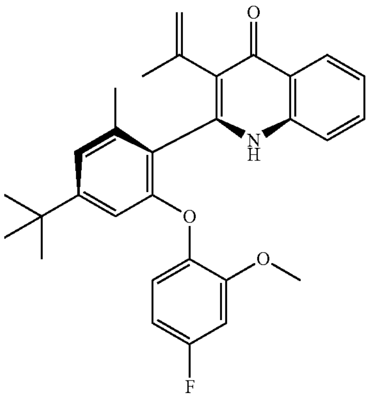

,

2-[4-tert-butyl-2-(4-fluoro-2-methoxy-phenoxy)-6-methyl-phenyl]-3-isopropenyl-1H-quinolin-4-one

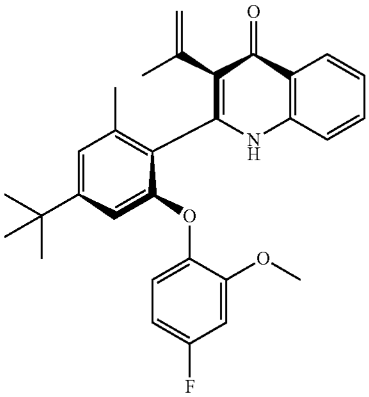

,

2-[4-tert-butyl-2-(4-fluoro-2-methoxy-phenoxy)-6-methyl-phenyl]-3-isopropenyl-1H-quinolin-4-one -continued

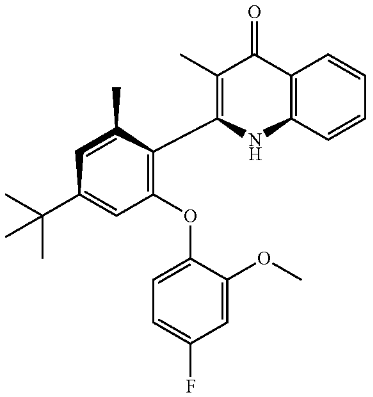

2-[4-tert-butyl-2-(4-fluoro-2-methoxy-phenoxy)-6-methyl-phenyl]-3-methyl-1H-quinolin-4-one

,

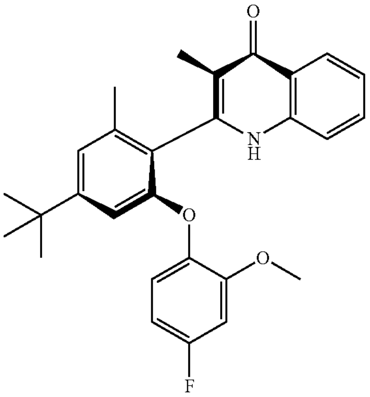

2-[4-tert-butyl-2-(4-fluoro-2-methoxy-phenoxy)-6-methyl-phenyl]-3-methyl-1H-quinolin-4-one

,

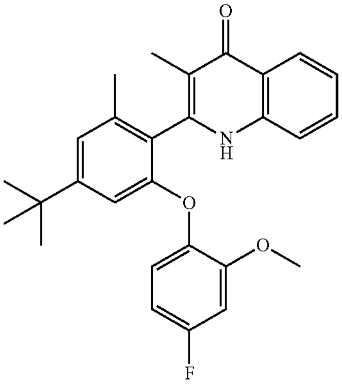

2-[4-tert-butyl-2-(4-fluoro-2-methoxy-phenoxy)-6-methyl-phenyl]-3-methyl-1H-quinolin-4-one

,

-continued

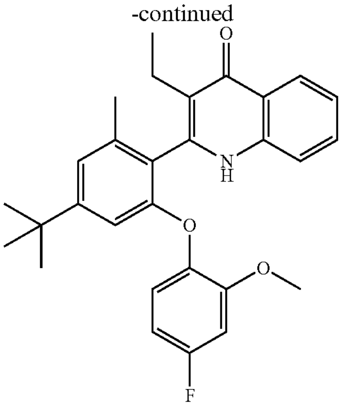

2-[4-tert-butyl-2-(4-fluoro-2-methoxy-phenoxy)-6-methyl-phenyl]-3-ethyl-1H-quinolin-4-one

,

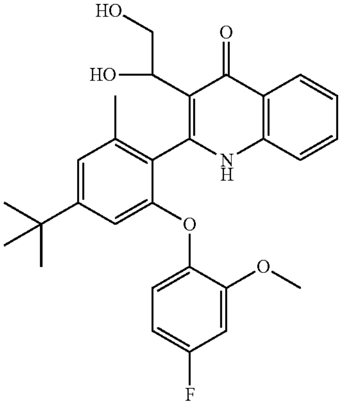

2-[4-tert-butyl-2-(4-fluoro-2-methoxy-phenoxy)-6-methyl-phenyl]-3-(1,2-dihydroxyethyl)-1H-quinolin-4-one

,

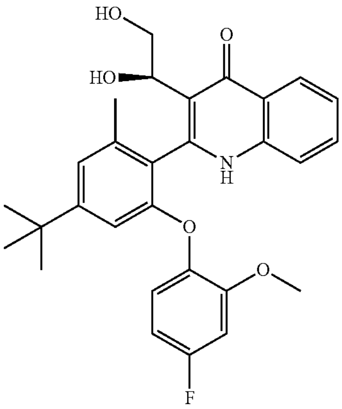

(R)-2-[4-tert-butyl-2-(4-fluoro-2-methoxy-phenoxy)-6-methyl-phenyl]-3-(1,2-dihydroxyethyl)-1H-quinolin-4-one

,

-continued

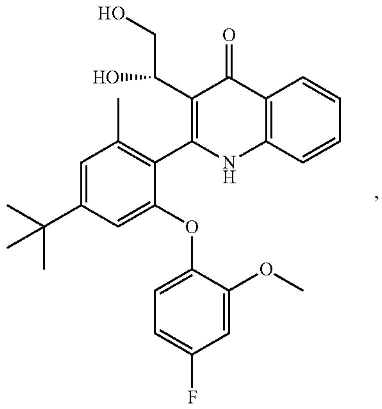

(S)-2-[4-tert-butyl-2-(4-fluoro-2-methoxy-phenoxy)-6-methyl-phenyl]-3-(1,2-dihydroxyethyl)-1H-quinolin-4-one

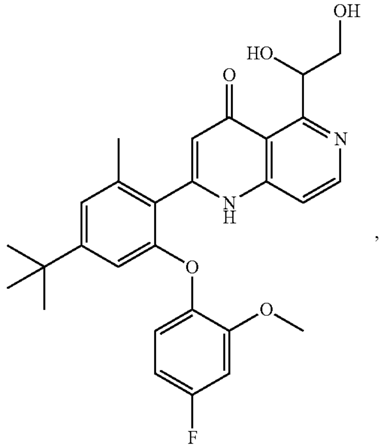

2-[4-tert-butyl-2-(4-fluoro-2-methoxy-phenoxy)-6-methyl-phenyl]-5-(1,2-dihydroxyethyl)-1H-1,6-naphthyridin-4-one

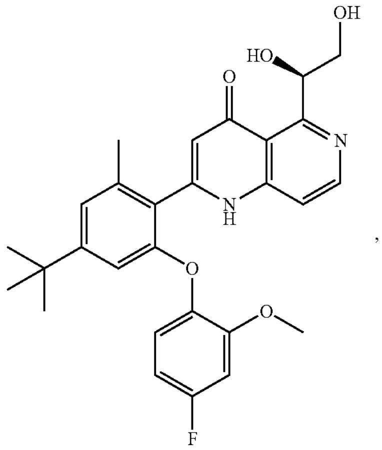

(R)-2-[4-tert-butyl-2-(4-fluoro-2-methoxy-phenoxy)-6-methyl-phenyl]-5-(1,2-dihydroxyethyl)-1H-1,6-naphthyridin-4-one -continued

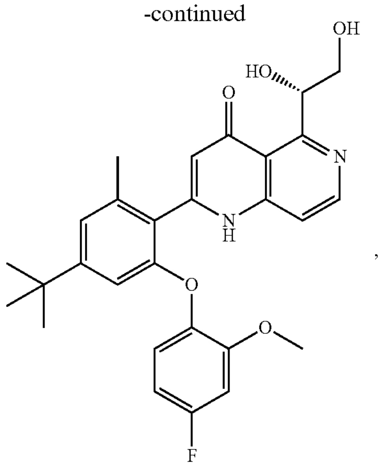

(S)-2-[4-tert-butyl-2-(4-fluoro-2-methoxy-phenoxy)-6-methyl-phenyl]-5-(1,2-dihydroxyethyl)-1H-1,6-naphthyridin-4-one

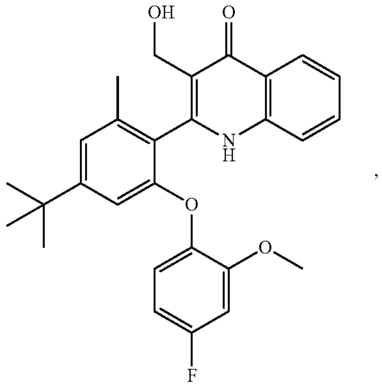

2-[4-tert-butyl-2-(4-fluoro-2-methoxy-phenoxy)-6-methyl-phenyl]-3-(1,2-hydroxymethyl)-1H-quinolin-4-one

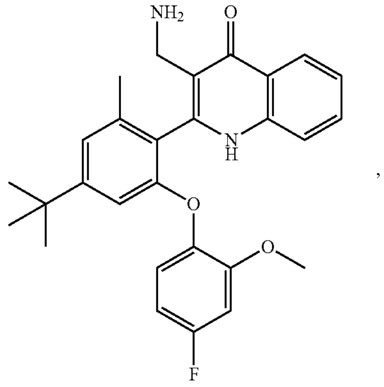

3-(aminomethyl)-2-[4-tert-butyl-2-(4-fluoro-2-methoxy-phenoxy)-6-methyl-phenyl]-1H-quinolin-4-one -continued

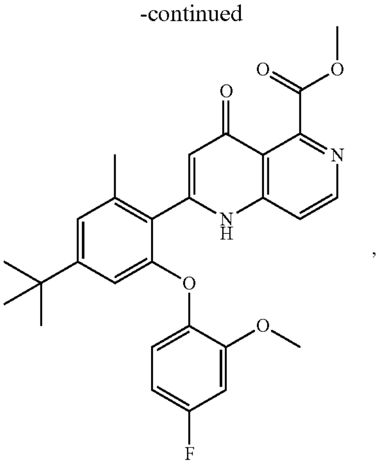

methyl 2-[4-tert-butyl-2-(4-fluoro-2-methoxy-phenoxy)-6-methyl-phenyl]-4-oxo-1H-1,6-naphthyridine-5-carboxylate

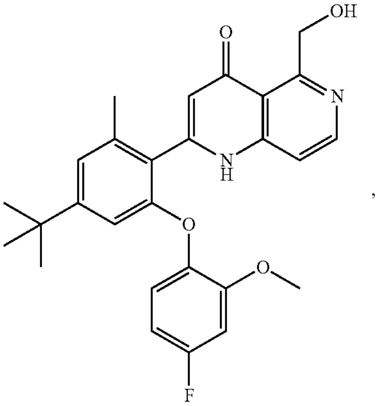

2-[4-tert-butyl-2-(4-fluoro-2-methoxy-phenoxy)-6-methyl-phenyl]-5-(hydroxymethyl)-1H-1,6-naphthyridin-4-one

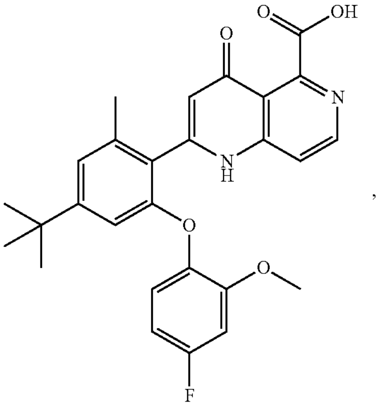

2-[4-tert-butyl-2-(4-fluoro-2-methoxy-phenoxy)-6-methyl-phenyl]-4-oxo-1H-1,6-naphthyridine-5-carboxylic acid -continued

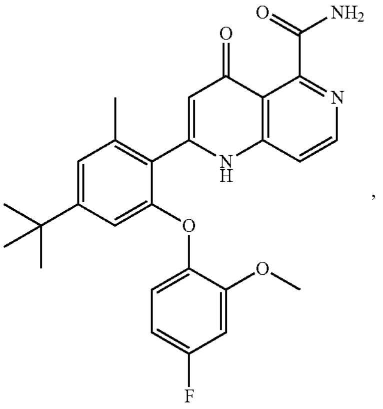

2-[4-tert-butyl-2-(4-fluoro-2-methoxy-phenoxy)-6-methyl-phenyl]-4-oxo-1H-1,6-naphthyridine-5-carboxamide

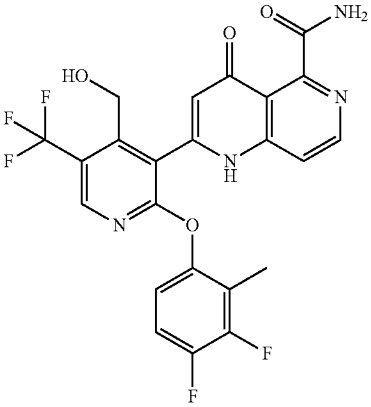

, and

2-[2-(3,4-difluoro-2-methyl-phenoxy)-4-(hydroxymethyl)-5-(trifluoromethyl)-3-pyridyl]-4-oxo-1H-1,6-naphthyridine-5-carboxamide

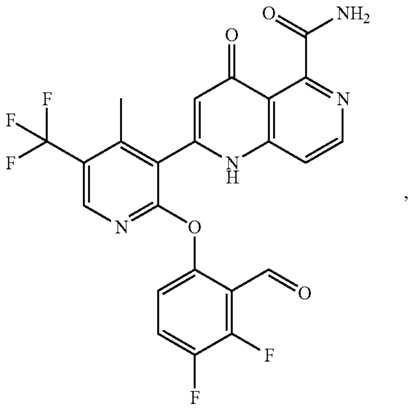

2-[2-(3,4-difluoro-2-formyl-phenoxy)-4-methyl-5-(trifluoromethyl)-3-pyridyl]-4-oxo-1H-1,6-naphthyridine-5-carboxamide or a pharmaceutically acceptable salt thereof.

5. The compound of claim 1, wherein the compound is selected from:

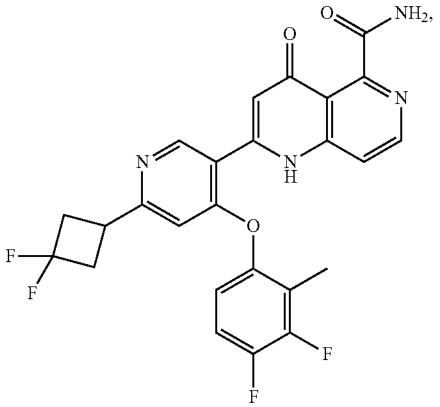

2-[6-(3,3-difluorocyclobutyl)-4-(3,4-difluoro-2-methyl-phenoxy)-3-pyridyl]-4-oxo-1H-1,6-naphthyridine-5-carboxamide

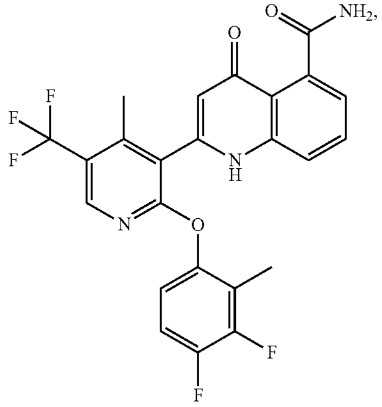

2-[2-(3,4-difluoro-2-methyl-phenoxy)-4-methyl-5-(trifluoromethyl)-3-pyridyl]-4-oxo-1H-quinoline-5-carboxamide

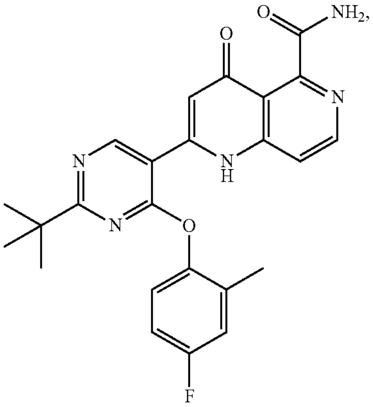

2-[2-tert-butyl-4-(4 -fluoro-2-methyl-phenoxy)pyrimidin-5-yl]-4-oxo-1H-1,6-naphthyridine-5-carboxamide -continued

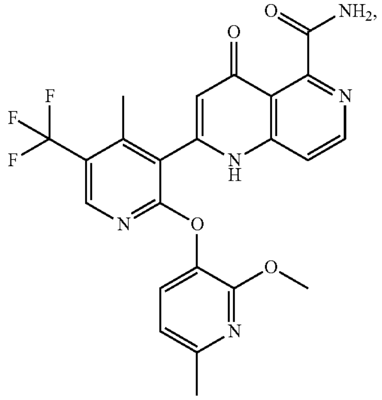

2-[2-[(2-methoxy-6-methyl-3-pyridyl)oxy]-4-methyl-5-(trifluoromethyl)-3-pyridyl]-4-oxo-1H-1,6-naphthyridine-5-carboxamide

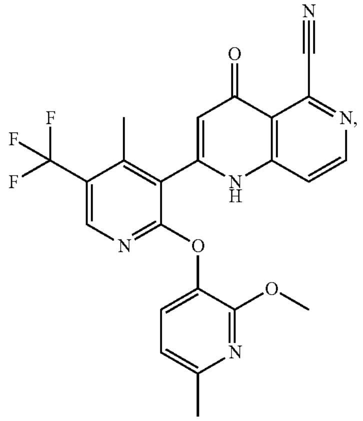

2-[2-[(2-methoxy-6-methyl-3-pyridyl)oxy]-4-methyl-5-(trifluoromethyl)-3-pyridyl]-4-oxo-1H-1,6-naphthyridine-5-carbonitrile

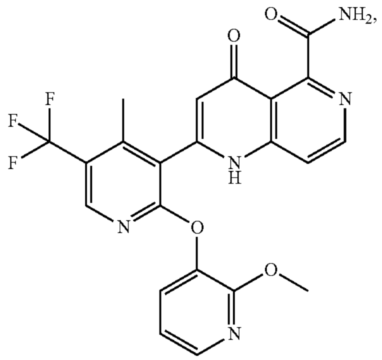

2-[2-[(2-methoxy-3-pyridyl)oxy]-4-methyl-5-(trifluoromethyl)-3-pyridyl]-4-oxo-1H-1,6-naphthyridine-5-carboxamide -continued

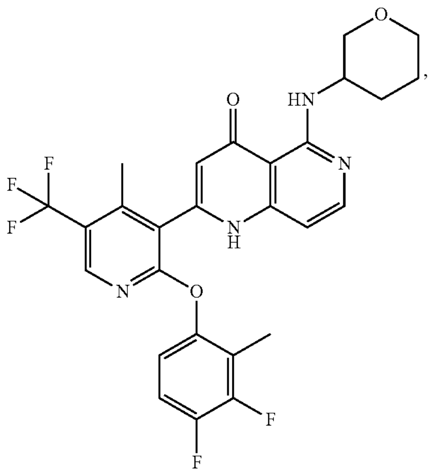

2-[2-(3,4-difluoro-2-methyl-phenoxy)-4-methyl-5-(trifluoromethyl)-3-pyridyl]-5-(tetrahydropyran-3-ylamino)-1H-1,6-naphthyridin-4-one

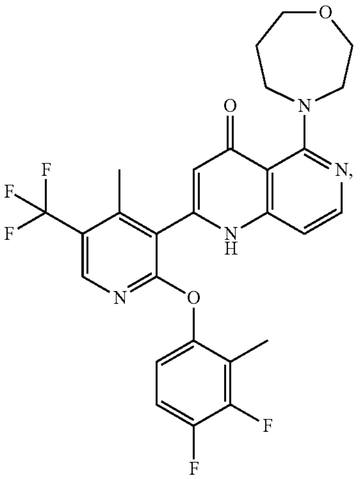

2-[2-(3,4-difluoro-2-methyl-phenoxy)-4-methyl-5-(trifluoromethyl)-3-pyridyl]-5-(1,4-oxazepan-4-yl)-1H-1,6-naphthyridin-4-one

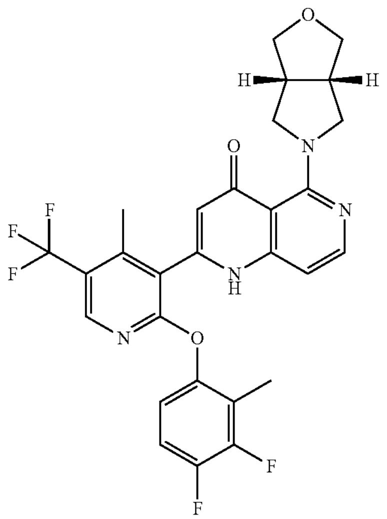

5-[(3aS,6aR)-1,3,3a,4,6,6a-hexahydrofurol[3,4-c]pyrrol-5-yl]-2-[2-(3,4-difluoro-2-methyl-phenoxy)-4-methyl-5-(trifluoromethyl)-3-pyridyl]-1H-1,6-naphthyridin-4-one -continued

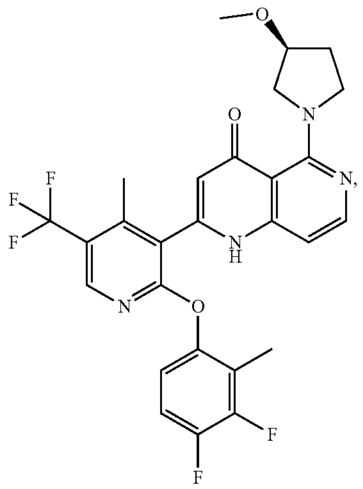

2-[2-(3,4-difluoro-2-methyl-phenoxy)-4-methyl-5-(trifluoromethyl)-3-pyridyl]-5-[(3S)-3-methoxypyrrolidin-l-yl]-1H-1,6-naphthyridin-4-one

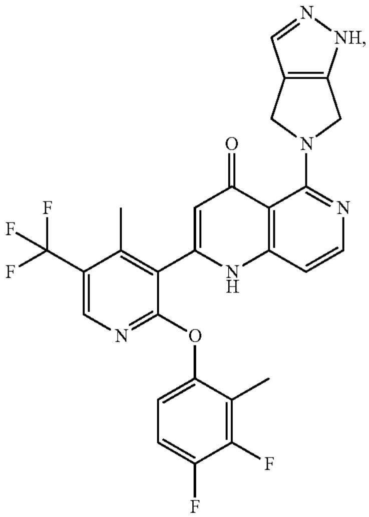

2-[2-(3,4-difluoro-2-methyl-phenoxy)-4-methyl-5-(trifluoromethyl)-3-pyridyl]-5-(4,6-dihydro-1H-pyrrolo[3,4-c]pyrazol-5-yl)-1H-1,6-naphthyridin-4-one -continued

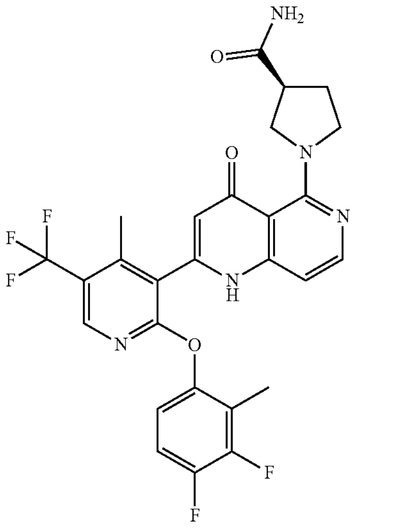

(3S)-1-[2-[2-(3,4-difluoro-2-methyl-phenoxy)-4-methyl-5-(trifluoromethyl)-3-pyridyl]-4-oxo-1H-1,6-naphthyridin-5-yl]pyrrolidine-3-carboxamide

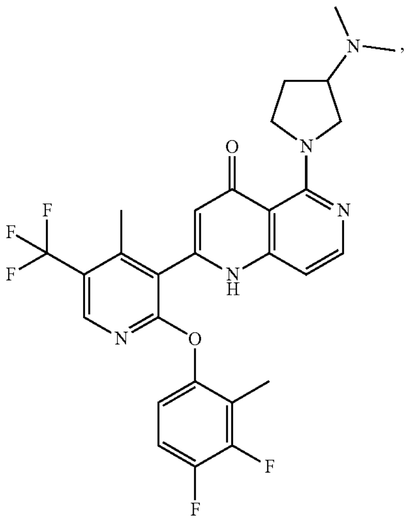

2-[2-(3,4-difluoro-2-methyl-phenoxy)-4-methyl-5-(trifluoromethyl)-3-pyridyl]-5-[3-(dimethylamino)pyrrolidin-1-yl]-1H-1,6-naphthyridin-4-one

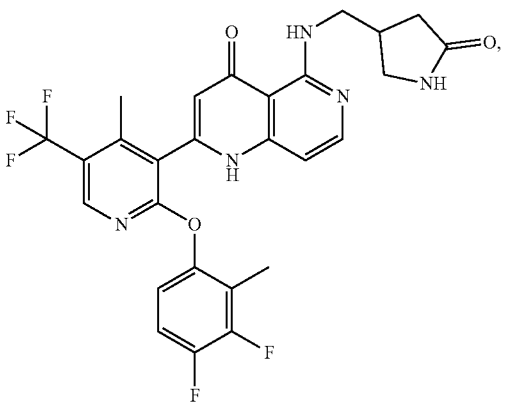

2-[2-(3,4-difluoro-2-methyl-phenoxy)-4-methyl-5-(trifluoromethyl)-3-pyridyl]-5-[(5-oxopyrrolidin-3-yl)methylamino]-1H-1,6-naphthyridin-4-one -continued

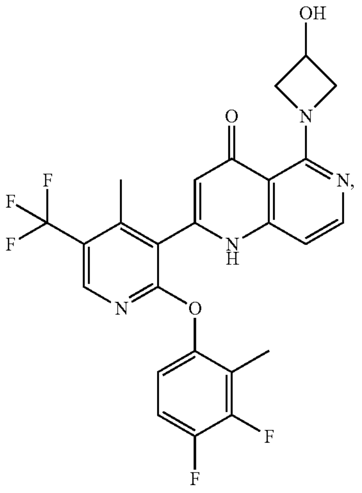

2-[2-(3,4-difluoro-2-methyl-phenoxy)-4-methyl-5-(trifluoromethyl)-3-pyridyl]-5-(3-hydroxyazetidin-1-yl)-1H-1,6-naphthyridin-4-one

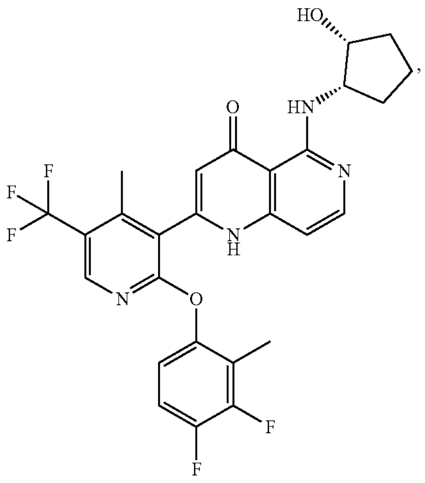

2-[2-(3,4-difluoro-2-methyl-phenoxy)-4-methyl-5-(trifluoromethyl)-3-pyridyl]-5-[[(1S,2R)-2-hydroxycyclopentyl]amino]-1H-1,6-naphthyridin-4-one

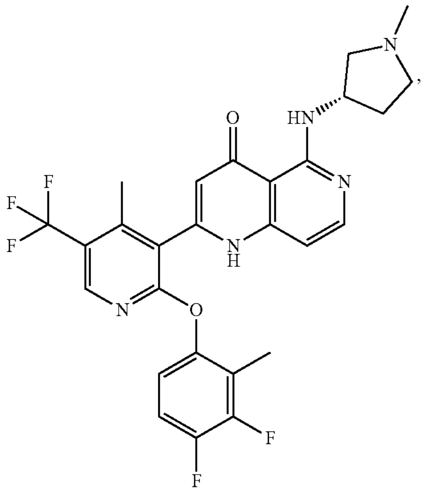

2-[2-(3,4-difluoro-2-methyl-phenoxy)-4-methyl-5-(trifluoromethyl)-3-pyridyl]-5-[[(3S)-1-methylpyrrolidin-3-yl]amino]-1H-1,6-naphthyridin-4-one -continued

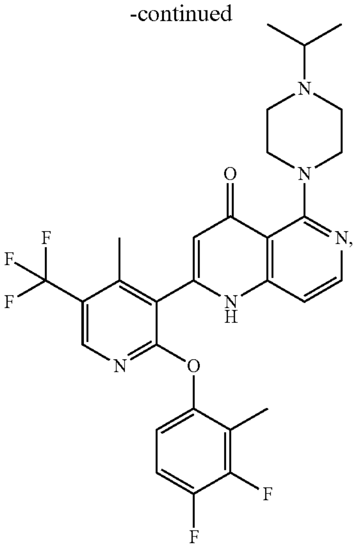

2-[2-(3,4-difluoro-2-methyl-phenoxy)-4-methyl-5-(trifluoromethyl)-3-pyridyl]-5-(4-isopropylpiperazin-1-yl)-1H-1,6-naphthyridin-4-one

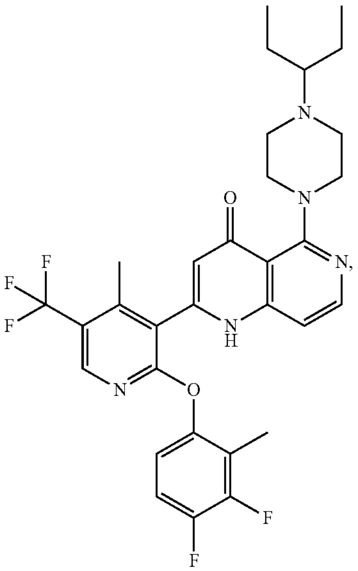

2-[2-(3,4-difluoro-2-methyl-phenoxy)-4-methyl-5-(trifluoromethyl)-3-pyridyl]-5-[4-(1-ethylpropyl)piperazin-1-yl]-1H-1,6-naphthyridin-4-one -continued

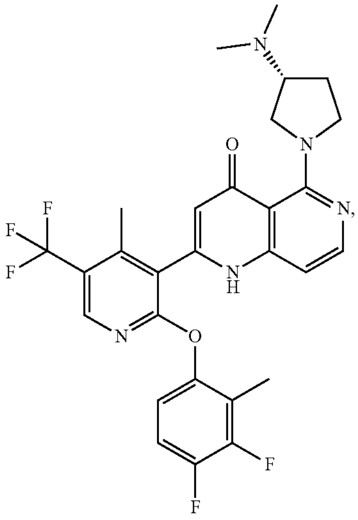

2-[2-(3,4-difluoro-2-methyl-phenoxy)-4-methyl-5-(trifluoromethyl)-3-pyridyl]-5-[(3R)-3-(dimethylamino)pyrrolidin-1-yl]-1H-1,6-naphthyridin-4-one

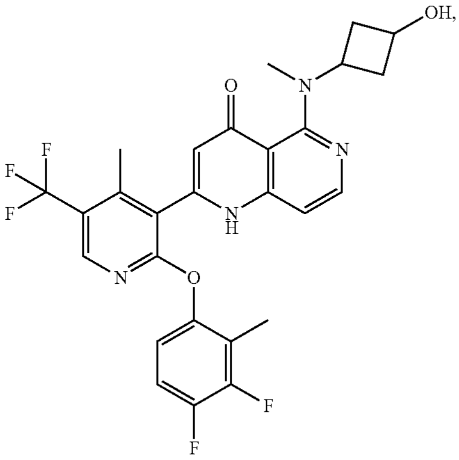

2-[2-(3,4-difluoro-2-methyl-phenoxy)-4-methyl-5-(trifluoromethyl)-3-pyridyl]-5-[(3-hydroxycyclobutyl)-methyl-amino]-1H-1,6-naphthyridin-4-one

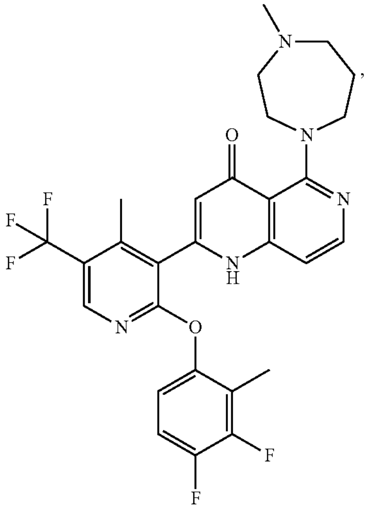

2-[2-(3,4-difluoro-2-methyl-phenoxy)-4-methyl-5-(trifluoromethyl)-3-pyridyl]-5-(4-methyl-1,4-diazepan-1-yl)-1H-1,6-naphthyridin-4-one -continued

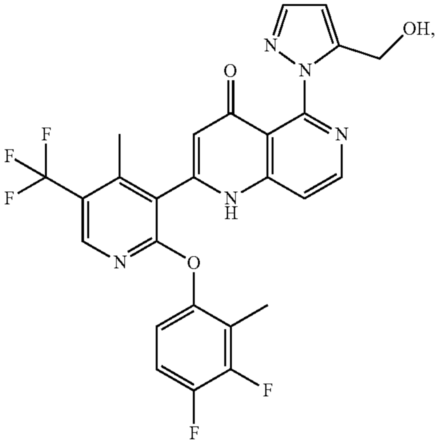

2-[2-(3,4-difluoro-2-methyl-phenoxy)-4-methyl-5-(trifluoromethyl)-3-pyridyl]-5-[5 -(hydroxymethyl)pyrazol-1-yl]-1H-1,6-naphthyridin-4-one

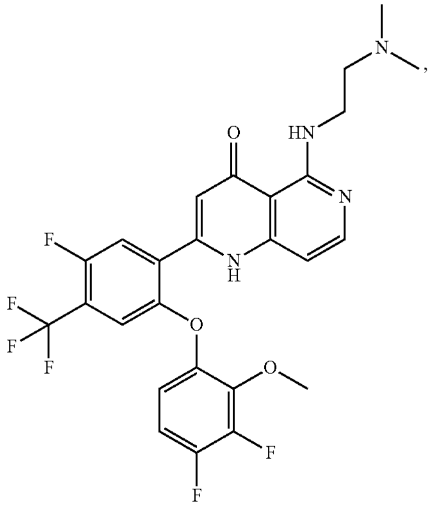

2-[2-(3,4-difluoro-2-methoxy-phenoxy)-5-fluoro-4-(trifluoromethyl)phenyl]-5-[2-(dimethylamino)ethylamino]-1H-1,6-naphthyridin-4-one

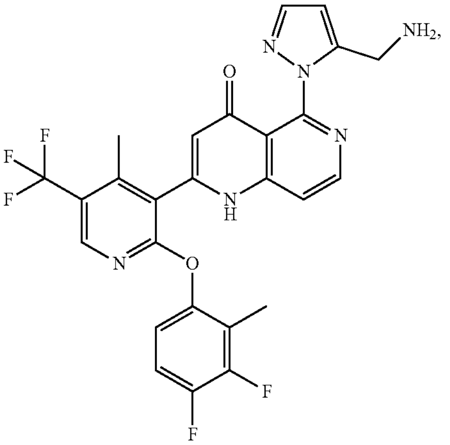

5-[5-(aminomethyl)pyrazol-1-yl]-2-[2-(3,4-difluoro-2-methyl-phenoxy)-4-methy1-5-(trifluoromethyl)-3-pyridyl]-1H-1,6-naphthyridin-4-one -continued

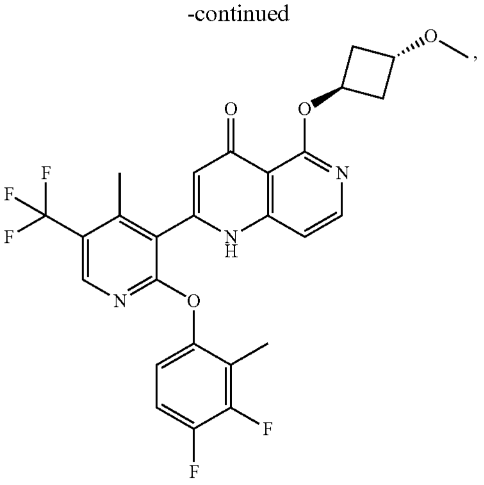

2-[2-(3,4-difluoro-2-methyl-phenoxy)-4-methyl-5-(trifluoromethyl)-3-pyridyl]-5-(3-methoxycyclobutoxy)-1H-1,6-naphthyridin-4-one

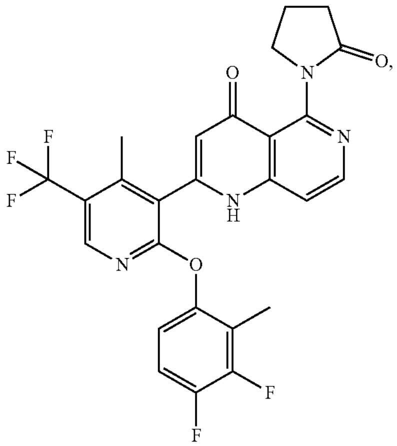

2-[2-(3,4-difluoro-2-methyl-phenoxy)-4-methyl-5-(trifluoromethyl)-3-pyridyl]-5-(2-oxopyrrolidin-1-yl)-1H-1,6-naphthyridin-4-one

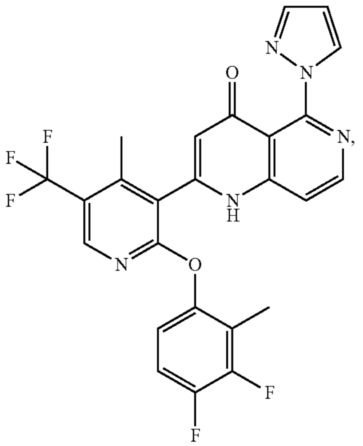

2-[2-(3,4-difluoro-2-methyl-phenoxy)-4-methyl-5-(trifluoromethyl)-3-pyridyl]-5-pyrazol-1-yl-1H-1,6-naphthyridin-4-one -continued

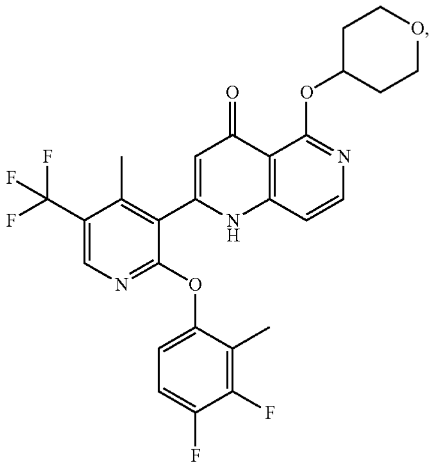

2-[2-(3,4-difluoro-2-methyl-phenoxy)-4-methyl-5-(trifluoromethyl)-3-pyridyl]-5-tetrahydropyran-4-yloxy-1H-1,6-naphthyridin-4-one

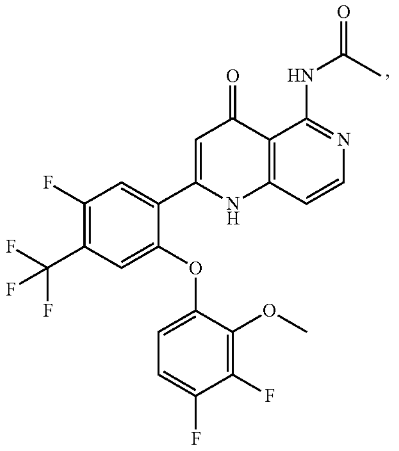

N-[2-[2-(3,4-difluoro-2-methoxy-phenoxy)-5-fluoro-4-(trifluoromethyl)phenyl]-4-oxo-1H-1,6-naphthyridin-5-yl]acetamide

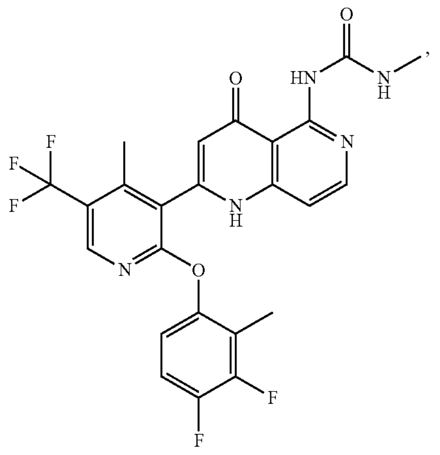

1-[2-[2-(3,4-difluoro-2-methyl-phenoxy)-4-methyl-5-(trifluoromethyl)-3-pyridyl]-4-oxo-1H-1,6-naphthyridin-5-yl]-3-methyl-urea -continued

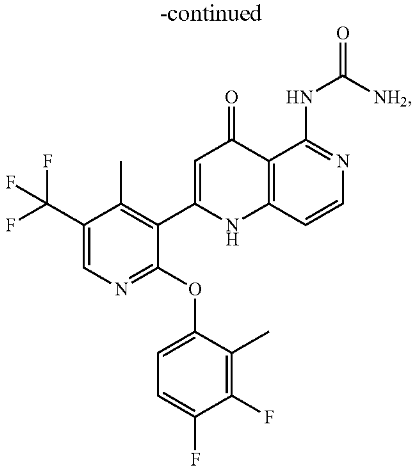

[2-[2-(3,4-difluoro-2-methyl-phenoxy)-4-methyl-5-(trifluoromethyl)-3-pyridyl]-4-oxo-1H-1,6-naphthyridin-5-yl]-urea

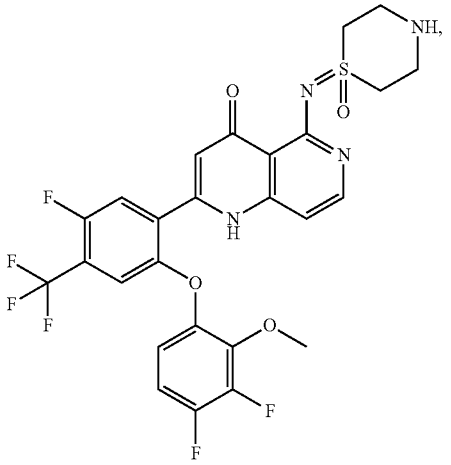

2-[2-(3,4-difluoro-2-methoxy-phenoxy)-5-fluoro-4-(trifluoromethyl)phenyl]-5-[(1-oxo-1,4-thiazinan-1-ylidene)amino]-1H-1,6-naphthyridin-4-one

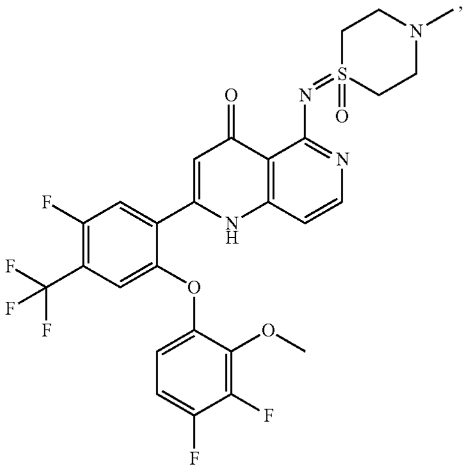

2-[2-(3,4-difluoro-2-methoxy-phenoxy)-5-fluoro-4-(trifluoromethyl)phenyl]-5-[(4-methyl-1-oxo-1,4-thiazinan-1-ylidene)amino]-1H-1,6-naphthyridin-4-one

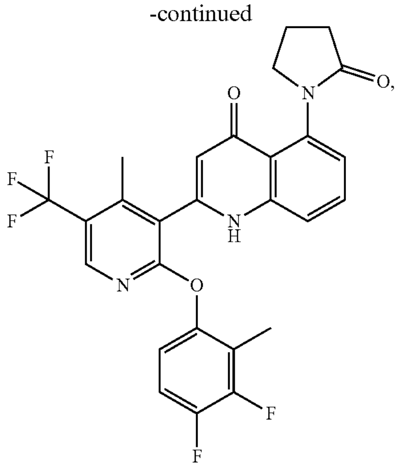

2-[2-(3,4-difluoro-2-methyl-phenoxy)-4-methyl-5-(trifluoromethyl)-3-pyridyl]-5-(2-oxopyrrolidin-1-yl)-1H-quinolin-4-one

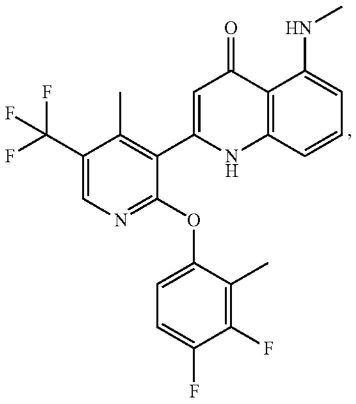

2-[2-(3,4-difluoro-2-methyl-phenoxy)-4-methyl-5-(trifluoromethyl)-3-pyridyl]-5-(methylamino)-1H-quinolin-4-one

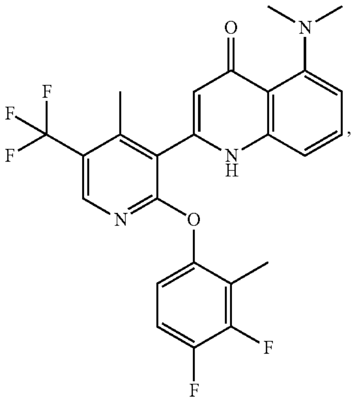

2-[2-(3,4-difluoro-2-methyl-phenoxy)-4-methyl-5-(trifluoromethyl)-3-pyridyl]-5-(dimethylamino )-1H-quinolin-4-one

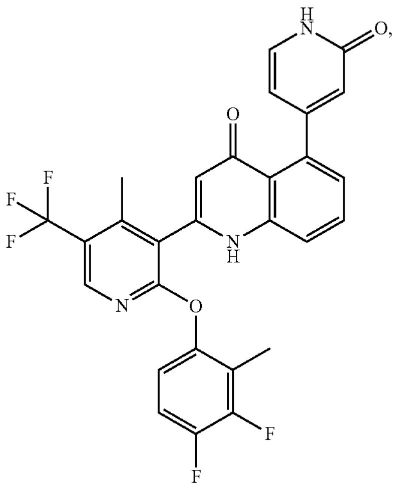

N-[2-[2-(3,4-difluoro-2-methoxy-phenoxy)-5-fluoro-4-(trifluoromethyl)phenyl]-4-oxo-1H-1,6-naphthyridin-5-yl]acetamide

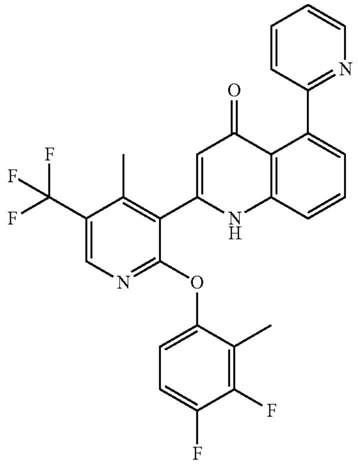

2-[2-(3,4-difluoro-2-methyl-phenoxy)-4-methyl-5-(trifluoromethyl)-3-pyridyl]-5-(2-pyridyl)-1H-quinolin-4-one,

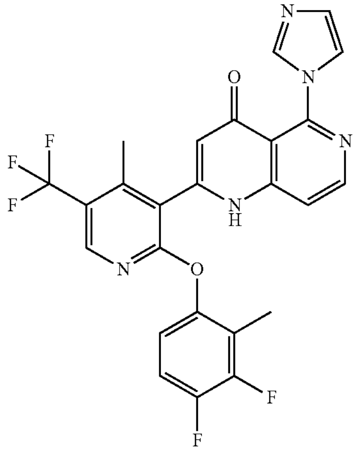

2-[2-(3,4-difluoro-2-methyl-phenoxy)-4-methyl-5-(trifluoromethyl)-3-pyridyl]-5-imidazol-1-yl-1H-1,6-naphthyridin-4-one, -continued

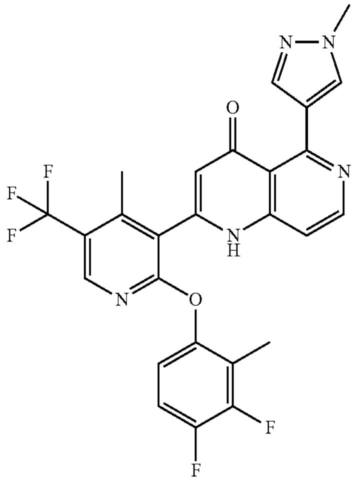

2-[2-(3,4-difluoro-2-methyl-phenoxy)-4-methyl-5-(trifluoromethyl)-3-pyridyl]-5-(1-methylpyrazol-4-yl)-1H-1,6-naphthyridin-4-one,

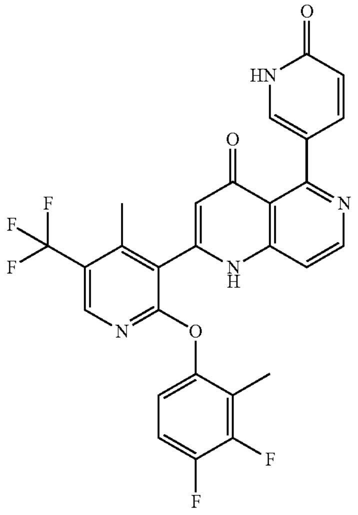

2-[2-(3,4-difluoro-2-methyl-phenoxy)-4-methyl-5-(trifluoromethyl)-3-pyridyl]-5-(6-oxo-1H-pyridin-3-yl)-1H-1,6-naphthyridin-4-one,

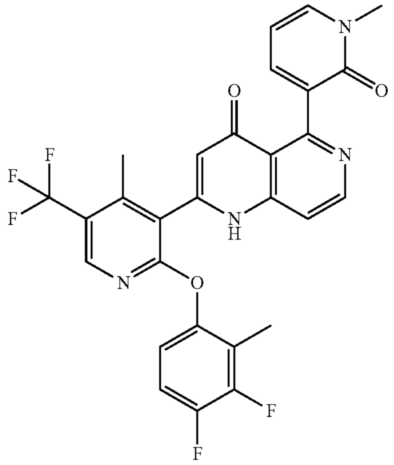

2-[2-(3,4-difluoro-2-methyl-phenoxy)-4-methyl-5-(trifluoromethyl)-3-pyridyl]-5-(1-methyl-2-oxo-3-pyridyl)-1H-1,6-naphthyridin-4-one, -continued

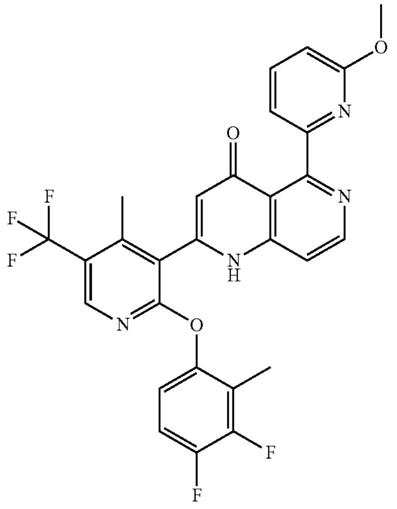

2-[2-(3,4-difluoro-2-methyl-phenoxy)-4-methyl-5-(trifluoromethyl)-3-pyridyl]-5-(6-methoxy-2-pyridyl)-1H-1,6-naphthyridin-4-one,

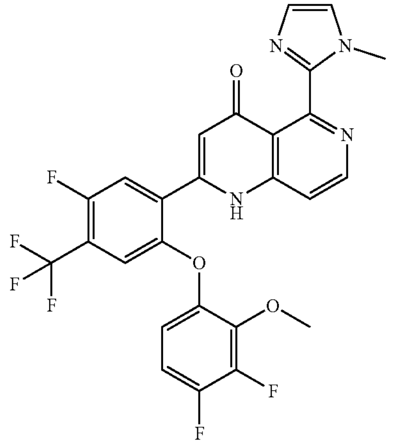

2-[2-(3,4-difluoro-2-methoxy-phenoxy)-5-fluoro-4-(trifluoromethyl)phenyl]-5-(1-methylimidazol-2-yl)-1H-1,6-naphthyridin-4-one,

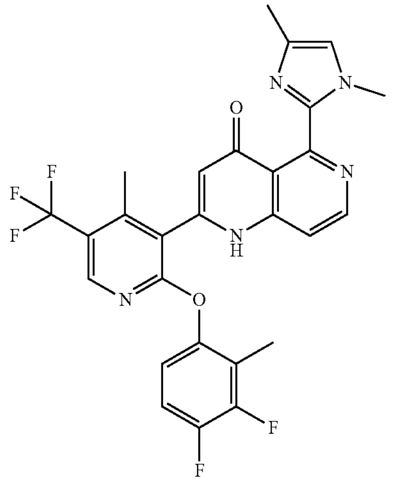

2-[2-(3,4-difluoro-2-methyl-phenoxy)-4-methyl-5-(trifluoromethyl)-3-pyridyl]-5-(1,4-dimethylimidazol-2-yl)-1H-1,6-naphthyridin-4-one, -continued

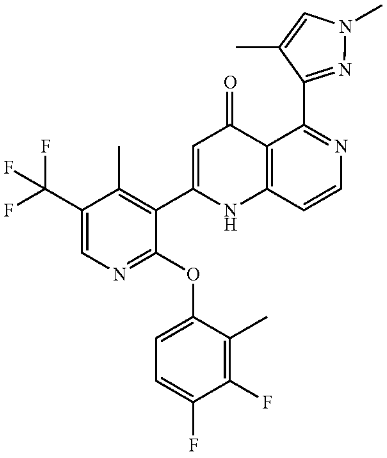

2-[2-(3,4-difluoro-2-methyl-phenoxy)-4-methyl-5-(trifluoromethyl)-3-pyridyl]-5-(1-4-dimethylpyrazol-3-yl)-1H-1,6-naphthyridin-4-one,

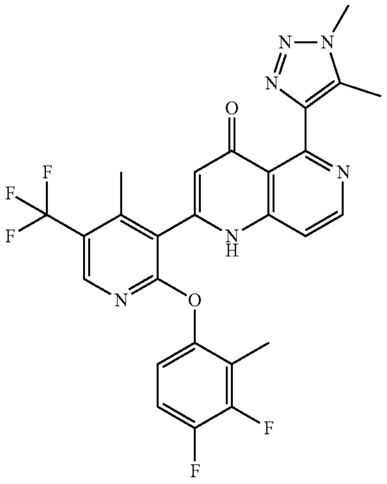

2-[2-(3,4-difluoro-2-methyl-phenoxy)-4-methyl-5-(trifluoromethyl)-3-pyridyl]-5-(1,5-dimethyltriazol-4-yl)-1H-1,6-naphthyridin-4-one,

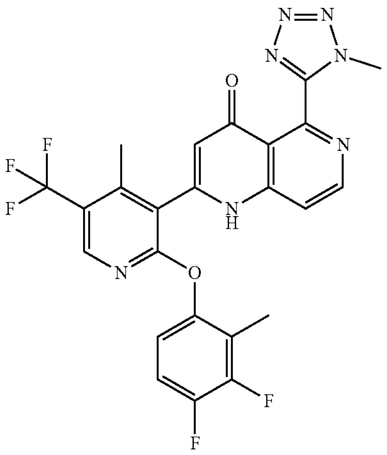

2-[2-(3,4-difluoro-2-methyl-phenoxy)-4-methyl-5-(trifluoromethyl)-3-pyridyl]-5-(1-methyltetrazol-5-yl)-1H-1,6-naphthyridin-4-one, -continued

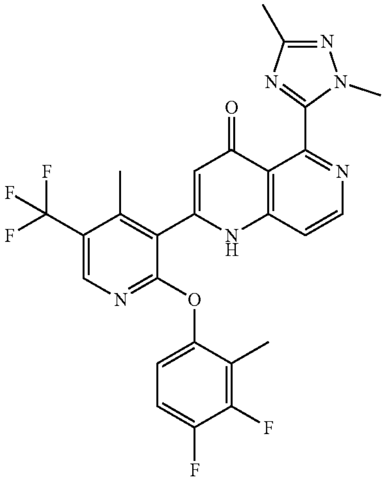

2-[2-(3,4-difluoro-2-methyl-phenoxy)-4-methyl-5-(trifluoromethyl)-3-pyridyl]-5-(2,5-dimethyl-1,2,4-triazol-3-yl)-1H-1,6-naphthyridin-4-one,

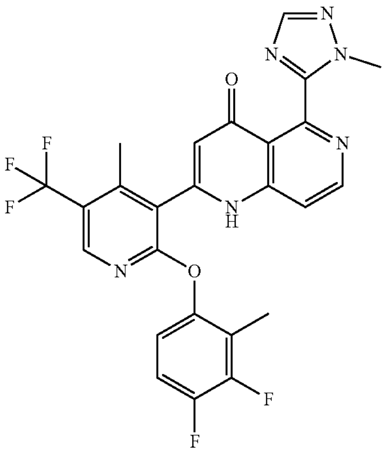

2-[2-(3,4-difluoro-2-methyl-phenoxy)-4-methyl-5-(trifluoromethyl)-3-pyridyl]-5-(2-methyl-,12,4-triazol-3-yl)-1H-1,6-naphthyridin-4-one,

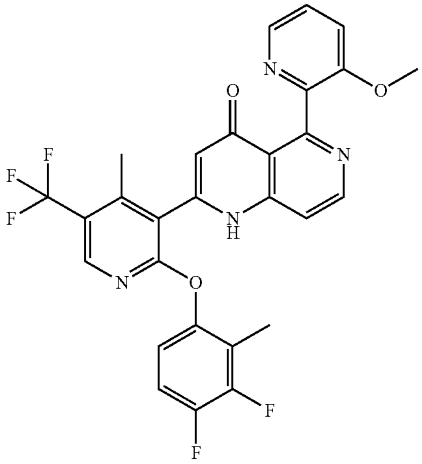

2-[2-(3,4-difluoro-2-methyl-phenoxy)-4-methyl-5-(trifluoromethyl)-3-pyridyl]-5-(3-methoxy-2-pyridyl)-1H-1,6-naphthyridin-4-one, -continued

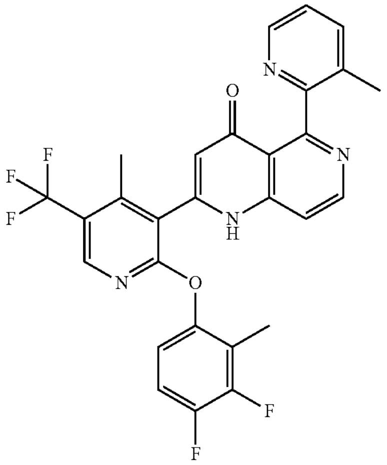

2-[2-(3,4-difluoro-2-methyl-phenoxy)-4-methyl-5-(trifluoromethyl)-3-pyridyl]-5-(3-methyl-2-pyridyl)-1H-1,6-naphthyridin-4-one,

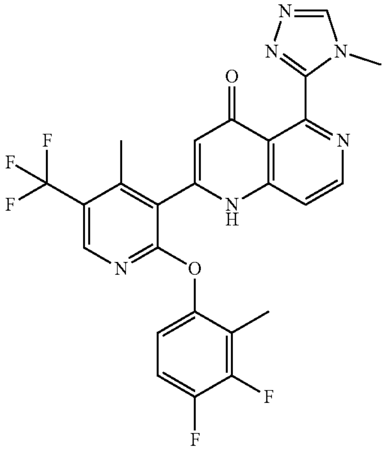

2-[2-(3,4-difluoro-2-methyl-phenoxy)-4-methyl-5-(trifluoromethyl)-3-pyridyl]-5-(4-methyl-1,2,4-triazol-3-yl)-1H-1,6-naphthyridin-4-one,

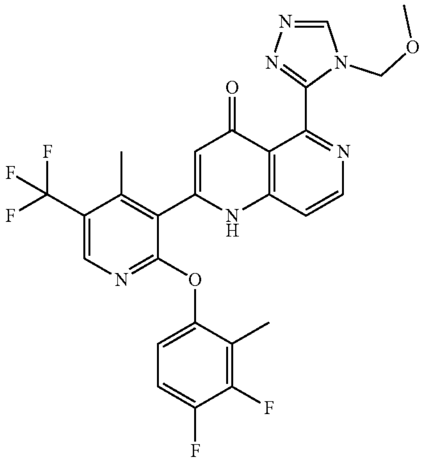

2-[2-(3,4-difluoro-2-methyl-phenoxy)-4-methyl-5-(trifluoromethyl)-3-pyridyl]-5-[1-(methoxymethyl)tetrazol-5-yl]-1H-1,6-naphthyridin-4-one, -continued

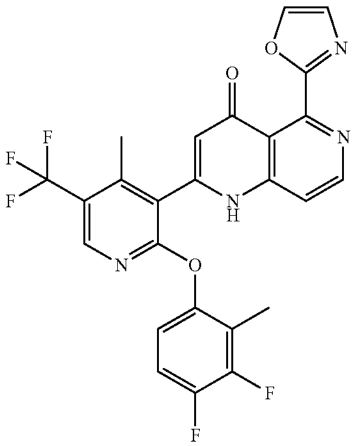

2-[2-(3,4-difluoro-2-methyl-phenoxy)-4-methyl-5-(trifluoromethyl)-3-pyridyl]-5-oxazol-2-yl-1H-1,6-naphthyridin-4-one,

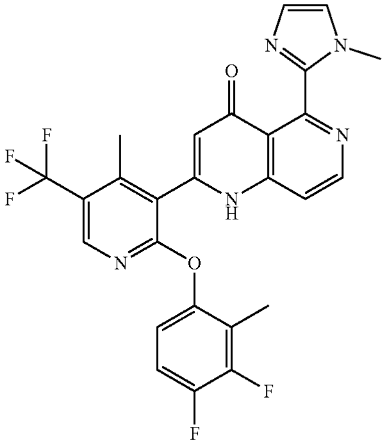

2-[2-(3,4-difluoro-2-methyl-phenoxy)-4-methyl-5-(trifluoromethyl)-3-pyridyl]-5-(1-methylimidazol-2-yl)-1H-1,6-naphthyridin-4-one,

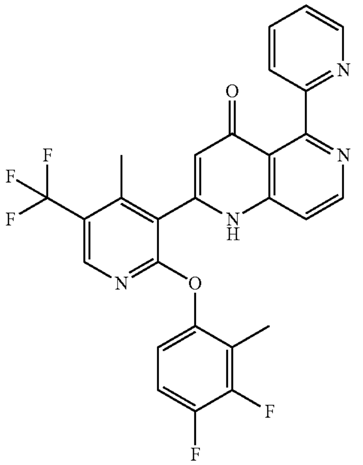

2-[2-(3,4-difluoro-2-methyl-phenoxy)-4-methyl-5-(trifluoromethyl)-3-pyridyl]-5-(2-pyridyl)-1H-1,6-naphthyridin-4-one, -continued

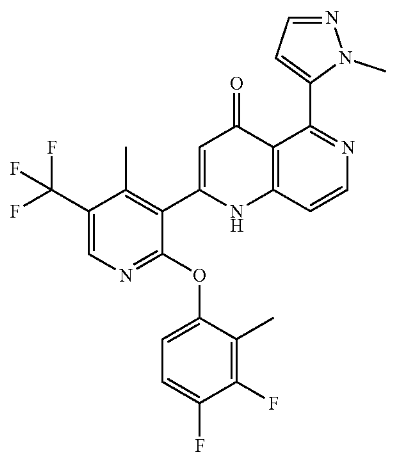

2-[2-(3,4-difluoro-2-methyl-phenoxy)-4-methyl-5-(trifluoromethyl)-3-pyridyl]-5-(2-methylpyrazol-3-yl)-1H-1,6-naphthyridin-4-one,

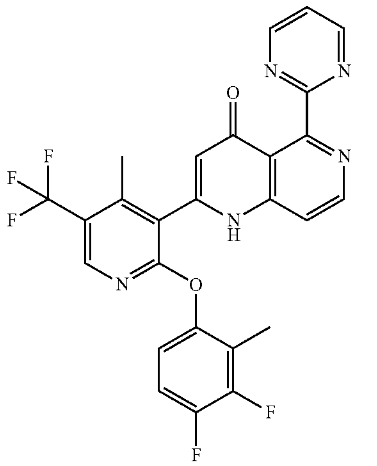

2-[2-(3,4-difluoro-2-methyl-phenoxy)-4-methyl-5-(trifluoromethyl)-3-pyridyl]-5-pyrimidin-2-yl-1H-1,6-naphthyridin-4-one,

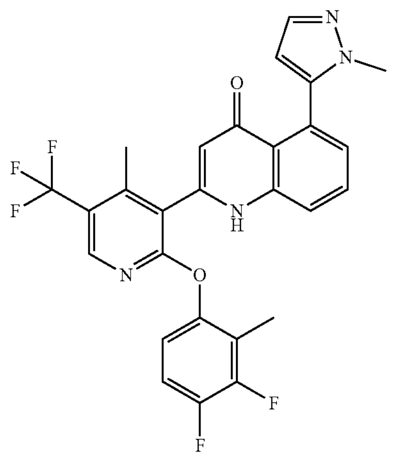

2-[2-(3,4-difluoro-2-methyl-phenoxy)-4-methyl-5-(trifluoromethyl)-3-pyridyl]-5-(2-methylpyrazol-3-yl)-1H-quinolin-4-one, -continued

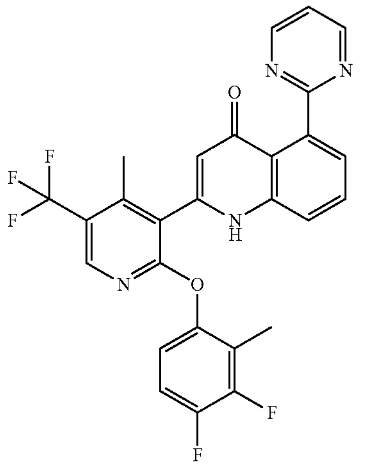

2-[2-(3,4-difluoro-2-methyl-phenoxy)-4-methyl-5-(trifluoromethyl)-3-pyridyl]-5-pyrimidin-2-yl-1H-quinolin-4-one,

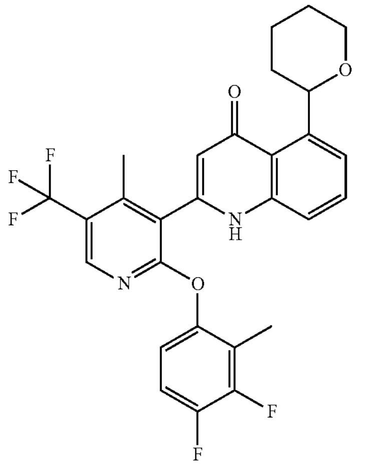

2-[2-(3,4-difluoro-2-methyl-phenoxy)-4-methyl-5-(trifluoromethyl)-3-pyridyl]-5-tetrahydropyran-2-yl-1H-quinolin-4-one,

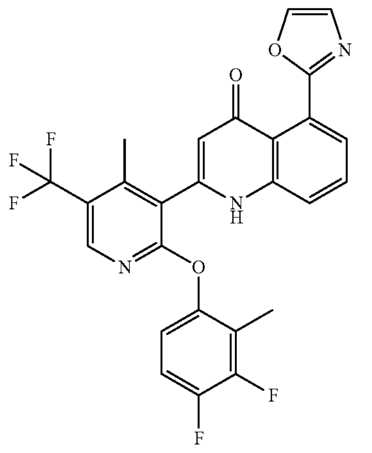

2-[2-(3,4-difluoro-2-methyl-phenoxy)-4-methyl-5-(trifluoromethyl)-3-pyridyl]-5-oxazol-2-yl-1H-quinolin-4-one, -continued

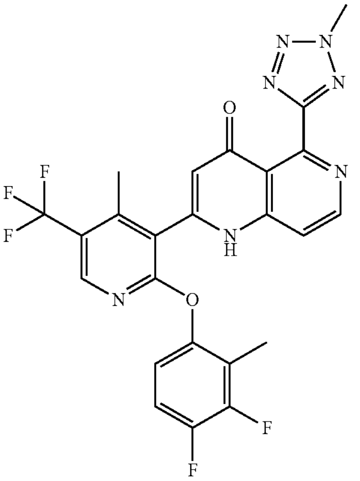

2-[2-(3,4-difluoro-2-methyl-phenoxy)-4-methyl-5-(trifluoromethyl)-3-pyridyl]-5-(2-methyltetrazol-5-yl)-1H-1,6-naphthyridin-4-one,

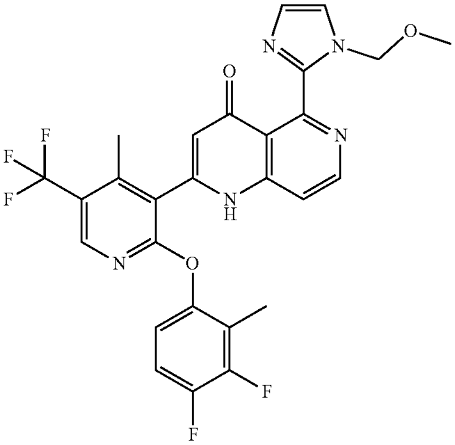

2-[2-(3,4-difluoro-2-methyl-phenoxy)-4-methyl-5-(trifluoromethyl)-3-pyridyl]-5-[1-(methoxymethyl)imidazol-2-yl]-1H-1,6-naphthyridin-4-one,

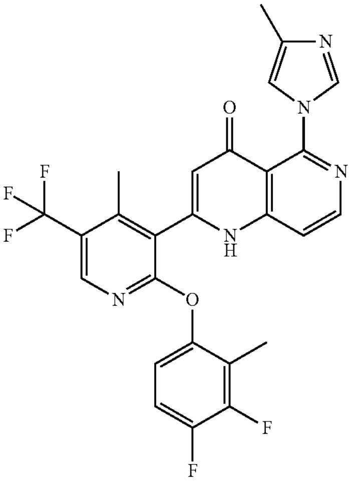

2-[2-(3,4-difluoro-2-methyl-phenoxy)-4-methyl-5-(trifluoromethyl)-3-pyridyl]-5-(4-methyltetrazol-1-yl)-1H-1,6-naphthyridin-4-one, -continued

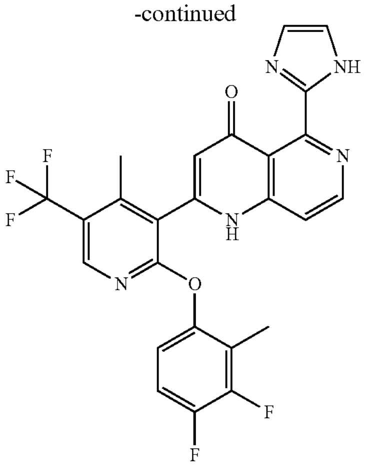

2-[2-(3,4-difluoro-2-methyl-phenoxy)-4-methyl-5-(trifluoromethyl)-3-pyridyl]-5-[1H-imidazol-2-yl]-1H-1,6-naphthyridin-4-one,

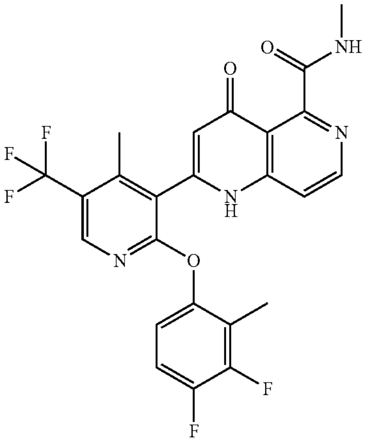

2-[2-(3,4-difluoro-2-methyl-phenoxy)-4-methyl-5-(trifluoromethyl)-3-pyridyl]-N-methyl-4-oxo-[1H-1,6-naphthyridine-5-carboxamide,

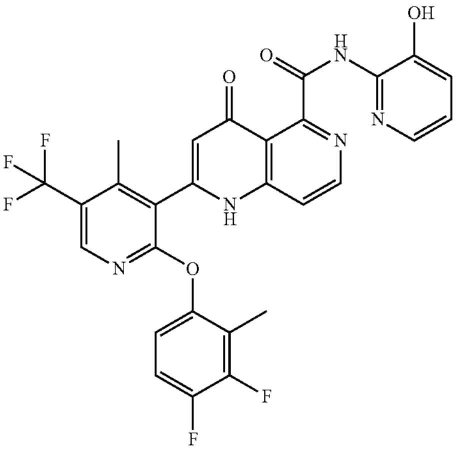

2-[2-(3,4-difluoro-2-methyl-phenoxy)-4-methyl-5-(trifluoromethyl)-3-pyridyl]-N-(3-hydroxy-2-pyridyl)-4-oxo-1H-1,6-naphthyridine-5-carboxamide, -continued

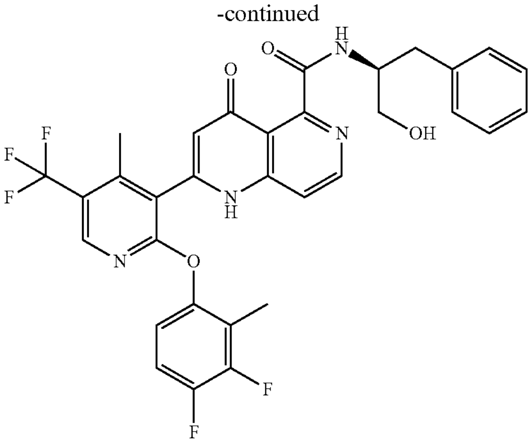

N-[(1S)-1-benzyl-2-hydroxy-ethyl]-2-[2-(3,4-difluoro-2-methyl-phenoxy)-4-methyl-5-(trifluoromethyl)-3-pyridyl]-4-oxo-1H-1,6-naphthyridine-5-carboxamide,

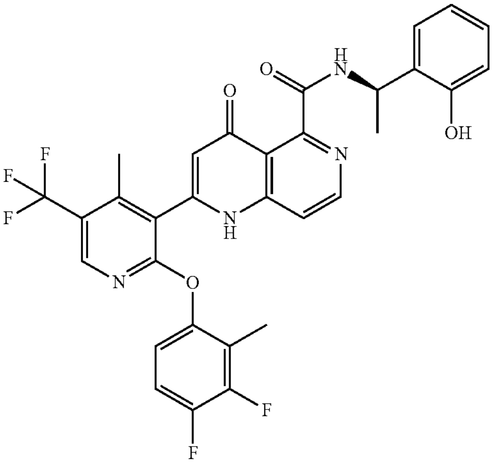

2-[2-(3,4-difluoro-2-methyl-phenoxy)-4-methyl-5-(trifluoromethyl)-3-pyridyl]-N-[(1R)-1-(2-hydroxyphenyl)ethyl]-4-oxo-1H-1,6-naphthyridine-5-carboxamide,

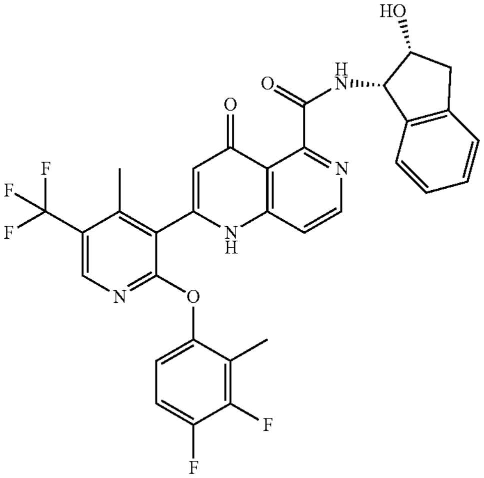

2-[2-(3,4-difluoro-2-methyl-phenoxy)-4-methyl-5-(trifluoromethyl)-3-pyridyl]-N-[(1S,2R)-2-hydroxyindan-1-yl)-4-oxo-1H-1,6-naphthyridine-5-carboxamide,

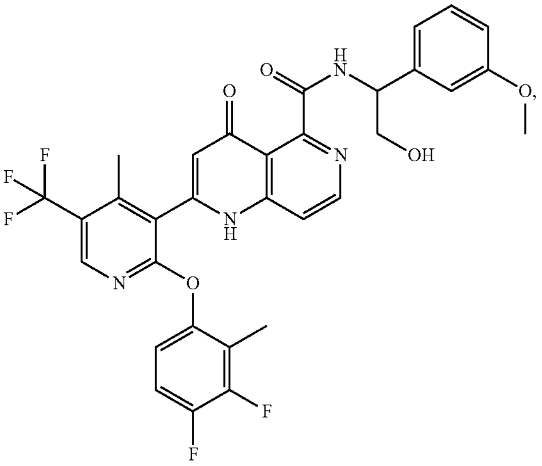

2-[2-(3,4-difluoro-2-methyl-phenoxy)-4-methyl-5-(trifluoromethyl)-3-pyridyl]-N-[2-hydroxy-1-(3-methoxyphenyl)ethyl]-4-oxo-1H-1,6-naphthyridine-5-carboxamide

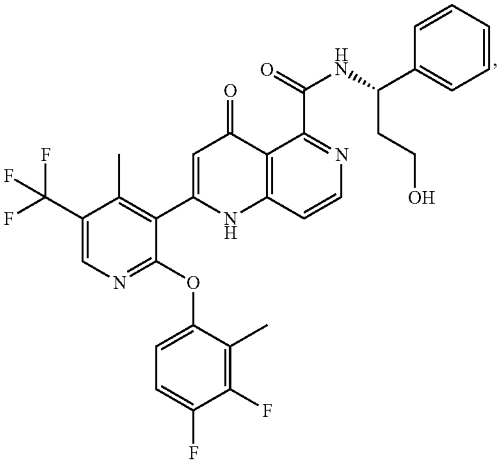

2-[2-(3,4-difluoro-2-methyl-phenoxy)-4-methyl-5-(trifluoromethyl)-3-pyridyl]-N-[(1S)-3-hydroxy-1-phenyl-propyl]-4-oxo-1H-1,6-naphthyridine-5-carboxamide

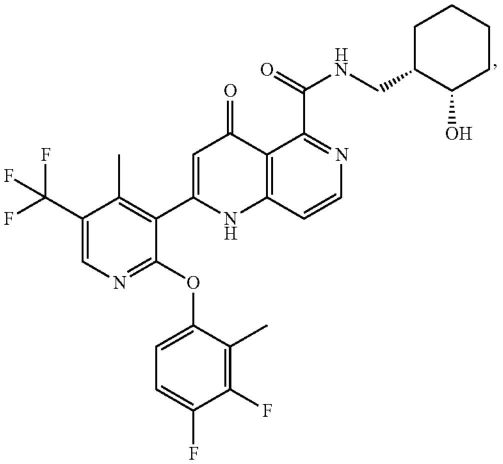

2-[2-(3,4-difluoro-2-methyl-phenoxy)-4-methyl-5-(trifluoromethyl)-3-pyridyl]-N-[[(1S,2S)-2-hydroxycyclohexyl]methyl]-4-oxo-1H-1,6-naphthyridine-5-carboxamide -continued

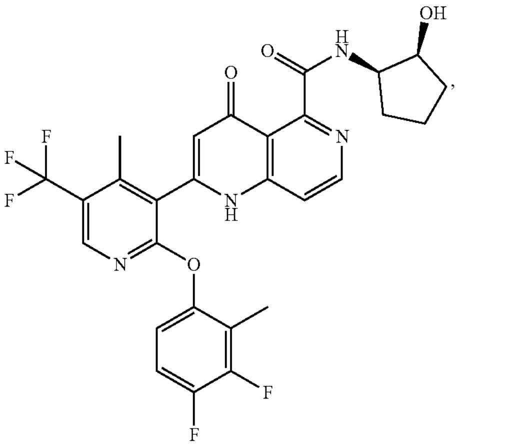

2-[2-(3,4-difluoro-2-methyl-phenoxy)-4-methyl-5-(trifluoromethyl)-3-pyridyl]-N-[(1R,2S)-2-hydroxycyclopentyl]-4-oxo-1H-1,6-naphthyridine-5-carboxamide

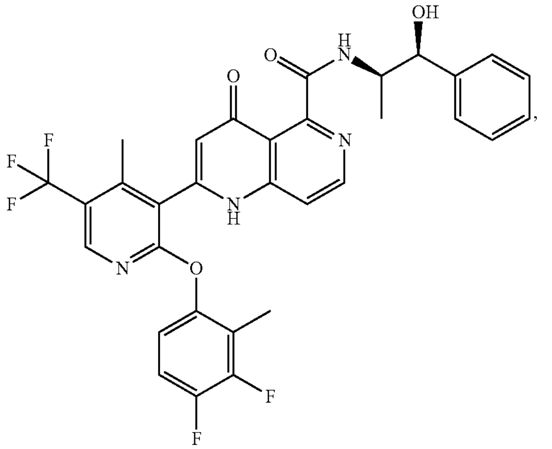

2-[2-(3,4-difluoro-2-methyl-phenoxy)-4-methyl-5-(trifluoromethyl)-3-pyridyl]-N-[[(1R,2S)-2-hydroxy-1-methyl-2-phenyl-ethyl]-4-oxo-1H-1,6-naphthyridine-5-carboxamide

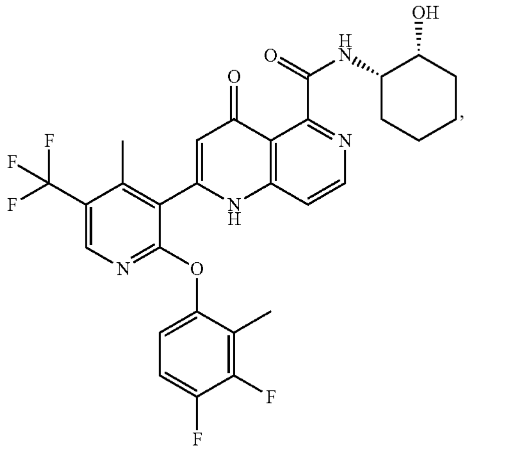

2-[2-(3,4-difluoro-2-methyl-phenoxy)-4-methyl-5-(trifluoromethyl)-3-pyridyl]-N-[[(1S,2R)-2-hydroxycyclohexyl]-4-oxo-1H-1,6-naphthyridine-5-carboxamide -continued

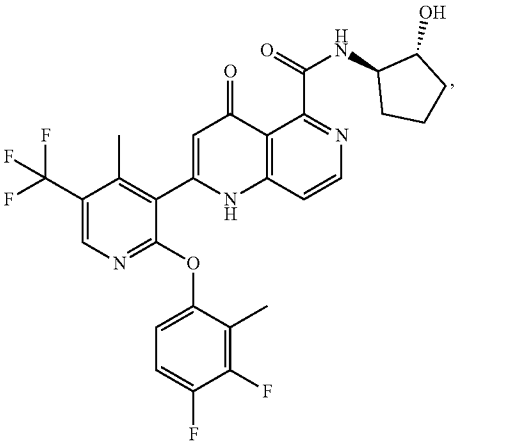

2-[2-(3,4-difluoro-2-methyl-phenoxy)-4-methyl-5-(trifluoromethyl)-3-pyridyl]-N-[(1R,2R)-2-hydroxycyclopentyl]-4-oxo-1H-1,6-naphthyridine-5-carboxamide

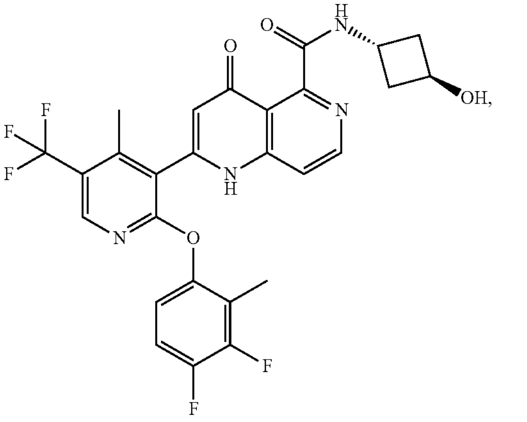

2-[2-(3,4-difluoro-2-methyl-phenoxy)-4-methyl-5-(trifluoromethyl)-3-pyridyl]-N-[(1R,2R)-2-hydroxycyclobutyl]-4-oxo-1H-1,6-naphthyridine-5-carboxamide (trans isomer)

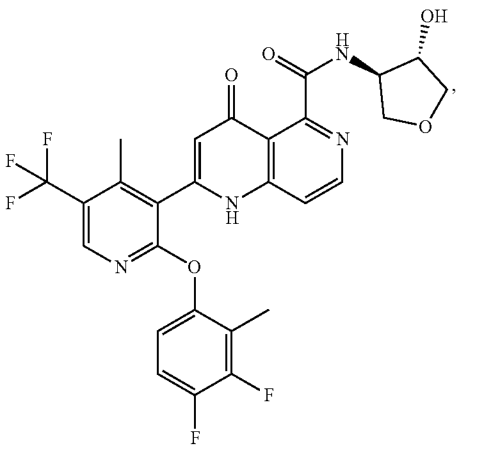

2-[2-(3,4-difluoro-2-methyl-phenoxy)-4-methyl-5-(trifluoromethyl)-3-pyridyl]-N-[(3R,4S)-4-oxo-1H-1,6-naphthyridine-5-carboxamide

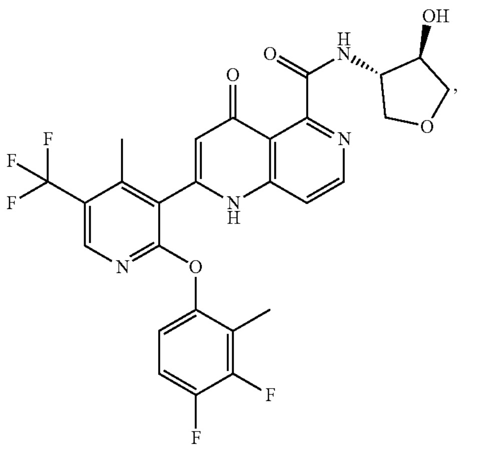

2-[2-(3,4-difluoro-2-methyl-phenoxy)-4-methyl-5-(trifluoromethyl)-3-pyridyl]-N-[(3S,4R)-4-hydroxytetrahydrofuran-3-yl]-4-oxo-1H-1,6-naphthyridine-5-carboxamide

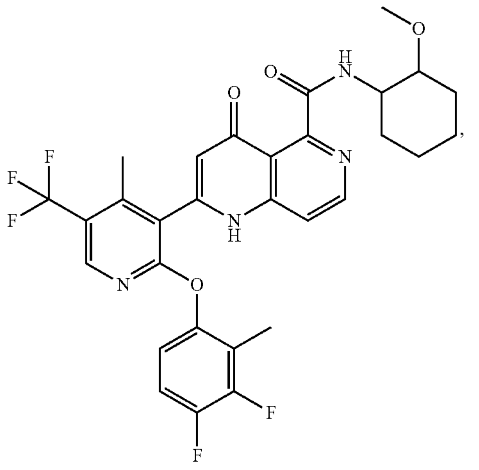

2-[2-(3,4-difluoro-2-methyl-phenoxy)-4-methyl-5-(trifluoromethyl)-3-pyridyl]-N-(2-methoxycyclohexyl)-4-oxo-1H-1,6-naphthyridine-5-carboxamide

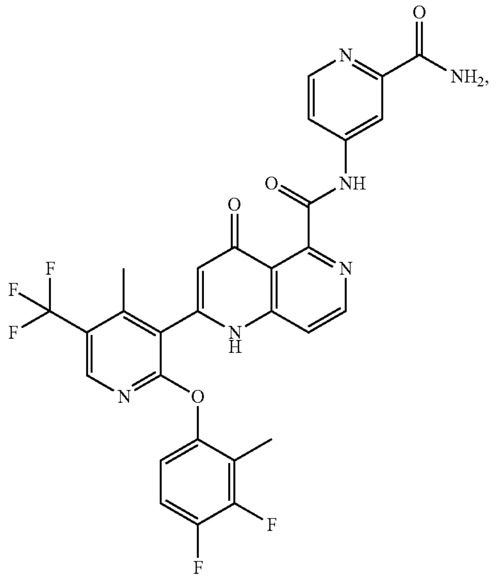

N-(2-carbamoyl-4-pyridyl)-2-[2-(3,4-difluoro-2-methyl-phenoxy)-4-methyl-5-(trifluoromethyl)-3-pyridyl]-4-oxo-1H-1,6-naphthyridine-5-carboxamide

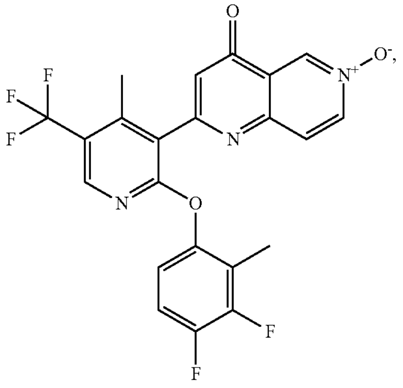

2-(2-(3,4-difluoro-2-methylphenoxy)-4-methyl-5-(trifluoromethyl)pyridin-3-yl)-4-oxo-4l5-1,6-naphthyridine-6-oxide

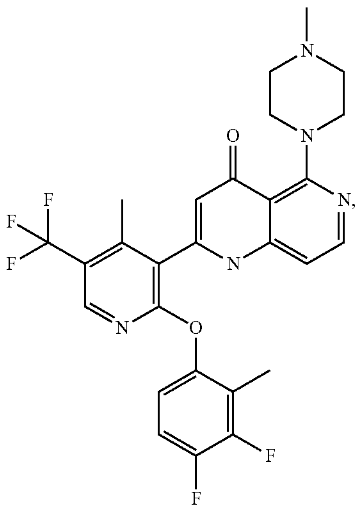

2-(2-(3,4-difluoro-2-methylphenoxy)-4-methyl-5-(trifluoromethyl)pyridin-3-yl)-5-(4-methylpiperazin-1-yl)-1,6-naphthyridin-4(1H)-one

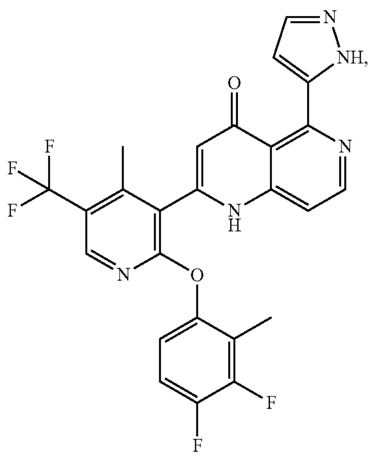

2-(2-(3,4-difluoro-2-methylphenoxy)-4-methyl-5-(trifluoromethyl)pyridin-3-yl)-5-(1H-pyrazol-5-yl)-1,6-naphthyridin-4(1H)-one -continued

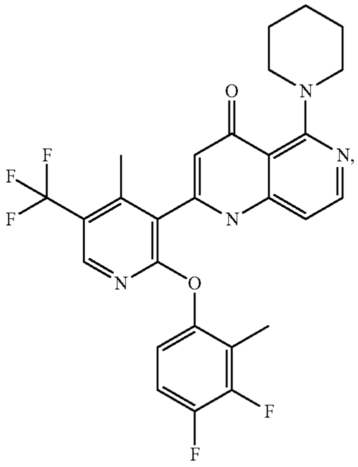

2-(2-(3,4-difluoro-2-methylphenoxy)-4-methyl-5-(trifluoromethyl)pyridin-3-yl)-5-(pyrazin-2-yl))-1,6-naphthyridin-4(1H)-one

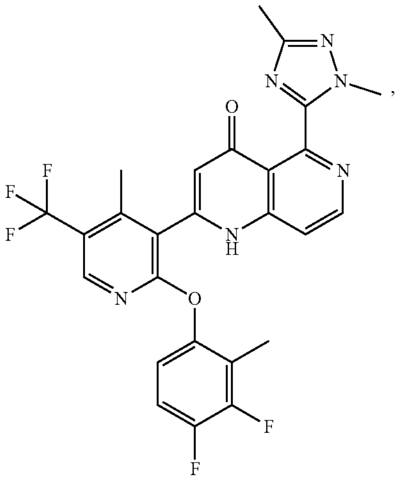

5-(1,3-dimethyl-1H-1,2,4-triazol-5-yl)-2-(3-(4-fluoro-2-methylphenoxy)-5-methyl-6-(trifluoromethyl)pyridazin-4-yl)-1,6-naphthyridin-4(1H)-one

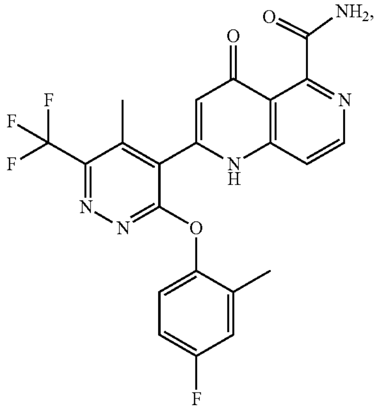

2-(3-(4-fluoro-2-methylphenoxy)-5-methyl-6-(trifluoromethyl)pyridazin-4-yl)-4-oxo-1,4-dihydro-1,6-naphthyridine-5-carboxamide -continued

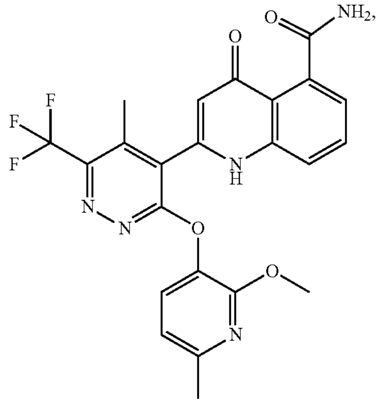

2-(3-((2-methoxy-6-methylpyeidin-3-yl)oxy)-5-methyl-6-(trifluoromethyl)pyridazin-4-yl)-4-oxo-1,4-dihydroquinoline-5-carboxamide

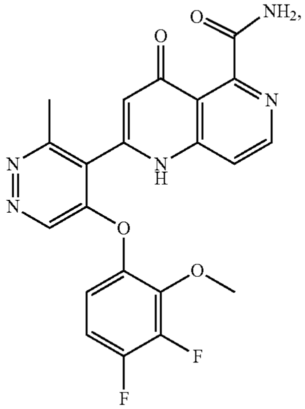

2-(5-(3,4-difluoro-2-methylphenoxy)-3-methylpyridazin-4-yl)-4-oxo-1,4-dihydro-1,6-naphthyridine-5-carboxamide

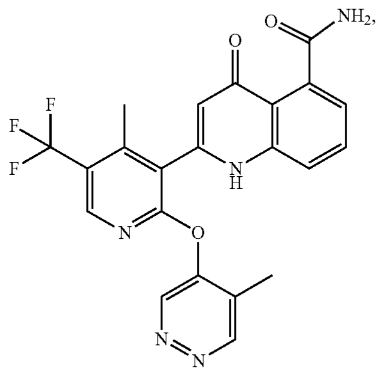

2-(4-methyl-2-((5-methylpyridazin-4-yl)oxy)-5-(trifluoromethyl)pyridin-3-yl)-4-oxo-1,4-dihydroquinaline-5-carboxamide -continued

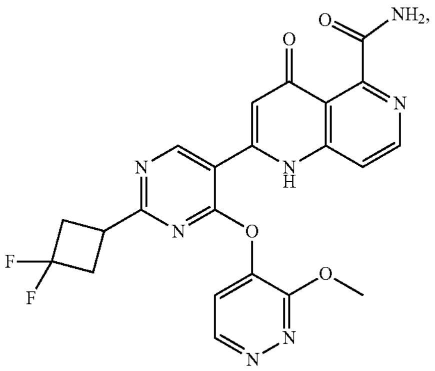

2-(2-(3,3difluorocyclobutyl)-4-((3-methylpyridazin-4-yl)oxy)pyrimidin-5-yl)-4-oxo-1,4-dihydro-1,6-naphthyridine-5-carboxamide

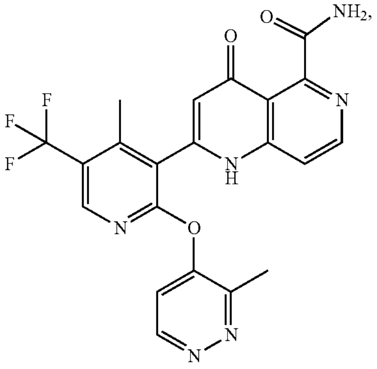

2-(4-methyl-2-((3-methylpyridazin-4-yl)oxy)-5-(trifluoromethyl)pyridin-3-yl)-4-oxo-1,4-dihydro-1,6-naphthyridine-5-carboxamide

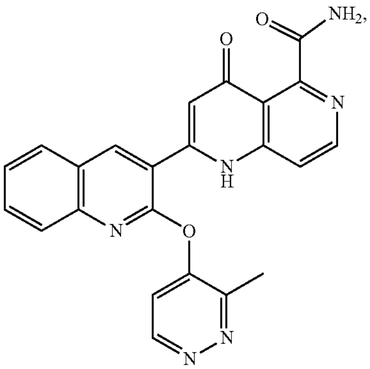

2-2-((3-methylpyridazin-4-yl)oxy)-5-(trifluoromethyl)pyridin-3-yl)-4-oxo-1,4-dihydro-1,6-naphthyridine-5-carboxamide -continued

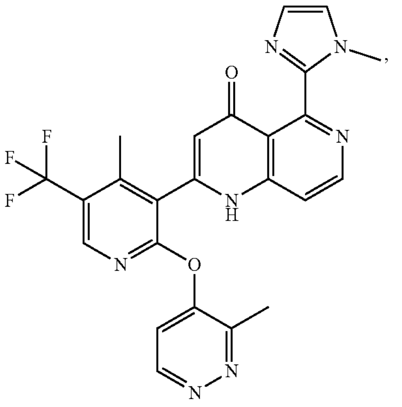

5-(1-methyl-1H-imidazol-2-yl)-2-(3-methyl-5-((3-methylpyridazin-4-yl)oxy)-2-(trifluoromethyl)pyridin-4-yl)-1,6-naphthyridin-4(1H)-one

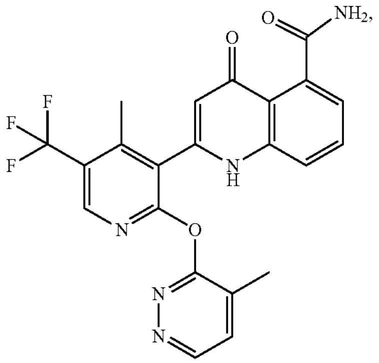

2-(4-methyl-2-((4-methylpyridazin-3-yl)oxy)-5-(trifluoromethyl)pyridin-3-yl)-4-oxo-1,4-dihydroquinoline-5-carboxamide

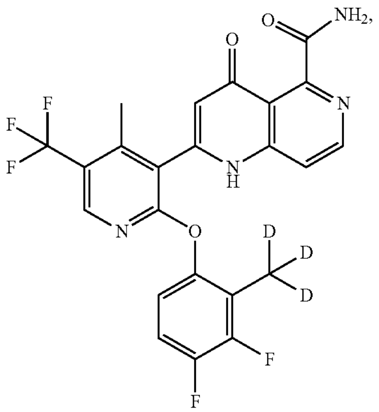

2-(2-(3,4-difluoro-2-(methyl-d3)phenoxy)-4-methyl-5-(trifluoromethyl)pyridin-3-yl)-4-oxo-1,4-dihydro-1,6naphthyridine-5-carboxamide -continued

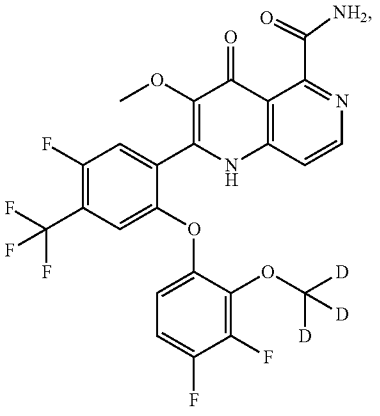

2-(2-(3,4-difluoro-2-(methyl-d3)phenoxy)-5-fluporo-4-(trifluoromethyl)phenyl)-3-methoxy-4-oxo-1,4-dihydro-1,6naphthyridine-5-carboxamide

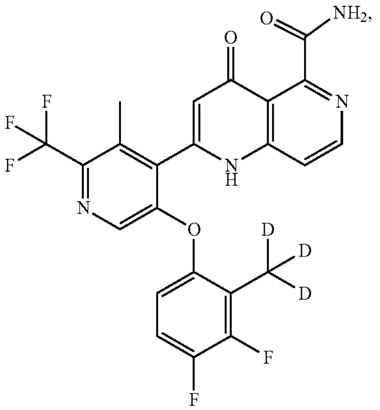

2-(5-(3,4-difluoro-2-(methyl-d3)phenoxy)-3-methyl-2-(trifluoromethyl)pyridin-4-yl)-4-oxo-1,4-dihydro-1,6naphthyridine-5-carboxamide and

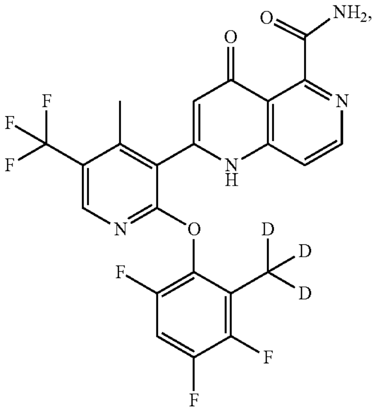

2-(2-(3,4-difluoro-2-(methyl-d3)phenoxy)6-d)-4-methyl-5-(trifluoromethyl)pyridin-3-yl)-4-oxo-1,4-dihydro-1,6naphthyridine-5-carboxamide or a pharmaceutically acceptable salt thereof.

6. The compound of claim 1, wherein the compound is selected from:

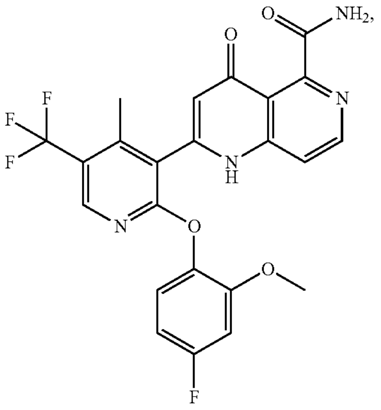 [SMILES: COc1cc(F)ccc1Oc1ncc(C(F)(F)F)c(C)c1-c1cc(=O)c2c(C(N)=O)nccc2[nH]1]

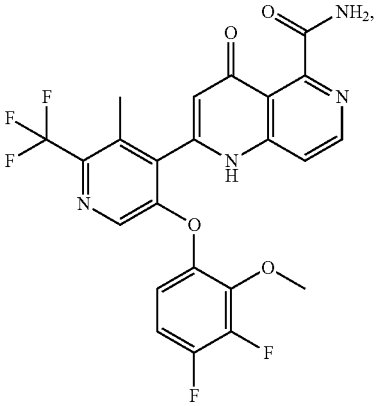

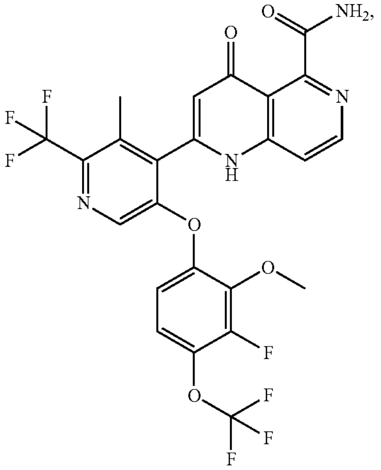

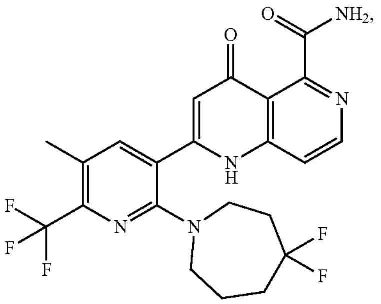

-continued
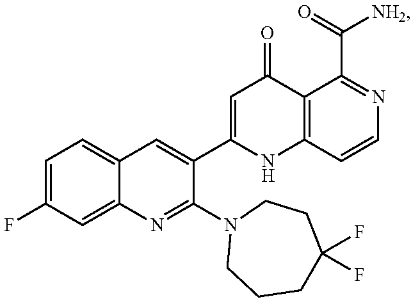
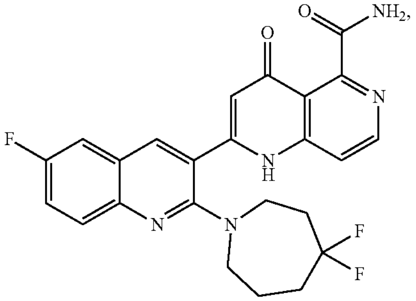
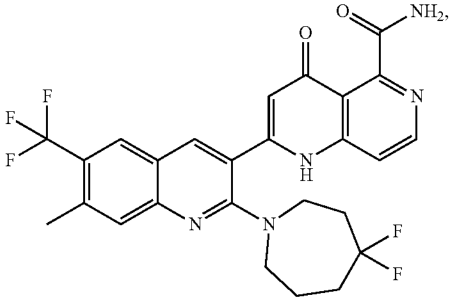
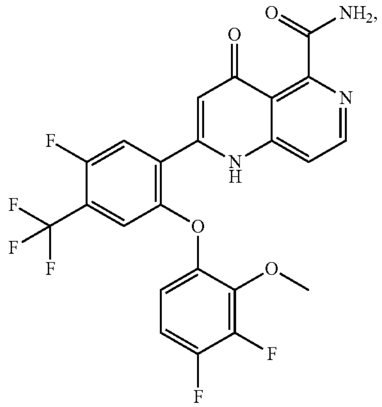
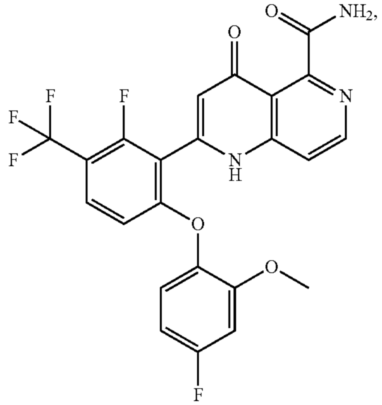
-continued
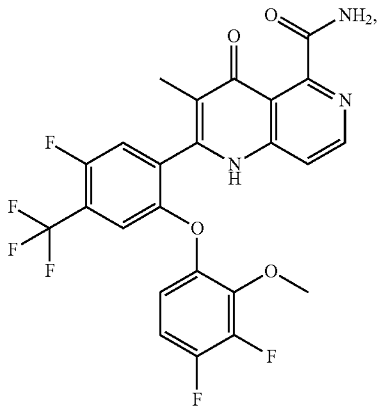
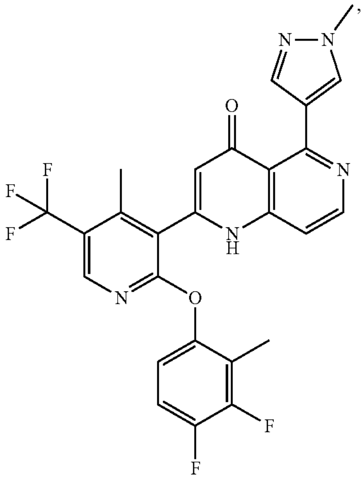
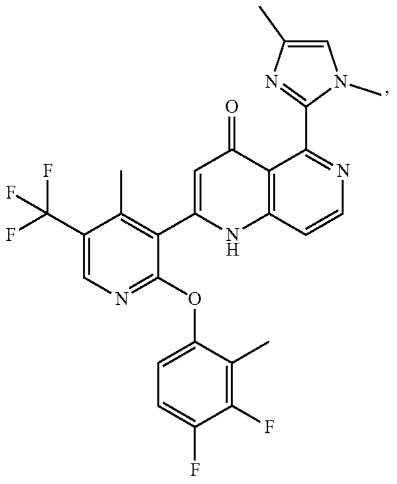

-continued
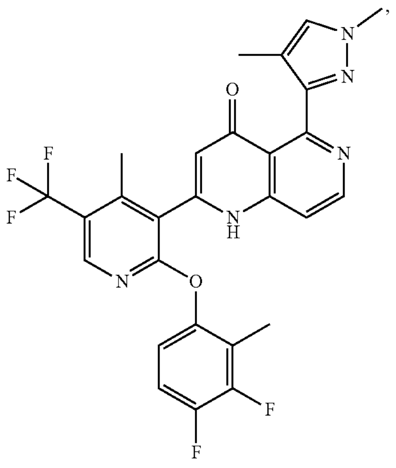
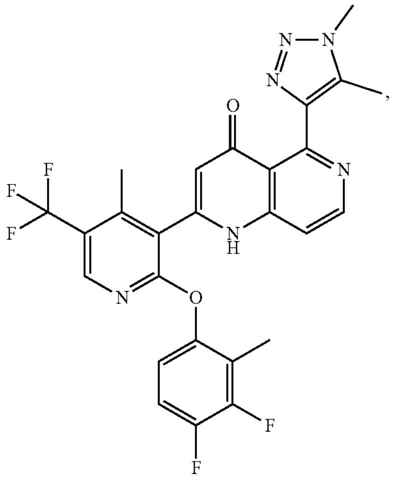
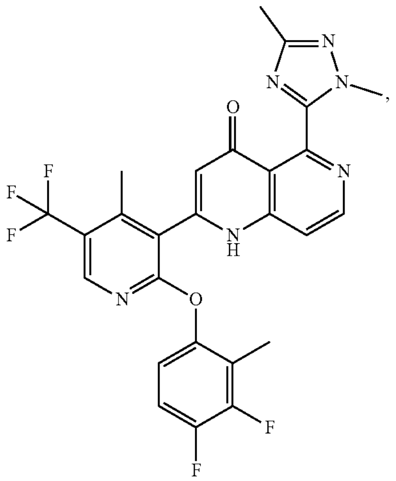
-continued
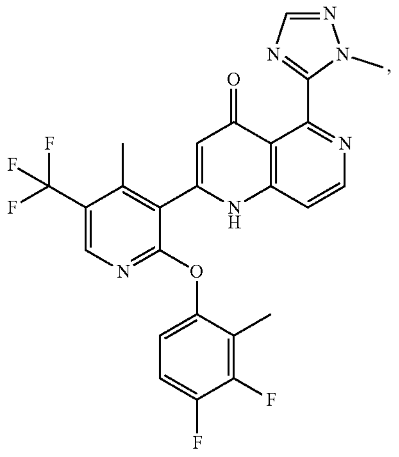
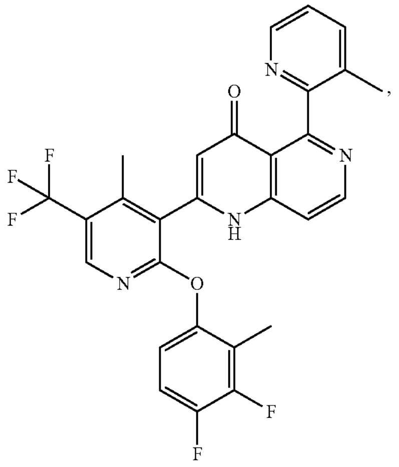
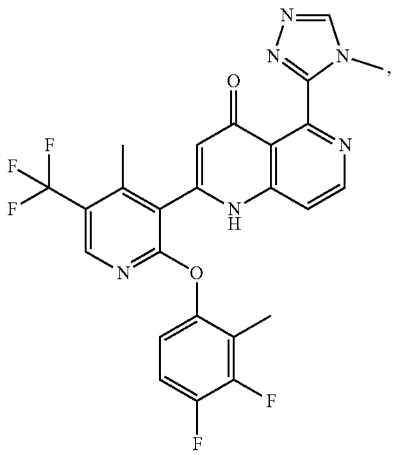

-continued
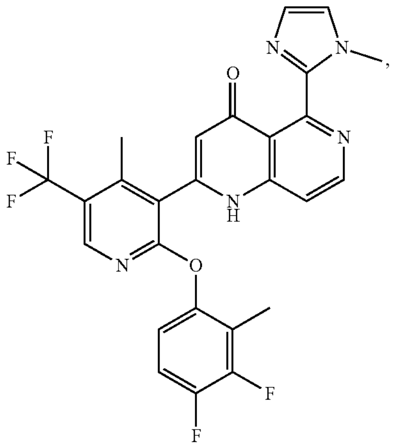
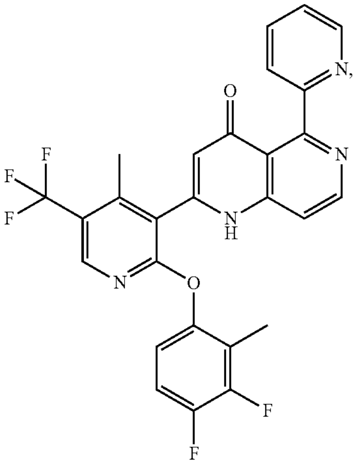
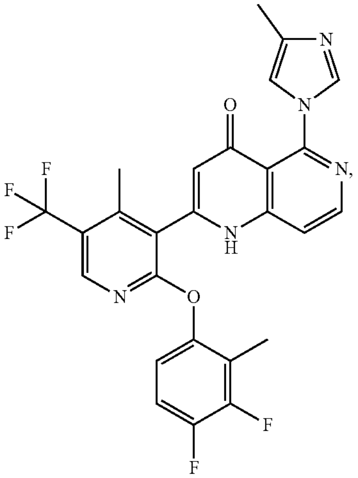
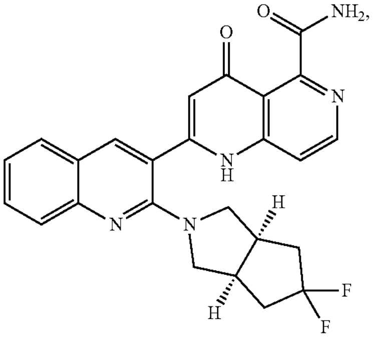
-continued
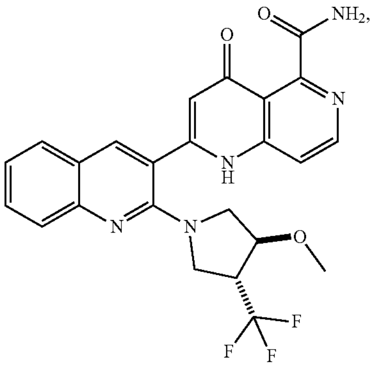
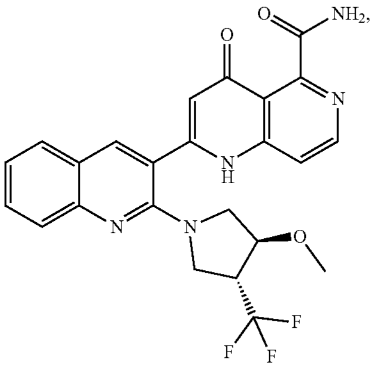
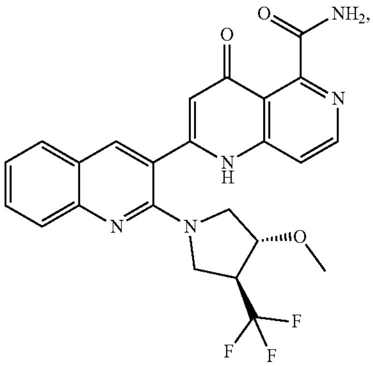
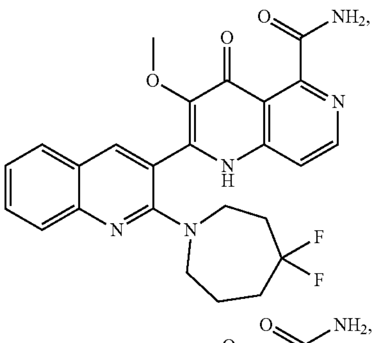
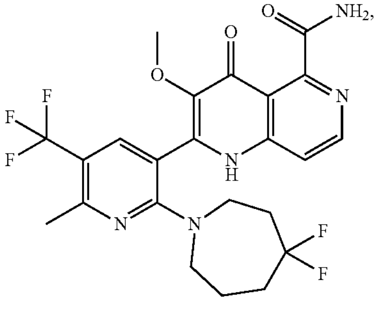

-continued
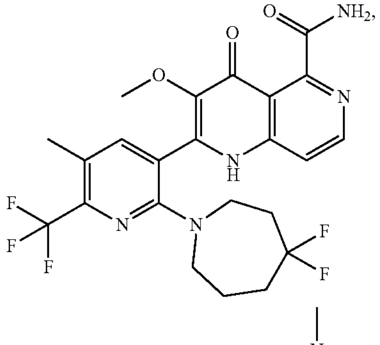
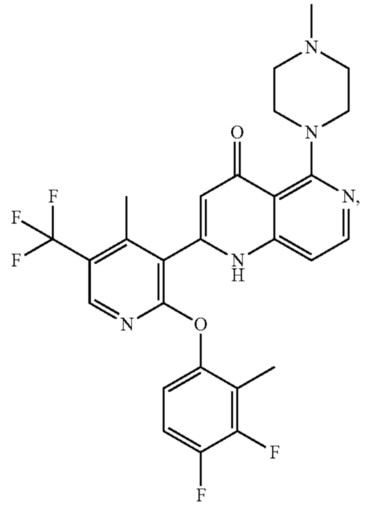
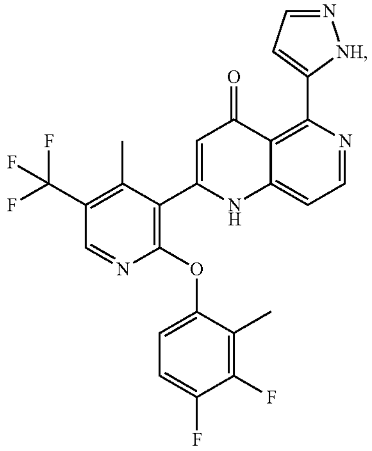
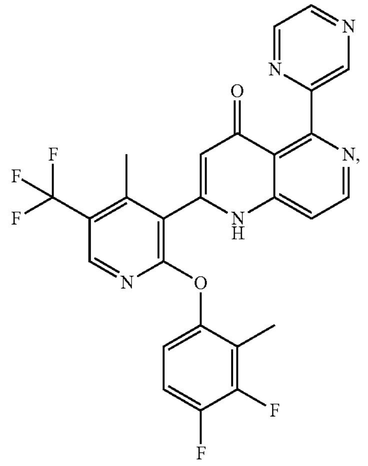
-continued
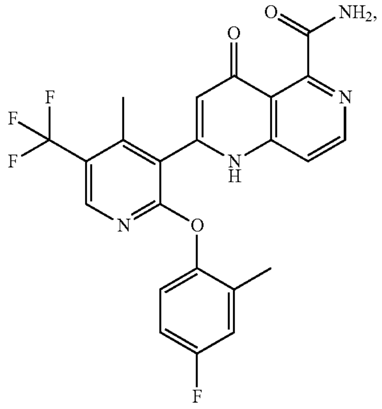
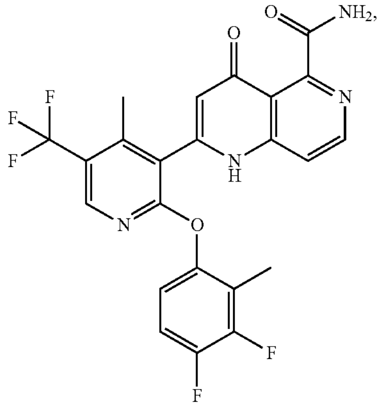
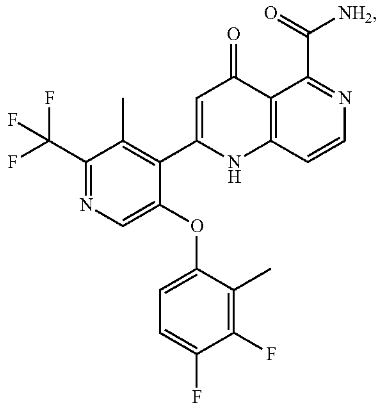
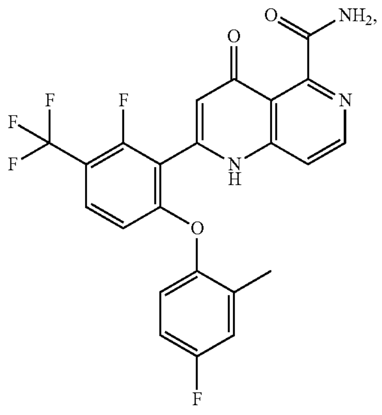

-continued

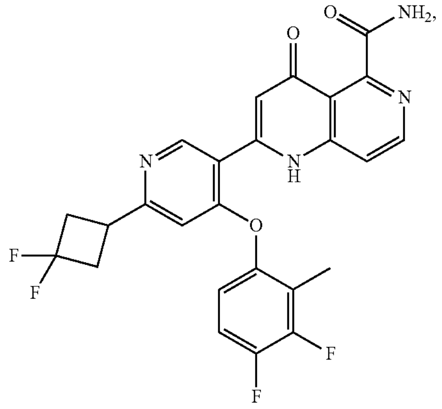

and

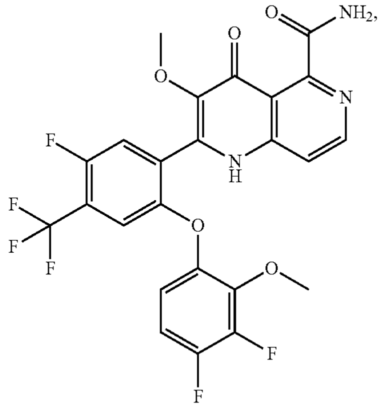

or a pharmaceutically acceptable salt thereof.

7. The compound of claim 1, wherein the compound is:

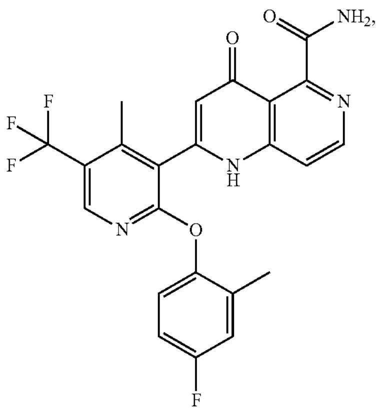

or a pharmaceutically acceptable salt thereof.

8. The compound of claim 1, wherein the compound is:

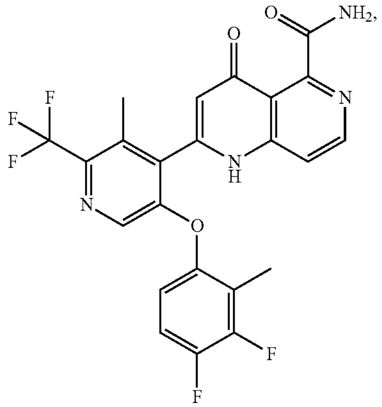

or a pharmaceutically acceptable salt thereof.

9. The compound of claim 1, wherein the compound is:

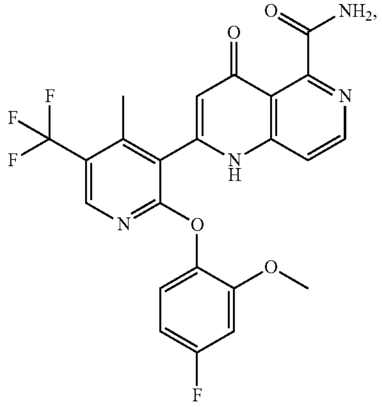

or a pharmaceutically acceptable salt thereof.

10. The compound of claim 1, wherein the compound is:

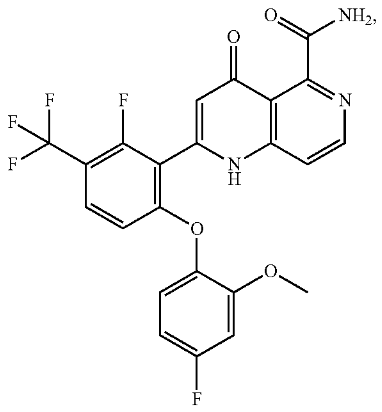 [SMILES: COc1cc(F)ccc1Oc1ccc(C(F)(F)F)c(F)c1-c1cc(=O)c2c(C(N)=O)nccc2[nH]1]

or a pharmaceutically acceptable salt thereof.

11. The compound of claim 1, or a pharmaceutically acceptable salt thereof, wherein $X_4$ is $CR_4$; $X_5$ is N; $X_6$ is $CR_6$; $X_7$ is $CR_7$.

12. The compound of claim 1, or a pharmaceutically acceptable salt thereof, wherein $X_4$ is $CR_4$; $X_5$ is N; $X_6$ is $CR_6$; $X_7$ is N.

13. The compound of claim 1, or a pharmaceutically acceptable salt thereof, wherein $X_4$ is $CR_4$; $X_5$ is $CR_5$; $X_6$ is N; $X_7$ is $CR_7$.

14. The compound of claim 1, or a pharmaceutically acceptable salt thereof, wherein $X_4$ is $CR_4$; $X_5$ is $CR_5$; $X_6$ is $CR_6$; $X_7$ is N.

15. The compound of claim 1, or a pharmaceutically acceptable salt thereof, wherein $X_2$ is $CR_2$;

$Y_1$ is $CR_{1a}$;

$Y_2$ is N or $CR_{2a}$;

$Y_3$ is $CR_{3a}$;

$R_{11}$, $R_{2a}$, and $R_{3a}$ are each H;

$R_{1a}$ is $C(O)NR_{12}R_{13}$, $NR_{12}R_{13}$, $NR_8C(O)NR_8R_9$, $OR_{12}$, N═S(═O)R'R", 5-10 membered heteroaryl, or 4-10 membered heterocyclyl, wherein the heterocyclyl or heteroaryl in said 5-10 membered heteroaryl or 4-10 membered heterocyclyl is optionally substituted with 1-4 substituents selected from OH, halo, oxo, C(O)$NR_8R_9$, $NR_8R_9$, $C_1$-$C_6$ alkyl, $C_1$-$C_6$ alkoxy, ($C_1$-$C_6$ alkylene)-OH, ($C_1$-$C_6$ alkylene)-O—($C_1C_6$ alkyl), and ($C_1$-$C_6$ alkylene)-$NR_8R_9$;

R' and R", together with the S atom to which they are attached, form a 4-7 membered heterocyclyl; and $R_{12}$ and $R_{13}$ are each independently H, C(O)($C_1$-$C_6$ alkyl), ($C_1$-$C_6$ alkylene)-$NR_8R_9$, $CH_2CH(OH)(CH_2)_m(CHOH)_n(CH_2)_pH$, $C_1$-$C_6$ alkyl optionally substituted with one or more OH, indanyl, ($C_1$-$C_6$ alkylene)-($C_3$-$C_6$ cycloalkyl), ($C_1$-$C_6$ alkylene)-phenyl, ($C_1$-$C_6$ alkylene)-(5 membered heterocyclyl), $C_4$-$C_7$ cycloalkyl, $C_6$-$C_{10}$ aryl, 5-6 membered heteroaryl, or 4-7 membered heterocyclyl, wherein the indanyl, ($C_1$-$C_6$ alkylene)-($C_3$-$C_6$ cycloalkyl), ($C_1$-$C_6$ alkylene)-phenyl, ($C_1$-$C_6$ alkylene)-(5-membered heterocyclyl), $C_4$-$C_7$ cycloalkyl, $C_6$-$C_{10}$ aryl, 5-6 membered heteroaryl, or 4-7 membered heterocyclyl is optionally substituted with 1-4 substituents selected from OH, oxo, $C_1$-$C_6$ alkyl, ($C_1$-$C_6$ alkylene)-OH, and $C_1$-$C_6$ alkoxy.

16. The compound of claim 15, or a pharmaceutically acceptable salt thereof, wherein $Y_2$ is N.

17. The compound of claim 16, or a pharmaceutically acceptable salt thereof, wherein $X_4$ is $CR_4$; $X_5$ is N; $X_6$ is $CR_6$; $X_7$ is $CR_7$.

18. The compound of claim 16, or a pharmaceutically acceptable salt thereof, wherein $X_4$ is $CR_4$; $X_5$ is N; $X_6$ is $CR_6$; $X_7$ is N.

19. The compound of claim 16, or a pharmaceutically acceptable salt thereof, wherein $X_4$ is $CR_4$; $X_5$ is $CR_5$; $X_6$ is N; $X_7$ is $CR_7$.

20. The compound of claim 16, or a pharmaceutically acceptable salt thereof, wherein $X_4$ is $CR_4$; $X_5$ is $CR_5$; $X_6$ is $CR_6$; $X_7$ is N.

21. The compound of claim 16, or a pharmaceutically acceptable salt thereof, wherein:

L is a single bond or —$C(R)_2$—;

$X_2$ is $CR_2$;

Z is 3-7 membered cycloalkenyl, phenyl, or 5-6 membered heteroaryl, wherein said 3-7 membered cycloalkenyl, phenyl, or 5-6 membered heteroaryl may be unsubstituted or may be substituted with 1-4 substituents selected from halo, OH, $C_1$-$C_6$ alkyl, $C_1$-$C_6$ alkoxy, $C_1$-$C_6$ haloalkyl, and $C_1$-$C_6$ haloalkoxy.

22. The compound of claim 16, or a pharmaceutically acceptable salt thereof, wherein:

L is a single bond;

$X_2$ is $CR_2$;

$R_{1a}$ is H, halo, CN, OH, $C(O)NR_{12}R_{13}$, $C_1$-$C_6$ alkoxy, —$NR_{12}R_{13}$, ($C_1$-$C_6$ alkylene)-$C(O)NR_8R_9$, ($C_1$-$C_6$ alkylene)-OH, $C(O)OR_{12}$, $CH(OH)(CH_2)_m(CHOH)_n(CH_2)_pH$, or N═S(═O)($CH_3$) 2; and $Z_1$ is 4-10 membered heterocyclyl, wherein said 4-10 membered heterocyclyl may be unsubstituted or may be substituted with 1-4 substituents selected from halo, OH, $C_1$-$C_6$ alkyl, $C_1$-$C_6$ alkoxy, $C_1$-$C_6$ haloalkyl, and $C_1$-$C_6$ haloalkoxy.

23. The compound of claim 22, wherein the compound has formula (I-B-2)

I-B-2

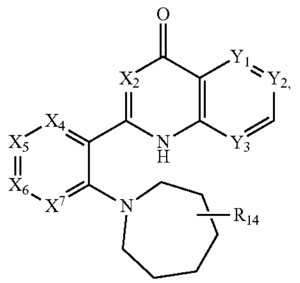

or a pharmaceutically acceptable salt thereof, wherein:

r is 0, 1, 2, 3, or 4; and each $R_{14}$ is independently selected from halo, OH, $C_1$-$C_6$ alkyl, $C_1$-$C_6$ alkoxy, $C_1$-$C_6$ haloalkyl, and $C_1$-$C_6$ haloalkoxy.

24. The compound of claim 16, or a pharmaceutically acceptable salt thereof, wherein:

L is O, —O—$C(R)_2$—, or —$C(R)_2$—O—;

$Z_1$ is phenyl, 4-10 membered heterocyclyl, or 5-6 membered heteroaryl, wherein said phenyl, 4-10 membered heterocyclyl, or 5-6 membered heteroaryl may be unsubstituted or may be substituted with 1-4 substituents selected from halo, OH, $C_1$-$C_6$ alkyl, $C_1$-$C_6$ alkoxy, $C_1$-$C_6$ haloalkyl, $CH_2OH$, C(O)H, and $C_1$-$C_6$ haloalkoxy.

25. The compound of claim 24, wherein the compound has formula (I-C-1)

I-C-1

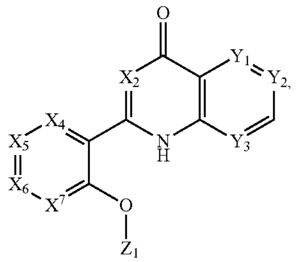

or a pharmaceutically acceptable salt thereof.

26. The compound of claim 24, wherein the compound has formula (I-C-2)

I-C-2

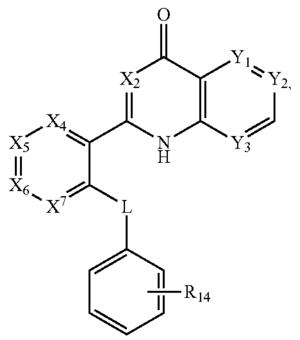

or a pharmaceutically acceptable salt thereof, wherein:

r is 0, 1, 2, 3, or 4; and each $R_{14}$ is independently selected from halo, OH, $C_1$-$C_6$ alkyl, $C_1$-$C_6$ alkoxy, $C_1$-$C_6$ haloalkyl, and $C_1$-$C_6$ haloalkoxy.

27. The compound of claim 24, or a pharmaceutically acceptable salt thereof, wherein $R_4$, $R_5$, $R_6$, and Ry are each independently H, halo, $C_1$-$C_6$ alkyl, $C_1$-$C_6$ haloalkyl, or $C_3$-$C_6$ cycloalkyl optionally substituted with one or more alkyl, halo, or OH.

28. A compound, wherein the compound is:

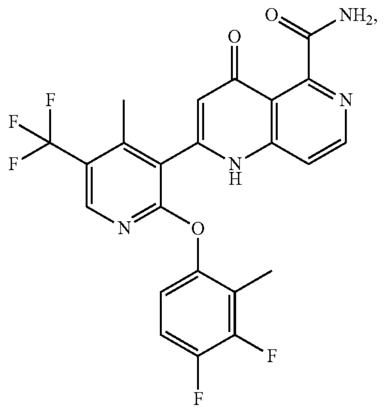 [SMILES: Cc1c(Oc2ncc(C(F)(F)F)c(C)c2-c2cc(=O)c3c(C(N)=O)nccc3[nH]2)ccc(F)c1F]

or a pharmaceutically acceptable salt thereof.

29. The compound of claim 28, wherein the compound is in non-salt form.

30. A pharmaceutical composition comprising the compound of claim 1, or a pharmaceutically acceptable salt thereof, and one or more pharmaceutically acceptable carriers or vehicles.

31. A method of inhibiting a voltage-gated sodium channel in a subject comprising administering to the subject the compound of claim 1, or a pharmaceutically acceptable salt thereof.

32. A method of treating or lessening the severity in a subject of chronic pain, gut pain, neuropathic pain, musculoskeletal pain, acute pain, inflammatory pain, cancer pain, idiopathic pain, postsurgical pain, visceral pain, multiple sclerosis, Charcot-Marie-Tooth syndrome, incontinence, pathological cough, or cardiac arrhythmia comprising administering to the subject an effective amount of the compound of claim 1, or a pharmaceutically acceptable salt thereof.

33. A pharmaceutical composition comprising the compound of claim 6, or a pharmaceutically acceptable salt thereof, and one or more pharmaceutically acceptable carriers or vehicles.

34. A method of inhibiting a voltage-gated sodium channel in a subject comprising administering to the subject the compound of claim 6, or a pharmaceutically acceptable salt thereof.

35. A method of treating or lessening the severity in a subject of chronic pain, gut pain, neuropathic pain, musculoskeletal pain, acute pain, inflammatory pain, cancer pain, idiopathic pain, postsurgical pain, visceral pain, multiple sclerosis, Charcot-Marie-Tooth syndrome, incontinence, pathological cough, or cardiac arrhythmia comprising administering to the subject an effective amount of the compound of claim 6, or a pharmaceutically acceptable salt thereof.

* * * * *